US006605592B2

(12) United States Patent
Ni et al.

(10) Patent No.: US 6,605,592 B2

(45) Date of Patent: Aug. 12, 2003

(54) PROTEIN HOFNF53

(75) Inventors: Jian Ni, Germantown, MD (US); Kevin P. Baker, Darnestown, MD (US); Charles E. Birse, North Potomac, MD (US); Reinhard Ebner, Gaithersburg, MD (US); Michele Fiscella, Bethesda, MD (US); George A. Komatsoulis, Silver Spring, MD (US); David W. LaFleur, Washington, DC (US); Paul A. Moore, Germantown, MD (US); Henrik S. Olsen, Gaithersburg, MD (US); Craig A. Rosen, Laytonsville, MD (US); Steven M. Ruben, Olney, MD (US); Daniel R. Soppet, Centreville, VA (US); Paul E. Young, Gaithersburg, MD (US); Ping Wei, Brookeville, MD (US); Kimberly A. Florence, Rockville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 56 days.

(21) Appl. No.: 09/800,729

(22) Filed: Mar. 8, 2001

(65) Prior Publication Data

US 2002/0068319 A1 Jun. 6, 2002

Related U.S. Application Data

(63) Continuation-in-part of application No. PCT/US00/26013, filed on Sep. 22, 2000.

(60) Provisional application No. 60/155,709, filed on Sep. 24, 1999.

(51) Int. Cl.[7] ........................ C07K 14/47; A61K 38/17; C12N 5/10; C12N 15/12; C12N 15/63

(52) U.S. Cl. .............................. 514/2; 530/350; 514/8; 514/12; 435/69.1; 435/71.1; 435/71.2; 435/471; 435/325; 435/252.3; 435/254.11; 435/320.1

(58) Field of Search .............................. 530/350; 514/2, 514/8, 12; 435/69.1, 71.1, 71.2, 325, 471, 252.3, 254.11, 320.1

(56) References Cited

FOREIGN PATENT DOCUMENTS

EP 022 267 A2 * 4/1987

OTHER PUBLICATIONS

Thomas E. Creighton, Proteins, Structures & Molecular Principles, Freeman & Co, N.Y. pp. 70–73, 1984.*

Reeck et al. Cell. vol. 50, p. 667, 1987.*

Ganong, Review of Medical Physiology, Appleton & Lange 17$^{th}$ edition, pp. 220 & 446, 1995.*

The Cytokine Facts Book, Callard & Gearing, Academic Pren. pp. 39–40, 1994.*

Skolnick et al. Nature Biotechnology vol. 18, pp. 283–287, Mar. 2000.*

U.S. patent application Ser. No. 09/912,293, Rosen et al., not published.

U.S. patent application Ser. No. 09/912,292, Rosen et al., not published.

* cited by examiner

*Primary Examiner*—Prema Mertz

(74) *Attorney, Agent, or Firm*—Human Genome Sciences, Inc.

(57) ABSTRACT

The present invention relates to novel human secreted proteins and isolated nucleic acids containing the coding regions of the genes encoding such proteins. In particular, the present application relates to a novel human protein, Protein HOFNF53. Also provided are vectors, host cells, antibodies, and recombinant methods for producing human secreted proteins. The invention further relates to diagnostic and therapeutic methods useful for diagnosing and treating diseases, disorders, and/or conditions related to these novel human secreted proteins.

19 Claims, 22 Drawing Sheets

```
  1  GGGCCATCAGGCCCACAGAGGAGGGCGGCCTCCACGTCCACATGGAGTTCCCGGGGGCGG   60
  1   A  I  R  P  T  E  E  G  G  L  H  V  H  M  E  F  P  G  A  D   20

 61  ACGGCTGTAACCAGGTGGATGCCGAGTACCTGAAGGTGGGCTCCGAGGGACACTTCAGAG  120
 21   G  C  N  Q  V  D  A  E  Y  L  K  V  G  S  E  G  H  F  R  V   40

121  TCCCGGCCTTGGGCTACCTGGACGTGCGCATCGTGGACACAGACTACAGCTCCTTCGCCG  180
 41   P  A  L  G  Y  L  D  V  R  I  V  D  T  D  Y  S  S  F  A  V   60

181  TCCTTTACATCTACAAGGAGCTGGAGGGGGCGCTCAGCACCATGGTGCAGCTCTACAGCC  240
 61   L  Y  I  Y  K  E  L  E  G  A  L  S  T  M  V  Q  L  Y  S  R   80

241  GGACCCAGGATGTGAGTCCCCAGGCTCTGAAGGCCTTCCAGGACTTCTACCCGACCCTGG  300
 81   T  Q  D  V  S  P  Q  A  L  K  A  F  Q  D  F  Y  P  T  L  G  100

301  GGCTCCCCGAGGACATGATGGTCATGCTGCCCCAGTCAGATGCATGCAACCCTGAGAGCA  360
101   L  P  E  D  M  M  V  M  L  P  Q  S  D  A  C  N  P  E  S  K  120

361  AGGAGGCGCCCTGACACCTCCGGAGCCCCACCCCCGCCCTTCCCAGGTGGAGCCAAAGCA  420
121   E  A  P  *                                                  124

421  GCAGGCGCCTTTGCCCCTGGAGTCAAGACCCACAGCCCTCGGGGACCACCTGGAGTCTCT  480

481  CCATCCTCCACCCCCCGCCTGTGGGATGCCTTGTGGACGTCTCTTTCTATTCAATAAAC  540

541  AGATGCTGCAGCCTCAAAAAAAAAAAAAAA  570
```

FIG. 1

```
                10        20        30        40
1   ----------------------------------------  Lipocolon.aa
1   MKGLVLSFAL-VALSALCVYGDVPIQPDFQEDKILGKWYG  emb|CAA48138.1
1   MMRILLALSLGVACCSLWVGAEVQVQPDFQKEKVLGKWYG  dbj|BAA12075.1
1   MMRILLALSLGVACCSLWVGAEVQVQPDFQKEKVLGKWYG  emb|CAA59132.1

                50        60        70        80
1   ----------------------AIRPTEEGGLHVHMEFPG  Lipocolon.aa
40  IGLASNSNWFQSKKQQLKMCTTVITPTADGNLDVVATFPK  emb|CAA48138.1
41  IGLASNSNWFKDRKSHMKMCTTIITPTADGNVEVTATYPK  dbj|BAA12075.1
41  IGLASNSNWFKDRKSHMKMCTTIITPTADGNLEVTATYPK  emb|CAA59132.1

                90       100       110       120
19  ADGCNQVDAEYLKVGSEGHFRVPALGY---LDVRIVDTDY  Lipocolon.aa
80  LDRCEKKSMTYIKTEQPGRFLSKSPRYGSDHVIRVVESNY  emb|CAA48138.1
81  MDRCETKSMTYFKTEQLGRFRAKSPRYGSEHDMRVVETNY  dbj|BAA12075.1
81  MDRCETKSMTYFKTEQLGGFRAKSPRYGSEHDMRVVETNY  emb|CAA59132.1

               130       140       150       160
56  SSFAVLYIYKELEGALSTMVQLYSRTQDVSPQALKAFQDF  Lipocolon.aa
120 DEYTLMHTIKTKGNEVNTIVSLFGRRKTLSPELLDKFQQF  emb|CAA48138.1
121 DEYILMYTVKTKGSETNQIVSLFGRDKDLRPELLDKFQNF  dbj|BAA12075.1
121 DEYILMYTVKTKGSETNQIVSLFGRDKDLRPELLDKFQNF  emb|CAA59132.1

               170       180
96  YPTLGLPEDMMVMLPQSDACNPESKEAP              Lipocolon.aa
160 AKEQGLTDDNILILPQTDSCMSEV                  emb|CAA48138.1
161 AKSQGLADDNIIILPHTDQCMTEA                  dbj|BAA12075.1
161 AKSQGLADDNIIILPHTDQCMTEA                  emb|CAA59132.1
```

FIG. 2

```
1    TCGACGGCAGAGGAGCACTTAGCAGCTTATTCAGTGTCCGATTCTGATTCCGGCAAGGAT   60

61   CCAAGCATGGAATGCTGCCGTCGGGCAACTCCTGGCACACTGCTCCTCTTTCTGGCTTTC   120
1          M  E  C  C  R  R  A  T  P  G  T  L  L  L  F  L  A  F     18

121  CTGCTCCTGAGTTCCAGGACCGCACGCTCCGAGGAGGACCGGGACGGCCTATGGGATGCC   180
19   L  L  L  S  S  R  T  A  R  S  E  E  D  R  D  G  L  W  D  A     38

181  TGGGGCCCATGGAGTGAATGCTCACGCACCTGCGGGGGTGGGGCCTCCTACTCTCTGAGG   240
39   W  G  P  W  S  E  C  S  R  T  C  G  G  G  A  S  Y  S  L  R     58

241  CGCTGCCTGAGCAGCAAGAGCTGTGAAGGAAGAAATATCCGATACAGAACATGCAGTAAT   300
59   R  C  L  S  S  K  S  C  E  G  R  N  I  R  Y  R  T  C  S  N     78

301  GTGGACTGCCCACCAGAAGCAGGTGATTTCCGAGCTCAGCAATGCTCAGCTCATAATGAT   360
79   V  D  C  P  P  E  A  G  D  F  R  A  Q  Q  C  S  A  H  N  D     98

361  GTCAAGCACCATGGCCAGTTTTATGAATGGCTTCCTGTGTCTAATGACCCTGACAACCCA   420
99   V  K  H  H  G  Q  F  Y  E  W  L  P  V  S  N  D  P  D  N  P     118

421  TGTTCACTCAAGTGCCAAGCCAAAGGAACAACCCTGGTTGTTGAACTAGCACCTAAGGTC   480
119  C  S  L  K  C  Q  A  K  G  T  T  L  V  V  E  L  A  P  K  V     138

481  TTAGATGGTACGCGTTGCTATACAGAATCTTTGGATATGTGCATCAGTGGTTTATGCCAA   540
139  L  D  G  T  R  C  Y  T  E  S  L  D  M  C  I  S  G  L  C  Q     158

541  ATTGTTGGCTGCGATCACCAGCTGGGAAGCACCGTCAAGGAAGATAACTGTGGGGTCTGC   600
159  I  V  G  C  D  H  Q  L  G  S  T  V  K  E  D  N  C  G  V  C     178

601  AACGGAGATGGGTCCACCTGCCGGCTGGTCCGAGGGCAGTATAAATCCCAGCTCTCCGCA   660
179  N  G  D  G  S  T  C  R  L  V  R  G  Q  Y  K  S  Q  L  S  A     198

661  ACCAAATCGGATGATACTGTGGTTGCAATTCCCTATGGAAGTAGACATATTCGCCTTGTC   720
199  T  K  S  D  D  T  V  V  A  I  P  Y  G  S  R  H  I  R  L  V     218
```

FIG. 4A

```
721  TTAAAAGGTCCTGATCACTTATATCTGGAAACCAAAACCCTCCAGGGGACTAAAGGTGAA  780
219  L  K  G  P  D  H  L  Y  L  E  T  K  T  L  Q  G  T  K  G  E   238

781  AACAGTCTCAGCTCCACAGGAACTTTCCTTGTGGACAATTCTAGTGTGGACTTCCAGAAA  840
239  N  S  L  S  S  T  G  T  F  L  V  D  N  S  S  V  D  F  Q  K   258

841  TTTCCAGACAAAGAGATACTGAGAATGGCTGGACCACTCACAGCAGATTTCATTGTCAAG  900
259  F  P  D  K  E  I  L  R  M  A  G  P  L  T  A  D  F  I  V  K   278

901  ATTCGTAACTCGGGCTCCGCTGACAGTACAGTCCAGTTCATCTTCTATCAACCCATCATC  960
279  I  R  N  S  G  S  A  D  S  T  V  Q  F  I  F  Y  Q  P  I  I   298

961  CACCGATGGAGGGAGACGGATTTCTTTCCTTGCTCAGCAACCTGTGGAGGAGGTTATCAG  1020
299  H  R  W  R  E  T  D  F  F  P  C  S  A  T  C  G  G  G  Y  Q   318

1021 CTGACATCGGCTGAGTGCTACGATCTGAGGAGCAACCGTGTGGTTGCTGACCAATACTGT  1080
319  L  T  S  A  E  C  Y  D  L  R  S  N  R  V  V  A  D  Q  Y  C   338

1081 CACTATTACCCAGAGAACATCAAACCCAAACCCAAGCTTCAGGAGTGCAACTTGGATCCT  1140
339  H  Y  Y  P  E  N  I  K  P  K  P  K  L  Q  E  C  N  L  D  P   358

1141 TGTCCAGCCAGGTGGGAGGCCACCCCATGGACCGCGTGCTCCTCCTCGTGTGGGGGGGGC  1200
359  C  P  A  R  W  E  A  T  P  W  T  A  C  S  S  S  C  G  G  G   378

1201 ATCCAGAGCCGGGCAGTTTCCTGTGTGGAGGAGGACATCCAGGGGCATGTCACTTCAGTG  1260
379  I  Q  S  R  A  V  S  C  V  E  E  D  I  Q  G  H  V  T  S  V   398

1261 GAAGAGTGGAAATGCATGTACACCCCTAAGATGCCCATCGCGCAGCCCTGCAACATTTTT  1320
399  E  E  W  K  C  M  Y  T  P  K  M  P  I  A  Q  P  C  N  I  F   418

1321 GACTGCCCTAAATGGCTGGCACAGGAGTGGTCTCCGTGCACAGTGACATGTGGCCAGGGC  1380
419  D  C  P  K  W  L  A  Q  E  W  S  P  C  T  V  T  C  G  Q  G   438

1381 CTCAGATACCGTGTGGTCCTCTGCATCGACCATCGAGGAATGCACACAGGAGGCTGTAGC  1440
439  L  R  Y  R  V  V  L  C  I  D  H  R  G  M  H  T  G  G  C  S   458
```

FIG. 4B

```
1441 CCAAAAACAAAGCCCCACATAAAAGAGGAATGCATCGTACCCACTCCCTGCTATAAACCC 1500
459  P  K  T  K  P  H  I  K  E  E  C  I  V  P  T  P  C  Y  K  P  478

1501 AAAGAGAAACTTCCAGTCGAGGCCAAGTTGCCATGGTTCAAACAAGCTCAAGAGCTAGAA 1560
479  K  E  K  L  P  V  E  A  K  L  P  W  F  K  Q  A  Q  E  L  E  498

1561 GAAGGAGCTGCTGTGTCAGAGGAGCCCTCGTTCATCCCAAAGGCCTGGTCGGCCTGCACA 1620
499  E  G  A  A  V  S  E  E  P  S  F  I  P  K  A  W  S  A  C  T  518

1621 GTCACCTGTGGTGTGGGGACCCAGGTGCGAATAGTCAGGTGCCAGGTGCTCCTGTCTTTC 1680
519  V  T  C  G  V  G  T  Q  V  R  I  V  R  C  Q  V  L  L  S  F  538

1681 TCTCAGTCCGTGGCTGACCTGCCTATTGACGAGTGTGAAGGGCCCAAGCCAGCATCCCAG 1740
539  S  Q  S  V  A  D  L  P  I  D  E  C  E  G  P  K  P  A  S  Q  558

1741 CGTGCCTGTTATGCAGGCCCATGCAGCGGGGAAATTCCTGAGTTCAACCCAGACGAGACA 1800
559  R  A  C  Y  A  G  P  C  S  G  E  I  P  E  F  N  P  D  E  T  578

1801 GATGGGCTCTTTGGTGGCCTGCAGGATTTCGACGAGCTGTATGACTGGGAGTATGAGGGG 1860
579  D  G  L  F  G  G  L  Q  D  F  D  E  L  Y  D  W  E  Y  E  G  598

1861 TTCACCAAGTGCTCCGAGTCCTGTGGAGGAGGTGTCCAGGAGGCTGTGGTGAGCTGCTTG 1920
599  F  T  K  C  S  E  S  C  G  G  G  V  Q  E  A  V  V  S  C  L  618

1921 AACAAACAGACTCGGGAGCCTGCTGAGGAGAACCTGTGCGTGACCAGCCGCCGGCCCCCA 1980
619  N  K  Q  T  R  E  P  A  E  E  N  L  C  V  T  S  R  R  P  P  638

1981 CAGCTCCTGAAGTCCTGCAATTTGGATCCCTGCCCAGCAAGGTGGGAAATTGGCAAGTGG 2040
639  Q  L  L  K  S  C  N  L  D  P  C  P  A  R  W  E  I  G  K  W  658

2041 AGTCCATGTAGTCTCACATGTGGGGTCGGCCTACAGACCAGAGACGTCTTCTGCAGCCAC 2100
659  S  P  C  S  L  T  C  G  V  G  L  Q  T  R  D  V  F  C  S  H  678

2101 CTGCTTTCCAGAGAGATGAATGAAACAGTCATCCTGGCTGATGAGCTGTGTCGCCAGCCC 2160
679  L  L  S  R  E  M  N  E  T  V  I  L  A  D  E  L  C  R  Q  P  698
```

FIG. 4C

```
2161 AAGCCCAGCACGGTGCAAGCTTGTAACCGCTTTAATTGCCCCCCAGCCTGGTACCCTGCA 2220
699  K  P  S  T  V  Q  A  C  N  R  F  N  C  P  P  A  W  Y  P  A  718

2221 CAGTGGCAGCCGTGTTCCAGAACGTGTGGCGGGGGTGTTCAGAAACGTGAGGTTCTTTGC 2280
719  Q  W  Q  P  C  S  R  T  C  G  G  G  V  Q  K  R  E  V  L  C  738

2281 AAGCAGCGCATGGCTGATGGCAGCTTCCTGGAGCTTCCTGAGACCTTCTGTTCAGCTTCA 2340
739  K  Q  R  M  A  D  G  S  F  L  E  L  P  E  T  F  C  S  A  S  758

2341 AAACCTGCCTGCCAGCAAGCATGCAAGAAAGATGACTGTCCCAGCGAGTGGCTTCTCTCA 2400
759  K  P  A  C  Q  Q  A  C  K  K  D  D  C  P  S  E  W  L  L  S  778

2401 GACTGGACAGAGTGTTCCACAAGCTGCGGGGAAGGCACCCAGACTCGAAGCGCCATTTGC 2460
779  D  W  T  E  C  S  T  S  C  G  E  G  T  Q  T  R  S  A  I  C  798

2461 CGAAAGATGCTGAAAACCGGCCTCTCAACGGTTGTCAATTCCACCCTGTGCCCGCCCCTG 2520
799  R  K  M  L  K  T  G  L  S  T  V  V  N  S  T  L  C  P  P  L  818

2521 CCTTTCTCTTCCTCCATCAGGCCCTGTATGCTGGCAACCTGTGCAAGGCCCGGGCGGCCA 2580
819  P  F  S  S  S  I  R  P  C  M  L  A  T  C  A  R  P  G  R  P  838

2581 TCCACGAAGCACAGCCCGCACATCGCGGCCGCCAGGAAGGTCTACATACAGACTCGCAGG 2640
839  S  T  K  H  S  P  H  I  A  A  A  R  K  V  Y  I  Q  T  R  R  858

2641 CAGAGGAAGCTGCACTTCGTGGTGGGGGGCTTCGCCTACCTGCTCCCCAAGACGGCGGTG 2700
859  Q  R  K  L  H  F  V  V  G  G  F  A  Y  L  L  P  K  T  A  V  878

2701 GTGCTGCGCTGCCCGGCGCGCAGGGTCCGCAAGCCCCTCATCACCTGGGAGAAGGACGGC 2760
879  V  L  R  C  P  A  R  R  V  R  K  P  L  I  T  W  E  K  D  G  898

2761 CAGCACCTCATCAGCTCGACGCACGTCACGGTGGCCCCCTTCGGCTATCTCAAGATCCAC 2820
899  Q  H  L  I  S  S  T  H  V  T  V  A  P  F  G  Y  L  K  I  H  918

2821 CGCCTCAAGCCCTCGGATGCAGGCGTCTACACCTGCTCAGCGGGCCCGGCCCGGGAGCAC 2880
919  R  L  K  P  S  D  A  G  V  Y  T  C  S  A  G  P  A  R  E  H  938
```

FIG. 4D

```
2881 TTTGTGATTAAGCTCATCGGAGGCAACCGCAAGCTCGTGGCCCGGCCCTTGAGCCCGAGA 2940
939  F  V  I  K  L  I  G  G  N  R  K  L  V  A  R  P  L  S  P  R  958

2941 AGTGAGGAAGAGGTGCTTGCGGGGAGGAAGGGCGGCCCGAAGGAGGCCCTGCAGACCCAC 3000
959  S  E  E  E  V  L  A  G  R  K  G  G  P  K  E  A  L  Q  T  H  978

3001 AAACACCAGAACGGGATCTTCTCCAACGGCAGCAAGGCGGAGAAGCGGGGCCTGGCCGCC 3060
979  K  H  Q  N  G  I  F  S  N  G  S  K  A  E  K  R  G  L  A  A  998

3061 AACCCGGGGAGCCGCTACGACGACCTCGTCTCCCGGCTGCTGGAGCAGGGCGGCTGGCCC 3120
999  N  P  G  S  R  Y  D  D  L  V  S  R  L  L  E  Q  G  G  W  P  1018

3121 GGAGAGCTGCTGGCCTCGTGGGAGGCGCAGGACTCTGCGGAAAGGAACACGACCTCGGAG 3180
1019 G  E  L  L  A  S  W  E  A  Q  D  S  A  E  R  N  T  T  S  E  1038

3181 GAGGACCCGGGTGCAGAGCAAGTGCTCCTGCACCTGCCCTTCACCATGGTGACCGAGCAG 3240
1039 E  D  P  G  A  E  Q  V  L  L  H  L  P  F  T  M  V  T  E  Q  1058

3241 CGGCGCCTGGACGACATCCTGGGGAACCTCTCCCAGCAGCCCGAGGAGCTGCGCGACCTC 3300
1059 R  R  L  D  D  I  L  G  N  L  S  Q  Q  P  E  E  L  R  D  L  1078

3301 TACAGCAAGCACCTGGTGGCCCAGCTGGCCCAGGAGATCTTCCGCAGCCACCTGGAGCAC 3360
1079 Y  S  K  H  L  V  A  Q  L  A  Q  E  I  F  R  S  H  L  E  H  1098

3361 CAGGACACGCTCCTGAAGCCCTCGGAGCGCAGGACTTCCCCAGTGACTCTCTCGCCTCAT 3420
1099 Q  D  T  L  L  K  P  S  E  R  R  T  S  P  V  T  L  S  P  H  1118

3421 AAACACGTGTCTGGCTTCAGCAGCTCCCTGCGGACCTCCTCCACCGGGGACGCCGGGGGA 3480
1119 K  H  V  S  G  F  S  S  S  L  R  T  S  S  T  G  D  A  G  G  1138

3481 GGCTCTCGAAGGCCACACCGCAAGCCCACCATCCTGCGCAAGATCTCAGCGGCCCAGCAG 3540
1139 G  S  R  R  P  H  R  K  P  T  I  L  R  K  I  S  A  A  Q  Q  1158

3541 CTCTCAGCCTCGGAGGTGGTCACCCACCTGGGGCAGACGGTGGCCCTGGCCAGCGGGACA 3600
1159 L  S  A  S  E  V  V  T  H  L  G  Q  T  V  A  L  A  S  G  T  1178
```

FIG. 4E

```
3601 CTGAGTGTTCTTCTGCACTGTGAGGCCATCGGCCACCCAAGGCCTACCATCAGCTGGGCC 3660
1179 L  S  V  L  L  H  C  E  A  I  G  H  P  R  P  T  I  S  W  A  1198

3661 AGGAATGGAGAAGAAGTTCAGTTCAGTGACAGGATTCTTCTACAGCCAGATGATTCCTTA 3720
1199 R  N  G  E  E  V  Q  F  S  D  R  I  L  L  Q  P  D  D  S  L  1218

3721 CAGATCTTGGCACCAGTGGAAGCAGATGTGGGTTTCTACACTTGCAATGCCACCAATGCC 3780
1219 Q  I  L  A  P  V  E  A  D  V  G  F  Y  T  C  N  A  T  N  A  1238

3781 TTGGGATACGACTCTGTCTCCATTGCCGTCACATTAGCAGGAAAGCCACTAGTGAAAACG 3840
1239 L  G  Y  D  S  V  S  I  A  V  T  L  A  G  K  P  L  V  K  T  1258

3841 TCACGAATGACAGTGATCAACACGGAGAAGCCTGCAGTCACAGTCGATATAGGAAGCACC 3900
1259 S  R  M  T  V  I  N  T  E  K  P  A  V  T  V  D  I  G  S  T  1278

3901 ATCAAAACAGTGCAGGGAGTGAATGTGACAATCAACTGCCAGGTTGCAGGAGTGCCTGAA 3960
1279 I  K  T  V  Q  G  V  N  V  T  I  N  C  Q  V  A  G  V  P  E  1298

3961 GCTGAAGTCACTTGGTTCAGGAATAAAAGCAAACTGGGCTCCCCGCACCATCTGCACGAA 4020
1299 A  E  V  T  W  F  R  N  K  S  K  L  G  S  P  H  H  L  H  E  1318

4021 GGCTCCTTGCTGCTCACAAACGTGTCCTCCTCGGATCAGGGCCTGTACTCCTGCAGGGCG 4080
1319 G  S  L  L  L  T  N  V  S  S  S  D  Q  G  L  Y  S  C  R  A  1338

4081 GCCAATCTTCATGGAGAGCTGACTGAGAGCACCCAGCTGCTGATCCTAGATCCCCCCCAA 4140
1339 A  N  L  H  G  E  L  T  E  S  T  Q  L  L  I  L  D  P  P  Q  1358

4141 GTCCCCACACAGTTGGAAGACATCAGGGCCTTGCTCGCTGCCACTGGACCGAACCTTCCT 4200
1359 V  P  T  Q  L  E  D  I  R  A  L  L  A  A  T  G  P  N  L  P  1378

4201 TCAGTGCTGACGTCTCCTCTGGGAACACAGCTGGTCCTGGATCCTGGGAATTCTGCTCTC 4260
1379 S  V  L  T  S  P  L  G  T  Q  L  V  L  D  P  G  N  S  A  L  1398

4261 CTTGGCTGCCCCATCAAAGGTCACCCTGTCCCTAATATCACCTGGTTTCATGGTGGTCAG 4320
1399 L  G  C  P  I  K  G  H  P  V  P  N  I  T  W  F  H  G  G  Q  1418
```

FIG. 4F

```
4321 CCAATTGTCACTGCCACAGGACTGACGCATCACATCTTGGCAGCTGGACAGATCCTTCAA 4380
1419 P I V T A T G L T H H I L A A G Q I L Q 1438

4381 GTTGCAAACCTTAGCGGTGGGTCTCAAGGGGAATTCAGCTGCCTTGCTCAGAATGAGGCA 4440
1439 V A N L S G G S Q G E F S C L A Q N E A 1458

4441 GGGGTGCTCATGCAGAAGGCATCTTTAGTGATCCAAGATTACTGGTGGTCTGTGGACAGA 4500
1459 G V L M Q K A S L V I Q D Y W W S V D R 1478

4501 CTGGCAACCTGCTCAGCCTCCTGTGGTAACCGGGGGGTTCAGCAGCCCCGCTTGAGGTGC 4560
1479 L A T C S A S C G N R G V Q Q P R L R C 1498

4561 CTGCTGAACAGCACGGAGGTCAACCCTGCCCACTGCGCAGGGAAGGTTCGCCCTGCGGTG 4620
1499 L L N S T E V N P A H C A G K V R P A V 1518

4621 CAGCCCATCGCGTGCAACCGGAGAGACTGCCCTTCTCGGTGGATGGTGACCTCCTGGTCT 4680
1519 Q P I A C N R R D C P S R W M V T S W S 1538

4681 GCCTGTACCCGGAGCTGTGGGGGAGGTGTCCAGACCCGCAGGGTGACCTGTCAAAAGCTG 4740
1539 A C T R S C G G G V Q T R R V T C Q K L 1558

4741 AAAGCCTCTGGGATCTCCACCCCTGTGTCCAATGACATGTGCACCCAGGTCGCCAAGCGG 4800
1559 K A S G I S T P V S N D M C T Q V A K R 1578

4801 CCTGTGGACACCCAGGCCTGTAACCAGCAGCTGTGTGTGGAGTGGGCCTTCTCCAGCTGG 4860
1579 P V D T Q A C N Q Q L C V E W A F S S W 1598

4861 GGCCAGTGCAATGGGCCTTGCATCGGGCCTCACCTAGCTGTGCAACACAGACAAGTCTTC 4920
1599 G Q C N G P C I G P H L A V Q H R Q V F 1618

4921 TGCCAGACACGGGATGGCATCACCTTACCATCAGAGCAGTGCAGTGCTCTTCCGAGGCCT 4980
1619 C Q T R D G I T L P S E Q C S A L P R P 1638

4981 GTGAGCACCCAGAACTGCTGGTCAGAGGCCTGCAGTGTACACTGGAGAGTCAGCCTGTGG 5040
1639 V S T Q N C W S E A C S V H W R V S L W 1658
```

FIG. 4G

```
5041 ACCCTGTGCACAGCTACCTGTGGCAACTACGGCTTCCAGTCCCGGCGTGTGGAGTGTGTG 5100
1659 T  L  C  T  A  T  C  G  N  Y  G  F  Q  S  R  R  V  E  C  V  1678

5101 CATGCCCGCACCAACAAGGCAGTGCCTGAGCACCTGTGCTCCTGGGGGCCCCGGCCTGCC 5160
1679 H  A  R  T  N  K  A  V  P  E  H  L  C  S  W  G  P  R  P  A  1698

5161 AACTGGCAGCGCTGCAACATCACCCCATGTGAAAACATGGAGTGCAGAGACACCACCAGG 5220
1699 N  W  Q  R  C  N  I  T  P  C  E  N  M  E  C  R  D  T  T  R  1718

5221 TACTGCGAGAAGGTGAAACAGCTGAAACTCTGCCAACTCAGCCAGTTTAAATCTCGCTGC 5280
1719 Y  C  E  K  V  K  Q  L  K  L  C  Q  L  S  Q  F  K  S  R  C  1738

5281 TGTGGAACTTGTGGCAAAGCGTGAAGATAGGGTGTGGGGAAAAACTCTACCCTGGCCACA 5340
1739 C  G  T  C  G  K  A  *                                       1746

5341 CGAAGGACTCACGCAACCACCTCGGACAGAACCTAAGCTTTCTTCATTTTATTTATTTAT 5400

5401 TTCCCCCTCCCCACTCCACACACACCCTTCCAACCTCCTCCACCTCCACCTTCAAGCATA 5460

5461 AGGACGTCCGCGTGTTTTCTCTTTCAGTTAGCTGGAGGACAGGATGTTGGGAAAGGAAAG 5520

5521 GACAGATGTCTAAAGGAGGTTGCAGAGCAGGCCAGGCAGACAGTGGGGGCTCCCTTGAAG 5580

5581 AGCTTCCTCCCTCCCAAACCTGGGTCTCAAAGACCTAGAAAGAGGCAGGCACAGCCCCTG 5640

5641 CGGACAGCAGGGAGCCAGAAGGTTTGTAGCCTATTGGTGCAAACATTGGACAAATTCCTG 5700

5701 TGTCTTTCCTAGAAGCGCAG 5720
```

```
                          10                  20                  30                  40
  1   M E C C R R A T P G T L L L F L A F L L L S S R T A R S E E D R D G L - W D A W   THRAP
  1   M K C - - - S Y T V V F L L F - - Y L L I A S F H V - - - - - - D A L S W A A W   emb CAB03121.1

                          50                  60                  70                  80
 40   G P W S E C S R T C G G G A S Y S L R R C L S S K S C E G R N I R Y R T C S N V   THRAP
 30   S P W S S C T K T C G G G V S R Q L R R C L T S K - C S G E S V R F K V C A Q K   emb CAB03121.1

                          90                 100                 110                 120
 80   D C P P E A G D F R A Q Q C S A H N D V K H H G Q F Y E W L P V S N D P D N P C   THRAP
 69   T C E S K S R L A R D T I C G G E - E I V S R G Q - - - - - - - - - - - - - - C   emb CAB03121.1

                         130                 140                 150                 160
120   S L K C Q A K G T T L V V E L A P K V L D G T R C - Y T E S L D M C I S G L C Q   THRAP
 94   E V V C R S R L T G - - A N F L W R V D D G T P C Q A A T S R A V C S K G S C Q   emb CAB03121.1

                         170                 180                 190                 200
159   I V G C D H Q L G S T V K E D N C G V C N G D G S T C R L V R G Q Y K S Q L S A   THRAP
132   I V G C D G L I S S S F R F D A C G V C G G R G D T C D - - - - - - - - - - - -   emb CAB03121.1

                         210                 220                 230                 240
199   T K S D D T V V A I P Y G S R H I R L V L K G P D H L Y L E T K T L Q G T K G E   THRAP
160   - - - - - - - - - - - - - - - N G K F I W K V S E E - Y - - - - T A C A S N C D   emb CAB03121.1

                         250                 260                 270                 280
239   N S L S S T G T F L V D N S S V D F Q K F P D K E I L R M A G P L T A D F I V K   THRAP
180   D I V D W S G A - - - - - - - - - - - - - - G R S I A S T S Q P I V V - - - - -   emb CAB03121.1

                         290                 300                 310                 320
279   I R N S G S A D S T V Q F I F Y Q P I I H R W R E T D F F P C S A T C G G G Y Q   THRAP
201   - - - - - - - - - - - - - - - - - - - - - - - - - - - - - - - - - - - - - - - -   emb CAB03121.1

                         330                 340                 350                 360
319   L T S A E C Y D L R S N R V V A D Q Y C H Y Y P E N I K P K P K L Q E C N L D P   THRAP
201   - - - - - C V N A I T G R V V P E K L C - - - A D K L R P K V E A R P C P M L I   emb CAB03121.1
```

FIG. 5B

```
                370       380       390       400
359 C P A R W E A T P W T A C S S S C G G G I Q S R A V S C V E E D I Q G H V T S V THRAP
233 C P S R W M A A D W T E C V P H C G E G T R K R E V Y C V Q T A H N V T V H V P emb CAB03121.1

                410       420       430       440
399 E E W K C M Y T P K M P I A Q P C N I F D C P K W L A Q E W S P C T V T C G Q G THRAP
273 D T F - C E N G T R P A A E E N C V S T S C G R W E A G K W S K C T A S C G Q G emb CAB03121.1

                450       460       470       480
439 L R Y R V V L C I D H R G M H T G G C S P K T K P H I K E E C I V P T P C Y K P THRAP
312 V R R R H V A C V G - - - - - - G S D C D E G G R P R Q E T T C Y A G I P C S I A emb CAB03121.1

                490       500       510       520
479 K E K L P V E A K L P W F K Q A Q E L E - - E G A A V S E E P S F I P K A W S A THRAP
347 T N S L D W N D R A - - Y L D G N T F G S M D N H N D W Q A P R L V A G E W S T emb CAB03121.1

                530       540       550       560
517 C T V T C G V G T Q V R I V R C Q V L L S F S Q S V A D L P I D E C E G P K P A THRAP
385 C S S T C G T G V M S R T V E C V A V N P I S S A P I K L P M S E C Q D Q E Q P emb CAB03121.1

                570       580       590       600
557 S Q - R A C Y A G P C S - G E I P E F N P D E T D G L F G G L Q D F D E L Y D W THRAP
425 K L F E S C E V R S C P L Q E D S K L S E D E A P - - - - - - - - - - - - Y Q W emb CAB03121.1

                610       620       630       640
595 E Y E G F T K C S E S C G G G V Q E A V V S C L N K Q T R E P A E E N L C V T S THRAP
453 R Y G D W T Q C S A S C L G G K Q K A A L K C I Q V S T G K S V Q W S Q C D A R emb CAB03121.1

                650       660       670       680
635 R R P P Q L L K S C N L D P C P A R W E I G K W S P C S L T C G V G L Q T R D V THRAP
493 R R P P E K S R P C N Q H P C P P F W L T S K Y S D C S M S C G S G T A R R S V emb CAB03121.1

                690       700       710       720
675 F C S H L L S R E - - M N E T V I L A D E L C R Q P K P S T V Q A C N R F N C P THRAP
533 K C A Q T V S K T D G A D A H I V L R D D R C H F K K P Q E T E T C N V V A C P emb CAB03121.1
```

FIG. 5C

```
                        730       740       750       760
 713  PAWYPAQWQPCSRTCGGGVQKREVLCKQRMADGSFLELPE  THRAP
 573  ATW------------VSSLNKRHNKIKLNKLKTA------  emb CAB03121.1

                        770       780       790       800
 753  TFCSASKPACQQACKKDDCPSEWLLSDWTECSTSCGEGTQ  THRAP
 595  --------------------------QWTECSRSCDSGER  emb CAB03121.1

                        810       820       830       840
 793  TRSAICRKMLKTGLSTVVNSTLCPPLPFSSSIRPCMLATC  THRAP
 609  RRQVWCEIRDSRGKTQRRPDVECDANTKPQTVEVCSFGSC  emb CAB03121.1

                        850       860       870       880
 833  ARPGRPSTKHSPHIAAARKVYIQTRRQRKLHFVVGGFAYL  THRAP
 649  SRPE----------LLSNRVFEQNAEQKKLTLGIGGVATL  emb CAB03121.1

                        890       900       910       920
 873  LPKTAVVLRCPARRVRKPLITWEKDGQHLISSTHVTVAPF  THRAP
 679  YQGTSIKIKCPAKKFDKKKIYWKKNGKKIKNDAHIKVSAN  emb CAB03121.1

                        930       940       950       960
 913  GYLKIHRLKPSDAGVYTCSAGPAREHFVIKLIGGNRKLVA  THRAP
 719  GNLRVFHARMEDAGVYEC--------FTDRLQG-------  emb CAB03121.1

                        970       980       990      1000
 953  RPLSPRSEEEVLAGRKGGPKEALQTHKHQNGIFSNGSKAE  THRAP
 744  ----------------------------------------  emb CAB03121.1

                       1010      1020      1030      1040
 993  KRGLAANPGSRYDDLVSRLLEQGGWPGELLASWEAQDSAE  THRAP
 744  ----------------------------------------  emb CAB03121.1

                       1050      1060      1070      1080
1033  RNTTSEEDPGAEQVLLHLPFTMVTEQRRLDDILGNLSQQP  THRAP
 744  ------------NVTLNFKY--------------------  emb CAB03121.1
```

FIG. 5D

```
                       1090       1100       1110       1120
1073 E E L R D L Y S K H L V A Q L A Q E I F R S H L E H Q D T L L K P S E R R T S P THRAP
752  - - - R D F - - - - - - - - - - - - - - - - - - - - - - - - - - P A S R - - - - emb CAB03121.1

                       1130       1140       1150       1160
1113 V T L S P H K H V S G F S S S L R T S S T G D A G G G S R R P H R K P T I L R K THRAP
759  - - - - - - - - - - - - - - - - - - - - - - - - - - - - - - - - - - - - - - - - emb CAB03121.1

                       1170       1180       1190       1200
1153 I S A A Q Q L S A S E V V T H L G Q T V A L A S G T L S V L L H C E A I G H P R THRAP
759  - - - - - - - - - - - - - - - - - - - V D L A - - - - - - - - - - - - - - - P K emb CAB03121.1

                       1210       1220       1230       1240
1193 P T I S W A R N G E E V Q F S D R I L L Q P D D S L Q I L A P V E A D V G F Y T THRAP
765  P Q I P S T K N R Q R V Q V S K E D V L R E Q A S V - - - - - - - - - - - - - - emb CAB03121.1

                       1250       1260       1270       1280
1233 C N A T N A L G Y D S V S I A V T L A G K P L V K T S R M T V I N T E K P A V T THRAP
791  - - - - - - - - - - - - - - - - - - - - - - - - - - - - - - - - - - - - - - - - emb CAB03121.1

                       1290       1300       1310       1320
1273 V D I G S T I K T V Q G V N V T I N C Q V A G V P E A E V T W F R N K S K L G S THRAP
791  - - - - - - - - - - - - - - - - - - - - - - - - - - - - - - - - - - - - - - - - emb CAB03121.1

                       1330       1340       1350       1360
1313 P H H L H E G S L L L T N V S S S D Q G L Y S C R A A N L H G E L T E S T Q L L THRAP
791  - - - L H - - - - - - - - - - - - - - - - - - - - - - K M N V S L I E A - - - - emb CAB03121.1

                       1370       1380       1390       1400
1353 I L D P P Q V P T Q L E D I R A L L A A T G P N L P S V L T S P L G T Q L V L D THRAP
802  L L T A P N D E K A R E Q L R K Y - - - - - - - - - - - - - - - - G N E L V - - emb CAB03121.1

                       1410       1420       1430       1440
1393 P G N S A L L G C P I K G H P V P N I T W F H G G Q P I V T A T G L T H H I L A THRAP
824  - - - - - - - - - - - - - - - - - - - - - - - - - - - - - - - - - - - - - - - - emb CAB03121.1
```

FIG. 5E

```
                       1450        1460        1470        1480
1433 AGQILQVANLSGGSQGEFSCLAQNEAGVLMQKASLVIQDY THRAP
824  ---------------------------------------- emb CAB03121.1

                       1490        1500        1510        1520
1473 WWSVDRLATCSASCGNRGVQQPRLRCLLNSTEVNPAHCAG THRAP
824  ---------------------------------------- emb CAB03121.1

                       1530        1540        1550        1560
1513 KVRPAVQPIACNRRDCPSRWMVTSWSACT-RSC-GGGVQT THRAP
824  -----------------ARWDIGHWSECRQKTCHVAGYQA emb CAB03121.1

                       1570        1580        1590        1600
1551 RRVTCQKLKASGISTPVSNDMCTQVAK-RPVDTQACNQQL THRAP
847  RGISC-KVTFHGEIRNVDNSICESLASVRPPETRPCHRED emb CAB03121.1

                       1610        1620        1630        1640
1590 CVEWAFSSWGQCNGP-CIGPHLAVQHRQVFCQTRDGITLP THRAP
886  CPRWEASQWSECSSQRCVSSMLAQKRRNVTCRFTNGTSVD emb CAB03121.1

                       1650        1660        1670        1680
1629 SEQCSALPRPVSTQNCWSEACSVHWRVSLWTLCTATCGNY THRAP
926  IQHCDITNRPATTMDCPNQNCKAEWRTSDWGSCSSECGTG emb CAB03121.1

                       1690        1700        1710        1720
1669 GFQSRRVECVHARTNKAVPEHLCSWGPRPANWQRC----N THRAP
966  GVQLRLLSCVWISSGRP-AGRNCEQMRRPHSARACVADEP emb CAB03121.1

                       1730        1740        1750        1760
1705 ITPC----------ENMECRDTTRYCEKVKQLKLCQLSQFK THRAP
1005 LPPCMPTASALYQRDASCQDQSRFCDIIKLFHSCDSLEVR emb CAB03121.1

                       1770
1736 SRCCGTCG----KA.                          THRAP
1045 QKCCSTCTFVERKKF                          emb CAB03121.1
```

```
  1  TGTCCCTTCGTCTCCTTCTTCCCCTAACCAGGCCTCCCTCCACCTGTCTTCTCAGAGCAG   60

 61  GTAATGGCAAGCATGGCTGCCGTGCTCACCTGGGCTCTGGCTCTTCTTTCAGCGTTTTCG  120
  1     M  A  S  M  A  A  V  L  T  W  A  L  A  L  L  S  A  F  S    19

121  GCCACCCAGGCACGGAAAGGCTTCTGGGACTACTTCAGCCAGACCAGCGGGGACAAAGGC  180
 20  A  T  Q  A  R  K  G  F  W  D  Y  F  S  Q  T  S  G  D  K  G    39

181  AGGGTGGAGCAGATCCATCAGCAGAAGATGGCTCGCGAGCCCGCGACCCTGAAAGACAGC  240
 40  R  V  E  Q  I  H  Q  Q  K  M  A  R  E  P  A  T  L  K  D  S    59

241  CTTGAGCAAGACCTCAACAATATGAACAAGTTCCTGGAAAAGCTGAGGCCTCTGAGTGGG  300
 60  L  E  Q  D  L  N  N  M  N  K  F  L  E  K  L  R  P  L  S  G    79

301  AGCGAGGCTCCTCGGCTCCCACAGGACCCGGTGGGCATGCGGCGGCAGCTGCAGGAGGAG  360
 80  S  E  A  P  R  L  P  Q  D  P  V  G  M  R  R  Q  L  Q  E  E    99

361  TTGGAGGAGGTGAAGGCTCGCCTCCAGCCCTACATGGCAGAGGCGCACGAGCTGGTGGGC  420
100  L  E  E  V  K  A  R  L  Q  P  Y  M  A  E  A  H  E  L  V  G   119

421  TGGAATTTGGAGGGCTTGCGGCAGCAACTGAAGCCCTACACGATGGATCTGATGGAGCAG  480
120  W  N  L  E  G  L  R  Q  Q  L  K  P  Y  T  M  D  L  M  E  Q   139

481  GTGGCCCTGCGCGTGCAGGAGCTGCAGGAGCAGTTGCGCGTGGTGGGGGAAGACACCAAG  540
140  V  A  L  R  V  Q  E  L  Q  E  Q  L  R  V  V  G  E  D  T  K   159

541  GCCCAGTTGCTGGGGGGCGTGGACGAGGCTTGGGCTTTGCTGCAGGGACTGCAGAGCCGC  600
160  A  Q  L  L  G  G  V  D  E  A  W  A  L  L  Q  G  L  Q  S  R   179

601  GTGGTGCACCACACCGGCCGCTTCAAAGAGCTCTTCCACCCATACGCCGAGAGCCTGGTG  660
180  V  V  H  H  T  G  R  F  K  E  L  F  H  P  Y  A  E  S  L  V   199

661  AGCGGCATCGGGCGCCACGTGCAGGAGCTGCACCGCAGTGTGGCTCCGCACGCCCCCGCC  720
```

```
200  S  G  I  G  R  H  V  Q  E  L  H  R  S  V  A  P  H  A  P  A    219

                    .         .         .         .         .         .
721  AGCCCCGCGCGCCTCAGTCGCTGCGTGCAGGTGCTCTCCCGGAAGCTCACGCTCAAGGCC   780
220  S  P  A  R  L  S  R  C  V  Q  V  L  S  R  K  L  T  L  K  A    239

                    .         .         .         .         .         .
781  AAGGCCCTGCACGCACGCATCCAGCAGAACCTGGACCAGCTGCGCGAAGAGCTTATCAGA   840
240  K  A  L  H  A  R  I  Q  Q  N  L  D  Q  L  R  E  E  L  I  R    259

                    .         .         .         .         .         .
841  GCCTTTGCAGGCACTGGGACTGAGGAAGGGGCCGGCCCGGACCCCCAGATGCTCTCCGAG   900
260  A  F  A  G  T  G  T  E  E  G  A  G  P  D  P  Q  M  L  S  E    279

                    .         .         .         .         .         .
901  GAGGTGCGCCAGCGACTTCAGGCTTTCCGCCAGGACACCTACCTGCAGATAGCTGCCTTC   960
280  E  V  R  Q  R  L  Q  A  F  R  Q  D  T  Y  L  Q  I  A  A  F    299

                    .         .         .         .         .         .
961  ACTCGCGCCATCGACCAGGAGACTGAGGAGGTCCAGCAGCAGCTGGCGCCACCTCCACCA   1020
300  T  R  A  I  D  Q  E  T  E  E  V  Q  Q  Q  L  A  P  P  P  P    319

                    .         .         .         .         .         .
1021 GGCCACAGTGCCTTCGCCCCAGAGTTTCAACAAACAGACAGTGGCAAGGTTCTGAGCAAG   1080
320  G  H  S  A  F  A  P  E  F  Q  Q  T  D  S  G  K  V  L  S  K    339

                    .         .         .         .         .         .
1081 CTGCAGGCCCGTCTGGATGACCTGTGGGAAGACATCACTCACAGCCTTCATGACCAGGGC   1140
340  L  Q  A  R  L  D  D  L  W  E  D  I  T  H  S  L  H  D  Q  G    359

                    .         .         .         .         .         .
1141 CACAGCCATCTGGGGGACCCCTGAGGATCTACCTGCCCAGGCCCATTCCCAGCTCCTTGT   1200
360  H  S  H  L  G  D  P  *                                         367

                    .         .         .         .         .         .
1201 CTGGGGAGCCTTGGCTCTGAGCCTCTAGCATGGTTCAGTCCTTGAAAGTGGCCTGTTGGG   1260

                    .         .         .         .         .         .
1261 TGGAGGGTGGAAGGTCCTGTGCAGGACAGGGAGGCCACCAAAGGGGCTGCTGTCTCCTGC   1320

                    .         .         .         .         .         .
1321 ATATCCAGCCTCCTGCGACTCCCCAATCTGGATGCATTACATTCACCAGGCTTTGCAAAA   1380

                    .
1381 AAAAAAAAAAAAA  1393
```

```
                      10                  20                  30
1    M A S M A A V L T W A L A L L S A - - - - F S A T Q A R K G  Apolipoprotein A-IV-Like
1    M F L K A V V L S L A L V A V T G A R A E V N A D Q V A T V  emb|CAA11020.1
1    M F L K A V V L T L A L V A V A G A R A E V S A D Q V A T V  gb|AAA51744.1
1    M F L K A A V L T L A L V A I T G T R A E V T S D Q V A N V  gb|AAA37214.1

                      40                  50                  60
27   F W D Y F S Q T S G D - K G R V E Q I H Q Q K M A R E P A T  Apolipoprotein A-IV-Like
31   M W D Y F S Q L G S N A K K A V E H L Q K S E L T Q Q L N T  emb|CAA11020.1
31   M W D Y F S Q L S N N A K E A V E H L Q K S E L T Q Q L N A  gb|AAA51744.1
31   V W D Y F T Q L S N N A K E A V E Q F Q K T D V T Q Q L S T  gb|AAA37214.1

                      70                  80                  90
56   L - K D S L E Q D L N N M N K F L E K L R P L S G S E A P R  Apolipoprotein A-IV-Like
61   L F Q D K L G E V N T Y T E D L Q K K L V P F A T E L H E R  emb|CAA11020.1
61   L F Q D K L G E V N T Y A G D L Q K K L V P F A T E L H E R  gb|AAA51744.1
61   L F Q D K L G D A S T Y A D G V H N K L V P F V V Q L S G H  gb|AAA37214.1

                      100                 110                 120
85   L P Q D P V G M R R Q L Q E E L E E V K A R L Q P Y M A E A  Apolipoprotein A-IV-Like
91   L T K D S E K L K E E I R R E L E E L R A R L L P H A T E V  emb|CAA11020.1
91   L A K D S E K L K E E I G K E L E E L R A R L L P H A N E V  gb|AAA51744.1
91   L A K E T E R V K E E I K K E L E D L R D R M M P H A N K V  gb|AAA37214.1

                      130                 140                 150
115  H E L V G W N L E G L R Q Q L K P Y T M D L M E Q V A L R V  Apolipoprotein A-IV-Like
121  S Q K I G D N V R E L Q Q R L G P F T G G L R T Q V N T Q V  emb|CAA11020.1
121  S Q K I G D N L R E L Q Q R L E P Y A D Q L R T Q V N T Q A  gb|AAA51744.1
121  T Q T F G E N M Q K L Q E H L K P Y A V D L Q D Q I N T Q T  gb|AAA37214.1

                      160                 170                 180
145  Q E L Q E Q L R V V G E D T K A Q L L G G V D E - - - - A W  Apolipoprotein A-IV-Like
151  Q Q L Q R Q L K P Y A E R M E S V L R Q N I R N L E A S V A  emb|CAA11020.1
151  E Q L R R Q L D P L A Q R M E R V L R E N A D S L Q A S L R  gb|AAA51744.1
151  Q E M K L Q L T P Y I Q R M Q T T I K E N V D N L H T S M M  gb|AAA37214.1

                      190                 200                 210
171  A L L Q G L Q S R V V H H T G R F K E L F H P Y A E S L V S  Apolipoprotein A-IV-Like
181  P Y A D E F K A K I D Q N V E E L K G S L T P Y A E E L K A  emb|CAA11020.1
181  P H A D E L K A K I D Q N V E E L K G R L T P Y A D E F K V  gb|AAA51744.1
181  P L A T N L K D K F N R N M E E L K G H L T P R A N E L K A  gb|AAA37214.1
```

FIG. 8B

```
                        220              230              240
201  G I G R H V Q E L H R S V A P H A P A S P A R L S R C V Q V   Apolipoprotein A-IV-Like
211  K I D Q N V E E L R R S L A P Y A Q D V Q E K L N H Q L E G   emb|CAA11020.1
211  K I D Q T V E E L R R S L A P Y A Q D T Q E K L N H Q L E G   gb|AAA51744.1
211  T I D Q N L E D L R R S L A P L T V G V Q E K L N H Q M E G   gb|AAA37214.1

                        250              260              270
231  L S R K L T L K A K A L H A R I Q Q N L D Q L R E E L I R A   Apolipoprotein A-IV-Like
241  L A F Q M K K Q A E E L K A K I S A N A D E L R Q K L V P V   emb|CAA11020.1
241  L T F Q M K K N A E E L K A R I S A S A E E L R Q R L A P L   gb|AAA51744.1
241  L A F Q M K K N A E E L Q T K V S A K I D Q L Q K N L A P L   gb|AAA37214.1

                        280              290              300
261  F A G T - - - - - G T E E G A G P D P Q M L S E E V R Q R L   Apolipoprotein A-IV-Like
271  A E N V H G H L K G N T E G L Q K S L L E L R S H L D Q Q V   emb|CAA11020.1
271  A E D V R G N L K G N T E G L Q K S L A E L G G H L D Q Q V   gb|AAA51744.1
271  V E D V Q S K V K G N T E G L Q K S L E D L N R Q L E Q Q V   gb|AAA37214.1

                        310              320              330
286  Q A F R Q D T Y L Q I A A F T R A I D Q E T E E V Q Q Q L A   Apolipoprotein A-IV-Like
301  E E F R L K V E P Y G E T F N K A L V Q Q V E D L R Q K L G   emb|CAA11020.1
301  E E F R R R V E P Y G E N F N K A L V Q Q M E Q L R Q K L G   gb|AAA51744.1
301  E E F R R T V E P M G E M F N K A L V Q Q L E Q F R Q Q L G   gb|AAA37214.1

                        340              350              360
316  P P P P G H S A F A P E F Q Q T D S G K V L S K L Q A R L D   Apolipoprotein A-IV-Like
331  P L A G D V E G H L S F L E K D L R D K V N T F F S T L K E   emb|CAA11020.1
331  P H A G D V E G H L S F L E K D L R D K V N S F F S T F K E   gb|AAA51744.1
331  P N S G E V E S H L S F L E K S L R E K V N S F M S T L E K   gb|AAA37214.1

                        370              380              390
346  D L W E D I T H S L - - - - - - - - - - H D Q G H S H L G -   Apolipoprotein A-IV-Like
361  E A S Q G Q S Q A L P A Q E K A Q - - - - - - - - - - - - -   emb|CAA11020.1
361  K E S Q D K T L S L P E L E Q Q Q E Q Q Q E Q Q Q E Q V Q M   gb|AAA51744.1
361  K G S P D Q P Q A L P L P E Q A Q E Q A Q E Q V Q P K - - -   gb|AAA37214.1

365  - - - - D P                                                  Apolipoprotein A-IV-Like
378  - A P L E G                                                  emb|CAA11020.1
391  L A P L E S                                                  gb|AAA51744.1
388  - - P L E S                                                  gb|AAA37214.1
```

PROTEIN HOFNF53

This application is a continuation-in-part of, and claims benefit under 35 U.S.C. §120 of copending PCT International Application Ser. No. PCT/US00/26013, filed Sep. 22, 2000, which is hereby incorporated by reference, which claims benefit under 35 U.S.C. §119(e) based on U.S. Provisional Application No. 60/155,709, filed Sep. 24, 1999, which is hereby incorporated by reference in its entirety.

FIELD OF THE INVENTION

This invention relates to newly identified polynucleotides, polypeptides encoded by these polynucleotides, antibodies that bind these polypeptides, uses of such polynucleotides, polypeptides, and antibodies, and their production.

BACKGROUND OF THE INVENTION

Unlike bacterium, which exist as a single compartment surrounded by a membrane, human cells and other eucaryotes are subdivided by membranes into many functionally distinct compartments. Each membrane-bounded compartment, or organelle, contains different proteins essential for the function of the organelle. The cell uses "sorting signals," which are amino acid motifs located within the protein, to target proteins to particular cellular organelles.

One type of sorting signal, called a signal sequence, a signal peptide, or a leader sequence, directs a class of proteins to an organelle called the endoplasmic reticulum (ER). The ER separates the membrane-bounded proteins from all other types of proteins. Once localized to the ER, both groups of proteins can be further directed to another organelle called the Golgi apparatus. Here, the Golgi distributes the proteins to vesicles, including secretory vesicles, the cell membrane, lysosomes, and the other organelles.

Proteins targeted to the ER by a signal sequence can be released into the extracellular space as a secreted protein. For example, vesicles containing secreted proteins can fuse with the cell membrane and release their contents into the extracellular space—a process called exocytosis. Exocytosis can occur constitutively or after receipt of a triggering signal. In the latter case, the proteins are stored in secretory vesicles (or secretory granules) until exocytosis is triggered. Similarly, proteins residing on the cell membrane can also be secreted into the extracellular space by proteolytic cleavage of a "linker" holding the protein to the membrane.

Despite the great progress made in recent years, only a small number of genes encoding human secreted proteins have been identified. These secreted proteins include the commercially valuable human insulin, interferon, Factor VIII, human growth hormone, tissue plasminogen activator, and erythropoeitin. Thus, in light of the pervasive role of secreted proteins in human physiology, a need exists for identifying and characterizing novel human secreted proteins and the genes that encode them. This knowledge will allow one to detect, to treat, and to prevent medical diseases, disorders, and/or conditions by using secreted proteins or the genes that encode them.

SUMMARY OF THE INVENTION

The present invention relates to novel polynucleotides and the encoded polypeptides. Moreover, the present invention relates to vectors, host cells, antibodies, and recombinant and synthetic methods for producing the polypeptides and polynucleotides. Also provided are diagnostic methods for detecting diseases, disorders, and/or conditions related to the polypeptides and polynucleotides, and therapeutic methods for treating such diseases, disorders, and/or conditions. The invention further relates to screening methods for identifying binding partners of the polypeptides.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In the present invention, a "secreted" protein refers to those proteins capable of being directed to the ER, secretory vesicles, or the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As used herein, a "polynucleotide" refers to a molecule having a nucleic acid sequence contained in SEQ ID NO:X or the cDNA contained within the clone deposited with the ATCC®. For example, the polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:X was often generated by overlapping sequences contained in multiple clones (contig analysis). A representative clone containing all or most of the sequence for SEQ ID NO:X was deposited with the American Type Culture Collection ("ATCC®"). As shown in Table 1, each clone is identified by a cDNA Clone ID (Identifier) and the ATCC® Deposit Number. The ATCC® is located at 10801 University Boulevard, Manassas, Va. 20110-2209, USA. The ATCC® deposit was made pursuant to the terms of the Budapest Treaty on the international recognition of the deposit of microorganisms for purposes of patent procedure.

A "polynucleotide" of the present invention also includes those polynucleotides capable of hybridizing, under stringent hybridization conditions, to sequences contained in SEQ ID NO:X, the complement thereof, or the cDNA within the clone deposited with the ATCC®. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65 degree C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20×SSPE=3M NaCl; 0.2M $NaH_2PO_4$; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single-and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

"SEQ ID NO:X" refers to a polynucleotide sequence while "SEQ ID NO:Y" refers to a polypeptide sequence, both sequences identified by an integer specified in Table 1.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

Many proteins (and translated DNA sequences) contain regions where the amino acid composition is highly biased toward a small subset of the available residues. For example, membrane spanning domains and signal peptides (which are also membrane spanning) typically contain long stretches where Leucine (L), Valine (V), Alanine (A), and Isoleucine (I) predominate. Poly-Adenosine tracts (polyA) at the end of cDNAs appear in forward translations as poly-Lysine (poly-K) and poly-Phenylalanine (poly-F) when the reverse complement is translated. These regions are often referred to as "low complexity" regions.

Such regions can cause database similarity search programs such as BLAST to find high-scoring sequence matches that do not imply true homology. The problem is exacerbated by the fact that most weight matrices (used to score the alignments generated by BLAST) give a match between any of a group of hydrophobic amino acids (L, V and I) that are commonly found in certain low complexity regions almost as high a score as for exact matches.

In order to compensate for this, BLASTX.2 (version 2.0a5MP-WashU) employs two filters ("seg" and "xnu") which "mask" the low complexity regions in a particular sequence. These filters parse the sequence for such regions, and create a new sequence in which the amino acids in the low complexity region have been replaced with the character "X". This is then used as the input sequence (sometimes referred to herein as "Query" and/or "Q") to the BLASTX program. While this regime helps to ensure that high-scoring matches represent true homology, there is a negative consequence in that the BLASTX program uses the query sequence that has been masked by the filters to draw alignments.

Thus, a stretch of "X"s in an alignment shown in the following application does not necessarily indicate that either the underlying DNA sequence or the translated protein sequence is unknown or uncertain. Nor is the presence of such stretches meant to indicate that the sequence is identical or not identical to the sequence disclosed in the alignment of the present invention. Such stretches may simply indicate that the BLASTX program masked amino acids in that region due to the detection of a low complexity region, as defined above. In all cases, the reference sequence (s) (sometimes referred to herein as "Subject", "Sbjct", and/or "S") indicated in the specification, sequence table (Table 1), and/or the deposited clone is (are) the definitive embodiment(s) of the present invention, and should not be construed as limiting the present invention to the partial sequence shown in an alignment, unless specifically noted otherwise herein.

Polynucleotides and Polypeptides of the Invention

Features of Protein Encoded by Gene No: 1

The translation product of this gene shares sequence homology with alloreaction associated antigen (ARAg), or V7, a transmembrane protein with an extracellular domain containing 7 immunoglobulin like domains. ARAg is present on the surface of alloantigen activated CD8+ T cells, monocytes, granulocytes and peripheral dendritic cells and can be used to screen potential immunosuppressants, identify and isolate ARAg receptors and generate MAb for suppressing an immune response. A mAb directed against V7 inhibits the proliferative response of T cells to allogenic cells or immobilized anti-CD3 Ab, but not lectin mitogens, suggesting that V7 plays a role in TCR/CD3-mediated T cell activation. Based on the sequence similarity, the translation product of this clone is expected to share at least some biological activities with T-cell activator proteins, and particularly V7. Such activities are known in the art, some of which are described elsewhere herein (See, for example, J. Immunol. 154 (9), 4434–4443 (1995); all the information available through this reference is hereby incorporated herein by reference).

A preferred polypeptide variant of the invention comprises the following amino acid sequence:

```
MGALRPTLLPPSLPLLLLLMLGMGCWAREVLVPEGPLYRVAGTAVSISCNVT   (SEQ ID NO: 153)
GYEGPAQQNFEWFLYRPEAPDTALGIVSTKDTQFSYAVFKSRVVAGEVQVQR
LQGDAVVLKIARLQAQDAGIYECHTPSTDTRYLGSYSGKVELRVLPDVLQVS
AAPPGPRGRQAPTSPPRMTVHEGQELALGCLARTSTQKHTHLAVSFGRSVPE
APVGRSTLQEVVGIRSDLAVEAGAPYAERLAAGELRLGKEGTDRYRMVV
GGAQAGDAGTYHCTAAEWIQDPDGSWAQIA.
```

Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that bind polypeptides of the invention are also encompassed by the invention. Polynucleotides encoding these polypeptides are also encompassed by the invention.

The polypeptide of this gene has been determined to have a transmembrane domain at about amino acid position 580–596 of the amino acid sequence referenced in Table 1 for this gene. Moreover, a cytoplasmic tail encompassing amino acids 597 to 648 of this protein has also been determined. Based upon these characteristics, it is believed that the protein product of this gene shares structural features to type Ia membrane proteins.

This gene is expressed primarily in brain and primary dendritic cells and to a lesser extent in activated T cells, as well as several other tissues.

Polynucleotides and polypeptides of the invention are useful as reagents for differential identification of the tissue (s) or cell type(s) present in a biological sample and for diagnosis of diseases and conditions which include but are not limited to: neurodegenerative disorders; immune system dysfunction; immunosuppression; transplant rejection; graft versus host disease; inflammatory disorders; and autoimmune diseases. Similarly, polypeptides and antibodies directed to these polypeptides are useful in providing immunological probes for differential identification of the tissue(s) or cell type(s). For a number of disorders of the above tissues or cells, particularly of the brain, CNS, and immune system, expression of this gene at significantly higher or lower levels may be routinely detected in certain tissues or cell types (e.g., neural, immune, hematopoietic, and cancerous and wounded tissues) or bodily fluids (e.g., lymph, serum, plasma, urine, synovial fluid and spinal fluid) or another tissue or sample taken from an individual having such a disorder, relative to the standard gene expression level, i.e., the expression level in healthy tissue or bodily fluid from an individual not having the disorder.

Preferred polypeptides of the present invention comprise, or alternatively consist of, one or more immunogenic epitopes immunogenic epitopes shown in SEQ ID NO: 82 as residues: Thr-52 to Phe-62, Pro-130 to Arg-135, Pro-160 to Arg-173, Thr-190 to His-195, Gly-246 to Arg-252, Arg-397 to Thr-403, Gly-414 to Arg-420, Arg-483 to Glu-488, Arg-525 to Arg-530, Gly-535 to Val-541. Polynucleotides encoding said polypeptides are also encompassed by the invention.

The tissue distribution in primary dendritic cells and activated T cells, combined with the homology to ARAg or V7 indicates that polynucleotides and polypeptides corresponding to this gene are useful for the diagnosis and/or treatment of a variety of immune disorders. Previous studies have indicated that V7 or ARAg is involved in T cell activation and in immune responses. Therefore, this gene may play similar roles, and may be involved in inflammation, autoimmunity, susceptibility to infection, tissue/graft rejection, and in the proliferation, survival, differentiation, or activation of a variety of hematopoietic cell lineages. Similarly, expression at elevated levels in the brain, and in other tissues, suggests that this protein may be involved in the proliferation, stimulation, or differentiation of other cell lineages as well, including neurons and mesenchymal cells. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lens tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:11 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2315 of SEQ ID NO:11, b is an integer of 15 to 2329, where both a and b correspond to the positions of nucleotide residues shown in SEQ ID NO:11, and where b is greater than or equal to a+14.

Features of Protein Encoded by Gene No: 2

The translation product of this gene shares sequence homology with the PC-1 protein, that is a membrane glycoprotein that is selectively expressed on the surface of antibody-secreting cells. It also displays homology with alkaline phosphodiesterase I, and autotaxin, a tumor cell motility-stimulating protein. Based on the sequence similarity, the translation product of this clone is expected to share at least some biological activities with membrane glycoprotein and/or autotaxin proteins. Such activities are known in the art, some of which are described elsewhere herein.

The polypeptide of this gene has been determined to have a transmembrane domain at about amino acid position 411–427 of the amino acid sequence referenced in Table 1 for this gene. Moreover, a cytoplasmic tail encompassing amino acids 428 to 453 of this protein has also been determined. Based upon these characteristics, it is believed that the protein product of this gene shares structural features to type Ia membrane proteins.

This gene is expressed primarily in human ovarian tumors.

Polynucleotides and polypeptides of the invention are useful as reagents for differential identification of the tissue(s) or cell type(s) present in a biological sample and for diagnosis of diseases and conditions which include but are not limited to: reproductive diseases and/or disorders, particularly ovarian cancer and tumor cell metastasis. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., reproductive, ovarian, and cancerous and wounded tissues) or bodily fluids (e.g., lymph, serum, plasma, urine, synovial fluid and spinal fluid) or another tissue or sample taken from an individual having such a disorder, relative to the standard gene expression level, i.e., the expression level in healthy tissue or bodily fluid from an individual not having the disorder.

Preferred polypeptides of the present invention comprise, or alternatively consist of, one or more immunogenic epitopes immunogenic epitopes shown in SEQ ID NO: 83 as residues: Gly-17 to His-22, Lys-100 to Asp-109, Gln-124 to Ser-130, Glu-186 to Glu-201, Asp-237 to Lys-247, His-304 to Ile-311, Asp-335 to Leu-342, Ala-355 to Thr-364, Pro-382 to His-391, Gln-444 to Leu-451. Polynucleotides encoding said polypeptides are also encompassed by the invention.

The tissue distribution in ovarian cancer and homology to autotaxin indicates that polynucleotides and polypeptides corresponding to this gene are useful for the diagnosis and/or treatment of cancer. Autotaxin is a tumor cell motility-stimulating protein. The gene described herein in this patent application is only detected in ovarian tumors. Therefore, it may represent a key player in the diagnosis or treatment in particular of ovarian cancer, and possibly of cancers in general. It may particularly represent a target for inhibitors to control the spread of such cancers. Similarly, the expression within cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Alternatively, this gene product may be involved in the pattern of cellular proliferation that accompanies early embryogenesis. Thus, aberrant expression of this gene product in tissues—particularly adult tissues—may correlate with patterns of abnormal cellular proliferation, such as found in various cancers. Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and would be useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:12 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2316 of SEQ ID NO:12, b is an integer of 15 to 2330, where both a and b correspond to the positions of nucleotide residues shown in SEQ ID NO:12, and where b is greater than or equal to a+14.

Features of Protein Encoded by Gene No: 3

The translation product of this gene shares sequence homology with murine proline-rich acidic protein (Genbank Accession No: AAC24897).

This gene is expressed primarily in fetal liver and tumors of the liver (hepatoma) and to a lesser extent in normal and malignant colon as well as breast cancer.

Polynucleotides and polypeptides of the invention are useful as reagents for differential identification of the tissue (s) or cell type(s) present in a biological sample and for diagnosis of diseases and conditions which include but are not limited to: inflammatory diseases and/or cancers of the liver, colon or breast. Similarly, polypeptides and antibodies directed to these polypeptides are useful in providing immunological probes for differential identification of the tissue(s) or cell type(s). For a number of disorders of the above tissues or cells, particularly of the gastrointestinal or hepatic system, expression of this gene at significantly higher or lower levels may be routinely detected in certain tissues or cell types (e.g., gastrointestinal, hepatic, metabolic, reproductive, endocrine, and cancerous and wounded tissues) or bodily fluids (e.g., lymph, breast milk, chyme, bile, serum, plasma, urine, synovial fluid and spinal fluid) or another tissue or sample taken from an individual having such a disorder, relative to the standard gene expression level, i.e., the expression level in healthy tissue or bodily fluid from an individual not having the disorder.

Preferred polypeptides of the present invention comprise, or alternatively consist of, one or more immunogenic epitopes immunogenic epitopes shown in SEQ ID NO: 84 as residues: Trp-35 to Trp-46, Pro-53 to Asp-58, Thr-74 to Arg-83, Pro-106 to Leu-113, Pro-116 to Arg-128, Pro-141 to Gln-152. Polynucleotides encoding said polypeptides are also encompassed by the invention.

The tissue distribution in human colon tissue indicates that polynucleotides and polypeptides corresponding to this gene are useful for diagnosis and or treatment of tumors of the colon or liver or for inflammatory disorders of theses tissues such as inflammatory bowel disease. Moreover, the protein product of this clone is useful for the detection and treatment of liver disorders and cancers. Representative uses are described in the "Hyperproliferative Disorders", "Infectious Disease", and "Binding Activity" sections below, in Example 11, and 27, and elsewhere herein. Briefly, the protein can be used for the detection, treatment, and/or prevention of hepatoblastoma, jaundice, hepatitis, liver metabolic diseases and conditions that are attributable to the differentiation of hepatocyte progenitor cells. In addition the expression in fetus would suggest a useful role for the protein product in developmental abnormalities, fetal deficiencies, pre-natal disorders and various would-healing models and/or tissue trauma. The protein is useful for modulating the immune response to aberrant polypeptides, as may exist in rapidly proliferating cells and tissues (e.g., colon, breast, and liver cancer tissue). Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:13 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 637 of SEQ ID NO:13, b is an integer of 15 to 651, where both a and b correspond to the positions of nucleotide residues shown in SEQ ID NO:13, and where b is greater than or equal to a+14.

Features of Protein Encoded by Gene No: 4

The translation product of this gene shares sequence homology with the human complement subcomponent C1q chain A precursor (see, e.g., GenBank accession AAD32626), which is thought to be important in immune responses.

It has been discovered that this gene is expressed primarily in immune and hemopoietic cells and to a lesser extent in various cancer cells.

Polynucleotides and polypeptides of the invention are useful as reagents for differential identification of the tissue (s) or cell type(s) present in a biological sample and for diagnosis of the following diseases and conditions: disorders of the immune and hemopoietic systems and cancer. Similarly, polypeptides and antibodies directed to those polypeptides are useful to provide immunological probes for differential identification of the tissue(s) or cell type(s). For a number of disorders of the above tissues or cells, particularly of the immune and hemopoietic systems, expression of this gene at significantly higher or lower levels may be detected in certain tissues (e.g., cancerous and wounded tissues) or bodily fluids (e.g., serum, plasma, urine, synovial fluid or spinal fluid) taken from an individual having such a disorder, relative to the standard gene expression level, i.e., the expression level in healthy tissue from an individual not having the disorder.

Preferred polypeptides of the present invention comprise, or alternatively consist of, one or more immunogenic epitopes immunogenic epitopes shown in SEQ ID NO: 85 as residues: Pro-29 to Gly-46, Lys-48 to Gly-55, Lys-67 to Gly-80, Lys-100 to Pro-115, Arg-121 to Gly-127, Asn-139 to Gly-149, Ser-179 to Arg-185, Asp-191 to Gly-196, Lys-219 to Gly-224. Polynucleotides encoding said polypeptides are also encompassed by the invention.

The tissue distribution and homology to complement subcomponent C1q chain A precursor suggests that the protein product of this clone would be useful for treatment and diagnosis of diseases of the immune and hemopoietic systems and cancers. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lens tissue injury, demyelination, systemic lupus erythematosis, drug induced hemolytic anemia, rheumatoid arthritis, Sjogren's disease, and scleroderma.

Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Based upon the tissue distribution of this protein, antagonists directed against this protein may be useful in blocking the activity of this protein. Accordingly, preferred are antibodies which specifically bind a portion of the translation product of this gene. Also provided is a kit for detecting tumors in which expression of this protein occurs. Such a kit comprises in one embodiment an antibody specific for the translation product of this gene bound to a solid support. Also provided is a method of detecting these tumors in an individual which comprises a step of contacting an antibody specific for the translation product of this gene to a bodily fluid from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker.

Many polynucleotide sequences, such as EST sequences, are publicly available and accessible through sequence databases. Some of these sequences are related to SEQ ID NO:14 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 983 of SEQ ID NO:14, b is an integer of 15 to 997, where both a and b correspond to the positions of nucleotide residues shown in SEQ ID NO:14, and where b is greater than or equal to a+14.

Features of Protein Encoded by Gene No: 5

The translation product of this gene shares sequence homology with, and is believed to be a novel homolog of, the human complement C1r protein (gb|AAA51851.1|human complement C1r [Homo sapiens]) an inactive precursor of a serine protease which is thought to be important in activation of the complement pathway in human immunity (See, for example, Biochemistry 25 (17), 4855–4863 (1986); all information within this reference is hereby incorporated herein by reference). The homologous regions are shown below:

```
>gb |AAA51851.1| human complement Clr [Homo sapiens] >pir|A24170|C1HURB
          complement subcomponent Clr (EC 3.4.21.41) precursor - human
          >sp |P00736|C1R_HUMAN COMPLEMENT C1R COMPONENT PRECURSOR (EC
          3.4.21.41).
          Length = 705
```

-continued

```
Plus Strand HSPs:
Score = 721 (253.8 bits), Expect = 7.4e-103, Sum P(2) = 7.4e-103
Identities = 127/230 (55%) Positives = 170/230 (73%) Frame = +1
Query:  574 AKVQNHCQEPYYQXXXXXXXXXX--------XXXXWKDRQDGEEVLQCMPVCGRPVTPIA   729
       A++Q +C EPYY+                       WK+ Q GE++ C+ ++PVCG+PV P+
Sbjct:  400 ARIQYYCHEPYYKMQTRAGSRESEQGVYTCTAQGIWKNEQKGEKIPRCLPVCGKPVNPVE   459

Query:  730 QNQTTLGSSRAKLGNFPWQAFTSIHGRGGGALLGDRWILTAAHTIYPKDSVSLRKNQSVN   909
            Q Q  +G  +AK+GNFPWQ FT+IHGRGGGALLGDRWILTAAHT+YPK+H   + + N S++
Sbjct:  460 QRQRIIGGQKAKMGNFPWQVFTNIHGRGGGALLGDRWILTAAHTLYPKEHEA-QSNASLD   518

Query:  910 VFLGHTAIDEMLKLGNHPVHRVVVHPDYRQNESHNFSGDIALLELQHSIPLGPNVLPVCL  1089
            VFLGHT ++E++KLGNHP+ RV VHPDYRQ+ES+NF GDIALLEL++S+ LGPN+LP+CL
Sbjct:  519 VFLGHTNVEELMKLGNHPIRRVSVHPDYRQDESYNFEGDIALLELENSVTLGPNLLPICL   578
Query: 1090 PDNETLYRSGLLGYVSGFGMEMGWLTTELKYSRLPVAPREACNAWLQKRQR          1242
           PDN+T Y  GL+GYVSGFG+    +  +L++ RLPVA  +AC  WL+ + R
Sbjct:  579 PDNDTFYDLGLMGYVSGFGVMEEKIAHDLRFVRLPVANPQACENWLRGKNR          629
Score = 325 (114.4 bits), Expect = 7.4e-103, Sum P(2) = 7.4e-103
Identities = 72/156 (46%), Positives = 94/156 (60%), Frame = +1
Query:   79 MWWLLLWGVLQACPTRGSVLLAQELPQQLTSPGYPEPYGKGQESSTDIKAPEGFAVRLVF   258
            MW L L      C   GS+ + Q+L  ++TSP +P+PY     E++T I  P G+ V+LVF
Sbjct:    1 MWLLYLLVPALFCRAGGSIPIPQKLFGEVTSPLFPKPYPNNFETTTVITVPTGYRVKLVF    60

Query:  259 QDFDLEPSQDCAGDSVTISFVGSDPSQFCGQQGSPLGRPPGQREFVSSGRSLRLTFRTQP   438
            Q FDLEPS+ C  D V IS       +FCGQ GSPLG PPG++EF+S G  + LTF T
Sbjct:   61 QQFDLEPSEGCFYDYVKISADKKSLGRFCGQLGSPLGNPPGKKEFMSQGNKMLLTFHTDF   120

Query:  439 SSE-NKTAHLHKGFLALYQTVAVNYSQPISEASRGSE                        546
             S+E N T   +KGFLA YQ  AV+  +  S +  G E
Sbjct:  121 SNEENGTIMFYKGFLAYYQ--AVDLDECASRSKSGEE                        155
```

Based on the sequence similarity, the translation product of this clone is expected to share at least some biological activities with serine protease zymogens such as C1r. Such activities are known in the art, some of which are described elsewhere herein.

In specific embodiments, polypeptides of the invention comprise, or alternatively consist of the following amino acid sequence:

```
MGLILTVVGVHNDTVDRVVPQFQHLIYGCVAQEHIHTLVLPERNTVLGVDGV    (SEQ ID NO: 154)

GSSEDPSVPQQGPAPTAVDTGEGLPGEVAQLGSGRTEGRLILGNGGDWPSAD

RHTLKNLLPILSVFPGPWGCTGECPCCRGLIIGLLAVVLDLGRVVSRCVDGLR

APAGLADGLTIVHSHGLVEGQEALVEVGSLVLRGRLCAEGQPQTPP
```

Polynucleotides encoding these polypeptides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that bind polypeptides of the invention are also encompassed by the invention. Polynucleotides encoding these polypeptides are also encompassed by the invention.

This gene is expressed primarily in kidney (e.g., fetal kidney, rejected Kidney transplant, and cancerous kidney tissue) Human OB MG63 control fraction I (osteosarcoma); Human Adult Testes, Large Inserts, Reexcision; and Rejected Kidney, lib 4.

Polynucleotides and polypeptides of the invention are useful as reagents for differential identification of the tissue (s) or cell type(s) present in a biological sample and for diagnosis of diseases and conditions which include but are not limited to: reproductive, and renal diseases and/or disorders, including immune suppression and other diseases of the immune system. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, renal, reproductive, and cancerous and wounded tissues) or bodily fluids (e.g., lymph, serum, seminal fluid, plasma, urine, synovial fluid and spinal fluid) or another tissue or sample taken from an individual having such a disorder, relative to the standard gene expression level, i.e., the expression level in healthy tissue or bodily fluid from an individual not having the disorder.

Preferred polypeptides of the present invention comprise, or alternatively consist of, one or more immunogenic epitopes immunogenic epitopes shown in SEQ ID NO: 86 as residues: Pro-32 to Lys-49, Glu-66 to Ala-72, Asp-84 to Gly-90, Arg-117 to Thr-126, Pro-161 to Tyr-176, Gly-191 to Glu-201, Leu-270 to Ser-275, Pro-303 to Ser-314, Asp-339 to Tyr-344, Gln-384 to Lys-396. Polynucleotides encoding said polypeptides are also encompassed by the invention.

The homology of the translation product of this gene to the human C1r indicates that polynucleotides and polypeptides corresponding to this gene are useful for diagnosis and treatment of diseases of the immune system including AIDS and other immune deficiencies, autoimmune disorders such as lupus, and other immune disorders. Alternatively, the distribution in testicular tissue indicates that polynucleotides and polypeptides corresponding to this gene are useful for the treatment and diagnosis of conditions concerning proper testicular function (e.g. endocrine function, sperm maturation), as well as cancer. Therefore, this gene product is useful in the treatment of male infertility and/or impotence. This gene product is also useful in assays designed to identify binding agents, as such agents (antagonists) are useful as male contraceptive agents. Similarly, the protein is believed to be useful in the treatment and/or diagnosis of testicular cancer. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications. Alternatively, the tissue distribution in kidney indicates that the protein product of this clone could be used in the treatment and/or detection of kidney diseases including renal failure, nephritis, renal tubular acidosis, proteinuria, pyuria, edema, pyelonephritis, hydronephritis, nephrotic syndrome, crush syndrome, glomerulonephritis, hematuria, renal colic and kidney stones, in addition to Wilm's Tumor Disease, and congenital kidney abnormalities such as horseshoe kidney, polycystic kidney, and Falconi's syndrome. The protein is useful in modulating the immune response to aberrant polypeptides (as may exist in rapidly proliferating cells and tissues), and presents a novel therapeutic for hemophiliacs and other patients presenting aberrant blood diseases and/or disorders. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:15 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1252 of SEQ ID NO:15, b is an integer of 15 to 1266, where both a and b correspond to the positions of nucleotide residues shown in SEQ ID NO:15, and where b is greater than or equal to a+14.

Features of Protein Encoded by Gene No: 6

The translation product of this gene shares sequence homology with Bos taurus mimecan (see GenBank accession AAB70264), which is though to be important in connective tissues. Based on this homology it is expected that these proteins will share some biological activity.

It has been discovered that this gene is expressed primarily in fetal tissues, aorta, cochlea and to a lesser extent in a variety of other tissues and cell types.

Polynucleotides and polypeptides of the invention are useful as reagents for differential identification of the tissue (s) or cell type(s) present in a biological sample and for diagnosis of the following diseases and conditions: heart disease, restenosis, atherosclerosis, stoke, angina, thrombosis, and wound healing, deafness and vertigo. Similarly, polypeptides and antibodies directed to those polypeptides are useful to provide immunological probes for differential identification of the tissue(s) or cell type(s). For a number of disorders of the above tissues or cells, particularly of the connective tissue, expression of this gene at significantly higher or lower levels may be detected in certain tissues (e.g., immune, nervous, cancerous and wounded tissues) or bodily fluids (e.g., serum, plasma, urine, synovial fluid or spinal fluid) taken from an individual having such a disorder, relative to the standard gene expression level, i.e., the expression level in healthy tissue from an individual not having the disorder.

Preferred polypeptides of the present invention comprise, or alternatively consist of, one or more immunogenic epitopes immunogenic epitopes shown in SEQ ID NO: 87 as residues: Pro-21 to Arg-28, Tyr-33 to Phe-38, Gln-45 to Glu-61, Pro-83 to Glu-90, Lys-195 to Ile-204, Thr-253 to Tyr-262. Polynucleotides encoding said polypeptides are also encompassed by the invention.

Mimecan is a member of a group of small, leucine-rich proteoglycans (SLRPs). These proteins share a common core structure which consists of a central domain with varying numbers of leucine-rich repeats flanked by cysteine-rich clusters. Seven members of SLRPs have been described so far. These include: keratocan, lumican, fibromodulin, decorin, biglycan, and epiphycan. A seventh member of the family, mimecan, is a proteoglycan expressed by many connective tissues. It was originally isolated in a truncated form as a bone-associated glycoprotein, osteoglycin. Mimecan has since been demonstrated to be expressed in a variety of tissues, with and without keratan sulfate chains. Numerous examples illustrate the ability of SLRPs to bind growth factors and/or growth factor receptors and therefore to modulate cell proliferation and differentiation.

The tissue distribution and homology to mimecan suggests that the protein product of this clone would be useful for the treatment and diagnosis of conditions involving tissue repair and wound healing. Tissue repair may be indicated in cases of injury to the skin or internal organs, ulceration, cellular necrosis or other conditions involving healing of both diseased or non-diseased, traumatized tissue.

More specifically, the expression in aorta would suggest a role in cardiovascular disorders such as, asthma, heart disease, restenosis, atherosclerosis, stoke, angina and thrombosis. The expression in cochlea would suggest a potential use in the treatment of conditions affecting the inner ear, such as deafness and vertigo. Based upon the tissue distribution of this protein, antagonists directed against this protein may be useful in blocking the activity of this protein. Accordingly, preferred are antibodies which specifically bind a portion of the translation product of this gene. Also provided is a kit for detecting tumors in which expression of this protein occurs. Such a kit comprises in one embodiment an antibody specific for the translation product of this gene bound to a solid support. Also provided is a method of detecting these tumors in an individual which comprises a step of contacting an antibody specific for the translation product of this gene to a bodily fluid from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein. In addition, because of the implications of tissue regeneration, remodeling and growth regulation, and in light of the high degree of expression in fetal and cancerous tissues, the protein product of this gene may have indications in the diagnosis and treatment of neoplasms and cancer. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:16 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2696 of SEQ ID NO:16, b is an integer of 15 to 2710, where both a and b correspond to the positions of nucleotide residues shown in SEQ ID NO:16, and where b is greater than or equal to a+14.

Features of Protein Encoded by Gene No: 7

The translation product of this gene shares sequence homology with the rat decay accelerating factor (see, e.g., GenBank accession AAC77439) which is thought to be important in modifying the activity and cellular response of complement proteins and thus attenuating complement mediated immune responses.

In specific embodiments, polypeptides of the invention comprise, or alternatively consists of, the following amino acid sequence:

```
MCLLGGLSAPPLLLLPLLPLLLCPPTAQGDCSFPPELPNAIQSVGDQQSFPEKFT    (SEQ ID NO: 213)
VTYKCKEGFVKVPGKADSVVCLNNKWSEVAEFCNRSCDVPTRLQFASLKKS
FTKQNYFPVGSVVEYECRPGYQRDHLLSGKLTCLLNFTWSKPDEFCKRKSCP
NPGDLRHGHVNIPTDILYAAVIHFSCNKGYRLVGAASSYCSIVNDDVGWSDPL
PECQEIFCPEPPKISNGVILDQQNTYVYQQAVKYECIKGFTLIGENSIYCTVKG
DQGEWSGRRLNAKVLRFLQSYQQQRHHHSKCFSYKAHISSSETHHCKCYRY
QSYISSSETHHRECSRYRSYINSSETHYSGCFRDPVSSPESHHGKCVCYTGHAS
NP
```

Moreover, fragments and variants of this polypeptide (such as, for example, fragments as described herein, polypeptides at least 80%, 85%, 90%, 95%, 96%, 97%, 98%, or 99% identical to these polypeptides and polypeptides encoded by the polynucleotide which hybridize, under stringent conditions, to the polynucleotide encoding this polypeptide are encompassed by the invention. Antibodies that bind polypeptides of the invention are also encompassed by the invention. Polynucleotides encoding this polypeptide are also encompassed by the invention.

In specific embodiments, polynucleotides of the invention comprise, or alternatively consists of, the following polynucleotide sequence:

```
gaactantnggtgacactataagaaggtacgcctgcaggtaccggtccggaattcccgggtcgacccacg   (SEQ ID NO: 214)
cgtccgcttaccgctgcttgctggagcgagcttccacttaactcccgtcccggtccccgcgcgccatgt
gcctcctcggcgggctgagcgccccgccgctgctgctgctgccgctgctgccgctgctgctgtgtccgc
ctacggcgcagggtgactgcagctttcccccagagctacctaatgccatacaaagtgtgggtgaccaac
agagttttcctgaaaaattcacagtaacatacaaatgtaaagaaggctttgtaaaggttcctggcaagg
cagactccgtggtctgtctcaacaataaatggtcagaggtggcagaattttgtaaccgtagctgtgatg
ttccaaccaggctacaatttgcatctctcaaaaagtctttcaccaaacagaattatttcccagtgggtt
ccgttgtggaatatgaatgccgacctggctaccaaagggaccatcttctctcaggaaaactaacttgcc
ttctgaattttacatggtccaaacccgatgaattttgtaaaagaaaatcatgtcctaatcctggagatt
taagacatggtcatgtcaacattccaactgacatattgtatgctgcagttatccacttctcgtgtaaca
aggggtacaggttagtcggtgcagcttctagttactgttccattgtaaatgacgatgttggctggagtg
atccattgcctgaatgccaagaaatttttgtccggaaccaccaaaaattagcaatggagtcattctag
```

-continued

```
atcaacagaacacttatgtgtatcaacaggctgtwaaatatgagtgtataaaaggcttcaccctgatcg

gagagaactctatttattgtactgttaagggtgaccaaggagaatggagtggccgccgcctgaatgcaa

aggttctcagatttctacagtcataccagcaacagagacaccaccacagtaagtgcttcagctacaaag

cccacatcagctcntcagaaacccaccactgcaaatgttacaggtaccaaagttacatcagctcctcag

aaacccaccacagggaatgttccaggtaccgaagctacatcaactcctcagaaacccactacagcggat

gtttcagagaccccgtcagcagtccagaatcccatcacggcaaatgcgtytgctacacaggccatgcca

gcaacccatagatcctccacagcaaaagcttcatttacacagagtcttccagcaacacgaaagtccact

gctatacatgccccagtgactaagggtctccatacaacaaaaagattgacctctgctcgtattacagca

aaacagagttcagctactcccaggacaaccagcgcacctcatggaagagggaccctctcttcagatgct

gccatcattgcagttggtaagtttggttcttcggcagttaaaaaaaattgtcatcactgtgggatgtac

aatccttattcctggaggagaatattgtctttttactgccttaggaatactattaagatgaaatgttta

aggtcagggagaagacgggtaaatgcattttatcgacgtgtttggtggaccccgttaggtactcggtac

gttcctaagtcttcccaaccgtgttcttgttccaaggtaattttagggcaacttcacatcatttggcca

gtcaatcaagtatccctgaacgcctattgtctcaatgcattatcattctaggggccaaaaacaacmata

aggaagctattatcaatacagtttttaagcctcaagtgktttacaagtactcacaaactactccttggt

tgkttctagacgtctgttccagataaaccagaatgctacytttgattacatcctgttctttttttccctt

tcctgtcagtgatttaaagcaaagatagctttaaaattattctgttgctatagacttaaggacatatct

atgttgcaaatttctttttcttgttcccnagtcttttgttgttcattaaatatattatttgatgttata

cattttaccaagaagattaataactcctaaagaagatggcaaaagaaatgtttaagaagcaatacagct

aagttggcatattaaaanggaatgcccagtagaaaatatgcacattaaaaagtgaatattttaaaatta

tgtccttataagctgaggtctcctatttatgcatgcatgagtgaaacaagggactgaagctgaaaaggt

gtttttttaattattattattatttatagttcttttatagttcttttatattttgaatgaacctctcctt

agctaaaatagttatcttgaaagatttgaacagttggattcactttgtttgtttgatattttcaataga

aataaatgcattctaaatgaaaaaaaaaaaaaaaaaaaaaagggcggcc.
```

Moreover, fragments and variants of this polynucleotide (such as, for example, fragments as described herein, polynucleotides at least 80%, 85%, 90%, 95%, 96%, 97%, 98%, or 99% identical to this polynucleotide and polynucleotides which hybridize, under stringent conditions, to this polynucleotide are encompassed by the invention. Polypeptides encoded by these polynucleotides are also encompassed by the invention as are antibodies which bind to such polypeptides.

It has been discovered that this gene is expressed primarily in ovarian tumor.

Polynucleotides and polypeptides of the invention are useful as reagents for differential identification of the tissue(s) or cell type(s) present in a biological sample and for diagnosis of the following diseases and conditions: reproductive diseases and/or disorders, particularly ovarian tumors. Similarly, polypeptides and antibodies directed to those polypeptides are useful to provide immunological probes for differential identification of the tissue(s) or cell type(s). For a number of disorders of the above tissues or cells, particularly of the reproductive system, expression of this gene at significantly higher or lower levels may be detected in certain tissues or cell types (e.g., reproductive, ovarian, and cancerous and wounded tissues) or bodily fluids (e.g., lymph, amniotic fluid, serum, plasma, urine, synovial fluid or spinal fluid) taken from an individual having such a disorder, relative to the standard gene expression level, i.e., the expression level in healthy tissue from an individual not having the disorder.

The tissue distribution in ovarian tumor tissue indicates that polynucleotides and polypeptides of the invention are useful for the detection, treatment, and/or prevention of proliferative diseases and/or disorders, and particularly for ovarian cancer. Moreover, the expression within cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Alternatively, this gene product may be involved in the pattern of cellular proliferation that accompanies early embryogenesis. Thus, aberrant expression of this gene product in tissues—particularly adult tissues— may correlate with patterns of abnormal cellular proliferation, such as found in various cancers. Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and would be useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation.

Based upon the tissue distribution of this protein, antagonists directed against this protein may be useful in blocking the activity of this protein. Accordingly, preferred are antibodies which specifically bind a portion of the translation product of this gene. Also provided is a kit for detecting tumors in which expression of this protein occurs. Such a kit comprises in one embodiment an antibody specific for the translation product of this gene bound to a solid support. Also provided is a method of detecting these tumors in an individual which comprises a step of contacting an antibody specific for the translation product of this gene to a bodily fluid from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:17 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2391 of SEQ ID NO:17, b is an integer of 15 to 2405, where both a and b correspond to the positions of nucleotide residues shown in SEQ ID NO:17, and where b is greater than or equal to a+14.

Features of Protein Encoded by Gene No: 8

Angiogenesis, the formation of new blood vessels from pre-existing vasculature, is a tightly regulated process in normal adults. Under physiological circumstances, growth of new capillaries is tightly controlled by an interplay of growth regulatory proteins which act either to stimulate or to inhibit blood vessel growth. Normally, the balance between these forces is tipped in favor of inhibition and consequently blood vessel growth is restrained. Under certain pathological circumstances, however, local inhibitory controls are unable to restrain the increased activity of angiogenic inducers. Angiogenesis is a key step in the metastasis of cancer (Folkman, *Nature Med.* 1:27–31 (1995)) and in abnormal wound healing, inflammation, rheumatoid arthritis, psoriasis, and diabetic retinopathy, it is integral to the pathology (Folkman et al., *Science* 235:442–447 (1987)), engendering the hope that these pathological entities could be regulated by pharmacological and/or genetic suppression of blood vessel growth (Iruela-Arispe et al., *Thromb. Haem.* 78:672–677 1997)).

Thrombospondin-1 (TSP-1) is a 450 kDa, anti-angiogenic adhesive glycoprotein released from activated platelets and secreted by growing cells (reviewed in Adams, *Int. J. Biochem. Cell Biol.* 29:861–865 (1997)). TSP-1 is a homotrimer, with each subunit comprised of a 1152 amino acid residue polypeptide, post-translationally modified by N-linked glycosylation and beta-hydroxylation of asparagine residues.

TSP-1 protein and mRNA levels are regulated by a variety of factors. TSP-1 protein levels are down-regulated by IL-1 alpha and TNF alpha. TSP-1 mRNA and protein levels are up-regulated by polypeptide growth factors including PDGF, TGF-beta, and bFGF (Bornstein, *FASEB J.* 6:3290–3299 (1992)) and are also regulated by the level of expression of the p53 tumor suppressor gene product (Dameron et al., *Science* 265:1582–1584 (1994)). At least four other members of the thrombospondin family have been identified: TSP-2, TSP-3, TSP-4, and TSP-5 (also called COMP). There is a need in the art to identify other molecules involved in the regulation of angiogenesis.

FIGS. 4A–4H shows the nucleotide sequence (SEQ ID NO:18) and the deduced amino acid sequence (SEQ ID NO:89) of THRAP. The predicted leader sequence located at about amino acid residues 1 to 28 is bolded in FIGS. 4A–4H. FIGS. 4A–4H also shows 13 TSP-1-like domains (indicated by single underlined amino acid residues), an IgG-like domain (indicated by bolded and double underlined amino acid residues), and a proteinase inhibitor-like domain (indicated by double underlined amino acid residues) of SEQ ID NO:89. In this context "about" includes the particularly recited ranges, larger or smaller by several (10, 9, 8, 7, 6, 5, 4, 3, 2, or 1) amino acids, at either extreme or at both extremes.

FIGS. 5A–5E shows the regions of identity between the amino acid sequence of THRAP and the translation product of Thrombospondin-like protein (MKCSYTVVFLLFYLLIASFHVDALSWAWSPWSSCTKTCGGGVSRQLRRCL (SEQ ID NO: 217)

TSKCSGESVRFKVCAQKTCESKSRLARDTICGGEEIVSRGQCEVVCRSRLTGA

NFLWRVDDGTPCQAATSRAVCSKGSCQIVGCDGLISSSFRFDACGVCGGRGD

TCDNGKFIWKVSEEYTACASNCDDIVDWSGAGRSIASTSQPIVVCVNAITGRV

-continued

```
VPEKLCADKLRPKVEARPCPMLICPSRWMAADWTECVPHCGEGTRKREVYC

VQTAHNVTVHVPDTFCENGTRPAAEENCVSTSCGRWEAGKWSKCTASCGQG

VRRRHVACVGGSDCDEGGRPRQETTCYAGIPCSIATNSLDWNDRAYLDGNTF

GSMDNHNDWQAPRLVAGEWSTCSSTCGTGVMSRTVECVAVNPISSAPIKLP

MSECQDQERQPKLFESCEVRSCPLQEDSKLSEDEAPYQWRYGDWTQCSASCLG

GKQKAALKCIQVSTGKSVQWSQCDARRRPPEKSRPCNQHPCPPFWLTSKYSD

CSMSCGSGTARRSVKCAQTVSKTDGADAHIVLRDDRCHFKKPQETETCNVV

ACPATWVSSLNKRHNKIKLNKLKTAQWTECSRSCDSGERRRQVWCEIRDSRG

KTQRRPDVECDANTKPQTVEVCSFGSCSRPELLSNRVFEQNAEQKKLTLGIGG

VATLYQGTSIKIKCPAKKFDKKKIYWKKNGKKIKNDAHIKVSANGNLRVFHA

RMEDAGVYECFTDRLQGNVTLNFKYRDFPASRVDLAPKPQIPSTKNRQRVQV

SKEDVLREQASVLHKMNVSLIEALLTAPNDEKAREQLRKYGNELVARWDIG

HWSECRQKTCHVAGYQARGISCKVTFHGEIRNVDNSICESLASVRPPETRPCH

REDCPRWEASQWSECSSQRCVSSMLAQKRRNVTCRFTNGTSVDIQHCDITNR

PATTMDCPNQNCKAEWRTSDWGSCSSECGTGGVQLRLLSCVWISSGRPAGR

NCEQMRRPHSARACVADEPLPPCMPTASALYQRDASCQDQSRFCDIIKLFHSC

DSLEVRQKCCSTCTFVERKKF;

Genbank accession CAB03212.1)
```

determined by BLAST analysis. Identical amino acids between the two polypeptides are boxed. By examining the regions of boxed amino acids, the skilled artisan can readily identify conserved domains between the two polypeptides. These conserved domains are preferred embodiments of the present invention.

FIG. 6 shows an analysis of the THRAP amino acid sequence. Alpha, beta, turn and coil regions; hydrophilicity and hydrophobicity; amphipathic regions; flexible regions; antigenic index and surface probability are shown, and all were generated using the default settings. In the "Antigenic Index or Jameson-Wolf" graph, the positive peaks indicate locations of the highly antigenic regions of the THRAP protein, i.e., regions from which epitope-bearing peptides of the invention can be obtained. The domains defined by these graphs are contemplated by the present invention.

The data presented in FIG. 6 are also represented in tabular form in Table 7. The columns are labeled with the headings "Res", "Position", and Roman Numerals I–XIV. The column headings refer to the following features of the amino acid sequence presented in FIG. 6, and Table 7: "Res": amino acid residue of SEQ ID NO:89 and FIGS. 4A–4H; "Position": position of the corresponding residue within SEQ ID NO:89 and FIGS. 4A–4H; I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Hydrophobicity Plot—Hopp-Woods; X: Alpha, Amphipathic Regions—Eisenberg; XI: Beta, Amphipathic Regions—Eisenberg; XII: Flexible Regions—Karplus-Schulz; XIII: Antigenic Index—Jameson-Wolf; and XIV: Surface Probability Plot—Emini.

A clone (HOHCA60) containing all or most of the sequence for SEQ ID NO:18 was deposited with the American Type Culture Collection ("ATCC®") on Sep. 7, 1999, and was given the ATCC Deposit Number PTA-627. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure. Clone HOHCA60 was isolated from a osteoblast II cDNA library. This clone contains the entire coding region identified as SEQ ID NO:18. The deposited clone contains a cDNA having a total of 5720 nucleotides, which encodes a predicted open reading frame of 1745 amino acid residues. (See FIGS. 4A–4H.) The open reading frame begins at a N-terminal methionine located at nucleotide position 67, and ends at a stop codon at nucleotide position 5302. The predicted molecular weight of the THRAP protein is about 191 kDa.

Subsequent Northern analysis also showed that this gene is expressed primarily in testes, fetal tissue (e.g., lung, heart), synovial sarcoma, brain, immune cells and tissues (e.g., lymph node, macrophage), colon, prostate, small intestine, thyroid and to a lesser extent in many other tissues.

DOMAINS: It has also been discovered that THRAP (SEQ ID NO:89) contains 13 TSP-1-like domains, an IgG-like domain, and a proteinase inhibitor-like domain. More particularly, (a) a predicted TSP-1-like domain1 (SEQ ID NO:161) located at about amino acids 33 to 82 of SEQ ID NO:89; (b) a predicted TSP-1-like domain2 (SEQ ID NO:162) located at about amino acids 301–360 of SEQ ID NO:89; (c) a predicted TSP-1-like domain3 (SEQ ID NO:163) located at about amino acids 363–421 of SEQ ID NO:89, (d) a predicted TSP-1-like domain4 (SEQ ID NO:164) located at about amino acids 423–475 of SEQ ID NO:89, (e) a predicted TSP-1-like domain5 (SEQ ID NO:165) located at about amino acids 514–566 of SEQ ID NO:89, (f) a predicted TSP-1-like domain6 (SEQ ID NO:166) located at about amino acids 590–650 of SEQ ID NO:89, (g) a predicted TSP-1-like domain7 (SEQ ID NO:167) located at about amino acids 653–712 SEQ ID NO:89, (h) a predicted TSP-1-like domain8 (SEQ ID NO:168) located at about amino acids 715–772 of SEQ ID NO:89, (i) a predicted TSP-1-like domain9 (SEQ ID NO:169) located at about amino acids 775–832 of SEQ ID NO:89, (j) a predicted TSP-1-like domain10 (SEQ ID NO: 170) located at about amino acids 1473–1529 SEQ ID NO:89, (k) a predicted TSP-1-like domain11 (SEQ ID NO:171) located at about amino acids 1532–1590 of SEQ ID NO:89, (l) a predicted TSP-1-like domain12 (SEQ ID NO:172) located at about amino acids 1593–1650 of SEQ ID NO:89, (m) a predicted TSP-1-like domain13 (SEQ ID NO:173) located at about amino acids 1653–1708 SEQ ID NO:89, (n) a predicted proteinase inhibitor domain (SEQ ID NO:174) located at about amino acids 83–220 of SEQ ID NO:89, and (o) a predicted IgG-like domain (SEQ ID NO:175) located at about amino acids 1180–1471 of SEQ ID NO:89. In this context "about" includes the particularly recited ranges, larger or smaller by several (10, 9, 8, 7, 6, 5, 4, 3, 2, or 1) amino acids, at either extreme or at both extremes. These polypeptide fragments of THRAP are specifically contemplated in the present invention.

SIGNAL SEQUENCE. Moreover, the encoded polypeptide has a THRAP leader sequence located at about amino acids 1–28. (See FIGS. 4A–4H.) Also shown in FIGS. 4A–4H, the THRAP secreted protein encompasses about amino acid residues 29–1745. In this context "about" includes the particularly recited ranges, larger or smaller by several (10, 9, 8, 7, 6, 5, 4, 3, 2, or 1) amino acids, at either extreme or at both extremes. These polypeptide fragments of THRAP are specifically contemplated in the present invention.

N-terminal deletions of the THRAP polypeptide can be described by the general formula m–1745, where m is an integer from 2 to 1739 where m corresponds to the position of the amino acid residue identified in SEQ ID NO:89. More in particular, the invention provides polynucleotides encoding polypeptides comprising, or alternatively consisting of, an amino acid sequence selected from the group: E-2 to A-1745; C-3 to A-1745; C-4 to A-1745; R-5 to A-1745; R-6 to A-1745; A-7 to A-1745; T-8 to A-1745; P-9 to A-1745; G-10 to A-1745; T-11 to A-1745; L-12 to A-1745; L-13 to A-1745; L-14 to A-1745; F-15 to A-1745; L-16 to A-1745; A-17 to A-1745; F-18 to A-1745; L-19 to A-1745; L-20 to A-1745; L-21 to A-1745; S-22 to A-1745; S-23 to A-1745; R-24 to A-1745; T-25 to A-1745; A-26 to A-1745; R-27 to A-1745; S-28 to A-1745; E-29 to A-1745; E-30 to A-1745; D-31 to A-1745; R-32 to A-1745; D-33 to A-1745; G-34 to A-1745; L-35 to A-1745; W-36 to A-1745; D-37 to A-1745; A-38 to A-1745; W-39 to A-1745; G-40 to A-1745; P-41 to A-1745; W-42 to A-1745; S-43 to A-1745; E-44 to A-1745; C-45 to A-1745; S-46 to A-1745; R-47 to A-1745; T-48 to A-1745; C-49 to A-1745; G-50 to A-1745; G-51 to A-1745; G-52 to A-1745; A-53 to A-1745; S-54 to A-1745; Y-55 to A-1745; S-56 to A-1745; L-57 to A-1745; R-58 to A-1745; R-59 to A-1745; C-60 to A-1745; L-61 to A-1745; S-62 to A-1745; S-63 to A-1745; K-64 to A-1745; S-65 to A-1745; C-66 to A-1745; E-67 to A-1745; G-68 to A-1745; R-69 to A-1745; N-70 to A-1745; I-71 to A-1745; R-72 to A-1745; Y-73 to A-1745; R-74 to A-1745; T-75 to A-1745; C-76 to A-1745; S-77 to A-1745; N-78 to A-1745; V-79 to A-1745; D-80 to A-1745; C-81 to A-1745; P-82 to A-1745; P-83 to A-1745; E-84 to A-1745; A-85 to A-1745; G-86 to A-1745; D-87 to A-1745; F-88 to A-1745; R-89 to A-1745; A-90 to A-1745; Q-91 to A-1745; Q-92 to A-1745; C-93 to A-1745; S-94 to A-1745; A-95 to A-1745; H-96 to A-1745; N-97 to A-1745; D-98 to A-1745; V-99 to A-1745; K-100 to A-1745; H-101 to A-1745; H-102 to A-1745; G-103 to A-1745; Q-104 to A-1745; F-105 to A-1745; Y-106 to A-1745; E-107 to A-1745; W-108 to A-1745; L-109 to A-1745; P-110 to A-1745; V-111 to A-1745; S-112 to A-1745; N-113 to A-1745; D-114 to A-1745; P-115 to A-1745; D-116 to A-1745; N-117 to A-1745; P-118 to A-1745; C-119 to A-1745; S-120 to A-1745; L-121 to A-1745; K-122 to A-1745; C-123 to A-1745; Q-124 to A-1745; A-125 to A-1745; K-126 to A-1745; G-127 to A-1745; T-128 to A-1745; T-129 to A-1745; L-130 to A-1745; V-131 to A-1745; V-132 to A-1745; E-133 to A-1745; L-134 to A-1745; A-135 to A-1745; P-136 to A-1745; K-137 to A-1745; V-138 to A-1745; L-139 to A-1745; D-140 to A-1745; G-141 to A-1745; T-142 to A-1745; R-143 to A-1745; C-144 to A-1745; Y-145 to A-1745; T-146 to A-1745; E-147 to A-1745; S-148 to A-1745; L-149 to A-1745; D-150 to A-1745; M-151 to A-1745; C-152 to A-1745; I-153 to A-1745; S-154 to A-1745; G-155 to A-1745; L-156 to A-1745; C-157 to A-1745; Q-158 to A-1745; I-159 to A-1745; V-160 to A-1745; G-161 to A-1745; C-162 to A-1745; D-163 to A-1745; H-164 to A-1745; Q-165 to A-1745; L-166 to A-1745; G-167 to A-1745; S-168 to A-1745; T-169 to A-1745; V-170 to A-1745; K-171 to A-1745; E-172 to A-1745; D-173 to A-1745; N-174 to A-1745; C-175 to A-1745; G-176 to A-1745; V-177 to A-1745; C-178 to A-1745; N-179 to A-1745; G-180 to A-1745; D-181 to A-1745; G-182 to A-1745; S-183 to A-1745; T-184 to A-1745; C-185 to A-1745; R-186 to A-1745; L-187 to A-1745; V-188 to A-1745; R-189 to A-1745; G-190 to A-1745; Q-191 to A-1745; Y-192 to A-1745; K-193 to A-1745; S-194 to A-1745; Q-195 to A-1745; L-196 to A-1745; S-197 to A-1745; A-198 to A-1745; T-199 to A-1745; K-200 to A-1745; S-201 to A-1745; D-202 to A-1745; D-203 to A-1745; T-204 to A-1745; V-205 to A-1745; V-206 to A-1745; A-207 to A-1745; I-208 to A-1745; P-209 to A-1745; Y-210 to A-1745; G-211 to A-1745; S-212 to A-1745; R-213 to A-1745; H-214 to A-1745; I-215 to A-1745; R-216 to A-1745; L-217 to A-1745; V-218 to A-1745; L-219 to A-1745; K-220 to A-1745; G-221 to A-1745; P-222 to A-1745; D-223 to A-1745; H-224 to A-1745; L-225 to A-1745; Y-226 to A-1745; L-227 to A-1745; E-228 to A-1745; T-229 to A-1745; K-230 to A-1745; T-231 to A-1745; L-232 to A-1745; Q-233 to A-1745; G-234 to A-1745; T-235 to A-1745; K-236 to A-1745; G-237 to A-1745; E-238 to A-1745; N-239 to A-1745; S-240 to A-1745; L-241 to A-1745; S-242 to A-1745; S-243 to A-1745; T-244 to A-1745; G-245 to A-1745; T-246 to A-1745; F-247 to A-1745; L-248 to A-1745; V-249 to A-1745; D-250 to A-1745; N-251 to A-1745; S-252 to A-1745; S-253 to A-1745; V-254 to A-1745; D-255 to A-1745; F-256 to A-1745; Q-257 to A-1745; K-258 to A-1745; F-259 to A-1745; P-260 to A-1745; D-261 to A-1745; K-262 to A-1745; E-263 to A-1745; I-264 to A-1745; L-265 to A-1745; R-266 to A-1745; M-267 to A-1745; A-268 to A-1745; G-269 to A-1745; P-270 to A-1745; L-271 to A-1745; T-272 to A-1745; A-273 to A-1745; D-274 to A-1745; F-275 to A-1745; I-276 to A-1745; V-277 to A-1745; K-278 to A-1745; I-279 to A-1745; R-280 to A-1745; N-281 to A-1745; S-282 to A-1745; G-283 to A-1745; S-284 to A-1745; A-285 to A-1745; D-286 to A-1745; S-287 to A-1745; T-288 to A-1745; V-289 to A-1745; Q-290 to A-1745; F-291 to A-1745; I-292 to A-1745; F-293 to A-1745; Y-294 to A-1745; Q-295 to A-1745; P-296 to A-1745; I-297 to A-1745; I-298 to A-1745; H-299 to A-1745; R-300 to A-1745; W-301 to A-1745; R-302 to A-1745; E-303 to A-1745; T-304 to A-1745; D-305 to A-1745; F-306 to A-1745; F-307 to A-1745; P-308 to A-1745; C-309 to A-1745; S-310 to A-1745; A-311 to A-1745; T-312 to A-1745; C-313 to A-1745; G-314 to A-1745; G-315 to A-1745; G-316 to A-1745; Y-317 to A-1745; Q-318 to A-1745; L-319 to A-1745; T-320 to A-1745; S-321 to A-1745; A-322 to A-1745; E-323 to A-1745; C-324 to A-1745; Y-325 to A-1745; D-326 to A-1745; L-327 to A-1745; R-328 to A-1745; S-329 to A-1745; N-330 to A-1745; R-331 to A-1745; V-332 to A-1745; V-333 to A-1745; A-334 to A-1745; D-335 to A-1745; Q-336 to A-1745; Y-337 to A-1745; C-338 to A-1745; H-339 to A-1745; Y-340 to A-1745; Y-341 to A-1745; P-342 to A-1745; E-343 to A-1745; N-344 to A-1745; I-345 to A-1745; K-346 to A-1745; P-347 to A-1745; K-348 to A-1745; P-349 to A-1745; K-350 to A-1745; L-351 to A-1745; Q-352 to A-1745; E-353 to A-1745; C-354 to A-1745; N-355 to A-1745; L-356 to A-1745; D-357 to A-1745; P-358 to A-1745; C-359 to A-1745; P-360 to A-1745; A-361 to A-1745; R-362 to A-1745; W-363 to A-1745; E-364 to A-1745; A-365 to A-1745; T-366 to A-1745; P-367 to A-1745; W-368 to A-1745; T-369 to A-1745; A-370 to A-1745; C-371 to A-1745; S-372 to A-1745; S-373 to A-1745; S-374 to A-1745; C-375 to A-1745; G-376 to A-1745; G-377 to A-1745; G-378 to A-1745; I-379 to A-1745; Q-380 to A-1745; S-381 to A-1745; R-382 to A-1745; A-383 to A-1745; V-384 to A-1745; S-385 to A-1745; C-386 to A-1745; V-387 to A-1745; E-388 to A-1745; E-389 to A-1745; D-390 to A-1745; W-396 to A-1745; Q-392 to A-1745; G-393 to A-1745; H-394 to A-1745; V-395 to A-1745; T-396 to A-1745; S-397 to A-1745; V-398 to A-1745; E-399 to A-1745; E-400 to A-1745; W-401 to A-1745; K-402 to A-1745; C-403 to A-1745; M-404 to A-1745; Y-405 to A-1745; T-406 to A-1745; P-407 to A-1745; K-408 to A-1745; M-409 to A-1745; P-410 to A-1745; I-411 to A-1745; A-412 to A-1745; Q-413 to A-1745; P-414 to A-1745; C-415 to A-1745; N-416 to A-1745; I-417 to A-1745; F-418 to A-1745; D-419 to A-1745; C-420 to A-1745; P-421 to A-1745; K-422 to A-1745; W-423 to A-1745; L-424 to A-1745; A-425 to A-1745; Q-426 to A-1745; Q-427 to A-1745; W-428 to A-1745; S-429 to A-1745; P-430 to A-1745; C-431 to A-1745; T-432 to A-1745; V-433 to A-1745; T-434 to A-1745; C-435 to A-1745; G-436 to A-1745; Q-437 to A-1745; G-438 to A-1745; L-439 to A-1745; R-440 to A-1745; Y-441 to A-1745; R-442 to A-1745; V-443 to A-1745; V-444 to A-1745; L-445 to A-1745; C-446 to A-1745; I-447 to A-1745; D-448 to A-1745; H-449 to A-1745; R-450 to A-1745; G-451 to A-1745; M-452 to A-1745; H-453 to A-1745; T-454 to A-1745; G-455 to A-1745; G-456 to A-1745; C-457 to A-1745; S-458 to A-1745; P-459 to A-1745; K-460 to A-1745; T-461 to A-1745; K-462 to A-1745; P-463 to A-1745; H-464 to A-1745; I-465 to A-1745; K-466 to A-1745; E-467 to A-1745; E-468 to A-1745; C-469 to A-1745; I-470 to A-1745; V-471 to A-1745; P-472 to A-1745; T-473 to A-1745; P-474 to A-1745; C-475 to A-1745; Y-476 to A-1745; K-477 to A-1745; P-478 to A-1745; K-479 to A-1745; E-480 to A-1745; K-481 to A-1745; L-482 to A-1745; P-483 to A-1745; V-484 to A-1745; E-485 to A-1745; A-486 to A-1745; K-487 to A-1745; L-488 to A-1745; P-489 to A-1745; W-490 to A-1745; F-491 to A-1745; K-492 to A-1745; Q-493 to A-1745; A-494 to A-1745; Q-495 to A-1745; E-496 to A-1745; L-497 to A-1745; E-498 to A-1745; E-499 to A-1745; G-500 to A-1745; A-501 to A-1745; A-502 to A-1745; V-503 to A-1745; S-504 to A-1745; E-505 to A-1745; E-506 to A-1745; P-507 to A-1745; S-508 to A-1745; F-509 to A-1745; I-510 to A-1745; P-511 to A-1745; K-512 to A-1745; A-513 to A-1745; W-514 to A-1745; S-515 to A-1745; A-516 to A-1745; C-517 to A-1745; T-518 to A-1745; V-519 to A-1745; T-520 to A-1745; C-521 to A-1745; G-522 to A-1745; V-523 to A-1745; G-524 to A-1745; T-525 to A-1745; Q-526 to A-1745; V-527 to A-1745; R-528 to A-1745; I-529 to A-1745; V-530 to A-1745; R-531 to A-1745; C-532 to A-1745; Q-533 to A-1745; V-534 to A-1745; L-535 to A-1745; L-536 to A-1745; S-537 to A-1745; F-538 to A-1745; S-539 to A-1745; Q-540 to A-1745; S-541 to A-1745; V-542 to A-1745; A-543 to A-1745; D-544 to A-1745; L-545 to A-1745; P-546 to A-1745; I-547 to A-1745; D-548 to A-1745; E-549 to A-1745; C-550 to A-1745; E-551 to A-1745; G-552 to A-1745; P-553 to A-1745; K-554 to A-1745; P-555 to A-1745; A-556 to A-1745; S-557 to A-1745; Q-558 to A-1745; R-559 to A-1745; A-560 to A-1745; C-561 to A-1745; Y-562 to A-1745; A-563 to A-1745; G-564 to A-1745; P-565 to A-1745; C-566 to A-1745; S-567 to A-1745; G-568 to A-1745; E-569 to A-1745; I-570 to A-1745; P-571 to A-1745; E-572 to A-1745; F-573 to A-1745; N-574 to A-1745; P-575 to A-1745; D-576 to A-1745; E-577 to A-1745; T-578 to A-1745; D-579 to A-1745; G-580 to A-1745; L-581 to A-1745; F-582 to A-1745; G-583 to A-1745; G-584 to A-1745; L-585 to A-1745; Q-586 to A-1745; D-587 to A-1745; F-588 to A-1745; D-589 to A-1745; E-590 to A-1745; L-591 to A-1745; Y-592 to A-1745; D-593 to A-1745; W-594 to A-1745; E-595 to A-1745; Y-596 to A-1745; E-597 to A-1745; G-598 to A-1745; F-599 to A-1745; T-600 to A-1745; K-601 to A-1745; C-602 to A-1745; S-603 to A-1745; E-604 to A-1745; S-605 to A-1745; C-606 to A-1745; G-607 to A-1745; G-608 to A-1745; G-609 to A-1745; V-610 to A-1745; Q-611 to A-1745; E-612 to A-1745; A-613 to A-1745; V-614 to A-1745; V-615 to A-1745; S-616 to A-1745; C-617 to A-1745; L-618 to A-1745; N-619 to A-1745; K-620 to A-1745; Q-621 to A-1745; T-622 to A-1745; R-623 to A-1745; E-624 to A-1745; P-625 to A-1745; A-626 to A-1745; E-627 to A-1745; E-628 to A-1745; N-629 to A-1745; L-630 to A-1745; C-631 to A-1745; V-632 to A-1745; T-633 to A-1745; S-634 to A-1745; R-635 to A-1745; R-636 to A-1745; P-637 to A-1745; P-638 to A-1745; Q-639 to A-1745; L-640 to A-1745; L-641 to A-1745; K-642 to A-1745; S-643 to A-1745; C-644 to A-1745; N-645 to A-1745; L-646 to A-1745; D-647 to A-1745; P-648 to A-1745; C-649 to A-1745; P-650 to A-1745; A-651 to A-1745; R-652 to A-1745; W-653 to A-1745; E-654 to A-1745; I-655 to A-1745; G-656 to A-1745; K-657 to A-1745; W-658 to A-1745; S-659 to A-1745; P-660 to A-1745; C-661 to A-1745; S-662 to A-1745; L-663 to A-1745; T-664 to A-1745; C-665 to A-1745; G-666 to A-1745; V-667 to A-1745; G-668 to A-1745; L-669 to A-1745; Q-670 to A-1745; T-671 to A-1745; R-672 to A-1745; D-673 to A-1745; V-674 to A-1745; F-675 to A-1745; C-676 to A-1745; S-677 to A-1745; H-678 to A-1745; L-679 to A-1745; L-680 to A-1745; S-681 to A-1745; R-682 to A-1745; E-683 to A-1745; M-684 to A-1745; N-685 to A-1745; E-686 to A-1745; T-687 to A-1745; V-688 to A-1745; I-689 to A-1745; L-690 to A-1745; A-691 to A-1745; D-692 to A-1745; E-693 to A-1745; L-694 to A-1745; C-695 to A-1745; R-696 to A-1745; Q-697 to A-1745; P-698 to A-1745; K-699 to A-1745; P-700 to A-1745; S-701 to A-1745; T-702 to A-1745; V-703 to A-1745; Q-704 to A-1745; A-705 to A-1745; C-706 to A-1745; N-707 to A-1745; R-708 to A-1745; F-709 to A-1745; N-710 to A-1745; C-711 to A-1745; P-712 to A-1745; P-713 to A-1745; A-714 to A-1745; W-715 to A-1745; Y-716 to A-1745; P-717 to A-1745; A-718 to A-1745; Q-719 to A-1745; W-720 to A-1745; Q-721 to A-1745; P-722 to A-1745; C-723 to A-1745; S-724 to A-1745; R-725 to A-1745; T-726 to A-1745; C-727 to A-1745; G-728 to A-1745; G-729 to A-1745; G-730 to A-1745; V-731 to A-1745; Q-732 to A-1745; K-733 to A-1745; R-734 to A-1745; E-735 to A-1745; V-736 to A-1745; L-737 to A-1745; C-738 to A-1745; K-739 to A-1745; Q-740 to A-1745; R-741 to A-1745; M-742 to A-1745; A-743 to A-1745; D-744 to A-1745; G-745 to A-1745; S-746 to A-1745; F-747 to A-1745; L-748 to A-1745; E-749 to A-1745; L-750 to A-1745; P-751 to A-1745; E-752 to A-1745; T-753 to A-1745; F-754 to A-1745; C-755 to A-1745; S-756 to A-1745; A-757 to A-1745; S-758 to A-1745; K-759 to A-1745; P-760 to A-1745; A-761 to A-1745; C-762 to A-1745; Q-763 to A-1745; Q-764 to A-1745; A-765 to A-1745; C-766 to A-1745; K-767 to A-1745; K-768 to A-1745; D-769 to A-1745; D-770 to A-1745; C-771 to A-1745; P-772 to A-1745; S-773 to A-1745; E-774 to A-1745; W-775 to A-1745; L-776 to A-1745; L-777 to A-1745; S-778 to A-1745; D-779 to A-1745; W-780 to A-1745; T-781 to A-1745; E-782 to A-1745; C-783 to A-1745; S-784 to A-1745; T-785 to A-1745; S-786 to A-1745; C-787 to A-1745; G-788 to A-1745; E-789 to A-1745; G-790 to A-1745; T-791 to A-1745; Q-792 to A-1745; T-793 to A-1745; R-794 to A-1745; S-795 to A-1745; A-796 to A-1745; I-797 to A-1745; C-798 to A-1745; R-799 to A-1745; K-800 to A-1745; M-801 to A-1745; L-802 to A-1745; K-803 to A-1745; T-804 to A-1745; G-805 to A-1745; L-806 to A-1745; S-807 to A-1745; T-808 to A-1745; V-809 to A-1745; V-810 to A-1745; N-811 to A-1745; S-812 to A-1745; T-813 to A-1745; L-814 to A-1745; C-815 to A-1745; P-816 to A-1745; P-817 to A-1745; L-818 to A-1745; P-819 to A-1745; F-820 to A-1745; S-821 to A-1745; S-822 to A-1745; S-823 to A-1745; I-824 to A-1745; R-825 to A-1745; P-826 to A-1745; C-827 to A-1745; M-828 to A-1745; L-829 to A-1745; A-830 to A-1745; T-831 to A-1745; C-832 to A-1745; A-833 to A-1745; R-834 to A-1745; P-835 to A-1745; G-836 to A-1745; R-837 to A-1745; P-838 to A-1745; S-839 to A-1745; T-840 to A-1745; K-841 to A-1745; H-842 to A-1745; S-843 to A-1745; P-844 to A-1745; H-845 to A-1745; I-846 to A-1745; A-847 to A-1745; A-848 to A-1745; A-849 to A-1745; R-850 to A-1745; K-851 to A-1745; V-852 to A-1745; Y-853 to A-1745; I-854 to A-1745; Q-855 to A-1745; T-856 to A-1745; R-857 to A-1745; R-858 to A-1745; Q-859 to A-1745; R-860 to A-1745; K-861 to A-1745; L-862 to A-1745; H-863 to A-1745; F-864 to A-1745; V-865 to A-1745; V-866 to A-1745; G-867 to A-1745; G-868 to A-1745; F-869 to A-1745; A-870 to A-1745; Y-871 to A-1745; L-872 to A-1745; L-873 to A-1745; P-874 to A-1745; K-875 to A-1745; T-876 to A-1745; A-877 to A-1745; V-878 to A-1745; V-879 to A-1745; L-880 to A-1745; R-881 to A-1745; C-882 to A-1745; P-883 to A-1745; A-884 to A-1745; R-885 to A-1745; R-886 to A-1745; V-887 to A-1745; R-888 to A-1745; K-889 to A-1745; P-890 to A-1745; L-891 to A-1745; I-892 to A-1745; T-893 to A-1745; W-894 to A-1745; E-895 to A-1745; K-896 to A-1745; D-897 to A-1745; G-898 to A-1745; Q-899 to A-1745; H-900 to A-1745; L-901 to A-1745; I-902 to A-1745; S-903 to A-1745; S-904 to A-1745; T-905 to A-1745; H-906 to A-1745; V-907 to A-1745; T-908 to A-1745; V-909 to A-1745; A-910 to A-1745; P-911 to A-1745; F-912 to A-1745; G-913 to A-1745; Y-914 to A-1745; L-915 to A-1745; K-916 to A-1745; I-917 to A-1745; H-918 to A-1745; R-919 to A-1745; L-920 to A-1745; K-921 to A-1745; P-922 to A-1745; S-923 to A-1745; D-924 to A-1745; A-925 to A-1745; G-926 to A-1745; V-927 to A-1745; Y-928 to A-1745; T-929 to A-1745; C-930 to A-1745; S-931 to A-1745; A-932 to A-1745; G-933 to A-1745; P-934 to A-1745; A-935 to A-1745; R-936 to A-1745; E-937 to A-1745; H-938 to A-1745; F-939 to A-1745; V-940 to A-1745; I-941 to A-1745; K-942 to A-1745; L-943 to A-1745; I-944 to A-1745; G-945 to A-1745; G-946 to A-1745; N-947 to A-1745; R-948 to A-1745; K-949 to A-1745; L-950 to A-1745; V-951 to A-1745; A-952 to A-1745; R-953 to A-1745; P-954 to A-1745; L-955 to A-1745; S-956 to A-1745; P-957 to A-1745; R-958 to A-1745; S-959 to A-1745; E-960 to A-1745; E-961 to A-1745; E-962 to A-1745; V-963 to A-1745; L-964 to A-1745; A-965 to A-1745; G-966 to A-1745; R-967 to A-1745; K-968 to A-1745; G-969 to A-1745; G-970 to A-1745; P-971 to A-1745; K-972 to A-1745; E-973 to A-1745; A-974 to A-1745; L-975 to A-1745; Q-976 to A-1745; T-977 to A-1745; H-978 to A-1745; K-979 to A-1745; H-980 to A-1745; Q-981 to A-1745; N-982 to A-1745; G-983 to A-1745; I-984 to A-1745; F-985 to A-1745; S-986 to A-1745; N-987 to A-1745; G-988 to A-1745; S-989 to A-1745; K-990 to A-1745; A-991 to A-1745; E-992 to A-1745; K-993 to A-1745; R-994 to A-1745; G-995 to A-1745; L-996 to A-1745; A-997 to A-1745; A-998 to A-1745; N-999 to A-1745; P-1000 to A-1745; G-1001 to A-1745; S-1002 to A-1745; R-1003 to A-1745; Y-1004 to A-1745; D-1005 to A-1745; D-1006 to A-1745; L-1007 to A-1745; V-1008 to A-1745; S-1009 to A-1745; R-1010 to A-1745; L-1011 to A-1745; L-1012 to A-1745; E-1013 to A-1745; Q-1014 to A-1745; G-1015 to A-1745; G-1016 to A-1745; W-1017 to A-1745; P-1018 to A-1745; G-1019 to A-1745; E-1020 to A-1745; L-1021 to A-1745; L-1022 to A-1745; A-1023 to A-1745; S-1024 to A-1745; W-1025 to A-1745; E-1026 to A-1745; A-1027 to A-1745; Q-1028 to A-1745; D-1029 to A-1745; S-1030 to A-1745; A-1031 to A-1745; E-1032 to A-1745; R-1033 to A-1745; N-1034 to A-1745; T-1035 to A-1745; T-1036 to A-1745; S-1037 to A-1745; E-1038 to A-1745; E-1039 to A-1745; D-1040 to A-1745; P-1041 to A-1745; G-1042 to A-1745; A-1043 to A-1745; E-1044 to A-1745; Q-1045 to A-1745; V-1046 to A-1745; L-1047 to A-1745; L-1048 to A-1745; H-1049 to A-1745; L-1050 to A-1745; P-1051 to A-1745; F-1052 to A-1745; T-1053 to A-1745; M-1054 to A-1745; V-1055 to A-1745; T-1056 to A-1745; E-1057 to A-1745; Q-1058 to A-1745; R-1059 to A-1745; R-1060 to A-1745; L-1061 to A-1745; D-1062 to A-1745; D-1063 to A-1745; I-1064 to A-1745; L-1065 to A-1745; G-1066 to A-1745; N-1067 to A-1745; L-1068 to A-1745; S-1069 to A-1745; Q-1070 to A-1745; Q-1071 to A-1745; P-1072 to A-1745; E-1073 to A-1745; E-1074 to A-1745; L-1075 to A-1745; R-1076 to A-1745; D-1077 to A-1745; L-1078 to A-1745; Y-1079 to A-1745; S-1080 to A-1745; K-1081 to A-1745; H-1082 to A-1745; L-1083 to A-1745; V-1084 to A-1745; A-1085 to A-1745; Q-1086 to A-1745; L-1087 to A-1745; A-1088 to A-1745; Q-1089 to A-1745; E-1090 to A-1745; I-1091 to A-1745; F-1092 to A-1745; R-1093 to A-1745; S-1094 to A-1745; H-1095 to A-1745; L-1096 to A-1745; E-1097 to A-1745; H-1098 to A-1745; Q-1099 to A-1745; D-1100 to A-1745; T-1101 to A-1745; L-1102 to A-1745; L-1103 to A-1745; K-1104 to A-1745; P-1105 to A-1745; S-1106 to A-1745; E-1107 to A-1745; R-1108 to A-1745; R-1109 to A-1745; T-1110 to A-1745; S-1111 to A-1745; P-1112 to A-1745; V-1113 to A-1745; T-1114 to A-1745; L-1115 to A-1745; S-1116 to A-1745; P-1117 to A-1745; H-1118 to A-1745; K-1119 to A-1745; H-1120 to A-1745; V-1121 to A-1745; S-1122 to A-1745; G-1123 to A-1745; F-1124 to A-1745; S-1125 to A-1745; S-1126 to A-1745; S-1127 to A-1745; L-1128 to A-1745; R-1129 to A-1745; T-1130 to A-1745; S-1131 to A-1745; S-1132 to A-1745; T-1133 to A-1745; G-1134 to A-1745; D-1135 to A-1745; A-1136 to A-1745; G-1137 to A-1745; G-1138 to A-1745; G-1139 to A-1745; S-1140 to A-1745; R-1141 to A-1745; R-1142 to A-1745; P-1143 to A-1745; H-1144 to A-1745; R-1145 to A-1745; K-1146 to A-1745; P-1147 to A-1745; T-1148 to A-1745; I-1149 to A-1745; L-1150 to A-1745; R-1151 to A-1745; K-1152 to A-1745; I-1153 to A-1745; S-1154 to A-1745; A-1155 to A-1745; A-1156 to A-1745; Q-1157 to A-1745; Q-1158 to A-1745; L-1159 to A-1745; S-1160 to A-1745; A-1161 to A-1745; S-1162 to A-1745; E-1163 to A-1745; V-1164 to A-1745; V-1165 to A-1745; T-1166 to A-1745; H-1167 to A-1745; L-1168 to A-1745; G-1169 to A-1745; Q-1170 to A-1745; T-1171 to A-1745; V-1172 to A-1745; A-1173 to A-1745; L-1174 to A-1745; A-1175 to A-1745; S-1176 to A-1745; G-1177 to A-1745; T-1178 to A-1745; L-1179 to A-1745; S-1180 to A-1745; V-1181 to A-1745; L-1182 to A-1745; L-1183 to A-1745; H-1184 to A-1745; C-1185 to A-1745; E-1186 to A-1745; A-1187 to A-1745; I-1188 to A-1745; G-1189 to A-1745; H-1190 to A-1745; P-1191 to A-1745; R-1192 to A-1745; P-1193 to A-1745; T-1194 to A-1745; I-1195 to A-1745; S-1196 to A-1745; W-1197 to A-1745; A-1198 to A-1745; R-1199 to A-1745; N-1200 to A-1745; G-1201 to A-1745; E-1202 to A-1745; E-1203 to A-1745; V-1204 to A-1745; Q-1205 to A-1745; F-1206 to A-1745; S-1207 to A-1745; D-1208 to A-1745; R-1209 to A-1745; I-1210 to A-1745; L-1211 to A-1745; L-1212 to A-1745; Q-1213 to A-1745; P-1214 to A-1745; D-1215 to A-1745; D-1216 to A-1745; S-1217 to A-1745; L-1218 to A-1745; Q-1219 to A-1745; I-1220 to A-1745; L-1221 to A-1745; A-1222 to A-1745; P-1223 to A-1745; V-1224 to A-1745; E-1225 to A-1745; A-1226 to A-1745; D-1227 to A-1745; V-1228 to A-1745; G-1229 to A-1745; F-1230 to A-1745; Y-1231 to A-1745; T-1232 to A-1745; C-1233 to A-1745; N-1234 to A-1745; A-1235 to A-1745; T-1236 to A-1745; N-1237 to A-1745; A-1238 to A-1745; L-1239 to A-1745; G-1240 to A-1745; Y-1241 to A-1745; D-1242 to A-1745; S-1243 to A-1745; V-1244 to A-1745; S-1245 to A-1745; I-1246 to A-1745; A-1247 to A-1745; V-1248 to A-1745; T-1249 to A-1745; L-1250 to A-1745; A-1251 to A-1745; G-1252 to A-1745; K-1253 to A-1745; P-1254 to A-1745; L-1255 to A-1745; V-1256 to A-1745; K-1257 to A-1745; T-1258 to A-1745; S-1259 to A-1745; R-1260 to A-1745; M-1261 to A-1745; T-1262 to A-1745; V-1263 to A-1745; I-1264 to A-1745; N-1265 to A-1745; T-1266 to A-1745; E-1267 to A-1745; K-1268 to A-1745; P-1269 to A-1745; A-1270 to A-1745; V-1271 to A-1745; T-1272 to A-1745; V-1273 to A-1745; D-1274 to A-1745; I-1275 to A-1745; G-1276 to A-1745; S-1277 to A-1745; T-1278 to A-1745; I-1279 to A-1745; K-1280 to A-1745; T-1281 to A-1745; V-1282 to A-1745; Q-1283 to A-1745; G-1284 to A-1745; V-1285 to A-1745; N-1286 to A-1745; V-1287 to A-1745; T-1288 to A-1745; I-1289 to A-1745; N-1290 to A-1745; C-1291 to A-1745; Q-1292 to A-1745; V-1293 to A-1745; A-1294 to A-1745; G-1295 to A-1745; V-1296 to A-1745; P-1297 to A-1745; E-1298 to A-1745; A-1299 to A-1745; E-1300 to A-1745; V-1301 to A-1745; T-1302 to A-1745; W-1303 to A-1745; F-1304 to A-1745; R-1305 to A-1745; N-1306 to A-1745; K-1307 to A-1745; S-1308 to A-1745; K-1309 to A-1745; L-1310 to A-1745; G-1311 to A-1745; S-1312 to A-1745; P-1313 to A-1745; H-1314 to A-1745; H-1315 to A-1745; L-1316 to A-1745; H-1317 to A-1745; E-1318 to A-1745; G-1319 to A-1745; S-1320 to A-1745; L-1321 to A-1745; L-1322 to A-1745; L-1323 to A-1745; T-1324 to A-1745; N-1325 to A-1745; V-1326 to A-1745; S-1327 to A-1745; S-1328 to A-1745; S-1329 to A-1745; D-1330 to A-1745; Q-1331 to A-1745; G-1332 to A-1745; L-1333 to A-1745; Y-1334 to A-1745; S-1335 to A-1745; C-1336 to A-1745; R-1337 to A-1745; A-1338 to A-1745; A-1339 to A-1745; N-1340 to A-1745; L-1341 to A-1745; H-1342 to A-1745; G-1343 to A-1745; E-1344 to A-1745; L-1345 to A-1745; T-1346 to A-1745; E-1347 to A-1745; S-1348 to A-1745; T-1349 to A-1745; Q-1350 to A-1745; L-1351 to A-1745; L-1352 to A-1745; I-1353 to A-1745; L-1354 to A-1745; D-1355 to A-1745; P-1356 to A-1745; P-1357 to A-1745; Q-1358 to A-1745; V-1359 to A-1745; P-1360 to A-1745; T-1361 to A-1745; Q-1362 to A-1745; L-1363 to A-1745; E-1364 to A-1745; D-1365 to A-1745; I-1366 to A-1745; R-1367 to A-1745; A-1368 to A-1745; L-1369 to A-1745; L-1370 to A-1745; A-1371 to A-1745; A-1372 to A-1745; T-1373 to A-1745; G-1374 to A-1745; P-1375 to A-1745; N-1376 to A-1745; L-1377 to A-1745; P-1378 to A-1745; S-1379 to A-1745; V-1380 to A-1745; L-1381 to A-1745; T-1382 to A-1745; S-1383 to A-1745; P-1384 to A-1745; L-1385 to A-1745; G-1386 to A-1745; T-1387 to A-1745; Q-1388 to A-1745; L-1389 to A-1745; V-1390 to A-1745; L-1391 to A-1745; D-1392 to A-1745; P-1393 to A-1745; G-1394 to A-1745; N-1395 to A-1745; S-1396 to A-1745; A-1397 to A-1745; L-1398 to A-1745; L-1399 to A-1745; G-1400 to A-1745; C-1401 to A-1745; P-1402 to A-1745; I-1403 to A-1745; K-1404 to A-1745; G-1405 to A-1745; H-1406 to A-1745; P-1407 to A-1745; V-1408 to A-1745; P-1409 to A-1745; N-1410 to A-1745; I-1411 to A-1745; T-1412 to A-1745; W-1413 to A-1745; F-1414 to A-1745; H-1415 to A-1745; G-1416 to A-1745; G-1417 to A-1745; Q-1418 to A-1745; P-1419 to A-1745; I-1420 to A-1745; V-1421 to A-1745; T-1422 to A-1745; A-1423 to A-1745; T-1424 to A-1745; G-1425 to A-1745; L-1426 to A-1745; T-1427 to A-1745; H-1428 to A-1745; H-1429 to A-1745; I-1430 to A-1745; L-1431 to A-1745; A-1432 to A-1745; A-1433 to A-1745; G-1434 to A-1745; Q-1435 to A-1745; I-1436 to A-1745; L-1437 to A-1745; Q-1438 to A-1745; V-1439 to A-1745; A-1440 to A-1745; N-1441 to A-1745; L-1442 to A-1745; S-1443 to A-1745; G-1444 to A-1745; G-1445 to A-1745; S-1446 to A-1745; Q-1447 to A-1745; G-1448 to A-1745; E-1449 to A-1745; F-1450 to A-1745; S-1451 to A-1745; C-1452 to A-1745; L-1453 to A-1745; A-1454 to A-1745; Q-1455 to A-1745; N-1456 to A-1745; E-1457 to A-1745; A-1458 to A-1745; G-1459 to A-1745; V-1460 to A-1745; L-1461 to A-1745; M-1462 to A-1745; Q-1463 to A-1745; K-1464 to A-1745; A-1465 to A-1745; S-1466 to A-1745; L-1467 to A-1745; V-1468 to A-1745; I-1469 to A-1745; Q-1470 to A-1745; D-1471 to A-1745; Y-1472 to A-1745; W-1473 to A-1745; W-1474 to A-1745; S-1475 to A-1745; V-1476 to A-1745; D-1477 to A-1745; R-1478 to A-1745; L-1479 to A-1745; A-1480 to A-1745; T-1481 to A-1745; C-1482 to A-1745; S-1483 to A-1745; A-1484 to A-1745; S-1485 to A-1745; C-1486 to A-1745; G-1487 to A-1745; N-1488 to A-1745; R-1489 to A-1745; G-1490 to A-1745; V-1491 to A-1745; Q-1492 to A-1745; Q-1493 to A-1745; P-1494 to A-1745; R-1495 to A-1745; L-1496 to A-1745; R-1497 to A-1745; C-1498 to A-1745; L-1499 to A-1745; L-1500 to A-1745; N-1501 to A-1745; S-1502 to A-1745; T-1503 to A-1745; E-1504 to A-1745; V-1505 to A-1745; N-1506 to A-1745; P-1507 to A-1745; A-1508 to A-1745; H-1509 to A-1745; C-1510 to A-1745; A-1511 to A-1745; G-1512 to A-1745; K-1513 to A-1745; V-1514 to A-1745; R-1515 to A-1745; P-1516 to A-1745; A-1517 to A-1745; V-1518 to A-1745; Q-1519 to A-1745; P-1520 to A-1745; I-1521 to A-1745; A-1522 to A-1745; C-1523 to A-1745; N-1524 to A-1745; R-1525 to A-1745; R-1526 to A-1745; D-1527 to A-1745; C-1528 to A-1745; P-1529 to A-1745; S-1530 to A-1745; R-1531 to A-1745; W-1532 to A-1745; M-1533 to A-1745; V-1534 to A-1745; T-1535 to A-1745; S-1536 to A-1745; W-1537 to A-1745; S-1538 to A-1745; A-1539 to A-1745; C-1540 to A-1745; T-1541 to A-1745; R-1542 to A-1745; S-1543 to A-1745; C-1544 to A-1745; G-1545 to A-1745; G-1546 to A-1745; G-1547 to A-1745; V-1548 to A-1745; Q-1549 to A-1745; T-1550 to A-1745; R-1551 to A-1745; R-1552 to A-1745; V-1553 to A-1745; T-1554 to A-1745; C-1555 to A-1745; Q-1556 to A-1745; K-1557 to A-1745; L-1558 to A-1745; K-1559 to A-1745; A-1560 to A-1745; S-1536 to A-1745; G-1562 to A-1745; I-1563 to A-1745; S-1564 to A-1745; T-1565 to A-1745; P-1566 to A-1745; V-1567 to A-1745; S-1568 to A-1745; N-1569 to A-1745; D-1570 to A-1745; M-1571 to A-1745; C-1572 to A-1745; T-1573 to A-1745; Q-1574 to A-1745; V-1575 to A-1745; A-1576 to A-1745; K-1577 to A-1745; R-1578 to A-1745; P-15579 to A-1745; V-1580 to A-1745; D-1581 to A-1745; T-1582 to A-1745; Q-1583 to A-1745; A-1584 to A-1745; C-1585 to A-1745; N-1586 to A-1745; Q-1587 to A-1745; Q-1588 to A-1745; L-1589 to A-1745; C-1590 to A-1745; V-1591 to A-1745; E-1592 to A-1745; W-1593 to A-1745; A-1594 to A-1745; F-1595 to A-1745; S-1596 to A-1745; S-1597 to A-1745; W-1598 to A-1745; G-1599 to A-1745; Q-1600 to A-1745; C-1601 to A-1745; N-1602 to A-1745; G-1603 to A-1745; P-1604 to A-1745; C-1605 to A-1745; I-1606 to A-1745; G-1607 to A-1745; P-1608 to A-1745; H-1609 to A-1745; L-1610 to A-1745; A-1611 to A-1745; V-1612 to A-1745; Q-1613 to A-1745; H-1614 to A-1745; R-1615 to A-1745; Q-1616 to A-1745; V-1617 to A-1745; F-1618 to A-1745; C-1619 to A-1745; Q-1620 to A-1745; T-1621 to A-1745; R-1622 to A-1745; D-1623 to A-1745; G-1624 to A-1745; I-1625 to A-1745; T-1626 to A-1745; L-1627 to A-1745; P-1628 to A-1745; S-1629 to A-1745; E-1630 to A-1745; Q-1631 to A-1745; C-1632 to A-1745; S-1633 to A-1745; A-1634 to A-1745; L-1635 to A-1745; P-1636 to A-1745; R-1637 to A-1745; P-1638 to A-1745; V-1639 to A-1745; S-1640 to A-1745; T-1641 to A-1745; Q-1642 to A-1745; N-1643 to A-1745; C-1644 to A-1745; W-1645 to A-1745; S-1646 to A-1745; E-1647 to A-1745; A-1648 to A-1745; C-1649 to A-1745; S-1650 to A-1745; V-1651 to A-1745; H-1652 to A-1745; W-1653 to A-1745; R-1654 to A-1745; V-1655 to A-1745; S-1656 to A-1745; L-1644 to A-1745; W-1658 to A-1745; T-1659 to A-1745; L-1660 to A-1745; C-1661 to A-1745; T-1662 to A-1745; A-1663 to A-1745; T-1664 to A-1745; C-1665 to A-1745; G-1666 to A-1745; N-1667 to A-1745; Y-1668 to A-1745; G-1669 to A-1745; F-1670 to A-1745; Q-1671 to A-1745; S-1672 to A-1745; R-1673 to A-1745; R-1674 to A-1745; V-1675 to A-1745; E-1676 to A-1745; C-1677 to A-1745; V-1678 to A-1745; H-1679 to A-1745; A-1680 to A-1745; R-1681 to A-1745; T-1682 to A-1745; N-1683 to A-1745; K-16684 to A-1745; A-1685 to A-1745; V-1686 to A-1745; P-1687 to A-1745; E-1688 to A-1745; H-1689 to A-1745; L-1690 to A-1745; C-1691 to A-1745; S-1692 to A-1745; W-1693 to A-1745; G-1694 to A-1745; P-1695 to A-1745; R-1696 to A-1745; P-1697 to A-1745; A-1698 to A-1745; N-1699 to A-1745; W-1700 to A-1745; Q-9701 to A-1745; R-1702 to A-1745; C-1703 to A-1745; N-1704 to A-1745; N-1705 to A-1745; T-1706 to A-1745; P-1707 to A-1745; C-1708 to A-1745; E-1709 to A-1745; N-1710 to A-1745; M-1711 to A-1745; E-1712 to A-1745; C-1713 to A-1745; R-1714 to A-1745; D-1715 to A-1745; T-1716 to A-1745; T-1717 to A-1745; R-1718 to A-1745; Y-1719 to A-1745; C-1720 to A-1745; E-1721 to A-1745; K-1722 to A-1745; V-1723 to A-1745; K-1724 to A-1745; Q-1725 to A-1745; L-1726 to A-1745; K-1727 to A-1745; L-1728 to A-1745; C-1729 to A-1745; Q-1730 to A-1745; L-1731 to A-1745; S-1732 to A-1745; Q-1733 to A-1745; F-1734 to A-1745; K-1735 to A-1745; S-1736 to A-1745; R-1737 to A-1745; C-1738 to A-1745; C-1739 to A-1745; and G-1740 to A-1745 of SEQ ID NO: 89. Polypeptides encoded by these polynucleotides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that bind polypeptides of the invention are also encompassed by the invention. Polynucleotides encoding these polypeptides are also encompassed by the invention.

The present invention further provides polypeptides having one or more residues deleted from the carboxy terminus of the amino acid sequence of the THRAP polypeptide shown in FIGS. 4A–4H (SEQ ID NO:89), as described by the general formula 1–n, where n is an integer from 6 to 1745 where n corresponds to the position of amino acid residue identified in SEQ ID NO:89. More in particular, the invention provides polynucleotides encoding polypeptides comprising, or alternatively consisting of, an amino acid sequence selected from the group: E-29 to K-1744; E-29 to G-1743; E-29 to C-1742; E-29 to T-1741; E-29 to G-1740; E-29 to C-1739; E-29 to C-1738; E-29 to R-1737; E-29 to S-1736; E-29 to K-1735; E-29 to F-1734; E-29 to Q-1733; E-29 to S-1732; E-29 to L-1731; E-29 to Q-1730; E-29 to C-1729; E-29 to L-1728; E-29 to K-1727; E-29 to L-1726; E-29 to Q-1725; E-29 to K-1724; E-29 to V-1723; E-29 to K-1722; E-29 to E-1721; E-29 to C-1720; E-29 to Y-1719; E-29 to R-1718; E-29 to T-1717; E-29 to T-1716; E-29 to D-1715; E-29 to R-1714; E-29 to C-1713; E-29 to E-1712; E-29 to E-29711; E-29 to N-1710; E-29 to E-1709; E-29 to C-1708; E-29 to P-1707; E-29 to T-1706; E-29 to I-1705; E-29 to N-1704; E-29 to C-1703; E-29 to R-1702; E-29 to Q-1701; E-29 to W-1700; E-29 to N-1699; E-29 to A-1698; E-29 to P-1697; E-29 to R-1696; E-29 to P-1695; E-29 to G-1694; E-29 to W-1693; E-29 to S-1692; E-29 to C-1691; E-29 to L-1690; E-29 to H-1689; E-29 to E-1688; E-29 to P-1687; E-29 to V-1686; E-29 to A-1685; E-29 to K-1684; E-29 to N-1683; E-29 to T-1682; E-29 to R-1681; E-29 to A-1680; E-29 to H-1679; E-29 to V-1678; E-29 to C-1677; E-29 to E-1676; E-29 to V-1675; E-29 to R-1674; E-29 to R-1673; E-29 to S-1672; E-29 to Q-1671; E-29 to F-1670; E-29 to G-1669; E-29 to Y-1668; E-29 to N-1667; E-29 to G-1666; E-29 to C-1665; E-29 to T-1664; E-29 to A-1663; E-29 to T-1662; E-29 to C-1661; E-29 to L-1660; E-29 to T-1659; E-29 to W-1658; E-29 to L-1657; E-29 to S-1656; E-29 to V-1655; E-29 to R-1654; E-29 to W-1653; E-29 to H-1652; E-29 to V-1651; E-29 to S-1650; E-29 to C-1649; E-29 to A-1648; E-29 to E-1647; E-29 to S-1646; E-29 to W-1645; E-29 to C-1644; E-29 to N-1643; E-29 to Q-1642; E-29 to T-1641; E-29 to S-1640; E-29 to V-1639; E-29 to P-1638; E-29 to R-1637; E-29 to P-1636; E-29 to L-1635; E-29 to A-1634; E-29 to S-1633; E-29 to C-1632; E-29 to Q-1631; E-29 to E-1630; E-29 to S-1629; E-29 to P-1628;

E-29 to L-1627; E-29 to T-1626; E-29 to I-1625; E-29 to G-1624; E-29 to D-1623; E-29 to R-1622; E-29 to T-1621; E-29 to Q-1620; E-29 to C-1619; E-29 to F-1618; E-29 to V-1617; E-29 to Q-1616; E-29 to R-1615; E-29 to H-1614; E-29 to Q-1613; E-29 to V-1612; E-29 to A-1611; E-29 to L-1610; E-29 to H-1609; E-29 to P-1608; E-29 to G-1607; E-29 to I-1606; E-29 to C-1605; E-29 to P-1604; E-29 to G-1603; E-29 to N-1602; E-29 to C-1601; E-29 to Q-1600; E-29 to G-1599; E-29 to W-1598; E-29 to S-1597; E-29 to S-1596; E-29 to F-1595; E-29 to A-1594; E-29 to W-1593; E-29 to E-1592; E-29 to V-1591; E-29 to C-1590; E-29 to L-1589; E-29 to Q-1588; E-29 to Q-1587; E-29 to N-1586; E-29 to C-1585; E-29 to A-1584; E-29 to Q-1583; E-29 to T-1582; E-29 to D-1581; E-29 to V-1580; E-29 to P-1579; E-29 to R-1578; E-29 to K-1577; E-29 to A-1576; E-29 to V-1575; E-29 to Q-1574; E-29 to T-1573; E-29 to C-1572; E-29 to E-29571; E-29 to D-1570; E-29 to N-1569; E-29 to S-1568; E-29 to V-1567; E-29 to P-1566; E-29 to T-1565; E-29 to S-1564; E-29 to I-1563; E-29 to G-1562; E-29 to S-2561; E-29 to A-1560; E-29 to K-1559; E-29 to L-1558; E-29 to K-1557; E-29 to Q-1556; E-29 to C-1555; E-29 to T-1554; E-29 to V-1553; E-29 to R-1552; E-29 to R-1551; E-29 to T-1550; E-29 to Q-1549; E-29 to V-1548; E-29 to G-1547; E-29 to G-1546; E-29 to G-1545; E-29 to C-1544; E-29 to S-1543; E-29 to R-1542; E-29 to T-1541; E-29 to C-1540; E-29 to A-1539; E-29 to S-1538; E-29 to W-1537; E-29 to S-1536; E-29 to T-1535; E-29 to V-1534; E-29 to E-29533; E-29 to W-1532; E-29 to R-1531; E-29 to S-1530; E-29 to P-1529; E-29 to C-1528; E-29 to D-1527; E-29 to R-1526; E-29 to R-1525; E-29 to N-1524; E-29 to C-1523; E-29 to A-1522; E-29 to I-1521; E-29 to P-1520; E-29 to Q-1519; E-29 to V-1518; E-29 to A-1517; E-29 to P-1516; E-29 to R-1515; E-29 to V-1514; E-29 to K-1513; E-29 to G-1512; E-29 to A-1511; E-29 to C-1510; E-29 to H-1509; E-29 to A-1508; E-29 to P-1507; E-29 to N-1506; E-29 to V-1505; E-29 to E-1504; E-29 to T-1503; E-29 to S-1502; E-29 to N-1501; E-29 to L-1500; E-29 to L-1499; E-29 to C-1498; E-29 to R-1497; E-29 to L-1496; E-29 to R-1495; E-29 to P-1494; E-29 to Q-1493; E-29 to Q-1492; E-29 to V-1491; E-29 to G-1490; E-29 to R-1489; E-29 to N-1488; E-29 to G-1487; E-29 to C-1486; E-29 to S-1485; E-29 to A-1484; E-29 to S-1483; E-29 to C-1482; E-29 to T-1481; E-29 to A-1480; E-29 to L-1479; E-29 to R-1478; E-29 to D-1477; E-29 to V-1476; E-29 to S-1475; E-29 to W-1474; E-29 to W-1473; E-29 to Y-1472; E-29 to D-1471; E-29 to Q-1470; E-29 to I-1469; E-29 to V-1468; E-29 to L-1467; E-29 to S-1466; E-29 to A-1465; E-29 to K-1464; E-29 to Q-1463; E-29 to E-29462; E-29 to L-1461; E-29 to V-1460; E-29 to G-1459; E-29 to A-1458; E-29 to E-1457; E-29 to N-1456; E-29 to Q-1455; E-29 to A-1454; E-29 to L-1453; E-29 to C-1452; E-29 to S-1451; E-29 to F-1450; E-29 to E-1449; E-29 to G-1448; E-29 to Q-1447; E-29 to S-1446; E-29 to G-1445; E-29 to G-1444; E-29 to S-1443; E-29 to L-1442; E-29 to N-1441; E-29 to A-1440; E-29 to V-1439; E-29 to Q-1438; E-29 to L-1437; E-29 to I-1436; E-29 to Q-1435; E-29 to G-1434; E-29 to A-1433; E-29 to A-1432; E-29 to L-1431; E-29 to I-1430; E-29 to G-1429; E-29 to H-1428; E-29 to T-1427; E-29 to L-1426; E-29 to G-1425; E-29 to T-1424; E-29 to A-1423; E-29 to T-1422; E-29 to V-1421; E-29 to I-1420; E-29 to P-1419; E-29 to Q-1418; E-29 to G-1417; E-29 to G-1416; E-29 to I-1415; E-29 to F-1414; E-29 to W-1413; E-29 to T-1412; E-29 to I-1411; E-29 to N-1410; E-29 to P-1409; E-29 to V-1408; E-29 to P-1407; E-29 to H-1406; E-29 to G-1405; E-29 to K-1404; E-29 to I-1403; E-29 to P-1402; E-29 to C-1401; E-29 to G-1400; E-29 to L-1399; E-29 to L-1398; E-29 to A-1397; E-29 to S-1396; E-29 to N-1395; E-29 to G-1394; E-29 to P-1393; E-29 to D-1392; E-29 to L-1391; E-29 to V-1390; E-29 to L-1389; E-29 to Q-1388; E-29 to T-1387; E-29 to G-1386; E-29 to L-1385; E-29 to P-1384; E-29 to S-1383; E-29 to T-1382; E-29 to L-1381; E-29 to V-1380; E-29 to P-1379; E-29 to P-1378; E-29 to L-1377; E-29 to N-1376; E-29 to P-1375; E-29 to G-1374; E-29 to T-1373; E-29 to A-1372; E-29 to A-1371; E-29 to L-1370; E-29 to L-1369; E-29 to A-1368; E-29 to R-1367; E-29 to I-1366; E-29 to D-1365; E-29 to E-1364; E-29 to L-1363; E-29 to Q-1362; E-29 to T-1361; E-29 to P-1360; E-29 to V-1359; E-29 to Q-1358; E-29 to P-1357; E-29 to P-1356; E-29 to D-1355; E-29 to L-1354; E-29 to I-1353; E-29 to L-1352; E-29 to L-1351; E-29 to Q-1350; E-29 to T-1349; E-29 to S-1348; E-29 to E-1347; E-29 to T-1346; E-29 to L-1345; E-29 to E-1344; E-29 to G-1343; E-29 to H-1342; E-29 to L-1341; E-29 to N-1340; E-29 to A-1339; E-29 to A-1338; E-29 to R-1337; E-29 to C-1336; E-29 to S-1335; E-29 to Y-1334; E-29 to L-1333; E-29 to G-1332; E-29 to Q-1331; E-29 to D-1330; E-29 to S-1329; E-29 to S-1328; E-29 to S-1327; E-29 to V-1326; E-29 to N-1325; E-29 to T-1324; E-29 to L-1323; E-29 to L-1322; E-29 to L-1321; E-29 to S-1320; E-29 to G-1319; E-29 to E-1318; E-29 to H-1317; E-29 to L-1316; E-29 to H-1315; E-29 to H-1314; E-29 to P-1313; E-29 to S-1312; E-29 to G-1311; E-29 to L-1310; E-29 to K-1309; E-29 to S-1308; E-29 to K-1307; E-29 to N-1306; E-29 to R-1305; E-29 to F-1304; E-29 to W-1303; E-29 to T-1302; E-29 to V-1301; E-29 to F-1300; E-29 to A-1299; E-29 to E-1298; E-29 to P-1297; E-29 to V-1296; E-29 to G-1295; E-29 to A-1294; E-29 to V-1293; E-29 to Q-1292; E-29 to C-1291; E-29 to N-1290; E-29 to I-1289; E-29 to T-1288; E-29 to V-1287; E-29 to N-1286; E-29 to V-1285; E-29 to G-1284; E-29 to Q-1283; E-29 to V-1282; E-29 to T-1281; E-29 to K-1280; E-29 to I-1279; E-29 to T-1278; E-29 to S-1277; E-29 to G-1276; E-29 to V-1275; E-29 to D-1274; E-29 to V-1273; E-29 to T-1272; E-29 to V-1271; E-29 to A-1270; E-29 to P-1269; E-29 to K-1268; E-29 to S-1267; E-29 to T-1266; E-29 to N-1265; E-29 to I-1264; E-29 to V-1263; E-29 to T-1262; E-29 to V-29261; E-29 to R-1260; E-29 to S-1259; E-29 to T-1258; E-29 to K-1257; E-29 to V-1256; E-29 to L-1255; E-29 to P-1254; E-29 to K-1253; E-29 to G-1252; E-29 to A-1251; E-29 to L-1250; E-29 to T-1249; E-29 to V-1248; E-29 to A-1247; E-29 to I-1246; E-29 to S-1245; E-29 to V-1244; E-29 to S-1243; E-29 to D-1242; E-29 to Y-1241; E-29 to G-1240; E-29 to L-1239; E-29 to A-1238; E-29 to N-1237; E-29 to T-1236; E-29 to A-1235; E-29 to N-1234; E-29 to C-1233; E-29 to T-1232; E-29 to Y-1231; E-29 to F-1230; E-29 to G-1229; E-29 to V-1228; E-29 to D-1227; E-29 to A-1226; E-29 to F-1225; E-29 to V-1224; E-29 to P-1223; E-29 to A-1222; E-29 to L-1221; E-29 to I-1220; E-29 to Q-1219; E-29 to L-1218; E-29 to S-1217; E-29 to D-1216; E-29 to D-1215; E-29 to P-1214; E-29 to Q-1213; E-29 to L-1212; E-29 to L-1211; E-29 to I-1210; E-29 to R-1209; E-29 to D-1208; E-29 to S-1207; E-29 to F-1206; E-29 to Q-1205; E-29 to V-1204; E-29 to E-1203; E-29 to E-1202; E-29 to G-1201; E-29 to N-1200; E-29 to R-1199; E-29 to A-1198; E-29 to W-1197; E-29 to S-1196; E-29 to I-1195; E-29 to T-1194; E-29 to P-1193; E-29 to R-1192; E-29 to P-1191; E-29 to H-1190; E-29 to G-1189; E-29 to I-1188; E-29 to A-1187; E-29 to E-1186; E-29 to C-1185; E-29 to H-1184; E-29 to L-1183; E-29 to L-1182; E-29 to V-1181; E-29 to S-1180; E-29 to L-1179; E-29 to T-1178; E-29 to G-1177; E-29 to S-1176; E-29 to A-1175; E-29 to L-1174; E-29 to A-1173; E-29 to V-1172; E-29 to T-1171; E-29 to Q-1170; E-29 to G-1169; E-29 to L-1168; E-29 to H-1167; E-29 to T-1166; E-29 to V-1165; E-29 to V-1164; E-29 to E-1163; E-29 to S-1162; E-29 to A-1161; E-29 to S-1160; E-29 to L-1159;

E-29 to Q-1158; E-29 to Q-1157; E-29 to A-1156; E-29 to A-1155; E-29 to S-1154; E-29 to I-1153; E-29 to K-1152; E-29 to R-1151; E-29 to L-1150; E-29 to I-1149; E-29 to T-1148; E-29 to P-1147; E-29 to K-1146; E-29 to R-1145; E-29 to H-1144; E-29 to P-1143; E-29 to R-1142; E-29 to R-1141; E-29 to S-1140; E-29 to G-1139; E-29 to G-1138; E-29 to G-1137; E-29 to A-1136; E-29 to D-1135; E-29 to G-1134; E-29 to T-1133; E-29 to S-1132; E-29 to S-1131; E-29 to T-1130; E-29 to R-1129; E-29 to L-1128; E-29 to S-1127; E-29 to S-1126; E-29 to S-1125; E-29 to F-1124; E-29 to G-1123; E-29 to S-1122; E-29 to V-1121; E-29 to H-1120; E-29 to K-1119; E-29 to H-1118; E-29 to P-1117; E-29 to S-1116; E-29 to L-1115; E-29 to T-1114; E-29 to V-1113; E-29 to P-1112; E-29 to S-1111; E-29 to T-1110; E-29 to R-1109; E-29 to R-1108; E-29 to E-1107; E-29 to S-1106; E-29 to P-1105; E-29 to K-1104; E-29 to L-1103; E-29 to L-1102; E-29 to T-1101; E-29 to D-1100; E-29 to Q-1099; E-29 to H-1098; E-29 to E-1097; E-29 to L-1096; E-29 to H-1095; E-29 to S-1094; E-29 to R-1093; E-29 to F-1092; E-29 to I-1091; E-29 to E-1090; E-29 to Q-1089; E-29 to A-1088; E-29 to L-1087; E-29 to Q-1086; E-29 to A-1085; E-29 to V-1084; E-29 to L-1083; E-29 to H-1082; E-29 to K-1081; E-29 to S-1080; E-29 to Y-1079; E-29 to L-1078; E-29 to D-1077; E-29 to R-1076; E-29 to L-1075; E-29 to E-1074; E-29 to E-1073; E-29 to P-1072; E-29 to Q-1071; E-29 to Q-1070; E-29 to S-1069; E-29 to L-1068; E-29 to N-1067; E-29 to G-1066; E-29 to L-1065; E-29 to I-1064; E-29 to D-1063; E-29 to D-1062; E-29 to L-1061; E-29 to R-1060; E-29 to R-1059; E-29 to Q-1058; E-29 to E-1057; E-29 to T-1056; E-29 to V-1055; E-29 to E-29054; E-29 to T-1053; E-29 to F-1052; E-29 to P-1051; E-29 to L-1050; E-29 to H-1049; E-29 to L-1048; E-29 to L-1047; E-29 to V-1046; E-29 to Q-1045; E-29 to E-1044; E-29 to A-1043; E-29 to G-1042; E-29 to P-1041; E-29 to D-1040; E-29 to E-1039; E-29 to E-1038; E-29 to S-1037; E-29 to T-1036; E-29 to T-1035; E-29 to N-1034; E-29 to R-1033; E-29 to E-1032; E-29 to A-1031; E-29 to S-1030; E-29 to D-1029; E-29 to Q-1028; E-29 to A-1027; E-29 to E-1026; E-29 to W-1025; E-29 to S-1024; E-29 to A-1023; E-29 to L-1022; E-29 to L-1021; E-29 to E-1020; E-29 to G-1019; E-29 to P-1018; E-29 to W-1017; E-29 to G-1016; E-29 to G-1015; E-29 to Q-1014; E-29 to E-1013; E-29 to L-1012; E-29 to L-1011; E-29 to R-1010; E-29 to S-1009; E-29 to V-1008; E-29 to L-1007; E-29 to D-1006; E-29 to D-1005; E-29 to Y-1004; E-29 to R-1003; E-29 to S-1002; E-29 to G-1001; E-29 to P-1000; E-29 to N-999; E-29 to A-998; E-29 to A-997; E-29 to L-996; E-29 to G-995; E-29 to R-994; E-29 to K-993; E-29 to E-992; E-29 to A-991; E-29 to K-990; E-29 to S-989; E-29 to G-988; E-29 to N-987; E-29 to S-986; E-29 to F-985; E-29 to I-984; E-29 to G-983; E-29 to N-982; E-29 to Q-981; E-29 to H-980; E-29 to K-979; E-29 to H-978; E-29 to T-977; E-29 to Q-976; E-29 to L-975; E-29 to A-974; E-29 to E-973; E-29 to K-972; E-29 to P-971; E-29 to G-970; E-29 to G-969; E-29 to K-968; E-29 to R-967; E-29 to G-966; E-29 to A-965; E-29 to L-964; E-29 to V-963; E-29 to E-962; E-29 to E-961; E-29 to E-960; E-29 to S-959; E-29 to R-958; E-29 to P-957; E-29 to S-956; E-29 to L-955; E-29 to P-954; E-29 to R-953; E-29 to A-952; E-29 to V-951; E-29 to L-950; E-29 to K-949; E-29 to R-948; E-29 to N-947; E-29 to G-946; E-29 to G-945; E-29 to I-944; E-29 to L-943; E-29 to K-942; E-29 to I-941; E-29 to V-940; E-29 to F-939; E-29 to H-938; E-29 to E-937; E-29 to R-936; E-29 to A-935; E-29 to P-934; E-29 to G-933; E-29 to A-932; E-29 to S-931; E-29 to C-930; E-29 to T-929; E-29 to Y-928; E-29 to V-927; E-29 to G-926; E-29 to A-925; E-29 to D-924; E-29 to S-923; E-29 to P-922; E-29 to K-921; E-29 to L-920; E-29 to R-919; E-29 to H-918; E-29 to I-917; E-29 to K-916; E-29 to L-915; E-29 to Y-914; E-29 to G-913; E-29 to F-912; E-29 to P-911; E-29 to A-910; E-29 to V-909; E-29 to T-908; E-29 to V-907; E-29 to H-906; E-29 to T-905; E-29 to S-904; E-29 to S-903; E-29 to I-902; E-29 to L-901; E-29 to H-900; E-29 to Q-899; E-29 to G-898; E-29 to D-897; E-29 to K-896; E-29 to E-895; E-29 to W-894; E-29 to T-893; E-29 to I-892; E-29 to L-891; E-29 to P-890; E-29 to K-889; E-29 to R-888; E-29 to V-887; E-29 to R-886; E-29 to R-885; E-29 to A-884; E-29 to P-883; E-29 to C-882; E-29 to R-881; E-29 to L-880; E-29 to V-879; E-29 to V-878; E-29 to A-877; E-29 to T-876; E-29 to K-875; E-29 to P-874; E-29 to L-873; E-29 to L-872; E-29 to Y-871; E-29 to A-870; E-29 to F-869; E-29 to G-868; E-29 to G-867; E-29 to V-866; E-29 to V-865; E-29 to F-864; E-29 to H-863; E-29 to L-862; E-29 to K-861; E-29 to R-860; E-29 to Q-859; E-29 to R-858; E-29 to R-857; E-29 to T-856; E-29 to Q-855; E-29 to I-854; E-29 to Y-853; E-29 to V-852; E-29 to K-851; E-29 to R-850; E-29 to A-849; E-29 to A-848; E-29 to A-847; E-29 to I-846; E-29 to H-845; E-29 to P-844; E-29 to S-843; E-29 to H-842; E-29 to K-841; E-29 to T-840; E-29 to S-839; E-29 to P-838; E-29 to R-837; E-29 to G-836; E-29 to P-835; E-29 to R-834; E-29 to A-833; E-29 to C-832; E-29 to T-831; E-29 to A-830; E-29 to L-829; E-29 to M-828; E-29 to C-827; E-29 to P-826; E-29 to R-825; E-29 to I-824; E-29 to S-823; E-29 to S-822; E-29 to S-821; E-29 to F-820; E-29 to P-819; E-29 to L-818; E-29 to P-817; E-29 to P-816; E-29 to C-815; E-29 to L-814; E-29 to T-813; E-29 to S-812; E-29 to N-811; E-29 to V-810; E-29 to V-809; E-29 to T-808; E-29 to S-807; E-29 to L-806; E-29 to G-805; E-29 to T-804; E-29 to K-803; E-29 to L-802; E-29 to M-801; E-29 to K-800; E-29 to R-799; E-29 to C-798; E-29 to I-797; E-29 to A-796; E-29 to S-795; E-29 to R-794; E-29 to T-793; E-29 to Q-792; E-29 to T-791; E-29 to G-790; E-29 to E-789; E-29 to G-788; E-29 to C-787; E-29 to S-786; E-29 to T-785; E-29 to S-784; E-29 to C-783; E-29 to E-782; E-29 to T-781; E-29 to W-780; E-29 to D-779; E-29 to S-778; E-29 to L-777; E-29 to L-776; E-29 to W-775; E-29 to E-774; E-29 to S-773; E-29 to P-772; E-29 to C-771; E-29 to D-770; E-29 to D-769; E-29 to K-768; E-29 to K-767; E-29 to C-766; E-29 to A-765; E-29 to Q-764; E-29 to Q-763; E-29 to C-762; E-29 to A-761; E-29 to P-760; E-29 to K-759; E-29 to S-758; E-29 to A-757; E-29 to S-756; E-29 to C-755; E-29 to F-754; E-29 to T-753; E-29 to E-752; E-29 to P-751; E-29 to L-750; E-29 to E-749; E-29 to L-748; E-29 to F-747; E-29 to S-746; E-29 to G-745; E-29 to D-744; E-29 to A-743; E-29 to M-742; E-29 to R-741; E-29 to Q-740; E-29 to K-739; E-29 to C-738; E-29 to L-737; E-29 to V-736; E-29 to E-735; E-29 to R-734; E-29 to K-733; E-29 to Q-732; E-29 to V-731; E-29 to G-730; E-29 to G-729; E-29 to G-728; E-29 to C-727; E-29 to T-726; E-29 to R-725; E-29 to S-724; E-29 to C-723; E-29 to P-722; E-29 to Q-721; E-29 to W-720; E-29 to Q-719; E-29 to A-718; E-29 to P-717; E-29 to Y-716; E-29 to W-715; E-29 to A-714; E-29 to P-713; E-29 to P-712; E-29 to C-711; E-29 to N-710; E-29 to F-709; E-29 to R-708; E-29 to N-707; E-29 to C-706; E-29 to A-705; E-29 to Q-704; E-29 to V-703; E-29 to T-702; E-29 to S-701; E-29 to P-700; E-29 to K-699; E-29 to P-698; E-29 to Q-697; E-29 to R-696; E-29 to C-695; E-29 to L-694; E-29 to E-693; E-29 to D-692; E-29 to A-691; E-29 to L-690; E-29 to I-689; E-29 to V-688; E-29 to T-687; E-29 to E-686; E-29 to N-685; E-29 to M-684; E-29 to E-683; E-29 to R-682; E-29 to S-681; E-29 to L-680; E-29 to L-679; E-29 to H-678; E-29 to S-677; E-29 to C-676; E-29 to F-675; E-29 to V-674; E-29 to D-673; E-29 to R-672; E-29 to T-671; E-29 to Q-670; E-29 to L-669; E-29 to G-668; E-29 to V-667; E-29 to

G-666; E-29 to C-665; E-29 to T-664; E-29 to L-663; E-29 to S-662; E-29 to C-661; E-29 to P-660; E-29 to S-659; E-29 to W-658; E-29 to K-657; E-29 to G-656; E-29 to I-655; E-29 to E-654; E-29 to W-653; E-29 to R-652; E-29 to A-651; E-29 to P-650; E-29 to C-649; E-29 to P-648; E-29 to D-647; E-29 to L-646; E-29 to N-645; E-29 to C-644; E-29 to S-643; E-29 to K-642; E-29 to L-641; E-29 to L-640; E-29 to Q-639; E-29 to P-638; E-29 to P-637; E-29 to R-636; E-29 to R-635; E-29 to S-634; E-29 to T-633; E-29 to V-632; E-29 to C-631; E-29 to L-630; E-29 to N-629; E-29 to E-628; E-29 to E-627; E-29 to A-626; E-29 to P-625; E-29 to E-624; E-29 to R-623; E-29 to T-622; E-29 to Q-621; E-29 to K-620; E-29 to N-619; E-29 to L-618; E-29 to C-617; E-29 to S-616; E-29 to V-615; E-29 to V-614; E-29 to A-613; E-29 to E-612; E-29 to Q-611; E-29 to V-610; E-29 to G-609; E-29 to G-608; E-29 to G-607; E-29 to C-606; E-29 to S-605; E-29 to E-604; E-29 to S-603; E-29 to C-602; E-29 to K-601; E-29 to T-600; E-29 to F-599; E-29 to G-598; E-29 to E-597; E-29 to Y-596; E-29 to E-595; E-29 to W-594; E-29 to D-593; E-29 to Y-592; E-29 to L-591; E-29 to E-590; E-29 to D-589; E-29 to F-588; E-29 to D-587; E-29 to Q-586; E-29 to L-585; E-29 to G-584; E-29 to G-583; E-29 to F-582; E-29 to L-581; E-29 to G-580; E-29 to D-579; E-29 to T-578; E-29 to E-577; E-29 to D-576; E-29 to P-575; E-29 to N-574; E-29 to F-573; E-29 to E-572; E-29 to P-571; E-29 to I-570; E-29 to E-569; E-29 to G-568; E-29 to S-567; E-29 to C-566; E-29 to P-565; E-29 to G-564; E-29 to A-563; E-29 to Y-562; E-29 to C-561; E-29 to A-560; E-29 to R-559; E-29 to Q-558; E-29 to S-557; E-29 to A-556; E-29 to P-555; E-29 to K-554; E-29 to P-553; E-29 to G-552; E-29 to E-551; E-29 to C-550; E-29 to E-549; E-29 to D-548; E-29 to I-547; E-29 to P-546; E-29 to L-545; E-29 to D-544; E-29 to A-543; E-29 to V-542; E-29 to S-541; E-29 to Q-540; E-29 to S-539; E-29 to F-538; E-29 to S-537; E-29 to L-536; E-29 to L-535; E-29 to V-534; E-29 to Q-533; E-29 to C-532; E-29 to R-531; E-29 to V-530; E-29 to I-529; E-29 to R-528; E-29 to V-527; E-29 to Q-526; E-29 to T-525; E-29 to G-524; E-29 to V-523; E-29 to G-522; E-29 to C-521; E-29 to T-520; E-29 to V-519; E-29 to T-518; E-29 to C-517; E-29 to A-516; E-29 to S-515; E-29 to W-514; E-29 to A-513; E-29 to K-512; E-29 to P-511; E-29 to I-510; E-29 to F-509; E-29 to S-508; E-29 to P-507; E-29 to E-506; E-29 to E-505; E-29 to S-504; E-29 to V-503 E-29 to A-502; E-29 to A-501; E-29 to G-500; E-29 to E-499; E-29 to E-498; E-29 to L-497; E-29 to E-496; E-29 to Q-495; E-29 to A-494; E-29 to Q-493; E-29 to K-492; E-29 to F-491; E-29 to W-490; E-29 to P-489; E-29 to L-488; E-29 to K-487; E-29 to A-486; E-29 to E-485; E-29 to V-484; E-29 to P-483; E-29 to L-482; E-29 to K-481; E-29 to E-480; E-29 to K-479; E-29 to P-478; E-29 to K-477; E-29 to Y-476; E-29 to C-475; E-29 to P-474; E-29 to T-473; E-29 to P-472; E-29 to V-471; E-29 to I-470; E-29 to C-469; E-29 to E-468; E-29 to E-467; E-29 to K-466; E-29 to I-465; E-29 to H-464; E-29 to P-463; E-29 to K-462; E-29 to T-461; E-29 to K-460; E-29 to P-459; E-29 to S-458; E-29 to C-457; E-29 to G-456; E-29 to G-455; E-29 to T-454; E-29 to H-453; E-29 to M-452; E-29 to G-451; E-29 to R-450; E-29 to H-449; E-29 to D-448; E-29 to I-447; E-29 to C-446; E-29 to L-445; E-29 to V-444; E-29 to V-443; E-29 to R-442; E-29 to Y-441; E-29 to R-440; E-29 to L-439; E-29 to G-438; E-29 to Q-437; E-29 to G-436; E-29 to C-435; E-29 to T-434; E-29 to V-433; E-29 to T-432; E-29 to C-431; E-29 to P-430; E-29 to S-429; E-29 to W-428; E-29 to G-427; E-29 to Q-426; E-29 to A-425; E-29 to L-424; E-29 to W-423; E-29 to K-422; E-29 to P-421; E-29 to C-420; E-29 to D-419; E-29 to F-418; E-29 to I-417; E-29 to N-416; E-29 to C-415; E-29 to P-414; E-29 to Q-413; E-29 to A-412; E-29 to I-411; E-29 to P-410; E-29 to M-409; E-29 to K-408; E-29 to P-407; E-29 to I-406; E-29 to Y-405; E-29 to M-404; E-29 to C-403; E-29 to K-402; E-29 to W-401; E-29 to E-400; E-29 to P-399; E-29 to V-398; E-29 to S-397; E-29 to T-396; E-29 to V-395; E-29 to H-394; E-29 to G-393; E-29 to Q-392; E-29 to I-391; E-29 to D-390; E-29 to E-389; E-29 to E-388; E-29 to V-387; E-29 to C-386; E-29 to S-385; E-29 to V-384; E-29 to A-383; E-29 to R-382; E-29 to S-381; E-29 to Q-380; E-29 to I-379; E-29 to G-378; E-29 to G-377; E-29 to G-376; E-29 to C-375; E-29 to S-374; E-29 to S-373; E-29 to S-372; E-29 to C-371; E-29 to A-370; E-29 to T-369; E-29 to W-368; E-29 to P-367; E-29 to T-366; E-29 to A-365; E-29 to E-364; E-29 to W-363; E-29 to R-362; E-29 to A-361; E-29 to P-360; E-29 to C-359; E-29 to P-358; E-29 to D-357; E-29 to L-356; E-29 to N-355; E-29 to C-354; E-29 to E-353; E-29 to Q-352; E-29 to L-351; E-29 to K-350; E-29 to P-349; E-29 to K-348; E-29 to P-347; E-29 to K-346; E-29 to I-345; E-29 to N-344; E-29 to E-343; E-29 to P-342; E-29 to Y-341; E-29 to Y-340; E-29 to H-339; E-29 to C-338; E-29 to Y-337; E-29 to Q-336; E-29 to D-335; E-29 to A-334; E-29 to V-333; E-29 to V-332; E-29 to R-331; E-29 to N-330; E-29 to S-329; E-29 to R-328; E-29 to L-327; E-29 to D-326; E-29 to Y-325; E-29 to C-324; E-29 to E-323; E-29 to A-322; E-29 to S-321; E-29 to T-320; E-29 to L-319; E-29 to Q-318; E-29 to Y-317; E-29 to G-316; E-29 to G-315; E-29 to G-314; E-29 to C-313; E-29 to T-312; E-29 to A-311; E-29 to S-310; E-29 to C-309; E-29 to P-308; E-29 to F-307; E-29 to F-306; E-29 to D-305; E-29 to T-304; E-29 to E-303; E-29 to R-302; E-29 to W-301; E-29 to R-300; E-29 to H-299; E-29 to I-298; E-29 to I-297; E-29 to P-296; E-29 to Q-295; E-29 to Y-294; E-29 to F-293; E-29 to I-292; E-29 to F-291; E-29 to Q-290; E-29 to V-289; E-29 to T-288; E-29 to S-287; E-29 to D-286; E-29 to A-285; E-29 to S-284; E-29 to G-283; E-29 to S-282; E-29 to N-281; E-29 to R-280; E-29 to I-279; E-29 to K-278; E-29 to V-277; E-29 to I-276; E-29 to F-275; E-29 to D-274; E-29 to A-273; E-29 to T-272; E-29 to L-271; E-29 to P-270; E-29 to G-269; E-29 to A-268; E-29 to M-267; E-29 to R-266; E-29 to L-265; E-29 to I-264; E-29 to E-263; E-29 to K-262; E-29 to D-261; E-29 to P-260; E-29 to F-259; E-29 to K-258; E-29 to Q-257; E-29 to F-256; E-29 to D-255; E-29 to V-254; E-29 to S-253; E-29 to S-252; E-29 to N-251; E-29 to D-250; E-29 to V-249; E-29 to L-248; E-29 to F-247; E-29 to T-246; E-29 to G-245; E-29 to T-244; E-29 to S-243; E-29 to S-242; E-29 to L-241; E-29 to S-240; E-29 to N-239; E-29 to E-238; E-29 to G-237; E-29 to K-236; E-29 to T-235; E-29 to G-234; E-29 to Q-233; E-29 to L-232; E-29 to T-231; E-29 to K-230; E-29 to T-229; E-29 to E-228; E-29 to L-227; E-29 to Y-226; E-29 to L-225; E-29 to H-224; E-29 to D-223; E-29 to P-222; E-29 to G-221; E-29 to K-220; E-29 to L-219; E-29 to V-218; E-29 to L-217; E-29 to R-216; E-29 to I-215; E-29 to H-214; E-29 to R-213; E-29 to S-212; E-29 to G-211; E-29 to Y-210; E-29 to P-209; E-29 to I-208; E-29 to A-207; E-29 to V-206; E-29 to V-205; E-29 to T-204; E-29 to D-203; E-29 to D-202; E-29 to S-201; E-29 to K-200; E-29 to T-199; E-29 to A-198; E-29 to S-197; E-29 to L-196; E-29 to Q-195; E-29 to S-194; E-29 to K-193; E-29 to Y-192; E-29 to Q-191; E-29 to G-190; E-29 to R-189; E-29 to V-188; E-29 to L-187; E-29 to R-186; E-29 to C-185; E-29 to T-184; E-29 to S-183; E-29 to G-182; E-29 to D-181; E-29 to G-180; E-29 to N-179; E-29 to C-178; E-29 to V-177; E-29 to G-176; E-29 to C-175; E-29 to N-174; E-29 to D-173; E-29 to E-172; E-29 to K-171; E-29 to V-170; E-29 to T-169; E-29 to S-168; E-29 to G-167; E-29 to L-166; E-29 to Q-165; E-29 to H-164; E-29 to D-163; E-29 to C-162; E-29 to G-161; E-29 to V-160; E-29 to I-159; E-29 to Q-158; E-29 to C-157; E-29 to L-156; E-29 to G-155; E-29 to S-154; E-29 to I-153; E-29 to C-152; E-29 to E-2951 E-29 to D-150; E-29 to L-149; E-29 to S-148; E-29 to E-147; E-29 to T-146; E-29 to Y-145; E-29 to C-144; E-29 to R-143; E-29 to T-142; E-29 to G-141; E-29 to D-140; E-29 to L-139; E-29 to V-138; E-29 to K-137; E-29 to P-136; E-29 to A-135; E-29 to L-134; E-29 to E-133; E-29 to V-132; E-29 to V-131; E-29 to L-130; E-29 to T-129; E-29 to T-128; E-29 to G-127; E-29 to K-126; E-29 to A-125; E-29 to Q-124; E-29 to C-123; E-29 to K-122; E-29 to L-121; E-29 to S-120; E-29 to C-119; E-29 to P-118; E-29 to N-117; E-29 to D-116; E-29 to P-115; E-29 to D-114; E-29 to N-113; E-20 to S-112; E-29 to V-111; E-29 to P-110; E-29 to L-109; E-29 to W-108; E-29 to E-107; E-29 to Y-106; E-29 to F-105; E-29 to Q-104; E-29 to G-103; E-29 to H-102; E-29 to H-101; E-29 to K-100; E-29 to V-99; E-29 to D-98; E-29 to N-97; E-29 to H-96; E-29 to A-95; E-29 to S-94; E-29 to C-93; E-29 to Q-92; E-29 to Q-91; E-29 to A-90; E-29 to R-89; E-29 to F-88; E-29 to D-87; E-29 to G-86; E-29 to A-85; E-29 to E-84; E-29 to P-83; E-29 to P-82; E-29 to C-81; E-29 to D-80; E-29 to V-79; E-29 to N-78; E-29 to S-77; E-29 to C-76; E-29 to T-75; E-29 to R-74; E-29 to Y-73; E-29 to R-72; E-29 to I-71; E-29 to N-70; E-29 to R-69; E-29 to G-68; E-29 to E-67; E-29 to C-66; E-29 to S-65; E-29 to K-64; E-29 to S-63; E-29 to S-62; E-29 to L-61; E-29 to C-60; E-29 to R-59; E-29 to R-58; E-29 to L-57; E-29 to S-56; E-29 to Y-55; E-29 to S-54; E-29 to A-53; E-29 to G-52; E-29 to G-51; E-29 to G-50; E-29 to C-49; E-29 to T-48; E-29 to R-47; E-29 to S-46; E-29 to C-45; E-29 to E-44; E-29 to S-43; E-29 to W-42; E-29 to P-41; E-29 to G-40; E-29 to W-39; E-29 to A-38; E-29 to D-37; E-29 to W-36; E-29 to L-35; E-29 to G-34; E-29 to D-33; E-29 to R-32; E-29 to D-31; or E-29 to E-30 of SEQ ID NO:89. Polypeptides encoded by these polynucleotides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that bind polypeptides of the invention are also encompassed by the invention. Polynucleotides encoding these polypeptides are also encompassed by the invention.

Moreover, a signal sequence may be added to these C-terminal constructs. For example, amino acids 1–28 of SEQ ID NO:89, amino acids 2–28 of SEQ ID NO:89, amino acids 3–28 of SEQ ID NO:89, amino acids 4–28 of SEQ ID NO:89, amino acids 5–28 of SEQ ID NO:89, amino acids 6–28 of SEQ ID NO:89, amino acids 7–28 of SEQ ID NO:89, amino acids 8–28 of SEQ ID NO:89, amino acids 9–28 of SEQ ID NO:89, amino acids 10–28 of SEQ ID NO:89, amino acids 11–28 of SEQ ID NO:89, amino acids 12–28 of SEQ ID NO:89, amino acids 13–28 of SEQ ID NO:89, amino acids 14–28 of SEQ ID NO:89, amino acids 15–28 of SEQ ID NO:89, amino acids 16–28 of SEQ ID NO:89, amino acids 17–28 of SEQ ID NO:89, amino acids 18–28 of SEQ ID NO:89, amino acids 19–28 of SEQ ID NO:89, amino acids 20–28 of SEQ ID NO:89, amino acids 21–28 of SEQ ID NO:89, amino acids 22–28 of SEQ ID NO:89, amino acids 23–28 of SEQ ID NO:89, amino acids 24–28 of SEQ ID NO:89, amino acids 25–28 of SEQ ID NO:89, amino acids 26–28 of SEQ ID NO:89, or amino acids 27–28 of SEQ ID NO:89 can be added to the N-terminus of each C-terminal constructs listed above.

In addition, any of the above listed N- or C-terminal deletions can be combined to produce a N- and C-terminal deleted THRAP polypeptide. The invention also provides polypeptides having one or more amino acids deleted from both the amino and the carboxyl termini, which may be described generally as having residues m–n of SEQ ID NO:89, where n and m are integers as described above. It is understood, however, that any N- and C-terminal deletion mutant is at least, preferably, 6 amino acids, 10 amino acids, 20 amino acids, or 50 amino acids in length. Polynucleotides encoding these polypeptides are also encompassed by the invention.

Moreover, the invention provides nucleic acid molecules having nucleotide sequences related to extensive portions of SEQ ID NO:18 which have been determined from the following related cDNA clones: HBINE55R (SEQ ID NO:156), HOEEW19R (SEQ ID NO:157), HSLAS01R (SEQ ID NO:158), HORBP08R (SEQ ID NO:159)and HAJBI67R (SEQ ID NO:160).

Also preferred polypeptide fragments of the invention comprise, or consist of, the following fragments: TSP-1-like domain1; TSP-1-like domain1 and the proteinase domain; TSP-1-like domain1, the proteinase domain, and the TSP-1-like domain2; TSP-1-like domain1, the proteinase domain, and the TSP-1-like domain2 to TSP-1-like domain3; TSP-1-like domain1, the proteinase domain, and the TSP-1-like domain2 to TSP-1-like domain4; TSP-1-like domain1, the proteinase domain, and the TSP-1-like domain2 to TSP-1-like domain5; TSP-1-like domain1, the proteinase domain, and the TSP-1-like domain2 to TSP-1-like domain6; TSP-1-like domain1, the proteinase domain, and the TSP-1-like domain2 to TSP-1-like domain7; TSP-1-like domain1, the proteinase domain, and the TSP-1-like domain2 to TSP-1-like domain8; TSP-1-like domain1, the proteinase domain, and the TSP-1-like domain2 to TSP-1-like domain9; TSP-1-like domain1, the proteinase domain, the TSP-1-like domain2 to TSP-1-like domain9, and the IgG-like domain; TSP-1-like domain1, the proteinase domain, the TSP-1-like domain2 to TSP-1-like domain9, the TgG-like domain and the TSP-1-like domain10; TSP-1-like domain1, the proteinase domain, the TSP-1-like domain2 to TSP-1-like domain9, the IgG-like domain, the TSP-1-like domain10, and the TSP-1-like domain 11; TSP-1-like domain1, the proteinase domain, the TSP-1-like domain2 to TSP-1-like domain9, the IgG-like domain, the TSP-1-like domain10 to the TSP-1-like domain12; or TSP-1-like domain1, the proteinase domain, the TSP-1-like domain2 to TSP-1-like domain9, the IgG-like domain, and the TSP-1-like domain10 to the TSP-1-like domain13.

Additionally, preferred polypeptide fragments of the invention comprise, or consist of, the following fragments: the proteinase domain; the proteinase domain, and the TSP-1-like domain2; the proteinase domain, and the TSP-1-like domain2 to TSP-1-like domain3; the proteinase domain, and the TSP-1-like domain2 to TSP-1-like domain4; the proteinase domain, and the TSP-1-like domain2 to TSP-1-like domain5; the proteinase domain, and the TSP-1-like domain2 to TSP-1-like domain6; the proteinase domain, and the TSP-1-like domain2 to TSP-1-like domain7; the proteinase domain, and the TSP-1-like domain2 to TSP-1-like domain8; the proteinase domain, and the TSP-1-like domain2 to TSP-1-like domain9; the proteinase domain, the TSP-1-like domain2 to TSP-1-like domain9, and the IgG-like domain; the proteinase domain, the TSP-1-like domain2 to TSP-1-like domain9, the IgG-like domain and the TSP-1-like domain10; the proteinase domain, the TSP-1-like domain2 to TSP-1-like domain9, the IgG-like domain, the TSP-1-like domain10 and the TSP-1-like domain11; the proteinase domain, the TSP-1-like domain2 to TSP-1-like domain9, the IgG-like domain, the TSP-1-like domain10 to the TSP-1-like domain12; or the proteinase domain, the TSP-1-like domain2 to TSP-1-like domain9, the IgG-like domain, and the TSP-1-like domain10 to the TSP-1-like domain13.

Additionally, preferred polypeptide fragments of the invention comprise, or consist of, the following fragments: TSP-1-like domain2; the TSP-1-like domain2 to TSP-1-like domain3; the TSP-1-like domain2 to TSP-1-like domain4; the TSP-1-like domain2 to TSP-1-like domain5; the TSP-1-like domain2 to TSP-1-like domain6; the TSP-1-like domain2 to TSP-1-like domain7; the TSP-1-like domain2 to TSP-1-like domain8; the TSP-1-like domain2 to TSP-1-like domain9; the TSP-1-like domain2 to TSP-1-like domain9, and the IgG-like domain; the TSP-1-like domain2 to TSP-1-like domain9, the IgG-like domain and the TSP-1-like domain10; the TSP-1-like domain2 to TSP-1-like domain9, the IgG-like domain, the TSP-1-like domain10 and the TSP-1-like domain11; the TSP-1-like domain2 to TSP-1-like domain9, the IgG-like domain, the TSP-1-like domain10 to the TSP-1-like domain12; or the TSP-1-like domain2 to TSP-1-like domain9, the IgG-like domain, and the TSP-1-like domain10 to the TSP-1-like domain13.

Additionally, preferred polypeptide fragments of the invention comprise, or consist of, the following fragments: the TSP-1-like domain3; the TSP-1-like domain3 to TSP-1-like domain4; the TSP-1-like domain3 to TSP-1-like domain5; the TSP-1-like domain3 to TSP-1-like domain6; the TSP-1-like domain3 to TSP-1-like domain7; the TSP-1-like domain3 to TSP-1-like domain8; the TSP-1-like domain3 to TSP-1-like domain9; the TSP-1-like domain3 to TSP-1-like domain9, and the IgG-like domain; the TSP-1-like domain3 to TSP-1-like domain9, the IgG-like domain and the TSP-1-like domain10; the TSP-1-like domain3 to TSP-1-like domain9, the IgG-like domain, the TSP-1-like domain10 and the TSP-1-like domain11; the TSP-1-like domain3 to TSP-1-like domain9, the IgG-like domain, the TSP-1-like domain10 to the TSP-1-like domain12; or the TSP-1-like domain3 to TSP-1-like domain9, the IgG-like domain, and the TSP-1-like domain10 to the TSP-1-like domain13.

Additionally, preferred polypeptide fragments of the invention comprise, or consist of, the following fragments: the TSP-1-like domain4; the TSP-1-like domain4 to TSP-1-like domain5; the TSP-1-like domain4 to TSP-1-like domain6; the TSP-1-like domain4 to TSP-1-like domain7; the TSP-1-like domain4 to TSP-1-like domain8; the TSP-1-like domain4 to TSP-1-like domain9; the TSP-1-like domain4 to TSP-1-like domain9, and the IgG-like domain; the TSP-1-like domain4 to TSP-1-like domain9, the IgG-like domain and the TSP-1-like domain10; the TSP-1-like domain4 to TSP-1-like domain9, the IgG-like domain, the TSP-1-like domain10 and the TSP-1-like domain11; the TSP-1-like domain4 to TSP-1-like domain9, the IgG-like domain, the TSP-1-like domain10 to the TSP-1-like domain12; or the TSP-1-like domain4 to TSP-1-like domain9, the IgG-like domain, and the TSP-1-like domain10 to the TSP-1-like domain13.

Additionally, preferred polypeptide fragments of the invention comprise, or consist of, the following fragments: the TSP-1-like domain5; the TSP-1-like domain5 to TSP-1-like domain6; the TSP-1-like domain5 to TSP-1-like domain7; the TSP-1-like domain5 to TSP-1-like domain8; the TSP-1-like domain5 to TSP-1-like domain9; the TSP-1-like domain5 to TSP-1-like domain9, and the IgG-like domain; the TSP-1-like domain5 to TSP-1-like domain9, the IgG-like domain and the TSP-1-like domain10; the TSP-1-like domain5 to TSP-1-like domain9, the IgG-like domain, the TSP-1-like domain10 and the TSP-1-like domain11; the TSP-1-like domain5 to TSP-1-like domain9, the IgG-like domain, the TSP-1-like domain10 to the TSP-1-like domain12; or the TSP-1-like domain5 to TSP-1-like domain9, the IgG-like domain, and the TSP-1-like domain10 to the TSP-1-like domain13.

Additionally, preferred polypeptide fragments of the invention comprise, or consist of, the following fragments: the TSP-1-like domain6; the TSP-1-like domain6 to TSP-1-like domain7; the TSP-1-like domain6 to TSP-1-like domain8; the TSP-1-like domain6 to TSP-1-like domain9; the TSP-1-like domain6 to TSP-1-like domain9, and the IgG-like domain; the TSP-1-like domain6 to TSP-1-like domain9, the IgG-like domain and the TSP-1-like domain10; the TSP-1-like domain6 to TSP-1-like domain9, the IgG-like domain, the TSP-1-like domain10 and the TSP-1-like domain11; the TSP-1-like domain6 to TSP-1-like domain9, the IgG-like domain, the TSP-1-like domain10 to the TSP-1-like domain12; or the TSP-1-like domain6 to TSP-1-like domain9, the IgG-like domain, and the TSP-1-like domain10 to the TSP-1-like domain13.

Additionally, preferred polypeptide fragments of the invention comprise, or consist of, the following fragments: the TSP-1-like domain7; the TSP-1-like domain7 to TSP-1-like domain8; the TSP-1-like domain7 to TSP-1-like domain9; the TSP-1-like domain7 to TSP-1-like domain9, and the IgG-like domain; the TSP-1-like domain7 to TSP-1-like domain9, the IgG-like domain and the TSP-1-like domain10; the TSP-1-like domain7 to TSP-1-like domain9, the IgG-like domain, the TSP-1-like domain10 and the TSP-1-like domain11; the TSP-1-like domain7 to TSP-1-like domain9, the IgG-like domain, the TSP-1-like domain10 to the TSP-1-like domain12; or the TSP-1-like domain7 to TSP-1-like domain9, the IgG-like domain, and the TSP-1-like domain10 to the TSP-1-like domain13.

Additionally, preferred polypeptide fragments of the invention comprise, or consist of, the following fragments: the TSP-1-like domain8; the TSP-1-like domain8 to TSP-1-like domain9; the TSP-1-like domain8 to TSP-1-like domain9, and the IgG-like domain; the TSP-1-like domain8 to TSP-1-like domain9, the IgG-like domain and the TSP-1-like domain10; the TSP-1-like domain8 to TSP-1-like domain9, the IgG-like domain, the TSP-1-like domain10 and the TSP-1-like domain11; the TSP-1-like domain8 to TSP-1-like domain9, the IgG-like domain, the TSP-1-like domain10 to the TSP-1-like domain12; or the TSP-1-like domain8 to TSP-1-like domain9, the IgG-like domain, and the TSP-1-like domain10 to the TSP-1-like domain13.

Additionally, preferred polypeptide fragments of the invention comprise, or consist of, the following fragments: the TSP-1-like domain9; TSP-1-like domain9 and the IgG-like domain; the TSP-1-like domain9, the IgG-like domain and the TSP-1-like domain10; the TSP-1-like domain9, the IgG-like domain, the TSP-1-like domain10 and the TSP-1-like domain11; the TSP-1-like domain9, the IgG-like domain, the TSP-1-like domain10 to the TSP-1-like domain12; or the TSP-1-like domain9, the IgG-like domain, and the TSP-1-like domain10 to the TSP-1-like domain13.

Additionally, preferred polypeptide fragments of the invention comprise, or consist of, the following fragments: the IgG-like domain; the IgG-like domain and the TSP-1-like domain10; the IgG-like domain, the TSP-1-like domain10 and the TSP-1-like domain11; the IgG-like domain, the TSP-1-like domain10 to the TSP-1-like domain12; or the IgG-like domain, and the TSP-1-like domain10 to the TSP-1-like domain13.

Additionally, preferred polypeptide fragments of the invention comprise, or consist of, the following fragments: the TSP-1-like domain10; the TSP-1-like domain10 and the TSP-1-like domain11; the TSP-1-like domain10 to the TSP-1-like domain12; and the TSP-1-like domain10 to the TSP-1-like domain13.

Additionally, preferred polypeptide fragments of the invention comprise, or consist of, the following fragments: the TSP-1-like domain11; the TSP-1-like domain11 to the TSP-1-like domain12; and the TSP-1-like domain11 to the TSP-1-like domain13.

Additionally, preferred polypeptide fragments of the invention comprise, or consist of, the following fragment: the TSP-1-like domain12; or the TSP-1-like domain12 to the TSP-1-like domain13.

Additionally, preferred polypeptide fragments of the invention comprise, or consist of, the following fragments: the TSP-1-like domain13.

Also included are a nucleotide sequence encoding a polypeptide consisting of a portion of the complete THRAP amino acid sequence encoded by the cDNA clone (HOHCA60) contained in ATCC® Deposit No. PTA-627, where this portion excludes any integer of amino acid residues from 1 to about 1735 amino acids from the amino terminus of the complete amino acid sequence encoded by the cDNA clone contained in ATCC® Deposit No. PTA-627, or any integer of amino acid residues from 1 to about 1735 amino acids from the carboxy terminus, or any combination of the above amino terminal and carboxy terminal deletions, of the complete amino acid sequence encoded by the cDNA clone contained in ATCC® Deposit No. PTA-627. Polynucleotides encoding all of the above deletion mutant polypeptide forms are also encompassed by the invention.

In additional embodiments, the polynucleotides of the invention encode functional attributes of THRAP. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of THRAP.

The data representing the structural or functional attributes of THRAP set forth in FIGS. 4A–4H and/or Table 7, as described above, was generated using the various modules and algorithms of the DNA*STAR set on default parameters. In a preferred embodiment, the data presented in columns VIII, IX, XIII, and XIV of Table 7 can be used to determine regions of THRAP which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response. The columns are labeled with the headings "Res", "Position", and Roman Numerals I–XIV. The column headings refer to the following features of the amino acid sequence presented in FIGS. 4A–H, and Table 7: "Res": amino acid residue of SEQ ID NO: 89 and FIGS. 4A–4H; "Position": position of the corresponding residue within SEQ ID NO: 89 and FIGS. 4A–4H; I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Hydrophobicity Plot—Hopp-Woods; X: Alpha, Amphipathic Regions—Eisenberg; XI: Beta, Amphipathic Regions—Eisenberg; XII: Flexible Regions—Karplus-Schulz; XIII: Antigenic Index—Jameson-Wolf; and XIV: Surface Probability Plot—Emini.

Certain preferred regions in these regards are set out in FIG. 6, but may, as shown in Table 7, be represented or identified by using tabular representations of the data presented in FIG. 6. The DNA*STAR computer algorithm used to generate FIG. 6 (set on the original default parameters) was used to present the data in FIG. 6 in a tabular format (See Table 7). The tabular format of the data in FIG. 6 may be used to easily determine specific boundaries of a preferred region.

The above-mentioned preferred regions set out in FIG. 6 and in Table 7 include, but are not limited to, regions of the aforementioned types identified by analysis of the amino acid sequence set out in FIGS. 4A–4H. As set out in FIG. 6 and in Table 7, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

Also preferred are THRAP polypeptide variants. For example, site directed changes at the amino acid level of THRAP (SEQ ID NO:89) can be made by replacing a particular amino acid with a conservative amino acid. Preferred conservative substitutions include: MI replaced with A, G, I, L, S, T, or V; E2 replaced with D; R5 replaced with H, or K; R6 replaced with H, or K; A7 replaced with G, I, L, S, T, M, or V; T8 replaced with A, G, I, L, S, M, or V; G10 replaced with A, I, L, S, T, M, or V; T11 replaced with A, G, I, L, S, M, or V; L12 replaced with A, G, I, S, T, M, or V; L13 replaced with A, G, I, S, T, M, or V; L14 replaced with A, G, I, S, T, M, or V; F15 replaced with W, or Y; L16 replaced with A, G, I, S, T, M, or V; A17 replaced with G, I, L, S, T, M, or V; F18 replaced with W, or Y; L19 replaced with A, G, I, S, T, M, or V; L20 replaced with A, G, I, S, T, M, or V; L21 replaced with A, G, I, S, T, M, or V; S22 replaced with A, G, I, L, T, M, or V; S23 replaced with A, G, I, L, T, M, or V; R24 replaced with H, or K; T25 replaced with A, G, I, L, S, M, or V; A26 replaced with G, I, L, S, T, M, or V; R27 replaced with H, or K; S28 replaced with A, G, I, L, T, M, or V; E29 replaced with D; E30 replaced with D; D31 replaced with E; R32 replaced with H, or K; D33 replaced with E; G34 replaced with A, I, L, S, T, M, or V; L35 replaced with A, G, I, S, T, M, or V; W36 replaced with F, or Y; D37 replaced with E; A38 replaced with G, I, L, S, T, M, or V; W39 replaced with F, or Y; G40 replaced with A, I, L, S, T, M, or V; W42 replaced with F, or Y; S43 replaced with A, G, I, L, T, M, or V; E44 replaced with D; S46 replaced with A, G, I, L, T, M, or V; R47 replaced with H, or K; T48 replaced with A, G, I, L, S, M, or V; G50 replaced with A, I, L, S, T, M, or V; G51 replaced with A, I, L, S, T, M, or V; G52 replaced with A, I, L, S, T, M, or V; A53 replaced with G, I, L, S, T, M, or V; S54 replaced with A, G, I, L, T, M, or V; Y55 replaced with F, or W; S56 replaced with A, G, I, L, T, M, or V; L57 replaced with A, G, I, S, T, M, or V; R58 replaced with H, or K; R59 replaced with H, or K; L61 replaced with A, G, I, S, T, M, or V; S62 replaced with A, G, I, L, T, M, or V; S63 replaced with A, G, I, L, T, M, or V; K64 replaced with H, or R; S65 replaced with A, G, I, L, T, M, or V; E67 replaced with D; G68 replaced with A, I, L, S, T, M, or V; R69 replaced with H, or K; N70 replaced with Q; I71 replaced with A, G, L, S, T, M, or V; R72 replaced with H, or K; Y73 replaced with F, or W; R74 replaced with H, or K; T75 replaced with A, G, I, L, S, M, or V; S77 replaced with A, G, I, L, T, M, or V; N78 replaced with Q; V79 replaced with A, G, I, L, S, T, or M; D80 replaced with E; E84 replaced with D; A85 replaced with G, I, L, S, T, M, or V; G86 replaced with A, I, L, S, T, M, or V; D87 replaced with E; F88 replaced with W, or Y; R89 replaced with H, or K; A90 replaced with G, I, L, S, T, M, or V; Q91 replaced with N; Q92 replaced with N; S94 replaced with A, G, I, L, T, M, or V; A95 replaced with G, I, L, S, T, M, or V; H96 replaced with K, or R; N97 replaced with Q; D98 replaced with E; V99 replaced with A, G, I, L, S, T, or M; K100 replaced with H, or R; H101 replaced with K, or R; H102 replaced with K, or R; G103 replaced with A, I, L, S, T, M, or V; Q104 replaced with N; F105 replaced with W, or Y; Y106 replaced with F, or W; E107 replaced with D; W108 replaced with F, or Y; L109 replaced with A, G, I, S, T, M, or V; V111 replaced with A, G, I, L, S, T, or M; S112 replaced with A, G, I, L, T, M, or V; N113 replaced with Q; D114 replaced with E; D116 replaced with E; N117 replaced with Q; S120 replaced with A, G, I, L, T, M, or V; L121 replaced with A, G, I, S, T, M, or V; K122 replaced with H, or R; Q124 replaced with N; A125 replaced with G, I, L, S, T, M, or V; K126 replaced with H, or R; G127 replaced with A, I, L, S, T, M, or V; T128 replaced with A, G, I, L, S, M, or V; T129 replaced with A, G, I, L, S, M, or V; L130 replaced with A, G, I, S, T, M, or V; V131 replaced with A, G, I, L, S, T, or M; V132 replaced with A, G, I, L, S, T, or M; E133 replaced with D; L134 replaced with A, G, I, S, T, M, or V; A135 replaced with G, I, L, S, T, M, or V; K137 replaced with H, or R; V138 replaced with A, G, I, L, S, T, or M; L139 replaced with A, G, I, S, T, M, or V; D140 replaced with E; G141 replaced with A, I, L, S, T, M, or V; T142 replaced with A, G, I, L, S, M, or V; R143 replaced with H, or K; Y145 replaced with F, or W; T146 replaced with A, G, I, L, S, M, or V; E147 replaced with D; S148 replaced with A, G, I, L, T, M, or V; L149 replaced with A, G, I, S, T, M, or V; D150 replaced with E; M151 replaced with A, G, I, L, S, T, or V; I153 replaced with A, G, L, S, T, M, or V; S154 replaced with A, G, I, L, T, M, or V; G155 replaced with A, I, L, S, T, M, or V; L156 replaced with A, G, I, S, T, M, or V; Q158 replaced with N; I159 replaced with A, G, L, S, T, M, or V; V160 replaced with A, G, I, L, S, T, or M; G161 replaced with A, I, L, S, T, M, or V; D 163 replaced with E; H 164 replaced with K, or R; Q165 replaced with N; L166 replaced with A, G, I, S, T, M, or V; G167 replaced with A, I, L, S, T, M, or V; S168 replaced with A, G, I, L, T, M, or V; T169 replaced with A, G, I, L, S, M, or V; V170 replaced with A, G, I, L, S, T, or M; K171 replaced with H, or R; E172 replaced with D; D173 replaced with E; N174 replaced with Q; G176 replaced with A, I, L, S, T, M, or V; V 177 replaced with A, G, I, L, S, T, or M; N179 replaced with Q; G180 replaced with A, I, L, S, T, M, or V; D181 replaced with E; G182 replaced with A, I, L, S, T, M, or V; S183 replaced with A, G, I, L, T, M, or V; T184 replaced with A, G, I, L, S, M, or V; R186 replaced with H, or K; L187 replaced with A, G, I, S, T, M, or V; V188 replaced with A, G, I, L, S, T, or M; R189 replaced with H, or K; G190 replaced with A, I, L, S, T, M, or V; Q191 replaced with N; Y192 replaced with F, or W; K193 replaced with H, or R; S194 replaced with A, G, I, L, T, M, or V; Q195 replaced with N; L196 replaced with A, G, I, S, T, M, or V; S197 replaced with A, G, I, L, T, M, or V; A198 replaced with G, I, L, S, T, M, or V; T199 replaced with A, G, I, L, S, M, or V; K200 replaced with H, or R; S201 replaced with A, G, I, L, T, M, or V; D202 replaced with E; D203 replaced with E; T204 replaced with A, G, I, L, S, M, or V; V205 replaced with A, G, I, L, S, T, or M; V206 replaced with A, G, I, L, S, T, or M; A207 replaced with G, I, L, S, T, M, or V; I208 replaced with A, G, L, S, T, M, or V; Y210 replaced with F, or W; G211 replaced with A, I, L, S, T, M, or V; S212 replaced with A, G, I, L, T, M, or V; R213 replaced with H, or K; H214 replaced with K, or R; I215 replaced with A, G, L, S, T, M, or V; R216 replaced with H, or K; L217 replaced with A, G, I, S, T, M, or V; V218 replaced with A, G, I, L, S, T, or M; L219 replaced with A, G, I, S, T, M, or V; K220 replaced with H, or R; G221 replaced with A, I, L, S, T, M, or V; D223 replaced with E; H224 replaced with K, or R; L225 replaced with A, G, I, S, T, M, or V; Y226 replaced with F, or W; L227 replaced with A, G, I, S, T, M, or V; E228 replaced with D; T229 replaced with A, G, I, L, S, M, or V; K230 replaced with H, or R; T231 replaced with A, G, I, L, S, M, or V; L232 replaced with A, G, I, S, T, M, or V; Q233 replaced with N; G234 replaced with A, I, L, S, T, M, or V; T235 replaced with A, G, I, L, S, M, or V; K236 replaced with H, or R; G237 replaced with A, I, L, S, T, M, or V; E238 replaced with D; N239 replaced with Q; S240 replaced with A, G, I, L, T, M, or V; L241 replaced with A, G, I, S, T, M, or V; S242 replaced with A, G, I, L, T, M, or V; S243 replaced with A, G, I, L, T, M, or V; T244 replaced with A, G, I, L, S, M, or V; G245 replaced with A, I, L, S, T, M, or V; T246 replaced with A, G, I, L, S, M, or V; F247 replaced with W, or Y; L248 replaced with A, G, I, S, T, M, or V; V249 replaced with A, G, I, L, S, T, or M; D250 replaced with E; N251 replaced with Q; S252 replaced with A, G, I, L, T, M, or V; S253 replaced with A, G, I, L, T, M, or V; V254 replaced with A, G, I, L, S, T, or M; D255 replaced with E; F256 replaced with W, or Y; Q257 replaced with N; K258 replaced with H, or R; F259 replaced with W, or Y; D261 replaced with E; K262 replaced with H, or R; E263 replaced with D; I264 replaced with A, G, L, S, T, M, or V; L265 replaced with A, G, I, S, T, M, or V; R266 replaced with H, or K; M267 replaced with A, G, I, L, S, T, or V; A268 replaced with G, I, L, S, T, M, or V; G269 replaced with A, I, L, S, T, M, or V; L271 replaced with A, G, I, S, T, M, or V; T272 replaced with A, G, I, L, S, M, or V; A273 replaced with G, I, L, S, T, M, or V; D274 replaced with E; F275 replaced with W, or Y; I276 replaced with A, G, L, S, T, M, or V; V277 replaced with A, G, I, L, S, T, or M; K278 replaced with H, or R; I279 replaced with A, G, L, S, T, M, or V; R280 replaced with H, or K; N281 replaced with Q; S282 replaced with A, G, I, L, T, M, or V; G283 replaced with A, I, L, S, T, M, or V; S284 replaced with A, G, I, L, T, M, or V; A285 replaced with G, I, L, S, T, M, or V; D286 replaced with E; S287 replaced with A, G, I, L, T, M, or V; T288 replaced with A, G, I, L, S, M, or V; V289 replaced with A, G, I, L, S, T, or M; Q290 replaced with N; F291 replaced with W, or Y; I292 replaced with A, G, L, S, T, M, or V; F293 replaced with W, or Y; Y294 replaced with F, or W; Q295 replaced with N; I297 replaced with A, G, L, S, T, M, or V; I298 replaced with A, G, L, S, T, M, or V; H299 replaced with K, or R; R300 replaced with H, or K; W301 replaced with F, or Y; R302 replaced with H, or K; E303 replaced with D; T304 replaced with A, G, I, L, S, M, or V; D305 replaced with E; F306 replaced with W, or Y; F307 replaced with W, or Y; S310 replaced with A, G, I, L, T, M, or V; A311 replaced with G, I, L, S, T, M, or V; T312 replaced with A, G, I, L, S, M, or V; G314 replaced with A, I, L, S, T, M, or V; G315 replaced with A, I, L, S, T, M, or V; G316 replaced with A, I, L, S, T, M, or V; Y317 replaced with F, or W; Q318 replaced with N; L319 replaced with A, G, I, S, T, M, or V; T320 replaced with A, G, I, L, S, M, or V; S321 replaced with A, G, I, L, T, M, or V; A322 replaced with G, I, L, S, T, M, or V; E323 replaced with D; Y325 replaced with F, or W; D326 replaced with E; L327 replaced with A, G, I, S, T, M, or V; R328 replaced with H, or K; S329 replaced with A, G, I, L, T, M, or V; N330 replaced with Q; R331 replaced with H, or K; V332 replaced with A, G, I, L, S, T, or M; V333 replaced with A, G, I, L, S, T, or M; A334 replaced with G, I, L, S, T, M, or V; D335 replaced with E; Q336 replaced with N; Y337 replaced with F, or W; H339 replaced with K, or R; Y340 replaced with F, or W; Y341 replaced with F, or W; E343 replaced with D; N344 replaced with Q; I345 replaced with A, G, L, S, T, M, or V; K346 replaced with H, or R; K348 replaced with H, or R; K350 replaced with H, or R; L351 replaced with A, G, I, S, T, M, or V; Q352 replaced with N; E353 replaced with D; N355 replaced with Q; L356 replaced with A, G, I, S, T, M, or V; D357 replaced with E; A361 replaced with G, I, L, S, T, M, or V; R362 replaced with H, or K; W363 replaced with F, or Y; E364 replaced with D; A365 replaced with G, I, L, S, T, M, or V; T366 replaced with A, G, I, L, S, M, or V; W368 replaced with F, or Y; T369 replaced with A, G, I, L, S, M, or V; A370 replaced with G, I, L, S, T, M, or V; S372 replaced with A, G, I, L, T, M, or V; S373 replaced with A, G, I, L, T, M, or V; S374 replaced with A, G, I, L, T, M, or V; G376 replaced with A, I, L, S, T, M, or V; G377 replaced with A, G, L, S, T, M, or V; G378 replaced with A, I, L, S, T, M, or V; I379 replaced with A, G, L, S, T, M, or V; Q380 replaced with N; S381 replaced with A, G, I, L, T, M, or V; R382 replaced with H, or K; A383 replaced with G, I, L, S, T, M, or V; V384 replaced with A, G, I, L, S, T, or M; S385 replaced with A, G, I, L, T, M, or V; V387 replaced with A, G, I, L, S, T, or M; E388 replaced with D; E389 replaced with D; D390 replaced with E; I391 replaced with A, G, L, S, T, M, or V; Q392 replaced with N; G393 replaced with A, I, L, S, T, M, or V; H394 replaced with K, or R; V395 replaced with A, G, I, L, S, T, or M; T396 replaced with A, G, I, L, S, M, or V; S397 replaced with A, G, I, L, T, M, or V; V398 replaced with A, G, I, L, S, T, or M; E399 replaced with D; E400 replaced with D; W401 replaced with F, or Y; K402 replaced with H, or R; M404 replaced with A, G, I, L, S, T, or V; Y405 replaced with F, or W; T406 replaced with A, G, I, L, S, M, or V; K408 replaced with H, or R; M409 replaced with A, G, I, L, S, T, or V; I411 replaced with A, G, L, S, T, M, or V; A412 replaced with G, I, L, S, T, M, or V; Q413 replaced with N; N416 replaced with Q; I417 replaced with A, G, L, S, T, M, or V; F418 replaced with W, or Y; D419 replaced with E; K422 replaced with H, or R; W423 replaced with F, or Y; L424 replaced with A, G, I, S, T, M, or V; A425 replaced with G, I, L, S, T, M, or V; Q426 replaced with N; E427 replaced with D; W428 replaced with F, or Y; S429 replaced with A, G, I, L, T, M, or V; T432 replaced with A, G, I, L, S, M, or V; V433 replaced with A, G, I, L, S, T, or M; T434 replaced with A, G, I, L, S, M, or V; G436 replaced with A, I, L, S, T, M, or V; Q437 replaced with N; G438 replaced with A, I, L, S, T, M, or V; L439 replaced with A, G, I, S, T, M, or V; R440 replaced with H, or K; Y441 replaced with F, or W; R442 replaced with H, or K; V443 replaced with A, G, I, L, S, T, or M; V444 replaced with A, G, I, L, S, T, or M; L445 replaced with A, G, I, S, T, M, or V; I447 replaced with A, G, L, S, T, M, or V; D448 replaced with E; H449 replaced with K, or R; R450 replaced with H, or K; G451 replaced with A, I, L, S, T, M, or V; M452 replaced with A, G, I, L, S, T, or V; H453 replaced with K, or R; T454 replaced with A, G, I, L, S, M, or V; G455 replaced with A, I, L, S, T, M, or V; G456 replaced with A, I, L, S, T, M, or V; S458 replaced with A, G, I, L, T, M, or V; K460 replaced with H, or R; T461 replaced with A, G, I, L, S, M, or V; K462 replaced with H, or R; H464 replaced with K, or R; I465 replaced with A, G, L, S, T, M, or V; K466 replaced with H, or R; E467 replaced with D; E468 replaced with D; I470 replaced with A, G, L, S, T, M, or V; V471 replaced with A, G, I, L, S, T, or M; T473 replaced with A, G, I, L, S, M, or V; Y476 replaced with F, or W; K477 replaced with H, or R; K479 replaced with H, or R; E480 replaced with D; K481 replaced with H, or R; L482 replaced with A, G, I, S, T, M, or V; V484 replaced with A, G, I, L, S, T, or M; E485 replaced with D; A486 replaced with G, I, L, S, T, M, or V; K487 replaced with H, or R; L488 replaced with A, G, I, S, T, M, or V; W490 replaced with F, or Y; F491 replaced with W, or Y; K492 replaced with H, or R; Q493 replaced with N; A494 replaced with G, I, L, S, T, M, or V; Q495 replaced with N; E496 replaced with D; L497 replaced with A, G, I, S, T, M, or V; E498 replaced with D; E499 replaced with D; G500 replaced with A, I, L, S, T, M, or V; A501 replaced with G, I, L, S, T, M, or V; A502 replaced with G, I, L, S, T, M, or V; V503 replaced with A, G, I, L, S, T, or M; S504 replaced with A, G, I, L, T, M, or V; E505 replaced with D; E506 replaced with D; S508 replaced with A, G, I, L, T, M, or V; F509 replaced with W, or Y; I510 replaced with A, G, L, S, T, M, or V; K512 replaced with H, or R; A513 replaced with G, I, L, S, T, M, or V; W514 replaced with F, or Y; S515 replaced with A, G, I, L, T, M, or V; A516 replaced with G, I, L, S, T, M, or V; T518 replaced with A, G, I, L, S, M, or V; V519 replaced with A, G, I, L, S, T, or M; T520 replaced with A, G, I, L, S, M, or V; G522 replaced with A, I, L, S, T, M, or V; V523 replaced with A, G, I, L, S, T, or M; G524 replaced with A, I, L, S, T, M, or V; T525 replaced with A, G, I, L, S, M, or V; Q526 replaced with N; V527 replaced with A, G, I, L, S, T, or M; R528 replaced with H, or K; I529 replaced with A, G, L, S, T, M, or V; V530 replaced with A, G, I, L, S, T, or M; R531 replaced with H, or K; Q533 replaced with N; V534 replaced with A, G, I, L, S, T, or M; L535 replaced with A, G, I, S, T, M, or V; L536 replaced with A, G, I, S, T, M, or V; S537 replaced with A, G, I, L, T, M, or V; F538 replaced with W, or Y; S539 replaced with A, G, I, L, T, M, or V; Q540 replaced with N; S541 replaced with A, G, I, L, T, M, or V; V542 replaced with A, G, I, L, S, T, or M; A543 replaced with G, I, L, S, T, M, or V; D544 replaced with E; L545 replaced with A, G, I, S, T, M, or V; I547 replaced with A, G, L, S, T, M, or V; D548 replaced with E; E549 replaced with D; E551 replaced with D; G552 replaced with A, I, L, S, T, M, or V; K554 replaced with H, or R; A556 replaced with G, I, L, S, T, M, or V; S557 replaced with A, G, I, L, T, M, or V; Q558 replaced with N; R559 replaced with H, or K; A560 replaced with G, I, L, S, T, M, or V; Y562 replaced with F, or W; A563 replaced with G, I, L, S, T, M, or V; G564 replaced with A, I, L, S, T, M, or V; S567 replaced with A, G, I, L, T, M, or V; G568 replaced with A, I, L, S, T, M, or V; E569 replaced with D; I570 replaced with A, G, L, S, T, M, or V; E572 replaced with D; F573 replaced with W, or Y; N574 replaced with Q; D576 replaced with E; E577 replaced with D; T578 replaced with A, G, I, L, S, M, or V; D579 replaced with E; G580 replaced with A, I, L, S, T, M, or V; L581 replaced with A, G, I, S, T, M, or V; F582 replaced with W, or Y; G583 replaced with A, I, L, S, T, M, or V; G584 replaced with A, I, L, S, T, M, or V; L585 replaced with A, G, I, S, T, M, or V; Q586 replaced with N; D587 replaced with E; F588 replaced with W, or Y; D589 replaced with E; E590 replaced with D; L591 replaced with A, G, I, S, T, M, or V; Y592 replaced with F, or W; D593 replaced with E; W594 replaced with F, or Y; E595 replaced with D; Y596 replaced with F, or W; E597 replaced with D; G598 replaced with A, I, L, S, T, M, or V; F599 replaced with W, or Y; T600 replaced with A, G, I, L, S, M, or V; K601 replaced with H, or R; S603 replaced with A, G, I, L, T, M, or V; E604 replaced with D; S605 replaced with A, G, I, L, T, M, or V; G607 replaced with A, I, L, S, T, M, or V; G608 replaced with A, I, L, S, T, M, or V; G609 replaced with A, I, L, S, T, M, or V; V610 replaced with A, G, I, L, S, T, or M; Q611 replaced with N; E612 replaced with D; A613 replaced with G, I, L, S, T, M, or V; V614 replaced with A, G, I, L, S, T, or M; V615 replaced with A, G, I, L, S, T, or M; S616 replaced with A, G, I, L, T, M, or V; L618 replaced with A, G, I, S, T, M, or V; N619 replaced with Q; K620 replaced with H, or R; Q621 replaced with N; T622 replaced with A, G, I, L, S, M, or V; R623 replaced with H, or K; E624 replaced with D; A626 replaced with G, I, L, S, T, M, or V; E627 replaced with D; E628 replaced with D; N629 replaced with Q; L630 replaced with A, G, I, S, T, M, or V; V632 replaced with A, G, I, L, S, T, or M; T633 replaced with A, G, I, L, S, M, or V; S634 replaced with A, G, I, L, T, M, or V; R635 replaced with H, or K; R636 replaced with H, or K; Q639 replaced with N; L640 replaced with A, G, I, S, T, M, or V; L641 replaced with A, G, I, S, T, M, or V; K642 replaced with H, or R; S643 replaced with A, G, I, L, T, M, or V; N645 replaced with Q; L646 replaced with A, G, I, S, T, M, or V; D647 replaced with E; A651 replaced with G, I, L, S, T, M, or V; R652 replaced with H, or K; W653 replaced with F, or Y; E654 replaced with D; I655 replaced with A, G, L, S, T, M, or V; G656 replaced with A, I, L, S, T, M, or V; K657 replaced with H, or R; W658 replaced with F, or Y; S659 replaced with A, G, I, L, T, M, or V; S662 replaced with A, G, I, L, T, M, or V; L663 replaced with A, G, I, S, T, M, or V; T664 replaced with A, G, I, L, S, M, or V; G666 replaced with A, I, L, S, T, M, or V; V667 replaced with A, G, I, L, S, T, or M; G668 replaced with A, I, L, S, T, M, or V; L669 replaced with A, G, I, S, T, M, or V; Q670 replaced with N; T671 replaced with A, G, I, L, S, M, or V; R672 replaced with H, or K; D673 replaced with E; V674 replaced with A, G, I, L, S, T, or M; F675 replaced with W, or Y; S677 replaced with A, G, I, L, T, M, or V; H678 replaced with K, or R; L679 replaced with A, G, I, S, T, M, or V; L680 replaced with A, G, I, S, T, M, or V; S681 replaced with A, G, I, L, T, M, or V; R682 replaced with H, or K; E683 replaced with D; M684 replaced with A, G, I, L, S, T, or V; N685 replaced with Q; E686 replaced with D; T687 replaced with A, G, I, L, S, M, or V; V688 replaced with A, G, I, L, S, T, or M; I689 replaced with A, G, L, S, T, M, or V; L690 replaced with A, G, I, S, T, M, or V; A691 replaced with G, I, L, S, T, M, or V; D692 replaced with E; E693 replaced with D; L694 replaced with A, G, I, S, T, M, or V; R696 replaced with H, or K; Q697 replaced with N; K699 replaced with H, or R; S701 replaced with A, G, I, L, T, M, or V; T702 replaced with A, G, I, L, S, M, or V; V703 replaced with A, G, I, L, S, T, or M; Q704 replaced with N; A705 replaced with G, I, L, S, T, M, or V; N707 replaced with Q; R708 replaced with H, or K; F709 replaced with W, or Y; N710 replaced with Q; A714 replaced with G, I, L, S, T, M, or V; W715 replaced with F, or Y; Y716 replaced with F, or W; A718 replaced with G, I, L, S, T, M, or V; Q719 replaced with N; W720 replaced with F, or Y; Q721 replaced with N; S724 replaced with A, G, I, L, T, M, or V; R725 replaced with H, or K; T726 replaced with A, G, I, L, S, M, or V; G728 replaced with A, I, L, S, T, M, or V; G729 replaced with A, I, L, S, T, M, or V; G730 replaced with A, I, L, S, T, M, or V; V731 replaced with A, G, I, L, S, T, or M; Q732 replaced with N; K733 replaced with H, or R; R734 replaced with H, or K; E735 replaced with D; V736 replaced with A, G, I, L, S, T, or M; L737 replaced with A, G, I, S, T, M, or V; K739 replaced with H, or R; Q740 replaced with N; R741 replaced with H, or K; M742 replaced with A, G, I, L, S, T, or V; A743 replaced with G, I, L, S, T, M, or V; D744 replaced with E; G745 replaced with A, I, L, S, T, M, or V; S746 replaced with A, G, I, L, T, M, or V; F747 replaced with W, or Y; L748 replaced with A, G, I, S, T, M, or V; E749 replaced with D; L750 replaced with A, G, I, S, T, M, or V; E752 replaced with D; T753 replaced with A, G, I, L, S, M, or V; F754 replaced with W, or Y; S756 replaced with A, G, I, L, T, M, or V; A757 replaced with G, I, L, S, T, M, or V; S758 replaced with A, G, I, L, T, M, or V; K759 replaced with H, or R; A761 replaced with G, I, L, S, T, M, or V; Q763 replaced with N; Q764 replaced with N; A765 replaced with G, I, L, S, T, M, or V; K767 replaced with H, or R; K768 replaced with H, or R; D769 replaced with E; D770 replaced with E; S773 replaced with A, G, I, L, T, M, or V; E774 replaced with D; W775 replaced with F, or Y; L776 replaced with A, G, I, S, T, M, or V; L777 replaced with A, G, I, S, T, M, or V; S778 replaced with A, G, I, L, T, M, or V; D779 replaced with E; W780 replaced with F, or Y; T781 replaced with A, G, I, L, S, M, or V; E782 replaced with D; S784 replaced with A, G, I, L, T, M, or V; T785 replaced with A, G, I, L, S, M, or V; S786 replaced with A, G, I, L, T, M, or V; G788 replaced with A, I, L, S, T, M, or V; E789 replaced with D; G790 replaced with A, I, L, S, T, M, or V; T791 replaced with A, G, I, L, S, M, or V; Q792 replaced with N; T793 replaced with A, G, I, L, S, M, or V; R794 replaced with H, or K; S795 replaced with A, G, I, L, T, M, or V; A796 replaced with G, I, L, S, T, M, or V; I797 replaced with A, G, L, S, T, M, or V; R799 replaced with H, or K; K800 replaced with H, or R. M801 replaced with A, G, I, L, S, T, or V; L802 replaced with A, G, I, S, T, M, or V; K803 replaced with H, or R; T804 replaced with A, G, I, L, S, M, or V; G805 replaced with A, I, L, S, T, M, or V; L806 replaced with A, G, I, S, T, M, or V; S807 replaced with A, G, I, L, T, M, or V; T808 replaced with A, G, I, L, S, M, or V; V809 replaced with A, G, I, L, S, T, or M; V810 replaced with A, G, I, L, S, T, or M; N811 replaced with Q; S812 replaced with A, G, I, L, T, M, or V; T813 replaced with A, G, I, L, S, M, or V; L814 replaced with A, G, I, S, T, M, or V; L818 replaced with A, G, I, S, T, M, or V; F820 replaced with W, or Y; S821 replaced with A, G, I, L, T, M, or V; S822 replaced with A, G, I, L, T, M, or V; S823 replaced with A, G, I, L, T, M, or V; I824 replaced with A, G, L, S, T, M, or V; R825 replaced with H, or K; M828 replaced with A, G, I, L, S, T, or V; L829 replaced with A, G, I, S, T, M, or V; A830 replaced with G, I, L, S, T, M, or V; T831 replaced with A, G, I, L, S, M, or V; A833 replaced with G, I, L, S, T, M, or V; R834 replaced with H, or K; G836 replaced with A, I, L, S, T, M, or V; R837 replaced with H, or K; S839 replaced with A, G, I, L, T, M, or V; T840 replaced with A, G, I, L, S, M, or V; K841 replaced with H, or R; H842 replaced with K, or R; S843 replaced with A, G, I, L, T, M, or V; H845 replaced with K, or R; I846 replaced with A, G, L, S, T, M, or V; A847 replaced with G, I, L, S, T, M, or V; A848 replaced with G, I, L, S, T, M, or V; A849 replaced with G, I, L, S, T, M, or V; R850 replaced with H, or K; K851 replaced with H, or R; V852 replaced with A, G, I, L, S, T, or M; Y853 replaced with F, or W; I854 replaced with A, G, L, S, T, M, or V; Q855 replaced with N; T856 replaced with A, G, I, L, S, M, or V; R857 replaced with H, or K; R858 replaced with H, or K; Q859 replaced with N; R860 replaced with H, or K; K861 replaced with H, or R; L862 replaced with A, G, I, S, T, M, or V; H863 replaced with K, or R; F864 replaced with W, or Y; V865 replaced with A, G, I, L, S, T, or M; V866 replaced with A, G, I, L, S, T, or M; G867 replaced with A, I, L, S, T, M, or V; G868 replaced with A, I, L, S, T, M, or V; F869 replaced with W, or Y; A870 replaced with G, I, L, S, T, M, or V; Y871 replaced with F, or W; L872 replaced with A, G, I, S, T, M, or V; L873 replaced with A, G, I, S, T, M, or V; K875 replaced with H, or R; T876 replaced with A, G, I, L, S, M, or V; A877 replaced with G, I, L, S, T, M, or V; V878 replaced with A, G, I, L, S, T, or M; V879 replaced with A, G, I, L, S, T, or M; L880 replaced with A, G, I, S, T, M, or V; R881 replaced with H, or K; A884 replaced with G, I, L, S, T, M, or V; R885 replaced with H, or K; R886 replaced with H, or K; V887 replaced with A, G, I, L, S, T, or M; R888 replaced with H, or K; K889 replaced with H, or R; L891 replaced with A, G, I, S, T, M, or V; I892 replaced with A, G, L, S, T, M, or V; T893 replaced with A, G, I, L, S, M, or V; W894 replaced with F, or Y; E895 replaced with D; K896 replaced with H, or R; D897 replaced with E; G898 replaced with A, I, L, S, T, M, or V; Q899 replaced with N; H900 replaced with K, or R; L901 replaced with A, G, I, S, T, M, or V; I902 replaced with A, G, L, S, T, M, or V; S903 replaced with A, G, I, L, T, M, or V; S904 replaced with A, G, I, L, T, M, or V; T905 replaced with A, G, I, L, S, M, or V; H906 replaced with K, or R; V907 replaced with A, G, I, L, S, T, or M; T908 replaced with A, G, I, L, S, M, or V; V909 replaced with A, G, I, L, S, T, or M; A910 replaced with G, I, L, S, T, M, or V; F912 replaced with W, or Y; G913 replaced with A, I, L, S, T, M, or V; Y914 replaced with F, or W; L915 replaced with A, G, I, S, T, M, or V; K916 replaced with H, or R; I917 replaced with A, G, L, S, T, M, or V; H918 replaced with K, or R; R919 replaced with H, or K; L920 replaced with A, G, I, S, T, M, or V; K921 replaced with H, or R; S923 replaced with A, G, I, L, T, M, or V; D924 replaced with E; A925 replaced with G, I, L, S, T, M, or V; G926 replaced with A, I, L, S, T, M, or V; V927 replaced with A, G, I, L, S, T, or M; Y928 replaced with F, or W; T929 replaced with A, G, I, L, S, M, or V; S931 replaced with A, G, I, L, T, M, or V; A932 replaced with G, I, L, S, T, M, or V; G933 replaced with A, I, L, S, T, M, or V; A935 replaced with G, I, L, S, T, M, or V; R936 replaced with H, or K; E937 replaced with D; H938 replaced with K, or R; F939 replaced with W, or Y; V940 replaced with A, G, I, L, S, T, or M; I941 replaced with A, G, L, S, T, M, or V; K942 replaced with H, or R; L943 replaced with A, G, I, S, T, M, or V; I944 replaced with A, G, L, S, T, M, or V; G945 replaced with A, I, L, S, T, M, or V; G946 replaced with A, I, L, S, T, M, or V; N947 replaced with Q; R948 replaced with H, or K; K949 replaced with H, or R; L950 replaced with A, G, I, S, T, M, or V; V951 replaced with A, G, I, L, S, T, or M; A952 replaced with G, I, L, S, T, M, or V; R953 replaced with H, or K; L955 replaced with A, G, I, S, T, M, or V; S956 replaced with A, G, I, L, T, M, or V; R958 replaced with H, or K; S959 replaced with A, G, I, L, T, M, or V; E960 replaced with D; E961 replaced with D; E962 replaced with D; V963 replaced with A, G, I, L, S, T, or M; L964 replaced with A, G, I, S, T, M, or V; A965 replaced with G, I, L, S, T, M, or V; G966 replaced with A, I, L, S, T, M, or V; R967 replaced with H, or K; K968 replaced with H, or R; G969 replaced with A, I, L, S, T, M, or V; G970 replaced with A, I, L, S, T, M, or V; K972 replaced with H, or R; E973 replaced with D; A974 replaced with G, I, L, S, T, M, or V; L975 replaced with A, G, I, S, T, M, or V; Q976 replaced with N; T977 replaced with A, G, I, L, S, M, or V; H978 replaced with K, or R; K979 replaced with H, or R; H980 replaced with K, or R; Q981 replaced with N; N982 replaced with Q; G983 replaced with A, I, L, S, T, M, or V; I984 replaced with A, G, L, S, T, M, or V; F985 replaced with W, or Y; S986 replaced with A, G, I, L, T, M, or V; N987 replaced with Q; G988 replaced with A, I, L, S, T, M, or V; S989 replaced with A, G, I, L, T, M, or V; K990 replaced with H, or R; A991 replaced with G, I, L, S, T, M, or V; E992 replaced with D; K993 replaced with H, or R; R994 replaced with H, or K; G995 replaced with A, I, L, S, T, M, or V; L996 replaced with A, G, I, S, T, M, or V; A997 replaced with G, I, L, S, T, M, or V; A998 replaced with G, I, L, S, T, M, or V; N999 replaced with Q; G1001 replaced with A, I, L, S, T, M, or V; S1002 replaced with A, G, I, L, T, M, or V; R1003 replaced with H, or K; Y1004 replaced with F, or W; D1005 replaced with E; D1006 replaced with E; L 1007 replaced with A, G, I, S, T, M, or V; V1008 replaced with A, G, I, L, S, T, or M; S1009 replaced with A, G, I, L, T, M, or V; R1010 replaced with H, or K; L1011 replaced with A, G, I, S, T, M, or V; L1012 replaced with A, G, I, S, T, M, or V; E1013 replaced with D; Q1014 replaced with N; G1015 replaced with A, I, L, S, T, M, or V; G1016 replaced with A, I, L, S, T, M, or V; W1017 replaced with F, or Y; G1019 replaced with A, I, L, S, T, M, or V; E1020 replaced with D; L1021 replaced with A, G, I, S, T, M, or V; L1022 replaced with A, G, I, S, T, M, or V; A1023 replaced with G, I, L, S, T, M, or V; S1024 replaced with A, G, I, L, T, M, or V; W1025 replaced with F, or Y; E1026 replaced with D; A1027 replaced with G, I, L, S, T, M, or V; Q1028 replaced with N; D1029 replaced with E; S1030 replaced with A, G, I, L, T, M, or V; A1031 replaced with G, I, L, S, T, M, or V; E1032 replaced with D; R1033 replaced with H, or K; N1034 replaced with Q; T1035 replaced with A, G, I, L, S, M, or V; T1036 replaced with A, G, I, L, S, M, or V; S1037 replaced with A, G, I, L, T, M, or V; E1038 replaced with D; E1039 replaced with D; D1040 replaced with E; G1042 replaced with A, I, L, S, T, M, or V; A1043 replaced with G, I, L, S, T, M, or V; E1044 replaced with D; Q1045 replaced with N; V1046 replaced with A, G, I, L, S, T, or M; L1047 replaced with A, G, I, S, T, M, or V; L1048 replaced with A, G, I, S, T, M, or V; H1049 replaced with K, or R; L1050 replaced with A, G, I, S, T, M, or V; F1052 replaced with W, or Y; T1053 replaced with A, G, I, L, S, M, or V; M1054 replaced with A, G, I, L, S, T, or V; V 1055 replaced with A, G, I, L, S, T, or M; T1056 replaced with A, G, I, L, S, M, or V; E1057 replaced with D; Q1058 replaced with N; R1059 replaced with H, or K; R1060 replaced with H, or K; L1061 replaced with A, G, I, S, T, M, or V; D1062 replaced with E; D1063 replaced with E; I1064 replaced with A, G, L, S, T, M, or V; L1065 replaced with A, G, I, S, T, M, or V; G1066 replaced with A, I, L, S, T, M, or V; N1067 replaced with Q; L1068 replaced with A, G, I, S, T, M, or V; S1069 replaced with A, G, I, L, T, M, or V; Q1070 replaced with N; Q1071 replaced with N; E1073 replaced with D; E1074 replaced with D; L1075 replaced with A, G, I, S, T, M, or V; R1076 replaced with H, or K; D1077 replaced with E; L1078 replaced with A, G, I, S, T, M, or V; Y1079 replaced with F, or W; S1080 replaced with A, G, I, L, T, M, or V; K1081 replaced with H, or R; H1082 replaced with K, or R; L1083 replaced with A, G, I, S, T, M, or V; V1084 replaced with A, G, I, L, S, T, or M; A1085 replaced with G, I, L, S, T, M, or V; Q1086 replaced with N; L1087 replaced with A, G, I, S, T, M, or V; A1088 replaced with G, I, L, S, T, M, or V; Q1089 replaced with N; E1090 replaced with D; I1091 replaced with A, G, L, S, T, M, or V; F1092 replaced with W, or Y; R1093 replaced with H, or K; S1094 replaced with A, G, I, L, T, M, or V; H1095 replaced with K, or R; L1096 replaced with A, G, I, S, T, M, or V; E1097 replaced with D; H1098 replaced with K, or R; Q1099 replaced with N; D1100 replaced with E; T1101 replaced with A, G, I, L, S, M, or V; L1102 replaced with A, G, I, S, T, M, or V; L1103 replaced with A, G, I, S, T, M, or V; K1104 replaced with H, or R; S1106 replaced with A, G, I, L, T, M, or V; E1107 replaced with D; R1108 replaced with H, or K; R 1109 replaced with H, or K; T1110 replaced with A, G, I, L, S, M, or V; S1111 replaced with A, G, I, L, T, M, or V; V1113 replaced with A, G, I, L, S, T, or M; T1114 replaced with A, G, I, L, S, M, or V; L1115 replaced with A, G, I, S, T, M, or V; S1116 replaced with A, G, I, L, T, M, or V; H1118 replaced with K, or R; K1119 replaced with H, or R; H1120 replaced with K, or R; V1121 replaced with A, G, I, L, S, T, or M; S1122 replaced with A, G, I, L, T, M, or V; G1123 replaced with A, I, L, S, T, M, or V; F1124 replaced with W, or Y; S1125 replaced with A, G, I, L, T, M, or V; S1126 replaced with A, G, I, L, T, M, or V; S1127 replaced with A, G, I, L, T, M, or V; L1128 replaced with A, G, I, S, T, M, or V; R1129 replaced with H, or K; T1130 replaced with A, G, I, L, S, M, or V; S1131 replaced with A, G, I, L, T, M, or V; S1132 replaced with A, G, I, L, T, M, or V; T1133 replaced with A, G, I, L, S, M, or V; G1134 replaced with A, I, L, S, T, M, or V; D1135 replaced with E; A1136 replaced with G, I, L, S, T, M, or V; G1137 replaced with A, I, L, S, T, M, or V; G1138 replaced with A, I, L, S, T, M, or V; G1139 replaced with A, I, L, S, T, M, or V; S1140 replaced with A, G, I, L, T, M, or V; R1141 replaced with H, or K; R1142 replaced with H, or K; H1144 replaced with K, or R; R1145 replaced with H, or K; K1146 replaced with H, or R; T1148 replaced with A, G, I, L, S, M, or V; I1149 replaced with A, G, L, S, T, M, or V; L1150 replaced with A, G, I, S, T, M, or V; R1151 replaced with H, or K; K1152 replaced with H, or R; I1153 replaced with A, G, L, S, T, M, or V; S1154 replaced with A, G, I, L, T, M, or V; A1155 replaced with G, I, L, S, T, M, or V; A1156 replaced with G, I, L, S, T, M, or V; Q1157 replaced with N; Q1158 replaced with N; L1159 replaced with A, G, I, S, T, M, or V; S1160 replaced with A, G, I, L, T, M, or V; A1161 replaced with G, I, L, S, T, M, or V; S1162 replaced with A, G, I, L, T, M, or V; E1163 replaced with D; V1164 replaced with A, G, I, L, S, T, or M; V1165 replaced with A, G, I, L, S, T, or M; T1166 replaced with A, G, I, L, S, M, or V; H1167 replaced with K, or R; L1168 replaced with A, G, I, S, T, M, or V; G1169 replaced with A, I, L, S, T, M, or V; Q1170 replaced with N; T1171 replaced with A, G, I, L, S, M, or V; V1172 replaced with A, G, I, L, S, T, or M; A1173 replaced with G, I, L, S, T, M, or V; L1174 replaced with A, G, I, S, T, M, or V; A1175 replaced with G, I, L, S, T, M, or V; S1176 replaced with A, G, I, L, T, M, or V; G1177 replaced with A, I, L, S, T, M, or V; T1178 replaced with A, G, I, L, S, M, or V; L1179 replaced with A, G, I, S, T, M, or V; S1180 replaced with A, G, I, L, T, M, or V; V 1181 replaced with A, G, I, L, S, T, or M; L1182 replaced with A, G, I, S, T, M, or V; L1183 replaced with A, G, I, S, T, M, or V; H1184 replaced with K, or R; E1186 replaced with D; A1187 replaced with G, I, L, S, T, M, or V; I1188 replaced with A, G, L, S, T, M, or V; G1189 replaced with A, I, L, S, T, M, or V; H1190 replaced with K, or R; R1192 replaced with H, or K; T1194 replaced with A, G, I, L, S, M, or V; I1195 replaced with A, G, L, S, T, M, or V; S1196 replaced with A, G, I, L, T, M, or V; W1197 replaced with F, or Y; A1198 replaced with G, I, L, S, T, M, or V; R1199 replaced with H, or K; N1200 replaced with Q; G1201 replaced with A, I, L, S, T, M, or V; E1202 replaced with D; E1203 replaced with D; V1204 replaced with A, G, I, L, S, T, or M; Q1205 replaced with N; F1206 replaced with W, or Y; S1207 replaced with A, G, I, L, T, M, or V; D1208 replaced with E; R1209 replaced with H, or K; I1210 replaced with A, G, L, S, T, M, or V; L1211 replaced with A, G, I, S, T, M, or V; L1212 replaced with A, G, I, S, T, M, or V; Q1213 replaced with N; D1215 replaced with E; D1216 replaced with E; S1217 replaced with A, G, I, L, T, M, or V; L1218 replaced with A, G, I, S, T, M, or V; Q1219 replaced with N; I1220 replaced with A, G, L, S, T, M, or V; L1221 replaced with A, G, I, S, T, M, or V; A1222 replaced with G, I, L, S, T, M, or V; V1224 replaced with A, G, I, L, S, T, or M; E1225 replaced with D; A1226 replaced with G, I, L, S, T, M, or V; D1227 replaced with E; V1228 replaced with A, G, I, L, S, T, or M; G1229 replaced with A, I, L, S, T, M, or V; F1230 replaced with W, or Y; Y1231 replaced with F, or W; T1232 replaced with A, G, I, L, S, M, or V; N1234 replaced with Q; A1235 replaced with G, I, L, S, T, M, or V; T1236 replaced with A, G, I, L, S, M, or V; N1237 replaced with Q; A1238 replaced with G, I, L, S, T, M, or V; L1239 replaced with A, G, I, S, T, M, or V; G1240 replaced with A, I, L, S, T, M, or V; Y1241 replaced with F, or W; D1242 replaced with E; S1243 replaced with A, G, I, L, T, M, or V; V1244 replaced with A, G, I, L, S, T, or M; S1245 replaced with A, G, I, L, T, M, or V; I1246 replaced with A, G, L, S, T, M, or V; A1247 replaced with G, I, L, S, T, M, or V; V1248 replaced with A, G, I, L, S, T, or M; T1249 replaced with A, G, I, L, S, M, or V; L1250 replaced with A, G, I, S, T, M, or V; A1251 replaced with G, I, L, S, T, M, or V; G1252 replaced with A, I, L, S, T, M, or V; K1253 replaced with H, or R; L1255 replaced with A, G, I, S, T, M, or V; V1256 replaced with A, G, I, L, S, T, or M; K1257 replaced with H, or R; T1258 replaced with A, G, I, L, S, M, or V; S1259 replaced with A, G, I, L, T, M, or V; R1260 replaced with H, or K; M1261 replaced with A, G, I, L, S, T, or V; T1262 replaced with A, G, I, L, S, M, or V; V1263 replaced with A, G, I, L, S, T, or M; I1264 replaced with A, G, L, S, T, M, or V; N1265 replaced with Q; T1266 replaced with A, G, I, L, S, M, or V; E1267 replaced with D; K1268 replaced with H, or R; A1270 replaced with G, I, L, S, T, M, or V; V1271 replaced with A, G, I, L, S, T, or M; T1272 replaced with A, G, I, L, S, M, or V; V1273 replaced with A, G, I, L, S, T, or M; D1274 replaced with E; I1275 replaced with A, G, L, S, T, M, or V; G1276 replaced with A, I, L, S, T, M, or V; S1277 replaced with A, G, I, L, T, M, or V; T1278 replaced with A, G, I, L, S, M, or V; I1279 replaced with A, G, L, S, T, M, or V; K1280 replaced with H, or R; T1281 replaced with A, G, I, L, S, M, or V; V1282 replaced with A, G, I, L, S, T, or M; Q1283 replaced with N; G1284 replaced with A, I, L, S, T, M, or V; V1285 replaced with A, G, I, L, S, T, or M; N1286 replaced with Q; V1287 replaced with A, G, I, L, S, T, or M; T1288 replaced with A, G, I, L, S, M, or V; I1289 replaced with A, G, L, S, T, M, or V; N1290 replaced with Q; Q1292 replaced with N; V1293 replaced with A, G, I, L, S, T, or M; A1294 replaced with G, I, L, S, T, M, or V; G1295 replaced with A, I, L, S, T, M, or V; V1296 replaced with A, G, I, L, S, T, or M; E1298 replaced with D; A1299 replaced with G, I, L, S, T, M; or V; E1300 replaced with D; V1301 replaced with A, G, I, L, S, T, or M; T1302 replaced with A, G, I, L, S, M, or V; W1303 replaced with F, or Y; F1304 replaced with W, or Y; R1305 replaced with H, or K; N1306 replaced with Q; K1307 replaced with H, or R; S1308 replaced with A, G, I, L, T, M, or V; K1309 replaced with H, or R; L1310 replaced with A, G, I, S, T, M, or V; G1311 replaced with A, I, L, S, T, M, or V; S1312 replaced with A, G, I, L, T, M, or V; H1314 replaced with K, or R; H1315 replaced with K, or R; L1316 replaced with A, G, I, S, T, M, or V; H1317 replaced with K, or R; E1318 replaced with D; G1319 replaced with A, I, L, S, T, M, or V; S1320 replaced with A, G, I, L, T, M, or V; L1321 replaced with A, G, I, S, T, M, or V; L1322 replaced with A, G, I, S, T, M, or V; L1323 replaced with A, G, I, S, T, M, or V; T1324 replaced with A, G, I, L, S, M, or V; N1325 replaced with Q; V1326 replaced with A, G, I, L, S, T, or M; S1327 replaced with A, G, I, L, T, M, or V; S1328 replaced with A, G, I, L, T, M, or V; S1329 replaced with A, G, I, L, T, M, or V; D1330 replaced with E; Q1331 replaced with N; G1332 replaced with A, I, L, S, T, M, or V; L1333 replaced with A, G, I, S, T, M, or V; Y1334 replaced with F, or W; S1335 replaced with A, G, I, L, T, M, or V; R1337 replaced with H, or K; A1338 replaced with G, I, L, S, T, M, or V; A1339 replaced with G, I, L, S, T, M, or V; N1340 replaced with Q; L1341 replaced with A, G, I, S, T, M, or V; H1342 replaced with K, or R; G1343 replaced with A, I, L, S, T, M, or V; E1344 replaced with D; L1345 replaced with A, G, I, S, T, M, or V; T1346 replaced with A, G, I, L, S, M, or V; E1347 replaced with D; S1348 replaced with A, G, I, L, T, M, or V; T1349 replaced with A, G, I, L, S, M, or V; Q1350 replaced with N; L1351 replaced with A, G, I, S, T, M, or V; L1352 replaced with A, G, I, S, T, M, or V; I1353 replaced with A, G, L, S, T, M, or V; L1354 replaced with A, G, I, S, T, M, or V; D1355 replaced with E; Q1358 replaced with N; V1359 replaced with A, G, I, L, S, T, or M; T1361 replaced with A, G, I, L, S, M, or V; Q1362 replaced with N; L1363 replaced with A, G, I, S, T, M, or V; E1364 replaced with D; D1365 replaced with E; I1366 replaced with A, G, L, S, T, M, or V; R1367 replaced with H, or K; A1368 replaced with G, I, L, S, T, M, or V; L1369 replaced with A, G, I, S, T, M, or V; L1370 replaced with A, G, I, S, T, M, or V; A1371 replaced with G, I, L, S, T, M, or V; A1372 replaced with G, I, L, S, T, M, or V; T1373 replaced with A, G, I, L, S, M, or V; G1374 replaced with A, I, L, S, T, M, or V; N1376 replaced with Q; L1377 replaced with A, G, I, S, T, M, or V; S1379 replaced with A, G, I, L, T, M, or V; V1380 replaced with A, G, I, L, S, T, or M; L1381 replaced with A, G, I, S, T, M, or V; T1382 replaced with A, G, I, L, S, M, or V; S1383 replaced with A, G, I, L, T, M, or V; L1385 replaced with A, G, I, S, T, M, or V; G1386 replaced with A, I, L, S, T, M, or V; T1387 replaced with A, G, I, L, S, M, or V; Q1388 replaced with N; L1389 replaced with A, G, I, S, T, M, or V; V1390 replaced with A, G, I, L, S, T, or M; L1391 replaced with A, G, I, S, T, M, or V; D1392 replaced with E; G1394 replaced with A, I, L, S, T, M, or V; N1395 replaced with Q; S1396 replaced with A, G, I, L, T, M, or V; A1397 replaced with G, I, L, S, T, M, or V; L1398 replaced with A, G, I, S, T, M, or V; L1399 replaced with A, G, I, S, T, M, or V; G1400 replaced with A, I, L, S, T, M, or V; I1403 replaced with A, G, L, S, T, M, or V; K1404 replaced with H, or R; G1405 replaced with A, I, L, S, T, M, or V; H1406 replaced with K, or R; V1408 replaced with A, G, I, L, S, T, or M; N1410 replaced with Q; I1411 replaced with A, G, L, S, T, M, or V; T1412 replaced with A, G, I, L, S, M, or V; W 1413 replaced with F, or Y; F1414 replaced with W, or Y; H1415 replaced with K, or R; G1416 replaced with A, I, L, S, T, M, or V; G1417 replaced with A, I, L, S, T, M, or V; Q1418 replaced with N; I1420 replaced with A, G, L, S, T, M, or V; V1421 replaced with A, G, I, L, S, T, or M; T1422 replaced with A, G, I, L, S, M, or V; A1423 replaced with G, I, L, S, T, M, or V; T1424 replaced with A, G, I, L, S, M, or V; G1425 replaced with A, I, L, S, T, M, or V; L1426 replaced with A, G, I, S, T, M, or V; T1427 replaced with A, G, I, L, S, M, or V; H1428 replaced with K, or R; H1429 replaced with K, or R; I1430 replaced with A, G, L, S, T, M, or V; L1431 replaced with A, G, I, S, T, M, or V; A1432 replaced with G, I, L, S, T, M, or V; A1433 replaced with G, I, L, S, T, M, or V; G1434 replaced with A, I, L, S, T, M, or V; Q1435 replaced with N; I1436 replaced with A, G, L, S, T, M, or V; L1437 replaced with A, G, I, S, T, M, or V; Q1438 replaced with N; V1439 replaced with A, G, I, L, S, T, or M; A1440 replaced with G, I, L, S, T, M, or V; N1441 replaced with Q; L1442 replaced with A, G, I, S, T, M, or V; S1443 replaced with A, G, I, L, T, M, or V; G1444 replaced with A, I, L, S, T, M, or V; G1445 replaced with A, I, L, S, T, M, or V; S1446 replaced with A, G, I, L, T, M, or V; Q1447 replaced with N; G1448 replaced with A, I, L, S, T, M, or V; E1449 replaced with D; F1450 replaced with W, or Y; S1451 replaced with A, G, I, L, T, M, or V; L1453 replaced with A, G, I, S, T, M, or V; A1454 replaced with G, I, L, S, T, M, or V; Q1455 replaced with N; N1456 replaced with Q; E1457 replaced with D; A1458 replaced with G, I, L, S, T, M, or V; G1459 replaced with A, I, L, S, T, M, or V; V1460 replaced with A, G, I, L, S, T, or M; L1461 replaced with A, G, I, S, T, M, or V; M1462 replaced with A, G, I, L, S, T, or V; Q1463 replaced with N; K1464 replaced with H, or R; A1465 replaced with G, I, L, S, T, M, or V; S1466 replaced with A, G, I, L, T, M, or V; L1467 replaced with A, G, I, S, T, M, or V; V1468 replaced with A, G, I, L, S, T, or M; I1469 replaced with A, G, L, S, T, M, or V; Q1470 replaced with N; D1471 replaced with E; Y1472 replaced with F, or W; W1473 replaced with F, or Y; W1474 replaced with F, or Y; S1475 replaced with A, G, I, L, T, M, or V; V1476 replaced with A, G, I, L, S, T, or M; D1477 replaced with E; R1478 replaced with H, or K; L1479 replaced with A, G, I, S, T, M, or V; A1480 replaced with G, I, L, S, T, M, or V; T1481 replaced with A, G, I, L, S, M, or V; S1483 replaced with A, G, I, L, T, M, or V; A1484 replaced with G, I, L, S, T, M, or V; S1485 replaced with A, G, I, L, T, M, or V; G1487 replaced with A, I, L, S, T, M, or V; N1488 replaced with Q; R1489 replaced with H, or K; G1490 replaced with A, I, L, S, T, M, or V; V1491 replaced with A, G, I, L, S, T, or M; Q1492 replaced with N; Q1493 replaced with N; R1495 replaced with H, or K; L1496 replaced with A, G, I, S, T, M, or V; R1497 replaced with H, or K; L1499 replaced with A, G, I, S, T, M, or V; L1500 replaced with A, G, I, S, T, M, or V; N1501 replaced with Q; S1502 replaced with A, G, I, L, T, M, or V; T1503 replaced with A, G, I, L, S, M, or V; E1504 replaced with D; V1505 replaced with A, G, I, L, S, T, or M; N1506 replaced with Q; A1508 replaced with G, I, L, S, T, M, or V; H1509 replaced with K, or R; A1511 replaced with G, I, L, S, T, M, or V; G1512 replaced with A, I, L, S, T, M, or V; K1513 replaced with H, or R; V1514 replaced with A, G, I, L, S, T, or M; R1515 replaced with H, or K; A1517 replaced with G, I, L, S, T, M, or V; V1518 replaced with A, G, I, L, S, T, or M; Q1519 replaced with N; I1521 replaced with A, G, L, S, T, M, or V; A1522 replaced with G, I, L, S, T, M, or V; N1524 replaced with Q; R1525 replaced with H, or K; R1526 replaced with H, or K; D1527 replaced with E; S1530 replaced with A, G, I, L, T, M, or V; R1531 replaced with H, or K; W1532 replaced with F, or Y; M1533 replaced with A, G, I, L, S, T, or V; V1534 replaced with A, G, I, L, S, T, or M; T1535 replaced with A, G, I, L, S, M, or V; S1536 replaced with A, G, I, L, T, M, or V; W1537 replaced with F, or Y; S1538 replaced with A, G, I, L, T, M, or V; A1539 replaced with G, I, L, S, T, M, or V; T1541 replaced with A, G, I, L, S, M, or V; R1542 replaced with H, or K; S1543 replaced with A, G, I, L, T, M, or V; G1545 replaced with A, I, L, S, T, M, or V; G1546 replaced with A, I, L, S, T, M, or V; G1547 replaced with A, I, L, S, T, M, or V; V1548 replaced with A, G, I, L, S, T, or M; Q1549 replaced with N; T1550 replaced with A, G, I, L, S, M, or V; R1551 replaced with H, or K; R1552 replaced with H, or K; V1553 replaced with A, G, I, L, S, T, or M; T1554 replaced with A, G, I, L, S, M, or V; Q1556 replaced with N; K1557 replaced with H, or R; L1558 replaced with A, G, I, S, T, M, or V; K1559 replaced with H, or R; A1560 replaced with G, I, L, S, T, M, or V; S1561 replaced with A, G, I, L, T, M, or V; G1562 replaced with A, I, L, S, T, M, or V; I1563 replaced with A, G, L, S, T, M, or V; S1564 replaced with A, G, I, L, T, M, or V; T1565 replaced with A, G, I, L, S, M, or V; V1567 replaced with A, G, I, L, S, T, or M; S1568 replaced with A, G, I, L, T, M, or V; N1569 replaced with Q; D1570 replaced with E; M1571 replaced with A, G, I, L, S, T, or V; T1573 replaced with A, G, I, L, S, M, or V; Q1574 replaced with N; V1575 replaced with A, G, I, L, S, T, or M; A1576 replaced with G, I, L, S, T, M, or V; K1577 replaced with H, or R; R1578 replaced with H, or K; V1580 replaced with A, G, I, L, S, T, or M; D1581 replaced with E; T1582 replaced with A, G, I, L, S, M, or V; Q1583 replaced with N; A1584 replaced with G, I, L, S, T, M, or V; N1586 replaced with Q; Q1587 replaced with N; Q1588 replaced with N; L1589 replaced with A, G, I, S, T, M, or V; V1591 replaced with A, G, I, L, S, T, or M; E1592 replaced with D; W1593 replaced with F, or Y; A1594 replaced with G, I, L, S, T, M, or V; F1595 replaced with W, or Y; S1596 replaced with A, G, I, L, T, M, or V; S1597 replaced with A, G, I, L, T, M, or V; W1598 replaced with F, or Y; G1599 replaced with A, I, L, S, T, M, or V; Q1600 replaced with N; N1602 replaced with Q; G1603 replaced with A, I, L, S, T, M, or V; I1606 replaced with A, G, L, S, T, M, or V; G1607 replaced with A, I, L, S, T, M, or V; H1609 replaced with K, or R; L1610 replaced with A, G, I, S, T, M, or V; A1611 replaced with G, I, L, S, T, M, or V; V1612 replaced with A, G, I, L, S, T, or M; Q1613 replaced with N; H1614 replaced with K, or R; R1615 replaced with H, or K; Q1616 replaced with N; V1617 replaced with A, G, I, L, S, T, or M; F1618 replaced with W, or Y; Q1620 replaced with N; T1621 replaced with A, G, I, L, S, M, or V; R1622 replaced with H, or K; D1623 replaced with E; G1624 replaced with A, I, L, S, T, M, or V; I1625 replaced with A, G, L, S, T, M, or V; T1626 replaced with A, G, I, L, S, M, or V; L1627 replaced with A, G, I, S, T, M, or V; S1629 replaced with A, G, I, L, T, M, or V; E1630 replaced with D; Q1631 replaced with N; S1633 replaced with A, G, I, L, T, M, or V; A1634 replaced with G, I, L, S, T, M, or V; L1635 replaced with A, G, I, S, T, M, or V; R1637 replaced with H, or K; V1639 replaced with A, G, I, L, S, T, or M; S1640 replaced with A, G, I, L, T, M, or V; T1641 replaced with A, G, I, L, S, M, or V; Q1642 replaced with N; N1643 replaced with Q; W1645 replaced with F, or Y; S1646 replaced with A, G, I, L, T, M, or V; E1647 replaced with D; A1648 replaced with G, I, L, S, T, M, or V; S1650 replaced with A, G, I, L, T, M, or V; V1651 replaced with A, G, I, L, S, T, or M; H1652 replaced with K, or R; W1653 replaced with F, or Y; R1654 replaced with H, or K; V1655 replaced with A, G, I, L, S, T, or M; S1656 replaced with A, G, I, L, T, M, or V; L1657 replaced with A, G, I, S, T, M, or V; W1658 replaced with F, or Y; T1659 replaced with A, G, I, L, S, M, or V; L1660 replaced with A, G, I, S, T, M, or V; T1662 replaced with A, G, I, L, S, M, or V; A1663 replaced with G, I, L, S, T, M, or V; T1664 replaced with A, G, I, L, S, M, or V; G1666 replaced with A, I, L, S, T, M, or V; N1667 replaced with Q; Y1668 replaced with F, or W; G1669 replaced with A, I, L, S, T, M, or V; F1670 replaced with W, or Y; Q1671 replaced with N; S1672 replaced with A, G, I, L, T, M, or V; R1673 replaced with H, or K; R1674 replaced with H, or K; V1675 replaced with A, G, I, L, S, T, or M; E1676 replaced with D; V1678 replaced with A, G, I, L, S, T, or M; H1679 replaced with K, or R; A1680 replaced with G, I, L, S, T, M, or V; R1681 replaced with H, or K; T1682 replaced with A, G, I, L, S, M, or V; N1683 replaced with Q; K1684 replaced with H, or R; A1685 replaced with G, I, L, S, T, M, or V; V1686 replaced with A, G, I, L, S, T, or M; E1688 replaced with D; H1689 replaced with K, or R; L1690 replaced with A, G, I, S, T, M, or V; S1692 replaced with A, G, I, L, T, M, or V; W1693 replaced with F, or Y; G1694 replaced with A, I, L, S, T, M, or V; R1696 replaced with H, or K; A1698 replaced with G, I, L, S, T, M, or V; N1699 replaced with Q; W1700 replaced with F, or Y; Q1701 replaced with N; R1702 replaced with H, or K; N1704 replaced with Q; I1705 replaced with A, G, L, S, T, M, or V; T1706 replaced with A, G, I, L, S, M, or V; E1709 replaced with D; N1710 replaced with Q; M1711 replaced with A, G, I, L, S, T, or V; E1712 replaced with D; R1714 replaced with H, or K; D1715 replaced with E; T1716 replaced with A, G, I, L, S, M, or V; T1717 replaced with A, G, I, L, S, M, or V; R1718 replaced with H, or K; Y1719 replaced with F, or W; E1721 replaced with D; K1722 replaced with H, or R; V1723 replaced with A, G, I, L, S, T, or M; K1724 replaced with H, or R; Q1725 replaced with N; L1726 replaced with A, G, I, S, T, M, or V; K1727 replaced with H, or R; L1728 replaced with A, G, I, S, T, M, or V; Q1730 replaced with N; L1731 replaced with A, G, I, S, T, M, or V; S1732 replaced with A, G, I, L, T, M, or V; Q1733 replaced with N; F1734 replaced with W, or Y; K1735 replaced with H, or R; S1736 replaced with A, G, I, L, T, M, or V; R1737 replaced with H, or K; G1740 replaced with A, I, L, S, T, M, or V; T1741 replaced with A, G, I, L, S, M, or V; G1743 replaced with A, I, L, S, T, M, or V; K1744 replaced with H, or R; or A1745 replaced with G, I, L, S, T, M, or V.

The resulting constructs can be routinely screened for activities or functions described throughout the specification and known in the art. Preferably, the resulting constructs have an increased THRAP activity or function, while the remaining THRAP activities or functions are maintained. More preferably, the resulting constructs have more than one increased THRAP activity or function, while the remaining THRAP activities or functions are maintained.

Besides conservative amino acid substitution, non-conservative substitutions are also preferred. For example, preferred non-conservative substitutions of THRAP (SEQ ID NO:89) include: M1 replaced with D, E, H, K, R, N, Q, F, W, Y, P, or C; E2 replaced with H, K, R, A, G, I, L, S, T, M, V, N, Q, F, W, Y, P, or C; C3 replaced with D, E, H, K, R, A, G, I, L, S, T, M, V, N, Q, F, W, Y, or P; C4 replaced with D, E, H, K, R, A, G, I, L, S, T, M, V, N, Q, F, W, Y, or P; R5 replaced with D, E, A, G, I, L, S, T, M, V, N, Q, F, W, Y, P, or C; R6 replaced with D, E, A, G, I, L, S, T, M, V, N, Q, F, W, Y, P, or C; A7 replaced with D, E, H, K, R, N, Q, F, W, Y, P, or C; T8 replaced with D, E, H, K, R, N, Q, F, W, Y, P, or C; P9 replaced with D, E, H, K, R, A, G, I, L, S, T, M, V, N, Q, F, W, Y, or C; G10 replaced with D, E, H, K, R, N, Q, F, W, Y, P, or C; T11 replaced with D, E, H, K, R, N, Q, F, W, Y, P, or C; L12 replaced with D, E, H, K, R, N, Q, F, W, Y, P, or C; L13 replaced with D, E, H, K, R, N, Q, F, W, Y, P, or C; L14 replaced with D, E, H, K, R, N, Q, F, W, Y, P, or C; F15 replaced with D, E, H, K, R, N, Q, A, G, I, L, S, T, M, V, P, or C; L16 replaced with D, E, H, K, R, N, Q, F, W, Y, P, or C; A17 replaced with D, E, H, K, R, N, Q, F, W, Y, P, or C; F18 replaced with D, E, H, K, R, N, Q, A, G, I, L, S, T, M, V, P, or C; L19 replaced with D, E, H, K, R, N, Q, F, W, Y, P, or C; L20 replaced with D, E, H, K, R, N, Q, F, W, Y, P, or C; L21 replaced with D, E, H, K, R, N, Q, F, W, Y, P, or C; S22 replaced with D, E, H, K, R, N, Q, F, W, Y, P, or C; S23 replaced with D, E, H, K, R, N, Q, F, W, Y, P, or C; R24 replaced with D, E, A, G, I, L, S, T, M, V, N, Q, F, W, Y, P, or C; T25 replaced with D, E, H, K, R, N, Q, F, W, Y, P, or C; A26 replaced with D, E, H, K, R, N, Q, F, W, Y, P, or C; R27 replaced with D, E, A, G, I, L, S, T, M, V, N, Q, F, W, Y, P, or C; S28 replaced with D, E, H, K, R, N, Q, F, W, Y, P, or C; E29 replaced with H, K, R, A, G, I, L, S, T, M, V, N, Q, F, W, Y, P, or C; E30 replaced with H, K, R, A, G, I, L, S, T, M, V, N, Q, F, W, Y, P, or C; D31 replaced with H, K, R, A, G, I, L, S, T, M, V, N, Q, F, W, Y, P, or C; R32 replaced with D, E, A, G, I, L, S, T, M, V, N, Q, F, W, Y, P, or C; D33 replaced with H, K, R, A, G, I, L, S, T, M, V, N, Q, F, W, Y, P, or C; G34 replaced with D, E, H, K, R, N, Q, F, W, Y, P, or C; L35 replaced with D, E, H, K, R, N, Q, F, W, Y, P, or C; W36 replaced with D, E, H, K, R, N, Q, A, G, I, L, S, T, M, V, P, or C; D37 replaced with H, K, R, A, G, I, L, S, T, M, V, N, Q, F, W, Y, P, or C; A38 replaced with D, E, H, K, R, N, Q, F, W, Y, P, or C; W39 replaced with D, E, H, K, R, N, Q, A, G, I, L, S, T, M, V, P, or C; G40 replaced with D, E, H, K, R, N, Q, F, W, Y, P, or C; P41 replaced with D, E, H, K, R, A, G, I, L, S, T, M, V, N, Q, F, W, Y, or C; W42 replaced with D, E, H, K, R, N, Q, A, G, I, L, S, T, M, V, P, or C; S43 replaced with D, E, H, K, R, N, Q, F, W, Y, P, or C; E44 replaced with H, K, R, A, G, I, L, S, T, M, V, N, Q, F, W, Y, P, or C; C45 replaced with D, E, H, K, R, A, G, I, L, S, T, M, V, N, Q, F, W, Y, or P; S46 replaced with D, E, H, K, R, N, Q, F, W, Y, P, or C; R47 replaced with D, E, A, G, I, L, S, T, M, V, N, Q, F, W, Y, P, or C; T48 replaced with D, E, H, K, R, N, Q, F, W, Y, P, or C; C49 replaced with D, E, H, K, R, A, G, I, L, S, T, M, V, N, Q, F, W, Y, or P; G50 replaced with D, E, H, K, R, N, Q, F, W, Y, P, or C; G51 replaced with D, E, H, K, R, N, Q, F, W, Y, P, or C; G52 replaced with D, E, H, K, R, N, Q, F, W, Y, P, or C; A53 replaced with D, E, H, K, R, N, Q, F, W, Y, P, or C; S54 replaced with D, E, H, K, R, N, Q, F, W, Y, P, or C; Y55 replaced with D, E, H, K, R, N, Q, A, G, I, L, S, T, M, V, P, or C; S56 replaced with D, E, H, K, R, N, Q, F, W, Y, P, or C; L57 replaced with D, E, H, K, R, N, Q, F, W, Y, P, or C; R58 replaced with D, E, A, G, I, L, S, T, M, V, N, Q, F, W, Y, P, or C; R59 replaced with D, E, A, G, I, L, S, T, M, V, N, Q, F, W, Y, P, or C; C60 replaced with D, E, H, K, R, A, G, I, L, S, T, M, V, N, Q, F, W, Y, or P; L61 replaced with D, E, H, K, R, N, Q, F, W, Y, P, or C; S62 replaced with D, E, H, K, R, N, Q, F, W, Y, P, or C; S63 replaced with D, E, H, K, R, N, Q, F, W, Y, P, or C; K64 replaced with D, E, A, G, I, L, S, T, M, V, N, Q, F, W, Y, P, or C; S65 replaced with D, E, H, K, R, N, Q, F, W, Y, P, or C; C66 replaced with D, E, H, K, R, A, G, I, L, S, T, M, V, N, Q, F, W, Y, or P; E67 replaced with H, K, R, A, G, I, L, S, T, M, V, N, Q, F, W, Y, P, or C; G68 replaced with D, E, H, K, R, N, Q, F, W, Y, P, or C; R69 replaced with D, E, A, G, I, L, S, T, M, V, N, Q, F, W, Y, P, or C; N70 replaced with D, E, H, K, R, A, G, I, L, S, T, M, V, F, W, Y, P, or C; I71 replaced with D, E, H, K, R, N, Q, F, W, Y, P, or C; R72 replaced with D, E, A, G, I, L, S, T, M, V, N, Q, F, W, Y, P, or C; Y73 replaced with D, E, H, K, R, N, Q, A, G, I, L, S, T, M, V, P, or C; R74 replaced with D, E, A, G, I, L, S, T, M, V, N, Q, F, W, Y, P, or C; T75 replaced with D, E, H, K, R, N, Q, F, W, Y, P, or C; C76 replaced with D, E, H, K, R, A, G, I, L, S, T, M, V, N, Q, F, W, Y, or P; S77 replaced with D, E, H, K, R, N, Q, F, W, Y, P, or C; N78 replaced with D, E, H, K, R, A, G, I, L, S, T, M, V, F, W, Y, P, or C; V79 replaced with D, E, H, K, R, N, Q, F, W, Y, P, or C; D80 replaced with H, K, R, A, G, I, L, S, T, M, V, N, Q, F, W, Y, P, or C; C81 replaced with D, E, H, K, R, A, G, I, L, S, T, M, V, N, Q, F, W, Y, or P; P82 replaced with D, E, H, K, R, A, G, I, L, S, T, M, V, N, Q, F, W, Y, or C; P83 replaced with D, E, H, K, R, A, G, I, L, S, T, M, V, N, Q, F, W, Y, or C; E84 replaced with H, K, R, A, G, I, L, S, T, M, V, N, Q, F, W, Y, P, or C; A85 replaced with D, E, H, K, R, N, Q, F, W, Y, P, or C; G86 replaced with D, E, H, K, R, N, Q, F, W, Y, P, or C; D87 replaced with H, K, R, A, G, I, L, S, T, M, V, N, Q, F, W, Y, P, or C; F88 replaced with D, E, H, K, R, N, Q, A, G, I, L, S, T, M, V, P, or C; R89 replaced with D, E, A, G, I, L, S, T, M, V, N, Q, F, W, Y, P, or C; A90 replaced with D, E, H, K, R, N, Q, F, W, Y, P, or C; Q91 replaced with D, E, H, K, R, A, G, I, L, S, T, M, V, F, W, Y, P, or C; Q92 replaced with D, E, H, K, R, A, G, I, L, S, T, M, V, F, W, Y, P, or C; C93 replaced with D, E, H, K, R, A, G, I, L, S, T, M, V, N, Q, F, W, Y, or P; S94 replaced with D, E, H, K, R, N, Q, F, W, Y, P, or C; A95 replaced with D, E, H, K, R, N, Q, F, W, Y, P, or C; H96 replaced with D, E, A, G, I, L, S, T, M, V, N, Q, F, W, Y, P, or C; N97 replaced with D, E, H, K, R, A, G, I, L, S, T, M, V, F, W, Y, P, or C; D98 replaced with H, K, R, A, G, I, L, S, T, M, V, N, Q, F, W, Y, P, or C; V99 replaced with D, E, H, K, R, N, Q, F, W, Y, P, or C; K100 replaced with D, E, A, G, I, L, S, T, M, V, N, Q, F, W, Y, P, or C; H101 replaced with D, E, A, G, I, L, S, T, M, V, N, Q, F, W, Y, P, or C; H102 replaced with D, E, A, G, I, L, S, T, M, V, N, Q, F, W, Y, P, or C; G103 replaced with D, E, H, K, R, N, Q, F, W, Y, P, or C; Q104 replaced with D, E, H, K, R, A, G, I, L, S, T, M, V, F, W, Y, P, or C; F105 replaced with D, E, H, K, R, N, Q, A, G, I, L, S, T, M, V, P, or C; Y106 replaced with D, E, H, K, R, N, Q, A, G, I, L, S, T, M, V, P, or C; E107 replaced with H, K, R, A, G, I, L, S, T, M, V, N, Q, F, W, Y, P, or C; W108 replaced with D, E, H, K, R, N, Q, A, G, I, L, S, T, M, V, P, or C; L109 replaced with D, E, H, K, R, N, Q, F, W, Y, P, or C; P110 replaced with D, E, H, K, R, A, G, I, L, S, T, M, V, N, Q, F, W, Y, or C; V111 replaced with D, E, H, K, R, N, Q, F, W, Y, P, or C; S112 replaced with D, E, H, K, R, N, Q, F, W, Y, P, or C; N 113 replaced with D, E, H, K, R, A, G, I, L, S, T, M, V, F, W, Y, P, or C; D114 replaced with H, K, R, A, G, I, L, S, T, M, V, N, Q, F, W, Y, P, or C; P115 replaced with D, E, H, K, R, A, G, I, L, S, T, M, V, N, Q, F, W, Y, or C; D116 replaced with H, K, R, A, G, I, L, S, T, M, V, N, Q, F, W, Y, P, or C; N 117 replaced with D, E, H, K, R, A, G, I, L, S, T, M, V, F, W, Y, P, or C; P118 replaced with D, E, H, K, R, A, G, I, L, S, T, M, V, N, Q, F, W, Y, or C; C119 replaced with D, E, H, K, R, A, G, I, L, S, T, M, V, N, Q, F, W, Y, or P; S120 replaced with D, E, H, K, R, N, Q, F, W, Y, P, or C; L121 replaced with D, E, H, K, R, N, Q, F, W, Y, P, or C; K122 replaced with D, E, A, G, I, L, S, T, M, V, N, Q, F, W, Y, P, or C; C123 replaced with D, E, H, K, R, A, G, I, L, S, T, M, V, N, Q, F, W, Y, or P; Q124 replaced with D, E, H, K, R, A, G, I, L, S, T, M, V, F, W, Y, P, or C; A125 replaced with D, E, H, K, R, N, Q, F, W, Y, P, or C; K126 replaced with D, E, A, G, I, L, S, T, M, V, N, Q, F, W, Y, P, or C; G127 replaced with D, E, H, K, R, N, Q, F, W, Y, P, or C; T128 replaced with D, E, H, K, R, N, Q, F, W, Y, P, or C; T129 replaced with D, E, H, K, R, N, Q, F, W, Y, P, or C; L130 replaced with D, E, H, K, R, N, Q, F, W, Y, P, or C; V131 replaced with D, E, H, K, R, N, Q, F, W, Y, P, or C; V132 replaced with D, E, H, K, R, N, Q, F, W, Y, P, or C; E133 replaced with H, K, R, A, G, I, L, S, T, M, V, N, Q, F, W, Y, P, or C; L134 replaced with D, E, H, K, R, N, Q, F, W, Y, P, or C; A135 replaced with D, E, H, K, R, N, Q, F, W, Y, P, or C; P136 replaced with D, E, H, K, R, A, G, I, L, S, T, M, V, N, Q, F, W, Y, or C; K137 replaced with D, E, A, G, I, L, S, T, M, V, N, Q, F, W, Y, P, or C; V138 replaced with D, E, H, K, R, N, Q, F, W, Y, P, or C; L139 replaced with D, E, H, K, R, N, Q, F, W, Y, P, or C; D140 replaced with H, K, R, A, G, I, L, S, T, M, V, N, Q, F, W, Y, P, or C; G141 replaced with D, E, H, K, R, N, Q, F, W, Y, P, or C; T142 replaced with D, E, H, K, R, N, Q, F, W, Y, P, or C; R143 replaced with D, E, A, G, I, L, S, T, M, V, N, Q, F, W, Y, P, or C; C144 replaced with D, E, H, K, R, A, G, I, L, S, T, M, V, N, Q, F, W, Y, or P; Y145 replaced with D, E, H, K, R, N, Q, A, G, I, L, S, T, M, V, P, or C; T146 replaced with D, E, H, K, R, N, Q, F, W, Y, P, or C; E147 replaced with H, K, R, A, G, I, L, S, T, M, V, N, Q, F, W, Y, P, or C; S148 replaced with D, E, H, K, R, N, Q, F, W, Y, P, or C; L149 replaced with D, E, H, K, R, N, Q, F, W, Y, P, or C; D150 replaced with H, K, R, A, G, I, L, S, T, M, V, N, Q, F, W, Y, P, or C; M151 replaced with D, E, H, K, R, N, Q, F, W, Y, P, or C; C152 replaced with D, E, H, K, R, A, G, I, L, S, T, M, V, N, Q, F, W, Y, or P; I153 replaced with D, E, H, K, R, N, Q, F, W, Y, P, or C; S154 replaced with D, E, H, K, R, N, Q, F, W, Y, P, or C; G155 replaced with D, E, H, K, R, N, Q, F, W, Y, P, or C; L156 replaced with D, E, H, K, R, N, Q, F, W, Y, P, or C; C157 replaced with D, E, H, K, R, A, G, I, L, S, T, M, V, N, Q, F, W, Y, or P; Q158 replaced with D, E, H, K, R, A, G, I, L, S, T, M, V, F, W, Y, P, or C; I159 replaced with D, E, H, K, R, N, Q, F, W, Y, P, or C; V160 replaced with D, E, H, K, R, N, Q, F, W, Y, P, or C; G161 replaced with D, E, H, K, R, N, Q, F, W, Y, P, or C; C162 replaced with D, E, H, K, R, A, G, I, L, S, T, M, V, N, Q, F, W, Y, or P; D163 replaced with H, K, R, A, G, I, L, S, T, M, V, N, Q, F, W, Y, P, or C; H164 replaced with D, E, A, G, I, L, S, T, M, V, N, Q, F, W, Y, P, or C; Q165 replaced with D, E, H, K, R, A, G, I, L, S, T, M, V, F, W, Y, P, or C; L166 replaced with D, E, H, K, R, N, Q, F, W, Y, P, or C; G167 replaced with D, E, H, K, R, N, Q, F, W, Y, P, or C; S168 replaced with D, E, H, K, R, N, Q, F, W, Y, P, or C; T169 replaced with D, E, H, K, R, N, Q, F, W, Y, P, or C; V170 replaced with D, E, H, K, R, N, Q, F, W, Y, P, or C; K171 replaced with D, E, A, G, I, L, S, T, M, V, N, Q, F, W, Y, P, or C; E172 replaced with H, K, R, A, G, I, L, S, T, M, V, N, Q, F, W, Y, P, or C; D173 replaced with H, K, R, A, G, I, L, S, T, M, V, N, Q, F, W, Y, P, or C; N174 replaced with D, E, H, K, R, A, G, I, L, S, T, M, V, F, W, Y, P, or C; C175 replaced with D, E, H, K, R, A, G, I, L, S, T, M, V, N, Q, F, W, Y, or P; G176 replaced with D, E, H, K, R, N, Q, F, W, Y, P, or C; V177 replaced with D, E, H, K, R, N, Q, F, W, Y, P, or C; C178 replaced with D, E, H, K, R, A, G, I, L, S, T, M, V, N, Q, F, W, Y, or P; N179 replaced with D, E, H, K, R, A, G, I, L, S, T, M, V, F, W, Y, P, or C; G180 replaced with D, E, H, K, R, N, Q, F, W, Y, P, or C; D181 replaced with H, K, R, A, G, I, L, S, T, M, V, N, Q, F, W, Y, P, or C; G182 replaced with D, E, H, K, R, N, Q, F, W, Y, P, or C; S183 replaced with D, E, H, K, R, N, Q, F, W, Y, P, or C; T184 replaced with D, E, H, K, R, N, Q, F, W, Y, P, or C; C185 replaced with D, E, H, K, R, A, G, I, L, S, T, M, V, N, Q, F, W, Y, or P; R186 replaced with D, E, A, G, I, L, S, T, M, V, N, Q, F, W, Y, P, or C; L187 replaced with, E, H, K, R, N, Q, F, W, Y, P, or C; V188 replaced with D, E, H, K, R, N, Q, F, W, Y, P, or C; R189 replaced with D, E, A, G, I, L, S, T, M, V, N, Q, F, W, Y, P, or C; G190 replaced with D, E, H, K, R, N, Q, F, W, Y, P, or C; Q191 replaced with D, E, H, K, R, A, G, I, L, S, T, M, V, F, W, Y, P, or C; Y192 replaced with D, E, H, K, R, N, Q, A, G, I, L, S, T, M, V, P, or C; K193 replaced with D, E, A, G, I, L, S, T, M, V, N, Q, F, W, Y, P, or C; S194 replaced with D, E, H, K, R, N, Q, F, W, Y, P, or C; Q195 replaced with D, E, H, K, R, A, G, I, L, S, T, M, V, F, W, Y, P, or C; L196 replaced with D, E, H, K, R, N, Q, F, W, Y, P, or C; S197 replaced with D, E, H, K, R, N, Q, F, W, Y, P, or C; A198 replaced with D, E, H, K, R, N, Q, F, W, Y, P, or C; T199 replaced with D, E, H, K, R, N, Q, F, W, Y, P, or C; K200 replaced with D, E, A, G, I, L, S, T, M, V, N, Q, F, W, Y, P, or C; S201 replaced with D, E, H, K, R, N, Q, F, W, Y, P, or C; D202 replaced with H, K, R, A, G, I, L, S, T, M, V, N, Q, F, W, Y, P, or C; D203 replaced with H, K, R, A, G, I, L, S, T, M, V, N, Q, F, W, Y, P, or C; T204 replaced with D, E, H, K, R, N, Q, F, W, Y, P, or C; V205 replaced with D, E, H, K, R, N, Q, F, W, Y, P, or C; V206 replaced with D, E, H, K, R, N, Q, F, W, Y, P, or C; A207 replaced with D, E, H, K, R, N, Q, F, W, Y, P, or C; I208 replaced with D, E, H, K, R, N, Q, F, W, Y, P, or C; P209 replaced with D, E, H, K, R, A, G, I, L, S, T, M, V, N, Q, F, W, Y, or C; Y210 replaced with D, E, H, K, R, N, Q, A, G, I, L, S, T, M, V, P, or C; G211 replaced with D, E, H, K, R, N, Q, F, W, Y, P, or C; S212 replaced with D, E, H, K, R, N, Q, F, W, Y, P, or C; R213 replaced with D, E, A, G, I, L, S, T, M, V, N, Q, F, W, Y, P, or C; H214 replaced with D, E, A, G, I, L, S, T, M, V, N, Q, F, W, Y, P, or C; I215 replaced with D, E, H, K, R, N, Q, F, W, Y, P, or C; R216 replaced with D, E, A, G, I, L, S, T, M, V, N, Q, F, W, Y, P, or C; L217 replaced with D, E, H, K, R, N, Q, F, W, Y, P, or C; V218 replaced with D, E, H, K, R, N, Q, F, W, Y, P, or C; L219 replaced with D, E, H, K, R, N, Q, F, W, Y, P, or C; K220 replaced with D, E, A, G, I, L, S, T, M, V, N, Q, F, W, Y, P, or C; G221 replaced with D, E, H, K, R, N, Q, F, W, Y, P, or C; P222 replaced with D, E, H, K, R, A, G, I, L, S, T, M, V, N, Q, F, W, Y, or C; D223 replaced with H, K, R, A, G, I, L, S, T, M, V, N, Q, F, W, Y, P, or C; H224 replaced with D, E, A, G, I, L, S, T, M, V, N, Q, F, W, Y, P, or C; L225 replaced with D, E, H, K, R, N, Q, F, W, Y, P, or C; Y226 replaced with D, E, H, K, R, N, Q, A, G, I, L, S, T, M, V, P, or C; L227 replaced with D, E, H, K, R, N, Q, F, W, Y, P, or C; E228 replaced with H, K, R, A, G, I, L, S, T, M, V, N, Q, F, W, Y, P, or C; T229 replaced with D, E, H, K, R, N, Q, F, W, Y, P, or C; K230 replaced with D, E, A, G, I, L, S, T, M, V, N, Q, F, W, Y, P, or C; T231 replaced with D, E, H, K, R, N, Q, F, W, Y, P, or C; L232 replaced with D, E, H, K, R, N, Q, F, W, Y, P, or C; Q233 replaced with D, E, H, K, R, A, G, I, L, S, T, M, V, F, W, Y, P, or C; G234 replaced with D, E, H, K, R, N, Q, F, W, Y, P, or C; T235 replaced with D, E, H, K, R, N, Q, F, W, Y, P, or C; K236 replaced with D, E, A, G, I, L, S, T, M, V, N, Q, F, W, Y, P, or C; G237 replaced with D, E, H, K, R, N, Q, F, W, Y, P, or C; E238 replaced with H, K, R, A, G, I, L, S, T, M, V, N, Q, F, W, Y, P, or C; N239 replaced with D, E, H, K, R, A, G, I, L, S, T, M, V, F, W, Y, P, or C; S240 replaced with D, E, H, K, R, N, Q, F, W, Y, P, or C; L241 replaced with D, E, H, K, R, N, Q, F, W, Y, P, or C; S242 replaced with D, E, H, K, R, N, Q, F, W, Y, P, or C; S243 replaced with D, E, H, K, R, N, Q, F, W, Y, P, or C; T244 replaced with D, E, H, K, R, N, Q, F, W, Y, P, or C; G245 replaced with D, E, H, K, R, N, Q, F, W, Y, P, or C; T246 replaced with D, E, H, K, R, N, Q, F, W, Y, P, or C; F247 replaced with D, E, H, K, R, N, Q, A, G, I, L, S, T, M, V, P, or C; L248 replaced with D, E, H, K, R, N, Q, F, W, Y, P, or C; V249 replaced with D, E, H, K, R, N, Q, F, W, Y, P, or C; D250 replaced with H, K, R, A, G, I, L, S, T, M, V, N, Q, F, W, Y, P, or C; N251 replaced with D, E, H, K, R, A, G, I, L, S, T, M, V, F, W, Y, P, or C; S252 replaced with D, E, H, K, R, N, Q, F, W, Y, P, or C; S253 replaced with D, E, H, K, R, N, Q, F, W, Y, P, or C; V254 replaced with D, E, H, K, R, N, Q, F, W, Y, P, or C; D255 replaced with H, K, R, A, G, I, L, S, T, M, V, N, Q, F, W, Y, P, or C; F256 replaced with D, E, H, K, R, N, Q, A, G, I, L, S, T, M, V, P, or C; Q257 replaced with D, E, H, K, R, A, G, I, L, S, T, M, V, F, W, Y, P, or C; K258 replaced with D, E, A, G, I, L, S, T, M, V, N, Q, F, W, Y, P, or C; F259 replaced with D, E, H, K, R, N, Q, A, G, I, L, S, T, M, V, P, or C; P260 replaced with D, E, H, K, R, A, G, I, L, S, T, M, V, N, Q, F, W, Y, or C; D261 replaced with H, K, R, A, G, I, L, S, T, M, V, N, Q, F, W, Y, P, or C; K262 replaced with D, E, A, G, I, L, S, T, M, V, N, Q, F, W, Y, P, or C; E263 replaced with H, K, R, A, G, I, L, S, T, M, V, N, Q, F, W, Y, P, or C; I264 replaced with D, E, H, K, R, N, Q, F, W, Y, P, or C; L265 replaced with D, E, H, K, R, N, Q, F, W, Y, P, or C; R266 replaced with D, E, A, G, I, L, S, T, M, V, N, Q, F, W, Y, P, or C; M267 replaced with D, E, H, K, R, N, Q, F, W, Y, P, or C; A268 replaced with D, E, H, K, R, N, Q, F, W, Y, P, or C; G269 replaced with D, E, H, K, R, N, Q, F, W, Y, P, or C; P270 replaced with D, E, H, K, R, A, G, I, L, S, T, M, V, N, Q, F, W, Y, or C; L271 replaced with D, E, H, K, R, N, Q, F, W, Y, P, or C; T272 replaced with D, E, H, K, R, N, Q, F, W, Y, P, or C; A273 replaced with D, E, H, K, R, N, Q, F, W, Y, P, or C; D274 replaced with H, K, R, A, G, I, L, S, T, M, V, N, Q, F, W, Y, P, or C; F275 replaced with D, E, H, K, R, N, Q, A, G, I, L, S, T, M, V, P, or C; I276 replaced with D, E, H, K, R, N, Q, F, W, Y, P, or C; V277 replaced with D, E, H, K, R, N, Q, F, W, Y, P, or C; K278 replaced with D, E, A, G, I, L, S, T, M, V, N, Q, F, W, Y, P, or C; I279 replaced with D, E, H, K, R, N, Q, F, W, Y, P, or C; R280 replaced with D, E, A, G, I, L, S, T, M, V, N, Q, F, W, Y, P, or C; N281 replaced with D, E, H, K, R, A, G, I, L, S, T, M, V, F, W, Y, P, or C; S282 replaced with D, E, H, K, R, N, Q, F, W, Y, P, or C; G283 replaced with D, E, H, K, R, N, Q, F, W, Y, P, or C; S284 replaced with D, E, H, K, R, N, Q, F, W, Y, P, or C; A285 replaced with D, E, H, K, R, N, Q, F, W, Y, P, or C; D286 replaced with H, K, R, A, G, I, L, S, T, M, V, N, Q, F, W, Y, P, or C; S287 replaced with D, E, H, K, R, N, Q, F, W, Y, P, or C; T288 replaced with D, E, H, K, R, N, Q, F, W, Y, P, or C; V289 replaced with D, E, H, K, R, N, Q, F, W, Y, P, or C; Q290 replaced with D, E, H, K, R, A, G, I, L, S, T, M, V, F, W, Y, P, or C; F291 replaced with D, E, H, K, R, N, Q, A, G, I, L, S, T, M, V, P, or C; I292 replaced with D, E, H, K, R, N, Q, F, W, Y, P, or C; F293 replaced with D, E, H, K, R, N, Q, A, G, I, L, S, T, M, V, P, or C; Y294 replaced with D, E, H, K, R, N, Q, A, G, I, L, S, T, M, V, P, or C; Q295 replaced with D, E, H, K, R, A, G, I, L, S, T, M, V, F, W, Y, P, or C; P296 replaced with D, E, H, K, R, A, G, I, L, S, T, M, V, N, Q, F, W, Y, or C; I297 replaced with D, E, H, K, R, N, Q, F, W, Y, P, or C; I298 replaced with D, E, H, K, R, N, Q, F, W, Y, P, or C; H299 replaced with D, E, A, G, I, L, S, T, M, V, N, Q, F, W, Y, P, or C; R300 replaced with D, E, A, G, I, L, S, T, M, V, N, Q, F, W, Y, P, or C; W301 replaced with D, E, H, K, R, N, Q, A, G, I, L, S, T, M, V, P, or C; R302 replaced with D, E, A, G, I, L, S, T, M, V, N, Q, F, W, Y, P, or C; E303 replaced with H, K, R, A, G, I, L, S, T, M, V, N, Q, F, W, Y, P, or C; T304 replaced with D, E, H, K, R, N, Q, F, W, Y, P, or C; D305 replaced with H, K, R, A, G, I, L, S, T, M, V, N, Q, F, W, Y, P, or C; F306 replaced with D, E, H, K, R, N, Q, A, G, I, L, S, T, M, V, P, or C; F307 replaced with D, E, H, K, R, N, Q, A, G, I, L, S, T, M, V, P, or C; P308 replaced with D, E, H, K, R, A, G, I, L, S, T, M, V, N, Q, F, W, Y, or C; C309 replaced with D, E, H, K, R, A, G, I, L, S, T, M, V, N, Q, F, W, Y, or P; S310 replaced with D, E, H, K, R, N, Q, F, W, Y, P, or C; A311 replaced with D, E, H, K, R, N, Q, F, W, Y, P, or C; T312 replaced with D, E, H, K, R, N, Q, F, W, Y, P, or C; C313 replaced with D, E, H, K, R, A, G, I, L, S, T, M, V, N, Q, F, W, Y, or P; G314 replaced with D, E, H, K, R, N, Q, F, W, Y, P, or C; G315 replaced with D, E, H, K, R, N, Q, F, W, Y, P, or C; G316 replaced with D, E, H, K, R, N, Q, F, W, Y, P, or C; Y317 replaced with D, E, H, K, R, N, Q, A, G, I, L, S, T, M, V, P, or C; Q318 replaced with D, E, H, K, R, A, G, I, L, S, T, M, V, F, W, Y, P, or C; L319 replaced with D, E, H, K, R, N, Q, F, W, Y, P, or C; T320 replaced with D, E, H, K, R, N, Q, F, W, Y, P, or C; S321 replaced with D, E, H, K, R, N, Q, F, W, Y, P, or C; A322 replaced with D, E, H, K, R, N, Q, F, W, Y, P, or C; E323 replaced with H, K, R, A, G, I, L, S, T, M, V, N, Q, F, W, Y, P, or C; C324 replaced with D, E, H, K, R, A, G, I, L, S, T, M, V, N, Q, F, W, Y, or P; Y325 replaced with D, E, H, K, R, N, Q, A, G, I, L, S, T, M, V, P, or C; D326 replaced with H, K, R, A, G, I, L, S, T, M, V, N, Q, F, W, Y, P, or C; L327 replaced with D, E, H, K, R, N, Q, F, W, Y, P, or C; R328 replaced with D, E, A, G, I, L, S, T, M, V, N, Q, F, W, Y, P, or C; S329 replaced with D, E, H, K, R, N, Q, F, W, Y, P, or C; N330 replaced with D, E, H, K, R, A, G, J, L, S, T, M, V, F, W, Y, P, or C; R331 replaced with D, E, A, G, I, L, S, T, M, V, N, Q, F, W, Y, P, or C; V332 replaced with D, E, H, K, R, N, Q, F, W, Y, P, or C; V333 replaced with D, E, H, K, R, N, Q, F, W, Y, P, or C; A334 replaced with D, E, H, K, R, N, Q, F, W, Y, P, or C; D335 replaced with H, K, R, A, G, I, L, S, T, M, V, N, Q, F, W, Y, P, or C; Q336 replaced with D, E, H, K, R, A, G, I, L, S, T, M, V, F, W, Y, P, or C; Y337 replaced with D, E, H, K, R, N, Q, A, G, I, L, S, T, M, V, P, or C; C338 replaced with D, E, H, K, R, A, G, I, L, S, T, M, V, N, Q, F, W, Y, or P; H339 replaced with D, E, A, G, I, L, S, T, M, V, N, Q, F, W, Y, P, or C; Y340 replaced with D, E, H, K, R, N, Q, A, G, I, L, S, T, M, V, P, or C; Y341 replaced with D, E, H, K, R, N, Q, A, G, I, L, S, T, M, V, P, or C; P342 replaced with D, E, H, K, R, A, G, I, L, S, T, M, V, N, Q, F, W, Y, or C; E343 replaced with H, K, R, A, G, I, L, S, T, M, V, N, Q, F, W, Y, P, or C; N344 replaced with D, E, H, K, R, A, G, I, L, S, T, M, V, F, W, Y, P, or C; I345 replaced with D, E, H, K, R, N, Q, F, W, Y, P, or C; K346 replaced with D, E, A, G, I, L, S, T, M, V, N, Q, F, W, Y, P, or C; P347 replaced with D, E, H, K, R, A, G, I, L, S, T, M, V, N, Q, F, W, Y, or C; K348 replaced with D, E, A, G, I, L, S, T, M, V, N, Q, F, W, Y, P, or C; P349 replaced with D, E, H, K, R, A, G, I, L, S, T, M, V, N, Q, F, W, Y, or C; K350 replaced with D, E, A, G, I, L, S, T, M, V, N, Q, F, W, Y, P, or C; L351 replaced with D, E, H, K, R, N, Q, F, W, Y, P, or C; Q352 replaced with D, E, H, K, R, A, G, I, L, S, T, M, V, F, W, Y, P, or C; E353 replaced with H, K, R, A, G, I, L, S, T, M, V, N, Q, F, W, Y, P, or C; C354 replaced with D, E, H, K, R, A, G, I, L, S, T, M, V, N, Q, F, W, Y, or P; N355 replaced with D, E, H, K, R, A, G, I, L, S, T, M, V, F, W, Y, P, or C; L356 replaced with D, E, H, K, R, N, Q, F, W, Y, P, or C; D357 replaced with H, K, R, A, G, I, L, S, T, M, V, N, Q, F, W, Y, P, or C; P358 replaced with D, E, H, K, R, A, G, I, L, S, T, M, V, N, Q, F, W, Y, or C; C359 replaced with D, E, H, K, R, A, G, I, L, S, T, M, V, N, Q, F, W, Y, or P; P360 replaced with D, E, H, K, R, A, G, I, L, S, T, M, V, N, Q, F, W, Y, or C; A361 replaced with D, E, H, K, R, N, Q, F, W, Y, P, or C; R362 replaced with D, E, A, G, I, L, S, T, M, V, N, Q, F, W, Y, P, or C; W363 replaced with D, E, H, K, R, N, Q, A, G, I, L, S, T, M, V, P, or C; E364 replaced with H, K, R, A, G, I, L, S, T, M, V, N, Q, F, W, Y, P, or C; A365 replaced with D, E, H, K, R, N, Q, F, W, Y, P, or C; T366 replaced with D, E, H, K, R, N, Q, F, W, Y, P, or C; P367 replaced with D, E, H, K, R, A, G, I, L, S, T, M, V, N, Q, F, W, Y, or C; W368 replaced with D, E, H, K, R, N, Q, A, G, I, L, S, T, M, V, P, or C; T369 replaced with D, E, H, K, R, N, Q, F, W, Y, P, or C; A370 replaced with D, E, H, K, R, N, Q, F, W, Y, P, or C; C371 replaced with D, E, H, K, R, A, G, I, L, S, T, M, V, N, Q, F, W, Y, or P; S372 replaced with D, E, H, K, R, N, Q, F, W, Y, P, or C; S373 replaced with D, E, H, K, R, N, Q, F, W, Y, P, or C; S374 replaced with D, E, H, K, R, N, Q, F, W, Y, P, or C; C375 replaced with D, E, H, K, R, A, G, I, L, S, T, M, V, N, Q, F, W, Y, or P; G376 replaced with D, E, H, K, R, N, Q, F, W, Y, P, or C; G377 replaced with D, E, H, K, R, N, Q, F, W, Y, P, or C; G378 replaced with D, E, H, K, R, N, Q, F, W, Y, P, or C; I379 replaced with D, E, H, K, R, N, Q, F, W, Y, P, or C; Q380 replaced with D, E, H, K, R, A, G, I, L, S, T, M, V, F, W, Y, P, or C; S381 replaced with D, E, H, K, R, N, Q, F, W, Y, P, or C; R382 replaced with D, E, A, G, I, L, S, T, M, V, N, Q, F, W, Y, P, or C; A383 replaced with D, E, H, K, R, N, Q, F, W, Y, P, or C; V384 replaced with D, E, H, K, R, N, Q, F, W, Y, P, or C; S385 replaced with D, E, H, K, R, N, Q, F, W, Y, P, or C; C386 replaced with D, E, H, K, R, A, G, I, L, S, T, M, V, N, Q, F, W, Y, or P; V387 replaced with D, E, H, K, R, N, Q, F, W, Y, P, or C; E388 replaced with H, K, R, A, G, I, L, S, T, M, V, N, Q, F, W, Y, P, or C; E389 replaced with H, K, R, A, G, I, L, S, T, M, V, N, Q, F, W, Y, P, or C;

D390 replaced with H, K, R, A, G, I, L, S, T, M, V, N, Q, F, W, Y, P, or C; I391 replaced with D, E, H, K, R, N, Q, F, W, Y, P, or C; Q392 replaced with D, E, H, K, R, A, G, I, L, S, T, M, V, F, W, Y, P, or C; G393 replaced with D, E, H, K, R, N, Q, F, W, Y, P, or C; H394 replaced with D, E, A, G, I, L, S, T, M, V, N, Q, F, W, Y, P, or C; V395 replaced with D, E, H, K, R, N, Q, F, W, Y, P, or C; T396 replaced with D, E, H, K, R, N, Q, F, W, Y, P, or C; S397 replaced with D, E, H, K, R, N, Q, F, W, Y, P, or C; V398 replaced with D, E, H, K, R, N, Q, F, W, Y, P, or C; E399 replaced with H, K, R, A, G, I, L, S, T, M, V, N, Q, F, W, Y, P, or C; E400 replaced with H, K, R, A, G, I, L, S, T, M, V, N, Q, F, W, Y, P, or C; W401 replaced with D, E, H, K, R, N, Q, A, G, I, L, S, T, M, V, P, or C; K402 replaced with D, E, A, G, I, L, S, T, M, V, N, Q, F, W, Y, P, or C; C403 replaced with D, E, H, K, R, A, G, I, L, S, T, M, V, N, Q, F, W, Y, or P; M404 replaced with D, E, H, K, R, N, Q, F, W, Y, P, or C; Y405 replaced with D, E, H, K, R, N, Q, A, G, I, L, S, T, M, V, P, or C; T406 replaced with D, E, H, K, R, N, Q, F, W, Y, P, or C; P407 replaced with D, E, H, K, R, A, G, I, L, S, T, M, V, N, Q, F, W, Y, or C; K408 replaced with D, E, A, G, I, L, S, T, M, V, N, Q, F, W, Y, P, or C; M409 replaced with D, E, H, K, R, N, Q, F, W, Y, P, or C; P410 replaced with D, E, H, K, R, A, G, I, L, S, T, M, V, N, Q, F, W, Y, or C; I411 replaced with D, E, H, K, R, N, Q, F, W, Y, P, or C; A412 replaced with D, E, H, K, R, N, Q, F, W, Y, P, or C; Q413 replaced with D, E, H, K, R, A, G, I, L, S, T, M, V, F, W, Y, P, or C; P414 replaced with D, E, H, K, R, A, G, I, L, S, T, M, V, N, Q, F, W, Y, or C; C415 replaced with D, E, H, K, R, A, G, I, L, S, T, M, V, N, Q, F, W, Y, or P; N416 replaced with D, E, H, K, R, A, G, I, L, S, T, M, V, F, W, Y, P, or C; I417 replaced with D, E, H, K, R, N, Q, F, W, Y, P, or C; F418 replaced with D, E, H, K, R, N, Q, A, G, I, L, S, T, M, V, P, or C; D419 replaced with H, K, R, A, G, I, L, S, T, M, V, N, Q, F, W, Y, P, or C; C420 replaced with D, E, H, K, R, A, G, I, L, S, T, M, V, N, Q, F, W, Y, or P; P421 replaced with D, E, H, K, R, A, G, I, L, S, T, M, V, N, Q, F, W, Y, or C; K422 replaced with D, E, A, G, I, L, S, T, M, V, N, Q, F, W, Y, P, or C; W423 replaced with D, E, H, K, R, N, Q, A, G, I, L, S, T, M, V, P, or C; L424 replaced with D, E, H, K, R, N, Q, F, W, Y, P, or C; A425 replaced with D, E, H, K, R, N, Q, F, W, Y, P, or C; Q426 replaced with D, E, H, K, R, A, G, I, L, S, T, M, V, F, W, Y, P, or C; E427 replaced with H, K, R, A, G, I, L, S, T, M, V, N, Q, F, W, Y, P, or C; W428 replaced with D, E, H, K, R, N, Q, A, G, I, L, S, T, M, V, P, or C; S429 replaced with D, E, H, K, R, N, Q, F, W, Y, P, or C; P430 replaced with D, E, H, K, R, A, G, I, L, S, T, M, V, N, Q, F, W, Y, or C; C431 replaced with D, E, H, K, R, A, G, I, L, S, T, M, V, N, Q, F, W, Y, or P; T432 replaced with D, E, H, K, R, N, Q, F, W, Y, P, or C; V433 replaced with D, E, H, K, R, N, Q, F, W, Y, P, or C; T434 replaced with D, E, H, K, R, N, Q, F, W, Y, P, or C; C435 replaced with D, E, H, K, R, A, G, I, L, S, T, M, V, N, Q, F, W, Y, or P; G436 replaced with D, E, H, K, R, N, Q, F, W, Y, P, or C; Q437 replaced with D, E, H, K, R, A, G, I, L, S, T, M, V, F, W, Y, P, or C; G438 replaced with D, E, H, K, R, N, Q, F, W, Y, P, or C; L439 replaced with D, E, H, K, R, N, Q, F, W, Y, P, or C; R440 replaced with D, E, A, G, I, L, S, T, M, V, N, Q, F, W, Y, P, or C; Y441 replaced with D, E, H, K, R, N, Q, A, G, I, L, S, T, M, V, P, or C; R442 replaced with D, E, A, G, I, L, S, T, M, V, N, Q, F, W, Y, P, or C; V443 replaced with D, E, H, K, R, N, Q, F, W, Y, P, or C; V444 replaced with D, E, H, K, R, N, Q, F, W, Y, P, or C; L445 replaced with D, E, H, K, R, N, Q, F, W, Y, P, or C; C446 replaced with D, E, H, K, R, A, G, I, L, S, T, M, V, N, Q, F, W, Y, or P; I447 replaced with D, E, H, K, R, N, Q, F, W, Y, P, or C; D448 replaced with H, K, R, A, G, I, L, S, T, M, V, N, Q, F, W, Y, P, or C; H449 replaced with D, E, A, G, I, L, S, T, M, V, N, Q, F, W, Y, P, or C; R450 replaced with D, E, A, G, I, L, S, T, M, V, N, Q, F, W, Y, P, or C; G451 replaced with D, E, H, K, R, N, Q, F, W, Y, P, or C; M452 replaced with D, E, H, K, R, N, Q, F, W, Y, P, or C; H453 replaced with D, E, A, G, I, L, S, T, M, V, N, Q, F, W, Y, P, or C; T454 replaced with D, E, H, K, R, N, Q, F, W, Y, P, or C; G455 replaced with D, E, H, K, R, N, Q, F, W, Y, P, or C; G456 replaced with D, E, H, K, R, N, Q, F, W, Y, P, or C; C457 replaced with D, E, H, K, R, A, G, I, L, S, T, M, V, N, Q, F, W, Y, or P; S458 replaced with D, E, H, K, R, N, Q, F, W, Y, P, or C; P459 replaced with D, E, H, K, R, A, G, I, L, S, T, M, V, N, Q, F, W, Y, or C; K460 replaced with D, E, A, G, I, L, S, T, M, V, N, Q, F, W, Y, P, or C; T461 replaced with D, E, H, K, R, N, Q, F, W, Y, P, or C; K462 replaced with D, E, A, G, I, L, S, T, M, V, N, Q, F, W, Y, P, or C; P463 replaced with D, E, H, K, R, A, G, I, L, S, T, M, V, N, Q, F, W, Y, or C; H464 replaced with D, E, A, G, I, L, S, T, M, V, N, Q, F, W, Y, P, or C; I465 replaced with D, E, H, K, R, N, Q, F, W, Y, P, or C; K466 replaced with D, E, A, G, I, L, S, T, M, V, N, Q, F, W, Y, P, or C; E467 replaced with H, K, R, A, G, I, L, S, T, M, V, N, Q, F, W, Y, P, or C; E468 replaced with H, K, R, A, G, I, L, S, T, M, V, N, Q, F, W, Y, P, or C; C469 replaced with D, E, H, K, R, A, G, I, L, S, T, M, V, N, Q, F, W, Y, or P; I470 replaced with D, E, H, K, R, N, Q, F, W, Y, P, or C; V471 replaced with D, E, H, K, R, N, Q, F, W, Y, P, or C; P472 replaced with D, E, H, K, R, A, G, I, L, S, T, M, V, N, Q, F, W, Y, or C; T473 replaced with D, E, H, K, R, N, Q, F, W, Y, P, or C; P474 replaced with D, E, H, K, R, A, G, I, L, S, T, M, V, N, Q, F, W, Y, or C; C475 replaced with D, E, H, K, R, A, G, I, L, S, T, M, V, N, Q, F, W, Y, or P; Y476 replaced with D, E, H, K, R, N, Q, A, G, I, L, S, T, M, V, P, or C; K477 replaced with D, E, A, G, I, L, S, T, M, V, N, Q, F, W, Y, P, or C; P478 replaced with D, E, H, K, R, A, G, I, L, S, T, M, V, N, Q, F, W, Y, or C; K479 replaced with D, E, A, G, I, L, S, T, M, V, N, Q, F, W, Y, P, or C; E480 replaced with H, K, R, A, G, I, L, S, T, M, V, N, Q, F, W, Y, P, or C; K481 replaced with D, E, A, G, I, L, S, T, M, V, N, Q, F, W, Y, P, or C; L482 replaced with D, E, H, K, R, N, Q, F, W, Y, P, or C; P483 replaced with D, E, H, K, R, A, G, I, L, S, T, M, V, N, Q, F, W, Y, or C; V484 replaced with D, E, H, K, R, N, Q, F, W, Y, P, or C; E485 replaced with H, K, R, A, G, I, L, S, T, M, V, N, Q, F, W, Y, P, or C; A486 replaced with D, E, H, K, R, N, Q, F, W, Y, P, or C; K487 replaced with D, E, A, G, I, L, S, T, M, V, N, Q, F, W, Y, P, or C; L488 replaced with D, E, H, K, R, N, Q, F, W, Y, P, or C; P489 replaced with D, E, H, K, R, A, G, I, L, S, T, M, V, N, Q, F, W, Y, or C; W490 replaced with D, E, H, K, R, N, Q, A, G, I, L, S, T, M, V, P, or C; F491 replaced with D, E, H, K, R, N, Q, A, G, I, L, S, T, M, V, P, or C; K492 replaced with D, E, A, G, I, L, S, T, M, V, N, Q, F, W, Y, P, or C; Q493 replaced with D, E, H, K, R, A, G, I, L, S, T, M, V, F, W, Y, P, or C; A494 replaced with D, E, H, K, R, N, Q, F, W, Y, P, or C; Q495 replaced with D, E, H, K, R, A, G, I, L, S, T, M, V, F, W, Y, P, or C; E496 replaced with H, K, R, A, G, I, L, S, T, M, V, N, Q, F, W, Y, P, or C; L497 replaced with D, E, H, K, R, N, Q, F, W, Y, P, or C; E498 replaced with H, K, R, A, G, I, L, S, T, M, V, N, Q, F, W, Y, P, or C; E499 replaced with H, K, R, A, G, I, L, S, T, M, V, N, Q, F, W, Y, P, or C; G500 replaced with D, E, H, K, R, N, Q, F, W, Y, P, or C; A501 replaced with D, E, H, K, R, N, Q, F, W, Y, P, or C; A502 replaced with D, E, H, K, R, N, Q, F, W, Y, P, or C; V503 replaced with D, E, H, K, R, N, Q, F, W, Y, P, or C; S504 replaced with D, E, H, K, R, N, Q, F, W, Y, P, or C; E505 replaced with H, K, R, A, G, I, L, S, T, M, V, N, Q, F, W, Y, P, or C; E506 replaced with H, K, R, A, G, I, L, S, T, M, V, N, Q, F, W, Y, P, or C; P507 replaced with D, E, H, K, R, A, G, I, L, S, T, M, V, N, Q, F, W, Y, or C; S508 replaced with D, E, H, K, R, N, Q, F, W, Y, P, or C; F509 replaced with D, E, H, K, R, N, Q, A, G, I, L, S, T, M, V, P, or C; I510 replaced with D, E, H, K, R, N, Q, F, W, Y, P, or C; P511 replaced with D, E, H, K, R, A, G, I, L, S, T, M, V, N, Q, F, W, Y, or C; K512 replaced with D, E, A, G, I, L, S, T, M, V, N, Q, F, W, Y, P, or C; A513 replaced with D, E, H, K, R, N, Q, F, W, Y, P, or C; W514 replaced with D, E, H, K, R, N, Q, A, G, I, L, S, T, M, V, P, or C; S515 replaced with D, E, H, K, R, N, Q, F, W, Y, P, or C; A516 replaced with D, E, H, K, R, N, Q, F, W, Y, P, or C; C517 replaced with D, E, H, K, R, A, G, I, L, S, T, M, V, N, Q, F, W, Y, or P; T518 replaced with D, E, H, K, R, N, Q, F, W, Y, P, or C; V519 replaced with D, E, H, K, R, N, Q, F, W, Y, P, or C; T520 replaced with D, E, H, K, R, N, Q, F, W, Y, P, or C; C521 replaced with D, E, H, K, R, A, G, I, L, S, T, M, V, N, Q, F, W, Y, or P; G522 replaced with D, E, H, K, R, N, Q, F, W, Y, P, or C; V523 replaced with D, E, H, K, R, N, Q, F, W, Y, P, or C; G524 replaced with D, E, H, K, R, N, Q, F, W, Y, P, or C; T525 replaced with D, E, H, K, R, N, Q, F, W, Y, P, or C; Q526 replaced with D, E, H, K, R, A, G, I, L, S, T, M, V, F, W, Y, P, or C; V527 replaced with D, E, H, K, R, N, Q, F, W, Y, P, or C; R528 replaced with D, E, A, G, I, L, S, T, M, V, N, Q, F, W, Y, P, or C; I529 replaced with D, E, H, K, R, N, Q, F, W, Y, P, or C; V530 replaced with D, E, H, K, R, N, Q, F, W, Y, P, or C; R531 replaced with D, E, A, G, I, L, S, T, M, V, N, Q, F, W, Y, P, or C; C532 replaced with D, E, H, K, R, A, G, I, L, S, T, M, V, N, Q, F, W, Y, or P; Q533 replaced with D, E, H, K, R, A, G, I, L, S, T, M, V, F, W, Y, P, or C; V534 replaced with D, E, H, K, R, N, Q, F, W, Y, P, or C; L535 replaced with D, E, H, K, R, N, Q, F, W, Y, P, or C; L536 replaced with D, E, H, K, R, N, Q, F, W, Y, P, or C; S537 replaced with D, E, H, K, R, N, Q, F, W, Y, P, or C; F538 replaced with D, E, H, K, R, N, Q, A, G, I, L, S, T, M, V, P, or C; S539 replaced with D, E, H, K, R, N, Q, F, W, Y, P, or C; Q540 replaced with D, E, H, K, R, A, G, I, L, S, T, M, V, F, W, Y, P, or C; S541 replaced with D, E, H, K, R, N, Q, F, W, Y, P, or C; V542 replaced with D, E, H, K, R, N, Q, F, W, Y, P, or C; A543 replaced with D, E, H, K, R, N, Q, F, W, Y, P, or C; D544 replaced with H, K, R, A, G, I, L, S, T, M, V, N, Q, F, W, Y, P, or C; L545 replaced with D, E, H, K, R, N, Q, F, W, Y, P, or C; P546 replaced with D, E, H, K, R, A, G, I, L, S, T, M, V, N, Q, F, W, Y, or C; I547 replaced with D, E, H, K, R, N, Q, F, W, Y, P, or C; D548 replaced with H, K, R, A, G, I, L, S, T, M, V, N, Q, F, W, Y, P, or C; E549 replaced with H, K, R, A, G, I, L, S, T, M, V, N, Q, F, W, Y, P, or C; C550 replaced with D, E, H, K, R, A, G, I, L, S, T, M, V, N, Q, F, W, Y, or P; E551 replaced with H, K, R, A, G, I, L, S, T, M, V, N, Q, F, W, Y, P, or C; G552 replaced with D, E, H, K, R, N, Q, F, W, Y, P, or C; P553 replaced with D, E, H, K, R, A, G, I, L, S, T, M, V, N, Q, F, W, Y, or C; K554 replaced with D, E, A, G, I, L, S, T, M, V, N, Q, F, W, Y, P, or C; P555 replaced with D, E, H, K, R, A, G, I, L, S, T, M, V, N, Q, F, W, Y, or C; A556 replaced with D, E, H, K, R, N, Q, F, W, Y, P, or C; S557 replaced with D, E, H, K, R, N, Q, F, W, Y, P, or C; Q558 replaced with D, E, H, K, R, A, G, I, L, S, T, M, V, F, W, Y, P, or C; R559 replaced with D, E, A, G, I, L, S, T, M, V, N, Q, F, W, Y, P, or C; A560 replaced with D, E, H, K, R, N, Q, F, W, Y, P, or C; C561 replaced with D, E, H, K, R, A, G, I, L, S, T, M, V, N, Q, F, W, Y, or P; Y562 replaced with D, E, H, K, R, N, Q, A, G, I, L, S, T, M, V, P, or C; A563 replaced with D, E, H, K, R, N, Q, F, W, Y, P, or C; G564 replaced with D, E, H, K, R, N, Q, F, W, Y, P, or C; P565 replaced with D, E, H, K, R, A, G, I, L, S, T, M, V, N, Q, F, W, Y, or C; C566 replaced with D, E, H, K, R, A, G, I, L, S, T, M, V, N, Q, F, W, Y, or P; S567 replaced with D, E, H, K, R, N, Q, F, W, Y, P, or C; G568 replaced with D, E, H, K, R, N, Q, F, W, Y, P, or C; E569 replaced with H, K, R, A, G, I, L, S, T, M, V, N, Q, F, W, Y, P, or C; I570 replaced with D, E, H, K, R, N, Q, F, W, Y, P, or C; P571 replaced with D, E, H, K, R, A, G, I, L, S, T, M, V, N, Q, F, W, Y, or C; E572 replaced with H, K, R, A, G, I, L, S, T, M, V, N, Q, F, W, Y, P, or C; F573 replaced with D, E, H, K, R, N, Q, A, G, I, L, S, T, M, V, P, or C; N574 replaced with D, E, H, K, R, A, G, I, L, S, T, M, V, F, W, Y, P, or C; P575 replaced with D, E, H, K, R, A, G, I, L, S, T, M, V, N, Q, F, W, Y, or C; D576 replaced with H, K, R, A, G, I, L, S, T, M, V, N, Q, F, W, Y, P, or C; E577 replaced with H, K, R, A, G, I, L, S, T, M, V, N, Q, F, W, Y, P, or C; T578 replaced with D, E, H, K, R, N, Q, F, W, Y, P, or C; D579 replaced with H, K, R, A, G, I, L, S, T, M, V, N, Q, F, W, Y, P, or C; G580 replaced with D, E, H, K, R, N, Q, F, W, Y, P, or C; L581 replaced with D, E, H, K, R, N, Q, F, W, Y, P, or C; F582 replaced with D, E, H, K, R, N, Q, A, G, I, L, S, T, M, V, P, or C; G583 replaced with D, E, H, K, R, N, Q, F, W, Y, P, or C; G584 replaced with D, E, H, K, R, N, Q, F, W, Y, P, or C; L585 replaced with D, E, H, K, R, N, Q, F, W, Y, P, or C; Q586 replaced with D, E, H, K, R, A, G, I, L, S, T, M, V, F, W, Y, P, or C; D587 replaced with H, K, R, A, G, I, L, S, T, M, V, N, Q, F, W, Y, P, or C; F588 replaced with D, E, H, K, R, N, Q, A, G, I, L, S, T, M, V, P, or C; D589 replaced with H, K, R, A, G, I, L, S, T, M, V, N, Q, F, W, Y, P, or C; E590 replaced with H, K, R, A, G, I, L, S, T, M, V, N, Q, F, W, Y, P, or C; L591 replaced with D, E, H, K, R, N, Q, F, W, Y, P, or C; Y592 replaced with D, E, H, K, R, N, Q, A, G, I, L, S, T, M, V, P, or C; D593 replaced with H, K, R, A, G, I, L, S, T, M, V, N, Q, F, W, Y, P, or C; W594 replaced with D, E, H, K, R, N, Q, A, G, I, L, S, T, M, V, P, or C; E595 replaced with H, K, R, A, G, I, L, S, T, M, V, N, Q, F, W, Y, P, or C; Y596 replaced with D, E, H, K, R, N, Q, A, G, I, L, S, T, M, V, P, or C; E597 replaced with H, K, R, A, G, I, L, S, T, M, V, N, Q, F, W, Y, P, or C; G598 replaced with D, E, H, K, R, N, Q, F, W, Y, P, or C; F599 replaced with D, E, H, K, R, N, Q, A, G, I, L, S, T, M, V, P, or C; T600 replaced with D, E, H, K, R, N, Q, F, W, Y, P, or C; K601 replaced with D, E, A, G, I, L, S, T, M, V, N, Q, F, W, Y, P, or C; C602 replaced with D, E, H, K, R, A, G, I, L, S, T, M, V, N, Q, F, W, Y, or P; S603 replaced with D, E, H, K, R, N, Q, F, W, Y, P, or C; E604 replaced with H, K, R, A, G, I, L, S, T, M, V, N, Q, F, W, Y, P, or C; S605 replaced with D, E, H, K, R, N, Q, F, W, Y, P, or C; C606 replaced with D, E, H, K, R, A, G, I, L, S, T, M, V, N, Q, F, W, Y, or P; G607 replaced with D, E, H, K, R, N, Q, F, W, Y, P, or C; G608 replaced with D, E, H, K, R, N, Q, F, W, Y, P, or C; G609 replaced with D, E, H, K, R, N, Q, F, W, Y, P, or C; V610 replaced with D, E, H, K, R, N, Q, F, W, Y, P, or C; Q611 replaced with D, E, H, K, R, A, G, I, L, S, T, M, V, F, W, Y, P, or C; E612 replaced with H, K, R, A, G, I, L, S, T, M, V, N, Q, F, W, Y, P, or C; A613 replaced with D, E, H, K, R, N, Q, F, W, Y, P, or C; V614 replaced with D, E, H, K, R, N, Q, F, W, Y, P, or C; V615 replaced with D, E, H, K, R, N, Q, F, W, Y, P, or C; S616 replaced with D E, H, K, R, N, Q, F, W, Y, P, or C; C617 replaced with D, E, H, K, R, A, G, I, L, S, T, M, V, N, Q, F, W, Y, or P; L618 replaced with D, E, H, K, R, N, Q, F, W, Y, P, or C; N619 replaced with D, E, H, K, R, A, G, I, L, S, T, M, V, F, W, Y, P, or C; K620 replaced with D, E, A, G, I, L, S, T, M, V, N, Q, F, W, Y, P, or C; Q621 replaced with D, E, H, K, R, A, G, I, L, S, T, M, V, F, W, Y, P, or C; T622 replaced with D, E, H, K, R, N, Q, F, W, Y, P, or C; R623 replaced with D, E, A, G, I, L, S, T, M, V, N, Q, F, W, Y, P, or C; E624 replaced with H, K, R, A, G, I, L, S, T, M, V, N, Q, F, W, Y, P, or C; P625 replaced with D, E, H, K, R, A, G, I, L, S, T, M, V, N, Q, F, W, Y, or C; A626 replaced with D, E, H, K, R, N, Q, F, W, Y, P, or C; E627 replaced with H, K, R, A, G, I, L, S, T, M, V, N, Q, F, W, Y, P, or C; E628 replaced with H, K, R, A, G, I, L, S, T, M, V, N, Q, F, W, Y, P, or C; N629 replaced with D, E, H, K, R, A, G, I, L, S, T, M, V, F, W, Y, P, or C; L630 replaced with D, E, H, K, R, N, Q, F, W, Y, P, or C; C631 replaced with D, E, H, K, R, A, G, I, L, S, T, M, V, N, Q, F, W, Y, or P; V632 replaced with D, E, H, K, R, N, Q, F, W, Y, P, or C; T633 replaced with D, E, H, K, R, N, Q, F, W, Y, P, or C; S634 replaced with D, E, H, K, R, N, Q, F, W, Y, P, or C; R635 replaced with D, E, A, G, I, L, S, T, M, V, N, Q, F, W, Y, P, or C; R636 replaced with D, E, A, G, I, L, S, T, M, V, N, Q, F, W, Y, P, or C; P637 replaced with D, E, H, K, R, A, G, I, L, S, T, M, V, N, Q, F, W, Y, or C; P638 replaced with D, E, H, K, R, A, G, I, L, S, T, M, V, N, Q, F, W, Y, or C; Q639 replaced with D, E, H, K, R, A, G, I, L, S, T, M, V, F, W, Y, P, or C; L640 replaced with D, E, H, K, R, N, Q, F, W, Y, P, or C; L641 replaced with D, E, H, K, R, N, Q, F, W, Y, P, or C; K642 replaced with D, E, A, G, I, L, S, T, M, V, N, Q, F, W, Y, P, or C; S643 replaced with D, E, H, K, R, N, Q, F, W, Y, P, or C; C644 replaced with D, E, H, K, R, A, G, I, L, S, T, M, V, N, Q, F, W, Y, or P; N645 replaced with D, E, H, K, R, A, G, I, L, S, T, M, V, F, W, Y, P, or C; L646 replaced with D, E, H, K, R, N, Q, F, W, Y, P, or C; D647 replaced with H, K, R, A, G, I, L, S, T, M, V, N, Q, F, W, Y, P, or C; P648 replaced with D, E, H, K, R, A, G, I, L, S, T, M, V, N, Q, F, W, Y, or C; C649 replaced with D, E, H, K, R, A, G, I, L, S, T, M, V, N, Q, F, W, Y, or P; P650 replaced with D, E, H, K, R, A, G, I, L, S, T, M, V, N, Q, F, W, Y, or C; A651 replaced with D, E, H, K, R, N, Q, F, W, Y, P, or C; R652 replaced with D, E, A, G, I, L, S, T, M, V, N, Q, F, W, Y, P, or C; W653 replaced with D, E, H, K, R, N, Q, A, G, I, L, S, T, M, V, P, or C; E654 replaced with H, K, R, A, G, I, L, S, T, M, V, N, Q, F, W, Y, P, or C; I655 replaced with D, E, H, K, R, N, Q, F, W, Y, P, or C; G656 replaced with D, E, H, K, R, N, Q, F, W, Y, P, or C; K657 replaced with D, E, A, G, I, L, S, T, M, V, N, Q, F, W, Y, P, or C; W658 replaced with D, E, H, K, R, N, Q, A, G, I, L, S, T, M, V, P, or C; S659 replaced with D, E, H, K, R, N, Q, F, W, Y, P, or C; P660 replaced with D, E, H, K, R, A, G, I, L, S, T, M, V, N, Q, F, W, Y, or C; C661 replaced with D, E, H, K, R, A, G, I, L, S, T, M, V, N, Q, F, W, Y, or P; S662 replaced with D, E, H, K, R, N, Q, F, W, Y, P, or C; L663 replaced with D, E, H, K, R, N, Q, F, W, Y, P, or C; T664 replaced with D, E, H, K, R, N, Q, F, W, Y, P, or C; C665 replaced with D, E, H, K, R, A, G, I, L, S, T, M, V, N, Q, F, W, Y, or P; G666 replaced with D, E, H, K, R, N, Q, F, W, Y, P, or C; V667 replaced with D, E, H, K, R, N, Q, F, W, Y, P, or C; G668 replaced with D, E, H, K, R, N, Q, F, W, Y, P, or C; L669 replaced with D, E, H, K, R, N, Q, F, W, Y, P, or C; Q670 replaced with D, E, H, K, R, A, G, I, L, S, T, M, V, F, W, Y, P, or C; T671 replaced with D, E, H, K, R, N, Q, F, W, Y, P, or C; R672 replaced with D, E, A, G, I, L, S, T, M, V, N, Q, F, W, Y, P, or C; D673 replaced with H, K, R, A, G, I, L, S, T, M, V, N, Q, F, W, Y, P, or C; V674 replaced with D, E, H, K, R, N, Q, F, W, Y, P, or C; F675 replaced with D, E, H, K, R, N, Q, A, G, I, L, S, T, M, V, P, or C; C676 replaced with D, E, H, K, R, A, G, I, L, S, T, M, V, N, Q, F, W, Y, or P; S677 replaced with D, E, H, K, R, N, Q, F, W, Y, P, or C; H678 replaced with D, E, A, G, I, L, S, T, M, V, N, Q, F, W, Y, P, or C; L679 replaced with D, E, H, K, R, N, Q, F, W, Y, P, or C; L680 replaced with D, E, H, K, R, N, Q, F, W, Y, P, or C; S681 replaced with D, E, H, K, R, N, Q, F, W, Y, P, or C; R682 replaced with D, E, A, G, I, L, S, T, M, V, N, Q, F, W, Y, P, or C; E683 replaced with H, K, R, A, G, I, L, S, T, M, V, N, Q, F, W, Y, P, or C; M684 replaced with D, E, H, K, R, N, Q, F, W, Y, P, or C; N685 replaced with D, E, H, K, R, A, G, I, L, S, T, M, V, F, W, Y, P, or C; E686 replaced with H, K, R, A, G, I, L, S, T, M, V, N, Q, F, W, Y, P, or C; T687 replaced with D, E, H, K, R, N, Q, F, W, Y, P, or C; V688 replaced with D, E, H, K, R, N, Q, F, W, Y, P, or C; 1689 replaced with D, E, H, K, R, N, Q, F, W, Y, P, or C; L690 replaced with D, E, H, K, R, N, Q, F, W, Y, P, or C; A691 replaced with D, E, H, K, R, N, Q, F, W, Y, P, or C; D692 replaced with H, K, R, A, G, I, L, S, T, M, V, N, Q, F, W, Y, P, or C; E693 replaced with H, K, R, A, G, I, L, S, T, M, V, N, Q, F, W, Y, P, or C; L694 replaced with D, E, H, K, R, N, Q, F, W, Y, P, or C; C695 replaced with D, E, H, K, R, A, G, I, L, S, T, M, V, N, Q, F, W, Y, or P; R696 replaced with D, E, A, G, I, L, S, T, M, V, N, Q, F, W, Y, P, or C; Q697 replaced with D, E, H, K, R, A, G, I, L, S, T, M, V, F, W, Y, P, or C; P698 replaced with D, E, H, K, R, A, G, I, L, S, T, M, V, N, Q, F, W, Y, or C; K699 replaced with D, E, A, G, I, L, S, T, M, V, N, Q, F, W, Y, P, or C; P700 replaced with D, E, H, K, R, A, G, I, L, S, T, M, V, N, Q, F, W, Y, or C; S701 replaced with D, E, H, K, R, N, Q, F, W, Y, P, or C; T702 replaced with D, E, H, K, R, N, Q, F, W, Y, P, or C; V703 replaced with D, E, H, K, R, N, Q, F, W, Y, P, or C; Q704 replaced with D, E, H, K, R, A, G, I, L, S, T, M, V, F, W, Y, P, or C; A705 replaced with D, E, H, K, R, N, Q, F, W, Y, P, or C; C706 replaced with D, E, H, K, R, A, G, I, L, S, T, M, V, N, Q, F, W, Y, or P; N707 replaced with D, E, H, K, R, A, G, I, L, S, T, M, V, F, W, Y, P, or C; R708 replaced with D, E, A, G, I, L, S, T, M, V, N, Q, F, W, Y, P, or C; F709 replaced with D, E, H, K, R, N, Q, A, G, I, L, S, T, M, V, P, or C; N710 replaced with D, E, H, K, R, A, G, I, L, S, T, M, V, F, W, Y, P, or C; C711 replaced with D, E, H, K, R, A, G, I, L, S, T, M, V, N, Q, F, W, Y, or P; P712 replaced with D, E, H, K, R, A, G, I, L, S, T, M, V, N, Q, F, W, Y, or C; P713 replaced with D, E, H, K, R, A, G, I, L, S, T, M, V, N, Q, F, W, Y, or C; A714 replaced with D, E, H, K, R, N, Q, F, W, Y, P, or C; W715 replaced with D, E, H, K, R, N, Q, A, G, I, L, S, T, M, V, P, or C; Y716 replaced with D, E, H, K, R, N, Q, A, G, I, L, S, T, M, V, P, or C; P717 replaced with D, E, H, K, R, A, G, I, L, S, T, M, V, N, Q, F, W, Y, or C; A718 replaced with D, E, H, K, R, N, Q, F, W, Y, P, or C; Q719 replaced with D, E, H, K, R, A, G, I, L, S, T, M, V, F, W, Y, P, or C; W720 replaced with D, E, H, K, R, N, Q, A, G, I, L, S, T, M, V, P, or C; Q721 replaced with D, E, H, K, R, A, G, I, L, S, T, M, V, F, W, Y, P, or C; P722 replaced with D, E, H, K, R, A, G, I, L, S, T, M, V, N, Q, F, W, Y, or C; C723 replaced with D, E, H, K, R, A, G, I, L, S, T, M, V, N, Q, F, W, Y, or P; S724 replaced with D, E, H, K, R, N, Q, F, W, Y, P, or C; R725 replaced with D, E, A, G, I, L, S, T, M, V, N, Q, F, W, Y, P, or C; T726 replaced with D, E, H, K, R, N, Q, F, W, Y, P, or C; C727 replaced with D, E, H, K, R, A, G, I, L, S, T, M, V, N, Q, F, W, Y, or P; G728 replaced with D, E, H, K, R, N, Q, F, W, Y, P, or C; G729 replaced with D, E, H, K, R, N, Q, F, W, Y, P, or C; G730 replaced with D, E, H, K, R, N, Q, F, W, Y, P, or C; V731 replaced with D, E, H, K, R, N, Q, F, W, Y, P, or C; Q732 replaced with D, E, H, K, R, A, G, I, L, S, T, M, V, F, W, Y, P, or C; K733 replaced with D, E, A, G, I, L, S, T, M, V, N, Q, F, W, Y, P, or C; R734 replaced with D, E, A, G, I, L, S, T, M, V, N, Q, F, W, Y, P, or C; E735 replaced with H, K, R, A, G, I, L, S, T, M, V, N, Q, F, W, Y, P, or C; V736 replaced with D, E, H, K, R, N, Q, F, W, Y, P, or C; L737 replaced with D, E, H, K, R, N, Q, F, W, Y, P, or C; C738 replaced with D, E, H, K, R, A, G, I, L, S, T, M, V, N, Q, F, W, Y, or P; K739 replaced with D, E, A, G, I, L, S, T, M, V, N, Q, F, W, Y, P, or C; Q740 replaced with D, E, H, K, R, A, G, I, L, S, T, M, V, F, W, Y, P, or C; R741 replaced with D, E, A, G, I, L, S, T, M, V, N, Q, F, W, Y, P, or C; M742 replaced with D, E, H, K, R, N, Q, F, W, Y, P, or C; A743 replaced with D, E, H, K, R, N, Q, F, W, Y, P, or C; D744 replaced with H, K, R, A, G, I, L, S, T, M, V, N, Q, F, W, Y, P, or C; G745 replaced with D, E, H, K, R, N, Q, F, W, Y, P, or C; S746 replaced with D, E, H, K, R, N, Q, F, W, Y, P, or C; F747 replaced with D, E, H, K, R, N, Q, A, G, I, L, S, T, M, V, P, or C; L748 replaced with D, E, H, K, R, N, Q, F, W, Y, P, or C; E749 replaced with H, K, R, A, G, I, L, S, T, M, V, N, Q, F, W, Y, P, or C; L750 replaced with D, E, H, K, R, N, Q, F, W, Y, P, or C; P751 replaced with D, E, H, K, R, A, G, I, L, S, T, M, V, N, Q, F, W, Y, or C; E752 replaced with H, K, R, A, G, I, L, S, T, M, V, N, Q, F, W, Y, P, or C; T753 replaced with D, E, H, K, R, N, Q, F, W, Y, P, or C; F754 replaced with D, E, H, K, R, N, Q, A, G, I, L, S, T, M, V, P, or C; C755 replaced with D, E, H, K, R, A, G, I, L, S, T, M, V, N, Q, F, W, Y, or P; S756 replaced with D, E, H, K, R, N, Q, F, W, Y, P, or C; A757 replaced with D, E, H, K, R, N, Q, F, W, Y, P, or C; S758 replaced with D, E, H, K, R, N, Q, F, W, Y, P, or C; K759 replaced with D, E, A, G, I, L, S, T, M, V, N, Q, F, W, Y, P, or C; P760 replaced with D, E, H, K, R, A, G, I, L, S, T, M, V, N, Q, F, W, Y, or C; A761 replaced with D, E, H, K, R, N, Q, F, W, Y, P, or C; C762 replaced with D, E, H, K, R, A, G, I, L, S, T, M, V, N, Q, F, W, Y, or P; Q763 replaced with D, E, H, K, R, A, G, I, L, S, T, M, V, F, W, Y, P, or C; Q764 replaced with D, E, H, K, R, A, G, I, L, S, T, M, V, F, W, Y, P, or C; A765 replaced with D, E, H, K, R, N, Q, F, W, Y, P, or C; C766 replaced with D, E, H, K, R, A, G, I, L, S, T, M, V, N, Q, F, W, Y, or P; K767 replaced with D, E, A, G, I, L, S, T, M, V, N, Q, F, W, Y, P, or C; K768 replaced with D, E, A, G, I, L, S, T, M, V, N, Q, F, W, Y, P, or C; D769 replaced with H, K, R, A, G, I, L, S, T, M, V, N, Q, F, W, Y, P, or C; D770 replaced with H, K, R, A, G, I, L, S, T, M, V, N, Q, F, W, Y, P, or C; C771 replaced with D, E, H, K, R, A, G, I, L, S, T, M, V, N, Q, F, W, Y, or P; P772 replaced with D, E, H, K, R, A, G, I, L, S, T, M, V, N, Q, F, W, Y, or C; S773 replaced with D, E, H, K, R, N, Q, F, W, Y, P, or C; E774 replaced with H, K, R, A, G, I, L, S, T, M, V, N, Q, F, W, Y, P, or C; W775 replaced with D, E, H, K, R, N, Q, A, G, I, L, S, T, M, V, P, or C; L776 replaced with D, E, H, K, R, N, Q, F, W, Y, P, or C; L777 replaced with D, E, H, K, R, N, Q, F, W, Y, P, or C; S778 replaced with D, E, H, K, R, N, Q, F, W, Y, P, or C; D779 replaced with H, K, R, A, G, I, L, S, T, M, V, N, Q, F, W, Y, P, or C; W780 replaced with D, E, H, K, R, N, Q, A, G, I, L, S, T, M, V, P, or C; T781 replaced with D, E, H, K, R, N, Q, F, W, Y, P, or C; E782 replaced with H, K, R, A, G, I, L, S, T, M, V, N, Q, F, W, Y, P, or C; C783 replaced with D, E, H, K, R, A, G, I, L, S, T, M, V, N, Q, F, W, Y, or P; S784 replaced with D, E, H, K, R, N, Q, F, W, Y, P, or C; T785 replaced with D, E, H, K, R, N, Q, F, W, Y, P, or C; S786 replaced with D, E, H, K, R, N, Q, F, W, Y, P, or C; C787 replaced with D, E, H, K, R, A, G, I, L, S, T, M, V, N, Q, F, W, Y, or P; G788 replaced with D, E, H, K, R, N, Q, F, W, Y, P, or C; E789 replaced with H, K, R, A, G, I, L, S, T, M, V, N, Q, F, W, Y, P, or C; G790 replaced with D, E, H, K, R, N, Q, F, W, Y, P, or C; T791 replaced with D, E, H, K, R, N, Q, F, W, Y, P, or C; Q792 replaced with D, E, H, K, R, A, G, I, L, S, T, M, V, F, W, Y, P, or C; T793 replaced with D, E, H, K, R, N, Q, F, W, Y, P, or C; R794 replaced with D, E, A, G, J, L, S, T, M, V, N, Q, F, W, Y, P, or C; S795 replaced with D, E, H, K, R, N, Q, F, W, Y, P, or C; A796 replaced with D, E, H, K, R, N, Q, F, W, Y, P, or C; I797 replaced with D, E, H, K, R, N, Q, F, W, Y, P, or C; C798 replaced with D, E, H, K, R, A, G, J, L, S, T, M, V, N, Q, F, W, Y, or P; R799 replaced with D, E, A, G, I, L, S, T, M, V, N, Q, F, W, Y, P, or C; K800 replaced with D, E, A, G, I, L, S, T, M, V, N, Q, F, W, Y, P, or C; M801 replaced with D, E, H, K, R, N, Q, F, W, Y, P, or C; L802 replaced with D, E, H, K, R, N, Q, F, W, Y, P, or C; K803 replaced with D, E, A, G, I, L, S, T, M, V, N, Q, F, W, Y, P, or C; T804 replaced with D, E, H, K, R, N, Q, F, W, Y, P, or C; G805 replaced with D, E, H, K, R, N, Q, F, W, Y, P, or C; L806 replaced with D, E, H, K, R, N, Q, F, W, Y, P, or C; S807 replaced with D, E, H, K, R, N, Q, F, W, Y, P, or C; T808 replaced with D, E, H, K, R, N, Q, F, W, Y, P, or C; V809 replaced with D, E, H, K, R, N, Q, F, W, Y, P, or C; V810 replaced with D, E, H, K, R, N, Q, F, W, Y, P, or C; N811 replaced with D, E, H, K, R, A, G, I, L, S, T, M, V, F, W, Y, P, or C; S812 replaced with D, E, H, K, R, N, Q, F, W, Y, P, or C; T813 replaced with D, E, H, K, R, N, Q, F, W, Y, P, or C; L814 replaced with D, E, H, K, R, N, Q, F, W, Y, P, or C; C815 replaced with D, E, H, K, R, A, G, I, L, S, T, M, V, N, Q, F, W, Y, or P; P816 replaced with D, E, H, K, R, A, G, I, L, S, T, M, V, N, Q, F, W, Y, or C; P817 replaced with D, E, H, K, R, A, G, I, L, S, T, M, V, N, Q, F, W, Y, or C; L818 replaced with D, E, H, K, R, N, Q, F, W, Y, P, or C; P819 replaced with D, E, H, K, R, A, G, I, L, S, T, M, V, N, Q, F, W, Y, or C; F820 replaced with D, E, H, K, R, N, Q, A, G, I, L, S, T, M, V, P, or C; S821 replaced with D, E, H, K, R, N, Q, F, W, Y, P, or C; S822 replaced with D, E, H, K, R, N, Q, F, W, Y, P, or C; S823 replaced with D, E, H, K, R, N, Q, F, W, Y, P, or C; I824 replaced with D, E, H, K, R, N, Q, F, W, Y, P, or C; R825 replaced with D, E, A, G, I, L, S, T, M, V, N, Q, F, W, Y, P, or C; P826 replaced with D, E, H, K, R, A, G, I, L, S, T, M, V, N, Q, F, W, Y, or C; C827 replaced with D, E, H, K, R, A, G, I, L, S, T, M, V, N, Q, F, W, Y, or P; M828 replaced with D, E, H, K, R, N, Q, F, W, Y, P, or C; L829 replaced with D, E, H, K, R, N, Q, F, W, Y, P, or C; A830 replaced with D, E, H, K, R, N, Q, F, W, Y, P, or C; T831 replaced with D, E, H, K, R, N, Q, F, W, Y, P, or C; C832 replaced with D, E, H, K, R, A, G, I, L, S, T, M, V, N, Q, F, W, Y, or P; A833 replaced with D, E, H, K, R, N, Q, F, W, Y, P, or C; R834 replaced with D, E, A, G, I, L, S, T, M, V, N, Q, F, W, Y, P, or C; P835 replaced with D, E, H, K, R, A, G, I, L, S, T, M, V, N, Q, F, W, Y, or C; G836 replaced with D, E, H, K, R, N, Q, F, W, Y, P, or C; R837 replaced with D, E, A, G, I, L, S, T, M, V, N, Q, F, W, Y, P, or C; P838 replaced with D, E, H, K, R, A, G, I, L, S, T, M, V, N, Q, F, W, Y, or C; S839 replaced with D, E, H, K, R, N, Q, F, W, Y, P, or C; T840 replaced with D, E, H, K, R, N, Q, F, W, Y, P, or C; K841 replaced with D, E, A, G, I, L, S, T, M, V, N, Q, F, W, Y, P, or C; H842 replaced with D, E, A, G, I, L, S, T, M, V, N, Q, F, W, Y, P, or C; S843 replaced with D, E, H, K, R, N, Q, F, W, Y, P, or C; P844 replaced with D, E, H, K, R, A, G, I, L, S, T, M, V, N, Q, F, W, Y, or C; H845 replaced with D, E, A, G, I, L, S, T, M, V, N, Q, F, W, Y, P, or C; I846 replaced with D, E, H, K, R, N, Q, F, W, Y, P, or C; A847 replaced with D, E, H, K, R, N, Q, F, W, Y, P, or C; A848 replaced with D, E, H, K, R, N, Q, F, W, Y, P, or C; A849 replaced with D, E, H, K, R, N, Q, F, W, Y, P, or C; R850 replaced with D, E, A, G, I, L, S, T, M, V, N, Q, F, W, Y, P, or C; K851 replaced with D, E, A, G, I, L, S, T, M, V, N, Q, F, W, Y, P, or C; V852 replaced with D, E, H, K, R, N, Q, F, W, Y, P, or C; Y853 replaced with D, E, H, K, R, N, Q, A, G, I, L, S, T, M, V, P, or C; I854 replaced with D, E, H, K, R, N, Q, F, W, Y, P, or C; Q855 replaced with D, E, H, K, R, A, G, I, L, S, T, M, V, F, W, Y, P, or C; T856 replaced with D, E, H, K, R, N, Q, F, W, Y, P, or C; R857 replaced with D, E, A, G, I, L, S, T, M, V, N, Q, F, W, Y, P, or C; R858 replaced with D, E, A, G, I, L, S, T, M, V, N, Q, F, W, Y, P, or C; Q859 replaced with D, E, H, K, R, A, G, I, L, S, T, M, V, F, W, Y, P, or C; R860 replaced with D, E, A, G, I, L, S, T, M, V, N, Q, F, W, Y, P, or C; K861 replaced with D, E, A, G, I, L, S, T, M, V, N, Q, F, W, Y, P, or C; L862 replaced with D, E, H, K, R, N, Q, F, W, Y, P, or C; H863 replaced with D, E, A, G, I, L, S, T, M, V, N, Q, F, W, Y, P, or C; F864 replaced with D, E, H, K, R, N, Q, A, G, I, L, S, T, M, V, P, or C; V865 replaced with D, E, H, K, R, N, Q, F, W, Y, P, or C; V866 replaced with D, E, H, K, R, N, Q, F, W, Y, P, or C; G867 replaced with D, E, H, K, R, N, Q, F, W, Y, P, or C; G868 replaced with D, E, H, K, R, N, Q, F, W, Y, P, or C; F869 replaced with D, E, H, K, R, N, Q, A, G, I, L, S, T, M, V, P, or C; A870 replaced with D, E, H, K, R, N, Q, F, W, Y, P, or C; Y871 replaced with D, E, H, K, R, N, Q, A, G, I, L, S, T, M, V, P, or C; L872 replaced with D, E, H, K, R, N, Q, F, W, Y, P, or C; L873 replaced with D, E, H, K, R, N, Q, F, W, Y, P, or C; P874 replaced with D, E, H, K, R, A, G, I, L, S, T, M, V, N, Q, F, W, Y, or C; K875 replaced with D, E, A, G, I, L, S, T, M, V, N, Q, F, W, Y, P, or C; T876 replaced with D, E, H, K, R, N, Q, F, W, Y, P, or C; A877 replaced with D, E, H, K, R, N, Q, F, W, Y, P, or C; V878 replaced with D, E, H, K, R, N, Q, F, W, Y, P, or C; V879 replaced with D, E, H, K, R, N, Q, F, W, Y, P, or C; L880 replaced with D, E, H, K, R, N, Q, F, W, Y, P, or C; R881 replaced with D, E, A, G, I, L, S, T, M, V, N, Q, F, W, Y, P, or C; C882 replaced with D, E, H, K, R, A, G, I, L, S, T, M, V, N, Q, F, W, Y, or P; P883 replaced with D, E, H, K, R, A, G, I, L, S, T, M, V, N, Q, F, W, Y, or C; A884 replaced with D, E, H, K, R, N, Q, F, W, Y, P, or C; R885 replaced with D, E, A, G, I, L, S, T, M, V, N, Q, F, W, Y, P, or C; R886 replaced with D, E, A, G, I, L, S, T, M, V, N, Q, F, W, Y, P, or C; V887 replaced with D, E, H, K, R, N, Q, F, W, Y, P, or C; R888 replaced with D, E, A, G, I, L, S, T, M, V, N, Q, F, W, Y, P, or C; K889 replaced with D, E, A, G, I, L, S, T, M, V, N, Q, F, W, Y, P, or C; P890 replaced with D, E, H, K, R, A, G, I, L, S, T, M, V, N, Q, F, W, Y, or C; L891 replaced with D, E, H, K, R, N, Q, F, W, Y, P, or C; I892 replaced with D, E, H, K, R, N, Q, F, W, Y, P, or C; T893 replaced with D, E, H, K, R, N, Q, F, W, Y, P, or C; W894 replaced with D, E, H, K, R, N, Q, A, G, I, L, S, T, M, V, P, or C; E895 replaced with H, K, R, A, G, I, L, S, T, M, V, N, Q, F, W, Y, P, or C; K896 replaced with D, E, A, G, I, L, S, T, M, V, N, Q, F, W, Y, P, or C; D897 replaced with H, K, R, A, G, I, L, S, T, M, V, N, Q, F, W, Y, P, or C; G898 replaced with D, E, H, K, R, N, Q, F, W, Y, P, or C; Q899 replaced with D, E, H, K, R, A, C, I, L, S, T, M, V, F, W, Y, P, or C; H900 replaced with D, E, A, G, I, L, S, T, M, V, N, Q, F, W, Y, P, or C; L901 replaced with D, B, H, K, R, N, Q, F, W, Y, P, or C; I902 replaced with D, B, H, K, R, N, Q, F, W, Y, P, or C; S903 replaced with D, E, H, K, R, N, Q, F, W, Y, P, or C; S904 replaced with D, E, H, K, R, N, Q, F, W, Y, P, or C; T905 replaced with D, E, H, K, R, N, Q, F, W, Y, P, or C; H906 replaced with D, E, A, C, I, L, S, T, M, V, N, Q, F, W, Y, P, or C; V 907 replaced with D, E, H, K, R, N, Q, F, W, Y, P, or C; T 908 replaced with D, E, H, K, R, N, Q, F, W, Y, P, or C; V909 replaced with D, E, H, K, R, N, Q, F, W, Y, P, or C; A910 replaced with D, B, H, K, R, N, Q, F, W, Y, P, or C; P911 replaced with D, E, H, K, R, A, G, I, L, S, T, M, V, N, Q, F, W, Y, or C; F912 replaced with D, E, H, K, R, N, Q, A, G, I, L, S, T, M, V, P, or C; G913 replaced with D, E, H, K, R, N, Q, F, W, Y, P, or C; Y914 replaced with D, E, H, K, R, N, Q, A, G, I, L, S, T, M, V, P, or C; L915 replaced with D, E, H, K, R, N, Q, F, W, Y, P, or C; K916 replaced with D, E, A, G, I, L, S, T, M, V, N, Q, F, W, Y, P, or C; I917 replaced with D, E, H, K, R, N, Q, F, W, Y, P, or C; H918 replaced with D, E, A, G, I, L, S, T, M, V, N, Q, F, W, Y, P, or C; R919 replaced with D, E, A, G, I, L, S, T, M, V, N, Q, F, W, Y, P, or C; L920 replaced with D, E, H, K, R, N, Q, F, W, Y, P, or C; K921 replaced with D, E, A, C, G, L, S, T, M, V, N, Q, F, W, Y, P, or C; P922 replaced with D, E, H, K, R, A, G, I, L, S, T, M, V, N, Q, F, W, Y, or C; S923 replaced with D, E, H, K, R, N, Q, F, W, Y, P, or C; D924 replaced with H, K, R, A, G, I, L, S, T, M, V, N, Q, F, W, Y, P, or C; A925 replaced with D, E, H, K, R, N, Q, F, W, Y, P, or C; G926 replaced with D, E, H, K, R, N, Q, F, W, Y, P, or C; V927 replaced with D, E, H, K, R, N, Q, F, W, Y, P, or C; Y928 replaced with D, E, H, K, R, N, Q, A, G, I, L, S, T, M, V, P, or C; T929 replaced with D, E, H, K, R, N, Q, F, W, Y, P, or C; C930 replaced with D, E, H, K, R, A, G, I, L, S, T, M, V, N, Q, F, W, Y, or P; S931 replaced with D, E, H, K, R, N, Q, F, W, Y, P, or C; A932 replaced with D, E, H, K, R, N, Q, F, W, Y, P, or C; G933 replaced with D, E, H, K, R, N, Q, F, W, Y, P, or C; P934 replaced with D, E, H, K, R, A, G, I, L, S, T, M, V, N, Q, F, W, Y, or C; A935 replaced with D, E, H, K, R, N, Q, F, W, Y, P, or C; R936 replaced with D, E, A, G, I, L, S, T, M, V, N, Q, F, W, Y, P, or C; E937 replaced with H, K, R, A, G, I, L, S, T, M, V, N, Q, F, W, Y, P, or C; H938 replaced with D, E, A, G, I, L, S, T, M, V, N, Q, F, W, Y, P, or C; F939 replaced with D, E, H, K, R, N, Q, A, G, I, L, S, T, M, V, P, or C; V940 replaced with D, E, H, K, R, N, Q, F, W, Y, P, or C; I941 replaced with D, E, H, K, R, N, Q, F, W, Y, P, or C; K942 replaced with D, E, A, G, I, L, S, T, M, V, N, Q, F, W, Y, P, or C; L943 replaced with D, E, H, K, R, N, Q, F, W, Y, P, or C; I944 replaced with D, E, H, K, R, N, Q, F, W, Y, P, or C; G945 replaced with D, E, H, K, R, N, Q, F, W, Y, P, or C; G946 replaced with D, E, H, K, R, N, Q, F, W, Y, P, or C; N947 replaced with D, E, H, K, R, A, G, I, L, S, T, M, V, F, W, Y, P, or C; R948 replaced with D, E, A, G, I, L, S, T, M, V, N, Q, F, W, Y, P, or C; K949 replaced with D, E, A, G, I, L, S, T, M, V, N, Q, F, W, Y, P, or C; L950 replaced with D, E, H, K, R, N, Q, F, W, Y, P, or C; V951 replaced with D, E, H, K, R, N, Q, F, W, Y, P, or C; A952 replaced with D, E, H, K, R, N, Q, F, W, Y, P, or C; R953 replaced with D, E, A, G, I, L, S, T, M, V, N, Q, F, W, Y, P, or C; P954 replaced with D, E, H, K, R, A, G, I, L, S, T, M, V, N, Q, F, W, Y, or C; L955 replaced with D, E, H, K, R, N, Q, F, W, Y, P, or C; S956 replaced with D, E, H, K, R, N, Q, F, W, Y, P, or C; P957 replaced with D, E, H, K, R, A, G, I, L, S, T, M, V, N, Q, F, W, Y, or C; R958 replaced with D, E, A, G, I, L, S, T, M, V, N, Q, F, W, Y, P, or C; S959 replaced with D, E, H, K, R, N, Q, F, W, Y, P, or C; E960 replaced with H, K, R, A, G, I, L, S, T, M, V, N, Q, F, W, Y, P, or C; E961 replaced with H, K, R, A, G, I, L, S, T, M, V, N, Q, F, W, Y, P, or C; E962 replaced with H, K, R, A, G, I, L, S, T, M, V, N, Q, F, W, Y, P, or C; V963 replaced with D, E, H, K, R, N, Q, F, W, Y, P, or C; L964 replaced with D, E, H, K, R, N, Q, F, W, Y, P, or C; A965 replaced with D, E, H, K, R, N, Q, F, W, Y, P, or C; G966 replaced with D, E, H, K, R, N, Q, F, W, Y, P, or C; R967 replaced with D, E, A, G, I, L, S, T, M, V, N, Q, F, W, Y, P, or C; K968 replaced with D, E, A, G, I, L, S, T, M, V, N, Q, F, W, Y, P, or C; G969 replaced with D, E, H, K, R, N, Q, F, W, Y, P, or C; G970 replaced with D, E, H, K, R, N, Q, F, W, Y, P, or C; P971 replaced with D, E, H, K, R, A, G, I, L, S, T, M, V, N, Q, F, W, Y, or C; K972 replaced with D, E, A, G, I, L, S, T, M, V, N, Q, F, W, Y, P, or C; E973 replaced with H, K, R, A, G, I, L, S, T, M, V, N, Q, F, W, Y, P, or C; A974 replaced with D, E, H, K, R, N, Q, F, W, Y, P, or C; L975 replaced with D, E, H, K, R, N, Q, F, W, Y, P, or C; Q976 replaced with D, E, H, K, R, A, G, I, L, S, T, M, V, F, W, Y, P, or C; T977 replaced with D, E, H, K, R, N, Q, F, W, Y, P, or C; H978 replaced with D, E, A, G, I, L, S, T, M, V, N, Q, F, W, Y, P, or C; K979 replaced with D, E, A, G, I, L, S, T, M, V, N, Q, F, W, Y, P, or C; H980 replaced with D, E, A, G, I, L, S, T, M, V, N, Q, F, W, Y, P, or C; Q981 replaced with D, E, H, K, R, A, G, I, L, S, T, M, V, F, W, Y, P, or C; N982 replaced with D, E, H, K, R, A, G, I, L, S, T, M, V, F, W, Y, P, or C; G983 replaced with D, E, H, K, R, N, Q, F, W, Y, P, or C; I984 replaced with D, E, H, K, R, N, Q, F, W, Y, P, or C; F985 replaced with D, E, H, K, R, N, Q, A, G, I, L, S, T, M, V, P, or C; S986 replaced with D, E, H, K, R, N, Q, F, W, Y, P, or C; N987 replaced with D, E, H, K, R, A, G, I, L, S, T, M, V, F, W, Y, P, or C; G988 replaced with D, E, H, K, R, N, Q, F, W, Y, P, or C; S989 replaced with D, E, H, K, R, N, Q, F, W, Y, P, or C; K990 replaced with D, E, A, G, I, L, S, T, M, V, N, Q, F, W, Y, P, or C; A991 replaced with D, E, H, K, R, N, Q, F, W, Y, P, or C; E992 replaced with H, K, R, A, G, I, L, S, T, M, V, N, Q, F, W, Y, P, or C; K993 replaced with D, E, A, G, I, L, S, T, M, V, N, Q, F, W, Y, P, or C; R994 replaced with D, E, A, G, I, L, S, T, M, V, N, Q, F, W, Y, P, or C; G995 replaced with D, E, H, K, R, N, Q, F, W, Y, P, or C; L996 replaced with D, E, H, K, R, N, Q, F, W, Y, P, or C; A997 replaced with D, E, H, K, R, N, Q, F, W, Y, P, or C; A998 replaced with D, E, H, K, R, N, Q, F, W, Y, P, or C; N999 replaced with D, E, H, K, R, A, G, I, L, S, T, M, V, F, W, Y, P, or C; P1000 replaced with D, E, H, K, R, A, G, I, L, S, T, M, V, N, Q, F, W, Y, or C; G1001 replaced with D, E, H, K, R, N, Q, F, W, Y, P, or C; S1002 replaced with D, E, H, K, R, N, Q, F, W, Y, P, or C; R1003 replaced with D, E, A, G, I, L, S, T, M, V, N, Q, F, W, Y, P, or C; Y1004 replaced with D, E, H, K, R, N, Q, A, G, I, L, S, T, M, V, P, or C; D1005 replaced with H, K, R, A, G, I, L, S, T, M, V, N, Q, F, W, Y, P, or C; D1006 replaced with H, K, R, A, G, I, L, S, T, M, V, N, Q, F, W, Y, P, or C; L1007 replaced with D, E, H, K, R, N, Q, F, W, Y, P, or C; V1008 replaced with D, E, H, K, R, N, Q, F, W, Y, P, or C; S1009 replaced with D, E, H, K, R, N, Q, F, W, Y, P, or C; R1010 replaced with D, E, A, G, I, L, S, T, M, V, N, Q, F, W, Y, P, or C; L1011 replaced with D, E, H, K, R, N, Q, F, W, Y, P, or C; L1012 replaced with D, E, H, K, R, N, Q, F, W, Y, P, or C; E1013 replaced with H, K, R, A, G, I, L, S, T, M, V, N, Q, F, W, Y, P, or C; Q1014 replaced with D, E, H, K, R, A, G, I, L, S, T, M, V, F, W, Y, P, or C; G1015 replaced with D, E, H, K, R, N, Q, F, W, Y, P, or C; G1016 replaced with D, E, H, K, R, N, Q, F, W, Y, P, or C; W1017 replaced with D, E, H, K, R, N, Q, A, G, I, L, S, T, M, V, P, or C; P1018 replaced with D, E, H, K, R, A, G, I, L, S, T, M, V, N, Q, F, W, Y, or C; G1019 replaced with D, E, H, K, R, N, Q, F, W, Y, P, or C; E1020 replaced with H, K, R, A, G, I, L, S, T, M, V, N, Q, F, W, Y, P, or C; L1021 replaced with D, E, H, K, R, N, Q, F, W, Y, P, or C; L1022 replaced with D, E, H, K, R, N, Q, F, W, Y, P, or C; A1023 replaced with D, E, H, K, R, N, Q, F, W, Y, P, or C; S1024 replaced with D, E, H, K, R, N, Q, F, W, Y, P, or C; W1025 replaced with D, E, H, K, R, N, Q, A, G, I, L, S, T, M, V, P, or C; E1026 replaced with H, K, R, A, G, I, L, S, T, M, V, N, Q, F, W, Y, P, or C; A1027 replaced with D, E, H, K, R, N, Q, F, W, Y, P, or C; Q1028 replaced with D, E, H, K, R, A, G, I, L, S, T, M, V, F, W, Y, P, or C; D1029 replaced with H, K, R, A, G, I, L, S, T, M, V, N, Q, F, W, Y, P, or C; S1030 replaced with D, E, H, K, R, N, Q, F, W, Y, P, or C; A1031 replaced with D, E, H, K, R, N, Q, F, W, Y, P, or C; E1032 replaced with H, K, R, A, G, I, L, S, T, M, V, N, Q, F, W, Y, P, or C; R1033 replaced with D, E, A, G, I, L, S, T, M, V, N, Q, F, W, Y, P, or C; N1034 replaced with D, E, H, K, R, A, G, I, L, S, T, M, V, F, W, Y, P, or C; T1035 replaced with D, E, H, K, R, N, Q, F, W, Y, P, or C; T1036 replaced with D, E, H, K, R, N, Q, F, W, Y, P, or C; S1037 replaced with D, E, H, K, R, N, Q, F, W, Y, P, or C; E1038 replaced with H, K, R, A, G, I, L, S, T, M, V, N, Q, F, W, Y, P, or C; E1039 replaced with H, K, R, A, G, I, L, S, T, M, V, N, Q, F, W, Y, P, or C; D1040 replaced with H, K, R, A, G, I, L, S, T, M, V, N, Q, F, W, Y, P, or C; P1041 replaced with D, E, H, K, R, A, G, I, L, S, T, M, V, N, Q, F, W, Y, or C; G1042 replaced with D, E, H, K, R, N, Q, F, W, Y, P, or C; A1043 replaced with D, E, H, K, R, N, Q, F, W, Y, P, or C; E1044 replaced with H, K, R, A, G, I, L, S, T, M, V, N, Q, F, W, Y, P, or C; Q1045 replaced with D, E, H, K, R, A, G, I, L, S, T, M, V, F, W, Y, P, or C; V1046 replaced with D, E, H, K, R, N, Q, F, W, Y, P, or C; L1047 replaced with D, E, H, K, R, N, Q, F, W, Y, P, or C; L1048 replaced with D, E, H, K, R, N, Q, F, W, Y, P, or C; H1049 replaced with D, E, A, G, I, L, S, T, M, V, N, Q, F, W, Y, P, or C; L1050 replaced with D, E, H, K, R, N, Q, F, W, Y, P, or C; P1051 replaced with D, E, H, K, R, A, G, I, L, S, T, M, V, N, Q, F, W, Y, or C; F1052 replaced with D, E, H, K, R, N, Q, A, G, I, L, S, T, M, V, P, or C; T1053 replaced with D, E, H, K, R, N, Q, F, W, Y, P, or C; M1054 replaced with D, E, H, K, R, N, Q, F, W, Y, P, or C; V1055 replaced with D, E, H, K, R, N, Q, F, W, Y, P, or C; T1056 replaced with D, E, H, K, R, N, Q, F, W, Y, P, or C; E1057 replaced with H, K, R, A, G, I, L, S, T, M, V, N, Q, F, W, Y, P, or C; Q1058 replaced with D, E, H, K, R, A, G, I, L, S, T, M, V, F, W, Y, P, or C; R1059 replaced with D, E, A, G, I, L, S, T, M, V, N, Q, F, W, Y, P, or C; R1060 replaced with D, E, A, G, I, L, S, T, M, V, N, Q, F, W, Y, P, or C; L1061 replaced with D, E, H, K, R, N, Q, F, W, Y, P, or C; D1062 replaced with H, K, R, A, G, I, L, S, T, M, V, N, Q, F, W, Y, P, or C; D1063 replaced with H, K, R, A, G, I, L, S, T, M, V, N, Q, F, W, Y, P, or C; I1064 replaced with D, E, H, K, R, N, Q, F, W, Y, P, or C; L1065 replaced with D, E, H, K, R, N, Q, F, W, Y, P, or C; G1066 replaced with D, E, H, K, R, N, Q, F, W, Y, P, or C; N1067 replaced with D, E, H, K, R, A, G, I, L, S, T, M, V, F, W, Y, P, or C; L1068 replaced with D, E, H, K, R, N, Q, F, W, Y, P, or C; S1069 replaced with D, E, H, K, R, N, Q, F, W, Y, P, or C; Q1070 replaced with D, E, H, K, R, A, G, I, L, S, T, M, V, F, W, Y, P, or C; Q1071 replaced with D, E, H, K, R, A, G, I, L, S, T, M, V, F, W, Y, P, or C; P1072 replaced with D, E, H, K, R, A, G, I, L, S, T, M, V, N, Q, F, W, Y, or C; E1073 replaced with H, K, R, A, G, I, L, S, T, M, V, N, Q, F, W, Y, P, or C; E1074 replaced with H, K, R, A, G, I, L, S, T, M, V, N, Q, F, W, Y, P, or C; L1075 replaced with D, E, H, K, R, N, Q, F, W, Y, P, or C; R1076 replaced with D, E, A, G, I, L, S, T, M, V, N, Q, F, W, Y, P, or C; D1077 replaced with H, K, R, A, G, I, L, S, T, M, V, N, Q, F, W, Y, P, or C; L1078 replaced with D, E, H, K, R, N, Q, F. W, Y, P, or C; Y1079 replaced with D, E, H, K, R, N, Q, A, G, I, L, S, T, M, V, P, or C; S1080 replaced with D, E, H, K, R, N, Q, F, W, Y, P, or C; K1081 replaced with D, E, A, G, I, L, S, T, M, V, N, Q, F, W, Y, P, or C; H1082 replaced with D, E, A, G, I, L, S, T, M, V, N, Q, F, W, Y, P, or C; L1083 replaced with D, E, H, K, R, N, Q, F, W, Y, P, or C; V1084 replaced with D, E, H, K, R, N, Q, F, W, Y, P, or C; A1085 replaced with D, E, H, K, R, N, Q, F, W, Y, P, or C; Q1086 replaced with D, E, H, K, R, A, G, I, L, S, T, M, V, F, W, Y, P, or C; L1087 replaced with D, E, H, K, R, N, Q, F, W, Y, P, or C; A1088 replaced with D, E, H, K, R, N, Q, F, W, Y, P, or C; Q1089 replaced with D, E, H, K, R, A, G, I, L, S, T, M, V, F, W, Y, P, or C; E1090 replaced with H, K, R, A, G, I, L, S, T, M, V, N, Q, F, W, Y, P, or C; I1091 replaced with D, E, H, K, R, N, Q, F, W, Y, P, or C; F1092 replaced with D, E, H, K, R, N, Q, A, G, I, L, S, T, M, V, P, or C; R1093 replaced with D, E, A, G, I, L, S, T, M, V, N, Q, F, W, Y, P, or C; S1094 replaced with D, E, H, K, R, N, Q, F, W, Y, P, or C; H1095 replaced with D, E, A, G, I, L, S, T, M, V, N, Q, F, W, Y, P, or C; L1096 replaced with D, E, H, K, R, N, Q, F, W, Y, P, or C; E1097 replaced with H, K, R, A, G, I, L, S, T, M, V, N, Q, F, W, Y, P, or C; H1098 replaced with D, E, A, G, I, L, S, T, M, V, N, Q, F, W, Y, P, or C; Q1099 replaced with D, E, H, K, R, A, G, I, L, S, T, M, V, F, W, Y, P, or C; D1100 replaced with H, K, R, A, G, I, L, S, T, M, V, N, Q, F, W, Y, P, or C; T1101 replaced with D, E, H, K, R, N, Q, F, W, Y, P, or C; L1102 replaced with D, E, H, K, R, N, Q, F, W, Y, P, or C; L1103 replaced with D, E, H, K, R, N, Q, F, W, Y, P, or C; K1104 replaced with D, E, A, G, I, L, S, T, M, V, N, Q, F, W, Y, P, or C; P1105 replaced with D, E, H, K, R, A, G, I, L, S, T, M, V, N, Q, F, W, Y, or C; S1106 replaced with D, E, H, K, R, N, Q, F, W, Y, P, or C; E1107 replaced with H, K, R, A, G, I, L, S, T, M, V, N, Q, F, W, Y, P, or C; R1108 replaced with D, E, A, G, I, L, S, T, M, V, N, Q, F, W, Y, P, or C; R1109 replaced with D, E, A, G, I, L, S, T, M, V, N, Q, F, W, Y, P, or C; T1110 replaced with D, E, H, K, R, N, Q, F, W, Y, P, or C; S1111 replaced with D, E, H, K, R, N, Q, F, W, Y, P, or C; P1112 replaced with D, E, H, K, R, A, G, I, L, S, T, M, V, N, Q, F, W, Y, or C; V1113 replaced with D, E, H, K, R, N, Q, F, W, Y, P, or C; T1114 replaced with D, E, H, K, R, N, Q, F, W, Y, P, or C; L1115 replaced with D, E, H, K, R, N, Q, F, W, Y, P, or C; S1116 replaced with D, E, H, K, R, N, Q, F, W, Y, P, or C; P1117 replaced with D, E, H, K, R, A, G, I, L, S, T, M, V, N, Q, F, W, Y, or C; H1118 replaced with D, E, A, G, I, L, S, T, M, V, N, Q, F, W, Y, P, or C; K1119 replaced with D, E, A, G, I, L, S, T, M, V, N, Q, F, W, Y, P, or C; H1120 replaced with D, E, A, G, I, L, S, T, M, V, N, Q, F, W, Y, P, or C; V1121 replaced with D, E, H, K, R, N, Q, F, W, Y, P, or C; S1122 replaced with D, E, H, K, R, N, Q, F, W, Y, P, or C; G1123 replaced with D, E, H, K, R, N, Q, F, W, Y, P, or C; F 1124 replaced with D, E, H, K, R, N, Q, A, G, I, L, S, T, M, V, P, or C; S1125 replaced with D, E, H, K, R, N, Q, F, W, Y, P, or C; S1126 replaced with D, E, H, K, R, N, Q, F, W, Y, P, or C; S1127 replaced with D, E, H, K, R, N, Q, F, W, Y, P, or C; L1128 replaced with D, E, H, K, R, N, Q, F, W, Y, P, or C; R1129 replaced with D, E, A, G, I, L, S, T, M, V, N, Q, F, W, Y, P, or C; T1130 replaced with D, E, H, K, R, N, Q, F, W, Y, P, or C; S1131 replaced with D, E, H, K, R, N, Q, F, W, Y, P, or C; S1132 replaced with D, E, H, K, R, N, Q, F, W, Y, P, or C; T1133 replaced with D, E, H, K, R, N, Q, F, W, Y, P, or C; G1134 replaced with D, E, H, K, R, N, Q, F, W, Y, P, or C; D1135 replaced with H, K, R, A, G, I, L, S, T, M, V, N, Q, F, W, Y, P, or C; A1136 replaced with D, E, H, K, R, N, Q, F, W, Y, P, or C; G1137 replaced with D, E, H, K, R, N, Q, F, W, Y, P, or C; G1138 replaced with D, E, H, K, R, N, Q, F, W, Y, P, or C; G 1139 replaced with D, E, H, K, R, N, Q, F, W, Y, P, or C; S1140 replaced with D, E, H, K, R, N, Q, F, W, Y, P, or C; R1141 replaced with D, E, A, G, I, L, S, T, M, V, N, Q, F, W, Y, P, or C; R1142 replaced with D, E, A, G, I, L, S, T, M, V, N, Q, F, W, Y, P, or C; P1143 replaced with D, E, H, K, R, A, G, I, L, S, T, M, V, N, Q, F, W, Y, or C; H1144 replaced with D, E, A, G, I, L, S, T, M, V, N, Q, F, W, Y, P, or C; R1145 replaced with D, E, A, G, I, L, S, T, M, V, N, Q, F, W, Y, P, or C; K1146 replaced with D, E, A, G, I, L, S, T, M, V, N, Q, F, W, Y, P, or C; P1147 replaced with D, E, H, K, R, A, G, I, L, S, T, M, V, N, Q, F, W, Y, or C; T1148 replaced with D, E, H, K, R, N, Q, F, W, Y, P, or C; I1149 replaced with D, E, H, K, R, N, Q, F, W, Y, P, or C; L1150 replaced with D, E, H, K, R, N, Q, F, W, Y, P, or C; R1151 replaced with D, E, A, G, I, L, S, T, M, V, N, Q, F, W, Y, P, or C; K1152 replaced with D, E, A, G, I, L, S, T, M, V, N, Q, F, W, Y, P, or C; I1153 replaced with D, E, H, K, R, N, Q, F, W, Y, P, or C; S1154 replaced with D, E, H, K, R, N, Q, F, W, Y, P, or C; A1155 replaced with D, E, H, K, R, N, Q, F, W, Y, P, or C; A1156 replaced with D, E, H, K, R, N, Q, F, W, Y, P, or C; Q1157 replaced with D, E, H, K, R, A, G, I, L, S, T, M, V, F, W, Y, P, or C; Q1158 replaced with D, E, H, K, R, A, G, I, L, S, T, M, V, F, W, Y, P, or C; L1159 replaced with D, E, H, K, R, N, Q, F, W, Y, P, or C; S1160 replaced with D, E, H, K, R, N, Q, F, W, Y, P, or C; A1161 replaced with D, E, H, K, R, N, Q, F, W, Y, P, or C; S1162 replaced with D, E, H, K, R, N, Q, F, W, Y, P, or C; E1163 replaced with H, K, R, A, G, I, L, S, T, M, V, N, Q, F, W, Y, P, or C; V1164 replaced with D, E, H, K, R, N, Q, F, W, Y, P, or C; V 1165 replaced with D, E, H, K, R, N, Q, F, W, Y, P, or C; T1166 replaced with D, E, H, K, R, N, Q, F, W, Y, P, or C; H1167 replaced with D, E, A, G, I, L, S, T, M, V, N, Q, F, W, Y, P, or C; L1168 replaced with D, E, H, K, R, N, Q, F, W, Y, P, or C; G1169 replaced with D, E, H, K, R, N, Q, F, W, Y, P, or C; Q1170 replaced with D, E, H, K, R, A, G, I, L, S, T, M, V, F, W, Y, P, or C; T1171 replaced with D, E, H, K, R, N, Q, F, W, Y, P, or C; V1172 replaced with D, E, H, K, R, N, Q, F, W, Y, P, or C; A1173 replaced with D, E, H, K, R, N, Q, F, W, Y, P, or C; L1174 replaced with D, E, H, K, R, N, Q, F, W, Y, P, or C; A1175 replaced with D, E, H, K, R, N, Q, F, W, Y, P, or C; S1176 replaced with D, E, H, K, R, N, Q, F, W, Y, P, or C; G1177 replaced with D, E, H, K, R, N, Q, F, W, Y, P, or C; T1178 replaced with D, E, H, K, R, N, Q, F, W, Y, P, or C; L1179 replaced with D, E, H, K, R, N, Q, F, W, Y, P, or C; S1180 replaced with D, E, H, K, R, N, Q, F, W, Y, P, or C; V1181 replaced with D, E, H, K, R, N, Q, F, W, Y, P, or C; L1182 replaced with D, E, H, K, R, N, Q, F, W, Y, P, or C; L1183 replaced with D, E, H, K, R, N, Q, F, W, Y, P, or C; H1184 replaced with D, E, A, G, I, L, S, T, M, V, N, Q, F, W, Y, P, or C; C1185 replaced with D, E, H, K, R, A, G, I, L, S, T, M, V, N, Q, F, W, Y, or P; E1186 replaced with H, K, R, A, G, I, L, S, T, M, V, N, Q, F, W, Y, P, or C; A1187 replaced with D, E, H, K, R, N, Q, F, W, Y, P, or C; I1188 replaced with D, E, H, K, R, N, Q, F, W, Y, P, or C; G1189 replaced with D, E, H, K, R, N, Q, F, W, Y, P, or C; H1190 replaced with D, E, A, G, I, L, S, T, M, V, N, Q, F, W, Y, P, or C; P1191 replaced with D, E, H, K, R, A, G, I, L, S, T, M, V, N, Q, F, W, Y, or C; R1192 replaced with D, E, A, G, I, L, S, T, M, V, N, Q, F, W, Y, P, or C; P1193 replaced with D, E, H, K, R, A, G, I, L, S, T, M, V, N, Q, F, W, Y, or C; T1194 replaced with D, E, H, K, R, N, Q, F, W, Y, P, or C; I1195 replaced with D, E, H, K, R, N, Q, F, W, Y, P, or C; S1196 replaced with D, E, H, K, R, N, Q, F, W, Y, P, or C; W1197 replaced with D, E, H, K, R, N, Q, A, G, I, L, S, T, M, V, P, or C; A1198 replaced with D, E, H, K, R, N, Q, F, W, Y, P, or C; R1199 replaced with D, E, A, G, I, L, S, T, M, V, N, Q, F, W, Y, P, or C; N1200 replaced with D, E, H, K, R, A, G, I, L, S, T, M, V, F, W, Y, P, or C; G1201 replaced with D, E, H, K, R, N, Q, F, W, Y, P, or C; E1202 replaced with H, K, R, A, G, I, L, S, T, M, V, N, Q, F, W, Y, P, or C; E1203 replaced with H, K, R, A, G, I, L, S, T, M, V, N, Q, F, W, Y, P, or C; V1204 replaced with D, E, H, K, R, N, Q, F, W, Y, P, or C; Q1205 replaced with D, E, H, K, R, A, G, I, L, S, T, M, V, F, W, Y, P, or C; F1206 replaced with D, E, H, K, R, N, Q, A, G, I, L, S, T, M, V, P, or C; S1207 replaced with D, E, H, K, R, N, Q, F, W, Y, P, or C; D1208 replaced with H, K, R, A, G, I, L, S, T, M, V, N, Q, F, W, Y, P, or C; R1209 replaced with D, E, A, G, I, L, S, T, M, V, N, Q, F, W, Y, P, or C; I1210 replaced with D, E, H, K, R, N, Q, F, W, Y, P, or C; L1211 replaced with D, E, H, K, R, N, Q, F, W, Y, P, or C; L1212 replaced with D, E, H, K, R, N, Q, F, W, Y, P, or C; Q1213 replaced with D, E, H, K, R, A, G, I, L, S, T, M, V, F, W, Y, P, or C; P1214 replaced with D, E, H, K, R, A, G, J, L, S, T, M, V, N, Q, F, W, Y, or C; D1215 replaced with H, K, R, A, G, I, L, S, T, M, V, N, Q, F, W, Y, P, or C; D1216 replaced with H, K, R, A, G, I, L, S, T, M, V, N, Q, F, W, Y, P, or C; S1217 replaced with D, E, H, K, R, N, Q, F, W, Y, P, or C; L1218 replaced with D, E, H, K, R, N, Q, F, W, Y, P, or C; Q1219 replaced with D, E, H, K, R, A, G, I, L, S, T, M, V, F, W, Y, P, or C; I1220 replaced with D, E, H, K, R, N, Q, F, W, Y, P, or C; L1221 replaced with D, E, H, K, R, N, Q, F, W, Y, P, or C; A1222 replaced with D, E, H, K, R, N, Q, F, W, Y, P, or C; P1223 replaced with D, E, H, K, R, A, G, I, L, S, T, M, V, N, Q, F, W, Y, or C; V1224 replaced with D, E, H, K, R, N, Q, F, W, Y, P, or C; E1225 replaced with H, K, R, A, G, I, L, S, T, M, V, N, Q, F, W, Y, P, or C; A1226 replaced with D, E, H, K, R, N, Q, F, W, Y, P, or C; D1227 replaced with H, K, R, A, G, I, L, S, T, M, V, N, Q, F, W, Y, P, or C; V1228 replaced with D, E, H, K, R, N, Q, F, W, Y, P, or C; G1229 replaced with D, E, H, K, R, N, Q, F, W, Y, P, or C; F1230 replaced with D, E, H, K, R, N, Q, A, G, I, L, S, T, M, V, P, or C; Y1231 replaced with D, E, H, K, R, N, Q, A, G, I, L, S, T, M, V, P, or C; T1232 replaced with D, E, H, K, R, N, Q, F, W, Y, P, or C; C1233 replaced with D, E, H, K, R, A, G, I, L, S, T, M, V, N, Q, F, W, Y, or P; N1234 replaced with D, E, H, K, R, A, G, I, L, S, T, M, V, F, W, Y, P, or C; A1235 replaced with D, E, H, K, R, N, Q, F, W, Y, P, or C; T1236 replaced with D, E, H, K, R, N, Q, F, W, Y, P, or C; N1237 replaced with D, E, H, K, R, A, G, I, L, S, T, M, V, F, W, Y, P, or C; A1238 replaced with D, E, H, K, R, N, Q, F, W, Y, P, or C; L1239 replaced with D, E, H, K, R, N, Q, F, W, Y, P, or C; G1240 replaced with D, E, H, K, R, N, Q, F, W, Y, P, or C; Y1241 replaced with D, E, H, K, R, N, Q, A, G, I, L, S, T, M, V, P, or C; D1242 replaced with H, K, R, A, G, I, L, S, T, M, V, N, Q, F, W, Y, P, or C; S1243 replaced with D, E, H, K, R, N, Q, F, W, Y, P, or C; V1244 replaced with D, E, H, K, R, N, Q, F, W, Y, P, or C; S1245 replaced with D, E, H, K, R, N, Q, F, W, Y, P, or C; I1246 replaced with D, E, H, K, R, N, Q, F, W, Y, P, or C; A1247 replaced with D, E, H, K, R, N, Q, F, W, Y, P, or C; V1248 replaced with D, E, H, K, R, N, Q, F, W, Y, P, or C; T1249 replaced with D, E, H, K, R, N, Q, F, W, Y, P, or C; L1250 replaced with D, E, H, K, R, N, Q, F, W, Y, P, or C; A1251 replaced with D, E, H, K, R, N, Q, F, W, Y, P, or C; G1252 replaced with D, E, H, K, R, N, Q, F, W, Y, P, or C; K1253 replaced with D, E, A, G, I, L, S, T, M, V, N, Q, F, W, Y, P, or C; P1254 replaced with D, E, H, K, R, A, G, I, L, S, T, M, V, N, Q, F, W, Y, or C; L1255 replaced with D, E, H, K, R, N, Q, F, W, Y, P, or C; V1256 replaced with D, E, H, K, R, N, Q, F, W, Y, P, or C; K1257 replaced with D, E, A, G, I, L, S, T, M, V, N, Q, F, W, Y, P, or C; T1258 replaced with D, E, H, K, R, N, Q, F, W, Y, P, or C; S1259 replaced with D, E, H, K, R, N, Q, F, W, Y, P, or C; R1260 replaced with D, E, A, G, I, L, S, T, M, V, N, Q, F, W, Y, P, or C; M1261 replaced with D, E, H, K, R, N, Q, F, W, Y, P, or C; T1262 replaced with D, E, H, K, R, N, Q, F, W, Y, P, or C; V1263 replaced with D, E, H, K, R, N, Q, F, W, Y, P, or C; I1264 replaced with D, E, H, K, R, N, Q, F, W, Y, P, or C; N1265 replaced with D, E, H, K, R, A, G, I, L, S, T, M, V, F, W, Y, P, or C; T1266 replaced with D, E, H, K, R, N, Q, F, W, Y, P, or C; E1267 replaced with H, K, R, A, G, I, L, S, T, M, V, N, Q, F, W, Y, P, or C; K1268 replaced with D, E, A, G, I, L, S, T, M, V, N, Q, F, W, Y, P, or C; P1269 replaced with D, E, H, K, R, A, G, I, L, S, T, M, V, N, Q, F, W, Y, or C; A1270 replaced with D, E, H, K, R, N, Q, F, W, Y, P, or C; V1271 replaced with D, E, H, K, R, N, Q, F, W, Y, P, or C; T1272 replaced with D, E, H, K, R, N, Q, F, W, Y, P, or C; V1273 replaced with D, E, H, K, R, N, Q, F, W, Y, P, or C; D1274 replaced with H, K, R, A, G, I, L, S, T, M, V, N, Q, F, W, Y, P, or C; I1275 replaced with D, E, H, K, R, N, Q, F, W, Y, P, or C; G1276 replaced with D, E, H, K, R, N, Q, F, W, Y, P, or C; S1277 replaced with D, E, H, K, R, N, Q, F, W, Y, P, or C; T1278 replaced with D, E, H, K, R, N, Q, F, W, Y, P, or C; I1279 replaced with D, E, H, K, R, N, Q, F, W, Y, P, or C; K1280 replaced with D, E, A, G, I, L, S, T, M, V, N, Q, F, W, Y, P, or C; T1281 replaced with D, E, H, K, R, N, Q, F, W, Y, P, or C; V1282 replaced with D, E, H, K, R, N, Q, F, W, Y, P, or C; Q1283 replaced with D, E, H, K, R, A, G, I, L, S, T, M, V, F, W, Y, P, or C; G1284 replaced with D, E, H, K, R, N, Q, F, W, Y, P, or C; V1285 replaced with D, E, H, K, R, N, Q, F, W, Y, P, or C; N1286 replaced with D, E, H, K, R, A, G, I, L, S, T, M, V, F, W, Y, P, or C; V1287 replaced with D, E, H, K, R, N, Q, F, W, Y, P, or C; T1288 replaced with D, E, H, K, R, N, Q, F, W, Y, P, or C; I1289 replaced with D, E, H, K, R, N, Q, F, W, Y, P, or C; N1290 replaced with D, E, H, K, R, A, G, I, L, S, T, M, V, F, W, Y, P, or C; C1291 replaced with D, E, H, K, R, A, G, I, L, S, T, M, V, N, Q, F, W, Y, or P; Q1292 replaced with D, E, H, K, R, A, G, I, L, S, T, M, V, F, W, Y, P, or C; V1293 replaced with D, E, H, K, R, N, Q, F, W, Y, P, or C; A1294 replaced with D, E, H, K, R, N, Q, F, W, Y, P, or C; G1295 replaced with D, E, H, K, R, N, Q, F, W, Y, P, or C; V1296 replaced with D, E, H, K, R, N, Q, F, W, Y, P, or C; P1297 replaced with D, E, H, K, R, A, G, I, L, S, T, M, V, N, Q, F, W, Y, or C; E1298 replaced with H, K, R, A, G, I, L, S, T, M, V, N, Q, F, W, Y, P, or C; A1299 replaced with D, E, H, K, R, N, Q, F, W, Y, P, or C; E1300 replaced with H, K, R, A, G, I, L, S, T, M, V, N, Q, F, W, Y, P, or C; V1301 replaced with D, E, H, K, R, N, Q, F, W, Y, P, or C; T1302 replaced with D, E, H, K, R, N, Q, F, W, Y, P, or C; W1303 replaced with D, E, H, K, R, N, Q, A, G, I, L, S, T, M, V, P, or C; F1304 replaced with D, E, H, K, R, N, Q, A, G, I, L, S, T, M, V, P, or C; R1305 replaced with D, E, A, G, I, L, S, T, M, V, N, Q, F, W, Y, P, or C; N1306 replaced with D, E, H, K, R, A, G, I, L, S, T, M, V, F, W, Y, P, or C; K1307 replaced with D, E, A, G, I, L, S, T, M, V, N, Q, F, W, Y, P, or C; S1308 replaced with D, E, H, K, R, N, Q, F, W, Y, P, or C; K1309 replaced with D, E, A, G, I, L, S, T, M, V, N, Q, F, W, Y, P, or C; L1310 replaced with D, E, H, K, R, N, Q, F, W, Y, P, or C; G1311 replaced with D, E, H, K, R, N, Q, F, W, Y, P, or C; S1312 replaced with D, E, H, K, R, N, Q, F, W, Y, P, or C; P1313 replaced with D, E, H, K, R, A, G, I, L, S, T, M, V, N, Q, F, W, Y, or C; H1314 replaced with D, E, A, G, I, L, S, T, M, V, N, Q, F, W, Y, P, or C; H1315 replaced with D, E, A, G, I, L, S, T, M, V, N, Q, F, W, Y, P, or C; L1316 replaced with D, E, H, K, R, N, Q, F, W, Y, P, or C; H1317 replaced with D, E, A, G, I, L, S, T, M, V, N, Q, F, W, Y, P, or C; E1318 replaced with H, K, R, A, G, I, L, S, T, M, V, N, Q, F, W, Y, P, or C; G1319 replaced with D, E, H, K, R, N, Q, F, W, Y, P, or C; S1320 replaced with D, E, H, K, R, N, Q, F, W, Y, P, or C; L1321 replaced with D, E, H, K, R, N, Q, F, W, Y, P, or C; L1322 replaced with D, E, H, K, R, N, Q, F, W, Y, P, or C; L1323 replaced with D, E, H, K, R, N, Q, F, W, Y, P, or C; T1324 replaced with D, E, H, K, R, N, Q, F, W, Y, P, or C; N1325 replaced with D, E, H, K, R, A, G, I, L, S, T, M, V, F, W, Y, P, or C; V1326 replaced with D, E, H, K, R, N, Q, F, W, Y, P, or C; S1327 replaced with D, E, H, K, R, N, Q, F, W, Y, P, or C; S1328 replaced with D, E, H, K, R, N, Q, F, W, Y, P, or C; S1329 replaced with D, E, H, K, R, N, Q, F, W, Y, P, or C; D1330 replaced with H, K, R, A, G, I, L, S, T, M, V, N, Q, F, W, Y, P, or C; Q1331 replaced with D, E, H, K, R, A, G, I, L, S, T, M, V, F, W, Y, P, or C; G1332 replaced with D, E, H, K, R, N, Q, F, W, Y, P, or C; L1333 replaced with D, E, H, K, R, N, Q, F, W, Y, P, or C; Y1334 replaced with D, E, H, K, R, N, Q, A, G, I, L, S, T, M, V, P, or C; S1335 replaced with D, E, H, K, R, N, Q, F, W, Y, P, or C; C1336 replaced with D, E, H, K, R, A, G, I, L, S, T, M, V, N, Q, F, W, Y, or P; R1337 replaced with D, E, A, G, I, L, S, T, M, V, N, Q, F, W, Y, P, or C; A1338 replaced with D, E, H, K, R, N, Q, F, W, Y, P, or C; A1339 replaced with D, E, H, K, R, N, Q, F, W, Y, P, or C; N1340 replaced with D, E, H, K, R, A, G, I, L, S, T, M, V, F, W, Y, P, or C; L1341 replaced with D, E, H, K, R, N, Q, F, W, Y, P, or C; H1342 replaced with D, E, A, G, I, L, S, T, M, V, N, Q, F, W, Y, P, or C; G1343 replaced with D, E, H, K, R, N, Q, F, W, Y, P, or C; E1344 replaced with H, K, R, A, G, I, L, S, T, M, V, N, Q, F, W, Y, P, or C; L1345 replaced with D, E, H, K, R, N, Q, F, W, Y, P, or C; T1346 replaced with D, E, H, K, R, N, Q, F, W, Y, P, or C; E1347 replaced with H, K, R, A, G, I, L, S, T, M, V, N, Q, F, W, Y, P, or C; S1348 replaced with D, E, H, K, R, N, Q, F, W, Y, P, or C; T1349 replaced with D, E, H, K, R, N, Q, F, W, Y, P, or C; Q1350 replaced with D, E, H, K, R, A, G, I, L, S, T, M, V, F, W, Y, P, or C; L1351 replaced with D, E, H, K, R, N, Q, F, W, Y, P, or C; L1352 replaced with D, E, H, K, R, N, Q, F, W, Y, P, or C; I1353 replaced with D, E, H, K, R, N, Q, F, W, Y, P, or C; L1354 replaced with D, E, H, K, R, N, Q, F, W, Y, P, or C; D1355 replaced with H, K, R, A, G, I, L, S, T, M, V, N, Q, F, W, Y, P, or C; P1356 replaced with D, E, H, K, R, A, G, I, L, S, T, M, V, N, Q, F, W, Y, or C; P1357 replaced with D, E, H, K, R, A, G, I, L, S, T, M, V, N, Q, F, W, Y, or C; Q1358 replaced with D, E, H, K, R, A, G, I, L, S, T, M, V, F, W, Y, P, or C; V1359 replaced with D, E, H, K, R, N, Q, F, W, Y, P, or C; P1360 replaced with D, E, H, K, R, A, G, I, L, S, T, M, V, N, Q, F, W, Y, or C; T1361 replaced with D, E, H, K, R, N, Q, F, W, Y, P, or C; Q1362 replaced with D, E, H, K, R, A, G, I, L, S, T, M, V, F, W, Y, P, or C; L1363 replaced with D, E, H, K, R, N, Q, F, W, Y, P, or C; E1364 replaced with H, K, R, A, G, I, L, S, T, M, V, N, Q, F, W, Y, P, or C; D1365 replaced with H, K, R, A, G, I, L, S, T, M, V, N, Q, F, W, Y, P, or C; I1366 replaced with D, E, H, K, R, N, Q, F, W, Y, P, or C; R1367 replaced with D, E, A, G, I, L, S, T, M, V, N, Q, F, W, Y, P, or C; A1368 replaced with D, E, H, K, R, N, Q, F, W, Y, P, or C; L1369 replaced with D, E, H, K, R, N, Q, F, W, Y, P, or C; L1370 replaced with D, E, H, K, R, N, Q, F, W, Y, P, or C; A1371 replaced with D, E, H, K, R, N, Q, F, W, Y, P, or C; A1372 replaced with D, E, H, K, R, N, Q, F, W, Y, P, or C; T1373 replaced with D, E, H, K, R, N, Q, F, W, Y, P, or C; G1374 replaced with D, E, H, K, R, N, Q, F, W, Y, P, or C; P1375 replaced with D, E, H, K, R, A, G, I, L, S, T, M, V, N, Q, F, W, Y, or C; N1376 replaced with D, E, H, K, R, A, G, I, L, S, T, M, V, F, W, Y, P, or C; L1377 replaced with D, E, H, K, R, N, Q, F, W, Y, P, or C; P1378 replaced with D, E, H, K, R, A, G, I, L, S, T, M, V, N, Q, F, W, Y, or C; S1379 replaced with D, E, H, K, R, N, Q, F, W, Y, P, or C; V1380 replaced with D, E, H, K, R, N, Q, F, W, Y, P, or C; L1381 replaced with D, E, H, K, R, N, Q, F, W, Y, P, or C; T1382 replaced with D, E, H, K, R, N, Q, F, W, Y, P, or C; S1383 replaced with D, E, H, K, R, N, Q, F, W, Y, P, or C; P1384 replaced with D, E, H, K, R, A, G, I, L, S, T, M, V, N, Q, F, W, Y, or C; L1385 replaced with D, E, H, K, R, N, Q, F, W, Y, P, or C; G1386 replaced with D, E, H, K, R, N, Q, F, W, Y, P, or C; T1387 replaced with D, E, H, K, R, N, Q, F, W, Y, P, or C; Q1388 replaced with D, E, H, K, R, A, G, I, L, S, T, M, V, F, W, Y, P, or C; L1389 replaced with D, E, H, K, R, N, Q, F, W, Y, P, or C; V1390 replaced with D, E, H, K, R, N, Q, F, W, Y, P, or C; L1391 replaced with D, E, H, K, R, N, Q, F, W, Y, P, or C; D1392 replaced with H, K, R, A, G, I, L, S, T, M, V, N, Q, F, W, Y, P, or C; P1393 replaced with D, E, H, K, R, A, G, I, L, S, T, M, V, N, Q, F, W, Y, or C; G1394 replaced with D, E, H, K, R, N, Q, F, W, Y, P, or C; N1395 replaced with D, E, H, K, R, A, G, I, L, S, T, M, V, F, W, Y, P, or C; S1396 replaced with D, E, H, K, R, N, Q, F, W, Y, P, or C; A1397 replaced with D, E, H, K, R, N, Q, F, W, Y, P, or C; L1398 replaced with D, E, H, K, R, N, Q, F, W, Y, P, or C; L1399 replaced with D, E, H, K, R, N, Q, F, W, Y, P, or C; G1400 replaced with D, E, H, K, R, N, Q, F, W, Y, P, or C; C1401 replaced with D, E, H, K, R, A, G, I, L, S, T, M, V, N, Q, F, W, Y, or P; P1402 replaced with D, E, H, K, R, A, G, I, L, S, T, M, V, N, Q, F, W, Y, or C; I1403 replaced with D, E, H, K, R, N, Q, F, W, Y, P, or C; K1404 replaced with D, E, A, G, I, L, S, T, M, V, N, Q, F, W, Y, P, or C; G1405 replaced with D, E, H, K, R, N, Q, F, W, Y, P, or C; H1406 replaced with D, E, A, G, I, L, S, T, M, V, N, Q, F, W, Y, P, or C; P1407 replaced with D, E, H, K, R, A, G, I, L, S, T, M, V, N, Q, F, W, Y, or C; V1408 replaced with D, E, H, K, R, N, Q, F, W, Y, P, or C; P1409 replaced with D, E, H, K, R, A, G, I, L, S, T, M, V, N, Q, F, W, Y, or C; N1410 replaced with D, E, H, K, R, A, G, I, L, S, T, M, V, F, W, Y, P, or C; I1141 replaced with D, E, H, K, R, N, Q, F, W, Y, P, or C; T1412 replaced with D, E, H, K, R, N, Q, F, W, Y, P, or C; W1413 replaced with D, E, H, K, R, N, Q, A, G, I, L, S, T, M, V, P, or C; F1414 replaced with D, E, H, K, R, N, Q, A, G, I, L, S, T, M, V, P, or C; H1415 replaced with D, E, A, G, I, L, S, T, M, V, N, Q, F, W, Y, P, or C; G1416 replaced with D, E, H, K, R, N, Q, F, W, Y, P, or C; G1417 replaced with D, E, H, K, R, N, Q, F, W, Y, P, or C; Q1418 replaced with D, E, H, K, R, A, G, I, L, S, T, M, V, F, W, Y, P, or C; P1419 replaced with D, E, H, K, R, A, G, I, L, S, T, M, V, N, Q, F, W, Y, or C; I1420 replaced with D, E, H, K, R, N, Q, F, W, Y, P, or C; V1421 replaced with D, E, H, K, R, N, Q, F, W, Y, P, or C; T1422 replaced with D, E, H, K, R, N, Q, F, W, Y, P, or C; A1423 replaced with D, E, H, K, R, N, Q, F, W, Y, P, or C; T1424 replaced with D, E, H, K, R, N, Q, F, W, Y, P, or C; G1425 replaced with D, E, H, K, R, N, Q, F, W, Y, P, or C; L1426 replaced with D, E, H, K, R, N, Q, F, W, Y, P, or C; T1427 replaced with D, E, H, K, R, N, Q, F, W, Y, P, or C; H1428 replaced with D, E, A, G, I, L, S, T, M, V, N, Q, F, W, Y, P, or C; H1429 replaced with D, E, A, G, I, L, S, T, M, V, N, Q, F, W, Y, P, or C; I1430 replaced with D, E, H, K, R, N, Q, F, W, Y, P, or C; L1431 replaced with D, E, H, K, R, N, Q, F, W, Y, P, or C; A1432 replaced with D, E, H, K, R, N, Q, F, W, Y, P, or C; A1433 replaced with D, E, H, K, R, N, Q, F, W, Y, P, or C; G1434 replaced with D, E, H, K, R, N, Q, F, W, Y, P, or C; Q1435 replaced with D, E, H, K, R, A, G, I, L, S, T, M, V, F, W, Y, P, or C; I1436 replaced with D, E, H, K, R, N, Q, F, W, Y, P, or C; L1437 replaced with D, E, H, K, R, N, Q, F, W, Y, P, or C; Q1438 replaced with D, E, H, K, R, A, G, I, L, S, T, M, V, F, W, Y, P, or C; V1439 replaced with D, E, H, K, R, N, Q, F, W, Y, P, or C; A1440 replaced with D, E, H, K, R, N, Q, F, W, Y, P, or C; N1441 replaced with D, E, H, K, R, A, G, I, L, S, T, M, V, F, W, Y, P, or C; L1442 replaced with D, E, H, K, R, N, Q, F, W, Y, P, or C; S1443 replaced with D, E, H, K, R, N, Q, F, W, Y, P, or C; G1444 replaced with D, E, H, K, R, N, Q, F, W, Y, P, or C; G1445 replaced with D, E, H, K, R, N, Q, F, W, Y, P, or C; S1446 replaced with D, E, H, K, R, N, Q, F, W, Y, P, or C; Q1447 replaced with D, E, H, K, R, A, G, I, L, S, T, M, V, F, W, Y, P, or C; G1448 replaced with D, E, H, K, R, N, Q, F, W, Y, P, or C; E1449 replaced with H, K, R, A, G, I, L, S, T, M, V, N, Q, F, W, Y, P, or C; F1450 replaced with D, E, H, K, R, N, Q, A, G, I, L, S, T, M, V, P, or C; S1451 replaced with D, E, H, K, R, N, Q, F, W, Y, P, or C; C1452 replaced with D, E, H, K, R, A, G, I, L, S, T, M, V, N, Q, F, W, Y, or P; L1453 replaced with D, E, H, K, R, N, Q, F, W, Y, P, or C; A1454 replaced with D, E, H, K, R, N, Q, F, W, Y, P, or C; Q1455 replaced with D, E, H, K, R, A, G, I, L, S, T, M, V, F, W, Y, P, or C; N1456 replaced with D, E, H, K, R, A, G, I, L, S, T, M, V, F, W, Y, P, or C; E1457 replaced with H, K, R, A, G, I, L, S, T, M, V, N, Q, F, W, Y, P, or C; A1458 replaced with D, E, H, K, R, N, Q, F, W, Y, P, or C; G1459 replaced with D, E, H, K, R, N, Q, F, W, Y, P, or C; V1460 replaced with D, E, H, K, R, N, Q, F, W, Y, P, or C; L1461 replaced with D, E, H, K, R, N, Q, F, W, Y, P, or C; M1462 replaced with D, E, H, K, R, N, Q, F, W, Y, P, or C; Q1463 replaced with D, E, H, K, R, A, G, I, L, S, T, M, V, F, W, Y, P, or C; K1464 replaced with D, E, A, G, I, L, S, T, M, V, N, Q, F, W, Y, P, or C; A1465 replaced with D, E, H, K, R, N, Q, F, W, Y, P, or C; S1466 replaced with D, E, H, K, R, N, Q, F, W, Y, P, or C; L1467 replaced with D, E, H, K, R, N, Q, F, W, Y, P, or C; V1468 replaced with D, E, H, K, R, N, Q, F, W, Y, P, or C; I1469 replaced with D, E, H, K, R, N, Q, F, W, Y, P, or C; Q1470 replaced with D, E, H, K, R, A, G, I, L, S, T, M, V, F, W, Y, P, or C; D1471 replaced with H, K, R, A, G, I, L, S, T, M, V, N, Q, F, W, Y, P, or C; Y1472 replaced with D, E, H, K, R, N, Q, A, G, I, L, S, T, M, V, P, or C; W1473 replaced with D, E, H, K, R, N, Q, A, G, I, L, S, T, M, V, P, or C; W1474 replaced with D, E, H, K, R, N, Q, A, G, I, L, S, T, M, V, P, or C; S1475 replaced with D, E, H, K, R, N, Q, F, W, Y, P, or C; V1476 replaced with D, E, H, K, R, N, Q, F, W, Y, P, or C; D1477 replaced with H, K, R, A, G, I, L, S, T, M, V, N, Q, F, W, Y, P, or C; R1478 replaced with D, E, A, G, I, L, S, T, M, V, N, Q, F, W, Y, P, or C; L1479 replaced with D, E, H, K, R, N, Q, F, W, Y, P, or C; A1480 replaced with D, E, H, K, R, N, Q, F, W, Y, P, or C; T1481 replaced with D, E, H, K, R, N, Q, F, W, Y, P, or C; C1482 replaced with D, E, H, K, R, A, G, I, L, S, T, M, V, N, Q, F, W, Y, or P; S1483 replaced with D, E, H, K, R, N, Q, F, W, Y, P, or C; A1484 replaced with D, E, H, K, R, N, Q, F, W, Y, P, or C; S1485 replaced with D, E, H, K, R, N, Q, F, W, Y, P, or C; C1486 replaced with D, E, H, K, R, A, G, I, L, S, T, M, V, N, Q, F, W, Y, or P; G1487 replaced with D, E, H, K, R, N, Q, F, W, Y, P, or C; N1488 replaced with D, E, H, K, R, A, G, I, L, S, T, M, V, F, W, Y, P, or C; R1489 replaced with D, E, A, G, I, L, S, T, M, V, N, Q, F, W, Y, P, or C; G1490 replaced with D, E, H, K, R, N, Q, F, W, Y, P, or C; V1491 replaced with D, E, H, K, R, N, Q, F, W, Y, P, or C; Q1492 replaced with D, E, H, K, R, A, G, I, L, S, T, M, V, F, W, Y, P, or C; Q1493 replaced with D, E, H, K, R, A, G, I, L, S, T, M, V, F, W, Y, P, or C; P1494 replaced with D, E, H, K, R, A, G, I, L, S, T, M, V, N, Q, F, W, Y, or C; R1495 replaced with D, E, A, G, I, L, S, T, M, V, N, Q, F, W, Y, P, or C; L1496 replaced with D, E, H, K, R, N, Q, F, W, Y, P, or C; R1497 replaced with D, E, A, G, I, L, S, T, M, V, N, Q, F, W, Y, P, or C; C1498 replaced with D, E, H, K, R, A, G, I, L, S, T, M, V, N, Q, F, W, Y, or P; L1499 replaced with D, E, H, K, R, N, Q, F, W, Y, P, or C; L1500 replaced with D, E, H, K, R, N, Q, F, W, Y, P, or C; N1501 replaced with D, E, H, K, R, A, G, I, L, S, T, M, V, F, W, Y, P, or C; S1502 replaced with D, E, H, K, R, N, Q, F, W, Y, P, or C; T1503 replaced with D, E, H, K, R, N, Q, F, W, Y, P, or C; E1504 replaced with H, K, R, A, G, I, L, S, T, M, V, N, Q, F, W, Y, P, or C; V1505 replaced with D, E, H, K, R, N, Q, F, W, Y, P, or C; N1506 replaced with D, E, H, K, R, A, G, I, L, S, T, M, V, F, W, Y, P, or C; P1507 replaced with D, E, H, K, R, A, G, I, L, S, T, M, V, N, Q, F, W, Y, or C; A1508 replaced with D, E, H, K, R, N, Q, F, W, Y, P, or C; H1509 replaced with D, E, A, G, I, L, S, T, M, V, N, Q, F, W, Y, P, or C; C1510 replaced with D, E, H, K, R, A, G, I, L, S, T, M, V, N, Q, F, W, Y, or P; A1511 replaced with D, E, H, K, R, N, Q, F, W, Y, P, or C; G1512 replaced with D, E, H, K, R, N, Q, F, W, Y, P, or C; K1513 replaced with D, E, A, G, I, L, S, T, M, V, N, Q, F, W, Y, P, or C; V1514 replaced with D, E, H, K, R, N, Q, F, W, Y, P, or C; R1515 replaced with D, E, A, G, I, L, S, T, M, V, N, Q, F, W, Y, P, or C; P1516 replaced with D, E, H, K, R, A, G, I, L, S, T, M, V, N, Q, F, W, Y, or C; A1517 replaced with D, E, H, K, R, N, Q, F, W, Y, P, or C; V1518 replaced with D, E, H, K, R, N, Q, F, W, Y, P, or C; Q1519 replaced with D, E, H, K, R, A, G, I, L, S, T, M, V, F, W, Y, P, or C; P1520 replaced with D, E, H, K, R, A, G, I, L, S, T, M, V, N, Q, F, W, Y, or C; I1521 replaced with D, E, H, K, R, N, Q, F, W, Y, P, or C; A1522 replaced with D, E, H, K, R, N, Q, F, W, Y, P, or C; C1523 replaced with D, E, H, K, R, A, G, I, L, S, T, M, V, N, Q, F, W, Y, or P; N1524 replaced with D, E, H, K, R, A, G, I, L, S, T, M, V, F, W, Y, P, or C; R1525 replaced with D, E, A, G, I, L, S, T, M, V, N, Q, F, W, Y, P, or C; R1526 replaced with D, E, A, G, I, L, S, T, M, V, N, Q, F, W, Y, P, or C; D1527 replaced with H, K, R, A, G, I, L, S, T, M, V, N, Q, F, W, Y, P, or C; C1528 replaced with D, E, H, K, R, A, G, I, L, S, T, M, V, N, Q, F, W, Y, or P; P1529 replaced with D, E, H, K, R, A, G, I, L, S, T, M, V, N, Q, F, W, Y, or C; S1530 replaced with D, E, H, K, R, N, Q, F, W, Y, P, or C; R1531 replaced with D, E, A, G, I, L, S, T, M, V, N, Q, F, W, Y, P, or C; W1532 replaced with D, E, H, K, R, N, Q, A, G, I, L, S, T, M, V, P, or C; M1533 replaced with D, E, H, K, R, N, Q, F, W, Y, P, or C; V1534 replaced with D, E, H, K, R, N, Q, F, W, Y, P, or C; T1535 replaced with D, E, H, K, R, N, Q, F, W, Y, P, or C; S1536 replaced with D, E, H, K, R, N, Q, F, W, Y, P, or C; W1537 replaced with D, E, H, K, R, N, Q, A, G, I, L, S, T, M, V, P, or C; S1538 replaced with D, E, H, K, R, N, Q, F, W, Y, P, or C; A1539 replaced with D, E, H, K, R, N, Q, F, W, Y, P, or C; C1540 replaced with D, E, H, K, R, A, G, I, L, S, T, M, V, N, Q, F, W, Y, or P; T1541 replaced with D, E, H, K, R, N, Q, F, W, Y, P, or C; R1542 replaced with D, E, A, G, I, L, S, T, M, V, N, Q, F, W, Y, P, or C; S1543 replaced with D, E, H, K, R, N, Q, F, W, Y, P, or C; C1544 replaced with D, E, H, K, R, A, G, I, L, S, T, M, V, N, Q, F, W, Y, or P; G1545 replaced with D, E, H, K, R, N, Q, F, W, Y, P, or C; G1546 replaced with D, E, H, K, R, N, Q, F, W, Y, P, or C; G1547 replaced with D, E, H, K, R, N, Q, F, W, Y, P, or C; V1548 replaced with D, E, H, K, R, N, Q, F, W, Y, P, or C; Q1549 replaced with D, E, H, K, R, A, G, I, L, S, T, M, V, F, W, Y, P, or C; T1550 replaced with D, E, H, K, R, N, Q, F, W, Y, P, or C; R1551 replaced with D, E, A, G, I, L, S, T, M, V, N, Q, F, W, Y, P, or C; R1552 replaced with D, E, A, G, I, L, S, T, M, V, N, Q, F, W, Y, P, or C; V1553 replaced with D, E, H, K, R, N, Q, F, W, Y, P, or C; T1554 replaced with D, E, H, K, R, N, Q, F, W, Y, P, or C; C1555 replaced with D, E, H, K, R, A, G, I, L, S, T, M, V, N, Q, F, W, Y, or P; Q1556 replaced with D, E, H, K, R, A, G, I, L, S, T, M, V, F, W, Y, P, or C; K1557 replaced with D, E, A, G, I, L, S, T, M, V, N, Q, F, W, Y, P, or C; L1558 replaced with D, E, H, K, R, N, Q, F, W, Y, P, or C; K1559 replaced with D, E, A, G, I, L, S, T, M, V, N, Q, F, W, Y, P, or C; A1560 replaced with D, E, H, K, R, N, Q, F, W, Y, P, or C; S1561 replaced with D, E, H, K, R, N, Q, F, W, Y, P, or C; G1562 replaced with D, E, H, K, R, N, Q, F, W, Y, P, or C; I1563 replaced with D, E, H, K, R, N, Q, F, W, Y, P, or C; S1564 replaced with D, E, H, K, R, N, Q, F, W, Y, P, or C; T1565 replaced with D, E, H, K, R, N, Q, F, W, Y, P, or C; P1566 replaced with D, E, H, K, R, A, G, I, L, S, T, M, V, N, Q, F, W, Y, or C; V1567 replaced with D, E, H, K, R, N, Q, F, W, Y, P, or C; S1568 replaced with D, E, H, K, R, N, Q, F, W, Y, P, or C; N1569 replaced with D, E, H, K, R, A, G, I, L, S, T, M, V, F, W, Y, P, or C; D1570 replaced with H, K, R, A, G, I, L, S, T, M, V, N, Q, F, W, Y, P, or C; M1571 replaced with D, E, H, K, R, N, Q, F, W, Y, P, or C; C1572 replaced with D, E, H, K, R, A, G, I, L, S, T, M, V, N, Q, F, W, Y, or P; T1573 replaced with D, E, H, K, R, N, Q, F, W, Y, P, or C; Q1574 replaced with D, E, H, K, R, A, G, I, L, S, T, M, V, F, W, Y, P, or C; V1575 replaced with D, E, H, K, R, N, Q, F, W, Y, P, or C; A1576 replaced with D, E, H, K, R, N, Q, F, W, Y, P, or C; K1577 replaced with D, E, A, G, I, L, S, T, M, V, N, Q, F, W, Y, P, or C; R1578 replaced with D, E, A, G, I, L, S, T, M, V, N, Q, F, W, Y, P, or C; P1579 replaced with D, E, H, K, R, A, G, I, L, S, T, M, V, N, Q, F, W, Y, or C; V1580 replaced with D, E, H, K, R, N, Q, F, W, Y, P, or C; D1581 replaced with H, K, R, A, G, I, L, S, T, M, V, N, Q, F, W, Y, P, or C; T1582 replaced with D, E, H, K, R, N, Q, F, W, Y, P, or C; Q1583 replaced with D, E, H, K, R, A, G, I, L, S, T, M, V, F, W, Y, P, or C; A1584 replaced with D, E, H, K, R, N, Q, F, W, Y, P, or C; C1585 replaced with D, E, H, K, R, A, G, I, L, S, T, M, V, N, Q, F, W, Y, or P; N1586 replaced with D, E, H, K, R, A, G, I, L, S, T, M, V, F, W, Y, P, or C; Q1587 replaced with D, E, H, K, R, A, G, I, L, S, T, M, V, F, W, Y, P, or C; Q1588 replaced with D, E, H, K, R, A, G, I, L, S, T, M, V, F, W, Y, P, or C; L1589 replaced with D, E, H, K, R, N, Q, F, W, Y, P, or C; C1590 replaced with D, E, H, K, R, A, G, I, L, S, T, M, V, N, Q, F, W, Y, or P; V1591 replaced with D, E, H, K, R, N, Q, F, W, Y, P, or C; E1592 replaced with H, K, R, A, G, I, L, S, T, M, V, N, Q, F, W, Y, P, or C; W1593 replaced with D, E, H, K, R, N, Q, A, G, I, L, S, T, M, V, P, or C; A1594 replaced with D, E, H, K, R, N, Q, F, W, Y, P, or C; F1595 replaced with D, E, H, K, R, N, Q, A, G, I, L, S, T, M, V, P, or C; S1596 replaced with D, E, H, K, R, N, Q, F, W, Y, P, or C; S1597 replaced with D, E, H, K, R, N, Q, F, W, Y, P, or C; W1598 replaced with D, E, H, K, R, N, Q, A, G, I, L, S, T, M, V, P, or C; G1599 replaced with D, E, H, K, R, N, Q, F, W, Y, P, or C; Q1600 replaced with D, E, H, K, R, A, G, I, L, S, T, M, V, F, W, Y, P, or C; C1601 replaced with D, E, H, K, R, A, G, I, L, S, T, M, V, N, Q, F, W, Y, or P; N1602 replaced with D, E, H, K, R, A, G, I, L, S, T, M, V, F, W, Y, P, or C; G1603 replaced with D, E, H, K, R, N, Q, F, W, Y, P, or C; P1604 replaced with D, E, H, K, R, A, G, I, L, S, T, M, V, N, Q, F, W, Y, or C; C1605 replaced with D, E, H, K, R, A, G, I, L, S, T, M, V, N, Q, F, W, Y, or P; I1606 replaced with D, E, H, K, R, N, Q, F, W, Y, P, or C; G1607 replaced with D, E, H, K, R, N, Q, F, W, Y, P, or C; P1608 replaced with D, E, H, K, R, A, G, I, L, S, T, M, V, N, Q, F, W, Y, or C; H1609 replaced with D, E, A, G, I, L, S, T, M, V, N, Q, F, W, Y, P, or C; L1610 replaced with D, E, H, K, R, N, Q, F, W, Y, P, or C; A1611 replaced with D, E, H, K, R, N, Q, F, W, Y, P, or C; V1612 replaced with D, E, H, K, R, N, Q, F, W, Y, P, or C; Q1613 replaced with D, E, H, K, R, A, G, I, L, S, T, M, V, F, W, Y, P, or C; H1614 replaced with D, E, A, G, I, L, S, T, M, V, N, Q, F, W, Y, P, or C; R1615 replaced with D, E, A, G, I, L, S, T, M, V, N, Q, F, W, Y, P, or C; Q1616 replaced with D, E, H, K, R, A, G, I, L, S, T, M, V, F, W, Y, P, or C; V1617 replaced with D, E, H, K, R, N, Q, F, W, Y, P, or C; F1618 replaced with D, E, H, K, R, N, Q, A, G, I, L, S, T, M, V, P, or C; C1619 replaced with D, E, H, K, R, A, G, I, L, S, T, M, V, N, Q, F, W, Y, or P; Q1620 replaced with D, E, H, K, R, A, G, I, L, S, T, M, V, F, W, Y, P, or C; T1621 replaced with D, E, H, K, R, N, Q, F, W, Y, P, or C; R1622 replaced with D, E, A, G, I, L, S, T, M, V, N, Q, F, W, Y, P, or C; D1623 replaced with H, K, R, A, G, I, L, S, T, M, V, N, Q, F, W, Y, P, or C; G1624 replaced with D, E, H, K, R, N, Q, F, W, Y, P, or C; I1625 replaced with D, E, H, K, R, N, Q, F, W, Y, P, or C; T1626 replaced with D, E, H, K, R, N, Q, F, W, Y, P, or C; L1627 replaced with D, E, H, K, R, N, Q, F, W, Y, P, or C; P1628 replaced with D, E, H, K, R, A, G, I, L, S, T, M, V, N, Q, F, W, Y, or C; S1629 replaced with D, E, H, K, R, N, Q, F, W, Y, P, or C; E1630 replaced with H, K, R, A, G, I, L, S, T, M, V, N, Q, F, W, Y, P, or C; Q1631 replaced with D, E, H, K, R, A, G, I, L, S, T, M, V, F, W, Y, P, or C; C1632 replaced with D, E, H, K, R, A, G, I, L, S, T, M, V, N, Q, F, W, Y, or P; S1633 replaced with D, E, H, K, R, N, Q, F, W, Y, P, or C; A1634 replaced with D, E, H, K, R, N, Q, F, W, Y, P, or C; L1635 replaced with D, E, H, K, R, N, Q, F, W, Y, P, or C; P1636 replaced with D, E, H, K, R, A, G, I, L, S, T, M, V, N, Q, F, W, Y, or C; R1637 replaced with D, E, A, G, I, L, S, T, M, V, N, Q, F, W, Y, P, or C; P1638 replaced with D, E, H, K, R, A, G, I, L, S, T, M, V, N, Q, F, W, Y, or C; V1639 replaced with D, E, H, K, R, N, Q, F, W, Y, P, or C; S1640 replaced with D, E, H, K, R, N, Q, F, W, Y, P, or C; T1641 replaced with D, E, H, K, R, N, Q, F, W, Y, P, or C; Q1642 replaced with D, E, H, K, R, A, G, I, L, S, T, M, V, F, W, Y, P, or C; N1643 replaced with D, E, H, K, R, A, G, I, L, S, T, M, V, F, W, Y, P, or C; C1644 replaced with D, E, H, K, R, A, G, I, L, S, T, M, V, N, Q, F, W, Y, or P; W1645 replaced with D, E, H, K, R, N, Q, A, G, I, L, S, T, M, V, P, or C; S1646 replaced with D, E, H, K, R, N, Q, F, W, Y, P, or C; E1647 replaced with H, K, R, A, G, I, L, S, T, M, V, N, Q, F, W, Y, P, or C; A1648 replaced with D, E, H, K, R, N, Q, F, W, Y, P, or C; C1649 replaced with D, E, H, K, R, A, G, I, L, S, T, M, V, N, Q, F, W, Y, or P; S1650 replaced with D, E, H, K, R, N, Q, F, W, Y, P, or C; V1651 replaced with D, E, H, K, R, N, Q, F, W, Y, P, or C; H1652 replaced with D, E, A, G, I, L, S, T, M, V, N, Q, F, W, Y, P, or C; W1653 replaced with D, E, H, K, R, N, Q, A, G, I, L, S, T, M, V, P, or C; R1654 replaced with D, E, A, G, I, L, S, T, M, V, N, Q, F, W, Y, P, or C; V1655 replaced with D, E, H, K, R, N, Q, F, W, Y, P, or C; S1656 replaced with D, E, H, K, R, N, Q, F, W, Y, P, or C; L1657 replaced with D, E, H, K, R, N, Q, F, W, Y, P, or C; W1658 replaced with D, E, H, K, R, N, Q, A, G, I, L, S, T, M, V, P, or C; T1659 replaced with D, E, H, K, R, N, Q, F, W, Y, P, or C; L1660 replaced with D, E, H, K, R, N, Q, F, W, Y, P, or C; C1661 replaced with D, E, H, K, R, A, G, I, L, S, T, M, V, N, Q, F, W, Y, or P; T1662 replaced with D, E, H, K, R, N, Q, F, W, Y, P, or C; A1663 replaced with D, E, H, K, R, N, Q, F, W, Y, P, or C; T1664 replaced with D, E, H, K, R, N, Q, F, W, Y, P, or C; C1665 replaced with D, E, H, K, R, A, G, I, L, S, T, M, V, N, Q, F, W, Y, or P; G1666 replaced with D, E, H, K, R, N, Q, F, W, Y, P, or C; N1667 replaced with D, E, H, K, R, A, G, I, L, S, T, M, V, F, W, Y, P, or C; Y1668 replaced with D, E, H, K, R, N, Q, A, G, I, L, S, T, M, V, P, or C; G1669 replaced with D, E, H, K, R, N, Q, F, W, Y, P, or C; F1670 replaced with D, E, H, K, R, N, Q, A, G, I, L, S, T, M, V, P, or C; Q1671 replaced with D, E, H, K, R, A, G, I, L, S, T, M, V, F, W, Y, P, or C; S1672 replaced with D, E, H, K, R, N, Q, F, W, Y, P, or C; R1673 replaced with D, E, A, G, I, L, S, T, M, V, N, Q, F, W, Y, P, or C; R1674 replaced with D, E, A, G, I, L, S, T, M, V, N, Q, F, W, Y, P, or C; V1675 replaced with D, E, H, K, R, N, Q, F, W, Y, P, or C; E1676 replaced with H, K, R, A, G, I, L, S, T, M, V, N, Q, F, W, Y, P, or C; C1677 replaced with D, E, H, K, R, A, G, I, L, S, T, M, V, N, Q, F, W, Y, or P; V1678 replaced with D, E, H, K, R, N, Q, F, W, Y, P, or C; H1679 replaced with D, E, A, G, I, L, S, T, M, V, N, Q, F, W, Y, P, or C; A1680 replaced with D, E, H, K, R, N, Q, F, W, Y, P, or C; R1681 replaced with D, E, A, G, I, L, S, T, M, V, N, Q, F, W, Y, P, or C; T1682 replaced with D, E, H, K, R, N, Q, F, W, Y, P, or C; N1683 replaced with D, E, H, K, R, A, G, I, L, S, T, M, V, F, W, Y, P, or C; K1684 replaced with D, E, A, G, I, L, S, T, M, V, N, Q, F, W, Y, P, or C; A1685 replaced with D, E, H, K, R, N, Q, F, W, Y, P, or C; V1686 replaced with D, E, H, K, R, N, Q, F, W, Y, P, or C; P1687 replaced with D, E, H, K, R, A, G, I, L, S, T, M, V, N, Q, F, W, Y, or C; E1688 replaced with H, K, R, A, G, I, L, S, T, M, V, N, Q, F, W, Y, P, or C; H1689 replaced with D, E, A, G, I, L, S, T, M, V, N, Q, F, W, Y, P, or C; L1690 replaced with D, E, H, K, R, N, Q, F, W, Y, P, or C; C1691 replaced with D, E, H, K, R, A, G, I, L, S, T, M, V, N, Q, F, W, Y, or P; S1692 replaced with D, E, H, K, R, N, Q, F, W, Y, P, or C; W1693 replaced with D, E, H, K, R, N, Q, A, G, I, L, S, T, M, V, P, or C; G1694 replaced with D, E, H, K, R, N, Q, F, W, Y, P, or C; P1695 replaced with D, E, H, K, R, A, G, I, L, S, T, M, V, N, Q, F, W, Y, or C; R1696 replaced with D, E, A, G, I, L, S, T, M, V, N, Q, F, W, Y, P, or C; P1697 replaced with D, E, H, K, R, A, G, I, L, S, T, M, V, N, Q, F, W, Y, or C; A1698 replaced with D, E, H, K, R, N, Q, F, W, Y, P, or C; N1699 replaced with D, E, H, K, R, A, G, I, L, S, T, M, V, F, W, Y, P, or C; W1700 replaced with D, E, H, K, R, N, Q, A, G, I, L, S, T, M, V, P, or C; Q1701 replaced with D, E, H, K, R, A, G, I, L, S, T, M, V, F, W, Y, P, or C; R1702 replaced with D, E, A, G, I, L, S, T, M, V, N, Q, F, W, Y, P, or C; C1703 replaced with D, E, H, K, R, A, G, I, L, S, T, M, V, N, Q, F, W, Y, or P; N1704 replaced with D, E, H, K, R, A, G, I, L, S, T, M, V, F, W, Y, P, or C; I1705 replaced with D, E, H, K, R, N, Q, F, W, Y, P, or C; T1706 replaced with D, E, H, K, R, N, Q, F, W, Y, P, or C; P1707 replaced with D, E, H, K, R, A, G, I, L, S, T, M, V, N, Q, F, W, Y, or C; C1708 replaced with D, E, H, K, R, A, G, I, L, S, T, M, V, N, Q, F, W, Y, or P; E1709 replaced with H, K, R, A, G, I, L, S, T, M, V, N, Q, F, W, Y, P, or C; N1710 replaced with D, E, H, K, R, A, G, I, L, S, T, M, V, F, W, Y, P, or C; M1711 replaced with D, E, H, K, R, N, Q, F, W, Y, P, or C; E1712 replaced with H, K, R, A, G, I, L, S, T, M, V, N, Q, F, W, Y, P, or C; C1713 replaced with D, E, H, K, R, A, G, I, L, S, T, M, V, N, Q, F, W, Y, or P; R1714 replaced with D, E, A, G, I, L, S, T, M, V, N, Q, F, W, Y, P, or C; D1715 replaced with H, K, R, A, G, I, L, S, T, M, V, N, Q, F, W, Y, P, or C; T1716 replaced with D, E, H, K, R, N, Q, F, W, Y, P, or C; T1717 replaced with D, E, H, K, R, N, Q, F, W, Y, P, or C; R1718 replaced with D, E, A, G, I, L, S, T, M, V, N, Q, F, W, Y, P, or C; Y1719 replaced with D, E, H, K, R, N, Q, A, G, I, L, S, T, M, V, P, or C; C1720 replaced with D, E, H, K, R, A, G, I, L, S, T, M, V, N, Q, F, W, Y, or P; E1721 replaced with H, K, R, A, G, I, L, S, T, M, V, N, Q, F, W, Y, P, or C; K1722 replaced with D, E, A, G, I, L, S, T, M, V, N, Q, F, W, Y, P, or C; V1723 replaced with D, E, H, K, R, N, Q, F, W, Y, P, or C; K1724 replaced with D, E, A, G, I, L, S, T, M, V, N, Q, F, W, Y, P, or C; Q1725 replaced with D, E, H, K, R, A, G, I, L, S, T, M, V, F, W, Y, P, or C; L1726 replaced with D, E, H, K, R, N, Q, F, W, Y, P, or C; K1727 replaced with D, E, A, G, I, L, S, T, M, V, N, Q, F, W, Y, P, or C; L1728 replaced with D, E, H, K, R, N, Q, F, W, Y, P, or C; C1729 replaced with D, E, H, K, R, A, G, I, L, S, T, M, V, N, Q, F, W, Y, or P; Q1730 replaced with D, E, H, K, R, A, G, I, L, S, T, M, V, F, W, Y, P, or C; L1731 replaced with D, E, H, K, R, N, Q, F, W, Y, P, or C; S1732 replaced with D, E, H, K, R, N, Q, F, W, Y, P, or C; Q1733 replaced with D, E, H, K, R, A, G, I, L, S, T, M, V, F, W, Y, P, or C; F1734 replaced with D, E, H, K, R, N, Q, A, G, I, L, S, T, M, V, P, or C; K1735 replaced with D, E, A, G, I, L, S, T, M, V, N, Q, F, W, Y, P, or C; S1736 replaced with D, E, H, K, R, N, Q, F, W, Y, P, or C; R1737 replaced with D, E, A, G, I, L, S, T, M, V, N, Q, F, W, Y, P, or C; C1738 replaced with D, E, H, K, R, A, G, I, L, S, T, M, V, N, Q, F, W, Y, or P; C1739 replaced with D, E, H, K, R, A, G, I, L, S, T, M, V, N, Q, F, W, Y, or P; G1740 replaced with D, E, H, K, R, N, Q, F, W, Y, P, or C; T1741 replaced with D, E, H, K, R, N, Q, F, W, Y, P, or C; C1742 replaced with D, E, H, K, R, A, G, I, L, S, T, M, V, N, Q, F, W, Y, or P; G1743 replaced with D, E, H, K, R, N, Q, F, W, Y, P, or C; K1744 replaced with D, E, A, G. I, L, S, T, M, V, N, Q, F, W, Y, P, or C; or A1745 replaced with D, E, H, K, R, N, Q, F, W, Y, P, or C. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that bind polypeptides of the invention are also encompassed by the invention. Polynucleotides encoding these polypeptides are also encompassed by the invention.

The resulting constructs can be routinely screened for activities or functions described throughout the specification and known in the art. Preferably, the resulting constructs have an decreased THRAP activity or function, while the remaining THRAP activities or functions are maintained. More preferably, the resulting constructs have more than one decreased THRAP activity or function, while the remaining THRAP activities or functions are maintained.

Polynucleotides and polypeptides of the invention are useful as reagents for differential identification of the tissue (s) or cell type(s) present in a biological sample and for diagnosis of diseases and conditions which include but are not limited to: prostate cancer, cancer of the gastrointestinal tract, disorders of the uterus, neurological disorders, synovial sarcoma, immune disorders, tumor growth, and/or cancer, in general. Similarly, polypeptides and antibodies directed to these polypeptides are useful in providing immunological probes for differential identification of the tissue(s) or cell type(s). For a number of disorders of the above tissues or cells, particularly of the immune, neural, gastrointestinal, bone, skeletal, connective, and/or reproductive system, expression of this gene at significantly higher or lower levels may be routinely detected in certain tissues or cell types (e.g., immune, neural, gastrointestinal, bone, skeletal, connective, reproductive, cancerous and wounded tissues) or bodily fluids (e.g., lymph, serum, plasma, urine, amniotic fluid, semen, synovial fluid and spinal fluid) or another tissue or sample taken from an individual having such a disorder, relative to the standard gene expression level, i.e., the expression level in healthy tissue or bodily fluid from an individual not having the disorder.

Preferred polypeptides of the present invention comprise, or alternatively consist of, one or more of the immunogenic epitopes shown in SEQ ID NO: 89 as residues: Cys-3 to Pro-9, Arg-24 to Leu-35, Pro-41 to Gly-50, Lys-64 to Ser-77, Cys-93 to His-102, Ser-112 to Cys-119, Thr-142 to Ser-148, Val-170 to Gly-176, Arg-189 to Gln-195, Thr-235 to Leu-241, Arg-300 to Asp-305, Tyr-325 to Asn-330, Pro-342 to Asn-355, His-449 to Cys-457, Pro-459 to Lys-466, Pro-474 to Leu-482, Lys-492 to Leu-497, Glu-549 to Ser-557, Phe-573 to Gly-580, Tyr-596 to Cys-606, Asn-619 to Glu-627, Ser-634 to Leu-640, Trp-653 to Trp-658, Cys-695 to Ser-701, Pro-722 to Cys-727, Ala-765 to Ser-773, Thr-781 to Arg-794, Pro-835 to Pro-844, Thr-856 to Lys-861, Pro-883 to Arg-888, Leu-955 to Glu-960, Arg-967 to Ile-984, Asn-987 to Gly-995, Pro-1000 to Leu-1007, Gln-1028 to Gly-1042, Thr-1056 to Asp-1062, Leu-1068 to Tyr-1079, Pro-1105 to Ser-1111, Leu-1128 to Thr-1148, Arg-1305 to Gly-1311, Ser-1327 to Gly-1332, Cys-1486 to Arg-1495, Cys-1523 to Ser-1530, Gly-1666 to Arg-1674, Arg-1681 to Val-1686, Pro-1695 to Asn-1704, Pro-1707 to Arg-1718, Gln-1733 to Cys-1738. Polynucleotides encoding these polypeptides are also encompassed by the invention. Antibodies that bind one or more of these epitopes, domains described herein, or other polypeptides of the invention are specifically, but nonexclusively preferred.

The ubiquitous tissue distribution, the homology to thrombospondin-related protein, and the presence of multiple TSP-1-like domains indicates that the THRAP polypeptide and/or fragments of the present invention possess anti-angiogenic activity and, therefore, can be used in the treatment, diagnosis, and/or prevention of solid tumors of many tissues including, but not limited to the prostate, lung, breast, ovarian, stomach, pancreas, larynx, esophagus, testes, liver, parotid, biliary tract, colon, rectum, cervix, uterus, endometrium, kidney, bladder, thyroid cancer. Additionally, the THRAP polypeptide and/or fragments of the present invention can be used in the treatment, diagnosis, and/or prevention of primary tumors and metastases; melanomas; glioblastoma; Kaposi's sarcoma; leiomyosarcoma; non-small cell lung cancer; colorectal cancer; advanced malignancies; and blood born tumors such as leukemias.

Additionally, the THRAP polypeptide and/or fragments of the present invention possess anti-angiogenic activity and, therefore, can be used in the treatment, diagnosis, and/or prevention of other disorders, besides cancers, which involve angiogenesis. These disorders include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, restenosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and/or atherosclerosis.

Moreover, the ubiquitous tissue distribution and the presence of proteinase inhibitor-like domains indicates that the THRAP polypeptide and/or fragments of the present invention are useful as a proteinase inhibitor.

The tissue distribution in brain and homology to thrombospondin-related protein indicates that the THRAP polypeptide and/or fragments of the present invention are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette's Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it may play a role in normal neural function. Potentially, THRAP polypeptide and/or fragments of the present invention may be involved in synapse formation, neurotransmission, learning, cognition, homeostasis, or neuronal differentiation or survival.

The tissue distribution in immune cells and tissues (e.g., macrophage, and lymph node) and homology to thrombospondin-related protein indicates that the THRAP polypeptide and/or fragments of the present invention are useful for the detection, treatment, and/or prevention of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this THRAP polypeptide and/or fragments of the present invention indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lens tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. The expression within fetal tissue and other cellular sources marked by proliferating cells and homology to thrombospondin-related proteins indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus the THRAP polypeptide and/or fragments of the present invention may modulate apoptosis or tissue differentiation and would be useful in the detection, treatment, and/or prevention of degenerative or proliferative conditions and diseases. The THRAP polypeptide and/or fragments of the present invention are useful in modulating the immune response to aberrant polypeptides, as may exist in proliferating and cancerous cells and tissues. The THRAP polypeptide and/or fragments of the present invention can also be used to gain new insight into the regulation of cellular growth and proliferation.

Additionally, the secreted protein can also be used to determine biological activity, to raise antibodies, as tissue markers, to isolate cognate ligands or receptors, to identify agents that modulate their interactions, and as nutritional supplements. It may also have a very wide range of biological activities. Representative uses are described in the "Chemotaxis" and "Binding Activity" sections below, in Examples 11, 12, 13, 14, 15, 16, 18, 19, and 20, and elsewhere herein. Briefly, the THRAP polypeptide and/or fragments of the present invention may possess the following activities: cytokine, cell proliferation/differentiation modulating activity or induction of other cytokines; immunostimulating/immunosuppressant activities (e.g. for treating human immunodeficiency virus infection, cancer, autoimmune diseases and allergy); regulation of hematopoiesis (e.g. for treating anemia or as adjunct to chemotherapy); stimulation or growth of bone, cartilage, tendons, ligaments and/or nerves (e.g. for treating wounds, stimulation of follicle stimulating hormone (for control of fertility); chemotactic and chemokinetic activities (e.g. for treating infections, tumors); hemostatic or thrombolytic activity (e.g. for treating hemophilia, cardiac infarction etc.); anti-inflammatory activity (e.g. for treating septic shock, Crohn's disease); as antimicrobials; for treating psoriasis or other hyperproliferative diseases; for regulation of metabolism, and behavior. Also contemplated is the use of the corresponding nucleic acid in gene therapy procedures. Polynucleotides of the invention may also be employed in gene therapy. Representative uses are of gene therapy are described in the section "Gene Therapy" below and elsewhere herein.

Additionally, the expression of this gene product in synovium and homology to thrombospondin-related protein would suggest a role in the detection and treatment of disorders and conditions afflicting the skeletal system, in particular osteoporosis, bone cancer, connective tissue disorders (e.g. arthritis, trauma, tendonitis, chrondomalacia and inflammation). The THRAP polypeptide and/or fragments of the present invention are also useful in the diagnosis or treatment of various autoimmune disorders (i.e., rheumatoid arthritis, lupus, scleroderma, and dermatomyositis), dwarfism, spinal deformation, joint abnormalities, and chondrodysplasias (i.e. spondyloepiphyseal dysplasia congenita, familial osteoarthritis, Atelosteogenesis type II, metaphyseal chondrodysplasia type Schmid, etc.). Furthermore, the THRAP polypeptide and/or fragments of the present invention may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:18 and may have been publicly available prior to conception of the present invention. Preferably, such related polynucleotides are specifically excluded from the scope of the present invention. To list every related sequence would be cumbersome. However, preferably excluded from the present invention includes Genseq accession numbers Y35899, X97684, and X97583 (WO/9931236), which are hereby incorporated by reference in its entirety. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 5706 of SEQ ID NO:18, b is an integer of 15 to 5720, where both a and b correspond to the positions of nucleotide residues shown in SEQ ID NO:18, and where b is greater than or equal to a+14.

Features of Protein Encoded by Gene No: 9

The translation product of this gene shares sequence homology with the mouse uterine-specific proline-rich acidic protein which may play an important role in pregnancy. Based on the sequence similarity, the translation product of this clone is expected to share at least some biological activities with proline-rich acidic proteins. Such activities are known in the art, some of which are described elsewhere herein.

This gene is expressed primarily in colon cancer and to a lesser extent in fetal liver and spleen.

Polynucleotides and polypeptides of the invention are useful as reagents for differential identification of the tissue (s) or cell type(s) present in a biological sample and for diagnosis of diseases and conditions which include but are not limited to: colon cancer; digestive disorders; hematopoietic disorders; immune system dysfunction; inflammation; inflammatory bowel disease. Similarly, polypeptides and antibodies directed to these polypeptides are useful in providing immunological probes for differential identification of the tissue(s) or cell type(s). For a number of disorders of the above tissues or cells, particularly of the colon and immune system, expression of this gene at significantly higher or lower levels may be routinely detected in certain tissues or cell types (e.g., cancerous and wounded tissues) or bodily fluids (e.g., serum, plasma, urine, synovial fluid and spinal fluid) or another tissue or sample taken from an individual having such a disorder, relative to the standard gene expression level, i.e., the expression level in healthy tissue or bodily fluid from an individual not having the disorder.

Preferred polypeptides of the present invention comprise, or alternatively consist of, one or more immunogenic epitopes immunogenic epitopes shown in SEQ ID NO: 90 as residues: Trp-35 to Trp-45, Pro-52 to Asp-57, Thr-73 to Thr-80, Pro-96 to Leu-103, Pro-106 to Arg-118, Pro-131 to Gln-142. Polynucleotides encoding said polypeptides are also encompassed by the invention.

The tissue distribution in colon cancer cells and tissues, combined with the homology to the mouse proline-rich acidic protein indicates that polynucleotides and polypeptides corresponding to this gene are useful for the diagnosis and/or treatment of disorders of the colon, including colon cancer. Elevated levels of this transcript in various colon tumors suggests that it may represent an important diagnostic or causative agent in the development or progression of colon cancer. Alternately, expression in the colon may be indicative of roles in normal colon or digestive function. Similarly, expression of this transcript in hematopoietic cells and tissues, such as fetal liver suggests that it may play a role in the proliferation, differentiation, survival, or activation of a variety of blood cell lineages. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:19 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 691 of SEQ ID NO:19, b is an integer of 15 to 705, where both a and b correspond to the positions of nucleotide residues shown in SEQ ID NO:19, and where b is greater than or equal to a+14.

Features of Protein Encoded by Gene No: 10

The translation product of this gene shares sequence homology with bovine vacuolar ATP synthase membrane sector associated protein (see, e.g., Genbank Accession No. sp|P811341|VATN_BOVIN; all references available through this accession are hereby incorporated by reference in their entirety herein). Vacuolar ATPase is composed of at least 10 subunits and is believed to be responsible for acidifying a variety of intracellular compartments in eukaryotic cells.

The polypeptide encoded by this gene has been determined to have a transmembrane domain at about amino acid position 307 to about 323 of the amino acid sequence referenced in Table 1 for this gene. Moreover, a cytoplasmic tail encompassing about amino acids 324 to about 350 of this protein has also been determined. Based upon these characteristics, it is believed that the protein product of this gene shares structural features to type Ia membrane proteins.

It has been discovered that this gene is expressed primarily in dendritic cells, human osteoclastoma, placenta, fetal liver spleen, infant brain, colon tumor, pancreatic tumor, and ovarian tumor.

Polynucleotides and polypeptides of the invention are useful as reagents for differential identification of the tissue (s) or cell type(s) present in a biological sample and for diagnosis of the following diseases and conditions: immune, skeletal, developmental, reproductive, and/or neural diseases or disorders. Similarly, polypeptides and antibodies directed to those polypeptides are useful to provide immunological probes for differential identification of the tissue(s) or cell type(s). For a number of disorders of the above tissues or cells, particularly of the immune, hematopoietic, and/or integumentary system(s), expression of this gene at significantly higher or lower levels may be detected in certain tissues or cell types (e.g., immune, skeletal, developmental, reproductive, neural, and cancerous and wounded tissues) or bodily fluids (e.g., lymph, serum, plasma, urine, synovial fluid or spinal fluid) taken from an individual having such a disorder, relative to the standard gene expression level, i.e., the expression level in healthy tissue from an individual not having the disorder.

Preferred polypeptides of the present invention comprise, or alternatively consist of, one or more immunogenic epitopes immunogenic epitopes shown in SEQ ID NO: 91 as residues: Gln-153 to Ser-163, Ser-172 to Glu-178, Ala-204 to Asp-210, Ile-222 to Ala-236, Lys-284 to Ser-291, Met-342 to Arg-348. Polynucleotides encoding said polypeptides are also encompassed by the invention.

The tissue distribution in immune cells and tissues indicates that polynucleotides and/or polypeptides corresponding to this gene would be useful for the treatment, prevention, detection and/or diagnosis of hematopoietic related disorders such as anemia, pancytopenia, leukopenia, thrombocytopenia or leukemia since stromal cells are important in the production of cells of hematopoietic lineages. Representative uses are described in the "Immune Activity" and "Infectious Disease" sections below, in Example 11, 13, 14, 16, 18, 19, 20, and 27, and elsewhere herein. Briefly, the uses include bone marrow cell ex-vivo culture, bone marrow transplantation, bone marrow reconstitution, radiotherapy or chemotherapy of neoplasia. Polynucleotides and/or polypeptides of the invention may also be involved in lymphopoiesis, and therefore, would be useful in treating, preventing, detecting and/or diagnosing immune disorders such as infection, inflammation, allergy, immunodeficiency etc. In addition, this gene product may have commercial utility in the expansion of stem cells and committed progenitors of various blood lineages, and in the differentiation and/or proliferation of various cell types.

Alternatively, polynucleotides and/or polypeptides corresponding to this gene would be useful in detecting, diagnosing, treating, and/or preventing congenital disorders (i.e., nevi, moles, freckles, Mongolian spots, hemangiomas, port-wine syndrome), integumentary tumors (i.e., keratoses, Bowen's disease, basal cell carcinoma, squamous cell carcinoma, malignant melanoma, Paget's disease, mycosis fungoides, and Kaposi's sarcoma), injuries and inflammation of the skin (i.e., wounds, rashes, prickly heat disorder, psoriasis, dermatitis), atherosclerosis, uticaria, eczema, photosensitivity, autoimmune disorders (i.e., lupus erythematosus, vitiligo, dermatomyositis, morphea, scleroderma, pemphigoid, and pemphigus), keloids, striae, erythema, petechiae, purpura, and xanthelasma. In addition, such disorders may predispose increased susceptibility to viral and bacterial infections of the skin (i.e., cold sores, warts, chickenpox, molluscum contagiosum, herpes zoster, boils, cellulitis, erysipelas, impetigo, tinea, althlete's foot, and ringworm). Moreover, the protein product of this clone may also be useful for the treatment or diagnosis of various connective tissue disorders (i.e., arthritis, trauma, tendonitis, chrondomalacia and inflammation, etc.), autoimmune disorders (i.e., rheumatoid arthritis, lupus, scleroderma, dermatomyositis, etc.), dwarfism, spinal deformation, joint abnormalities, and chondrodysplasias (i.e., spondyloepiphyseal dysplasia congenita, familial osteoarthritis, Atelosteogenesis type II, metaphyseal chondrodysplasia type Schmid). The predicted membrane localization indicates that polynucleotides and/or polypeptides corresponding to this gene would be a good target for antagonists, particularly small molecules or antibodies, which block functional activity (such as, for example, transport function; complex formation; binding of the receptor by its cognate ligand(s); signaling function). Accordingly, preferred are antibodies and or small molecules which specifically bind an extracellular portion of the translation product of this gene. The extracellular regions can be ascertained from the information regarding the transmembrane domains as set out above. Also provided is a kit for detecting tumors in which expression of this protein occurs (such as, for example, ovarian cancer). Such a kit comprises in one embodiment an antibody specific for the translation product of this gene bound to a solid support. Also provided is a method of detecting these tumors in an individual which comprises a step of contacting an antibody specific for the translation product of this gene to a bodily fluid from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:20 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2094 of SEQ ID NO:20, b is an integer of 15 to 2108, where both a and b correspond to the positions of nucleotide residues shown in SEQ ID NO:20, and where b is greater than or equal to a+14.

Features of Protein Encoded by Gene No: 11

In specific embodiments, polypeptides of the invention comprise, or alternatively consist of, an amino acid sequence selected from the group consisting of:

```
MKPATASALLLLLLGLAWTQGSHGWGADASSLQKRAGRADQPGAGWQEVA,        (SEQ ID NO: 176)

MKPATASALLLLLLGLAWTQGSHGWGADASSLQKRA                       (SEQ ID NO: 177)

GRADQPGAGWQEVAAVTSKNYNYNQHAYPTA,

MKPATA

SALLLLLLGLAWTQGSHGWAGADASSLQKRAGRADQPGAGWQEVAAVTS          (SEQ ID NO: 178)

KNYNYNQHAYPTAYGGKYSVKTPAKGGVS,

SCNFQELQLQPACVSHCLWWEVLSQDPCKGGSLTFFLGFPGATWPAAVGEVL       (SEQ ID NO: 179)

VGNFLQPPPRPRKALVVRELLPLAPSLCQPWPGCHTSVS.
```

Polynucleotides encoding these polypeptides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that bind polypeptides of the invention are also encompassed by the invention. Polynucleotides encoding these polypeptides are also encompassed by the invention.

This gene is expressed primarily in fetal heart, healing wounds, and keratinocytes.

Polynucleotides and polypeptides of the invention are useful as reagents for differential identification of the tissue (s) or cell type(s) present in a biological sample and for diagnosis of diseases and conditions which include but are not limited to: developmental, cardiovascular, and integumentary diseases and/or disorders, particularly vascular disorders and impaired wound healing. Similarly, polypeptides and antibodies directed to these polypeptides are useful in providing immunological probes for differential identification of the tissue(s) or cell type(s). For a number of disorders of the above tissues or cells, particularly of the integumentary and immune systems, expression of this gene at significantly higher or lower levels may be routinely detected in certain tissues or cell types (e.g., developmental, cardiovascular, integumentary, and cancerous and wounded tissues) or bodily fluids (e.g., serum, plasma, urine, synovial fluid and spinal fluid) or another tissue or sample taken from an individual having such a disorder, relative to the standard gene expression level, i.e., the expression level in healthy tissue or bodily fluid from an individual not having the disorder.

Preferred polypeptides of the present invention comprise, or alternatively consist of, one or more immunogenic epitopes immunogenic epitopes shown in SEQ ID NO: 92 as residues: Ser-31 to Gly-45, Ser-54 to Gln-61, Ala-67 to Val-74. Polynucleotides encoding said polypeptides are also encompassed by the invention.

The tissue distribution in fetal heart indicates that polynucleotides and polypeptides corresponding to this gene are useful for the detection and/or treatment of vascular disorders including heart disease, myocardial infarction, ischemia, stroke, tumorigenesis, wound healing, ulcerative colitis, and skin disorders including psoriasis.

The tissue distribution in keratinocytes and healing wounds indicates that the protein product of this clone is useful for the treatment, diagnosis, and/or prevention of various skin disorders. Representative uses are described in the "Biological Activity", "Hyperproliferative Disorders", "Infectious Disease", and "Regeneration" sections below, in Example 11, 19, and 20, and elsewhere herein. Briefly, the protein is useful in detecting, treating, and/or preventing congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e. wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma. In addition, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, athletes foot, and ringworm).

Moreover, the protein product of this clone may also be useful for the treatment or diagnosis of various connective tissue disorders (i.e., arthritis, trauma, tendonitis, chrondomalacia and inflammation, etc.), autoimmune disorders (i.e., rheumatoid arthritis, lupus, scleroderma, dermatomyositis, etc.), dwarfism, spinal deformation, joint abnormalities, and chondrodysplasias (i.e. spondyloepiphyseal dysplasia congenita, familial osteoarthritis, Atelosteogenesis type II, metaphyseal chondrodysplasia type Schmid). Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:21 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 661 of SEQ ID NO:21, b is an integer of 15 to 675, where both a and b correspond to the positions of nucleotide residues shown in SEQ ID NO:21, and where b is greater than or equal to a+14.

Features of Protein Encoded by Gene No: 12

Translation products corresponding to this gene share sequence homology with sodium hydrogen exchanger proteins(See, e.g., Genbank Accession AAC39643), which are thought to be involved in the electroneutral exchange of protons for Na+ and K+ across the mitochondrial inner membrane contributing to organelle volume and Ca2+ homeostasis Based on the sequence similarity, the translation product of this clone is expected to share at least some biological activities with sodium hydrogen exchanger proteins. Such activities are known in the art, some of which are described elsewhere herein.

The polypeptide of this gene has been determined to have potential transmembrane domains at about amino acid position 19–35, 50–66, 158–174, 201–217, 235–251, 271–285, 320–336, 387–403, 430–446, and 456–472 of the amino acid sequence referenced in Table 1 for this gene. Based upon these characteristics, it is believed that the protein product of this gene shares structural features to type IIIb membrane proteins.

In a specific embodiment, polypeptides comprising the amino acid sequence of the open reading frame upstream of the predicted signal peptide are contemplated by the present invention. Specifically, polypeptides of the invention comprise, or alternatively consist of the following amino acid sequence:

```
RPRLGSSSGAAAEDSSAMEELATEKEAEESHRQDSVXLLTFILLLTLTILTIWLF(SEQ ID NO: 180)

KHRRVRFLHETGLAMIYGLIVGVILRYGTPATSGRDKSLSCTQEDRAFSTLLV

NVSGKFFEYTLKGEISPGKINSVEQNDMLRKVTFDPEVFFNILLPPIIFHAGYSL

KKRHFFRNLGSILAYAFLGTAXSCFIIGNLMYGVVKLMKIMGQLSDKFYYTX

XLFFGAIISATDPVTVLAIFNELHADVDLYALLFGESVLNDAVAIXLXSSIVAY

QPAGLNTHAFDAAAFFKSVGIFLGIFSGSFTMGAVTGVVTAXVTKFTKXHXFP

LLETALFFLMSWSTFLLAEACGFTGVVAVLFCGITQAHYTYNNLSVESRSRTK

QLFEVLHFLAENFIFSYMGLALFTFQKH-
VFSPIFIIGAFVAIFLGRAAHIYPLSFF

LNLGRRHKIGWNFQHMMMFSGLRGAMAFALAIRDTASYARQMMFTTTLLIV

FFTVWIIGGGTTPMLSWLNIRVGVDPDXDPPPXXDSFAFXTETA.
```

-

In a further specific embodiment, polypeptides of the invention comprise, or alternatively consist of, the following amino acid sequence:

```
MGAVTGVVTALVTKFTKLHCFPLLETALFFLMSWSTFLLAEACGFTGVVAVL   (SEQ ID NO: 215)

FCGITQAHYTYNNLSVESRSRTKQLFEVLHFLAENFIFSYMGLALFTFQKHVFS

PIFIIGAFVAIFLGRAAHIYPLSFFLNLGRRHKIGWNFQHMMMFSGLRGAMAF

ALAIRDTASYARQMMFTTTLLIVFFTVWIIGGGTTPMLSWLNIRVGVDPDQDP

PPNNDSFQVLQGDGPDSARGNRTKQESAWIFRLWYSFDHNYLKPILTHSGPPL

TTTLPAWCGLLARCLTSPQVYDNQEPLREEDSDFILTEGDLTLTYGDSTVTAN

GSSSSHTASTSLEGSRRTKSSSEEVLERDLGMGDQKVSSRGTRLVFPLEDNA.
```

Polynucleotides encoding these polypeptides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that bind polypeptides of the invention are also encompassed by the invention. Polynucleotides encoding these polypeptides are also encompassed by the invention.

It has been discovered that this gene is expressed primarily in germinal center B cell, and other cells of the immune system (e.g., thymus stromal cells, bone marrow stromal cells, dendritic cells and T cells) and to a lesser extent in stromal cells and brain.

Polynucleotides and polypeptides of the invention are useful as reagents for differential identification of the tissue(s) or cell type(s) present in a biological sample and for diagnosis of the following diseases and conditions: including arthritis, asthma, immunodeficiency diseases and leukemia. Similarly, polypeptides and antibodies directed to those polypeptides are useful to provide immunological probes for differential identification of the tissue(s) or cell type(s). For a number of disorders of the above tissues or cells, particularly of the immune, expression of this gene at significantly higher or lower levels may be detected in certain tissues (e.g., cancerous and wounded tissues) or bodily fluids (e.g., serum, plasma, urine, synovial fluid or spinal fluid) taken from an individual having such a disorder, relative to the standard gene expression level, i.e., the expression level in healthy tissue from an individual not having the disorder.

Preferred polypeptides of the present invention comprise, or alternatively consist of, one or more immunogenic epitopes immunogenic epitopes shown in SEQ ID NO: 93 as residues: Leu-4 to Ser-18. Polynucleotides encoding said polypeptides are also encompassed by the invention.

The homology of this gene to a sodium/hydrogen exchanger protein suggests that this gene is involved in cellular metabolism and maintaining Calcium homeostasis. The balance of calcium in the cell is extremely important with regards to signal transduction. Thus, expression of this gene in cells of the immune and nervous systems indicates that this gene may have a role in helping cells respond to extracellular signals to proliferate, differentiate, migrate, survive or die. Accordingly, the polynucleotides and/or polypeptides corresponding to this gene (and/or antibodies raised against those polypeptides) would be useful for treatment/detection of immune disorders such as arthritis, asthma, immune deficiency diseases such as AIDS, and leukemia, allergy, graft rejection, systemic lupus erythematosus (SLE), rheumatoid arthritis (RA) and other autoimmune conditions, infections, chronic variable immune deficiency (CVID) and other immune deficiency syndromes, respiratory distress syndrome and inflammation, neoplasms of the immune/hematopoietic system including leukemias, lymphomas and other proliferative disorders such as multiple myeloma, Hodgkin's and non-Hodgkin's lymphoma, and myelodypsplastic syndromes.

Further, the expression of this gene in the nervous system of the human indicates that the polynucleotides and/or polypeptides corresponding to this gene, (and/or antibodies raised against those polypeptides) are useful in the detection, diagnosis and treatment of neurological conditions such as manic depression, Alzheimer's, Huntington's, and Parkinson's disease, Tourette's syndrome and other neurodegenerative diseases including but not limited to, demyelinating diseases, epilepsy, headache, migraine, CNS infections, neurological trauma and neural regrowth following trauma, CNS neoplasms, stroke and reperfusion injury following stroke. It may also be useful for the treatment and diagnosis of learning and cognitive diseases, depression, dementia, pyschosis, mania, bipolar syndromes, schizophrenia and other psychiatric conditions. Potentially, this gene product is involved in synapse formation, neurotransmission, learning, cognition, homeostasis, or neuronal differentiation or survival.

The polynucleotides and/or polypeptides corresponding to this gene (and/or antibodies raised against those polypeptides) would be useful for treatment/detection in the treatment/detection of thymus disorders such as Graves Disease, lymphocytic thyroiditis, hyperthyroidism and hypothyroidism; and in the treatment/detection of pineal gland disorders such as the circadian rhythm disturbances associated with shift work, jet lag, blindness, insomnia and old age.

Based upon the tissue distribution of this protein, antagonists directed against this protein may be useful in blocking the activity of this protein. Accordingly, preferred are antibodies which specifically bind a portion of the translation product of this gene. Also provided is a kit for detecting tumors in which expression of this protein occurs. Such a kit comprises in one embodiment an antibody specific for the translation product of this gene bound to a solid support. Also provided is a method of detecting these tumors in an individual which comprises a step of contacting an antibody specific for the translation product of this gene to a bodily fluid from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:22 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1567 of SEQ ID NO:22, b is an integer of 15 to 1581, where both a and b correspond to the positions of nucleotide residues shown in SEQ ID NO:22, and where b is greater than or equal to a+14.

Features of Protein Encoded by Gene No: 13

The translation product of this gene shares sequence homology with a novel protein with a calcium binding motif (See, e.g., Genbank Accession number J30027) which may be important in calcium mediated signaling events. Based on the sequence similarity, the translation product of this clone is expected to share at least some biological activities with calcium binding proteins. Such activities are known in the art, some of which are described elsewhere herein.

In a specific embodiment, polypeptides comprising the amino acid sequence of the open reading frame upstream of the predicted signal peptide are contemplated by the present invention. Specifically, polypeptides of the invention comprise, or alternatively consist of the following amino acid sequence:

```
NGKISPYYWEQKLELHRGGGRSRTSGSPGLQEFGTSRGRAFWGRGLVRLTLE    (SEQ ID NO: 181)
GFASASETVRILMTMRSLLRTPFLCGLLWAFCAPGARAEEPAASFSQPGSMGL
DKNTVHDQEHIMEHLEGVINKPEAEMSPQELQLHYFKMHDYDGNNLLDGLE
LSTAITHVHKEEGSEQAPLMSEDELINIIDGVLRDDDKNNDGYIDYAEFAKSL
Q
```

Polynucleotides encoding these polypeptides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that bind polypeptides of the invention are also encompassed by the invention. Polynucleotides encoding these polypeptides are also encompassed by the invention.

In specific embodiments, polypeptides of the invention comprise, or alternatively consist of, an amino acid sequence selected from the group consisting of:

```
MLHDMLLVVHCVLIQAHAAGLGEAGCRLLSPGAWGTKGPEAQATQEGGSEQ     (SEQ ID NO: 182)
GSHGHQYPYGLRSRREALQREPHQPPSPKRSSSARAEFLQPGGSTSSRAAATA
VELQLLFPIVRGDFXV
and
MTPSRCSMICSWSCTVFLSRPMLPGWEKLAAGSSALAPGAQKAQSRPHRKGV     (SEQ ID NO: 183)
LSRDLMVINILTVSEADAKPSNVSLTSPRPQNALPRLVPNSCSPGDPLVLERPPP
RWSSSFCSQ.
```

Polynucleotides encoding these polypeptides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that bind polypeptides of the invention are also encompassed by the invention. Polynucleotides encoding these polypeptides are also encompassed by the invention.

It has been discovered that this gene is expressed primarily in bone marrow stroma and arthritic bone and to a lesser extent in pregnant uterus, retina, brain, dendritic cells and several other tissues and cell lines.

Polynucleotides and polypeptides of the invention are useful as reagents for differential identification of the tissue (s) or cell type(s) present in a biological sample and for diagnosis of the following diseases and conditions: osteoporosis, osteoarthritis or other bone related diseases. Similarly, polypeptides and antibodies directed to those polypeptides are useful to provide immunological probes for differential identification of the tissue(s) or cell type(s). For a number of disorders of the above tissues or cells, particularly of the skeletal system and blood forming tissues, expression of this gene at significantly higher or lower levels may be detected in certain tissues (e.g., cancerous and wounded tissues) or bodily fluids (e.g., serum, plasma, urine, synovial fluid or spinal fluid) taken from an individual having such a disorder, relative to the standard gene expression level, i.e., the expression level in healthy tissue from an individual not having the disorder.

Preferred polypeptides of the present invention comprise, or alternatively consist of, one or more immunogenic epitopes immunogenic epitopes shown in SEQ ID NO: 94 as residues: Ala-24 to Pro-29, Asp-42 to Glu-50, Asp-81 to Asn-86, Lys-102 to Gln-108, Arg-126 to Tyr-135. Polynucleotides encoding said polypeptides are also encompassed by the invention.

The tissue distribution and homology to calcium binding proteins suggests that the protein product of this clone would be useful for diagnosis, treatment and monitoring of diseases of the bone and joints including osteoporosis, osteoarthritis, bone cancers, and diseases of the bone marrow leading to alterations in the cells of the circulatory system. Based upon the tissue distribution of this protein, antagonists directed against this protein may be useful in blocking the activity of this protein. Accordingly, preferred are antibodies which specifically bind a portion of the translation product of this gene. Also provided is a kit for detecting tumors in which expression of this protein occurs. Such a kit comprises in one embodiment an antibody specific for the translation product of this gene bound to a solid support. Also provided is a method of detecting these tumors in an individual which comprises a step of contacting an antibody specific for the translation product of this gene to a bodily fluid from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:23 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 908 of SEQ ID NO:23, b is an integer of 15 to 922, where both a and b correspond to the positions of nucleotide residues shown in SEQ ID NO:23, and where b is greater than or equal to a+14.

Features of Protein Encoded by Gene No: 14

The translation product of this gene appears to be the human homolog of a mouse interferon-gamma (IFN-g)-induced protein expressed in peritoneal macrophages (see GenBank accession AAA66219, and Lafuse et al. (J. Leukocyte Biol. 57(3):477–83). When tested against T-cells, polypeptides of the present invention stimulated IL-5 release.

It has been discovered that this gene is expressed in bone marrow, activated T-cells and monocytes, as well as in fetal tissues, placenta, infant brain, corneal stromal cells, and a number of cancerous tissues (including ovary and colon cancers, and T-cell lymphoma).

Polynucleotides and polypeptides of the invention are useful as reagents for differential identification of the tissue(s) or cell type(s) present in a biological sample and for diagnosis of the following diseases and conditions: neurological, immune and hematopoietic disorders as well as developmental and proliferative disorders, including cancer. Similarly, polypeptides and antibodies directed to those polypeptides are useful to provide immunological probes for differential identification of the tissue(s) or cell type(s). For a number of disorders of the above tissues or cells, particularly of the immune, hemopoietic and central nervous system, expression of this gene at significantly higher or lower levels may be detected in certain tissues (e.g., bone marrow, neural, immune, cancerous and wounded tissues) or bodily fluids (e.g., lymph, serum, plasma, urine, synovial fluid or spinal fluid) taken from an individual having such a disorder, relative to the standard gene expression level, i.e., the expression level in healthy tissue from an individual not having the disorder.

Preferred polypeptides of the present invention comprise, or alternatively consist of, one or more immunogenic epitopes immunogenic epitopes shown in SEQ ID NO: 95 as residues: Met-1 to Ala-28, Pro-40 to Glu-48, Ile-68 to Ile-73, Gly-183 to Glu-188, Pro-286 to Ser-295, Val-301 to Gly-307, Asp-311 to His-321. Polynucleotides encoding said polypeptides are also encompassed by the invention.

The tissue distribution and homology to a mouse interferon-induced gene suggests that the protein product of this clone would be useful for treatment and diagnosis of disorders of the immune and hematopoietic systems, as well as neurological disorders, including epilepsy, Alzheimer's Disease, Parkinson's Disease, Huntington's Disease, Tourette's Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lens tissue injury, demyelination, systemic lupus erythematosis, drug induced hemolytic anemia, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Based upon the tissue distribution of this protein, antagonists directed against this protein may be useful in blocking the activity of this protein. Accordingly, preferred are antibodies which specifically bind a portion of the translation product of this gene. Also provided is a kit for detecting tumors in which expression of this protein occurs. Such a kit comprises in one embodiment an antibody specific for the translation product of this gene bound to a solid support. Also provided is a method of detecting these tumors in an individual which comprises a step of contacting an antibody specific for the translation product of this gene to a bodily fluid from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein. Furthermore, the protein may also be used to determine biological activity, raise antibodies, as tissue markers, to isolate cognate ligands or receptors, to identify agents that modulate their interactions, in addition to its use as a nutritional supplement. The expression of this gene in highly proliferative tissues (e.g. fetus, placental, infant brain, cancers) suggests that translation products of this gene may be involved in cell differentiation and/or proliferation. Therefore, protein, as well as antibodies directed against the protein, may show utility as tumor markers and/or immunotherapy targets for the above listed tissues.

Many polynucleotide sequences, such as EST sequences, are publicly available and accessible through sequence databases. Some of these sequences are related to SEQ ID NO:24 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2274 of SEQ ID NO:24, b is an integer of 15 to 2288, where both a and b correspond to the positions of nucleotide residues shown in SEQ ID NO:24, and where b is greater than or equal to a+14.

Features of Protein Encoded by Gene No: 15

The polypeptide of this gene has been determined to have a transmembrane domain at about amino acid position 3–19 of the amino acid sequence referenced in Table 1 for this gene. Moreover, a cytoplasmic tail encompassing amino acids 20–81 of this protein has also been determined. Based upon these characteristics, it is believed that the protein product of this gene shares structural features to type Ib membrane proteins.

In specific embodiments, polypeptides of the invention comprise, or alternatively consists of, the following amino acid sequence:

```
SGXPGSTHASAHASAQLPSQDVKICLLTMRLLVLSSLLCILLLCFSIFSTEGKRR  (SEQ ID NO: 184)

PAKAWSGRRTRLCCHRVPSPNSTNLKGHHVRLCKPCKLEPEPRLWVVPGA

LPQV.
```

Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that bind polypeptides of the invention are also encompassed by the invention. Polynucleotides encoding these polypeptides are also encompassed by the invention.

This gene is expressed primarily in colon and to a lesser extent in prostate, dendritic cells, healing groin wound, keratinocytes, and ovary.

Polynucleotides and polypeptides of the invention are useful as reagents for differential identification of the tissue(s) or cell type(s) present in a biological sample and for diagnosis of diseases and conditions which include but are not limited to: gastrointestinal system, colorectal cancer, reproductive system. Similarly, polypeptides and antibodies directed to these polypeptides are useful in providing immunological probes for differential identification of the tissue(s) or cell type(s). For a number of disorders of the above tissues or cells, particularly of the gastrointestinal system, reproductive and immune system expression of this gene at significantly higher or lower levels may be routinely detected in certain tissues or cell types (e.g., immune, cancerous and wounded tissues) or bodily fluids (e.g., serum, plasma, urine, synovial fluid and spinal fluid) or another tissue or sample taken from an individual having such a disorder, relative to the standard gene expression level, i.e., the expression level in healthy tissue or bodily fluid from an individual not having the disorder.

Preferred polypeptides of the present invention comprise, or alternatively consist of, one or more immunogenic epitopes immunogenic epitopes shown in SEQ ID NO: 96 as residues: Thr-22 to Cys-40, Val-44 to His-56. Polynucleotides encoding said polypeptides are also encompassed by the invention.

The tissue distribution in colon, colon cancer and ovary tumor indicates that polynucleotides and polypeptides corresponding to this gene are useful for diagnosis, treatment and/or detection of tumors, especially of the intestine, such as, carcinoid tumors, lymphomas, cancer of the colon and cancer of the rectum, as well as cancers of the ovary and other tissues where the expression has been indicated. The expression in the colon and ovary tissues, and immune cells may indicate the gene or its products can be used to treat and/or diagnose other disorders of the gastrointestinal, reproductive, and immune including inflammatory disorders such as, diverticular colon disease (DCD), inflammatory colonic disease, Crohn's disease (CD), non-inflammatory bowel disease (non-IBD) colonic inflammation; ulcerative disorders such as, ulcerative colitis (UC), amebic colitis, eosinophilic colitis; non-cancerous tumors, such as, polyps in the colon, adenomas, leiomyomas, lipomas, and angiomas. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:25 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 894 of SEQ ID NO:25, b is an integer of 15 to 908, where both a and b correspond to the positions of nucleotide residues shown in SEQ ID NO:25, and where b is greater than or equal to a+14.

Features of Protein Encoded by Gene No: 16

This gene is expressed primarily in developing lung, hemangiopericytoma and merkel cells.

Polynucleotides and polypeptides of the invention are useful as reagents for differential identification of the tissue(s) or cell type(s) present in a biological sample and for diagnosis of diseases and conditions which include but are not limited to: disorders of the skin, peripheral neuropathy, diseases of the lung, and cancers, particularly of the connective tissues (for example, involving pericytes) and soft tissues. Similarly, polypeptides and antibodies directed to these polypeptides are useful in providing immunological probes for differential identification of the tissue(s) or cell type(s). For a number of disorders of the above tissues or cells, particularly of the skin, pulmonary, and peripheral nervous systems, expression of this gene at significantly higher or lower levels may be routinely detected in certain tissues or cell types (e.g., pulmonary, cancerous and wounded tissues) or bodily fluids (e.g., lymph, serum, plasma, urine, synovial fluid and spinal fluid) or another tissue or sample taken from an individual having such a disorder, relative to the standard gene expression level, i.e., the expression level in healthy tissue or bodily fluid from an individual not having the disorder.

Preferred polypeptides of the present invention comprise, or alternatively consist of, one or more immunogenic epitopes immunogenic epitopes shown in SEQ ID NO: 97 as residues: Ala-55 to Ser-60. Polynucleotides encoding said polypeptides are also encompassed by the invention.

The tissue distribution in Merkel cells indicates that polynucleotides and polypeptides corresponding to this gene are useful for treatment of disorders involving sensory innervation such as peripheral neuropathy and sensory loss associated with leprosy. Moreover, the protein product of this clone is useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette's Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival.

Alternatively, the protein is useful for the treatment of disorders involving loss of lung function such as emphysema, ARDS, and cystic fibrosis. The protein is also useful for the treatment, detection, and/or prevention of pain disorders. The tissue distribution in Merkel cells also indicates that polynucleotides and polypeptides corresponding to this gene are useful for treatment of disorders involving: the skin (particularly, but not limited to, skin cancer); the lungs (for example lung cancer); and pericytes (particularly, but not limited to, hemangiopericytoma). Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:26 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2076 of SEQ ID NO:26, b is an integer of 15 to 2090, where both a and b correspond to the positions of nucleotide residues shown in SEQ ID NO:26, and where b is greater than or equal to a+14.

Features of Protein Encoded by Gene No: 17

A supernatant from a transfection of this gene has been shown to induce transcription in Jurkat T-cells by the SEAP assay. Specifically, when tested against Jurkat T-cell lines, supernatants removed from cells containing this gene activated the GAS (gamma activating sequence) promoter element. Thus, it is likely that this gene activates T-cells, and to a lesser extent, in immune and hematopoietic cells and tissue cell types, through the Jak-Stat signal transduction pathway. GAS is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

In specific embodiments, polypeptides of the invention comprise, or alternatively consists of, the following amino acid sequence:

```
MWGWGSLVSARGGWGVFIYLYNGLYIVLWGMGEPAGGENPPLSPHPPGRA      (SEQ ID NO: 185)
NVKLLIFVLYIFYINISIFFLQNQFINGRGVWGGHMELPLWGGPLHYPTYRPFP
HPPHSPPPGCDCCKMGV.
```

Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that bind polypeptides of the invention are also encompassed by the invention. Polynucleotides encoding these polypeptides are also encompassed by the invention.

This gene is expressed primarily in neurological tissue (including cerebellum, adult brain, epileptic frontal cortex, corpus colosum, and fetal brain) and to a lesser extent in T-cells and other immunological tissues, as well as a variety of tumors and other normal adult and fetal tissues.

Polynucleotides and polypeptides of the invention are useful as reagents for differential identification of the tissue(s) or cell type(s) present in a biological sample and for diagnosis of diseases and conditions which include but are not limited to: neural diseases and/or disorders, particularly cancer and other proliferative disorders. Similarly, polypeptides and antibodies directed to these polypeptides are useful in providing immunological probes for differential identification of the tissue(s) or cell type(s). For a number of disorders of the above tissues or cells, particularly of the neurological and immune systems, expression of this gene at significantly higher or lower levels may be routinely detected in certain tissues or cell types (e.g., neural, immune, hematopoietic, and cancerous and wounded tissues) or bodily fluids (e.g., lymph, serum, plasma, urine, synovial fluid and spinal fluid) or another tissue or sample taken from an individual having such a disorder, relative to the standard gene expression level, i.e., the expression level in healthy tissue or bodily fluid from an individual not having the disorder.

Preferred polypeptides of the present invention comprise, or alternatively consist of, one or more immunogenic epitopes immunogenic epitopes shown in SEQ ID NO: 98 as residues: Thr-52 to Phe-62, Pro-130 to Arg-135, Pro-160 to Arg-173, Thr-190 to His-195, Gly-246 to Arg-252, Arg-397 to Thr-403, Gly-414 to Arg-420, Arg-483 to Glu-488. Polynucleotides encoding said polypeptides are also encompassed by the invention.

The tissue distribution in neurological tissue indicates that polynucleotides and polypeptides corresponding to this gene are useful for diagnosis and treatment of cancer and other proliferative disorders, particularly of neural and immune tissues. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette's Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:27 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2341 of SEQ ID NO:27, b is an integer of 15 to 2355, where both a and b correspond to the positions of nucleotide residues shown in SEQ ID NO:27, and where b is greater than or equal to a+14.

Features of Protein Encoded by Gene No: 18

Supernatants from cells expressing this gene stimulate T cells and or NK cells to secrete interferon-gamma. Interferon gamma is an immunomodulatory cytokine that, for example, regulates inflammation and inhibits Th2 immune responses.

In specific embodiments, polypeptides of the invention comprise, or alternatively consist of, an amino acid sequence selected from the group consisting of:

```
GTRYAAASPAWAAAQQRSHPAMSPGTPGPTMGRSQGSPMDPMVMKRPQLY        (SEQ ID NO: 186)
GMGSNPHSQPQQSSPYPGGYGPPGPQRYPIGIQGRTPGAMAGMQYPQQQMP
PQYGQQGVSGYCQQGQQPYYSQQPQPPHLPPQAQYLPSQSQQRYQPQQVST
VHCPAGPVFSTKADPALNHLPVLY,
PSFSASAEQSVPRRFLWPSRPTAVSNWHPGSDSRQHGRNAVPSAADATSVWT      (SEQ ID NO: 187)
ARCEWLLPAGPTAILQPAAAAPAPPTPGAVSAVPVPAEVPAAAGEHSALPRRP
CFLHQGRPGSESSSCPLLKIMFWWKKN,
and/or
MIQSRVCLGGENRACGAVHCAHLLRLVPLLGLGRQILRLGWEVRGLRLLAVI      (SEQ ID NO: 188)
WLLALLAVTTHTLLSILRWHLLLRVLHSGHGPGSPTLDANWIPLWAWRAIGT
SWVRTALLRLRMRVTAHAIQLRSLHHHWIHWAALGSAHGRSGGAGAHRRV
TPLLRGRPGRAGSGVPRA.
```

Polynucleotides encoding these polypeptides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that bind polypeptides of the invention are also encompassed by the invention. Polynucleotides encoding these polypeptides are also encompassed by the invention.

This gene is expressed primarily in glioblastoma and fetal tissues (including fetal heart, fetal lung and fetal liver/spleen) and to a lesser extent in retina, germinal center B cells (from chronic lymphocytic leukemia and germinal center), and apoptotic T-cells.

Polynucleotides and polypeptides of the invention are useful as reagents for differential identification of the tissue(s) or cell type(s) present in a biological sample and for diagnosis of diseases and conditions which include but are not limited to: neural, developmental, and immune diseases and/or disorders, particularly cancer and other proliferative disorders, including glioblastoma. Similarly, polypeptides and antibodies directed to these polypeptides are useful in providing immunological probes for differential identification of the tissue(s) or cell type(s). For a number of disorders of the above tissues or cells, particularly of the brain and fetal tissues, expression of this gene at significantly higher or lower levels may be routinely detected in certain tissues or cell types (e.g., neural, developmental, immune, and cancerous and wounded tissues) or bodily fluids (e.g., lymph, amniotic fluid, serum, plasma, urine, synovial fluid and spinal fluid) or another tissue or sample taken from an individual having such a disorder, relative to the standard gene expression level, i.e., the expression level in healthy tissue or bodily fluid from an individual not having the disorder.

The tissue distribution in neural tissues indicates that polynucleotides and polypeptides corresponding to this gene are useful for diagnosis and treatment of cancer and other proliferative disorders, particularly of the brain and fetal tissue. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette's Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Alternatively, the expression within developmental tissues indicates that the protein may play a role in the regulation of cellular division, and may show utility in the diagnosis, treatment, and/or prevention of developmental diseases and disorders, including cancer, and other proliferative conditions.

Additionally, the homology of the ability of this gene to stimulate the secretion of interferon-gamma indicates that the polynucleotides and/or polypeptides corresponding to this gene (and/or antibodies raised against those polypeptides) are useful for the diagnosis and treatment of diseases and disorders associated with the immune system, including, but not limited to, allergy, asthma, graft rejection, systemic lupus erythematosus (SLE), rheumatoid arthritis (RA) and other autoimmune conditions, infections, AIDS, chronic variable immune deficiency (CVID) and other immune deficiency syndromes, respiratory distress syndrome and inflammation, neoplasms of the immune/hematopoietic system including leukemias, lymphomas and other proliferative disorders such as multiple myeloma, Hodgkin's and non-Hodgkin's lymphoma, and myelodysplastic syndromes. The polynucleotides and/or polypeptides corresponding to this gene (and/or antibodies raised against those polypeptides) may also be useful for stimulating the immune response to bolster the immune response to diseases such as cancer or infection.

Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:28 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1666 of SEQ ID NO:28, b is an integer of 15 to 1680, where both a and b correspond to the positions of nucleotide residues shown in SEQ ID NO:28, and where b is greater than or equal to a+14.

Features of Protein Encoded by Gene No: 19

Contact of MVEC cells with supernatant expressing the product of this gene was shown to increase the expression of a soluble adhesion molecule, specifically, ICAM-1. Thus it is likely that the product of this gene is involved in the activation of MVEC, in addition to other endothelial cell-lines or tissue cell types. Thus, polynucleotides and polypeptides related to this gene have uses which include, but are not limited to, activating vascular endothelial cells, such as during an inflammatory response.

The polypeptide encoded by this gene has been determined to have a transmembrane domain at about amino acid position 61 to about 77 of the amino acid sequence referenced in Table 1 for this gene. Moreover, a cytoplasmic tail encompassing about amino acids 1 to about 60 of this protein has also been determined. Based upon these characteristics, it is believed that the protein product of this gene shares structural features to type II membrane proteins.

It has been discovered that this gene is expressed primarily in Soares infant brain 1NIB and to a lesser extent in normalized infant brain cDNA.

Polynucleotides and polypeptides of the invention are useful as reagents for differential identification of the tissue(s) or cell type(s) present in a biological sample and for diagnosis of the following diseases and conditions: neurodevelopmental and/or neurodegenerative diseases or disorders. Similarly, polypeptides and antibodies directed to those polypeptides are useful to provide immunological probes for differential identification of the tissue(s) or cell type(s). For a number of disorders of the above tissues or cells, particularly of the central nervous system, expression of this gene at significantly higher or lower levels may be detected in certain tissues (e.g., nervous, neural, neuronal, cancerous and wounded tissues) or bodily fluids (e.g., serum, plasma, urine, lymph, synovial fluid or spinal fluid) taken from an individual having such a disorder, relative to the standard gene expression level, i.e., the expression level in healthy tissue from an individual not having the disorder.

Preferred polypeptides of the present invention comprise, or alternatively consist of, one or more immunogenic epitopes immunogenic epitopes shown in SEQ ID NO: 100 as residues: Leu-27 to Glu-32. Polynucleotides encoding said polypeptides are also encompassed by the invention.

The tissue distribution in fetal brain indicates that polynucleotides and/or polypeptides corresponding to this gene would be useful for the detection, diagnosis, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, diagnosis, treatment, and/or prevention of Alzheimer's Disease, Parkinson's Disease, Huntington's Disease, Tourette's Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception.

In addition, elevated expression of polynucleotides and/or polypeptides corresponding to this gene in regions of the brain indicates that polynucleotides and/or polypeptides of the invention may play a role in normal neural function. Potentially, polynucleotides and/or polypeptides of the invention are involved in synapse formation, neurotransmission, learning, cognition, homeostasis, or neuronal differentiation or survival.

The predicted membrane localization indicates that polynucleotides and/or polypeptides corresponding to this gene would be a good target for antagonists, particularly small molecules or antibodies, which block functional activity (such as, for example, binding of the receptor by its cognate ligand(s); transport function; signaling function). Accordingly, preferred are antibodies and or small molecules which specifically bind an extracellular portion of the translation product of this gene. The extracellular regions can be ascertained from the information regarding the transmembrane domains as set out above. Also provided is a kit for detecting tumors in which expression of polynucleotides and/or polypeptides corresponding to this gene occurs. Such a kit comprises in one embodiment an antibody specific for polynucleotides and/or polypeptides corresponding to this gene bound to a solid support. Also provided is a method of detecting these tumors in an individual which comprises a step of contacting an antibody specific for the translation product of this gene to a bodily fluid from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:29 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1604 of SEQ ID NO:29, b is an integer of 15 to 1618, where both a and b correspond to the positions of nucleotide residues shown in SEQ ID NO:29, and where b is greater than or equal to a+14.

Features of Protein Encoded by Gene No: 20

The translation product of this gene shares sequence homology with, and is believed to be a novel homolog of, GDNF. GDNF, neurturin (see, e.g., Genbank Accession No. gb|AAC50898.1|; all references available through this accession are hereby incorporated in their entirety by reference herein), persephin (see, e.g., Genbank Accession No. gb|AAC39640.1|(AF040962); all references available through this accession are hereby incorporated in their entirety by reference herein) and related family members serve useful roles as survival factors for neurons, particularly dopaminergic neurons. They can also have neurotrophic effects on neurons. GDNF and Neurturin (NTN) can each activate the MAP kinase signaling pathway in cultured sympathetic neurons and support the survival of sympathetic neurons, as well as of sensory neurons and dorsal root ganglia. Persephin, like GDNF and NTN, promotes the survival of ventral midbrain dopaminergic neurons in culture and prevents their degeneration after 6-hydroxydopamine treatment in vivo. Persephin also supports the survival of motor neurons in culture and in vivo after sciatic nerve axotomy and, like GDNF, promotes ureteric bud branching. However, in contrast to GDNF and NTN, persephin does not support peripheral neurons. Fibroblasts transfected with Ret and one of the coreceptors GFRalpha-1 or GFRalpha-2 do not respond to persephin, suggesting that persephin utilizes additional, or different, receptor components than GDNF and NTN. For these reasons, they may play key roles in mediating outcome of neurodegenerative disorders, such asamyotrophic lateral sclerosis (ALS) and Parkinson's disease. Potentially, it may turn out that GDNF-like molecules (i.e., novel family members) will exert survival, proliferation, or trophic effects on other cell types besides neurons. Thus, based on the sequence similarity, the translation product of this clone is expected to share at least some biological activities with GDNF family member proteins. Such activities are known in the art, some of which are described elsewhere herein.

It has been discovered that this gene is expressed primarily in smooth muscle.

Polynucleotides and polypeptides of the invention are useful as reagents for differential identification of the tissue(s) or cell type(s) present in a biological sample and for diagnosis of the following diseases and conditions: neural and vascular diseases and/or disorders. Similarly, polypeptides and antibodies directed to those polypeptides are useful to provide immunological probes for differential identification of the tissue(s) or cell type(s). For a number of disorders of the above tissues or cells, particularly of the CNS, PNS, and vascular systems, expression of this gene at significantly higher or lower levels may be detected in certain tissues (e.g., vascular, neural, and cancerous and wounded tissues) or bodily fluids (e.g., lymph, serum, plasma, urine, synovial fluid or spinal fluid) taken from an individual having such a disorder, relative to the standard gene expression level, i.e., the expression level in healthy tissue from an individual not having the disorder.

Preferred polypeptides of the present invention comprise, or alternatively consist of, one or more immunogenic epitopes immunogenic epitopes shown in SEQ ID NO: 101 as residues: Pro-75 to Cys-84. Polynucleotides encoding said polypeptides are also encompassed by the invention.

The homology to GDNF indicates that polynucleotides and/or polypeptides corresponding to this gene would be useful for the detection, diagnosis, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, diagnosis, treatment, and/or prevention of Alzheimer's Disease, Parkinson's Disease, Huntington's Disease, Tourette's Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Moreover, the protein is useful in the detection, treatment, and/or prevention of a variety of vascular disorders and conditions, which include, but are not limited to microvascular disease, vascular leak syndrome, aneurysm, stroke, embolism, thrombosis, coronary artery disease, arteriosclerosis, and/or atherosclerosis. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:30 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 959 of SEQ ID NO:30, b is an integer of 15 to 973, where both a and b correspond to the positions of nucleotide residues shown in SEQ ID NO:30, and where b is greater than or equal to a+14.

Features of Protein Encoded by Gene No: 21

The translation product of this clone shares sequence homology to the NADH oxidoreductase complex I subunit of Caenorhabditis elegans (See Genbank Accession No. gi|5019819|gb|AAD37863.1|AF143152_1 and Nucleic Acids Res. 27 (17), 3424–3432 (1999); all information contained within this accession and publication is hereby incorporated herein by reference). Based on the sequence similarity, the translation product of this clone is expected to share at least some biological activities with NADH oxidoreductase proteins. Such activities are known in the art, some of which are described elsewhere herein.

The polypeptide of this gene has been determined to have five transmembrane domains at about amino acid position 62–78, 95–111, 113–129, 149–65, and 169–185 of the amino acid sequence referenced in Table 1 for this gene. Based upon these characteristics, it is believed that the protein product of this gene shares structural features to type IIIa membrane proteins.

A preferred polypeptide fragment of the invention comprises the following amino acid sequence:

```
MTLFGLFVSLVFLGQAFTIMLVYVWSRRNPYVRMNFFGLLNFQAPFLPWVL        (SEQ ID NO: 189)

MGFSLLLGNSIIVDLLGIAVGHIYFFLEDVFPNQPGGIRILKTPSILKAIFDTPDE

DPNYNPLPEERPGGFAWGEGQRLGG.
```

Polynucleotides encoding these polypeptides are also encompassed by the invention.

This gene is expressed primarily in fetal liver spleen and to a lesser extent in most tissues and/or cell types examined.

Polynucleotides and polypeptides of the invention are useful as reagents for differential identification of the tissue(s) or cell type(s) present in a biological sample and for diagnosis of diseases and conditions which include but are not limited to: hematopoietic and immune diseases and/or disorders, particularly multiple myeloma, leukemia, and hemophilia. Similarly, polypeptides and antibodies directed to these polypeptides are useful in providing immunological probes for differential identification of the tissue(s) or cell type(s). For a number of disorders of the above tissues or cells, particularly of the immune and hematopoietic systems, expression of this gene at significantly higher or lower levels may be routinely detected in certain tissues or cell types (e.g., hematopoietic, immune, developmental, and cancerous and wounded tissues) or bodily fluids (e.g., lymph, amniotic fluid, serum, plasma, urine, synovial fluid and spinal fluid) or another tissue or sample taken from an individual having such a disorder, relative to the standard gene expression level, i.e., the expression level in healthy tissue or bodily fluid from an individual not having the disorder.

Preferred polypeptides of the present invention comprise, or alternatively consist of, one or more immunogenic epitopes immunogenic epitopes shown in SEQ ID NO: 102 as residues: Gly-88 to Arg-93, Ser-133 to Tyr-138, Phe-189 to Gly-195, Thr-211 to Gly-227. Polynucleotides encoding said polypeptides are also encompassed by the invention.

The tissue distribution enrichment in fetal liver spleen indicates that polynucleotides and polypeptides corresponding to this gene are useful for the treatment and/or detection of immune and/or hematopoietic disorders including arthritis, asthma, immunodeficiency diseases, leukemia, transplant rejection, and microbial infections. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lens tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Additionally this gene's homology to the NADH oxidoreductase complex I subunit protein indicates that this gene may play a role in cellular metabolism. Thus, the polynucleotides and/or polypeptides corresponding to this gene (and/or antibodies raised against those polypeptides) may be useful in detecting, diagnosing, and or treating complex I deficiencies. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:31 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1175 of SEQ ID NO:31, b is an integer of 15 to 1189, where both a and b correspond to the positions of nucleotide residues shown in SEQ ID NO:31, and where b is greater than or equal to a+14.

Features of Protein Encoded by Gene No: 22

In specific embodiments, polypeptides of the invention comprise, or alternatively consists of, an amino acid sequence selected from the group:

Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that bind polypeptides of the invention are also encompassed by the invention. Polynucleotides encoding these polypeptides are also encompassed by the invention.

This gene is expressed primarily in Soares adult brain N2b4HB55Y and to a lesser extent in epididymus, soares testis NHT, macrophage, and dendritic cells, placenta, tonsils, helper T-cells, embryo, and amniotic cells.

Polynucleotides and polypeptides of the invention are useful as reagents for differential identification of the tissue(s) or cell type(s) present in a biological sample and for diagnosis of diseases and conditions which include but are not limited to: neurodegenerative and immune disorders. Similarly, polypeptides and antibodies directed to these polypeptides are useful in providing immunological probes for differential identification of the tissue(s) or cell type(s). For a number of disorders of the above tissues or cells, particularly of the central nervous system and immune system, expression of this gene at significantly higher or lower levels may be routinely detected in certain tissues or

```
HASALALGPPGAAAPWPRPGCSSASAPPTPASAPWPASPSSSSGRWSTDSRGP      (SEQ ID NO: 192)
RLMGGLAGVLALWVLVTHVMYMQDYWRTWLKGLRGFFFVGVLFSAVSIAA
FCTFLVLAITRHQSLTDPTSYYLSSVWSFISFKWAFLLSLYAHRYRADFADISIL
SDF
and
CTCKIIGGPGSRGCAASSSWASSSRPSPSLPSAPSSCWPSPGIRASQTPPATTSPA   (SEQ ID NO: 190)
SGASFPSSGPSCSASMPTATGLTLLTSASSAISDPGGEVSAPWGGLRTWTQPLR
CWERLLPPPGDPRTVAENTQQDECGLPGSCPARPLSRKPECGREGILPCCSSSA
WPEGSFRPFQMNLFSFLSFFFLFFFFLRWSLTLSPRLESSAISAHCNLRLPGSS
NSPALASQVAGITGICHHARQIFVFLVETGFCHVGQAGLELLISGDSPASAFQS
AGIIGVSHRARPGSVFLARSEESLYLRPGQQSQEVKV,
MRPGPMLQARVSIPAALGTLFPRPGWAPGEVSSEISSRDLLNPHPSTPSCCSQS     (SEQ ID NO: 191)
WSPMSVLEPDSRGPPPISLTHTGIHTPQKTSQMRPDSGSRGMCFCPCKGFGEG
GNIVEAGKSPQTCAHAPPALRFHSAFSEGPCCTQTTGQERPCLPLQPLSLPFN,
MPTATGLTLLTSASSAISDPGGEVSAPWGGLRTWTQPLRCWERLLPPPGDPRT      (SEQ ID NO: 193)
VAENTQQDECGLPGSCPARPLSRKPECGREGILPCCSSSAWPEGSFRPFQMNL
FSFLSFFFLFFFFLRWSLTLSPRLECSSAISAHCNLRLPGSSNSPALASQVAGITG
ICHHARQIFVFLVETGFCHVGQAGLELLISGDSPASAFQSAGIIGVSHRARPGS
VFLARSEESLYLRPGQQSQEVKV,
and
MAPSRLQLGLRAAYSGISSVAGFSIFLVWTVVYRQPGTAAHGRARRGAGTVG       (SEQ ID NO: 194)
PGDARNVHARLLEDLAQGAARLLLRGRPLLGRLHRCLLHLPRAGHHPASEPH
RPHQLLPLQRLELHFLQVGLPAQPLCPPLPG.
```

cell types (e.g., neural, immune, cancerous and wounded tissues) or bodily fluids (e.g., serum, plasma, urine, synovial fluid and spinal fluid) or another tissue or sample taken from an individual having such a disorder, relative to the standard gene expression level, i.e., the expression level in healthy tissue or bodily fluid from an individual not having the disorder.

Preferred polypeptides of the present invention comprise, or alternatively consist of, one or more immunogenic epitopes immunogenic epitopes shown in SEQ ID NO: 103 as residues: Tyr-2 to Trp-7, Arg-42 to Thr-50. Polynucleotides encoding said polypeptides are also encompassed by the invention.

The tissue distribution in brain indicates the protein product of this clone is useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette's Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival.

The tissue distribution in immune cells (e.g., T-cells and macrophage) indicates the protein product of this clone is useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lens tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:32 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1898 of SEQ ID NO:32, b is an integer of 15 to 1912, where both a and b correspond to the positions of nucleotide residues shown in SEQ ID NO:32, and where b is greater than or equal to a+14.

Features of Protein Encoded by Gene No: 23

The translation product of this gene shares sequence homology with zinc finger proteins (see, e.g., Genbank Accession numbers CAA17278.1 and AAC51180; all references available through this accession are hereby incorporated by reference herein.). Additionally, the translation product of this gene shares sequence homology with OTIC 18 brain-specific nucleosome assembly protein and BRCA1-associated protein (see, e.g., Genseq accession numbers W37504 and W52187, respectively) which are important for diagnosis or therapy of hereditary disease and cancers, particularly of the brain, ovaries, and breast.

In specific embodiments, polypeptides of the invention comprise, or alternatively consists of, an amino acid sequence selected from the group:

```
PRVRGKGKKIFIHMHEIIQIDGHIYQCLECKQNFCENLALIMCQRTHTGEKPYK   (SEQ ID NO: 195)

CDMCEKTFVQSSDLTSHQRIHNYEKPYKCSKCEKSFWHHLALSGHQRTHAG

KKFYTCDICGKNFGQSSDLLVHQRSHTGEKPYLCSECDKCFSRSTNLIRHRRT

HTGEKPFKCLDVKKLLVGNQILLATRELTLGKGPTNVISVRKVTDTVQPSLYI

KEFILGRSPISVEPVKNALARNQTLSVHQRVHTGEKPYKCLECMRSFTRSANLI

RHQATHTHTFKCLEYEKSFNCSSRSNCTSVEFTWKRTPTSVVWRLESGFLLRN

GLCCPTRK
```

-continued and

```
MHEIIQIDGHIYQCLECKQNFCENLALIMCQRTHTGEKPYKCDMCEKTFVQSS    (SEQ ID NO: 196)

DLTSHQRIHNYEKPYKCSKCEKSFWHHLALSGHQRTHAGKKFYTCDICGKNF

GQSSDLLVHQRSHTGEKPYLCSECDKCFSRSTNLIRHRRTHTGEKPFKCLECE

KAFSGKSDLISHQRTHTGERPYKCNKCEDSYRHRSAFIVHKRVHTGEKPYKC

GACEKCFGQKSDLIVHQRVHTGEKPYKCLECMRSFTRSANLIRHQATHTHTF

KCLEYEKSFNCSSRSNCTSVEFTWKKTPTSVVWRLESGFLLRNGLCCPTRK.
```

Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides) are encompassed by the invention. Antibodies that bind polypeptides of the invention are also encompassed by the invention. Polynucleotides encoding these polypeptides are also encompassed by the invention.

This gene is expressed primarily in brain frontal cortex, ovary, skin, dendritic cells, skin, bone marrow and to a lesser extent in colon.

Polynucleotides and polypeptides of the invention are useful as reagents for differential identification of the tissue(s) or cell type(s) present in a biological sample and for diagnosis of diseases and conditions which include but are not limited to: ovarian cancer, brain cancer, neurodegenerative and immune disorders. Similarly, polypeptides and antibodies directed to these polypeptides are useful in providing immunological probes for differential identification of the tissue(s) or cell type(s). For a number of disorders of the above tissues or cells, particularly of the central nervous system, ovaries, colon, and immune cells, expression of this gene at significantly higher or lower levels may be routinely detected in certain tissues or cell types (e.g., immune, ovarian, neural, cancerous and wounded tissues) or bodily fluids (e.g., serum, plasma, urine, synovial fluid and spinal fluid) or another tissue or sample taken from an individual having such a disorder, relative to the standard gene expression level, i.e., the expression level in healthy tissue or bodily fluid from an individual not having the disorder.

The tissue distribution in brain and homology to OTIC 18 indicates the protein product of this clone is useful for the detection, treatment, and/or prevention of neurodegenerative disease states, behavioral disorders, inflammatory conditions, or brain cancer. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette's Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. The tissue distribution in ovaries and homology to BRCA1-associated protein indicates that polynucleotides and polypeptides corresponding to this gene are useful for detection, treatment, and/or prevention of ovarian and/or breast cancer.

The tissue distribution in bone marrow and dendritic cells indicates the protein product of this clone is useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lens tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:33 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2380 of SEQ ID NO:33, b is an integer of 15 to 2394, where both a and b correspond to the positions of nucleotide residues shown in SEQ ID NO:33, and where b is greater than or equal to a+14.

Features of Protein Encoded by Gene No: 24

The polypeptide of this gene has been determined to have a transmembrane domain at about amino acid position 2–18 of the amino acid sequence referenced in Table 1 for this gene. Moreover, a cytoplasmic tail encompassing amino acids 19–49 of this protein has also been determined. Based upon these characteristics, it is believed that the protein product of this gene shares structural features to type Ib membrane proteins.

In specific embodiments, polypeptides of the invention comprise, or alternatively consists of, the following amino acid sequence:

GTRERGLRTPQMVLVFAYLCVLLIVCWVTSKTSLALKYTVYKNFKRLIWNKS (SEQ ID NO: 197)

ILIITLTP.

Moreover, fragments and variants of this polypeptide (such as, for example, fragments as described herein, polypeptides at least 80%, 85%, 90%, 95%, 96%, 97%, 98%, or 99% identical to these polypeptides and polypeptides encoded by the polynucleotide which hybridize, under stringent conditions, to the polynucleotide encoding this polypeptide are encompassed by the invention. Antibodies that bind polypeptides of the invention are also encompassed by the invention. Polynucleotides encoding this polypeptide are also encompassed by the invention.

This gene is expressed primarily in brain frontal cortex

Polynucleotides and polypeptides of the invention are useful as reagents for differential identification of the tissue(s) or cell type(s) present in a biological sample and for diagnosis of diseases and conditions which include but are not limited to: neurological conditions. Similarly, polypeptides and antibodies directed to these polypeptides are useful in providing immunological probes for differential identification of the tissue(s) or cell type(s). For a number of disorders of the above tissues or cells, particularly of the nervous system, expression of this gene at significantly higher or lower levels may be routinely detected in certain tissues or cell types (e.g., neural, cancerous and wounded tissues) or bodily fluids (e.g., serum, plasma, urine, synovial fluid and spinal fluid) or another tissue or sample taken from an individual having such a disorder, relative to the standard gene expression level, i.e., the expression level in healthy tissue or bodily fluid from an individual not having the disorder.

The tissue distribution in brain indicates the protein product of this clone is useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette's Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:34 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2104 of SEQ ID NO:34, b is an integer of 15 to 2118, where both a and b correspond to the positions of nucleotide residues shown in SEQ ID NO:34, and where b is greater than or equal to a+14.

Features of Protein Encoded by Gene No: 25

The translation product of this gene shares sequence homology with Alix from Mus musculus, which is thought to be important in activation of apoptosis. According to Vito, et. al, J.Biol Chem (1999) Mouse ALIX (or AIP1 according to the authors' nomenclature) interacts with ALG-2 and is required for the calcium dependent step of apoptosis.

In specific embodiments, polypeptides of the invention comprise, or alternatively consist of the following amino acid sequence selected from the group consisting of:

VGAPGKLPDPERRRSASLSASQSASPPAQYLSLLGPRKLSAVCLARTAAEALI (SEQ ID NO: 199)

MATFISVQLKKTSEVDLAKPLVKFIQQTYPLGGEEQAQYCRAAEELSKLRRAA

VGRPLDKHEGALETLLRYYDQICSIEPKFPFSENQICLTFTWKDAFDKGSLFGG

-continued

SVKLALASLGYEKSCVLFNCAALASQIAAEQNLDNDEGLKIAAKHYQFASGA

FLHIKETVLSALSREPTVDISPDTVGTLSLIMLAXAQEVFFLKATRDKMKDAII

AKLANQAADYFGDAFKQCQYKDTLPKEVFPVLAAKHCIMQANAEYHQSILA

KQQKKFGEEIARLQHAAELIKTVASRYDEYVNVKDFSDKINRALXAAKKDND

FIYHDRVPDLKDLDPIGKATLVKSTPVNVPISQKFTDLFEKMVPVSVQQSLAA

YNQRKADLVNRSIAQMREATTLANGVLASLNLPAAIEDVSGDTVPQSILTKSR

SVIEQGGIQTVDQLIKELPELLQRNREILDESLRLLDEEEATDNDLRAKFKERW

QRTPSNELYKPLRAEGTNFRTVLDKAVQADGQVKECYQSHRDTIVLLCKPEP

ELNAAIPSANPAKTMQGSEVVXVLKSLLSNLDEVKKEREGLENDLKSVNFDM

TSKFLTALAQDGVINEEALSVTELDRVYGGLTTKVQESLKKQEGLLKNIQVSH

QEFSKMKQSNNEANLREEVLKNLATAYDNFVELVANLKEGTKFYNELTEILV

RFQNKCSDIVFARKTERDELLKDLQQSIAREPSAPSIPTPAYQSLPAGGHAPTPP

TPAPRTMPPTKPQPPARPPPPVLPANRAPSATAPSPVGAGTAAPAPSQTPGSAP

PPQAQGPPYPTYPGYPGYCQMPMPMGYNPYAYGQYNMPYPPVYHQSPGQAP

YPGPQQPSYPFP QPPQQSYYPQQ.

Polynucleotides encoding these polypeptides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that bind polypeptides of the invention are also encompassed by the invention. Polynucleotides encoding these polypeptides are also encompassed by the invention.

In specific embodiments, polypeptides of the invention comprise, or alternatively consist of the following amino acid sequence:

MHQLLQLQRQEPCRLLSPSPQPGLHHLCFQQIELLLLLLHLQWGLGLLRQLHH (SEQ ID NO: 198)

KRLAQLLLHRRRDHPIPPIQDILGIAKCPCPWAIILMRMASIICHIHQCITRVLDR

LRTRDPSSLHTPSLSPHSSLTIHSSNMSAQQLS.

Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that bind polypeptides of the invention are also encompassed by the invention. Polynucleotides encoding these polypeptides are also encompassed by the invention.

The gene encoding the disclosed cDNA is believed to reside on chromosome 3. Accordingly, polynucleotides related to this invention are useful as a marker in linkage analysis for chromosome 3.

This gene is expressed primarily in prostate cancer, osteoblasts, microvascular endothelial cells, umbilical vein, breast, fetal cochlea, pancreas tumor, fetal heart, testes, 8 week whole embryo, fetal liver spleen, and primary dendritic cells and to a lesser extent in a variety of normal and transformed adult and fetal tissues and cell lines.

Polynucleotides and polypeptides of the invention are useful as reagents for differential identification of the tissue(s) or cell type(s) present in a biological sample and for diagnosis of diseases and conditions which include but are not limited to: vascular, hematopoietic, reproductive, and developmental diseases and/or disorders, particularly cancer and other proliferative disorders. Similarly, polypeptides and antibodies directed to these polypeptides are useful in providing immunological probes for differential identification of the tissue(s) or cell type(s). For a number of disorders of the above tissues or cells, particularly of the prostate skeletal system, breast, pancreas, testes, and the immune system, expression of this gene at significantly higher or lower levels may be routinely detected in certain tissues or cell types (e.g., vascular, hematopoietic, and developmental, and cancerous and wounded tissues) or bodily fluids (e.g., lymph, serum, amniotic fluid, seminal fluid, plasma, urine, synovial fluid and spinal fluid) or another tissue or sample taken from an individual having such a disorder, relative to the standard gene expression level, i.e., the expression level in healthy tissue or bodily fluid from an individual not having the disorder.

Preferred polypeptides of the present invention comprise, or alternatively consist of, one or more immunogenic epitopes immunogenic epitopes shown in SEQ ID NO: 106 as residues: Thr-28 to Gln-36, Gln-138 to Gly-145. Polynucleotides encoding said polypeptides are also encompassed by the invention.

The tissue distribution in microvascular endothelial cells and umbilical vein, combined with the homology to the Alix protein, a factor which is required for apoptosis, indicates that polynucleotides and polypeptides corresponding to this gene are useful for treatment and diagnosis of cancer and other proliferative disorders, especially prostate cancer, since such a protein product could potentially be used to induce programmed cell death in tumors. Moreover, this protein may represent a protein which is constitutively down regulated in proliferative cells and tissues, and primarily in vascular tissues. Thus, agonizes of this protein may inhibit vascularization in tumors by returning the cellular control of this protein to basal, non-transformed levels. Moreover, the protein is useful in the detection, treatment, and/or prevention of a variety of vascular disorders and conditions, which include, but are not limited to microvascular disease, vascular leak syndrome, aneurysm, stroke, embolism, thrombosis, coronary artery disease, arteriosclerosis, and/or atherosclerosis. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:35 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 6051 of SEQ ID NO:35, b is an integer of 15 to 6065, where both a and b correspond to the positions of nucleotide residues shown in SEQ ID NO:35, and where b is greater than or equal to a+14.

Features of Protein Encoded by Gene No: 26

In specific embodiments, polypeptides of the invention comprise, or alternatively consists of, the following amino acid sequence:

VAVSNNSQAQVTWNLGAALCSGSQWLPERASAKCEMRGHITTLLTTSFLVFG (SEQ ID NO: 200)

LHIIFFLNISCFNFRVFILFETRPEDSRLYRERPVLPRY.

Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that bind polypeptides of the invention are also encompassed by the invention. Polynucleotides encoding these polypeptides are also encompassed by the invention.

The polypeptide of this gene has been determined to have a transmembrane domain at about amino acid position 13–29 of the amino acid sequence referenced in Table 1 for this gene. Moreover, a cytoplasmic tail encompassing amino acids 30–56 of this protein has also been determined. Based upon these characteristics, it is believed that the protein product of this gene shares structural features to type Ia membrane proteins.

This gene is expressed primarily in fetal tissue (e.g., liver, spleen), prostate, brain, colon, bone marrow and T-cells.

Polynucleotides and polypeptides of the invention are useful as reagents for differential identification of the tissue(s) or cell type(s) present in a biological sample and for diagnosis of diseases and conditions which include but are not limited to: developmental, immune, and neurodegenerative disorders. Similarly, polypeptides and antibodies directed to these polypeptides are useful in providing immunological probes for differential identification of the tissue(s) or cell type(s). For a number of disorders of the above tissues or cells, particularly of the central nervous system and immune system, expression of this gene at significantly higher or lower levels may be routinely detected in certain tissues or cell types (e.g., neural, immune, cancerous and wounded tissues) or bodily fluids (e.g., serum, plasma, urine, synovial fluid and spinal fluid) or another tissue or sample taken from an individual having such a disorder, relative to the standard gene expression level, i.e., the expression level in healthy tissue or bodily fluid from an individual not having the disorder.

Preferred polypeptides of the present invention comprise, or alternatively consist of, one or more immunogenic epitopes immunogenic epitopes shown in SEQ ID NO: 107 as residues: Thr-39 to Leu-53. Polynucleotides encoding said polypeptides are also encompassed by the invention.

The tissue distribution in brain indicates the protein product of this clone is useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette's Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival.

The tissue distribution in immune cells (e.g., T-cells) and bone marrow indicates the protein product of this clone is useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lens tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types.

Moreover, the expression within fetal tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and would be useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:36 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1351 of SEQ ID NO:36, b is an integer of 15 to 1365, where both a and b correspond to the positions of nucleotide residues shown in SEQ ID NO:36, and where b is greater than or equal to a+14.

Features of Protein Encoded by Gene No: 27

This invention relates to newly identified Lipocolon polynucleotides, polypeptides encoded by such polynucleotides, the use of such polynucleotides and polypeptides, as well as the production of such polynucleotides and polypeptides. The polypeptide of the present invention has been putatively identified as a human lipocalin homolog derived from colon carcinoma cDNA library. More particularly, the polypeptide of the present invention has been putatively identified as a human lipocalin colon carcinoma-derived protein, sometimes hereafter referred to as "Lipocolon" and/or "LPC". The invention also relates to inhibiting the action of such polypeptides.

The lipocalin protein family is a large group of small extracellular proteins. The family demonstrates great diversity at the sequence level, though most lipocalins share three characteristic conserved sequence motifs. The kernel lipocalins represent a more divergent family member as they share only a single conserved sequence motif. Belying this sequence dissimilarity, lipocalin crystal structures are highly conserved and comprise a single eight-stranded continuously hydrogen-bonded anti-parallel beta-barrel, which encloses an internal ligand-binding site. Together with two other families of ligand-binding proteins, the fatty-acid-binding proteins (FABPs) and the avidins, the lipocalins form part of an overall structural superfamily: the calycins.

Members of the lipocalin family are characterized by several common molecular-recognition properties: the ability to bind a range of small hydrophobic molecules, binding to specific cell-surface receptors and the formation of complexes with soluble macromolecules. The varied biological functions of the lipocalins are mediated by one or more of these properties. In the past, the lipocalins have been classified as transport proteins; however, it is now clear that the lipocalins exhibit great functional diversity, with roles in retinol transport, invertebrate cryptic coloration, olfaction and pheromone transport, and prostaglandin synthesis. These general properties suggest such proteins as appropriate transporters transferring biologically hazardous molecules in a safe and controlled manner between cells. Moreover, many lipocalins have been implicated in the regulation of cell homeostasis: apolipoprotein D, quiescience specific protein, purpurin, alpha-1-microglobulin, and NGAL. This combination of direct and indirect evidence indicates that the lipocalin protein family is involved, in a quite general way, in the mediation of cell regulation and that many presently functionless family members might act in this way.

The lipocalins have also been implicated in the regulation of cell homoeostasis and the modulation of the immune response, and, as carrier proteins, to act in the general clearance of endogenous and exogenous compounds. Roles for lipocalins in cell regulation have been proposed. Recently, NGAL (Neutrophil gelatinase-associated lipocalin) has been attributed to the pathogenesis of certain pathologic conditions in the colonic mucosa (See Nielsen BS, et al., Gut Mar;38(3):414–20; which is hereby incorporated herein). Interestingly, NGAL was found in a variety of normal and pathological human tissues. Neoplastic human tissues showed a very heterogeneous expression of NGAL protein. High NGAL levels were found in adenocarcinomas of lung, colon and pancreas. In contrast, renal cell carcinomas of various subtypes and prostate cancers contained low NGAL levels. Lymphomas and thymic tumors were negative for NGAL immuno-labeling.

Certain lipocalins are able to induce strong allergic responses. The molecular mimicry between lipocalin allergens and endogenous lipocalins at the T-cell level may explain why the immune response against lipocalins is Th2-dominated and results in allergy. This view is supported by recent studies of autoimmune and parasitic diseases and peptide analogues. The literature has intriguing references to members of the lipocalin family. For example, experiments have shown that the serum measurement of a protein from the neutrophil, human neutrophil lipocalin (HNL), is a superior means to distinguish acute bacterial and viral infections. Prostaglandin (PG) D2 is recognized as the most potent endogenous sleep-promoting substance whose action mechanism is the best characterized among the various sleep-substances thus far reported. Lipocalin-type PGD synthase is dominantly produced in the arachnoid membrane and choroid plexus of the brain, and is secreted into the CSF to become beta-trace, a major protein component of the CSF. The PGD synthase as well as the PGD2 thus produced circulates in the ventricular system, subarachnoidal space, and extracellular space in the brain system. PGD2 then interacts with DP receptors in the chemosensory region of the ventro-medial surface of the rostral basal forebrain to initiate the signal to promote sleep probably via the activation of adenosine A2A receptive neurons.

The polypeptide of the present invention has been putatively identified as a member of the lipocalin family and has been termed Lipocolon ("LPC"). This identification has been made as a result of amino acid sequence homology to lipocalin of Bufo marinus, prostaglandin D synthase, and cpl-1 proteins of Xenopus laevis, in combination with its isolation from a human colon carcinoma cDNA library.

FIG. 1 shows the nucleotide (SEQ ID NO:37) and deduced amino acid sequence (SEQ ID NO:201) of LPC. Predicted amino acids from about 48 to about 62 constitute the predicted lipocalin motif II (amino acid residues from about 48 to about 62 in SEQ ID NO:201) and are represented by the underlined amino acid regions; amino acids from about 77 to about 92 constitute the lipocalin motif III (amino acid residues from about 77 to about 92 in SEQ ID NO:201) and are represented by the double underlined amino acids.

FIG. 2 shows the regions of similarity between the amino acid sequences of the Lipocolon (LPC) protein (SEQ ID NO:201), the lipocalin of Bufo marinus, emb|CAA48138.1 (SEQ ID NO: 202); the Xenopus prostaglandin D synthase, dbj|BAA12075.1 (SEQ ID NO: 203); and the Xenopus cpl-1 proteins, emb|CAA59132.1 (SEQ ID NO: 204).

Figure 3:
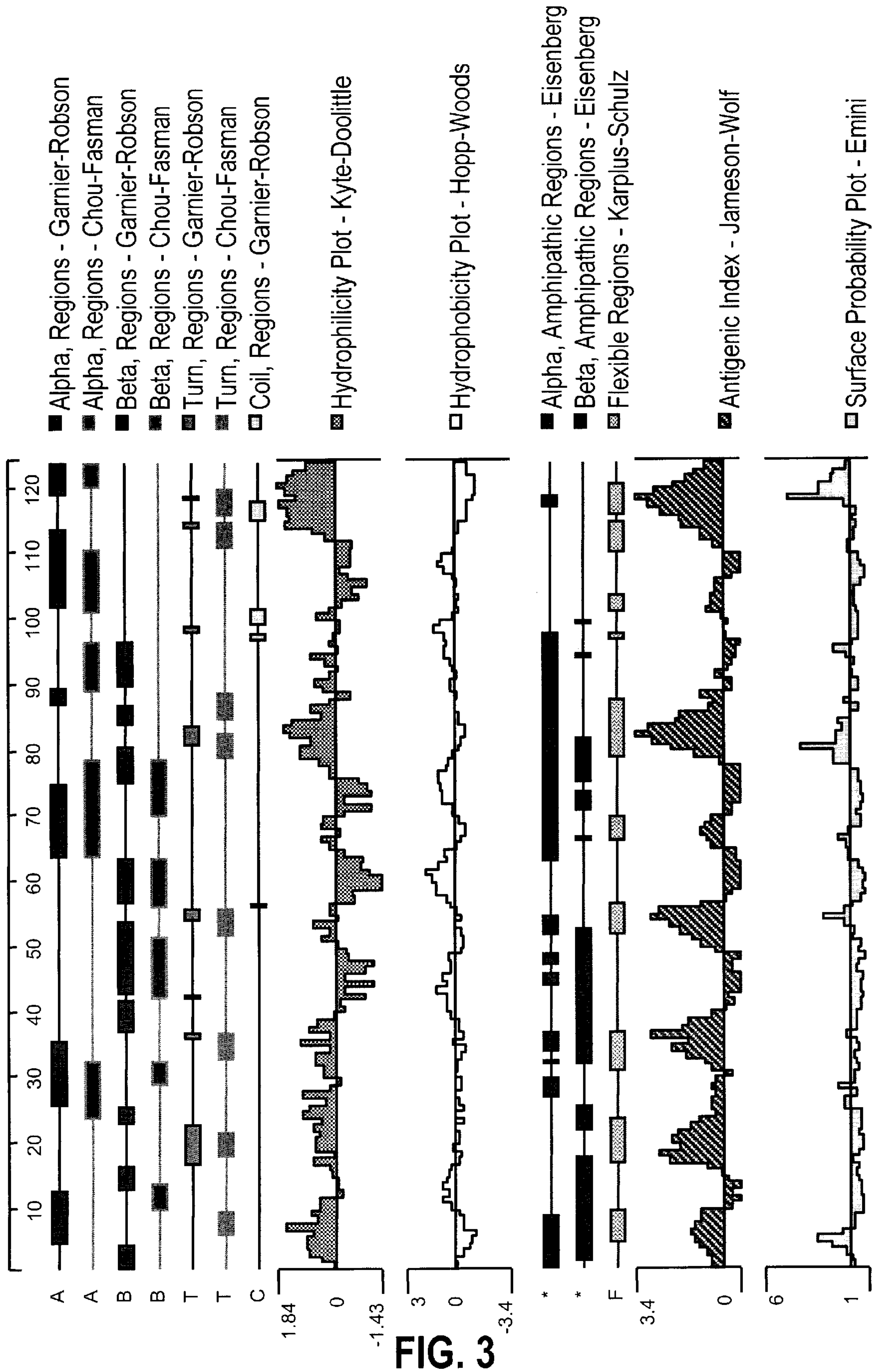
FIG. 3 shows an analysis of the Lipocolon (LPC) amino acid sequence. Alpha, beta, turn and coil regions; hydrophilicity and hydrophobicity; amphipathic regions; flexible regions; antigenic index and surface probability are shown.
Figure 6:
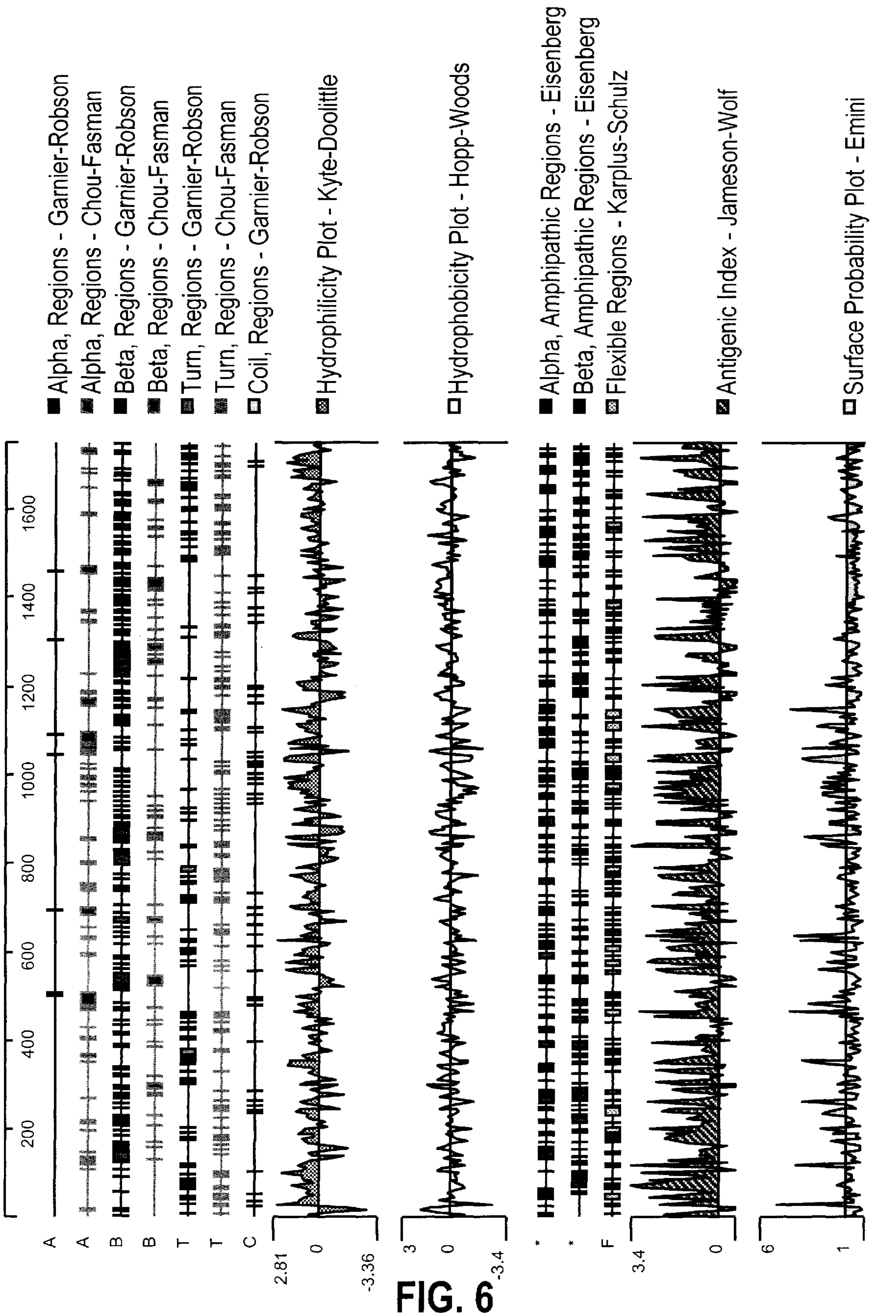

A polynucleotide encoding a polypeptide of the present invention is obtained from human colon adenocarcinoma, colon carcinoma, and cervical adenocarcinoma tissues, in addition to HeLa S3 cell line cells. The polynucleotide of this invention was discovered in a human colon carcinoma cDNA library. Its translation product has homology to the characteristic lipocalin domains. As shown in FIG. 1 and FIG. 2, LCP has two lipocalin domains (the lipocalin domains comprise amino acids 48–62 and/or 77–92 of SEQ ID NO:201; which correspond to amino acids 48 ñ 62 and/or 77–92 of FIG. 1) with strong conservation between other members of the lipocalin family. The polynucleotide contains an open reading frame encoding a portion of the LPC polypeptide of 123 amino acids. LCP exhibits a high degree of homology at the amino acid level to the lipocalin of Bufo marinus, prostaglandin D synthase and cpl-1 proteins of Xenopus laevis (as shown in FIG. 2).

The present invention provides isolated nucleic acid molecules comprising a polynucleotide encoding the LCP polypeptide having the amino acid sequence shown in FIG. 1 (SEQ ID NO:201), which was determined by sequencing a cloned cDNA, gene HWNFG66. The nucleotide sequence shown in FIG. 1 (SEQ ID NO:37) was obtained by sequencing a cDNA gene (HWNFG66), which was deposited on Sep. 27, 1999 at the American Type Culture Collection, and given Accession Number PTA-797. The deposited gene (HWNFG66) is inserted in the pSport plasmid (Life Technologies, Rockville, Md.) using the SalI/NotI restriction endonuclease cleavage sites.

The present invention is further directed to fragments of the isolated nucleic acid molecules described herein. By a fragment of an isolated DNA molecule having the nucleotide sequence of the deposited cDNA or the nucleotide sequence shown in SEQ ID NO:37 is intended DNA fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–1500 nt in length are also useful according to the present invention, as are fragments corresponding to most, if not all, of the nucleotide sequence of the deposited cDNA or as shown in SEQ ID NO:37. By a fragment at least 20 nt in length, for example, is intended fragments which include 20 or more contiguous bases from the nucleotide sequence of the deposited cDNA or the nucleotide sequence as shown in SEQ ID NO:37 (FIG. 1). In this context "about" includes the particularly recited size, larger or smaller by several (5, 4, 3, 2, or 1) nucleotides, at either terminus or at both termini.

Representative examples of LCP polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, from about 501 to about 550, from about 551 to about 570, from about 1 to about 236, from about 144 to about 188, from about 231 to about 276 of SEQ ID NO:37 (FIG. 1), or the complementary strand thereto, or the cDNA contained in the deposited gene. In this context "about" includes the particularly recited ranges, larger or smaller by several (5, 4, 3, 2, or 1) nucleotides, at either terminus or at both termini.

Preferred nucleic acid fragments of the present invention include nucleic acid molecules encoding a member selected from the group: a polypeptide comprising or alternatively, consisting of, any one of the lipocalcin domains (amino acid residues from about 48 to about 62 and/or 77 to about 92 in FIG. 1 (amino acids from about 48 to about 62 and/or 77 to about 92 in SEQ ID NO:201). Since the location of these domains have been predicted by computer analysis, one of ordinary skill would appreciate that the amino acid residues constituting these domains may vary slightly (e.g., by about 1 to 15 amino acid residues) depending on the criteria used to define each domain.

In additional embodiments, the polynucleotides of the invention encode functional attributes of LCP. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of LCP.

The data representing the structural or functional attributes of LCP set forth in FIG. 3 and/or Table 8, as described above, was generated using the various modules and algorithms of the DNA*STAR set on default parameters. In a preferred embodiment, the data presented in columns VIII, IX, XIII, and XIV of Table 8 can be used to determine regions of LCP which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 3, but may, as shown in Table 8, be represented or identified by using tabular representations of the data presented in FIG. 3. The DNA*STAR computer algorithm used to generate FIG. 3 (set on the original default parameters) was used to present the data in FIG. 3 in a tabular format (See Table 8). The tabular format of the data in FIG. 3 is used to easily determine specific boundaries of a preferred region.

The above-mentioned preferred regions set out in FIG. 3 and in Table 8 include, but are not limited to, regions of the aforementioned types identified by analysis of the amino acid sequence set out in FIG. 1. As set out in FIG. 3 and in Table 8, such preferred regions include Garnier-Robson alpha-regions, beta-regions, turn-regions, and coil-regions, Chou-Fasman alpha-regions, beta-regions, and turn-regions, Kyte-Doolittle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions.

Even if deletion of one or more amino acids from the N-terminus of a protein results in modification of loss of one or more biological functions of the protein, other functional activities (e.g., biological activities, ability to multimerize, etc.) may still be retained. For example, the ability of shortened LCP muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an LCP mutein with a large number of deleted N-terminal amino acid residues may retain some biological or immunogenic activities. In fact, peptides composed of as few as six LCP amino acid residues may often evoke an immune response.

Accordingly, the present invention further provides polypeptides having one or more residues deleted from the amino terminus of the LCP amino acid sequence shown in FIG. 1, up to the proline residue at position number 117 and polynucleotides encoding such polypeptides. In particular, the present invention provides polypeptides comprising the amino acid sequence of residues n1–123 of FIG. 1, where n1 is an integer from 2 to 117 corresponding to the position of the amino acid residue in FIG. 1 (which is identical to the sequence shown as SEQ ID NO:201).

In another embodiment, N-terminal deletions of the LCP polypeptide can be described by the general formula n2–123, where n2 is a number from 2 to 117, corresponding to the position of amino acid identified in FIG. 1. N-terminal deletions of the LCP polypeptide of the invention shown as SEQ ID NO:201 (FIG. 1) include polypeptides comprising, or alternatively consisting of, the amino acid sequence of residues: I-2 to P-117; R-3 to P-117; P-4 to P-117; T-5 to P-117; E-6 to P-117; E-7 to P-117; G-8 to P-117; G-9 to P-117; L-10 to P-117; H-11 to P-117; V-12 to P-117; H-13 to P-117; M-14 to P-117; E-15 to P-117; F-16 to P-117; P-17 to P-117; G-18 to P-117; A-19 to P-117; D-20 to P-117; G-21 to P-117; C-22 to P-117; N-23 to P-117; Q-24 to P-117; V-25 to P-117; D-26 to P-117; A-27 to P-117; E-28 to P-117; Y-29 to P-117; L-30 to P-117; K-31 to P-117; V-32 to P-117; G-33 to P-117; S-34 to P-117; E-35 to P-117; G-36 to P-117; H-37 to P-117; F-38 to P-117; R-39 to P-117 V-40 to P-117; P-41 to P-117; A-42 to P-117; L-43 to P-117; G-44 to P-117; Y-45 to P-117; L-46 to P-117; D-47 to P-117; V-48 to P-117; R-49 to P-117; I-50 to P-117; V-51 to P-117; D-52 to P-117; T-53 to P-117; D-54 to P-117; Y-55 to P-117; S-56 to P-117; S-57 to P-117; F-58 to P-117; A-59 to P-117; V-60 to P-117; L-61 to P-117; Y-62 to P-117; I-63 to P-117; Y-64 to P-117; K-65 to P-117; E-66 to P-117; L-67 to P-117; E-68 to P-117; G-69 to P-117; A-70 to P-117; L-71 to P-117; S-72 to P-117; T-73 to P-117; M-74 to P-117; V-75 to P-117; Q-76 to P-117; L-77 to P-117; Y-78 to P-117; S-79 to P-117; R-80 to P-117; T-81 to P-117; Q-82 to P-117; D-83 to P-117; V-84 to P-117; S-85 to P-117; P-86 to P-117; Q-87 to P-117; A-88 to P-117; L-89 to P-117; K-90 to P-117; A-91 to P-117; F-92 to P-117; Q-93 to P-117; D-94 to P-117; F-95 to P-117; Y-96 to P-117; P-97 to P-117; T-98 to P-117; L-99 to P-117; G-100 to P-117; L-101 to P-117; P-102 to P-117; E-103 to P-117; D-104 to P-117; M-105 to P-117; M-106 to P-117; V-107 to P-117; M-108 to P-117; L-109 to P-117; P-110 to P-117; Q-111 to P-117; or S-112 to P-117; of SEQ ID NO:201 (FIG. 1). Polypeptides encoded by these polynucleotides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that these bind polypeptides of the invention are also encompassed by the invention. Polynucleotides encoding these polypeptides are also encompassed by the invention.

Also as mentioned above, even if deletion of one or more amino acids from the C-terminus of a protein results in modification or loss of one or more biological functions of the protein, other functional activities (e.g., biological activities (e.g., ability to illicit mitogenic activity, induce differentiation of normal or malignant cells, bind to retinal, bind to retinoic acid, ability to bind small lipophilic molecules, etc.), ability to multimerize, ability to bind small lipophilic molecules receptors may still be retained. For example the ability of the shortened LCP mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an LCP mutein with a large number of deleted C-terminal amino acid residues may retain some biological or immunogenic activities. In fact, peptides composed of as few as six LCP amino acid residues may often evoke an immune response.

Accordingly, the present invention further provides polypeptides having one or more residues deleted from the carboxy terminus of the amino acid sequence of the LCP polypeptide shown in FIG. 1, up to the glutamine residue at position number 7, and polynucleotides encoding such polypeptides. In particular, the present invention provides polypeptides comprising the amino acid sequence of residues 1–m1 of FIG. 1, where m1 is an integer from 7 to 117 corresponding to the position of the amino acid residue in FIG. 1.

Moreover, the invention provides polynucleotides encoding polypeptides comprising, or alternatively consisting of, the amino acid sequence of C-terminal deletions of the LCP polypeptide of the invention shown as SEQ ID NO:201 (FIG. 1) include polypeptides comprising the amino acid sequence of residues: A-1 to N-116; A-1 to C-115; A-1 to A-114; A-1 to D-113; A-1 to S-112; A-1 to Q-111; A-1 to P-110; A-1 to L-109; A-1 to M-108; A-1 to V-107; A-1 to M-106; A-1 to M-105; A-1 to D-104; A-1 to E-103; A-1 to P-102; A-1 to L-101; A-1 to G-100; A-1 to L-99; A-1 to T-98; A-1 to P-97; A-1 to Y-96; A-1 to F-95; A-1 to D-94; A-1 to Q-93; A-1 to F-92; A-1 to A-91; A-1 to K-90; A-1 to L-89; A-1 to A-88; A-1 to Q-87; A-1 A-1 to P-86; A-1 to S-85; A-1 to V-84; A-1 to D-83; A-1 to Q-82; A-1 to T-81; A-1 to R-80; A-1 to S-79; A-1 to Y-78; A-1 to L-77; A-1 to Q-76; A-1 to V-75; A-1 to M-74; A-1 to T-73; A-1 to S-72; A-1 to L-71; A-1 to A-70; A-1 to G-69; A-1 to E-68; A-1 to L-67; A-1 to E-66; A-1 to K-65; A-1 to Y-64; A-1 to I-63; A-1 to Y-62; A-1 to L-61; A-1 to V-60; A-1 to A-59; A-1 to F-58; A-1 to S-57; A-1 to S-56; A-1 to Y-55; A-1 to D-54; A-1 to T-53; A-1 to D-52; A-1 to V-51; A-1 to I-50; A-1 to R-49; A-1 to V-48; A-1 to D-47; A-1 to L-46; A-1 to Y-45; A-1 to G-44; A-1 to L-43; A-1 to A-42; A-1 to P-41; A-1 to V-40; A-1 to R-39; A-1 to F-38; A-1 to H-37; A-1 to G-36; A-1 to E-35; A-1 to S-34; A-1 to G-33; A-1 to V-32; A-1 to K-31; A-1 to L-30; A-1 to Y-29; A-1 to E-28; A-1 to A-27; A-1 to D-26; A-1 to V-25; A-1 to Q-24; A-1 to N-23; A-1 to C-22; A-1 to G-21; A-1 to D-20; A-1 to A-19; A-1 to G-18; A-1 to P-17; A-1 to F-16; A-1 to E-15; A-1 to M-14; A-1 to H-13; A-1 to V-12; A-1 to H-1; A-1 to L-10; A-1 to G-9; A-1 to G-8; or A-1 to E-7 of SEQ ID NO:201 (FIG. 1). Polypeptides encoded by these polynucleotides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that these bind polypeptides of the invention are also encompassed by the invention. Polynucleotides encoding these polypeptides are also encompassed by the invention.

Based on the sequence similarity to lipocalin of *Bufo marinus*, and the prostaglandin D synthase and cpl-1 proteins of *Xenopus laevis*, translation product of this gene is expected to share at least some biological activities with lipocalin motif-containing proteins, and specifically lipocalin, cpl-1, and prostaglandin D synthase proteins. Such activities are known in the art, some of which are described elsewhere herein.

Specifically, polynucleotides and polypeptides of the invention are also useful for modulating the differentiation of normal and malignant cells, binding to and activating small lipophilic molecules (e.g., retinal, retinoic acid, D/L thyroxine, etc.), modulating the synthesis of prostaglandin D, hormones, etc., and modulating the proliferation and/or dedifferentiation of cancer and neoplastic cells, particularly adenocarcinoma. Polynucleotides and polypeptides of the invention may represent a diagnostic marker for colon adenocarcinoma, and adenocarcinoma in general. The full-length protein should be a secreted protein, based upon homology to the lipocalin family.

Therefore, it is secreted into serum, urine, or feces and thus the levels is assayable from patient samples. Assuming specific expression levels are reflective of the presence of adenocarcinoma, this would provide a convenient diagnostic for early detection. In addition, expression of this gene product may also be linked to the progression of the disease, and therefore may itself actually represent a therapeutic or therapeutic target for the treatment of cancer. Therefore, based upon the tissue distribution of this protein in adenocarcinoma cells and tissues, antagonists directed against this protein is useful in blocking the activity of this protein. Accordingly, preferred are antibodies which specifically bind a portion of the translation product of this gene.

Also provided is a kit for detecting tumors in which expression of this protein occurs. Such a kit comprises in one embodiment an antibody specific for the translation product of this gene bound to a solid support. Also provided is a method of detecting these tumors in an individual which comprises a step of contacting an antibody specific for the translation product of this gene to a bodily fluid from the individual, preferably serum, lymph, urine, seminal fluid, or feces and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein. Polynucleotides and polypeptides of the invention may play an important role in the pathogenesis of human cancers and cellular transformation, particularly those of the gastrointestinal, endocrine, and immune systems, and specifically of colon adenocarcinoma, cervical adenocarcinoma, and blood cells. Polynucleotides and polypeptides of the invention may also be involved in the pathogenesis of developmental abnormalities based upon its potential effects on proliferation and differentiation of cells and tissue cell types. Due to the potential proliferating and differentiating activity of said polynucleotides and polypeptides, the invention is useful as a therapeutic agent in inducing tissue regeneration, for treating inflammatory conditions (e.g., inflammatory bowel syndrome, diverticulitis, etc.). Moreover, the invention is useful in modulating the immune response to aberrant polypeptides, as may exist in rapidly proliferating cells and tissue cell types, particularly in adenocarcinoma cells, and other cancers.

This gene is expressed primarily in colon adenocarcinoma, cervical adenocarcinoma, and cell line HeLa S3.

Polynucleotides and polypeptides of the invention are useful as reagents for differential identification of the tissue(s) or cell type(s) present in a biological sample and for diagnosis of diseases and conditions which include but are not limited to: proliferative diseases and/or disorders, particularly adenocarcinomas. Similarly, polypeptides and antibodies directed to these polypeptides are useful in providing immunological probes for differential identification of the tissue(s) or cell type(s). For a number of disorders of the above tissues or cells, particularly of the gastrointestinal, endocrine, and immune systems, expression of this gene at significantly higher or lower levels is routinely detected in certain tissues or cell types (e.g., gastrointestinal, reproductive, endocrine, immune, and cancerous and wounded tissues) or bodily fluids (e.g., lymph, serum, plasma, urine, synovial fluid and spinal fluid) or another tissue or sample taken from an individual having such a disorder, relative to the standard gene expression level, i.e., the expression level in healthy tissue or bodily fluid from an individual not having the disorder.

Preferred polypeptides of the present invention comprise, or alternatively consist of, one or more immunogenic epitopes shown in SEQ ID NO: 108 as residues: Ser-66 to Ser-72, Pro-104 to Pro-110 (amino acid residues Ser-79 to Ser-85, Pro-117 to 123 of SEQ ID NO:201). Polynucleotides encoding said polypeptides are also encompassed by the invention as are antibodies that bind said epitopes, domains, or other polypeptides of the invention.

The tissue distribution in colon adenocarcinoma indicates polynucleotides and polypeptides corresponding to this gene are useful for the diagnosis and treatment of a variety of immune system disorders. Representative uses are described in the "Immune Activity" and "infectious disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses).

Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous Disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lens tissue injury, demyelination, systemic lupus erythematosis, drug induced hemolytic anemia, rheumatoid arthritis, Sjogren's Disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. The protein product of this gene is thought to be involved in allergy and Th2 mediated responses. Therefore, antagonists of this protein is useful therapeutically for the treatment, detection, and/or prevention of allergic responses, inhibiting eosinophil and basophil activation and release of mediators, and toxic shock syndromes.

Alternatively, the expression within cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation.

Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA).

Alternatively, this gene product is involved in the pattern of cellular proliferation that accompanies early embryogenesis. Thus, aberrant expression of this gene product in tissues—particularly adult tissues—may correlate with patterns of abnormal cellular proliferation, such as found in various cancers. In addition, other lipocalin family members, specifically cpl1, have been associated with playing a key role in early embryonic development. Through homology, it is expected that polypeptides and polynucleotides of the present invention may also play similar roles. Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases.

The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:37 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 556 of SEQ ID NO:37, b is an integer of 15 to 570, where both a and b correspond to the positions of nucleotide residues shown in SEQ ID NO:37, and where b is greater than or equal to a+14.

Features of Protein Encoded by Gene No: 28

The gene encoding the disclosed cDNA is believed to reside on chromosome 6. Accordingly, polynucleotides related to this invention are useful as a marker in linkage analysis for chromosome 6.

In specific embodiments, polypeptides of the invention comprise, or alternatively consists of, the following amino acid sequence:

```
PRVRNRKRRLSAVPAGGGEAAVGSLGCVSPVMEPGPTAAQRRCSLPPWLPLG     (SEQ ID NO: 205)
LLLWSGLALGALPRGSSPHRVFHDLLSEQQLLEVEDLSLSLLQGGGLGPLSLPP
DLPDLDPECRELLLDFANSSAELTGCLVRSARPVRLCQTCYPLFQQVVSKMD
NISRAAGNTSESQSCARSLLMADRMQIVVILSEFFNTTWQEANCANCLTNNSE
ELSNSTVYFLKSI
and
MEPGPTAAQRRCSLPPWLPLGLLLWSGLALGALPFGSSPHRVFHDLLSEQQLL    (SEQ ID NO: 140)
EVEDLSLSLLQGGGLGPLSLPPDLPDLDPECRELLLDFANSSAELTGCLVRSAR
PVRLCQTCYPLFQQVVSKMDNISRAAGNTSESQSCARSLLMADRMQIVVILSE
FFNTTWQEANCANCLTNNSEELSNSTVYFLKSI.
```

Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides) are encompassed by the invention. Antibodies that bind polypeptides of the invention are also encompassed by the invention. Polynucleotides encoding these polypeptides are also encompassed by the invention.

This gene is expressed primarily in osteoclastoma, T-cell, pineal gland, adipose tissue, placenta, dendritic cells, fetal tissue (e.g., heart) and to a lesser extent in many other tissues.

Polynucleotides and polypeptides of the invention are useful as reagents for differential identification of the tissue(s) or cell type(s) present in a biological sample and for diagnosis of diseases and conditions which include but are not limited to: immune disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., serum, plasma, urine, synovial fluid and spinal fluid) or another tissue or sample taken from an individual having such a disorder, relative to the standard gene expression level, i.e., the expression level in healthy tissue or bodily fluid from an individual not having the disorder.

Preferred polypeptides of the present invention comprise, or alternatively consist of, one or more immunogenic epitopes immunogenic epitopes shown in SEQ ID NO: 109 as residues: Glu-2 to Ser-13, Pro-75 to Leu-80. Polynucleotides encoding said polypeptides are also encompassed by the invention.

The tissue distribution in immune cells (e.g., T-cells) indicates the protein product of this clone is useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lens tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:38 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 3215 of SEQ ID NO:38, b is an integer of 15 to 3229, where both a and b correspond to the positions of nucleotide residues shown in SEQ ID NO:38, and where b is greater than or equal to a+14.

Features of Protein Encoded by Gene No: 29

The polypeptide of this gene has been determined to have a transmembrane domain at about amino acid position 3–19 of the amino acid sequence referenced in Table 1 for this gene. Moreover, a cytoplasmic tail encompassing amino acids 20–75 of this protein has also been determined. Based upon these characteristics, it is believed that the protein product of this gene shares structural features to type Ib membrane proteins.

This gene is expressed primarily in parathyroid tumor, brain, placenta, ovarian cancer, healing groin wound, osteoclastoma and to a lesser extent in many other tissues.

Polynucleotides and polypeptides of the invention are useful as reagents for differential identification of the tissue(s) or cell type(s) present in a biological sample and for diagnosis of diseases and conditions which include but are not limited to: ovarian cancer, neurological disorders, and/or parathyroid cancer. Similarly, polypeptides and antibodies directed to these polypeptides are useful in providing immunological probes for differential identification of the tissue(s) or cell type(s). For a number of disorders of the above tissues or cells, particularly of the female reproductive system, endocrine and exocrine system, expression of this gene at significantly higher or lower levels may be routinely detected in certain tissues or cell types (e.g., ovaries, cancerous and wounded tissues) or bodily fluids (e.g., serum, plasma, urine, synovial fluid and spinal fluid) or another tissue or sample taken from an individual having such a disorder, relative to the standard gene expression level, i.e., the expression level in healthy tissue or bodily fluid from an individual not having the disorder.

The tissue distribution in parathyroid tumor and ovarian cancer tissue indicates the protein product of this clone would be useful for the detection, treatment, and/or prevention of various endocrine and reproductive disorders and cancers. Representative uses are described in the "Biological Activity", "Hyperproliferative Disorders", and "Binding Activity" sections below, in Example 11, 17, 18, 19, 20 and 27, and elsewhere herein. Briefly, the protein can be used for the detection, treatment, and/or prevention of Addison's disease, Cushing's Syndrome, and disorders and/or cancers of the pancreas (e.g. diabetes mellitus), adrenal cortex, ovaries, pituitary (e.g., hyper-, hypopituitarism), thyroid (e.g. hyper-, hypothyroidism), parathyroid (e.g. hyper-, hypoparathyroidism), hypothalamus, and testes. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:39 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 497 of SEQ ID NO:39, b is an integer of 15 to 511, where both a and b correspond to the positions of nucleotide residues shown in SEQ ID NO:39, and where b is greater than or equal to a+14.

Features of Protein Encoded by Gene No: 30

The translation product of this gene shares sequence homology with apolipoprotein A-IV (see, e.g., Genbank Accession Nos. emb|CAA11020.1|(AJ222966) and gb|AAA35379.1|; all references available through these accessions are hereby incorporated in their entirety by reference herein).

```
(Genbank Accession Nos. emb CAA11020.1 polypeptide sequence:
MFLKAVVLSLALVAVTGARAEVNADQVATVMWDYFSQLGSNAKKAVEHLQ          (SEQ ID NO: 206)

KSELTQQLNTLFQDKLGEVNTYTEDLQKKLVPFATELHERLTKDSEKLKEEIR

RELEELRARLLPHATEVSQKIGDNVRELQQRLGPFTGGLRTQVNTQVQQLQR

QLKPYAERMESVLRQNIRNLEASVAPYADEFKAKIDQNVEELKGSLTPYAEEL

KAKIDQNVEELRRSLAPYAQDVQEKLNHQLEGLAFQMKKQAEELKAKISAN

ADELRQKLVPVAENVHGHLKGNTEGLQKSLLELRSHLDQQVEEFRLKVEPYG

ETFNKALVQQVEDLRQKLGPLAGDVEGHLSFLEKDLRDKVNTFFSTLKEEAS

QGQSQALPAQEKAQAPLEG.

Genbank Accession Nos. gb AAA35379.1:
MFLKAVVLTLALVAVAGARAEVSADQVATVMWDYFSQLSNNAKEAVEHLQ          (SEQ ID NO: 207)

KSELTQQLNALFQDKLGEVNTYAGDLQKKLVPFATELHERLAKDSEKLKEEI

GKELEELRARLLPHANEVSQKIGDNLRELQQRLEPYADQLRTQVNTQAEQLR

RQLDPLAQRMERVLRENADSLQASLRPHADELKAKIDQNVEELKGRLTPYAD

EFKVKIDQTVEELRRSLAPYAQDTQEKLNHQLEGLTFQMKKNAEELKARISA

SAEELRQRLAPLAEDVRGNLKGNTEGLQKSLAELGGHLDQQVEEFRRRVEPY

GENFNKALVQQMEQLRQKLGPHAGDVEGHLSFLEKDLRDKVNSFFSTFKEKE

SQDKTLSLPELEQQQEQQQEQQQEQVQMLAPLES.
```

-continued

```
Genbank Accession No. gb AAA37214.1:
MFLKAAVLTLALVAITGTRAEVTSDQVANVVWDYFTQLSNNAKEAVEQFQK          (SEQ ID NO: 208)

TDVTQQLSTLFQDKLGDASTYADGVHNKLVPFVVQLSGHLAKETERVKEEIK

KELEDLRDRMMPHANKVTQTFGENMQKLQEHLKPYAVDLQDQINTQTQEM

KLQLTPYIQRMQTTIKENVDNLHTSMMPLATNLKDKFNRNMEELKGHLTPRA

NELKATIDQNLEDLRRSLAPLTVGVQEKLNHQMEGLAFQMKKNAEELQTKV

SAKIDQLQKNLAPLVEDVQSKVKGNTEGLQKSLEDLNRQLEQQVEEFRRTVE

PMGEMFNKALVQQLEQFRQQLGPNSGEVESHLSFLEKSLREKVNSFMSTLEK

KGSPDQPQALPLPEQAQEQAQEQVQPKPLES.).
```

This invention relates to newly identified Apolipoprotein polynucleotides, polypeptides encoded by such polynucleotides, the use of such polynucleotides and polypeptides, as well as the production of such polynucleotides and polypeptides. The polypeptide of the present invention has been putatively identified as a human apolipoprotein A-IV homolog derived from a normal human liver cDNA library, sometimes hereafter referred to as "Apolipoprotein A-IV-Like" and/or "ApoA-IV-L". The invention also relates to inhibiting the action of such polypeptides.

Apolipoproteins are protein constituents of plasma lipid transport particles. ApoA-IV is associated with triglyceride-rich lipoproteins and HDL, and also occurs in a lipoprotein-free form. It has been proposed to play a role in reverse cholesterol transport on the basis of in vitro properties. It has been demonstrated that apoA-IV can bind to hepatocytes. Since it appears that the expression of our homolog, apoA-IV-L, is liver-enriched, if not liver-specific, perhaps there is some "hand-off" mechanism, whereby HDL/cholesterol is transported to the liver by apoA-IV and transferred to apoA-IV-L for elimination from the liver. Therefore, apoA-IV-L is intimately involved in cholesterol metabolism, cholesterol transport, and removal of cholesterol from the body. The ApoA-IV protein has also been attributed to regulating food-intake (J Nutr. 1999 Aug;129(8):1503–6).

In transgenic mice that are expressing apoA-IV in the liver, it appears that apoA-IV can protect against atherosclerosis by a mechanism that does not involve an increase in HDL cholesterol concentration. Therefore, perhaps our homolog, apoA-IV-L can also provide protection against atherosclerosis.

Studies have demonstrated that dietary fat clearance is modulated by genetic variation in the apolipoprotein A-IV gene locus. For example, the A-IV-347Ser polymorphism is associated with the variability in low density lipoprotein (LDL)-cholesterol response to dietary therapy. A putative polymorphism has been specifically identified within the present invention (a serine to isoleucine polymorphism at amino acid residue 258 of FIGS. 7A–B (amino acid residue 258 of SEQ ID NO: 212). Perhaps this possible polymorphism, or others as yet undetected in the gene locus for apoA-IV-L may likewise provide a diagnostic for altered lipid/cholesterol/bile metabolism.

Interestingly, other apolipoproteins, specifically apolipoprotein(a) ("apo(a)") is a recognized cardiovascular risk factor. Apo(a) is characterized by a high genetic polymorphism with at least 34 isoforms in plasma. Recent studies have shown that in atherothrombosis apo(a) polymorphism could play a role independent of Lp(a) levels. In particular, apo(a) phenotypes seem to have their highest predictive value for coronary heart disease, when apo(a) isoforms are detected by high resolution phenotyping methods and when an adequate operative cut-off of apo(a) polymorphism is used. A strong association between apo(a) phenotypes and coronary heart disease has been also found in hypertensive, diabetic, and uremic patients. Moreover, apo(a) phenotypes seem to correlate well with the severity of coronary atherosclerosis and the age of clinical onset of coronary heart disease. These studies suggest that apo(a) polymorphism may have a great clinical usefulness in a primary prevention setting, since apo(a) phenotypes could be used together with Lp(a) levels as strong genetic predictors of atherothrombosis. The analysis of apo(a) polymorphism appears to be particularly useful in healthy subjects with a family history of atherothrombotic diseases, in patients with diseases at high cardiovascular risk (diabetes, hypertension, hypercholesterolemia) and in subjects with conditions modifying Lp(a) levels (Cardiologia. 1999 Apr;44(4):347–54, and Am J Cardiol. 1999 May 13;83(9B) :3F–12F). Thus, it is anticipated that at the present apolipoprotein A-IV-like protein, and/or polymorphisms thereof, may portray similar clinical phenotypes, whose expression levels may also serve as a diagnostic for cardiovascular diseases and/or disorders, if not also for liver diseases and/or disorders.

The polypeptide of the present invention has been putatively identified as a member of the apolipoprotein family and has been termed Apolipoprotein A-IV-Like protein ("ApoA-IV-L"). This identification has been made as a result of amino acid sequence homology to the apolipoprotein A-IV of Sus scrofa (emb|CAA11020.1), the human apolipoprotein A-IV (gb|AAA51744.1), and the mouse apolipoprotein A-IV (gb|AAA37214.1).

FIGS. 7A–B show the nucleotide (SEQ ID NO: 40) and deduced amino acid sequence (SEQ ID NO: 212) of ApoA-IV-L. Predicted amino acids from about 1 to about 23 constitute the predicted signal sequence (amino acid residues from about 1 to about 23 in SEQ ID NO: 212) and are represented by the underlined amino acid regions; and nucleic acid residues from about 781 to about 885 (nucleic acid residues from about 781 to about 885 in SEQ ID NO:212 which constitutes the putative polymorphism domain as is represented by the double underlined nucleic acids; and amino acid 258 which constitutes a putative Serine to Isoleucine polymorphism (amino acid residue 258 in SEQ ID NO155 and is represented by the bold amino acid.

FIGS. 8A–8B shows the regions of similarity between the amino acid sequences of the Apolipoprotein A-IV-Like (ApoA-IV-L) protein (SEQ ID NO:212) the apolipoprotein A-IV of Sus scrofa (SEQ ID NO: 206), the human apolipoprotein A-IV (SEQ ID NO: 207), and the mouse apolipoprotein A-IV (SEQ ID NO: 208).

Figure 9:
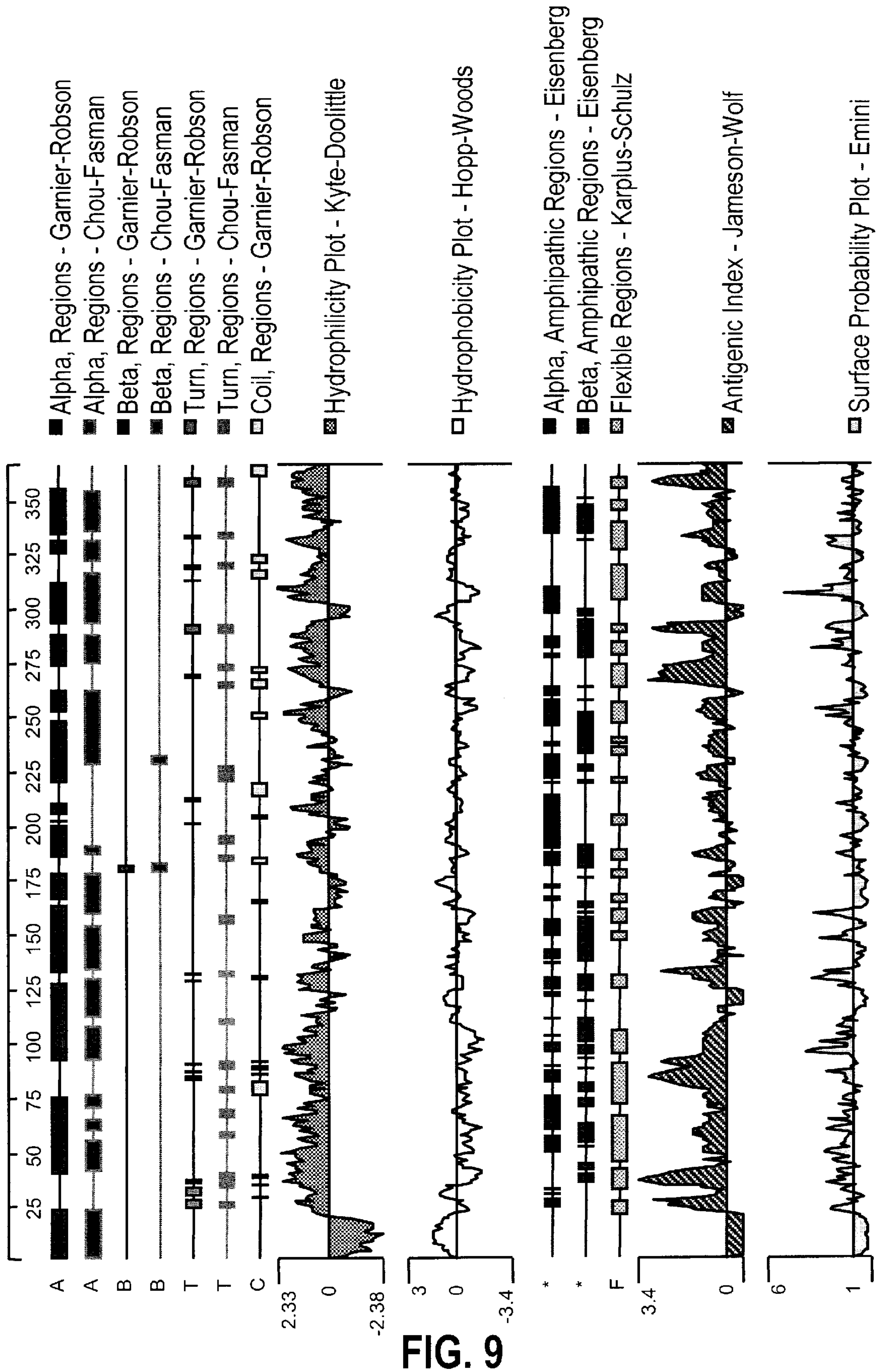

FIG. 9 shows an analysis of the Apolipoprotein A-IV-Like (ApoA-IV-L) amino acid sequence. Alpha, beta, turn and coil regions; hydrophilicity and hydrophobicity; amphipathic regions; flexible regions; antigenic index and surface probability are shown.

A polynucleotide encoding a polypeptide of the present invention is obtained from human normal liver, hepatoma, and pancreas tumor tissues. The polynucleotide of this invention was discovered in a human normal liver cDNA library. As shown in FIGS. 7A–B and FIG. 8, ApoA-IV-L has strong conservation between other members of the apolipoprotein A-IV family. The polynucleotide contains an open reading frame encoding the full-length apolipoprotein A-IV polypeptide of 366 amino acids, and a predicted molecular weight of 41.237 kilodaltons. ApoA-IV-L exhibits a high degree of homology at the amino acid level to the apolipoprotein A-IV of Sus scrofa, the human apolipoprotein A-IV, and the mouse apolipoprotein A-IV (as shown in FIG. 8).

The present invention provides isolated nucleic acid molecules comprising a polynucleotide encoding the ApoA-IV-L polypeptide having the amino acid sequence shown in FIGS. 7A–B (SEQ ID NO: 212). The nucleotide sequence shown in FIGS. 7A–B (SEQ ID NO: 40) was obtained by sequencing a cDNA gene (HLDRR08), which was deposited on Sep. 27, 1999 at the American Type Culture Collection, and given Accession Number PTA-796. The deposited gene (HLDRR08) is inserted in the pCMV Sport 3.0 plasmid (Life Technologies, Rockville, Md.) using the SalI/NotI restriction endonuclease cleavage sites.

The present invention is further directed to fragments of the isolated nucleic acid molecules described herein. By a fragment of an isolated DNA molecule having the nucleotide sequence of the deposited cDNA or the nucleotide sequence shown in SEQ ID NO: 40 is intended DNA fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–1500 nt in length are also useful according to the present invention, as are fragments corresponding to most, if not all, of the nucleotide sequence of the deposited cDNA or as shown in SEQ ID NO: 40. By a fragment at least 20 nt in length, for example, is intended fragments which include 20 or more contiguous bases from the nucleotide sequence of the deposited cDNA or the nucleotide sequence as shown in SEQ ID NO: 40. In this context "about" includes the particularly recited size, larger nucleotides, at either terminus or at both termini.

Representative examples of ApoA-IV-L polynucleotide fragments of the invention include, for example, fragments that comprise, or Alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, from about 501 to about 550, from about 551 to about 600, from about 601 to about 650, from about 651 to about 700, from about 701 to about 750, from about 751 to about 800, from about 801 to about 850, from about 851 to about 900, from about 901 to about 950, from about 951 to about 1000, from about 1001 to about 1050, from about 1051 to about 1100, from about 1101 to about 1150, from about 1151 to about 1200, from about 1201 to about 1250, from about 1251 to about 1300, from about 1301 to about 1350, from about 1351 to about 1393, from about 64 to about 129, from about 67 to about 1161, and from about 130 to about 1161 of SEQ ID NO: 40 (FIGS. 7A–B), or the complementary strand thereto, or the cDNA contained in the deposited gene. In this context "about" includes the particularly recited ranges, larger or smaller by several (5, 4, 3, 2, or 1) nucleotides, at either terminus or at both termini.

Alternatively, consisting of, the predicted mature apolipoprotein A-IV-L (amino acid residues from about 24 to about 366 in FIGS. 7A–B (amino acids from about 24 to about 366 in SEQ ID NO: 212); the full-length apolipoprotein A-IV-L (amino acid residues from about 1 to about 366 in FIGS. 7A–B (amino acid residues from about 1 to about 366 in SEQ ID NO: 212); the full-length apolipoprotein A-IV-L minus the start methionine (amino acid residues from about 2 to about 366 in FIGS. 7A–B (amino acid residues from about 2 to about 366 in SEQ ID NO: 212). In this context "about" includes the particularly recited ranges, larger or smaller by several (5, 4, 3, 2, or 1) nucleotides, at either terminus or at both termini.

Alternatively, consist of, the putative polymorphic domain, and specifically polynucleotide fragments having a sequence from about nucleotide 825 to about 846, from about 822 to about 849, from about 820 to about 852, from about 817 to about 855, from about 814 to about 858, from about 811 to about 861, from about 808 to about 864, from about 805 to about 867, from about 802 to about 870, from about 799 to about 873, from about 796 to about 876, from about 793 to about 879, from about 790 to about 882, from about 787 to about 885, from about 784 to about 888, and from about 781 to about 891 of SEQ ID NO: 40 (FIGS. 7A–B). In this context "about" includes the particularly recited ranges, larger or smaller by several (5, 4, 3, 2, or 1) nucleotides, at either terminus or at both termini, and potentially as many as 10, 20, 30, 40, 50, or 100 nucleotides, at either terminus or at both termini. Such polynucleotide fragments could be used diagnostically to identify individuals, organisms, and/or cells at risk for metabolic, liver, and cardiovascular diseases and/or disorders through the application of such fragments in modern RFLP and SSLP polymorphism analysis. The methodology of such an analysis would readily be apparent to the skilled artisan. Though a few examples are referenced in Methods Mol Biol. 1998;110:1–34, J Clin Lab Anal. 1999;13(5):205–208, and Am. J. Hum. Genet. 44:388–396.

In additional embodiments, the polynucleotides of the invention encode functional attributes of ApoA-IV-L. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of ApoA-IV-L.

The data representing the structural or functional attributes of ApoA-IV-L set forth in FIG. 9 and/or Table 9, as described above, was generated using the various modules and algorithms of the DNA*STAR set on default parameters. In a preferred embodiment, the data presented in columns VIII, IX, XIII, and XIV of Table 9 can be used to determine regions of ApoA-IV-L which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 9, but may, as shown in Table 9, be represented or identified by using tabular representations of the data presented in FIG. 9. The DNA*STAR computer algorithm used to generate FIG. 9 (set on the original default parameters) was used to present the data in FIG. 9 in a tabular format (See Table 9). The tabular format of the data in FIG. 9 is used to easily determine specific boundaries of a preferred region.

The above-mentioned preferred regions set out in FIG. 9 and in Table 9 include, but are not limited to, regions of the aforementioned types identified by analysis of the amino acid sequence set out in FIGS. 7A–7B. As set out in FIG. 9 and in Table 9, such preferred regions include Garnier-Robson alpha-regions, beta-regions, turn-regions, and coil-regions, Chou-Fasman alpha-regions, beta-regions, and turn-regions, Kyte-Doolittle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions.

Even if deletion of one or more amino acids from the N-terminus of a protein results in modification of loss of one or more biological functions of the protein, other functional activities (e.g., biological activities, ability to multimerize, etc.) may still be retained. For example, the ability of shortened ApoA-IV-L muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an ApoA-IV-L mutein with a large number of deleted N-terminal amino acid residues may retain some biological or immunogenic activities. In fact, peptides composed of as few as six ApoA-IV-L amino acid residues may often evoke an immune response.

Accordingly, the present invention further provides polypeptides having one or more residues deleted from the amino terminus of the ApoA-IV-L amino acid sequence shown in FIGS. 7A–7B, up to the serine residue at position number 361 and polynucleotides encoding such polypeptides. In particular, the present invention provides polypeptides comprising the amino acid sequence of residues n1–366 of FIGS. 7A–7B, where n1 is an integer from 2 to 361 corresponding to the position of the amino acid residue in FIGS. 7A–7B (which is identical to the sequence shown as SEQ ID NO: 212).

In another embodiment, N-terminal deletions of the ApoA-IV-L polypeptide can be described by the general formula n2–361, where n2 is a number from 2 to 361, corresponding to the position of amino acid identified in FIGS. 7A–7B. N-terminal deletions of the ApoA-IV-L polypeptide of the invention shown as SEQ ID NO: 212 include polypeptides comprising the amino acid sequence of residues: N-terminal deletions of the ApoA-IV-L polypeptide of the invention shown as SEQ ID NO: 212 include polypeptides comprising, or alternatively consisting of, the amino acid sequence of residues: A-2 to P-366; S-3 to P-366; M-4 to P-366; A-5 to P-366; A-6 to P-366; V-7 to P-366; L-8 to P-366; T-9 to P-366; W-10 to P-366; A-11 to P-366; L-12 to P-366; A-13 to P-366; L-14 to P-366; L-15 to P-366; S-16 to P-366; A-17 to P-366; F-18 to P-366; S-19 to P-366; A-20 to P-366; T-21 to P-366; Q-22 to P-366; A-23 to P-366; R-24 to P-366; K-25 to P-366; G-26 to P-366; F-27 to P-366; W-28 to P-366; D-29 to P-366; Y-30 to P-366; F-31 to P-366; S-32 to P-366; Q-33 to P-366; T-34 to P-366; S-35 to P-366; G-36 to P-366; D-37 to P-366; K-38 to P-366; G-39 to P-366; R-40 to P-366; V-41 to P-366; E-42 to P-366; Q-43 to P-366; I-44 to P-366; H-45 to P-366; Q-46 to P-366; Q-47 to P-366; K-48 to P-366; M-49 to P-366; A-50 to P-366; R-51 to P-366; E-52 to P-366; P-53 to P-366; A-54 to P-366; T-55 to P-366; L-56 to P-366; K-57 to P-366; D-58 to P-366; S-59 to P-366; L-60 to P-366; E-61 to P-366; Q-62 to P-366; D-63 to P-366; L-64 to P-366; N-65 to P-366; N-66 to P-366; M-67 to P-366; N-68 to P-366; K-69 to P-366; F-70 to P-366; L-71 to P-366; E-72 to P-366; K-73 to P-366; L-74 to P-366; R-75 to P-366; P-76 to P-366; L-77 to P-366; S-78 to P-366; G-79 to P-366; S-80 to P-366; E-81 to P-366; A-82 to P-366; P-83 to P-366; R-84 to P-366; L-85 to P-366; P-86 to P-366; Q-87 to P-366; D-88 to P-366; P-89 to P-366; V-90 to P-366; G-91 to P-366; M-92 to P-366; R-93 to P-366; R-94 to P-366; Q-95 to P-366; L-96 to P-366; Q-97 to P-366; E-98 to P-366; E-99 to P-366; L-100 to P-366; E-101 to P-366; E-102 to P-366; V-103 to P-366; K-104 to P-366; A-105 to P-366; R-106 to P-366; L-107 to P-366; Q-108 to P-366; P-109 to P-366; Y-110 to P-366; M-111 to P-366; A-112 to P-366; E-113 to P-366; A-114 to P-366; H-115 to P-366; E-116 to P-366; L-117 to P-366; V-118 to P-366; G-119 to P-366; W-120 to P-366; N-121 to P-366; L-122 to P-366; E-123 to P-366; G-124 to P-366; L-125 to P-366; R-126 to P-366; Q-127 to P-366; Q-128 to P-366; L-129 to P-366; K-130 to P-366; P-131 to P-366; Y-132 to P-366; T-133 to P-366; M-134 to P-366; D-135 to P-366; L-136 to P-366; M-137 to P-366; E-138 to P-366; Q-139 to P-366; V-140 to P-366; A-141 to P-366; L-142 to P-366; R-143 to P-366; V-144 to P-366; Q-145 to P-366; E-146 to P-366; L-147 to P-366; Q-148 to P-366; E-149 to P-366; Q-150 to P-366; L-151 to P-366; R-152 to P-366; V-153 to P-366; V-154 to P-366; G-155 to P-366; E-156 to P-366; D-157 to P-366; T-158 to P-366; K-159 to P-366; A-160 to P-366; Q-161 to P-366; L-162 to P-366; L-163 to P-366; G-164 to P-366; G-165 to P-366; V-166 to P-366; D-167 to P-366; E-168 to P-366; A-169 to P-366; W-170 to P-366; A-171 to P-366; L-172 to P-366; L-173 to P-366; Q-174 to P-366; G-175 to P-366; L-176 to P-366; Q-177 to P-366; S-178 to P-366; R-179 to P-366; V-180 to P-366; V-181 to P-366; H-182 to P-366; H-183 to P-366; T-184 to P-366; G-185 to P-366; R-186 to P-366; F-187 to P-366; K-188 to P-366; E-189 to P-366; L-190 to P-366; F-191 to P-366; H-192 to P-366; P-193 to P-366; Y-194 to P-366; A-195 to P-366; E-196 to P-366; S-197 to P-366; L-198 to P-366; V-199 to P-366; S-200 to P-366; G-201 to P-366; I-202 to P-366; G-203 to P-366; R-204 to P-366; H-205 to P-366; V-206 to P-366; Q-207 to P-366; E-208 to P-366; L-209 to P-366; H-210 to P-366; R-211 to P-366; S-212 to P-366; V-213 to P-366; A-214 to P-366; P-215 to P-366; H-216 to P-366; A-217 to P-366; P-218 to P-366; A-219 to P-366; S-220 to P-366; P-221 to P-366; A-222 to P-366; R-223 to P-366; L-224 to P-366; S-225 to P-366; R-226 to P-366; C-227 to P-366; V-228 to P-366; Q-229 to P-366; V-230 to P-366; L-231 to P-366; S-232 to P-366; R-233 to P-366; K-234 to P-366; L-235 to P-366; T-236 to P-366; L-237 to P-366; K-238 to P-366; A-239 to P-366; K-240 to P-366; A-241 to P-366; L-242 to P-366; H-243 to P-366; A-244 to P-366; R-245 to P-366; I-246 to P-366; Q-247 to P-366; Q-248 to P-366; N-249 to P-366; L-250 to P-366; D-251 to P-366; Q-252 to P-366; L-253 to P-366; R-254 to P-366; E-255 to P-366; E-256 to P-366; L-257 to P-366; I-258 to P-366; R-259 to P-366; A-260 to P-366; F-261 to P-366; A-262 to P-366; G-263 to P-366; T-264 to P-366; G-265 to P-366; T-266 to P-366; E-267 to P-366; E-268 to P-366; G-269 to P-366; A-270 to P-366; G-271 to P-366; P-272 to P-366; D-273 to P-366; P-274 to P-366; Q-275 to P-366; M-276 to P-366; L-277 to P-366; S-278 to P-366; E-279 to P-366; E-280 to P-366; V-281 to P-366; R-282 to P-366; Q-283 to P-366; R-284 to P-366; L-285 to P-366; Q-286 to P-366; A-287 to P-366; F-288 to P-366; R-289 to P-366; Q-290 to P-366; D-291 to P-366; T-292 to P-366; Y-293 to P-366; L-294 to P-366; Q-295 to P-366; I-296 to P-366; A-297 to P-366; A-298 to P-366; F-299 to P-366; T-300 to P-366; R-301 to P-366; A-302 to P-366; I-303 to P-366; D-304 to P-366; Q-305 to P-366; E-306 to P-366; T-307 to P-366; E-308 to P-366; E-309 to P-366; V-310 to P-366; Q-311 to P-366; Q-312 to P-366; Q-313 to P-366; L-314 to P-366; A-315 to P-366; P-316 to P-366; P-317 to P-366; P-318 to P-366; P-319 to P-366; G-320 to P-366; H-321 to P-366; S-322 to P-366; A-323 to P-366; F-324 to P-366; A-325 to P-366; P-326 to P-366; E-327 to P-366; F-328 to P-366; Q-329 to P-366; Q-330 to P-366; T-331 to P-366; D-332 to P-366; S-333 to P-366; G-334 to P-366; K-335 to P-366; V-336 to P-366; L-337 to P-366; S-338 to P-366; K-339 to P-366; L-340 to P-366; Q-341 to P-366; A-342 to P-366; R-343 to P-366; L-344 to P-366; D-345 to P-366; D-346 to P-366; L-347 to P-366; W-348 to P-366; E-349 to P-366; D-350 to P-366; I-351 to P-366; T-352 to P-366; H-353 to P-366; S-354 to P-366; L-355 to P-366; H-356 to P-366; D-357 to P-366; Q-358 to P-366; G-359 to P-366; H-360 to P-366; or S-361 to P-366; of SEQ ID NO: 212. Polypeptides encoded by these polynucleotides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that these bind polypeptides of the invention are also encompassed by the invention. Polynucleotides encoding these polypeptides are also encompassed by the invention.

Also as mentioned above, even if deletion of one or more amino acids from the C-terminus of a protein results in modification or loss of one or more biological functions of the protein, other functional activities (e.g., biological activities (e.g., ability to transport lipids, cholesterol transport, metabolize lipoprotein, etc.), ability to multimerize, and the ability to activate lecithin cholesterol actltransferase may still be retained. For example the ability of the shortened ApoA-IV-L mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an ApoA-IV-L mutein with a large number of deleted C-terminal amino acid residues may retain some biological or immunogenic activities. In fact, peptides composed of as few as six ApoA-IV-L amino acid residues may often evoke an immune response.

Preferred polypeptides of the invention comprise the following amino acid sequence:

```
MASMAAVLTWALALLSAFSATQARKGFWDYFSQTSGDKGRVEQIHQQKMA      (SEQ ID NO: 155)
REPATLKDSLEQDLNNMNKFLEKLRPLSGSEAPRLPQDPVGMRRQLQEELEE
VKARLQPYMAEAHELVGWNLEGLRQQLKPYTMDLMEQVALRVQELQEQLR
VVGEDTKAQLLGGVDEAWALLQGLQSRVVHHTGRFKELFHPYAESLVSGIG
RHVQELHRSVAPHAPASPARLSRCVQVLSRKLTLKAKALHARIQQNLDQLRE
ELIRAFAGTGTEEGAGPDPQMLSEEVRQRLQAFRQDTYLQIAAFTRAIDQETE
EVQQQLAPPPPGHSAFAPEFQQTDSGKVLSKLQARLDDLWEDITHSLHDQGH
SHLGDP.
```

Polynucleotides encoding these polypeptides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that these bind polypeptides of the invention are also encompassed by the invention. Polynucleotides encoding these polypeptides are also encompassed by the invention.

In another embodiment, the polypeptide sequence illustrated in Table I for this gene (SEQ ID NO:96) represents a potential alternative secreted form of the protein. Based upon the location of the start methionine of this polypeptide sequence with respect to the start methionine of the sequence shown in FIGS. 7A–B (SEQ ID NO: 212), it is unclear which start methionine the cell will utilize during expression. Thus, both SEQ ID NO: 212 and SEQ ID NO:96 are contemplated by the present invention.

Accordingly, the present invention further provides polypeptides having one or more residues deleted from the carboxy terminus of the amino acid sequence of the ApoA-IV-L polypeptide shown in FIGS. 7A–7B, up to the valine residue at position number 7, and polynucleotides encoding such polypeptides. In particular, the present invention provides polypeptides comprising the amino acid sequence of residues 1–m1 of FIGS. 7A–7B, where m1 is an integer from 7 to 336 corresponding to the position of the amino acid residue in FIGS. 7A–7B.

Moreover, the invention provides polynucleotides encoding polypeptides comprising, or alternatively consisting of, the amino acid sequence of C-terminal deletions of the ApoA-IV-L polypeptide of the invention shown as SEQ ID NO: 212 (FIGS. 7A–B) include polypeptides comprising, or alternatively consisting of the amino acid sequence of residues: M-1 to D-365; M-1 to G-364; M-1 to L-363; M-1 to H-362; M-1 to S-361; M-1 to H-360; M-1 to G-359; M-1 to Q-358; M-1 to D-357; M1 to H-356; M-1 to L-355; M-1 to S-354; M-1 to H-353; M-1 to T-352; M-1 to I-351; M-1 to D-350; M-1 to E-349; M-1 to W-348; M-1 to L-347; M-1 to D-346; M-1 to D-345; M-1 to L-344; M-1 to R-343; M-1 to A-342; M-1 to Q-341; M-1 to L-340; M-1 to K-339; M-1 to S-338; M-1 to L-337; M-1 to V-336; M-1 to K-335; M-1 to G-334; M-1 to S-333; M-1 to D-332; M-1 to T-331; M-1 to Q-330; M-1 to Q-329; M-1 to F-328; M-1 to E-327; M-1 to P-326; M-1 to A-325; M-1 to F-324; M-1 to A-323; M-1 to S-322; M-1 to H-321; M-1 to G-320; M-1 to P-319; M-1 to P-318; M-1 to P-317; M-1 to P-316; M-1 to A-315; M-1 to L-314; M-1 to Q-313; M-1 to Q-312; M-1 to Q-311; M-1 to V-310; M-1 to E-309; M-1 to E-308; M-1 to T-307; M-1 to E-306; M-1 to Q-305; M-1 to D-304; M-1 to I-303; M-1 to A-302; M-1 to R-301; M-1 to T-300; M-1 to F-299; M-1 to A-298; M-1 to A-297; M-1 to I-296; M-1 to Q-295; M-1 to L-294; M-1 to Y-293; M-1 to T-292; M-1 to D-291; M-1 to Q-290; M-1 to R-289; M-1 to F-288; M-1 to A-287; M-1 to Q-286; M-1 to L-285; M-1 to R-284; M-1 to Q-283; M-1 to R-282; M-1 to V-281; M-1 to E-280; M-1 to E-279; M-1 to S-278; M-1 to L-277; M-1 to M-276; M-1 to Q-275; M-1 to P-274; M-1 to D-273; M-1 to P-272; M-1 to G-271; M-1 to A-270; M-1 to G-269; M-1 to E-268; M-1 to E-267; M-1 to T-266; M-1 to G-265; M-1 to T-264; M-1 to G-263; M-1 to A-262; M-1 to F-261; M-1 to A-260; M-1 to R-259; M-1 to I-258; M-1 to L-257; M-1 to E-256; M-1 to E-255; M-1 to R-254; M-1 to L-253; M-1 to Q-252; M-1 to D-251; M-1 to L-250; M-1 to N-249; M-1 to Q-248; M-1 to Q-247; M-1 to I-246; M-1 to R-245; M-1 to A-244; M-1 to H-243; M-1 to L-242; M-1 to A-241; M-1 to K-240; M-1 to A-239; M-1 to K-238; M-1 to L-237; M-1 to T-236; M-1 to L-235; M-1 to K-234; M-1 to R-233; M-1 to S-232; M-1 to L-231; M-1 to V-230; M-1 to Q-229; M-1 to V-228; M-1 to C-227; M-1 to R-226; M-1 to S-225; M-1 to L-224; M-1 to R-223; M-1 to A-222; M-1 to P-221; M-1 to S-220; M-1 to A-219; M-1 to P-218; M-1 to A-217; M-1 to H-216; M-1 to P-215; M-1 to A-214; M-1 to V-213; M-1 to S-212; M-1 to R-211; M-1 to H-210; M-1 to L-209; M-1 to E-208; M-1 to Q-207; M-1 to V-206; M-1 to H-205; M-1 to R-204; M-1 to G-203; M-1 to I-202; M-1 to G-201; M-1 to S-200; M-1 to V-199; M-1 to L-198; M-1 to S-197; M-1 to E-196; M-1 to A-195; M-1 to Y-194; M-1 to P-193; M-1 to H-192; M-1 to F-191; M-1 to L-190; M-1 to E-189; M-1 to K-188; M-1 to F-187; M-1 to R-186; M-1 to G-185; M-1 to T-184; M-1 to H-183; M-1 to H-182; M-1 to V-181; M-1 to V-180; M-1 to R-179; M-1 to S-178; M-1 to Q-177; M-1 to L-176; M-1 to G-175; M-1 to Q-174; M-1 to L-173; M-1 to L-172; M-1 to A-171; M-1 to W-170; M-1 to A-169; M-1 to E-168; M-1 to D-167; M-1 to V-166; M-1 to G-165; M-1 to G-164; M-1 to L-163; M-1 to L-162; M-1 to Q-161; M-1 to A-160; M-1 to K-159; M-1 to T-158; M-1 to D-157; M-1 to E-156; M-1 to G-155; M-1 to V-154; M-1 to V-153; M-1 to R-152; M-1 to L-151; M-1 to Q-150; M-1 to E-149; M-1 to Q-148; M-1 to L-147; M-1 to E-146; M-1 to Q-145; M-1 to V-144; M-1 to R-143; M-1 to L-142; M-1 to A-141; M-1 to V-140; M-1 to Q-139; M-1 to E-138; M-1 to M-137; M-1 to L-136; M-1 to D-135; M-1 to M-134; M-1 to T-133; M-1 to Y-132; M-1 to P-131; M-1 to K-130; M-1 to L-129; M-1 to Q-128; M-1 to Q-127; M-1 to R-126; M-1 to L-125; M-1 to G-124; M-1 to E-123; M-1 to L-122; M-1 to N-121; M-1 to W-120; M-1 to G-119; M-1 to V-118; M-1 to L-117; M-1 to E-116; M-1 to H-115; M-1 to A-114; M-1 to E-113; M-1 to A-112; M-1 to M-111; M-1 to Y-110; M-1 to P-109; M-1 to Q-108; M-1 to L-107; M-1 to R-106; M-1 to A-105; M-1 to K-104; M-1 to V-103; M-1 to E-102; M-1 to E-101; M-1 to L-100; M-1 to E-99; M-1 to E-98; M-1 to Q-97; M-1 to L-96; M-1 to Q-95; M-1 to R-94; M-1 to R-93; M-1 to M-92; M-1 to G-91; M-1 to V-90; M-1 to P-89; M-1 to D-88; M-1 to Q-87; M-1 to P-86; M-1 to L-85; M-1 to R-84; M-1 to P-83; M-1 to A-82; M-1 to E-81; M-1 to S-80; M-1 to G-79; M-1 to S-78; M-1 to L-77; M-1 to P-76; M-1 to R-75; M-1 to L-74; M-1 to K-73; M-1 to E-72; M-1 to L-71; M-1 to F-70; M-1 to K-69; M-1 to N-68; M-1 to M-67; M-1 to N-66; M-1 to N-65; M-1 to L-64; M-1 to D-63; M-1 to Q-62; M-1 to E-61; M-1 to L-60; M-1 to S-59; M-1 to D-58; M-1 to K-57; M-1 to L-56; M-1 to T-55; M-1 to A-54; M-1 to P-53; M-1 to E-52; M-1 to R-51; M-1 to A-50; M-1 to M-49; M-1 to K-48; M-1 to Q-47; M-1 to Q-46; M-1 to H-45; M-1 to I-44; M-1 to Q-43; M-1 to E-42; M-1 to V-41; M-1 to R-40; M-1 to G-39; M-1 to K-38; M-1 to D-37; M-1 to G-36; M-1 to S-35; M-1 to T-34; M-1 to Q-33; M-1 to S-32; M-1 to F-31; M-1 to Y-30; M-1 to D-29; M-1 to W-28; M-1 to F-27; M-1 to G-26; M-1 to K-25; M-1 to R-24; M-1 to A-23; M-1 to Q-22; M-1 to T-21; M-1 to A-20; M-1 to S-19; M-1 to F-18; M-1 to A-17; M-1 to S-16; M-1 to L-15; M-1 to L-14; M-1 to A-13; M-1 to L-12; M-1 to A-11; M-1 to W-10; M-1 to T-9; M-1 to L-8; M-1 to V-7; and M-1 to A-6; of SEQ ID NO: 212. Polypeptides encoded by these polynucleotides are also encompassed by the invention.

Moreover, the invention provides polynucleotides encoding polypeptides comprising, or alternatively consisting of, the following amino acid sequences of C-terminal deletions of the mature ApoA-IV-L polypeptide of the invention shown as SEQ ID NO: 212 (FIGS. 7A–B): R-24 to D-365; R-24 to G-364; R-24 to L-363; R-24 to H-362; R-24 to S-361; R-24 to H-360; R-24 to G-359; R-24 to Q-358; R-24 to D-357; R-24 to H-356; R-24 to L-355; R-24 to S-354; R-24 to H-353; R-24 to T-352; R-24 to I-351; R-24 to D-350; R-24 to E-349; R-24 to W-348; R-24 to L-347; R-24 to D-346; R-24 to D-345; R-24 to L-344; R-24 to R-343; R-24 to A-342; R-24 to Q-341; R-24 to L-340; R-24 to K-339; R-24 to S-338; R-24 to L-337; R-24 to V-336; R-24 to K-335; R-24 to G-334; R-24 to S-333; R-24 to D-332; R-24 to T-331; R-24 to Q-330; R-24 to Q-329; R-24 to F-328; R-24 to E-327; R-24 to P-326; R-24 to A-325; R-24 to F-324; R-24 to A-323; R-24 to S-322; R-24 to H-321; R-24 to G-320; R-24 to P-319; R-24 to P-318; R-24 to P-317; R-24 to P-316; R-24 to A-315; R-24 to L-314; R-24 to Q-313; R-24 to Q-312; R-24 to Q-311; R-24 to V-310; R-24 to E-309; R-24 to E-308; R-24 to T-307; R-24 to E-306; R-24 to Q-305; R-24 to D-304; R-24 to I-303; R-24 to A-302; R-24 to R-301; R-24 to T-300; R-24 to F-299; R-24 to A-298; R-24 to A-297; R-24 to I-296; R-24 to Q-295; R-24 to L-294; R-24 to Y-293; R-24 to T-292; R-24 to D-291; R-24 to Q-290; R-24 to R-289; R-24 to F-288; R-24 to A-287; R-24 to Q-286; R-24 to L-285; R-24 to R-284; R-24 to Q-283; R-24 to R-282; R-24 to V-281; R-24 to E-280; R-24 to E-279; R-24 to S-278; R-24 to L-277; R-24 to M-276; R-24 to Q-275; R-24 to P-274; R-24 to D-273; R-24 to P-272; R-24 to G-271; R-24 to A-270; R-24 to G-269; R-24 to E-268; R-24 to E-267; R-24 to T-266; R-24 to G-265; R-24 to T-264; R-24 to G-263; R-24 to A-262; R-24 to F-261; R-24 to A-260; R-24 to R-259; R-24 to I-258; R-24 to L-257; R-24 to E-256; R-24 to E-255; R-24 to R-254; R-24 to L-253; R-24 to Q-252; R-24 to D-251; R-24 to L-250; R-24 to N-249; R-24 to Q-248; R-24 to Q-247; R-24 to I-246; R-24 to R-245; R-24 to A-244; R-24 to H-243; R-24 to L-242; R-24 to A-241; R-24 to K-240; R-24 to A-239; R-24 to K-238; R-24 to L-237; R-24 to T-236; R-24 to L-235; R-24 to K-234; R-24 to R-233; R-24 to S-232; R-24 to L-231; R-24 to V-230; R-24 to Q-229; R-24 to V-228; R-24 to C-227; R-24 to R-226; R-24 to S-225; R-24 to L-224; R-24 to R-223; R-24 to A-222; R-24 to P-221; R-24 to S-220; R-24 to A-219; R-24 to P-218; R-24 to A-217; R-24 to H-216; R-24 to P-215; R-24 to A-214; R-24 to V-213; R-24 to S-212; R-24 to R-211; R-24 to H-210; R-24 to L-209; R-24 to E-208; R-24 to Q-207; R-24 to V-206; R-24 to H-205; R-24 to R-204; R-24 to G-203; R-24 to I-202; R-24 to G-201; R-24 to S-200; R-24 to V-199; R-24 to L-198; R-24 to S-197; R-24 to E-196; R-24 to A-195; R-24 to Y-194; R-24 to P-193; R-24 to H-192; R-24 to F-191; R-24 to L-190; R-24 to E-189; R-24 to K-188; R-24 to F-187; R-24 to R-186; R-24 to G-185; R-24 to T-184; R-24 to H-183; R-24 to H-182; R-24 to V-181; R-24 to V-180; R-24 to R-179; R-24 to S-178; R-24 to Q-177; R-24 to L-176; R-24 to G-175; R-24 to Q-174; R-24 to L-173; R-24 to L-172; R-24 to A-171; R-24 to W-170; R-24 to A-169; R-24 to E-168; R-24 to D-167; R-24 to V-166; R-24 to G-165; R-24 to G-164; R-24 to L-163; R-24 to L-162; R-24 to Q-161; R-24 to A-160; R-24 to K-159; R-24 to T-158; R-24 to D-157; R-24 to E-156; R-24 to G-155; R-24 to V-154; R-24 to V-153; R-24 to R-152; R-24 to L-151; R-24 to Q-150; R-24 to E-149; R-24 to Q-148; R-24 to L-147; R-24 to E-146; R-24 to Q-145; R-24 to V-144; R-24 to R-143; R-24 to L-142; R-24 to A-141; R-24 to V-140; R-24 to Q-139; R-24 to E-138; R-24 to M-137; R-24 to L-136; R-24 to D-135; R-24 to M-134; R-24 to T-133; R-24 to Y-132; R-24 to P-131; R-24 to K-130; R-24 to L-129; R-24 to Q-128; R-24 to Q-127; R-24 to R-126; R-24 to L-125; R-24 to G-124; R-24 to E-123; R-24 to L-122; R-24 to N-121; R-24 to W-120; R-24 to G-119; R-24 to V-118; R-24 to L-117; R-24 to E-116; R-24 to H-115; R-24 to A-114; R-24 to E-113; R-24 to A-112; R-24 to M-111; R-24 to Y-110; R-24 to P-109; R-24 to Q-108; R-24 to L-107; R-24 to R-106; R-24 to A-105; R-24 to K-104; R-24 to V-103; R-24 to E-102; R-24 to E-101; R-24 to L-100; R-24 to E-99; R-24 to E-98; R-24 to Q-97; R-24 to L-96; R-24 to Q-95; R-24 to R-94; R-24 to R-93; R-24 to M-92; R-24 to G-91; R-24 to V-90; R-24 to P-89; R-24 to D-88; R-24 to Q-87; R-24 to P-86; R-24 to L-85; R-24 to R-84; R-24 to P-83; R-24 to A-82; R-24 to E-81; R-24 to S-80; R-24 to G-79; R-24 to S-78; R-24 to L-77; R-24 to P-76; R-24 to R-75; R-24 to L-74; R-24 to K-73; R-24 to E-72; R-24 to L-71; R-24 to F-70; R-24 to K-69; R-24 to N-68; R-24 to M-67; R-24 to N-66; R-24 to N-65; R-24 to L-64; R-24 to D-63; R-24 to Q-62; R-24 to E-61; R-24 to L-60; R-24 to S-59; R-24 to D-58; R-24 to K-57; R-24 to L-56; R-24 to T-55; R-24 to A-54; R-24 to P-53; R-24 to E-52; R-24 to R-51; R-24 A-50; R-24 to M-49; R-24 to K-48; R-24 to Q-47; R-24 to Q-46; R-24 to H-45; R-24 to I-44; R-24 to Q-43; R-24 to E-42; R-24 to V-41; R-24 to R-40; R-24 to G-39; R-24 to K-38; R-24 to D-37; R-24 to G-36; R-24 to S-35; R-24 to T-34; R-24 to Q-33; R-24 to S-32; R-24 to F-31; R-24 to Y-30; of SEQ ID NO: 212. Polypeptides encoded by these polynucleotides are also encompassed by the invention. Moreover, fragments and variants of these polypeptides (such as, for example, fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement there of are encompassed by the invention. Antibodies that bind polypeptides of the invention are also encompassed by the invention. Polynucleotides encoding these polypeptides are also encompassed by the invention.

In addition, the invention provides nucleic acid molecules having nucleotide sequences related to extensive portions of SEQ ID NO:19 which have been determined from the following related cDNA genes: HLDOE40R (SEQ ID NO:209), HLDOU12R (SEQ ID NO:210), and HLDBC83RA (SEQ ID NO:211).

Based on the sequence similarity to apolipoprotein A-IV of Sus scrofa, the human apolipoprotein A-IV, and the mouse apolipoprotein A-IV, translation product of this gene is expected to share at least some biological activities with apolipoproteins, and specifically apolipoprotein A-IV proteins. Such activities are known in the art, some of which are described elsewhere herein.

Specifically, polynucleotides and polypeptides of the invention are useful for the treatment, detection, and/or prevention of lipid transport & lipoprotein metabolism disorders. Polynucleotides and polypeptides are proposed to be associated with triglyceride-rich lipoproteins & HDL and may play a role in reverse cholesterol transport (cholesterol transport from tissues back to the liver for elimination). Thus, polynucleotides and polypeptides of the invention are useful for treating, detecting, and/or preventing hypercholesterolemia and related disorders. Polynucleotides and polypeptides of the invention are useful for activating lecithin cholesterol acyltransferase and the promotion of cholesterol efflux from cholesterol-preloaded cells. Polymorphisms in apoA-IV are associated with variability in low density lipoprotein (LDL)-cholesterol response to dietary therapy. Moreover, the levels of such polymorphisms (of the 32 currently known to exist in plasma) also appear to correlate with increased incidence and risk for coronary heart disease. Thus, polynucleotides and polypeptides of the invention are useful for the treatment, detection, and/or prevention of cardiovascular diseases and/or disorders, particularly in the protection against atherogenesis in mice. Polynucleotides and polypeptides of the invention are useful as a satiating factor for controlling appetite and long-term regulation of food intake and body weight (chronic ingestion of a high fat diet blunts apoA-IV response to lipid feeding and may explain why chronic ingestion of a high fat diet predisposes animals and human to obesity).

Polynucleotides and polypeptides of the invention is involved in bile metabolism and is useful in the treatment, detection, and/or prevention of metabolism diseases and/or disorders, particularly for lipid metabolism and lipid emulsification. As inferred above, expression levels and/or polymorphisms in apoA-IV-L may represent diagnostic markers for such conditions as variability in low density lipoprotein (LDL)-cholesterol response to dietary therapy or bile disorders.

Polynucleotides and polypeptides of the invention may represent a diagnostic marker for atherogenesis, atherosclerosis, aberrant cholesterol/LDL/HDL plasma level regulation, obesity, hepatoma, liver diseases and/or disorders, metabolic diseases and/or disorders, obesity, and cardiovascular disease, in general. The full-length protein should be a secreted protein, based upon homology to the apolipoprotein family. Therefore, it is secreted into serum, urine, or feces and thus the levels is assayable from patient samples. Assuming specific expression levels are reflective of the presence of metabolic dysfunction (e.g., aberrant cholesterol/LDL/HDL levels, bile synthesis dysfunction, lipoprotein metabolism dysfunction, etc.), this would provide a convenient diagnostic for early detection. In addition, expression of this gene product may also be linked to the progression of metabolic disease, and therefore may itself actually represent a therapeutic or therapeutic target for the treatment of cancer.

Therefore, based upon the tissue distribution of this protein in liver, hepatoma, and pancreatic cells and tissues, in combination with its homology to apolipoproteins, indicates that this protein represents a novel, central player in lipid transport and metabolism. Therefore, antagonists directed against this protein is useful in blocking the activity of this protein. Accordingly, preferred are antibodies which specifically bind a portion of the translation product of this gene.

Also provided is a kit for detecting tumors in which expression of this protein occurs. Such a kit comprises in one embodiment an antibody specific for the translation product of this gene bound to a solid support. Also provided is a method of detecting these tumors in an individual which comprises a step of contacting an antibody specific for the translation product of this gene to a bodily fluid from the individual, preferably serum, lymph, urine, seminal fluid, or feces and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein.

Polynucleotides and polypeptides of the invention may play an important role in the pathogenesis of human cancers and cellular transformation, particularly those of the gastrointestinal, endocrine, and metabolic systems, and specifically of hepatoma and pancreatic cancers. Polynucleotides and polypeptides of the invention may also be involved in the pathogenesis of developmental abnormalities based upon its potential effects on proliferation and differentiation of cells and tissue cell types. Due to the potential proliferating and differentiating activity of said polynucleotides and polypeptides, the invention is useful as a therapeutic agent in inducing tissue regeneration, for treating inflammatory conditions (e.g., inflammatory bowel syndrome, diverticulitis, etc.). Moreover, the invention is useful in modulating the immune response to aberrant polypeptides, as may exist in rapidly proliferating cells and tissue cell types, particularly in hepatoma cells, tissues, and other cancers.

The tissue distribution in hepatoma. Liver, and pancreatic cancer indicates polynucleotides and polypeptides corresponding to this gene are useful for the diagnosis and treatment of a variety of metabolic and liver disorders. Representative uses are described in the "Hyperproliferative Disorders", "infectious disease", and "Binding Activity" sections below, in Example 11, and 27, and elsewhere herein. Briefly, the protein can be used for the detection, treatment, and/or prevention of hepatoblastoma, jaundice, hepatitis, liver metabolic diseases and conditions that are attributable to the differentiation of hepatocyte progenitor cells.

Alternatively, the expression within cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation.

Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA).

Alternatively, this gene product is involved in the pattern of cellular proliferation that accompanies early embryogenesis. Thus, aberrant expression of this gene product in tissues—particularly adult tissues—may correlate with patterns of abnormal cellular proliferation, such as found in various cancers. In addition, other lipocalin family members, specifically cpl1, have been associated with playing a key role in early embryonic development. Through homology, it is expected that polypeptides and polynucleotides of the present invention may also play similar roles. Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions.

Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Preferred polypeptides of the present invention comprise, or alternatively consist of, one or more immunogenic epitopes immunogenic epitopes shown in SEQ ID NO: 111 as residues: Gln-19 to Trp-25, Tyr-27 to Arg-37, His-42 to Glu-49, Asp-55 to Asn-65, Glu-78 to Gln-84, Arg-91 to Glu-98, Glu-120 to Tyr-129, Gln-244 to Arg-251, Glu-265 to Gln-272, Ile-300 to Pro-313, Glu-324 to Gly-331. Polynucleotides encoding said polypeptides are also encompassed by the invention.

Many polynucleotide sequences, such as EST sequences, are publicly available and accessible through sequence databases. Some of these sequences are related to SEQ ID NO:40 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1379 of SEQ ID NO:40, b is an integer of 15 to 1393, where both a and b correspond to the positions of nucleotide residues shown in SEQ ID NO:40, and where b is greater than or equal to a+14.

Features of Protein Encoded by Gene No: 31

In specific embodiments, polypeptides of the invention comprise, or alternatively consists of, the following amino acid sequence:

MEFGLTWVFLVALLRGVHCQVQLVESGGAVVQPGGSLRLSCAASGFTFSRY (SEQ ID NO: 216)

GMHWVRQAPGKGLQWLALVLHDGGQKYNEDVVKGRFTISRDNSNNKVYL

-continued

QMDSLRGEDTATYYCVRGMWEQLPSYYFDYWGQGTLVTVSSASPTSPKVFP

LSLCSTQPDGNVVIACLVQGFFPQEPSLVTWSESGQGVTARNFPPSQDASGDL

YTTSSQLTLPATQCLAGKSVTCHVKHYTNPSQDVTVPCPVPSTPPTPSPSTPPT

PSPSCCHPRLSLHRPALEDLLLGSEANLTCTLTGLRDASGATFTWTPSSGKSAV

QGPPERDLCGCYSVSSVLPGCAPQWNHGETFTCTAAYPELKTPLTANITKSGN

TFRPEVHLLPPPSEELALNELVTLTCLARGFSPKDVLVRWLQGSQELPREKYL

TWASRQEPSQGTTTFAVTSILRVAAEDWKKGDTSCMVGHEALPLAFTQKTI

DRLAGKPTHVNVSVVMAEVDGTCY.

Moreover, fragments and variants of this polypeptide (such as, for example, fragments as described herein, polypeptides at least 80%, 85%, 90%, 95%, 96%, 97%, 98%, or 99% identical to these polypeptides and polypeptides encoded by the polynucleotide which hybridize, under stringent conditions, to the polynucleotide encoding this polypeptide are encompassed by the invention. Antibodies that bind polypeptides of the invention are also encompassed by the invention. Polynucleotides encoding this polypeptide are also encompassed by the invention.

The gene encoding the disclosed cDNA is believed to reside on chromosome 14. Accordingly, polynucleotides related to this invention are useful as a marker in linkage analysis for chromosome 14.

It has been discovered that this gene is expressed in normal colon, colon cancer, and ulcerative colitis. This gene is also expressed in normal breast tissue, breast lymph node, breast cancer, bone marrow, thymus, and tonsils.

Polynucleotides and polypeptides of the invention are useful as reagents for differential identification of the tissue(s) or cell type(s) present in a biological sample and for diagnosis of the following diseases and conditions: gastrointestinal, hematopoietic, immunological, and proliferative diseases and/or disorders, particularly colon cancer, and other cancers. Similarly, polypeptides and antibodies directed to those polypeptides are useful to provide immunological probes for differential identification of the tissue(s) or cell type(s). For a number of disorders of the above tissues or cells, particularly of the gastrointestinal, hematopoietic, and immune systems, expression of this gene at significantly higher or lower levels may be detected in certain tissues or cell types (e.g., bone marrow, gastrointestinal, digestive, immune, breast, cancerous and wounded tissues) or bodily fluids (e.g., lymph, bile, chyme, serum, plasma, urine, synovial fluid or spinal fluid) taken from an individual having such a disorder, relative to the standard gene expression level, i.e., the expression level in healthy tissue from an individual not having the disorder.

Preferred polypeptides of the present invention comprise, or alternatively consist of, one or more immunogenic epitopes immunogenic epitopes shown in SEQ ID NO: 112 as residues: Asp-73 to Asn-79, Ser-90 to Lys-97, Leu-105 to Ala-111, Tyr-127 to Gln-133, Ser-143 to Lys-148, Ser-156 to Gly-161, Arg-192 to Gly-202, Leu-204 to Ser-209, Lys-229 to Asp-237, Pro-248 to Cys-264, Val-312 to Asp-319, Pro-336 to Thr-342, Lys-362 to Pro-369, Gly-408 to Tyr-417, Ser-422 to Thr-430, Asp-445 to Thr-451. Polynucleotides encoding said polypeptides are also encompassed by the invention.

The tissue distribution in ulcerative colitis and colon cancer tissues indicates that polynucleotides and polypeptides of the invention, as well as antibodies directed to polypeptides of the invention, are useful in the treatment, detection, and/or prevention of gastrointestinal disorders, including inflammatory bowel disorders and proliferative diseases, particularly colon cancer. Furthermore, the expression of this gene in bone marrow, thymus, lymph node, and tonsil tissues suggests that polynucleotides and polypeptides of the invention, as well as antibodies directed to polypeptides of the invention, are useful in the detection, treatment, and/or prevention of hematopoietic and immunological disorders. Moreover, the expression within cellular sources marked by proliferating cells indicates this protein may play a role in the regulation of cellular division, and may show utility in the diagnosis, treatment, and/or prevention of developmental diseases and disorders, including cancer, and other proliferative conditions, including colon and breast cancers. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Alternatively, this gene product may be involved in the pattern of cellular proliferation that accompanies early embryogenesis. Thus, aberrant expression of this gene product in tissues—particularly adult tissues—may correlate with patterns of abnormal cellular proliferation, such as found in various cancers. Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and would be useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Based upon the tissue distribution of this protein, antagonists directed against this protein may be useful in blocking the activity of this protein. Accordingly, preferred are antibodies which specifically bind a portion of the translation product of this gene. Also provided is a kit for detecting tumors in which expression of this protein occurs. Such a kit comprises in one embodiment an antibody specific for the translation product of this gene bound to a solid support. Also provided is a method of detecting these tumors in an individual which comprises a step of contacting an antibody specific for the translation product of this gene to a bodily fluid from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:41 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1637 of SEQ ID NO:41, b is an integer of 15 to 1651, where both a and b correspond to the positions of nucleotide residues shown in SEQ ID NO:41, and where b is greater than or equal to a+14.

Features of Protein Encoded by Gene No: 32

The translation product of this gene shares sequence homology with complement subcomponent C1q chain C precursor (see Genbank accession S14351), which is thought to be important in immune responses.

It has been discovered that this gene is expressed primarily in immune and hemopoietic cells and to a lesser extent in various cancer cells.

Polynucleotides and polypeptides of the invention are useful as reagents for differential identification of the tissue(s) or cell type(s) present in a biological sample and for diagnosis of the following diseases and conditions: disorders of the immune and hemopoietic systems and cancer. Similarly, polypeptides and antibodies directed to those polypeptides are useful to provide immunological probes for differential identification of the tissue(s) or cell type(s). For a number of disorders of the above tissues or cells, particularly of the immune and hemopoietic systems, expression of this gene at significantly higher or lower levels may be detected in certain tissues (e.g., cancerous and wounded tissues) or bodily fluids (e.g., serum, plasma, urine, synovial fluid or spinal fluid) taken from an individual having such a disorder, relative to the standard gene expression level, i.e., the expression level in healthy tissue from an individual not having the disorder.

Preferred polypeptides of the present invention comprise, or alternatively consist of, one or more immunogenic epitopes immunogenic epitopes shown in SEQ ID NO: 113 as residues: Arg-25 to Gly-31, Pro-45 to Gly-52. Polynucleotides encoding said polypeptides are also encompassed by the invention.

The tissue distribution and homology to complement subcomponent C1q chain C precursor suggests that the protein product of this clone would be useful for treatment and diagnosis of diseases of the immune and hemopoietic systems and cancers. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lens tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Based upon the tissue distribution of this protein, antagonists directed against this protein may be useful in blocking the activity of this protein. Accordingly, preferred are antibodies which specifically bind a portion of the translation product of this gene. Also provided is a kit for detecting tumors in which expression of this protein occurs. Such a kit comprises in one embodiment an antibody specific for the translation product of this gene bound to a solid support. Also provided is a method of detecting these tumors in an individual which comprises a step of contacting an antibody specific for the translation product of this gene to a bodily fluid from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker Many polynucleotide sequences, such as EST sequences, are publicly available and accessible through sequence databases. Some of these sequences are related to SEQ ID NO:42 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1094 of SEQ ID NO:42, b is an integer of 15 to 1108, where both a and b correspond to the positions of nucleotide residues shown in SEQ ID NO:42, and where b is greater than or equal to a+14.

TABLE 1

| Gene No. | cDNA Clone ID | ATCC Deposit No:Z and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 1 | HSSDM23 | PTA-736 09/21/99 | Uni-ZAP XR | 11 | 2329 | 1 | 2329 | 147 | 147 | 82 | 1 | 27 | 28 | 613 |
| 1 | H55DM23 | PTA-736 09/21/99 | Uni-ZAP XR | 43 | 2286 | 1 | 2286 | 147 | 147 | 114 | 1 | 30 | 31 | 287 |
| 2 | HOFNX30 | PTA-736 09/21/99 | pCMVSport 2.0 | 12 | 2330 | 1 | 2330 | 247 | 247 | 83 | 1 | 18 | 19 | 453 |
| 3 | HLQFB12 | PTA-736 09/21/99 | Lambda ZAP II | 13 | 651 | 1 | 651 | 52 | 52 | 84 | 1 | 20 | 21 | 152 |
| 4 | HDPUM13 | PTA-736 09/21/99 | pCMVSport 3.0 | 14 | 997 | 1 | 997 | 16 | 16 | 85 | 1 | 22 | 23 | 245 |
| 4 | HPLAT62 | PTA-736 09/21/99 | Uni-ZAP XR | 44 | 1138 | 119 | 1075 | 128 | 128 | 115 | 1 | 24 | 25 | 245 |
| 4 | HE6DI14 | PTA-736 09/21/99 | Uni-ZAP XR | 45 | 1071 | 27 | 1071 | 50 | 50 | 116 | 1 | 24 | 25 | 245 |
| 4 | HACBG19 | PTA-2071 06/09/99 | Uni-ZAP XR | 46 | 1050 | 101 | 1002 | 107 | 107 | 117 | 1 | 22 | 23 | 229 |
| 4 | HACBG19 | PTA-2071 06/09/99 | Uni-ZAP XR | 47 | 1149 | 155 | 1149 | 128 | 128 | 118 | 1 | 22 | 23 | 245 |
| 4 | HAPQT56 | PTA-909 11/02/99 | Uni-ZAP XR | 48 | 1086 | 45 | 1012 | 64 | 64 | 119 | 1 | 22 | 23 | 245 |
| 4 | HLYAN43 | 209226 08/28/97 | pSport1 | 49 | 971 | 26 | 946 | 135 | 135 | 120 | 1 | 23 | 24 | 32 |
| 5 | HTLGV19 | PTA-736 09/21/99 | Uni-ZAP XR | 15 | 1266 | 1 | 1266 | 79 | 79 | 86 | 1 | 17 | 18 | 396 |
| 6 | HTTCT46 | PTA-736 09/21/99 | Uni-ZAP XR | 16 | 2710 | 93 | 2694 | 133 | 133 | 87 | 1 | 24 | 25 | 298 |
| 6 | HSDEE58 | PTA-909 11/02/99 | Uni-ZAP XR | 50 | 2752 | 97 | 1707 | 175 | 175 | 121 | 1 | 24 | 25 | 298 |
| 7 | HOFNF53 | PTA-736 09/21/99 | pCMVSport 2.0 | 17 | 2405 | 1 | 2405 | 76 | 76 | 88 | 1 | 27 | 28 | 263 |
| 7 | HOFNF53 | PTA-736 09/21/99 | pCMVSport 2.0 | 51 | 2389 | 1 | 2389 | 72 | 72 | 122 | 1 | 27 | 28 | 55 |
| 8 | HOHCA60 | PTA-627 09/07/99 | pCMVSport 2.0 | 18 | 5720 | 1 | 5720 | 67 | 67 | 89 | 1 | 28 | 29 | 1745 |
| 8 | HOHCA60 | PTA-627 09/07/99 | pCMVSport 2.0 | 52 | 2254 | 1177 | 2254 | 1021 | 123 | 1 | | | | 19 |
| 8 | HOHCA60 | PTA-627 09/07/99 | pCMVSport 2.0 | 53 | 3559 | 1 | 3559 | | 1873 | 124 | 1 | 27 | 28 | 514 |
| 8 | HOHCA60 | PTA-627 09/07/99 | pCMVSport 2.0 | 54 | 852 | 1 | 852 | 65 | 65 | 125 | 1 | 28 | 29 | 262 |
| 8 | HOHCA60 | PTA-627 09/07/99 | pCMVSport 2.0 | 55 | 609 | 45 | 609 | | 109 | 126 | 1 | 1 | 2 | 115 |
| 9 | HLQFT18 | PTA-736 09/21/99 | Lambda ZAP II | 19 | 705 | 1 | 705 | 16 | 16 | 90 | 1 | 20 | 21 | 142 |
| 10 | HBXFT65 | PTA-736 09/21/99 | ZAP Express | 20 | 2108 | 1 | 2085 | 130 | 130 | 91 | 1 | 16 | 17 | 350 |
| 10 | HMSEO15 | PTA-736 09/21/99 | Uni-ZAP XR | 56 | 2099 | 111 | 2027 | 114 | 114 | 127 | 1 | 17 | 18 | 350 |
| 11 | HWHGK36 | PTA-736 09/21/99 | pCMVSport 3.0 | 21 | 675 | 1 | 675 | 12 | 12 | 92 | 1 | 24 | 25 | 102 |
| 12 | HAGDA35 | PTA-736 09/21/99 | Uni-ZAP XR | 22 | 1581 | 945 | 1581 | 53 | 53 | 93 | 1 | 37 | 38 | 509 |
| 12 | HAGDA35 | PTA-736 09/21/99 | Uni-ZAP XR | 57 | 1688 | 316 | 1688 | 366 | 366 | 128 | 1 | 28 | 29 | 339 |
| 12 | HAGDA35 | PTA-736 09/21/99 | Uni-ZAP XR | 58 | 1354 | 1 | 1354 | 39 | 39 | 129 | 1 | 28 | 29 | 339 |
| 13 | HRODQ04 | PTA-736 09/21/99 | Uni-ZAP XR | 23 | 922 | 1 | 922 | 193 | 193 | 94 | 1 | 26 | 27 | 146 |
| 14 | HDPOL27 | PTA-736 09/21/99 | pCMVSport 3.0 | 24 | 2288 | 484 | 2271 | 115 | 115 | 95 | 1 | 30 | 31 | 626 |
| 14 | HDPOL27 | PTA-736 09/21/99 | pCMVSport 3.0 | 59 | 1821 | 1 | 1821 | 137 | 137 | 130 | 1 | 29 | 30 | 472 |
| 14 | HEBCV31 | 209194 08/01/97 | Uni-ZAP XR | 60 | 803 | 1 | 803 | 149 | 149 | 131 | 1 | | | 42 |
| 15 | HWLHZ79 | PTA-736 09/21/99 | pSport1 | 25 | 908 | 1 | 871 | 85 | 85 | 96 | 1 | 24 | 25 | 81 |
| 16 | HKGDP17 | PTA-736 09/21/99 | pSport1 | 26 | 2090 | 1 | 2090 | 348 | 348 | 97 | 1 | 14 | 15 | 86 |
| 17 | HSVBD67 | PTA-736 09/21/99 | Uni-ZAP XR | 27 | 2355 | 1588 | 2341 | 183 | 183 | 98 | 1 | 27 | 28 | 613 |
| 17 | HSVBD67 | PTA-736 09/21/99 | Uni-ZAP XR | 61 | 1499 | 1 | 1499 | 100 | 100 | 132 | 1 | 37 | 38 | 122 |

TABLE 1-continued

| Gene No. | cDNA Clone ID | ATCC Deposit No:Z and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 18 | HTGAT51 | PTA-736 09/21/99 | Uni-ZAP XR | 28 | 1680 | 1 | 1680 | 149 | 149 | 99 | 1 | 17 | 18 | 60 |
| 19 | HFCEQ37 | PTA-736 09/21/99 | Uni-ZAP XR | 29 | 1618 | 1 | 1577 | 78 | 78 | 100 | 1 | 18 | 19 | 167 |
| 20 | HSKNP59 | PTA-736 09/21/99 | pBluescript | 30 | 973 | 1 | 973 | 218 | 218 | 101 | 1 | 21 | 22 | 183 |
| 20 | HSKNP59 | PTA-736 09/21/99 | pBluescript | 62 | 974 | 1 | 974 | 218 | 218 | 133 | 1 | 21 | 22 | 252 |
| 21 | HWMBB68 | PTA-736 09/21/99 | pSport1 | 31 | 1189 | 318 | 1189 | 50 | 50 | 102 | 1 | 30 | 31 | 239 |
| 21 | HWMBB68 | PTA-736 09/21/99 | pSport1 | 63 | 872 | 1 | 871 | 64 | 64 | 134 | 1 | 18 | 19 | 132 |
| 21 | HDTGF15 | 203570 01/11/99 | pCMVSport 2.0 | 64 | 1208 | 27 | 1165 | 275 | 275 | 135 | 1 | 40 | 41 | 156 |
| 21 | HLWAD77 | 209651 03/04/98 | pCMVSport 3.0 | 65 | 1167 | 304 | 1167 | 326 | 326 | 136 | 1 | 24 | 25 | 140 |
| 22 | HWABL61 | PTA-736 09/21/99 | pCMVSport 3.0 | 32 | 1912 | 1 | 1912 | 218 | 218 | 103 | 1 | 39 | 40 | 89 |
| 23 | HWDAQ83 | PTA-736 09/21/99 | pCMVSport 3.0 | 33 | 2394 | 1 | 2394 | 308 | 308 | 104 | 1 | 28 | 29 | 50 |
| 23 | HWDAQ83 | PTA-736 09/21/99 | pCMVSport 3.0 | 66 | 2311 | 1 | 2311 | 308 | 308 | 137 | 1 | 31 | 32 | 50 |
| 24 | HFXLF67 | PTA-736 09/21/99 | Lambda ZAP II | 34 | 2118 | 1 | 2118 | 34 | 34 | 105 | 1 | 19 | 20 | 49 |
| 25 | HTPHH74 | PTA-736 09/21/99 | Uni-ZAP XR | 35 | 6065 | 2257 | 3272 | 162 | 162 | 106 | 1 | 30 | 31 | 868 |
| 25 | HTPHH74 | PTA-736 09/21/99 | Uni-ZAP XR | 67 | 1049 | 1 | 1016 | | 1 | 138 | 1 | 1 | 2 | 172 |
| 25 | HTFOB75 | PTA-1838 05/09/00 | pSport1 | 68 | 3299 | 1996 | 3274 | 2365 | 2365 | 139 | 1 | 46 | 47 | 142 |
| 26 | HWABW88 | PTA-736 09/21/99 | pCMVSport 3.0 | 36 | 1365 | 1 | 1365 | 142 | 142 | 107 | 1 | 28 | 29 | 56 |
| 27 | HWNFG66 | PTA-797 09/27/99 | pSport1 | 37 | 570 | 1 | 570 | 42 | 42 | 108 | 1 | 1 | 2 | 110 |
| 28 | HDPQG01 | PTA-736 09/21/99 | pCMVSport 3.0 | 38 | 3229 | 1 | 3229 | 84 | 84 | 109 | 1 | 31 | 32 | 334 |
| 28 | HDPQG01 | PTA-736 09/21/99 | pCMVSport 3.0 | 69 | 1772 | 1 | 1772 | 94 | 94 | 140 | 1 | 31 | 32 | 193 |
| 28 | HJPAD80 | PTA-840 10/13/99 | Uni-ZAP XR | 70 | 1121 | 1 | 1121 | 247 | 247 | 141 | 1 | 1 | 2 | 134 |
| 28 | HTXJM94 | PTA-181 06/07/99 | Uni-ZAP XR | 71 | 938 | 1 | 938 | 44 | 44 | 142 | 1 | 46 | 47 | 73 |
| 29 | HE21O57 | PTA-736 09/21/99 | Uni-ZAP XR | 39 | 511 | 1 | 511 | 146 | 146 | 110 | 1 | 25 | 26 | 75 |
| 30 | HLDRR08 | PTA-796 09/27/99 | pCMVSport 3.0 | 40 | 1393 | 1 | 1393 | 73 | 73 | 111 | 1 | 20 | 21 | 363 |
| 31 | HTOJV86 | PTA-736 09/21/99 | Uni-ZAP XR | 41 | 1651 | 1 | 1651 | 60 | 60 | 112 | 1 | 19 | 20 | 530 |
| 31 | HHBGE77 | PTA-736 09/21/99 | pCMVSport 1 | 72 | 943 | 1 | 943 | 34 | 34 | 143 | 1 | 1 | 2 | 144 |
| 31 | HCEFZ82 | PTA-792 09/27/99 | Uni-ZAP XR | 73 | 1810 | 45 | 1780 | 215 | 215 | 144 | 1 | 18 | 19 | 189 |
| 31 | HSIED48 | PTA-987 11/24/99 | Uni-ZAP XR | 74 | 1543 | 1 | 1543 | 18 | 18 | 145 | 1 | 19 | 20 | 487 |
| 31 | HADFW77 | 203980 04/29/99 | pSport1 | 75 | 1806 | 935 | 1806 | 437 | 437 | 146 | 1 | 1 | 2 | 294 |
| 31 | HNGFW58 | 203517 12/10/98 | Uni-ZAP XR | 76 | 1547 | 1 | 1547 | 279 | 279 | 147 | 1 | 28 | 29 | 99 |
| 31 | HCEFZ82 | 203917 04/08/99 | Uni-ZAP XR | 77 | 1811 | 44 | 1781 | 215 | 215 | 148 | 1 | 18 | 19 | 265 |
| 32 | HLYAV34 | PTA-736 09/21/99 | pSport1 | 42 | 1108 | 20 | 1108 | 117 | 117 | 113 | 1 | 32 | 33 | 207 |
| 32 | HLYAV34 | PTA-736 09/21/99 | pSport1 | 78 | 1141 | 24 | 1141 | 105 | 105 | 149 | 1 | 32 | 33 | 206 |
| 32 | HTOCG60 | 209368 10/16/97 | Uni-ZAP XR | 79 | 990 | 1 | 936 | 8 | 8 | 150 | 1 | 20 | 21 | 234 |
| 32 | HDPWX42 | 203364 10/19/98 | pCMVSport 3.0 | 80 | 1297 | 104 | 1237 | 184 | 184 | 151 | 1 | 28 | 29 | 208 |
| 32 | HCNSM85 | 209300 09/25/97 | pBluescript | 81 | 941 | 1 | 941 | 16 | 16 | 152 | 1 | 22 | 23 | 235 |

Table 1 summarizes the information corresponding to each "Gene No." described above. The nucleotide sequence identified as "NT SEQ ID NO:X" was assembled from partially homologous ("overlapping") sequences obtained from the "cDNA clone ID" identified in Table 1 and, in some cases, from additional related DNA clones. The overlapping sequences were assembled into a single contiguous sequence of high redundancy (usually three to five overlapping sequences at each nucleotide position), resulting in a final sequence identified as SEQ ID NO:X.

The cDNA Clone ID was deposited on the date and given the corresponding deposit number listed in "ATCC® Deposit No:Z and Date." Some of the deposits contain multiple different clones corresponding to the same gene. "Vector" refers to the type of vector contained in the cDNA Clone ID.

"Total NT Seq." refers to the total number of nucleotides in the contig identified by "Gene No." The deposited clone may contain all or most of these sequences, reflected by the nucleotide position indicated as "5' NT of Clone Seq." and the "3' NT of Clone Seq." of SEQ ID NO:X. The nucleotide position of SEQ ID NO:X of the putative start codon (methionine) is identified as "5' NT of Start Codon." Similarly, the nucleotide position of SEQ ID NO:X of the predicted signal sequence is identified as "5' NT of First AA of Signal Pep."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The first and last amino acid position of SEQ ID NO:Y of the predicted signal peptide is identified as "First AA of Sig Pep" and "Last AA of Sig Pep." The predicted first amino acid position of SEQ ID NO:Y of the secreted portion is identified as "Predicted First AA of Secreted Portion." Finally, the amino acid position of SEQ ID NO:Y of the last amino acid in the open reading frame is identified as "Last AA of ORF."

SEQ ID NO:X (where X may be any of the polynucleotide sequences disclosed in the sequence listing) and the translated SEQ ID NO:Y (where Y may be any of the polypeptide sequences disclosed in the sequence listing) are sufficiently accurate and otherwise suitable for a variety of uses well known in the art and described further below. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used, for example, to generate antibodies which bind specifically to proteins containing the polypeptides and the secreted proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a human cDNA of the invention deposited with the ATCC®, as set forth in Table 1. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited human cDNA, collecting the protein, and determining its sequence.

The present invention also relates to the genes corresponding to SEQ ID NO:X, SEQ ID NO:Y, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to SEQ ID NO:X, SEQ ID NO:Y, or a deposited clone, using information from the sequences disclosed herein or the clones deposited with the ATCC®. For example, allelic variants and/or species homologs may be isolated and identified by making suitable probes or primers from the sequences provided herein and screening a suitable nucleic acid source for allelic variants and/or the desired homologue.

Table 2 summarizes the expression profile of polynucleotides corresponding to the clones disclosed in Table 1. The first column provides a unique clone identifier, "Clone ID", for a cDNA clone related to each contig sequence disclosed in Table 1. Column 2, "Library Codes" shows the expression profile of tissue and/or cell line libraries which express the polynucleotides of the invention. Each Library Code in column 2 represents a tissue/cell source identifier code corresponding to the Library Code and Library description provided in Table 4. Expression of these polynucleotides was not observed in the other tissues and/or cell libraries tested. One of skill in the art could routinely use this information to identify tissues which show a predominant expression pattern of the corresponding polynucleotide of the invention or to identify polynucleotides which show predominant and/or specific tissue expression.

Table 3, column 1, provides a nucleotide sequence identifier, "SEQ ID NO:X," that matches a nucleotide SEQ ID NO:X disclosed in Table 1, column 5. Table 3, column 2, provides the chromosomal location, "Cytologic Band or Chromosome," of polynucleotides corresponding to SEQ ID NO:X. Chromosomal location was determined by finding exact matches to EST and cDNA sequences contained in the NCBI (National Center for Biotechnology Information) UniGene database. Given a presumptive chromosomal location, disease locus association was determined by comparison with the Morbid Map, derived from Online Mendelian Inheritance in Man (Online Mendelian Inheritance in Man, OMIM™. McKusick-Nathans Institute for Genetic Medicine, Johns Hopkins University (Baltimore, Md.) and National Center for Biotechnology Information, National Library of Medicine (Bethesda, Md.) 2000. World Wide Web URL: http://www.ncbi.nlm.nih.gov/omim/). If the putative chromosomal location of the Query overlapped with the chromosomal location of a Morbid Map entry, the OMIM reference identification number of the morbid map entry is provided in Table 3, column 3, labelled "OMIM ID." A key to the OMIM reference identification numbers is provided in Table 5.

Table 4 provides a key to the Library Code disclosed in Table 2. Column 1 provides the Library Code disclosed in Table 2, column 2. Column 2 provides a description of the tissue or cell source from which the corresponding library was derived.

Table 5 provides a key to the OMIM reference identification numbers disclosed in Table 3, column 3. OMIM reference identification numbers (Column 1) were derived from Online Mendelian Inheritance in Man (Online Mendelian inheritance in Man, OMIM. McKusick-Nathans Institute for Genetic Medicine, Johns Hopkins University (Baltimore, Md.) and National Center for Biotechnology Information, National Library of Medicine, (Bethesda, Md.) 2000. World Wide Web URL: http://www.ncbi.nlm.nih.gov/omim/). Column 2 provides diseases associated with the cytologic band disclosed in Table 3, column 2, as determined using the Morbid Map database.

TABLE 2

| Clone ID | Library Codes |
|---|---|
| HSSDM23 | H0008 H0012 H0040 H0052 H0059 H0087 H0135 H0140 H0166 H0252 H0253 H0254 H0265 H0309 H0327 H0333 H0370 H0483 H0484 H0486 H0494 H0506 H0509 H0520 H0521 H0539 H0542 H0545 H0547 H0556 H0586 H0617 H0619 H0620 H0646 H0658 H0672 H0673 H0684 H0689 L1290 S0007 S0011 S0031 S0038 S0040 S0053 S0144 S0222 S0282 S0356 S0358 S0376 S0388 S6016 |
| HOFNX30 | H0415 |
| HLQFB12 | H0059 H0150 H0204 H0331 H0393 H0509 H0510 H0574 H0615 H0661 L1290 S0358 S0360 S0374 S0410 S0444 |
| HDPUM13 | H0009 H0015 H0030 H0031 H0039 H0042 H0045 H0087 H0100 H0120 H0124 H0252 H0254 H0255 H0309 H0318 H0327 H0352 H0375 H0411 H0421 H0424 H0427 H0445 H0455 H0506 H0509 H0510 H0521 H0522 H0538 H0550 H0555 H0575 H0581 H0583 H0587 H0602 H0617 H0632 H0637 H0638 H0641 H0647 H0649 H0653 H0661 H0663 H0672 H0687 H0689 L1290 S0044 S0116 S0260 S0280 S0292 S0332 S0356 S0358 S0360 S0374 S0376 S0380 S0404 S0408 S6022 T0082 |
| HTLGV19 | H0284 H0555 H0618 H0620 L1290 |
| HTTCT46 | H0013 H0024 H0039 H0040 H0048 H0099 H0123 H0144 H0170 H0171 H0244 H0328 H0329 H0339 H0369 H0402 H0486 H0521 H0595 H0622 H0624 H0669 H0687 H0691 L1290 S0028 S0031 S0037 S0053 S0192 S0194 S0312 S0318 S0358 S0374 S0378 T0003 T0069 |
| HOFNF53 | H0415 |
| HOHCA60 | H0012 H0013 H0014 H0024 H0031 H0036 H0038 H0039 H0052 H0083 H0123 H0135 H0208 H0253 H0264 H0270 H0292 H0327 H0370 H0423 H0494 H0506 H0545 H0547 H0561 H0581 H0591 H0593 H0596 H0607 H0616 H0618 H0634 H0644 H0650 H0659 H0687 H0690 L0022 L1290 S0002 S0027 S0028 S0037 S0040 S0049 S0126 S0152 S0192 S0194 S0212 S0242 S0250 S0342 S0344 S0356 S0366 S0374 S0420 T0010 T0067 T0115 |
| HLQFT18 | H0059 H0150 H0204 H0331 H0393 H0509 H0510 H0574 H0615 H0661 L0022 S0358 S0360 S0374 S0410 S0444 |
| HBXFT65 | H0013 H0031 H0038 H0040 H0046 H0090 H0096 H0144 H0156 H0163 H0171 H0179 H0264 H0265 H0266 H0305 H0327 H0341 H0359 H0393 H0409 H0412 H0413 H0415 H0421 H0438 H0494 H0506 H0509 H0521 H0522 H0547 H0551 H0553 H0555 H0560 H0575 H0580 H0581 H0586 H0591 H0615 H0619 H0622 H0624 H0638 H0648 H0658 H0659 H0661 H0667 H0672 H0674 H0684 H0696 H0707 L0022 S0001 S0002 S0003 S0010 S0011 S0022 S0028 |

TABLE 2-continued

| Clone ID | Library Codes |
|---|---|
| | S0031 S0037 S0040 S0045 S0046 S0051 S0114 S0126 S0132 S0134 S0142 S0152 S0192 S0196 S0212 S0214 S0222 S0278 S0330 S0360 S0374 S0376 S0380 S0404 S0418 S0456 S0665 S6028 T0010 T0067 T0110 |
| HWHGK36 | H0024 H0032 H0087 H0150 H0188 H0379 H0392 H0494 H0555 H0586 H0587 H0592 H0600 H0604 H0620 H0670 H0689 L0022 S0126 S0192 S0352 S6024 T0067 |
| HAGDA35 | H0156 H0251 H0521 H0551 H0556 H0580 L0022 S0010 S0026 S0212 S0282 |
| HRODQ04 | H0494 H0497 H0519 H0551 H0580 H0586 H0598 H0599 H0624 L0022 S0040 S0150 S0180 S0212 S0312 S0314 S0380 S0386 T0040 T0082 |
| HDPOL27 | H0069 H0306 H0423 H0436 H0445 H0521 H0522 H0542 H0580 H0581 H0591 H0596 H0624 H0638 H0648 L0022 S0002 S0007 S0222 S0426 |
| HWLHZ79 | H0232 H0512 H0597 L0022 S0044 S0330 S0354 S0358 S0374 |
| HKGDP17 | H0208 H0333 H0538 L0022 |
| HSVBD67 | H0008 H0012 H0013 H0014 H0040 H0052 H0059 H0087 H0135 H0140 H0166 H0179 H0252 H0253 H0254 H0265 H0266 H0268 H0309 H0327 H0333 H0370 H0392 H0483 H0484 H0486 H0494 H0506 H0509 H0519 H0520 H0521 H0539 H0542 H0545 H0547 H0551 H0556 H0580 H0581 H0586 H0593 H0617 H0619 H0620 H0643 H0646 H0657 H0658 H0659 H0660 H0672 H0673 H0674 H0684 H0689 H0690 L0022 S0007 S0011 S0031 S0038 S0040 S0053 S0140 S0144 S0192 S0222 S0282 S0356 S0358 S0376 S0388 S0424 S6016 S6022 S6024 |
| HTGAT51 | H0619 L0022 S0134 |
| HFCEQ37 | H0009 H0253 H0486 L0022 S0028 S0222 S0346 |
| HSKNP59 | L0022 S3012 |
| HWMBB68 | H0038 H0046 H0052 H0083 H0100 H0150 H0250 H0251 H0261 H0266 H0341 H0372 H0412 H0435 H0485 H0486 H0494 H0522 H0529 H0539 H0553 H0574 H0580 H0581 H0599 H0616 H0641 H0642 H0648 H0659 H0660 H0673 H0687 H0689 L0022 S0007 S0027 S0028 S0045 S0112 S0116 S0126 S0142 S0150 S0152 S0196 S0214 S0276 S0328 S0330 S0360 S0376 S0428 T0002 T0040 T0110 |
| HWABL61 | H0008 H0009 H0150 H0244 H0250 H0255 H0263 H0264 H0265 H0266 H0295 H0318 H0349 H0413 H0435 H0445 H0449 H0486 H0520 H0521 H0542 H0553 H0556 H0580 H0581 H0597 H0624 H0650 H0657 H0670 H0677 H0682 H0687 L0022 S0044 S0051 S0115 S0116 S0142 S0144 S0222 S0250 S0278 S0282 S0344 S0468 S6022 S6028 T0006 |
| HWDAQ83 | H0522 H0547 H0561 H0600 L0022 |
| HFXLF67 | S0282 |
| HTPHH74 | H0008 H0013 H0029 H0032 H0036 H0038 H0039 H0046 H0050 H0056 H0068 H0123 H0124 H0144 H0156 H0169 H0220 H0264 H0266 H0268 H0316 H0328 H0341 H0349 H0355 H0374 H0393 H0413 H0423 H0431 H0437 H0445 H0485 H0486 H0494 H0497 H0509 H0518 H0519 H0520 H0521 H0522 H0529 H0539 H0543 H0547 H0551 H0553 H0555 H0556 H0561 H0574 H0581 H0586 H0591 H0592 H0593 H0615 H0619 H0622 H0623 H0638 H0641 H0644 H0646 H0650 H0653 H0656 H0657 H0658 H0659 H0665 H0670 H0672 H0688 H0689 H0694 L0022 S0010 S0011 S0016 S0026 S0027 S0044 S0045 S0114 S0116 S0126 S0132 S0142 S0150 S0152 S0194 S0222 S0242 S0250 S0276 S0280 S0330 S0344 S0350 S0354 S0356 S0358 S0360 S0374 S0378 S0390 S0414 S0424 S0426 T0006 T0042 T0048 T0049 |
| HWABW88 | H0030 H0041 H0052 H0136 H0163 H0170 H0266 H0341 H0427 H0478 H0494 H0510 H0521 H0529 H0556 H0561 H0581 H0597 H0606 H0617 L0022 S0001 S0036 S0046 S0152 S0222 S0358 S0468 T0042 T0049 |
| HWNFG66 | S0360 |
| HDPQG01 | H0013 H0032 H0040 H0052 H0083 H0187 H0274 H0365 H0445 H0486 H0509 H0522 H0539 H0542 H0556 H0580 H0581 H0586 H0590 H0624 H0635 H0644 H0687 L0022 S0003 S0031 S0116 S0152 S0196 S0214 S0280 S0330 S0360 S0420 S0422 S0426 S6022 T0006 |
| HE2IO57 | H0031 H0050 H0170 H0263 H0318 H0327 H0341 H0411 H0412 H0413 H0422 H0506 H0521 H0545 H0547 H0556 H0575 H0580 H0581 H0586 H0599 H0623 H0638 H0646 |

TABLE 2-continued

| Clone ID | Library Codes |
|---|---|
| | H0659 H0672 H0687 L0022 S0003 S0040 S0114 S0208 S0212 S0214 S0242 S0418 S0420 S0422 S0458 S3014 T0004 T0071 |
| HLDRR08 | H0509 H0510 S0380 |
| HTOJV86 | H0014 H0015 H0030 H0036 H0038 H0039 H0040 H0042 H0056 H0063 H0085 H0087 H0090 H0135 H0144 H0163 H0179 H0183 H0188 H0194 H0204 H0205 H0231 H0232 H0234 H0235 H0251 H0252 H0254 H0255 H0263 H0264 H0271 H0272 H0274 H0318 H0328 H0355 H0373 H0375 H0383 H0402 H0421 H0427 H0436 H0444 H0478 H0479 H0485 H0486 H0488 H0489 H0506 H0510 H0518 H0519 H0521 H0522 H0538 H0551 H0553 H0560 H0575 H0581 H0586 H0587 H0590 H0596 H0597 H0614 L0022 S0003 S0026 S0031 S0044 S0052 S0116 S0122 S0216 S0282 S0312 S0314 S0328 S0330 S0354 S0356 S0358 S0360 S0372 S0374 S0376 S0382 S0394 S0404 S0406 S0430 S0432 S0440 S0442 S0444 S0446 S0448 S0456 S0464 T0002 T0023 T0082 |
| HLYAV34 | H0009 H0014 H0031 H0039 H0062 H0063 H0090 H0108 H0122 H0123 H0163 H0189 H0213 H0252 H0264 H0309 H0333 H0343 H0345 H0352 H0375 H0376 H0393 H0427 H0444 H0445 H0486 H0506 H0509 H0510 H0521 H0522 H0553 H0555 H0575 H0597 H0619 H0620 H0638 H0644 H0652 H0658 H0661 H0662 H0663 H0668 H0672 L0022 S0106 S0190 S0212 S0354 S0358 S0360 S0362 S0376 S0378 S0384 |

TABLE 3

| SEQ ID NO: X | Cytologic Band or Chromosome: | OMIM Reference(s): |
|---|---|---|
| 40 | 14q32.33 | 144120 147020 147110 |

TABLE 4

| Library Code | Library Description |
|---|---|
| H0008 | Whole 6 Week Old Embryo |
| H0009 | Human Fetal Brain |
| H0012 | Human Fetal Kidney |
| H0013 | Human 8 Week Whole Embryo |
| H0014 | Human Gall Bladder |
| H0015 | Human Gall Bladder, fraction II |
| H0024 | Human Fetal Lung III |
| H0029 | Human Pancreas |
| H0030 | Human Placenta |
| H0031 | Human Placenta |
| H0032 | Human Prostate |
| H0036 | Human Adult Small Intestine |
| H0038 | Human Testes |
| H0039 | Human Pancreas Tumor |
| H0040 | Human Testes Tumor |
| H0041 | Human Fetal Bone |
| H0042 | Human Adult Pulmonary |
| H0045 | Human Esophagus, Cancer |
| H0046 | Human Endometrial Tumor |
| H0048 | Human Pineal Gland |
| H0050 | Human Fetal Heart |
| H0052 | Human Cerebellum |
| H0056 | Human Umbilical Vein, Endo. remake |
| H0059 | Human Uterine Cancer |
| H0062 | Human Thymus |
| H0063 | Human Thymus |
| H0068 | Human Skin Tumor |
| H0069 | Human Activated T-Cells |
| H0083 | HUMAN JURKAT MEMBRANE BOUND POLYSOMES |
| H0085 | Human Colon |
| H0087 | Human Thymus |
| H0090 | Human T-Cell Lymphoma |
| H0096 | Human Parotid Cancer |

TABLE 4-continued

| Library Code | Library Description |
|---|---|
| H0099 | Human Lung Cancer, subtracted |
| H0100 | Human Whole Six Week Old Embryo |
| H0108 | Human Adult Lymph Node, subtracted |
| H0120 | Human Adult Spleen, subtracted |
| H0122 | Human Adult Skeletal Muscle |
| H0123 | Human Fetal Dura Mater |
| H0124 | Human Rhabdomyosarcoma |
| H0135 | Human Synovial Sarcoma |
| H0136 | Supt Cells, cyclohexamide treated |
| H0140 | Activated T-Cells, 8 hrs. |
| H0144 | Nine Week Old Early Stage Human |
| H0150 | Human Epididymus |
| H0156 | Human Adrenal Gland Tumor |
| H0163 | Human Synovium |
| H0166 | Human Prostate Cancer, Stage B2 fraction |
| H0169 | Human Prostate Cancer, Stage C fraction |
| H0170 | 12 Week Old Early Stage Human |
| H0171 | 12 Week Old Early Stage Human, II |
| H0179 | Human Neutrophil |
| H0183 | Human Colon Cancer |
| H0187 | Resting T-Cell |
| H0188 | Human Normal Breast |
| H0189 | Human Resting Macrophage |
| H0194 | Human Cerebellum, subtracted |
| H0204 | Human Colon Cancer, subtracted |
| H0205 | Human Colon Cancer, differential |
| H0208 | Early Stage Human Lung, subtracted |
| H0213 | Human Pituitary, subtracted |
| H0220 | Activated T-Cells, 4 hrs, subtracted |
| H0231 | Human Colon, subtraction |
| H0232 | Human Colon, differential expression |
| H0234 | human colon cancer, metastatic to liver, differentially expressed |
| H0235 | Human colon cancer, metaticized to liver, subtraction |
| H0244 | Human 8 Week Whole Embryo, subtracted |
| H0250 | Human Activated Monocytes |
| H0251 | Human Chondrosarcoma |
| H0252 | Human Osteosarcoma |
| H0253 | Human adult testis, large inserts |
| H0254 | Breast Lymph node cDNA library |
| H0255 | breast lymph node CDNA library |
| H0261 | H. cerebellum, Enzyme subtracted |
| H0263 | human colon cancer |
| H0264 | human tonsils |
| H0265 | Activated T-Cell (12 hs)/Thiouridine labelledEco |
| H0266 | Human Microvascular Endothelial Cells, fract. A |
| H0268 | Human Umbilical Vein Endothelial Cells, fract. A |
| H0270 | HPAS (human pancreas, subtracted) |
| H0271 | Human Neutrophil, Activated |
| H0272 | HUMAN TONSILS, FRACTION 2 |
| H0274 | Human Adult Spleen, fractionII |
| H0284 | Human OB MG63 control fraction I |
| H0292 | Human OB HOS treated (10 nM E2) fraction I |
| H0295 | Amniotic Cells - Primary Culture |
| H0305 | CD34 positive cells (Cord Blood) |
| H0306 | CD34 depleted Buffy Coat (Cord Blood) |
| H0309 | Human Chronic Synovitis |
| H0316 | HUMAN STOMACH |
| H0318 | HUMAN B CELL LYMPHOMA |
| H0327 | human corpus colosum |
| H0328 | human ovarian cancer |
| H0329 | Dermatofibrosarcoma Protuberance |
| H0331 | Hepatocellular Tumor |
| H0333 | Hemangiopericytoma |
| H0339 | Duodenum |
| H0341 | Bone Marrow Cell Line (RS4,11) |
| H0343 | stomach cancer (human) |
| H0345 | SKIN |
| H0349 | human adult liver cDNA library |
| H0352 | wilm's tumor |
| H0355 | Human Liver |
| H0359 | KMH2 cell line |
| H0365 | Osteoclastoma-normalized B |
| H0369 | H. Atrophic Endometrium |
| H0370 | H. Lymph node breast Cancer |
| H0372 | Human Testes |
| H0373 | Human Heart |

TABLE 4-continued

| Library Code | Library Description |
|---|---|
| H0374 | Human Brain |
| H0375 | Human Lung |
| H0376 | Human Spleen |
| H0379 | Human Tongue, frac 1 |
| H0383 | Human Prostate BPH, re-excision |
| H0392 | H. Meningima, M1 |
| H0393 | Fetal Liver, subtraction II |
| H0402 | CD34 depleted Buffy Coat (Cord Blood), re-excision |
| H0409 | H. Striatum Depression, subtracted |
| H0411 | H Female Bladder, Adult |
| H0412 | Human umbilical vein endothelial cells, IL-4 induced |
| H0413 | Human Umbilical Vein Endothelial Cells, uninduced |
| H0415 | H. Ovarian Tumor, II, OV5232 |
| H0421 | Human Bone Marrow, re-excision |
| H0422 | T-Cell PHA 16 hrs |
| H0423 | T-Cell PHA 24 hrs |
| H0424 | Human Pituitary, subt IX |
| H0427 | Human Adipose |
| H0431 | H. Kidney Medulla, re-excision |
| H0435 | Ovarian Tumor 10-3-95 |
| H0436 | Resting T-Cell Library, II |
| H0437 | H Umbilical Vein Endothelial Cells, frac A, re-excision |
| H0438 | H. Whole Brain #2, re-excision |
| H0444 | Spleen metastic melanoma |
| H0445 | Spleen, Chronic lymphocytic leukemia |
| H0449 | CD34+ cell, I |
| H0455 | H. Striatum Depression, subt |
| H0478 | Salivary Gland, Lib 2 |
| H0479 | Salivary Gland, Lib 3 |
| H0483 | Breast Cancer cell line, MDA 36 |
| H0484 | Breast Cancer Cell line, angiogenic |
| H0485 | Hodgkin's Lymphoma I |
| H0486 | Hodgkin's Lymphoma II |
| H0488 | Human Tonsils, Lib 2 |
| H0489 | Crohn's Disease |
| H0494 | Keratinocyte |
| H0497 | HEL cell line |
| H0506 | Ulcerative Colitis |
| H0509 | Liver, Hepatoma |
| H0510 | Human Liver, normal |
| H0512 | Keratinocyte, lib 3 |
| H0518 | pBMC stimulated w/poly I/C |
| H0519 | NTERA2, control |
| H0520 | NTERA2 + retinoic acid, 14 days |
| H0521 | Primary Dendritic Cells, lib 1 |
| H0522 | Primary Dendritic cells, frac 2 |
| H0529 | Myoloid Progenitor Cell Line |
| H0538 | Merkel Cells |
| H0539 | Pancreas Islet Cell Tumor |
| H0542 | I Cell helper I |
| H0543 | T cell helper II |
| H0545 | Human endometrial stromal cells-treated with progesterone |
| H0547 | NTERA2 teratocarcinoma cell line + retinoic acid (14 days) |
| H0550 | H. Epididiymus, cauda |
| H0551 | Human Thymus Stromal Cells |
| H0553 | Human Placenta |
| H0555 | Rejected Kidney, lib 4 |
| H0556 | Activated T-cell(12 h)/Thiouridine-re-excision |
| H0560 | KMH2 |
| H0561 | L428 |
| H0574 | Hepatocellular Tumor, re-excision |
| H0575 | Human Adult Pulmonary, re-excision |
| H0580 | Dendritic cells, pooled |
| H0581 | Human Bone Marrow, treated |
| H0583 | B Cell lymphoma |
| H0586 | Healing groin wound, 6.5 hours post incision |
| H0587 | Healing groin wound, 7.5 hours post incision |
| H0590 | Human adult small intestine, re-excision |
| H0591 | Human T-cell lymphoma, re-excision |
| H0592 | Healing groin wound - zero hr post-incision (control) |
| H0593 | Olfactory epithelium, nasalcavity |
| H0595 | Stomach cancer (human), re-excision |
| H0596 | Human Colon Cancer, re-excision |
| H0597 | Human Colon, re-excision |
| H0598 | Human Stomach, re-excision |
| H0599 | Human Adult Heart, re-excision |

TABLE 4-continued

| Library Code | Library Description |
|---|---|
| H0600 | Healing Abdomen wound, 70 & 90 min post incision |
| H0602 | Healing Abdomen Wound, 21 & 29 days post incision |
| H0604 | Human Pituitary, re-excision |
| H0606 | Human Primary Breast Cancer, re-excision |
| H0607 | H. Leukocytes, normalized cot 50A3 |
| H0614 | H. Leukocytes, normalized cot 500 A |
| H0615 | Human Ovarian Cancer Reexcision |
| H0616 | Human Testes, Reexcision |
| H0617 | Human Primary Breast Cancer Reexcision |
| H0618 | Human Adult Testes, Large Inserts, Reexcision |
| H0619 | Fetal Heart |
| H0620 | Human Fetal Kidney, Reexcision |
| H0622 | Human Pancreas Tumor, Reexcision |
| H0623 | Human Umbilical Vein, Reexcision |
| H0624 | 12 Week Early Stage Human II, Reexcision |
| H0632 | Hepatocellular Tumor, re-excision |
| H0634 | Human Testes Tumor, re-excision |
| H0635 | Human Activated T-Cells, re-excision |
| H0637 | Dendritic Cells From CD34 Cells |
| H0638 | CD40 activated monocyte dendridic cells |
| H0641 | LPS activated derived dendritic cells |
| H0642 | Hep G2 Cells, lambda library |
| H0643 | Hep G2 Cells, PCR library |
| H0644 | Human Placenta (re-excision) |
| H0646 | Lung, Cancer (4005313 A3): Invasive Poorly Differentiated Lung Adenocarcinoma, |
| H0647 | Lung, Cancer (4005163 B7): Invasive, Poorly Diff. Adenocarcinoma, Metastatic |
| H0648 | Ovary, Cancer: (4004562 B6) Papillary Serous Cystic Neoplasm, Low Malignant Pot |
| H0649 | Lung, Normal: (4005313 B1) |
| H0650 | B-Cells |
| H0652 | Lung, Normal: (4005313 B1) |
| H0653 | Stromal Cells |
| H0656 | B-cells (unstimulated) |
| H0657 | B-cells (stimulated) |
| H0658 | Ovary, Cancer (9809C332): Poorly differentiated adenocarcinoma |
| H0659 | Ovary, Cancer (15395A1F): Grade II Papillary Carcinoma |
| H0660 | Ovary, Cancer: (15799A1F) Poorly differentiated carcinoma |
| H0661 | Breast, Cancer: (4004943 A5) |
| H0662 | Breast, Normal: (4005522B2) |
| H0663 | Breast, Cancer: (4005522 A2) |
| H0665 | Stromal cells 3.88 |
| H0667 | Stromal cells(HBM3.18) |
| H0668 | stromal cell clone 2.5 |
| H0669 | Breast, Cancer: (4005385 A2) |
| H0670 | Ovary, Cancer(4004650 A3): Well-Differentiated Micropapillary Serous Carcinoma |
| H0672 | Ovary, Cancer: (4004576 A8) |
| H0673 | Human Prostate Cancer, Stage B2, re-excision |
| H0674 | Human Prostate Cancer, Stage C, re-excission |
| H0677 | TNFR degenerate oligo |
| H0682 | Ovarian cancer, Serous Papillary Adenocarcinoma |
| H0684 | Ovarian cancer, Serous Papillary Adenocarcinoma |
| H0687 | Human normal ovary(#9610G215) |
| H0688 | Human Ovarian Cancer(#9807G017) |
| H0689 | Ovarian Cancer |
| H0690 | Ovarian Cancer, #9702G001 |
| H0691 | Normal Ovary, #9710G208 |
| H0694 | Prostate cancer (adenocarcinoma) |
| H0696 | Prostate Adenocarcinoma |
| H0707 | Stomach Cancer(S007635) |
| L0022 | Soares_pregnant_uterus_NbHPU |
| L1290 | Soares_NFL_T_GBC_S1 |
| S0001 | Brain frontal cortex |
| S0002 | Monocyte activated |
| S0003 | Human Osteoclastoma |
| S0007 | Early Stage Human Brain |
| S0010 | Human Amygdala |
| S0011 | STROMAL -OSTEOCLASTOMA |
| S0016 | Kidney Pyramids |
| S0022 | Human Osteoclastoma Stromal Cells - unamplified |
| S0026 | Stromal cell TF274 |
| S0027 | Smooth muscle, serum treated |
| S0028 | Smooth muscle,control |

TABLE 4-continued

| Library Code | Library Description |
|---|---|
| S0031 | Spinal cord |
| S0036 | Human Substantia Nigra |
| S0037 | Smooth muscle, IL1b induced |
| S0038 | Human Whole Brain #2 - Oligo dT > 1.5 Kb |
| S0040 | Adipocytes |
| S0044 | Prostate BPH |
| S0045 | Endothelial cells-control |
| S0046 | Endothelial-induced |
| S0049 | Human Brain, Striatum |
| S0051 | Human Hypothalmus, Schizophrenia |
| S0052 | neutrophils control |
| S0053 | Neutrophils IL-1 and LPS induced |
| S0106 | STRIATUM DEPRESSION |
| S0112 | Hypothalamus |
| S0114 | Anergic T-cell |
| S0116 | Bone marrow |
| S0122 | Osteoclastoma-normalized A |
| S0126 | Osteoblasts |
| S0132 | Epithelial-TNFa and INF induced |
| S0134 | Apoptotic T-cell |
| S0140 | eosinophil-IL5 induced |
| S0142 | Macrophage-oxLDL |
| S0144 | Macrophage (GM-CSF treated) |
| S0150 | LNCAP prostate cell line |
| S0152 | PC3 Prostate cell line |
| S0180 | Bone Marrow Stroma, TNF & LPS ind |
| S0190 | Prostate BPH, Lib 2, subtracted |
| S0192 | Synovial Fibroblasts (control) |
| S0194 | Synovial hypoxia |
| S0196 | Synovial IL-1/TNF stimulated |
| S0208 | Messangial cell, frac 1 |
| S0212 | Bone Marrow Stromal Cell, untreated |
| S0214 | Human Osteoclastoma, re-excision |
| S0216 | Neutrophils IL-1 and LPS induced |
| S0222 | H. Frontal cortex, epileptic, re-excision |
| S0242 | Synovial Fibroblasts (Il1/TNF), subt |
| S0250 | Human Osteoblasts II |
| S0260 | Spinal Cord, re-excision |
| S0276 | Synovial hypoxia-RSF subtracted |
| S0278 | H Macrophage (GM-CSF treated), re-excision |
| S0280 | Human Adipose Tissue, re-excision |
| S0282 | Brain Frontal Cortex, re-excision |
| S0292 | Osteoarthritis (OA-4) |
| S0312 | Human osteoarthritic, fraction II |
| S0314 | Human osteoarthritis, fraction I |
| S0318 | Human Normal Cartilage Fraction II |
| S0328 | Palate carcinoma |
| S0330 | Palate normal |
| S0332 | Pharynx carcinoma |
| S0342 | Adipocytes, re-excision |
| S0344 | Macrophage-oxLDL, re-excision |
| S0346 | Human Amygdala, re-excision |
| S0350 | Pharynx Carcinoma |
| S0352 | Larynx Carcinoma |
| S0354 | Colon Normal II |
| S0356 | Colon Carcinoma |
| S0358 | Colon Normal III |
| S0360 | Colon Tumor II |
| S0362 | Human Gastrocnemius |
| S0366 | Human Soleus |
| S0372 | Larynx carcinoma III |
| S0374 | Normal colon |
| S0376 | Colon Tumor |
| S0378 | Pancreas normal PCA4 No |
| S0380 | Pancreas Tumor PCA4 Tu |
| S0382 | Larynx carcinoma IV |
| S0384 | Tongue carcinoma |
| S0386 | Human Whole Brain, re-excision |
| S0388 | Human Hypothalamus, schizophrenia, re-excision |
| S0390 | Smooth muscle, control, re-excision |
| S0394 | Stomach, normal |
| S0404 | Rectum normal |
| S0406 | Rectum tumour |
| S0408 | Colon, normal |
| S0410 | Colon, tumour |
| S0414 | Hippocampus, Alzheimer Subtracted |
| S0418 | CHME Cell Line, treated 5 hrs |
| S0420 | CHME Cell Line, untreated |
| S0422 | Mo7e Cell Line GM-CSF treated (1 ng/ml) |
| S0424 | TF-1 Cell Line GM-CSF Treated |
| S0426 | Monocyte activated, re-excision |
| S0428 | Neutrophils control, re-excision |
| S0430 | Aryepiglottis Normal |
| S0432 | Sinus piriformis Tumour |
| S0440 | Liver Tumour Met 5 Tu |
| S0442 | Colon Normal |
| S0444 | Colon Tumor |
| S0446 | Tongue Tumour |
| S0448 | Larynx Normal |
| S0456 | Tongue Normal |
| S0458 | Thyroid Normal (SDCA2 No) |
| S0464 | Larynx Normal |
| S0468 | Ea.hy.926 cell line |
| S0665 | Human Amygdala, re-excission |
| S3012 | Smooth Muscle Serum Treated, Norm |
| S3014 | Smooth muscle, serum induced, re-exc |
| S6016 | H. Frontal Cortex, Epileptic |
| S6022 | H. Adipose Tissue |
| S6024 | Alzheimers, spongy change |
| S6028 | Human Manic Depression Tissue |
| T0002 | Activated T-cells |
| T0003 | Human Fetal Lung |
| T0004 | Human White Fat |
| T0006 | Human Pineal Gland |
| T0010 | Human Infant Brain |
| T0023 | Human Pancreatic Carcinoma |
| T0040 | HSC172 cells |
| T0042 | Jurkat T-Cell, S phase |
| T0048 | Human Aortic Endothelium |
| T0049 | Aorta endothelial cells + TNF-a |
| T0067 | Human Thyroid |
| T0069 | Human Uterus, normal |
| T0071 | Human Bone Marrow |
| T0082 | Human Adult Retina |
| T0110 | Human colon carcinoma (HCC) cell line, remake |
| T0115 | Human Colon Carcinoma (HCC) cell line |

TABLE 5

| OMIM ID | OMIM Description |
|---|---|
| 144120 | Hyperimmunoglobulin G1 syndrome (2) (?) |
| 147020 | Agammaglobulinemia, 601495 (3) |
| 147110 | IgG2 deficiency, selective (3) |

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the secreted protein, including the mature form, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, including the secreted polypeptide, can be substantially purified using techniques described herein or otherwise known in the art, such as, for example, by the one-step method described in Smith and Johnson, Gene 67:31–40 (1988). Polypeptides of the invention also can be purified from natural, synthetic or recombinant sources using techniques described herein or otherwise known in the art, such as, for example, antibodies of the invention raised against the secreted protein.

The present invention provides a polynucleotide comprising, or alternatively consisting of, the nucleic acid sequence of SEQ ID NO:X, and/or a cDNA contained in ATCC® deposit Z. The present invention also provides a polypeptide comprising, or alternatively, consisting of, the polypeptide sequence of SEQ ID NO:Y and/or a polypeptide encoded by the cDNA contained in ATCC® deposit Z. Polynucleotides encoding a polypeptide comprising, or alternatively consisting of the polypeptide sequence of SEQ ID NO:Y and/or a polypeptide sequence encoded by the cDNA contained in ATCC® deposit Z are also encompassed by the invention.

Signal Sequences and Mature Polypeptides

The present invention also encompasses mature forms of a polypeptide having the amino acid sequence of SEQ ID NO:Y and/or the amino acid sequence encoded by the cDNA in a deposited clone. Polynucleotides encoding the mature forms (such as, for example, the polynucleotide sequence in SEQ ID NO:X and/or the polynucleotide sequence contained in the cDNA of a deposited clone) are also encompassed by the invention. Moreover, fragments or variants of these polypeptides (such as, fragments as described herein, polypeptides at least 80%, 85%, 90%, 95%, 96%, 97%, 98%, 99%, or 100% identical to these polypeptides, or polypeptides encoded by a polynucleotide that hybridizes under stringent conditions to the complementary strand of the polynucleotide encoding these polypeptides) are also encompassed by the invention. In preferred embodiments, these fragments or variants retain one or more functional activities of the full-length or mature form of the polypeptide (e.g., biological activity, antigenicity (i.e., ability to bind polypeptide specific antibodies), immunogenicity (i.e., ability to elicit generation of polypeptide specific antibodies), ability to form heteromeric or homomeric multimers/oligomers, and ability to bind cognate receptors or ligands). Antibodies that bind the polypeptides of the invention, and polynucleotides encoding these polypeptides are also encompassed by the invention.

According to the signal hypothesis, proteins secreted by mammalian cells have a signal or secretary leader sequence which is cleaved from the mature protein once export of the growing protein chain across the rough endoplasmic reticulum has been initiated. Most mammalian cells, and even insect cells, cleave secreted proteins with the same specificity. However, in some cases, cleavage of a secreted protein is not entirely uniform, which results in two or more mature species of the protein. Further, it has long been known that cleavage specificity of a secreted protein is ultimately determined by the primary structure of the complete protein, that is, cleavage specificity is inherent in the amino acid sequence of the polypeptide.

Methods for predicting whether a protein has a signal sequence, as well as the cleavage point for that sequence, are available. For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues −13 to +2, where +1 indicates the amino terminus of the cleaved protein. The accuracy of predicting the cleavage points of known mammalian secretory proteins by each of these methods is in the range of 75–80%. (von Heinje, supra.) However, the two methods do not always produce the same predicted cleavage point(s) for a given protein.

In the present case, the deduced amino acid sequence of the secreted polypeptide was analyzed by a computer program called SignalP (Henrik Nielsen et al., Protein Engineering 10:1–6 (1997)), which predicts the sub-cellular localization of a protein based on the amino acid sequence. As part of this computational prediction of localization, the methods of McGeoch and von Heinje are incorporated. The analysis of the amino acid sequences of the secreted proteins described herein by this program provided the results shown in Table 1.

In specific embodiments, polypeptides of the invention comprise, or alternatively consist of, the predicted mature form of the polypeptide as delineated in columns 14 and 15 of Table 1. Moreover, fragments or variants of these polypeptides (such as, fragments as described herein, polypeptides at least 80%, 85%, 90%, 95%, 96%, 97%, 98%, 99%, or 100% identical to these polypeptides, or polypeptides encoded by a polynucleotide that hybridizes under stringent conditions to the complementary strand of the polynucleotide encoding these polypeptides) are also encompassed by the invention. In preferred embodiments, these fragments or variants retain one or more functional activities of the full-length or mature form of the polypeptide (e.g., biological activity, antigenicity (i.e., ability to bind polypeptide specific antibodies), immunogenicity (i.e., ability to elicit generation of polypeptide specific antibodies), ability to form heteromeric or homomeric multimers/oligomers, and ability to bind cognate receptors or ligands). Antibodies that bind the polypeptides of the invention, and polynucleotides encoding these polypeptides are also encompassed by the invention.

Polynucleotides encoding proteins comprising, or consisting of, the predicted mature form of polypeptides of the invention (e.g., polynucleotides having the sequence of SEQ ID NO: X (Table 1, column 5), the sequence delineated in columns 7 and 8 of Table 1, and a sequence encoding the mature polypeptide delineated in columns 14 and 15 of Table 1 (e.g., the sequence of SEQ ID NO:X encoding the mature polypeptide delineated in columns 14 and 15 of Table 1)) are also encompassed by the invention, as are fragments or variants of these polynucleotides (such as, fragments as described herein, polynucleotides at least 80%, 85%, 90%, 95%, 96%, 97%, 98%, 99%, or 100% identical to these polynucleotides, and nucleic acids which hybridizes under stringent conditions to the complementary strand of the polynucleotide).

As one of ordinary skill would appreciate, however, polypeptide signal sequence cleavage sites cannot be predicted with absolute certainty. For example, within any given organism cleavage of the signal sequence is often not entirely uniform (resulting in more than one mature polypeptide species). Moreover, signal cleavage sites may also vary from organism to organism (also resulting in multiple species of mature polypeptides). Accordingly, the present invention provides secreted polypeptides having a sequence shown in SEQ ID NO:Y which have an N-terminus beginning within 15 residues of the predicted cleavage point (i.e., having 1, 2, 3, 4, 5, 6, 7, 8, 9, 10, 11, 12, 13, 14, or 15 more or less contiguous residues of SEQ ID NO:Y at the N-terminus when compared to the predicted mature form of the polypeptide (e.g., the mature polypeptide delineated in columns 14 and 15 of Table 1). These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the endoplasmic reticulum. Nonetheless, the present invention provides the mature protein produced by expression of the polynucleotide sequence of SEQ ID NO:X and/or the polynucleotide sequence contained in the cDNA of a deposited clone, in a mammalian cell (e.g., COS cells, as described below). These polypeptides, and the polynucleotides encoding such polypeptides, are contemplated by the present invention.

Mature forms of the polypeptide of the present invention also include polypeptides processed at the carboxyl terminus (C-terminus). For example, post-translational processing within any given cell type or organism can also result in polypeptides with truncated C-termini (as compared to the full-length or secreted polypeptides delineated in columns 12 and 15 or columns 14 and 15, respectively, of Table 1). Therefore, in further specific embodiments, polypeptides of the invention comprise, or alternatively consist of, the mature form of the polypeptide having a C-terminus ending within 15 residues of the predicted carboxyl-terminus (i.e., having 1, 2, 3, 4, 5, 6, 7, 8, 9, 10, 11, 12, 13, 14, or 15 C-terminal residues less than the mature polypeptide delineated in columns 14 and 15 of Table 1).

Thus, mature forms of polypeptides of the present invention include, but are not limited to, polypeptides with amino-terminal and/or carboxyl-terminal truncations of the polypeptide sequences delineated in Table 1, columns 12 and 15. Accordingly, these polypeptides, polynucleotides encoding such polypeptides, and antibodies binding such polypeptides, are contemplated by the present invention.

Polynucleotide and Polypeptide Variants

The present invention is directed to variants of the polynucleotide sequence disclosed in SEQ ID NO:X, the complementary strand thereto, and/or the cDNA sequence contained in a deposited clone.

The present invention also encompasses variants of the polypeptide sequence disclosed in SEQ ID NO:Y and/or encoded by a deposited clone.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

The present invention is also directed to nucleic acid molecules which comprise, or alternatively consist of, a nucleotide sequence which is at least 80%, 85%, 90%, 95%, 96%, 97%, 98% or 99% identical to, for example, the nucleotide coding sequence in SEQ ID NO:X or the complementary strand thereto, the nucleotide coding sequence contained in a deposited cDNA clone or the complementary strand thereto, a nucleotide sequence encoding the polypeptide of SEQ ID NO:Y, a nucleotide sequence encoding the polypeptide encoded by the cDNA contained in a deposited clone, and/or polynucleotide fragments of any of these nucleic acid molecules (e.g., those fragments described herein). Polynucleotides which hybridize to these nucleic acid molecules under stringent hybridization conditions or lower stringency conditions are also encompassed by the invention, as are polypeptides encoded by these polynucleotides.

The present invention is also directed to polypeptides which comprise, or alternatively consist of, an amino acid sequence which is at least 80%, 85%, 90%, 95%, 96%, 97%, 98%, 99% identical to, for example, the polypeptide sequence shown in SEQ ID NO:Y, the polypeptide sequence encoded by the cDNA contained in a deposited clone, and/or polypeptide fragments of any of these polypeptides (e.g., those fragments described herein).

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown in Table 1, the ORF (open reading frame), or any fragment specified as described herein.

As a practical matter, whether any particular nucleic acid molecule or polypeptide is at least 80%, 85%, 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237–245(1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, an amino acid sequences shown in Table 1 (SEQ ID NO:Y) or to the amino acid sequence encoded by cDNA contained in a deposited clone can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237–245(1990)). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as *E. coli*).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the secreted protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification or (v) fusion of the polypeptide with another compound, such as albumin (including, but not limited to, recombinant albumin (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1–5, 5–10, 5–25, 5–50, 10–50 or 50–150, conservative amino acid substitutions are preferable.

Polynucleotide and Polypeptide Fragments

The present invention is also directed to polynucleotide fragments of the polynucleotides of the invention.

In the present invention, a "polynucleotide fragment" refers to a short polynucleotide having a nucleic acid sequence which: is a portion of that contained in a deposited clone, or encoding the polypeptide encoded by the cDNA in a deposited clone; is a portion of that shown in SEQ ID NO:X or the complementary strand thereto, or is a portion of a polynucleotide sequence encoding the polypeptide of SEQ ID NO:Y. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the cDNA sequence contained in a deposited clone or the nucleotide sequence shown in SEQ ID NO:X. In this context "about" includes the particularly recited value, a value larger or smaller by several (5, 4, 3, 2, or 1) nucleotides, at either terminus or at both termini. These nucleotide fragments have uses that include, but are not limited to, as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments comprising, or alternatively consisting of, a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 to the end of SEQ ID NO:X, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Polynucleotides which hybridize to these nucleic acid molecules under stringent hybridization conditions or lower stringency conditions are also encompassed by the invention, as are polypeptides encoded by these polynucleotides.

In the present invention, a "polypeptide fragment" refers to an amino acid sequence which is a portion of that contained in SEQ ID NO:Y or encoded by the cDNA contained in a deposited clone. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Preferred polypeptide fragments include the secreted protein as well as the mature form. Further preferred polypeptide fragments include the secreted protein or the mature form having a continuous series of deleted residues from the amino or the carboxy terminus, or both. For example, any number of amino acids, ranging from 1–60, can be deleted from the amino terminus of either the secreted polypeptide or the mature form. Similarly, any number of amino acids, ranging from 1–30, can be deleted from the carboxy terminus of the secreted protein or mature form. Furthermore, any combination of the above amino and carboxy terminus deletions are preferred. Similarly, polynucleotides encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

Preferably, the polynucleotide fragments of the invention encode a polypeptide which demonstrates a functional activity. By a polypeptide demonstrating a "functional activity" is meant, a polypeptide capable of displaying one or more known functional activities associated with a full-length (complete) polypeptide of invention protein. Such functional activities include, but are not limited to, biological activity, antigenicity [ability to bind (or compete with a polypeptide of the invention for binding) to an antibody to the polypeptide of the invention], immunogenicity (ability to generate antibody which binds to a polypeptide of the invention), ability to form multimers with polypeptides of the invention, and ability to bind to a receptor or ligand for a polypeptide of the invention.

The functional activity of polypeptides of the invention, and fragments, variants derivatives, and analogs thereof, can be assayed by various methods.

For example, in one embodiment where one is assaying for the ability to bind or compete with full-length polypeptide of the invention for binding to an antibody of the polypeptide of the invention, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a ligand for a polypeptide of the invention identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., 1995, Microbiol. Rev. 59:94–123. In another embodiment, physiological correlates of binding of a polypeptide of the invention to its substrates (signal transduction) can be assayed.

In addition, assays described herein (see Examples) and otherwise known in the art may routinely be applied to measure the ability of polypeptides of the invention and fragments, variants derivatives and analogs thereof to elicit related biological activity related to that of the polypeptide of the invention (either in vitro or in vivo). Other methods will be known to the skilled artisan and are within the scope of the invention.

Epitopes and Antibodies

The present invention encompasses polypeptides comprising, or alternatively consisting of, an epitope of the polypeptide having an amino acid sequence of SEQ ID NO:Y, or an epitope of the polypeptide sequence encoded by a polynucleotide sequence contained in ATCC® deposit No. Z or encoded by a polynucleotide that hybridizes to the complement of the sequence of SEQ ID NO:X or contained in ATCC® deposit No. Z under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:X), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767–778 (1984); Sutcliffe et al., Science 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 $\mu$g of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof), or albumin (including but not limited to recombinant albumin (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2): 76–82 (1998); Hansson, et al., J. Mol. Biol. 287:265–76 (1999); and Lorenzo and Blasco, Biotechniques 24(2) :308–13 (1998) (each of these patents and publications are hereby incorporated by reference in its entirety). In one embodiment, alteration of polynucleotides corresponding to SEQ ID NO:X and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NO:Y, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. In preferred embodiments, the immunoglobulin molecules of the invention are IgG1. In other preferred embodiments, the immunoglobulin molecules of the invention are IgG4.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{7}$ M, $5\times10^{-8}$ M, $10^{-8}$ M, $5\times10^{-9}$ M, $10^{-9}$ M, $5\times10^{-10}$ M, $10^{-10}$ M, $5\times-11$ M, $10\times^{-11}$ M, $5\times10^{-12}$ M, $^{10-12}$M, $5\times10^{-13}$ M, $10^{-13}$ M, $5\times10^{-14}$ M, $10^{-14}$ M, $5\times10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161 (4):1786–1794 (1998); Zhu et al., Cancer Res. 58(15): 3209–3214 (1998); Yoon et al., J. Immunol. 160(7): 3170–3179 (1998); Prat et al., J. Cell. Sci. 111(Pt2): 237–247 (1998); Pitard et al., J. Immunol. Methods 205(2): 177–190 (1997); Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples (e.g., Example 16). In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC®. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5): 489–498 (1991); Studnicka et al., Protein Engineering 7(6) :805–814 (1994); Roguska. et al., PNAS91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:Y.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*)

transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5): 155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a polypeptide, polypeptide fragment, or a variant of SEQ ID NO:Y may be fused or conjugated to the above antibody portions to increase the in vivo half life of the polypeptides or for use in immunoassays using methods known in the art. Further, the polypeptides corresponding to SEQ ID NO:Y may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al, *Int. Immunol.,* 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell,* 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5):155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342:435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contains nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92m (1985) and maybe used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J.Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell. Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).) Polynucleotides comprising or alternatively consisting of nucleic acids which encode these fusion proteins are also encompassed by the invention.

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995).)

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells (e.g., *Saccharomyces cerevisiae* or *Pichia pastoris* (ATCC® Accession No. 201178)); insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast *Pichia pastoris* is used to express the polypeptide of the present invention in a eukaryotic system. *Pichia pastoris* is a methylotrophic yeast which can metabolize methanol as its sole carbon source. A main step in the methanol metabolization pathway is the oxidation of methanol to formaldehyde using $O_2$. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for $O_2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis, S. B., et al, *Mol. Cell. Biol.* 5:1111–21 (1985); Koutz, P. J. et al., *Yeast* 5:167–77 (1989); Tschopp, J. F., et al., *Nucl. Acids Res.* 15:3859–76 (1987). Thus, a heterologous coding sequence, such as, for example, a polynucleotide of the present invention, under the transcriptional regulation of all or part of the AOX1 regulatory sequence is expressed at exceptionally high levels in Pichia yeast grown in the presence of methanol.

In one example, the plasmid vector pPIC9K is used to express DNA encoding a polypeptide of the invention, as set forth herein, in a Pichea yeast system essentially as described in "Pichia Protocols: Methods in Molecular Biology," D. R. Higgins and J. Cregg, eds. The Humana Press, Totowa, N.J., 1998. This expression vector allows expression and secretion of a protein of the invention by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W. H. Freeman & Co., N.Y., and Hunkapiller et al., *Nature,* 310:105–111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59–72 (1996); Vorobjev et al., *Nucleosides Nucleotides* 18:2745–2750 (1999); and Caliceti et al., *Bioconjug. Chem.* 10:638–646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249–304 (1992); Francis et al., *Intern. J. of Hematol.* 68:1–18 (1998); U.S. Pat. Nos. 4,002,531; 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1–3, 2–4, 3–5, 4–6, 5–7, 6–8, 7–9, 8–10, 9–11, 10–12, 11–13, 12–14, 13–15, 14–16, 15–17, 16–18, 17–19, or 18–20 polyethylene glycol moieties per protein molecule. Methods for determining the degree of substitution are discussed, for example, in Delgado et al., *Crit. Rev. Thera. Drug Carrier Sys.* 9:249–304 (1992).

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:Y or encoded by the cDNA contained in a deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, oseteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide sequence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (see, e.g., U.S. Pat. No. 5,478, 925, which is herein incorporated by reference in its entirety).

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ ID NO:X. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, preselection by hybridization to construct chromosome specific-cDNA libraries and computer mapping techniques (See, e.g., Shuler, Trends Biotechnol 16:456–459 (1998) which is hereby incorporated by reference in its entirety).

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., “Human Chromosomes: a Manual of Basic Techniques,” Pergamon Press, New York (1988).

For chromosome mapping, the polynucleotides can be used individually (to mark a single chromosome or a single site on that chromosome) or in panels (for marking multiple sites and/or multiple chromosomes).

The polynucleotides of the present invention would likewise be useful for radiation hybrid mapping, HAPPY mapping, and long range restriction mapping. For a review of these techniques and others known in the art, see, e.g., Dear, “Genome Mapping: A Practical Approach,” IRL Press at Oxford University Press, London (1997); Aydin, J. Mol. Med. 77:691–694 (1999); Hacia et al., Mol. Psychiatry 3:483–492 (1998); Herrick et al., Chromosome Res. 7:409–423 (1999); Hamilton et al., Methods Cell Biol. 62:265–280 (2000); and/or Ott, J. Hered. 90:68–70 (1999) each of which is hereby incorporated by reference in its entirety.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using polynucleotides of the present invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an individual and comparing the measured gene expression level with a standard level of polynucleotide expression level, whereby an increase or decrease in the gene expression level compared to the standard is indicative of a disorder.

In still another embodiment, the invention includes a kit for analyzing samples for the presence of proliferative and/or cancerous polynucleotides derived from a test subject. In a general embodiment, the kit includes at least one polynucleotide probe containing a nucleotide sequence that will specifically hybridize with a polynucleotide of the present invention and a suitable container. In a specific embodiment, the kit includes two polynucleotide probes defining an internal region of the polynucleotide of the present invention, where each probe has one strand containing a 31'mer-end internal to the region. In a further embodiment, the probes may be useful as primers for polymerase chain reaction amplification.

Where a diagnosis of a disorder, has already been made according to conventional methods, the present invention is useful as a prognostic indicator, whereby patients exhibiting enhanced or depressed polynucleotide of the present invention expression will experience a worse clinical outcome relative to patients expressing the gene at a level nearer the standard level.

By "measuring the expression level of polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of individuals not having a disorder. As will be appreciated in the art, once a standard polypeptide level or mRNA level is known, it can be used repeatedly as a standard for comparison.

By "biological sample" is intended any biological sample obtained from an individual, body fluid, cell line, tissue culture, or other source which contains the polypeptide of the present invention or mRNA. As indicated, biological samples include body fluids (such as semen, lymph, sera, plasma, urine, synovial fluid and spinal fluid) which contain the polypeptide of the present invention, and other tissue sources found to express the polypeptide of the present invention. Methods for obtaining tissue biopsies and body fluids from mammals are well known in the art. Where the biological sample is to include mRNA, a tissue biopsy is the preferred source.

The method(s) provided above may preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including cancerous diseases and conditions. Such a method is described in U.S. Pat. Nos. 5,858,659 and 5,856,104. The U.S. Patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point (T.sub.m) by 8°–20° C., vs. 4°–16° C. for the DNA/DNA 15-mer duplex. Also, the absence of charge groups in PNA means that hybridization can be done at low ionic strengths and reduce possible interference by salt during the analysis.

The present invention is useful for detecting cancer in mammals. In particular the invention is useful during diagnosis of pathological cell proliferative neoplasias which include, but are not limited to: acute myelogenous leukemias including acute monocytic leukemia, acute myeloblastic leukemia, acute promyelocytic leukemia, acute myelomonocytic leukemia, acute erythroleukemia, acute megakaryocytic leukemia, and acute undifferentiated leukemia, etc.; and chronic myelogenous leukemias including chronic myelomonocytic leukemia, chronic granulocytic leukemia, etc. Preferred mammals include monkeys, apes, cats, dogs, cows, pigs, horses, rabbits and humans. Particularly preferred are humans.

Pathological cell proliferative diseases, disorders, and/or conditions are often associated with inappropriate activation of proto-oncogenes. (Gelmann, E. P. et al., "The Etiology of Acute Leukemia: Molecular Genetics and Viral Oncology," in Neoplastic Diseases of the Blood, Vol 1., Wiernik, P. H. et al. eds., 161–182 (1985)). Neoplasias are now believed to result from the qualitative alteration of a normal cellular gene product, or from the quantitative modification of gene expression by insertion into the chromosome of a viral sequence, by chromosomal translocation of a gene to a more actively transcribed region, or by some other mechanism. (Gelmann et al., supra) It is likely that mutated or altered expression of specific genes is involved in the pathogenesis of some leukemias, among other tissues and cell types. (Gelmann et al., supra) Indeed, the human counterparts of the oncogenes involved in some animal neoplasias have been amplified or translocated in some cases of human leukemia and carcinoma. (Gelmann et al., supra) For example, c-myc expression is highly amplified in the non-lymphocytic leukemia cell line HL-60. When HL-60 cells are chemically induced to stop proliferation, the level of c-myc is found to be downregulated. (International Publication Number WO 91/15580) However, it has been shown that exposure of HL-60 cells to a DNA construct that is complementary to the 5' end of c-myc or c-myb blocks translation of the corresponding mRNAs which downregulates expression of the c-myc or c-myb proteins and causes arrest of cell proliferation and differentiation of the treated cells. (International Publication Number WO 91/15580; Wickstrom et al., Proc. Natl. Acad. Sci. 85:1028 (1988); Anfossi et al., Proc. Natl. Acad. Sci. 86:3379 (1989)). However, the skilled artisan would appreciate the present invention's usefulness would not be limited to treatment of proliferative diseases, disorders, and/or conditions of hematopoietic cells and tissues, in light of the numerous cells and cell types of varying origins which are known to exhibit proliferative phenotypes.

In addition to the foregoing, a polynucleotide can be used to control gene expression through triple helix formation or antisense DNA or RNA. Antisense techniques are discussed, for example, in Okano, J. Neurochem. 56: 560 (1991); "Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxynucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell.

The polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, synovial fluid, amniotic fluid, breast milk, lymph, pulmonary sputum or surfactant, urine, fecal matter, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, polynucleotides of the present invention can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell. Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, polypeptides of the present invention can be used to treat, prevent, and/or diagnose disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor supressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to a polypeptide of the present invention can also be used to treat, prevent, and/or diagnose disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Gene Therapy Methods

Another aspect of the present invention is to gene therapy methods for treating or preventing disorders, diseases and conditions. The gene therapy methods relate to the introduction of nucleic acid (DNA, RNA and antisense DNA or RNA) sequences into an animal to achieve expression of a polypeptide of the present invention. This method requires a polynucleotide which codes for a polypeptide of the invention that operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a polynucleotide of the invention ex vivo, with the engineered cells then being provided to a patient to be treated with the polypeptide. Such methods are well-known in the art. For example, see Belldegrun et al., J. Natl. Cancer Inst., 85:207–216 (1993); Ferrantini et al., Cancer Research, 53:107–1112 (1993); Ferrantini et al., J. Immunology 153: 4604–4615 (1994); Kaido, T., et al., Int. J. Cancer 60: 221–229 (1995); Ogura et al., Cancer Research 50: 5102–5106 (1990); Santodonato, et al., Human Gene Therapy 7:1–10 (1996); Santodonato, et al., Gene Therapy 4:1246–1255 (1997); and Zhang, et al., Cancer Gene Therapy 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the polynucleotide constructs can be delivered by any method that delivers injectable materials to the cells of an animal, such as, injection into the interstitial space of tissues (heart, muscle, skin, lung, liver, and the like). The polynucleotide constructs may be delivered in a pharmaceutically acceptable liquid or aqueous carrier.

In one embodiment, the polynucleotide of the invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotides of the invention can also be delivered in liposome formulations and lipofectin formulations and the like can be prepared by methods well known to those skilled in the art. Such methods are described, for example, in U.S. Pat. Nos.

5,593,972, 5,589,466, and 5,580,859, which are herein incorporated by reference.

The polynucleotide vector constructs of the invention used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of polynucleotide sequence of the invention. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for the polynucleotides of the invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct of the invention can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the polynucleotide constructs of the invention are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA, 84:7413–7416 (1987), which is herein incorporated by reference); mRNA (Malone et al., Proc. Natl. Acad. Sci. USA, 86:6077–6081 (1989), which is herein incorporated by reference); and purified transcription factors (Debs et al., J. Biol. Chem., 265:10189–10192 (1990), which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl Acad. Sci. USA, 84:7413–7416 (1987), which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication NO: WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., Felgner et al., Proc. Natl. Acad. Sci. USA, 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology, 101:512–527 (1983), which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., Biochim. Biophys. Acta, 394:483 (1975); Wilson et al., Cell, 17:77 (1979)); ether injection (Deamer et al., Biochim. Biophys. Acta, 443:629 (1976); Ostro et al., Biochem. Biophys. Res. Commun., 76:836 (1977); Fraley et al., Proc. Natl. Acad. Sci. USA, 76:3348 (1979)); detergent dialysis (Enoch et al., Proc. Natl. Acad. Sci. USA, 76:145 (1979)); and reverse-phase evaporation (REV) (Fraley et al., J. Biol. Chem., 255:10431 (1980); Szoka et al., Proc. Natl. Acad. Sci. USA, 75:145 (1978); Schaefer-Ridder et al., Science, 215:166 (1982)), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding polypeptides of the invention. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy, 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding polypeptides of the invention. Such retroviral vector particles then may be employed, to transduce eukaryotic cells, either in vitro or in vivo. The transduced eukaryotic cells will express polypeptides of the invention.

In certain other embodiments, cells are engineered, ex vivo or in vivo, with polynucleotides of the invention contained in an adenovirus vector. Adenovirus can be manipulated such that it encodes and expresses polypeptides of the invention, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz et al., Am. Rev. Respir. Dis., 109:233–238 (1974)). Finally, adenovirus mediated gene transfer has been demonstrated in a number of instances including transfer of alpha-1-antitrypsin and CFTR to the lungs of cotton rats (Rosenfeld et al., Science, 252:431–434 (1991); Rosenfeld et al., Cell, 68:143–155 (1992)). Furthermore, extensive studies to attempt to establish adenovirus as a causative agent in human cancer were uniformly negative (Green et al. Proc. Natl. Acad. Sci. USA, 76:6606 (1979)).

Suitable adenoviral vectors useful in the present invention are described, for example, in Kozarsky and Wilson, Curr. Opin. Genet. Devel., 3:499–503 (1993); Rosenfeld et al., Cell, 68:143–155 (1992); Engelhardt et al., Human Genet. Ther., 4:759–769 (1993); Yang et al., Nature Genet., 7:362–369 (1994); Wilson et al., Nature, 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, Curr. Topics in Microbiol. Immunol., 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The polynucleotide construct containing polynucleotides of the invention is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct of the invention. These viral particles are then used to transduce eukaryotic cells, either ex vivo or in vivo. The transduced cells will contain the polynucleotide construct integrated into its genome, and will express the desired gene product.

Another method of gene therapy involves operably associating heterologous control regions and endogenous polynucleotide sequences (e.g. encoding the polypeptide sequence of interest) via homologous recombination (see, e.g., U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932–8935 (1989); and Zijlstra et al., Nature, 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

The polynucleotides encoding polypeptides of the present invention may be administered along with other polynucleotides encoding other angiongenic proteins. Angiogenic proteins include, but are not limited to, acidic and basic fibroblast growth factors, VEGF-1, VEGF-2 (VEGF-C), VEGF-3 (VEGF-B), epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding a polypeptide of the invention contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers. (Kaneda et al., Science, 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA, 189:11277–11281(1992), which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian. Therapeutic compositions of the present invention can be administered to any animal, preferably to mammals and birds. Preferred mammals include humans, dogs, cats, mice, rats, rabbits sheep, cattle, horses and pigs, with humans being particularly Biological Activities The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

Immune Activity

Polynucleotides, polypeptides, antibodies, and/or agonists or antagonists of the present invention may be useful in treating, preventing, and/or diagnosing diseases, disorders, and/or conditions of the immune system, by, for example, activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer and some autoimmune diseases, acquired (e.g., by chemotherapy or toxins), or infectious. Moreover, polynucleotides, polypeptides, antibodies, and/or agonists or antagonists of the present invention can be used as a marker or detector of a particular immune system disease or disorder.

Polynucleotides, polypeptides, antibodies, and/or agonists or antagonists of the present invention may be useful in treating, preventing, and/or diagnosing diseases, disorders, and/or conditions of hematopoietic cells. Polynucleotides, polypeptides, antibodies, and/or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g., agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, polynucleotides, polypeptides, antibodies, and/or agonists or antagonists of the present invention could also be used to modulate hemostatic (the stopping of bleeding) or thrombolytic activity (clot formation). For example, by increasing hemostatic or thrombolytic activity, polynucleotides or polypeptides, and/or agonists or antagonists of the present invention could be used to treat or prevent blood coagulation diseases, disorders, and/or conditions (e.g., afibrinogenemia, factor deficiencies), blood platelet diseases, disorders, and/or conditions (e.g., thrombocytopenia), or wounds resulting from trauma, surgery, or other causes. Alternatively, polynucleotides, polypeptides, antibodies, and/or agonists or antagonists of the present invention that can decrease hemostatic or thrombolytic activity could be used to inhibit or dissolve clotting. These molecules could be important in the treatment or prevention of heart attacks (infarction), strokes, or scarring.

The polynucleotides, polypeptides, antibodies, and/or agonists or antagonists of the present invention may be useful in treating, preventing, and/or diagnosing autoimmune disorders. Many autoimmune disorders result from inappropriate recognition of self as foreign material by immune cells. This inappropriate recognition results in an immune response leading to the destruction of the host tissue. Therefore, the administration of polynucleotides and polypeptides of the invention that can inhibit an immune response, particularly the proliferation, differentiation, or chemotaxis of T-cells, may be an effective therapy in preventing autoimmune disorders.

Autoimmune diseases or disorders that may be treated, prevented, and/or diagnosed by polynucleotides, polypeptides, antibodies, and/or agonists or antagonists of the present invention include, but are not limited to, one or more of the following: autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g, IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Autism, Guillain-Barre Syndrome, insulin dependent diabetes mellitis, and autoimmune inflammatory eye, autoimmune thyroiditis, hypothyroidism (i.e., Hashimoto's thyroiditis, systemic lupus erhythematosus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, scleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders.

Additional autoimmune disorders (that are probable) that may be treated, prevented, and/or diagnosed with the compositions of the invention include, but are not limited to, rheumatoid arthritis (often characterized, e.g., by immune complexes in joints), scleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell-mediated adrenal cytotoxicity, infertility (often characterized, e.g., by antispermatozoal antibodies), glomerulonephritis (often characterized, e.g., by glomerular basement membrane antibodies or immune complexes), bullous pemphigoid (often characterized, e.g., by IgG and complement in basement membrane), Sjogren's syndrome (often characterized, e.g., by multiple tissue antibodies, and/or a specific nonhistone ANA (SS-B)), diabetes millitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies).

Additional autoimmune disorders (that are possible) that may be treated, prevented, and/or diagnosed with the compositions of the invention include, but are not limited to, chronic active hepatitis (often characterized, e.g., by smooth muscle antibodies), primary biliary cirrhosis (often characterized, e.g., by mitchondrial antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and IgM antibodies to IgE), and many other inflammatory, granulamatous, degenerative, and atrophic disorders.

In a preferred embodiment, the autoimmune diseases and disorders and/or conditions associated with the diseases and disorders recited above are treated, prevented, and/or diagnosed using for example, antagonists or agonists, polypeptides or polynucleotides, or antibodies of the present invention.

In a preferred embodiment polynucleotides, polypeptides, antibodies, and/or agonists or antagonists of the present invention could be used as an agent to boost immunoresponsiveness among B cell and/or T cell immunodeficient individuals.

B cell immunodeficiencies that may be ameliorated or treated by administering the polypeptides or polynucleotides of the invention, and/or agonists thereof, include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVI) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymophoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

T cell deficiencies that may be ameliorated or treated by administering the polypeptides or polynucleotides of the invention, and/or agonists thereof include, but are not limited to, for example, DiGeorge anomaly, thymic hypoplasia, third and fourth pharyngeal pouch syndrome, 22q 11.2 deletion, chronic mucocutaneous candidiasis, natural killer cell deficiency (NK), idiopathic CD4+ T-lymphocytopenia, immunodeficiency with predominant T cell defect (unspecified), and unspecified immunodeficiency of cell mediated immunity. In specific embodiments, DiGeorge anomaly or conditions associated with DiGeorge anomaly are ameliorated or treated by, for example, administering the polypeptides or polynucleotides of the invention, or antagonists or agonists thereof.

Other immunodeficiencies that may be ameliorated or treated by administering polypeptides or polynucleotides of the invention, and/or agonists thereof, include, but are not limited to, severe combined immunodeficiency (SCID; e.g., X-linked SCID, autosomal SCID, and adenosine deaminase deficiency), ataxia-telangiectasia, Wiskott-Aldrich syndrome, short-limber dwarfism, X-linked lymphoproliferative syndrome (XLP), Nezelof syndrome (e.g., purine nucleoside phosphorylase deficiency), MHC Class II deficiency. In specific embodiments, ataxia-telangiectasia or conditions associated with ataxia-telangiectasia are ameliorated or treated by administering the polypeptides or polynucleotides of the invention, and/or agonists thereof.

In a specific preferred embodiment, rheumatoid arthritis is treated, prevented, and/or diagnosed using polynucleotides, polypeptides, antibodies, and/or agonists or antagonists of the present invention. In another specific preferred embodiment, systemic lupus erythemosus is treated, prevented, and/or diagnosed using polynucleotides, polypeptides, antibodies, and/or agonists or antagonists of the present invention. In another specific preferred embodiment, idiopathic thrombocytopenia purpura is treated, prevented, and/or diagnosed using polynucleotides, polypeptides, antibodies, and/or agonists or antagonists of the present invention. In another specific preferred embodiment IgA nephropathy is treated, prevented, and/or diagnosed using polynucleotides, polypeptides, antibodies, and/or agonists or antagonists of the present invention. In a preferred embodiment, the autoimmune diseases and disorders and/or conditions associated with the diseases and disorders recited above are treated, prevented, and/or diagnosed using antibodies against the protein of the invention.

Similarly, allergic reactions and conditions, such as asthma (particularly allergic asthma) or other respiratory problems, may also be treated, prevented, and/or diagnosed using polypeptides, antibodies, or polynucleotides of the invention, and/or agonists or antagonists thereof. Moreover, these molecules can be used to treat, prevent, and/or diagnose anaphylaxis, hypersensitivity to an antigenic molecule, or blood group incompatibility.

Moreover, inflammatory conditions may also be treated, diagnosed, and/or prevented with polynucleotides, polypeptides, antibodies, and/or agonists or antagonists of the present invention. Such inflammatory conditions include, but are not limited to, for example, respiratory disorders (such as, e.g., asthma and allergy); gastrointestinal disorders (such as, e.g., inflammatory bowel disease); cancers (such as, e.g., gastric, ovarian, lung, bladder, liver, and breast); CNS disorders (such as, e.g., multiple sclerosis, blood-brain barrier permeability, ischemic brain injury and/or stroke, traumatic brain injury, neurodegenerative disorders (such as, e.g., Parkinson's disease and Alzheimer's disease), AIDS-related dementia, and prion disease); cardiovascular disorders (such as, e.g., atherosclerosis, myocarditis, cardiovascular disease, and cardiopulmonary bypass complications); as well as many additional diseases, conditions, and disorders that are characterized by inflammation (such as, e.g., chronic hepatitis (B and C), rheumatoid arthritis, gout, trauma, septic shock, pancreatitis, sarcoidosis, dermatitis, renal ischemia-reperfusion injury, Grave's disease, systemic lupus erythematosis, diabetes mellitus (i.e., type 1 diabetes), and allogenic transplant rejection).

In specific embodiments, polypeptides, antibodies, or polynucleotides of the invention, and/or agonists or antagonists thereof, are useful to treat, diagnose, and/or prevent transplantation rejections, graft-versus-host disease, autoimmune and inflammatory diseases (e.g., immune complex-induced vasculitis, glomerulonephritis, hemolytic anemia, myasthenia gravis, type II collagen-induced arthritis, experimental allergic and hyperacute xenograft rejection, rheumatoid arthritis, and systemic lupus erythematosus (SLE). Organ rejection occurs by host immune cell destruction of the transplanted tissue through an immune response. Similarly, an immune response is also involved in GVHD, but, in this case, the foreign transplanted immune cells destroy the host tissues. Polypeptides, antibodies, or polynucleotides of the invention, and/or agonists or antagonists thereof, that inhibit an immune response, particularly the activation, proliferation, differentiation, or chemotaxis of T-cells, may be an effective therapy in preventing organ rejection or GVHD.

Similarly, polynucleotides, polypeptides, antibodies, and/or agonists or antagonists of the present invention may also be used to modulate and/or diagnose inflammation. For example, since polypeptides, antibodies, or polynucleotides of the invention, and/or agonists or antagonists of the invention may inhibit the activation, proliferation and/or differentiation of cells involved in an inflammatory response, these molecules can be used to treat, diagnose, or prognose, inflammatory conditions, both chronic and acute conditions, including, but not limited to, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, and resulting from over production of cytokines (e.g., TNF or IL-1.).

Polypeptides, antibodies, polynucleotides and/or agonists or antagonists of the invention can be used to treat, detect, and/or prevent infectious agents. For example, by increasing the immune response, particularly increasing the proliferation activation and/or differentiation of B and/or T cells, infectious diseases may be treated, detected, and/or prevented. The immune response may be increased by either enhancing an existing immune response, or by initiating a new immune response. Alternatively, polynucleotides, polypeptides, antibodies, and/or agonists or antagonists of the present invention may also directly inhibit the infectious agent (refer to section of application listing infectious agents, etc), without necessarily eliciting an immune response.

Additional preferred embodiments of the invention include, but are not limited to, the use of polypeptides, antibodies, polynucleotides and/or agonists or antagonists in the following applications:

Administration to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production (e.g., IgG, IgA, IgM, and IgE), and/or to increase an immune response.

Administration to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO/9634096, WO/9633735, and WO/9110741.

A vaccine adjuvant that enhances immune responsiveness to specific antigen.

An adjuvant to enhance tumor-specific immune responses.

An adjuvant to enhance anti-viral immune responses. Anti-viral immune responses that may be enhanced using the compositions of the invention as an adjuvant, include virus and virus associated diseases or symptoms described herein or otherwise known in the art. In specific embodiments, the compositions of the invention are used as an adjuvant to enhance an immune response to a virus, disease, or symptom selected from the group consisting of: AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of: HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex, and yellow fever.

An adjuvant to enhance anti-bacterial or anti-fungal immune responses. Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of: tetanus, Diphtheria, botulism, and meningitis type B. In another specific embodiment, the compositions of the invention are used as an adjuvant to enhance an immune response to a bacteria or fungus, disease, or symptom selected from the group consisting of: *Vibrio cholerae, Mycobacterium leprae, Salmonella typhi, Salmonella paratyphi, Meisseria meningitidis, Streptococcus pneumoniae*, Group B streptococcus, Shigella spp., Enterotoxigenic *Escherichia coli*, Enterohemorrhagic *E. coli, Borrelia burgdorferi*, and Plasmodium (malaria).

An adjuvant to enhance anti-parasitic immune responses. Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to Plasmodium (malaria).

As a stimulator of B cell responsiveness to pathogens.

As an activator of T cells.

As an agent that elevates the immune status of an individual prior to their receipt of immunosuppressive therapies.

As an agent to induce higher affinity antibodies.

As an agent to increase serum immunoglobulin concentrations.

As an agent to accelerate recovery of immunocompromised individuals.

As an agent to boost immunoresponsiveness among aged populations.

As an immune system enhancer prior to, during, or after bone marrow transplant and/or other transplants (e.g., allogeneic or xenogeneic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

As an agent to boost immunoresponsiveness among individuals having an acquired loss of B cell function. Conditions resulting in an acquired loss of B cell function that may be ameliorated or treated by administering the polypeptides, antibodies, polynucleotides and/or agonists or antagonists thereof, include, but are not limited to, HIV Infection, AIDS, bone marrow transplant, and B cell chronic lymphocytic leukemia (CLL).

As an agent to boost immunoresponsiveness among individuals having a temporary immune deficiency. Conditions resulting in a temporary immune deficiency that may be ameliorated or treated by administering the polypeptides, antibodies, polynucleotides and/or agonists or antagonists thereof, include, but are not limited to, recovery from viral infections (e.g., influenza), conditions associated with malnutrition, recovery from infectious mononucleosis, or conditions associated with stress, recovery from measles, recovery from blood transfusion, recovery from surgery.

As a regulator of antigen presentation by monocytes, dendritic cells, and/or B-cells. In one embodiment, polynucleotides, polypeptides, antibodies, and/or agonists or antagonists of the present invention enhance antigen presentation or antagonizes antigen presentation in vitro or in vivo. Moreover, in related embodiments, said enhancement or antagonization of antigen presentation may be useful as an anti-tumor treatment or to modulate the immune system.

As an agent to direct an individuals immune system towards development of a humoral response (i.e. TH2) as opposed to a TH1 cellular response.

As a means to induce tumor proliferation and thus make it more susceptible to anti-neoplastic agents. For example, multiple myeloma is a slowly dividing disease and is thus refractory to virtually all anti-neoplastic regimens. If these cells were forced to proliferate more rapidly their susceptibility profile would likely change.

As a stimulator of B cell production in pathologies such as AIDS, chronic lymphocyte disorder and/or Common Variable Immunodificiency.

As a therapy for generation and/or regeneration of lymphoid tissues following surgery, trauma or genetic defect.

As a gene-based therapy for genetically inherited disorders resulting in immuno-incompetence such as observed among SCID patients.

As an antigen for the generation of antibodies to inhibit or enhance immune mediated responses against polypeptides of the invention.

As a means of activating T cells.

As a means of activating monocytes/macrophages to defend against parasitic diseases that effect monocytes such as Leshmania.

As pretreatment of bone marrow samples prior to transplant. Such treatment would increase B cell representation and thus accelerate recover.

As a means of regulating secreted cytokines that are elicited by polypeptides of the invention.

Additionally, polypeptides or polynucleotides of the invention, and/or agonists thereof, may be used to treat or prevent IgE-mediated allergic reactions. Such allergic reactions include, but are not limited to, asthma, rhinitis, and eczema.

All of the above described applications as they may apply to veterinary medicine.

Antagonists of the invention include, for example, binding and/or inhibitory antibodies, antisense nucleic acids, or ribozymes. These would be expected to reverse many of the activities of the ligand described above as well as find clinical or practical application as:

A means of blocking various aspects of immune responses to foreign agents or self. Examples include autoimmune disorders such as lupus, and arthritis, as well as immunoresponsiveness to skin allergies, inflammation, bowel disease, injury and pathogens.

A therapy for preventing the B cell proliferation and Ig secretion associated with autoimmune diseases such as idiopathic thrombocytopenic purpura, systemic lupus erythramatosus and MS.

An inhibitor of B and/or T cell migration in endothelial cells. This activity disrupts tissue architecture or cognate responses and is useful, for example in disrupting immune responses, and blocking sepsis.

An inhibitor of graft versus host disease or transplant rejection.

A therapy for B cell and/or T cell malignancies such as ALL, Hodgkins disease, non-Hodgkins lymphoma, Chronic lymphocyte leukemia, plasmacytomas, multiple myeloma, Burkitt's lymphoma, and EBV-transformed diseases.

A therapy for chronic hypergammaglobulinemeia evident in such diseases as monoclonalgammopathy of undetermined significance (MGUS), Waldenstrom's disease, related idiopathic monoclonalgammopathies, and plasmacytomas.

A therapy for decreasing cellular proliferation of Large B-cell Lymphomas.

A means of decreasing the involvement of B cells and Ig associated with Chronic Myelogenous Leukemia.

An immunosuppressive agent(s).

Polynucleotides, polypeptides, antibodies, and/or agonists or antagonists of the present invention may be used to modulate IgE concentrations in vitro or in vivo.

In another embodiment, administration of polypeptides, antibodies, polynucleotides and/or agonists or antagonists of the invention, may be used to treat or prevent IgE-mediated allergic reactions including, but not limited to, asthma, rhinitis, and eczema.

The agonists and antagonists may be employed in a composition with a pharmaceutically acceptable carrier, e.g., as described herein.

The agonists or antagonists may be employed for instance to inhibit polypeptide chemotaxis and activation of macrophages and their precursors, and of neutrophils, basophils, B lymphocytes and some T-cell subsets, e.g., activated and CD8 cytotoxic T cells and natural killer cells, in certain auto-immune and chronic inflammatory and infective diseases. Examples of autoimmune diseases are described herein and include multiple sclerosis, and insulin-dependent diabetes. The antagonists or agonists may also be employed to treat infectious diseases including silicosis, sarcoidosis, idiopathic pulmonary fibrosis by, for example, preventing the recruitment and activation of mononuclear phagocytes. They may also be employed to treat idiopathic hypereosinophilic syndrome by, for example, preventing eosinophil production and migration. The antagonists or agonists or may also be employed for treating atherosclerosis, for example, by preventing monocyte infiltration in the artery wall.

Antibodies against polypeptides of the invention may be employed to treat ARDS.

Agonists and/or antagonists of the invention also have uses in stimulating wound and tissue repair, stimulating angiogenesis, stimulating the repair of vascular or lymphatic diseases or disorders. Additionally, agonists and antagonists of the invention may be used to stimulate the regeneration of mucosal surfaces.

In a specific embodiment, polynucleotides or polypeptides, and/or agonists thereof are used to treat or prevent a disorder characterized by primary or acquired immunodeficiency, deficient serum immunoglobulin production, recurrent infections, and/or immune system dysfunction. Moreover, polynucleotides or polypeptides, and/or agonists thereof may be used to treat or prevent infections of the joints, bones, skin, and/or parotid glands, blood-borne infections (e.g., sepsis, meningitis, septic arthritis, and/or osteomyelitis), autoimmune diseases (e.g., those disclosed herein), inflammatory disorders, and malignancies, and/or any disease or disorder or condition associated with these infections, diseases, disorders and/or malignancies) including, but not limited to, CVID, other primary immune deficiencies, HIV disease, CLL, recurrent bronchitis, sinusitis, otitis media, conjunctivitis, pneumonia, hepatitis, meningitis, herpes zoster (e.g., severe herpes zoster), and/or pneumocystis carnii.

In another embodiment, polynucleotides, polypeptides, antibodies, and/or agonists or antagonists of the present invention are used to treat, and/or diagnose an individual having common variable immunodeficiency disease ("CVID"; also known as "acquired agammaglobulinemia" and "acquired hypogammaglobulinemia") or a subset of this disease.

In a specific embodiment, polynucleotides, polypeptides, antibodies, and/or agonists or antagonists of the present invention may be used to treat, diagnose, and/or prevent (1) cancers or neoplasms and (2) autoimmune cell or tissue-related cancers or neoplasms. In a preferred embodiment, polynucleotides, polypeptides, antibodies, and/or agonists or antagonists of the present invention conjugated to a toxin or a radioactive isotope, as described herein, may be used to treat, diagnose, and/or prevent acute myelogeneous leukemia. In a further preferred embodiment, polynucleotides, polypeptides, antibodies, and/or agonists or antagonists of the present invention conjugated to a toxin or a radioactive isotope, as described herein, may be used to treat, diagnose, and/or prevent, chronic myelogeneous leukemia, multiple myeloma, non-Hodgkins lymphoma, and/or Hodgkins disease.

In another specific embodiment, polynucleotides or polypeptides, and/or agonists or antagonists of the invention may be used to treat, diagnose, prognose, and/or prevent selective IgA deficiency, myeloperoxidase deficiency, C2 deficiency, ataxia-telangiectasia, DiGeorge anomaly, common variable immunodeficiency (CVI), X-linked agammaglobulinemia, severe combined immunodeficiency (SCID), chronic granulomatous disease (CGD), and Wiskott-Aldrich syndrome.

Examples of autoimmune disorders that can be treated or detected are described above and also include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

In a preferred embodiment, the autoimmune diseases and disorders and/or conditions associated with the diseases and disorders recited above are treated, prognosed, prevented, and/or diagnosed using antibodies against the polypeptide of the invention.

As an agent to boost immunoresponsiveness among B cell immunodeficient individuals, such as, for example, an individual who has undergone a partial or complete splenectomy.

Additionally, polynucleotides, polypeptides, and/or antagonists of the invention may affect apoptosis, and therefore, would be useful in treating a number of diseases associated with increased cell survival or the inhibition of apoptosis. For example, diseases associated with increased cell survival or the inhibition of apoptosis that could be treated or detected by polynucleotides, polypeptides, and/or antagonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, polynucleotides, polypeptides, and/or antagonists of the invention are used to inhibit growth, progression, and/or metastisis of cancers, in particular those listed above.

Additional diseases or conditions associated with increased cell survival that could be treated or detected by polynucleotides, polypeptides, and/or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated or detected by polynucleotides, polypeptides, and/or antagonists of the invention, include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Hyperproliferative diseases and/or disorders that could be detected and/or treated by polynucleotides, polypeptides, and/or antagonists of the invention, include, but are not limited to neoplasms located in the: liver, abdomen, bone, breast, digestive system, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by polynucleotides, polypeptides, and/or antagonists of the invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Hyperproliferative Disorders

A polynucleotides or polypeptides, or agonists or antagonists of the invention can be used to treat, prevent, and/or diagnose hyperproliferative diseases, disorders, and/or conditions, including neoplasms. A polynucleotides or polypeptides, or agonists or antagonists of the present invention may inhibit the proliferation of the disorder through direct or indirect interactions. Alternatively, a polynucleotides or polypeptides, or agonists or antagonists of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative diseases, disorders, and/or conditions can be treated, prevented, and/or diagnosed. This immune response may be increased by either enhancing an existing immune response, or by initiating a new immune response. Alternatively, decreasing an immune response may also be a method of treating, preventing, and/or diagnosing hyperproliferative diseases, disorders, and/or conditions, such as a chemotherapeutic agent.

Examples of hyperproliferative diseases, disorders, and/or conditions that can be treated, prevented, and/or diagnosed by polynucleotides or polypeptides, or agonists or antagonists of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative diseases, disorders, and/or conditions can also be treated, prevented, and/or diagnosed by a polynucleotides or polypeptides, or agonists or antagonists of the present invention. Examples of such hyperproliferative diseases, disorders, and/or conditions include, but are not limited to: hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating or preventing cell proliferative diseases, disorders, and/or conditions by inserting into an abnormally proliferating cell a polynucleotide of the present invention, wherein said polynucleotide represses said expression.

Another embodiment of the present invention provides a method of treating or preventing cell-proliferative diseases, disorders, and/or conditions in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the poynucleotides of the present invention is inserted into cells to be treated utilizing a retrovirus, or more preferably an adenoviral vector (See G J. Nabel, et. al., PNAS1999 96: 324–326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to, transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating, preventing, and/or diagnosing one or more of the described diseases, disorders, and/or conditions. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating, preventing, and/or diagnosing a subject having or developing cell proliferative and/or differentiation diseases, disorders, and/or conditions as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of diseases, disorders, and/or conditions related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5\times10^{-6}$ M, $10^{-6}$ M, $5\times10^{-7}$ M, $10^{-7}$ M, $5\times10^{-8}$ M $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Moreover, polypeptides of the present invention are useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph I B, et al. J Natl Cancer Inst, 90(21):1648–53 (1998), which is hereby incorporated by reference). Antibodies directed to polypeptides or polynucleotides of the present invention may also result in inhibition of angiogenesis directly, or indirectly (See Witte L, et al., Cancer Metastasis Rev. 17(2):155–61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et. al., Eur J Biochem 254(3):439–59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuviants, such as apoptonin, galectins, thioredoxins, anti-inflammatory proteins (See for example, Mutat Res 400 (1–2):447–55 (1998), Med Hypotheses.50(5):423–33 (1998), Chem Biol Interact. Apr 24;111–112:23–34 (1998), J Mol Med.76(6):402–12 (1998), Int J Tissue React;20(1): 3–15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewere herein, or indirectly, such as activating the expression of proteins known to inhibit metastasis, for example alpha 4 integrins, (See, e.g., Curr Top Microbiol Immunol 1998;231:125–41, which is hereby incorporated by reference). Such therapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodes associated with heterologous polypeptides, heterologous nucleic acids, toxins, or prodrugs) to targeted cells expressing the polypeptide of the present invention. Polypeptides or polypeptide antibodes of the invention may be associated with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Cardiovascular Disorders

Polynucleotides or polypeptides, or agonists or antagonists of the invention may be used to treat, prevent, and/or diagnose cardiovascular diseases, disorders, and/or conditions, including peripheral artery disease, such as limb ischemia.

Cardiovascular diseases, disorders, and/or conditions include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular diseases, disorders, and/or conditions also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular diseases, disorders, and/or conditions include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Polynucleotides or polypeptides, or agonists or antagonists of the invention, are especially effective for the treatment of critical limb ischemia and coronary disease.

Polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides of the invention may be administered as part of a Therapeutic, described in more detail below. Methods of delivering polynucleotides of the invention are described in more detail herein.

Anti-Angiogenesis Activity

The naturally occurring balance between endogenous stimulators and inhibitors of angiogenesis is one in which inhibitory influences predominate. Rastinejad et al., *Cell* 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye diseases, disorders, and/or conditions, and psoriasis. See, e.g., reviews by Moses et al., *Biotech.* 9:630–634 (1991); Folkman et al., *N. Engl. J Med.,* 333:1757–1763 (1995); Auerbach et al., *J. Microvasc. Res.* 29:401–411 (1985); Folkman, Advances in Cancer Research, eds. Klein and Weinhouse, Academic Press, New York, pp. 175–203 (1985); Patz, *Am. J. Opthalmol.* 94:715–743 (1982); and Folkman et al., Science 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442–447 (1987).

The present invention provides for treatment of diseases, disorders, and/or conditions associated with neovascularization by administration of the polynucleotides and/or polypeptides of the invention, as well as agonists or antagonists of the present invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)).Thus, the present invention provides a method of treating, preventing, and/or diagnosing an angiogenesis-related disease and/or disorder, comprising administering to an individual in need thereof a therapeutically effective amount of a polynucleotide, polypeptide, antagonist and/or agonist of the invention. For example, polynucleotides, polypeptides, antagonists and/or agonists may be utilized in a variety of additional methods in order to therapeutically treator prevent a cancer or tumor. Cancers which may be treated, prevented, and/or diagnosed with polynucleotides, polypeptides, antagonists and/or agonists include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias. For example, polynucleotides, polypeptides, antagonists and/or agonists may be delivered topically, in order to treat or prevent cancers such as skin cancer, head and neck tumors, breast tumors, and Kaposi's sarcoma.

Within yet other aspects, polynucleotides, polypeptides, antagonists and/or agonists may be utilized to treat superficial forms of bladder cancer by, for example, intravesical administration. Polynucleotides, polypeptides, antagonists and/or agonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Polynucleotides, polypeptides, antagonists and/or agonists may be useful in treating, preventing, and/or diagnosing other diseases, disorders, and/or conditions, besides cancers, which involve angiogenesis. These diseases, disorders, and/or conditions include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention methods are provided for treating, preventing, and/or diagnosing hypertrophic scars and keloids, comprising the step of administering a polynucleotide, polypeptide, antagonist and/or agonist of the invention to a hypertrophic scar or keloid.

Within one embodiment of the present invention polynucleotides, polypeptides, antagonists and/or agonists are directly injected into a hypertrophic scar or keloid, in order to prevent the progression of these lesions. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development. As noted above, the present invention also provides methods for treating, preventing, and/or diagnosing neovascular diseases of the eye, including for example, corneal neovascularization, neovascular glaucoma, proliferative diabetic retinopathy, retrolental fibroplasia and macular degeneration.

Moreover, Ocular diseases, disorders, and/or conditions associated with neovascularization which can be treated, prevented, and/or diagnosed with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704–710 (1978) and Gartner et al., *Surv. Ophthal.* 22:291–312 (1978).

Thus, within one aspect of the present invention methods are provided for treating or preventing neovascular diseases of the eye such as corneal neovascularization (including corneal graft neovascularization), comprising the step of administering to a patient a therapeutically effective amount of a compound (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of diseases, disorders, and/or conditions can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali bums, trauma, inflammation (of any cause), toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a muco-adhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2–3 times per year. A steroid could also be added to the injection solution to reduce inflammation resulting from the injection itself.

Within another aspect of the present invention, methods are provided for treating or preventing neovascular glaucoma, comprising the step of administering to a patient a therapeutically effective amount of a polynucleotide, polypeptide, antagonist and/or agonist to the eye, such that the formation of blood vessels is inhibited. In one embodiment, the compound may be administered topically to the eye in order to treat or prevent early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating or preventing proliferative diabetic retinopathy, comprising the step of administering to a patient a therapeutically effective amount of a polynucleotide, polypeptide, antagonist and/or agonist to the eyes, such that the formation of blood vessels is inhibited.

Within particularly preferred embodiments of the invention, proliferative diabetic retinopathy may be treated by injection into the aqueous humor or the vitreous, in order to increase the local concentration of the polynucleotide, polypeptide, antagonist and/or agonist in the retina. Preferably, this treatment should be initiated prior to the acquisition of severe disease requiring photocoagulation.

Within another aspect of the present invention, methods are provided for treating or preventing retrolental fibroplasia, comprising the step of administering to a patient a therapeutically effective amount of a polynucleotide, polypeptide, antagonist and/or agonist to the eye, such that the formation of blood vessels is inhibited. The compound may be administered topically, via intravitreous injection and/or via intraocular implants.

Additionally, diseases, disorders, and/or conditions which can be treated, prevented, and/or diagnosed with the polynucleotides, polypeptides, agonists and/or agonists include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, diseases, disorders, and/or conditions and/or states, which can be treated, prevented, and/or diagnosed with the polynucleotides, polypeptides, agonists and/or agonists include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (*Rochele minalia quintosa*), ulcers (*Helicobacter pylori*), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. Polynucleotides, polypeptides, agonists and/or agonists may also be used in controlling menstruation or administered as either a peritoneal lavage fluid or for peritoneal implantation in the treatment of endometriosis.

Polynucleotides, polypeptides, agonists and/or agonists of the present invention may be incorporated into surgical sutures in order to prevent stitch granulomas.

Polynucleotides, polypeptides, agonists and/or agonists may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiogenesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a polynucleotide, polypeptide, agonist and/or agonist to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention, polynucleotides, polypeptides, agonists and/or agonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The polynucleotides, polypeptides, agonists and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22–26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321–17326, 1992); Chymostatin (Tomkinson et al., Biochem J. 286:475–480, 1992); Cyclodextrin Tetradecasulfate; Eponemycin; Camptothecin; Fumagillin (Ingber et al., Nature 348:555–557, 1990); Gold Sodium Thiomalate ("GST"; Matsubara and Ziff, J. Clin. Invest. 79:1440–1446, 1987); anticollagenase-serum; alpha2-antiplasmin (Holmes et al., J. Biol. Chem. 262(4): 1659–1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312–316, 1992); Thalidomide; Angostatic steroid; AGM-1470; carboxynaminolmidazole; and metalloproteinase inhibitors such as BB94.

Diseases at the Cellular Level

Diseases associated with increased cell survival or the inhibition of apoptosis that could be treated, prevented, and/or diagnosed by the polynucleotides or polypeptides and/or antagonists or agonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, the polynucleotides or polypeptides, and/or agonists or antagonists of the invention are used to inhibit growth, progression, and/or metasis of cancers, in particular those listed above.

Additional diseases or conditions associated with increased cell survival that could be treated, prevented or diagnosed by the polynucleotides or polypeptides, or agonists or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated, prevented, and/or diagnosed by the polynucleotides or polypeptides, and/or agonists or antagonists of the invention, include AIDS; neurodegenerative diseases, disorders, and/or conditions (such as Alzheimer's disease, Parkinson's disease, Amyotrophic lateral sclerosis, Retinitis pigmentosa, Cerebellar degeneration and brain tumor or prior associated disease); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing the polynucleotides or polypeptides, and/or agonists or antagonists of the invention, for therapeutic purposes, for example, to stimulate epithelial cell proliferation and basal keratinocytes for the purpose of wound healing, and to stimulate hair follicle production and healing of dermal wounds. Polynucleotides or polypeptides, as well as agonists or antagonists of the invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, bums resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. Polynucleotides or polypeptides, and/or agonists or antagonists of the invention, could be used to promote dermal reestablishment subsequent to dermal loss The polynucleotides or polypeptides, and/or agonists or antagonists of the invention, could be used to increase the adherence of skin grafts to a wound bed and to stimulate re-epithelialization from the wound bed. The following are a non-exhaustive list of grafts that polynucleotides or polypeptides, agonists or antagonists of the invention, could be used to increase adherence to a wound bed: autografts, artificial skin, allografts, autodermic graft, autoepdermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. The polynucleotides or polypeptides, and/or agonists or antagonists of the invention, can be used to promote skin strength and to improve the appearance of aged skin.

It is believed that the polynucleotides or polypeptides, and/or agonists or antagonists of the invention, will also produce changes in hepatocyte proliferation, and epithelial cell proliferation in the lung, breast, pancreas, stomach, small intesting, and large intestine. The polynucleotides or polypeptides, and/or agonists or antagonists of the invention, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. The polynucleotides or polypeptides, and/or agonists or antagonists of the invention, may promote proliferation of endothelial cells, keratinocytes, and basal keratinocytes.

The polynucleotides or polypeptides, and/or agonists or antagonists of the invention, could also be used to reduce the side effects of gut toxicity that result from radiation, chemotherapy treatments or viral infections. The polynucleotides or polypeptides, and/or agonists or antagonists of the invention, may have a cytoprotective effect on the small intestine mucosa. The polynucleotides or polypeptides, and/or agonists or antagonists of the invention, may also stimulate healing of mucositis (mouth ulcers) that result from chemotherapy and viral infections.

The polynucleotides or polypeptides, and/or agonists or antagonists of the invention, could further be used in full regeneration of skin in full and partial thickness skin defects, including burns, (i.e., repopulation of hair follicles, sweat glands, and sebaceous glands), treatment of other skin defects such as psoriasis. The polynucleotides or polypeptides, and/or agonists or antagonists of the invention, could be used to treat epidermolysis bullosa, a defect in adherence of the epidermis to the underlying dermis which results in frequent, open and painful blisters by accelerating reepithelialization of these lesions. The polynucleotides or polypeptides, and/or agonists or antagonists of the invention, could also be used to treat gastric and doudenal ulcers and help heal by scar formation of the mucosal lining and regeneration of glandular mucosa and duodenal mucosal lining more rapidly. Inflammatory bowel diseases, such as Crohn's disease and ulcerative colitis, are diseases which result in destruction of the mucosal surface of the small or large intestine, respectively. Thus, the polynucleotides or polypeptides, and/or agonists or antagonists of the invention, could be used to promote the resurfacing of the mucosal surface to aid more rapid healing and to prevent progression of inflammatory bowel disease. Treatment with the polynucleotides or polypeptides, and/or agonists or antagonists of the invention, is expected to have a significant effect on the production of mucus throughout the gastrointestinal tract and could be used to protect the intestinal mucosa from injurious substances that are ingested or following surgery. The polynucleotides or polypeptides, and/or agonists or antagonists of the invention, could be used to treat diseases associate with the under expression of the polynucleotides of the invention.

Moreover, the polynucleotides or polypeptides, and/or agonists or antagonists of the invention, could be used to prevent and heal damage to the lungs due to various pathological states. A growth factor such as the polynucleotides or polypeptides, and/or agonists or antagonists of the invention, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated, prevented, and/or diagnosed using the polynucleotides or polypeptides, and/or agonists or antagonists of the invention. Also, the polynucleotides or polypeptides, and/or agonists or antagonists of the invention, could be used to stimulate the proliferation of and differentiation of type II pneumocytes, which may help treat or prevent disease such as hyaline membrane diseases, such as infant respiratory distress syndrome and bronchopulmonary displasia, in premature infants.

The polynucleotides or polypeptides, and/or agonists or antagonists of the invention, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, the polynucleotides or polypeptides, and/or agonists or antagonists of the invention, could be used treat or prevent the onset of diabetes mellitus. In patients with newly diagnosed Types I and II diabetes, where some islet cell function remains, the polynucleotides or polypeptides, and/or agonists or antagonists of the invention, could be used to maintain the islet function so as to alleviate, delay or prevent permanent manifestation of the disease. Also, the polynucleotides or polypeptides, and/or agonists or antagonists of the invention, could be used as an auxiliary in islet cell transplantation to improve or promote islet cell function.

Neurological Diseases

Nervous system diseases, disorders, and/or conditions, which can be treated, prevented, and/or diagnosed with the compositions of the invention (e.g., polypeptides, polynucleotides, and/or agonists or antagonists), include, but are not limited to, nervous system injuries, and diseases, disorders, and/or conditions which result in either a disconnection of axons, a diminution or degeneration of neurons, or demyelination. Nervous system lesions which may be treated, prevented, and/or diagnosed in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a preferred embodiment, the polypeptides, polynucleotides, or agonists or antagonists of the invention are used to protect neural cells from the damaging effects of cerebral hypoxia. According to this embodiment, the compositions of the invention are used to treat, prevent, and/or diagnose neural cell injury associated with cerebral hypoxia. In one aspect of this embodiment, the polypeptides, polynucleotides, or agonists or antagonists of the invention are used to treat, prevent, and/or diagnose neural cell injury associated with cerebral ischemia. In another aspect of this embodiment, the polypeptides, polynucleotides, or agonists or antagonists of the invention are used to treat, prevent, and/or diagnose neural cell injury associated with cerebral infarction. In another aspect of this embodiment, the polypeptides, polynucleotides, or agonists or antagonists of the invention are used to treat, prevent, and/or diagnose or prevent neural cell injury associated with a stroke. In a further aspect of this embodiment, the polypeptides, polynucleotides, or agonists or antagonists of the invention are used to treat, prevent, and/or diagnose neural cell injury associated with a heart attack.

The compositions of the invention which are useful for treating or preventing a nervous system disorder may be selected by testing for biological activity in promoting the survival or differentiation of neurons. For example, and not by way of limitation, compositions of the invention which elicit any of the following effects may be useful according to the invention: (1) increased survival time of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, the method set forth in Arakawa et al. (J. Neurosci. 10:3507–3515 (1990)); increased sprouting of neurons may be detected by methods known in the art, such as, for example, the methods set forth in Pestronk et al. (Exp. Neurol. 70:65–82 (1980)) or Brown et al. (Ann. Rev. Neurosci. 4:17–42 (1981)); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron diseases, disorders, and/or conditions that may be treated, prevented, and/or diagnosed according to the invention include, but are not limited to, diseases, disorders, and/or conditions such as infarction, infection, exposure to toxin, trauma, surgical damage, degenerative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Further, polypeptides or polynucleotides of the invention may play a role in neuronal survival; synapse formation; conductance; neural differentiation, etc. Thus, compositions of the invention (including polynucleotides, polypeptides, and agonists or antagonists) may be used to diagnose and/or treat or prevent diseases or disorders associated with these roles, including, but not limited to, learning and/or cognition disorders. The compositions of the invention may also be useful in the treatment or prevention of neurodegenerative disease states and/or behavioural disorders. Such neurodegenerative disease states and/or behavioral disorders include, but are not limited to, Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, compositions of the invention may also play a role in the treatment, prevention and/or detection of developmental disorders associated with the developing embryo, or sexually-linked disorders.

Additionally, polypeptides, polynucleotides and/or agonists or antagonists of the invention, may be useful in protecting neural cells from diseases, damage, disorders, or injury, associated with cerebrovascular disorders including, but not limited to, carotid artery diseases (e.g., carotid artery thrombosis, carotid stenosis, or Moyamoya Disease), cerebral amyloid angiopathy, cerebral aneurysm, cerebral anoxia, cerebral arteriosclerosis, cerebral arteriovenous malformations, cerebral artery diseases, cerebral embolism and thrombosis (e.g., carotid artery thrombosis, sinus thrombosis, or Wallenberg's Syndrome), cerebral hemorrhage (e.g., epidural or subdural hematoma, or subarachnoid hemorrhage), cerebral infarction, cerebral ischemia (e.g., transient cerebral ischemia, Subclavian Steal Syndrome, or vertebrobasilar insufficiency), vascular dementia (e.g., multi-infarct), leukomalacia, periventricular, and vascular headache (e.g., cluster headache or migraines).

In accordance with yet a further aspect of the present invention, there is provided a process for utilizing polynucleotides or polypeptides, as well as agonists or antagonists of the present invention, for therapeutic purposes, for example, to stimulate neurological cell proliferation and/or differentiation. Therefore, polynucleotides, polypeptides, agonists and/or antagonists of the invention may be used to treat and/or detect neurologic diseases. Moreover, polynucleotides or polypeptides, or agonists or antagonists of the invention, can be used as a marker or detector of a particular nervous system disease or disorder.

Examples of neurologic diseases which can be treated or detected with polynucleotides, polypeptides, agonists, and/or antagonists of the present invention include brain diseases, such as metabolic brain diseases which includes phenylketonuria such as maternal phenylketonuria, pyruvate carboxylase deficiency, pyruvate dehydrogenase complex deficiency, Wernicke's Encephalopathy, brain edema, brain neoplasms such as cerebellar neoplasms which include infratentorial neoplasms, cerebral ventricle neoplasms such as choroid plexus neoplasms, hypothalamic neoplasms, supratentorial neoplasms, canavan disease, cerebellar diseases such as cerebellar ataxia which include spinocerebellar degeneration such as ataxia telangiectasia, cerebellar dyssynergia, Friederich's Ataxia, Machado-Joseph Disease, olivopontocerebellar atrophy, cerebellar neoplasms such as infratentorial neoplasms, diffuse cerebral sclerosis such as encephalitis periaxialis, globoid cell leukodystrophy, metachromatic leukodystrophy and subacute sclerosing panencephalitis.

Additional neurologic diseases which can be treated or detected with polynucleotides, polypeptides, agonists, and/or antagonists of the present invention include cerebrovascular disorders (such as carotid artery diseases which include carotid artery thrombosis, carotid stenosis and Moyamoya Disease), cerebral amyloid angiopathy, cerebral aneurysm, cerebral anoxia, cerebral arteriosclerosis, cerebral arteriovenous malformations, cerebral artery diseases, cerebral embolism and thrombosis such as carotid artery thrombosis, sinus thrombosis and Wallenberg's Syndrome, cerebral hemorrhage such as epidural hematoma, subdural hematoma and subarachnoid hemorrhage, cerebral infarction, cerebral ischemia such as transient cerebral ischemia, Subclavian Steal Syndrome and vertebrobasilar insufficiency, vascular dementia such as multi-infarct dementia, periventricular leukomalacia, vascular headache such as cluster headache and migraine.

Additional neurologic diseases which can be treated or detected with polynucleotides, polypeptides, agonists, and/or antagonists of the present invention include dementia such as AIDS Dementia Complex, presenile dementia such as Alzheimer's Disease and Creutzfeldt-Jakob Syndrome, senile dementia such as Alzheimer's Disease and progressive supranuclear palsy, vascular dementia such as multi-infarct dementia, encephalitis which include encephalitis periaxialis, viral encephalitis such as epidemic encephalitis, Japanese Encephalitis, St. Louis Encephalitis, tick-borne encephalitis and West Nile Fever, acute disseminated encephalomyelitis, meningoencephalitis such as uveomeningoencephalitic syndrome, Postencephalitic Parkinson Disease and subacute sclerosing panencephalitis, encephalomalacia such as periventricular leukomalacia, epilepsy such as generalized epilepsy which includes infantile spasms, absence epilepsy, myoclonic epilepsy which includes MERRF Syndrome, tonic-clonic epilepsy, partial epilepsy such as complex partial epilepsy, frontal lobe epilepsy and temporal lobe epilepsy, post-traumatic epilepsy, status epilepticus such as Epilepsia Partialis Continua, and Hallervorden-Spatz Syndrome.

Additional neurologic diseases which can be treated or detected with polynucleotides, polypeptides, agonists, and/or antagonists of the present invention include hydrocephalus such as Dandy-Walker Syndrome and normal pressure hydrocephalus, hypothalamic diseases such as hypothalamic neoplasms, cerebral malaria, narcolepsy which includes cataplexy, bulbar poliomyelitis, cerebri pseudotumor, Rett Syndrome, Reye's Syndrome, thalamic diseases, cerebral toxoplasmosis, intracranial tuberculoma and Zellweger Syndrome, central nervous system infections such as AIDS Dementia Complex, Brain Abscess, subdural empyema, encephalomyelitis such as Equine Encephalomyelitis, Venezuelan Equine Encephalomyelitis, Necrotizing Hemorrhagic Encephalomyelitis, Visna, and cerebral malaria.

Additional neurologic diseases which can be treated or detected with polynucleotides, polypeptides, agonists, and/or antagonists of the present invention include meningitis such as arachnoiditis, aseptic meningtitis such as viral meningtitis which includes lymphocytic choriomeningitis, Bacterial meningtitis which includes Haemophilus Meningtitis, Listeria Meningtitis, Meningococcal Meningtitis such as Waterhouse-Friderichsen Syndrome, Pneumococcal Meningtitis and meningeal tuberculosis, fungal meningitis such as Cryptococcal Meningtitis, subdural effusion, meningoencephalitis such as uvemeningoencephalitic syndrome, myelitis such as transverse myelitis, neurosyphilis such as tabes dorsalis, poliomyelitis which includes bulbar poliomyelitis and postpoliomyelitis syndrome, prion diseases (such as Creutzfeldt-Jakob Syndrome, Bovine Spongiform Encephalopathy, Gerstmann-Straussler Syndrome, Kuru, Scrapie), and cerebral toxoplasmosis.

Additional neurologic diseases which can be treated or detected with polynucleotides, polypeptides, agonists, and/or antagonists of the present invention include central nervous system neoplasms such as brain neoplasms that include cerebellar neoplasms such as infratentorial neoplasms, cerebral ventricle neoplasms such as choroid plexus neoplasms, hypothalamic neoplasms and supratentorial neoplasms, meningeal neoplasms, spinal cord neoplasms which include epidural neoplasms, demyelinating diseases such as Canavan Diseases, diffuse cerebral sceloris which includes adrenoleukodystrophy, encephalitis periaxialis, globoid cell leukodystrophy, diffuse cerebral sclerosis such as metachromatic leukodystrophy, allergic encephalomyelitis, necrotizing hemorrhagic encephalomyelitis, progressive multifocal leukoencephalopathy, multiple sclerosis, central pontine myelinolysis, transverse myelitis, neuromyelitis optica, Scrapie, Swayback, Chronic Fatigue Syndrome, Visna, High Pressure Nervous Syndrome, Meningism, spinal cord diseases such as amyotonia congenita, amyotrophic lateral sclerosis, spinal muscular atrophy such as Werdnig-Hoffmnann Disease, spinal cord compression, spinal cord neoplasms such as epidural neoplasms, syringomyelia, Tabes Dorsalis, Stiff-Man Syndrome, mental retardation such as Angelman Syndrome, Cri-du-Chat Syndrome, De Lange's Syndrome, Down Syndrome, Gangliosidoses such as gangliosidoses G(M1), Sandhoff Disease, Tay-Sachs Disease, Hartnup Disease, homocystinuria, Laurence-Moon-Biedl Syndrome, Lesch-Nyhan Syndrome, Maple Syrup Urine Disease, mucolipidosis such as fucosidosis, neuronal ceroid-lipofuscinosis, oculocerebrorenal syndrome, phenylketonuria such as maternal phenylketonuria, Prader-Willi Syndrome, Rett Syndrome, Rubinstein-Taybi Syndrome, Tuberous Sclerosis, WAGR Syndrome, nervous system abnormalities such as holoprosencephaly, neural tube defects such as anencephaly which includes hydrangencephaly, Arnold-Chairi Deformity, encephalocele, meningocele, meningomyelocele, spinal dysraphism such as spina bifida cyistica and spina bifida occulta.

Additional neurologic diseases which can be treated or detected with polynucleotides, polypeptides, agonists, and/or antagonists of the present invention include hereditary motor and sensory neuropathies which include Charcot-Marie Disease, Hereditary optic atrophy, Refsum's Disease, hereditary spastic paraplegia, Werdnig-Hoffmann Disease, Hereditary Sensory and Autonomic Neuropathies such as Congenital Analgesia and Familial Dysautonomia, Neurologic manifestations (such as agnosia that include Gerstmann's Syndrome, Amnesia such as retrograde amnesia, apraxia, neurogenic bladder, cataplexy, communicative disorders such as hearing disorders that includes deafness, partial hearing loss, loudness recruitment and tinnitus, language disorders such as aphasia which include agraphia, anomia, broca aphasia, and Wernicke Aphasia, Dyslexia such as Acquired Dyslexia, language development disorders, speech disorders such as aphasia which includes anomia, broca aphasia and Wernicke Aphasia, articulation disorders, communicative disorders such as speech disorders which include dysarthria, echolalia, mutism and stuttering, voice disorders such as aphonia and hoarseness, decerebrate state, delirium, fasciculation, hallucinations, meningism, movement disorders such as angelman syndrome, ataxia, athetosis, chorea, dystonia, hypokinesia, muscle hypotonia, myoclonus, tic, torticollis and tremor, muscle hypertonia such as muscle rigidity such as stiff-man syndrome, muscle spasticity, paralysis such as facial paralysis which includes Herpes Zoster Oticus, Gastroparesis, Hemiplegia, ophthalmoplegia such as diplopia, Duane's Syndrome, Homer's Syndrome, Chronic progressive external ophthalmoplegia such as Kearns Syndrome, Bulbar Paralysis, Tropical Spastic Paraparesis, Paraplegia such as Brown-Sequard Syndrome, quadriplegia, respiratory paralysis and vocal cord paralysis, paresis, phantom limb, taste disorders such as ageusia and dysgeusia, vision disorders such as amblyopia, blindness, color vision defects, diplopia, hemianopsia, scotoma and subnormal vision, sleep disorders such as hypersomnia which includes Kleine-Levin Syndrome, insomnia, and somnambulism, spasm such as trismus, unconsciousness such as coma, persistent vegetative state and syncope and vertigo, neuromuscular diseases such as amyotonia congenita, amyotrophic lateral sclerosis, Lambert-Eaton Myasthenic Syndrome, motor neuron disease, muscular atrophy such as spinal muscular atrophy, Charcot-Marie Disease and Werdnig-Hoffmann Disease, Postpoliomyelitis Syndrome, Muscular Dystrophy, Myasthenia Gravis, Myotonia Atrophica, Myotonia Confenita, Nemaline Myopathy, Familial Periodic Paralysis, Multiplex Paramyloclonus, Tropical Spastic Paraparesis and Stiff-Man Syndrome, peripheral nervous system diseases such as acrodynia, amyloid neuropathies, autonomic nervous system diseases such as Adie's Syndrome, Barre-Lieou Syndrome, Familial Dysautonomia, Horner's Syndrome, Reflex Sympathetic Dystrophy and Shy-Drager Syndrome, Cranial Nerve Diseases such as Acoustic Nerve Diseases such as Acoustic Neuroma which includes Neurofibromatosis 2, Facial Nerve Diseases such as Facial Neuralgia, Melkersson-Rosenthal Syndrome, ocular motility disorders which includes amblyopia, nystagmus, oculomotor nerve paralysis, ophthalmoplegia such as Duane's Syndrome, Homer's Syndrome, Chronic Progressive External Ophthalmoplegia which includes Kearns Syndrome, Strabismus such as Esotropia and Exotropia, Oculomotor Nerve Paralysis, Optic Nerve Diseases such as Optic Atrophy which includes Hereditary Optic Atrophy, Optic Disk Drusen, Optic Neuritis such as Neuromyelitis Optica, Papilledema, Trigeminal Neuralgia, Vocal Cord Paralysis, Demyelinating Diseases such as Neuromyelitis Optica and Swayback, and Diabetic neuropathies such as diabetic foot.

Additional neurologic diseases which can be treated or detected with polynucleotides, polypeptides, agonists, and/or antagonists of the present invention include nerve compression syndromes such as carpal tunnel syndrome, tarsal tunnel syndrome, thoracic outlet syndrome such as cervical rib syndrome, ulnar nerve compression syndrome, neuralgia such as causalgia, cervico-brachial neuralgia, facial neuralgia and trigeminal neuralgia, neuritis such as experimental allergic neuritis, optic neuritis, polyneuritis, polyradiculoneuritis and radiculities such as polyradiculitis, hereditary motor and sensory neuropathies such as Charcot-Marie Disease, Hereditary Optic Atrophy, Refsum's Disease, Hereditary Spastic Paraplegia and Werdnig-Hoffmnann Disease, Hereditary Sensory and Autonomic Neuropathies which include Congenital Analgesia and Familial Dysautonomia, POEMS Syndrome, Sciatica, Gustatory Sweating and Tetany).

Infectious Disease

A polypeptide or polynucleotide and/or agonist or antagonist of the present invention can be used to treat, prevent, and/or diagnose infectious agents. For example, by increasing the immune response, particularly increasing the proliferation and differentiation of B and/or T cells, infectious diseases may be treated, prevented, and/or diagnosed. The immune response may be increased by either enhancing an existing immune response, or by initiating a new immune response. Alternatively, polypeptide or polynucleotide and/or agonist or antagonist of the present invention may also directly inhibit the infectious agent, without necessarily eliciting an immune response.

Viruses are one example of an infectious agent that can cause disease or symptoms that can be treated, prevented, and/or diagnosed by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxyiridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat, prevent, and/or diagnose AIDS.

Similarly, bacterial or fungal agents that can cause disease or symptoms and that can be treated, prevented, and/or diagnosed by a polynucleotide or polypeptide and/or agonist or antagonist of the present invention include, but not limited to, include, but not limited to, the following Gram-Negative and Gram-positive bacteria and bacterial families and fungi: Actinomycetales (e.g., Corynebacterium, Mycobacterium, Norcardia), Cryptococcus neoformans, Aspergillosis, Bacillaceae (e.g., Anthrax, Clostridium), Bacteroidaceae, Blastomycosis, Bordetella, Borrelia (e.g., *Borrelia burgdorferi*), Brucellosis, Candidiasis, Campylobacter, Coccidioidomycosis, Cryptococcosis, Dermatocycoses, *E. coli* (e.g., Enterotoxigenic *E. coli* and Enterohemorrhagic *E. coli*), Enterobacteriaceae (Klebsiella, Salmonella (e.g., *Salmonella typhi*, and *Salmonella paratyphi*), Serratia, Yersinia), Erysipelothrix, Helicobacter, Legionellosis, Leptospirosis, Listeria, Mycoplasmatales, *Mycobacterium leprae, Vibrio cholerae*, Neisseriaceae (e.g., Acinetobacter, Gonorrhea, Menigococcal), *Meisseria meningitidis*, Pasteurellacea Infections (e.g., Actinobacillus, Heamophilus (e.g., Heamophilus influenza type B), Pasteurella), Pseudomonas, Rickettsiaceae, Chlamydiaceae, Syphilis, Shigella spp., Staphylococcal, Meningiococcal, Pneumococcal and Streptococcal (e.g., *Streptococcus pneumoniae* and Group B Streptococcus). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Polynucleotides or polypeptides, agonists or antagonists of the invention, can be used to treat, prevent, and/or diagnose any of these symptoms or diseases. In specific embodiments, polynucleotides, polypeptides, agonists or antagonists of the invention are used to treat, prevent, and/or diagnose: tetanus, Diptheria, botulism, and/or meningitis type B.

Moreover, parasitic agents causing disease or symptoms that can be treated, prevented, and/or diagnosed by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose malaria.

Preferably, treatment or prevention using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide and/or agonist or antagonist of the present invention can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, bums, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide and/or agonist or antagonist of the present invention may increase regeneration of tissues difficult to heal. For example, increased tendon/ligament regeneration would quicken recovery time after damage. A polynucleotide or polypeptide and/or agonist or antagonist of the present invention could also be used prophylactically in an effort to avoid damage. Specific diseases that could be treated, prevented, and/or diagnosed include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide and/or agonist or antagonist of the present invention to proliferate and differentiate nerve cells. Diseases that could be treated, prevented, and/or diagnosed using this method include central and peripheral nervous system diseases, neuropathies, or mechanical and traumatic diseases, disorders, and/or conditions (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated, prevented, and/or diagnosed using the polynucleotide or polypeptide and/or agonist or antagonist of the present invention.

Chemotaxis

A polynucleotide or polypeptide and/or agonist or antagonist of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide and/or agonist or antagonist of the present invention may increase chemotaxic activity of particular cells. These chemotactic molecules can then be used to treat, prevent, and/or diagnose inflammation, infection, hyperproliferative diseases, disorders, and/or conditions, or any immune system disorder by increasing the number of cells targeted to a particular location in the body. For example, chemotaxic molecules can be used to treat, prevent, and/or diagnose wounds and other trauma to tissues by attracting immune cells to the injured location. Chemotactic molecules of the present invention can also attract fibroblasts, which can be used to treat, prevent, and/or diagnose wounds.

It is also contemplated that a polynucleotide or polypeptide and/or agonist or antagonist of the present invention may inhibit chemotactic activity. These molecules could also be used to treat, prevent, and/or diagnose diseases, disorders, and/or conditions. Thus, a polynucleotide or polypeptide and/or agonist or antagonist of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, Drosophila, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labelled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of polypeptides of the invention thereby effectively generating agonists and antagonists of polypeptides of the invention. See generally, U.S. Pat. Nos. 5,605,793, 5,811,238, 5,830,721, 5,834,252, and 5,837,458, and Patten, P. A., et al., Curr. Opinion Biotechnol. 8:724–33 (1997); Harayama, S. Trends Biotechnol. 16(2):76–82 (1998); Hansson, L. O., et al., J. Mol. Biol. 287:265–76 (1999); and Lorenzo, M. M. and Blasco, R. Biotechniques 24(2):308–13 (1998) (each of these patents and publications are hereby incorporated by reference). In one embodiment, alteration of polynucleotides and corresponding polypeptides of the invention may be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention may be alterred by being subjected to random mutagenesis by error-prone PCR, random nucleotide insertion or other methods prior to recombination. In another embodiment, one or more components, motifs, sections, parts, domains, fragments, etc., of the polypeptides of the invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermnal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptides of the invention. Biologically active fragments are those exhibiting activity similar, but not necessarily identical, to an activity of the polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and 3[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of 3[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues. Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of: (a) incubating a candidate compound with the polypeptide, (b) assaying a biological activity, and (b) determining if a biological activity of the polypeptide has been altered.

Also, one could identify molecules bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of, any combination or all of the beta pleated sheet regions in one of the polypeptide sequences of the invention.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

Polypeptides of the Invention Binding Peptides and Other Molecules

The invention also encompasses screening methods for identifying polypeptides and nonpolypeptides that bind polypeptides of the invention, and the polypeptide of the invention binding molecules identified thereby. These binding molecules are useful, for example, as agonists and antagonists of the polypeptides of the invention. Such agonists and antagonists can be used, in accordance with the invention, in the therapeutic embodiments described in detail, below.

This method comprises the steps of:

a. contacting a polypeptide of the invention with a plurality of molecules; and b. identifying a molecule that binds the polypeptide of the invention.

The step of contacting the polypeptide of the invention with the plurality of molecules may be effected in a number of ways. For example, one may contemplate immobilizing the polypeptide of the invention on a solid support and bringing a solution of the plurality of molecules in contact with the immobilized polypeptide of the invention. Such a procedure would be akin to an affinity chromatographic process, with the affinity matrix being comprised of the immobilized polypeptide of the invention. The molecules having a selective affinity for the polypeptide of the invention can then be purified by affinity selection. The nature of the solid support, process for attachment of the polypeptide of the invention to the solid support, solvent, and conditions of the affinity isolation or selection are largely conventional and well known to those of ordinary skill in the art.

Alternatively, one may also separate a plurality of polypeptides into substantially separate fractions comprising a subset of or individual polypeptides. For instance, one can separate the plurality of polypeptides by gel electrophoresis, column chromatography, or like method known to those of ordinary skill for the separation of polypeptides. The individual polypeptides can also be produced by a transformed host cell in such a way as to be expressed on or about its outer surface (e.g., a recombinant phage). Individual isolates can then be "probed" by the polypeptide of the invention, optionally in the presence of an inducer should one be required for expression, to determine if any selective affinity interaction takes place between the polypeptide of the invention and the individual clone. Prior to contacting the polypeptide of the invention with each fraction comprising individual polypeptides, the polypeptides could first be transferred to a solid support for additional convenience. Such a solid support may simply be a piece of filter membrane, such as one made of nitrocellulose or nylon. In this manner, positive clones could be identified from a collection of transformed host cells of an expression library, which harbor a DNA construct encoding a polypeptide having a selective affinity for a polypeptide of the invention. Furthermore, the amino acid sequence of the polypeptide having a selective affinity for the polypeptide of the invention can be determined directly by conventional means or the coding sequence of the DNA encoding the polypeptide can frequently be determined more conveniently. The primary sequence can then be deduced from the corresponding DNA sequence. If the amino acid sequence is to be determined from the polypeptide itself, one may use microsequencing techniques. The sequencing technique may include mass spectroscopy.

In certain situations, it may be desirable to wash away any unbound polypeptide of the invention, or alterntatively, unbound polypeptides, from a mixture of the polypeptide of the invention and the plurality of polypeptides prior to attempting to determine or to detect the presence of a selective affinity interaction. Such a wash step may be particularly desirable when the polypeptide of the invention or the plurality of polypeptides is bound to a solid support.

The plurality of molecules provided according to this method may be provided by way of diversity libraries, such as random or combinatorial peptide or nonpeptide libraries which can be screened for molecules that specifically bind to a polypeptide of the invention. Many libraries are known in the art that can be used, e.g., chemically synthesized libraries, recombinant (e.g., phage display libraries), and in vitro translation-based libraries. Examples of chemically synthesized libraries are described in Fodor et al., 1991, Science 251:767–773; Houghten et al., 1991, Nature 354:84–86; Lam et al., 1991, Nature 354:82–84; Medynski, 1994, Bio/Technology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lerner, 1992, Proc. Natl. Acad. Sci. USA 89:5381–5383.

Examples of phage display libraries are described in Scott and Smith, 1990, Science 249:386–390; Devlin et al., 1990, Science, 249:404–406; Christian, R. B., et al., 1992, J. Mol. Biol. 227:711–718); Lenstra, 1992, J. Immunol. Meth. 152:149–157; Kay et al., 1993, Gene 128:59–65; and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., 1994, Proc. Natl. Acad. Sci. USA 91:9022–9026.

By way of examples of nonpeptide libraries, a benzodiazepine library (see e.g., Bunin et al., 1994, Proc. Natl. Acad. Sci. USA 91:4708–4712) can be adapted for use. Peptoid libraries (Simon et al., 1992, Proc. Natl. Acad. Sci. USA 89:9367–9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

The variety of non-peptide libraries that are useful in the present invention is great. For example, Ecker and Crooke, 1995, Bio/Technology 13:351–360 list benzodiazepines, hydantoins, piperazinediones, biphenyls, sugar analogs, beta-mercaptoketones, arylacetic acids, acylpiperidines, benzopyrans, cubanes, xanthines, aminimides, and oxazolones as among the chemical species that form the basis of various libraries.

Non-peptide libraries can be classified broadly into two types: decorated monomers and oligomers. Decorated monomer libraries employ a relatively simple scaffold structure upon which a variety functional groups is added. Often the scaffold will be a molecule with a known useful pharmacological activity. For example, the scaffold might be the benzodiazepine structure.

Non-peptide oligomer libraries utilize a large number of monomers that are assembled together in ways that create new shapes that depend on the order of the monomers. Among the monomer units that have been used are carbamates, pyrrolinones, and morpholinos. Peptoids, peptide-like oligomers in which the side chain is attached to the alpha amino group rather than the alpha carbon, form the basis of another version of non-peptide oligomer libraries. The first non-peptide oligomer libraries utilized a single type of monomer and thus contained a repeating backbone. Recent libraries have utilized more than one monomer, giving the libraries added flexibility.

Screening the libraries can be accomplished by any of a variety of commonly known methods. See, e.g., the following references, which disclose screening of peptide libraries: Parmley and Smith, 1989, Adv. Exp. Med. Biol. 251:215–218; Scott and Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. No. 5,096,815, U.S. Pat. No. 5,223,409, and U.S. Pat. No. 5,198,346, all to Ladner et al.; Rebar and Pabo, 1993, Science 263:671–673; and CT Publication No. WO 94/18318.

In a specific embodiment, screening to identify a molecule that binds a polypeptide of the invention can be carried out by contacting the library members with a polypeptide of the invention immobilized on a solid phase and harvesting those library members that bind to the polypeptide of the invention. Examples of such screening methods, termed "panning" techniques are described by way of example in Parmley and Smith, 1988, Gene 73:305–318; Fowlkes et al., 1992, BioTechniques 13:422–427; PCT Publication No. WO 94/18318; and in references cited herein.

In another embodiment, the two-hybrid system for selecting interacting proteins in yeast (Fields and Song, 1989, Nature 340:245–246; Chien et al., 1991, Proc. Natl. Acad. Sci. USA 88:9578–9582) can be used to identify molecules that specifically bind to a polypeptide of the invention.

Where the polypeptide of the invention binding molecule is a polypeptide, the polypeptide can be conveniently selected from any peptide library, including random peptide libraries, combinatorial peptide libraries, or biased peptide libraries. The term "biased" is used herein to mean that the method of generating the library is manipulated so as to restrict one or more parameters that govern the diversity of the resulting collection of molecules, in this case peptides.

Thus, a truly random peptide library would generate a collection of peptides in which the probability of finding a particular amino acid at a given position of the peptide is the same for all 20 amino acids. A bias can be introduced into the library, however, by specifying, for example, that a lysine occur every fifth amino acid or that positions 4, 8, and 9 of a decapeptide library be fixed to include only arginine. Clearly, many types of biases can be contemplated, and the present invention is not restricted to any particular bias. Furthermore, the present invention contemplates specific types of peptide libraries, such as phage displayed peptide libraries and those that utilize a DNA construct comprising a lambda phage vector with a DNA insert.

As mentioned above, in the case of a polypeptide of the invention binding molecule that is a polypeptide, the polypeptide may have about 6 to less than about 60 amino acid residues, preferably about 6 to about 10 amino acid residues, and most preferably, about 6 to about 22 amino acids. In another embodiment, a polypeptide of the invention binding polypeptide has in the range of 15–100 amino acids, or 20–50 amino acids.

The selected polypeptide of the invention binding polypeptide can be obtained by chemical synthesis or recombinant expression.

Antisense And Ribozyme (Antagonists)

In specific embodiments, antagonists according to the present invention are nucleic acids corresponding to the sequences contained in SEQ ID NO:X, or the complementary strand thereof, and/or to nucleotide sequences contained a deposited clone. In one embodiment, antisense sequence is generated internally by the organism, in another embodiment, the antisense sequence is separately administered (see, for example, O'Connor, Neurochem., 56:560 (1991). Oligodeoxynucleotides as Anitsense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, Neurochem., 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research, 6:3073 (1979); Cooney et al., Science, 241:456 (1988); and Dervan et al., Science, 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2×ligation buffer (2 mM TRIS HCl pH 7.5, 10 mM MgCl2, 10 MM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense nucleic acid of the invention. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding a polypeptide of the invention, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature, 29:304–310 (1981), the promoter contained in the 3' long terminal repeat of Rous sarcoma virus (Yamamoto et al., Cell, 22:787–797 (1980), the herpes thymidine promoter (Wagner et al., Proc. Natl. Acad. Sci. U.S.A., 78:1441–1445 (1981), the regulatory sequences of the metallothionein gene (Brinster et al., Nature, 296:39–42 (1982)), etc.

The antisense nucleic acids of the invention comprise a sequence complementary to at least a portion of an RNA transcript of a gene of interest. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded antisense nucleic acids of the invention, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., Nature, 372:333–335 (1994). Thus, oligonucleotides complementary to either the 5'- or 3'-non-translated, non-coding regions of a polynucleotide sequence of the invention could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553–6556 (1989); Lemaitre et al., Proc. Natl. Acad. Sci., 84:648–652 (1987); PCT Publication NO: WO88/09810, published Dec. 15, 1988) or the blood-brain barrier (see, e.g., PCT Publication NO: WO89/10134, published Apr. 25, 1988), hybridization-triggered cleavage agents. (See, e.g., Krol et al., BioTechniques, 6:958–976 (1988)) or intercalating agents. (See, e.g., Zon, Pharm. Res., 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., Nucl. Acids Res., 15:6625–6641 (1987)). The oligonucleotide is a 2-0-methylribonucleotide (Inoue et al., Nucl. Acids Res., 15:6131–6148 (1987)), or a chimeric RNA-DNA analogue (Inoue et al., FEBS Lett. 215:327–330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res., 16:3209 (1988)), methylphosphonate oligonucleotides can be prepared by use of controlled pore glass polymer supports (Sarin et al., Proc. Natl. Acad. Sci. U.S.A., 85:7448–7451 (1988)), etc.

While antisense nucleotides complementary to the coding region sequence of the invention could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science, 247:1222–1225 (1990). While ribozymes that cleave mRNA at site specific recognition sequences can be used to destroy mRNAs corresponding to the polynucleotides of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature, 334:585–591 (1988). There are numerous potential hammerhead ribozyme cleavage sites within each nucleotide sequence disclosed in the sequence listing. Preferably, the ribozyme is engineered so that the cleavage recognition site is located near the 5' end of the mRNA corresponding to the polynucleotides of the invention; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express the polynucleotides of the invention in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat, prevent, and/or diagnose the diseases described herein.

Thus, the invention provides a method of treating or preventing diseases, disorders, and/or conditions, including but not limited to the diseases, disorders, and/or conditions listed throughout this application, associated with overexpression of a polynucleotide of the present invention by administering to a patient (a) an antisense molecule directed to the polynucleotide of the present invention, and/or (b) a ribozyme directed to the polynucleotide of the present invention. invention, and/or (b) a ribozyme directed to the polynucleotide of the present invention Other Activities The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptide may also be employed to stimulate angiogenesis and limb regeneration, as discussed above.

The polypeptide may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat, prevent, and/or diagnose neuronal damage which occurs in certain neuronal disorders or neuro-degenerative conditions such as Alzheimer's disease, Parkinson's disease, and AIDS-related complex. The polypeptide of the invention may have the ability to stimulate chondrocyte growth, therefore, they may be employed to enhance bone and periodontal regeneration and aid in tissue transplants or bone grafts.

The polypeptide of the present invention may be also be employed to prevent skin aging due to sunburn by stimulating keratinocyte growth.

The polypeptide of the invention may also be employed for preventing hair loss, since FGF family members activate hair-forming cells and promotes melanocyte growth. Along the same lines, the polypeptides of the present invention may be employed to stimulate growth and differentiation of hematopoietic cells and bone marrow cells when used in combination with other cytokines.

The polypeptide of the invention may also be employed to maintain organs before transplantation or for supporting cell culture of primary tissues.

The polypeptide of the present invention may also be employed for inducing tissue of mesodermal origin to differentiate in early embryos.

The polypeptide or polynucleotides and/or agonist or antagonists of the present invention may also increase or decrease the differentiation or proliferation of embryonic stem cells, besides, as discussed above, hematopoietic lineage.

The polypeptide or polynucleotides and/or agonist or antagonists of the present invention may also be used to modulate mammalian characteristics, such as body height, weight, hair color, eye color, skin, percentage of adipose tissue, pigmentation, size, and shape (e.g., cosmetic surgery). Similarly, polypeptides or polynucleotides and/or agonist or antagonists of the present invention may be used to modulate mammalian metabolism affecting catabolism, anabolism, processing, utilization, and storage of energy.

Polypeptide or polynucleotides and/or agonist or antagonists of the present invention may be used to change a mammal's mental state or physical state by influencing biorhythms, caricadic rhythms, depression (including depressive diseases, disorders, and/or conditions), tendency for violence, tolerance for pain, reproductive capabilities (preferably by Activin or Inhibin-like activity), hormonal or endocrine levels, appetite, libido, memory, stress, or other cognitive qualities.

Polypeptide or polynucleotides and/or agonist or antagonists of the present invention may also be used as a food additive or preservative, such as to increase or decrease storage capabilities, fat content, lipid, protein, carbohydrate, vitamins, minerals, cofactors or other nutritional components.

Other Preferred Embodiments

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:X wherein X is any integer as defined in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Clone Sequence and ending with the nucleotide at about the position of the 3' Nucleotide of the Clone Sequence as defined for SEQ ID NO:X in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Start Codon and ending with the nucleotide at about the position of the 3' Nucleotide of the Clone Sequence as defined for SEQ ID NO:X in Table 1.

Similarly preferred is a nucleic acid molecule wherein said sequence of contiguous nucleotides is included in the nucleotide sequence of SEQ ID NO:X in the range of positions beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

Also preferred is an isolated nucleic acid molecule comprising a nucleotide sequence which is at least 95% identical to a sequence of at least about 150 contiguous nucleotides in the nucleotide sequence of SEQ ID NO:X.

Further preferred is an isolated nucleic acid molecule comprising a nucleotide sequence which is at least 95% identical to a sequence of at least about 500 contiguous nucleotides in the nucleotide sequence of SEQ ID NO:X.

A further preferred embodiment is a nucleic acid molecule comprising a nucleotide sequence which is at least 95% identical to the nucleotide sequence of SEQ ID NO:X beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

A further preferred embodiment is an isolated nucleic acid molecule comprising a nucleotide sequence which is at least 95% identical to the complete nucleotide sequence of SEQ ID NO:X.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a human cDNA clone identified by a cDNA Clone Identifier in Table 1, which DNA molecule is contained in the material deposited with the American Type Culture Collection and given the ATCC® Deposit Number shown in Table 1 for said cDNA Clone Identifier.

Also preferred is an isolated nucleic acid molecule comprising a nucleotide sequence which is at least 95% identical to a sequence of at least 50 contiguous nucleotides in the nucleotide sequence of a human cDNA clone identified by a cDNA Clone Identifier in Table 1, which DNA molecule is contained in the deposit given the ATCC® Deposit Number shown in Table 1.

Also preferred is an isolated nucleic acid molecule, wherein said sequence of at least 50 contiguous nucleotides is included in the nucleotide sequence of the complete open reading frame sequence encoded by said human cDNA clone.

Also preferred is an isolated nucleic acid molecule comprising a nucleotide sequence which is at least 95% identical to sequence of at least 150 contiguous nucleotides in the nucleotide sequence encoded by said human cDNA clone.

A further preferred embodiment is an isolated nucleic acid molecule comprising a nucleotide sequence which is at least 95% identical to sequence of at least 500 contiguous nucleotides in the nucleotide sequence encoded by said human cDNA clone.

A further preferred embodiment is an isolated nucleic acid molecule comprising a nucleotide sequence which is at least 95% identical to the complete nucleotide sequence encoded by said human cDNA clone.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC® Deposit Number shown for said cDNA clone in Table 1; which method comprises a step of comparing a nucleotide sequence of at least one nucleic acid molecule in said sample with a sequence selected from said group and determining whether the sequence of said nucleic acid molecule in said sample is least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC® Deposit Number shown for said cDNA clone in Table 1.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a secreted protein identified in Table 1, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC® Deposit Number shown for said cDNA clone in Table 1.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC® Deposit Number shown for said cDNA clone in Table 1. The nucleic acid molecules can comprise DNA molecules or RNA molecules.

Also preferred is an isolated polypeptide comprising an amino acid sequence at least 90% identical to a sequence of at least about 10 contiguous amino acids in the amino acid sequence of SEQ ID NO:Y wherein Y is any integer as defined in Table 1.

Also preferred is a polypeptide, wherein said sequence of contiguous amino acids is included in the amino acid sequence of SEQ ID NO:Y in the range of positions beginning with the residue at about the position of the First Amino Acid of the Secreted Portion and ending with the residue at about the Last Amino Acid of the Open Reading Frame as set forth for SEQ ID NO:Y in Table 1.

Also preferred is an isolated polypeptide comprising an amino acid sequence at least 95% identical to a sequence of at least about 30 contiguous amino acids in the amino acid sequence of SEQ ID NO:Y.

Further preferred is an isolated polypeptide comprising an amino acid sequence at least 95% identical to a sequence of at least about 100 contiguous amino acids in the amino acid sequence of SEQ ID NO:Y.

Further preferred is an isolated polypeptide comprising an amino acid sequence at least 95% identical to the complete amino acid sequence of SEQ ID NO:Y.

Further preferred is an isolated polypeptide comprising an amino acid sequence at least 90% identical to a sequence of at least about 10 contiguous amino acids in the complete amino acid sequence of a secreted protein encoded by a human cDNA clone identified by a cDNA Clone Identifier in Table 1 and contained in the deposit with the ATCC® Deposit Number shown for said cDNA clone in Table 1.

Also preferred is a polypeptide wherein said sequence of contiguous amino acids is included in the amino acid sequence of a secreted portion of the secreted protein encoded by a human cDNA clone identified by a cDNA Clone Identifier in Table 1 and contained in the deposit with the ATCC® Deposit Number shown for said cDNA clone in Table 1.

Also preferred is an isolated polypeptide comprising an amino acid sequence at least 95% identical to a sequence of at least about 30 contiguous amino acids in the amino acid sequence of the secreted portion of the protein encoded by a human cDNA clone identified by a cDNA Clone Identifier in Table 1 and contained in the deposit with the ATCC® Deposit Number shown for said cDNA clone in Table 1.

Also preferred is an isolated polypeptide comprising an amino acid sequence at least 95% identical to a sequence of at least about 100 contiguous amino acids in the amino acid sequence of the secreted portion of the protein encoded by a human cDNA clone identified by a cDNA Clone Identifier in Table 1 and contained in the deposit with the ATCC® Deposit Number shown for said cDNA clone in Table 1.

Also preferred is an isolated polypeptide comprising an amino acid sequence at least 95% identical to the amino acid sequence of the secreted portion of the protein encoded by a human cDNA clone identified by a cDNA Clone Identifier in Table 1 and contained in the deposit with the ATCC® Deposit Number shown for said cDNA clone in Table 1.

Further preferred is an isolated antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC® Deposit Number shown for said cDNA clone in Table 1.

Further preferred is a method for detecting in a biological sample a polypeptide comprising an amino acid sequence which is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC® Deposit Number shown for said cDNA clone in Table 1; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC® Deposit Number shown for said cDNA clone in Table 1.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC® Deposit Number shown for said cDNA clone in Table 1.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing in a subject a pathological condition associated with abnormal structure or expression of a gene encoding a secreted protein identified in Table 1, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC® Deposit Number shown for said cDNA clone in Table 1.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at east 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC® Deposit Number shown for said cDNA clone in Table 1.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC® Deposit Number shown for said cDNA clone in Table 1.

Further preferred is a method of making a recombinant vector comprising inserting any of the above isolated nucleic acid molecule into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a secreted portion of a human secreted protein comprising an amino acid sequence selected from the group consisting of: an amino acid sequence of SEQ ID NO:Y beginning with the residue at the position of the First Amino Acid of the Secreted Portion of SEQ ID NO:Y wherein Y is an integer set forth in Table 1 and said position of the First Amino Acid of the Secreted Portion of SEQ ID NO:Y is defined in Table 1; and an amino acid sequence of a secreted portion of a protein encoded by a human cDNA clone identified by a cDNA Clone Identifier in Table 1 and contained in the deposit with the ATCC® Deposit Number shown for said cDNA clone in Table 1. The isolated polypeptide produced by this method is also preferred.

Also preferred is a method of treatment of an individual in need of an increased level of a secreted protein activity, which method comprises administering to such an individual a pharmaceutical composition comprising an amount of an isolated polypeptide, polynucleotide, or antibody of the claimed invention effective to increase the level of said protein activity in said individual.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

In specific embodiments of the invention, for each "Contig ID" listed in the fourth column of Table 6, preferably excluded are one or more polynucleotides comprising, or alternatively consisting of, a nucleotide sequence referenced in the fifth column of Table 6 and described by the general formula of a–b, whereas a and b are uniquely determined for the corresponding SEQ ID NO:X referred to in column 3 of Table 6. Further specific embodiments are directed to polynucleotide sequences excluding one, two, three, four, or more of the specific polynucleotide sequences referred to in the fifth column of Table 6. In no way is this listing meant to encompass all of the sequences which may be excluded by the general formula, it is just a representative example. All references available through these accessions are hereby incorporated by reference in their entirety.

TABLE 6

| Gene No. | cDNA Clone ID | NT SEQ ID NO: X | Contig ID | Public Accession Numbers |
|---|---|---|---|---|
| 1 | HSSDM23 | 11 | 904824 | AI814485, AI872286, AI085288, AI871915, D55959, AI815039, AI863123, AI336860, H17328, AA044426, AA604984, AI633049, AW189982, AW025903, AL039802, AI620041, AW161698, F19322, AI357312, D54424, AW161017, D52832, F25495, AA703238, AI249687, C15890, R87515, H41877, D52711, AI910243, AA972364, AW002448, AI223172, H17356, AI419944, C15914, AA043060, AW137423, AA837263, D53580, AA285001, AA437366, AI884896, N62793, AI630922, AW139983, N93907, T06071, AI700165, AI934044, R87602, R90815, R87601, D80607, T23962, AA852308, AW393830, R90816, AA322589, AA330874, AI040803, F35183, AW393886, T12056, AI367549, D80888, AW204276, AA290964, AW389410, H50473, AW205735, AI356969, AI804924, AI619947, AW300654, AI948525, AI619622, AW050474, AI880215, AA224082, F34413, Z17406, F37450, AI540674, AW161156, AI797538, AW087199, AL047100, AI961414, AI254727, AI590043, AW051088, AW169671, AW162194, AI802542, AI352274, AI623941, AI624293, AI536685, AI859991, AI538885, AW020397, AI800473, AI538829, AW189716, AI621341, AI868931, AI890574, AI521594, AW088560, AA470491, AI241923, AI499963, AW105460, AW169784, AL036361, AI345778, AI285732, AI345543, AI521560, AI637584, AI927233, AI270183, AI271796, AI500714, AI684021, AW238688, A1687362, AI961589, C00462, AI918449, AL119863, AI587156, AI580214, AI470674, AI432969, AI583558, AA464646, AI636170, AI571439, AL110306, AI433157, AL036631, AI702073, AI687809, AI698391, AI567582, AI783504, AI929108, AL046466, AI281757, AI950892, AW151714, AL036673, AI609409, AI818353, AI434741, AI679266, AL121564, AI633125, AW059828, AI886181, AW303152, AI589428, AI538564, |

TABLE 6-continued

| Gene No. | cDNA Clone ID | NT SEQ ID NO: X | Contig ID | Public Accession Numbers |
|---|---|---|---|---|
| | | | | AI816884, AI915291, AI630252, AW152182, AW089275, AI973152, AI582932, AI433590, AI872423, AW129230, AI537677, AL037558, AI889189, AI435253, AI473536, AI610446, AW169618, AI318280, AI446023, A1866469, AI612913, AI961278, AI884318, AI452560, AI446046, AA641818, W74529, AA502794, AI537261, AI254042, AI587121, AW167918, AI612750, AW051044, AW008353, AI445992, AI581033, AI583578, AI696611, AI923370, AI355849, AI524654, AI288050, AL046618, AI932794, AI475371, AW080402, AI620284, AW163834, AI445990, AI827154, AI500061, AI473799, AL037030, AI866770, AI950729, AI539800, AI632408, AL040241, AW131999, AW152550, AW151136, AL046944, AI312428, AL138386, AI863191, AL039086, AI270295, AI335214, AI590120, AI473451, AI445611, AL119791, AL045500, AI670015, AI890907, AL043355, AI538637, AI267185, AI690687, AW161579, AL046595, AL040169, AI832245, AW149925, AC005815, AL137480, I48978, AF177401, AL17435, I89947, AF026008, AF017790, AL023657, I48979, A03736, I09499, X72889, AR038854, AL133637, AR034821, A08910, A08909, A77033, A77035, AL122110, A08908, AF079763, Z97214, AB019565, S83456, A08916, A08913, AF087943, I17544, A08912, AF090896, AL137488, AF102578, E12747, Z72491, AL080110, AF183393, AR013797, AL137271, AL133112, AF097996, AJ003118, AL133113, L04504, AL133665, AL050155, S36676, A65341, I03321, AL117460, AF067790, I26207, A18777, AF111849, AL050092, AF008439, AL049339, AF176651, AL117416, AL133640, AL080154, AL080148, U75932, A21103, AF118094, X52128, AF026124, Z37987, AL122100, AL137533, AL080126, AL096751, U35846, AL137665, AL110218, AF026816, I89931, AF061943, AL049430, AL137550, AL137574, AF090903, X99717, AL137292, D83032, AL080124, I49625, AF090934, AL137478, A76335, A23630, AL137459, X65873, S76508, AF113019, AL137530, AL050172, Y14314, AL117440, AF185576, L19437, AL137560, E07108, AF061795, AF151685, A45787, AL137641, AJ005690, AL050138, Y16645, Y11254, AL049314, AF111851, M96857, I33392, AL096744, AL110225, AL117394, I32738, AL133619, AL133565, AF106862, Y10655, A08907, Z82022, AF159615, AF146568, X82434, I89934, AF113690, AF065135, AL110196, AF031147, AL137529, AL110221, AF090900, AL137547, E01614, E13364, X63574, I68732, AL050277, AR020905, M86826, AF126247, AL080159, E06743, AF153205, AF106697, AL050149, AF061981, S78214, AL133010, AL122121, AL137476, AL110280, AL133560, AF111112, AF162270, AF017437, A86558, X66871, A65340, X79812, AL049283, X62580, AR029490, D16301, M27260, A07647, S68736, AL050393, AF079765, M92439, A08911, AF113694, AL122050, AL050116, Y07905, AF032666, AJ012755, I89944, I80064, AF012536, AL049300, U95114, AL049466, X70685, AL049452, U77594, Y10080, U80742, X83508, AC004200, X00861, AL133558, AL050024, U67958, AF113699, AL133557, AF090886, AL137558, AF139986, AL137537, A15345, AF003737, AF118064, AF067728, Y11587, AJ000937, L30117, AL137538, AL133016, AF125948, AL137521, AR011880, AB016226, AF113689, AL049938, AL133080, AF118090, E02349, AF210052, X84990, A93350, I66342, AL050108, AL122118, X96540, U42766, AL133606, AL137548, AL137479, A58524, AF061573, A58523, AL078630, and AF113677. |
| 2 | HOFNX30 | 12 | 899523 | AW270089, AB020686, and AL035701. |
| 3 | HLQFB12 | 13 | 899489 | AA502331, AW444616, AI017393, AA568450, T85589, AA503839, T72043, T78178, T85588, AI699382, T86494, AA335186, AA299977, AA551860, AW079940, and AR027051. |
| 4 | HDPUM13 | 14 | 651321 | AW007501, AA902287, AI858092, AI005351, AW083940, AI870864, AI032697, AW149115, AA829811, AA709070, AW264612, AA614344, |

TABLE 6-continued

| Gene No. | cDNA Clone ID | NT SEQ ID NO: X | Contig ID | Public Accession Numbers |
|---|---|---|---|---|
| | | | | AA643392, AI951841, AI312642, AA533443, AI799536, AA991955, AI830766, AA594172, AI289881, AW088660, AI276207, AW268666, AI741805, AI749660, AI369678, AI264768, AA625243, AI190367, AI816740, AI510691, AW168615, AI817506, AI792359, AW089929, AI609047, AI291890, AI268176, AA617718, AI394498, AI913963, F34379, AA985480, AI282722, AA864826, AI494152, AW050814, AI868440, AW129114, AA991995, AA937062, AA877343, AA737786, AI335628, AA335122, AI708280, AA318733, AA642608, AI245599, AI074177, AA603928, AW080143, AI768186, AA936631, AA569858, AA317892, AA995511, AI718073, AA345519, AI963480, AA318753, AI915027, AI291076, AA335136, A1830861, AI739187, AI340221, W87494, AI351218, AW054951, AI266613, AA779248, AI950591, T53694, AA335121, AW083985, AW148663, AA746624, R23643, AA804997, AA740560, AI749854, AA961830, AW168417, R35066, AA878942, AA983420, AA367958, T53693, AA804991, AI198965, AA862333, AA632062, AI828465, AW005612, AA729782, AA554005, AW080896, AI538203, H89138, AI918424, AA769697, AW084151, AI654137, AI540179, AI816976, AL045421, AA172258, AI817244, AI699175, AW020619, AA743358, AA587590, H95782, AI540606, AI865040, AW021662, AA767177, AI582822, AA811656, AW022593, AA824435, AL047172, AI913476, AW236186, AL118620, AI307557, AW084873, AW023928, AI376797, AI926593, AF135157, AF158248, AL049452, S70057, AL133049, X53587, X68560, AF130342, A15345, AL050170, AF131814, AR050959, AB026995, AF111851, AF150103, AF061573, AC006115, AL080074, AL096709, X79812, AF058921, A21625, X67813, AL133010, AF067223, AF113676, U80919, AC006112, AL080110, AF106697, AC004805, AL137539, AF067728, U66075, AF139986, AC002558, AF004162, AF211175, AF007142, AL133608, I48978, AF119336, A41575, AL133053, AF094480, AF107018, A57389, AL133088, E01357, AL133016, S68736, AF137367, E01314, AF098162, M79462, AF192522, AF161413, AL022165, A86558, S36676, D44497, AL080154, X51694, AF039202, AF126372, I80062, X60769, X76228, X99257, AJ006039, AL137284, X68249, Y00093, E15568, AC005156, AF179633, X98066, Y11254, A83556, AF199509, X66113, E13998, AL137641, and S69510. |
| 4 | HPLAT62 | 44 | 839292 | AW007501, AA902287, AI858092, AI005351, AW083940, AI870864, AI032697, AA829811, AA709070, AW264612, AA643392, AI951841, AW149115, AI312642, AA614344, AA533443, AI799536, AA991955, AI830766, AA594172, AI289881, AI741805, AI276207, AW088660, AW268666, AI749660, AI369678, AI264768, AA625243, AI190367, AI816740, AI510691, AW168615, AI817506, AI792359, AI291890, AW089929, AI268176, AI609047, AA617718, AI913963, F34379, AA985480, AI282722, AI394498, AA864826, AW050814, AI494152, AI868440, AA991995, AA937062, AW129114, AA877343, AI335628, AA335122, AA737786, AI708280, AA642608, AA318733, AI245599, AW054951, AA603928, AI074177, AA936631, AA569858, AW080143, AI768186, AA995511, AA317892, AI718073, AA345519, AI915027, AI963480, AA318753, AW083985, AI291076, AA335136, AI340221, W87494, AI739187, AI830861, AI351218, AI266613, AA779248, T53694, AA335121, AI950591, AA746624, R23643, AA804997, AA740560, AI749854, AW148663, AA961830, R35066, AW168417, AI299182, AA878942, AA983420, AA367958, T53693, AA804991, AI198965, AI913330, AA862333, AA632062, AI590043, AI887775, |

TABLE 6-continued

| Gene No. | cDNA Clone ID | NT SEQ ID NO: X | Contig ID | Public Accession Numbers |
|---|---|---|---|---|
| | | | | AI500714, AW089557, AL039390, AI433157, AI648567, AI554821, AW151136, AI539771, AL045626, AI274759, AI537677, AI494201, AI500659, AI866465, AI815232, AI801325, AI500523, AI538850, AI582932, AI872423, AI284517, AI923989, AI500706, AI491710, AI445237, AI491776, AW151138, AI889189, AI521560, AI500662, AI539800, AW172723, AI284509, AI538885, AI889168, AI440263, AI866573, AI633493, AI434256, AI866469, AI434242, AI805769, AI888661, AI284513, AI888118, AI570169, AI436429, AI859991, AI889147, AI355779, AI371228, AI581033, AI440252, AL047422, AI866786, AI860003, AI610557, AI242736, AI828574, AI887499, AI539781, AI539707, AI559957, AI521571, AI281867, AI620284, AI345416, AI345612, AI582912, AI671642, AI345415, AI866461, AL079960, AI623736, AI469775, AI866820, AL045500, AL045421, AI433976, AI890907, AI355008, AI273179, AI371251, AI866510, AI923046, AI950664, AI335426, AI348777, AW151979, AI885949, AW302924, AI690946, AI249946, AI366900, AI432644, AW105601, AI285419, AL047187, AL042488, AW191003, AI922550, AW023590, AW197139, H89138, AL048375, AI364788, AW129230, AW169604, AI432666, AI866581, AW005612, AA641818, AI815150, AI275175, AI633125, AI499463, AW073697, AL046942, AI670009, AI610362, AW083804, AI049851, AI955906, AI440239, AI817244, AI521596, AL134712, AI590686, AW193467, AL042551, AW162194, AL048644, AI537273, AA715307, AI436456, AI371265, AA809974, AI963846, AI567940, AI610357, AF135157, AF158248, AL049452, X53587, AL122106, AL137461, A15345, S75997, I48978, A52563, AF118070, AL137548, AF111851, AF061573, AL080074, X79812, AF183393, A08916, AL133010, AF162270, AF026816, I89947, A08913, AL137476, AR038854, AF113676, A08912, A08910, AL122110, I89931, A08909, Y11587, AL133014, I49625, AF067728, A08908, AF139986, AL122049, AI8777, E15324, Z82022, AF003737, AF153205, AL122098, AL133016, S68736, AF137367, E12747, S36676, U67958, A77033, A77035, AL133640, AL080154, E02349, AF026124, AL122118, AF030513, AJ012755, AF113677, L30117, AL137538, AF058921, Y11254, E01314, AL133077, I48979, AL080148, AF113013, AL133072, AL137665, AF078844, AF113690, AL133080, Z72491, Y08769, AL133081, U96683, AF081195, AR011880, E07361, X81464, I89934, I89944, AC002467, AJ242859, AL117460, AF106697, AF000301, AF090900, S76508, AL050138, X80340, AL137574, S69510, AL137558, AL137488, AR020905, AL133067, AL137556, AL133558, AL080159, AL137560, X52128, AJ238278, AB007812, AF061795, AF151685, AL137658, E15569, AF008439, AL137537, I80064, AF113694, A65341, AR000496, U39656, AL110221, L31396, AL049465, AL080140, AL050393, AL137641, X93495, X65873, E01614, E13364, AF057300, AF057299, A21103, X63410, AF091084, AF113019, X82434, AF017437, AF126247, AL137526, AF118094, AF097996, E06743, AF210052, AL117583, AF176651, AL137459, AF159615, AL117585, AL122100, AL117578, M27260, AL050170, AF125948, AF125949, U49434, AL122093, AL133113, U42766, AL080163, AJ005690, AL137479, X96540, AL110280, AL122123, X72889, A58524, A58523, AF012536, AL080060, AF113689, L19437, I26207, U95114, AF090943, U00763, AL137478, AL049314, L31397, AF111849, U68233, 192592, AF090903, Y14314, AL117440, U80742, A12297, AL110222, E02221, AF032666, I68732, AL050366, D83032, AL137539, AL049464, AF067790, E03348, X00861, AL137557, AF215669, E02253, AL049466, E03349, AR029490, AL137550, D16301, |

TABLE 6-continued

| Gene No. | cDNA Clone ID | NT SEQ ID NO: X | Contig ID | Public Accession Numbers |
|---|---|---|---|---|
| | | | | E07108, AL050149, AL080137, AF113691, AL137292, AF061943, AL080124, AL137463, U75932, AL080086, AB016226, A65340, AL049382, X70514, AL133557, Z37987, AL080127, A07647, AL133665, U68387, S77771, AF146568, AL137705, AL050092, AR034821, S78214, AL137521, AF000145, AF104032, I00734, AR068751, A08911, AB019565, AL050277, AF119337, AL133104, AF090934, Y16645, AL110196, X62580, AF118090, I42402, AL117416, A90832, AR059958, and AL117649. |
| 4 | HE6DI14 | 45 | 361400 | AW007501, AA902287, AI858092, AI005351, AW083940, AI870864, AI032697, AA829811, AW264612, AA709070, AA614344, AA643392, AI951841, AW149115, AI312642, AA533443, AI799536, AA991955, AI830766, AA594172, AI289881, AI741805, AI276207, AW088660, AW268666, AI749660, AI369678, AI816740, AA625243, AI264768, AI190367, AI510691, AW168615, AI817506, AI792359, AI291890, AW089929, AI268176, AI609047, AA617718, AI913963, F34379, AI282722, AI394498, AA985480, AA864826, AI494152, AW050814, AI868440, AW129114, AA991995, AA937062, AA877343, AA335122, AI335628, AA737786, AI708280, AA642608, AA318733, AW054951, AI245599, AA603928, AI074177, AW080143, AA936631, AA569858, AI768186, AA995511, AA317892, AI718073, AA345519, AI915027, AI963480, AA318753, AI291076, AA335136, AI340221, W87494, AI739187, AI830861, AI351218, AA779248, AI266613, T53694, AA335121, AI950591, AW083985, AW148663, AA746624, R23643, AA804997, AA740560, AI749854, AA961830, R35066, AW168417, AA878942, AA983420, AA367958, T53693, AA804991, AI198965, AA862333, AA632062, AI557082, AI541321, AI541205, AI557808, AI557238, T18597, D51002, AI557258, AI525856, AI557602, AI541027, AI557731, AW023469, AI525500, AW020592, AI557533, AI540890, AW020328, AW022874, AI541048, AI535660, AI828465, AI525556, AW021693, AI557426, AI557222, AI557241, AW023351, AW022593, AW022981, AW021182, AW023863, AW021178, AW022826, AI557697, AI557285, AI526078, AW020397, AW022456, AW020480, AI525656, AI541346, AW019988, H65400, AI557084, AW023617, AW020425, AW021561, AW020543, AW022299, AW080896, AW022571, AW411235, AW021466, AW022727, AI557234, AW021059, AI541056, AI525669, AW020931, AW022308, AW411265, AW410902, AA729782, D50992, AI557041, Z32887, AW020406, AL045453, AW411351, AW020295, AI612885, AI557262, Z33559, AW005612, AI469764, AW189802, AI654137, AI540179, AA554005, AW411043, AW023884, D59751, AW020634, AW020629, AW021717, AW265004, AI699175, AW022760, AA127565, AI535639, AA743358, AA259207, H95782, AA769697, AF135157, AR050070, S68736, A62298, Y08991, A91160, AF158248, A82595, A82593, Z30183, U94592, Y11505, S73498, AL133049, E12888, AL049452, S70057, AR030544, E12579, A62300, A15345, S71381, X53587, D44497, A93016, AC004213, AF111851, AF061573, AF130342, AF006072, AR068753, AR050959, AR068751, Y11254, AF065135, A76337, A76335, I92592, U80919, AL050170, AF131814, AL080110, AF150103, AR038854, L40386, A21625, AF139986, I48978, AB026995, A41575, AF094480, AF067223, AC004399, AC006115, AE192522, AF161413, AL080074, AL137539, E01314, A86558, S36676, AF067728, X79812, AL133053, AF058921, AF004162, X67813, AL133010, AF107018, AC005156, I80062, AF211175, AF113676, AC006112, X98066, AF106697, U45328, E01357, AL133016, AF098162, M79462, AF141976, AL110221, AL080154, X51694, AF007142, AF039202, AL137574, AF124396, AL137641, AC005209, I48979, X60769, X76228, |

TABLE 6-continued

| Gene No. | cDNA Clone ID | NT SEQ ID NO: X | Contig ID | Public Accession Numbers |
|---|---|---|---|---|
| | | | | A41579, X99257, AL137560, E03168, AL133607, AJ006039, L12407, AL137284, X66113, AL133608, J05277, AL022165, AC004554, AF119336, A83556, AF199509, AF044323, E13998, S82852, AF081825, X82434, and A57389. |
| 4 | HACBG19 | 46 | 1050384 | AW007501, AA902287, AI858092, AI005351, AW083940, AI032697, AI870864, AW149115, AA829811, AA709070, AW264612, AI951841, AA643392, AA614344, AI312642, AA533443, AI799536, AA991955, AI830766, AA594172, AI289881, AI741805, AI276207, AW088660, AW268666, AI749660, AI369678, AI264768, AA625243, AI816740, AI190367, AI510691, AW168615, AI817506, AI291890, AW089929, AI268176, AI792359, AA617718, AI913963, F34379, AA985480, AI282722, AA864826, AW050814, AI868440, AA991995, AA937062, AI494152, AA877343, AA737786, AI609047, AW129114, AI394498, AI335628, AA335122, AI708280, AA642608, AA318733, AI245599, AA603928, AA936631, AW054951, AA995511, AA317892, AI718073, AA569858, AI915027, AI768186, AI963480, AA318753, AW080143, AI291076, AA335136, AI340221, W87494, AI830861, AI351218, AI266613, AA779248, T53694, AA335121, AI950591, AA746624, R23643, AA804997, AA740560, AI749854, AA961830, AA345519, R35066, AA878942, AI739187, AA983420, AA367958, T53693, AA804991, AI198965, AA862333, AA632062, AI828465, AA078636, AI557262, AI541205, AI525556, AI557082, AI557602, AI535828, AI541075, AI557084, AI557474, AI557809, AI541034, AI557258, AI541321, AI546829, AI541346, and AF135157. |
| 4 | HACBG19 | 47 | 1050383 | AW007501, AA902287, AI858092, AI005351, AW083940, AI870864, AI032697, AA829811, AA709070, AW264612, AA643392, AI951841, AW149115, AI312642, AA614344, AA533443, AI799536, AA991955, AI830766, AA594172, AI289881, AI741805, AI276207, AW088660, AW268666, AI749660, AI369678, AI264768, AA625243, AI190367, AI816740, AI510691, AW168615, AI817506, AI792359, AI291890, AW089929, AI268176, AI609047, AA617718, AI913963, F34379, AA985480, AI282722, AI394498, AA864826, AW050814, AI494152, AI868440, AA991995, AA937062, AW129114, AA877343, AI335628, AA335122, AA737786, AI708280, AA642608, AA318733, AI245599, AW054951, AA603928, AI074177, AA936631, AA569858, AW080143, AI768186, AA995511, AA317892, AI718073, AA345519, AI915027, AI963480, AA318753, AI291076, AA335136, AI340221, W87494, AI739187, AI830861, AI351218, AI266613, AA779248, T53694, AA335121, AI950591, AA746624, AW083985, AW148663, R23643, AA804997, AA740560, AI749854, AA961830, R35066, AW168417, AA878942, AA983420, AA367958, T53693, AA804991, AI198965, AA862333, AA632062, AI557082, AI541321, AI541205, AI557808, AI557238, T18597, D51002, AI557258, AI557602, AI525856, AI541027, AI557731, AW023469, AI525500, AW020592, AI557533, AI540890, AI541048, AI828465, AI535660, AW020328, AW022874, AW022593, AI525556, AW021693, AI557426, AI557222, AI557241, AW023351, AW022981, AW021182, AW023863, AW021178, AW022826, AI557697, AI557285, AI526078, AW020397, AW022456, AW020480, AI525656, AW023617, AI557084, AI541346, AW019988, H65400, AW020425, AW021561, AW020543, AW022299, AW022571, AW411235, AW021466, AW022727, AI557234, AW021059, AI541056, AI525669, AW020931, AW022308, AW411265, AW410902, AA729782, D50992, Z32887, AW020406, AW080896, AA554005, AW411351, |

TABLE 6-continued

| Gene No. | cDNA Clone ID | NT SEQ ID NO: X | Contig ID | Public Accession Numbers |
|---|---|---|---|---|
| | | | | AW020295, AW022760, AI612885, AI557262, Z33559, AW189802, AI557041, AW411043, AW023884, D59751, AW020634, AI538203, AW020629, AW021717, H89138, AW265004, AL045453, AA127565, AI535639, AA259207, AI918424, AA769697, AA100772, AW264964, AF135157, AR050070, S68736, A62298, Y08991, A91160, AF158248, A82595, A82593, Z30183, S73498, Y11505, U94592, AL049452, S70057, E12888, AL133049, AR030544, E12579, X53587, A62300, D44497, S71381, X68560, AF130342, A93016, AC004213, A15345, AL050170, AF006072, AF131814, AR068753, AR050959, AR068751, AB026995, Y11254, AF065135, A76337, A76335, I92592, AF111851, AF150103, AF061573, AC004399, AC006115, L40386, A21625, AL080074, AL096709, X79812, AF058921, X67813, AL133010, AF107018, AF113676, U80919, AC006112, AF067223, AL080110, AF106697, AL137539, AF067728, AL133053, U66075, AF139986, AC005156, AF211175, AF007142, AF004162, AL133608, AC004554, I48978, AF119336, A41575, AF094480, U45328, A57389, AL133088, E01357, AL133016, AF137367, AF098162, M79462, AF192522, AF161413, AL022165, AF141976, A86558, S36676, AL080154, X51694, E01314, AF039202, AF126372, AC005209, I80062, X60769, X76228, AL031295, X99257, A59344, AJ006039, L12407, AL137284, X68249, J05277, Y00093, E15568, and AF179633. |
| 4 | HAPQT56 | 48 | 902207 | AW007501, AA902287, AI858092, AI005351, AW083940, AI870864, AI032697, AW149115, AA829811, AA709070, AW264612, AA643392, AI951841, AA614344, AI312642, AA533443, AI799536, AA991955, AI830766, AA594172, AI289881, AI741805, AI276207, AW088660, AW268666, AI749660, AI369678, AI264768, AA625243, AI816740, AI190367, AI510691, AW168615, AI817506, AI792359, AI291890, AW089929, AI268176, AA617718, AI609047, AI913963, F34379, AA985480, AI282722, AI394498, AA864826, AW050814, AI494152, AI868440, AA991995, AA937062, AW129114, AA877343, AI335628, AA335122, AA737786, AI708280, AA642608, AA318733, AI245599, AW054951, AA603928, AI074177, AA936631, AA569858, AW080143, AI768186, AA995511, AA317892, AI718073, AA345519, AI915027, AI963480, AA318753, AI291076, AA335136, AI340221, W87494, AI739187, AI830861, AI351218, AI266613, AA779248, T53694, AA335121, AI950591, AW083985, AA746624, AW148663, R23643, AA804997, AA740560, AI749854, AA961830, R35066, AW168417, AA878942, AA983420, AA367958, T53693, AA804991, AI198965, AA862333, AA632062, AI557082, AI541321, AI541205, AI557808, AI557238, D51002, AI557258, AI525653, AI541027, AI557731, AI557602, AI525856, AW020592, AI525500, T18597, AI541048, AW021693, AI557533, AI540890, AI828465, AW022874, AI535660, AA585439, AI557426, AI557222, AI557241, AW023351, AW023469, AI525556, AW022981, AW021182, AW021561, AW023863, AW021178, AW022826, AI305283, AW020397, AW022593, AW020480, AW020328, AI557697, AI525656, AI583584, AW019988, AI557285, AI525499, AI526078, AW020931, AW022571, AW022456, AW020425, AW022760, AI557084, AW022299, AI541346, H65400, AW411235, AW021059, AI541056, AI525669, AW411265, AW410902, AW023884, AA729782, AW020543, AW020406, AA554005, AW022727, AI557234, AW022308, AL138459, AW023617, AW411351, AW020295, AI612885, AW189802, D50992, AW411043, Z32887, AI273179, AW020629, AW021717, H89138, AW265004, AW411337, AW021466, AA127565, AA259207, AW084151, AL121328, AA100772, AW264964, AI557262, AW020876, |

TABLE 6-continued

| Gene No. | cDNA Clone ID | NT SEQ ID NO: X | Contig ID | Public Accession Numbers |
|---|---|---|---|---|
| | | | | AI673184, Z33559, AF135157, S68736, AR050070, A62298, Y08991, A91160, AF158248, E12888, AL133049, A82595, A82593, Z30183, U94592, AL049452, Y11505, S70057, AF107847, E12579, X53587, X96757, S73498, AF130342, A62300, A93016, AC004213, A15345, X68560, U45328, AL122049, AL022165, A18777, AF131814, D44497, AR068753, AL137548, AR050959, AR068751, AB026995, Y11254, AF065135, A76337, A76335, I92592, AC006115, AL050170, AF111851, AF150103, AF061573, AF006072, U67813, A21625, AL080074, X79812, AF058921, X67813, AL133010, AL133014, S71381, AF113676, AR030544, U80919, AF141976, AC006112, L40386, AL080110, D00174, AF106697, AL137539, AF067728, AF139986, AF169202, S65585, AP000081, AL096709, AF211175, A59344, AF007142, AL080150, AF029728, AF004162, I48978, AR005195, AL133608, AF072933, AF119336, A41575, AL133053, AF153205, AF094480, AL080129, AF067223, Y08769, A57389, AL133088, AF030165, AL133016, AF137367, AF098162, M79462, AF192522, AF161413, Z93784, AF022813, E01314, A86558, S36676, AL137562, AL080154, AF039202, U66075, AL137665, AF126372, AB014082, AP00514, AC006203, U69730, I80062, Y17327, X60769, X76228, X99257, AJ006039, AL137284, AL137534, J05277, Y00093, E15568, AF179633, X98066, A83556, M85165, AF082324, AF199509, AL137641, and AL050322. |
| 4 | HLYAN43 | 49 | 513179 | AA449296, AA449556, AI524150, AI984842, AI609927, AI819436, AW009733, AA465450, AI948444, AI277802, R41061, AI672999, AI056173, AI557436, AI277801, AI189314, AI581709, AA954708, AA683571, AA933818, AW079525, AI078401, AA379775, AA369058, AI634327, AA742493, AI950621, AI365075, AA663732, AA877647, AA862700, AA877471, AI391456, AW089003, R18095, AI566394, AA912462, AI301746, AA028143, AW102581, AI914810, AA737984, AA369057, H83569, AI376709, AA028180, AA969789, AI889818, AI446023, AI590043, AI524179, AA916033, AW182790, AI590686, AI744985, AI950729, AI627866, AA761557, AW195943, AW024594, AW163834, AI498067, AI373276, AI866624, AL138457, AA676361, AI472536, AI932739, AW089844, AW194014, AW130356, AI689470, AA767177, AW081383, AI345415, AI653402, AW080992, AI401697, AW080290, AI673301, AI922543, AW193288, AI799313, AI933574, AI288050, AI688858, AI638644, AI381676, AW051088, AI890907, AI565048, AA743430, W45039, AI952145, AI693016, AI357599, AI539800, AI763414, AW191844, AI174394, AI633198, AI932794, AI673297, AI499570, AI584140, AL047100, AI338427, AI282688, AI365256, AI609556, AI499963, AI474146, AW262557, AI522052, AI637584, AI583578, AW089006, AI619691, AW198090, AI922561, AI432969, AI872423, AI696583, AI864836, AI677646, AI620944, AI973152, AI434468, AI571980, AI583584, AI633300, AI146568, AI671673, AI872472, AA835966, AI961414, N25033, AW008226, AI673363, AI624154, AW078606, AW081298, AW083572, AI933903, AI590755, AI367328, AI422080, AL040449, AI798351, AI500061, AI440399, AW084233, AI633125, AI473799, AA587590, AI690813, AI619426, AI658566, AI783504, AI927233, AI367705, AI922707, AW088691, AI479292, AI571439, AI559752, AI802244, AI245008, AI624693, AI609360, AI972944, AI521100, AW129264, AI678602, AI554411, AI553645, AI799189, AI762707, AI350880, AI537967, AI669612, AI800648, AI824576, AW088560, AW075382, AI263584, AI954095, AI345612, AW029238, AI866691, |

TABLE 6-continued

| Gene No. | cDNA Clone ID | NT SEQ ID NO: X | Contig ID | Public Accession Numbers |
|---|---|---|---|---|
| | | | | AI096613, AI279628, AI863047, AI679069, AI345416, AW025279, AI570056, AI681985, AI434731, AI683270, AI651840, AI678446, AW075305, AW078777, T69241, AW196720, AW166979, AI589428, AW085786, AA502794, AA831948, AI679778, AI538686, AA514684, AI284484, AI343582, AI440238, AI961310, AI611810, AI811603, AI860817, AW080076, AW150578, AI887381, AI539260, AI536563, AI559596, AW055081, AI633061, AI680066, AW026477, AI274655, AI889306, AI356868, R41605, AI582932, AW082532, AI689614, AI362537, AA743385, AW151714, AI687362, AL137554, AF090903, D83032, Y14314, AR059883, X63162, AI5345, AC005992, I22272, AF183393, AL080110, AF113694, AL122049, AL137560, AF107847, S77771, AL050143, AL117443, AF061981, AL137550, AR038854, AL031984, AL137463, Z72491, A18777, E12747, A77033, A77035, AF153205, AL050138, AL049452, X98066, AL137530, AL133062, AL110228, AL137527, Z97214, AF169154, X80340, AF031147, AF161413, AL133623, E12579, AL080140, AL133619, AL137292, AR029490, U90884, AL049460, U37359, A45787, E12580, A08913, I89947, A52563, X53587, L19437, AF159615, AF094480, AL133557, AL080139, AL137574, AL133075, AL050149, A08912, U49434, AL080150, AL133608, AL080150, AL133608, U79523, AF032666, A08910, A08911, A08909, X66871, Z13966, AL080154, AL110226, AL137294, AF057300, AF057299, AR029580, A08907, I48978, A08908, AR068466, S76508, AC004227, A32826, A30330, A32827, A30331, AL133084, AB026995, U89906, AL080159, X84990, AB007812, AL080158, AL137533, I32738, Z48796, U75378, X81464, AF054986, AR009628, AF115392, X92070, AF047716, X57084, AL133568, A27171, AL133049, AL137548, AL137665, AF000145, A18788, E02152, AF091084, AB016226, AL133637, AL122050, A76337, E02349, AL110296, AF079763, AF017790, M27260, I26207, AF205861, I09499, U78525, AL137268, AF008439, AR036183, AL137300, AR068751, AF067728, L13297, E07108, AF177401, AF044323, X67813, AL110224, AL050393, AL137662, AJ012755, AL137471, S54890, A21103, AF090900, AL133069, E03348, AF028823, A86558, A41575, AL117435, AL137562, E03349, AL110221, AF090896, Z82022, U95738, AF026816, I41145, AF022813, AL096709, AF215669, AL137478, U83980, X89102, AL117416, E00984, I04527, AL050116, AJ003118, AL080148, AF043642, AF115410, AF077051, A65965, X63410, AL137627, A92311, X82434, AF114170, AF131773, AL133558, Y11587, U76419, AL133070, A76335, AF141289, AL050172, AF200464, AL133624, E01314, U83172, AF199027, A65943, AF030513, AL049466, AL110222, AJ005690, AF098162, AL137539, AF003737, Y10823, AL137557, A65340, X62580, AF200416, AL137538, AF061795, AF151685, S82852, AF180525, AF019298, X87224, AC002467, AC002464, M84133, E01573, E02319, AF106945, AL096728, AL080146, Y13350, AF114784, I17544, AF106697, U42031, AF199509, AF036268, AB028451, and AL137273. |
| 5 | HTLGV19 | 15 | 901886 | AI392811, AI302099, AA478198, AI435141, AI803046, AI928295, AA478040, AI928292, AW206706, AW367708, and AA846117. |
| 6 | HTTCT46 | 16 | 423038 | AW014933, AW021164, AW020116, AI453569, AW338670, AI424992, AI922706, AI742885, AI521511, AI342112, AI342123, AA864962, AI916681, N48528, AI813984, AI570185, H30104, AW305161, AI088387, D62133, N69067, D62597, AW020789, AA977334, AI745211, N67892, AW262786, N63231, W56148, N39415, AI093708, AA904959, D61737, D62236, AI218410, W06903, AI280284, AI287305, AA227767, N91349, N69076, N67939, AA227951, AI381291, W39563, D62569, D62771, D62982, AW264446, AA045327, W20008, D62028, AW263349, AA889218, W15431, AA332364, AA774515, H30466, AA219100, AI263713, N75186, AI394180, AW104259, |

TABLE 6-continued

| Gene No. | cDNA Clone ID | NT SEQ ID NO: X | Contig ID | Public Accession Numbers |
|---|---|---|---|---|
| | | | | AI700865, AI537351, D62862, AI926000, D54372, D61808, AI261756, D62929, D62584, H88893, AA861328, D62870, D62749, AW022422, AW023728, AA358198, D62922, D62565, D62880, AW026876, AA219099, N22301, AA367442, H88894, D62754, D62519, D62119, H30183, D62912, D79392, AA781602, AA295227, D79802, H88966, H88940, H90645, D61934, AA329940, D62847, D62721, D79695, D62811, AW339960, AI610487, H89049, D63133, AA625257, D61880, H89169, D62813, AA045385, D79492, D79678, AA327731, D62551, AA243742, AA708797, AA328664, D79421, D63063, D63015, AA193444, D61758, D79830, H91568, D62382, AW020090, AI934365, D62456, D62755, D62809, D79356, AI127717, D62911, D62707, D79638, W21015, D62685, D79491, AW262616, D62836, D61876, D79741, AA329804, N89676, D79241, D61920, N67575, H27453, D79609, AA296367, D62256, D79293, R06414, D62973, AA249597, D79825, D79456, D79904, AA903304, D62958, D79460, D61750, D62080, T97739, N66456, R06469, AW244004, AI040141, T97846, C16149, AA332194, AI270264, AW302407, AW023330, N56025, AW361429, AL133114, AL110267, AF100758, AF192483, M37974, AF017339, AF105150, D31951, AF088023, AF112465, AF192478, AF192481, AF192480, AF192482, AF192479, and AF192477. |
| 6 | HSDEE58 | 50 | 905256 | AW014933, AW021164, AW020116, AI453569, AW338670, AI424992, AI922706, AI742885, AI521511, AI342112, AI342123, AA864962, AI916681, N48528, AI813984, AI570185, H30104, AW305161, AI088387, D62133, N69067, AW020789, D62597, AA977334, AI745211, N67892, AW262786, N63231, W56148, N39415, AI093708, AA904959, D61737, D62236, AI218410, W06903, AI280284, AA227767, AI287305, N91349, N69076, N67939, AI381291, AA227951, W39563, D62569, D62771, D62982, AW264446, W20008, AA045327, D62028, AW263349, AA889218, W15431, AA332364, AA774515, H30466, AA219100, AI263713, N75186, AI394180, AW104259, AI700865, AI537351, D62862, D54372, AI926000, D61808, AI261756, D62929, D62584, H88893, AA861328, D62870, D62749, AW022422, AW023728, D62922, D62565, AA358198, D62880, AW026876, AA219099, N22301, AA367442, H88894, D62754, D62519, D62119, H30183, D62912, D79392, AA781602, AA295227, D79802, H88966, AI934365, H88940, H90645, D61934, AA329940, D62847, D62721, D79695, D62811, AW339960, AI610487, H89049, D63133, AA625257, D61880, H89169, D62813, AA045385, D79492, D79678, AA327731, D62551, AA243742, AA708797, AA328664, D79421, D63063, D63015, AA193444, D61758, D79830, H91568, D62382, AW020090, D62456, D62755, D62809, D79356, AI127717, D62911, D62707, D79638, W21015, D62685, D79491, AW262616, D62836, D61876, D79741, AA329804, N89676, D79241, D61920, N67575, H27453, D79609, AA296367, D62256, D79293, R06414, D62973, AA249597, D79825, D79456, D79904, AA903304, D62958, D79460, D61750, D62080, T97739, N66456, R06469, AW244004, AI040141, T97846, C16149, AA332194, AI270264, AW302407, N56025, AW023330, AW361429, AL133114, AL110267, AF100758, AF192483, M37974, AF017339, AF105150, D31951, AF088023, AF112465, AF192478, AF192481, AF192480, AF192482, AF192479, AF192477, and D79422. |
| 8 | HOHCA60 | 18 | 906064 | AI917724, AI342006, AI261611, AI750970, N33407, AI825646, AA482392, AI459225, W47029, AA971699, N44869, W47220, AA284278, AI905640, AI905601, AI005408, AI806281, and AW137913. |
| 8 | HOHCA60 | 52 | 906419 | AI608789, AA411541, AW150272, AI991149, AI934755, AI763268, AI090866, AA464314, AI277953, AI624414, AI954973, AI167471, W96217, AI675874, AA604659, W93790, AW016493, AA813712, AW082293, AI159950, AI038163, AA834939, AI279359, AA297727, AW004853, AA297726, AA550765, H91883, AA456486, W96311, |

TABLE 6-continued

| Gene No. | cDNA Clone ID | NT SEQ ID NO: X | Contig ID | Public Accession Numbers |
|---|---|---|---|---|
| | | | | T16058, T36190, AA412342, AA382771, AA412452, AA781072, AA377166, AA344749, Z38920, AA369026, AA326408, AA341054, R41523, AI435982, AW016126, R18534, AA477934, AA664345, AI144001, AA722624, AA628669, W93789, Z42768, D45660, T52089, H06991, AL080162, AF097484, AF056183, AC005089, AF097485, and AF097523. |
| 8 | HOHCA60 | 53 | 904949 | AI917724, AI342006, AI261611, N33407, AI825646, AA482392, W47029, AI750970, N44869, W47220, AI459225, AA284278, AA971699, AI905640, AI905601, and AW137913. |
| 8 | HOHCA60 | 54 | 904948 | AA482392, AI459225, AA971699, and AW137913. |
| 9 | HLQFT18 | 19 | 899439 | AA502331, AA503839, AW444616, AI699382, AA568450, AI017393, T72043, T85589, T78178, T85588, AA299977, T86494, AA335186, AA551860, AI421755, AA525331, AW019964, AI567391, AA558404, AI671077, AI279417, T95676, AI200649, AA828730, AA586433, AI821273, T51743, AI355246, H43183, AI923052, AI565084, AA524616, AA371410, AW166641, AA937809, AA482792, AA904211, AI049676, AA630854, H65213, AA834799, R93919, AW023111, AI267356, AL041375, AA658934, AA304858, AI831172, T84567, AW265688, AI280266, AL138431, AA515939, AA349937, F01222, T08386, AI267450, AI335963, AA641112, AI114733, AI133552, AA707747, AI310464, F31867, AL119247, AI914713, R70883, AA343894, D51877, AI866580, R70884, AW316599, AA384911, AA582060, AA878407, AI064843, AA582746, T62078, AI133612, AA654874, AI306717, AW151541, AA936718, AA445908, AI885465, W24312, AA650447, AI609972, AW439703, AA553570, AL110373, AA493947, AI889579, AI185990, AA837771, R99613, AI749306, AA947369, AI133514, H67064, AI471808, AI620354, AR027051, AC006966, AC006275, AC008116, AC005696, U95739, AC000097, AC004922, AC006547, AC006512, U16812, AL022320, I34294, AL031984, |

TABLE 6-continued

| Gene No. | cDNA Clone ID | NT SEQ ID NO: X | Contig ID | Public Accession Numbers |
|---|---|---|---|---|
| | | | | U10868, AL049856, AC006979, AC006277, AC005821, AC005339, S42653, AL022316, AL022336, AL049795, AC006581, U02047, AC007226, Z83838, Z86090, AL117344, AL049557, AF184110, AF108459, AC005288, AC002550, AF102137, Z98052, AC004020, AC007993, AP001063, AF069291, AF024534, AC020663, X51956, AL031848, AC004828, U75931, AC002477, AF049895, AC004263, AL035462, AL049793, AL022337, AF196969, AL031282, Z82245, Z98886, AC004002, AC008012, Z98946, AL022719, Z95115, M57627, AC000393, Z98200, U16720, AL050306, AL135959, AL034369, AC000003, AC006071, Z83822, U62293, AC006057, AL078634, Z81010, AC005859, AC005480, AL031311, AC005899, AF024533, AC005264, AL121769, Z92542, AC000378, AC007200, AC005231, I40899, AC005775, AC004912, Z83846, AC005546, Z94802, AC004651, X71896, AC006487, AC005086, AC004612, Z98882, AL049576, AC005519, AC004760, AC004148, AC005488, U07561, AC005295, AC004031, AC007227, AL031466, Z84496, AC007201, AC004131, AC007057, AL049872, AC006450, AC005207, AF149773, AC006121, X55448, AC006059, AL034548, Z84813, AC007786, AC007551, AL132712, AC006112, AL109628, Z82179, AL021155, AL023807, Z82900, L78810, AC005778, AP000295, AL031681, AP000350, AF090931, AC008041, AP000274, AL022238, AC004232, AC006251, AC004876, AC004257, AC006241, AL023803, AC006473, AP000286, AC005057, Z84487, AC005795, AC007938, AC005544, Z98051, Z97630, AL031005, AC004935, AC004216, AC005391, AL021546, AC006014, U02052, AP000268, AL031432, AF118079, AC006449, AC007565, AL133275, AC002128, AC004150, AL008730, AC004262, D88268, AP000034, AF111170, M88004, AC009113, Z96074, AC002546, AP000501, AC005486, AC005291, AL035703, AC005294, AL031904, Z98304, AL109758, AC005383, AC000039, AC005225, |

TABLE 6-continued

| Gene No. | cDNA Clone ID | NT SEQ ID NO: X | Contig ID | Public Accession Numbers |
|---|---|---|---|---|
| | | | | AP000109, AP000041, AC006084, AC005081, Z82172, AB001523, AC006536, AB033024, U52111, AC005988, AC004801, AL031291, AC004883, AL035400, AC002563, AF038458, AF015723, AC005796, Z82217, AC003992, AC006211, AC005827, AC005372, U78027, Z84484, AC006396, AL079342, AJ006995, AC000079, AC005365, AC005919, AC000068, AC007663, AC007637, AL035418, AC005943, AL049699, AF015416, AP001056, AC011331, AL031905, AL023575, AC009247, and AL050338. |
| 10 | HBXFT65 | 20 | 784062 | AW249865, AI091273, AA313317, AA854119, AA479605, AA528178, AI741720, AI949241, W37670, AI041810, AA427616, AI678997, AI421428, AI376945, AI682011, AI018757, AW024459, AA843850, AA148013, AA115177, AI088836, AA397898, AA164656, AI817629, AI419386, AW340310, AI031676, AW166105, AI653966, N41633, AI805755, W55938, AA164657, W58241, AW057816, AA417296, AA833840, AI220471, W58242, AA576267, N29628, AI333667, AI446780, AA416560, AI040265, AA947478, AA255918, AW392222, AW003884, AI051395, AI304937, AI347635, AA988744, AW020149, AA772434, AW130885, AA713478, AA903306, AI023956, AA470629, N54515, AA974783, AA393599, AA465651, AI033986, AA459425, AI344527, AA437350, AI081927, W37530, AA584287, AI571215, AI493440, N51885, H07998, N48016, N35368, AA281406, AI159809, AI573012, AI039904, AI028502, N41531, AA554092, AA770637, AA574012, AI366997, N29516, N36022, N20818, N27425, W39255, AI092581, AA251015, AI366775, AA147985, AI022504, AA313617, AI417192, AA928947, AA773339, AI084384, W42526, AA902741, AI276064, AI344624, N63383, AI348399, A1128976, N24900, AI022495, W94541, AW438835, N30124, R51426, AA846586, AI682889, AA976669, AI095352, AI567371, W52608, AI983274, |

TABLE 6-continued

| Gene No. | cDNA Clone ID | NT SEQ ID NO: X | Contig ID | Public Accession Numbers |
|---|---|---|---|---|
| | | | | AA652023, AA605267, AA890442, N30541, AA599849, AA131635, R79812, AA903999, T74223, AI797520, R78826, AA504313, R25326, R62705, H96859, AI200275, AA890540, N35735, AI625128, N57460, T33335, AA788773, AA255919, AI564312, R51314, W15286, AA825307, AA411697, AA878389, AA489232, R77590, AW370869, R79321, AA417822, AI242587, AA084106, W27971, D51241, AA652014, F10105, AA844543, AA298831, H10190, AI275474, R17981, AI075460, AI439760, AI879862, AA854083, H56745, F12487, H10236, H59133, AI702447, AA952967, R44801, H59176, AI034047, AI750027, AI186656, N27239, AI689439, AI214761, AA298846, AA298119, N76218, W39007, R34849, AI205633, H85240, AI963141, R63080, AW023054, H12551, AI372808, AI349539, AA636009, AA025912, AI220862, AA410980, H65558, AI567231, W92614, AA406563, R66608, AW020210, W42449, AA035073, R66609, AA025751, AA725062, R63665, R63122, R24623, AA298829, AA298870, H96444, AA890510, R43470, AI948455, N34708, AI352243, AI051513, AA084217, H07906, T88945, N52199, H12550, T61909, AI864333, AI084246, AA638966, R19136, N73409, AI349546, AW392267, D20253, AI244926, AI471226, AA788679, AA298825, AA298852, F13756, AA169533, AA095751, AA053862, H59100, H86728, AL049929, Y17975, A74463, A74460, A74462, AF039698, S78798, T61972, R24520, R34946, R77591, R79912, H56665, H89873, H89872, H96709, H89873, N55129, AA035490, AA169729, AA194554, and AA419372. |
| 10 | HMSEO15 | 56 | 384344 | AW249865, AI091273, AA313317, AA854119, AA479605, AA528178, AI741720, AI949241, W37670, AI041810, AA427616, AI678997, AI421428, AI376945, AI682011, AI018757, AW024459, AI805755, AA843850, AA148013, AA115177, AI088836, AA397898, W55938, AA164656, AI817629, AI419386, AW340310, AI031676, AW166105, AI653966, N41633, AA833840, AA164657, W58241, AW057816, AA417296, |

TABLE 6-continued

| Gene No. | cDNA Clone ID | NT SEQ ID NO: X | Contig ID | Public Accession Numbers |
|---|---|---|---|---|
| | | | | AI220471, W58242, AA576267, N29628, AI446780, AA416560, AA947478, AA255918, AI040265, AI333667, AW392222, AW003884, AI051395, AI304937, AI347635, AA988744, AW020149, AA772434, AW130885, AA713478, AA903306, AI023956, AA470629, N54515, AA974783, AA393599, AA465651, AI081927, AI033986, AA459425, AI344527, AA437350, W37530, AI571215, AA584287, AI493440, N51885, H07998, N48016, N35368, AA281406, AI159809, AI573012, AI039904, AI028502, N41531, AA554092, AA770637, AA574012, N29516, N36022, N20818, N27425, AI366997, W39255, AA251015, AI366775, AI084384, AA147985, AI022504, AA313617, AI417192, AI092581, AA928947, AA773339, W42526, AA902741, AI276064, AI344624, N63383, AI348399, AI128976, N24900, AI022495, W94541, AW438835, N30124, R51426, AA846586, AI682889, AA976669, AI095352, AI567371, W52608, AI983274, AA652023, AA605267, AA890442, N30541, AA131635, AA599849, R79812, AA903999, T74223, AI797520, R78826, AA504313, R62705, R25326, H96859, AI200275, AA890540, N35735, AI625128, N57460, T33335, AA788773, AA255919, AI564312, R51314, W15286, AA825307, AA411697, AA878389, AA489232, R77590, AW370869, R79321, AA417822, AI242587, AA084106, W27971, D51241, AA652014, F10105, AA844543, AA298831, H10190, AI275474, R17981, AI075460, AI439760, AI879862, AA854083, H56745, F12487, H10236, H59133, AI702447, AA952967, R44801, H59176, AI034047, AI750027, AI186656, N27239, AI689439, AI214761, AA298846, N76218, W39007, R34849, AI205633, H85240, AI963141, R63080, AW023054, H12551, AI372808, AA636009, AA025912, AI220862, AA410980, AI349539, H65558, AI567231, W92614, AA406563, R66608, AW020210, W42449, AA035073, R66609, AA025751, AA725062, R63665, R63122, R24623, AA298119, AA298829, AA298870, H96444, AA890510, R43470, AI948455, N34708, AI352243, AI051513, AA084217, H07906, T88945, AI864333, N52199, H12550, T61909, AI084246, AA638966, R19136, N73409, AI349546, AW392267, D20253, AI244926, AI471226, AA788679, AA298825, AA298852, F13756, AA169533, AA095751, AA053862, AW241187, H59100, AL049929, Y17975, A74463, A74460, A74462, X84990, E12888, D44497, J05277, X80340, AL080060, AC005520, AL122049, AL049423, AL133015, AR055519, AL133075, A03736, AL133053, AL133049, AL133623, AF113691, X66417, I29004, AL122106, AL133607, AF029750, AC006582, AL133072, AF026008, L19437, AF094480, AL122101, AL050138, E01614, E13364, T61972, R24520, R34946, R77591, R79912, H56665, H86728, H89873, H89872, H96709, H89873, N55129, AA035490, and AA169729. |
| 11 | HWHGK36 | 21 | 899442 | AA846828, W73821, W73855, AI131566, AA706316, AI141167, AA854719, AW009909, AA480817, AI161236, AW001367, W95733, AI148339, AW009219, AA740424, AI144221, AI092860, W94659, AI150077, W92535, AI884343, AI092290, AI127118, W02504, AI160306, AI146274, AI093208, W69100, AI659437, AA457707, W68286, AA683607, W68306, AI201606, W69381, AI807653, AA025788, AA723266, W69101, AI090543, AW129599, AI968950, W95987, AA732945, AI920791, AI243460, AI191440, AI040335, AA733131, W58747, AA559049, AA025948, AI276343, AI140412, AI288161, W25575, AI217041, AI240970, AI311411, AI123650, W35291, W94668, AA369872, AA022504, AI914430, W95776, AA897755, C00662, W69380, AW002963, AI915707, AA777022, AI270114, AA022503, AA722946, AA359882, H27527, H45934, AI283931, AI961281, AW073996, AI674627, AW089638, AI623941, AI627714, AI918809, AI287827, AI950892, AI587257, AI445256, AL036802, AI540752, AL120756, AI422002, AI687725, AF086315, AD001502, AL137716, AF103804, I89947, AL137550, |

TABLE 6-continued

| Gene No. | cDNA Clone ID | NT SEQ ID NO: X | Contig ID | Public Accession Numbers |
|---|---|---|---|---|
| | | | | M79462, AF087943, X83544, U95114, L35261, X69026, and U72621. |
| 12 | HAGDA35 | 22 | 1070597 | AI685285, AA648924, AA215679, AI241084, AA279477, AA810583, AI885510, AA769118, AA810311, W47115, AA662537, AL022165, AL050307, and AA278532. |
| 12 | HAGDA35 | 57 | 618529 | AA278194, AW297646, AA279477, W47116, W47115, AA662537, T05300, AA832156, and AL022165. |
| 12 | HAGDA35 | 58 | 637487 | AA278194, AW297646, AA279477, W47116, W47115, AA662537, T05300, AA832156, and AL022165. |
| 13 | HRODQ04 | 23 | 777923 | AI065139, AI686204, AI766943, AI623280, AA425583, AI678169, AA425387, AI032814, AI220994, AA595016, AI240411, AI758161, AA132163, AI271565, AI332512, AA451730, AI393086, AI961133, AA135504, AA424150, AA468862, AA135505, H12316, AW299404, AW207017, AA132078, AA318401, AI474190, AA375142, AW069070, AI381324, AA552888, AI373040, AI905235, AW138311, AI816870, D80045, C14331, C14429, D59275, D80253, C14389, D80227, D59467, D51799, D80195, D59502, D80164, D80366, D80269, D58283, D80166, D51423, D59619, D80210, D80391, D80240, D80043, D80038, D59859, D80212, D80193, D80196, D80188, D80022, C15076, D80219, D59927, D81030, D57483, D51060, D80024, D59610, AW366296, D50979, D59889, D59787, D80378, D50995, AW177440, AA305409, D80241, C14014, C75259, T03269, AA514188, D51022, AA305578, AW178893, D81026, D80251, C14407, AW179328, D80248, D80134, AA514186, AW378532, AW360811, D80522, D51250, AW178775, D80133, AW177501, AW177511, AW369651, D52291, F13647, AW375405, AW178762, AW378540, D58253, D59695, AW352158, D80168, AW377671, AW360844, D80268, AI535686, AW360817, AW375406, AW378534, AW179332, AW377672, AW179023, AW178905, C05695, AW352117, C14227, AW176467, C06015, D80302, AI910186, D81111, AI905856, D80132, AW352171, D80439, AW377676, AW178906, AW352170, AW177731, C14298, AW178907, AW179019, AW179024, D80247, D80064, Z21582, AW177505, AW360841, AW179020, AW178909, D59373, AW177456, AW179329, AW178980, AW177733, AW378528, AW178908, AW178754, AW179018, AW352174, AI557751, D51103, T48593, AA809122, AW179004, AW179012, AW178914, AW378525, AW360834, D80157, T11417, AW177722, AW367967, AW177728, D51097, AA285331, AW179009, D51759, AW178774, AW178911, AW378543, AW352163, AW178983, D58246, D59503, AW178781, C14344, D58101, AW352120, AW177723, D59653, D59627, AI535850, D80258, D45260, AI525923, C14975, AW367950, AW378533, AW177734, H67854, C03092, H67866, AW177508, AW178986, D45273, T03116, D59317, C14973, AW177497, D51213, AI525917, D80228, D80014, D51221, AI525920, AI557774, N66429, D60214, D60010, D59551, M23161, AL031118, A62298, A62300, A84916, Y17188, AR018138, A82595, AJ132110, AR016808, AB028859, Y17187, X67155, AF058696, AR008278, A67220, D89785, A78862, D26022, A25909, D34614, X82626, D88547, A94995, I82448, Y12724, AR025207, X68127, AR060385, AB002449, AR016514, AR008443, A30438, A43190, AB012117, I50126, I50132, I50128, I50133, AR066488, AR060138, A45456, A26615, AR052274, A85396, A44171, AR066482, AR038669, A85477, Y09669, I19525, A43192, A86792, AR066487, AR066490, X93549, I14842, I18367, AR054175, AR008277, AR008281, D50010, A63261, AR016691, AR016690, U46128, D88507, AR008408, AR062872, A70867, I79511, AF135125, D13509, A64136, A68321, U79457, AR060133, AF123263, AR032065, AR060382, and AR008382. |
| 14 | HDPOL27 | 24 | 1163002 | AI936172, AI341137, AI635373, AI650516, AA496235, AA993067, AW140139, AA496236, AI823907, AA534789, AI694980, AI337223, AI493181, AA649205, AI337224, AI246486, |

TABLE 6-continued

| Gene No. | cDNA Clone ID | NT SEQ ID NO: X | Contig ID | Public Accession Numbers |
|---|---|---|---|---|
| | | | | AA478751, AA479971, AA421603, AI744621, AW194078, H28871, H22744, AA516280, R26128, R72261, R25510, R45574, W20038, R62652, M86047, AA381555, AA381682, AA381593, AI572487, AA381497, R26340, AA057695, AA057610, AA381478, H47862, AI014588, AI675309, AW277012, AI288285, AW263796, AA806757, AW151132, AW090498, AI804586, AA908294, AI590043, AI440210, AW025279, AI537516, AI628325, AW162194, AI370623, AI401697, AI669864, AI148256, AI421252, AW081866, AI978703, AI493836, AI818353, AI004911, AW074172, AI285439, AI289791, AI624520, AA749425, AI886355, AA088789, AW008166, AI918637, AI491710, AI538342, AW085786, AI500714, AI433611, AI348901, AA514684, AI738762, AI452876, AA835966, N25033, AI095113, AI539800, AI469516, AA904121, AA575874, AW168875, AI917994, AI434656, AW026707, AI655932, AI658566, AI697178, AI471429, AI590755, AW088793, AW169671, AL039716, AI624154, AI075885, AI859310, AI417790, AI610086, AI963846, AW027898, AI912297, AI926593, AL044725, AW076124, AI245008, AI689096, AI524652, AI590601, AI631095, AI491852, AI272973, AI583558, AI439020, AI625444, AW051088, AI225000, AW085373, AI539028, AI583611, AW079334, AI863197, AA824435, AI648663, AI267492, AI539153, AI431962, AW411363, AW302924, AI372009, AW020592, AI672861, AI570861, AI287476, AW022494, AW020288, AI680347, AI362537, AI345688, AI440399, AI611743, AI584118, AW083804, AW021717, AI357599, AW020381, AI309306, AW079432, AI619607, AI479292, AI478123, AI923559, AI627600, AI355779, AW020046, AI697207, AW263804, AI521005, N75779, AI096771, |

TABLE 6-continued

| Gene No. | cDNA Clone ID | NT SEQ ID NO: X | Contig ID | Public Accession Numbers |
|---|---|---|---|---|
| | | | | AW087566, AI524654, AI241901, AI927233, AI560536, AI472566, AI698391, AI499279, AI669639, AL048499, AI345415, AI805688, AI619820, AW021662, AI249877, AI859644, AI688854, AW080076, AW150762, AI244380, AI921379, AI291601, AI860027, AW411235, AWI51979, AI684164, AI344928, AW176261, AW079706, AI282346, AI696714, AI689614, AI336592, AI114703, AI468872, AA127565, AI264299, AW151451, AI469081, AI344933, AI224373, AI367705, AW411351, AI247298, AI866469, AI589428, AI889306, AI539863, AI648699, AI335449, AA782332, AA555145, AI446124, AI625589, AW089029, AI376376, AI863002, AW168602, AL118781, AI125109, AI095119, AI865320, AI370945, AA493923, AA761557, AI560099, AI582396, AI866573, AI446829, AI696340, AI434760, AI697045, AW411265, AL036265, AW410902, AI678688, AW131999, F26535, AL050267, AF228421, U15635, AF147427, I22272, AR029580, S69510, AL133619, X79812, S82852, S79832, AR068466, AF022363, U89906, AJ005690, AF111849, X66871, AL137530, AL122098, AL096720, A08456, I68732, U77594, E12579, AF061795, AF151685, AF081197, AF081195, AF167995, AF078844, I48978, AL137557, AL137480, A31057, U67958, U95114, AF169154, E06743, AL133015, AI8777, I09499, M64936, AF013214, AF113019, AF026124, S36676, U92068, AF067420, AL117626, AL137711, AF044323, Z97214, AF059612, A08913, AF131821, AL080147, AR038854, AC004987, A21103, X76228, X61399, E12580, A08912, AF026008, X99226, A08911, AF030165, S77771, AF151109, AL133014, AL133559, AL137627, AR068753, Y11587, AL122100, S76508, AL133067, X66862, AF114168, AR068751, AL137478, AL133062, AF16573, AL050366, Y11254, AF065135, A76337, A76335, |

TABLE 6-continued

| Gene No. | cDNA Clone ID | NT SEQ ID NO: X | Contig ID | Public Accession Numbers |
|---|---|---|---|---|
| | | | | AL080110, AL117416, I92592, A91160, AL050149, S68736, A08910, A93016, I89931, A08909, AF119337, AF119336, X65873, U36585, M79462, AF126372, I49625, A08907, A32826, A30330, A32827, A30331, AF100781, AF117959, A08908, A57389, AL133084, A86558, I89947, A65340, AF067728, A65341, AF030635, AL080159, AL133088, AL049382, X80340, AF069506, I42402, AB025103, AF076633, S59519, E01314, AF061981, I32738, AF106657, AL080148, AL133072, AF102578, AL137665, X62773, AL122121, AF032666, AF008439, AJ012755, AC004554, AF113694, AL122110, AF145233, X75295, AL137495, AL133665, I89934, A77033, A77035, M19658, AF109155, AF039138, AF039137, AL137476, AP000130, AP000208, AP000247, S54890, AL050143, AL080162, AR012379, AL117587, Z82022, AF183393, I36502, I22020, U57352, I25049, I25048, X06146, Y14634, U51124, AL137705, AF139986, AF019298, X72889, A70386, AL137556, AL049339, AL133080, U13676, AF047716, U42031, AL137529, U87620, Y14314, AF205861, AF015958, AB029065, A91162, AL137463, L13297, X98066, AF067790, AL080086, AF113690, A20553, L19437, AL133070, X83544, E12806, I46765, AL137536, AL137574, U83172, AL096728, AL117443, J05277, AF113676, U75604, AC006112, AL133560, I48979, AF114170, AL137640, Z13966, AL133624, AF185614, J05032, AF090886, I18358, I34395, AL080156, AL137660, AF185576, AF108357, AL117432, AF040723, AL137268, U72620, AC003032, AL022170, AC006371, AF130342, AR016469, AF111112, AR013797, and AI276219. |
| 14 | HDPOL27 | 59 | 637587 | AI936172, AI341137, AI635373, AI650516, AA496235, AA993067, AW140139, AI823907, AA534789, AI694980, AI337223, AI493181, AA649205, AI337224, AI246486, AA478751, AA479971, AA421603, AW194078, H28871, H22744, AA516280, R26128, R72261, R25510, R45574, R62652, W20038, AA381555, M86047, AA381682, AI572487, AA381593, AA381497, R26340, AA057695, AA057610, AI744621, AA381478, AA496236, AI014588, H47862, AI675309, AW277012, AL050267, AF228421, U15635, and AF147427. |
| 14 | HEBCV31 | 60 | 469522 | AI936172, AI635373, AI650516, AA993067, AA496235, AW140139, AI823907, AA534789, AI694980, AI493181, AA479971, AA421603, AW194078, AI337223, AI246486, H28871, AI341137, AI337224, H22744, AA516280, AA649205, R26128, R72261, R45574, R62652, AI572487, R26340, AA057695, AA057610, AI014588, AA478751, AI288285, N75771, AW263796, AW090498, N71180, AA806757, AW151132, AI804586, AA908294, AI590043, AI440210, AW025279, AI537516, AI628325, AW162194, AI370623, AI401697, AI669864, AI148256, AI421252, AW081866, AI978703, AI493836, AI818353, AI004911, AW074172, AI285439, AI624520, AI289791, AA749425, AI886355, AA088789, AW008166, AI918637, AI491710, AI538342, AW085786, AI500714, AI433611, AI348901, AA514684, AI738762, AI452876, AA835966, N25033, AI095113, AI539800, AI469516, AA904121, AW168875, AA575874, AI917994, AI434656, AW026707, AI655932, AI697178, AI658566, AI471429, AI590755, AW088793, AW169671, AL039716, AI624154, AI075885, AI859310, AI417790, AI610086, AI963846, AW027898, AI912297, AI926593, AL044725, AW076124, AI245008, AI689096, AI524652, AI590601, AI631095, AI491852, AI272973, AI583558, AI439020, AI625444, AW051088, AI225000, AW085373, AI539028, AI583611, AW079334, AI863197, AA824435, AI648663, AI267492, AI431962, AW411363, AI539153, AW302924, AI372009, AI672861, AW020592, AI570861, AI287476, AW022494, AI680347, AW020288, AI362537, AI345688, AI440399, AI611743, AI584118, AW083804, AW021717, |

TABLE 6-continued

| Gene No. | cDNA Clone ID | NT SEQ ID NO: X | Contig ID | Public Accession Numbers |
|---|---|---|---|---|
| | | | | AI357599, AW020381, AI309306, AI619607, AW079432, AI479292, AI478123, AI923559, AI627600, AI355779, AW020046, AI697207, AW263804, AI521005, AW087566, N75779, AI096771, AI524654, AI241901, AI927233, AI560536, AI698391, AI472566, AI499279, AI669639, AL048499, AI345415, AI805688, AI619820, AW021662, AI249877, AI859644, AI688854, AW150762, AW080076, AI921379, AI244380, AI291601, AI860027, AW411235, AW151979, AI684164, AI344928, AW176261, AW079706, AI282346, AI696714, AI336592, AI689614, AI468872, AI114703, AI264299, AA127565, AW151451, AI469081, AI344933, AI367705, AI224373, AW411351, AI247298, AI889306, AI866469, AI589428, AI539863, AI335449, AA782332, AI648699, AA555145, AI446124, AI625589, AW089029, AI376376, AW168602, AI863002, AI125109, AI095119, AL118781, AI370945, AI865320, AI560099, AI582396, AA493923, AA761557, AI446829, AI866573, AI696340, AI697045, AI434760, AW411265, AL036265, AI678688, AW410902, AW131999, F26535, AI345010, AL121037, AI678480, AW020164, AI830024, AW150225, AA837930, AI306610, AI915295, AI400725, AI677646, AL050267, AF228421, I22272, AR029580, S69510, AL133619, X79812, S82852, S79832, AF022363, AR068466, U89906, AJ005690, AF111849, X66871, AL137530, AL122098, AL096720, A08456, I68732, U77594, E12579, AF061795, AF151685, AF081197, AF081195, AF167995, AF078844, I48978, AL137557, AL137480, A31057, U67958, U95114, E06743, AL133015, A18777, I09499, M64936, AF013214, AF113019, S36676, U92068, AF067420, AL117626, AL137711, AF044323, Z97214, Y11254, AF059612, AF131821, A08913, AL080147, AR038854, AC004987, A21103, X76228, X61399, E12580, AF026008, A08912, X99226, A08911, AF030165, AF151109, S77771, AL133014, AF113694, AL133559, AL137627, AR068753, Y11587, AL122100, S76508, AL133067, X66862, AF114168, AR068751, AL137478, AL133062, AF116573, AL034400, AF065135, A76337, A76335, AL080110, AL117416, I92592, A91160, AL050149, S68736, A08910, A93016, AF169154, I89931, A08909, AF119337, AF119336, AF038847, A77033, A77035, AL137271, X66975, X66975, AR034821, X65873, U36585, M79462, AF126372, I49625, A32826, A30330, A32827, A30331, A08907, AF100781, AF117959, A57389, AL133084, A86558, A08908, A65340, AF067728, A65341, AF030635, I89947, AL080159, AL133088, AL049382, X80340, AF069506, I42402, AB025103, AF076633, S59519, E01314, AF061981, I32738, AF106657, AL080148, AL133072, AF102578, AL137665, X62773, AL122121, AF008439, AJ012755, AC004554, AL122110, AF145233, X75295, AL137495, AL050366, AL133665, Z49258, I89934, M19658, AF109155, AF039138, AF039137, AL137476, AP000130, AP000208, AP000247, S54890, AR012379, AL117587, Z82022, AF183393, I22020, I36502, AF032666, U57352, I25049, I25048, X06146, Y14634, U51124, AL137705, AF139986, X72889, A70386, AL137556, AL049339, AL133080, U13676, AF047716, U42031, AL137529, U87620, Y14314, AF205861, AF015958, AL050143, AB029065, A91162, AL137463, X98066, AF067790, L13297, AF113690, A20553, L19437, AF124435, AL133070, X83544, E12806, I46765, AL137536, AL137574, U83172, AL096728, AL117443, J05277, AC009286, U75604, AF109906, AC006112, AL133560, AF114170, I48979, AF019298, U62807, AL137640, Z13966, AL133624, AF185614, J05032, AF090886, I18358, I34395, AL080156, AL137660, AF185576, AF108357, AL117432, AF040723, AL137268, U72620, AC003032, AL022170, AC006371, AF130342, AR016469, and AF111112. |
| 15 | HWLHZ79 | 25 | 897839 | AW134688, AA422178, AA553959, AI831407, AI304380, AI983767, AI948903, AI832391, |

TABLE 6-continued

| Gene No. | cDNA Clone ID | NT SEQ ID NO: X | Contig ID | Public Accession Numbers |
|---|---|---|---|---|
| | | | | AW206923, AI833297, AI339648, AA587764, AI283185, AI813445, AI832498, AA857922, AI336470, AA938765, AW361498, AW361500, AI833021, AI285352, AW361502, AI744428, AI336626, AI732376, AI732377, AA534511, AI864896, AA422086, AW351839, AI766378, AA283751, AI833288, AI246768, AW351854, AW361503, AA535314, AI720988, T25111, AL134524, AL119511, AL042488, AL046356, AL045891, AL043089, AI432644, AI432666, AL041862, AL043321, AL040207, AI431307, AL042787, AI431316, AL047675, AI431238, AL135012, AL042853, AL042515, AI431323, AL047163, AL047611, AL042655, AL043091, AL042898, AL042729, AI432656, AL047092, AL045327, AL042533, AL042744, AI623302, AI432653, AW197139, AL046990, AL042508, AI431321, AL133049, AF019249, AL133053, AL122101, AL133074, Y17793, AL133068, AL133076, and AL133082. |
| 16 | HKGDP17 | 26 | 899502 | AI804162, AI340667, AI038755, AW150209, AF108083, AC005486, AC005969, Z98946, AC006160, AL031255, AC007216, AF003529, U95742, and AC005291. |
| 17 | HSVBD67 | 27 | 905861 | AI814485, AI872286, AI085288, AI871915, D55959, AI815039, AI863123, H17328, AI336860, AA044426, AA604984, AW189982, AI633049, AW025903, AL039802, AI620041, AW161698, F19322, AI357312, D54424, D52832, AW161017, F25495, AA703238, AI249687, C15890, R87515, H41877, AI910243, D52711, AA972364, AW002448, AI223172, H17356, AW137423, AA043060, C15914, AA837263, D53580, AI419944, AA285001, AA437366, AI884896, N62793, AI630922, AW139983, N93907, T06071, AI700165, R87602, AI934044, R90815, R87601, D80607, T23962, AA322589, AA852308, AW393830, R90816, AA330874, AI040803, F35183, AW393886, T12056, AI367549, AW204276, D80888, AA290964, AW389410, H50473, |

TABLE 6-continued

| Gene No. | cDNA Clone ID | NT SEQ ID NO: X | Contig ID | Public Accession Numbers |
|---|---|---|---|---|
| | | | | AW205735, AI356969, AI804924, AI619947, AW300654, AI948525, AI619622, AW050474, AA224082, AI880215, F34413, Z17406, C00462, AL119457, AL119324, AW392670, AL134524, AW084080, AL119443, AL119391, AL119484, AL119444, U46347, AL134527, AL119319, U46350, AL119439, U46351, AL119522, AI499335, AL119418, AL134528, AW372827, AW363220, AL119363, Z99396, AL119497, AL037205, U46341, AI586959, AW384394, AL119341, AL119396, AL134531, AW148743, AL119401, AR060234, AB026436, AR066494, AR054110, A81671, and AR069079. |
| 18 | HTGAT51 | 28 | 901883 | AI359208, AI955765, AI161200, AI359311, AI475753, AI807659, AI1568380, AI831934, AW136763, AW024272, W73250, AW137878, AI140648, AW172670, AI421717, AW076016, AI924345, H38677, AI381518, AA648734, AA041273, AA814021, H86339, R85891, AI183710, R85524, AI523567, AW137491, AI438962, AI494366, AI052410, AI383876, AI798097, AW237472, AW008866, T97359, AA836063, W72941, AA041189, AI907543, AA533768, AI821467, AA595522, AA489081, AA548692, AI952900, N39953, AL022313, AC007649, AJ001216, AL031662, AL021069, Z81370, Z85986, AL132716, AC005153, AL109802, AP000689, AC006138, AC000039, AC005288, AC005831, Z83822, AC005823, AC005209, AC005690, AL035419, AL050338, AC005747, Z96568, AC004983, AC005520, AL121657, AC004817, AC004596, AC004967, AF037338, AC004997, AC004685, AC002488, AC007429, U73638, AC007191, Z93096, AL133245, AC004921, AP000348, AC006054, AC005058, Z83845, AC005318, AC004819, AC006293, Z84489, AC003051, AC006141, AL035706, AC004590, AL133163, AF165124, AC005585, AL021453, AC000003, AP000555, AL050348, and AC006950. |
| 19 | HFCEQ37 | 29 | 746860 | AW297465, R37473, R20618, H08151, H09566, H11386, |

TABLE 6-continued

| Gene No. | cDNA Clone ID | NT SEQ ID NO: X | Contig ID | Public Accession Numbers |
|---|---|---|---|---|
| | | | | R60580, H05295, Z40466, AA013396, H24061, R44488, Z39576, R60633, AA885521, AA812965, F03288, R49325, F03287, T17067, H05345, Z44590, F05379, F05979, R40430, R21026, F05378, R11881, AI500061, AI927233, AI621341, AI521596, AI888317, AI610446, AI289791, AI432570, AI561170, AI537273, AI539260, AI440238, AI553645, AI624693, AI888575, AI866503, AI696603, AI571439, AI433157, AI648567, AI690946, AI554821, AW151136, AI539771, AI432644, AI537677, AI494201, AI567971, AI500659, AI909697, AI866465, AI815232, AI801325, AI500523, AI417790, AI538850, AI285439, AI887775, AI582932, AI590043, AI872423, AI923989, AI284517, AI500706, AI491776, AI445237, AW151138, AI889189, AI521560, AI500662, AI539800, AW172723, AI284509, AI582912, AI538885, AI889168, AI440263, AI866573, AI633493, AI434256, AI866469, AI434242, AI805769, AI625926, AI888661, AI500714, AI284513, AI888118, AI859991, AI436429, AI355779, AI889147, AI623736, AI581033, AI371228, AI491710, AI440252, AI431307, AI866786, AI860003, AI610557, AI431316, AI242736, AI828574, AI887499, AW151979, AI539781, AI702065, AI539707, AI885949, AI285419, AI559957, AW089557, AI521571, AI469775, AI866581, AI524654, AI567953, AI815150, AI446495, AI867068, AW074057, AI804505, AI499508, AL046466, AI963846, AW129106, AI572021, AA916133, AL045500, AI866820, AI225248, AW020397, AI890907, AI436438, AI371243, AI570056, AW075382, AW089844, AW172878, R15416, AL079799, AI284516, AI371251, AI866510, AI926593, AI866461, AI923046, AI874261, AI624293, AL047422, AI917963, AI089782, AL048403, AW151131, AA848053, AI469784, AI702073, AI469516, AI690748, AI698391, AL039390, AI493559, AI918435, AI819545, AI698352, AW051088, AI434255, AI633125, AI284060, AI479292, AI274759, AI538564, AI969655, AI915291, AW152182, AI537191, AI623941, AI933992, AI696570, AL042365, AI433976, AI884318, AI638644, AL039716, AI434731, W74529, AI366910, AL045413, AI701097, AI281757, AI499570, AL039274, AI797538, AI440260, AI699823, AI955441, AI241901, AI804531, AI919593, AI978703, AI539863, AI356505, AI366900, AI432666, AI524179, AI521005, AW008166, AA502794, AI538878, AW027374, AI620056, AL121365, AW238688, AI561177, AW129310, AI632850, AW197139, AI355008, AL119319, AI049856, AL042944, AI582926, AI802695, AI275175, AW024594, AI249389, AI610667, AA806719, AL040011, AL046595, AI273179, AI866691, AI499463, AI434969, AL118781, AI471282, AL039287, AI610362, AI868931, AI890507, AL046618, AL137530, S82852, Y11587, I89947, A77033, A77035, I48978, AF106657, AL133080, AL137480, Z13966, AL122104, AR038854, AL117587, I09499, I32738, S36676, AL080148, AL023657, AL133049, Z97214, AF111849, A08910, A08909, AF159615, A08908, X63162, AL137271, AL122100, AF061795, AF151685, AJ005690, A08907, AL133070, A08913, AF002985, A30330, A30331, I33392, A08912, U35846, A08911, I17544, U75932, X80340, AL117435, AL110224, AL133665, AL133010, AR034821, S76508, AL110280, I48979, A76335, Z82022, AL117416, AL137529, AF004162, AL137537, AL049324, AL133084, E01314, U30290, A57389, AF090900, S77771, AF185576, AF139986, AL133637, X76228, A07588, X79812, AF151109, U57352, X82434, AL122049, AF067728, AL050159, AL080110, |

TABLE 6-continued

| Gene No. | cDNA Clone ID | NT SEQ ID NO: X | Contig ID | Public Accession Numbers |
|---|---|---|---|---|
| | | | | AF126488, AL137574, A91160, A58545, AF177401, AF061981, A18777, A65340, AF079763, A93350, AL110158, AL137533, A21103, AF113019, A08456, Y11254, AF065135, AF117657, AL050155, E01614, E13364, A91162, L04849, I89931, L04852, AL050277, AL049283, AL137550, AF194030, AR029580, I49625, AL122110, X66871, AF094480, AL137711, AF044323, AL080126, X83508, M92439, AF026816, A65341, A76337, AF087943, X89102, AF183393, AF026008, AL137488, U78525, A23630, A58524, A58523, A08916, I89934, AR020905, AL049339, AL122050, AF069506, AJ012755, AL080163, S54890, AL080060, AF107847, E02349, AL031346, AF106697, E06743, AL049430, AL137560, AF017152, U87620, Y14314, AL050149, AF199027, U77594, X53587, X98066, AL137627, S78453, AJ000937, AF131821, AF153205, U86379, AB007812, AF047716, AL133075, AL133062, A03736, AL110218, AL050366, AR068753, AF002672, E12747, A32826, A32827, AF118092, D44497, AF115392, E12806, AL110296, AL117460, AL080162, AF106862, AF113677, L13297, A86558, AL133558, AR029490, AL049452, A07647, S83440, AL050393, A21101, AL133072, L04504, AR013797, AF100931, Y10936, U53505, AL080154, AL133081, AL050172, U58996, AF205861, AF125948, AL133077, AF032666, AF081195, S78214, E07361, I89944, A15345, AL080124, AL137463, AF013214, AF078844, Y10080, AF091084, AB016226, AF131773, X66862, AF215669, AL137478, AF141289, AF111851, AF200464, AL110221, M27260, A45787, AJ003118, U73682, AL096720, A52563, AL133619, AL050138, AL137555, AF061573, AL137665, AL122121, AL137292, X98834, X72889, AF106945, AL049996, AF090934, AF119336, AL117583, X06146, AF017790, AF090903, and AL050116. |
| 20 | HSKNP59 | 30 | 626946 | AA480375, AI251419, AI270846, AI308612, AI270979, AA953100, AI340555, AI250202, AI309146, AW023232, AW020543, AW021400, AW021890, AI557082, AI541205, AI557697, AW022571, AW022456, AW022086, AW023469, AW021729, AW020666, AW020196, AW023029, AW022983, AI557426, AW023351, AW021816, AW022727, AW021693, AW021930, AW022981, AW021182, AW022874, AW021466, AW022593, AW023235, AW021121, AW020480, AW021059, AI541321, AW021585, AW021561, AI547225, AF040962, Y11505, S68736, Y08991, and A91160. |
| 20 | HSKNP59 | 62 | 768694 | AA480375, AI251419, AI270846, AI308612, AI270979, AA953100, AI340555, AI250202, AI309146, AW023232, AW020543, AW021400, AW021890, AI557082, AI541205, AI557697, AW022571, AW022456, AW022086, AW023469, AW021729, AW020666, AW020196, AW023029, AW022983, AI557426, AW023351, AW021816, AW022727, AW021693, AW021930, AW022981, AW021182, AW022874, AW021466, AW022593, AW023235, AW021121, AW020480, AW021059, AI541321, AW021585, AW021561, AI547225, AF040962, Y11505, S68736, Y08991, and A91160. |
| 21 | HWMBB68 | 31 | 897852 | AI148564, AI911259, W60958, AI683823, AW268612, AW275920, AA404358, AA443743, AI271616, AI675766, AA936391, AA403095, AI311856, AI695003, AI082141, AI079408, AA503819, AA393808, AI189388, T86418, N30670, AA393892, AA974212, AA827290, AA910984, AI014740, AA804216, AI219049, AI566294, H96780, R21152, AI374805, H23300, AI299755, R99539, N75557, R99538, AA476793, AI094470, AA417638, W05584, AI133161, AI089034, AA905867, AA677753, T86508, AI240536, R99550, AI538267, AA335337, AA918453, AA313386, AW445161, Z40615, H92649, W87796, T33983, AW298229, R08382, H23186, R08329, H96103, H97711, H80948, T99199, N24555, AA375092, T99198, H92437, AA383378, AA419545, AF151859, AC004148, AC009263, and AI085108. |
| 21 | HDTGF15 | 64 | 834675 | AI148564, AI911259, W60958, AI683823, AW268612, AW275920, AA404358, AI271616, AI675766, |

TABLE 6-continued

TABLE 6-continued

| Gene No. | cDNA Clone ID | NT SEQ ID NO: X | Contig ID | Public Accession Numbers |
|---|---|---|---|---|
| | | | | AA443743, AA936391, AA403095, AI695003, AI082141, AI311856, AA503819, T86418, N30670, AI079408, AA974212, AA393892, AA393808, AA827290, AA910984, AI014740, AI219049, AI566294, H96780, R21152, AA804216, AI189388, H23300, R99539, AI299755, N75557, R99538, AA476793, AI374805, WQ5584, AI133161, AI094470, AI089034, AA905867, AA677753, T86508, AI240536, R99550, AA335337, AI538267, AA918453, AA313386, Z40615, AW445161, H92649, W87796, T33983, AW298229, R08382, H96103, H97711, R08329, H23186, H80948, T99199, N24555, AA375092, T99198, H92437, AA383378, AA419545, AF151859, AC004148, and AC009263. |
| 21 | HLWAD77 | 65 | 653513 | AI148564, AI911259, W60958, AI683823, AW268612, AW275920, AA404358, AA443743, AI271616, AA936391, AI675766, AI695003, AA403095, AI311856, AI082141, AA503819, N30670, T86418, AI079408, AA393808, AA393892, AA827290, AI189388, AA910984, R21152, H96780, AI014740, AA804216, AI219049, H23300, AI566294, R99539, N75557, R99538, AI299755, AA476793, AA974212, AA417638, AI374805, AI094470, AI133161, W05584, AI089034, AA905867, T86508, AA677753, R99550, AA335337, AI240536, AA313386, AI538267, AA918453, H23186, H92649, W87796, AW445161, Z40615, T33983, AW298229, R08382, R08329, H97711, H96103, H80948, T99199, N24555, AA375092, T99198, H92437, AA383378, AA419545, AF151859, AC004148, and AC009263. |
| 22 | HWABL61 | 32 | 897731 | AW328370, AW328371, AI261280, AI051959, AW044642, AI360169, AI631013, AI631025, AI091459, H18096, N53583, AA431621, AI654433, AI800320, T08343, AI399636, AI658637, AA335273, AA975921, H18136, AW005692, N54625, AA335317, H14185, AA938896, R88236, AI025281, AI439225, AI536975, AA336012, H30304, H14241, AA431334, AI090613, AI761098, AL119563, AL079734, AI085035, AI538345, AW304580, AI251034, AI887235, AI250552, AW303098, AI251284, AI251203, AA515728, AI970917, AI284543, AA410788, AL037856, AA715814, AW029515, AI962030, AI613389, AI733856, AA530958, AA579179, AI114557, AL038842, AI254770, AA169245, AW103406, AI891080, AI889995, AI249853, AL042756, AA335303, AA719073, AA365021, AW080436, AI583142, AA595499, AW438542, AI669910, H14266, AL042667, AL042670, AW327624, AI251241, AA904211, AA746911, AI310787, AI610360, AI912401, AW270771, AA228778, AW021583, AA229935, AL138182, AW022897, N23504, AL038936, AL036909, AI358089, AA084609, AI753672, AC004466, AL049839, AL035455, AF037338, AC006088, AL096766, L44140, AL049694, AC004883, AL109627, AC002314, AF124523, AL031659, AP000505, AL020997, AC005015, AC003692, AF196779, AC002477, AL033521, U80017, AL132777, AL031577, AC005412, AL031283, AL049779, AL031984, AL049831, AC005231, AL031602, Z82194, AL031589, AC007227, AL031368, AC008009, AL023575, AC007686, AC005274, AC000353, AL121652, AC005962, AC004263, AC007536, AC004656, Z94056, AC007055, AP000133, AP000211, AC006530, AL021154, AC006449, AC002115, Z98742, AP000563, U62293, AC002301, Z83844, AP000104, AC004526, AC002369, AC008179, AC005399, AC004491, AC007308, AC006285, AL049780, AC005696, AC000041, AC006487, AC006277, Z98884, AC007707, AC007021, AC004983, U47924, Z73359, AL049874, AL031295, AC004470, AC005261, AC005291, Z85987, AC005932, AC004804, AC004598, AC016025, AC007541, AC003101, AL080243, AC006077, AL049749, Z80896, U95742, AC006312, |

TABLE 6-continued

| Gene No. | cDNA Clone ID | NT SEQ ID NO: X | Contig ID | Public Accession Numbers |
|---|---|---|---|---|
| | | | | AC004531, AC005736, AP000547, AC008012, AC008116, AC004990, AL049871, AC004895, AC002300, U85195, AC005726, AC002316, AL109984, AC005519, AL031427, AL049539, AC007546, AC006509, AC006064, Z85986, AC005057, AL035072, AE000658, AL008631, U91326, AC005088, AL049776, AL031230, Y14768, AC004000, AL031228, AL022237, AP000359, AC005921, AC005058, AC006057, AC005332, AL049699, AL031311, AL049872, AL133448, AP000037, AP000105, AC009247, AL133244, AL035587, AF001549, AL023803, AC004975, AC002563, AL121825, AC005225, AC007216, AP000240, AC002457, AC005901, AF088219, AL021326, AC002059, AC005920, AC002429, AF207550, AC005874, AF134471, Z83838, AC005200, AL050318, AL022165, AC004675, AF111169, AC011311, AC002432, AL049696, AL024498, AC002425, AC005280, AC006539, AC007666, AC006026, AC007919, AC004534, AL008718, AC002551, D88270, AC009731, AC006061, AC006252, AP000245, AC012099, AC004477, AC006013, AC002375, AL109802, AC004966, AC003669, Z85996, AC007435, AF038458, AC003029, AC005859, AC003043, AC006581, U07562, AC006538, AC005082, Z98946, AC005048, AC002350, AC007565, AC005881, AL132992, AC006001, AC007731, AC002558, AL078638, Z83733, AC007052, AL034554, AL022320, AF030453, AC005479, AC005971, U80460, AL034420, AC004822, AC005207, AL024508, AC005387, AL137100, AC005591, AC006480, AL008732, AL133246, AC007199, AF047825, AC004967, AJ011930, AC005531, AL034549, AL031774, AC002476, AC005209, AC002996, AL022316, AC007450, AC002472, AC005324, AC004106, AC005071, AL022721, AC006130, AC002565, AF205588, and AL035422. |
| 23 | HWDAQ83 | 33 | 1126378 | AL135118, AI083551, AA081133, AA148143, AI869871, H28944, AA143781, AW089526, AW188903, AW198015, N51465, AI580927, N45114, AI906328, AW166645, AI349772, AI907070, AL119049, AI149592, AI815383, AI873768, AI624859, AW080838, AA081212, AI868831, AW071349, AL047042, AW132121, AI907061, AI349645, AI345111, AI220734, AI207510, AI340582, AI909662, AI344182, AI684265, AL121270, AI682106, AI064830, AI343112, AW268253, AA528822, AI349614, AL135661, AL120854, AL045500, AI345860, AI500553, AI590482, AI687376, AI436456, AI673256, AI525064, AI702406, AL046849, AI334902, AI690751, AI349598, AL036396, AW168591, AW162071, AL036146, AA613907, AI907056, AI909666, AI251485, AL036802, AI608667, AI580190, AI312152, AI349937, AI500077, AI567351, AI863014, AI433976, AI349256, AW074993, AL036759, AL119791, AW303152, AI920968, AI813914, AI433157, AI866608, AI799305, AI567632, AI679724, AW089572, AI873731, AI349933, AI440426, AI568870, AL036980, AL047763, AI687415, AI569870, AW117882, AW302965, AI934036, AI687728, AI857296, AI027531, AI524991, AI345735, AI249257, AI538716, AI309401, AI699857, AW238730, AI547175, AL135308, AL121365, AI282655, AI609592, AW235035, AA528491, AL040169, AI307466, AA603930, AI889203, AI633419, AL036274, AL120736, AI886532, AW301409, AI475371, AI469532, AI521012, AI583316, AI702433, AL119748, AI499463, AA640779, AI281779, AW071417, AL043326, AI753683, AI340519, AI560012, AI818683, AI499393, AI969601, AW103371, AI366991, AI349004, AI686926, AI345744, AI343059, |

TABLE 6-continued

| Gene No. | cDNA Clone ID | NT SEQ ID NO: X | Contig ID | Public Accession Numbers |
|---|---|---|---|---|
| | | | | AI969567, AI631107, AL036240, AL038778, AI285735, AI222742, AI696846, AI557728, AL038605, AI612913, AA585422, AI919058, AI539153, AA572758, AI590128, AI597918, AW195957, AI690835, AI811863, AI250293, AI307558, AI678302, AW274192, AI275175, AI348897, AL040243, AI366549, AI697137, AW169653, AW148320, I48979, AF113691, S78214, AF090934, AL133640, L31396, L31397, AF090900, AL049938, AF118064, and AL050393. |
| 23 | HWDAQ83 | 66 | 897735 | AL135118, AI083551, AA148143, AA081133, AI869871, AA143781, AW089526, H28944, AW188903, AW198015, N51465, N45114, AI873768, AA081212, AL135308, AA585237, N53605, AI433157, AI868831, AI698401, AI539153, AW089179, AW151785, AI633419, AI469532, AI866608, AI345111, AI538342, AI933785, AI955866, AI828731, AI499393, AL046926, AI802833, AI648663, AI886753, AI174394, AI365256, AI888953, AI538716, AI610645, AI886124, AW088899, AI648684, AI696819, AI539771, AI699011, AL045500, AI564719, and U67082. |
| 25 | HTPHH74 | 35 | 1155925 | AI718282, AI709383, AW368622, AW272235, AW392816, AW392815, AW076072, AW392813, AI671707, AI628226, AL138202, AI887486, AI984572, AA732450, AW080807, AI859535, AI523527, AI752689, AI693382, AI984050, AW131290, AI922765, AA777248, AI832002, AI346505, AA922780, AA521201, AI954924, AA557382, AI888131, AW269811, AI608617, W72219, AI681187, AA932106, AW181955, AW392812, AA527142, AA745501, AW021226, AI889591, AW069693, AI769962, AI912432, AI419435, AI688405, AW391835, AA916772, AW168916, AI400751, N53751, AI375686, AA984515, AI690156, AI422357, AA448336, AI218693, AW392811, AI752688, AI754303, AI379872, AA988930, AW117350, AA576006, AI540975, AA196632, AA452324, AW008558, AI858111, AI300865, W44724, AA055218, AA569878, AI860850, W77963, N40921, AW130787, AI087219, AW135054, AA553499, AA156791, AI985931, AA651871, AW168405, AI700311, AW338074, AA988997, AA700296, AA621239, AI798053, AA729147, AW406945, AI351536, AA653632, AA814336, AI038164, AA570128, AI123294, AW007940, AA459461, AI914233, AL138350, AA199821, AA514830, W76103, R60314, AI168835, W72868, AA199822, AA847366, AI291058, R60370, N73108, AW026583, R18782, AA081063, AA363711, Z39606, AI798240, AA088472, AI286285, H71287, AA452102, AI061410, AA262748, AI274565, H93030, C06200, H88379, AA196914, AI434525, AA370299, AI524979, AA843973, D79669, AA621516, AW373716, T53791, AI597813, H88445, H88385, Z46043, AW021466, AI096826, AA363712, H06978, T35853, F06614, AA137043, AI886534, AA301555, W38656, D20097, AI537191, AA332019, D61785, AI609647, AA747404, AI434523, AA337670, H06473, AA452798, AI798826, AW340046, D58251, R37068, AA332974, R82990, H88453, AI903866, AA055248, AA356131, H06979, AA047786, AI566428, AA319514, AI363742, AA911435, AA100043, AA506127, Z43878, H51656, AA305992, AA330152, AA156880, AI874086, AA364351, AI017533, D62111, N56435, D79451, AA057621, AI001735, T23483, R82991, T53906, AW392806, AI681094, AA761608, AA747690, AI242747, AA330851, AA649156, AA262641, H68666, AA994628, AA988479, AI272065, AI457369, H70885, AI090525, AI525669, C02181, AL045500, AW302854, AL036802, AW089405, AA291453, AI525653, AI927755, AI815232, AI541056, AW169653, AI873731, AL121270, AI557426, AI590043, AW020397, AI345735, AI917253, AI335209, |

TABLE 6-continued

| Gene No. | cDNA Clone ID | NT SEQ ID NO: X | Contig ID | Public Accession Numbers |
|---|---|---|---|---|
| | | | | AI349944, AW271119, AI469532, AW268220, AI538885, AW149925, AI866608, AI698391, AI620284, AI553645, AI500061, AW073655, AW268253, AL134259, AI613548, AL040241, AI702073, AL046466, AF151793, AF119955, AJ005073, AF115497, AF192757, AJ005074, AF176514, S68736, AF113694, AL122050, AF113690, I89947, I03321, AF118090, I48978, AL110221, A03736, Y09972, Y16645, D16301, AL137529, AL133640, AF090896, I89931, M86826, A08916, AL137479, AL050146, AF090934, AF176651, AF097996, AL110196, AF132676, AF061836, A08913, L31396, L31397, AJ005690, AF104032, S78214, A08910, A08909, AB016226, AF090903, AL096744, AL050116, AL080060, AL117435, AL117460, AL117585, AL137533, AL133606, AF113013, AR011880, A93016, AL133080, AF113699, AF125948, AL049452, AL133560, I48979, AF067790, I49625, AF118070, AL023657, AF090900, AL133113, AL050393, AF026816, AF090943, AL133016, A08912, AF158248, A65340, AL137538, AL117457, AF039138, AF039137, AL080137, AF113677, Y11587, AL050024, AL133557, AF087943, X82434, S76508, AR038854, U67813, AF118064, X84990, AF090886, AL133619, AL122123, AF078844, AL133067, U53505, AJ000937, AL049466, AF106827, U58996, Z82022, AL133075, AF113676, AL050108, X70685, AF182215, AI8777, Y10823, A08908, AR029490, Z72491, AJ242859, AB007812, AL117649, A91160, AF061795, AF151685, AF146568, AL122121, AR068751, AL122110, AF106862, A65341, AL049430, AL049382, AL049314, AL137527, AR020905, AL080234, AL049938, U67958, AF065135, AL137560, AF111849, AL137550, AL110225, AL080057, AF115410, AL137283, X72889, E01573, E02319, AF113019, AF017437, E15569, A77033, A77035, AL137459, M85164, AJ238278, S77771, U91329, AF102578, AF113691, AL122049, S63521, A86558, AF067728, I33392, AF141289, AF111851, AL122098, U00763, AF125949, AL133568, U80742, AF028823, AF183393, AF079765, L04849, S75997, AR013797, AF113689, AF175903, AL049300, AF215669, X62580, I42402, AR059958, AL050155, Y07905, AL133565, AL137463, AB019565, AL117648, AL137556, AL117583, AF026124, AL137521, Y10080, S61953, AF119337, AF118094, A83556, AL117626, E02349, AL137648, AL133098, AF177401, AL137488, A12297, U72620, AL050149, I89934, AL050277, AF100931, X66862, AL049347, AL137557, Y11254, AR000496, U39656, AL050172, I17767, E07108, M92439, AL122093, I08319, X63574, Z97214, E06743, U88966, U42766, E05822, AL080159, AF090901, AF079763, U55017, AL117394, U78525, AL137548, X83508, AL137539, AL133104, X87582, M30514, AL110218, AR034821, I09499, A08907, AL133093, AL137271, X52128, U68233, I92592, X93495, AJ012755, I00734, E08263, E08264, AA401830, AW467902, AW470101, AW470123, AW572680, AW629754, and AW769234. |
| 25 | HTPHH74 | 67 | 899440 | AI718282, AI709383, AW272235, AI887486, AI859535, AI984572, AW131290, AI523527, AI628226, AA777248, AI922765, AI346505, AA922780, AA557382, W72219, AW080807, AI608617, AA527142, AI832002, AI688405, AW391835, AA988930, AW069693, AA196632, W44724, AI300865, AA569878, AI087219, N53751, AA651871, AA553499, AI700311, AW338074, AI985931, AW168405, AW406945, AA988997, AA621239, AA700296, AI754303, AA729147, AA814336, AI351536, AA570128, AA653632, AI038164, AI123294, AI798240, AI858111, W76103, AA514830, N40921, AI168835, AW130787, AW026583, H71287, H88445, AW007940, D79669, AA847366, AI524979, W72868, T35853, W77963, AA088472, F06614, D20097, AA363711, AA081063, Z39606, D61785, H88379, H88385, AA262748, AI274565, W38656, T53791, AI798826, AW340046, D58251, H88453, AI597813, N73108, AA843973, |

TABLE 6-continued

| Gene No. | cDNA Clone ID | NT SEQ ID NO: X | Contig ID | Public Accession Numbers |
|---|---|---|---|---|
| | | | | AI096826, AW021466, AA305992, AI537191, AA747404, N56435, AA301555, D79451, AI363742, AA506127, D62111, AI889591, AA649156, AI874086, AA262641, AW392806, AA994628, C02181, AA902147, AL047100, AA370299, AI824648, AI581033, AA401830, AA291453, AA641818, AI698391, AW022636, AL037454, AL079963, AI624543, AI889189, AI473536, AW161156, AW051088, AA809897, AL046618, AI818353, AI923989, AI553640, AI500061, AI624293, AI620643, AL046466, AW020095, AA580663, AI533065, AI587121, AW020046, AI932794, AI918449, AA928539, AI250852, AI633125, AI538564, AI915291, AW152182, AL047344, AI267162, AW088697, AI679506, AI499890, AI637584, AW151136, AI884318, AI473451, AI452560, AI538764, AI538885, AI801152, AI866469, AW087445, AI953562, AW149925, AW021717, AI890907, W74529, AI866465, AI540674, AW303089, AW191003, AI281757, AL118781, AW162189, AI859991, AW089275, AI686576, AI623941, AL037649, AI859464, AI582932, AI872423, AI590043, AL046227, AI521560, AI969655, AI934035, AW104141, AW020397, AL120853, AA502794, AA001397, AL036361, AI340519, AI355779, AI241901, AI345543, AW238688, AI270429, AI742728, AI860003, AI498067, AW080746, AA259207, AA579618, AI284517, AI340533, AI863382, AI344935, AI800155, AI310575, AW054885, AW006032, AI554343, AI439087, AI371251, AW020693, AI702073, N71180, AI868204, AW129659, AI365256, AW051258, AI567582, AI929108, AW081513, AW020419, AI805603, AL045620, AW021667, AA908294, AI568374, AI499986, AI439995, AI345745, AI567769, AA857847, AL135607, |

TABLE 6-continued

| Gene No. | cDNA Clone ID | NT SEQ ID NO: X | Contig ID | Public Accession Numbers |
|---|---|---|---|---|
| | | | | AI801325, AI553645, AI500523, AI433157, AI349932, AI525653, AI815855, AI798303, AW118373, AI612750, AI500662, AI630252, AA806754, AI824576, AI815232, AI888661, AF151793, AF176514, AF192757, AJ005073, AJ005074, I89947, AF113690, M86826, AL133560, I48978, E06743, AL137479, AL023657, I33392, X70685, AL049314, AF090901, X82434, AL137529, AL049283, X65873, X72624, AF183393, AL122100, Y16645, AF097996, AR038854, A08913, A08912, AL133113, AL133640, Y09972, AF125949, AL122121, A08910, A08909, AF113677, AF087943, AF114784, AL137533, AF026816, A77033, A77035, AL080074, AL050116, AL117394, Y10655, I48979, A49139, AL133557, M96857, AF090903, AL137488, AF106657, U35846, AF100781, AF126247, A08908, I33391, AL137480, AF031147, AL080234, Z37987, AL133016, Y07905, AF113019, A57389, I09499, AL050155, E12747, A21103, AL133104, AL117416, AJ005690, AL080118, AF078844, AI8777, I89931, AF028823, AL133080, X80340, U95114, AL117460, AL050149, S83440, AF180525, AL137527, I89934, AF111112, I49625, AL122110, AF100931, A08916, AL137459, AL133075, AF090900, AF177401, AL137550, AL117648, E07108, AJ003118, AL096751, A03736, S78214, AL080124, AL133637, AL049430, AL096744, AF090896, AL133665, X76228, A65340, AL117457, AL049426, AF104032, AR011880, U73682, E04233, U58996, AL137574, Y14314, AF061981, AF139986, D83032, U88966, A65965, A08907, L13297, AL050024, Y11254, AL110196, Y10936, A76335, AF079763, AL133568, A65943, D16301, AL137267, A08911, AL110159, AF113694, AR013797, AF090934, S36676, AL049382, AL117626, AF143957, AF210052, AF111849, AF137367, AL133565, AL137521, AL049347, AC004883, AF118094, AL137530, AF132676, AF069506, E02349, AF061836, U68233, I92592, AR034821, S76508, Z97214, AF061943, AR068753, AL050146, L19437, AL137557, A65341, Y11587, |

TABLE 6-continued

| Gene No. | cDNA Clone ID | NT SEQ ID NO: X | Contig ID | Public Accession Numbers |
|---|---|---|---|---|
| | | | | AL080159, AL137271, AL122106, Z82022, S77771, AE185576, AL080148, U42766, AL137292, AF106862, AF032666, AJ012755, A18788, I89944, AR029580, AL136884, AL050172, AL117583, AF126488, A93350, AF026124, AL049466, AF125948, X99717, AL080156, I32738, AF030513, AL110218, AF161418, U75932, Y18680, AF054599, AJ000937, AL122050, X83544, AF113699, AF118090, AL133081, AL117649, X92070, A91160, A91162, X83508, AL110280, X72889, S61953, AF031903, X87582, E05822, AL137523, AR029490, AL137538, U78525, AL117435, AL110222, AJ006417, AF057300, AF008439, AF057299, AL133112, I68732, S63521, AL049938, I80064, AL133558, AL137478, X01775, AL080154, U55017, AF047443, U96683, AL137471, AF061795, AF151685, and AL050393. |
| 25 | HTFOB75 | 68 | 900824 | AI718282, AI709383, AW368622, AW272235, AW392816, AW392815, AI628226, AW076072, AW392813, AW080807, AL138202, AI887486, AI984572, AI859535, AI523527, AI832002, AW131290, AA777248, AI922765, AI346505, AA922780, AA557382, AW069693, AW269811, W72219, AI608617, AW392812, AA527142, AW391835, AI688405, N53751, AI754303, AA984515, AW392811, AI752688, AA988930, AA196632, AI540975, AI858111, W44724, AI300865, AW130787, AA569878, AI087219, N40921, W77963, AA651871, AA553499, AW338074, AI985931, AW168405, AI700311, AA988997, AA621239, AA700296, AW406945, AA729147, AA814336, AW007940, AI351536, AA653632, AI038164, AI123294, AA570128, AL138350, AA514830, W76103, W72868, AI168835, AA847366, N73108, AA081063, AW026583, AA363711, Z39606, AI798240, AA088472, H71287, AI274565, AA262748, AA196914, AA843973, H88379, C06200, AA370299, AI524979, AI597813, D79669, T53791, H88445, H88385, AI096826, AA363712, T35853, |

TABLE 6-continued

| Gene No. | cDNA Clone ID | NT SEQ ID NO: X | Contig ID | Public Accession Numbers |
|---|---|---|---|---|
| | | | | AW021466, F06614, AA137043, AA301555, W38656, D20097, AA332019, D61785, AI609647, AI537191, AA747404, AA337670, AI798826, AW340046, AA332974, D58251, H88453, AI903866, AA356131, AI363742, AA100043, AA506127, AA911435, AA305992, AI889591, AI874086, AI017533, D62111, N56435, D79451, AI001735, T53906, AW392806, AI681094, AA649156, AA330851, AA262641, H68666, AA994628, AA988479, H70885, AI090525, C02181, AA291453, AA902147, AL047100, AW172723, AL045500, AI433157, AI815232, AI889189, AI582932, AI581033, AA401830, AI824648, AI633125, AA641818, AI698391, AW022636, AL037454, AL079963, AI624543, AI702073, AI915291, AI583065, AI473536, AI918435, AW161156, AW051088, AL046618, AI923989, AI553640, AI500061, AI624293, AL046466, AW020095, AA580663, AI587121, AW020046, AI620643, AI918449, AI678496, AA928539, AI250852, AI538564, AA809897, AI863382, AW152182, AL047344, AI267162, AI679506, AI499890, AW151136, Z21709, AI884318, AI473451, AI452560, AI538764, AI538885, AI866469, AW087445, AI953562, AW021717, AI890907, W74529, AI866465, AL046593, AI540674, AW303089, AW191003, AI281757, AL118781, AW162189, AI859991, AW089275, AI623941, AI345131, AL037649, AL119863, AI859464, AI872423, AI590043, AI521560, AL046227, AI969655, AI934035, AW104141, AW020397, AL120853, AI637584, AA502794, AA001397, AI340519, AL036361, AI355779, AI241901, AW238688, AI345543, AI270429, AI742728, AI537273, AI860003, AA259207, AW080746, AA579618, AI537303, AI284517, AI340533, AI923833, AI344935, AW088697, AW149925, AI800155, |

TABLE 6-continued

| Gene No. | cDNA Clone ID | NT SEQ ID NO: X | Contig ID | Public Accession Numbers |
|---|---|---|---|---|
| | | | | AI310575, AF151793, AF119955, AJ005073, AF115497, AF192757, AF176514, AJ005074, I33392, AL133640, I89947, I33391, AL137479, AF113690, AL049314, AF090901, AL133560, I48978, X70685, M86826, AF113699, AL137529, E06743, AL023657, AL049283, X72624, AF183393, AL122100, Y16645, AR038854, A08913, X82434, A08912, AL133113, AF118094, Y09972, AF026816, AF125949, A08910, A08909, AF113677, AF087943, AF114784, AL137533, AL050146, AL080074, AL050116, AL117394, Y10655, I48979, A49139, AL133557, M96857, AF090903, AL137488, AF106657, U35846, AL122121, AF100781, AF126247, A08908, AF031147, AL080234, Z37987, AL133016, Y07905, AF113019, A57389, X65873, ALO050155, E12747, AL133104, U88966, AL117416, U91329, AJ005690, AL080118, A18777, AF078844, I89931, AF028823, AL133080, X80340, U95114, AL117460, S83440, AF180525, AL137527, I89934, I49625, AF111112, AL122110, A08916, AF100931, AL050024, AL137459, AL133075, AF090900, AF177401, AL133568, AL137480, AL137550, A03736, AL117648, E07108, AJ003118, AL096751, S78214, AL050092, AL080124, AL133637, AL049430, AL096744, AF090896, U42766, X76228, A65340, A77033, A77035, AL117457, AF139986, AR011880, I09499, L19437, E04233, U58996, AL137574, Y14314, AF061981, AL133665, AL050149, A08907, A65965, L13297, Y11254, AL110196, Y10936, A76335, AF079763, A65943, D16301, AF104032, AL137267, A08911, AL110159, AF113694, AR013797, AF090934, S36676, AL049382, AL117626, AF143957, AE111849, AF137367, AL133565, AL137521, AL049347, I08319, AF132676, AF069506, E02349, AF061836, AR034821, S76508, Z97214, AF061943, AR068753, AL137557, A65341, Y11587, AL080159, AL137271, AL122106, Z82022, S77771, AL049452, AF185576, AL080148, AL137292, AF032666, AJ012755, I89944, AI8788, AR029580, AL136884, AF118090, AL050172, AL117583, AJ238278, AF126488, A93350, AF026124, AL049466, AF125948, AL080156, I32738, AF030513, A12297, AL110218, U75932, A21103, AF054599, AJ000937, AL122050, X83544, AL133081, AF210052, U68233, AL117649, I92592, X92070, A91160, AF146568, U73682, A91162, X83508, AL110280, X72889, S61953, AF106862, AF031903, X87582, E05822, X60786, AF161418, AR029490, AL137538, U78525, AL110222, AJ006417, AF057300, AF008439, AF057299, AL133112, I68732, A58524, A58523, S63521, I80064, AF097996, AL049938, AL133558, AL137478, X01775, AL080154, U55017, AF047443, U96683, and AL137471. |
| 26 | HWABW88 | 36 | 897798 | AW250365, AA447429, AW246687, AA447430, AA191517, AI292051, AW085725, AA804949, AA831450, AA582562, AI459407, H15486, H17698, AA257978, AW084939, AA457567, AA457764, AW250961, AI538335, AA642333, AA598900, AI198312, AI538216, AA312579, AA834950, AA367576, AA521042, AI248763, AI056798, AA858336, R16685, AI218663, AA682862, T83917, W87588, AA642911, F03073, W17264, AA191511, F37811, AA894565, AI375815, AA303405, AI041443, H85468, AW198159, U89387, U85510, AC006011, AC002288, AP001067, Z97053, AJ011930, AC006111, U91323, AC004841, AL096791, AP001068, and AL049835. |
| 27 | HWNFG66 | 37 | 906070 | AW009446, AW273128, AA524501, and AI917291. |
| 28 | HDPQG01 | 38 | 1069521 | Z78342, AW275036, AI820780, AW020115, AA150284, N27708, AA016281, D80611, AA151597, AI523050, AI668603, AI185997, AI148307, N33979, AI277822, AA150386, AA458926, AI709233, AA446724, AA862368, AA946706, AA421931, W48862, AA722005, AA906072, N36527, AA045034, H16873, AA149477, AI749931, N35107, AA040052, AA861846, AA805628, N62848, W48734, AI623374, AA831459, AA446595, AW193460, AI183326, AI423718, AW296493, AI051843, AI025497, R18558, N33053, H12026, |

TABLE 6-continued

| Gene No. | cDNA Clone ID | NT SEQ ID NO: X | Contig ID | Public Accession Numbers |
|---|---|---|---|---|
| | | | | Z44707, AA609262, H00771, H25402, AA017689, H26331, R62292, Z24971, AI263557, AI123259, AI382929, H25802, H25403, H03535, AI932614, AA312980, H03451, AI803852, AW439934, C21502, H16764, N77755, R33770, AI580671, D79660, Z28673, T30082, D80610, H25761, N24537, Z40541, AA452707, R62291, N43850, D61217, AA459144, R33656, AA428166, AI017010, H11769, AA718983, N48776, R41425, AA092336, T34768, AI245435, N20866, AF077205, Z98200, and AW475060. |
| 28 | HDPQG01 | 69 | 899434 | AW275036, N33979, AA446724, AA906072, AA609262, AA017689, AI123259, AI382929, AW439934, Z24971, N24537, N43850, AA459144, AA092336, T34768, N27708, T30082, H16873, AF077205, and Z98200. |
| 28 | HJPAD80 | 70 | 901861 | AI953485, AI150769, AI271369, W56090, AA100484, F10393, AA297759, AI752351, F03251, AI752444, AA905365, AA047585, AW183209, AA447403, AI160655, N48800, R45278, AI366812, AW089943, AI918806, AA446920, AW352020, AW178617, N45592, AW178643, AI810715, AW440022, AA350505, AB029024, AB017642, AB026898, and AP000499. |
| 28 | HTXJM94 | 71 | 853413 | AW275036, AA906072, AA446724, AA609262, AI123259, AI382929, AA017689, AW439934, Z24971, N24537, N33979, N43850, AA459144, T34768, N27708, T30082, H16873, AF077205, and Z98200. |
| 29 | HE2IO57 | 39 | 899432 | AI675275, AA411339, AW418908, AI432460, AI417263, AI765331, AA441930, AI089276, AA446408, AA775550, R54099, AI088019, AI056121, R15968, C00373, AI400530, AI569092, AI631289, AA976916, AA748034, AW054705, AA191592, AA262484, AA843198, AW001599, AI376109, AI242622, AW105442, AI572192, AA165533, AI573163, AI338951, AI421105, AI493050, AI800245, AI051345, T35143, AI582470, AI279355, AL135735, AI381688, AI808098, W46353, AA947055, AI082835, AI378592, AA863118, AI864893, AI148300, |

TABLE 6-continued

| Gene No. | cDNA Clone ID | NT SEQ ID NO: X | Contig ID | Public Accession Numbers |
|---|---|---|---|---|
| | | | | AA525936, AA159671, AA992359, N98515, AI962766, AI952609, AI039115, AW130051, AI215162, AW338369, AI264471, AI927999, AA994439, AA404561, AI632889, AI741573, AI268634, AA846089, AI337932, AI741665, AI042366, AI858583, AW261838, AI273271, AI589195, AI972862, AA772295, AA169639, AI088234, AI289638, AI492897, AA156611, AA515061, AI360854, AA261946, AI634144, AI859022, AW264573, AI168736, AA262236, AI631684, AA977642, AA278726, AA079653, AI224998, AW025711, AW241626, AA766851, AI094200, N32558, AI432208, T32659, AI224943, AA569555, AA029224, AI823576, AW138107, AW008185, AI337940, T30097, AA448698, AI948724, AW272954, AI971220, AA526501, AI766247, AI697277, N95634, AA079618, R45930, AI978987, AI885114, AI394586, AA748054, AI862044, R59062, AW151592, AI419203, Z38227, W33017, AI560111, AA911012, AI261210, AA368031, AA410514, AW130735, AA911014, AI796397, AW162071, AW163823, H42768, and AI041407. |
| 30 | HLDRR08 | 40 | 906270 | AF202890, AF202889, and AC007707. |
| 31 | HTOJV86 | 41 | 762837 | AI685121, AI991095, AI913168, AI735017, AI302085, AI956168, AI991865, AI679903, AI620545, AI829197, AI685204, AW190397, AI833028, AI991250, AA554973, AI927762, AI459598, AW337144, AI583526, AI692817, AI963817, AI660628, AI956075, AI880450, AI518588, AI829230, AW275867, AI978631, AI814847, AI453734, AW190012, AW190228, AI625231, AI471500, AI539178, AW337938, AW192935, AW150194, AW001210, AI220226, AW273057, AI635246, AI696804, AI720447, AA402884, AI801496, AW007637, AW058222, AW338132, AI921422, AI435281, AI538691, AI735170, AI744441, AI708758, AW170593, |

TABLE 6-continued

| Gene No. | cDNA Clone ID | NT SEQ ID NO: X | Contig ID | Public Accession Numbers |
|---|---|---|---|---|
| | | | | AA402890, AW001217, AI963743, AI679773, AI539857, AI559206, AI748802, AW261992, AI829410, AI818229, AI923867, AW188532, AI923346, AW338661, AW338635, AI697171, AW189223, AI683465, AI623982, AW057732, AA610130, AI923926, AI983170, AA503365, AW131218, AI554519, AW007281, AW404803, AW190375, AI628855, AI571456, AW263007, AI804591, AA578566, AI572069, AI677647, AI565900, AI986124, AA576348, AW268534, AI811453, AI683834, AW316762, AI572084, AI624432, AI828420, AI022765, AW150841, AI446302, AW276427, AI570200, AI962904, AA573868, AI696908, AI701060, AI689647, AA523408, AI860853, AW364700, AI911650, AI587423, AW262111, AI680059, AI571990, AW194314, AI285655, AI799325, AI687917, AI151114, AA844940, AI581862, AI678689, AI570284, AI275227, AI625655, AA664201, AA523119, AI819138, AI911645, AI682577, AI749266, AA595758, AA401360, AA401336, AI572628, AW193314, AW264686, AI952262, AA410694, AI573201, AI813866, AI991849, AI559261, AA568920, AI921019, AW001504, AI811754, AA523390, AI189942, AI587047, AI521342, AA659897, AI587186, AI590385, AA522613, AA429352, AI281742, AI598095, AA477091, AI829224, AW085666, AI275814, AA522776, AI677995, AI445522, AI961478, AI459910, AA845885, AI984847, AI673632, AI986014, AI431417, AI983983, AI697003, AA662295, AI683481, AI984126, AI570045, AI697246, AI571646, AW191013, AI983804, AI922800, AI696995, AI673816, AI635785, AA428763, AI686934, AI955753, AW193403, AI567553, AI281596, AI627913, AI570063, AI690842, AI598025, |

TABLE 6-continued

| Gene No. | cDNA Clone ID | NT SEQ ID NO: X | Contig ID | Public Accession Numbers |
|---|---|---|---|---|
| | | | | AA290845, AI660451, AI624165, AI697243, AI696969, AI439833, AI986042, AI125317, AI660213, AI587494, AI566478, AI805478, AI597973, AA581445, AI453141, AI610183, AI566489, AI832603, AI564660, AI632055, AA578833, AW405737, AI991212, AW406672, AI624660, AI280825, AI858139, AI640792, AI750165, AI880818, AI865827, AI694180, AI460298, AI631417, AI640877, AI673199, AW084943, AI571607, AI963186, AW050723, AI968517, AI524657, AI708951, AW380195, AI446131, AI583601, AI921670, AI685184, AF067420, S71043, J00220, X53707, X53703, X15045, X53702, X53704, X53706, X53708, X53709, X53705, S55735, AF024645, AJ012264, U12594, AF109167, U07986, X82119, Z98733, X08044, X82117, Z98731, M60192, Z98734, Z98736, Z98735, Z98732, Y14737, Z98714, Z98725, Z98713, Z98693, Z98684, Z98686, Z98683, Z98688, Z98694, Z98703, Z98706, Z98690, Z98689, Z98699, Z98702, Z98708, Z98738, X00353, Z98700, Z98701, M18517, Z98692, Z98687, Z98704, Z98737, M34031, Z98698, Z98691, Z98696, Z98697, X53385, Z98685, M18508, AJ010443, M34026, M34030, X53387, X53386, Z14203, X53388, D11018, E01699, U43759, AB019439, Z14204, U43757, X81728, L23557, M83134, AF062180, AF062099, AF062277, U24081, Z14168, L26399, AF052383, Z14170, X80305, X65901, X81745, X81738, AF135164, L23571, Z14192, L38427, I27679, A21385, Z80846, M99665, X61014, L38429, X81747, AF174010, Z14173, AF062281, L01276, X65899, AF174033, Z14174, M99663, AB019438, X61013, M62729, X81741, L21958, AF027159, Z14177, I52258, X81696, M28074, AF165100, L08085, AF062171, X81727, A44323, L26960, M34032, AF115125, M62737, X53389, AF026931, L29153, L29154, AJ234181, AJ234183, AJ234159, X92214, Z80855, AB019440, X81753, X62967, AF115128, A40944, AJ234265, L23564, AF115127, M99652, |

TABLE 6-continued

| Gene No. | cDNA Clone ID | NT SEQ ID NO: X | Contig ID | Public Accession Numbers |
|---|---|---|---|---|
| | | | | U80090, U43761, X64238, AF062287, X70208, AF115111, AJ239341, AJ245279, and AJ245350. |
| 31 | HHBGE77 | 72 | 836039 | AI741776, AI937181, AA142834, AA115742, AA449297, W07748, AI185171, AI189560, AA044208, AI127627, AA133448, AI093329, AA099349, AA040461, AI266553, W74689, N80688, AI052641, AI969190, W74787, AA043947, AA101880, AA745759, AA057190, AA678275, AI800774, T79148, AA040462, AA705309, AI277738, R05522, AI611334, AI122879, T79229, AA862428, T49145, C02622, R05630, AA046501, AA426483, AA045459, AA057125, AA035598, AI057255, AI271978, AF098269, T48600, T64288, T94106, T94194, R48539, R50308, R50595, R54836, R72044, R72788, R81845, H00997, H01634, H14534, H14621, H14914, H15754, H15902, H21803, H21804, H21946, H22030, H22241, H22276, H22339, H22340, H24583, H24760, H24805, H24952, H25060, H25142, H25143, H25234, H25437, H25439, H25447, H25481, H25484, H25552, H25575, H25581, H25597, H25667, H25723, H25873, H26093, H26123, H26170, H26171, H26188, H26253, H27449, H27498, H27570, H27706, H27707, H27758, H28405, H28468, H28675, H28682, H28687, H41899, H41904, H41938, H41943, H42228, H42347, H42482, H42486, H42825, H43015, H43016, H43117, H43612, H43672, H43724, H43726, H43905, H43988, H44045, H44288, H44317, H44407, H44445, H44541, H44599, H44656, H45249, H45272, H45437, H45458, H45465, H45524, H45552, H45794, H46631, R83358, R83490, R83794, R85978, R86022, R86091, H51902, H51910, H64505, H64518, H67527, H70718, H70719, H64505, N22028, N25275, N25316, AA235488, AA235521, AA235584, AA458497, AA464199, AA419097, AA421863, AA422158, AA428763, AA429352, AA471061, AA484184, AA484194, AA502213, AA503365, AA505465, AA507425, AA507877, AA13093, AA513282, AA522776, AA523119, AA523390, AA523408, AA534124, AA535255, AA554167, AA554973, AA581245, AA581445, AA595658, AA595758, AA610130, AA613100, AA568920, AA627124, AA639889, AA573868, AA576348, AA578566, AA578833, AA659897, AA662295, AA687945, AA740508, AA808990, AA865256, AA916021, AA916046, AA916721, AA916791, AA916874, AA931793, AA932497, AA935803, AA938643, AA948644, AA961083, AA988030, AA999945, AI000523, C02563, AA649916, AA649932, AA283741, AA290777, AA290778, AA291723, AA292541, AA400808, AA401105, and AA403266. |
| 31 | HCEFZ82 | 73 | 879185 | AI672493, N21040, AW386160, AI672483, AI693512, AI138621, AA778387, AA173791, AA209239, AI022755, AI077708, AI824069, AI936432, AI038303, N39250, AI927782, AI457926, AI436138, AI056772, AI079503, N58793, AI016045, AA210850, AI096581, AA062719, W88815, AA725072, AI375410, W31742, AA669791, AA173843, W88816, AI740977, AI086937, AA704681, AI190844, AI341909, AI365029, N46695, AI086941, AI676179, AA826493, AA554932, AA789007, AA917998, R08679, AA889734, W04647, AA321894, AI912831, AI239655, AI368377, AA992261, H71960, H78240, H78440, AI470391, R37067, AI700804, R44781, H96434, R10835, N77482, AA314780, R44068, R08587, AI419628, N90646, H65409, AA836620, W26811, R10834, AA905784, AI086303, H84253, AI086248, AI312428, AW051059, AI538885, AW301865, AL036802, AI345612, AI345415, AA568405, AL118781, AI581033, AL041573, AI343059, AI361701, AI345416, AA614183, AI349933, AI340519, AI349937, AI340603, AW129264, AW022636, AL036631, AL040169, |

TABLE 6-continued

| Gene No. | cDNA Clone ID | NT SEQ ID NO: X | Contig ID Public Accession Numbers |
|---|---|---|---|
| | | | AA572758, AW403717, AI859991, AI241901, AW161579, AI815232, AL036396, AI064830, AL119836, AL045413, AI698391, AW302988, AL039086, AI433157, AI349645, AI698391, N71199, AI312152, AI267162, AW162194, AI923989, AI284517, AI623941, AI318569, AW089572, AA225339, AW161202, AI567582, AI500523, AW268253, AL043345, AI538764, AW020397, AI866465, AL079741, AW075084, AI345688, AL121365, AI348897, AI307708, AA579232, AA635382, AI310575, AI916419, AW023590, AI340533, AI521244, AL036274, AL038529, AI345735, AI348777, AI540845, AL037454, AL038605, AA580663, AW161156, AL121328, AI702073, AL047675, AL079963, AL119748, AA494167, AL047344, AI699865, AI554245, AW302965, AL036980, AA613907, AL047422, AW238730, AA641818, AA640779, AI366549, AI636719, AI539153, AI539771, AI446373, AL047275, AI335426, AL046466, AL036187, AI866608, AL045500, AI537677, AI382201, AW083804, AI696626, AI589993, AL040390, AL044192, AW150578, AL036403, AW082623, AI349814, AW160905, AI282508, AI251830, AI623682, AA420722, AI685005, AI590043, R81679, AL119791, AI494201, AW129106, AI583578, AI349256, AI801605, AI345347, AW068845, T99953, AI538850, AW020693, AL120853, AW268251, AL049085, AW151138, AI690813, AW071417, AI207572, AI815855, AW051088, AL036146, AI440263, AI906328, AI952217, AI343091, AL121463, AI538637, AI251221, AI371251, AI950664, AW071380, AL038715, AW169234, AI364788, AW239449, AI560012, AI500659, AI282326, AW059638, AW269097, AI635492, AL036780, AW268072, AW022494, AW071349, AI929108, AA493647, |

TABLE 6-continued

| Gene No. | cDNA Clone ID | NT SEQ ID NO: X | Contig ID Public Accession Numbers |
|---|---|---|---|
| | | | AW162189, AI345608, AL133067, I48978, AL049300, AL110196, AL122050, AL096744, AF090934, AF100931, AL137529, U42766, AL133565, A08916, AL117457, U35846, I48979, S61953, I89947, AF113694, AF097996, AF090900, AL050393, S78214, AL133557, A08910, AL133080, AL133640, AF210052, AL137459, AL035458, AF078844, I89931, AL050116, AF113690, A08909, U87620, AL133606, A03736, S36676, AL049314, AL050146, X72387, AL137527, Y07905, AF113013, AF022813, U95114, AF118070, AL049382, A08913, AF090896, AL122121, AL049430, AF017152, Z37987, AL133016, AF158248, AL122118, X93495, AL137283, Y16645, AF090943, A65341, I49625, AF118064, AL133093, I26207, Y11587, AF146568, AL137705, AL122123, AF106827, AL049452, AL117460, AF090886, AF090903, AL137292, AF113699, AF118090, AL117583, AL110221, AF102578, AF104032, AF091084, AR068753, AF125949, AL137488, AF182215, AF107847, AL080124, AL137276, AL050277, AF113689, I09360, AL137271, AF120268, AJ242859, AF026124, AL080127, AL137550, U72621, A12297, A21103, AL049283, E05822, Y10936, AL122100, I66342, AL110225, E01614, E13364, X63574, AB029065, D83032, AR011880, I00734, A18788, A18777, AL136884, AF113019, A86558, A77033, A77035, AF087943, AL049466, AF176651, AF200464, I09499, E00617, E00717, E00778, AF177401, AF090901, AL122093, AL096751, AF113691, A93016, AL080060, AF067790, Y10823, AL049938, E03671, AF069506, AF111851, AF079763, AL133075, AF113676, L31396, AL137533, A23630, AL137548, L31397, AF106862, AR038854, AL133560, AF118094, A65340, A08908, U92068, Y11254, AL137648, AF017790, A08912, U72620, U75604, E15582, AB019565, S78453, AF113677, AF132676, AF061836, AF111849, M96857, S68736, X83508, I68732, A58524, A58523, AF207750, AF065135, X80340, AL137538, AL050108, A21101, AJ012755, U00763, |

TABLE 6-continued

| Gene No. | cDNA Clone ID | NT SEQ ID NO: X | Contig ID | Public Accession Numbers |
|---|---|---|---|---|
| | | | | I41145, AL122110, AR013797, AF100781, AF017437, X79812, X70685, U58996, AF026030, X52128, AL117585, AL117649, AL080158, M27260, S77771, AL133113, E02221, AF079765, AL137521, S76508, M92439, U51587, I89934, E02349, AL122098, AF125948, AL137547, AL117435, X65873, AL133104, AF003737, AF126247, U67958, AL080137, U90884, AL122111, AJ238278, X84990, E07108, AL080126, AL110224, X62773, X98834, X72889, AL049464, AJ000937, Z82022, Y09972, AL137256, AL117394, AR034821, AL137479, X96540, AF061943, E12747, A15345, U75932, AL117648, AL137429, AL050024, AF159615, AJ003118, AL137656, AL133568, and AL133031. |
| 31 | HSIED48 | 74 | 872569 | AI735017, AI991095, AI833028, AI302085, AI991250, AI913168, AI459598, AI685121, AI956075, AI991865, AI880450, AI956168, AI620545, AI679903, AI539178, AW170593, AW001210, AA554973, AI927762, AI720447, AW337144, AI744441, AI685204, AI538691, AI963817, AI220226, AW190397, AI692817, AI829197, AI583526, AI735170, AI453734, AI660628, AW275867, AI748802, AI818588, AI814847, AW190012, AI978631, AW001217, AI559206, AI471500, AI923926, AW337938, AW192935, AI623982, AI696804, AI635246, AW273057, AI801496, AW007637, AW058222, AA402884, AI435281, AW338132, AI708758, AI829230, AA402890, AW150194, AI818229, AI829410, AI679773, AW261992, AW338661, AW188532, AW190228, AW338635, AW190375, AW057732, AW189223, AI923346, AI923867, AI963743, AA573868, AI539857, AA610130, AI697171, AI983170, AW131218, AI570200, AW276427, AI921422, AA503365, AI554519, AI687917, AW263007, AA578566, AI625231, AA664201, AI022765, AI986124, AW193314, AI565900, AW268534, AW404803, AI446302, |

TABLE 6-continued

| Gene No. | cDNA Clone ID | NT SEQ ID NO: X | Contig ID | Public Accession Numbers |
|---|---|---|---|---|
| | | | | AI749266, AI828420, AI696908, AW316762, AI572069, AW007281, AW150841, AI459910, AW194314, AA523408, AI680059, AI799325, AI682577, AI572084, AI571990, AI571456, AI819138, AI986014, AI624432, AA576348, AI151114, AI689647, AI860853, AI275227, AI285655, AI625655, AA844940, AI581862, AA523119, AI572628, AI683834, AI804591, AA578833, AI991849, AI587047, AI570284, AI628855, AI673632, AI811754, AW401348, AW001504, AA581445, AI275814, AA429352, AW084943, AW364700, AI587186, AI598095, AI281742, AA523390, AA568920, AI984847, AI678689, AI573201, AI983804, AI911650, AI697003, AI683481, AI984126, AA595758, AI829224, AI587423, AI983983, AI571646, AI677647, AI660451, AA522776, AI922800, AI696995, AI673816, AI559261, AI660213, AA845885, AI686934, AI521342, AI570045, AI955753, AI567553, AI697246, AI125317, AI624660, AI986042, AI962904, AW191013, AW193403, AI627913, AI690842, AI598025, AI701060, AI624165, AI597973, AI632055, AI439833, AW085666, AI991212, AW264686, AW405737, AI566478, AI570063, AI805478, AA659897, AI564660, AI811453, AI453141, AI566489, AI677995, AI858139, AI587494, AI750165, AI635785, AI610183, AI460298, AI961478, AA464199, AI631417, AI813866, AW050723, AI963186, AI708951, AI865827, AI968517, AI921019, AW402116, AI921670, AI832603, AI952262, AA662295, AI673199, AI640792, AI801796, AI694180, AI683465, AI280825, AI431417, AI708021, AI640877, AI189942, AI446131, AI445522, AI571607, AI880818, AA428763, AW192084, AI640911, AI358568, AI583601, |

TABLE 6-continued

| Gene No. | cDNA Clone ID | NT SEQ ID NO: X | Contig ID | Public Accession Numbers |
|---|---|---|---|---|
| | | | | AW193373, AI289398, AI832862, AI270569, AW243648, AW338788, AI687794, AF067420, S71043, J00220, X53707, X53703, X15045, X53702, X53704, X53706, X53708, X53709, X53705, S55735, AF024645, AJ012264, U12594, AF109167, X82119, M60192, X82117, U07986, X00353, Z75394, Z75365, AF062149, X08044, Z75378, AF174022, Z75377, AF062148, AF062112, AF064879, AF062201, Z75385, Z75383, Z75362, AF062278, M99601, X67906, X56158, Z75381, AJ234160, Z75379, Z35126, Z75367, Z75375, Z75397, M99683, AF013616, Z82883, Z75363, AF062239, AF062126, Z75387, L29122, U38663, AF062228, Z75364, Z74671, Z75405, AF062129, S50735, Z14237, Z82892, Z14193, AF062132, Z75388, AF062120, AF174036, X65903, Z75366, X65910, M97921, AF174013, Z82868, U24691, U24689, U86523, Z14195, X69866, Z14182, Z47349, AF013619, U86524, X80303, X92269, S55017, AB019439, AF062204, X69860, Z75380, Z14196, AF062106, AF062207, Z82886, X92270, X92271, X92272, X65911, AF062266, M18518, L38425, Z98714, M37058, U57568, Z14235, Z14238, AF013621, AF062209, Z75404, X65905, Z75399, X65908, Z14194, X54445, AF062220, U86525, AF062166, Z82875, X92273, AF062185, X95660, U24688, Z14239, X92274, AJ234190, AF062252, M99609, AF062245, U68227, M99607, AF062258, AF062203, AF062173, M12071, Z75370, AF062158, AF013622, U57563, AF062192, U57560, AJ234189, AF062152, AF062109, AF062181, X05715, AJ244965, U80131, Z14206, X53388, AF062218, M29811, X92275, AF062144, AF021954, AF062232, U80129, AF062146, U24683, Z47241, X92222, X05714, Z75392, AF126269, AF062272, AF062101, U80110, AJ244976, U71106, AF174020, AJ244949, M74018, S39381, Z75372, AF062196, X64234, U80132, X05711, AJ245012, X65907, AF062102, Z75401, U80111, M26997, Z82893, Z14198, L25291, L26965, Z75368, X65902, Z75400, M88500, AF062108, AF013620, X65909, X92230, Z47221, L23556, AB019437, X54437, AJ244930, Z75374, AF103795, AF062183, U03896, Z14248, L43087, Y08303, S59161, AJ279518, X95659, M17777, Z47234, Z14236, M33061, U80113, S67826, L28053, AF062240, Z75386, AJ245010, AF062264, U80167, X62112, M98868, X92249, X92251, L22587, U80127, X79172, AF062169, AR068123, U80166, Z75395, and X53387. |
| 31 | HADFW77 | 75 | 847205 | AI741776, AI937181, AA142834, AA449297, AA115742, W07748, AI185171, AI189560, AA044208, AI127627, AA133448, AI093329, AA099349, AI266553, AA040461, W74689, N80688, AI052641, AI969190, AA745759, AA043947, AA101880, W74787, AA057190, AA678275, AI800774, T79148, AA040462, AA705309, AI277738, T49144, R05522, AI611334, AI122879, D78874, AA862428, T79229, T49145, C02622, R05630, AA046501, AA449557, AA426483, AA045459, AA057125, AA035598, AI057255, AI271978, and AF098269. |
| 31 | HNGFW58 | 76 | 833074 | AL044254, AA641592, AL044209, AL135706, AI800268, AA584638, AW238615, AA533107, AA489896, AI936549, AL043065, AA714323, AI554666, AA577860, AA584801, AI922061, AA569180, AI868368, AA121904, AI052560, AI349954, AA501775, AA664366, AA553442, AA258511, AI061445, AW270592, AA333509, AA778649, AA487808, AA481809, AA679179, AA736957, AA640504, AA612822, AA657354, AA227298, AI401729, AI821285, H80568, AA766720, D59168, AA280232, AA769976, AW075927, AA084302, AA055576, AI923902, T63143, AA602337, AA720668, AA376315, AA551539, C16656, AI033961, T07820, AI525330, AA744577, T66926, AL134095, D56198, AA377887, AA780457, AA744267, AA745439, AA744408, T02931, AA883167, AA283645, N57818, F25744, AW028252, AF088219, AL136520, AC007344, AC003658, AP000034, AP000101, AP000264, AC005386, AC006364, AC007317, U66059, AC002449, AL049710, AL031286, AL049743, AC002070, AL049834, AL023875, |

TABLE 6-continued

| Gene No. | cDNA Clone ID | NT SEQ ID NO: X | Contig ID | Public Accession Numbers |
|---|---|---|---|---|
| | | | | AC006203, AC005019, AL110505, AC000119, AC002080, AL109628, AL132994, AC007402, AP000460, AL133162, U69730, AL034400, AC004823, AL049734, AC004677, AC004470, AC004894, AC003686, AC004072, AC005588, AC004949, Z68326, Z80774, AC008394, AC006249, AC004158, AL021068, AC002463, Z68280, L11910, AC007632, AL035671, AC002454, AC004908, AL133500, AC004842, AL049565, AL132777, AC004852, AC005794, AC004544, AC007065, AC007690, AL030996, AC003986, AC006336, AC003081, AL031274, AP000566, AC005739, AC007253, AC005034, AL035695, AC005823, AC005686, AP000692, Z84720, AC007319, U40455, AL022345, AL035699, AC007748, AC000378, AC007446, AP000457, AC005859, AL009176, Z82899, Z84470, AL031114, AL049838, AC005273, AL049641, AC006204, AC006461, L29074, AL033521, AC004774, AL034377, AC005064, AL023495, Z96074, AF101874, U01882, AC004454, AC005230, Z68871, AC005050, AL035688, AJ225782, AC010072, AC007243, AL121694, AL031663, Z83745, AL050334, AC006356, AL033517, AL109853, AC016831, AC008122, AL133312, AL050401, AB020861, AC007007, AP000476, AC007567, AF172277, Z84487, Z82194, AC006152, Y15155, AC000055, AL031116, AC005213, Z70274, AC006377, Z98255, AC003075, AL049557, AL109764, AL136363, AC007671, AC007091, AL080239, AL078588, AL035563, AC008179, AL022146, AL121790, AL135879, AC004055, AC005900, AC006265, Z83848, AC005498, AF001905, AL022241, AL021451, AC005076, Z77249, AL034347, AC009784, AC003082, AL034410, AL031782, Z73986, AC006043, AL049794, AC005199, Z82211, AC005201, AC004628, AF109076, AL132985, AF044083, AL049551, AC003693, AJ006343, AC000377, AC007250, AL035252, AC004959, AL121825, |

TABLE 6-continued

| Gene No. | cDNA Clone ID | NT SEQ ID NO: X | Contig ID | Public Accession Numbers |
|---|---|---|---|---|
| | | | | AL034399, AL096773, AL078600, Z82215, AC004810, AL096827, AC007970, AC004053, AP000083, AC007051, AL049859, U82828, AC006029, Z83313, AC003099, AL079305, AC007126, AC008929, AC005922, AC006840, AC009405, Z93403, AC007032, AC007286, AC004535, AC005378, AL031074, AL049778, Z70227, AC006548, AL023806, AJ239329, AC004063, AL121782, AL136018, AC000125, AC005094, Z82210, AC002429, AC005029, AC007392, Z82900, AC004613, AC008009, AC006455, AC007327, U80459, AC005177, AL009173, AL022576, and U78045. |
| 31 | HCEFZ82 | 77 | 831745 | AI672493, N21040, AW386160, AI672483, AI693512, AI138621, AA778387, AA173791, AI022755, AA209239, AI077708, AI824069, AI936432, AI038303, N39250, AI927782, AI457926, AI436138, AI056772, AI079503, N58793, AI016045, AA210850, AI096581, AA062719, W88815, AA725072, AI375410, AA669791, AA173843, W31742, W88816, AI740977, AI086937, AA704681, AI190844, AI341909, AI365029, N46695, AI086941, AI676179, AA826493, AA554932, AA789007, AA917998, R08679, AA889734, W04647, AA321894, AI912831, AI239655, AI368377, AA992261, H71960, H78240, H78440, AI470391, R37067, AI700804, R44781, R10835, H96434, N77482, AA314780, R44068, R08587, AI419628, N90646, H65409, AA836620, W26811, R10834, AA905784, AI086303, H84253, AI086248, AI312428, AW051059, AI538885, AW301865, AL036802, AI345612, AI345415, AA568405, AL118781, AI581033, AL041573, AI343059, AI361701, AI345416, AA614183, AI349933, AI340519, AI349937, AI340603, AW129264, AW022636, AL036631, AL040169, AA572758, AW403717, AI859991, AI241901, AW161579, AI815232, AL036396, AI064830, AL045413, AL119836, AI698391, |

TABLE 6-continued

| Gene No. | cDNA Clone ID | NT SEQ ID NO: X | Contig ID Public Accession Numbers |
|---|---|---|---|
| | | | AW302988, AL039086, AI433157, AI349645, AI683395, N71199, AI312152, AI267162, AW162194, AI923989, AI284517, AI623941, AI318569, AW089572, AA225339, AW161202, AI567582, AI500523, AW268253, AL043345, AI538764, AW020397, AI866465, AL079741, AW075084, AI345688, AL121365, AI348897, AI307708, AA579232, AA635382, AI310575, AI916419, AW023590, AI340533, AI521244, AL036274, AL038529, AI345735, AI348777, AI540845, AL037454, AL038605, AA580663, AW161156, AL121328, AI702073, AL047675, AL079963, AL119748, AA494167, AL047344, AI699865, AI554245, AW302965, AL036980, AA613907, AL047422, AW238730, AA641818, AA640779, AI366549, AI636719, AI539153, AI539771, AI446373, AL047275, AI335426, AL046466, AL036187, AI866608, AL045500, AI537677, AI382201, AW083804, AI696626, AI589993, AL040390, AL044192, AW150578, AL036403, AW082623, AI349814, AW160905, AI282508, AI251830, AI623682, AA420722, AI685005, AI590043, R81679, AL119791, AI494201, AW129106, AI583578, AI349256, AI801605, AI345347, AW068845, T99953, AI538850, AW020693, AL120853, AW268251, AL049085, AW151138, AI690813, AW071417, AI207572, AI815855, AW051088, AL036146, AI440263, AI906328, AI952217, AI343091, AL121463, AL538637, AI251221, AI371251, AI950664, AW071380, AL038715, AW169234, AI364788, AW239449, AI560012, AI500659, AI282326, AW059638, AW269097, AI635492, AL036780, AW268072, AW022494, AW071349, AA493647, AI929108, AW162189, AI345608, AL133067, I48978, AL049300, AL110196, AL122050, AL096744, AF090934, AF100931, |

TABLE 6-continued

| Gene No. | cDNA Clone ID | NT SEQ ID NO: X | Contig ID Public Accession Numbers |
|---|---|---|---|
| | | | AL137529, U42766, AL133565, A08916, AL117457, U35846, I48979, S61953, I89947, AF113694, AF097996, AF090900, AL050393, S78214, AL133557, A08910, AL133080, AL133640, AF210052, AL137459, AL035458, AF078844, I89931, AL050116, AF113690, A08909, U87620, AL133606, A03736, S36676, AL049314, AL050146, X72387, AL137527, Y07905, AF113013, AF022813, U95114, AF118070, AL049382, A08913, AF090896, AL122121, AL049430, AF017152, Z37987, AL133016, AF158248, AL122118, X93495, AL137283, Y16645, AF090943, A65341, I49625, AF118064, AL133093, I26207, Y11587, AF146568, AL137705, AL122123, AF106827, AL049452, AL117460, AF090886, AF090903, AL137292, AF113699, AF118090, AL117583, AL110221, AF102578, AF104032, AF091084, AR068753, AF125949, AL137488, AF182215, AF107847, AL080124, AL137276, AL050277, AF113689, I09360, AL137271, AF120268, AJ242859, AF026124, AL080127, AL137550, U72621, A12297, A21103, AL049283, E05822, Y10936, AL122100, I66342, AL110225, E01614, E13364, X63574, AB029065, D83032, AR011880, I00734, A18788, A18777, AL136884, AF113019, A86558, A77033, A77035, AF087943, AL049466, AF176651, AF200464, I09499, E00617, E00717, E00778, AF177401, AF090901, AL122093, AL096751, AF113691, A93016, AL080060, AF067790, Y10823, AL049938, E03671, AF069506, AF111851, AF079763, AL133075, AF113676, L31396, AL137533, A23630, AL137548, L31397, AF106862, AR038854, AL133560, AF118094, A65340, A08908, U92068, Y11254, AL137648, AF017790, A08912, U72620, U75604, E15582, AB019565, S78453, AF113677, AF132676, AF061836, AF111849, M96857, S68736, X83508, I68732, A58524, A58523, AF207750, AF065135, X80340, AL137538, AL050108, A21101, AJ012755, U00763, I41145, AL122110, AR013797, AF100781, AF017437, X79812, X70685, U58996, AF026030, X52128, |

TABLE 6-continued

| Gene No. | cDNA Clone ID | NT SEQ ID NO: X | Contig ID | Public Accession Numbers |
|---|---|---|---|---|
| | | | | AL117585, AL117649, AL080158, M27260, S77771, AL133113, E02221, AF079765, AL137521, S76508, M92439, U51587, I89934, E02349, AL122098, AF125948, AL137547, AL117435, X65873, AL133104, AF003737, AF126247, U67958, AL080137, U90884, AL122111, AJ238278, X84990, E07108, AL080126, AL110224, X62773, X98834, X72889, AL049464, AJ000937, Z82022, Y09972, AL137256, AL117394, AR034821, AL137479, X96540, AF061943, E12747, A15345, U75932, AL117648, AL137429, AL050024, AF159615, AJ003118, AL137656, AL133568, and AL133031. |
| 32 | HLYAV34 | 42 | 430780 | AI300176, AI561024, AI749282, AA894528, AA917673, AI193100, AA577400, AI184968, AA703086, N32601, AA922077, AI141075, AI200645, AI274361, AI291153, AI815092, W92736, AA922163, AI682589, AW001112, AW000838, AI687717, AI346224, AI283829, AI342526, AI718510, AA609464, AI285277, N38801, AA827271, AI274203, AI278912, AI598054, AA954441, T95291, C17007, AI523358, AI272748, AI582743, AA508675, AA485613, AI304507, AA443822, AI811138, R71353, W92820, AI749077, AA025765, H66699, AI459266, H66689, H90673, H78056, R66274, AI336608, R47872, AA383872, R24350, H64116, AI088641, T95371, AI749260, AA025953, H01871, N90491, H64951, T27046, AI873364, T72087, R47871, D31533, H42114, AI352318, R62666, R72785, H78057, H73228, AA368991, H89819, AA295668, AW374237, H01130, AW277068, N69227, R72786, AW135690, H26462, R24669, T23681, AI202813, H27838, H70128, AW374232, R43349, H83150, N47826, T16823, N45434, AA371827, H64952, T72232, AA640081, AI281745, AW105588, R17629, AI281707, H27773, AA835433, AR068753, S77771, and AL122110. |
| 32 | HLYAV34 | 78 | 731872 | AI300176, AA894528, AI561024, AI749282, AI193100, AA917673, AA577400, AA703086, N32601, AA922077, AI141075, AI274361, AI291153, AI200645, AI815092, AI184968, AA922163, W92736, AI682589, AW001112, AI687717, AW000838, AI346224, AI283829, AI342526, AI718510, AA609464, AI285277, AA827271, N38801, AI274203, AI278912, AI811138, AI598054, AA954441, C17007, T95291, AA485613, AI272748, AI523358, AI582743, AA508675, AI304507, AA443822, R71353, W92820, AI749077, AA025765, H66699, AI459266, R66274, H78056, H66689, H90673, AI336608, T95371, R47872, AA383872, R24350, T72087, AI749260, AA025953, AW029317, H64116, R47871, AI088641, D31533, AI352318, AA368991, AI872250, AI873364, T27046, H64951, R72785, H78057, R62666, H73228, H89819, AW374237, H42114, AA295668, H01130, N90491, AW277068, H01871, AW374232, N69227, AW135690, R72786, H26462, R24669, T23681, AI202813, H27838, AI476021, AA371827, H70128, R43349, H83150, T16823, AA640081, T72232, N45434, H64952, N47826, AI281745, AI874109, AI282655, AI619502, AI696846, AI560012, AW148320, AI669609, AI634737, AI630928, AI432969, AI648663, AI631107, AI653541, AI282281, AW085673, AI758437, AW105588, AI869367, AW075413, AW188539, AI862144, AI609592, AI872711, AW026882, AI475134, AI500077, AI569583, AI572787, AW075351, AI799199, AI538716, AI097248, AI567351, AW301409, AI499381, AI671679, AI828367, AI590128, AW075667, AI285735, AI270183, AI680498, AI800433, AI289937, AW167776, AI925156, AI632033, AI818206, AI699857, AI635461, AI862142, AI469532, AI475451, AI274508, AI349645, AI583316, AW268253, AI828731, AI281762, AI434468, AI597918, AW102785, AI281773, AI274013, AI686926, AI453322, AI249323, AI859511, AL036396, AI924971, |

TABLE 6-continued

| Gene No. | cDNA Clone ID | NT SEQ ID NO: X | Contig ID | Public Accession Numbers |
|---|---|---|---|---|
| | | | | AW089572, AI686808, AI887450, AI919058, AW167410, AI561254, AI620284, AW074993, AI273142, AI312152, AI345735, AI340519, AI349937, AI499285, AI628205, AI697137, AI613017, AW243820, AI934036, AI922365, AI800453, AA640779, AW082623, AI623396, AW166970, AI887396, AW300889, AI952114, AW085799, AI699865, AW169653, AI920968, AW169527, AL079963, AI597750, AI539808, AI446606, AI500553, AL041772, AI349614, AI580190, AI280637, AI270707, AW074869, AI680113, AI348897, AI536685, AI580984, AI524671, AI537303, AI513579, AW274192, AI497733, AL036146, AI476046, I48979, AJ242859, AF090943, I89947, AF113019, L31396, AF090896, L31397, Y11587, I89931, AL050116, AL122050, AL117457, AL050108, AF113694, AF090903, AL137527, A08916, AL137459, AL050146, AF090900, I48978, AF078844, AF113690, Y11254, AL133016, Z82022, AL133606, AF106862, AJ000937, I33392, S78214, AL133640, AL122121, AL049452, AF090934, Y16645, AF118064, S68736, AF118070, AF113691, AF113013, U42766, AF125949, AL050393, AL133080, AL049314, AL110221, AL050149, AF113677, AL110196, A77033, A77035, AF090901, AF104032, AL133075, AF113699, AL080060, AL133565, A93016, AL049938, AR011880, AR059958, E07108, AL096744, A08913, AF113689, A08910, AF097996, AL049382, AL080124, AL049466, AF146568, AL122093, AF113676, AF177401, AB019565, I49625, X84990, A65341, AL117460, AL049300, AL133560, AJ238278, AF017152, AF125948, AF091084, AL050277, AF111851, AL133557, X63574, AL122123, A08909, AL117394, U91329, E03348, AF017437, AL049430, AL137557, AL117585, E02349, AF183393, AL080137, AL137283, AL110225, AL137550, AF158248, AL122110, AL133093, X82434, X96540, AF087943, AL137648, AL117435, AL117583, AF079765, E07361, AF061943, A58524, A58523, AL122098, AL049464, AL133113, AL050024, X70685, AL137271, AL050138, I03321, A03736, U00763, AL137521, AF118094, AL137538, AL137463, A12297, U35846, AL080127, X72889, X65873, U72620, U80742, AF067728, X93495, AL049283, A08912, AL133072, U67958, S61953, AL080074, AL137560, I42402, I09360, AL080159, I26207, AF111112, E05822, A93350, Y09972, AF106657, AL110197, AR038969, X98834, E15569, AF106827, AJ012755, AF057300, AF057299, E08263, E08264, AL133014, AF119337, AF210052, AF026124, AL133568, AR013797, AF111849, AL137429, I66342, AR000496, U39656, AL050172, I00734, E00617, E00717, E00778, AL133077, A07647, AF026816, AL137526, AF153205, AL122049, M30514, AL133104, U58996, Y14314, AL137476, AF079763, AF003737, E04233, AL110280, AL137556, AF000145, AF132676, AL137523, AF061836, AF185576, AL137480, AF118090, Z72491, AL122111, I17767, E02221, X83508, AF008439, AL133067, AF126247, AL133098, Z37987, AR038854, U96683, E08631, U78525, X87582, I09499, Y07905, AJ006417, AF162270, U68387, U49908, AL117649, AL023657, AL137533, AL117440, A45787, AL137488, AL117432, AF067790, AF100931, E06743, AL122118, AL031346, AF081197, and A90832. |
| 32 | HTOCG60 | 79 | 560657 | AW406521, AA522693, AI354387, AI569037, AI921456, AW383594, AW406562, AI432569, AI694098, AW406564, AW369231, AI208910, AI355534, AI254719, AI250870, T58152, AW404417, AI990966, R69401, AW383598, AW404714, AI749799, AW405980, AW383597, AW383602, T89673, AI347602, T89330, AI933674, AW380142, AW383625, AW383564, AW383591, AW383536, AI469554, AW383452, AI582367, AW383549, AW406495, AW383454, AW383450, AW383559, AW379839, AA402992, AW377416, AI499556, H24569, AW382758, AW383543, AW383600, |

TABLE 6-continued

| Gene No. | cDNA Clone ID | NT SEQ ID NO: X | Contig ID | Public Accession Numbers |
|---|---|---|---|---|
| | | | | AW405634, AW377823, AW406081, AW383446, AW369150, AI619620, AA720572, AW377831, AW369233, AW368484, AW382749, AW369213, AW383603, R79142, AW382752, AW405723, AW382762, AW383550, AW406512, AW382718, T93086, AW405821, AA845297, AI001204, R53592, R49985, AW369237, AW383557, AW382727, AW391436, AW369144, AW383447, AI264770, T90680, AW383555, AW383539, AW369143, AW383620, AW377815, AW268531, R72655, AI864507, AI160771, AI860287, AA845791, T63859, AI634335, AI619481, AW383635, AA464511, AW383451, AA866065, AA996362, AI799618, AI281629, AW050835, AW383441, T93060, R76324, H61210, AW391263, AW406384, AW369127, AW368722, AW406133, AA715256, R67501, AW382733, AW393797, AA650531, AI803772, H44799, AW404498, AW405198, AA411496, H15909, N68865, AI886509, AW383444, H22016, AI621190, AW405603, AW190841, AW190839, AI861982, AI287256, AI589408, AW405499, AA622612, AW404101, AW337632, AI247306, AW071245, AW369190, AI624583, H61152, AW366307, AW190383, AW369147, AA235513, R83659, AA377245, AA679280, AI597789, AA463968, H21647, AW404099, AA507908, AW369083, AW369210, AI707746, T72175, AW368477, AW405753, AI249372, AW189898, AA496437, AA295982, AW377828, AA643483, R83657, AA633900, AI708967, AW393776, AI311104, AW383579, AW369188, AW368471, H44321, AW369085, AW380184, AA526013, AI355284, R73415, T57678, AW368478, AW383578, AW369082, AW368465, AA345900, AW369223, AW190956, AW368464, AW405023, R52162, AW378453, AW377819, AW369166, AW369197, R64694, T64210, AW369215, |

TABLE 6-continued

| Gene No. | cDNA Clone ID | NT SEQ ID NO: X | Contig ID | Public Accession Numbers |
|---|---|---|---|---|
| | | | | AW369214, H70727, AW369133, AA782276, AW405817, R47934, AW368524, AW368485, AA886456, AW405295, AW088815, AW377824, H24882, AW404748, AW368523, AI922607, AI869934, AW369141, AW369209, AW384359, AW405301, AA715871, AA501599, R48142, AW369145, AW383448, AW369154, AW369151, AA291844, AA485725, AW377826, AA580005, AI001852, AW369081, AW405187, H28430, AI523353, AW369146, AW368454, AW169031, AW369121, H44560, AA662263, AA565066, C02031, AW368526, H45129, AW369181, Y14736, AJ010442, A21386, M63438, E07333, AR035237, A94054, A94046, AF017732, AF113887, AR031183, AR031185, E08292, AB022656, X67858, E08293, M11937, L01411, X95750, E08291, U07989, X95749, AB022654, X95748, S49006, AR035236, AR035234, V00557, X96754, U07990, AB004304, AF026381, X95747, U72063, E08294, M11737, M11736, AB022651, AJ010446, AJ010444, L01413, AF027158, A07738, A07739, AR048108, AR018924, A51597, S79311, AB012910, U91942, A33044, L13309, L13317, L13316, I26930, L13315, A67260, L13310, L13312, A67295, A83197, AF051099, I69460, A67342, AB022653, I07074, L13308, AR015961, A27396, AR000007, A83232, AR051652, L13313, AR051553, AR051554, L22157, A67340, A70359, I69484, A57359, A07560, AR038305, AR038319, A51868, AR038307, AR038321, A99060, AR000006, AR015960, X75612, X72475, S74681, I65403, L03150, L03156, AF103775, L03152, AF198257, AF103774, L13314, A67290, L13311, A94038, M74019, L01279, E01513, U43770, AF113889, S59162, X80304, U43764, U43767, X85995, AF026918, M87478, Z68992, X65287, X64133, U57577, AR035977, AR035978, L33034, X72458, M64856, X72444, X67322, U57579, M64855, E12918, AF124196, AF124199, AF050635, X72427, X85997, M64857, AF054661, X72477, AF103773, AF054662, AF115362, I19518, Z27173, Z69004, U86790, L03555, |

TABLE 6-continued

| Gene No. | cDNA Clone ID | NT SEQ ID NO: X | Contig ID | Public Accession Numbers |
|---|---|---|---|---|
| | | | | L06158, X64163, X85996, X72426, AF103772, X72441, L26890, X72424, A44324, U57572, K02135, U43773, AF026933, Z68958, Z68969, M33060, X72446, X72480, S73911, X79834, S67637, Z37332, T59642, T59961, T60034, T61902, T61987, T62514, T64021, T64100, T64185, T64374, T64399, T64667, T69915, T69967, T70081, T72256, T87728, T87732, T87733, T89331, T89943, T89966, T91549, T91635, T92733, T92812, T93145, T93270, T93484, T93529, T93553, T94575, T94613, T94761, T94762, T94868, T94914, T95024, T96188, T96397, T96481, R10121, T85409, R31179, R48846, R49882, R53005, R53006, R54661, R54662, R66359, R66360, R69406, R69525, R70249, R70375, R72237, R73918, R76323, H15939, H21548, H24540, H24693, H24696, H25288, H25329, H25745, H25837, H26217, H26358, H26362, H26427, H267S1, H27472, H27649, H28387, H28892, H39S34, H39556, H42611, H42665, H42883, H44320, H44423, H44460, H44507, H45432, H45808, H46620, R83047, R83107, R83214, R83590, R96848, H53707, H58960, H61190, H61200, H61359, H62094, H62104, H62386, H67211, H68237, H68597, H69079, H71059, H71573, H81531, H95062, H81531, N22430, N23085, N23918, N30840, N54795, W58760, AA235514, AA236699, AA236700, AA458504, AA458958, AA459084, AA459173, AA464027, AA464364, AA464407, and AA464546. |
| 32 | HDPWX42 | 80 | 815656 | AI300176, AI193100, AI184968, AW001112, AA703086, AI561024, AA577400, AI342526, N32601, AI749282, AA894528, AI200645, AA922163, W92736, AA917673, AI687717, AW000838, C17007, AI141075, AI815092, AI346224, AA485613, AA922077, AI291153, AI718510, N38801, AI274361, AI523358, AI598054, AI582743, AA508675, AA443822, AI682589, AA827271, AI283829, R47871, AI285277, AA609464, R71353, AI811138, R47872, AI459266, W92820, AI274203, AA640081, AI278912, T95291, AI873364, AA954441, AI352318, H90673, T27046, AI749077, AA025765, AI272748, H66699, R66274, H64116, H42114, AI304507, H78056, H66689, R24350, AA025953, AA371827, T95371, AA383872, N90491, H64951, T72087, D31533, R72785, H01130, AI749260, AA368991, H89819, R62666, H01871, AI088641, N45434, AI872250, AW374237, AA295668, H78057, H73228, AI336608, AW277068, AW135690, AI202813, H64952, H26462, R24669, T72232, H27838, AI476021, T23681, H70128, AW374232, N47826, N69227, H83150, R43349, T16823, R72786, AL119457, AI281745, AW029317, AW085673, AL119399, AL042544, AI925156, AW082623, AI420521, AI632033, AW105588, AW087534, AL042382, AW075413, AW083175, AI572787, AI923357, AI571861, AW188539, AL079794, AI824648, AI874109, AI621209, AI282281, AI669609, AI653541, AI619502, AI282655, AW087160, AI680435, AI628316, AI249323, AI634224, AL119324, AI828818, AI869367, AW148320, AW080992, AI439089, AI824764, AI273142, AI684234, AI648663, AI634737, AL037081, AI499285, AI631107, AL119511, AI285448, AI569583, AI357316, AI783504, AI862139, AW087938, AL079741, AW002362, AW131282, AI560012, AI564719, AW104790, AI886206, AW075351, AI475455, AI889953, AI568900, AI564992, AI433157, AI871923, AI539808, AI812107, AI630928, AW084786, AW149851, AI680498, AI524671, AI828731, AI097248, AI862144, AI699865, AI696846, AI434468, AI591420, AI828568, AL036187, AW243820, AW026882, AI433384, AI587056, AI500077, AI566479, AI609592, AI654672, AI475134, AI306613, AI636719, AI648684, AI671679, AI432969, AI249962, AI887450, AI439920, AL038565, AI281707, AW090700, AW170635, AI932794, AI619754, AI567351, |

TABLE 6-continued

| Gene No. | cDNA Clone ID | NT SEQ ID NO: X | Contig ID | Public Accession Numbers |
|---|---|---|---|---|
| | | | | AI800433, AI619716, AI469532, AI890628, AW102785, AI493567, AA833760, AI499131, AI340627, AI859915, AI274508, Y11587, AR060234, Z82022, A08916, AR066494, AJ242859, A08910, AF090943, I89947, I48978, AL137459, A08913, AF113019, E02349, L31396, AF090896, L31397, I89931, A08909, AL050149, AL050108, AL049314, U42766, I49625, AL050116, AF113699, AL117435, I33392, AF017437, Y16645, AL122050, AL117457, AF177401, AL049466, AF113694, AF090903, AL110225, AL137527, E02221, AF091084, I48979, AL050146, X70685, AF090900, AL133557, AL117394, AF078844, AF113690, AL133080, AF125948, Y11254, AJ000937, AL049430, AF111851, AL049464, AL133016, AF106862, U77594, AL137271, AL133640, S78214, AL117585, E07108, AL133560, AL122121, AB019565, AF126247, AL137557, AL049382, I00734, AL096744, AF158248, AF146568, AL133606, X63574, AL122123, AF090934, AL049452, AL137648, E00617, E00717, E00778, AL080124, AF118064, X96540, S68736, AF118070, AL137538, AF113691, AF113013, AL122093, AF113677, AL137550, AL117460, AF125949, AL050393, X82434, AF100931, AF079763, A93350, AL110221, I09360, AL122110, A65341, AL110196, AF183393, AL133075, AF090901, AF079765, AF104032, A58524, A58523, AL137479, AL117583, AF026124, AL050277, AF097996, AF113676, AF061943, AL133565, A03736, U91329, AL080060, A93016, E03348, AF113689, AL049300, AL049938, AL133093, AR011880, A77033, A77035, AR059958, AJ238278, X84990, AF017152, AL080137, E07361, AR038854, AL049283, AF087943, U58996, AR038969, AL133081, M30514, U00763, AL122098, Z37987, AF118094, AL050024, AR000496, U39656, U78525, I26207, AL137429, AL137521, A07647, AL133568, AL133113, X65873, AJ006417, AF111112, I03321, Z72491, AI2297, AL050092, AF026816, AL133072, E06743, AF132676, AL137523, AF061836, AL122111, AL117649, AL137529, A08912, I66342, |

TABLE 6-continued

| Gene No. | cDNA Clone ID | NT SEQ ID NO: X | Contig ID | Public Accession Numbers |
|---|---|---|---|---|
| | | | | AL050138, AL110280, X98834, S61953, AL133104, AL137478, X92070, U35846, AF162270, AL122118, AL137488, AL137463, AL080159, AL137560, AF118090, AF111849, AF185576, X93495, AL137476, AF067790, AF003737, X87582, AL050172, AF061795, AF151685, U68387, Y07905, AL133098, AL035458, AL137283, U72620, I42402, AL080127, U80742, AC002467, AL133067, L19437, X72889, L30117, Y14314, AL137533, AL117440, AL117432, AF119337, AR013797, AL137526, AF067728, E05822, U67958, E15569, U68233, I92592, AJ012755, AL133665, AR020905, AL122049, X52128, AF153205, AL080158, Y09972, AL137480, AF057300, AF057299, X83508, X81464, and I41145. |
| 32 | HCNSM85 | 81 | 544723 | AW406521, AW406562, AI569037, AI354387, AW404714, AW379839, AA522693, AW383594, AI208910, AW369231, AI355534, AI990966, AI250870, T58152, AW406081, AI432569, AW404417, R69401, AI749799, T89673, T89330, AW405980, AW380142, AI933674, AW382752, AW406564, AI347602, AW382758, AW383602, AA650531, AI254719, AI469554, AI499556, AW383446, AW383450, AW383564, AW406495, AI921456, AA402992, AW377416, AA845791, H24569, AA845297, AW405634, AW377823, AW383597, T90680, AW383598, AW383600, R53592, AW383625, AW405817, AW369150, AW369233, AW368484, AW383536, AW369213, AW383549, AW383603, AW377831, R79142, AW383452, AW383454, AI864507, T93086, AI001204, AW383559, AW406512, AW382718, AI694098, AW382762, AA720572, AW383591, AI264770, R72655, AA866065, AW391263, R49985, AW369237, AW382749, AW383557, AI634335, AW383550, AW369144, AW391436, AW405821, AW383539, AW369143, AI619620, AW383555, AW377815, AW383447, AW382727, AW268531, AW405753, AW383620, AA464511, |

TABLE 6-continued

| Gene No. | cDNA Clone ID | NT SEQ ID NO: X | Contig ID | Public Accession Numbers |
|---|---|---|---|---|
| | | | | AI160771, AW383543, T93060, AW404099, AA996362, T63859, R76324, H61210, AW369127, AI860287, AW383451, AW382733, AA715256, AW405723, R67501, H44799, AI281629, AW337632, AA679280, AW405198, AI886509, AW404910, AW368722, AW406384, AW393797, N68865, H15909, AW406133, AW050835, H22016, AW405301, AA411496, AI799618, AI803772, AW404498, AI589408, AW383441, AW071245, H61152, AW190839, AW190841, AI287256, AW405603, AA507908, AW405499, AA235513, R83659, AA377245, T72175, AW369190, H21647, AW369147, AI619481, AW404101, AA633900, AW383635, AA463968, AA643483, AI707746, AW190383, AA496437, AW369083, AW366307, AA295982, H44321, AW369210, AI249372, R83657, AW406294, AW377828, AI708967, AW393776, AW368477, AW189898, T57678, R73415, AI355284, AW369082, AW369188, AW368478, AW190956, R52162, AA526013, AW368464, AW369141, AW368471, AW369223, AW369166, AW369197, AW377819, AW368465, R64694, T64210, AW404748, AA345900, AW369133, AA782276, R48142, H70727, AW380184, AW368524, R47934, AW368485, AA886456, AW369214, H24882, AW369085, AW088815, AW368523, AW369215, AW405023, AW369145, AA622612, AW369154, AW369151, AI621190, AW369209, AA715871, AI869934, AI311104, AA501599, AA485725, H28430, AW368454, AW383578, AW405906, AW405601, AA580005, AW378453, AI001852, AW406323, AW377824, AW368526, H45129, AI523353, AW369146, R48846, AW169031, AW383444, AW369121, AW378449, AW384359, AW369129, H44560, AW369081, AA662263, AA565066, AW384391, AI432004, AW369181, AW377814, AW364991, AW369132, AJ010442, Y14736, A21386, M63438, AR035237, E07333, AF017732, A94046, AR031183, AR031185, A94054, AP113887, X95750, X95749, AJ010446, E08292, AB022656, AB022654, X95748, E08291, E08294, E08293, U07990, X67858, AB004304, X95747, AR035236, AR035234, V00557, X96754, L01411, U72063, M11937, AF026381, S49006, U07989, M11737, M11736, AJ010444, AB022651, AF027158, L01413, AB012910, U91942, AB022653, L13309, L13316, L13312, A51597, L13317, AR048108, A07739, A07738, L13308, L13315, S79311, L13310, A33044, L13313, I26930, I69460, AR018924, A67260, A83197, A07560, AR051553, AR051554, I65403, L22157, A57359, I07074, A83232, AR015961, AR000007, AR051652, A27396, AF051099, AR038319, AR038305, A51868, AR038321, AR038307, I69484, AF103775, AR000006, AR015960, A67295, A67342, L01279, S74681, M74019, A70359, X75612, A67340, L03156, AF103774, L03152, A99060, U43770, A67290, AF198257, X72475, M87478, L13314, U43767, A94038, L03150, E01513, AF113889, E12918, S59162, X72477, X72427, U43765, X65287, L06158, U43764, X72441, X67322, D90158, Z68958, S67637, AF026933, E13178, L13311, AR035977, AR035978, X85997, M33060, K02135, L26891, L33034, U57579, M74020, L38434, Z27173, X00965, X72424, X59315, L33036, X59312, U86790, X72444, X72480, X80304, AF103771, AF050635, X85996, U43773, Y14865, X85995, X59318, Z37332, X72463, Z37336, X72446, AF103773, AF103772, M64858, Z37334, L26890, X72459, X72460, L03555, X64163, S73911, X93695, I19518, Z69026, X64133, X97481, Z37335, X72425, U57577, X72445, AF026918, U57574, Z68992, A44324, X51887, X00966, D88255, X72808, M64856, X94431, X72423, Z00013, K02096, D88254, Z68969, M64855, X72818, X79834, L03174, E12557, A68511, and X72819. |

Having generally described the invention, the same will be more readily understood by reference to the following examples, which are provided by way of illustration and are not intended as limiting.

EXAMPLES

Example 1

Isolation of a Selected cDNA Clone From the Deposited Sample

Each cDNA clone in a cited ATCC® deposit is contained in a plasmid vector. Table 1 identifies the vectors used to construct the cDNA library from which each clone was isolated. In many cases, the vector used to construct the library is a phage vector from which a plasmid has been excised. The table immediately below correlates the related plasmid for each phage vector used in constructing the cDNA library. For example, where a particular clone is identified in Table 1 as being isolated in the vector "Lambda Zap," the corresponding deposited clone is in "pBluescript."

| Vector Used to Construct Library Plasmid | Corresponding Deposited |
|---|---|
| Lambda Zap | pBluescript (pBS) |
| Uni-Zap XR | pBluescript (pBS) |
| Zap Express | pBK |
| lafmid BA | plafmid BA |
| pSport1 | pSport1 |
| pCMVSport2.0 | pCMVSport 2.0 |
| pCMVSport 3.0 | pCMVSport 3.0 |
| pCR ® 2.1 | pCR ® 2.1 |

Vectors Lambda Zap (U.S. Pat. Nos. 5,128,256 and 5,286,636), Uni-Zap XR (U.S. Pat. Nos. 5,128,256 and 5,286,636), Zap Express (U.S. Pat. Nos. 5,128,256 and 5,286,636), pBluescript (pBS) (Short, J. M. et al., Nucleic Acids Res. 16:7583–7600 (1988); Alting-Mees, M. A. and Short, J. M., Nucleic Acids Res. 17:9494 (1989)) and pBK (Alting-Mees, M. A. et al., Strategies 5:58–61 (1992)) are commercially available from Stratagene Cloning Systems, Inc., 11011 N. Torrey Pines Road, La Jolla, Calif., 92037. pBS contains an ampicillin resistance gene and pBK contains a neomycin resistance gene. Both can be transformed into *E. coli* strain XL-1 Blue, also available from Stratagene. pBS comes in 4 forms SK+, SK−, KS+ and KS. The S and K refers to the orientation of the polylinker to the T7 and T3 primer sequences which flank the polylinker region ("S" is for SacI and "K" is for KpnI which are the first sites on each respective end of the linker). "+" or "−" refer to the orientation of the f1 origin of replication ("ori"), such that in one orientation, single stranded rescue initiated from the f1 ori generates sense strand DNA and in the other, antisense.

Vectors pSport1, pCMVSport 2.0 and pCMVSport 3.0, were obtained from Life Technologies, Inc., P.O. Box 6009, Gaithersburg, Md. 20897. All Sport vectors contain an ampicillin resistance gene and may be transformed into *E. coli* strain DH10B, also available from Life Technologies. (See, for instance, Gruber, C. E., et al., Focus 15:59 (1993).) Vector lafmid BA (Bento Soares, Columbia University, NY) contains an ampicillin resistance gene and can be transformed into *E. coli* strain XL-1 Blue. Vector pCR®2.1, which is available from Invitrogen, 1600 Faraday Avenue, Carlsbad, Calif. 92008, contains an ampicillin resistance gene and may be transformed into *E. coli* strain DH10B, available from Life Technologies. (See, for instance, Clark, J. M., Nuc. Acids Res. 16:9677–9686 (1988) and Mead, D. et al., Bio/Technology 9: (1991).) Preferably, a polynucleotide of the present invention does not comprise the phage vector sequences identified for the particular clone in Table 1, as well as the corresponding plasmid vector sequences designated above.

The deposited material in the sample assigned the ATCC® Deposit Number cited in Table 1 for any given cDNA clone also may contain one or more additional plasmids, each comprising a cDNA clone different from that given clone. Thus, deposits sharing the same ATCC® Deposit Number contain at least a plasmid for each cDNA clone identified in Table 1. Typically, each ATCC® deposit sample cited in Table 1 comprises a mixture of approximately equal amounts (by weight) of about 50 plasmid DNAs, each containing a different cDNA clone; but such a deposit sample may include plasmids for more or less than 50 cDNA clones, up to about 500 cDNA clones.

Two approaches can be used to isolate a particular clone from the deposited sample of plasmid DNAs cited for that clone in Table 1. First, a plasmid is directly isolated by screening the clones using a polynucleotide probe corresponding to SEQ ID NO:X.

Particularly, a specific polynucleotide with 30–40 nucleotides is synthesized using an Applied Biosystems DNA synthesizer according to the sequence reported. The oligonucleotide is labeled, for instance, with $^{32}P$-γ-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:X (i.e., within the region of SEQ ID NO:X bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 ul of reaction mixture with 0.5 ug of the above cDNA template. A convenient reaction mixture is 1.5–5 mM $MgCl_2$, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to, filter probing, clone enrichment using specific probes, and protocols similar or identical to 5' and 3 ' "RACE" protocols which are well known in the art. For instance, a method similar to 5' RACE is available for generating the missing 5' end of a desired full-length transcript. (Fromont-Racine et al., Nucleic Acids Res. 21(7):1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2

Isolation of Genomic Clones Corresponding to a Polynucleotide

A human genomic P1 library (Genomic Systems, Inc.) is screened by PCR using primers selected for the cDNA sequence corresponding to SEQ ID NO:X., according to the method described in Example 1. (See also, Sambrook.)

Example 3

Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 1 is labeled with $P^{32}$ using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT1190-1. Following hybridization and washing, the blots are mounted and exposed to film at −70 degree C. overnight, and the films developed according to standard procedures.

Example 4

Chromosomal Mapping of the Polynucleotides

An oligonucleotide primer set is designed according to the sequence at the 5' end of SEQ ID NO:X. This primer preferably spans about 100 nucleotides. This primer set is then used in a polymerase chain reaction under the following set of conditions: 30 seconds,95 degree C.; 1 minute, 56 degree C.; 1 minute, 70 degree C. This cycle is repeated 32 times followed by one 5 minute cycle at 70 degree C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 5

Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance ($Amp^r$), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, which expresses the lacI repressor and also confers kanamycin resistance ($Kan^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 ($O.D.^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000× g). The cell pellet is solubilized in the chaotropic agent 6 Molar Guanidine HCl by stirring for 3–4 hours at 4 degree C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 MM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified protein is stored at 4 degree C. or frozen at −80 degree C.

In addition to the above expression vector, the present invention further includes an expression vector comprising phage operator and promoter elements operatively linked to a polynucleotide of the present invention, called pHE4a. (ATCC® Accession Number 209645, deposited on Feb. 25, 1998.) This vector contains: 1) a neomycinphosphotransferase gene as a selection marker, 2) an *E. coli* origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

Purification of a Polypeptide From an Inclusion Body

The following alternative method can be used to purify a polypeptide expressed in *E coli* when it is present in the form of inclusion bodies. Unless otherwise specified, all of the following steps are conducted at 4–10 degree C.

Upon completion of the production phase of the *E. coli* fermentation, the cell culture is cooled to 4–10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCl solubilized protein is refolded by quickly mixing the GuHCl extract with volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 ug of purified protein is loaded. The purified protein can also be tested for endotoxin/LPS contamination, and typically the LPS content is less than 0.1 ng/ml according to LAL assays.

Example 7

Cloning and Expression of a Polypeptide in a Baculovirus Expression System

In this example, the plasmid shuttle vector pA2 is used to insert a polynucleotide into a baculovirus to express a polypeptide. This expression vector contains the strong polyhedrin promoter of the *Autographa californica* nuclear polyhedrosis virus (AcMNPV) followed by convenient restriction sites such as BamHI, XbaI and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the cDNA sequence contained in the deposited clone, including the AUG initiation codon and the naturally associated leader sequence identified in Table 1, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transfected with 1.0 ug of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). One ug of BaculoGold™ virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC® CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of $^{35}$S-methionine and 5 uCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 8

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC® 37152), pSV2dhfr (ATCC® 37146), pBC12MI (ATCC® 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-dhfr (ATCC® Accession No. 37146), the expression vectors pC4 (ATCC Accession No. 209646) and pC6 (ATCC Accession No.209647) contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985).) Multiple cloning sites, e.g., with the restriction enzyme cleavage sites BamHI, XbaI and Asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide of the present invention is amplified according to the protocol outlined in Example 1. If the naturally occurring signal sequence is used to produce the secreted protein, the vector does not need a second signal peptide. Alternatively, if the naturally occurring signal sequence is not used, the vector can be modified to include a heterologous signal sequence. (See, e.g., WO 96/34891.)

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transfection. Five μg of the expression plasmid pC6 a pC4 is cotransfected with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100–200 uM. Expression of the desired gene product is analyzed, for instance, by SDS-PAGE and Western blot or by reversed phase HPLC analysis.

Example 9

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example 5; see also EP A 394,827; Traunecker, et al., Nature 331:84–86 (1988).) Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc region:

```
GGGATCCGGAGCCCAAATCTTCTGACAAAACTCACACATGCCCACCGTGC    (SEQ ID NO: 1)

CCAGCACCTGAATTCGAGGGTGCACCGTCAGTCTTCCTCTTCCCCCCAAAA

CCCAAGGACACCCTCATGATCTCCCGGACTCCTGAGGTCACATGCGTGGT

GGTGGACGTAAGCCACGAAGACCCTGAGGTCAAGTTCAACTGGTACGTGG

ACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT
```

-continued

```
GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAAC

CACAGGTGTACACCCTGCCCCCATCCCGGGATGAGCTGACCAGAACCAG

GTCAGCCTGACCTGCCTGGTCAAAGGCTTCTATCCAAGCGACATCGCCGT

GGAGTGGGAGAGCAATGGGCAGCCGGAGAACAACTACAAGACCACGCCT

CCCGTGCTGGACTCCGACGGCTCCTTCTTCCTCTACAGCAAGCTCACCGTG

GACAAGAGCAGGTGGCAGCAGGGGAACGTCTTCTCATGCTCCGTGATGCA

TGAGGCTCTGCACAACCACTACACGCAGAAGAGCCTCTCCCTGTCTCCGG

GTAAATGAGTGCGACGGCCGCGACTCTAGAGGAT
```

Example 10

Production of an Antibody From a Polypeptide

The antibodies of the present invention can be prepared by a variety of methods. (See, Current Protocols, Chapter 2.) As one example of such methods, cells expressing a polypeptide of the present invention is administered to an animal to induce the production of sera containing polyclonal antibodies. In a preferred method, a preparation of the secreted protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC®. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 11

Production of Secreted Protein For High-Throughput Screening Assays

The following protocol produces a supernatant containing a polypeptide to be tested. This supernatant can then be used in the Screening Assays described herein.

First, dilute Poly-D-Lysine (644 587 Boehringer-Mannheim) stock solution (1 mg/ml in PBS) 1:20 in PBS (w/o calcium or magnesium 17-516F Biowhittaker) for a working solution of 50 ug/ml. Add 200 ul of this solution to each well (24 well plates) and incubate at RT for 20 minutes.

Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2\times10^5$ cells/well in 0.5 ml DMEM (Dulbecco's Modified Eagle Medium)(with 4.5 G/L glucose and L-glutamine (12-604F Biowhittaker))/10% heat inactivated FBS(14-503F Biowhittaker)/1×Penstrep(17-602E Biowhittaker). Let the cells grow overnight.

The next day, mix together in a sterile solution basin: 300 ul Lipofectamine (18324-012 Gibco/BRL) and 5 ml Optimem I (31985070 Gibco/BRL)/96-well plate. With a small volume multi-channel pipetter, aliquot approximately 2 ug of an expression vector containing a polynucleotide insert, produced by the methods described in Examples 8 or 9, into an appropriately labeled 96-well round bottom plate. With a multi-channel pipetter, add 50 ul of the Lipofectamine/Optimem I mixture to each well. Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a 12-channel pipetter with tips on every other channel, adds the 200 ul of DNA/Lipofectamine/Optimem I complex to the odd wells first, then to the even wells, to each row on the 24-well plates. Incubate at 37 degrees C. for 6 hours.

While cells are incubating, prepare appropriate media, either 1% BSA in DMEM with 1×penstrep, or CHO-5 media (116.6 mg/L of CaCl2 (anhyd); 0.00130 mg/L $CuSO_4$-$5H_2O$; 0.050 mg/L of $Fe(NO_3)_3$-$9H_2O$; 0.417 mg/L of $FeSO_4$-$7H_2O$; 311.80 mg/L of Kcl; 28.64 mg/L of $MgCl_2$; 48.84 mg/L of $MgSO_4$; 6995.50 mg/L of NaCl; 2400.0 mg/L of $NaHCO_3$; 62.50 mg/L of $NaH_2PO_4$—$H_2O$; 71.02 mg/L of $Na_2HPO4$; 0.4320 mg/L of $ZnSO_4$-$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL-$H_2O$; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-$H_2O$; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-$2H_2O$; 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; and 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; and 10 mg/L of Methyl-B-Cyclodextrin complexed with Retinal) with 2 mm glutamine and 1×penstrep. (BSA (81-068-3 Bayer) 100 gm dissolved in 1 L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37 degrees C. for 45 or 72 hours depending on the media used: 1% BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 13–20.

It is specifically understood that when activity is obtained in any of the assays described below using a supernatant, the activity originates from either the polypeptide directly (e.g., as a secreted protein) or by the polypeptide inducing expression of other proteins, which are then secreted into the supernatant. Thus, the invention further provides a method of identifying the protein in the supernatant characterized by an activity in a particular assay.

Example 12

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Damell, Ann. Rev. Biochem. 64:621–51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proximal region encoding Trp-Ser-Xxx-Trp-Ser (SEQ ID NO:2)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

| | | JAKs | | | | |
|---|---|---|---|---|---|---|
| Ligand | tyk2 | Jak1 | Jak2 | Jak3 | STATS | GAS (elements) or ISRE |
| IFN family | | | | | | |
| IFN-a/B | + | + | − | − | 1,2,3 | ISRE |
| IFN-g | | + | + | − | 1 | GAS (IRF1>Lys6>IFP) |
| I1-10 | + | ? | ? | − | 1,3 | |
| gp130 family | | | | | | |
| IL-6 (Pleiotrophic) | + | + | + | ? | 1,3 | GAS (IRF1>Lys6>IFP) |
| I1-11 (Pleiotrophic) | ? | + | ? | ? | 1,3 | |
| OnM (Pleiotrophic) | ? | + | + | ? | 1,3 | |
| LIF (Pleitrophic) | ? | + | + | ? | 1,3 | |
| CNTF (Pleitrophic) | −/+ | + | + | ? | 1,3 | |
| G-CSF (Pleiotrophic) | ? | − | ? | ? | 1,3 | |
| IL-12 (Pleiotrophic) | + | − | + | + | 1,3 | |
| g-C family | | | | | | |
| IL-2 (lymphocytes) | − | + | − | + | 1,3,5 | GAS |
| IL-4 (lymph/myeloid) | − | + | − | + | 6 | GAS (IRF1 = IFP >>Lys6)(IgH) |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp140 family | | | | | | |
| IL-3 (myeloid) | − | − | + | − | 5 | GAS (IRF1>IFP>>Lys6) |
| IL-5 (myeloid) | − | − | + | − | 5 | GAS |
| GM-CSF (myeloid) | − | − | + | − | 5 | GAS |
| Growth hormone family | | | | | | |
| GH | ? | − | + | − | 5 | |
| PRL | ? | +/− | + | − | 1,3,5 | |
| EPO | ? | − | + | − | 5 | GAS(B-CAS>IRF1=IFP>>Lys6) |
| Receptor Tyrosine Kinases | | | | | | |
| EGF | ? | + | + | − | 1,3 | GAS (IRF1) |
| PDGF | ? | + | + | − | 1,3 | |
| CSF-1 | ? | + | + | − | 1,3 | GAS (not IRF1) |

To construct a synthetic GAS containing promoter element, which is used in the Biological Assays described in Examples 13–14, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used instead. The 5' primer also contains 18 bp of sequence complementary to the SV40 early promoter sequence and is flanked with an XhoI site. The sequence of the 5' primer is:

```
5':GCGCCTCGAGATTTCCCCGAAATCTAGATTTCCCCGAAATGATTTCCCC (SEQ ID NO: 3)

GAAATGATTTCCCCGAAATATCTGCCATCTCAATTAG:3'
```

The downstream primer is complementary to the SV40 promoter and is flanked with a Hind III site: 5':GCG-GCAAGCTTTTTGCAAAGCCTAGGC:3' (SEQ ID NO:4)

PCR amplification is performed using the SV40 promoter template present in the B-gal:promoter plasmid obtained from Clontech. The resulting PCR fragment is digested with XhoI/Hind III and subcloned into BLSK2-. (Stratagene.) Sequencing with forward and reverse primers confirms that the insert contains the following sequence:

5':CTCGAGATTTCCCCGAAATCTAGATTTCCCCGAAATGATTTCCCCGAAA (SEQ ID NO: 5)

TGATTTCCCCGAAATATCTGCCATCTCAATTAGTCAGCAACCATAGTCCCG

CCCCTAACTCCGCCCATCCCGCCCCTAACTCCGCCCAGTTCCGCCCATTCT

CCGCCCCATGGCTGACTAATTTTTTTTATTTATGCAGAGGCCGAGGCCGCC

TCGGCCTCTGAGCTATTCCAGAAGTAGTGAGGAGGCTTTTTTGGAGGCCT

AGGCTTTTC(SEQ ID NO: 1)                         GCAAAAAGCTT:3'

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using Hind III and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 13-14.

Other constructs can be made using the above description and replacing GAS with a different promoter sequence. For example, construction of reporter molecules containing NFK-B and EGR promoter sequences are described in Examples 15 and 16. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, I1-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 13

High-Throughput Screening Assay for T-cell Activity

The following protocol is used to assess T-cell activity by identifying factors, and determining whether supernate containing a polypeptide of the invention proliferates and/or differentiates T-cells. T-cell activity is assessed using the GAS/SEAP/Neo construct produced in Example 12. Thus, factors that increase SEAP activity indicate the ability to activate the Jaks-STATS signal transduction pathway. The T-cell used in this assay is Jurkat T-cells (ATCC® Accession No. TIB-152), although Molt-3 cells (ATCC® Accession No. CRL-1552) and Molt-4 cells (ATCC® Accession No. CRL-1582) cells can also be used.

Jurkat T-cells are lymphoblastic CD4+ Th1 helper cells. In order to generate stable cell lines, approximately 2 million Jurkat cells are transfected with the GAS-SEAP/neo vector using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1% Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15–45 mins.

During the incubation period, count cell concentration, spin down the required number of cells ($10^7$ per transfection), and resuspend in OPTI-MEM to a final concentration of $10^7$ cells/ml. Then add 1 ml of $1\times10^7$ cells in OPTI-MEM to T25 flask and incubate at 37 degrees C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing polypeptides of the invention and/or induced polypeptides of the invention as produced by the protocol described in Example 11.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20 degrees C. until SEAP assays are performed according to Example 17. The plates containing the remaining treated cells are placed at 4 degrees C. and serve as a source of material for repeating the assay on a specific well if desired.

As a positive control, 100 Unit/ml interferon gamma can be used which is known to activate Jurkat T cells. Over 30 fold induction is typically observed in the positive control wells.

The above protocol may be used in the generation of both transient, as well as, stable transfected cells, which would be apparent to those of skill in the art.

Example 14

High-Throughput Screening Assay Identifying Myeloid Activity

The following protocol is used to assess myeloid activity by determining whether polypeptides of the invention proliferates and/or differentiates myeloid cells. Myeloid cell activity is assessed using the GAS/SEAP/Neo construct produced in Example 12. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 12, a DEAE-Dextran method (Kharbanda et. al., 1994, Cell Growth & Differentiation, 5:259–265) is used. First, harvest $2\times10e^7$ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4.7H_2O$, 1 mM $MgCl_2$, and 675 uM $CaCl_2$. Incubate at 37 degrees C. for 45 min.

Wash the cells with RPMI 1640 medium containing 10% FBS and then resuspend in 10 ml complete medium and incubate at 37 degrees C. for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1\times10^8$ cells (this is enough for ten 96-well plates assay) and wash with PBS. Suspend the cells in 200 ml above described growth medium, with a final density of $5\times10^5$ cells/ml. Plate 200 ul cells per well in the 96-well plate (or $1\times10^{5}$ cells/well).

Add 50 ul of the supernatant prepared by the protocol described in Example 11. Incubate at 37 degrees C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 17.

Example 15

High-Throughput Screening Assay Identifying Neuronal Activity

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells can be assessed.

The EGR/SEAP reporter construct can be assembled by the following protocol. The EGR-1 promoter sequence (−633 to +1)(Sakamoto K et al., Oncogene 6:867–871 (1991)) can be PCR amplified from human genomic DNA using the following primers:

```
                                   (SEQ ID NO: 6)
5' GCGCTCGAGGGATGACAGCGATAGAACCCCGG-3'
                                   (SEQ ID NO: 7)
GCGAAGCTTCGCGACTCCCCGGATCCGCCTC-3'
```

Using the GAS:SEAP/Neo vector produced in Example 12, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat#08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. #12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 11. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5\times10^5$ cells/ml.

Add 200 ul of the cell suspension to each well of 96-well plate (equivalent to $1\times10^5$ cells/well). Add 50 ul supernatant produced by Example 11, 37° C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 17.

Example 16

High-Throughput Screening Assay for T-cell Activity

NF-KB (Nuclear Factor KB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-KB regulates the expression of genes involved in immune cell activation, control of apoptosis (NF-KB appears to shield cells from apoptosis), B and T-cell development, anti-viral and antimicrobial responses, and multiple stress responses.

In non-stimulated conditions, NF-KB is retained in the cytoplasm with I-KB (Inhibitor KB). However, upon stimulation, I-KB is phosphorylated and degraded, causing NF-KB to shuttle to the nucleus, thereby activating transcription of target genes. Target genes activated by NF-KB include IL-2, IL-6, GM-CSF, ICAM-1 and class 1 MHC.

Due to its central role and ability to respond to a range of stimuli, reporter constructs utilizing the NF-KB promoter element are used to screen the supernatants produced in Example 11. Activators or inhibitors of NF-KB would be useful in treating diseases. For example, inhibitors of NF-KB could be used to treat those diseases related to the acute or chronic activation of NF-KB, such as rheumatoid arthritis.

To construct a vector containing the NF-KB promoter element, a PCR based strategy is employed. The upstream primer contains four tandem copies of the NF-KB binding site (GGGGACTTTCCC) (SEQ ID NO:8), 18 bp of sequence complementary to the 5' end of the SV40 early promoter sequence, and is flanked with an XhoI site:

```
5':GCGGCCTCGAGGGGACTTTCCCGGG-                       (SEQ ID NO: 9)
GACTTTCCCGGGGACTTTCCGGGGACTTTCCGGGAC

TTTCCATCCTGCCATCTCAATTAG:3'
```

The downstream primer is complementary to the 3' end of the SV40 promoter and is flanked with a Hind III site: 5':GCGGCAAGCTTTTTGCAAAGCCTAGGC:3' (SEQ ID NO:4)

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence:

```
5':CTCGAGGGGACTTTCCCGGGGACTTTCCGGGGACTTTCCGGGACTTTCC (SEQ ID NO:10)

ATCTGCCATCTCAATTAGTCAGCAACCATAGTCCCGCCCCTAACTCCGCCC

ATCCCGCCCCTAACTCCGCCCAGTTCCGCCCATTCTCCGCCCCATGGCTGA

CTAATTTTTTTTATTTATGCAGAGGCCGAGGCCGCCTCGGCCTCTGAGCTA

TTCCAGAAGTAGTGAGGAGGCTTTTTTGGAGGCCTAGGCTTTTGCAAAAA

GCTT:3'
```

Next, replace the SV40 minimal promoter element present in the pSEAP2-promoter plasmid (Clontech) with this NF-KB/SV40 fragment using XhoI and HindIII. However, this vector does not contain a neomycin resistance gene, and therefore, is not preferred for mammalian expression systems.

In order to generate stable mammalian cell lines, the NF-KB/SV40/SEAP cassette is removed from the above NF-KB/SEAP vector using restriction enzymes SalI and NotI, and inserted into a vector containing neomycin resistance. Particularly, the NF-KB/SV40/SEAP cassette was inserted into pGFP-1 (Clontech), replacing the GFP gene, after restricting pGFP-1 with SalI and NotI.

Once NF-KB/SV40/SEAP/Neo vector is created, stable Jurkat T-cells are created and maintained according to the protocol described in Example 13. Similarly, the method for assaying supernatants with these stable Jurkat T-cells is also described in Example 13. As a positive control, exogenous TNF alpha (0.1, 1, 10 ng) is added to H9, H10, and H11, with a 5–10 fold activation typically observed.

Example 17

Assay for SEAP Activity

As a reporter molecule for the assays described in Examples 13–16, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5×Dilution Buffer and dispense 15 ul of 2.5×dilution buffer into Optiplates containing 35 ul of a supernatant. Seal the plates with a plastic sealer and incubate at 65 degree C. for 30 min. Separate the Optiplates to avoid uneven heating.

Cool the samples to room temperature for 15 minutes. Empty the dispenser and prime with the Assay Buffer. Add 50 ml Assay Buffer and incubate at room temperature 5 min. Empty the dispenser and prime with the Reaction Buffer (see the table below). Add 50 ul Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

Reaction Buffer Formulation:

| # of plates | Rxn buffer diluent (ml) | CSPD (ml) |
|---|---|---|
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 18

High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-4 (Molecular Probes, Inc.; catalog no. F-14202), used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-4 is made in 10% pluronic acid DMSO. To load the cells with fluo-4, 50 ul of 12 ug/ml fluo-4 is added to each well. The plate is incubated at 37 degrees C. in a $CO_2$ incubator for 60 min. The plate is washed four times in the Biotek washer with HBSS leaving 100 ul of buffer.

For non-adherent cells, the cells are spun down from culture media. Cells are re-suspended to $2–5\times10^6$ cells/ml with HBSS in a 50-ml conical tube. 4 ul of 1 mg/ml fluo-4 solution in 10% pluronic acid DMSO is added to each ml of cell suspension. The tube is then placed in a 37 degrees C. water bath for 30–60 min. The cells are washed twice with HBSS, resuspended to $1\times10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-4. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event which has resulted in an increase in the intracellular Ca++ concentration.

Example 19

High-Throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, the identification of novel human secreted proteins capable of activating tyrosine kinase signal transduction pathways are of interest. Therefore, the following protocol is designed to identify those novel human secreted proteins capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4 degree C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 11, the medium was removed and 100 ml of extraction buffer ((20 mM HEPES pH 7.5, 0.15 M NaCl, 1% Triton X-100, 0.1% SDS, 2 mM Na3VO4, 2 mM Na4P2O7 and a cocktail of protease inhibitors (#1836170) obtained from Boeheringer Mannheim (Indianapolis, Ind.) is added to each well and the plate is shaken on a rotating shaker for 5 minutes at 4 degrees C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4 degrees C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/$Mg_{2+}$ (5 mM ATP/50 mM $MgCl_2$), then 10 ul of 5×Assay Buffer (40 mM imidazole hydrochloride, pH7.3, 40 mM beta-glycerophosphate, 1 mM EGTA, 100 mM $MgCl_2$, 5 mM $MnCl_2$, 0.5 mg/ml BSA), then 5 ul of Sodium Vanadate(1 mM), and then 5 ul of water. Mix the components gently and preincubate the reaction mix at 30 degrees C. for 2 min. Initial the reaction by adding 10 ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37 degrees C. for 20 min. This allows the streptavadin coated 96 well plate to associate with the biotinylated peptide. Wash the MTP module with 300 ul/well of PBS four times. Next add 75 ul of anti-phospotyrosine antibody conjugated to horse radish peroxidase(anti-P-Tyr-POD(0.5 u/ml)) to each well and incubate at 37 degrees C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 20

High-Throughput Screening Assay Identifying Phosphorylation Activity

As a potential alternative and/or compliment to the assay of protein tyrosine kinase activity described in Example 19, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4 degrees C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 11 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation.

Example 21

Method of Determining Alterations in a Gene Corresponding to a Polynucleotide

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:X. Suggested PCR conditions consist of 35 cycles at 95 degrees C. for 30 seconds; 60–120 seconds at 52–58 degrees C.; and 60–120 seconds at 70 degrees C., using buffer solutions described in Sidransky et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton et al., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (Boehringer Manheim), and FISH performed as described in Johnson et al., Methods Cell Biol. 35:73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 22

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described in Example 10. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 23

Formulation

The invention also provides methods of treatment and/or prevention diseases, disorders, and/or conditions (such as, for example, any one or more of the diseases or disorders disclosed herein) by administration to a subject of an effective amount of a Therapeutic. By therapeutic is meant a polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547–556 (1983)), poly (2-hydroxyethyl methacrylate) (Langer et al., J. Biomed. Mater. Res. 15:167–277 (1981), and Langer, Chem. Tech. 12:98–105 (1982)), ethylene vinyl acetate (Langer et al., Id.) or poly-D-(−)-3-hydroxybutyric acid (EP 133,988).

Sustained-release Therapeutics also include liposomally entrapped Therapeutics of the invention (see generally, Langer, *Science* 249:1527–1533 (1990); Treat et al., in *Liposomes in the Therapy of Infectious Disease and Cancer*, Lopez-Berestein and Fidler (eds.), Liss, New York, pp. 317–327 and 353–365 (1989)). Liposomes containing the Therapeutic are prepared by methods known per se: DE 3,218,121; Epstein et al., Proc. Natl. Acad. Sci. (USA) 82:3688–3692 (1985); Hwang et al., Proc. Natl. Acad. Sci.(USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (*Science* 249:1527–1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Generally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The Therapeutic is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (ImmunoAg), MTP-PE (Biocine Corp.), QS21 (Genentech, Inc.), BCG, and MPL. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892),TR10 (International Publication No. WO 98/54202), 312C2 (International Publication No. WO 98/06842), and TR12, and soluble forms CD154, CD70, and CD153.

In certain embodiments, Therapeutics of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the Therapeutics of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVTR™ (zidovudine/lamivudine). Non-nucleoside reverse transcriptase inhibitors that may be administered in combination with the Therapeutics of the invention, include, but are not limited to, VIRAMUNE™ (nevirapine), RESCRIPTOR™ (delavirdine), and SUSTIVA™ (efavirenz). Protease inhibitors that may be administered in combination with the Therapeutics of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In other embodiments, Therapeutics of the invention may be administered in combination with anti-opportunistic infection agents. Anti-opportunistic agents that may be administered in combination with the Therapeutics of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, Therapeutics of the invention are used in any combination with TRIMETHOPRIM-SULFAMETHOXAZOLE™, DAPSONE™, PENTAMIDINE™, and/or ATOVAQUONE™ to prophylactically treat or prevent an opportunistic *Pneumocystis carinii* pneumonia infection. In another specific embodiment, Therapeutics of the invention are used in any combination with ISONIAZID™, RIFAMPIN™, PYRAZINAMIDE™, and/or ETHAMBUTOL™ to prophylactically treat or prevent an opportunistic *Mycobacterium avium* complex infection. In another specific embodiment, Therapeutics of the invention are used in any combination with RIFABUTIN™, CLARITHROMYCIN™, and/or AZITHROMYCN™ to prophylactically treat or prevent an opportunistic *Mycobacterium tuberculosis* infection. In another specific embodiment, Therapeutics of the invention are used in any combination with GANCICLOVIR™, FOSCARNET™, and/or CIDOFOVIR™ to prophylactically treat or prevent an opportunistic cytomegalovirus infection. In another specific embodiment, Therapeutics of the invention are used in any combination with FLUCONAZOLE™, ITRACONAZOLE™, and/or KETO- CONAZOLE™ to prophylactically treat or prevent an opportunistic fungal infection. In another specific embodiment, Therapeutics of the invention are used in any combination with ACYCLOVIR™ and/or FAMCICOLVIR™ to prophylactically treat or prevent an opportunistic herpes simplex virus type I and/or type II infection. In another specific embodiment, Therapeutics of the invention are used in any combination with PYRIMETHAMINE™ and/or LEUCOVORIN™ to prophylactically treat or prevent an opportunistic *Toxoplasma gondii* infection. In another specific embodiment, Therapeutics of the invention are used in any combination with LEUCOVORIN™ and/or NEUPOGEN™ to prophylactically treat or prevent an opportunistic bacterial infection.

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Therapeutics of the invention are administered in combination with immunosuppressants. Immunosuppressants preparations that may be administered with the Therapeutics of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In an additional embodiment, Therapeutics of the invention are administered alone or in combination with one or more intravenous immune globulin preparations. Intravenous immune globulin preparations that may be administered with the Therapeutics of the invention include, but not limited to, GAMMAR™, IVEEGAM™, SANDOGLOBULIN™, GAMMAGARD S/D™, and GAMIMUNE™. In a specific embodiment, Therapeutics of the invention are administered in combination with intravenous immune globulin preparations in transplantation therapy (e.g., bone marrow transplant).

In an additional embodiment, the Therapeutics of the invention are administered alone or in combination with an anti-inflammatory agent. Anti-inflammatory agents that may be administered with the Therapeutics of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the Therapeutics of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, Therapeutics of the invention are administered in combination with CHOP (cyclophosphamide, doxorubicin, vincristine, and prednisone) or any combination of the components of CHOP. In another embodiment, Therapeutics of the invention are administered in combination with Rituximab. In a further embodiment, Therapeutics of the invention are administered with Rituxmab and CHOP, or Rituxmab and any combination of the components of CHOP.

In an additional embodiment, the Therapeutics of the invention are administered in combination with cytokines. Cytokines that may be administered with the Therapeutics of the invention include, but are not limited to, IL2, IL3, IL4, IL5, IL6, IL7, IL10, IL12, IL13, IL15, anti-CD40, CD40L, IFN-gamma and TNF-alpha. In another embodiment, Therapeutics of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Growth Factors, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the Therapeutics of the invention are administered in combination with hematopoietic growth factors. Hematopoietic growth factors that may be administered with the Therapeutics of the invention include, but are not limited to, LEUKINE™ (SARGRAMOSTIM™) and NEUPOGEN™ (FILGRASTIM™).

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the Therapeutics of the invention are administered in combination with other therapeutic or prophylactic regimens, such as, for example, radiation therapy.

Example 24

Method of Treating Decreased Levels of the Polypeptide

The present invention relates to a method for treating an individual in need of an increased level of a polypeptide of the invention in the body comprising administering to such an individual a composition comprising a therapeutically effective amount of an agonist of the invention (including polypeptides of the invention). Moreover, it will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a Therapeutic comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided in Example 23.

Example 25

Method of Treating Increased Levels of the Polypeptide

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of a polypeptide of the present invention. This technology is one example of a method of decreasing levels of a polypeptide, preferably a secreted form, due to a variety of etiologies, such as cancer. For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 23.

Example 26

Method of Treatment Using Gene Therapy-Ex Vivo

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1 using primers and having appropriate restriction sites and initiation/stop codons, if necessary. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 27

Gene Therapy Using Endogenous Genes Corresponding to Polynucleotides of the Invention Another method of gene therapy according to the present invention involves operably associating the endogenous polynucleotide sequence of the invention with a promoter via homologous recombination as described, for example, in U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., *Proc. Natl. Acad. Sci. USA,* 86:8932–8935 (1989); and Zijlstra et al., *Nature,* 342:435–438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous polynucleotide sequence, flanking the promoter. The targeting sequence will be sufficiently near the 5' end of the polynucleotide sequence so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous polynucleotide sequence. This results in the expression of polynucleotide corresponding to the polynucleotide in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3\times10^6$ cells/ml. Electroporation should be performed immediately following resuspension.

Plasmid DNA is prepared according to standard techniques. For example, to construct a plasmid for targeting to the locus corresponding to the polynucleotide of the invention, plasmid pUC18 (MBI Fermentas, Amherst, N.Y.) is digested with HindIII. The CMV promoter is amplified by PCR with an XbaI site on the 5' end and a BamHI site on the 3'end. Two non-coding sequences are amplified via PCR: one non-coding sequence (fragment 1) is amplified with a HindIII site at the 5'end and an Xba site at the 3'end; the other non-coding sequence (fragment 2) is amplified with a BamHI site at the 5'end and a HindIII site at the 3'end. The CMV promoter and the fragments (1 and 2) are digested with the appropriate enzymes (CMV promoter-XbaI and BamHI; fragment 1—XbaI; fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 $\mu$g/ml. 0.5 ml of the cell suspension (containing approximately $1.5.\times10^6$ cells) is then added to the cuvette, and the cell suspension and DNA solutions are gently mixed. Electroporation is performed with a Gene-Pulser apparatus (Bio-Rad). Capacitance and voltage are set at 960 $\mu$F and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 28

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. The polynucleotide of the present invention may be operatively linked to a promoter or any other genetic elements necessary for the expression of the polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata et al., Cardiovasc.

Res. 35(3):470–479 (1997); Chao et al., Pharmacol. Res. 35(6):517–522 (1997); Wolff, Neuromuscul. Disord. 7(5): 314–318 (1997); Schwartz et al., Gene Ther. 3(5):405–411 (1996); Tsurumi et al., Circulation 94(12):3281–3290 (1996) (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. NY Acad. Sci. 772:126–139 and Abdallah B. et al. (1995) Biol. Cell 85(1):I-7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 29

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 30

Knock-Out Animals

Endogenous gene expression can also be reduced by inactivating or "knocking out" the gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 31

Production of an Antibody a) Hybridoma Technology

The antibodies of the present invention can be prepared by a variety of methods. (See, Current Protocols, Chapter 2.) As one example of such methods, cells expressing polypeptide(s) of the invention are administered to an animal to induce the production of sera containing polyclonal antibodies. In a preferred method, a preparation of polypeptide(s) of the invention is prepared and purified to render it substantially free of natural contaminants. Such a preparation is then introduced into an animal in order to produce polyclonal antisera of greater specific activity.

Monoclonal antibodies specific for polypeptide(s) of the invention are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563–681 (1981)). In general, an animal (preferably a mouse) is immunized with polypeptide(s) of the invention, or, more preferably, with a secreted polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 $\mu$g/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC®. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the polypeptide(s) of the invention.

Alternatively, additional antibodies capable of binding polypeptide(s) of the invention can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the polypeptide(s) of the invention protein-specific antibody can be blocked by polypeptide(s) of the invention. Such antibodies comprise anti-idiotypic antibodies to the polypeptide(s) of the invention protein-specific antibody and are used to immunize an animal to induce formation of further polypeptide(s) of the invention protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

b) Isolation of Antibody Fragments Directed Polypeptide(s) of the Invention from a Library of scFvs Naturally occurring V-genes isolated from human PBLs are constructed into a library of antibody fragments which contain reactivities against polypeptide(s) of the invention to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 *E. coli* harboring the phagemid are used to inoculate 50 ml of 2×TY containing 1% glucose and 100 $\mu$g/ml of ampicillin (2×TY-AMP-GLU) and grown to an O.D. of 0.8 with shaking. Five ml of this culture is used to innoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 $\mu$g/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 μg ampicillin/ml and 25 μg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 μm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 μg/ml or 10 μg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0 M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 μg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect *E. coli* HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Example 32

Assays Detecting Stimulation or Inhibition of B cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro Assay—Purified polypeptides of the invention, or truncated forms thereof, is assessed for its ability to induce activation, proliferation, differentiation or inhibition and/or death in B-cell populations and their precursors. The activity of the polypeptides of the invention on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed *Staphylococcus aureus* Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220).

Various dilutions of each sample are placed into individual wells of a 96-well plate to which are added $10^5$ B-cells suspended in culture medium (RPMI 1640 containing 10% FBS, $5\times10^{-5}$M 2ME, 100 U/ml penicillin, 10 ug/ml streptomycin, and $10^{-5}$ dilution of SAC) in a total volume of 150 ul. Proliferation or inhibition is quantitated by a 20 h pulse (1 uCi/well) with 3H-thymidine (6.7 Ci/mM) beginning 72 h post factor addition. The positive and negative controls are IL2 and medium respectively.

In Vivo Assay—BALB/c mice are injected (i.p.) twice per day with buffer only, or 2 mg/Kg of a polypeptide of the invention, or truncated forms thereof. Mice receive this treatment for 4 consecutive days, at which time they are sacrificed and various tissues and serum collected for analyses. Comparison of H&E sections from normal spleens and spleens treated with polypeptides of the invention identify the results of the activity of the polypeptides on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from mice treated with polypeptide is used to indicate whether the polypeptide specifically increases the proportion of ThB+, CD45R (B220)dull B cells over that which is observed in control mice.

Likewise, a predicted consequence of increased mature B-cell representation in vivo is a relative increase in serum Ig titers. Accordingly, serum IgM and IgA levels are compared between buffer and polypeptide-treated mice.

The studies described in this example tested activity of a polypeptide of the invention. However, one skilled in the art could easily modify the exemplified studies to test the activity of polynucleotides of the invention (e.g., gene therapy), agonists, and/or antagonists of polynucleotides or polypeptides of the invention.

Example 33

T Cell Proliferation Assay

Proliferation Assay for Resting PBLs

A CD3-induced proliferation assay is performed on PBMCs and is measured by the uptake of $^{3}$H-thymidine. The assay is performed as follows. Ninety-six well plates are coated with 100 microliters per well of mAb to CD3 (HIT3a, Pharmingen) or isotype-matched control mAb (B33.1) overnight at 4 C (1 microgram/ml in 0.05M bicarbonate buffer, pH 9.5), then washed three times with PBS. PBMC are isolated by F/H gradient centrifugation from human peripheral blood and added to quadruplicate wells ($5\times10^{4}$/well) of mAb coated plates in RPMI containing 10% FCS and P/S in the presence of varying concentrations of TNF Delta and/or TNF Epsilon protein (total volume 200 microliters). Relevant protein buffer and medium alone are controls. After 48 hr. culture at 37 C, plates are spun for 2 min. at 1000 rpm and 100 microliters of supernatant is removed and stored −20 C for measurement of IL-2 (or other cytokines) if effect on proliferation is observed. Wells are supplemented with 100 microliters of medium containing 0.5 microcuries of $^{3}$H-thymidine and cultured at 37 C for 18–24 hr. Wells are harvested and incorporation of $^{3}$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of TNF Delta and/or TNF Epsilon proteins.

Alternatively, a proliferation assay on resting PBL (peripheral blood lymphocytes) is measured by the up-take of $^{3}$H-thymidine. The assay is performed as follows. PBMC are isolated by Ficoll (LSM, ICN Biotechnologies, Aurora, Ohio) gradient centrifugation from human peripheral blood, and are cultured overnight in 10% (Fetal Calf Serum, Biofluids, Rockville, Md.)/RPMI (Gibco BRL, Gaithersburg, Md.). This overnight incubation period allows the adherent cells to attach to the plastic, which results in a lower background in the assay as there are fewer cells that can act as antigen presenting cells or that might be producing growth factors. The following day the non-adherent cells are collected, washed and used in the proliferation assay. The assay is performed in a 96 well plate using $2\times10^{4}$ cells/well in a final volume of 200 microliters. The supernatants (e.g., CHO or 293T supernatants) expressing the protein of interest are tested at a 30% final dilution, therefore 60 ul are added to 140 ul of 10% FCS/RPMI containing the cells. Control supernatants are used at the same final dilution and express the following proteins: vector (negative control), IL-2 (*), IFNγ, TNFα, IL-10 and TR2. In addition to the control supernatants, recombinant human IL-2 (R & D Systems, Minneapolois, Minn.) at a final concentration of 100 ng/ml is also used. After 24 hours of culture, each well is pulsed with 1 uCi of $^{3}$H-thymidine (Nen, Boston, Mass.). Cells are then harvested 20 hours following pulsing and incorporation of $^{3}$H-thymidine is used as a measure of proliferation. Results are expressed as an average of triplicate samples plus or minus standard error.

(*) The amount of the control cytokines IL-2, IFNγ, TNFα and IL-10 produced in each transfection varies between 300 pg to 5 ng/ml.

Costimulation Assay

A costimulation assay on resting PBL (peripheral blood lymphocytes) is performed in the presence of immobilized antibodies to CD3 and CD28. The use of antibodies specific for the invariant regions of CD3 mimic the induction of T cell activation that would occur through stimulation of the T cell receptor by an antigen. Cross-linking of the TCR (first signal) in the absence of a costimulatory signal (second signal) causes very low induction of proliferation and will eventually result in a state of "anergy", which is characterized by the absence of growth and inability to produce cytokines. The addition of a costimulatory signal such as an antibody to CD28, which mimics the action of the costimulatory molecule. B7-1 expressed on activated APCs, results in enhancement of T cell responses including cell survival and production of IL-2. Therefore this type of assay allows to detect both positive and negative effects caused by addition of supernatants expressing the proteins of interest on T cell proliferation.

The assay is performed as follows. Ninety-six well plates are coated with 100 ng/ml anti-CD3 and 5 ug/ml anti-CD28 (Pharmingen, San Diego, Calif.) in a final volume of 100 ul and incubated overnight at 4 C. Plates are washed twice with PBS before use. PBMC are isolated by Ficoll (LSM, ICN Biotechnologies, Aurora, Ohio) gradient centrifugation from human peripheral blood, and are cultured overnight in 10% FCS(Fetal Calf Serum, Biofluids, Rockville, Md.)/RPMI (Gibco BRL, Gaithersburg, Md.). This overnight incubation period allows the adherent cells to attach to the plastic, which results in a lower background in the assay as there are fewer cells that can act as antigen presenting cells or that might be producing growth factors. The following day the non adherent cells are collected, washed and used in the proliferation assay. The assay is performed in a 96 well plate using $2\times10^{4}$ cells/well in a final volume of 200 ul. The supernatants (e.g., CHO or 293T supernatants) expressing the protein of interest are tested at a 30% final dilution, therefore 60 ul are added to 140 ul of 10% FCS/RPMI containing the cells. Control supernatants are used at the same final dilution and express the following proteins: vector only (negative control), IL-2, IFNγ, TNFα, IL-10 and TR2. In addition to the control supernatants recombinant human IL-2 (R & D Systems, Minneapolis, Minn.) at a final concentration of 10 ng/ml is also used. After 24 hours of culture, each well is pulsed with 1 uCi of $^{3}$H-thymidine (Nen, Boston, Mass.). Cells are then harvested 20 hours following pulsing and incorporation of $^{3}$H-thymidine is used as a measure of proliferation. Results are expressed as an average of triplicate samples plus or minus standard error.

Costimulation Assay: IFNγ and IL-2 ELISA

The assay is performed as follows. Twenty-four well plates are coated with either 300 ng/ml or 600 ng/ml anti-CD3 and 5 ug/ml anti-CD28 (Pharmingen, San Diego, Calif.) in a final volume of 500 ul and incubated overnight at 4 C. Plates are washed twice with PBS before use. PBMC are isolated by Ficoll (LSM, ICN Biotechnologies, Aurora, Ohio) gradient centrifugation from human peripheral blood, and are cultured overnight in 10% FCS(Fetal Calf Serum, Biofluids, Rockville, Md.)/RPMI (Gibco BRL, Gaithersburg, Md.). This overnight incubation period allows the adherent cells to attach to the plastic, which results in a lower background in the assay as there are fewer cells that can act as antigen presenting cells or that might be producing growth factors. The following day the non adherent cells are collected, washed and used in the costimulation assay. The assay is performed in the pre-coated twenty-four well plate using $1\times10^{5}$ cells/well in a final volume of 900 ul. The supernatants (293T supernatants) expressing the protein of interest are tested at a 30% final dilution, therefore 300 ul are added to 600 ul of 10% FCS/RPMI containing the cells. Control supernatants are used at the same final dilution and express the following proteins: vector only(negative control), IL-2, IFNγ, IL-12 and IL-18. In addition to the control supernatants recombinant human IL-2 (all cytokines were purchased from R & D Systems, Minneapolis, Minn.) at a final concentration of 10 ng/ml, IL-12 at a final concentration of 1 ng/ml and IL-18 at a final concentration of 50 ng/ml are also used. Controls and unknown samples are tested in duplicate. Supernatant samples (250 ul) are collected 2 days and 5 days after the beginning of the assay. ELISAs to test for IFNγ and IL-2 secretion are performed using kits purchased from R & D Systems, (Minneapolis, Minn.). Results are expressed as an average of duplicate samples plus or minus standard error.

Proliferation Assay for Preactivated-Resting T Cells

A proliferation assay on preactivated-resting T cells is performed on cells that are previously activated with the lectin phytohemagglutinin (PHA). Lectins are polymeric plant proteins that can bind to residues on T cell surface glycoproteins including the TCR and act as polyclonal activators. PBLs treated with PHA and then cultured in the presence of low doses of IL-2 resemble effector T cells. These cells are generally more sensitive to further activation induced by growth factors such as IL-2. This is due to the expression of high affinity IL-2 receptors that allows this population to respond to amounts of IL-2 that are 100 fold lower than what would have an effect on a naïve T cell. Therefore the use of this type of cells might enable to detect the effect of very low doses of an unknown growth factor, that would not be sufficient to induce proliferation on resting (naïve) T cells.

The assay is performed as follows. PBMC are isolated by F/H gradient centrifugation from human peripheral blood, and are cultured in 10% FCS(Fetal Calf Serum, Biofluids, Rockville, Md.)/RPMI (Gibco BRL, Gaithersburg, Md.) in the presence of 2 ug/ml PHA (Sigma, Saint Louis, Mo.) for three days. The cells are then washed in PBS and cultured in 10% FCS/RPMI in the presence of 5 ng/ml of human recombinant IL-2 (R & D Systems, Minneapolis, Minn.) for 3 days. The cells are washed and rested in starvation medium (1% FCS/RPMI) for 16 hours prior to the beginning of the proliferation assay. An aliquot of the cells is analyzed by FACS to determine the percentage of T cells (CD3 positive cells) present; this usually ranges between 93–97% depending on the donor. The assay is performed in a 96 well plate using $2\times10^4$ cells/well in a final volume of 200 ul. The supernatants (e.g., CHO or 293T supernatants) expressing the protein of interest are tested at a 30% final dilution, therefore 60 ul are added to 140 ul of in 10% FCS/RPMI containing the cells. Control supernatants are used at the same final dilution and express the following proteins: vector (negative control), IL-2, IFNγ, TNFα, IL-10 and TR2. In addition to the control supernatants recombinant human IL-2 at a final concentration of 10 ng/ml is also used. After 24 hours of culture, each well is pulsed with 1 uCi of $^3$H-thymidine(Nen, Boston, Mass.). Cells are then harvested 20 hours following pulsing and incorporation of $^3$H-thymidine is used as a measure of proliferation. Results are expressed as an average of triplicate samples plus or minus standard error.

The studies described in this example test activity of polypeptides of the invention. However, one skilled in the art could easily modify the exemplified studies to test the activity of polynucleotides of the invention (e.g., gene therapy), agonists, and/or antagonists of polynucleotides or polypeptides of the invention.

Example 34

Effect of Polypeptides of the Invention on the Expression of MHC Class II Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-α, causes a rapid change in surface phenotype (increased expression of MHC class I and II, costimulatory and adhesion molecules, downregulation of FCγRII, upregulation of CD83). These changes correlate with increased antigen-presenting capacity and with functional maturation of the dendritic cells.

FACS analysis of surface antigens is performed as follows. Cells are treated 1–3 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Effect on the Production of Cytokines

Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells ($10^6$/ml) are treated with increasing concentrations of polypeptides of the invention for 24 hours. LPS (100 ng/ml) is added to the cell culture as positive control. Supernatants from the cell cultures are then collected and analyzed for IL-12 content using commercial ELISA kit (e.g, R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Monocyte Activation and/or Increased Survival.

Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. Polypeptides, agonists, or antagonists of the invention can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

Monocyte Survival Assay

Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of $2\times10^6$/ml in PBS containing PI at a final concentration of 5 $\mu$g/ml, and then incubaed at room temperature for 5 minutes before FACScan analysis. PI uptake has been demonstrated to correlate with DNA fragmentation in this experimental paradigm.

Effect on Cytokine Release

An important function of monocytes/macrophages is their regulatory activity on other cellular populations of the immune system through the release of cytokines after stimulation. An ELISA to measure cytokine release is performed as follows. Human monocytes are incubated at a density of $5\times10^5$ cells/ml with increasing concentrations of the a polypeptide of the invention and under the same conditions, but in the absence of the polypeptide. For IL-12 production, the cells are primed overnight with IFN (100 U/ml) in presence of a polypeptide of the invention. LPS (10 ng/ml) is then added. Conditioned media are collected after 24 h and kept frozen until use. Measurement of TNF-alpha, IL-10, MCP-1 and IL-8 is then performed using a commercially available ELISA kit (e.g, R & D Systems (Minneapolis, Minn.)) and applying the standard protocols provided with the kit.

Oxidative Burst

Purified monocytes are plated in 96-w plate at $2–1\times10^5$ cell/well. Increasing concentrations of polypeptides of the invention are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37° C. for 2 hours and the reaction is stopped by adding 20 $\mu$l 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example tested activity of a polypeptide of the invention. However, one skilled in the art could easily modify the exemplified studies to test the activity of polypeptides, polynucleotides (e.g., gene therapy), agonists, and/or antagonists of the invention.

Example 35

Biological Effects of Polypeptides of the Invention

Astrocyte and Neuronal Assays

Recombinant polypeptides of the invention, expressed in *Escherichia coli* and purified as described above, can be tested for activity in promoting the survival, neurite outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment. A thymidine incorporation assay, for example, can be used to elucidate a polypeptide of the invention's activity on these cells.

Moreover, previous reports describing the biological effects of FGF-2 (basic FGF) on cortical or hippocampal neurons in vitro have demonstrated increases in both neuron survival and neurite outgrowth (Walicke et al., "Fibroblast growth factor promotes survival of dissociated hippocampal neurons and enhances neurite extension." *Proc. Natl. Acad. Sci. USA* 83:3012–3016. (1986), assay herein incorporated by reference in its entirety). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of a polypeptide of the invention to induce neurite outgrowth can be compared to the response achieved with FGF-2 using, for example, a thymidine incorporation assay.

Fibroblast and Endothelial Cell Assays

Human lung fibroblasts are obtained from Clonetics (San Diego, Calif.) and maintained in growth media from Clonetics. Dermal microvascular endothelial cells are obtained from Cell Applications (San Diego, Calif.). For proliferation assays, the human lung fibroblasts and dermal microvascular endothelial cells can be cultured at 5,000 cells/well in a 96-well plate for one day in growth medium. The cells are then incubated for one day in 0.1% BSA basal medium. After replacing the medium with fresh 0.1% BSA medium, the cells are incubated with the test proteins for 3 days. Alamar Blue (Alamar Biosciences, Sacramento, Calif.) is added to each well to a final concentration of 10%. The cells are incubated for 4 hr. Cell viability is measured by reading in a CytoFluor fluorescence reader. For the $PGE_2$ assays, the human lung fibroblasts are cultured at 5,000 cells/well in a 96-well plate for one day. After a medium change to 0.1% BSA basal medium, the cells are incubated with FGF-2 or polypeptides of the invention with or without IL-1α for 24 hours. The supernatants are collected and assayed for $PGE_2$ by EIA kit (Cayman, Ann Arbor, Mich.). For the IL-6 assays, the human lung fibroblasts are cultured at 5,000 cells/well in a 96-well plate for one day. After a medium change to 0.1% BSA basal medium, the cells are incubated with FGF-2 or with or without polypeptides of the invention IL-1α for 24 hours. The supernatants are collected and assayed for IL-6 by ELISA kit (Endogen, Cambridge, Mass.).

Human lung fibroblasts are cultured with FGF-2 or polypeptides of the invention for 3 days in basal medium before the addition of Alamar Blue to assess effects on growth of the fibroblasts. FGF-2 should show a stimulation at 10–2500 ng/ml which can be used to compare stimulation with polypeptides of the invention.

Parkinson Models

The loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4 phenyl 1,2,3,6-tetrahydropyridine (MPTP). In the CNS, MPTP is taken-up by astrocytes and catabolized by monoamine oxidase B to 1-methyl-4-phenyl pyridine ($MPP^+$) and released. Subsequently, $MPP^+$ is actively accumulated in dopaminergic neurons by the high-affinity reuptake transporter for dopamine. $MPP^+$ is then concentrated in mitochondria by the electrochemical gradient and selectively inhibits nicotidamide adenine disphosphate:ubiquinone oxidoreductionase (complex I), thereby interfering with electron transport and eventually generating oxygen radicals.

It has been demonstrated in tissue culture paradigms that FGF-2 (basic FGF) has trophic activity towards nigral dopaminergic neurons (Ferrari et al., Dev. Biol. 1989). Recently, Dr. Unsicker's group has demonstrated that administering FGF-2 in gel foam implants in the striatum results in the near complete protection of nigral dopaminergic neurons from the toxicity associated with MPTP exposure (Otto and Unsicker, J. Neuroscience, 1990).

Based on the data with FGF-2, polypeptides of the invention can be evaluated to determine whether it has an action similar to that of FGF-2 in enhancing dopaminergic neuronal survival in vitro and it can also be tested in vivo for protection of dopaminergic neurons in the striatum from the damage associated with MPTP treatment. The potential effect of a polypeptide of the invention is first examined in vitro in a dopaminergic neuronal cell culture paradigm. The cultures are prepared by dissecting the midbrain floor plate from gestation day 14 Wistar rat embryos. The tissue is dissociated with trypsin and seeded at a density of 200,000 cells/$cm^2$ on polyorthinine-laminin coated glass coverslips. The cells are maintained in Dulbecco's Modified Eagle's medium and F12 medium containing hormonal supplements (N1). The cultures are fixed with paraformaldehyde after 8 days in vitro and are processed for tyrosine hydroxylase, a specific marker for dopminergic neurons, immunohistochemical staining. Dissociated cell cultures are prepared from embryonic rats. The culture medium is changed every third day and the factors are also added at that time.

Since the dopaminergic neurons are isolated from animals at gestation day 14, a developmental time which is past the stage when the dopaminergic precursor cells are proliferating, an increase in the number of tyrosine hydroxylase immunopositive neurons would represent an increase in the number of dopaminergic neurons surviving in vitro. Therefore, if a polypeptide of the invention acts to prolong the survival of dopaminergic neurons, it would suggest that the polypeptide may be involved in Parkinson's Disease.

The studies described in this example tested activity of a polypeptide of the invention. However, one skilled in the art could easily modify the exemplified studies to test the activity of polynucleotides (e.g., gene therapy), agonists, and/or antagonists of the invention.

Example 36

The Effect of Polypeptides of the Invention on the Growth of Vascular Endothelial Cells On day 1, human umbilical vein endothelial cells (HUVEC) are seeded at 2–5x$10^4$ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. A polypeptide having the amino acid sequence of SEQ ID NO:Y, and positive controls, such as VEGF and basic FGF (bFGF) are added, at varying concentrations. On days 4 and 6, the medium is replaced. On day 8, cell number is determined with a Coulter Counter.

An increase in the number of HUVEC cells indicates that the polypeptide of the invention may proliferate vascular endothelial cells.

The studies described in this example tested activity of a polypeptide of the invention. However, one skilled in the art could easily modify the exemplified studies to test the activity of polynucleotides (e.g., gene therapy), agonists, and/or antagonists of the invention.

Example 37

Stimulatory Effect of Polypeptides of the Invention on the Proliferation of Vascular Endothelial Cells For evaluation of mitogenic activity of growth factors, the calorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, Promega). Cells are seeded in a 96-well plate (5,000 cells/well) in 0.1 mL serum-supplemented medium and are allowed to attach overnight. After serum-starvation for 12 hours in 0.5% FBS, conditions (bFGF, $VEGF_{165}$ or a polypeptide of the invention in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. *In Vitro Cell. Dev. Biol* 30A:512–518 (1994).

The studies described in this example tested activity of a polypeptide of the invention. However, one skilled in the art could easily modify the exemplified studies to test the activity of polynucleotides (e.g., gene therapy), agonists, and/or antagonists of the invention.

Example 38

Inhibition of PDGF-Induced Vascular Smooth Muscle Cell Proliferation Stimulatory Effect HAoSMC proliferation can be measured, for example, by BrdUrd incorporation. Briefly, subconfluent, quiescent cells grown on the 4-chamber slides are transfected with CRP or FITC-labeled AT2-3LP. Then, the cells are pulsed with 10% calf serum and 6 mg/ml BrdUrd. After 24 h, immunocytochemistry is performed by using BrdUrd Staining Kit (Zymned Laboratories). In brief, the cells are incubated with the biotinylated mouse anti-BrdUrd antibody at 4 degrees C. for 2 h after being exposed to denaturing solution and then incubated with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., J. Biol. Chem. 6:271(36) :21985–21992 (1996).

The studies described in this example tested activity of a polypeptide of the invention. However, one skilled in the art could easily modify the exemplified studies to test the activity of polynucleotides (e.g., gene therapy), agonists, and/or antagonists of the invention.

Example 39

Stimulation of Endothelial Migration

This example will be used to explore the possibility that a polypeptide of the invention may stimulate lymphatic endothelial cell migration.

Endothelial cell migration assays are performed using a 48 well microchemotaxis chamber (Neuroprobe Inc., Cabin John, Md.; Falk, W., et al., J. Immunological Methods 1980;33:239–247). Polyvinylpyrrolidone-free polycarbonate filters with a pore size of 8 um (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2–6) HUVEC or BMEC cultures are washed and trypsinized for the minimum time required to achieve cell detachment. After placing the filter between lower and upper chamber, $2.5\times10^5$ cells suspended in 50 ul M199 containing 1% FBS are seeded in the upper compartment. The apparatus is then incubated for 5 hours at 37° C. in a humidified chamber with 5% CO2 to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

The studies described in this example tested activity of a polypeptide of the invention. However, one skilled in the art could easily modify the exemplified studies to test the activity of polynucleotides (e.g., gene therapy), agonists, and/or antagonists of the invention.

Example 40

Stimulation of Nitric Oxide Production by Endothelial Cells

Nitric oxide released by the vascular endothelium is believed to be a mediator of vascular endothelium relaxation. Thus, activity of a polypeptide of the invention can be assayed by determining nitric oxide production by endothelial cells in response to the polypeptide.

Nitric oxide is measured in 96-well plates of confluent microvascular endothelial cells after 24 hours starvation and a subsequent 4 hr exposure to various levels of a positive control (such as VEGF-1) and the polypeptide of the invention. Nitric oxide in the medium is determined by use of the Griess reagent to measure total nitrite after reduction of nitric oxide-derived nitrate by nitrate reductase. The effect of the polypeptide of the invention on nitric oxide release is examined on HUVEC.

Briefly, NO release from cultured HUVEC monolayer is measured with a NO-specific polarographic electrode connected to a NO meter (Iso-NO, World Precision Instruments Inc.) (1049). Calibration of the NO elements is performed according to the following equation:

$$2KNO_2+2KI+2H_2SO_462NO+I_2+2H_2O+2K_2SO_4$$

The standard calibration curve is obtained by adding graded concentrations of $KNO_2$ (0, 5, 10, 25, 50, 100, 250, and 500 nmol/L) into the calibration solution containing KI and $H_2SO_4$. The specificity of the Iso-NO electrode to NO is previously determined by measurement of NO from authentic NO gas (1050). The culture medium is removed and HUVECs are washed twice with Dulbecco's phosphate buffered saline. The cells are then bathed in 5 ml of filtered Krebs-Henseleit solution in 6-well plates, and the cell plates are kept on a slide warmer (Lab Line Instruments Inc.) To maintain the temperature at 37° C. The NO sensor probe is inserted vertically into the wells, keeping the tip of the electrode 2 mm under the surface of the solution, before addition of the different conditions. S-nitroso acetyl penicillamin (SNAP) is used as a positive control. The amount of released NO is expressed as picomoles per $1\times10^6$ endothelial cells. All values reported are means of four to six measurements in each group (number of cell culture wells). See, Leak et al. *Biochem. and Biophys. Res. Comm.* 217:96–105 (1995).

The studies described in this example tested activity of polypeptides of the invention. However, one skilled in the art could easily modify the exemplified studies to test the activity of polynucleotides (e.g., gene therapy), agonists, and/or antagonists of the invention.

Example 41

Effect of Polypepides of the Invention on Cord Formation in Angiogenesis

Another step in angiogenesis is cord formation, marked by differentiation of endothelial cells. This bioassay measures the ability of microvascular endothelial cells to form capillary-like structures (hollow structures) when cultured in vitro.

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 ml/well) for 30 min. at 37° C. CADMEC are seeded onto the coated wells at 7,500 cells/well and cultured overnight in Growth Medium. The Growth Medium is then replaced with 300 mg Cell Applications' Chord Formation Medium containing control buffer or a polypeptide of the invention (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. b-esteradiol (1 ng/ml) is used as a negative control. The appropriate buffer (without protein) is also utilized as a control.

The studies described in this example tested activity of a polypeptide of the invention. However, one skilled in the art could easily modify the exemplified studies to test the activity of polynucleotides (e.g., gene therapy), agonists, and/or antagonists of the invention.

Example 42

Angiogenic Effect on Chick Chorioallantoic Membrane

Chick chorioallantoic membrane (CAM) is a well-established system to examine angiogenesis. Blood vessel formation on CAM is easily visible and quantifiable. The ability of polypeptides of the invention to stimulate angiogenesis in CAM can be examined.

Fertilized eggs of the White Leghorn chick (*Gallus gallus*) and the Japanese qual (*Coturnix coturnix*) are incubated at 37.8° C. and 80% humidity. Differentiated CAM of 16-day-old chick and 13-day-old qual embryos is studied with the following methods.

On Day 4 of development, a window is made into the egg shell of chick eggs. The embryos are checked for normal development and the eggs sealed with cellotape. They are further incubated until Day 13. Thermanox coverslips (Nunc, Naperville, Ill.) are cut into disks of about 5 mm in diameter. Sterile and salt-free growth factors are dissolved in distilled water and about 3.3 mg/5 ml are pipetted on the disks. After air-drying, the inverted disks are applied on CAM. After 3 days, the specimens are fixed in 3% glutaraldehyde and 2% formaldehyde and rinsed in 0.12 M sodium cacodylate buffer. They are photographed with a stereo microscope [Wild M8] and embedded for semi- and ultrathin sectioning as described above. Controls are performed with carrier disks alone.

The studies described in this example tested activity of a polypeptide of the invention. However, one skilled in the art could easily modify the exemplified studies to test the activity of polynucleotides (e.g., gene therapy), agonists, and/or antagonists of the invention.

Example 43

Angiogenesis Assay Using a Matrigel Implant in Mouse

In vivo angiogenesis assay of a polypeptide of the invention measures the ability of an existing capillary network to form new vessels in an implanted capsule of murine extracellular matrix material (Matrigel). The protein is mixed with the liquid Matrigel at 4 degree C. and the mixture is then injected subcutaneously in mice where it solidifies. After 7 days, the solid "plug" of Matrigel is removed and examined for the presence of new blood vessels. Matrigel is purchased from Becton Dickinson Labware/Collaborative Biomedical Products.

When thawed at 4 degree C. the Matrigel material is a liquid. The Matrigel is mixed with a polypeptide of the invention at 150 ng/ml at 4 degrees C. and drawn into cold 3 ml syringes. Female C57B1/6 mice approximately 8 weeks old are injected with the mixture of Matrigel and experimental protein at 2 sites at the midventral aspect of the abdomen (0.5 ml/site). After 7 days, the mice are sacrificed by cervical dislocation, the Matrigel plugs are removed and cleaned (i.e., all clinging membranes and fibrous tissue is removed). Replicate whole plugs are fixed in neutral buffered 10% formaldehyde, embedded in paraffin and used to produce sections for histological examination after staining with Masson's Trichrome. Cross sections from 3 different regions of each plug are processed. Selected sections are stained for the presence of vWF. The positive control for this assay is bovine basic FGF (150 ng/ml). Matrigel alone is used to determine basal levels of angiogenesis.

The studies described in this example tested activity of a polypeptide of the invention. However, one skilled in the art could easily modify the exemplified studies to test the activity of polynucleotides (e.g., gene therapy), agonists, and/or antagonists of the invention.

Example 44

Rescue of Ischemia in Rabbit Lower Limb Model

To study the in vivo effects of polynucleotides and polypeptides of the invention on ischemia, a rabbit hindlimb ischemia model is created by surgical removal of one femoral arteries as described previously (Takeshita et al., *Am J. Pathol* 147:1649–1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita et al. *Am J. Pathol* 147:1649–1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked expression plasmid containing a polynucleotide of the invention by arterial gene transfer technology using a hydrogel-coated balloon catheter as described (Riessen et al. *Hum Gene Ther.* 4:749–758 (1993); Leclerc et al. *J. Clin. Invest.* 90: 936–944 (1992)). When a polypeptide of the invention is used in the treatment, a single bolus of 500 mg polypeptide of the invention or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score—This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

The studies described in this example tested activity of polynucleotides and polypeptides of the invention. However, one skilled in the art could easily modify the exemplified studies to test the agonists, and/or antagonists of the invention.

Example 45

Effect of Polypeptides of the Invention on Vasodilation

Since dilation of vascular endothelium is important in reducing blood pressure, the ability of polypeptides of the invention to affect the blood pressure in spontaneously hypertensive rats (SHR) is examined. Increasing doses (0, 10, 30, 100, 300, and 900 mg/kg) of the polypeptides of the invention are administered to 13–14 week old spontaneously hypertensive rats (SHR). Data are expressed as the mean+/−SEM. Statistical analysis are performed with a paired t-test and statistical significance is defined as $p<0.05$ vs. the response to buffer alone.

The studies described in this example tested activity of a polypeptide of the invention. However, one skilled in the art could easily modify the exemplified studies to test the activity of polynucleotides (e.g., gene therapy), agonists, and/or antagonists of the invention.

Example 46

Rat Ischemic Skin Flap Model

The evaluation parameters include skin blood flow, skin temperature, and factor VIII immunohistochemistry or endothelial alkaline phosphatase reaction. Expression of polypeptides of the invention, during the skin ischemia, is studied using in situ hybridization.

The study in this model is divided into three parts as follows:

a) Ischemic skin b) Ischemic skin wounds c) Normal wounds

The experimental protocol includes:

a) Raising a 3×4 cm, single pedicle full-thickness random skin flap (myocutaneous flap over the lower back of the animal).

b) An excisional wounding (4–6 mm in diameter) in the ischemic skin (skin-flap).

c) Topical treatment with a polypeptide of the invention of the excisional wounds (day 0, 1, 2, 3, 4 post-wounding) at the following various dosage ranges: 1 mg to 100 mg.

d) Harvesting the wound tissues at day 3, 5, 7, 10, 14 and 21 post-wounding for histological, immunohistochemical, and in situ studies.

The studies described in this example tested activity of a polypeptide of the invention. However, one skilled in the art could easily modify the exemplified studies to test the activity of polynucleotides (e.g., gene therapy), agonists, and/or antagonists of the invention.

Example 47

Peripheral Arterial Disease Model

Angiogenic therapy using a polypeptide of the invention is a novel therapeutic strategy to obtain restoration of blood flow around the ischemia in case of peripheral arterial diseases. The experimental protocol includes:

a) One side of the femoral artery is ligated to create ischemic muscle of the hindlimb, the other side of hindlimb serves as a control.

b) a polypeptide of the invention, in a dosage range of 20 mg–500 mg, is delivered intravenously and/or intramuscularly 3 times (perhaps more) per week for 2–3 weeks.

c) The ischemic muscle tissue is collected after ligation of the femoral artery at 1, 2, and 3 weeks for the analysis of expression of a polypeptide of the invention and histology. Biopsy is also performed on the other side of normal muscle of the contralateral hindlimb.

The studies described in this example tested activity of a polypeptide of the invention. However, one skilled in the art could easily modify the exemplified studies to test the activity of polynucleotides (e.g., gene therapy), agonists, and/or antagonists of the invention.

Example 48

Ischemic Myocardial Disease Model

A polypeptide of the invention is evaluated as a potent mitogen capable of stimulating the development of collateral vessels, and restructuring new vessels after coronary artery occlusion. Alteration of expression of the polypeptide is investigated in situ. The experimental protocol includes:

a) The heart is exposed through a left-side thoracotomy in the rat. Immediately, the left coronary artery is occluded with a thin suture (6-0) and the thorax is closed.

b) a polypeptide of the invention, in a dosage range of 20 mg–500 mg, is delivered intravenously and/or intramuscularly 3 times (perhaps more) per week for 2–4 weeks.

c) Thirty days after the surgery, the heart is removed and cross-sectioned for morphometric and in situ analyzes.

The studies described in this example tested activity of a polypeptide of the invention. However, one skilled in the art could easily modify the exemplified studies to test the activity of polynucleotides (e.g., gene therapy), agonists, and/or antagonists of the invention.

Example 49

Rat Corneal Wound Healing Model

This animal model shows the effect of a polypeptide of the invention on neovascularization. The experimental protocol includes:

a) Making a 1–1.5 mm long incision from the center of cornea into the stromal layer.

b) Inserting a spatula below the lip of the incision facing the outer corner of the eye.

c) Making a pocket (its base is 1–1.5 mm form the edge of the eye).

d) Positioning a pellet, containing 50 ng–5 ug of a polypeptide of the invention, within the pocket.

e) Treatment with a polypeptide of the invention can also be applied topically to the corneal wounds in a dosage range of 20 mg–500 mg (daily treatment for five days).

The studies described in this example tested activity of a polypeptide of the invention. However, one skilled in the art could easily modify the exemplified studies to test the activity of polynucleotides (e.g., gene therapy), agonists, and/or antagonists of the invention.

Example 50

Diabetic Mouse and Glucocorticoid-Impaired Wound Healing Models

A. Diabetic db+/db+ Mouse Model

To demonstrate that a polypeptide of the invention accelerates the healing process, the genetically diabetic mouse model of wound healing is used. The fall thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al., *J. Surg. Res.* 52:389 (1992); Greenhalgh, D. G. et al., *Am. J. Pathol* 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. *Proc. Natl. Acad. Sci. USA* 77:283–293 (1982)). Animals show polyphagia, polydipsia and polyuria. Mutant diabetic mice (db+/db+) have elevated blood glucose, increased or normal insulin levels, and suppressed cell-mediated immunity (Mandel et al., *J. Immunol.* 120:1375 (1978); Debray-Sachs, M. et al., *Clin. Exp. Immunol.* 51(1):1–7 (1983); Leiter et al, *Am. J. of Pathol.* 114:46–55 (1985)). Peripheral neuropathy, myocardial complications, and microvascular lesions, basement membrane thickening and glomerular filtration abnormalities have been described in these animals (Norido, F. et al.,

*Exp. Neurol.* 83 (2):221–232 (1984); Robertson et al., *Diabetes* 29(1):60–67 (1980); Giacomelli et al., *Lab Invest.* 40(4):460–473 (1979); Coleman, D. L., *Diabetes* 31 (*Suppl*) :1–6 (1982)). These homozygous diabetic mice develop hyperglycemia that is resistant to insulin analogous to human type II diabetes (Mandel et al., *J. Immunol.* 120:1375–1377 (1978)).

The characteristics observed in these animals suggests that healing in this model may be similar to the healing observed in human diabetes (Greenhalgh, et al., *Am. J. of Pathol.* 136:1235–1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and are 8 weeks old at the beginning of the study. Animals are individually housed and received food and water ad libitum. All manipulations are performed using aseptic techniques. The experiments are conducted according to the rules and guidelines of Human Genome Sciences, Inc. Institutional Animal Care and Use Committee and the Guidelines for the Care and Use of Laboratory Animals.

Wounding protocol is performed according to previously reported methods (Tsuboi, R. and Rifkin, D. B., *J. Exp. Med.* 172:245–251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

A polypeptide of the invention is administered using at a range different doses, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Three groups of 10 animals each (5 diabetic and 5 non-diabetic controls) are evaluated: 1) Vehicle placebo control, 2) untreated group, and 3) treated group.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 is 64 $mm^2$, the corresponding size of the dermal punch. Calculations are made using the following formula:

[Open area on day 8]–[Open area on day 1]/[Open area on day 1]

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with a polypeptide of the invention. This assessment included verification of the presence of cell accumulation, inflammatory cells, capillaries, fibroblasts, re-epithelialization and epidermal maturity (Greenhalgh, D. G. et al., *Am. J Pathol.* 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer can serve as a positive tissue control and human brain tissue can be used as a negative tissue control. Each specimen includes a section with omission of the primary antibody and substitution with non-immune mouse IgG. Ranking of these sections is based on the extent of proliferation on a scale of 0–8, the lower side of the scale reflecting slight proliferation to the higher side reflecting intense proliferation.

Experimental data are analyzed using an unpaired t test. A p value of <0.05 is considered significant.

B. Steroid Impaired Rat Model

The inhibition of wound healing by steroids has been well documented in various in vitro and in vivo systems (Wahl, Glucocorticoids and Wound healing. In: Anti-Inflammatory Steroid Action: Basic and Clinical Aspects. 280–302 (1989); Wahl et al., *J. Immunol.* 115: 476–481 (1975); Werb et al., *J. Exp. Med.* 147:1684–1694 (1978)). Glucocorticoids retard wound healing by inhibiting angiogenesis, decreasing vascular permeability (Ebert et al., *An. Intern. Med.* 37:701–705 (1952)), fibroblast proliferation, and collagen synthesis (Beck et al., *Growth Factors.* 5: 295–304 (1991); Haynes et al., *J. Clin. Invest.* 61: 703–797 (1978)) and producing a transient reduction of circulating monocytes (Haynes et al., *J. Clin. Invest.* 61: 703–797 (1978); Wahl, "Glucocorticoids and wound healing", In: Antiinflammatory Steroid Action: Basic and Clinical Aspects, Academic Press, New York, pp. 280–302 (1989)). The systemic administration of steroids to impaired wound healing is a well establish phenomenon in rats (Beck et al., *Growth Factors.* 5: 295–304 (1991); Haynes et al., *J. Clin. Invest.* 61: 703–797 (1978); Wahl, "Glucocorticoids and wound healing", In: Antiinflammatory Steroid Action: Basic and Clinical Aspects, Academic Press, New York, pp. 280–302 (1989); Pierce et al., *Proc. Natl. Acad. Sci. USA* 86: 2229–2233 (1989)).

To demonstrate that a polypeptide of the invention can accelerate the healing process, the effects of multiple topical applications of the polypeptide on full thickness excisional skin wounds in rats in which healing has been impaired by the systemic administration of methylprednisolone is assessed.

Young adult male Sprague Dawley rats weighing 250–300 g (Charles River Laboratories) are used in this example. The animals are purchased at 8 weeks of age and are 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study is conducted according to the rules and guidelines of Human Genome Sciences, Inc. Institutional Animal Care and Use Committee and the Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

The polypeptide of the invention is administered using at a range different doses, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Four groups of 10 animals each (5 with methylprednisolone and 5 without glucocorticoid) are evaluated: 1) Untreated group 2) Vehicle placebo control 3) treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 is 64 $mm^2$, the corresponding size of the dermal punch. Calculations are made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using an Olympus microtome. Routine hematoxylin-eosin (H&E) staining is performed on cross-sections of bisected wounds. Histologic examination of the wounds allows assessment of whether the healing process and the morphologic appearance of the repaired skin is improved by treatment with a polypeptide of the invention. A calibrated lens micrometer is used by a blinded observer to determine the distance of the wound gap.

Experimental data are analyzed using an unpaired t test. A p value of <0.05 is considered significant.

The studies described in this example tested activity of a polypeptide of the invention. However, one skilled in the art could easily modify the exemplified studies to test the activity of polynucleotides (e.g., gene therapy), agonists, and/or antagonists of the invention.

Example 51

Lymphadema Animal Model

The purpose of this experimental approach is to create an appropriate and consistent lymphedema model for testing the therapeutic effects of a polypeptide of the invention in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7–10 days. Perhaps more importantly, the chronic progress of the edema is followed for up to 3–4 weeks.

Prior to beginning surgery, blood sample is drawn for protein concentration analysis. Male rats weighing approximately ~350 g are dosed with Pentobarbital. Subsequently, the right legs are shaved from knee to hip. The shaved area is swabbed with gauze soaked in 70% EtOH. Blood is drawn for serum total protein testing. Circumference and volumetric measurements are made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated suture ligated.

Using a microscope, muscles in back of the leg (near the semitendinosis and adductors) are bluntly dissected. The popliteal lymph node is then located. The 2 proximal and 2 distal lymphatic vessels and distal blood supply of the popliteal node are then and ligated by suturing. The popliteal lymph node, and any accompanying adipose tissue, is then removed by cutting connective tissues.

Care is taken to control any mild bleeding resulting from this procedure. After lymphatics are occluded, the skin flaps are sealed by using liquid skin (Vetbond) (AJ Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals are checked daily through the optimal edematous peak, which typically occurred by day 5–7. The plateau edematous peak are then observed. To evaluate the intensity of the lymphedema, the circumference and volumes of 2 designated places on each paw before operation and daily for 7 days are measured. The effect plasma proteins on lymphedema is determined and whether protein analysis is a useful testing perimeter is also investigated. The weights of both control and edematous limbs are evaluated at 2 places. Analysis is performed in a blind manner.

Circumference Measurements: Under brief gas anesthetic to prevent limb movement, a cloth tape is used to measure limb circumference. Measurements are done at the ankle bone and dorsal paw by 2 different people then those 2 readings are averaged. Readings are taken from both control and edematous limbs.

Volumetric Measurements: On the day of surgery, animals are anesthetized with Pentobarbital and are tested prior to surgery. For daily volumetrics animals are under brief halothane anesthetic (rapid immobilization and quick recovery), both legs are shaved and equally marked using waterproof marker on legs. Legs are first dipped in water, then dipped into instrument to each marked level then measured by Buxco edema software(Chen/Victor). Data is recorded by one person, while the other is dipping the limb to marked area.

Blood-plasma protein measurements: Blood is drawn, spun, and serum separated prior to surgery and then at conclusion for total protein and Ca2+ comparison.

Limb Weight Comparison: After drawing blood, the animal is prepared for tissue collection. The limbs are amputated using a quillitine, then both experimental and control legs are cut at the ligature and weighed. A second weighing is done as the tibio-cacaneal joint is disarticulated and the foot is weighed.

Histological Preparations: The transverse muscle located behind the knee (popliteal) area is dissected and arranged in a metal mold, filled with freezeGel, dipped into cold methylbutane, placed into labeled sample bags at −80 EC until sectioning. Upon sectioning, the muscle is observed under fluorescent microscopy for lymphatics.

The studies described in this example tested activity of a polypeptide of the invention. However, one skilled in the art could easily modify the exemplified studies to test the activity of polynucleotides (e.g., gene therapy), agonists, and/or antagonists of the invention.

Example 52

Suppression of TNF Alpha-Induced Adhesion Molecule Expression by a Polypeptide of the Invention The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-a), a potent proinflammatory cytokine, is a stimulator of all three CAMs on endothelial cells and may be involved in a wide variety of inflammatory responses, often resulting in a pathological outcome.

The potential of a polypeptide of the invention to mediate a suppression of TNF-a induced CAM expression can be examined. A modified ELISA assay which uses ECs as a solid phase absorbent is employed to measure the amount of CAM expression on TNF-a treated ECs when co-stimulated with a member of the FGF family of proteins.

To perform the experiment, human umbilical vein endothelial cell (HUVEC) cultures are obtained from pooled cord harvests and maintained in growth medium (EGM-2; Clonetics, San Diego, Calif.) supplemented with 10% FCS and 1% penicillin/streptomycin in a 37 degree C. humidified incubator containing 5% $CO_2$. HUVECs are seeded in 96-well plates at concentrations of $1\times10^4$ cells/well in EGM medium at 37 degree C. for 18–24 hrs or until confluent. The monolayers are subsequently washed 3 times with a serum-free solution of RPMI-1640 supplemented with 100 U/ml penicillin and 100 mg/ml streptomycin, and treated with a given cytokine and/or growth factor(s) for 24 h at 37 degree C. Following incubation, the cells are then evaluated for CAM expression.

Human Umbilical Vein Endothelial cells (HUVECs) are grown in a standard 96 well plate to confluence. Growth medium is removed from the cells and replaced with 90 ul of 199 Medium (10% FBS). Samples for testing and positive or negative controls are added to the plate in triplicate (in 10 ul volumes). Plates are incubated at 37 degree C. for either 5 h (selectin and integrin expression) or 24 h (integrin expression only). Plates are aspirated to remove medium and 100 μl of 0.1% paraformaldehyde-PBS(with Ca++ and Mg++) is added to each well. Plates are held at 4° C. for 30 min.

Fixative is then removed from the wells and wells are washed 1×with PBS(+Ca, Mg)+0.5% BSA and drained. Do not allow the wells to dry. Add 10 μl of diluted primary antibody to the test and control wells. Anti-ICAM-1-Biotin, Anti-VCAM-1-Biotin and Anti-E-selectin-Biotin are used at a concentration of 10 μg/ml (1:10 dilution of 0.1 mg/ml stock antibody). Cells are incubated at 37° C. for 30 min. in a humidified environment. Wells are washed ×3 with PBS (+Ca, Mg)+0.5% BSA.

Then add 20 μl of diluted ExtrAvidin-Alkaline Phosphotase (1:5,000 dilution) to each well and incubated at 37° C. for 30 min. Wells are washed ×3 with PBS(+Ca, Mg)+0.5% BSA. 1 tablet of p-Nitrophenol Phosphate pNPP is dissolved in 5 ml of glycine buffer (pH 10.4). 100 μl of pNPP substrate in glycine buffer is added to each test well. Standard wells in triplicate are prepared from the working dilution of the ExtrAvidin-Alkaline Phosphotase in glycine buffer: 1:5,000 $(10^0)>10^{-0.5}>10^{-1}>10^{-1.5}$. 5 μl of each dilution is added to triplicate wells and the resulting AP content in each well is 5.50 ng, 1.74 ng, 0.55 ng, 0.18 ng. 100 μl of pNNP reagent must then be added to each of the standard wells. The plate must be incubated at 37° C. for 4 h. A volume of 50 μl of 3M NaOH is added to all wells. The results are quantified on a plate reader at 405 nm. The background subtraction option is used on blank wells filled with glycine buffer only. The template is set up to indicate the concentration of AP-conjugate in each standard well [5.50 ng; 1.74 ng; 0.55 ng; 0.18 ng]. Results are indicated as amount of bound AP-conjugate in each sample.

The studies described in this example tested activity of a polypeptide of the invention. However, one skilled in the art could easily modify the exemplified studies to test the activity of polynucleotides (e.g., gene therapy), agonists, and/or antagonists of the invention.

Example 53

Assay for the Stimulation of Bone Marrow CD34+ Cell Proliferation

This assay is based on the ability of human CD34+ to proliferate in the presence of hematopoietic growth factors and evaluates the ability of isolated polypeptides expressed in mammalian cells to stimulate proliferation of CD34+ cells.

It has been previously shown that most mature precursors will respond to only a single signal. More immature precursors require at least two signals to respond. Therefore, to test the effect of polypeptides on hematopoietic activity of a wide range of progenitor cells, the assay contains a given polypeptide in the presence or absence of other hematopoietic growth factors. Isolated cells are cultured for 5 days in the presence of Stem Cell Factor (SCF) in combination with tested sample. SCF alone has a very limited effect on the proliferation of bone marrow (BM) cells, acting in such conditions only as a "survival" factor. However, combined with any factor exhibiting stimulatory effect on these cells (e.g., IL-3), SCF will cause a synergistic effect. Therefore, if the tested polypeptide has a stimulatory effect on a hematopoietic progenitors, such activity can be easily detected. Since normal BM cells have a low level of cycling cells, it is likely that any inhibitory effect of a given polypeptide, or agonists or antagonists thereof, might not be detected. Accordingly, assays for an inhibitory effect on progenitors is preferably tested in cells that are first subjected to in vitro stimulation with SCF+IL+3, and then contacted with the compound that is being evaluated for inhibition of such induced proliferation.

Briefly, CD34+ cells are isolated using methods known in the art. The cells are thawed and resuspended in medium (QBSF 60 serum-free medium with 1% L-glutamine (500 ml) Quality Biological, Inc., Gaithersburg, Md. Cat#160-204-101). After several gentle centrifugation steps at 200× g, cells are allowed to rest for one hour. The cell count is adjusted to $2.5\times10^5$ cells/ml. During this time, 100 $\mu$l of sterile water is added to the peripheral wells of a 96-well plate. The cytokines that can be tested with a given polypeptide in this assay is rhSCF (R&D Systems, Minneapolis, Minn., Cat#255-SC) at 50 ng/ml alone and in combination with rhSCF and rhIL-3 (R&D Systems, Minneapolis, Minn., Cat#203 ML) at 30 ng/ml. After one hour, 10 $\mu$l of prepared cytokines, 50 $\mu$l SID (supernatants at 1:2 dilution=50 $\mu$l) and 20 $\mu$l of diluted cells are added to the media which is already present in the wells to allow for a final total volume of 100 $\mu$l. The plates are then placed in a 37° C./5% $CO_2$ incubator for five days.

Eighteen hours before the assay is harvested, 0.5 $\mu$Ci/well of [3H] Thymidine is added in a 10 $\mu$l volume to each well to determine the proliferation rate. The experiment is terminated by harvesting the cells from each 96-well plate to a filtermat using the Tomtec Harvester 96. After harvesting, the filtermats are dried, trimmed and placed into OmniFilter assemblies consisting of one OmniFilter plate and one OmniFilter Tray. 60 $\mu$l Microscint is added to each well and the plate sealed with TopSeal-A press-on sealing film A bar code 15 sticker is affixed to the first plate for counting. The sealed plates is then loaded and the level of radioactivity determined via the Packard Top Count and the printed data collected for analysis. The level of radioactivity reflects the amount of cell proliferation.

The studies described in this example test the activity of a given polypeptide to stimulate bone marrow CD34+ cell proliferation. One skilled in the art could easily modify the exemplified studies to test the activity of polynucleotides (e.g., gene therapy), antibodies, agonists, and/or antagonists and fragments and variants thereof. As a nonlimiting example, potential antagonists tested in this assay would be expected to inhibit cell proliferation in the presence of cytokines and/or to increase the inhibition of cell proliferation in the presence of cytokines and a given polypeptide. In contrast, potential agonists tested in this assay would be expected to enhance cell proliferation and/or to decrease the inhibition of cell proliferation in the presence of cytokines and a given polypeptide.

The ability of a gene to stimulate the proliferation of bone marrow CD34+ cells indicates that polynucleotides and polypeptides corresponding to the gene are useful for the diagnosis and treatment of disorders affecting the immune system and hematopoiesis. Representative uses are described in the "Immune Activity" and "Infectious Disease" sections above, and elsewhere herein.

Example 54

Assay for Extracellular Matrix Enhanced Cell Response (EMECR)

The objective of the Extracellular Matrix Enhanced Cell Response (EMECR) assay is to identify gene products (e.g., isolated polypeptides) that act on the hematopoietic stem cells in the context of the extracellular matrix (ECM) induced signal.

Cells respond to the regulatory factors in the context of signal(s) received from the surrounding microenvironment. For example, fibroblasts, and endothelial and epithelial stem cells fail to replicate in the absence of signals from the ECM. Hematopoietic stem cells can undergo self-renewal in the bone marrow, but not in in vitro suspension culture. The ability of stem cells to undergo self-renewal in vitro is dependent upon their interaction with the stromal cells and the ECM protein fibronectin (fn). Adhesion of cells to fn is mediated by the $\alpha_5.\beta_1$ and $\alpha_4.\beta_1$ integrin receptors, which are expressed by human and mouse hematopoietic stem cells. The factor(s) which integrate with the ECM environment and responsible for stimulating stem cell self-renewal has not yet been identified. Discovery of such factors should be of great interest in gene therapy and bone marrow transplant applications Briefly, polystyrene, non tissue culture treated, 96-well plates are coated with fn fragment at a coating concentration of 0.2 $\mu g/cm^2$. Mouse bone marrow cells are plated (1,000 cells/well) in 0.2 ml of serum-free medium. Cells cultured in the presence of IL-3 (5 ng/ml)+SCF (50 ng/ml) would serve as the positive control, conditions under which little self-renewal but pronounced differentiation of the stem cells is to be expected. Gene products are tested with appropriate negative controls in the presence and absence of SCF(5.0 ng/ml), where test factor supernates represent 10% of the total assay volume. The plated cells are then allowed to grow by incubating in a low oxygen environment (5% $CO_2$, 7% $O_2$, and 88% $N_2$) tissue culture incubator for 7 days. The number of proliferating cells within the wells is then quantitated by measuring thymidine incorporation into cellular DNA. Verification of the positive hits in the assay will require phenotypic characterization of the cells, which can be accomplished by scaling up of the culture system and using appropriate antibody reagents against cell surface antigens and FACScan.

One skilled in the art could easily modify the exemplified studies to test the activity of polynucleotides (e.g., gene therapy), antibodies, agonists, and/or antagonists and fragments and variants thereof.

If a particular gene product is found to be a stimulator of hematopoietic progenitors, polynucleotides and polypeptides corresponding to the gene may be useful for the diagnosis and treatment of disorders affecting the immune system and hematopoiesis. Representative uses are described in the "Immune Activity" and "Infectious Disease" sections above, and elsewhere herein. The gene product may also be useful in the expansion of stem cells and committed progenitors of various blood lineages, and in the differentiation and/or proliferation of various cell types.

Additionally, the polynucleotides and/or polypeptides of the gene of interest and/or agonists and/or antagonists thereof, may also be employed to inhibit the proliferation and differentiation of hematopoietic cells and therefore may be employed to protect bone marrow stem cells from chemotherapeutic agents during chemotherapy. This antiproliferative effect may allow administration of higher doses of chemotherapeutic agents and, therefore, more effective chemotherapeutic treatment.

Moreover, polynucleotides and polypeptides corresponding to the gene of interest may also be useful for the treatment and diagnosis of hematopoietic related disorders such as, for example, anemia, pancytopenia, leukopenia, thrombocytopenia or leukemia since stromal cells are important in the production of cells of hematopoietic lineages. The uses include bone marrow cell ex-vivo culture, bone marrow transplantation, bone marrow reconstitution, radiotherapy or chemotherapy of neoplasia.

Example 55

Human Dermal Fibroblast and Aortic Smooth Muscle Cell Proliferation

The polypeptide of interest is added to cultures of normal human dermal fibroblasts (NHDF) and human aortic smooth muscle cells (AoSMC) and two co-assays are performed with each sample. The first assay examines the effect of the polypeptide of interest on the proliferation of normal human dermal fibroblasts (NHDF) or aortic smooth muscle cells (AoSMC). Aberrant growth of fibroblasts or smooth muscle cells is a part of several pathological processes, including fibrosis, and restenosis. The second assay examines IL6 production by both NHDF and SMC. IL6 production is an indication of functional activation. Activated cells will have increased production of a number of cytokines and other factors, which can result in a proinflammatory or immunomodulatory outcome. Assays are run with and without co-TNFa stimulation, in order to check for costimulatory or inhibitory activity.

Briefly, on day 1, 96-well black plates are set up with 1000 cells/well (NHDF) or 2000 cells/well (AoSMC) in 100 μl culture media. NHDF culture media contains: Clonetics FB basal media, 1 mg/ml hFGF, 5 mg/ml insulin, 50 mg/ml gentamycin, 2% FBS, while AoSMC culture media contains Clonetics SM basal media, 0.5 μg/ml hEGF, 5 mg/ml insulin, 1 μg/ml hFGF, 50 mg/ml gentamycin, 50 μg/ml Amphotericin B, 5% FBS. After incubation @ 37° C. for at least 4–5 hours culture media is aspirated and replaced with growth arrest media. Growth arrest media for NHDF contains fibroblast basal media, 50 mg/ml gentamycin, 2% FBS, while growth arrest media for AoSMC contains SM basal media, 50 mg/ml gentamycin, 50 μg/ml Amphotericin B, 0.4% FBS. Incubate at 37 C. until day 2.

On day 2, serial dilutions and templates of the polypeptide of interest are designed which should always include media controls and known-protein controls. For both stimulation and inhibition experiments, proteins are diluted in growth arrest media. For inhibition experiments, TNFa is added to a final concentration of 2 ng/ml (NHDF) or 5 ng/ml (AoSMC). Then add 1/3 vol media containing controls or supernatants and incubate at 37 C./5% $CO_2$ until day 5.

Transfer 60 μl from each well to another labeled 96-well plate, cover with a plate-sealer, and store at 4C until Day 6 (for IL6 ELISA). To the remaining 100 μl in the cell culture plate, aseptically add Alamar Blue in an amount equal to 10% of the culture volume (10 μl). Return plates to incubator for 3 to 4 hours. Then measure fluorescence with excitation at 530 nm and emission at 590 nm using the CytoFluor. This yields the growth stimulation/inhibition data.

On day 5, the IL6 ELISA is performed by coating a 96 well plate with 50–100 ul/well of Anti-Human IL6 Monoclonal antibody diluted in PBS, pH 7.4, incubate ON at room temperature.

On day 6, empty the plates into the sink and blot on paper towels. Prepare Assay Buffer containing PBS with 4% BSA. Block the plates with 200 μl/well of Pierce Super Block blocking buffer in PBS for 1–2 hr and then wash plates with wash buffer (PBS, 0.05% Tween-20). Blot plates on paper towels. Then add 50 μl/well of diluted Anti-Human IL-6 Monoclonal, Biotin-labeled antibody at 0.50 mg/ml. Make dilutions of IL-6 stock in media (30, 10, 3, 1, 0.3, 0 ng/ml). Add duplicate samples to top row of plate. Cover the plates and incubate for 2 hours at RT on shaker.

Wash plates with wash buffer and blot on paper towels. Dilute EU-labeled Streptavidin 1:1000 in Assay buffer, and add 100 μl/well. Cover the plate and incubate 1 h at RT. Wash plates with wash buffer. Blot on paper towels.

Add 100 μl/well of Enhancement Solution. Shake for 5 minutes. Read the plate on the Wallac DELFIA Fluorometer. Readings from triplicate samples in each assay were tabulated and averaged.

A positive result in this assay suggests AoSMC cell proliferation and that the gene product of interest may be involved in dermal fibroblast proliferation and/or smooth muscle cell proliferation. A positive result also suggests many potential uses of polypeptides, polynucleotides, agonists and/or antagonists of the gene/gene product of interest. For example, inflammation and immune responses, wound healing, and angiogenesis, as detailed throughout this specification. Particularly, polypeptides of the gene product and polynucleotides of the gene may be used in wound healing and dermal regeneration, as well as the promotion of vasculargenesis, both of the blood vessels and lymphatics. The growth of vessels can be used in the treatment of, for example, cardiovascular diseases. Additionally, antagonists of polypeptides of the gene product and polynucleotides of the gene may be useful in treating diseases, disorders, and/or conditions which involve angiogenesis by acting as an anti-vascular (e.g., anti-angiogenesis). These diseases, disorders, and/or conditions are known in the art and/or are described herein, such as, for example, malignancies, solid tumors, benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis. Moreover, antagonists of polypeptides of the gene product and polynucleotides of the gene may be useful in treating anti-hyperproliferative diseases and/or anti-inflammatory known in the art and/or described herein.

One skilled in the art could easily modify the exemplified studies to test the activity of polynucleotides (e.g., gene therapy), antibodies, agonists, and/or antagonists and fragments and variants thereof.

Example 56

Cellular Adhesion Molecule (CAM) Expression on Endothelial Cells

The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Briefly, endothelial cells (e.g., Human Umbilical Vein Endothelial cells (HUVECs)) are grown in a standard 96 well plate to confluence, growth medium is removed from the cells and replaced with 100 μl of 199 Medium (10% fetal bovine serum (FBS)). Samples for testing and positive or negative controls are added to the plate in triplicate (in 10 μl volumes). Plates are then incubated at 37° C. for either 5 h (selectin and integrin expression) or 24 h (integrin expression only). Plates are aspirated to remove medium and 100 μl of 0.1% paraformaldehyde-PBS(with Ca++ and Mg++) is added to each well. Plates are held at 4° C. for 30 min. Fixative is removed from the wells and wells are washed 1× with PBS(+Ca, Mg)+0.5% BSA and drained. 10 μl of diluted primary antibody is added to the test and control wells. Anti-ICAM-1-Biotin, Anti-VCAM-1-Biotin and Anti-E-selectin-Biotin are used at a concentration of 10 μg/ml (1:10 dilution of 0.1 mg/ml stock antibody). Cells are incubated at 37° C. for 30 min. in a humidified environment. Wells are washed three times with PBS(+Ca, Mg)+0.5% BSA. 20 μl of diluted ExtrAvidin-Alkaline Phosphotase (1:5,000 dilution, referred to herein as the working dilution) are added to each well and incubated at 37° C. for 30 min. Wells are washed three times with PBS(+Ca, Mg)+0.5% BSA. Dissolve 1 tablet of p-Nitrophenol Phosphate pNPP per 5 ml of glycine buffer (pH 10.4). 100 μl of pNPP substrate in glycine buffer is added to each test well. Standard wells in triplicate are prepared from the working dilution of the ExtrAvidin-Alkaline Phosphotase in glycine buffer: 1:5,000 ($10^0$)>$10^{-}$ $_{0.5}$>$10^{-1}$>$10^{-1.5}$. 5 μl of each dilution is added to triplicate wells and the resulting AP content in each well is 5.50 ng, 1.74 ng, 0.55 ng, 0.18 ng. 100 μl of pNNP reagent is then added to each of the standard wells. The plate is incubated at 37° C. for 4 h. A volume of 50 μl of 3M NaOH is added to all wells. The plate is read on a plate reader at 405 nm using the background subtraction option on blank wells filled with glycine buffer only. Additionally, the template is set up to indicate the concentration of AP-conjugate in each standard well [5.50 ng; 1.74 ng; 0.55 ng; 0.18 ng]. Results are indicated as amount of bound AP-conjugate in each sample.

Example 57

Alamar Blue Endothelial Cells Proliferation Assay

This assay may be used to quantitatively determine protein mediated inhibition of bFGF-induced proliferation of Bovine Lymphatic Endothelial Cells (LECs), Bovine Aortic Endothelial Cells (BAECs) or Human Microvascular Uterine Myometrial Cells (UTMECs). This assay incorporates a fluorometric growth indicator based on detection of metabolic activity. A standard Alamar Blue Proliferation Assay is prepared in EGM-2MV with 10 ng/ml of bFGF added as a source of endothelial cell stimulation. This assay may be used with a variety of endothelial cells with slight changes in growth medium and cell concentration. Dilutions of the protein batches to be tested are diluted as appropriate. Serum-free medium (GIBCO SFM) without bFGF is used as a non-stimulated control and Angiostatin or TSP-1 are included as a known inhibitory controls.

Briefly, LEC, BAECs or UTMECs are seeded in growth media at a density of 5000 to 2000 cells/well in a 96 well plate and placed at 37-C overnight. After the overnight incubation of the cells, the growth media is removed and replaced with GIBCO EC-SFM. The cells are treated with the appropriate dilutions of the protein of interest or control protein sample(s) (prepared in SFM) in triplicate wells with additional bFGF to a concentration of 10 ng/ml. Once the cells have been treated with the samples, the plate(s) is/are placed back in the 37° C. incubator for three days. After three days 10 ml of stock alamar blue (Biosource Cat# DAL1100) is added to each well and the plate(s) is/are placed back in the 37° C. incubator for four hours. The plate(s) are then read at 530 nm excitation and 590 nm emission using the CytoFluor fluorescence reader. Direct output is recorded in relative fluorescence units.

Alamar blue is an oxidation-reduction indicator that both fluoresces and changes color in response to chemical reduction of growth medium resulting from cell growth. As cells grow in culture, innate metabolic activity results in a chemical reduction of the immediate surrounding environment. Reduction related to growth causes the indicator to change from oxidized (non-fluorescent blue) form to reduced (fluorescent red) form. i.e. stimulated proliferation will produce a stronger signal and inhibited proliferation will produce a weaker signal and the total signal is proportional to the total number of cells as well as their metabolic activity. The background level of activity is observed with the starvation medium alone. This is compared to the output observed from the positive control samples (bFGF in growth medium) and protein dilutions.

Example 58

Detection of Inhibition of a Mixed Lymphocyte Reaction

This assay can be used to detect and evaluate inhibition of a Mixed Lymphocyte Reaction (MLR) by gene products (e.g., isolated polypeptides). Inhibition of a MLR may be due to a direct effect on cell proliferation and viability, modulation of costimulatory molecules on interacting cells, modulation of adhesiveness between lymphocytes and accessory cells, or modulation of cytokine production by accessory cells. Multiple cells may be targeted by these polypeptides since the peripheral blood mononuclear fraction used in this assay includes T, B and natural killer lymphocytes, as well as monocytes and dendritic cells.

Polypeptides of interest found to inhibit the MLR may find application in diseases associated with lymphocyte and monocyte activation or proliferation. These include, but are not limited to, diseases such as asthma, arthritis, diabetes, inflammatory skin conditions, psoriasis, eczema, systemic lupus erythematosus, multiple sclerosis, glomerulonephritis, inflammatory bowel disease, crohn's disease, ulcerative colitis, arteriosclerosis, cirrhosis, graft vs. host disease, host vs. graft disease, hepatitis, leukemia and lymphoma.

Briefly, PBMCs from human donors are purified by density gradient centrifugation using Lymphocyte Separation Medium (LSM®, density 1.0770 g/ml, Organon Teknika Corporation, West Chester, Pa.). PBMCs from two donors are adjusted to $2\times10^6$ cells/ml in RPMI-1640 (Life Technologies, Grand Island, N.Y.) supplemented with 10% FCS and 2 mM glutamine. PBMCs from a third donor is adjusted to $2\times10^5$ cells/ml. Fifty microliters of PBMCs from each donor is added to wells of a 96-well round bottom microtiter plate. Dilutions of test materials (50 $\mu$l) is added in triplicate to microtiter wells. Test samples (of the protein of interest) are added for final dilution of 1:4; rhuIL-2 (R&D Systems, Minneapolis, Minn., catalog number 202-IL) is added to a final concentration of 1 $\mu$g/ml; anti-CD4 mAb (R&D Systems, clone 34930.11, catalog number MAB379) is added to a final concentration of 10 $\mu$g/ml. Cells are cultured for 7–8 days at 37° C. in 5% $CO_2$, and 1 $\mu$C of [$^3$H]thymidine is added to wells for the last 16 hrs of culture. Cells are harvested and thymidine incorporation determined using a Packard TopCount. Data is expressed as the mean and standard deviation of triplicate determinations.

Samples of the protein of interest are screened in separate experiments and compared to the negative control treatment, anti-CD4 mAb, which inhibits proliferation of lymphocytes and the positive control treatment, IL-2 (either as recombinant material or supernatant), which enhances proliferation of lymphocytes.

One skilled in the art could easily modify the exemplified studies to test the activity of polynucleotides (e.g., gene therapy), antibodies, agonists, and/or antagonists and fragments and variants thereof.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties. Additionally, the specifications and sequence listings of PCT International Application No. PCT/US00/26013 and of U.S. provisional application Ser. No. 60/155,709 is hereby incorporated by reference in their entirety.

TABLE 7

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | . | . | 0.12 | 0.04 | * | . | . | −0.10 | 0.18 |
| Glu | 2 | . | . | B | . | . | . | . | 0.62 | −0.39 | * | . | . | 0.50 | 0.28 |
| Cys | 3 | . | . | B | . | . | . | . | 0.42 | −0.81 | * | . | . | 1.10 | 0.43 |
| Cys | 4 | . | . | B | . | . | . | . | 0.50 | −0.74 | * | . | . | 1.40 | 0.44 |
| Arg | 5 | . | . | . | . | T | . | . | 0.68 | −0.87 | * | . | . | 2.10 | 0.37 |
| Arg | 6 | . | . | . | . | T | . | . | 0.93 | −0.44 | * | . | F | 2.40 | 1.06 |
| Ala | 7 | . | . | . | . | T | . | . | 0.62 | −0.59 | * | . | F | 3.00 | 1.96 |
| Thr | 8 | . | . | . | . | . | T | C | 0.48 | −0.67 | . | . | F | 2.70 | 1.45 |
| Pro | 9 | . | . | . | . | T | T | . | 0.33 | 0.01 | * | . | F | 1.55 | 0.61 |
| Gly | 10 | . | . | . | . | T | T | . | −0.59 | 0.70 | * | . | F | 0.95 | 0.50 |
| Thr | 11 | . | . | B | . | . | T | . | −1.40 | 0.89 | . | * | F | 0.25 | 0.28 |
| Leu | 12 | . | A | B | . | . | . | . | −1.62 | 1.19 | . | . | . | −0.60 | 0.16 |
| Leu | 13 | . | A | B | . | . | . | . | −1.90 | 1.44 | . | . | . | −0.60 | 0.13 |
| Leu | 14 | . | A | B | . | . | . | . | −2.39 | 1.51 | . | . | . | −0.60 | 0.09 |
| Phe | 15 | . | A | B | . | . | . | . | −2.86 | 1.81 | . | . | . | −0.60 | 0.10 |
| Leu | 16 | . | A | B | . | . | . | . | −3.36 | 1.81 | . | . | . | −0.60 | 0.10 |
| Ala | 17 | . | A | B | . | . | . | . | −3.36 | 1.81 | . | . | . | −0.60 | 0.10 |
| Phe | 18 | . | A | B | . | . | . | . | −2.84 | 1.81 | . | . | . | −0.60 | 0.09 |
| Leu | 19 | . | A | B | . | . | . | . | −2.33 | 1.41 | . | * | . | −0.60 | 0.15 |
| Leu | 20 | . | A | B | . | . | . | . | −1.52 | 1.11 | . | . | . | −0.60 | 0.20 |
| Leu | 21 | . | A | B | . | . | . | . | −1.02 | 0.61 | . | . | . | −0.60 | 0.45 |
| Ser | 22 | . | . | . | . | . | T | C | −1.02 | 0.31 | * | . | F | 0.45 | 0.79 |
| Ser | 23 | . | . | . | . | . | T | C | −0.21 | 0.13 | * | . | F | 0.45 | 0.97 |
| Arg | 24 | . | . | . | . | . | T | C | 0.30 | −0.56 | * | . | F | 1.50 | 2.30 |
| Thr | 25 | . | . | . | . | . | T | C | 1.11 | −0.86 | * | . | F | 1.50 | 2.30 |
| Ala | 26 | . | A | . | . | . | . | C | 1.92 | −1.24 | * | . | F | 1.10 | 2.98 |
| Arg | 27 | . | A | . | . | . | . | C | 2.22 | −1.63 | * | . | F | 1.44 | 2.63 |
| Ser | 28 | . | A | B | . | . | . | . | 2.63 | −1.63 | * | . | F | 1.58 | 3.04 |
| Glu | 29 | . | A | B | . | . | . | . | 2.52 | −2.11 | * | . | F | 1.92 | 5.90 |
| Glu | 30 | . | A | B | . | . | . | . | 2.49 | −2.61 | . | * | F | 2.26 | 5.03 |
| Asp | 31 | . | . | . | . | T | T | . | 2.27 | −2.19 | . | . | F | 3.40 | 3.72 |
| Arg | 32 | . | . | . | . | T | T | . | 1.87 | −1.89 | . | . | F | 3.06 | 1.77 |
| Asp | 33 | . | . | . | . | T | T | . | 2.17 | −0.97 | . | . | F | 2.72 | 1.07 |
| Gly | 34 | . | . | . | . | T | T | . | 1.58 | −0.97 | . | . | F | 2.38 | 1.07 |
| Leu | 35 | . | . | . | . | T | . | . | 1.29 | −0.47 | . | . | . | 1.24 | 0.55 |
| Trp | 36 | . | . | . | . | . | . | C | 0.94 | 0.44 | . | . | . | −0.20 | 0.35 |
| Asp | 37 | . | . | . | . | . | . | C | 0.62 | 0.87 | * | . | . | −0.20 | 0.35 |
| Ala | 38 | . | . | . | . | T | . | . | 0.33 | 0.87 | * | . | . | 0.00 | 0.65 |
| Irp | 39 | . | . | . | . | . | . | C | 0.38 | 1.10 | * | . | . | −0.20 | 0.65 |
| Gly | 40 | . | . | . | . | . | T | C | 1.19 | 0.57 | * | . | . | 0.00 | 0.53 |
| Pro | 41 | . | . | . | . | T | T | . | 0.81 | 0.57 | . | . | F | 0.35 | 0.90 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Tip | 42 | . | . | . | . | T | T | . | 0.51 | 0.64 | * | . | F | 0.66 | 0.46 |
| Ser | 43 | . | . | . | . | . | T | C | 1.21 | 0.11 | * | . | F | 1.07 | 0.62 |
| Glu | 44 | . | . | . | . | T | . | . | 1.19 | −0.31 | * | . | F | 1.98 | 0.79 |
| Cys | 45 | . | . | . | . | T | T | . | 0.87 | −0.26 | * | . | F | 2.64 | 1.08 |
| Ser | 46 | . | . | . | . | T | T | . | 0.73 | −0.60 | * | . | F | 3.10 | 0.43 |
| Mg | 47 | . | . | . | . | T | T | . | 0.68 | −0.56 | * | . | F | 2.79 | 0.25 |
| Thr | 48 | . | . | . | . | T | T | . | 0.63 | −0.13 | * | . | F | 2.18 | 0.46 |
| Cys | 49 | . | . | . | . | T | T | . | 0.04 | −0.27 | * | . | F | 1.87 | 0.34 |
| Gly | 50 | . | . | . | . | T | T | . | 0.41 | −0.16 | * | . | F | 1.56 | 0.17 |
| Gly | 51 | . | . | . | . | T | T | . | 0.47 | 0.23 | . | . | F | 0.65 | 0.16 |
| Gly | 52 | . | . | . | . | T | T | . | 0.06 | 0.50 | . | * | F | 0.35 | 0.47 |
| Ala | 53 | . | . | . | . | . | T | C | −0.44 | 0.31 | * | * | F | 0.45 | 0.64 |
| Ser | 54 | . | . | B | . | . | T | . | 0.33 | 0.57 | * | . | . | −0.20 | 0.53 |
| Tyr | 55 | . | . | B | . | . | T | . | 0.79 | 0.14 | * | . | . | 0.25 | 1.05 |
| Ser | 56 | . | . | B | . | . | T | . | 0.47 | −0.29 | * | * | . | 0.85 | 2.04 |
| Leu | 57 | . | . | B | . | . | . | . | 0.00 | −0.21 | * | . | . | 0.50 | 0.82 |
| Arg | 58 | . | . | B | . | . | . | . | 0.29 | 0.09 | * | * | . | −0.10 | 0.43 |
| Arg | 59 | . | . | B | . | . | . | . | 0.29 | −0.29 | * | * | . | 0.50 | 0.43 |
| Cys | 60 | . | . | B | . | . | . | . | 0.58 | −0.29 | * | * | . | 0.84 | 0.70 |
| Leu | 61 | . | . | . | . | T | . | . | 0.58 | −0.97 | * | . | F | 2.03 | 0.71 |
| Ser | 62 | . | . | . | . | T | . | . | 0.72 | −0.59 | * | . | F | 2.37 | 0.49 |
| Ser | 63 | . | . | . | . | T | T | . | 0.61 | −0.01 | . | . | F | 2.61 | 0.49 |
| Lys | 64 | . | . | . | . | T | T | . | 0.16 | −0.59 | * | . | F | 3.40 | 1.02 |
| Ser | 65 | . | . | . | . | T | T | . | 0.93 | −0.84 | . | . | F | 2.91 | 0.76 |
| Cys | 66 | . | . | . | . | T | T | . | 1.74 | −1.23 | . | . | F | 3.06 | 1.11 |
| Glu | 67 | . | . | . | . | T | . | . | 1.16 | −1.21 | * | . | F | 2.71 | 0.89 |
| Gly | 68 | . | . | . | . | T | T | . | 1.57 | −0.53 | * | . | F | 2.91 | 0.46 |
| Arg | 69 | . | . | . | . | T | T | . | 1.28 | −0.91 | . | * | F | 3.06 | 1.70 |
| Asn | 70 | . | . | . | . | T | T | . | 1.69 | −0.73 | . | * | F | 3.40 | 1.54 |
| Ile | 71 | . | . | B | . | . | T | . | 2.04 | −0.73 | . | * | . | 2.51 | 3.04 |
| Arg | 72 | . | . | B | . | . | . | . | 1.38 | −0.67 | . | * | . | 1.97 | 2.24 |
| Tyr | 73 | . | . | . | . | T | . | . | 1.42 | −0.10 | . | * | . | 1.89 | 0.75 |
| Arg | 74 | . | . | . | . | T | . | . | 1.31 | −0.11 | . | * | . | 2.01 | 1.43 |
| Thr | 75 | . | . | . | . | T | . | . | 0.46 | −0.40 | . | * | F | 2.13 | 1.17 |
| Cys | 76 | . | . | . | . | T | T | . | 1.34 | 0.24 | . | * | F | 1.89 | 0.56 |
| Ser | 77 | . | . | . | . | T | T | . | 0.57 | −0.51 | . | * | F | 3.10 | 0.47 |
| Asn | 78 | . | . | . | . | T | T | . | 0.60 | 0.06 | * | * | . | 1.74 | 0.18 |
| Val | 79 | . | . | . | . | T | T | . | 0.28 | 0.00 | * | * | . | 2.03 | 0.51 |
| Asp | 80 | . | . | . | . | T | . | . | 0.59 | −0.14 | . | * | . | 1.86 | 0.59 |
| Cys | 81 | . | . | B | . | . | . | . | 0.67 | −0.53 | . | * | F | 1.94 | 0.63 |
| Pro | 82 | . | . | B | . | . | T | . | 0.62 | −0.43 | * | * | F | 1.87 | 0.86 |
| Pro | 83 | . | . | . | . | T | T | . | 0.62 | −0.64 | . | * | F | 2.91 | 0.51 |
| Gln | 84 | . | . |  | . | T | T | . | 0.78 | −0.64 | . | * | F | 3.40 | 1.58 |
| Ala | 85 | . | . | . | . | T | T | . | 0.89 | −0.43 | . | * | F | 2.61 | 0.89 |
| Gly | 86 | . | . | . | . | T | . | . | 0.97 | −0.86 | . | * | F | 2.52 | 1.12 |
| Asp | 87 | . | A | . | . | T | . | . | 1.18 | −0.79 | . | * | F | 1.83 | 0.66 |
| Phe | 88 | . | A | B | . | . | . | . | 1.39 | −0.39 | . | * | . | 0.79 | 1.12 |
| Arg | 89 | . | A | B | . | . | . | . | 0.72 | −0.49 | . | * | . | 0.45 | 1.97 |
| Ala | 90 | . | A | B | . | . | . | . | 1.01 | −0.34 | . | * | . | 0.30 | 0.63 |
| Gln | 91 | . | . | B | . | . | T | . | 0.77 | 0.04 | . | * | . | 0.10 | 0.98 |
| Gln | 92 | . | . | B | . | . | T | . | 0.73 | −0.24 | . | * | . | 0.70 | 0.50 |
| Cys | 93 | . | . | . | . | T | T | . | 1.43 | 0.26 | . | * | . | 0.50 | 0.68 |
| Ser | 94 | . | . | . | . | T | T | . | 1.32 | 0.16 | . | * | . | 0.50 | 0.63 |
| Ala | 95 | . | . | . | . | T | . | . | 1.06 | −0.24 | . | * | . | 0.90 | 0.61 |
| His | 96 | . | . | . | . | T | T | . | 1.10 | 0.00 | . | * | . | 0.80 | 0.84 |
| Asn | 97 | . | . | . | . | T | T | . | 1.07 | −0.57 | . | * | . | 2.15 | 1.26 |
| Asp | 98 | . | . | . | . | T | T | . | 1.70 | −0.46 | * | * | F | 2.30 | 1.69 |
| Val | 99 | . |  | B | . | . | T | . | 1.66 | −0.46 | * | * | F | 2.20 | 1.69 |
| Lys | 100 | . | . | . | . | T | . | . | 2.24 | −0.53 | * | * | F | 3.00 | 1.04 |
| His | 101 | . | . | . | . | . | T | C | 1.58 | −0.53 | * | * | F | 2.55 | 1.08 |
| His | 102 | . | . | . | . | . | T | C | 1.33 | 0.26 | * | * | . | 1.35 | 1.26 |
| Gly | 103 | . | . | . | . | . | T | C | 1.33 | 0.37 | . | * | . | 0.90 | 0.99 |
| Gln | 104 | . | . | B | . | . | T | . | 1.90 | 0.37 | * | * | . | 0.55 | 1.26 |
| Phe | 105 | . | A | B | . | . | . | . | 1.04 | 0.79 | * | * | . | −0.60 | 0.97 |
| Tyr | 106 | . | A | B | . | . | . | . | 0.87 | 0.97 | . | . | . | −0.60 | 0.81 |
| Glu | 107 | . | A | B | . | . | . | . | 0.04 | 0.97 | . | . | . | −0.60 | 0.72 |
| Trp | 108 | . | A | B | . | . | . | . | 0.09 | 1.21 | . | . | . | −0.60 | 0.62 |
| Leu | 109 | . | . | B | . | . | . | . | 0.09 | 0.81 | * | . | . | −0.40 | 0.53 |
| Pro | 110 | . | . | . | . | T | . | . | 0.79 | 0.46 | * | . | . | 0.00 | 0.49 |
| Val | 111 | . | . | . | . | T | . | . | 0.82 | 0.46 | . | . | . | 0.34 | 0.78 |
| Ser | 112 | . | . |  | . | T | . | . | 0.82 | −0.03 | . | . | F | 1.88 | 1.46 |
| Asn | 113 | . | . | . | . | T | . | . | 1.11 | −0.71 | . | . | F | 2.52 | 1.58 |
| Asp | 114 | . | . | . | . | . | T | C | 1.71 | −0.74 | . | . | F | 2.86 | 3.43 |
| Pro | 115 | . | . | . | . | T | T | . | 1.26 | −0.96 | * | . | F | 3.40 | 3.95 |
| Asp | 116 | . | . | . | . | T | T | . | 1.81 | −0.77 | * | . | F | 3.06 | 1.32 |
| Asn | 117 | . | . | . | . | . | T | C | 1.30 | −0.79 | . | * | F | 2.52 | 1.06 |
| Pro | 118 | . | . | . | . | T | . | . | 1.34 | −0.10 | . | * | F | 1.73 | 0.56 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Cys | 119 | . | A | . | . | T | . | . | 0.68 | −0.53 | . | * | F | 1.49 | 0.68 |
| Ser | 120 | . | A | B | . | . | . | . | 0.89 | 0.04 | . | * | . | −0.30 | 0.23 |
| Leu | 121 | . | A | B | | . | . | . | 0.30 | 0.04 | . | * | . | −0.30 | 0.25 |
| Lys | 122 | . | A | B | | . | . | . | 0.34 | 0.11 | . | * | . | −0.30 | 0.48 |
| Cys | 123 | . | A | B | . | . | . | . | 0.21 | −0.46 | . | * | . | 0.55 | 0.71 |
| Gln | 124 | . | A | B | . | . | . | . | 0.57 | −0.41 | . | * | . | 0.80 | 0.85 |
| Ala | 125 | . | . | B | . | . | T | . | 0.56 | −0.61 | . | * | F | 1.90 | 0.61 |
| Lys | 126 | . | . | B | . | . | T | . | 0.56 | −0.13 | * | * | F | 2.00 | 1.65 |
| Gly | 127 | . | . | . | . | T | T | . | −0.34 | −0.01 | . | * | F | 2.50 | 0.79 |
| Thr | 128 | . | . | B | . | . | T | . | −0.53 | 0.23 | * | F | 1.25 | 0.58 | |
| Thr | 129 | . | A | B | B | . | . | . | −0.53 | 0.37 | . | * | F | 0.60 | 0.21 |
| Len | 130 | . | A | B | B | . | . | . | −0.76 | 0.37 | * | . | . | 0.20 | 0.38 |
| Val | 131 | . | A | B | B | . | . | . | −1.39 | 0.63 | * | . | . | −0.35 | 0.21 |
| Val | 132 | . | A | B | B | . | . | . | −1.26 | 0.64 | * | * | . | −0.60 | 0.15 |
| Glu | 133 | . | A | B | B | . | . | . | −0.90 | 0.59 | * | * | . | −0.60 | 0.28 |
| Leu | 134 | . | A | B | . | . | . | . | −1.44 | −0.10 | * | * | . | 0.30 | 0.76 |
| Ala | 135 | . | A | B | . | . | . | . | −1.44 | −0.10 | * | * | . | 0.30 | 0.76 |
| Pro | 136 | . | A | B | . | . | . | . | −0.59 | −0.06 | * | . | F | 0.45 | 0.36 |
| Lys | 137 | . | A | B | . | . | . | . | −0.08 | −0.06 | * | * | F | 0.45 | 0.73 |
| Val | 138 | . | A | B | . | . | . | . | −0.39 | −0.31 | * | . | F | 0.45 | 0.72 |
| Len | 139 | . | A | B | . | . | . | . | 0.53 | −0.33 | * | . | F | 0.45 | 0.67 |
| Asp | 140 | . | A | B | . | . | . | . | 0.46 | −0.76 | * | . | F | 0.75 | 0.66 |
| Gly | 141 | . | . | B | . | . | T | . | 0.42 | −0.19 | * | . | F | 0.85 | 0.47 |
| Thr | 142 | . | . | B | . | . | T | . | 0.07 | −0.07 | * | . | F | 0.85 | 0.90 |
| Arg | 143 | . | . | B | . | . | T | . | 0.92 | −0.27 | * | . | F | 0.85 | 0.78 |
| Cys | 144 | . | . | B | . | . | T | . | 1.43 | −0.27 | * | . | . | 0.85 | 1.36 |
| Tyr | 145 | . | . | B | . | . | . | . | 0.62 | −0.31 | * | . | . | 0.65 | 1.26 |
| Thr | 146 | . | A | B | . | . | . | . | 0.97 | −0.11 | * | . | F | 0.45 | 0.53 |
| Gln | 147 | . | A | B | . | . | . | . | 0.68 | −0.11 | * | . | F | 0.60 | 1.66 |
| Ser | 148 | . | A | B | . | . | . | . | −0.10 | −0.07 | * | * | F | 0.60 | 1.05 |
| Len | 149 | . | A | B | . | . | . | . | −0.32 | −0.26 | . | * | . | 0.30 | 0.39 |
| Asp | 150 | . | A | . | . | T | . | . | −0.38 | −0.06 | * | * | . | 0.70 | 0.16 |
| Met | 151 | . | A | B | . | . | . | . | −0.41 | 0.33 | * | * | . | −0.30 | 0.16 |
| Cys | 152 | . | . | B | . | . | T | . | −1.22 | 0.37 | * | * | . | 0.10 | 0.19 |
| Ile | 153 | . | . | B | . | . | T | . | −1.59 | 0.37 | * | * | . | 0.10 | 0.09 |
| Ser | 154 | . | . | B | . | . | T | . | −0.78 | 0.94 | * | * | . | −0.20 | 0.05 |
| Gly | 155 | . | . | . | . | T | T | . | −1.67 | 0.73 | * | * | . | 0.20 | 0.16 |
| Len | 156 | . | . | B | B | . | . | . | −1.92 | 0.84 | * | . | . | −0.60 | 0.16 |
| Cys | 157 | . | . | B | B | . | . | . | −1.60 | 0.80 | * | . | . | −0.60 | 0.09 |
| Gln | 158 | . | . | B | B | . | . | . | −1.38 | 0.84 | * | . | . | −0.60 | 0.09 |
| Ile | 159 | . | . | B | B | . | . | . | −1.08 | 0.99 | . | . | . | −0.60 | 0.06 |
| Val | 160 | . | . | B | B | . | . | . | −0.77 | 0.30 | . | . | . | −0.30 | 0.18 |
| Gly | 161 | . | . | B | . | . | . | . | 0.04 | 0.23 | * | . | . | −0.10 | 0.14 |
| Cys | 162 | . | . | B | . | . | T | . | −0.10 | 0.23 | . | . | . | 0.10 | 0.36 |
| Asp | 163 | . | . | B | . | . | T | . | −0.44 | 0.23 | . | . | . | 0.10 | 0.39 |
| His | 164 | . | . | B | . | . | T | . | 0.14 | 0.01 | . | . | . | 0.10 | 0.39 |
| Gln | 165 | . | . | . | . | T | T | . | 0.69 | −0.03 | . | * | . | 1.10 | 0.99 |
| Leu | 166 | . | . | B | B | . | . | . | 0.18 | −0.11 | * | * | . | 0.30 | 0.85 |
| Gly | 167 | . | . | . | B | T | . | . | 0.89 | 0.53 | * | * | F | −0.05 | 0.47 |
| Ser | 168 | . | . | B | B | . | . | . | 0.89 | 0.03 | * | * | F | −0.15 | 0.54 |
| Thr | 169 | . | . | B | B | . | . | . | 0.92 | −0.37 | * | * | F | 0.94 | 1.13 |
| Val | 170 | . | . | B | B | . | . | . | 0.92 | −1.06 | . | * | F | 1.58 | 1.90 |
| Lys | 171 | . | . | B | B | . | . | . | 1.07 | −1.09 | . | . | F | 1.92 | 2.28 |
| Gln | 172 | . | . | B | . | . | . | . | 1.07 | −0.90 | . | . | F | 2.31 | 0.85 |
| Asp | 173 | . | . | . | . | T | T | . | 0.51 | −0.96 | . | . | F | 3.40 | 1.13 |
| Asn | 174 | . | . | . | . | T | T | . | 0.16 | −0.96 | . | . | F | 2.91 | 0.42 |
| Cys | 175 | . | . | . | . | T | T | . | 1.01 | −0.39 | * | . | . | 2.12 | 0.13 |
| Gly | 176 | . | . | B | . | . | T | . | 0.62 | 0.01 | . | . | . | 0.78 | 0.13 |
| Val | 177 | . | . | B | . | . | . | . | 0.62 | 0.44 | . | . | . | −0.06 | 0.08 |
| Cys | 178 | . | . | B | . | . | . | . | 0.28 | 0.04 | . | . | . | −0.10 | 0.24 |
| Asn | 179 | . | . | . | . | T | T | . | −0.02 | −0.10 | . | . | F | 1.56 | 0.24 |
| Gly | 180 | . | . | . | . | T | T | . | 0.33 | −0.14 | . | . | F | 1.87 | 0.43 |
| Asp | 181 | . | . | . | . | T | T | . | 0.01 | −0.30 | * | . | F | 2.33 | 1.17 |
| Gly | 182 | . | . | . | . | T | T | . | 0.98 | −0.30 | * | . | F | 2.49 | 0.39 |
| Ser | 183 | . | . | . | . | T | T | . | 0.83 | −0.70 | * | . | F | 3.10 | 0.77 |
| Thr | 184 | | . | B | . | . | T | . | −0.02 | −0.44 | * | . | F | 2.09 | 0.38 |
| Cys | 185 | . | . | B | . | . | T | . | 0.43 | 0.20 | * | . | F | 1.18 | 0.28 |
| Mg | 186 | . | . | B | . | . | T | . | 0.09 | −0.23 | * | . | . | 1.32 | 0.42 |
| Leu | 187 | . | . | B | B | . | . | . | 0.43 | −0.19 | * | | . | 0.61 | 0.29 |
| Val | 188 | . | . | B | B | . | . | . | 0.49 | −0.27 | * | * | . | 0.56 | 0.92 |
| Arg | 189 | . | . | B | B | . | . | . | 0.84 | −0.09 | . | * | F | 0.97 | 0.74 |
| Gly | 190 | . | . | . | . | T | . | . | 1.21 | −0.09 | * | * | F | 1.98 | 1.79 |
| Gln | 191 | . | . | . | . | T | . | . | 1.10 | −0.39 | * | * | F | 2.24 | 3.23 |
| Tyr | 192 | . | . | B | . | . | T | . | 1.10 | −0.63 | . | * | F | 2.60 | 2.86 |
| Lys | 193 | . | . | B | . | . | T | . | 1.66 | 0.06 | . | * | F | 1.44 | 2.38 |
| Ser | 194 | . | . | B | . | . | T | . | 0.96 | 0.01 | . | * | F | 1.18 | 1.84 |
| Gln | 195 | . | . | B | . | . | T | . | 0.99 | 0.11 | . | * | F | 0.92 | 1.19 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 196 | . | A | B | . | . | . | . | 1.03 | −0.16 | . | * | F | 0.71 | 0.86 |
| Ser | 197 | . | A | B | . | . | . | . | 0.98 | −0.16 | . | * | F | 0.94 | 1.28 |
| Ala | 198 | . | A | B | . | . | . | . | 0.93 | −0.16 | . | * | F | 1.13 | 0.99 |
| Thr | 199 | . | A | B | . | . | . | . | 1.23 | −0.56 | . | . | F | 1.92 | 2.00 |
| Lys | 200 | . | A | . | . | T | . | . | 0.92 | −1.24 | . | . | F | 2.66 | 2.50 |
| Ser | 201 | . | . | . | . | T | T | . | 0.88 | −1.14 | . | . | F | 3.40 | 3.57 |
| Asp | 202 | . | . | . | . | T | T | . | 0.32 | −1.00 | . | . | F | 3.06 | 1.84 |
| Asp | 203 | . | . | B | . | . | T | . | 0.32 | −0.84 | * | . | F | 2.17 | 0.68 |
| Thr | 204 | . | . | B | . | . | T | . | −0.26 | −0.34 | . | . | F | 1.53 | 0.51 |
| Val | 205 | . | . | B | B | . | . | . | −0.51 | −0.04 | . | . | . | 0.64 | 0.22 |
| Val | 206 | . | . | B | B | . | . | . | −0.46 | 0.39 | . | . | . | −0.30 | 0.20 |
| Ala | 207 | . | . | B | B | . | . | . | −0.80 | 1.14 | . | . | . | −0.60 | 0.22 |
| Ile | 208 | . | . | B | . | . | T | . | −1.10 | 1.09 | * | * | . | −0.20 | 0.29 |
| Pro | 209 | . | . | B | . | . | T | . | −0.68 | 0.83 | . | . | . | −0.20 | 0.52 |
| Tyr | 210 | . | . | . | . | T | T | . | 0.14 | 0.19 | * | . | . | 0.65 | 1.01 |
| Gly | 211 | . | . | . | . | T | T | . | 0.11 | 0.19 | * | * | F | 0.80 | 1.96 |
| Ser | 212 | . | . | B | . | . | . | . | 0.81 | 0.19 | * | * | F | 0.05 | 0.89 |
| Arg | 213 | . | A | B | . | . | . | . | 0.89 | −0.24 | * | * | F | 0.60 | 1.11 |
| His | 214 | . | A | B | . | . | . | . | 0.24 | −0.31 | * | * | . | 0.30 | 0.93 |
| Ile | 215 | . | A | B | . | . | . | . | −0.32 | −0.10 | * | * | . | 0.30 | 0.51 |
| Arg | 216 | . | A | B | . | . | . | . | 0.07 | 0.20 | * | * | . | −0.30 | 0.22 |
| Leu | 217 | . | A | B | . | . | . | . | 0.02 | 0.20 | * | * | . | −0.30 | 0.32 |
| Val | 218 | . | A | B | . | . | . | . | −0.30 | 0.13 | * | * | . | −0.30 | 0.45 |
| Leu | 219 | . | A | B | . | . | . | . | −0.27 | −0.13 | * | * | . | 0.58 | 0.35 |
| Lys | 220 | . | A | . | . | . | . | C | 0.59 | −0.13 | * | * | F | 1.21 | 0.72 |
| Gly | 221 | . | . | . | . | . | T | C | −0.33 | −0.31 | * | * | F | 2.04 | 1.31 |
| Pro | 222 | . | . | . | . | . | T | C | 0.23 | −0.27 | * | * | F | 2.32 | 1.31 |
| Asp | 223 | . | . | . | . | T | T | . | 0.28 | −0.20 | * | * | F | 2.80 | 1.03 |
| His | 224 | . | . | B | . | . | T | . | 1.09 | 0.49 | . | * | . | 0.92 | 0.86 |
| Leu | 225 | . | . | B | . | . | . | . | 0.73 | 0.06 | * | * | . | 0.74 | 0.96 |
| Tyr | 226 | . | . | B | . | . | . | . | 1.12 | 0.11 | . | * | . | 0.46 | 0.83 |
| Leu | 227 | . | . | B | . | . | . | . | 1.02 | 0.11 | . | . | . | 0.33 | 1.22 |
| Glu | 228 | . | . | B | . | . | . | . | 0.21 | 0.10 | * | . | F | 0.20 | 2.14 |
| Thr | 229 | . | . | B | B | . | . | . | 0.24 | 0.10 | . | * | F | 0.00 | 1.12 |
| Lys | 230 | . | . | B | B | . | . | . | 0.71 | −0.26 | . | * | F | 0.60 | 2.36 |
| Thr | 231 | . | . | B | B | . | . | . | 0.64 | −0.51 | . | . | F | 0.90 | 1.35 |
| Leu | 232 | . | . | B | B | . | . | . | 1.50 | −0.03 | . | . | F | 0.60 | 1.35 |
| Gln | 233 | . | . | B | B | . | . | . | 1.16 | −0.51 | . | . | F | 1.20 | 1.35 |
| Gly | 234 | . | . | . | B | . | . | C | 1.47 | −0.09 | . | . | F | 1.25 | 0.93 |
| Thr | 235 | . | . | . | . | . | . | C | 1.42 | −0.57 | . | . | F | 2.20 | 1.94 |
| Lys | 236 | . | . | . | . | . | . | C | 1.43 | −0.86 | . | . | F | 2.50 | 1.80 |
| Gly | 237 | . | . | . | . | . | T | C | 1.43 | −0.87 | . | . | F | 3.00 | 2.44 |
| Giu | 238 | . | . | B | . | . | T | . | 1.13 | −0.61 | * | . | F | 2.50 | 1.40 |
| Asn | 239 | . | . | . | . | . | T | C | 1.18 | −0.71 | * | . | F | 2.25 | 0.94 |
| Ser | 240 | . | . | . | . | . | T | C | 1.18 | −0.33 | * | * | F | 1.80 | 1.27 |
| Leu | 241 | . | . | B | . | . | . | . | 0.79 | −0.27 | * | * | F | 1.10 | 1.06 |
| Ser | 242 | . | . | . | . | . | . | C | 0.82 | 0.16 | . | . | F | 0.25 | 0.65 |
| Ser | 243 | . | . | . | . | . | T | C | 0.12 | 0.24 | * | . | F | 0.45 | 0.70 |
| Thr | 244 | . | . | B | . | T | T | . | −0.69 | 0.64 | * | . | F | 0.35 | 0.73 |
| Gly | 245 | . | . | B | . | . | T | . | −1.24 | 0.64 | * | * | F | −0.05 | 0.45 |
| Thr | 246 | . | . | B | . | . | T | . | −0.43 | 0.90 | * | . | F | −0.05 | 0.25 |
| Phe | 247 | . | . | B | B | . | . | . | −0.13 | 0.51 | . | . | . | −0.60 | 0.29 |
| Leu | 248 | . | . | B | B | . | . | . | −0.13 | 0.43 | . | . | . | −0.60 | 0.47 |
| Val | 249 | . | . | B | B | . | . | . | −0.12 | 0.39 | . | . | F | −0.15 | 0.44 |
| Asp | 250 | . | . | B | . | . | T | . | −0.63 | 0.29 | . | . | F | 0.25 | 0.68 |
| Asn | 251 | . | . | . | . | . | T | C | −0.32 | 0.14 | . | * | F | 0.45 | 0.61 |
| Ser | 252 | . | . | . | . | . | T | C | −0.32 | −0.54 | . | * | F | 1.50 | 1.37 |
| Ser | 253 | . | . | . | . | . | T | C | 0.49 | −0.40 | * | . | F | 1.05 | 0.71 |
| Val | 254 | . | . | B | . | . | . | . | 139 | 0.00 | * | . | F | 0.65 | 0.77 |
| Asp | 255 | . | . | B | . | . | . | . | 0.69 | −0.40 | * | . | . | 0.95 | 1.14 |
| Phe | 256 | . | . | B | . | . | . | . | 0.48 | 0.00 | * | * | . | 1.10 | 0.74 |
| Gln | 257 | . | . | B | . | . | . | . | 0.78 | 0.04 | * | . | . | 0.95 | 1.54 |
| Lys | 258 | . | . | B | . | . | . | . | 1.12 | −0.60 | * | . | F | 2.30 | 1.54 |
| Phe | 259 | . | . | . | . | . | T | C | 1.98 | −0.60 | * | . | F | 3.00 | 3.55 |
| Pro | 260 | . | . | . | . | . | T | C | 1.09 | −1.39 | * | . | F | 2.70 | 3.55 |
| Asp | 261 | . | . | . | . | T | T | . | 0.98 | −1.10 | * | * | F | 2.60 | 1.24 |
| Lys | 262 | . | . | . | . | . | T | C | 1.09 | −0.41 | * | * | F | 1.80 | 1.19 |
| Glu | 263 | . | A | B | . | . | . | . | 0.44 | −1.20 | * | * | F | 1.20 | 1.50 |
| Ile | 264 | . | A | B | . | . | . | . | 0.56 | −1.01 | * | * | . | 0.60 | 0.89 |
| Leu | 265 | . | A | B | . | . | . | . | 0.42 | −0.51 | * | . | . | 0.60 | 0.45 |
| Arg | 266 | . | A | B | . | . | . | . | 0.21 | −0.09 | * | * | . | 0.30 | 0.26 |
| Met | 267 | . | A | B | . | . | . | . | −0.64 | 0.34 | * | * | . | −0.30 | 0.57 |
| Ala | 268 | . | A | B | . | . | . | . | −0.96 | 0.34 | * | * | . | −0.30 | 0.57 |
| Gly | 269 | . | . | . | . | . | T | C | −0.66 | 0.14 | * | * | . | 0.30 | 0.42 |
| Pro | 270 | . | . | . | . | . | T | C | 0.16 | 0.64 | * | * | F | 0.15 | 0.43 |
| Leu | 271 | . | . | . | . | . | T | C | −0.66 | 0.03 | * | * | . | 0.30 | 0.70 |
| Thr | 272 | . | . | B | . | . | T | . | −0.94 | 0.31 | . | * | . | 0.10 | 0.62 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Ala | 273 | . | . | B | B | . | . | . | −1.21 | 0.57 | * | * | . | −0.60 | 0.28 |
| Asp | 274 | . | . | B | B | . | . | . | −0.82 | 0.79 | * | * | . | −0.60 | 0.25 |
| Phe | 275 | . | . | B | B | . | . | . | −1.50 | 0.10 | * | * | . | −0.30 | 0.35 |
| Ile | 276 | . | . | B | B | . | . | . | −0.58 | 0.30 | * | * | . | −0.30 | 0.24 |
| Val | 277 | . | . | B | B | . | . | . | −0.27 | −0.20 | * | * | . | 0.30 | 0.28 |
| Lys | 278 | . | . | B | B | . | . | . | 0.02 | 0.20 | * | * | . | −0.30 | 0.53 |
| Ile | 279 | . | . | B | B | . | . | . | −0.32 | −0.20 | * | * | F | 0.90 | 1.01 |
| Arg | 280 | . | . | B | B | . | . | . | 0.08 | −0.46 | * | * | F | 1.20 | 1.34 |
| Asn | 281 | . | . | . | . | T | T | . | 0.38 | −0.71 | . | * | F | 2.45 | 0.90 |
| Ser | 282 | . | . | . | . | . | T | C | 1.23 | −0.21 | . | * | F | 2.40 | 1.30 |
| Gly | 283 | . | . | . | . | . | T | C | 0.89 | −0.90 | . | * | F | 3.00 | 1.11 |
| Ser | 284 | . | . | . | . | . | T | C | 1.47 | −0.51 | * | * | F | 2.55 | 0.92 |
| Ala | 285 | . | . | . | . | . | . | C | 0.50 | −0.43 | * | * | F | 1.75 | 0.99 |
| Asp | 286 | . | . | . | B | . | . | C | 0.50 | −0.17 | . | * | F | 1.25 | 0.74 |
| Ser | 287 | . | . | B | B | . | . | . | 0.10 | −0.20 | * | * | F | 0.75 | 0.96 |
| Thr | 288 | . | . | B | B | . | . | . | −0.44 | 0.20 | * | * | F | −0.15 | 0.82 |
| Val | 289 | . | . | B | B | . | . | . | −0.84 | 0.39 | * | * | . | −0.30 | 0.35 |
| Gln | 290 | . | . | B | B | . | . | . | −0.50 | 1.17 | . | * | . | −0.60 | 0.22 |
| Phe | 291 | . | . | B | B | . | . | . | −0.50 | 1.54 | . | * | . | −0.60 | 0.24 |
| Ile | 292 | . | . | B | B | . | . | . | −0.41 | 1.46 | . | . | . | −0.60 | 0.57 |
| Phe | 293 | . | . | B | B | . | . | . | −0.99 | 1.24 | . | . | . | −0.60 | 0.51 |
| Tyr | 294 | . | . | B | B | . | . | . | −1.02 | 1.53 | . | . | . | −0.60 | 0.41 |
| Gln | 295 | . | . | B | B | . | . | . | −1.06 | 1.43 | . | . | . | −0.60 | 0.41 |
| Pro | 296 | . | . | B | B | . | . | . | −0.24 | 1.24 | * | . | . | −0.60 | 0.64 |
| Ile | 297 | . | . | . | B | T | . | . | 0.36 | 0.46 | * | * | . | −0.20 | 0.80 |
| Ile | 298 | . | . | . | B | . | . | C | 1.17 | 0.61 | * | * | . | −0.40 | 0.49 |
| His | 299 | . | . | . | B | . | . | C | 1.41 | 0.21 | * | * | . | 0.20 | 0.62 |
| Arg | 300 | . | . | . | B | T | . | . | 1.10 | −0.21 | * | * | . | 1.45 | 1.53 |
| Trp | 301 | . | . | . | B | T | . | . | 1.31 | −0.41 | . | * | . | 1.75 | 3.14 |
| Arg | 302 | . | . | . | B | T | . | . | 1.50 | −1.10 | . | * | F | 2.50 | 3.86 |
| G1u | 303 | . | . | . | . | T | . | . | 1.69 | −0.81 | . | . | F | 3.00 | 1.71 |
| Thr | 304 | . | . | . | . | T | . | . | 1.51 | −0.03 | . | * | F | 2.40 | 1.41 |
| Asp | 305 | . | . | . | . | T | . | . | 0.73 | −0.51 | . | * | F | 2.40 | 1.11 |
| Phe | 306 | . | . | . | . | T | . | . | 0.72 | 0.06 | * | . | . | 0.90 | 0.34 |
| Phe | 307 | . | . | . | . | . | T | C | 0.02 | 0.44 | * | . | . | 0.30 | 0.32 |
| Pro | 308 | . | . | . | . | T | T | . | −0.29 | 0.46 | . | . | . | 0.20 | 0.19 |
| Cys | 309 | . | . | . | . | T | T | . | −0.64 | 0.94 | . | . | . | 0.20 | 0.32 |
| Ser | 310 | . | . | . | . | T | T | . | −0.99 | 0.73 | . | . | . | 0.20 | 0.20 |
| Ala | 311 | . | . | . | . | T | . | . | −0.63 | 0.37 | . | . | . | 0.30 | 0.13 |
| Thr | 312 | . | . | . | . | T | . | . | −0.28 | 0.37 | . | . | . | 0.30 | 0.24 |
| Cys | 313 | . | . | . | . | T | T | . | −0.31 | 0.23 | . | . | F | 0.65 | 0.17 |
| Gly | 314 | . | . | . | . | T | T | . | 0.36 | 0.60 | . | . | F | 0.35 | 0.27 |
| Gly | 315 | . | . | . | . | T | T | . | −0.16 | 0.50 | . | . | F | 0.35 | 0.32 |
| Gly | 316 | . | . | . | . | T | T | . | 0.12 | 0.70 | . | . | F | 0.35 | 0.50 |
| Tyr | 317 | . | . | B | B | . | . | . | 0.13 | 0.61 | . | . | . | −0.60 | 0.73 |
| Gln | 318 | . | . | B | B | . | . | . | 0.21 | 0.57 | . | . | . | −0.60 | 0.98 |
| Leu | 319 | . | . | B | B | . | . | . | 0.56 | 0.64 | . | . | . | −0.45 | 1.00 |
| Thr | 320 | . | . | B | B | . | . | . | 0.23 | 0.21 | . | . | . | −0.15 | 1.11 |
| Ser | 321 | . | . | B | B | . | . | . | 0.33 | 0.03 | . | . | F | −0.15 | 0.34 |
| Ala | 322 | . | . | B | . | . | . | . | 0.58 | 0.39 | . | . | . | −0.10 | 0.65 |
| Glu | 323 | . | . | B | . | . | . | . | −0.23 | −0.30 | . | * | . | 0.50 | 0.75 |
| Cys | 324 | . | . | B | . | . | T | . | 0.69 | −0.10 | . | * | . | 1.04 | 0.46 |
| Tyr | 325 | . | . | B | . | . | T | . | 0.70 | −0.49 | . | * | . | 1.38 | 0.90 |
| Asp | 326 | . | . | . | . | T | T | . | 1.00 | −0.60 | . | . | . | 2.42 | 0.70 |
| Leu | 327 | . | . | . | . | T | T | . | 1.70 | −0.20 | . | . | . | 2.61 | 2.09 |
| Arg | 328 | . | . | . | . | T | T | . | 0.84 | −0.77 | * | . | F | 3.40 | 2.61 |
| Ser | 329 | . | . | . | . | T | T | . | 0.66 | −0.89 | . | * | F | 3.06 | 1.16 |
| Asn | 330 | . | . | . | . | T | T | . | 0.31 | −0.24 | * | * | F | 2.42 | 1.04 |
| Arg | 331 | . | . | B | . | . | T | . | 0.31 | −0.43 | * | * | F | 1.53 | 0.54 |
| Val | 332 | . | . | B | . | . | . | . | 1.12 | −0.43 | * | . | . | 0.84 | 0.67 |
| Val | 333 | . | . | B | . | . | . | . | 0.77 | −0.41 | * | . | . | 0.50 | 0.72 |
| Ala | 334 | . | . | B | . | . | . | . | 0.40 | −0.06 | * | . | . | 0.50 | 0.58 |
| Asp | 335 | . | . | B | . | . | T | . | 0.37 | 0.51 | * | . | . | −0.20 | 0.42 |
| Gln | 336 | . | . | B | . | . | T | . | 0.01 | 0.37 | * | * | . | 0.10 | 0.77 |
| Tyr | 337 | . | . | B | . | . | T | . | 0.62 | 0.49 | . | . | . | −0.05 | 1.19 |
| Cys | 338 | . | . | B | . | . | T | . | 1.27 | 0.74 | * | . | . | −0.05 | 1.11 |
| His | 339 | . | . | B | . | . | . | . | 1.86 | 1.17 | * | . | . | −0.40 | 0.99 |
| Tyr | 340 | . | . | B | . | . | . | . | 1.86 | 0.77 | * | . | . | −0.25 | 1.10 |
| Tyr | 341 | . | . | B | . | . | T | . | 0.97 | 0.41 | * | . | . | −0.05 | 3.30 |
| Pro | 342 | . | . | . | . | T | T | . | 1.26 | 0.53 | * | * | . | 0.35 | 1.70 |
| Glu | 343 | . | . | . | . | T | T | . | 1.71 | 0.03 | . | * | F | 1.14 | 2.17 |
| Asn | 344 | . | . | . | . | T | T | . | 1.79 | −0.30 | . | * | F | 2.08 | 2.14 |
| Ile | 345 | . | . | . | . | T | . | . | 1.82 | −1.06 | * | * | F | 2.52 | 2.77 |
| Lys | 346 | . | . | . | . | . | T | C | 2.11 | −1.06 | * | * | F | 2.86 | 2.47 |
| Pro | 347 | . | . | . | . | T | T | . | 1.51 | −1.06 | . | * | F | 3.40 | 3.07 |
| Lys | 348 | . | . | . | . | . | T | C | 1.51 | −0.77 | . | * | F | 2.86 | 3.62 |
| Pro | 349 | . | . | . | . | . | T | C | 1.51 | −1.06 | . | * | F | 2.52 | 3.13 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Lys | 350 | . | A | . | . | T | . | . | 1.73 | −1.06 | . | * | F | 1.98 | 3.51 |
| Leu | 351 | . | A | B | . | . | . | . | 1.69 | −0.91 | . | * | F | 1.09 | 0.94 |
| Gln | 352 | . | A | B | . | . | . | . | 1.09 | −0.51 | . | * | F | 0.96 | 0.98 |
| Glu | 353 | . | A | B | . | . | . | . | 1.04 | −0.26 | . | * | . | 0.72 | 0.40 |
| Cys | 354 | . | A | B | . | . | . | . | 1.04 | −0.26 | . | . | . | 0.93 | 0.82 |
| Asn | 355 | . | A | . | . | T | . | . | 0.33 | −0.51 | . | . | . | 1.84 | 0.73 |
| Leu | 356 | . | . | . | . | T | . | . | 0.93 | −0.34 | . | . | F | 2.10 | 0.23 |
| Asp | 357 | . | . | . | . | . | T | C | 0.34 | 0.09 | . | * | F | 1.29 | 0.65 |
| Pro | 358 | . | . | . | . | T | T | . | 0.46 | 0.01 | . | * | F | 1.28 | 0.41 |
| Cys | 359 | . | . | . | . | . | T | C | 0.83 | −0.39 | * | * | F | 1.47 | 0.97 |
| Pro | 360 | . | . | . | . | . | T | C | 0.83 | −0.16 | . | * | . | 1.11 | 0.61 |
| Ala | 361 | . | A | . | . | T | . | . | 1.06 | −0.16 | . | * | . | 0.70 | 0.68 |
| Arg | 362 | . | A | B | . | . | . | . | 0.74 | −0.09 | . | * | . | 0.45 | 1.29 |
| Trp | 363 | . | A | B | . | . | . | . | 0.74 | −0.17 | . | * | . | 0.45 | 1.20 |
| Glu | 364 | . | A | B | . | . | . | . | 1.12 | −0.17 | . | * | . | 0.45 | 1.84 |
| Ala | 365 | . | A | . | . | T | . | C | 1.02 | 0.24 | . | * | . | 0.10 | 0.99 |
| Thr | 366 | . | A | . | . | . | . | C | 1.02 | 0.73 | . | * | F | −0.10 | 1.36 |
| Pro | 367 | . | A | . | . | T | . | . | 0.24 | 0.31 | . | * | F | 0.25 | 0.79 |
| Trp | 368 | . | . | . | . | T | . | . | 0.23 | 0.89 | . | . | . | 0.00 | 0.42 |
| Thr | 369 | . | . | . | . | T | T | . | −0.07 | 0.77 | . | . | . | 0.20 | 0.39 |
| Ala | 370 | . | . | . | . | T | T | . | 0.22 | 0.67 | . | . | . | 0.20 | 0.34 |
| Cys | 371 | . | . | . | . | T | T | . | −0.13 | 0.63 | . | . | . | 0.20 | 0.43 |
| Ser | 372 | . | . | . | . | T | T | . | −0.27 | 0.29 | . | . | F | 0.65 | 0.16 |
| Ser | 373 | . | . | . | . | T | . | . | −0.32 | 0.23 | . | . | F | 0.45 | 0.16 |
| Ser | 374 | . | . | . | . | T | . | . | −0.36 | 0.16 | . | . | F | 0.45 | 0.29 |
| Cys | 375 | . | . | . | . | T | T | . | −0.66 | 0.01 | . | . | F | 0.65 | 0.21 |
| Gly | 376 | . | . | . | . | T | T | . | 0.01 | 0.31 | . | . | F | 0.65 | 0.11 |
| Gly | 377 | . | . | . | . | T | T | . | 0.01 | 0.33 | . | * | F | 0.65 | 0.14 |
| Gly | 378 | . | . | . | . | T | T | . | 0.42 | 0.33 | . | * | F | 0.65 | 0.36 |
| Ile | 379 | . |  | B | B | . | . | . | 0.13 | −0.24 | . | * | F | 0.45 | 0.72 |
| Gln | 380 | . | . | B | B | . | . | . | −0.06 | −0.17 | . | * | F | 0.45 | 0.73 |
| Ser | 381 | . | . | B | B | . | . | . | −0.01 | 0.04 | . | * | F | −0.15 | 0.55 |
| Arg | 382 | . | . | B | B | . | . | . | −0.33 | 0.00 | * | * | F | 0.60 | 1.05 |
| Ala | 383 | . | . | B | B | . | . | . | −0.84 | −0.11 | * | * | . | 0.30 | 0.32 |
| Val | 384 | . | . | B | B | . | . | . | 0.04 | 0.13 | * | * | . | −0.30 | 0.18 |
| Ser | 385 | . | . | B | B | . | . | . | 0.04 | −0.26 | * | * | . | 0.30 | 0.16 |
| Cys | 386 | . | . | B | B | . | . | . | 0.34 | −0.26 | * | * | . | 0.56 | 0.27 |
| Val | 387 | . | . | B | B | . | . | . | −0.66 | −0.76 | * | * | . | 1.12 | 0.61 |
| Glu | 388 | . | . | B | B | . | . | . | −0.07 | −0.7i | * | * | F | 1.53 | 0.32 |
| Glu | 389 | . | . | B | . | . | . | . | 0.44 | −0.70 | * | * | F | 2.14 | 1.03 |
| Asp | 390 | . | . | . | B | T | . | . | 0.71 | −0.84 | * | * | F | 2.60 | 1.38 |
| Ile | 391 | . | . | B | B | . | . | . | 0.52 | −0.99 | * | * | F | 1.94 | 1.08 |
| Gln | 392 | . | . | . | B | T | . | . | 1.07 | −0.34 | * | * | F | 1.63 | 0.46 |
| Gly | 393 | . | . | . | B | . | . | C | 0.77 | 0.14 | * | * | F | 0.57 | 0.40 |
| His | 394 | . | . | . | B | . | . | C | −0.09 | 0.53 | * | * | . | −0.14 | 0.77 |
| Val | 395 | . | . | . | B | . | . | C | −0.09 | 0.49 | * | * | . | −0.40 | 0.33 |
| Thr | 396 | . | . | . | B | . | . | C | 0.80 | 0.09 | * | * | F | 0.05 | 0.58 |
| Ser | 397 | . | A | . | . | . | . | C | 0.51 | −0.34 | . | . | F | 0.65 | 0.73 |
| Val | 398 | . | A | B | . | . | . | . | 0.90 | 0.07 | . | . | F | 0.00 | 1.04 |
| Glu | 399 | . | A | . | . | T | . | . | 0.27 | −0.57 | . | . | F | 1.30 | 1.44 |
| Glu | 400 | . | A | . | . | T | . | . | 0.52 | −0.49 | . | . | F | 0.85 | 0.58 |
| Trp | 401 | . | A | . | . | T | . | . | 0.59 | −0.26 | . | . | . | 0.70 | 0.77 |
| Lys | 402 | . | A | . | . | T | . | . | 0.58 | −0.14 | . | . | . | 0.70 | 0.69 |
| Cys | 403 | . | A | . | . | T | . | . | 1.22 | 0.34 | . | * | . | 0.10 | 0.58 |
| Met | 404 | . | A | . | . | T | . | . | 1.27 | 0.77 | . | * | . | −0.20 | 0.85 |
| Tyr | 405 | . | A | . | . | T | . | . | 0.67 | −0.14 | . | * | . | 0.70 | 0.85 |
| Thr | 406 | . | . | . | . | . | T | C | 0.74 | 0.47 | . | * | . | 0.15 | 1.57 |
| Pro | 407 | . | . | . | . | T | T | . | −0.19 | 0.33 | . | * | F | 0.80 | 2.45 |
| Lys | 408 | . | . | . | . | T | T | . | −0.11 | 0.40 | . | . | F | 0.80 | 1.10 |
| Met | 409 | . | . | B | . | . | T | . | 0.49 | 0.14 | . | . | . | 0.10 | 0.77 |
| Pro | 410 | . | . | B | . | . | . | . | 0.52 | 0.06 | . | . | . | −0.10 | 0.86 |
| Ile | 411 | . | . | B | . | . | . | . | 0.17 | 0.06 | . | . | . | −0.10 | 0.67 |
| Ala | 412 | . | . | B | . | . | . | . | 0.38 | 0.63 | . | * | . | −0.40 | 0.36 |
| Gln | 413 | . | . | B | . | . | T | . | −0.56 | 0.41 | * | . | . | −0.20 | 0.37 |
| Pro | 414 | . | . | B | . | . | T | . | −0.66 | 0.67 | * | . | . | −0.20 | 0.37 |
| Cys | 415 | . | . | B | . | . | T | . | −0.44 | 0.77 | * | . | . | −0.20 | 0.32 |
| Asn | 416 | . | . | B | . | . | T | . | −0.22 | 0.27 | * | . | . | 0.10 | 0.31 |
| Ile | 417 | . | . | B | . | . | . | . | 0.16 | 0.44 | . | . | . | −0.40 | 0.11 |
| Phe | 418 | . | . | B | . | . | . | . | 0.20 | 0.44 | . | . | . | −0.40 | 0.31 |
| Asp | 419 | . | . | . | . | T | . | . | 0.12 | −0.13 | * | . | . | 0.90 | 0.39 |
| Cys | 420 | . | . | B | . | . | T | . | −0.02 | 0.39 | * | . | . | 0.10 | 0.58 |
| Pro | 421 | . | . | . | . | T | T | . | −0.61 | 0.39 | * | . | . | 0.50 | 0.55 |
| Lys | 422 | . | . | . | . | T | T | . | 0.28 | 0.10 | * | . | . | 0.50 | 0.33 |
| Trp | 423 | . | . | . | . | T | T | . | 0.98 | 0.50 | * | . | . | 0.35 | 1.08 |
| Leu | 424 | . | A | . | . | . | . | C | 0.69 | −0.07 | * | . | . | 0.65 | 1.20 |
| Ala | 425 | . | A | . | . | T | . | . | 1.06 | 0.41 | * | . | . | −0.20 | 0.63 |
| Gln | 426 | . | A | . | . | T | . | . | 1.06 | 0.80 | * | . | . | −0.20 | 0.81 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Glu | 427 | . | A | . | . | T | . | . | 0.34 | 0.31 | * | . | . | 0.25 | 1.51 |
| Trp | 428 | . | A | . | . | T | . | . | 0.32 | 0.20 | . | . | F | 0.25 | 0.80 |
| Ser | 429 | . | . | . | . | . | T | C | 0.28 | 0.19 | . | . | F | 0.45 | 0.67 |
| Pro | 430 | . | . | . | . | T | T | . | 0.56 | 0.43 | . | . | F | 0.35 | 0.29 |
| Cys | 431 | . | . | . | . | T | T | . | −0.11 | 0.91 | . | . | . | 0.20 | 0.39 |
| Thr | 432 | . | . | B | . | . | T | | −0.46 | 0.57 | . | . | . | −0.20 | 0.16 |
| Val | 433 | . | . | B | B | . | . | . | −0.17 | 0.61 | . | . | . | −0.60 | 0.10 |
| Thr | 434 | . | . | B | B | . | . | . | −0.21 | 0.59 | . | . | . | −0.60 | 0.33 |
| Cys | 435 | . | . | B | B | . | . | . | −0.81 | 0.44 | * | . | F | −0.45 | 0.22 |
| Gly | 436 | . | . | . | . | T | T | . | −0.03 | 0.64 | * | * | F | 0.35 | 0.25 |
| Gln | 437 | . | . | B | . | . | T | . | 0.03 | 0.00 | . | * | F | 0.85 | 0.34 |
| Gly | 438 | . | . | . | . | T | T | . | 1.00 | 0.27 | . | * | F | 0.65 | 0.98 |
| Len | 439 | . | . | B | . | . | T | . | 0.46 | −0.30 | . | * | . | 0.85 | 1.95 |
| Arg | 440 | . | . | B | B | . | . | | 0.27 | −0.09 | . | * | . | 0.30 | 0.83 |
| Tyr | 441 | . | . | B | B | . | . | . | −0.20 | 0.16 | . | * | . | −0.30 | 0.63 |
| Arg | 442 | . | . | B | B | . | . | . | −0.87 | 0.41 | . | * | . | −0.60 | 0.63 |
| Val | 443 | . | | B | B | . | . | . | −1.41 | 0.30 | . | * | . | −0.30 | 0.17 |
| Val | 444 | . | . | B | B | . | . | . | −0.60 | 0.99 | . | * | . | −0.60 | 0.08 |
| Len | 445 | . | . | B | B | . | . | . | −0.74 | 0.23 | . | * | . | −0.30 | 0.07 |
| Cys | 446 | . | . | B | B | . | . | . | −0.39 | 0.73 | * | * | . | −0.35 | 0.12 |
| Ile | 447 | . | . | B | B | . | . | . | −0.84 | 0.09 | * | * | . | 0.20 | 0.32 |
| Asp | 448 | . | . | B | . | . | T | . | −0.59 | −0.13 | * | * | . | 1.45 | 0.38 |
| His | 449 | . | . | . | . | T | T | . | 0.23 | −0.20 | * | * | . | 2.10 | 0.70 |
| Arg | 450 | . | . | . | . | T | T | . | 0.73 | −0.27 | * | * | . | 2.50 | 1.36 |
| Gly | 451 | . | . | . | . | T | T | . | 1.06 | −0.47 | . | * | . | 2.25 | 1.18 |
| Met | 452 | . | . | . | . | T | . | . | 1.60 | −0.04 | . | * | . | 1.65 | 0.85 |
| His | 453 | . | . | . | . | T | T | . | 0.93 | −0.11 | . | . | . | 1.60 | 0.43 |
| Thr | 454 | . | . | . | . | T | T | . | 0.67 | 0.46 | * | . | F | 0.60 | 0.23 |
| Gly | 455 | . | . | . | . | T | T | . | 0.34 | 0.41 | * | . | F | 0.69 | 0.32 |
| Gly | 456 | . | . | . | . | T | T | . | 0.73 | 0.23 | . | . | F | 1.33 | 0.36 |
| Cys | 457 | . | . | . | . | T | . | . | 1.02 | −0.27 | . | * | F | 2.07 | 0.50 |
| Ser | 458 | . | . | . | . | . | T | C | 1.10 | −0.27 | . | * | F | 2.41 | 0.73 |
| Pro | 459 | . | . | . | . | T | T | . | 1.20 | −0.70 | . | * | F | 3.40 | 1.47 |
| Lys | 460 | . | . | . | . | T | T | . | 1.51 | −0.70 | . | * | F | 3.06 | 4.24 |
| Thr | 461 | . | . | . | . | . | T | C | 0.97 | −0.77 | . | * | F | 2.52 | 4.30 |
| Lys | 462 | . | . | . | . | . | . | C | 1.68 | −0.47 | . | * | F | 1.68 | 1.95 |
| Pro | 463 | . | . | . | . | . | . | C | 1.98 | −0.90 | . | * | F | 1.64 | 1.95 |
| His | 464 | . | A | . | . | T | . | . | 2.19 | −0.90 | . | * | F | 1.30 | 2.34 |
| Ile | 465 | . | A | B | . | . | . | . | 1.48 | −1.39 | . | * | F | 0.90 | 2.03 |
| Lys | 466 | . | A | B | . | . | . | . | 0.90 | −0.81 | . | * | F | 0.75 | 0.70 |
| Glu | 467 | . | A | B | . | . | . | . | 0.00 | −0.56 | . | * | F | 0.75 | 0.36 |
| Glu | 468 | . | A | B | B | . | . | . | 0.00 | −0.41 | . | * | . | 0.30 | 0.38 |
| Cys | 469 | . | A | B | B | . | . | . | −0.28 | −0.67 | . | * | . | 0.60 | 0.30 |
| Ile | 470 | . | A | B | B | . | . | . | 0.40 | −0.19 | . | . | . | 0.30 | 0.25 |
| Val | 471 | . | A | B | B | . | . | . | −0.31 | 0.24 | . | . | . | −0.30 | 0.22 |
| Pro | 472 | . | A | B | B | . | . | . | −0.56 | 0.81 | . | . | F | −0.45 | 0.22 |
| Thr | 473 | . | . | B | . | . | T | . | −0.51 | 1.00 | . | . | F | −0.05 | 0.49 |
| Pro | 474 | . | . | . | . | T | T | . | −0.06 | 0.31 | . | * | F | 0.80 | 1.33 |
| Cys | 475 | . | . | . | . | T | T | . | 0.88 | 0.10 | . | . | F | 0.80 | 1.33 |
| Tyr | 476 | . | . | . | . | T | T | . | 1.73 | −0.33 | . | * | F | 1.40 | 1.84 |
| Lys | 477 | . | A | . | . | . | . | C | 1.99 | −0.81 | * | * | F | 1.10 | 2.06 |
| Pro | 478 | . | A | . | . | T | . | . | 1.49 | −1.24 | * | * | F | 1.30 | 7.69 |
| Lys | 479 | . | A | . | . | T | . | . | 1.49 | −1.13 | . | * | F | 1.30 | 4.05 |
| Glu | 480 | . | A | B | . | . | . | . | 1.30 | −1.46 | . | * | F | 0.90 | 3.13 |
| Lys | 481 | . | A | B | . | . | . | . | 1.54 | −0.81 | . | * | F | 0.90 | 1.50 |
| Leu | 482 | . | A | B | . | . | . | . | 0.91 | −1.24 | . | * | F | 0.90 | 1.30 |
| Pro | 483 | . | A | B | . | . | . | . | 1.17 | −0.74 | . | * | . | 0.60 | 0.76 |
| Val | 484 | . | A | B | . | . | . | . | 0.31 | −0.74 | . | * | . | 0.60 | 0.76 |
| Glu | 485 | A | A | . | . | . | . | . | 0.10 | −0.06 | . | * | . | 0.30 | 0.76 |
| Ala | 486 | . | A | B | . | . | . | . | −0.23 | −0.31 | . | * | . | 0.30 | 0.76 |
| Lys | 487 | A | A | . | . | . | . | . | −0.12 | 0.17 | . | * | . | −0.15 | 1.08 |
| Leu | 488 | . | A | . | . | . | . | C | 0.13 | 0.31 | . | * | . | −0.10 | 0.54 |
| Pro | 489 | . | A | . | . | T | . | . | 0.99 | 0.31 | . | * | . | 0.25 | 1.06 |
| Trp | 490 | . | A | . | . | T | . | . | 0.40 | 0.21 | . | * | . | 0.10 | 0.92 |
| Phe | 491 | A | A | . | . | . | . | . | 0.99 | 0.71 | . | . | . | −0.45 | 1.13 |
| Lys | 492 | A | A | . | . | . | . | . | 0.94 | 0.43 | . | . | F | −0.30 | 1.26 |
| Gln | 493 | . | A | . | . | . | . | C | 0.94 | 0.00 | * | . | F | 0.80 | 2.08 |
| Ala | 494 | . | A | . | . | . | . | C | 1.16 | −0.23 | * | . | F | 0.80 | 1.98 |
| Gln | 495 | . | A | . | . | . | . | C | 1.44 | −1.01 | * | . | F | 1.10 | 1.72 |
| Gln | 496 | . | A | . | . | . | . | C | 1.80 | −1.01 | * | . | F | 1.10 | 1.72 |
| Len | 497 | A | A | . | . | . | . | . | 1.17 | −0.99 | * | . | F | 0.90 | 1.68 |
| Glu | 498 | A | A | . | . | . | . | . | 0.58 | −0.99 | . | . | F | 0.75 | 0.98 |
| Gln | 499 | A | A | . | . | . | . | . | 0.31 | −0.89 | . | . | F | 0.75 | 0.57 |
| Gly | 500 | A | A | . | . | . | . | . | 0.01 | −0.24 | . | . | F | 0.45 | 0.52 |
| Ala | 501 | A | A | . | . | . | . | . | 0.01 | −0.54 | . | . | . | 0.60 | 0.40 |
| Ala | 502 | A | A | . | . | . | . | . | 0.82 | −0.54 | . | . | . | 0.60 | 0.40 |
| Val | 503 | A | A | . | . | . | . | . | 0.61 | −0.54 | . | . | . | 0.85 | 0.70 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Ser | 504 | A | A | . | . | . | . | . | 0.31 | −0.54 | . | . | F | 1.40 | 1.07 |
| Glu | 505 | . | A | B | . | . | . | . | −0.04 | −0.66 | . | . | F | 1.65 | 1.42 |
| Glu | 506 | . | . | B | . | . | T | . | −0.34 | −0.37 | . | . | F | 2.00 | 1.65 |
| Pro | 507 | . | . | . | . | T | T | . | 0.03 | −0.33 | * | . | F | 2.50 | 0.86 |
| Ser | 508 | . | . | . | . | T | T | . | 0.93 | −0.29 | * | . | F | 2.25 | 0.77 |
| Phe | 509 | . | . | B | . | . | T | . | 0.64 | −0.29 | * | . | . | 1.45 | 0.89 |
| Lie | 510 | . | . | B | . | . | . | . | 0.36 | 0.21 | * | . | . | 0.40 | 0.58 |
| Pro | 511 | . | . | . | . | T | . | . | 0.06 | 0.70 | * | . | . | 0.25 | 0.46 |
| Lys | 512 | . | . | . | . | T | . | . | −0.32 | 0.70 | * | . | . | 0.00 | 0.71 |
| Ala | 513 | . | . | . | . | T | . | . | −0.69 | 0.41 | * | . | . | 0.15 | 1.02 |
| Trp | 514 | . | . | . | . | T | . | . | −0.30 | 0.30 | . | . | . | 0.30 | 0.35 |
| Ser | 515 | . | . | B | . | . | T | . | −0.27 | 0.36 | . | . | . | 0.10 | 0.26 |
| Ala | 516 | . | . | B | . | . | T | . | −0.37 | 1.00 | . | . | . | −0.20 | 0.19 |
| Cys | 517 | . | . | B | . | . | T | . | −1.08 | 0.99 | . | . | . | −0.20 | 0.26 |
| Thr | 518 | . | . | B | . | . | T | . | −0.83 | 0.64 | . | . | . | −0.20 | 0.10 |
| Val | 519 | . | . | B | B | . | . | . | −1.40 | 0.69 | . | . | . | −0.60 | 0.10 |
| Thr | 520 | . | . | B | B | . | . | . | −1.44 | 0.83 | . | . | . | −0.60 | 0.14 |
| Cys | 521 | . | . | B | B | . | . | . | −1.17 | 0.69 | . | . | . | −0.60 | 0.10 |
| Gly | 522 | . | . | . | B | T | . | . | −0.50 | 0.69 | . | * | . | −0.20 | 0.19 |
| Val | 523 | . | . | B | B | . | . | . | −1.04 | 0.44 | * | * | . | −0.60 | 0.22 |
| Gly | 524 | . | . | B | B | . | . | . | −0.08 | 0.60 | * | * | F | −0.45 | 0.31 |
| Thr | 525 | . | . | B | B | . | . | . | −0.66 | 0.03 | * | * | F | −0.15 | 0.61 |
| Gln | 526 | . | . | B | B | . | . | . | −0.84 | 0.29 | * | * | F | −0.15 | 0.58 |
| Val | 527 | . | . | B | B | . | . | . | −0.39 | 0.29 | * | * | . | −0.30 | 0.43 |
| Atg | 528 | . | . | B | B | . | . | . | −0.20 | −0.14 | * | * | . | 0.30 | 0.59 |
| Ile | 529 | . | . | B | B | . | . | . | 0.14 | −0.06 | * | * | . | 0.30 | 0.18 |
| Val | 530 | . | . | B | B | . | . | . | −0.40 | −0.06 | * | * | . | 0.30 | 0.42 |
| Arg | 531 | . | . | B | B | . | . | . | −1.21 | −0.06 | * | * | . | 0.30 | 0.16 |
| Cys | 532 | . | . | B | B | . | . | . | −1.17 | 0.63 | * | * | . | −0.60 | 0.19 |
| Gln | 533 | . | . | B | B | . | . | . | −1.58 | 0.63 | * | * | . | −0.60 | 0.21 |
| Val | 534 | . | . | B | B | . | . | . | −1.39 | 0.37 | . | * | . | −0.30 | 0.14 |
| Leu | 535 | . | . | B | B | . | . | . | −0.83 | 1.16 | . | * | . | −0.60 | 0.23 |
| Leu | 536 | . | . | B | B | . | . | . | −0.94 | 0.97 | . | * | . | −0.60 | 0.18 |
| Ser | 537 | . | . | B | B | . | . | . | −0.58 | 0.97 | * | * | . | −0.60 | 0.42 |
| Phe | 538 | . | . | B | B | . | . | . | −1.43 | 0.71 | * | * | . | −0.60 | 0.68 |
| Ser | 539 | . | . | B | B | . | . | . | −1.17 | 0.67 | * | . | F | −0.45 | 0.61 |
| Gln | 540 | . | . | B | B | . | . | . | −0.36 | 0.49 | * | . | F | −0.45 | 0.46 |
| Ser | 541 | . | . | B | B | . | . | . | −0.36 | 0.10 | * | . | F | −0.15 | 0.89 |
| Val | 542 | . | . | B | B | . | . | . | −0.27 | 0.00 | * | * | . | 0.30 | 0.55 |
| Ala | 543 | . | . | B | B | . | . | . | −0.46 | 0.04 | * | * | . | −0.30 | 0.49 |
| Asp | 544 | . | . | B | B | . | . | . | −0.16 | 0.33 | . | * | . | −0.30 | 0.26 |
| Leu | 545 | . | . | B | B | . | . | . | −0.16 | −0.06 | * | * | . | 0.30 | 0.58 |
| Pro | 546 | . | . | B | . | . | . | . | −0.52 | −0.70 | * | . | . | 0.80 | 0.99 |
| Ile | 547 | . | . | B | . | . | . | . | 0.33 | −0.63 | . | . | . | 0.80 | 0.32 |
| Asp | 548 | . | . | B | . | . | . | . | 0.58 | −0.63 | . | * | F | 0.95 | 0.67 |
| Glu | 549 | . | . | B | . | . | . | . | 0.37 | −0.89 | . | . | F | 1.29 | 0.43 |
| Cys | 550 | . | . | . | . | T | . | . | 1.22 | −0.89 | . | . | F | 2.03 | 0.94 |
| Glu | 551 | . | . | . | . | T | . | . | 1.22 | −1.57 | . | . | F | 2.52 | 1.13 |
| Gly | 552 | . | . | . | . | . | T | C | 1.52 | −1.14 | . | . | F | 2.86 | 1.01 |
| Pro | 553 | . | . | . | . | T | T | . | 1.22 | −0.64 | . | . | F | 3.40 | 1.90 |
| Lys | 554 | . | . | . | . | . | T | C | 1.22 | −0.83 | . | . | F | 2.86 | 1.47 |
| Pro | 555 | . | . | . | . | T | T | . | 2.00 | −0.43 | * | | F | 2.42 | 2.57 |
| Ala | 556 | . | A | . | . | T | . | . | 1.41 | −0.86 | * | | F | 1.98 | 3.26 |
| Ser | 557 | . | A | B | . | . | . | . | 1.09 | −0.79 | . | . | F | 1.24 | 1.64 |
| Gln | 558 | . | A | B | . | . | . | . | 1.06 | −0.21 | * | . | F | 0.45 | 0.57 |
| Arg | 559 | . | A | B | . | . | . | . | 0.42 | 0.11 | * | . | F | −0.15 | 0.88 |
| Ala | 560 | . | . | B | . | . | . | . | 0.29 | 0.11 | . | . | . | −0.10 | 0.67 |
| Cys | 561 | . | . | B | . | . | . | . | 0.67 | 0.16 | . | * | . | −0.10 | 0.38 |
| Tyr | 562 | . | . | B | . | . | . | . | 0.30 | 0.19 | . | . | . | −0.10 | 0.30 |
| Ala | 563 | . | . | B | . | T | . | . | 0.00 | 0.76 | * | . | . | 0.00 | 0.16 |
| Gly | 564 | . | . | . | . | . | T | C | −0.46 | 0.64 | * | * | . | 0.00 | 0.40 |
| Pro | 565 | . | . | . | . | T | T | . | 0.13 | 0.50 | . | * | F | 0.35 | 0.25 |
| Cys | 566 | . | . | . | . | T | T | . | −0.09 | −0.26 | . | * | F | 1.25 | 0.43 |
| Ser | 567 | . | . | . | . | T | T | . | −0.06 | −0.07 | . | . | F | 1.25 | 0.31 |
| Gly | 568 | . | . | B | . | . | . | . | 0.53 | −0.07 | . | . | F | 0.65 | 0.31 |
| Glu | 569 | . | . | B | . | . | . | . | 0.18 | −0.50 | . | . | F | 0.65 | 0.99 |
| Ile | 570 | . | . | B | . | . | . | . | 0.39 | −0.29 | . | . | F | 0.95 | 0.64 |
| Pro | 571 | . | . | B | . | . | . | . | 0.84 | −0.27 | . | * | F | 1.40 | 1.04 |
| Glu | 572 | . | . | . | . | T | . | . | 1.14 | −0.27 | . | . | F | 1.95 | 0.93 |
| Phe | 573 | . | . | . | . | . | . | C | 1.49 | −0.27 | . | . | F | 2.20 | 2.21 |
| Asn | 574 | . | . | . | . | . | T | C | 1.18 | −0.96 | . | . | F | 3.00 | 2.47 |
| Pro | 575 | . | . | . | . | . | T | C | 2.07 | −0.90 | . | . | F | 2.70 | 2.06 |
| Asp | 576 | . | . | . | . | T | T | . | 1.93 | −0.90 | . | . | F | 2.85 | 3.97 |
| Glu | 577 | . | . | . | . | T | T | . | 1.12 | −1.26 | . | * | F | 2.80 | 2.45 |
| Thr | 578 | . | . | . | . | T | T | . | 1.12 | −0.97 | . | . | F | 2.75 | 1.30 |
| Asp | 579 | . | . | . | . | T | T | . | 0.78 | −0.61 | . | . | F | 2.55 | 0.68 |
| Gly | 580 | . | . | . | . | T | T | . | 0.64 | −0.19 | . | . | F | 2.50 | 0.39 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 581 | . | . | B | . | . | T | . | −0.17 | 0.24 | * | . | . | 1.10 | 0.26 |
| Phe | 582 | . | . | B | . | . | . | . | −0.17 | 0.44 | * | . | . | 0.35 | 0.13 |
| Gly | 583 | . | . | . | . | . | . | C | 0.14 | 0.84 | * | . | . | 0.30 | 0.23 |
| Gly | 584 | . | A | . | . | . | . | C | −0.56 | 0.41 | * | . | F | 0.00 | 0.46 |
| Leu | 585 | . | A | . | . | . | . | C | −0.21 | 0.51 | * | . | F | −0.25 | 0.46 |
| Gln | 586 | . | A | . | . | . | . | C | 0.60 | −0.27 | * | . | F | 0.65 | 0.78 |
| Asp | 587 | . | A | B | . | . | . | . | 0.49 | −0.70 | * | . | F | 0.90 | 1.37 |
| Phe | 588 | . | A | B | . | . | . | . | 0.59 | −0.44 | * | . | F | 0.60 | 1.37 |
| Asp | 589 | . | A | B | . | . | . | . | 0.93 | −0.37 | * | . | F | 0.60 | 1.24 |
| Glu | 590 | . | A | B | . | . | . | . | 1.46 | −0.77 | * | . | F | 0.90 | 1.24 |
| Leu | 591 | . | A | . | . | . | . | C | 1.46 | 0.14 | * | * | . | 0.05 | 1.50 |
| Tyr | 592 | . | A | . | . | . | . | C | 1.21 | −0.64 | * | * | . | 0.95 | 1.56 |
| Asp | 593 | . | A | . | . | T | . | . | 1.91 | 0.11 | * | * | . | 0.25 | 1.41 |
| Trp | 594 | . | A | . | . | T | . | . | 1.57 | 0.11 | * | . | . | 0.25 | 2.96 |
| Glu | 595 | A | A | . | . | . | . | . | 0.87 | −0.14 | * | . | . | 0.45 | 1.87 |
| lyr | 596 | . | . | . | . | T | . | . | 1.37 | −0.11 | * | * | . | 0.90 | 0.97 |
| Glu | 597 | . | . | . | . | T | . | . | 1.66 | 0.37 | * | * | . | 0.45 | 1.33 |
| Gly | 598 | . | . | . | . | T | . | . | 0.99 | −0.54 | . | * | F | 1.50 | 1.54 |
| Phe | 599 | . | . | . | . | T | . | . | 0.98 | 0.03 | . | * | F | 0.76 | 0.53 |
| Thr | 600 | . | . | . | . | T | T | . | 0.98 | −0.34 | * | . | F | 1.87 | 0.41 |
| Lys | 601 | . | . | . | . | T | T | . | 0.92 | −0.34 | * | . | F | 2.18 | 0.71 |
| Cys | 602 | . | . | . | . | T | T | . | 0.26 | −0.39 | * | . | F | 2.64 | 1.10 |
| 8cr | 603 | . | . | . | . | T | T | . | 0.26 | −0.60 | * | . | F | 3.10 | 0.41 |
| Gln | 604 | . | . | . | . | T | . | . | 0.61 | −0.66 | * | . | F | 2.59 | 0.20 |
| Ser | 605 | . | . | . | . | T | . | . | 0.58 | −0.23 | * | . | F | 1.98 | 0.37 |
| Cys | 606 | . | . | . | . | T | T | . | −0.32 | −0.37 | * | . | F | 2.00 | 0.28 |
| Gly | 607 | . | . | . | . | T | T | . | 0.34 | −0.11 | . | . | F | 1.82 | 0.12 |
| Gly | 608 | . | . | . | . | T | T | . | 0.64 | 0.29 | * | . | F | 1.04 | 0.15 |
| Gly | 609 | . | . | . | . | . | T | C | 0.06 | −0.10 | * | . | F | 1.57 | 0.49 |
| Val | 610 | . | . | B | . | . | . | . | −0.50 | −0.17 | . | . | F | 1.30 | 0.50 |
| Gln | 611 | . | . | B | . | . | . | . | −0.69 | 0.04 | . | . | F | 0.57 | 0.38 |
| Glu | 612 | . | . | B | . | . | . | . | −0.64 | 0.26 | . | . | . | 0.29 | 0.28 |
| Ala | 613 | . | . | B | B | . | . | . | −0.97 | 0.21 | . | . | . | −0.04 | 0.51 |
| Val | 614 | . | . | B | B | . | . | . | −1.43 | 0.14 | * | . | . | −0.17 | 0.16 |
| Val | 615 | . | . | B | B | . | . | . | −0.58 | 0.43 | * | . | . | −0.60 | 0.08 |
| 8cr | 616 | . | . | B | . | . | . | . | −0.53 | 0.83 | * | . | . | −0.40 | 0.12 |
| Cys | 617 | . | . | B | . | . | . | . | −0.53 | 0.33 | * | . | . | 0.16 | 0.32 |
| Leu | 618 | . | . | . | . | T | . | . | −0.26 | 0.09 | * | * | . | 0.82 | 0.76 |
| Asa | 619 | . | . | . | . | T | . | . | 0.71 | −0.07 | * | . | F | 1.83 | 0.81 |
| Lys | 620 | . | . | . | . | T | . | . | 1.57 | −0.46 | * | . | F | 2.24 | 2.98 |
| Gln | 621 | . | . | . | . | . | . | C | 1.66 | −1.03 | * | . | F | 2.60 | 6.25 |
| Thr | 622 | . | . | . | . | . | . | C | 1.73 | −1.29 | * | * | F | 2.34 | 6.01 |
| Arg | 623 | . | A | . | . | . | . | C | 2.54 | −1.19 | * | * | F | 1.88 | 3.04 |
| Glu | 624 | . | A | . | . | . | . | C | 2.54 | −1.19 | * | * | F | 1.62 | 3.04 |
| Pro | 625 | . | A | . | . | . | . | C | 2.50 | −1.59 | * | * | F | 1.36 | 3.64 |
| Ala | 626 | . | A | . | . | T | . | . | 1.69 | −1.67 | . | * | F | 1.30 | 2.99 |
| Gln | 627 | . | A | . | . | T | . | . | 1.33 | −0.99 | . | . | F | 1.30 | 1.42 |
| Glu | 628 | A | A | . | . | . | . | . | 0.37 | −0.41 | . | * | F | 0.45 | 0.49 |
| Asn | 629 | . | A | B | B | . | . | . | 0.06 | −0.20 | . | . | F | 0.45 | 0.36 |
| Leu | 630 | . | A | B | B | . | . | . | −0.03 | −0.21 | * | * | . | 0.58 | 0.30 |
| Cys | 631 | . | A | B | B | . | . | . | 0.67 | 0.17 | * | * | . | 0.26 | 0.23 |
| Val | 632 | . | A | B | B | . | . | . | 0.78 | 0.17 | * | * | . | 0.54 | 0.28 |
| Thr | 633 | . | . | B | . | . | T | . | 0.57 | −0.23 | * | . | F | 1.97 | 0.68 |
| Ser | 634 | . | . | . | . | T | T | . | 0.36 | −0.49 | * | * | F | 2.80 | 1.95 |
| Arg | 635 | . | . | . | . | T | T | . | 1.17 | −0.63 | * | . | F | 2.82 | 4.07 |
| Arg | 636 | . | . | B | . | . | T | . | 1.02 | −0.87 | * | . | F | 2.14 | 4.88 |
| Pro | 637 | . | . | . | . | . | T | C | 1.07 | −0.67 | * | . | F | 2.06 | 3.00 |
| Pro | 638 | . | . | . | . | T | T | . | 1.42 | −0.37 | * | . | F | 1.68 | 1.26 |
| Gln | 639 | . | . | . | . | T | T | . | 1.42 | −0.37 | * | . | F | 1.40 | 1.29 |
| Leu | 640 | . | . | B | . | . | T | . | 0.64 | 0.01 | * | . | F | 0.40 | 1.12 |
| Leu | 641 | . | . | B | . | . | T | . | 0.53 | 0.16 | * | * | F | 0.49 | 0.39 |
| Lys | 642 | . | . | B | . | . | T | . | −0.07 | 0.13 | . | . | F | 0.73 | 0.36 |
| Ser | 643 | . | . | B | . | . | T | . | 0.14 | 0.41 | . | . | F | 0.67 | 0.36 |
| Cys | 644 | . | . | . | . | T | T | . | −0.07 | −0.27 | . | . | . | 2.06 | 0.73 |
| Asn | 645 | . | . | . | . | T | . | . | 0.08 | −0.53 | . | . | . | 2.40 | 0.56 |
| Leu | 646 | . | . | . | . | T | . | . | 0.68 | 0.04 | . | . | F | 1.41 | 0.23 |
| Asp | 647 | . | . | . | . | . | T | C | 0.04 | 0.09 | * | . | F | 1.17 | 0.65 |
| Pro | 648 | . | . | . | . | T | T | . | 0.46 | 0.01 | * | * | F | 1.13 | 0.41 |
| Cys | 649 | . | . | . | . | . | T | C | 0.83 | −0.39 | * | * | F | 1.29 | 0.97 |
| Pro | 650 | . | . | B | . | . | T | . | 0.83 | −0.16 | . | * | . | 0.70 | 0.61 |
| Ala | 651 | . | A | B | . | . | . | . | 0.76 | −0.16 | . | * | . | 0.30 | 0.68 |
| Arg | 652 | . | A | B | . | . | . | . | 0.41 | 0.10 | . | * | . | −0.30 | 0.90 |
| Trp | 653 | . | A | B | . | . | . | . | 0.67 | −0.04 | . | * | . | 0.30 | 0.57 |
| Glu | 654 | . | A | B | . | . | . | . | 1.04 | −0.47 | . | * | . | 0.45 | 1.13 |
| Ile | 655 | . | A | . | . | T | . | . | 0.96 | −0.06 | . | * | . | 0.70 | 0.61 |
| Gly | 656 | . | A | . | . | T | . | . | 1.33 | 0.33 | . | * | F | 0.38 | 0.78 |
| Lys | 657 | . | . | . | . | T | . | . | 0.56 | −0.16 | . | * | F | 1.31 | 0.69 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Trp | 658 | . | . | . | . | T | . | . | 0.54 | 0.41 | * | . | F | 0.54 | 0.53 |
| Ser | 659 | . | . | . | . | . | T | C | −0.27 | 0.11 | * | . | F | 0.97 | 0.72 |
| Pro | 660 | . | . | . | . | T | T | . | 0.31 | 0.37 | * | . | F | 1.30 | 0.30 |
| Cys | 661 | . | . | . | . | T | T | . | −0.01 | 0.86 | . | . | . | 0.72 | 0.41 |
| Ser | 662 | . | . | . | . | T | T | . | −0.40 | 0.51 | . | . | . | 0.59 | 0.16 |
| Leu | 663 | . | . | B | B | . | . | . | −0.97 | 0.56 | . | . | . | −0.34 | 0.10 |
| Thr | 664 | . | . | B | B | . | . | . | −1.01 | 0.77 | . | . | . | −0.47 | 0.14 |
| Cys | 665 | . | . | B | B | . | . | . | −1.61 | 0.63 | . | * | . | −0.60 | 0.11 |
| Gly | 666 | . | . | B | B | . | . | . | −0.94 | 0.93 | . | * | . | −0.60 | 0.11 |
| Val | 667 | . | . | B | B | . | . | . | −0.96 | 0.64 | . | * | . | −0.60 | 0.13 |
| Gly | 668 | . | . | B | B | . | . | . | −0.03 | 0.64 | . | * | . | −0.60 | 0.34 |
| Leu | 669 | . | . | B | B | . | . | . | 0.28 | 0.07 | . | * | . | −0.30 | 0.68 |
| Gln | 670 | . | . | B | B | . | . | . | 0.09 | −0.36 | . | * | F | 0.60 | 1.53 |
| Thr | 671 | . | . | B | B | . | . | . | −0.27 | −0.36 | . | * | F | 0.60 | 1.15 |
| Arg | 672 | . | . | B | B | . | . | . | −0.08 | 0.00 | * | * | F | 0.00 | 1.20 |
| Asp | 673 | . | . | B | B | . | . | . | −0.03 | −0.11 | . | * | F | 0.45 | 0.37 |
| Va1 | 674 | . | . | B | B | . | . | . | 0.74 | −0.13 | . | * | . | 0.30 | 0.35 |
| Phe | 675 | . | . | B | B | . | . | . | −0.07 | −0.11 | . | . | . | 0.30 | 0.24 |
| Cys | 676 | . | . | B | . | . | T | . | −0.57 | 0.57 | . | . | . | −0.20 | 0.12 |
| Ser | 677 | . | . | B | . | . | T | . | −0.98 | 1.26 | . | . | . | −0.20 | 0.13 |
| His | 678 | . | . | B | . | . | T | . | −0.87 | 1.00 | . | . | . | −0.20 | 0.20 |
| Leu | 679 | . | . | . | . | . | T | C | −0.01 | 0.21 | . | . | . | 0.30 | 0.75 |
| Leu | 680 | . | A | . | . | . | . | C | 0.09 | −0.36 | * | . | . | 0.50 | 0.96 |
| Ser | 681 | . | A | . | . | . | . | C | 0.76 | −0.13 | * | . | F | 0.65 | 0.70 |
| Arg | 682 | . | A | . | . | . | . | C | 1.06 | −0.23 | * | . | F | 0.80 | 1.37 |
| Glu | 683 | . | A | . | . | . | . | C | 0.78 | −0.91 | * | . | F | 1.10 | 2.87 |
| Met | 684 | . | A | . | . | T | . | . | 0.73 | −1.11 | * | . | F | 1.30 | 3.09 |
| Asn | 685 | . | A | . | . | . | . | C | 0.66 | −0.86 | * | . | F | 1.10 | 1.17 |
| Glu | 686 | . | A | B | . | . | . | . | 0.14 | −0.17 | * | . | F | 0.45 | 0.47 |
| Thr | 687 | . | A | B | . | . | . | . | −0.56 | 0.51 | * | . | . | −0.60 | 0.40 |
| Val | 688 | . | A | B | . | . | . | . | −0.56 | 0.40 | . | . | . | −0.60 | 0.25 |
| Ile | 689 | . | A | B | . | . | . | . | 0.04 | 0.00 | . | . | . | −0.30 | 0.24 |
| Leu | 690 | . | A | B | . | . | . | . | −0.77 | 0.00 | . | . | . | −0.30 | 0.29 |
| Ala | 691 | A | A | . | . | . | . | . | −1.43 | 0.20 | * | . | . | −0.30 | 0.32 |
| Asp | 692 | A | A | . | . | . | . | . | −1.01 | 0.13 | * | . | . | −0.30 | 0.24 |
| Glu | 693 | . | A | B | . | . | . | . | −0.16 | −0.56 | * | . | . | 0.60 | 0.58 |
| Leu | 694 | . | A | B | . | . | . | . | 0.52 | −0.84 | * | . | . | 0.60 | 0.99 |
| Cys | 695 | . | A | . | . | T | . | . | 1.38 | −0.91 | * | . | F | 1.45 | 0.92 |
| Arg | 696 | . | A | . | . | T | . | . | 1.76 | −0.91 | * | . | F | 1.90 | 1.06 |
| Gln | 697 | . | A | . | . | . | . | C | 1.46 | −0.49 | * | . | F | 1.70 | 1.99 |
| Pro | 698 | . | A | . | . | T | . | . | 1.14 | −0.79 | * | . | F | 2.50 | 4.98 |
| Lys | 699 | . | . | . | . | . | T | C | 1.10 | −0.87 | * | . | F | 3.00 | 3.67 |
| Pro | 700 | . | . | . | . | T | T | . | 1.77 | −0.23 | . | . | F | 2.60 | 1.57 |
| Ser | 701 | . | . | . | . | T | T | . | 1.07 | −0.23 | . | . | F | 2.30 | 1.76 |
| Thr | 702 | . | . | B | . | . | T | . | 0.40 | −0.16 | . | . | F | 1.45 | 0.89 |
| Val | 703 | . | . | B | B | . | . | . | 0.61 | 0.41 | . | * | . | −0.30 | 0.31 |
| Gln | 704 | . | . | B | B | . | . | . | 0.68 | 0.39 | * | * | . | −0.30 | 0.37 |
| Ala | 705 | . | . | B | B | . | . | . | 0.19 | 0.00 | * | * | . | −0.30 | 0.50 |
| Cys | 706 | . | . | B | . | . | . | . | 0.49 | 0.30 | * | * | . | −0.10 | 0.59 |
| Asn | 707 | . | . | . | . | T | T | . | 0.13 | 0.06 | * | * | . | 0.50 | 0.54 |
| Arg | 708 | . | . | . | . | T | T | . | 0.78 | 0.23 | * | * | . | 0.50 | 0.29 |
| Phe | 709 | . | . | . | . | T | T | . | 0.57 | 0.16 | * | * | . | 0.50 | 0.83 |
| Asn | 710 | . | . | . | . | T | T | . | 0.57 | 0.01 | . | * | . | 0.50 | 0.80 |
| Cys | 711 | . | . | . | . | . | . | C | 0.94 | 0.11 | . | * | . | 0.10 | 0.41 |
| Pro | 712 | . | . | . | . | . | T | C | 0.70 | 1.03 | . | * | . | 0.00 | 0.50 |
| Pro | 713 | . | . | . | . | T | T | . | 0.38 | 1.00 | . | * | . | 0.20 | 0.49 |
| Ala | 714 | . | . | . | . | T | T | . | 0.49 | 1.03 | . | . | . | 0.35 | 1.41 |
| Trp | 715 | . | . | . | . | T | T | . | 0.49 | 0.96 | . | . | . | 0.20 | 0.92 |
| Tyr | 716 | . | . | B | . | . | T | . | 0.87 | 0.93 | . | * | . | −0.05 | 1.03 |
| Pro | 717 | . | . | . | . | T | T | . | 1.08 | 1.41 | . | * | . | 0.35 | 1.07 |
| Ala | 718 | . | . | . | . | T | T | . | 1.08 | 1.31 | . | * | . | 0.35 | 1.77 |
| Gln | 719 | . | . | . | . | T | T | . | 1.00 | 0.83 | . | . | . | 0.35 | 1.75 |
| Trp | 720 | . | . | . | . | T | . | . | 0.99 | 0.64 | * | * | . | 0.00 | 0.61 |
| Gln | 721 | . | . | B | . | . | T | C | 1.34 | 0.60 | * | * | . | 0.00 | 0.80 |
| Pro | 722 | . | . | . | . | T | T | . | 1.24 | 0.10 | * | * | F | 0.65 | 0.91 |
| Cys | 723 | . | . | . | . | T | T | . | 1.17 | 0.19 | * | * | F | 1.05 | 1.25 |
| Ser | 724 | . | . | . | . | T | T | . | 0.82 | −0.16 | * | * | F | 1.75 | 0.39 |
| Arg | 725 | . | . | . | . | T | . | . | 0.77 | −0.13 | * | * | F | 1.80 | 0.25 |
| Thr | 726 | . | . | . | . | T | . | . | 0.42 | −0.13 | * | . | F | 2.05 | 0.46 |
| Cys | 727 | . | . | . | . | T | T | . | −0.22 | −0.27 | * | . | F | 2.50 | 0.34 |
| Gly | 728 | . | . | . | . | T | T | . | 0.44 | −0.01 | * | . | F | 2.25 | 0.13 |
| Gly | 729 | . | . | . | . | T | T | . | 0.79 | 0.39 | . | * | F | 1.40 | 0.15 |
| Gly | 730 | . | . | . | . | . | T | C | 0.79 | −0.10 | . | . | F | 1.55 | 0.57 |
| Val | 731 | . | A | . | . | . | . | C | 1.10 | −0.67 | . | . | F | 1.35 | 1.13 |
| Gln | 732 | . | A | B | . | . | . | . | 0.91 | −1.10 | . | . | F | 0.90 | 1.98 |
| Lys | 733 | . | A | B | . | . | . | . | 0.44 | −0.89 | . | . | F | 0.90 | 1.48 |
| Arg | 734 | . | A | B | . | . | . | . | 0.12 | −0.63 | . | . | F | 0.90 | 1.65 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Glu | 735 | . | A | B | . | . | . | . | 0.51 | −0.70 | . | . | . | 0.60 | 0.51 |
| Val | 736 | . | A | B | . | . | . | . | 1.37 | −1.10 | . | * | . | 0.60 | 0.51 |
| Leu | 737 | . | A | B | . | . | . | . | 1.48 | −0.70 | . | * | . | 0.60 | 0.45 |
| Cys | 738 | . | A | B | . | . | . | . | 0.83 | −0.70 | * | * | . | 0.60 | 0.51 |
| Lys | 739 | . | A | B | . | . | . | . | 0.13 | −0.09 | * | . | F | 0.45 | 0.68 |
| Gln | 740 | . | A | B | . | . | . | . | 0.13 | −0.23 | . | * | F | 0.70 | 0.83 |
| Arg | 741 | . | A | B | . | . | . | . | 0.64 | −0.91 | . | . | F | 1.40 | 2.60 |
| Met | 742 | . | A | B | . | . | . | . | 1.16 | −1.06 | . | . | F | 1.65 | 1.28 |
| Ala | 743 | . | . | B | . | . | T | . | 1.12 | −0.67 | . | . | F | 2.15 | 0.99 |
| Asp | 744 | . | . | . | . | T | T | . | 0.27 | −0.29 | . | . | F | 2.50 | 0.44 |
| Gly | 745 | . | . | . | . | . | T | C | 0.27 | 0.40 | * | . | F | 1.15 | 0.37 |
| Ser | 746 | . | . | . | . | . | T | C | −0.66 | −0.21 | * | . | F | 1.80 | 0.63 |
| Phe | 747 | . | A | B | . | . | . | . | −0.27 | −0.03 | . | . | . | 0.80 | 0.31 |
| Leu | 748 | . | A | B | . | . | . | . | 0.32 | 0.40 | . | . | . | −0.35 | 0.48 |
| Glu | 749 | . | A | B | . | . | . | . | 0.01 | −0.03 | * | . | . | 0.30 | 0.63 |
| Leu | 750 | . | A | B | . | . | . | . | −0.34 | 0.07 | * | . | . | −0.15 | 1.04 |
| Pro | 751 | . | A | . | . | T | . | . | −0.71 | 0.07 | * | . | F | 0.40 | 1.10 |
| Glu | 752 | . | A | . | . | T | . | . | −0.31 | −0.04 | * | . | F | 0.85 | 0.34 |
| Thr | 753 | . | A | . | . | T | . | . | −0.09 | 0.34 | * | . | F | 0.25 | 0.55 |
| Phe | 754 | . | A | . | . | T | . | . | −0.39 | 0.16 | * | . | . | 0.10 | 0.36 |
| Cys | 755 | . | A | . | . | T | . | . | 0.47 | 0.11 | * | . | . | 0.10 | 0.28 |
| Ser | 756 | . | . | . | . | T | T | . | 0.47 | 0.11 | * | . | . | 0.50 | 0.39 |
| Ala | 757 | . | . | . | . | T | T | . | −0.12 | 0.06 | * | . | R | 0.65 | 0.69 |
| Ser | 758 | . | . | . | . | T | T | . | −0.48 | −0.23 | * | . | R | 1.40 | 1.30 |
| Lys | 759 | . | . | . | . | . | T | C | 0.22 | −0.23 | * | . | F | 1.05 | 0.52 |
| Pro | 760 | . | . | . | . | T | T | . | 0.89 | −0.21 | * | . | F | 1.25 | 0.89 |
| Ala | 761 | . | . | . | . | T | T | . | 0.60 | −0.31 | * | . | . | 1.25 | 1.15 |
| Cys | 762 | . | . | B | . | . | T | . | 0.52 | −0.20 | * | . | . | 1.01 | 0.58 |
| Gln | 763 | . | . | B | . | . | T | . | 0.87 | 0.37 | * | . | . | 0.72 | 0.20 |
| Gln | 764 | . | . | B | . | . | . | . | 0.87 | −0.06 | . | . | . | 1.43 | 0.40 |
| Ala | 765 | . | . | B | . | . | . | . | 1.08 | −0.56 | * | . | . | 2.19 | 1.49 |
| Cys | 766 | . | . | . | . | T | T | . | 1.67 | −1.13 | . | . | . | 3.10 | 1.44 |
| Lys | 767 | . | . | . | . | T | T | . | 1.67 | −1.53 | . | . | F | 2.94 | 1.38 |
| Lys | 768 | . | . | . | . | T | T | . | 1.46 | −1.36 | . | . | F | 2.48 | 0.73 |
| Asp | 769 | . | . | . | . | T | T | . | 1.16 | −1.43 | . | . | F | 2.57 | 2.12 |
| Asp | 770 | . | . | . | . | T | . | . | 1.74 | −1.61 | . | . | F | 2.31 | 1.42 |
| Cys | 771 | . | . | B | . | . | T | . | 2.12 | −1.61 | . | . | F | 2.05 | 1.23 |
| Pro | 772 | . | . | B | . | . | T | . | 1.27 | −0.70 | . | . | F | 2.15 | 0.77 |
| Ser | 773 | . | . | B | . | T | T | . | 0.41 | −0.01 | . | . | F | 2.50 | 0.38 |
| Glu | 774 | . | . | B | . | . | T | . | 0.11 | 0.67 | . | . | F | 0.95 | 0.59 |
| Trp | 775 | . | . | B | . | . | . | . | 0.11 | 0.49 | . | . | . | 0.35 | 0.51 |
| Leu | 776 | . | . | B | . | . | . | . | 0.49 | 0.06 | . | . | . | 0.40 | 0.64 |
| Leu | 777 | . | . | . | . | T | T | . | 0.30 | 0.59 | . | . | . | 0.45 | 0.39 |
| Ser | 778 | . | . | . | . | T | T | . | 0.69 | 1.07 | * | . | F | 0.35 | 0.53 |
| Asp | 779 | . | . | . | . | T | T | . | 0.02 | 0.16 | * | . | F | 0.80 | 1.11 |
| Trp | 780 | . | . | . | . | T | T | . | 0.01 | 0.04 | . | . | F | 0.65 | 0.72 |
| Thr | 781 | . | . | . | . | T | . | . | 0.51 | −0.26 | * | . | F | 1.30 | 0.72 |
| Glu | 782 | . | . | . | . | T | . | . | 1.02 | −0.16 | * | . | F | 1.55 | 0.62 |
| Cys | 783 | . | . | . | . | T | . | . | 0.66 | 0.23 | . | . | F | 1.20 | 0.80 |
| Ser | 784 | . | . | . | . | T | . | . | 0.31 | −0.11 | * | . | F | 2.05 | 0.30 |
| Thr | 785 | . | . | . | . | T | T | . | 0.60 | −0.17 | . | . | F | 2.50 | 0.17 |
| Ser | 786 | . | . | . | . | T | T | . | 0.57 | −0.17 | . | . | F | 2.25 | 0.55 |
| Cys | 787 | . | . | . | . | T | T | . | 0.26 | −0.31 | . | . | F | 2.30 | 0.40 |
| Gly | 788 | . | . | . | . | T | T | . | 0.92 | −0.21 | . | . | F | 2.35 | 0.40 |
| Glu | 789 | . | . | . | . | T | . | . | 0.91 | −0.30 | . | . | F | 2.20 | 0.52 |
| Gly | 790 | . | . | . | . | T | . | . | 1.33 | −0.20 | . | . | F | 2.40 | 1.40 |
| Thr | 791 | . | . | . | . | T | . | . | 1.33 | −0.77 | . | . | F | 3.00 | 2.78 |
| Gln | 792 | . | . | B | . | . | T | . | 1.41 | −0.81 | . | * | F | 2.50 | 2.15 |
| Thr | 793 | . | . | B | . | . | T | . | 0.87 | −0.31 | . | . | F | 1.90 | 2.19 |
| Arg | 794 | . | . | B | . | . | T | . | 0.20 | −0.06 | * | . | F | 1.60 | 1.06 |
| Ser | 795 | . | . | B | . | . | T | . | 0.66 | 0.03 | . | . | F | 0.55 | 0.33 |
| Ala | 796 | . | A | B | . | . | . | . | 1.01 | −0.37 | . | * | . | 0.30 | 0.45 |
| Ile | 797 | . | A | B | . | . | . | . | 0.41 | −0.86 | . | * | . | 0.60 | 0.46 |
| Cys | 798 | . | A | B | . | . | . | . | −0.09 | −0.24 | . | * | . | 0.30 | 0.34 |
| Arg | 799 | . | A | B | . | . | . | . | −0.16 | 0.06 | . | * | . | −0.30 | 0.28 |
| Lys | 800 | . | A | B | . | . | . | . | −0.17 | −0.44 | * | . | . | 0.30 | 0.79 |
| Met | 801 | . | A | B | . | . | . | . | 0.08 | −0.64 | * | . | . | 0.75 | 2.12 |
| Leu | 802 | . | A | B | . | . | . | . | 0.16 | −0.79 | * | . | F | 0.90 | 1.07 |
| Lys | 803 | . | . | B | . | . | T | . | 0.52 | −0.10 | * | * | F | 0.85 | 0.44 |
| Thr | 804 | . | . | B | . | . | T | . | 0.10 | 0.29 | * | * | F | 0.25 | 0.60 |
| Gly | 805 | . | . | B | . | . | T | . | −0.80 | 0.16 | * | . | F | 0.40 | 1.04 |
| Leu | 806 | . | . | B | . | . | T | . | −1.06 | 0.11 | * | * | F | 0.25 | 0.39 |
| Ser | 807 | . | . | B | B | . | . | . | −0.24 | 0.76 | * | * | F | −0.45 | 0.20 |
| Thr | 808 | . | . | B | B | . | . | . | −0.59 | 0.67 | * | . | . | −0.60 | 0.32 |
| Val | 809 | . | . | B | B | . | . | . | −0.59 | 0.63 | * | . | . | −0.60 | 0.53 |
| Val | 810 | . | . | B | B | . | . | . | −1.06 | 0.43 | * | . | F | −0.45 | 0.57 |
| Asn | 811 | . | . | B | . | . | T | . | −0.91 | 0.73 | * | . | F | −0.05 | 0.32 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Ser | 812 | . | . | B | . | . | T | . | −0.82 | 0.81 | . | . | F | −0.05 | 0.23 |
| Thr | 813 | . | . | B | . | . | T | . | −0.72 | 0.60 | . | . | F | −0.05 | 0.49 |
| Leu | 814 | . | . | B | . | . | T | . | −0.68 | 0.39 | . | . | F | 0.25 | 0.47 |
| Cys | 815 | . | . | B | . | . | . | . | −0.03 | 0.67 | . | * | F | −0.25 | 0.29 |
| Pro | 816 | . | . | B | . | . | . | . | −0.73 | 0.71 | . | * | F | −0.25 | 0.31 |
| Pro | 817 | . | . | B | . | . | . | . | −0.73 | 1.01 | . | . | F | −0.25 | 0.32 |
| Leu | 818 | . | | B | . | . | T | . | −0.72 | 0.71 | . | * | . | −0.20 | 0.81 |
| Pro | 819 | . | . | . | . | T | T | . | −0.21 | 0.53 | . | * | . | 0.20 | 0.70 |
| Phe | 820 | . | . | . | . | T | T | . | −0.43 | 0.49 | * | * | F | 0.35 | 0.61 |
| Ser | 821 | . | . | B | . | . | T | . | −0.11 | 0.74 | * | * | F | −0.05 | 0.52 |
| Ser | 822 | . | . | . | B | T | . | . | −0.11 | 0.06 | * | * | F | 0.25 | 0.66 |
| Ser | 823 | . | . | . | B | T | . | . | 0.03 | 0.06 | * | * | F | 0.40 | 1.17 |
| Ile | 824 | . | . | B | B | . | . | . | −0.36 | −0.16 | * | * | F | 0.45 | 0.47 |
| Arg | 825 | . | . | B | . | . | T | . | −0.47 | 0.07 | * | * | F | 0.25 | 0.35 |
| Pro | 826 | . | . | . | . | T | T | . | −0.76 | 0.37 | . | * | . | 0.50 | 0.21 |
| Cys | 827 | . | . | . | . | T | T | . | −0.77 | 0.49 | . | * | . | 0.20 | 0.31 |
| Met | 828 | . | . | B | . | . | T | . | −1.13 | 0.29 | . | * | . | 0.10 | 0.23 |
| Leu | 829 | . | . | B | . | . | . | . | −0.83 | 0.86 | . | * | . | −0.40 | 0.08 |
| Ala | 830 | . | . | B | . | . | . | . | −0.83 | 0.93 | . | * | . | −0.40 | 0.15 |
| Thr | 831 | . | . | B | . | . | . | . | −0.83 | 0.36 | * | . | . | 0.24 | 0.29 |
| Cys | 832 | . | . | B | . | . | . | . | −0.51 | 0.17 | * | . | . | 0.58 | 0.55 |
| Ala | 833 | . | . | B | . | . | . | . | 0.20 | −0.09 | * | . | . | 1.52 | 0.54 |
| Arg | 834 | . | . | B | . | . | T | . | 0.80 | −0.59 | * | . | F | 2.51 | 0.73 |
| Pro | 835 | . | . | . | . | T | T | . | 1.09 | −0.64 | * | . | F | 3.40 | 2.10 |
| Gly | 836 | . | . | . | . | T | T | . | 1.09 | −0.83 | * | * | F | 3.06 | 2.79 |
| Arg | 837 | . | . | . | . | . | T | C | 1.80 | −0.84 | * | . | F | 2.80 | 2.05 |
| Pro | 838 | . | . | . | . | T | T | . | 2.36 | −0.84 | * | * F | . | 2.94 | 2.66 |
| Ser | 839 | . | . | . | . | T | T | . | 1.94 | −0.77 | * | * F | . | 2.88 | 3.65 |
| Thr | 840 | . | . | . | . | T | T | . | 1.94 | −0.81 | * | * F | . | 2.82 | 2.50 |
| Lys | 841 | . | . | . | . | T | T | . | 2.26 | −0.39 | * | * F | . | 2.80 | 2.50 |
| His | 842 | . | . | . | . | . | . | C | 1.26 | −0.31 | * | * F | . | 2.12 | 2.54 |
| Ser | 843 | . | . | . | . | . | T | C | 0.88 | −0.01 | . | * F | . | 2.04 | 1.23 |
| Pro | 844 | . | . | B | . | . | T | . | 0.59 | 0.00 | . | . | F | 0.81 | 0.62 |
| His | 845 | . | . | B | . | . | T | . | 0.31 | 0.50 | . | * | . | 0.08 | 0.46 |
| Ile | 846 | . | . | B | . | . | T | . | 0.38 | 0.50 | . | . | . | −0.20 | 0.35 |
| Ala | 847 | A | A | . | . | . | . | . | 0.46 | 0.11 | * | . | . | −0.30 | 0.44 |
| Ala | 848 | A | A | . | . | . | . | . | −0.10 | −0.31 | * | . | . | 0.30 | 0.65 |
| Ala | 849 | . | A | B | B | . | . | . | −0.13 | −0.17 | . | . | . | 0.30 | 0.69 |
| Arg | 850 | . | A | B | B | . | . | . | −0.99 | −0.10 | . | . | . | 0.45 | 1.07 |
| Lys | 851 | . | A | B | B | . | . | . | −0.10 | 0.09 | . | . | . | −0.30 | 0.74 |
| Val | 852 | . | A | B | B | . | . | . | 0.18 | −0.01 | * | . | . | 0.45 | 1.27 |
| Tyr | 853 | . | A | B | B | . | . | . | 0.88 | −0.03 | * | . | . | 0.30 | 0.93 |
| Ile | 854 | . | . | B | B | . | . | . | 1.58 | −0.03 | * | * | . | 0.30 | 0.91 |
| Gln | 855 | . | . | B | B | . | . | . | 1.47 | −0.03 | * | . | . | 0.45 | 2.41 |
| Thr | 856 | . | . | B | B | . | . | . | 1.53 | −0.27 | * | * | F | 0.60 | 2.67 |
| Arg | 857 | . | A | B | B | . | . | . | 2.43 | −1.03 | * | * | F | 0.90 | 7.46 |
| Arg | 858 | . | A | B | B | . | . | . | 1.87 | −1.71 | . | . | F | 0.90 | 8.61 |
| Gln | 859 | . | A | . | B | T | . | . | 2.72 | −1.43 | . | * | F | 1.30 | 4.92 |
| Arg | 860 | . | A | . | B | T | . | . | 2.02 | −1.41 | . | . | F | 1.30 | 3.42 |
| Lys | 861 | . | A | B | . | . | . | . | 1.48 | −0.63 | * | . | F | 0.90 | 1.51 |
| Leu | 862 | . | . | B | B | . | . | . | 0.51 | 0.01 | * | . | . | −0.30 | 0.65 |
| His | 863 | . | . | B | B | . | . | . | 0.06 | 0.26 | . | . | . | −0.30 | 0.25 |
| Phe | 864 | . | . | B | B | . | . | . | −0.29 | 0.69 | * | . | . | −0.60 | 0.12 |
| Val | 865 | . | . | B | B | . | . | . | −1.10 | 1.11 | * | . | . | −0.60 | 0.15 |
| Val | 866 | . | . | B | B | . | . | | −1.73 | 1.21 | . | * | . | −0.60 | 0.09 |
| Gly | 867 | . | . | B | B | . | . | . | −1.17 | 1.21 | . | . | . | −0.60 | 0.11 |
| Gly | 868 | . | . | B | B | . | . | . | −1.94 | 1.19 | . | . | . | −0.60 | 0.23 |
| Phe | 869 | . | . | B | B | . | . | . | −2.06 | 1.23 | . | . | . | −0.60 | 0.25 |
| Ala | 870 | . | . | B | B | . | . | . | −1.41 | 1.27 | * | . | . | −0.60 | 0.21 |
| Tyr | 871 | . | . | B | B | . | . | . | −0.51 | 1.27 | * | . | . | −0.60 | 0.33 |
| Leu | 872 | . | . | B | B | . | . | . | −0.48 | 0.84 | * | . | . | −0.60 | 0.76 |
| Leu | 873 | . | . | B | . | . | T | . | −0.72 | 0.54 | . | . | . | −0.05 | 1.09 |
| Pro | 874 | . | . | B | . | . | T | . | −0.88 | 0.54 | . | . | F | −0.05 | 0.70 |
| Lys | 875 | . | . | . | . | T | T | . | −1.14 | 0.43 | . | . | F | 0.35 | 0.63 |
| Thr | 876 | . | . | B | . | . | T | . | −1.71 | 0.39 | * | * | F | 0.25 | 0.57 |
| Ala | 877 | . | . | B | B | . | . | . | −0.79 | 0.39 | * | * | . | −0.30 | 0.30 |
| Val | 878 | . | . | B | B | . | . | . | −0.64 | −0.04 | . | * | . | 0.30 | 0.30 |
| Val | 879 | . | . | B | B | . | . | . | −0.64 | 0.53 | . | * | . | −0.60 | 0.11 |
| Leu | 880 | . | . | B | B | . | . | . | −1.28 | 0.47 | * | * | . | −0.32 | 0.17 |
| Arg | 881 | . | . | B | B | . | . | . | −0.86 | 0.47 | * | * | . | −0.04 | 0.23 |
| Cys | 882 | . | . | B | . | . | T | . | −0.16 | −0.17 | * | * | . | 1.54 | 0.61 |
| Pro | 883 | . | . | B | . | . | T | . | −0.16 | −0.81 | * | * | . | 2.27 | 1.44 |
| Ala | 884 | . | . | . | . | T | T | . | 0.81 | −0.86 | * | * | . | 2.80 | 0.55 |
| Arg | 885 | . | . | B | . | . | T | . | 1.67 | −0.86 | * | * | F | 2.42 | 2.00 |
| Arg | 886 | . | . | B | B | . | . | . | 1.34 | −1.43 | * | * | F | 1.74 | 2.58 |
| Val | 887 | . | . | B | B | . | . | . | 1.20 | −1.43 | * | . | F | 1.46 | 3.95 |
| Arg | 888 | . | . | B | B | . | . | . | 0.52 | −1.24 | * | . | F | 1.18 | 1.66 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Lys | 889 | . | . | B | . | . | . | . | 0.80 | −0.56 | * | . | F | 0.95 | 0.60 |
| Pro | 890 | . | . | B | . | . | . | . | 0.40 | −0.07 | * | . | F | 0.80 | 1.16 |
| Leu | 891 | . | A | B | . | . | . | . | 0.29 | 0.20 | * | * | . | −0.30 | 0.62 |
| Ile | 892 | . | A | B | . | . | . | . | 1.19 | 0.20 | * | . | . | 0.04 | 0.54 |
| Thr | 893 | . | A | B | . | . | . | . | 1.08 | 0.20 | * | . | . | 0.38 | 0.70 |
| Trp | 894 | . | A | B | . | . | . | . | 0.69 | −0.23 | * | * | . | 1.47 | 1.41 |
| Glu | 895 | . | . | B | . | . | T | . | 0.90 | −0.49 | * | . | F | 2.36 | 1.99 |
| Lys | 896 | . | . | . | . | T | T | . | 1.68 | −0.77 | * | . | F | 3.40 | 2.39 |
| Asp | 897 | . | . | . | . | T | T | . | 1.76 | −0.76 | * | * | F | 3.06 | 3.09 |
| Gly | 898 | . | . | . | . | T | T | . | 1.18 | −0.99 | * | . | F | 2.72 | 1.47 |
| Gln | 899 | . | . | . | B | T | . | . | 1.17 | −0.30 | * | . | F | 1.53 | 0.52 |
| His | 900 | . | . | . | B | . | . | C | 0.87 | 0.09 | * | . | . | 0.24 | 0.41 |
| Leu | 901 | . | . | B | B | . | . | . | 0.51 | 0.47 | * | . | . | −0.60 | 0.56 |
| Ile | 902 | . | . | B | B | . | . | . | 0.48 | 0.53 | . | . | . | −0.60 | 0.47 |
| Ser | 903 | . | . | B | B | . | . | . | −0.03 | 0.63 | . | . | F | −0.45 | 0.47 |
| Ser | 904 | . | . | B | B | . | . | . | −0.34 | 0.77 | . | . | F | −0.45 | 0.42 |
| Thr | 905 | . | . | B | B | . | . | . | −1.17 | 0.57 | . | . | F | −0.45 | 0.87 |
| His | 906 | . | . | B | B | . | . | . | −0.94 | 0.53 | . | . | . | −0.60 | 0.48 |
| Val | 907 | . | . | B | B | . | . | . | −0.27 | 0.64 | . | . | . | −0.60 | 0.36 |
| Thr | 908 | . | . | B | B | . | . | . | −0.67 | 0.69 | . | . | . | −0.60 | 0.39 |
| Val | 909 | . | . | B | B | . | . | . | −0.71 | 0.99 | . | . | . | −0.60 | 0.25 |
| Ala | 910 | . | . | B | . | . | T | . | −0.64 | 0.91 | . | . | . | −0.20 | 0.33 |
| Pro | 911 | . | . | B | . | . | T | . | −1.42 | 1.03 | . | . | . | −0.20 | 0.36 |
| Phe | 912 | . | . | . | . | T | T | . | −0.52 | 1.23 | . | * | . | 0.20 | 0.40 |
| Gly | 913 | . | . | B | . | . | T | . | −1.10 | 0.59 | . | * | . | −0.20 | 0.78 |
| Tyr | 914 | . | . | B | B | . | . | . | −0.28 | 0.77 | * | . | . | −0.60 | 0.36 |
| Leu | 915 | . | . | B | B | . | . | . | 0.42 | 0.84 | * | . | . | −0.60 | 0.56 |
| Lys | 916 | . | . | B | B | . | . | . | −0.18 | 0.06 | . | . | . | −0.15 | 1.11 |
| Ile | 917 | . | . | B | B | . | . | . | 0.57 | 0.31 | . | . | . | −0.30 | 0.58 |
| His | 918 | . | . | B | B | . | . | . | 0.70 | −0.44 | * | * | . | 0.79 | 1.41 |
| Arg | 919 | . | . | B | B | . | . | . | 0.64 | −0.70 | . | . | . | 1.43 | 1.09 |
| Leu | 920 | . | . | B | B | . | . | . | 1.46 | −0.31 | . | . | . | 1.47 | 2.09 |
| Lys | 921 | . | . | B | . | . | T | . | 0.82 | −1.00 | . | . | F | 2.66 | 2.56 |
| Pro | 922 | . | . | . | . | T | T | . | 1.37 | −1.00 | . | . | F | 3.40 | 1.32 |
| Ser | 923 | . | . | . | . | T | T | . | 0.54 | −0.57 | . | * | F | 3.06 | 1.59 |
| Asp | 924 | . | . | . | . | T | T | . | 0.19 | −0.61 | . | * | F | 2.57 | 0.59 |
| Ala | 925 | . | . | B | B | . | . | . | 0.69 | 0.14 | . | . | F | 0.53 | 0.60 |
| G1y | 926 | . | . | B | B | . | . | . | −0.02 | 0.20 | . | . | . | 0.040 | 64 |
| Val | 927 | . | . | B | B | . | . | . | −0.11 | 0.39 | . | . | . | −0.30 | 0.21 |
| Tyr | 928 | . | . | B | B | . | . | . | −0.40 | 0.77 | . | . | . | −0.60 | 0.27 |
| Thr | 929 | . | . | B | B | . | . | . | −0.74 | 0.77 | . | . | . | −0.60 | 0.28 |
| Cys | 930 | . | . | B | B | . | . | . | −0.37 | 0.77 | . | . | . | −0.30 | 0.37 |
| Ser | 931 | . | . | . | . | T | T | . | −0.61 | 0.56 | * | . | . | 0.80 | 0.37 |
| Ala | 932 | . | . | . | . | . | T | C | 0.36 | 0.30 | * | . | F | 1.35 | 0.26 |
| Gly | 933 | . | . | . | . | . | T | C | 0.60 | −0.19 | . | . | F | 2.25 | 0.94 |
| Pro | 934 | . | . | . | . | . | T | C | 0.88 | −0.76 | . | * | F | 3.00 | 1.21 |
| Ala | 935 | . | A | . | . | . | . | C | 0.84 | −0.64 | . | . | F | 2.30 | 1.64 |
| Arg | 936 | A | A | . | . | . | . | . | 0.29 | −0.36 | . | * | F | 1.50 | 1.43 |
| Glu | 937 | . | A | B | . | . | . | . | −0.01 | −0.14 | . | * | . | 0.90 | 0.69 |
| His | 938 | . | A | B | . | . | . | . | 0.38 | 0.11 | . | * | . | 0.00 | 0.48 |
| Phe | 939 | . | A | B | . | . | . | . | −0.22 | −0.39 | . | * | . | 0.30 | 0.49 |
| Val | 940 | . | A | B | . | . | . | . | −0.52 | 0.30 | . | * | . | −0.30 | 0.23 |
| Ile | 941 | . | A | B | . | . | . | . | −0.98 | 0.99 | . | * | . | −0.60 | 0.12 |
| Lys | 942 | . | A | B | . | . | . | . | −1.32 | 0.91 | . | . | . | −0.35 | 0.14 |
| Leu | 943 | . | A | B | . | . | . | . | −1.29 | 0.56 | . | * | . | −0.10 | 0.18 |
| Ile | 944 | . | A | . | . | T | . | . | −0.48 | 0.31 | * | * | . | 0.85 | 0.42 |
| Gly | 945 | . | . | . | . | . | T | C | 0.42 | −0.37 | * | . | F | 2.05 | 0.41 |
| Gly | 946 | . | . | . | . | T | T | . | 0.50 | −0.37 | * | . | F | 2.50 | 0.99 |
| Asn | 947 | . | . | . | . | . | T | C | −0.40 | −0.37 | * | . | F | 2.20 | 1.17 |
| Arg | 948 | . | . | B | . | . | T | . | −0.18 | −0.41 | * | * | F | 1.60 | 0.87 |
| Lys | 949 | . | . | B | B | . | . | . | 0.82 | −0.34 | * | * | F | 0.95 | 0.89 |
| Leu | 950 | . | . | B | B | . | . | . | 0.96 | −0.77 | * | . | . | 1.00 | 1.09 |
| Val | 951 | . | . | B | B | . | . | . | 0.49 | −0.74 | * | . | . | 0.60 | 0.86 |
| Ala | 952 | . | . | B | B | . | . | . | 0.19 | −0.06 | * | . | . | 0.60 | 0.35 |
| Arg | 953 | . | . | B | . | . | . | . | −0.13 | 0.33 | . | . | . | 0.50 | 0.58 |
| Pro | 954 | . | . | B | . | . | . | . | −0.07 | 0.07 | * | * | F | 1.10 | 1.20 |
| Leu | 955 | . | . | . | . | . | . | C | 0.44 | −0.57 | . | * | F | 2.50 | 2.32 |
| Ser | 956 | . | . | . | . | . | T | C | 1.30 | −0.69 | * | . | F | 3.00 | 1.59 |
| Pro | 957 | . | . | . | . | . | T | C | 1.89 | −0.69 | * | * | F | 2.70 | 1.78 |
| Arg | 958 | . | . | . | . | . | T | C | 1.78 | −1.11 | * | * | F | 2.40 | 3.74 |
| Ser | 959 | . | . | . | . | . | T | C | 1.13 | −1.80 | * | * | F | 2.10 | 4.83 |
| GLu | 960 | . | A | B | . | . | . | . | 1.13 | −1.54 | . | * | F | 1.20 | 2.32 |
| Glu | 961 | . | A | B | . | . | . | . | 0.84 | −1.29 | * | * | F | 0.75 | 0.98 |
| Glu | 962 | . | A | B | . | . | . | . | 0.71 | −0.79 | . | * | F | 0.75 | 0.74 |
| Val | 963 | . | A | B | . | . | . | . | 0.71 | −0.74 | . | * | . | 0.60 | 0.42 |
| Leu | 964 | A | A | . | . | . | . | . | 1.06 | −0.74 | . | . | . | 0.94 | 0.48 |
| Ala | 965 | A | A | . | . | . | . | . | 0.71 | −0.74 | . | . | . | 1.28 | 0.55 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Gly | 966 | . | . | . | . | T | . | . | 0.37 | −0.31 | . | . | F | 2.07 | 0.73 |
| Arg | 967 | . | . | . | . | T | T | . | 0.16 | −0.53 | . | . | F | 2.91 | 0.88 |
| Lys | 968 | . | . | . | . | T | T | . | 1.06 | −0.79 | . | . | F | 3.40 | 1.35 |
| Gly | 969 | . | . | . | . | . | T | C | 1.87 | −1.29 | . | . | F | 2.86 | 2.72 |
| Gly | 970 | . | . | . | . | . | T | C | 1.87 | −1.71 | . | . | F | 2.52 | 2.40 |
| Pro | 971 | . | A | . | . | . | . | C | 1.40 | −1.21 | . | . | F | 1.78 | 1.21 |
| Lys | 972 | . | A | . | . | . | . | C | 1.29 | −0.53 | . | . | F | 1.44 | 1.01 |
| Glu | 973 | . | A | B | . | . | . | . | 0.93 | −0.56 | * | * | F | 0.90 | 1.77 |
| Ala | 974 | A | A | . | . | . | . | . | 1.24 | −0.50 | * | . | F | 0.60 | 1.65 |
| Leu | 975 | . | A | B | . | . | . | . | 1.63 | −0.43 | * | . | F | 0.60 | 1.12 |
| Gln | 976 | . | A | B | . | . | . | . | 1.81 | −0.43 | * | . | F | 0.60 | 1.30 |
| Thr | 977 | . | A | B | . | . | . | . | 1.77 | 0.07 | . | . | F | 0.28 | 1.75 |
| His | 978 | . | A | . | . | . | . | C | 1.77 | −0.03 | . | . | F | 1.36 | 3.67 |
| Lys | 979 | . | A | . | . | . | . | C | 2.01 | −0.31 | . | . | F | 1.64 | 3.41 |
| His | 980 | . | . | . | . | . | T | C | 1.93 | −0.29 | . | . | F | 2.32 | 2.34 |
| Gln | 981 | . | . | . | . | T | T | . | 1.23 | −0.09 | . | . | F | 2.80 | 1.21 |
| Asn | 982 | . | . | . | . | T | T | . | 1.24 | 0.20 | . | . | F | 1.77 | 0.52 |
| Gly | 983 | . | . | B | . | . | T | . | 1.28 | 0.59 | * | . | F | 079 | 0.51 |
| Ile | 984 | . | . | B | . | . | . | . | 0.89 | 0.49 | * | . | . | 0.16 | 0.48 |
| Phe | 985 | . | . | B | . | . | T | . | 0.62 | 0.51 | * | . | F | 0.23 | 0.29 |
| Ser | 986 | . | . | . | . | . | T | C | 0.67 | 0.50 | * | . | F | 0.15 | 0.40 |
| Asn | 987 | . | . | . | . | . | T | C | 0.08 | 0.07 | * | . | F | 0.60 | 1.13 |
| Gly | 988 | . | . | . | . | . | T | C | 0.42 | −0.11 | * | . | F | 1.20 | 1.32 |
| Ser | 989 | . | A | . | . | . | . | C | 1.36 | −0.90 | * | * | F | 1.10 | 1.71 |
| Lys | 990 | . | A | . | . | . | . | C | 2.17 | −1.29 | * | * | F | 1.10 | 2.13 |
| Ala | 991 | . | A | . | . | . | . | C | 2.12 | −1.69 | * | . | F | 1.10 | 4.21 |
| Glu | 992 | . | A | B | . | . | . | . | 1.31 | −1.69 | * | . | F | 0.90 | 3.11 |
| Lys | 993 | . | A | B | . | . | . | . | 1.07 | −1.39 | * | . | F | 0.90 | 1.28 |
| Arg | 994 | . | A | B | . | . | . | . | 0.78 | −0.89 | * | * | F | 0.90 | 1.28 |
| Gly | 995 | . | A | B | . | . | . | . | 0.73 | −0.89 | * | * | F | 0.75 | 0.75 |
| Leu | 996 | . | A | B | . | . | . | . | 1.11 | −0.49 | . | . | . | 0.30 | 0.60 |
| Ala | 997 | . | A | B | . | . | . | . | 0.77 | −0.06 | . | . | . | 0.30 | 0.47 |
| Ala | 998 | . | A | . | . | . | . | C | 0.42 | 0.37 | . | . | . | 0.24 | 0.47 |
| Asn | 999 | . | . | . | . | . | T | C | 0.42 | 0.33 | . | * | F | 1.13 | 0.77 |
| Pro | 1000 | . | . | . | . | . | T | C | 0.52 | −0.36 | . | * | F | 2.22 | 1.50 |
| Gly | 1001 | . | . | . | . | T | T | . | 1.33 | −0.10 | * | * | F | 2.76 | 2.32 |
| Ser | 1002 | . | . | B | . | T | T | . | 1.92 | −0.60 | * | . | F | 3.40 | 2.41 |
| Arg | 1003 | . | . | B | . | . | . | . | 1.70 | −1.00 | * | * | F | 2.46 | 2.60 |
| Tyr | 1004 | . | . | B | . | . | T | . | 0.84 | −0.74 | * | * | F | 2.51 | 2.17 |
| Asp | 1005 | . | . | B | . | . | T | . | 0.76 | −0.53 | * | . | F | 2.36 | 1.20 |
| Asp | 1006 | . | . | B | . | . | T | . | 1.21 | −0.53 | * | * | F | 2.06 | 0.82 |
| Leu | 1007 | . | . | B | . | . | T | . | 0.70 | −0.53 | * | . | F | 2.06 | 1.03 |
| Val | 1008 | . | . | B | . | . | . | . | −0.22 | −0.60 | * | . | F | 1.90 | 0.51 |
| Ser | 1009 | . | A | B | . | . | . | . | 0.02 | 0.09 | * | . | . | 0.46 | 0.25 |
| Arg | 1010 | . | A | B | . | . | . | . | 0.02 | 0.09 | * | . | . | 0.27 | 0.53 |
| Leu | 1011 | . | A | B | . | . | . | . | −0.32 | −0.20 | * | * | F | 0.98 | 1.23 |
| Leu | 1012 | . | A | B | . | . | . | . | 0.14 | −0.41 | * | . | F | 0.64 | 0.91 |
| Glu | 1013 | . | . | B | . | . | T | . | 0.71 | −0.37 | * | . | F | 0.85 | 0.46 |
| Gln | 1014 | . | . | . | . | T | T | . | 0.80 | 0.54 | * | * | F | 0.35 | 0.58 |
| Gly | 1015 | . | . | . | . | T | T | . | 0.34 | 0.29 | * | * | F | 0.80 | 1.09 |
| Gly | 1016 | . | . | . | . | . | T | C | 1.16 | 0.03 | . | * | F | 0.45 | 0.63 |
| Trp | 1017 | . | . | . | . | . | T | C | 1.16 | 0.03 | . | . | F | 0.45 | 0.63 |
| Pro | 1018 | . | . | . | . | . | T | C | 0.34 | 0.31 | . | . | F | 0.45 | 0.52 |
| Gly | 1019 | . | . | . | . | . | T | C | −0.24 | 0.57 | . | * | F | 0.15 | 0.43 |
| Glu | 1020 | . | . | B | . | . | T | . | −0.20 | 0.64 | . | * | F | −0.05 | 0.42 |
| Leu | 1021 | . | A | B | . | . | . | . | −0.14 | 0.11 | . | * | . | −0.30 | 0.36 |
| Leu | 1022 | . | A | . | . | . | . | C | 0.14 | 0.60 | . | * | . | −0.40 | 0.38 |
| Ala | 1023 | . | A | . | . | . | . | C | −0.23 | 0.17 | . | * | . | −0.10 | 0.38 |
| Ser | 1024 | . | A | . | . | . | . | C | 0.11 | 0.67 | . | * | . | −0.40 | 0.47 |
| Trp | 1025 | A | A | . | . | . | . | . | 0.11 | 0.39 | . | * | . | 0.00 | 0.99 |
| Glu | 1026 | A | A | . | . | . | . | . | 0.62 | −0.30 | . | * | . | 1.05 | 1.63 |
| Ala | 1027 | A | . | . | . | . | T | . | 0.84 | −0.41 | . | * | . | 1.75 | 1.63 |
| Gln | 1028 | . | . | . | . | . | T | C | 1.43 | −0.30 | * | * | F | 2.40 | 1.57 |
| Asp | 1029 | . | . | . | . | . | T | C | 1.84 | −1.21 | * | . | F | 3.00 | 1.57 |
| Ser | 1030 | . | . | . | . | . | T | C | 2.13 | −1.21 | * | . | F | 2.70 | 3.04 |
| Ala | 1031 | . | . | . | . | . | . | C | 1.82 | −1.31 | * | . | F | 2.20 | 2.83 |
| Glu | 1032 | . | . | . | . | . | . | C | 2.10 | −1.23 | * | . | F | 1.90 | 2.44 |
| Arg | 1033 | . | . | . | . | T | . | . | 1.80 | −0.74 | . | . | F | 1.80 | 2.63 |
| Asn | 1034 | . | . | . | . | . | T | C | 1.80 | −0.74 | . | . | F | 1.50 | 3.49 |
| Thr | 1035 | . | . | . | . | . | T | C | 2.10 | −1.24 | * | . | F | 1.50 | 3.49 |
| Thr | 1036 | . | . | . | . | . | T | C | 2.69 | −1.24 | . | . | F | 1.50 | 3.09 |
| Ser | 1037 | . | . | . | . | . | T | C | 2.48 | −1.24 | . | . | F | 1.50 | 3.20 |
| Glu | 1038 | . | . | . | . | . | . | C | 2.02 | −1.21 | . | . | F | 1.64 | 3.43 |
| Glu | 1039 | . | . | . | . | . | . | C | 1.43 | −1.27 | . | . | F | 1.98 | 2.35 |
| Asp | 1040 | . | . | . | . | . | T | C | 1.74 | −1.26 | . | . | F | 2.52 | 1.77 |
| Pro | 1041 | . | . | . | . | . | T | C | 2.06 | −1.64 | . | . | F | 2.86 | 1.77 |
| Gly | 1042 | . | . | . | . | T | T | . | 1.50 | −1.24 | . | . | F | 3.40 | 1.77 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Ala | 1043 | A | . | . | . | . | T | . | 0.69 | −0.60 | . | . | F | 2.51 | 0.79 |
| Glu | 1044 | A | A | . | . | . | . | . | −0.12 | 0.09 | . | . | F | 0.87 | 0.42 |
| Gln | 1045 | A | A | . | . | . | . | . | −0.16 | 0.34 | . | . | . | 0.38 | 0.35 |
| Val | 1046 | . | A | B | . | . | . | . | −0.76 | 0.41 | * | . | . | −0.26 | 0.47 |
| Leu | 1047 | . | A | B | . | | . | . | −0.62 | 0.60 | . | * | . | −0.60 | 0.22 |
| Leu | 1048 | . | A | B | . | . | . | . | −0.73 | 1.03 | . | * | . | −0.60 | 0.20 |
| His | 1049 | . | A | B | . | . | . | . | −1.04 | 1.41 | . | * | | −0.60 | 0.23 |
| Leu | 1050 | . | A | . | . | . | . | C | −1.64 | 1.26 | . | * | . | −0.40 | 0.41 |
| Pro | 1051 | . | A | . | . | . | . | C | −1.64 | 1.19 | . | * | . | −0.40 | 0.49 |
| Phe | 1052 | . | . | B | B | . | . | . | −1.14 | 1.14 | * | . | . | −0.60 | 0.27 |
| Thr | 1053 | . | . | B | B | . | . | . | −0.33 | 1.13 | . | * | . | −0.60 | 0.47 |
| Met | 1054 | . | A | B | B | . | . | . | −0.30 | 0.44 | . | * | . | −0.60 | 0.53 |
| Val | 1055 | . | A | B | B | . | . | . | 0.62 | 0.41 | . | . | . | −0.45 | 1.05 |
| Thr | 1056 | . | A | B | B | . | . | . | 0.94 | −0.37 | * | . | F | 0.60 | 1.43 |
| Glu | 1057 | . | A | B | B | . | . | . | 0.83 | −0.86 | . | * | F | 0.90 | 2.83 |
| Gln | 1058 | . | A | B | . | . | . | . | 1.14 | −0.79 | * | . | F | 0.90 | 3.14 |
| Arg | 1059 | . | A | B | . | . | . | . | 1.74 | −1.43 | * | . | F | 0.90 | 3.63 |
| Aig | 1060 | . | A | B | . | . | . | . | 1.71 | −1.91 | * | . | F | 0.90 | 3.50 |
| Leu | 1061 | . | A | B | . | . | . | . | 1.21 | −1.23 | * | . | F | 0.90 | 1.42 |
| Asp | 1062 | . | A | B | . | . | . | . | 0.87 | −0.94 | * | . | F | 0.75 | 0.60 |
| Asp | 1063 | . | A | B | . | . | . | . | 0.87 | −0.51 | * | . | F | 0.75 | 0.30 |
| Ile | 1064 | . | A | B | . | . | . | . | −0.06 | −0.11 | * | . | . | 0.30 | 0.59 |
| Leu | 1065 | . | A | B | . | . | . | . | −0.47 | −0.11 | * | * | . | 0.30 | 0.29 |
| Gly | 1066 | . | A | . | . | T | . | . | 0.34 | 0.27 | * | . | . | 0.10 | 0.23 |
| Asn | 1067 | . | . | . | . | . | . | C | 0.34 | 0.67 | * | * | F | −0.05 | 0.58 |
| Leu | 1068 | . | . | . | . | . | . | C | 0.13 | 0.39 | * | * | F | 0.40 | 1.21 |
| Ser | 1069 | . | . | . | . | . | . | C | 1.02 | 0.13 | * | * | F | 0.40 | 1.89 |
| Gln | 1070 | . | A | . | . | . | . | C | 1.83 | −030 | * | . | F | 0.80 | 2.03 |
| Gln | 1071 | . | A | . | . | . | . | C | 1.37 | −0.70 | . | * | F | 1.10 | 4.27 |
| Pro | 1072 | . | A | B | . | . | . | . | 1.48 | −070 | * | * | F | 0.90 | 2.63 |
| Glu | 1073 | . | A | B | . | . | . | . | 2.29 | −1.09 | * | . | F | 0.90 | 2.97 |
| Glu | 1074 | . | A | B | . | . | . | . | 1.78 | −1.49 | * | . | F | 0.90 | 2.87 |
| Leu | 1075 | . | A | B | . | . | . | . | 1.53 | −1.20 | * | . | F | 0.90 | 1.53 |
| Arg | 1076 | . | A | . | . | T | . | . | 1.23 | −0.87 | * | . | F | 1.30 | 1.38 |
| Asp | 1077 | . | A | . | . | T | . | . | 1.49 | −0.49 | * | . | F | 1.00 | 1.07 |
| Leu | 1078 | A | A | . | . | . | . | . | 1.46 | −0.49 | * | . | F | 0.60 | 2.60 |
| Tyr | 1079 | . | A | . | . | T | . | . | 0.64 | −0.67 | . | . | F | 1.30 | 1.80 |
| Ser | 1080 | . | A | . | . | T | . | . | 0.60 | 0.01 | * | . | F | 0.25 | 0.89 |
| Lys | 1081 | . | A | B | . | . | . | . | −0.10 | 0.66 | . | . | . | −0.60 | 0.80 |
| His | 1082 | . | A | B | . | . | . | . | −0.10 | 0.47 | . | * | . | −0.60 | 0.52 |
| Leu | 1083 | . | A | B | . | . | . | . | −0.10 | 0.11 | . | . | . | −0.30 | 0.67 |
| Val | 1084 | . | A | B | . | . | . | . | −0.44 | 0.41 | * | . | . | −0.60 | 0.28 |
| Ala | 1085 | . | A | B | . | . | . | . | −0.14 | 0.91 | * | . | . | −0.60 | 0.20 |
| Gln | 1086 | . | A | B | . | . | . | . | −0.19 | 0.81 | * | . | . | −0.60 | 0.43 |
| Leu | 1087 | . | A | B | . | . | . | . | −1.04 | 0.13 | * | . | . | −0.15 | 1.00 |
| Ala | 1088 | A | A | . | . | . | . | . | −0.93 | 0.17 | * | * | . | −0.30 | 0.70 |
| Gln | 1089 | A | A | . | . | . | . | . | 0.03 | 0.46 | * | . | . | −0.60 | 0.35 |
| Glu | 1090 | . | A | B | . | . | . | . | 0.32 | 0.06 | * | * | . | −0.30 | 0.83 |
| Ile | 1091 | . | A | B | . | . | . | . | 0.29 | −0.24 | * | * | . | 0.45 | 1.10 |
| Phe | 1092 | . | A | B | . | . | . | . | 0.29 | −0.24 | * | * | . | 0.30 | 0.86 |
| Arg | 1093 | . | A | B | . | . | . | . | 0.88 | 0.04 | * | * | . | −0.30 | 0.41 |
| Ser | 1094 | . | A | . | . | . | . | C | 0.84 | 0.04 | * | * | . | 0.05 | 1.01 |
| His | 1095 | . | A | . | . | . | . | C | 0.84 | −0.14 | * | * | . | 0.65 | 1.59 |
| Leu | 1096 | . | A | . | . | . | . | C | 1.73 | −0.53 | * | * | . | 0.95 | 1.41 |
| Glu | 1097 | . | A | . | . | . | . | C | 2.12 | −0.53 | * | * | . | 0.95 | 1.75 |
| His | 1098 | . | . | . | . | T | T | . | 1.20 | −0.43 | * | * | . | 1.25 | 1.86 |
| Gln | 1099 | . | . | . | . | T | T | . | 0.69 | −0.24 | * | . | F | 1.40 | 1.86 |
| Asp | 1100 | . | . | . | . | T | T | . | 0.77 | −0.24 | * | . | F | 1.25 | 0.89 |
| Thr | 1101 | . | . | B | . | . | T | . | 1.37 | −0.24 | * | . | F | 1.30 | 1.30 |
| Leu | 1102 | . | . | . | . | . | . | C | 1.07 | −0.31 | * | . | F | 1.60 | 1.16 |
| Leu | 1103 | . | . | . | . | . | . | C | 1.10 | −0.33 | * | * | F | 1.75 | 0.93 |
| Lys | 1104 | . | . | . | . | . | T | C | 1.21 | −0.33 | * | . | F | 2.40 | 1.12 |
| Pro | 1105 | . | . | . | . | . | T | C | 1.32 | −0.81 | * | . | F | 3.00 | 2.66 |
| Ser | 1106 | . | . | . | . | . | T | C | 1.32 | −1.50 | * | . | F | 2.70 | 6.31 |
| Glu | 1107 | . | . | . | . | T | T | . | 1.83 | −1.70 | * | . | F | 2.60 | 4.55 |
| Arg | 1108 | . | . | . | . | T | . | . | 2.43 | −1.31 | * | . | F | 2.10 | 3.95 |
| Arg | 1109 | . | . | . | . | T | . | . | 1.53 | −1.31 | * | . | F | 1.80 | 4.55 |
| Thr | 1110 | . | . | B | B | . | . | . | 1.43 | −1.06 | . | . | F | 0.90 | 1.95 |
| Ser | 1111 | . | . | B | B | . | . | . | 0.92 | −0.57 | . | . | F | 0.90 | 1.44 |
| Pro | 1112 | . | . | B | B | . | . | . | 0.62 | 0.11 | . | . | F | −0.15 | 0.61 |
| Val | 1113 | . | . | B | B | . | . | . | 0.30 | 0.50 | . | . | F | −0.45 | 0.56 |
| Thr | 1114 | . | . | B | B | . | . | . | 0.16 | 0.44 | . | . | F | −0.45 | 0.65 |
| Leu | 1115 | . | . | B | B | . | . | . | 0.51 | 0.56 | . | . | F | −0.25 | 0.57 |
| Ser | 1116 | . | . | B | . | . | T | . | 0.78 | 0.13 | . | . | F | 0.80 | 1.54 |
| Pro | 1117 | . | . | B | . | . | T | . | 0.13 | −0.01 | . | . | F | 1.60 | 1.45 |
| His | 1118 | . | . | . | . | T | T | . | 0.69 | 0.14 | . | . | F | 1.60 | 1.31 |
| Lys | 1119 | . | . | B | . | . | T | . | 0.66 | −0.16 | . | . | F | 2.00 | 1.31 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| His | 1120 | . | . | B | . | . | T | . | 0.77 | −0.11 | . | . | . | 1.50 | 0.84 |
| Val | 1121 | . | . | B | . | . | T | . | 0.77 | 0.24 | * | . | . | 0.70 | 0.53 |
| Ser | 1122 | . | . | B | . | . | T | . | 0.68 | 0.13 | * | . | . | 0.50 | 0.36 |
| Gly | 1123 | . | . | B | . | . | T | . | 0.41 | 0.51 | * | . | F | 0.15 | 0.35 |
| Phe | 1124 | . | . | B | . | . | . | . | −0.44 | 0.40 | * | * | F | −0.25 | 0.63 |
| Ser | 1125 | . | . | B | . | . | T | . | −0.30 | 0.44 | * | * | F | −0.05 | 0.39 |
| Ser | 1126 | . | . | B | . | . | T | . | 0.24 | 0.06 | * | * | F | 0.25 | 0.77 |
| Ser | 1127 | . | . | B | . | . | T | . | 0.24 | 0.11 | * | * | F | 0.40 | 1.29 |
| Leu | 1128 | . | . | B | . | . | T | . | 0.29 | −0.29 | * | * | F | 1.26 | 1.29 |
| Arg | 1129 | . | . | B | . | . | . | . | 0.68 | −0.29 | * | * | F | 1.32 | 1.29 |
| Thr | 1130 | . | . | B | . | . | . | . | 0.63 | −0.19 | . | * | F | 1.58 | 1.39 |
| Ser | 1131 | . | . | . | . | . | T | C | 0.93 | −0.14 | . | * | F | 2.24 | 1.66 |
| Ser | 1132 | . | . | B | . | . | T | . | 0.64 | −0.83 | . | * | F | 2.60 | 1.42 |
| Thr | 1133 | . | . | B | . | . | T | . | 1.11 | −0.33 | . | * | F | 1.89 | 0.99 |
| Gly | 1134 | . | . | B | . | . | T | . | 0.66 | −0.39 | . | * | F | 1.63 | 0.73 |
| Asp | 1135 | . | . | . | . | T | T | . | 0.62 | −0.34 | . | . | F | 1.77 | 0.54 |
| Ala | 1136 | . | . | . | . | . | T | C | 0.62 | −0.30 | . | * | F | 1.31 | 0.37 |
| Gly | 1137 | . | . | . | . | T | T | . | 1.03 | −0.40 | * | . | F | 1.25 | 0.50 |
| Gly | 1138 | . | . | . | . | T | T | . | 1.46 | −0.83 | * | . | F | 1.55 | 0.59 |
| Gly | 1139 | . | . | . | . | . | . | C | 1.59 | −0.83 | * | . | F | 1.64 | 1.14 |
| Ser | 1140 | . | . | . | . | . | . | C | 1.56 | −0.90 | * | . | F | 1.98 | 1.78 |
| Arg | 1141 | . | . | B | . | . | . | . | 2.26 | −0.83 | * | . | F | 2.12 | 2.45 |
| Arg | 1142 | . | . | B | . | . | T | . | 2.64 | −1.26 | * | . | F | 2.66 | 4.86 |
| Pro | 1143 | . | . | . | . | T | T | . | 2.78 | −1.69 | * | . | F | 3.40 | 7.25 |
| His | 1144 | . | . | . | . | T | T | . | 2.81 | −1.64 | * | . | F | 3.06 | 5.72 |
| Arg | 1145 | . | . | . | . | . | T | C | 2.22 | −1.16 | * | . | F | 2.52 | 4.22 |
| Lys | 1146 | . | . | B | B | . | . | . | 1.30 | −0.47 | * | . | F | 1.28 | 1.91 |
| Pro | 1147 | . | . | B | B | . | . | . | 1.30 | −0.21 | * | . | F | 0.94 | 1.16 |
| Thr | 1148 | . | . | B | B | . | . | . | 1.56 | −0.71 | * | . | F | 0.90 | 1.16 |
| Ile | 1149 | . | . | B | B | . | . | . | 0.70 | −0.71 | * | . | . | 0.75 | 1.16 |
| Leu | 1150 | . | . | B | B | . | . | . | 0.29 | −0.03 | * | . | . | 0.30 | 0.53 |
| Arg | 1151 | . | . | B | B | . | . | . | −0.34 | −0.07 | * | . | F | 0.45 | 0.49 |
| Lys | 1152 | . | . | B | B | . | . | . | −0.72 | −0.06 | * | . | F | 0.45 | 0.70 |
| Ile | 1153 | . | . | B | B | . | . | . | −0.41 | −0.24 | * | . | . | 0.30 | 0.86 |
| Ser | 1154 | . | A | B | . | . | . | . | 0.48 | −0.53 | * | . | . | 0.60 | 0.76 |
| Ala | 1155 | . | A | B | . | . | . | . | 0.48 | −0.13 | * | . | . | 0.30 | 0.66 |
| Ala | 1156 | . | A | B | . | . | . | . | 0.07 | 0.56 | * | . | . | −0.60 | 0.78 |
| Gln | 1157 | . | A | B | . | . | . | . | −0.57 | 0.26 | . | . | . | −0.30 | 0.78 |
| Gln | 1158 | . | A | B | . | . | . | . | 0.02 | 0.37 | . | . | . | −0.30 | 0.78 |
| Len | 1159 | . | A | . | . | . | . | C | 0.32 | 0.26 | . | . | . | 0.05 | 1.03 |
| Ser | 1160 | . | A | . | . | . | . | C | 0.06 | −0.24 | . | . | . | 0.65 | 1.03 |
| Ala | 1161 | . | A | B | . | . | . | . | −0.21 | 0.00 | . | . | F | −0.15 | 0.44 |
| Ser | 1162 | . | A | B | B | . | . | . | −0.52 | 0.24 | . | . | F | −0.15 | 0.40 |
| Gln | 1163 | . | A | B | B | . | . | . | −0.56 | 0.04 | . | . | . | −0.30 | 0.43 |
| Val | 1164 | . | A | B | B | . | . | . | −0.56 | 0.16 | * | . | . | −0.30 | 0.58 |
| Val | 1165 | . | A | B | B | . | . | . | −0.60 | 0.34 | * | . | . | −0.30 | 0.35 |
| Thr | 1166 | . | A | B | B | . | . | . | −0.01 | 0.39 | * | . | . | −0.30 | 0.20 |
| His | 1167 | . | A | B | B | . | . | . | −0.02 | 0.79 | * | . | . | −0.60 | 0.47 |
| Len | 1168 | . | A | B | B | . | . | . | −0.88 | 0.63 | * | . | F | −0.45 | 0.92 |
| Gly | 1169 | . | A | B | B | . | . | . | −0.61 | 0.63 | * | . | F | −0.45 | 0.47 |
| Gln | 1170 | . | A | B | B | . | . | . | −0.57 | 0.64 | * | . | F | −0.45 | 0.35 |
| Thr | 1171 | . | A | B | B | . | . | . | −0.84 | 0.83 | . | . | F | −0.45 | 0.35 |
| Val | 1172 | . | A | B | B | . | . | . | −1.11 | 0.64 | . | . | . | −0.60 | 0.36 |
| Ala | 1173 | . | A | B | B | . | . | . | −0.64 | 0.60 | . | . | . | −0.60 | 0.28 |
| Leu | 1174 | . | A | B | B | . | . | . | −0.61 | 0.63 | . | . | . | −0.60 | 0.19 |
| Ala | 1175 | . | . | B | . | . | T | . | −1.42 | 0.63 | . | . | . | −0.20 | 0.37 |
| Ser | 1176 | . | . | . | . | . | T | C | −1.41 | 0.67 | . | * | F | 0.15 | 0.30 |
| Gly | 1177 | . | . | . | . | T | T | . | −1.41 | 0.56 | . | . | F | 0.35 | 0.49 |
| Thr | 1178 | . | . | B | . | . | T | . | −1.63 | 0.51 | . | * | F | −0.05 | 0.36 |
| Leu | 1179 | . | A | B | . | . | . | . | −1.63 | 0.70 | . | * | . | −0.60 | 0.22 |
| Ser | 1180 | . | A | B | . | . | . | . | −1.08 | 1.00 | . | * | . | −0.60 | 0.18 |
| Val | 1181 | . | A | B | . | . | . | . | −1.44 | 1.07 | . | * | . | −0.60 | 0.17 |
| Leu | 1182 | . | A | B | . | . | . | . | −1.10 | 1.16 | . | * | . | −0.60 | 0.11 |
| Leu | 1183 | . | A | B | . | . | . | . | −1.38 | 0.47 | . | * | . | −0.60 | 0.15 |
| His | 1184 | . | A | B | . | . | . | . | −1.46 | 0.59 | . | * | . | −0.60 | 0.20 |
| Cys | 1185 | . | A | B | . | . | . | . | −1.50 | 0.63 | . | . | . | −0.60 | 0.17 |
| Glu | 1186 | . | A | B | . | . | . | . | −0.68 | 0.37 | . | . | . | −0.30 | 0.20 |
| Ala | 1187 | . | A | B | . | . | . | . | −0.08 | 0.19 | . | * | . | −0.06 | 0.20 |
| Ile | 1188 | . | A | . | . | T | . | . | 0.84 | 0.11 | . | * | . | 0.58 | 0.59 |
| Gly | 1189 | . | A | . | . | T | . | . | 0.67 | −0.46 | . | * | . | 1.42 | 0.66 |
| His | 1190 | . | . | . | . | . | T | C | 1.02 | −0.03 | . | * | . | 2.01 | 1.01 |
| Pro | 1191 | . | . | . | . | . | T | C | 0.13 | −0.04 | * | * | F | 2.40 | 2.09 |
| Arg | 1192 | . | . | . | . | . | T | C | 0.42 | −0.04 | . | * | F | 2.16 | 1.48 |
| Pro | 1193 | . | . | . | . | . | T | C | 1.02 | −0.09 | . | * | F | 1.92 | 1.46 |
| Thr | 1194 | . | . | . | . | T | . | . | 0.78 | 0.33 | * | * | F | 0.93 | 0.99 |
| Ile | 1195 | . | . | B | . | . | . | . | 0.92 | 0.40 | * | * | . | −0.16 | 0.51 |
| Ser | 1196 | . | . | B | . | . | . | . | 1.13 | 0.40 | * | * | . | −0.10 | 0.65 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Trp | 1197 | . | . | B | . | . | . | . | 0.68 | 0.37 | * | * | . | 0.50 | 0.72 |
| Ala | 1198 | . | . | . | . | . | T | C | 0.89 | 0.31 | * | . | . | 1.35 | 1.02 |
| Arg | 1199 | . | . | . | . | . | T | C | 1.20 | −0.37 | * | . | F | 2.40 | 1.31 |
| Asn | 1200 | . | . | . | . | . | T | C | 1.23 | −1.76 | * | . | F | 3.00 | 2.17 |
| Gly | 1201 | . | . | . | . | . | T | C | 1.53 | −1.03 | * | * | F | 2.70 | 1.59 |
| Glu | 1202 | . | . | . | . | . | . | C | 1.41 | −0.34 | . | * | F | 1.45 | 0.76 |
| Val | 1204 | . | . | G | . | . | . | . | 1.30 | −0.36 | * | * | . | 0.95 | 1.03 |
| Gln | 1205 | . | . | B | . | . | . | . | 1.41 | −0.79 | * | * | . | 0.80 | 0.99 |
| Phe | 1206 | . | . | B | . | . | T | . | 0.06 | −0.10 | * | * | . | 0.85 | 1.06 |
| Ser | 1207 | . | . | B | . | . | T | . | 0.06 | −0.10 | * | * | . | 0.85 | 1.06 |
| Asp | 1208 | . | . | B | . | . | T | . | −0.76 | −0.06 | * | * | . | 0.70 | 0.50 |
| Arg | 1209 | . | . | B | . | . | T | . | 0.10 | 0.23 | * | * | . | 0.10 | 0.48 |
| Ile | 1210 | . | . | B | . | . | . | . | −0.11 | −0.16 | * | * | . | 0.74 | 0.62 |
| Leu | 1211 | . | . | B | . | . | . | . | 0.59 | −0.11 | * | * | . | 0.98 | 0.57 |
| Leu | 1212 | . | . | B | . | . | . | . | 0.89 | −0.11 | * | * | . | 1.22 | 0.49 |
| Gln | 1213 | . | . | B | . | . | T | . | 0.59 | −0.11 | * | * | . | 1.81 | 1.16 |
| Pro | 1214 | . | . | . | . | . | T | C | −0.33 | −0.41 | * | * | F | 2.40 | 1.89 |
| Asp | 1215 | . | . | . | . | T | T | . | 0.56 | −0.41 | . | * | F | 2.36 | 1.89 |
| Asp | 1216 | . | . | . | . | T | T | . | 0.48 | −0.70 | . | * | F | 2.42 | 1.89 |
| Ser | 1217 | . | . | B | B | . | . | . | 0.48 | −0.41 | . | * | . | 0.78 | 0.86 |
| Leu | 1218 | . | . | B | B | . | . | . | −0.11 | −0.16 | * | * | . | 0.54 | 0.42 |
| Gln | 1219 | . | . | B | B | . | . | . | −0.11 | 0.34 | * | * | . | −0.30 | 0.26 |
| Ile | 1220 | . | . | B | B | . | . | . | −0.97 | 0.77 | * | * | . | −0.60 | 0.30 |
| Leu | 1221 | . | . | B | B | . |  | . | −0.97 | 1.03 | . | * | . | −0.60 | 0.27 |
| Ala | 1222 | . | . | B | B | . | . | . | −1.26 | 0.34 | . | * | . | −0.30 | 0.27 |
| Pro | 1223 | . | A | B | . | . | . | . | −0.44 | 0.44 | * | * | . | −0.60 | 0.38 |
| Val | 1224 | . | A | B | . | . | . | . | −1.30 | −0.24 | . | * | . | 0.30 | 0.78 |
| Glu | 1225 | . | A | B | . | . | . | . | −0.76 | −0.29 | . | * | . | 0.30 | 0.57 |
| Ala | 1226 | . | A | B | . | . | . | . | −0.64 | −0.36 | . | * | . | 0.30 | 0.37 |
| Asp | 1227 | . | A | B | B | . | . | . | −0.30 | 0.00 | . | * | . | −0.30 | 0.43 |
| Val | 1228 | . | A | B | B | . |  | . | −0.40 | 0.11 | . | * | . | −0.30 | 0.39 |
| Gly | 1229 | . | A | B | B | . | . | . | −0.21 | 0.60 | . | * | . | −0.60 | 0.55 |
| Phe | 1230 | . | . | B | B | . | . | . | −0.21 | 0.67 | . | * | . | −0.60 | 0.18 |
| Tyr | 1231 | . | . | B | . | . | T | . | −0.21 | 1.07 | . | . | . | −0.20 | 0.38 |
| Thr | 1232 | . | . | B | . | . | T | . | −0.52 | 0.93 | . | . | . | −0.20 | 0.39 |
| Cys | 1233 | . | . | B | . | . | T | . | 0.33 | 0.99 | . | . | . | −0.20 | 0.65 |
| Asn | 1234 | . | . | . | . | T | T | . | 0.09 | 0.60 | . | . | . | 0.20 | 0.67 |
| Ala | 1235 | . | . | B | . | . | . | . | −0.02 | 0.34 | . | . | . | −0.10 | 0.47 |
| Thr | 1236 | . | . | B | . | . | . | . | −0.12 | 0.54 | . | . | F | −0.25 | 0.72 |
| Asn | 1237 | . | . | B | . | . | . | . | −0.06 | 0.40 | . | . | . | −0.40 | 0.44 |
| Ala | 1238 | . | . | B | . | . | . | . | 0.61 | 0.76 | . | . | . | −0.40 | 0.69 |
| Leu | 1239 | . | . | B | . | . | . | . | 0.31 | 0.26 | . | . | . | −0.10 | 0.80 |
| Gly | 1240 | . | . | B | . | . | T | . | 0.04 | 0.16 | . | . | . | 0.10 | 0.66 |
| Tyr | 1241 | . | . | B | . | . | T | . | 0.06 | 0.40 | . | . | . | −0.20 | 0.49 |
| Asp | 1242 | . | . | B | . | . | T | . | −0.83 | 0.29 | . | . | F | 0.25 | 0.79 |
| Ser | 1243 | . | . | B | . | . | T | . | −0.83 | 0.29 | . | . | . | 0.10 | 0.56 |
| Val | 1244 | . | . | B | B | . | . | . | −0.88 | 0.36 | . | . | . | −0.30 | 0.36 |
| Ser | 1245 | . | . | B | B | . | . | . | −0.84 | 0.24 | . | * | . | −0.30 | 0.16 |
| Ile | 1246 | . | . | B | B | . | . | . | −1.41 | 0.73 | . | * | . | −0.60 | 0.17 |
| Ala | 1247 | . | . | B | B | . | . | . | −2.00 | 1.03 | . | * | . | −0.60 | 0.19 |
| Val | 1248 | . | . | B | B | . | . | . | −2.04 | 0.89 | . | * | . | −0.60 | 0.14 |
| Thr | 1249 | . | . | B | B | . | . | . | −1.14 | 0.93 | * | * | . | −0.60 | 0.20 |
| Leu | 1250 | . | . | B | B | . | . | . | −1.06 | 0.24 | . | * | . | −0.30 | 0.40 |
| Ala | 1251 | . | . | B | B | . | . | . | −0.98 | 0.17 | . | * |  | −0.30 | 0.84 |
| Gly | 1252 | . | . | . | B | . | . | C | −1.24 | 0.21 | * | * | F | 0.05 | 0.48 |
| Lys | 1253 | . | . | . | B | . | . | C | −0.34 | 0.37 | * | * | F | 0.05 | 0.43 |
| Pro | 1254 | . | . | B | B | . | . | . | −0.34 | −0.31 | * | * | F | 0.45 | 0.86 |
| Leu | 1255 | . | . | B | B | . | . | . | 0.17 | −0.33 | * | * | F | 0.60 | 1.25 |
| Val | 1256 | . | . | B | B | . | . | . | 0.87 | −0.37 | * | . | F | 0.45 | 0.84 |
| Lys | 1257 | . | . | B | B | . | . | . | 0.61 | −0.37 | * | * | F | 0.60 | 1.06 |
| Thr | 1258 | . | . | B | B | . | . | . | −0.26 | −0.19 | * | * | F | 0.60 | 1.28 |
| Ser | 1259 | . | . | B | B | . | . | . | −0.39 | −0.39 | . | . | F | 0.60 | 2.48 |
| Arg | 1260 | . | . | B | B | . | . | . | −0.47 | −0.39 | . | . | F | 0.45 | 0.92 |
| Met | 1261 | . | . | B | B | . | . | . | 0.39 | 0.30 | . | . | . | −0.30 | 0.45 |
| Thr | 1262 | . | . | B | B | . | . | . | 0.03 | 0.21 | . | . | . | −0.30 | 0.54 |
| Val | 1263 | . | . | B | B | . | . | . | 0.34 | 0.31 | . | . | . | −0.30 | 0.40 |
| Ile | 1264 | . | . | B | B | . | . | . | 0.69 | 0.31 | . | . | . | 0.00 | 0.69 |
| Asn | 1265 | . | . | B | . | . | G | . | 0.37 | −0.30 | . | . | . | 1.30 | 0.96 |
| Thr | 1266 | . | . | . | . | . | T | C | 0.38 | −0.36 | . | . | F | 2.10 | 2.00 |
| Glu | 1267 | . | . | . | . | . | T | C | −0.17 | −0.50 | * | . | F | 2.40 | 2.88 |
| Lys | 1268 | . | . | . | . | . | T | C | 0.38 | −0.54 | * | . | F | 3.00 | 1.33 |
| Pro | 1269 | . | . | . | B | . | . | C | 0.41 | −0.46 | . | * | F | 2.00 | 1.33 |
| Ala | 1270 | . | . | B | B | . | . | . | 0.41 | −0.30 | . | * | . | 1.20 | 0.57 |
| Val | 1271 | . | . | B | B | . | . | . | −0.17 | −0.30 | . | * | . | 0.90 | 0.48 |
| Thr | 1272 | . | . | B | B | . | . | . | −0.51 | 0.39 | . | * | . | 0.00 | 0.22 |
| Val | 1273 | . | . | B | B | . | . | . | −0.86 | 0.39 | . | * | . | −0.30 | 0.21 |
| Asp | 1274 | . | . | B | . | . | T | . | −0.96 | 0.27 | . | * | . | 0.10 | 0.38 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Ile | 1275 | . | . | B | . | . | T | . | −1.26 | 0.11 | * | * | F | 0.25 | 0.38 |
| Gly | 1276 | . | . | B | . | . | T | . | −0.36 | 0.31 | * | * | F | 0.25 | 0.36 |
| Ser | 1277 | . | . | B | . | . | T | . | −0.36 | −0.33 | * | * | F | 0.85 | 0.43 |
| Thr | 1278 | . | . | B | B | . | . | . | −0.36 | 0.16 | * | * | F | −0.15 | 0.89 |
| Ile | 1279 | . | . | B | B | . | . | . | −0.36 | 0.11 | * | * | F | −0.15 | 0.67 |
| Lys | 1280 | . | . | B | B | . | . | . | 0.19 | 0.09 | * | . | F | −0.15 | 0.86 |
| Thr | 1281 | . | . | B | B | . | . | . | −0.32 | 0.13 | * | . | F | −0.15 | 0.59 |
| Val | 1282 | . | . | B | B | . | . | . | −0.20 | 0.29 | . | . | F | −0.15 | 0.62 |
| Gln | 1283 | . | . | B | B | . | . | . | −0.57 | 0.00 | . | . | F | −0.15 | 0.50 |
| Gly | 1284 | . | . | B | B | . | . | . | 0.01 | 0.64 | * | * | F | −0.45 | 0.26 |
| Val | 1285 | . | . | B | B | . | . | . | −0.92 | 0.64 | * | * | . | −0.60 | 0.50 |
| Asn | 1286 | . | . | B | B | . | . | . | −0.61 | 0.69 | * | * | . | −0.60 | 0.20 |
| Val | 1287 | . | . | B | B | . | . | . | −0.42 | 0.69 | . | * | . | −0.60 | 0.33 |
| Thr | 1288 | . | . | B | B | . | . | . | −0.42 | 0.83 | . | * | . | −0.60 | 0.24 |
| Ile | 1289 | . | . | B | B | . | . | . | −0.93 | 0.59 | . | * | . | −0.60 | 0.26 |
| Asn | 1290 | . | . | B | B | . | . | . | −0.67 | 0.83 | . | * | . | −0.60 | 0.26 |
| Cys | 1291 | . | . | B | B | . | . | . | −1.01 | 0.69 | . | * | . | −0.60 | 0.18 |
| Gln | 1292 | . | . | B | B | . | . | . | −1.01 | 0.63 | . | * | . | −0.60 | 0.25 |
| Val | 1293 | . | . | B | B | . | . | . | −0.91 | 0.59 | . | * | . | −0.60 | 0.12 |
| Ala | 1294 | . | . | B | B | . | . | . | −0.02 | 0.61 | . | * | . | −0.60 | 0.34 |
| Gly | 1295 | . | . | . | B | . | . | C | −0.61 | 0.04 | . | * | . | −0.10 | 0.34 |
| Val | 1296 | . | . | . | . | . | . | C | 0.06 | 0.14 | . | * | . | 0.10 | 0.46 |
| Pro | 1297 | . | . | B | . | . | . | . | −0.80 | −0.50 | . | * | F | 0.65 | 0.79 |
| Glu | 1298 | . | . | B | . | . | . | . | −0.26 | −0.36 | . | * | F | 0.65 | 0.59 |
| Ala | 1299 | . | . | B | B | . | . | . | 0.04 | −0.30 | . | . | F | 0.60 | 1.15 |
| Glu | 1300 | . | . | B | B | . | . | . | −0.31 | −0.03 | * | . | . | 0.30 | 0.78 |
| Val | 1301 | A | . | . | B | . | . | . | 0.66 | 0.33 | * | . | . | −0.30 | 0.39 |
| Thr | 1302 | A | . | . | B | . | . | . | 0.87 | 0.33 | . | * | . | 0.04 | 0.76 |
| Trp | 1303 | A | . | . | B | . | . | . | 0.91 | 0.23 | . | * | . | 0.38 | 0.70 |
| Phe | 1304 | A | . | . | B | . | . | . | 1.20 | 0.23 | . | * | . | 0.87 | 1.90 |
| Arg | 1305 | . | . | . | B | T | . | . | 1.24 | ‘0.03 | * | * | F | 2.36 | 1.76 |
| Asn | 1306 | . | . | . | . | T | T | . | 1.29 | −0.51 | * | * | F | 3.40 | 3.35 |
| Lys | 1307 | . | . | . | . | T | T | . | 1.26 | −0.74 | * | * | F | 3.06 | 3.19 |
| Ser | 1308 | . | . | . | . | T | T | . | 1.24 | −1.10 | * | * | F | 2.93 | 1.61 |
| Lys | 1309 | . | . | . | . | T | T | . | 1.73 | −0.71 | * | * | F | 2.80 | 1.34 |
| Leu | 1310 | . | . | . | . | T | . | . | 1.59 | −0.69 | * | * | F | 2.47 | 1.04 |
| Gly | 1311 | . | . | . | . | . | . | C | 1.56 | −0.19 | . | * | F | 1.84 | 1.05 |
| Ser | 1312 | . | . | . | . | . | T | C | 0.70 | −0.07 | . | * | F | 2.10 | 0.72 |
| Pro | 1313 | . | . | B | . | . | T | . | 0.97 | 0.61 | . | . | F | 0.79 | 0.72 |
| His | 1314 | . | . | B | . | . | T | . | 0.92 | 0.43 | . | . | . | 0.43 | 0.99 |
| His | 1315 | . | . | B | . | . | T | . | 1.39 | 0.00 | . | . | . | 0.67 | 1.28 |
| Leu | 1316 | . | . | B | . | . | . | . | 1.43 | 0.04 | . | . | . | 0.11 | 0.82 |
| His | 1317 | . | . | B | . | . | T | . | 0.92 | 0.00 | . | . | . | 0.10 | 0.80 |
| Glu | 1318 | . | . | B | . | . | T | . | 0.32 | 0.19 | . | . | F | 0.25 | 0.49 |
| Gly | 1319 | . | . | . | . | T | T | . | −0.46 | 0.37 | . | . | F | 0.65 | 0.49 |
| Ser | 1320 | . | . | B | . | . | T | . | −0.73 | 0.37 | . | . | F | 0.25 | 0.30 |
| Leu | 1321 | . | . | B | B | . | . | . | 0.08 | 0.36 | * | . | F | −0.15 | 0.25 |
| Leu | 1322 | . | . | B | B | . | . | . | −0.74 | 0.76 | . | . | . | −0.60 | 0.40 |
| Len | 1323 | . | . | B | B | . | . | . | −1.04 | 0.97 | . | . | . | −0.60 | 0.22 |
| Thr | 1324 | . | . | B | B | . | . | . | −1.00 | 0.97 | . | . | . | −0.60 | 0.36 |
| Asn | 1325 | . | . | B | B | . | . | . | −1.00 | 0.67 | . | . | F | −0.17 | 0.58 |
| Val | 1326 | . | . | B | B | . | . | . | −0.19 | 0.37 | . | . | F | 0.41 | 0.95 |
| Ser | 1327 | . | . | B | . | . | . | . | 0.62 | −0.31 | . | . | F | 1.64 | 1.10 |
| Ser | 1328 | . | . | B | . | . | T | . | 1.09 | −0.40 | . | . | F | 2.12 | 1.18 |
| Ser | 1329 | . | . | . | . | T | T | . | 0.59 | −0.37 | . | . | F | 2.80 | 1.58 |
| Asp | 1330 | . | . | . | . | T | T | . | 0.34 | −0.33 | . | . | F | 2.37 | 0.97 |
| Gln | 1331 | . | . | . | . | T | T | . | 0.90 | 0.04 | . | . | F | 1.64 | 1.14 |
| Gly | 1332 | . | . | | . | T | . | . | 0.53 | 0.04 | * | . | F | 1.16 | 1.14 |
| Leu | 1333 | . | . | B | . | . | . | . | 0.94 | 0.23 | . | * | . | 0.18 | 0.36 |
| Tyr | 1334 | . | . | B | . | . | T | . | 0.66 | 0.23 | * | * | . | 0.10 | 0.41 |
| Ser | 1335 | . | . | B | . | . | T | . | 0.07 | 0.33 | * | | . | 0.10 | 0.42 |
| Cys | 1336 | . | . | B | . | . | T | . | 0.07 | 0.40 | . | . | . | −0.20 | 0.52 |
| Arg | 1337 | . | . | B | . | . | T | . | −0.40 | 0.11 | . | . | . | 0.10 | 0.53 |
| Ala | 1338 | . | A | B | . | . | . | . | 0.38 | 0.04 | . | . | . | −0.30 | 0.33 |
| Ala | 1339 | . | A | B | . | . | . | . | 0.28 | 0.16 | * | * | . | −0.30 | 0.83 |
| Asn | 1340 | . | A | . | . | . | . | C | 0.58 | 0.01 | * | * | . | −0.10 | 0.42 |
| Len | 1341 | . | A | . | . | . | . | C | 0.43 | 0.01 | * | * | . | −0.10 | 0.72 |
| His | 1342 | . | A | . | . | . | . | C | 0.01 | 0.20 | * | * | . | −0.10 | 0.58 |
| Gly | 1343 | . | A | . | . | . | . | C | 0.60 | 0.19 | * | * | . | −0.10 | 0.52 |
| Glu | 1344 | . | A | . | . | . | . | C | 0.89 | −0.21 | . | * | F | 0.80 | 1.10 |
| Len | 1345 | . | A | . | . | . | . | C | 0.58 | −0.51 | * | * | F | 1.10 | 1.09 |
| Thr | 1346 | . | A | B | . | . | . | . | 1.39 | −0.53 | . | * | F | 0.90 | 1.58 |
| Gln | 1347 | . | A | B | . | . | . | . | 0.61 | −0.56 | . | * | F | 0.90 | 1.58 |
| 8cr | 1348 | . | . | B | B | . | . | . | 0.14 | 0.13 | . | * | F | 0.00 | 1.58 |
| Thr | 1349 | . | . | B | B | . | . | . | −0.74 | 0.13 | . | . | F | −0.15 | 0.90 |
| Gln | 1350 | . | . | B | B | . | . | . | −0.74 | 0.33 | . | . | F | −0.15 | 0.37 |
| Len | 1351 | . | . | B | B | . | . | . | −0.43 | 1.01 | . | . | . | −0.60 | 0.23 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Len | 1352 | . | . | B | B | . | . | . | −0.64 | 0.63 | . | . | . | −0.60 | 0.26 |
| Ile | 1353 | . | . | B | B | . | . | . | −0.56 | 0.57 | . | . | . | −0.60 | 0.23 |
| Len | 1354 | . | . | B | B | . | . | . | −0.24 | 0.60 | . | . | . | −0.60 | 0.44 |
| Asp | 1355 | . | . | . | . | . | T | C | −1.10 | 0.31 | . | . | F | 0.45 | 0.92 |
| Pro | 1356 | . | . | . | . | . | T | C | −0.50 | 0.27 | . | . | F | 0.45 | 0.97 |
| Pro | 1357 | . | . | . | . | T | T | . | 0.00 | 0.01 | * | . | F | 0.80 | 1.82 |
| Gln | 1358 | . | . | . | . | . | T | C | 0.89 | −0.19 | * | * | F | 1.20 | 1.57 |
| Val | 1359 | . | . | B | . | . | . | . | 0.89 | 0.21 | . | * | F | 0.20 | 1.76 |
| Pro | 1360 | . | . | B | . | . | . | . | 0.89 | 0.47 | * | * | F | −0.25 | 0.94 |
| Thr | 1361 | . | A | B | . | . | . | . | 1.10 | 0.04 | * | * | F | −0.15 | 0.94 |
| Gln | 1362 | . | A | B | . | . | . | . | 0.42 | −0.36 | * | * | F | 0.60 | 2.11 |
| Len | 1363 | . | A | B | . | . | . | . | 0.53 | −0.31 | * | * | F | 0.45 | 0.96 |
| Glu | 1364 | . | A | B | . | . | . | . | 0.80 | −0.74 | * | * | F | 0.90 | 1.30 |
| Asp | 1365 | . | A | B | . | . | . | . | 0.20 | −0.73 | * | * | F | 0.75 | 0.76 |
| Ile | 1366 | . | A | B | . | . | . | . | −0.30 | −0.44 | * | * | . | 0.30 | 0.76 |
| Arg | 1367 | . | A | B | . | . | . | . | −0.89 | −0.44 | . | * | . | 0.30 | 0.36 |
| Ala | 1368 | . | A | B | . | . | . | . | −0.67 | 0.06 | * | * | . | −0.30 | 0.22 |
| Len | 1369 | . | A | B | . | . | . | . | −0.98 | 0.56 | * | * | . | −0.60 | 0.31 |
| Len | 1370 | . | A | B | . | . | . | . | −1.32 | 0.36 | . | * | . | −0.30 | 0.23 |
| Ala | 1371 | . | A | B | . | . | . | . | −0.64 | 0.79 | . | * | . | −0.60 | 0.23 |
| Ala | 1372 | . | A | B | . | . | . | . | −0.76 | 0.71 | . | * | . | −0.60 | 0.43 |
| Thr | 1373 | . | A | . | . | . | . | C | −0.98 | 0.43 | . | . | F | −0.25 | 0.83 |
| Gly | 1374 | . | . | . | . | . | T | C | −0.38 | 0.43 | . | . | F | 0.15 | 0.68 |
| Pro | 1375 | . | . | . | . | . | T | C | 0.13 | 0.36 | . | . | F | 0.60 | 1.04 |
| Asn | 1376 | . | . | . | . | . | T | C | −0.13 | 0.24 | . | . | F | 0.45 | 0.96 |
| Len | 1377 | . | . | B | . | . | T | . | −0.36 | 0.40 | . | . | F | −0.05 | 0.72 |
| Pro | 1378 | . | . | B | B | . | . | . | −0.36 | 0.66 | * | . | F | −0.45 | 0.39 |
| Ser | 1379 | . | . | B | B | . | . | . | −0.31 | 0.71 | * | . | F | −0.45 | 0.35 |
| Val | 1380 | . | . | B | B | . | . | . | −0.31 | 0.70 | * | . | F | −0.45 | 0.56 |
| Len | 1381 | . | . | B | B | . | . | . | −1.12 | 0.44 | * | . | F | −0.45 | 0.56 |
| Thr | 1382 | . | . | B | B | . | . | . | −0.66 | 0.70 | . | . | F | −0.45 | 0.35 |
| Ser | 1383 | . | . | B | . | . | T | . | −0.76 | 0.74 | . | . | F | −0.05 | 0.46 |
| Pro | 1384 | . | . | B | . | . | T | . | −0.46 | 0.59 | . | . | F | −0.05 | 0.81 |
| Leu | 1385 | . | . | . | . | T | T | . | −0.41 | 0.30 | . | . | F | 0.65 | 0.97 |
| Gly | 1386 | . | . | B | . | . | T | . | −0.46 | 0.50 | . | . | F | −0.05 | 0.60 |
| Thr | 1387 | . | . | B | B | . | . | . | −0.96 | 0.76 | . | * | F | −0.45 | 0.29 |
| Gln | 1388 | . | . | B | B | . | . | . | −0.66 | 1.01 | . | * | F | −0.45 | 0.29 |
| Leu | 1389 | . | . | B | B | . | . | . | −0.66 | 0.33 | . | . | . | −0.30 | 0.48 |
| Val | 1390 | . | . | B | B | . | . | . | −0.19 | 0.33 | * | . | . | −0.02 | 0.52 |
| Leu | 1391 | . | . | B | B | . | . | . | 0.16 | 0.27 | * | . | F | 0.41 | 0.30 |
| Asp | 1392 | . | . | B | . | . | T | . | 0.17 | 0.27 | * | . | F | 1.09 | 0.58 |
| Pro | 1393 | . | . | . | . | T | T | . | −0.42 | −0.03 | * | . | F | 2.52 | 1.04 |
| Gly | 1394 | . | . | . | . | T | T | . | −0.42 | −0.17 | . | . | F | 2.80 | 1.28 |
| Asn | 1395 | . | . | . | . | T | T | . | −0.38 | −0.17 | * | . | F | 2.37 | 0.63 |
| Ser | 1396 | . | . | B | . | . | . | . | 0.09 | 0.51 | . | . | F | 0.59 | 0.34 |
| Ala | 1397 | . | . | B | . | . | . | . | −0.58 | 0.51 | . | . | . | 0.16 | 0.34 |
| Leu | 1398 | . | . | B | . | . | . | . | −0.58 | 0.66 | . | . | . | −0.12 | 0.11 |
| Leu | 1399 | . | . | B | . | . | . | . | −1.12 | 0.69 | . | * | . | −0.40 | 0.13 |
| Gly | 1400 | . | . | B | . | . | . | . | −1.08 | 0.99 | . | * | . | −0.40 | 0.09 |
| Cys | 1401 | . | . | B | . | . | . | . | −1.12 | 0.49 | . | * | . | −0.40 | 0.22 |
| Pro | 1402 | . | . | B | . | . | . | . | −0.57 | 0.23 | . | * | . | −0.10 | 0.26 |
| Ile | 1403 | . | . | . | . | T | . | . | 0.03 | 0.04 | . | * | . | 0.30 | 0.36 |
| Lys | 1404 | . | . | B | . | . | . | . | −0.01 | 0.04 | . | * | F | 0.20 | 1.03 |
| Gly | 1405 | . | . | B | . | . | . | . | 0.12 | 0.11 | . | * | F | 0.05 | 0.50 |
| His | 1406 | . | . | B | . | . | T | . | 0.79 | 0.11 | . | * | F | 0.40 | 1.10 |
| Pro | 1407 | . | . | . | . | . | T | C | 0.11 | −0.17 | . | * | . | 0.90 | 0.88 |
| Val | 1408 | . | . | . | . | . | T | C | 0.69 | 0.51 | . | * | . | 0.00 | 0.62 |
| Pro | 1409 | . | . | B | . | . | T | . | 0.36 | 0.57 | . | * | F | −0.05 | 0.66 |
| Asn | 1410 | . | . | B | B | . | . | . | 0.00 | 0.99 | . | . | . | −0.60 | 0.45 |
| Ile | 1411 | . | . | B | B | . | . | . | 0.00 | 1.34 | . | . | . | −0.60 | 0.53 |
| Thr | 1412 | . | . | B | B | . | . | . | −0.13 | 1.20 | . | . | . | −0.60 | 0.46 |
| Trp | 1413 | . | . | B | B | . | . | . | 0.38 | 1.20 | . | . | . | −0.60 | 0.28 |
| Phe | 1414 | . | . | B | B | . | . | . | 0.59 | 1.23 | . | . | . | −0.60 | 0.40 |
| His | 1415 | . | . | . | . | T | T | . | 0.38 | 0.94 | . | . | . | 0.20 | 0.48 |
| Gly | 1416 | . | . | . | . | T | T | . | 0.38 | 0.89 | . | . | F | 0.35 | 0.71 |
| Gly | 1417 | . | . | . | . | . | T | C | −0.17 | 0.66 | * | . | F | 0.15 | 0.57 |
| Gln | 1418 | . | . | . | . | . | T | C | −0.19 | 0.51 | * | . | F | 0.15 | 0.31 |
| Pro | 1419 | . | . | . | B | . | . | C | −0.08 | 0.50 | * | . | F | −0.25 | 0.46 |
| Ile | 1420 | . | . | B | B | . | . | . | −0.36 | 0.57 | * | . | . | −0.60 | 0.47 |
| Val | 1421 | . | . | B | B | . | . | . | −0.36 | 0.63 | . | . | . | −0.60 | 0.39 |
| Thr | 1422 | . | . | B | B | . | . | . | −0.82 | 0.66 | . | . | . | −0.60 | 0.25 |
| Ala | 1423 | . | . | B | B | . | . | . | −1.13 | 0.91 | . | . | . | −0.60 | 0.29 |
| Thr | 1424 | . | . | B | B | . | . | . | −0.96 | 0.71 | . | . | F | −0.45 | 0.57 |
| Gly | 1425 | . | . | B | B | . | . | . | −0.10 | 0.57 | . | . | F | −0.45 | 0.54 |
| Leu | 1426 | . | . | B | B | . | . | . | −0.13 | 0.59 | . | . | . | −0.60 | 0.72 |
| Thr | 1427 | . | . | B | B | . | . | . | −0.63 | 0.77 | . | . | . | −0.60 | 0.35 |
| His | 1428 | . | . | B | B | . | . | . | −0.63 | 0.97 | . | . | . | −0.60 | 0.29 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| His | 1429 | . | . | B | B | . | . | . | −0.91 | 1.04 | . | . | . | −0.60 | 0.36 |
| Ile | 1430 | . | . | B | B | . | . | . | −0.91 | 0.86 | . | . | . | −0.60 | 0.25 |
| Leu | 1431 | . | . | B | B | . | . | . | −0.10 | 0.80 | * | * | . | −0.60 | 0.18 |
| Ala | 1432 | . | . | B | B | . | . | . | −0.68 | 0.70 | * | . | . | −0.60 | 0.23 |
| Ala | 1433 | . | . | B | B | . | . | . | −1.46 | 0.89 | * | . | . | −0.60 | 0.23 |
| Gly | 1434 | . | . | B | B | . | . | . | −1.42 | 0.89 | . | . | . | −0.60 | 0.23 |
| Gln | 1435 | . | . | B | B | . | . | . | −1.39 | 0.60 | * | . | . | −0.60 | 0.40 |
| Ile | 1436 | . | . | B | B | . | . | . | −1.17 | 0.74 | * | . | . | −0.60 | 0.29 |
| Leu | 1437 | . | . | B | B | . | . | . | −0.58 | 0.74 | * | . | . | −0.60 | 0.30 |
| Gln | 1438 | . | . | B | B | . | . | . | −0.80 | 0.71 | * | . | . | −0.60 | 0.28 |
| Val | 1439 | . | . | B | B | . | . | . | −0.76 | 1.00 | . | . | . | −0.60 | 0.33 |
| Ala | 1440 | . | . | B | B | . | . | . | −1.10 | 0.70 | . | . | . | −0.60 | 0.53 |
| Asn | 1441 | . | . | B | B | . | . | . | −0.56 | 0.44 | . | . | . | −0.60 | 0.30 |
| Leu | 1442 | . | . | . | . | . | T | C | −0.04 | 0.47 | . | . | F | 0.15 | 0.40 |
| Ser | 1443 | . | . | . | . | . | T | C | −0.04 | 0.21 | . | . | F | 0.45 | 0.53 |
| Gly | 1444 | . | . | . | . | T | T | . | 0.47 | 0.11 | . | * | F | 0.89 | 0.58 |
| Gly | 1445 | . | . | . | . | . | T | C | 1.06 | 0.14 | | * | F | 0.93 | 0.69 |
| Ser | 1446 | . | . | . | . | . | T | C | 0.36 | −0.54 | . | * | F | 2.07 | 0.89 |
| Gln | 1447 | . | . | . | . | . | T | C | 0.87 | −0.14 | . | * | F | 2.01 | 0.78 |
| Gly | 1448 | . | . | . | . | . | T | C | 0.50 | −0.19 | . | . | F | 2.40 | 1.06 |
| Glu | 1449 | . | . | B | . | . | T | . | 0.03 | −0.04 | . | * | F | 1.81 | 0.42 |
| phe | 1450 | . | A | B | . | . | . | . | −0.21 | 0.26 | . | * | . | 0.42 | 0.20 |
| Ser | 1451 | . | A | B | . | . | . | . | 0.09 | 0.36 | . | * | . | 0.18 | 0.21 |
| Cys | 1452 | . | A | B | . | . | . | . | 0.09 | 0.33 | . | * | . | −0.06 | 0.21 |
| Leu | 1453 | . | A | B | . | . | . | . | 0.43 | 0.73 | . | * | . | −0.60 | 0.38 |
| Ala | 1454 | . | A | . | . | . | . | C | −0.16 | −0.06 | . | . | . | 0.50 | 0.49 |
| Gln | 1455 | . | A | . | . | . | . | C | 0.20 | 0.06 | . | . | F | 0.05 | 0.93 |
| Asn | 1456 | . | A | . | . | . | . | C | −0.36 | −0.09 | . | . | F | 0.80 | 1.12 |
| Glu | 1457 | A | A | . | . | . | . | . | −0.50 | −0.13 | . | . | F | 0.45 | 0.82 |
| Ala | 1458 | A | A | . | . | . | . | . | −0.29 | 0.06 | . | . | F | −0.15 | 0.39 |
| Gly | 1459 | . | A | B | . | . | . | . | 0.30 | 0.27 | . | . | . | −0.30 | 0.24 |
| Val | 1460 | . | A | B | . | . | . | . | 0.34 | 0.27 | * | . | . | −0.30 | 0.24 |
| Leu | 1461 | . | A | B | . | . | . | . | −0.24 | 0.27 | * | . | . | −0.30 | 0.48 |
| Met | 1462 | . | A | B | . | . | . | . | −0.54 | 0.27 | . | . | . | −0.30 | 0.49 |
| Gln | 1463 | . | A | B | . | . | . | . | −0.77 | 0.23 | . | . | . | −0.30 | 0.88 |
| Lys | 1464 | . | A | B | . | . | . | . | −1.28 | 0.27 | . | . | . | −0.30 | 0.88 |
| Ala | 1465 | . | A | B | B | . | . | . | −1.31 | 0.23 | * | * | . | −0.30 | 0.66 |
| Ser | 1466 | . | A | B | B | . | . | . | −0.50 | 0.30 | * | * | . | −0.30 | 0.27 |
| Leu | 1467 | . | A | B | B | . | . | . | 0.10 | 0.30 | * | . | . | −0.30 | 0.23 |
| Val | 1468 | . | A | B | B | . | . | . | −0.14 | 0.30 | * | * | . | −0.30 | 0.38 |
| Ile | 1469 | . | A | B | B | . | . | . | −0.48 | 0.56 | . | * | . | −0.60 | 0.45 |
| Gln | 1470 | . | . | B | . | . | T | . | −0.18 | 1.09 | . | . | . | −0.20 | 0.57 |
| Asp | 1471 | . | . | B | . | . | T | . | −0.18 | 1.31 | . | . | . | −0.20 | 0.81 |
| Tyr | 1472 | . | . | . | . | T | T | . | −0.22 | 1.06 | . | . | . | 0.35 | 1.54 |
| Trp | 1473 | . | . | . | . | T | T | . | 0.63 | 1.01 | * | . | . | 0.20 | 0.66 |
| Trp | 1474 | . | . | B | . | . | . | . | 1.63 | 0.61 | * | . | . | −0.40 | 0.66 |
| Ser | 1475 | . | . | B | . | . | T | . | 0.82 | 0.61 | * | . | . | −0.20 | 0.82 |
| Val | 1476 | . | . | B | . | . | T | . | 0.23 | 0.54 | * | . | . | −0.20 | 0.65 |
| Asp | 1477 | . | . | . | . | T | T | . | 0.17 | 0.13 | * | . | F | 0.65 | 0.62 |
| Arg | 1478 | . | . | . | . | T | T | . | −0.21 | −0.30 | * | . | . | 1.10 | 0.67 |
| Leu | 1479 | . | . | . | . | T | . | | −0.22 | −0.11 | * | . | . | 0.90 | 0.48 |
| Ala | 1480 | . | . | . | . | T | T | . | −0.51 | −0.37 | * | . | . | 1.10 | 0.39 |
| Thr | 1481 | . | . | . | . | T | T | . | 0.04 | 0.13 | * | . | . | 0.50 | 0.20 |
| Cys | 1482 | . | . | B | . | . | T | . | −0.62 | 0.51 | * | . | . | 0.05 | 0.33 |
| Ser | 1483 | . | . | B | . | . | T | . | −1.08 | 0.40 | * | . | . | 0.30 | 0.17 |
| Ala | 1484 | . | . | B | . | . | . | . | −0.27 | 0.33 | * | . | . | 0.65 | 0.12 |
| Ser | 1485 | . | . | . | . | T | . | . | 0.43 | 0.24 | * | * | . | 1.30 | 0.35 |
| Cys | 1486 | . | . | . | . | T | T | . | 0.40 | −0.33 | * | . | F | 2.50 | 0.52 |
| Gly | 1487 | . | . | . | . | T | T | . | 0.21 | −0.29 | * | . | F | 2.25 | 0.51 |
| Asn | 1488 | . | . | . | . | T | T | . | 0.51 | −0.14 | * | . | F | 2.00 | 0.28 |
| Arg | 1489 | . | . | . | . | T | T | . | 1.10 | −0.13 | * | . | F | 1.75 | 0.91 |
| Gly | 1490 | . | . | . | . | T | . | . | 1.19 | −0.30 | * | * | F | 1.45 | 1.59 |
| Val | 1491 | . | . | B | . | . | . | . | 1.97 | −0.30 | * | * | F | 1.06 | 1.53 |
| Gln | 1492 | . | . | B | . | . | . | . | 1.50 | −0.70 | * | * | F | 1.62 | 1.53 |
| Gln | 1493 | . | . | B | . | . | T | . | 1.61 | −0.01 | * | * | F | 1.78 | 1.27 |
| Pro | 1494 | . | . | B | . | . | T | . | 0.83 | −0.44 | * | * | F | 2.04 | 3.36 |
| Arg | 1495 | . | . | B | . | . | T | . | 0.37 | −0.51 | . | * | F | 2.60 | 1.04 |
| Leu | 1496 | . | . | B | . | . | T | . | 0.41 | −0.23 | . | * | . | 1.74 | 0.50 |
| Arg | 1497 | . | A | B | . | . | . | . | 0.41 | 0.06 | . | * | . | 0.48 | 0.26 |
| Cys | 1498 | . | A | B | . | . | . | . | 0.11 | 0.03 | * | * | . | 0.22 | 0.22 |
| Leu | 1499 | . | A | B | . | . | . | . | 0.01 | 0.41 | * | * | . | −0.34 | 0.35 |
| Leu | 1500 | . | A | B | . | . | . | . | −0.10 | 0.21 | . | * | F | 0.25 | 0.84 |
| Asn | 1501 | . | . | B | . | . | T | . | −0.14 | 0.21 | * | * | F | 0.25 | 0.84 |
| Ser | 1502 | . | . | . | . | . | T | C | −0.26 | 0.29 | * | * | F | 0.45 | 0.76 |
| Thr | 1503 | . | . | . | . | T | T | . | 0.20 | 0.00 | . | . | F | 0.80 | 1.47 |
| Glu | 1504 | . | . | . | . | T | T | . | 0.42 | −0.26 | . | . | F | 1.40 | 1.42 |
| Val | 1505 | . | . | B | . | . | . | . | 1.20 | −0.16 | . | . | F | 0.80 | 1.07 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Asn | 1506 | . | . | B | . | . | T | . | 0.53 | −0.04 | . | . | F | 1.22 | 1.01 |
| Pro | 1507 | . | . | B | . | . | T | . | 0.24 | 0.04 | . | . | . | 0.54 | 0.31 |
| Ala | 1508 | . | . | B | . | T | T | . | 0.21 | 0.54 | * | . | . | 0.86 | 0.42 |
| His | 1509 | . | . | . | . | T | T | . | 0.26 | 0.33 | . | * | . | 1.38 | 0.26 |
| Cys | 1510 | . | . | . | . | T | T | . | 0.26 | −0.07 | . | * | . | 2.20 | 0.34 |
| Ala | 1511 | . | . | . | . | T | T | . | 0.37 | 0.14 | . | * | . | 1.38 | 0.25 |
| Gly | 1512 | . | . | . | . | T | T | . | 0.37 | −0.36 | . | * | . | 1.76 | 0.36 |
| Lys | 1513 | . | . | . | . | T | T | . | 0.37 | −0.43 | . | * | F | 1.84 | 1.03 |
| Val | 1514 | . | . | B | . | . | . | . | −0.46 | −0.50 | * | * | F | 1.02 | 1.03 |
| Arg | 1515 | . | . | B | . | . | . | . | 0.21 | −0.36 | * | * | F | 0.65 | 0.77 |
| Pro | 1516 | . | . | B | . | . | . | . | 0.59 | −0.39 | * | * | F | 0.65 | 0.67 |
| Ala | 1517 | | . | B | . | . | . | . | 0.04 | 0.04 | * | * | . | 0.05 | 1.39 |
| Val | 1518 | | . | B | . | . | . | . | −0.59 | 0.09 | * | * | . | −0.10 | 0.50 |
| Gln | 1519 | . | . | B | . | . | . | . | −0.40 | 0.59 | * | * | . | −0.40 | 0.33 |
| Pro | 1520 | . | . | B | . | . | . | . | −0.51 | 0.73 | * | * | . | −0.40 | 0.17 |
| Ile | 1521 | . | . | B | . | . | . | . | −0.19 | 0.63 | * | . | . | −0.40 | 0.37 |
| Ala | 1522 | . | . | B | . | . | . | . | 0.51 | −0.01 | * | . | . | 0.84 | 0.42 |
| Cys | 1523 | . | . | B | . | . | . | . | 1.37 | −0.41 | . | . | . | 1.18 | 0.54 |
| Asn | 1524 | . | . | B | . | . | T | . | 0.70 | −0.84 | . | . | . | 2.17 | 1.28 |
| Arg | 1525 | . | . | . | . | T | T | . | 0.70 | −0.96 | . | . | F | 2.91 | 0.68 |
| Arg | 1526 | . | . | . | . | T | T | . | 1.29 | −1.03 | . | * | F | 3.40 | 1.96 |
| Asp | 1527 | . | . | . | . | T | T | . | 1.99 | −1.21 | . | * | F | 3.06 | 1.63 |
| Cys | 1528 | . | . | . | . | . | T | C | 2.37 | −1.61 | . | . | F | 2.52 | 1.63 |
| Pro | 1529 | . | . | . | . | T | T | . | 1.77 | −0.70 | . | * | F | 2.23 | 0.88 |
| Ser | 1530 | . | . | . | . | T | T | . | 0.80 | −0.09 | . | * | F | 1.59 | 0.52 |
| Arg | 1531 | . | . | B | . | . | T | . | 0.38 | 0.56 | . | * | F | −0.05 | 0.72 |
| Trp | 1532 | . | . | B | B | . | . | . | 0.08 | 0.47 | * | * | . | −0.60 | 0.67 |
| Met | 1533 | . | . | B | B | . | . | . | 0.46 | 0.43 | * | * | . | −0.60 | 0.67 |
| Val | 1534 | . | . | B | B | . | . | . | 0.37 | 0.96 | * | * | . | −0.60 | 0.36 |
| Thr | 1535 | . | . | B | . | . | T | . | 0.08 | 1.34 | * | * | . | −0.20 | 0.46 |
| Ser | 1536 | . | . | . | . | T | T | . | −0.70 | 0.93 | * | * | . | 0.20 | 0.47 |
| Trp | 1537 | . | . | . | . | T | T | . | −0.72 | 0.89 | * | * | . | 0.20 | 0.34 |
| Ser | 1538 | . | . | . | . | T | T | . | −0.01 | 0.73 | * | * | . | 0.20 | 0.34 |
| Ala | 1539 | . | . | . | . | T | . | . | 0.54 | 0.24 | * | * | . | 0.55 | 0.49 |
| Cys | 1540 | . | . | . | . | T | T | . | 0.19 | 0.24 | * | * | . | 1.00 | 0.63 |
| Thr | 1541 | . | . | B | . | . | T | . | 0.14 | −0.10 | . | * | . | 1.45 | 0.25 |
| Arg | 1542 | . | . | . | . | T | T | . | 0.09 | −0.06 | * | * | F | 2.25 | 0.25 |
| Ser | 1543 | . | . | . | . | T | T | . | 0.04 | −0.13 | * | . | F | 2.50 | 0.46 |
| Cys | 1544 | . | . | . | . | T | T | . | −0.22 | −0.27 | * | . | F | 2.25 | 0.31 |
| Gly | 1545 | . | . | . | . | T | T | . | 0.44 | −0.11 | * | . | F | 2.00 | 0.12 |
| Gly | 1546 | . | . | . | . | T | T | . | 0.44 | 0.29 | . | * | F | 1.15 | 0.15 |
| Gly | 1547 | . | . | . | . | T | T | . | 0.44 | 0.39 | . | . | F | 0.90 | 0.41 |
| Val | 1548 | . | . | B | B | . | . | . | 0.86 | −0.19 | . | . | F | 0.45 | 0.82 |
| Gln | 1549 | . | . | B | B | . | . | . | 0.67 | −0.61 | . | . | F | 0.90 | 1.61 |
| Thr | 1550 | . | . | B | B | . | . | . | 0.70 | −0.40 | . | . | F | 0.60 | 1.21 |
| Arg | 1551 | . | . | B | B | . | . | . | 0.38 | −0.34 | * | . | F | 0.60 | 2.35 |
| Aig | 1552 | . | . | B | B | . | . | . | 0.72 | −0.41 | . | . | F | 0.45 | 0.73 |
| Val | 1553 | . | . | B | B | . | . | . | 1.62 | −0.41 | . | . | . | 0.30 | 0.87 |
| Thr | 1554 | . | . | B | B | . | . | . | 0.81 | −0.90 | * | . | . | 0.60 | 0.89 |
| Cys | 1555 | . | . | B | B | . | . | . | 1.17 | −0.21 | * | * | . | 0.30 | 0.38 |
| Gln | 1556 | . | . | B | B | . | . | . | 0.47 | −0.21 | * | * | F | 0.60 | 1.01 |
| Lys | 1557 | . | . | B | B | . | . | . | 0.06 | −0.36 | * | * | F | 0.45 | 0.71 |
| Leu | 1558 | . | . | B | . | . | . | . | 0.57 | −0.46 | . | . | F | 0.80 | 1.77 |
| Lys | 1559 | . | . | B | . | . | T | . | −0.01 | −0.60 | . | * | F | 1.30 | 1.01 |
| Ala | 1560 | . | | B | . | . | T | . | 0.36 | −0.31 | . | * | F | 0.85 | 0.36 |
| Ser | 1561 | . | . | B | . | . | T | . | 0.04 | 0.07 | . | * | F | 0.25 | 0.58 |
| Gly | 1562 | . | . | B | . | . | T | . | −0.21 | −0.13 | . | * | F | 0.85 | 0.42 |
| Ile | 1563 | . | . | B | B | . | . | . | −0.26 | 0.30 | . | * | F | 0.13 | 0.64 |
| Ser | 1564 | . | . | B | B | . | . | . | −0.60 | 0.44 | . | . | F | 0.11 | 0.35 |
| Thr | 1565 | . | . | B | B | . | . | . | −0.01 | 0.44 | . | . | F | 0.39 | 0.48 |
| Pro | 1566 | . | . | B | . | . | . | . | 0.29 | 0.41 | . | . | F | 1.02 | 1.10 |
| Val | 1567 | . | . | . | . | T | T | . | 0.03 | −0.27 | . | . | F | 2.80 | 1.37 |
| Ser | 1568 | . | . | . | . | T | T | . | 0.26 | −0.04 | . | . | F | 2.37 | 0.94 |
| Asn | 1569 | . | . | . | . | T | T | . | 0.24 | 0.04 | . | . | F | 1.49 | 0.32 |
| Asp | 1570 | . | . | . | . | T | T | . | 0.56 | 0.10 | * | * | F | 1.21 | 0.63 |
| Met | 1571 | . | . | B | B | . | . | . | −0.09 | −0.14 | . | . | . | 0.58 | 0.82 |
| Cys | 1572 | . | . | B | B | . | . | . | 0.18 | 0.11 | * | . | . | −0.30 | 0.38 |
| Thr | 1573 | . | . | B | B | . | . | . | 0.52 | 0.21 | * | . | . | −0.30 | 0.23 |
| Gln | 1574 | . | . | B | B | . | . | . | 0.63 | 0.21 | * | . | . | −0.30 | 0.46 |
| Val | 1575 | . | . | B | B | . | . | . | 0.42 | −0.40 | * | . | . | 0.45 | 1.68 |
| Ala | 1576 | . | . | B | B | . | . | . | 0.17 | −0.54 | * | . | F | 1.20 | 1.80 |
| Lys | 1577 | . | . | B | . | . | . | . | 0.83 | −0.39 | . | . | F | 1.25 | 0.77 |
| Arg | 1578 | . | . | B | . | . | . | . | 0.83 | −0.79 | * | . | F | 2.00 | 1.74 |
| Pro | 1579 | . | . | B | . | . | . | . | 0.83 | −0.94 | * | . | F | 2.30 | 2.48 |
| Val | 1580 | . | . | . | . | T | . | . | 1.10 | −1.04 | * | . | F | 3.00 | 2.15 |
| Asp | 1581 | . | A | B | . | . | . | . | 1.02 | −0.54 | * | . | F | 2.10 | 1.11 |
| Thr | 1582 | . | A | B | . | . | . | . | 0.98 | 0.03 | . | . | F | 0.75 | 0.38 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Gln | 1583 | . | A | B | . | . | . | . | 0.87 | 0.00 | . | . | F | 0.45 | 0.83 |
| Ala | 1584 | . | A | B | . | . | . | . | 1.08 | −0.24 | . | * | . | 0.60 | 0.86 |
| Cys | 1585 | . | A | . | . | T | . | . | 1.12 | 0.16 | . | * | . | 0.25 | 1.04 |
| Asn | 1586 | . | A | . | . | T | . | . | 0.46 | 0.36 | . | . | F | 0.25 | 0.49 |
| Gln | 1587 | . | A | B | . | . | . | . | −0.09 | 0.53 | . | * | F | −0.45 | 0.26 |
| Gln | 1588 | . | A | B | . | . | . | . | −0.09 | 0.67 | . | * | F | −0.45 | 0.36 |
| Leu | 1589 | . | A | B | . | . | . | . | 0.21 | 0.10 | . | * | . | −0.30 | 0.39 |
| Cys | 1590 | . | A | B | . | . | . | . | 0.29 | 0.61 | . | * | . | −0.60 | 0.24 |
| Val | 1591 | . | A | B | . | . | . | . | −0.41 | 0.71 | . | * | . | −0.60 | 0.14 |
| Glu | 1592 | . | A | B | . | . | . | . | −0.71 | 1.10 | . | * | . | −0.60 | 0.15 |
| Trp | 1593 | . | A | B | . | . | . | . | −1.01 | 0.80 | . | * | . | −0.60 | 0.36 |
| Ala | 1594 | . | A | B | . | . | . | . | −0.49 | 0.61 | . | * | . | −0.60 | 0.66 |
| Phe | 1595 | . | . | . | . | T | T | . | −0.17 | 0.89 | * | * | . | 0.20 | 0.40 |
| Ser | 1596 | . | . | . | . | T | T | . | 0.69 | 1.31 | * | * | . | 0.20 | 0.37 |
| Ser | 1597 | . | . | . | . | T | T | . | 0.02 | 0.80 | . | * | . | 0.20 | 0.64 |
| Trp | 1598 | . | . | . | . | T | T | . | 0.31 | 0.87 | . | . | . | 0.20 | 0.40 |
| Gly | 1599 | . | . | . | . | T | T | . | 0.56 | 0.49 | . | . | F | 0.35 | 0.48 |
| Gln | 1600 | . | . | . | . | T | T | . | 1.04 | 0.53 | . | * | F | 0.35 | 0.35 |
| Cys | 1601 | . | . | . | . | T | T | . | 0.68 | 0.57 | . | . | F | 0.35 | 0.52 |
| Asn | 1602 | . | . | . | . | T | T | . | 0.09 | 0.23 | . | . | F | 0.65 | 0.28 |
| Gly | 1603 | . | . | . | . | . | T | C | 0.03 | 0.49 | . | . | F | 0.15 | 0.11 |
| Pro | 1604 | . | . | . | . | T | T | . | 0.17 | 0.51 | . | . | F | 0.35 | 0.21 |
| Cys | 1605 | . | . | . | . | T | T | . | 0.13 | 0.37 | . | . | . | 0.50 | 0.20 |
| Ile | 1606 | . | . | B | . | . | T | . | −0.01 | 0.47 | . | . | . | −0.20 | 0.28 |
| Gly | 1607 | . | . | B | . | . | T | . | −0.60 | 0.73 | . | . | . | −0.20 | 0.15 |
| Pro | 1608 | . | . | B | . | . | T | . | −1.11 | 0.80 | . | * | . | −0.20 | 0.28 |
| His | 1609 | . | . | B | . | . | T | . | −0.90 | 0.87 | . | * | . | −0.20 | 0.30 |
| Leu | 1610 | . | . | B | . | . | T | . | −0.27 | 0.59 | . | * | . | −0.20 | 0.52 |
| Ala | 1611 | . | . | B | B | . | . | . | 0.73 | 0.66 | . | * | . | −0.60 | 0.45 |
| Val | 1612 | . | . | B | B | . | . | . | 1.08 | 0.23 | . | * | . | −0.30 | 0.65 |
| Gln | 1613 | . | . | B | B | . | . | . | 0.43 | 0.13 | * | * | . | −0.15 | 1.37 |
| His | 1614 | . | . | B | B | . | . | . | −0.23 | 0.09 | . | * | . | −0.15 | 1.01 |
| Arg | 1615 | . | . | B | B | . | . | . | −0.09 | 0.37 | . | * | . | −0.15 | 1.18 |
| Gln | 1616 | . | . | B | B | . | . | . | 0.50 | 0.30 | . | . | . | −0.30 | 0.36 |
| Val | 1617 | . | . | B | B | . | . | . | 1.04 | 0.30 | . | * | . | −0.30 | 0.46 |
| Phe | 1618 | . | . | B | B | . | . | . | 1.16 | 0.29 | * | . | . | −0.30 | 0.34 |
| Cys | 1619 | . | . | B | B | . | . | . | 1.19 | 0.29 | * | . | . | 0.04 | 0.39 |
| Gln | 1620 | . | . | B | B | . | . | . | 0.73 | −0.11 | * | * | . | 0.98 | 0.87 |
| Thr | 1621 | . | . | . | . | T | T | . | −0.16 | −0.33 | * | * | F | 2.27 | 0.99 |
| Arg | 1622 | . | . | . | . | T | T | . | 0.39 | −0.43 | * | * | F | 2.76 | 1.30 |
| Asp | 1623 | . | . | . | . | T | T | . | 0.28 | −0.51 | . | * | F | 3.40 | 1.08 |
| Gly | 1624 | . | . | . | . | T | T | . | 0.73 | −0.23 | . | * | F | 2.61 | 0.62 |
| Ile | 1625 | . | . | . | . | T | . | . | 0.43 | −0.29 | * | * | F | 2.07 | 0.49 |
| Thr | 1626 | . | . | . | . | . | . | C | 0.74 | 0.10 | * | * | F | 1.21 | 0.39 |
| Leu | 1627 | . | . | B | . | . | T | . | 0.63 | 0.10 | * | * | F | 1.15 | 0.69 |
| Pro | 1628 | . | . | B | . | . | T | . | −0.03 | 0.07 | . | . | F | 1.24 | 1.70 |
| Ser | 1629 | . | . | . | . | T | T | . | 0.01 | −0.04 | . | . | F | 2.37 | 0.63 |
| Glu | 1630 | . | . | . | . | T | T | . | 0.31 | −0.14 | . | . | F | 2.80 | 1.02 |
| Gln | 1631 | . | . | . | . | T | . | . | −0.19 | −0.33 | . | . | F | 2.17 | 0.67 |
| Cys | 1632 | . | . | . | . | T | . | . | 0.41 | −0.07 | * | * | . | 1.74 | 0.41 |
| Ser | 1633 | . | . | B | . | . | . | . | 0.73 | −0.03 | * | * | . | 1.06 | 0.37 |
| Ala | 1634 | . | . | B | . | . | . | . | 0.82 | −0.03 | * | . | . | 0.78 | 0.42 |
| Leu | 1635 | . | . | B | . | . | T | . | −0.03 | 0.00 | * | . | . | 0.25 | 1.20 |
| Pro | 1636 | . | . | . | . | . | T | C | −0.33 | 0.07 | * | . | F | 0.61 | 0.66 |
| Arg | 1637 | . | . | B | . | . | T | . | 0.02 | 0.07 | * | . | F | 0.57 | 0.88 |
| Pro | 1638 | . | . | . | . | T | T | . | 0.32 | 0.06 | * | . | F | 1.28 | 1.54 |
| Val | 1639 | . | . | . | . | T | . | . | 0.91 | −0.23 | * | . | F | 1.84 | 1.73 |
| Ser | 1640 | . | . | B | . | . | . | . | 1.06 | −0.26 | * | . | F | 1.60 | 1.42 |
| Thr | 1641 | . | . | B | . | . | T | . | 0.98 | 0.31 | . | . | F | 0.89 | 0.49 |
| Gln | 1642 | . | . | . | . | T | T | . | 0.57 | 0.80 | . | . | F | 0.83 | 0.70 |
| Asn | 1643 | . | . | . | . | T | T | . | 0.78 | 0.54 | . | . | F | 0.67 | 0.70 |
| Cys | 1644 | . | . | . | . | T | T | . | 1.04 | 0.16 | . | . | . | 0.66 | 0.84 |
| Trp | 1645 | . | A | . | . | T | . | . | 0.68 | 0.17 | * | . | . | 0.10 | 0.49 |
| Ser | 1646 | . | A | . | . | . | . | C | 0.69 | 0.34 | * | . | . | −0.10 | 0.16 |
| Glu | 1647 | . | A | . | . | T | . | . | −0.17 | 0.33 | . | . | . | 0.10 | 0.41 |
| Ala | 1648 | . | A | . | B | T | . | . | −0.20 | 0.40 | . | . | . | −0.20 | 0.29 |
| Cys | 1649 | . | A | . | B | T | . | . | 0.18 | −0.01 | * | * | . | 0.70 | 0.29 |
| Ser | 1650 | . | . | . | B | T | . | . | 0.58 | 0.51 | * | * | . | −0.20 | 0.18 |
| Val | 1651 | . | . | B | B | . | . | . | 0.02 | 0.51 | * | * | . | −0.60 | 0.34 |
| His | 1652 | . | . | . | B | T | . | . | −0.28 | 0.66 | . | * | . | −0.20 | 0.47 |
| Trp | 1653 | . | . | B | B | . | . | . | −0.50 | 0.47 | . | * | . | −0.60 | 0.47 |
| Arg | 1654 | . | . | B | B | . | . | . | −0.12 | 0.77 | . | * | . | −0.60 | 0.53 |
| Val | 1655 | . | . | B | B | . | . | . | −0.13 | 1.04 | . | . | . | −0.60 | 0.41 |
| Ser | 1656 | . | . | . | B | T | . | . | −0.09 | 1.03 | . | * | . | −0.20 | 0.56 |
| Leu | 1657 | . | . | . | B | T | . | . | −0.72 | 0.80 | . | * | . | −0.20 | 0.24 |
| Trp | 1658 | . | . | . | B | T | . | . | −0.74 | 1.37 | . | * | . | −0.20 | 0.17 |
| Thr | 1659 | . | . | B | B | . | . | . | −1.44 | 1.21 | . | * | . | −0.60 | 0.18 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 1660 | . | . | B | B | . | . | . | −0.90 | 1.33 | . | . | . | −0.60 | 0.22 |
| Cys | 1661 | . | . | B | B | . | . | . | −1.27 | 1.13 | . | . | . | −0.60 | 0.31 |
| Thr | 1662 | . | . | B | B | . | . | . | −0.80 | 0.79 | . | . | . | −0.60 | 0.11 |
| Ala | 1663 | . | . | B | B | . | . | . | −0.51 | 0.73 | . | . | . | −0.60 | 0.14 |
| Thr | 1664 | . | . | . | B | T | . | . | −0.44 | 0.44 | . | . | . | −0.20 | 0.41 |
| Cys | 1665 | . | . | . | . | T | T | . | 0.02 | 0.63 | . | . | . | 0.20 | 0.45 |
| Gly | 1666 | . | . | . | . | T | T | . | −0.01 | 0.57 | . | . | . | 0.20 | 0.44 |
| Asn | 1667 | . | . | . | . | T | T | . | 0.30 | 0.86 | . | . | . | 0.20 | 0.26 |
| Tyr | 1668 | . | . | . | . | T | T | . | 0.59 | 0.77 | . | * | . | 0.20 | 0.85 |
| Gly | 1669 | . | . | . | . | T | . | . | 1.01 | 0.59 | . | * | . | 0.41 | 1.15 |
| Phe | 1670 | . | . | . | . | T | . | . | 1.79 | 0.16 | * | . | . | 0.97 | 1.40 |
| Gln | 1671 | . | . | B | . | . | T | . | 1.28 | −0.24 | . | * | F | 1.78 | 1.75 |
| Ser | 1672 | . | . | B | . | . | T | . | 1.28 | −0.36 | . | * | F | 2.04 | 1.31 |
| Arg | 1673 | . | . | B | . | . | T | . | 0.86 | −0.79 | . | . | F | 2.60 | 2.62 |
| Arg | 1674 | . | . | B | . | . | T | . | 0.34 | −1.00 | . | . | F | 2.19 | 0.81 |
| Val | 1675 | . | A | B | . | . | . | . | 1.01 | −0.76 | . | . | . | 1.38 | 0.45 |
| Glu | 1676 | . | A | B | . | . | . | . | 0.42 | −0.64 | * | . | . | 1.12 | 0.31 |
| Cys | 1677 | . | A | B | . | . | . | . | 0.83 | −0.14 | * | * | . | 0.56 | 0.16 |
| Val | 1678 | . | A | B | . | . | . | . | 0.41 | −0.14 | * | * | . | 0.64 | 0.43 |
| His | 1679 | . | A | B | . | . | . | . | 0.30 | −0.30 | * | * | . | 0.98 | 0.35 |
| Ala | 1680 | . | A | . | . | T | . | . | 1.20 | 0.10 | * | . | . | 1.27 | 1.06 |
| Arg | 1681 | . | . | . | . | T | T | . | 0.6 | −0.47 | * | * | F | 2.76 | 2.86 |
| Thr | 1682 | . | . | . | . | T | T | . | 0.42 | −0.61 | * | * | F | 3.40 | 2.13 |
| Asn | 1683 | . | . | . | . | T | T | . | 1.07 | −0.47 | * | * | F | 2.76 | 1.56 |
| Lys | 1684 | . | . | . | . | T | T | . | 1.10 | −0.54 | * | * | F | 2.72 | 1.23 |
| Ala | 1685 | . | A | . | . | . | . | C | 1.66 | −0.54 | * | . | F | 1.78 | 1.48 |
| Val | 1686 | . | A | B | . | . | . | . | 0.73 | −0.53 | * | . | F | 1.24 | 1.25 |
| Pro | 1687 | . | A | B | . | . | . | . | 0.38 | −0.24 | * | . | F | 0.45 | 0.52 |
| Glu | 1688 | . | A | B | . | . | . | . | 0.08 | 0.33 | * | . | . | −0.30 | 0.27 |
| His | 1689 | . | A | B | . | . | . | . | −026 | 0.21 | * | . | . | −0.30 | 0.49 |
| Leu | 1690 | . | A | B | . | . | . | . | −0.01 | 0.49 | * | . | . | −0.60 | 0.34 |
| Cys | 1691 | . | . | . | . | T | T | . | 0.63 | 0.49 | * | * | . | 0.20 | 0.19 |
| Ser | 1692 | . | . | . | . | T | T | . | 0.96 | 0.91 | * | . | . | 0.20 | 0.22 |
| Trp | 1693 | . | . | . | . | T | T | . | 0.74 | 0.41 | * | . | . | 0.20 | 0.52 |
| Gly | 1694 | . | . | . | . | . | T | C | 0.19 | 0.16 | * | . | . | 0.45 | 1.50 |
| Pro | 1695 | . | . | . | . | . | . | C | 1.00 | 0.09 | * | . | F | 0.40 | 1.13 |
| Mg | 1696 | | . | . | . | . | . | C | 1.38 | 0.10 | . | . | F | 0.40 | 1.73 |
| Pro | 1697 | . | . | . | . | T | T | . | 1.68 | 0.10 | * | . | F | 0.80 | 1.83 |
| Ala | 1698 | . | . | . | . | T | T | . | 2.08 | 0.07 | * | . | F | 0.80 | 2.05 |
| Asn | 1699 | . | . | . | . | T | T | . | 1.76 | −0.36 | . | . | . | 1.25 | 2.05 |
| Trp | 1700 | . | . | . | . | T | T | . | 1.97 | 0.21 | . | * | . | 0.50 | 0.71 |
| Gln | 1701 | . | . | . | . | T | T | . | 0.97 | 0.19 | . | * | . | 0.65 | 1.13 |
| Arg | 1702 | . | . | . | . | T | T | . | 0.87 | 0.37 | . | * | . | 0.50 | 0.49 |
| Cys | 1703 | . | . | . | . | T | T | . | 1.24 | 0.46 | . | * | . | 0.45 | 0.68 |
| Asn | 1704 | . | . | . | . | T | T | . | 0.58 | −0.03 | * | . | . | 1.60 | 0.61 |
| Ile | 1705 | . | . | . | . | . | . | C | 0.87 | 0.14 | . | * | F | 1.00 | 0.17 |
| Thr | 1706 | . | . | . | . | . | T | C | 0.87 | 0.14 | . | * | F | 1.45 | 0.54 |
| Pro | 1707 | . | . | . | . | T | T | . | 0.16 | −0.03 | * | * | F | 2.50 | 0.54 |
| Cys | 1708 | . | . | . | . | T | T | . | 0.82 | 0.19 | . | * | F | 1.65 | 0.76 |
| Glu | 1709 | . | . | . | . | T | T | . | 0.16 | −0.50 | * | * | F | 2.00 | 0.91 |
| Asn | 1710 | . | . | . | . | T | . | . | 1.16 | −0.41 | . | * | . | 1.74 | 0.31 |
| Met | 1711 | . | . | . | . | T | . | . | 1.47 | −0.84 | . | * | . | 2.28 | 1.15 |
| Glu | 1712 | . | . | . | . | T | . | . | 1.37 | −1.41 | . | * | . | 2.37 | 1.11 |
| Cys | 1713 | . | . | . | . | T | T | . | 1.72 | −0.93 | * | * | . | 2.76 | 0.99 |
| Arg | 1714 | . | . | . | . | T | T | . | 1.83 | −0.84 | * | * | F | 3.40 | 1.45 |
| Asp | 1715 | . | . | . | . | T | T | . | 1.59 | −1.46 | * | * | F | 3.06 | 1.64 |
| Thr | 1716 | . | . | . | . | T | T | . | 1.52 | −0.70 | * | * | F | 2.72 | 4.79 |
| Thr | 1717 | . | A | . | . | T | . | . | 1.52 | −0.70 | * | * | F | 1.98 | 1.31 |
| Arg | 1718 | . | A | . | . | T | . | . | 2.23 | −0.70 | * | * | F | 1.64 | 1.36 |
| lyr | 1719 | . | A | . | . | T | . | . | 1.27 | −0.70 | * | * | . | 1.15 | 1.88 |
| Cys | 1720 | . | A | B | . | . | . | . | 1.31 | −0.54 | * | * | . | 0.60 | 0.97 |
| Glu | 1721 | . | A | B | . | . | . | . | 1.62 | −1.03 | * | * | . | 0.60 | 0.99 |
| Lys | 1722 | . | A | B | . | T | . | . | 1.12 | −0.63 | * | * | F | 1.30 | 1.09 |
| Val | 1723 | . | A | . | . | T | . | . | 1.06 | −0.70 | * | * | F | 1.30 | 1.68 |
| Lys | 1724 | . | A | B | . | T | . | . | 0.49 | −1.27 | . | . | F | 1.30 | 1.94 |
| Gln | 1725 | . | A | B | . | . | . | . | 0.49 | −0.59 | . | . | F | 0.75 | 0.80 |
| Leu | 1726 | . | A | B | . | . | . | . | 0.49 | −0.01 | . | . | F | 0.45 | 0.58 |
| Lys | 1727 | . | A | B | . | . | . | . | −0.37 | −0.26 | . | . | . | 0.30 | 0.50 |
| Leu | 1728 | . | A | B | B | . | . | . | 0.19 | 0.43 | . | . | . | −0.60 | 0.24 |
| Cys | 1729 | . | A | B | B | . | . | . | 0.14 | 0.41 | . | . | . | −0.60 | 0.39 |
| Gln | 1730 | . | A | B | B | . | . | . | −0.56 | 0.13 | . | * | . | −0.30 | 0.34 |
| Leu | 1731 | . | A | B | B | . | . | . | 0.30 | 0.91 | . | * | . | −0.60 | 0.35 |
| Ser | 1732 | . | A | . | . | T | . | . | −0.04 | 0.23 | * | * | . | 0.25 | 1.32 |
| Gln | 1733 | . | A | . | . | T | . | . | 0.88 | 0.04 | * | * | F | 0.40 | 1.02 |
| Phe | 1734 | . | A | . | . | T | . | . | 0.88 | −0.36 | * | * | F | 1.28 | 2.42 |
| Lys | 1735 | . | A | . | . | T | . | . | 0.21 | −0.47 | * | * | F | 1.41 | 0.97 |
| Ser | 1736 | . | . | . | . | T | T | . | 0.68 | −0.29 | . | * | F | 2.09 | 0.30 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Arg | 1737 | . | . | . | . | T | T | . | 0.67 | −0.26 | . | * | F | 2.37 | 0.34 |
| Cys | 1738 | . | . | . | . | T | T | . | 0.00 | −0.56 | . | * | . | 2.80 | 0.25 |
| Cys | 1739 | . | . | . | . | T | T | . | 0.36 | 0.01 | . | * | . | 1.62 | 0.10 |
| Gly | 1740 | . | . | . | . | T | T | . | 0.36 | 0.06 | * | * | . | 1.34 | 0.05 |
| Thr | 1741 | . | . | . | . | T | T | . | 0.07 | 0.06 | * | * | F | 1.21 | 0.19 |
| Cys | 1742 | . | . | . | . | T | T | . | −0.43 | −0.01 | * | * | F | 1.66 | 0.35 |
| Gly | 1743 | . | . | . | . | T | T | . | −0.16 | −0.16 | . | . | F | 1.51 | 0.45 |
| Lys | 1744 | . | . | B | . | . | . | . | 0.12 | −0.16 | . | . | . | 0.89 | 0.40 |
| Ala | 1745 | . | . | B | . | . | . | . | 0.08 | −0.21 | . | . | . | 1.02 | 0.96 |

TABLE 8

| Res | Position | I | II | III | IV | V | VI | VII | VIII | IX | X | XI | XII | XIII | XIV |
|---|---|---|---|---|---|---|---|---|---|---|---|---|---|---|---|
| Ala | 1 | . |  | B | . | . | . | . | 0.06 | −0.10 | * | . | . | 0.50 | 0.80 |
| Ile | 2 | . | . | B | . | . | . | . | 0.44 | −0.04 | * | * | . | 0.50 | 0.91 |
| Arg | 3 | . | . | B | . | . | . | . | 0.83 | −0.47 | * | * | . | 0.65 | 1.23 |
| Pro | 4 | . | . | B | . | . | . | . | 0.88 | −0.90 | * | * | . | 0.95 | 2.11 |
| Thr | 5 | A | . | . | . | . | . | . | 0.92 | −0.97 | * | * | F | 1.10 | 2.97 |
| Glu | 6 | A | . | . | . | . | T | . | 0.70 | −1.23 | * | * | F | 1.30 | 1.50 |
| Glu | 7 | A | . | . | . | . | T | . | 1.56 | −0.54 | * | * | F | 1.15 | 0.80 |
| Gly | 8 | A | . | . | . | . | T | . | 0.59 | −0.47 | * | * | F | 0.85 | 0.76 |
| Gly | 9 | A | . | . | . | . | T | . | 0.77 | −0.31 | . | * | F | 0.85 | 0.32 |
| Leu | 10 | A | . | . | B | . | . | . | 0.48 | 0.19 | . | * | . | −0.30 | 0.25 |
| His | 11 | A | . | . | B | . | . | . | 0.48 | 0.80 | . | * | . | −0.60 | 0.25 |
| Val | 12 | A | . | . | B | . | . | . | −0.22 | 0.37 | . | * | . | −0.30 | 0.45 |
| His | 13 | . | . | B | B | . | . | . | −0.09 | 0.73 | . | * | . | −0.60 | 0.47 |
| Met | 14 | . | . | B | . | . | . | . | −0.09 | 0.47 | . | * | . | −0.15 | 0.53 |
| Glu | 15 | . | . | B | . | . | . | . | 0.13 | 0.40 | . | * | . | 0.10 | 0.71 |
| Phe | 16 | . | . | B | . | . | . | . | 0.17 | 0.26 | . | * | . | 0.65 | 0.53 |
| Pro | 17 | . | . | . | . | T | . | . | 0.68 | −0.24 | . | * | F | 2.05 | 0.89 |
| Gly | 18 | . | . | . | . | T | T | . | 0.04 | −0.43 | . | . | F | 2.50 | 0.51 |
| Ala | 19 | . | . | . | . | T | T | . | 0.64 | 0.14 | . | . | F | 1.65 | 0.31 |
| Asp | 20 | . | . | . | . | T | T | . | 0.64 | −0.24 | . | . | F | 2.00 | 0.33 |
| Gly | 21 | . | . | . | . | T | T | . | 0.49 | −0.27 | . | . | F | 1.75 | 0.57 |
| Cys | 22 | . | . | . | . | T | . | . | 0.70 | −0.06 | . | * | F | 1.30 | 0.42 |
| Asn | 23 | . | . | B | . | . | . | . | 0.46 | −0.56 | . | * | F | 0.95 | 0.42 |
| Gln | 24 | . | A | B | . | . | . | . | 1.04 | −0.06 | . | * | . | 0.30 | 0.43 |
| Val | 25 | . | A | B | . | . | . | . | 0.80 | −0.49 | . | * | . | 0.45 | 1.38 |
| Asp | 26 | A | A | . | . | . | . | . | 0.33 | −0.30 | . | . | . | 0.45 | 1.35 |
| Ala | 27 | A | A | . | . | . | . | . | 1.04 | −0.01 | * | . | . | 0.30 | 0.64 |
| Glu | 28 | A | A | . | . | . | . | . | 0.19 | −0.41 | * | . | . | 0.45 | 1.73 |
| Tyr | 29 | A | A | . | B | . | . | . | −0.16 | −0.41 | * | . | . | 0.30 | 0.77 |
| Leu | 30 | A | A | . | B | . | . | . | 0.40 | 0.01 | . | . | . | −0.30 | 0.75 |
| Lys | 31 | A | A | . | B | . | . | . | 0.40 | −0.10 | . | . | F | 0.45 | 0.58 |
| Val | 32 | A | A | . | B | . | . | . | 0.64 | −0.10 | * | * | F | 0.73 | 0.64 |
| Gly | 33 | A | . | . | . | . | T | . | 0.61 | −0.43 | * | * | F | 1.41 | 0.77 |
| Ser | 34 | A | . | . | . | . | T | . | 0.16 | −0.61 | * | * | F | 1.99 | 0.53 |
| Glu | 35 | A | . | . | . | . | T | . | 1.08 | 0.17 | * | * | F | 1.37 | 0.61 |
| Gly | 36 | . | . | . | . | T | T | . | 0.18 | −0.47 | * | * | F | 2.80 | 1.22 |
| His | 37 | . | . | B | . | . | . | . | 0.82 | −0.26 | . | * | . | 1.62 | 0.67 |
| Phe | 38 | . | . | B | . | . | . | . | 0.58 | −0.21 | . | * | . | 1.34 | 0.60 |
| Arg | 39 | . | . | B | . | . | . | . | 0.07 | 0.29 | . | * | . | 0.46 | 0.61 |
| Val | 40 | . | . | B | . | . | . | . | −0.28 | 0.54 | . | * | . | −0.12 | 0.37 |
| Pro | 41 | . | . | B | . | . | . | . | −0.18 | 0.47 | . | * | . | −0.40 | 0.42 |
| Ala | 42 | . | . | . | B | T | . | . | −0.96 | 0.44 | . | * | . | −0.20 | 0.34 |
| Leu | 43 | . | . | B | B | . | . | . | −0.26 | 1.13 | . | * | . | −0.60 | 0.38 |
| Gly | 44 | . | . | B | B | . | . | . | −1.22 | 0.49 | * | * | . | −0.60 | 0.41 |
| Tyr | 45 | . | . | B | B | . | . | . | −0.26 | 0.70 | * | * | . | −0.60 | 0.30 |
| Leu | 46 | . | . | B | B | . | . | . | −0.93 | 0.20 | . | * | . | −0.30 | 0.71 |
| Asp | 47 | . | . | B | B | . | . | . | −1.20 | 0.20 | * | * | . | −0.30 | 0.50 |
| Val | 48 | . | . | B | B | . | . | . | −0.39 | 0.41 | * | * | . | −0.60 | 0.24 |
| Arg | 49 | . | . | B | B | . | . | . | −0.36 | −0.34 | . | * | . | 0.30 | 0.48 |
| Ile | 50 | . | . | B | B | . | . | . | −0.11 | −0.54 | . | * | . | 0.88 | 0.42 |
| Val | 51 | . | . | B | B | . | . | . | 0.46 | −0.54 | . | * | . | 1.16 | 0.94 |
| Asp | 52 | . | . | B | . | . | T | . | 0.16 | −0.43 | * | * | F | 1.69 | 0.75 |
| Thr | 53 | . | . | B | . | . | T | . | 0.71 | −0.04 | * | . | F | 2.12 | 1.44 |
| Asp | 54 | . | . | . | . | T | T | . | −0.10 | −0.34 | * | . | F | 2.80 | 2.60 |
| Tyr | 55 | . | . | . | . | T | T | . | 0.20 | −0.20 | . | . | F | 2.52 | 1.35 |
| Ser | 56 | . | . | . | B |  | . | C | 0.20 | 0.30 | . | . | F | 0.89 | 0.94 |
| Ser | 57 | . | . | B | B | . | . | . | −0.61 | 0.46 | . | . | . | −0.04 | 0.42 |
| Phe | 58 | . | . | B | B | . | . | . | −0.54 | 1.14 | . |  | . | −0.32 | 0.22 |
| Ala | 59 | . | . | B | B | . | . | . | −1.43 | 1.14 | . | . | . | −0.60 | 0.26 |
| Val | 60 | . | . | B | B | . | . | . | −1.43 | 1.44 | . | . | . | −0.60 | 0.13 |

TABLE 8-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 61 | . | . | B | B | . | . | . | −1.09 | 1.81 | . | . | . | −0.60 | 0.24 |
| Tyr | 62 | . | . | B | B | . | . | . | −0.79 | 1.03 | . | . | . | −0.60 | 0.48 |
| Ile | 63 | . | . | B | B | . | . | . | −0.90 | 0.53 | * | . | . | −0.45 | 1.13 |
| Tyr | 64 | A | A | . | . | . | . | . | −0.31 | 0.57 | * | . | . | −0.45 | 1.13 |
| Lys | 65 | A | A | . | . | . | . | . | 0.20 | −0.11 | * | . | . | 0.45 | 1.25 |
| Glu | 66 | A | A | . | . | . | . | . | 0.42 | −0.44 | * | * | F | 0.60 | 1.76 |
| Leu | 67 | A | A | . | . | . | . | . | −0.14 | −0.63 | * | . | F | 0.90 | 1.13 |
| Glu | 68 | A | A | . | . | . | . | . | 0.44 | −0.70 | * | . | F | 0.75 | 0.47 |
| Gly | 69 | A | A | . | . | . | . | . | 0.38 | −0.31 | * | . | F | 0.45 | 0.36 |
| Ala | 70 | A | A | . | B | . | . | . | −0.27 | 0.17 | * | . | . | −0.30 | 0.63 |
| Leu | 71 | A | A | . | B | . | . | . | −1.12 | 0.10 | * | * | . | −0.30 | 0.36 |
| Ser | 72 | A | A | . | B | . | . | . | −0.31 | 0.74 | * | * | . | −0.60 | 0.27 |
| Thr | 73 | A | A | . | B | . | . | . | −1.12 | 0.71 | * | * | . | −0.60 | 0.47 |
| Met | 74 | A | A | . | B | . | . | . | −1.02 | 0.90 | * | . | . | −0.60 | 0.47 |
| Val | 75 | . | A | B | B | . | . | . | −0.73 | 0.97 | * | * | . | −0.60 | 0.54 |
| Gln | 76 | . | A | B | B | . | . | . | 0.19 | 0.97 | * | * | . | −0.60 | 0.50 |
| Leu | 77 | . | A | B | B | . | . | . | 0.18 | 0.49 | * | * | . | −0.60 | 1.00 |
| Tyr | 78 | . | A | B | B | . | . | . | 0.49 | 0.36 | * | * | . | 0.19 | 1.94 |
| Ser | 79 | . | . | B | . | . | T | . | 1.09 | 0.11 | * | * | F | 1.08 | 1.94 |
| Arg | 80 | . | . | B | . | . | T | . | 1.09 | −0.29 | * | * | F | 2.02 | 3.94 |
| Thr | 81 | . | . | . | . | T | T | . | 0.79 | −0.33 | * | * | F | 2.76 | 1.86 |
| Gln | 82 | . | . | . | . | T | T | . | 1.39 | −0.70 | * | . | F | 3.40 | 1.86 |
| Asp | 83 | . | . | . | . | T | . | . | 1.63 | −0.66 | * | . | F | 2.86 | 1.47 |
| Val | 84 | . | . | B | . | . | . | . | 1.34 | −0.26 | * | . | F | 1.82 | 1.77 |
| Ser | 85 | . | . | B | . | . | T | . | 0.42 | −0.24 | * | . | F | 1.68 | 1.03 |
| Pro | 86 | . | . | B | . | . | T | . | 0.78 | 0.04 | * | . | F | 0.59 | 0.51 |
| Gln | 87 | A | . | . | . | . | T | . | 0.19 | 0.04 | * | . | F | 0.40 | 1.37 |
| Ala | 88 | A | . | . | . | . | T | . | −0.51 | −0.10 | * | . | . | 0.85 | 1.03 |
| Leu | 89 | A | A | . | . | . | . | . | 0.34 | 0.30 | * | . | . | −0.30 | 0.58 |
| Lys | 90 | . | A | B | . | . | . | . | 0.64 | 0.27 | * | . | . | −0.30 | 0.58 |
| Ala | 91 | . | A | B | . | . | . | . | 0.16 | −0.13 | * | . | . | 0.30 | 0.96 |
| Phe | 92 | . | A | B | . | . | . | . | −0.09 | 0.16 | * | . | . | −0.15 | 1.00 |
| Gln | 93 | . | A | B | . | . | . | . | 0.29 | 0.23 | * | . | . | −0.30 | 0.79 |
| Asp | 94 | . | A | B | . | . | . | . | 0.79 | 0.66 | * | * | . | −0.45 | 1.20 |
| Phe | 95 | . | A | B | . | . | . | . | −0.07 | 0.64 | * | . | . | −0.45 | 2.01 |
| Tyr | 96 | . | A | B | . | . | . | . | 0.18 | 0.54 | * | . | . | −0.60 | 0.96 |
| Pro | 97 | . | . | . | . | . | . | C | 0.07 | 0.57 | * | . | F | −0.05 | 0.57 |
| Thr | 98 | . | . | . | . | T | . | . | −0.14 | 1.26 | . | . | . | 0.00 | 0.54 |
| Leu | 99 | . | . | . | . | . | . | C | −0.14 | 0.90 | . | * | . | −0.20 | 0.53 |
| Gly | 100 | . | . | . | . | . | . | C. | 0.56 | 0.14 | . | . | . | 0.10 | 0.60 |
| Leu | 101 | . | A | . | . | . | . | C. | 0.20 | −0.29 | . | . | F | 0.65 | 0.69 |
| Pro | 102 | A | A | . | . | . | . | . | −0.19 | −0.16 | . | . | F | 0.45 | 0.83 |
| Glu | 103 | A | A | . | . | . | . | . | −0.73 | −0.23 | . | . | F | 0.45 | 0.83 |
| Asp | 104 | A | A | . | . | . | . | . | −0.52 | −0.01 | . | . | . | 0.30 | 0.75 |
| Met | 105 | A | A | . | . | . | . | . | −0.99 | −0.09 | . | . | . | 0.30 | 0.48 |
| Met | 106 | A | A | . | . | . | . | . | −0.39 | 0.17 | . | . | . | −0.30 | 0.23 |
| Val | 107 | A | A | . | . | . | . | . | −0.18 | 0.60 | . | . | . | −0.60 | 0.21 |
| Met | 108 | A | A | . | . | . | . | . | −0.48 | 1.00 | . | . | . | −0.60 | 0.37 |
| Leu | 109 | A | A | . | . | . | . | . | −0.48 | 0.77 | . | . | . | −0.60 | 0.50 |
| Pro | 110 | A | A | . | . | . | . | . | −0.47 | 0.16 | . | . | F | 0.00 | 1.12 |
| Gln | 111 | A | . | . | . | . | T | . | −0.53 | 0.01 | . | . | F | 0.40 | 1.14 |
| Ser | 112 | A | . | . | . | . | T | . | 0.32 | −0.03 | . | . | F | 0.85 | 0.74 |
| Asp | 113 | A | . | . | . | . | T | . | 0.71 | −0.31 | . | . | F | 0.85 | 0.77 |
| Ala | 114 | . | . | . | . | T | T | . | 1.52 | −0.31 | . | . | F | 1.59 | 0.69 |
| Cys | 115 | . | . | . | . | . | . | C. | 1.43 | −0.71 | . | . | . | 1.68 | 0.89 |
| Asn | 116 | . | . | . | . | . | T | C. | 1.48 | −0.71 | . | . | F | 2.37 | 0.72 |
| Pro | 117 | . | . | . | . | . | T | C. | 1.78 | −0.71 | * | . | F | 2.86 | 1.42 |
| Glu | 118 | . | . | . | . | T | T | . | 1.19 | −1.21 | * | . | F | 3.40 | 4.58 |
| Ser | 119 | A | . | . | . | . | T | . | 1.57 | −1.29 | . | . | F | 2.66 | 2.88 |
| Lys | 120 | A | A | . | . | . | . | . | 1.84 | −1.26 | . | . | F | 1.92 | 2.88 |
| Glu | 121 | A | A | . | . | . | . | . | 1.46 | −1.26 | . | . | . | 1.43 | 2.12 |
| Ala | 122 | A | A | . | . | . | . | . | 1.28 | −0.83 | . | . | . | 1.09 | 2.03 |
| Pro | 123 | A | A | . | . | . | . | . | 0.89 | −0.79 | . | . | . | 0.75 | 1.30 |

TABLE 9

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | A | . | . | . | . | . | −0.73 | 0.40 | . | . | . | −0.60 | 0.50 |
| Ala | 2 | A | A | . | . | . | . | . | −0.93 | 0.47 | . | . | . | −0.60 | 0.39 |
| Ser | 3 | A | A | . | . | . | . | . | −1.40 | 0.54 | . | . | . | −0.60 | 0.31 |
| Met | 4 | A | A | . |  | . | . | . | −1.82 | 0.76 | . | . | . | −0.60 | 0.23 |
| Ala | 5 | A | A | . | . | . | . | . | −1.74 | 0.83 | . | . | . | −0.60 | 0.19 |
| Ala | 6 | A | A | . | . | . | . | . | −1.43 | 0.81 | . | . | . | −0.60 | 0.20 |

TABLE 9-continued

| Res | Position | I | II | III | IV | V | VI | VII | VIII | IX | X | XI | XII | XIII | XIV |
|---|---|---|---|---|---|---|---|---|---|---|---|---|---|---|---|
| Val | 7 | A | A | . | . | . | . | . | −1.43 | 1.34 | . | . | . | −0.60 | 0.22 |
| Leu | 8 | A | A | . | . | . | . | . | −1.94 | 1.23 | . | . | | −0.60 | 0.22 |
| Thy | 9 | A | A | . | . | . | . | . | −1.93 | 1.41 | . | . | . | −0.60 | 0.18 |
| Trp | 10 | A | A | . | . | . | . | . | −2.16 | 1.41 | . | . | | −0.60 | 0.24 |
| Ala | 11 | A | A | . | . | . | . | . | −2.38 | 1.46 | . | . | . | −0.60 | 0.24 |
| Leu | 12 | A | A | . | . | . | . | . | −1.82 | 1.46 | . | . | . | −0.60 | 0.14 |
| Ala | 13 | A | A | . | . | . | . | . | −1.60 | 1.36 | . | . | . | −0.60 | 0.18 |
| Len | 14 | A | A | . | . | . | . | . | −1.99 | 0.94 | . | . | . | −0.60 | 0.18 |
| Len | 15 | A | A | . | . | . | . | . | −2.00 | 1.23 | . | . | . | −0.60 | 0.18 |
| Ser | 16 | A | A | . | . | . | . | . | −2.00 | 0.93 | . | . | . | −0.60 | 0.24 |
| Ala | 17 | A | A | . | . | . | . | . | −1.50 | 0.93 | . | . | . | −0.60 | 0.30 |
| Phe | 18 | A | A | . | . | . | . | . | −0.91 | 0.73 | . | . | . | −0.60 | 0.53 |
| Ser | 19 | A | A | . | . | . | . | . | −0.69 | 0.44 | . | . | . | −0.60 | 0.68 |
| Ala | 20 | A | A | . | . | . | . | . | 0.23 | 0.56 | . | . | . | −0.60 | 0.68 |
| Thr | 21 | A | A | . | . | . | . | . | 0.58 | 0.06 | . | . | F | 0.00 | 1.53 |
| Gln | 22 | A | A | . | . | . | . | . | 0.82 | −0.73 | . | . | F | 1.18 | 2.29 |
| Ala | 23 | A | A | . | . | . | . | . | 0.82 | −0.69 | . | . | F | 1.46 | 2.24 |
| Arg | 24 | . | . | . | . | T | T | . | 0.83 | −0.40 | * | . | F | 2.24 | 1.35 |
| Lys | 25 | . | . | . | . | T | T | . | 1.42 | 0.03 | * | . | F | 1.77 | 0.82 |
| Gly | 26 | . | . | . | . | T | T | . | 1.49 | −0.37 | * | . | F | 2.80 | 1.35 |
| Phe | 27 | . | . | . | . | T | T | . | 0.79 | −0.11 | * | . | . | 2.37 | 1.08 |
| Trp | 28 | . | . | . | . | T | . | . | 1.08 | 0.67 | * | . | . | 0.84 | 0.47 |
| Asp | 29 | . | . | . | . | . | . | C | 0.97 | 1.06 | . | . | . | 0.36 | 0.63 |
| Tyr | 30 | . | . | . | . | T | . | . | 0.61 | 1.03 | * | . | . | 0.43 | 1.27 |
| Phe | 31 | . | . | . | . | T | . | . | 0.66 | 0.73 | . | . | . | 0.15 | 1.74 |
| Ser | 32 | . | . | . | . | T | . | . | 1.01 | 0.20 | * | . | F | 0.94 | 1.40 |
| Gln | 33 | . | . | . | . | T | T | . | 1.30 | 0.63 | . | . | F | 1.03 | 0.88 |
| Thr | 34 | . | . | . | . | T | T | . | 1.34 | −0.13 | . | . | F | 2.42 | 1.70 |
| Ser | 35 | . | . | . | . | . | T | C | 1.24 | −0.91 | . | . | F | 2.86 | 2.54 |
| Gly | 36 | . | . | . | . | T | T | . | 2.06 | −0.87 | . | * | F | 3.40 | 1.45 |
| Asp | 37 | . | . | . | . | T | T | . | 1.50 | −1.27 | . | * | F | 3.06 | 1.97 |
| Lys | 38 | . | . | . | . | . | T | C | 1.50 | −1.11 | . | * | F | 2.52 | 1.09 |
| Gly | 39 | . | . | . | . | . | T | C | 1.81 | −150 | . | * | F | 2.18 | 1.91 |
| Arg | 40 | A | . | . | . | . | T | . | 1.22 | −1.53 | . | . | F | 1.64 | 1.98 |
| Val | 41 | A | A | . | . | . | . | . | 1.53 | −0.84 | . | * | F | 0.75 | 0.69 |
| GIu | 42 | A | A | . | . | . | . | . | 1.53 | −0.34 | . | * | F | 0.45 | 0.95 |
| Gln | 43 | A | A | . | . | . | . | . | 1.49 | −0.37 | . | * | . | 0.30 | 0.84 |
| Ile | 44 | A | A | . | . | . | . | . | 1.88 | 0.03 | . | * | . | −0.15 | 1.97 |
| His | 45 | A | A | . | . | . | . | . | 1.17 | −0.61 | . | . | F | 0.90 | 2.27 |
| GIn | 46 | A | A | . | . | . | . | . | 1.43 | 0.00 | . | . | F | 0.00 | 1.30 |
| GIn | 47 | A | A | . | . | . | . | . | 1.54 | 0.10 | . | . | F | 0.00 | 1.87 |
| Lys | 48 | A | A | . | . | . | . | . | 1.54 | −0.59 | . | . | F | 0.90 | 2.69 |
| Met | 49 | A | A | . | . | . | . | . | 2.22 | −1.09 | . | . | F | 0.90 | 2.69 |
| Ala | 50 | A | A | . | . | . | . | . | 1.67 | −1.06 | * | . | F | 0.90 | 2.40 |
| Arg | 51 | A | A | . | . | . | . | . | 1.36 | −0.96 | * | . | F | 0.90 | 1.21 |
| Glu | 52 | A | A | . | . | . | . | . | 0.54 | −0.47 | * | * | F | 0.60 | 1.77 |
| Pro | 53 | A | A | . | . | . | . | . | 0.54 | −0.40 | * | . | F | 0.60 | 1.45 |
| Ala | 54 | A | A | . | . | . | . | . | 1.14 | −0.90 | * | * | F | 0.90 | 1.48 |
| Thr | 55 | A | A | . | . | . | . | . | 1.43 | −0.90 | * | * | F | 0.90 | 1.42 |
| Leu | 56 | A | . | . | . | . | T | . | 0.51 | −0.51 | * | * | F | 1.30 | 1.23 |
| Lys | 57 | A | . | . | . | . | T | . | 0.51 | −0.26 | . | . | F | 1.00 | 1.01 |
| Asp | 58 | A | . | . | . | . | T | . | 0.72 | −0.76 | . | * | F | 1.30 | 1.21 |
| Ser | 59 | A | . | . | . | . | T | . | 1.31 | −0.84 | . | * | F | 1.30 | 2.54 |
| Leu | 60 | A | A | . | . | . | . | . | 0.81 | −1.53 | * | * | F | 0.90 | 2.12 |
| Glu | 61 | A | A | . | . | . | . | . | 1.62 | −0.84 | * | * | F | 0.90 | 1.05 |
| Gln | 62 | A | A | . | . | . | . | . | 1.58 | −0.44 | * | * | F | 0.60 | 1.26 |
| Asp | 63 | A | A | . | . | . | . | . | 0.98 | −0.43 | * | . | F | 0.60 | 2.45 |
| Leu | 64 | A | A | . | . | . | . | . | 1.28 | −0.50 | * | . | F | 0.60 | 1.40 |
| Asn | 65 | A | A | . | . | . | . | . | 2.13 | −0.10 | * | . | F | 0.60 | 1.30 |
| Asn | 66 | A | . | . | . | . | T | . | 1.43 | −0.50 | * | . | F | 0.85 | 1.56 |
| Met | 67 | A | . | . | . | . | T | . | 0.62 | 0.29 | * | . | . | 0.25 | 1.63 |
| Asn | 68 | A | . | . | . | . | T | . | 0.62 | 0.29 | * | . | . | 0.10 | 0.84 |
| Lys | 69 | A | . | . | . | . | T | . | 1.48 | −0.11 | * | . | . | 0.70 | 0.90 |
| Phe | 70 | A | A | . | . | . | . | . | 0.67 | −0.51 | * | * | . | 0.75 | 1.82 |
| Leu | 71 | A | A | . | . | . | . | . | 0.78 | −0.44 | * | * | . | 0.30 | 0.94 |
| Glu | 72 | A | A | . | . | . | . | . | 1.17 | −0.84 | * | * | F | 0.75 | 0.92 |
| Lys | 73 | A | A | . | . | . | . | . | 0.36 | −0.41 | * | * | F | 0.60 | 1.64 |
| Leu | 74 | A | A | . | . | . | . | . | 0.01 | −0.51 | * | * | F | 0.90 | 1.64 |
| Arg | 75 | A | A | . | . | . | . | . | 0.37 | −0.81 | * | . | F | 0.90 | 1.27 |
| Pro | 76 | . | A | . | . | . | . | C | 0.88 | −0.39 | . | . | F | 0.65 | 0.63 |
| Leu | 77 | . | . | . | . | . | T | C | 0.88 | 0.00 | . | * | F | 0.60 | 1.02 |
| Ser | 78 | . | . | . | . | . | T | C | 0.24 | −0.69 | . | * | F | 1.35 | 0.90 |
| Gly | 79 | . | . | . | . | . | T | C | 0.84 | −0.19 | . | * | F | 1.35 | 0.59 |
| Ser | 80 | . | . | . | . | . | T | C | 0.84 | −0.19 | . | * | F | 1.80 | 1.10 |
| Glu | 81 | . | . | . | . | . | . | C | 0.24 | −0.87 | . | * | F | 2.20 | 1.61 |
| Ala | 82 | . | . | . | . | . | . | C | 0.84 | −0.57 | * | . | F | 2.50 | 1.34 |
| Pro | 83 | . | . | . | . | T | . | . | 1.14 | −0.57 | * | . | F | 3.00 | 1.55 |

TABLE 9-continued

| Res | Position | I | II | III | IV | V | VI | VII | VIII | IX | X | XI | XII | XIII | XIV |
|---|---|---|---|---|---|---|---|---|---|---|---|---|---|---|---|
| Arg | 84 | . | . | . | . | T | . | . | 1.49 | −0.56 | * | . | F | 2.70 | 1.55 |
| Leu | 85 | . | . | . | . | . | . | C | 1.58 | −0.56 | * | . | F | 2.20 | 2.56 |
| Pro | 86 | . | . | . | . | T | . | . | 0.72 | −0.63 | * | . | F | 2.35 | 2.56 |
| Gln | 87 | . | . | . | . | T | . | . | 0.97 | −0.41 | * | . | F | 1.85 | 0.97 |
| Asp | 88 | . | . | . | . | . | T | C | 0.58 | 0.01 | . | * | F | 1.35 | 1.16 |
| Pro | 89 | . | . | . | . | . | T | C | 0.58 | −0.06 | * | . | F | 2.05 | 0.75 |
| Val | 90 | . |  | . | . | T | T | . | 1.50 | −0.49 | . | . | F | 2.50 | 0.84 |
| Gly | 91 | . | . | . | . | . | T | C | 1.71 | −0.89 | . | . | . | 2.20 | 0.99 |
| Met | 92 | A | A | . | . | . | . | . | 0.90 | −0.49 | . | * | . | 1.20 | 1.11 |
| Arg | 93 | A | A | . | . | . | . | . | 0.90 | −0.23 | . | . | . | 0.95 | 1.23 |
| Arg | 94 | A | A | . | . | . | . | . | 1.11 | −0.47 | . | * | F | 0.85 | 2.15 |
| Gln | 95 | A | A | . | . | . | . | . | 1.97 | −0.90 | . | * | F | 0.90 | 3.77 |
| Leu | 96 | A | A | . | . | . | . | . | 1.50 | −1.51 | * | * | F | 0.90 | 3.33 |
| Gln | 97 | A | A | . | . | . | . | . | 2.10 | −0.83 | * | * | F | 0.90 | 1.40 |
| Glu | 98 | A | A | . | . | . | . | . | 1.99 | −0.83 | * | * | F | 0.90 | 1.40 |
| Glu | 99 | A | A | . | . | . | . | . | 1.02 | −1.23 | * | . | F | 0.90 | 2.95 |
| Leu | 100 | A | A | . | . | . | . | . | 1.07 | −1.27 | . | * | F | 0.90 | 1.26 |
| Glu | 101 | A | A | . | . | . | . | . | 1.29 | −1.67 | . | * | F | 0.90 | 1.46 |
| Glu | 102 | A | A | . | . | . | . | . | 1.40 | −1.17 | . | * | F | 0.75 | 0.85 |
| Val | 103 | A | A | . | . | . | . | . | 0.59 | −1.17 | * | * | F | 0.90 | 2.02 |
| Lys | 104 | A | A | . | . | . | . | . | 0.59 | −1.17 | . | * | F | 0.75 | 0.96 |
| Ala | 105 | A | A | . | . | . | . | . | 1.19 | −0.77 | . | * | F | 0.60 | 0.96 |
| Arg | 106 | A | A | . | . | . | . | . | 0.94 | −0.34 | . | * | . | 0.45 | 2.00 |
| Leu | 107 | A | A | . | . | . | . | . | 0.34 | −0.23 | . | * | . | 0.45 | 1.57 |
| Gln | 108 | A | . | . | . | . | T | . | 0.61 | 0.39 | . | * | . | 0.25 | 1.54 |
| Pro | 109 | A | . | . | . | . | T | . | 0.57 | 0.39 | . | * | . | 0.10 | 0.79 |
| Tyr | 110 | A | . | . | . | . | T | . | 0.57 | 0.39 | . | * | . | 0.25 | 1.67 |
| Met | 111 | A | . | . | . | . | T | . | 0.42 | 0.20 | * | * | . | 0.10 | 0.97 |
| Ala | 112 | A | A | . | . | . | . | . | 1.23 | 0.30 | . | . | . | −0.30 | 0.85 |
| Glu | 113 | A | A | . | . | . | . | . | 0.42 | −0.13 | . | . | . | 0.30 | 0.94 |
| Ala | 114 | A | A | . | . | . | . | . | −0.22 | −0.20 | . | . | . | 0.30 | 0.79 |
| His | 115 | A | A | . | . | . | . | . | −0.32 | −0.17 | . | . | . | 0.30 | 0.58 |
| Glu | 116 | A | A | . | . | . | . | . | −0.01 | −0.24 | . | . | . | 0.30 | 0.33 |
| Leu | 117 | A | A | . | . | . | . | . | 0.58 | 0.67 | . | . | . | −0.60 | 0.34 |
| Val | 118 | A | A | . | . | . | . | . | −0.23 | 0.57 | . | . |  | −0.60 | 0.41 |
| Gly | 119 | A | A | . | . | . | . | . | 0.36 | 0.76 | . | * | . | −0.60 | 0.19 |
| Trp | 120 | A | A | . | . | . | . | . | 0.04 | 0.76 | . | . | . | −0.60 | 0.41 |
| Asn | 121 | A | A | . | . | . | . | . | −0.77 | 0.50 | * | . | . | −0.60 | 0.54 |
| Leu | 122 | A | A | . | . | . | . | . | 0.16 | 0.54 | * | . | . | −0.60 | 0.45 |
| Glu | 123 | A | A | . | . | . | . | . | 1.01 | 0.11 | . | * | . | −0.30 | 0.84 |
| Gly | 124 | A | A | . | . | . | . | . | 1.36 | −0.40 | . | * | F | 0.45 | 0.91 |
| Leu | 125 | A | A |  | . | . | . | . | 0.83 | −0.40 | * | * | F | 0.60 | 1.90 |
| Arg | 126 | A | A | . | . | . | . | . | 0.88 | −0.40 | * | * | F | 0.45 | 0.91 |
| Gln | 127 | A | A | . | . | . | . | . | 1.48 | −0.40 | * | * | F | 0.60 | 1.83 |
| Gln | 128 | . | A | . | . | T | . | . | 1.23 | −0.40 | * | * | F | 1.25 | 3.43 |
| Leu | 129 | . | A | . | . | . | . | C | 1.27 | −0.33 | * | * | F | 1.30 | 2.75 |
| Lys | 130 | . | . | . | . | . | T | C | 1.48 | 0.16 | . | * | F | 1.35 | 2.29 |
| Pro | 131 | . | . | . | . | . | T | C | 1.37 | 0.37 | . | * | F | 1.60 | 1.31 |
| Tyr | 132 | . | . | . | . | T | T | . | 0.56 | −0.03 | . | . | . | 2.50 | 2.65 |
| Thr | 133 | A | . | . | . | . | T | . | −0.04 | −0.03 | . | . | . | 1.85 | 1.09 |
| Met | 134 | A | A | . | . | . | . | . | 0.77 | 0.59 | . | . | . | 0.15 | 0.70 |
| Asp | 135 | A | A | . | . | . | . | . | 0.72 | 0.16 | . | . | . | 0.20 | 0.77 |
| Leu | 136 | A | A | . | . | . | . | . | 0.08 | −0.20 | * | . | . | 0.55 | 0.93 |
| Met | 137 | A | A | . | . | . | . | . | −0.27 | −0.04 | . | * | . | 0.30 | 0.70 |
| Glu | 138 | A | A | . | . | . | . | . | −0.77 | −0.16 | * | * | . | 0.30 | 0.42 |
| Gln | 139 | A | A | . | . | . | . | . | −0.06 | 0.53 | * | * | . | −0.60 | 0.42 |
| Val | 140 | A | A | . | . | . | . | . | −0.91 | −0.16 | * | * | . | 0.30 | 0.83 |
| Ala | 141 | A | A | . | . | . |  | . | −0.10 | −0.13 | * | * | . | 0.30 | 0.36 |
| Leu | 142 | A | A | . | . | . | . | . | 0.50 | 0.27 | * | * | . | −0.30 | 0.36 |
| Arg | 143 | A | A | . | . | . | . | . | −0.31 | −0.13 | . | * | . | 0.30 | 0.83 |
| Val | 144 | A | A | . | . | . | . | . | −0.31 | −0.09 | . | * | . | 0.30 | 0.68 |
| Gln | 145 | A | A | . | . | . | . | . | 0.54 | −0.19 | . | * | . | 0.45 | 1.43 |
| Glu | 146 | A | A | . | . | . | . | . | 1.13 | −0.87 | * | * | F | 0.90 | 1.26 |
| Leu | 147 | A | A | . | . | . | . | . | 1.13 | −0.47 | . | * | F | 0.60 | 2.95 |
| Gln | 148 | A | A | . | . | . | . | . | 1.13 | −0.43 | . | * | F | 0.60 | 1.40 |
| Glu | 149 | A | A | . | . | . | . | . | 1.13 | −0.83 | * | * | F | 0.90 | 1.59 |
| Gln | 150 | A | A | . | . | . | . | . | 0.28 | −0.19 | * | * | F | 0.60 | 1.43 |
| Leu | 151 | A | A | . | . | . | . | . | −0.07 | −0.23 | * | * | . | 0.30 | 0.61 |
| Arg | 152 | A | A | . | . | . | . | . | 0.74 | −0.20 | * | * | . | 0.30 | 0.35 |
| Val | 153 | A | A | . | . | . | . | . | 0.74 | −0.20 | * | * | . | 0.30 | 0.35 |
| Val | 154 | A | A | . | . | . | . | . | 0.43 | −0.60 | * | * | . | 0.60 | 0.71 |
| Gly | 155 | A | . | . | . | . | T | . | 0.48 | −0.80 | * | * | F | 1.15 | 0.52 |
| Glu | 156 | A | . | . | . | . | T | . | 0.70 | −0.80 | * | * | F | 1.30 | 1.41 |
| Asp | 157 | A | . | . | . | . | T | . | 0.59 | −0.94 | . | * | F | 1.30 | 1.91 |
| Thr | 158 | A | . | . | . | . | T | . | 0.63 | −1.19 | . | . | F | 1.30 | 3.35 |
| Lys | 159 | A | A | . | . | . | . | . | 0.68 | −0.93 | . | * | F | 0.90 | 1.59 |
| Ala | 160 | A | A | . | . | . | . | . | 0.68 | −0.24 | . | . | F | 0.45 | 0.79 |

TABLE 9-continued

| Res | Position | I | II | III | IV | V | VI | VII | VIII | IX | X | XI | XII | XIII | XIV |
|---|---|---|---|---|---|---|---|---|---|---|---|---|---|---|---|
| Gln | 161 | A | A | . | . | . | . | . | 0.33 | 0.19 | . | * | . | −0.30 | 0.54 |
| Leu | 162 | A | A | . | . | . | . | . | −0.52 | 0.13 | . | * | . | −0.30 | 0.27 |
| Leu | 163 | A | A | . | . | . | . | . | −0.21 | 0.77 | . | * | . | −0.60 | 0.20 |
| Gly | 164 | . | A | . | . | . | . | C | −0.26 | 0.27 | . | * | F | 0.05 | 0.19 |
| Gly | 165 | . | A | . | . | . | . | C | −0.26 | −0.13 | * | . | F | 0.65 | 0.40 |
| Val | 166 | A | A | . | . | . | . | . | −0.54 | −0.31 | * | . | F | 0.45 | 0.49 |
| Asp | 167 | A | A | . | . | . | . | . | −0.32 | −0.09 | . | . | F | 0.45 | 0.52 |
| Glu | 168 | A | A | . | . | . | . | . | −0.32 | −0.01 | . | . | . | 0.30 | 0.53 |
| Ala | 169 | A | A | . | . | . | . | . | −0.79 | 0.24 | . | . | . | −0.30 | 0.59 |
| Trp | 170 | A | A | . | . | . | . | . | −0.44 | 0.29 | . | . | . | −0.30 | 0.29 |
| Ala | 171 | A | A | . | . | . | . | . | 0.07 | 0.69 | * | . | . | −0.60 | 0.29 |
| Leu | 172 | A | A | . | . | . | . | . | −0.74 | 1.11 | * | . | . | −0.60 | 0.28 |
| Leu | 173 | A | A | . | . | . | . | . | −0.74 | 1.30 | . | . | . | −0.60 | 0.22 |
| Gln | 174 | A | A | . | . | . | . | . | −0.46 | 0.79 | . | . | . | −0.60 | 0.38 |
| Gly | 175 | A | A | . | . | . | . | . | −0.06 | 0.67 | . | * | F | −0.45 | 0.62 |
| Leu | 176 | A | A | . | . | . | . | . | −0.32 | −0.01 | . | . | F | 0.60 | 1.47 |
| Gln | 177 | A | A | . | . | . | . | . | −0.37 | −0.06 | . | . | F | 0.45 | 0.63 |
| Ser | 178 | A | A | . | . | . | . | . | 0.41 | 0.19 | . | . | F | −0.15 | 0.47 |
| Arg | 179 | . | . | B | B | . | . | . | 0.38 | 0.26 | . | . | F | −0.15 | 0.78 |
| Val | 180 | . | . | B | B | . | . | . | 0.41 | 0.07 | . | * | . | −0.30 | 0.61 |
| Val | 181 | . | . | B | B | . | . | . | 0.88 | 0.16 | * | * | . | −0.30 | 0.66 |
| His | 182 | . | . | . | B | . | . | C | 0.99 | 0.20 | * | * | . | −0.10 | 0.33 |
| His | 183 | . | . | . | . | . | T | C | 0.59 | 0.20 | * | * | . | 0.30 | 0.88 |
| Thr | 184 |  | . | . | . | . | T | C | 0.52 | 0.34 | * | * | F | 0.60 | 1.03 |
| Gly | 185 | . | . | . | . | . | T | C | 1.38 | −0.30 | * | * | F | 1.20 | 1.51 |
| Arg | 186 | A | . | . | . | . | T | . | 1.42 | −0.80 | * | * | F | 1.30 | 1.92 |
| Phe | 187 | A | A | . | . | . | . | . | 0.76 | −0.61 | * | * | F | 0.90 | 1.10 |
| Lys | 188 | A | A | . | . | . | . | . | 0.76 | −0.31 | . | * | F | 0.45 | 0.96 |
| Glu | 189 | A | A | . | . | . | . | . | 0.86 | −0.24 | * | * | . | 0.30 | 0.67 |
| Leu | 190 | A | A | . | . | . | . | . | 0.96 | 0.19 | * | * | . | −0.15 | 1.19 |
| Phe | 191 | A | A | . | . | . | . | . | 0.26 | 0.16 | * | * | . | −0.30 | 0.93 |
| His | 192 | A | . | . | . | . | T | . | 0.96 | 0.66 | * | . | . | −0.20 | 0.55 |
| Pro | 193 | A | . | . | . | . | T | . | 0.61 | 0.66 | * | . | . | −0.05 | 1.14 |
| Tyr | 194 | A | . | . | . | . | T | . | −0.20 | 0.36 | * | . | . | 0.25 | 1.77 |
| Ala | 195 | A | . | . | . | . | T | . | −0.24 | 0.26 | * | . | . | 0.25 | 1.07 |
| Glu | 196 | A | . | . | . | . | . | . | 0.16 | 0.40 | * | . | . | −0.40 | 0.52 |
| Ser | 197 | A | . | . | . | . | . | . | −0.16 | 0.36 | * | . | . | −0.10 | 0.44 |
| Leu | 198 | A | . | . | . | . | . | . | −0.83 | 0.03 | * | . | . | −0.10 | 0.43 |
| Val | 199 | A | . | . | . | . | . | . | −0.93 | 0.21 | * | . | . | −0.10 | 0.17 |
| Ser | 200 | A | . | . | . | . | . | . | −0.23 | 0.64 | * | . | F | −0.25 | 0.13 |
| Gly | 201 | . | . | . | . | T | . | . | −0.27 | 0.26 | * | . | F | 0.45 | 0.31 |
| Ile | 202 | A | . | . | . | . | . | . | −0.82 | 0.07 | * | . | F | 0.05 | 0.56 |
| Gly | 203 | . | . | . | . | . | . | C | −0.01 | 0.07 | * | . | F | 0.25 | 0.31 |
| Arg | 204 | . | . | . | . | . | . | C | 0.84 | 0.09 | * | . | F | 0.25 | 0.54 |
| His | 205 | A | . | . | . | . | . | . | 0.33 | −0.34 | * | . | . | 0.65 | 1.35 |
| Val | 206 | A | . | . | . | . | . | . | 0.64 | −0.34 | * | . | . | 0.65 | 1.12 |
| Gln | 207 | A | . | . | . | . | . | . | 1.64 | −0.27 | * | . | . | 0.50 | 0.78 |
| Glu | 208 | A | . | . | . | . | . | . | 1.69 | −0.27 | * | . | . | 0.65 | 1.12 |
| Leu | 209 | A | . | . | . | . | . | . | 0.72 | −0.39 | * | . | . | 0.65 | 2.03 |
| His | 210 | A | . | . | . | . | . | . | 0.17 | −0.39 | * | . | . | 0.50 | 0.87 |
| Arg | 211 | . | . | . | . | T | . | . | 0.81 | −0.29 | * | . | . | 0.90 | 0.51 |
| Ser | 212 | . | . | . | . | T | . | . | 0.78 | 0.14 | * | . | . | 0.30 | 0.95 |
| Val | 213 | A | . | . | . | . | . | . | 0.19 | −0.04 | * | . | . | 0.50 | 0.95 |
| Ala | 214 | . | . | . | . | . | . | C | 0.79 | −0.04 | * | . | . | 0.70 | 0.49 |
| Pro | 215 | . | . | . | . | . | . | C | 0.23 | 0.39 | . | . | . | 0.10 | 0.56 |
| His | 216 | . | . | . | . | . | . | C | −0.18 | 0.50 | . | . |  | −0.20 | 0.77 |
| Ala | 217 | . | . | . | . | . | . | C | −0.09 | 0.24 | . | . | . | 0.25 | 1.02 |
| Pro | 218 | . | . | . | . | . | . | C | 0.18 | 0.17 | . | . | . | 0.25 | 1.02 |
| Ala | 219 | . | . | . | . | . | . | C | 0.88 | 0.24 | * | * | F | 0.25 | 0.76 |
| Ser | 220 | A | . | . | . | . | T | . | 0.28 | −0.26 | . | * | F | 1.00 | 1.47 |
| Pro | 221 | A | . | . | . | . | T | . | 0.01 | −0.07 | * | . | F | 0.85 | 0.78 |
| Ala | 222 | A | . | . | . | . | T | . | 0.71 | −0.11 | * | . | F | 1.00 | 1.04 |
| Arg | 223 | A | . | . | . | . | T | . | 0.26 | −0.61 | * | . | . | 1.15 | 1.52 |
| Leu | 224 | A | . | . | . | . | T | . | −0.01 | −0.43 | * | . | . | 0.70 | 0.53 |
| Ser | 225 | A | . | . | . | . | T | . | 0.29 | −0.21 | * | * | . | 0.70 | 0.39 |
| Arg | 226 | A | . | . | . | . | T | . | −0.36 | −0.31 | * | * | . | 0.70 | 0.34 |
| Cys | 227 | A | . | . | . | . | T | . | −0.58 | 0.33 | * | * | . | 0.10 | 0.31 |
| Val | 228 | A | A | . | B | . | . | . | −0.99 | 0.33 | * | * | . | −0.30 | 0.19 |
| Gln | 229 | A | A | . | B | . | . | . | −0.07 | 0.33 | * | . | . | −0.30 | 0.13 |
| Val | 230 | A | A | . | B | . | . | . | 0.28 | 0.33 | * | . | . | −0.30 | 0.47 |
| Leu | 231 | A | A | . | B | . | . | . | −0.64 | −0.24 | * | . | . | 0.45 | 1.28 |
| Ser | 232 | A | A | . | B | . | . | . | −0.29 | −0.20 | * | . | F | 0.45 | 0.61 |
| Arg | 233 | A | A | . | . | . | . | . | −0.24 | −0.11 | . | * | F | 0.60 | 1.18 |
| Lys | 234 | A | A | . | . | . | . | . | −0.20 | −0.07 | . | * | F | 0.60 | 1.18 |
| Leu | 235 | A | A | . | . | . | . | . | 0.07 | −0.76 | . | * | F | 0.90 | 1.76 |
| Thr | 236 | A | A | . | . | . | . | . | 0.92 | −0.64 | * | * | . | 0.60 | 0.91 |
| Leu | 237 | A | A | . | . | . | . | . | 0.63 | −0.64 | * | * | . | 0.60 | 0.91 |

TABLE 9-continued

| Res | Position | I | II | III | IV | V | VI | VII | VIII | IX | X | XI | XII | XIII | XIV |
|---|---|---|---|---|---|---|---|---|---|---|---|---|---|---|---|
| Lys | 238 | A | A | . | . | . | . | . | −0.29 | −0.14 | * | * | F | 0.60 | 1.11 |
| Ala | 239 | A | A | . | . | . | . | . | −0.37 | −0.14 | . | * | F | 0.45 | 0.64 |
| Lys | 240 | A | A | . | . | . | . | . | −0.14 | −0.13 | . | * | F | 0.60 | 1.05 |
| Ala | 241 | A | A | . | . | . | . | . | 0.28 | −0.31 | . | * | . | 0.30 | 0.53 |
| Leu | 242 | A | A | . | . | . | . | . | 0.20 | −0.31 | . | * | . | 0.45 | 1.03 |
| His | 243 | A | A | . | . | . | . | . | 0.16 | −0.13 | . | * | . | 0.30 | 0.36 |
| Ala | 244 | A | A | . | . | . | . | . | 0.74 | 0.27 | . | * | . | −0.30 | 0.62 |
| Arg | 245 | A | A | . | . | . | . | . | 0.70 | 0.17 | . | * | . | −0.15 | 1.30 |
| Ile | 246 | A | A | . | . | . | . | . | 0.48 | −0.11 | * | * | . | 0.45 | 1.53 |
| Gln | 247 | A | A | . | . | . | . | . | 1.29 | 0.07 | * | * | F | 0.00 | 1.25 |
| Gln | 248 | A | A | . | . | . | . | . | 1.32 | −0.43 | * | * | F | 0.60 | 1.07 |
| Asn | 249 | . | A | . | . | . | . | C | 1.10 | −0.03 | * | * | F | 0.80 | 2.64 |
| Leu | 250 | . | A | | . | . | . | C | 1.10 | −0.03 | * | * | F | 0.80 | 1.26 |
| Asp | 251 | . | A | . | . | . | . | C | 1.99 | −0.43 | * | * | F | 0.80 | 1.42 |
| Gln | 252 | . | A | . | . | . | . | C | 1.99 | −0.83 | * | * | F | 1.10 | 1.53 |
| Leu | 253 | A | A | . | . | . | . | . | 1.18 | −1.23 | * | . | F | 0.90 | 3.21 |
| Arg | 254 | A | A | . | . | . | . | . | 0.29 | −1.23 | * | . | F | 0.90 | 1.59 |
| Glu | 255 | A | A | . | . | . | . | . | 1.21 | −0.54 | * | . | F | 0.75 | 0.64 |
| Glu | 256 | A | A | . | . | . | . | . | 0.62 | −0.94 | * | . | F | 0.90 | 1.52 |
| Leu | 257 | A | A | . | . | . | . | . | −0.08 | −1.13 | * | * | . | 0.60 | 0.79 |
| Ile | 258 | A | A | . | . | . | . | . | 0.14 | −0.34 | * | . | . | 0.30 | 0.39 |
| Arg | 259 | A | A | . | . | . | . | . | −0.31 | 0.16 | . | . | . | −0.30 | 0.23 |
| Ala | 260 | A | A | . | . | . | . | . | −0.62 | 0.59 | * | . | . | −0.60 | 0.28 |
| Phe | 261 | A | A | . | . | . | . | . | −0.97 | 0.39 | * | . | . | −0.30 | 0.57 |
| Ala | 262 | A | A | . | . | . | . | . | −0.47 | 0.13 | * | . | . | 0.00 | 0.29 |
| Gly | 263 | . | . | . | . | . | T | C | 0.42 | 0.61 | * | * | F | 0.75 | 0.41 |
| Thr | 264 | . | . | . | . | . | T | C | 0.31 | 0.11 | . | . | F | 1.35 | 0.82 |
| Gly | 265 | . | . | . | . | . | T | C | 0.56 | −0.67 | . | . | F | 2.70 | 1.40 |
| Thr | 266 | . | . | . | . | . | T | C | 0.67 | −0.74 | . | . | F | 3.00 | 1.40 |
| Glu | 267 | . | . | . | . | . | . | C | 0.91 | −0.67 | . | . | F | 2.35 | 0.98 |
| Glu | 268 | . | . | . | . | T | . | . | 1.04 | −0.73 | . | . | F | 2.49 | 0.98 |
| Gly | 269 | . | . | . | . | T | . | . | 1.36 | −0.73 | . | . | F | 2.58 | 1.05 |
| Ala | 270 | . | . | . | . | . | . | C | 1.49 | −1.21 | . | . | F | 2.32 | 1.01 |
| Gly | 271 | . | . | . | . | . | T | C | 1.80 | −0.79 | . | . | F | 2.31 | 0.91 |
| Pro | 272 | . | . | . | . | . | T | C | 1.20 | −0.39 | . | . | F | 2.40 | 1.58 |
| Asp | 273 | . | . | . | . | . | T | C | 0.39 | −0.20 | . | . | F | 2.16 | 1.55 |
| Pro | 274 | A | . | . | . | . | T | . | 0.43 | −0.01 | . | . | F | 1.72 | 1.29 |
| Gln | 275 | A | A | . | . | . | . | . | 1.02 | −0.06 | . | . | . | 0.93 | 1.12 |
| Met | 276 | A | A | . | . | . | . | . | 1.37 | −0.49 | . | . | . | 0.69 | 1.16 |
| Leu | 277 | A | A | . | . | . | . | . | 0.72 | −0.49 | * | * | . | 0.45 | 1.30 |
| Ser | 278 | A | A | . | . | . | . | . | 0.83 | −0.27 | * | * | F | 0.45 | 0.56 |
| Glu | 279 | A | A | . | . | . | . | . | 1.04 | −0.67 | . | * | F | 0.90 | 1.10 |
| G1u | 280 | A | A | . | . | . | . | . | 1.16 | −0.89 | . | * | F | 0.90 | 2.32 |
| Val | 281 | A | A | . | . | . | . | . | 0.94 | −1.57 | * | * | F | 0.90 | 3.39 |
| Arg | 282 | A | A | . | . | . | . | . | 1.76 | −1.27 | * | * | F | 0.90 | 1.61 |
| Gln | 283 | A | A | . | . | . | . | . | 1.47 | −0.87 | * | * | F | 0.90 | 1.61 |
| Arg | 284 | A | A | . | . | . | . | . | 0.77 | −0.37 | * | * | F | 0.60 | 2.20 |
| Leu | 285 | A | A | . | . | . | . | . | 0.88 | −0.23 | * | * | . | 0.30 | 0.97 |
| Gln | 286 | A | A | . | . | . | . | . | 1.73 | −0.23 | * | * | . | 0.73 | 1.10 |
| Ala | 287 | A | A | . | . | . | . | . | 1.62 | −0.23 | . | * | . | 0.86 | 0.97 |
| Phe | 288 | . | A | . | . | T | . | . | 1.31 | −0.23 | . | . | . | 1.69 | 1.97 |
| Mg | 289 | . | . | . | . | T | T | . | 0.96 | −0.43 | . | * | F | 2.52 | 1.64 |
| Gln | 290 | . | . | . | . | T | T | . | 0.96 | −0.07 | . | * | F | 2.80 | 2.54 |
| Asp | 291 | . | . | . | . | T | T | . | 0.96 | 0.11 | . | * | F | 1.92 | 2.42 |
| Thr | 292 | . | . | . | . | T | T | . | 0.66 | −0.27 | . | * | F | 2.24 | 2.14 |
| Tyr | 293 | A | A | . | . | . | . | . | 0.77 | 0.41 | . | * | . | −0.04 | 0.87 |
| Leu | 294 | A | A | . | . | . | . | . | 0.07 | 0.51 | . | * | . | −0.32 | 0.52 |
| Gln | 295 | A | A | . | . | . | . | . | −0.63 | 1.01 | . | . | . | −0.60 | 0.37 |
| Ile | 296 | A | A | . | . | . | . | . | −0.94 | 1.31 | . | * | . | −0.60 | 0.20 |
| Ala | 297 | A | A | . | . | . | . | . | −0.52 | 1.04 | . | * | . | −0.60 | 0.35 |
| Ala | 298 | A | A | . | . | . | . | . | −0.87 | 0.36 | * | * | . | −0.30 | 0.40 |
| Phe | 299 | A | A | . | . | . | . | . | −0.94 | 0.46 | * | * | . | −0.60 | 0.58 |
| TIn | 300 | A | A | . | . | . | . | . | −0.94 | 0.46 | * | . | . | −0.60 | 0.40 |
| Arg | 301 | A | A | . | . | . | . | . | −0.06 | −0.04 | * | . | . | 0.30 | 0.66 |
| Ala | 302 | A | A | . | . | . | . | . | 0.53 | −0.14 | * | . | . | 0.45 | 1.33 |
| Lie | 303 | A | A | . | . | | . | . | 0.81 | −0.93 | * | . | F | 0.90 | 1.59 |
| Asp | 304 | A | A | . | . | . | . | . | 1.51 | −0.93 | * | . | F | 0.90 | 1.17 |
| Gln | 305 | A | A | . | . | . | . | . | 1.82 | −0.93 | * | . | F | 0.90 | 2.01 |
| Glu | 306 | A | A | . | . | . | . | . | 0.86 | −1.43 | * | . | F | 0.90 | 4.97 |
| Thr | 307 | A | A | . | . | . | . | . | 1.44 | −1.47 | * | . | F | 0.90 | 2.21 |
| Glu | 308 | A | A | . | . | . | . | . | 2.33 | −1.07 | * | . | F | 0.90 | 2.21 |
| Glu | 309 | A | A | . | . | . | . | . | 2.33 | −1.07 | * | . | F | 0.90 | 2.21 |
| Val | 310 | A | A | . | . | . | . | . | 1.52 | −0.67 | * | . | F | 0.90 | 2.65 |
| Gln | 311 | A | A | . | . | . | . | . | 0.93 | −0.47 | . | . | F | 0.60 | 1.26 |
| Gln | 312 | A | A | . | . | . | . | . | 1.03 | 0.03 | . | . | F | −0.15 | 0.74 |
| Gln | 313 | . | A | . | . | T | . | . | 0.82 | 0.46 | . | . | F | 0.10 | 1.53 |
| Leu | 314 | . | A | . | . | . | . | C | 0.61 | 0.24 | . | . | F | 0.20 | 1.37 |

TABLE 9-continued

| Res | Position | I | II | III | IV | V | VI | VII | VIII | IX | X | XI | XII | XIII | XIV |
|---|---|---|---|---|---|---|---|---|---|---|---|---|---|---|---|
| Ala | 315 | . | A | . | . | . | . | C | 1.26 | 0.27 | . | . | F | 0.20 | 1.22 |
| Pro | 316 | . | A | . | . | . | . | C | 0.91 | 0.30 | . | . | F | 0.20 | 1.09 |
| Pro | 317 | . | . | . | . | . | . | C | 0.88 | 0.33 | . | . | F | 0.40 | 1.31 |
| Pro | 318 | . | . | . | . | . | T | C | 0.58 | 0.14 | . | . | F | 0.60 | 1.76 |
| Pro | 319 | . | . | . | . | T | T | . | 0.80 | 0.03 | . | . | F | 0.80 | 1.53 |
| Gly | 320 | . | . | . | . | T | T | . | 0.69 | 0.10 | . | . | F | 0.65 | 1.00 |
| His | 321 | . | . | . | . | . | T | C | 0.31 | 0.46 | . | . | . | 0.00 | 0.56 |
| Ser | 322 | . | A | . | . | . | . | C | 0.31 | 0.53 | . | . | . | −0.40 | 0.37 |
| Ala | 323 | . | A | . | . | . | . | C | 0.52 | 0.53 | . | . | . | −0.40 | 0.57 |
| Phe | 324 | . | A | . | . | . | . | C | 0.03 | 0.10 | . | . | . | −0.10 | 0.73 |
| Ala | 325 | A | A | . | . | . | . | . | 0.38 | 0.39 | . | . | . | −0.30 | 0.47 |
| Pro | 326 | A | A | . | . | . | . | . | 0.41 | 0.40 | . | . | . | −0.30 | 0.81 |
| Glu | 327 | A | A | . | . | . | . | . | 0.40 | 0.30 | . | . | F | 0.00 | 1.61 |
| Phe | 328 | A | A | . | . | . | . | . | 0.99 | 0.00 | . | . | F | 0.60 | 2.30 |
| Gln | 329 | A | A | . | . | . | . | . | 1.39 | −0.50 | . | . | F | 0.60 | 2.48 |
| Gln | 330 | A | A | . | . | . | . | . | 1.63 | −0.54 | . | . | F | 0.90 | 1.92 |
| Thr | 331 | A | A | . | . | . | . | . | 1.89 | −0.11 | . | * | F | 0.60 | 2.20 |
| Asp | 332 | . | . | . | . | T | T | . | 1.03 | −0.90 | . | . | F | 1.70 | 2.54 |
| Ser | 333 | A | . | . | . | T | T | . | 0.92 | −0.66 | . | . | F | 1.70 | 1.09 |
| Gly | 334 | . | . | . | . | T | T | . | 0.62 | −0.37 | . | . | F | 1.25 | 0.62 |
| Lys | 335 | A | . | . | . | . | T | . | 0.67 | −0.47 | * | * | F | 0.85 | 0.50 |
| Val | 336 | A | A | . | . | . | . | . | 0.17 | −0.47 | * | * | F | 0.45 | 0.74 |
| Leu | 337 | A | A | . | . | . | . | . | 0.17 | −0.17 | * | * | F | 0.45 | 0.62 |
| Ser | 338 | A | A | . | . | . | . | . | −0.12 | −0.20 | * | * | F | 0.45 | 0.54 |
| Lys | 339 | A | A | . | . | . | . | . | 0.33 | 0.30 | * | * | F | −0.15 | 0.73 |
| Leu | 340 | A | A | . | . | . | . | . | −0.52 | −0.34 | * | * | . | 0.45 | 1.74 |
| Gln | 341 | A | A | . | . | . | . | . | 0.33 | −0.34 | * | * | . | 0.45 | 1.07 |
| Ala | 342 | A | A | . | . | . | . | . | 1.14 | −0.73 | * | * | . | 0.60 | 0.89 |
| Arg | 343 | A | A | . | . | . | . | . | 0.63 | −0.73 | * | * | . | 0.75 | 1.81 |
| Leu | 344 | A | A | . | . | . | . | . | 0.30 | −0.73 | * | * | . | 0.60 | 0.86 |
| Asp | 345 | A | A | . | . | . | . | . | 1.11 | −0.21 | * | * | F | 0.45 | 0.90 |
| Asp | 346 | A | A | . | . | . | . | . | 1.11 | −0.71 | * | * | F | 0.75 | 0.79 |
| Leu | 347 | A | A | . | . | . | . | . | 0.81 | −0.71 | * | * | F | 0.90 | 1.60 |
| Trp | 348 | A | A | . | . | . | . | . | 0.39 | −0.71 | * | * | F | 0.75 | 0.67 |
| Glu | 349 | A | A | . | . | . | . | . | 1.17 | −0.23 | * | . | F | 0.45 | 0.58 |
| Asp | 350 | A | A | . | . | . | . | . | 0.87 | 0.27 | * | . | F | −0.15 | 0.96 |
| Ile | 351 | A | A | . | . | . | . | . | 0.06 | −0.03 | * | * | . | 0.45 | 1.22 |
| Thr | 352 | A | A | . | . | . | . | . | 0.83 | −0.26 | * | . | . | 0.30 | 0.58 |
| His | 353 | A | A | . | . | . | . | . | 1.12 | 0.24 | * | . | . | −0.30 | 0.47 |
| Ser | 354 | A | A | . | . | . | . | . | 1.12 | 0.24 | * | . | . | 0.13 | 1.13 |
| Leu | 355 | A | . | . | . | . | . | . | 0.78 | −0.04 | * | * | . | 1.21 | 1.36 |
| His | 356 | A | . | . | . | . | . | . | 1.63 | −0.10 | * | . | F | 1.49 | 0.99 |
| Asp | 357 | . | . | . | . | T | T | . | 1.64 | −0.10 | . | . | F | 2.52 | 1.00 |
| Gln | 358 | . | . | . | . | T | T | . | 1.64 | −0.10 | . | . | F | 2.80 | 1.63 |
| Gly | 359 | . | . | . | . | T | T | . | 1.13 | −0.29 | . | . | F | 2.52 | 1.63 |
| His | 360 | . | . | . | . | T | T | . | 1.60 | −0.10 | . | . | F | 2.09 | 0.80 |
| Ser | 361 | . | . | . | . | . | . | C | 1.63 | 0.33 | . | . | . | 0.66 | 0.46 |
| His | 362 | . | . | . | . | . | . | C | 1.42 | −0.07 | . | . | . | 0.98 | 0.78 |
| Leu | 363 | . | . | . | . | . | . | C | 1.03 | −0.07 | . | . | . | 0.70 | 0.88 |
| Gly | 364 | . | . | . | . | . | . | C | 0.99 | −0.14 | . | . | . | 0.70 | 0.84 |
| Asp | 365 | . | . | . | . | . | . | C | 0.63 | −0.10 | . | . | . | 0.70 | 0.79 |
| Pro | 366 | . | . | . | . | . | . | C | 0.54 | −0.17 | . | . | . | 0.85 | 1.22 |

What is claimed is:

1. An isolated polypeptide comprising amino acid residues 28 to 263 of SEQ ID NO:88.

2. The isolated polypeptide of claim 1 which comprises amino acid residues 2 to 263 of SEQ ID NO:88.

3. The isolated polypeptide of claim 1 which comprises amino acid residues 1 to 263 of SEQ ID NO:88.

4. The polypeptide of claim 1 which further comprises a polypeptide sequence heterologous to SEQ ID NO:88.

5. A composition comprising the polypeptide of claim 1 and an acceptable carrier.

6. An isolated protein produced by the method comprising:

(a) synthesizing the polypeptide of claim 3 in a cell; and (b) recovering the protein secreted from the cell.

7. An isolated polypeptide comprising the amino acid sequence of the complete polypeptide, Protein HOFNF53, encoded by the cDNA contained in ATCC Deposit No. PTA-736, excepting the N-terminal methionine.

8. The isolated polypeptide of claim 7 which comprises the amino acid sequence of the complete polypeptide, Protein HOFNF53, encoded by the cDNA contained in ATCC Deposit No. PTA-736.

9. An isolated protein produced by the method comprising:

(a) synthesizing the polypeptide of claim 8 in a cell; and (b) recovering said protein secreted from the cell.

10. The isolated protein of claim 9 which further comprises a polypeptide sequence heterologous to the complete polypeptide, Protein HOFNF53, encoded by the cDNA contained in ATCC Deposit No. PTA-736.

11. A composition comprising the isolated protein of claim 9 and an acceptable carrier.

12. An isolated polypeptide consisting of at least 30 contiguous amino acid residues of amino acid residues 1 to 263 of SEQ ID NO:88.

13. The isolated polypeptide of claim 12 which consists of at least 50 contiguous amino acid residues of amino acid residues 1 to 263 of SEQ ID NO:88.

14. The polypeptide of claim 12 which further comprises a polypeptide sequence heterologous to SEQ ID NO:88.

15. A composition comprising the polypeptide of claim 12 and an acceptable carrier.

16. An isolated polypeptide consisting of at least 30 contiguous amino acid residues of the complete polypeptide, Protein HOFNF53, encoded by the cDNA contained in ATCC Deposit No. PTA-736.

17. The isolated polypeptide of claim 16 which consists of at least 50 contiguous amino acid residues of the complete polypeptide, Protein HOFNF53, encoded by the cDNA contained in ATCC Deposit No. PTA-736.

18. The polypeptide of claim 16 which further comprises a polypeptide sequence heterologous to the complete polypeptide, Protein HOFNF53, encoded by the cDNA contained in ATCC Deposit No. PTA-736.

19. A composition comprising the polypeptide of claim 16 and an acceptable carrier.

* * * * *

SEQUENCE LISTING

<160> NUMBER OF SEQ ID NOS: 217

<210> SEQ ID NO 1
<211> LENGTH: 733
<212> TYPE: DNA
<213> ORGANISM: Homo sapiens

<400> SEQUENCE: 1

```
gggatccgga gcccaaatct tctgacaaaa ctcacacatg cccaccgtgc ccagcacctg      60

aattcgaggg tgcaccgtca gtcttcctct tccccccaaa acccaaggac accctcatga     120

tctcccggac tcctgaggtc acatgcgtgg tggtggacgt aagccacgaa gaccctgagg     180

tcaagttcaa ctggtacgtg gacggcgtgg aggtgcataa tgccaagaca aagccgcggg     240
```

-continued aggagcagta caacagcacg taccgtgtgg tcagcgtcct caccgtcctg caccaggact 300
ggctgaatgg caaggagtac aagtgcaagg tctccaacaa agccctccca acccccatcg 360
agaaaaccat ctccaaagcc aaagggcagc cccgagaacc acaggtgtac accctgcccc 420
catcccggga tgagctgacc aagaaccagg tcagcctgac ctgcctggtc aaaggcttct 480
atccaagcga catcgccgtg gagtgggaga gcaatgggca gccggagaac aactacaaga 540
ccacgcctcc cgtgctggac tccgacggct ccttcttcct ctacagcaag ctcaccgtgg 600
acaagagcag gtggcagcag gggaacgtct tctcatgctc cgtgatgcat gaggctctgc 660
acaaccacta cacgcagaag agcctctccc tgtctccggg taaatgagtg cgacggccgc 720
gactctagag gat 733

<210> SEQ ID NO 2
<211> LENGTH: 5
<212> TYPE: PRT
<213> ORGANISM: Homo sapiens
<220> FEATURE:
<221> NAME/KEY: Site
<222> LOCATION: (3)
<223> OTHER INFORMATION: Xaa equals any of the twenty naturally ocurring
L-amino acids

<400> SEQUENCE: 2

Trp Ser Xaa Trp Ser
1 5

<210> SEQ ID NO 3
<211> LENGTH: 86
<212> TYPE: DNA
<213> ORGANISM: Homo sapiens

<400> SEQUENCE: 3
gcgcctcgag atttccccga aatctagatt tccccgaaat gatttccccg aaatgatttc 60
cccgaaatat ctgccatctc aattag 86

<210> SEQ ID NO 4
<211> LENGTH: 27
<212> TYPE: DNA
<213> ORGANISM: Homo sapiens

<400> SEQUENCE: 4
gcggcaagct ttttgcaaag cctaggc 27

<210> SEQ ID NO 5
<211> LENGTH: 271
<212> TYPE: DNA
<213> ORGANISM: Homo sapiens

<400> SEQUENCE: 5
ctcgagattt ccccgaaatc tagatttccc cgaaatgatt tccccgaaat gatttccccg 60
aaatatctgc catctcaatt agtcagcaac catagtcccg cccctaactc cgcccatccc 120
gcccctaact ccgcccagtt ccgcccattc tccgccccat ggctgactaa ttttttttat 180
ttatgcagag gccgaggccg cctcggcctc tgagctattc cagaagtagt gaggaggctt 240
ttttggaggc ctaggctttt gcaaaaagct t 271

<210> SEQ ID NO 6
<211> LENGTH: 32
<212> TYPE: DNA

-continued

<213> ORGANISM: Homo sapiens

<400> SEQUENCE: 6
gcgctcgagg gatgacagcg atagaacccc gg 32

<210> SEQ ID NO 7
<211> LENGTH: 31
<212> TYPE: DNA
<213> ORGANISM: Homo sapiens

<400> SEQUENCE: 7
gcgaagcttc gcgactcccc ggatccgcct c 31

<210> SEQ ID NO 8
<211> LENGTH: 12
<212> TYPE: DNA
<213> ORGANISM: Homo sapiens

<400> SEQUENCE: 8
ggggactttc cc 12

<210> SEQ ID NO 9
<211> LENGTH: 73
<212> TYPE: DNA
<213> ORGANISM: Homo sapiens

<400> SEQUENCE: 9
gcggcctcga ggggactttc ccggggactt tccggggact ttccgggact ttccatcctg 60
ccatctcaat tag 73

<210> SEQ ID NO 10
<211> LENGTH: 256
<212> TYPE: DNA
<213> ORGANISM: Homo sapiens

<400> SEQUENCE: 10
ctcgagggga ctttcccggg gactttccgg ggactttccg ggactttcca tctgccatct 60
caattagtca gcaaccatag tcccgcccct aactccgccc atcccgcccc taactccgcc 120
cagttccgcc cattctccgc cccatggctg actaattttt tttatttatg cagaggccga 180
ggccgcctcg gcctctgagc tattccagaa gtagtgagga ggcttttttg gaggcctagg 240
cttttgcaaa aagctt 256

<210> SEQ ID NO 11
<211> LENGTH: 2329
<212> TYPE: DNA
<213> ORGANISM: Homo sapiens

<400> SEQUENCE: 11
ggcacgagct ccagttcagc tcgctcggcg cacccacgcc tcgctgcccc gcttcctgcc 60
ctcaacctgg gcatgcgccc cccacccttc cggcccccca gaacccgcgc catccccccgg 120 agcctcccca gagctggccg cgcaggatgg gcgccctcag gcccacgctg ctgccgcctt 180
cgctgccgct gctgctgctg ctaatgctag gaatgggatg ctgggcccgg gaggtgctgg 240
tccccgaggg gcccttgtac cgcgtggctg gcacagctgt ctccatctcc tgcaatgtga 300
ccggctatga gggccctgcc cagcagaact tcgagtggtt cctgtatagg cccgaggccc 360
cagatactgc actgggcatt gtcagtacca aggataccca gttctcctat gctgtcttca 420
agtcccgagt ggtggcgggt gaggtgcagg tgcagcgcct acaaggtgat gccgtggtgc 480

-continued

```
tcaagattgc ccgcctgcag gcccaggatg ccggcattta tgagtgccac acccccctcca    540
ctgatacccg ctacctgggc agctacagcg gcaaggtgga gctgagagtt cttccagatg    600
tcctccaggt gtctgctgcc cccccagggc cccgaggccg ccaggcccca acctcacccc    660
cacgcatgac ggtgcatgag gggcaggagc tggcactggg ctgcctggcg aggacaagca    720
cacagaagca cacacacctg gcagtgtcct ttgggcgatc tgtgcccgag gcaccagttg    780
ggcggtcaac tctgcaggaa gtggtgggaa tccggtcaga cttggccgtg gaggctggag    840
ctccctatgc tgagcgattg gctgcagggg agcttcgtct gggcaaggaa gggaccgatc    900
ggtaccgcat ggtagtaggg ggtgcccagg caggggacgc aggcacctac cactgcactg    960
ccgctgagtg gattcaggat cctgatggca gctgggccca gattgcagag aaaagggccg   1020
tcctggccca cgtggatgtg cagacgctgt ccagccagct ggcagtgaca gtggggcctg   1080
gtgaacgtcg gatcggccca ggggagccct tggaactgct gtgcaatgtg tcaggggcac   1140
ttcccccagc aggccgtcat gctgcatact ctgtaggttg ggagatggca cctgcggggg   1200
cacctgggcc cggccgcctg gtagcccagc tggacacaga gggtgtgggc agcctgggcc   1260
ctggctatga gggccgacac attgccatgg agaaggtggc atccagaaca taccggctac   1320
ggctagaggc tgccaggcct ggtgatgcgg gcacctaccg ctgcctcgcc aaagcctatg   1380
ttcgagggtc tgggacccgg cttcgtgaag cagccagtgc ccgttcccgg cctctccctg   1440
tacacgtgcg ggaggaaggt gtggtgctgg aagctgtggc atggctagca ggaggcacag   1500
tgtaccgcgg ggagactgcc tccctgctgt gcaacatctc tgtgcggggt ggccccccag   1560
gactgcggct ggccgccagc tggtgggtgg agcgaccaga ggatggagag ctcagctctg   1620
tccctgccca gctggtgggt ggcgtaggcc aggatggtgt ggcagagctg ggagtccggc   1680
ctggaggagg ccctgtcagc gtagagctgg tggggccccg aagccatcgg ctgagactac   1740
acagcttggg gcccgaggat gaaggcgtgt accactgtgc ccccagcgcc tgggtgcagc   1800
atgccgacta cagctggtac caggcgggca gtgcccgctc agggcctgtt acagtctacc   1860
cctacatgca tgccctggac accctatttg tgcctctgct ggtgggtaca ggggtggccc   1920
tagtcactgg tgccactgtc cttggtacca tcacttgctg cttcatgaag aggcttcgaa   1980
aacggtgatc ccttactccc caggtcttgc aggtgtcaac tgtcttccgg cccagctcca   2040
agccctcctc tggttgcctg gacaccctct ccctctgtcc actcttcctt taatttattt   2100
gacctcccac tacccagaat gggagacgtg cctccccttc cccactcctt ccctcccaag   2160
cccctccctc tggccttctg ttcttgatct cttagggatc ctatagggag gccatttcct   2220
gtcctggaat tagtttttct aaaatgtgaa taaacttgtt ttataaaaaa aaaaaaaaaa   2280
aaaaaaaaaa aaaaaaaaaa aaaaaaaaaa aaaaaaaaaa aaaaaaaaa               2329
```

<210> SEQ ID NO 12
<211> LENGTH: 2330
<212> TYPE: DNA
<213> ORGANISM: Homo sapiens

<400> SEQUENCE: 12

```
ccacgcgtcc gggcggctgc gcacactcca gagtgcccgc aacaaagcgg ttctggggga     60
ggttggggct gttacccgcg gcgggggcgc ccgctattgc gcaggcgcct caggaagatc    120
tctgcctcgc gcagagatca ggtcggcgtc gtccccaggg cccacgagcg cggggttccg    180
ccagtgctga gttccgcgcg ccggctgcag cgggaaccct gattgctttc cttcaacacg    240
```

-continued

```
ttcattatga agttattagt aatacttata ttttctggac ttataacttg ttgtggaggt    300

aactcttccc atagcctgcc atccaagctg ctgctggtgt cctttgatgg tttcagagct    360

gactatctac agaactatga atttcctcat ctccagaatt ttatcaaaga aggagtcctg    420

gtagagcatg ttaaaaatgt ttttatcaca aaaacatttc ctaaccacta cagcattgtg    480

acgggcttgt atgaagaaag tcatggcatc gtggctaatt ccatgtatga tgtaatcaca    540

aagaaacatt tttctgactt tgatgacaag gatccttttt ggtggaatga ggcggtacct    600

atttgggtga ccaatcagct tcaggaaaac agatcaagcg ccgccgctat gtggcctggt    660

actgatgtac ccattcacaa taccacacct tcctatttta tgaattatag ctcttcagtg    720

tcatttgagg agagactaaa taatattacc atgtggctga tgaattcgaa cccaccagtt    780

acctttgcaa cactctactg ggaagaacca gatgcaagtg gccacaaata tggacctgaa    840

gataaagaaa acatgtacag agtgttgaag gaagtagatg accttattgg tgagctagtc    900

cacaaactca aggtgctagg attgtgggaa aatctcaatg tgatcattac cagtgatcat    960

gggatgaccc agtgctctaa ggacaaattg ataaacctgg atctctgcat tgatcgctca   1020

agctacactc ttgtagatct gactccagtt gctgctgtcc ttcccaaaat aaatacaaca   1080

gaggtttata acaaactgaa agtctgtaac cctcacatga atgtttatct caaagaagac   1140

attcctgcca gatttcatta ccaacataat gatcgaattc agcctattat tttggttgct   1200

gatgaaggct ggacaattgt gttaaataaa tcattaccaa aattaggtga ccatggttat   1260

gacaattctt tgtcaagtat gcatccgttt ctagctgccc atggtccagc atttcacaaa   1320

ggctacaaac acagcacaat taacagtgtg gatatttatc cgatgatgtg ccacatcctg   1380

ggattaaaac cacatcccaa taacggaacc tttggtcata ctaagtgttt gttagttgac   1440

cagtggtgca ttaatctccc ggaagccatt ggaattgtga ttggtgcgct cttggtccta   1500

accacgctaa catgcctgat tataatcatg cagaatagac tgtctgtacc gcgtccgttt   1560

tcccgacttc agctgcaaga ggacgacgac gatcctttaa ttgagtagca tgtgctggag   1620

tttatagagt gtctttgatc agtcacgata ctgaggacac actcaagaat ggtattctaa   1680

cgatgaaaaa tacaccttga gaggcaaaga acttagaccg agcatgctag aattattttg   1740

gttttccttg tgctttgttt tactgcatca gctaatacat aaaaccctga ccatagcaaa   1800

aattgctagt aaatcagtag ttaacaccaa ctatttctcc aactagaaac tttttgtaag   1860

aaaaataatg cctctgcctt ttttttgcaa tgaagatttg acacattttt aaataaaaat   1920

ctatcaaaat ttaataggca tgcttttcta ataaactttt atatttgtaa ctgaaataac   1980

agaaatcttt atgcaattag tggattttgt gtatcaggaa ggaaaagttt tctatatttt   2040

tatatttaat aactttaata gagtttgtat cccaggtaaa cctatgacat tggaagacct   2100

ctgtgaaggt taataaaatt agttaagcag gcagaacaga tctagcatat gaagaaatta   2160

ttttaagaaa agctattata agaaaaacaa caaaaaccat gtgatacaaa gcttgagtct   2220

ttaccattgt ctttgttaag attcctaagc tgttgaagcc aggaaagata tctttcaaag   2280

actgttgcta taagaaatta agaaaatgga aagaaaaaaa aaaaaaaaaa              2330
```

```
<210> SEQ ID NO 13
<211> LENGTH: 651
<212> TYPE: DNA
<213> ORGANISM: Homo sapiens

<400> SEQUENCE: 13

ggcacgagtg cagctccctg agcactctct acagagacgc ggaccccaga catgaggagg     60
```

-continued

```
ctcctcctgg tcaccagcct ggtggttgtg ctgctgtggg aggcaggtgc agtcccagca    120
cccaaggtcc ctatcaagat gcaagtcaaa cactggccct cagagcagga cccagagaac    180
agggcctggg gcgcccgtgt ggtggagcct ccggagaagg acgaccagct ggtggtgctg    240
ttccctgtcc agaagccgaa actcttgacc accgaggaga agccacgagg tcagggcagg    300
ggccccatcc ttccaggcac caaggcctgg atggagaccg aggacaccct gggccgtgtc    360
ctgagtcccg agcccgacca tgacagcctg taccaccctc cgcctgagga ggaccagggc    420
gaggagaggc cccggttgtg ggtgatgcca aatcaccagg tgctcctggg accggaggaa    480
gaccaagacc acatctacca cccccagtag ggctccaggg gccatcactg cccccgccct    540
gtcccaaggc ccaggctgtt gggactggga ccctccctac cctgccccag ctagacaaat    600
aaaccccagc aggccgggaa aaaaaaaaaa aaaaaaaaaa aaaaaaaaaa a             651
```

<210> SEQ ID NO 14
<211> LENGTH: 997
<212> TYPE: DNA
<213> ORGANISM: Homo sapiens

<400> SEQUENCE: 14

```
ggaggcagag gcatcatgga gggtccccgg ggatggctgg tgctctgtgt gctggccata     60
tcgctggcct ctatggtgac cgaggacttg tgccgagcac cagacgggaa gaaaggggag    120
gcaggaagac ctggcagacg ggggcggcca ggcctcaagg gggagcaagg ggagccgggg    180
gcccctggca tccggacagg catccaaggc cttaaaggag accaggggga acctgggccc    240
tctggaaacc ccggcaaggt gggctaccca gggcccagcg gcccccctcgg ggcccgtggc    300
atcccgggaa ttaaaggcac caagggcagc ccaggaaaca tcaaggacca gccgaggcca    360
gccttctccg ccattcggcg gaaccccccca atgggggggca acgtggtcat cttcgacacg    420
gtcatcacca accaggaaga accgtaccag aaccactccg gccgattcgt ctgcactgta    480
cccggctact actacttcac cttccaggtg ctgtcccagt gggaaatctg cctgtccatc    540
gtctcctcct caaggggcca ggtccgacgc tccctgggct tctgtgacac caccaacaag    600
gggctcttcc aggtggtgtc agggggcatg gtgcttcagc tgcagcaggg tgaccaggtc    660
tgggttgaaa aagaccccaa aaagggtcac atttaccagg gctctgaggc cgacagcgtt    720
ttcagcggtt tcctcatttt cccatctgcc tgagccaggg aaggaccccc tcccccaccc    780
acctctctgg cttccatgct ccgcctgtaa aatgggggcg ctattgcttc agctgctgaa    840
gggagggggc tggctctgag agccccagga ctggctgccc cgtgacacat gctctaagaa    900
gctcgtttct tagacctctt cctggaataa acatctgtgt ctgtgtctgc tgaaaaaaaa    960
aaaaaaaaaa aaaaaaaaaa aaaaaaaaaa aaaaaaa                             997
```

<210> SEQ ID NO 15
<211> LENGTH: 1266
<212> TYPE: DNA
<213> ORGANISM: Homo sapiens

<400> SEQUENCE: 15

```
ggcacgagga tgcctggacc cagagtgtgg gggaaatatc tctggagaag ccctcactcc     60
aaaggctgtc caggcgcaat gtggtggctg cttctctggg gagtcctcca ggcttgccca    120
acccggggct ccgtcctctt ggcccaagag ctaccccagc agctgacatc cccgggtac     180
ccagagccgt atggcaaagg ccaagagagc agcacggaca tcaaggctcc agagggcttt    240
```

-continued

```
gctgtgaggc tcgtcttcca ggacttcgac ctggagccgt cccaggactg tgcaggggac    300
tctgtcacaa tctcattcgt cggttcggat ccaagccagt tctgtggtca gcaaggctcc    360
cctctgggca ggccccctgg tcagagggag tttgtatcct cagggaggag tttgcggctg    420
accttccgca cacagccttc ctcggagaac aagactgccc acctccacaa gggcttcctg    480
gccctctacc aaaccgtggc tgtgaactat agtcagccca tcagcgaggc cagcaggggc    540
tctgaggcca tcaacgcacc tggagacaac cctgccaagg tccagaacca ctgccaggag    600
ccctattatc aggccgcggc agcaggggca ctcacctgtg caaccccagg gacctggaaa    660
gacagacagg atggggagga ggttcttcag tgtatgcctg tctgcggacg gccagtcacc    720
cccattgccc agaatcagac gaccctcggt tcttccagag ccaagctggg caacttcccc    780
tggcaagcct tcaccagtat ccacggccgt gggggcgggg ccctgctggg ggacagatgg    840
atcctcactg ctgcccacac catctacccc aaggacagtg tttctctcag gaagaaccag    900
agtgtgaatg tgttcttggg ccacacagcc atagatgaga tgctgaaact ggggaaccac    960
cctgtccacc gtgtcgttgt gcaccccgac taccgtcaga atgagtccca taactttagc   1020
ggggacatcg ccctcctgga gctgcagcac agcatccccc tgggccccaa cgtcctcccg   1080
gtctgtctgc ccgataatga gaccctctac cgcagcggct tgttgggcta cgtcagtggg   1140
tttggcatgg agatgggctg gctaactact gagctgaagt actcgaggct gcctgtagct   1200
cccagggagg cctgcaacgc ctggctccaa aagagacaga gacccgaaaa aaaaaaaaaa   1260
aaaaaa                                                              1266
```

<210> SEQ ID NO 16
<211> LENGTH: 2710
<212> TYPE: DNA
<213> ORGANISM: Homo sapiens

<400> SEQUENCE: 16

```
ggcagacatg aacatctatt gaggaaaacc acaaaaaact tcaaaacagc tacaacggga     60
aaaagagagt tttgtcccac agtcagcagg ccactagttt attaacttcc agtcaccttg    120
atttttgcta aaatgaagac tctgcagtct acacttctcc tgttactgct tgtgcctctg    180
ataaagccag caccaccaac ccagcaggac tcacgcatta tctatgatta tggaacagat    240
aattttgaag aatccatatt tagccaagat tatgaggata aatacctgga tggaaaaaat    300
attaaggaaa aagaaactgt gataataccc aatgagaaaa gtcttcaatt acaaaaagat    360
gaggcaataa caccattacc tcccaagaaa gaaaatgatg aaatgcccac gtgtctgctg    420
tgtgtttgtt taagtggctc tgtatactgt gaagaagttg acattgatgc tgtaccaccc    480
ttaccaaagg aatcagccta tctttacgca cgattcaaca aaattaaaaa gctgactgcc    540
aaagattttg cagacatacc taacttaaga agactcgatt ttacaggaaa tttgatagaa    600
gatatagaag atggtacttt ttcaaaactt tctctgttag aagaactttc acttgctgaa    660
aatcaactac taaaacttcc agttcttcct cccaagctca ctttatttaa tgcaaaatac    720
aacaaaatca agagtagggg aatcaaagca aatgcattca aaaaactgaa taacctcacc    780
ttcctctact tggaccataa tgccctggaa tccgtgcctc ttaatttacc agaaagtcta    840
cgtgtaattc atcttcagtt caacaacata gcttcaatta cagatgacac attctgcaag    900
gctaatgaca ccagttacat ccgggaccgc attgaagaga tacgcctgga gggcaatcca    960
atcgtcctgg gaaagcatcc aaacagtttt atttgcttaa aaagattacc gataggtca   1020
tacttttaac ctctattggt acaacatata aatgaaagta cacctacact aatagtctgt   1080
```

-continued

```
ctcaacaatg agtaaaggaa cttaagtatt ggtttaatat taaccttgta tctcattttg   1140

aaggrattta atattttaag caaggatgtt caaaatctta catataataa gtaaaaagta   1200

agactgaatg tctacgttcg aaacaaagta atatgaaaat atttaaacag cattacaaaa   1260

tcctagttta tactagacta ccatttaaaa atcatgtttt tatataaatg cccaaatttg   1320

agatgcatta ttcctattac taatgatgta agtacgagga taaatccaag aaactttcaa   1380

ctctttgcct ttcctggcct ttactggatc ccaaaagcat ttaaggtaca tgttccaaaa   1440

actttgaaaa gctaaatgtt tcccatgatc gctcattctt cttttatgat tcatacgtta   1500

ttccttataa agtaagaact ttgttttcct cctatcaagg cagctatttt attaaatttt   1560

tcacttagtc tgagaaatag cagatagtct catatttagg aaaactttcc aaataaaata   1620

aatgttattc tctgataaag agctaataca gaaatgttca agttatttta ctttctggta   1680

atgtcttcag taaaatattt tctttatcta aatattaaca ttctaagtct accaaaaaaa   1740

gttttaaact caagcaggcc aaaaccaata tgcttataag aaataatgaa aagttcatcc   1800

atttctgata aagttctcta tggcaaagtc tttcaaatac gagataactg caaaatattt   1860

tccttttata ctacagaaat gagaatctca tcaataaatt agttcaagca taagatgaaa   1920

acagaatatt ctgtggtgcc agtgcacact accttcccac ccatacacat ccatgttcac   1980

tgtaacaaac tgaatattca caataaagct tctgagtaac actttctgat tactcatgat   2040

aaactgacat ggctaactgc argaattaaa tcttctatct gagagtaata atttatgatg   2100

actcagtggt gccagagtaa agtttctaaa ataacattcc tctcacttgt accccactaa   2160

aagtattagt ctacacatta cattgaagtt aaacacaaaa ttatcagtgt tttagaaaca   2220

tgagtccgga ctgtgtaagt aaaagtacaa acattatttc caccataaag tatgtattga   2280

aatcaagttg tctctgtgta cagaatacat acttattccc atttttaagc atttgcttct   2340

gttttcccta cctagaatgt cagatgtttt tcagttatct ccccatttgt caaagttgac   2400

ctcaagataa catttttcat taaagcatct gagatctaag aacacaatta ttattctaac   2460

aatgattatt agctcattca cttattttga taactaatga tcacagctat tatactactt   2520

tctcgttatt ttgtgtgcat gcctcatttc cctgacttaa acctcactga gagcgcaaaa   2580

tgcagcttta tactttttac tttcaattgc ctagcacaat agtgagtaca tttgaattga   2640

atatataata aatattgcaa aataaaatcc atctaaatag aaaaaaaaaa aaaaaaaaaa   2700

aaaaactcga                                                          2710
```

<210> SEQ ID NO 17
<211> LENGTH: 2405
<212> TYPE: DNA
<213> ORGANISM: Homo sapiens
<220> FEATURE:
<221> NAME/KEY: SITE
<222> LOCATION: (155)
<223> OTHER INFORMATION: n equals a,t,g, or c
<221> NAME/KEY: SITE
<222> LOCATION: (409)
<223> OTHER INFORMATION: n equals a,t,g, or c
<221> NAME/KEY: SITE
<222> LOCATION: (1971)
<223> OTHER INFORMATION: n equals a,t,g, or c
<221> NAME/KEY: SITE
<222> LOCATION: (2051)
<223> OTHER INFORMATION: n equals a,t,g, or c

<400> SEQUENCE: 17

```
tcgacccacg cgtccgctta ccgctgcttg ctggagcgag cttccactta actcccgtcc     60
```

-continued

```
cggtccccgc gcgccatgtg cctcctcggc gggctgagcg ccccgccgct gctgctgctg    120
ccgctgctgc cgctgctgct gtgtccgcct acggngcagg gtgactgcag ctttccccca    180
gagctaccta atgccataca aagtgtgggt gaccaacaga gttttcctga aaaattcaca    240
gtaacataca aatgtaaaga aggctttgta aaggttcctg gcaaggcaga ctccgtggtc    300
tgtctcaaca ataaatggtc agaggtggca gaattttgta accgtagctg tgatgttcca    360
accaggctac aatttgcatc tctcaaaaag tctttcacca aacagaatna tttcccagtg    420
ggttccgttg tggaatatga atgccgacct ggctaccaaa gggaccatct tctctcagga    480
aaactaactt gccttctgaa ttttacatgg tccaaacccg atgaattttg taaaagaaaa    540
tcatgtccta atcctggaga tttaagacat ggtcatgtca acattccaac tgacatattg    600
tatgctgcag ttatccactt ctcgtgtaac aaggggtaca ggttagtcgg tgcagcttct    660
agttactgtt ccattgtaaa tgacgatgtt ggctggagtg atccattgcc tgaatgccaa    720
gaaatttttt gtccggaacc accaaaaatt agcaatggag tcattctaga tcaacagaac    780
acttatgtgt atcaacaggc tgtwaaatat gartgtataa aaggcttcac cctgatcggr    840
gagaactctg atttattgta ctgttaaggs tgaccaagga gaatggrgtg gccgccgcct    900
gaatgcaaag gtkcwcwgaw ttctacagtc ataccagcaa cagagacacc accacagtaa    960
gtgcttcagc tacaaagccc acatcagctc tcagaaaccc accactgcaa atgttacagg   1020
taccaaagtt acatcagctc ctcagaaacc caccacaggg aatgttccag gtaccgaagc   1080
tacatcaact cctcagaaac ccactacagc ggatgtttca gagaccccgt cagcagtcca   1140
gaatcccatc acggcaaatg cgtytgtaca caggccatgc cagcaaccca tagatcctcc   1200
acagcaaaag cttcatttac acagagtctt ccagcaacac gaaagtccac tgctatacat   1260
gccccagtga ctaagggtct ccatacaaca aaaagattga cctctgctcg tattacagca   1320
aaacagagtt cagctactcc caggacaacc agcgcacctc atggaagagg gaccctctct   1380
tcagatgctg ccatcattgc agttggtaag tttggttctt cggcagttaa aaaaaattgt   1440
catcactgtg ggatgtacaa tccttattcc tggaggagaa tattgtcttt ttactgcctt   1500
aggaatacta ttaagatgaa atgtttaagg tcagggagaa gacgggtaaa tgcattttat   1560
cgacgtgttt ggtggacccc gttaggtact cggtacgttc ctaagtcttc ccaaccgtgt   1620
tcttgttcca aggtaatttt agggcaactt cacatcattt ggccagtcaa tcaagtatcc   1680
ctgaacgcct attgtctcaa tgcattatca ttctaggggc caaaaacaac aataaggaag   1740
ctattatcaa tacagttttt aagcctcaag tgktttacaa gtactcacaa actactyctt   1800
ggttgkttct agacgtctgt tccagataaa ccagaatgyt acytttgawt acatcctgkt   1860
cctttttcc ctttcctgtc agkgatttaa agcaaagata gctttaaaat tattctgttg   1920
ctatagactt aaggacatat ctatgttgca aatttctttt tcttgttccc nagtcttttg   1980
ttgttcatta aatatattat ttgatgttat acattttacc aagaagatta ataactccta   2040
agaagatggc naaaagaaat gtttaagaag caatacagct aagttggcat attaaaaagg   2100
aatgcccagt agaaaatatg cacattaaaa agtgaatatt ttaaaattat gtccttataa   2160
gctgaggtct cctatttatg catgcatgag tgaaacaagg gactgaagct gaaaaggtgt   2220
tttttaatta ttattattat ttatagttct tttatagttc ttttatattt tgaatgaacc   2280
tctccttagc taaaatagtt atcttgaaag atttgaacag ttggattcac tttgtttgtt   2340
tgatattttc aatagaaata aatgcattct aaatgaaaaa aaaaaaaaaa aaaaaaaggg   2400
```

-continued cggcc 2405

<210> SEQ ID NO 18
<211> LENGTH: 5720
<212> TYPE: DNA
<213> ORGANISM: Homo sapiens

<400> SEQUENCE: 18
tcgacggcag aggagcactt agcagcttat tcagtgtccg attctgattc cggcaaggat 60
ccaagcatgg aatgctgccg tcgggcaact cctggcacac tgctcctctt tctggctttc 120
ctgctcctga gttccaggac cgcacgctcc gaggaggacc gggacggcct atgggatgcc 180
tggggcccat ggagtgaatg ctcacgcacc tgcgggggtg ggcctcccta ctctctgagg 240
cgctgcctga gcagcaagag ctgtgaagga agaaatatcc gatacagaac atgcagtaat 300
gtggactgcc caccagaagc aggtgatttc cgagctcagc aatgctcagc tcataatgat 360
gtcaagcacc atggccagtt ttatgaatgg cttcctgtgt ctaatgaccc tgacaaccca 420
tgttcactca agtgccaagc caaaggaaca accctggttg ttgaactagc acctaaggtc 480
ttagatggta cgcgttgcta tacagaatct ttggatatgt gcatcagtgg tttatgccaa 540
attgttggct gcgatcacca gctgggaagc accgtcaagg aagataactg tggggtctgc 600
aacggagatg ggtccacctg ccggctggtc cgagggcagt ataaatccca gctctccgca 660
accaaatcgg atgatactgt ggttgcaatt ccctatggaa gtagacatat tcgccttgtc 720
ttaaaaggtc ctgatcactt atatctggaa accaaaaccc tccaggggac taaaggtgaa 780
aacagtctca gctccacagg aactttcctt gtggacaatt ctagtgtgga cttccagaaa 840
tttccagaca aagagatact gagaatggct ggaccactca cagcagattt cattgtcaag 900
attcgtaact cgggctccgc tgacagtaca gtccagttca tcttctatca acccatcatc 960
caccgatgga gggagacgga tttctttcct tgctcagcaa cctgtggagg aggttatcag 1020
ctgacatcgg ctgagtgcta cgatctgagg agcaaccgtg tggttgctga ccaatactgt 1080
cactattacc cagagaacat caaacccaaa cccaagcttc aggagtgcaa cttggatcct 1140
tgtccagcca ggtgggaggc caccccatgg accgcgtgct cctcctcgtg tggggggggc 1200
atccagagcc gggcagtttc ctgtgtggag gaggacatcc aggggcatgt cacttcagtg 1260
gaagagtgga aatgcatgta cacccctaag atgcccatcg cgcagccctg caacattttt 1320
gactgcccta aatggctggc acaggagtgg tctccgtgca cagtgacatg tggccagggc 1380
ctcagatacc gtgtggtcct ctgcatcgac catcgaggaa tgcacacagg aggctgtagc 1440
ccaaaaacaa agccccacat aaaagaggaa tgcatcgtac ccactccctg ctataaaccc 1500
aaagagaaac ttccagtcga ggccaagttg ccatggttca aacaagctca agagctagaa 1560
gaaggagctg ctgtgtcaga ggagccctcg ttcatcccaa aggcctggtc ggcctgcaca 1620
gtcacctgtg gtgtggggac ccaggtgcga atagtcaggt gccaggtgct cctgtctttc 1680
tctcagtccg tggctgacct gcctattgac gagtgtgaag ggcccaagcc agcatcccag 1740
cgtgcctgtt atgcaggccc atgcagcggg gaaattcctg agttcaaccc agacgagaca 1800
gatgggctct ttggtggcct gcaggatttc gacgagctgt atgactggga gtatgagggg 1860
ttcaccaagt gctccgagtc ctgtggagga ggtgtccagg aggctgtggt gagctgcttg 1920
aacaaacaga ctcgggagcc tgctgaggag aacctgtgcg tgaccagccg ccggccccca 1980
cagctcctga agtcctgcaa tttggatccc tgcccagcaa ggtgggaaat tggcaagtgg 2040
agtccatgta gtctcacatg tggggtcggc ctacagacca gagacgtctt ctgcagccac 2100

-continued

```
ctgctttcca gagagatgaa tgaaacagtc atcctggctg atgagctgtg tcgccagccc   2160
aagcccagca cggtgcaagc ttgtaaccgc tttaattgcc ccccagcctg gtaccctgca   2220
cagtggcagc cgtgttccag aacgtgtggc gggggtgttc agaaacgtga ggttctttgc   2280
aagcagcgca tggctgatgg cagcttcctg gagcttcctg agaccttctg ttcagcttca   2340
aaacctgcct gccagcaagc atgcaagaaa gatgactgtc ccagcgagtg gcttctctca   2400
gactggacag agtgttccac aagctgcggg gaaggcaccc agactcgaag cgccatttgc   2460
cgaaagatgc tgaaaaccgg cctctcaacg gttgtcaatt ccaccctgtg cccgcccctg   2520
cctttctctt cctccatcag gccctgtatg ctggcaacct gtgcaaggcc cgggcggcca   2580
tccacgaagc acagcccgca catcgcggcc gccaggaagg tctacataca gactcgcagg   2640
cagaggaagc tgcacttcgt ggtgggggc ttcgcctacc tgctccccaa gacggcggtg   2700
gtgctgcgct gcccggcgcg cagggtccgc aagcccctca tcacctggga gaaggacggc   2760
cagcacctca tcagctcgac gcacgtcacg gtggccccct tcggctatct caagatccac   2820
cgcctcaagc cctcggatgc aggcgtctac acctgctcag cgggcccggc ccgggagcac   2880
tttgtgatta agctcatcgg aggcaaccgc aagctcgtgg cccggccctt gagcccgaga   2940
agtgaggaag aggtgcttgc ggggaggaag ggcggcccga aggaggccct gcagacccac   3000
aaacaccaga acgggatctt ctccaacggc agcaaggcgg agaagcgggg cctggccgcc   3060
aacccgggga gccgctacga cgacctcgtc tcccggctgc tggagcaggg cggctggccc   3120
ggagagctgc tggcctcgtg ggaggcgcag gactctgcgg aaaggaacac gacctcggag   3180
gaggacccgg gtgcagagca agtgctcctg cacctgccct tcaccatggt gaccgagcag   3240
cggcgcctgg acgacatcct ggggaacctc tcccagcagc ccgaggagct gcgcgacctc   3300
tacagcaagc acctggtggc ccagctggcc caggagatct tccgcagcca cctggagcac   3360
caggacacgc tcctgaagcc ctcggagcgc aggacttccc cagtgactct ctcgcctcat   3420
aaacacgtgt ctggcttcag cagctccctg cggacctcct ccaccgggga cgccgggggga   3480
ggctctcgaa ggccacaccg caagcccacc atcctgcgca agatctcagc ggcccagcag   3540
ctctcagcct cggaggtggt cacccacctg gggcagacgg tggccctggc cagcgggaca   3600
ctgagtgttc ttctgcactg tgaggccatc ggccacccaa ggcctaccat cagctgggcc   3660
aggaatggag aagaagttca gttcagtgac aggattcttc tacagccaga tgattcctta   3720
cagatcttgg caccagtgga agcagatgtg ggtttctaca cttgcaatgc caccaatgcc   3780
ttgggatacg actctgtctc cattgccgtc acattagcag gaaagccact agtgaaaacg   3840
tcacgaatga cagtgatcaa cacggagaag cctgcagtca cagtcgatat aggaagcacc   3900
atcaaaacag tgcagggagt gaatgtgaca atcaactgcc aggttgcagg agtgcctgaa   3960
gctgaagtca cttggttcag gaataaaagc aaactgggct ccccgcacca tctgcacgaa   4020
ggctccttgc tgctcacaaa cgtgtcctcc tcggatcagg gcctgtactc ctgcagggcg   4080
gccaatcttc atggagagct gactgagagc acccagctgc tgatcctaga tcccccccaa   4140
gtccccacac agttggaaga catcagggcc ttgctcgctg ccactggacc gaaccttcct   4200
tcagtgctga cgtctcctct gggaacacag ctggtcctgg atcctgggaa ttctgctctc   4260
cttggctgcc ccatcaaagg tcaccctgtc cctaatatca cctggtttca tggtggtcag   4320
ccaattgtca ctgccacagg actgacgcat cacatcttgg cagctggaca gatccttcaa   4380
gttgcaaacc ttagcggtgg gtctcaaggg gaattcagct gccttgctca gaatgaggca   4440
```

-continued

```
ggggtgctca tgcagaaggc atctttagtg atccaagatt actggtggtc tgtggacaga   4500

ctggcaacct gctcagcctc ctgtggtaac cggggggttc agcagccccg cttgaggtgc   4560

ctgctgaaca gcacggaggt caaccctgcc cactgcgcag ggaaggttcg ccctgcggtg   4620

cagcccatcg cgtgcaaccg gagagactgc ccttctcggt ggatggtgac ctcctggtct   4680

gcctgtaccc ggagctgtgg gggaggtgtc cagacccgca gggtgacctg tcaaaagctg   4740

aaagcctctg ggatctccac ccctgtgtcc aatgacatgt gcacccaggt cgccaagcgg   4800

cctgtggaca cccaggcctg taaccagcag ctgtgtgtgg agtgggcctt ctccagctgg   4860

ggccagtgca atgggccttg catcgggcct cacctagctg tgcaacacag acaagtcttc   4920

tgccagacac gggatggcat caccttacca tcagagcagt gcagtgctct tccgaggcct   4980

gtgagcaccc agaactgctg gtcagaggcc tgcagtgtac actggagagt cagcctgtgg   5040

accctgtgca cagctacctg tggcaactac ggcttccagt cccggcgtgt ggagtgtgtg   5100

catgcccgca ccaacaaggc agtgcctgag cacctgtgct cctgggggcc ccggcctgcc   5160

aactggcagc gctgcaacat caccccatgt gaaaacatgg agtgcagaga caccaccagg   5220

tactgcgaga aggtgaaaca gctgaaactc tgccaactca gccagtttaa atctcgctgc   5280

tgtggaactt gtggcaaagc gtgaagatag ggtgtgggga aaaactctac cctggccaca   5340

cgaaggactc acgcaaccac ctcggacaga acctaagctt tcttcatttt atttatttat   5400

ttccccctcc ccactccaca cacacccttc caacctcctc cacctccacc ttcaagcata   5460

aggacgtccg cgtgttttct ctttcagtta gctggaggac aggatgttgg gaaaggaaag   5520

gacagatgtc taaaggaggt tgcagagcag gccaggcaga cagtgggggc tcccttgaag   5580

agcttcctcc ctcccaaacc tgggtctcaa agacctagaa agaggcaggc acagcccctg   5640

cggacagcag ggagccagaa ggtttgtagc ctattggtgc aaacattgga caaattcctg   5700

tgtctttcct agaagcgcag                                                5720
```

<210> SEQ ID NO 19
<211> LENGTH: 705
<212> TYPE: DNA
<213> ORGANISM: Homo sapiens

<400> SEQUENCE: 19

```
ggcacgagcc cagacatgag gaggctcctc ctggtcacca gcctggtggt tgtgctgctg     60

tgggaggcag gtgcagtccc agcacccaag gtccctatca agatgcaagt caaacactgg    120

ccctcagagc aggacccaga gaaggcctgg ggcgcccgtg tggtggagcc tccggagaag    180

gacgaccagc tggtggtgct gttccctgtc cagaagccga aactcttgac caccgaggag    240

aagccacgag gcaccaaggc ctggatggag accgaggaca ccctgggccg tgtcctgagt    300

cccgagcccg accatgacag cctgtaccac cctccgcctg aggaggacca gggcgaggag    360

aggccccggt tgtgggtgat gccaaatcac caggtgctcc tgggaccgga ggaagaccaa    420

gaccacatct accacccccca gtagggctcc aggggccatc actgcccccg ccctgtccca    480

aggcccaggc tgttgggact gggaccctcc ctaccctgcc ccagctagac aaataaaccc    540

cagcaggccg ggcgcggtgg ctcacctctg taatcccagc acttttagag gccgaggcag    600

gcggatcacc tgaaatcagg agttccagac cagcctgggc aacatggtga aaccccgtct    660

ctactaaaaa tacaaaaatt agccgggaaa aaaaaaaaaa aaaaa                    705
```

<210> SEQ ID NO 20
<211> LENGTH: 2108

-continued

<212> TYPE: DNA
<213> ORGANISM: Homo sapiens
<220> FEATURE:
<221> NAME/KEY: SITE
<222> LOCATION: (18)
<223> OTHER INFORMATION: n equals a,t,g, or c
<221> NAME/KEY: SITE
<222> LOCATION: (34)
<223> OTHER INFORMATION: n equals a,t,g, or c

<400> SEQUENCE: 20

```
gcgcctgcag gtcgacanta gtggatccaa aganttcggc acgaggtcac ctcctcacgc     60
tgcggctgtc gcccgtgtcc cgccggcccg ttccgtgtcg ccccgcagtg ctgcggccgc    120
cgcggcacca tggctgtgtt tgtcgtgctc ctggcgttgg tggcgggtgt tttggggaac    180
gagtttagta tattaaaatc accagggtct gttgttttcc gaaatggaaa ttggcctata    240
ccaggagagc ggatcccaga cgtggctgca ttgtccatgg gcttctctgt gaaagaagac    300
ctttcttggc caggactcgc agtgggtaac ctgtttcatc gtcctcgggc taccgtcatg    360
gtgatggtga agggagtgaa caaactggct ctacccccag gcagtgtcat ttcgtaccct    420
ttggagaatg cagttccttt tagtcttgac agtgttgcaa attccattca ctccttattt    480
tctgaggaaa ctcctgttgt tttgcagttg gctcccagtg aggaaagagt gtatatggta    540
gggaaggcaa actcagtgtt tgaagacctt tcagtcacct tgcgccagct ccgtaatcgc    600
ctgtttcaag aaaactctgt tctcagttca ctcccccctca attctctgag taggaacaat    660
gaagttgacc tgctctttct ttctgaactg caagtgctac atgatatttc aagcttgctg    720
tctcgtcata agcatctagc caaggatcat tctcctgatt tatattcact ggagctggca    780
ggtttggatg aaattgggaa gcgttatggg gaagactctg aacaattcag agatgcttct    840
aagatccttg ttgacgctct gcaaaagttt gcagatgaca tgtacagtct ttatggtggg    900
aatgcagtgg tagagttagt cactgtcaag tcatttgaca cctccctcat taggaagaca    960
aggactatcc ttgaggcaaa acaagcgaag aacccagcaa gtccctataa ccttgcatat   1020
aagtataatt ttgaatattc cgtggttttc aacatggtac tttggataat gatcgccttg   1080
gccttggctg tgattatcac ctcttacaat atttggaaca tggatcctgg atatgatagc   1140
atcatttata ggatgacaaa ccagaagatt cgaatggatt gaatgttacc tgtgccagaa   1200
ttagaaaagg gggttggaaa ttggctgttt tgttaaaata tatcttttag tgtgctttaa   1260
agtagatagt atactttaca tttataaaaa aaaatcaaat tttgttcttt attttgtgtg   1320
tgcctgtgat gtttttctag agtgaattat agtattgacg tgaatcccac tgtggtatag   1380
attccataat atgcttgaat attatgatat agccatttaa taacattgat ttcattctgt   1440
ttaatgaatt tggaaatatg cactgaaaga aatgtaaaac atttagaata gctcgtgtta   1500
tggaaaaaag tgcactgaat ttattagaca aacttacgaa tgcttaactt ctttacacag   1560
cataggtgaa aatcatattt gggctattgt atactatgaa caatttgtaa atgtcttaat   1620
ttgatgtaaa taactctgaa acaagagaaa aggtttttaa cttagagtag ccctaaaata   1680
tggatgtgct tatataatcg cttagttttg gaactgtatc tgagtaacag aggacagctg   1740
tttttaacc ctcttctgca agtttgttga cctacatggg ctaatatgga tactaaaaat   1800
actacattga tctaagaaga aactagcctt gtggagtata tagatgcttt tcattataca   1860
cacaaaaatc cctgagggac attttgaggc atgaatataa aacattttta tttcagtaac   1920
ttttcccccct gtgtaagtta ctatggtttg tggtacaact tcattctata gaatattaag   1980
tggaagtggg tgaattctac tttttatgtt ggagtggacc aatgtctatc aagagtgaca   2040
```

-continued aataaagtta atgatgattc caaaaaaaaa aaaaaaaaty cgatatcaag cttatcgata 2100
ccgtcgac 2108

<210> SEQ ID NO 21
<211> LENGTH: 675
<212> TYPE: DNA
<213> ORGANISM: Homo sapiens

<400> SEQUENCE: 21
ccacgcgtcc gatgaagccg gccactgcct ctgctctgct cctgctcctg ctgggcctgg 60
cctggaccca ggggagccac ggctggggtg cggacgcgtc atcactgcag aaacgtgcag 120
gcagagccga tcagccgggt gcaggatggc aggaggtggc agctgtaact tccaagaact 180
acaattacaa ccagcatgcg tatcccactg cctatggtgg gaagtactca gtcaagaccc 240
ctgcaaaggg gggagtctca ccttcttcct cggcttcccg ggtgcaacct ggcctgctgc 300
agtgggtgaa gttttggtag gcaatttctt gcaaccacca ccgaggcccc gaaaagcact 360
ggtcgtcagg gagctcctcc ccttggcccc cagcctgtgc cagccctggc ccggctgcca 420
cacctctgtt tcctaggctg gggacccagc ttgtctctcc ttgtttcttc ccactgcact 480
gtggtgcttc agtggccacc agcctcgtca catacaccag catctttctg tacctcctcc 540
ctttggtgac ctgaagtcac tgtgacagtt ctccaggaag gaggagcttc ctacttttga 600
gtttctctgt ggaaataaaa catgaatctt gttaaaaaaa aaaaaaaaaa aaaaaaaaaa 660
aaaaaaaaaa aaaaa 675

<210> SEQ ID NO 22
<211> LENGTH: 1581
<212> TYPE: DNA
<213> ORGANISM: Homo sapiens
<220> FEATURE:
<221> NAME/KEY: SITE
<222> LOCATION: (112)
<223> OTHER INFORMATION: n equals a,t,g, or c
<221> NAME/KEY: SITE
<222> LOCATION: (959)
<223> OTHER INFORMATION: n equals a,t,g, or c
<221> NAME/KEY: SITE
<222> LOCATION: (1565)
<223> OTHER INFORMATION: n equals a,t,g, or c

<400> SEQUENCE: 22
gcggccgcgg ctcggctcct cctctggggc ggcggcsgag gacagcagcg ccatggagga 60
gctcgctact gagaaggagg cggaggagag ccaccggcaa gacagcgtga gnctgctcac 120
cttcatcctg ctgctcacgc tcaccatcct caccatctgg ctcttcaagc accgccgggt 180
gcgctttctg cacgagaccg ggctggccat gatctatggg ctcatcgttg gggtgatcct 240
gaggtatggt acccctgcta ccagtggccg tgacaaatca ctcagctgca ctcaggaaga 300
cagggccttc agtaccttat tagtgaatgt cagcggaaag ttcttcgaat acactctgaa 360
aggagaaatc agtcctggca agatcaacag cgtagagcag aatgatatgc tacggaaggt 420
aacattcgat ccagaagtat ttttcaacat tcttctgcct ccaattattt ttcatgctgg 480
atacagctta aagaagagac actttttcag aaatcttgga tctatactgg cctatgcctt 540
cttggggact gctgkttcat gcttcattat tggaaatctc atgtatggtg tggtgaagct 600
catgaagatt atgggacagc tctcagataa attttactac acagawtgkc tctttttttgg 660 agcaatcatc tctgccactg acccagtgac tgtgctggcg atatttaatg aattgcatgc 720

-continued

```
agacgtggat ctttacgcac ttctttttgg agagagcgtc ctaaatgatg ctgttgccat    780

tgkactgkcc tcgtctattg ttgcctacca gccagcggga ctgaacactc acgcctttga    840

tgctgctgcc ttttttaagt cagttggcat ttttctaggt atatttagtg gctcttttac    900

catgggagct gtgactggtg ttgtgactgc tcyagtgact aagtttacca aackgcacng    960

cttccccctg ctggagacgg cgctgttctt cctcatgtcc tggagcacgt ttctcttggc   1020

agaagcctgc ggatttacag gtgttgtagc tgtccttttc tgtggaatca cacaagctca   1080

ttacacctac aacaatctgt cggtggaatc aagaagtcga accaagcagc tctttgaggt   1140

gttacatttc ctggcagaga acttcatctt ctcctacatg ggcctggcac tgtttacctt   1200

ccagaagcac gttttcagcc ccattttcat catcggagct tttgttgcca tcttcctggg   1260

cagagccgcg cacatctacc cgctctcctt cttcctcaac ttgggcagaa ggcataagat   1320

tggctggaat tttcaacaca tgatgatgtt ttcaggcctc aggggagcaa tggcatttgc   1380

gttggccatc cgtgacacgg catcctatgc tcgccagatg atgttcacga ccacccttct   1440

cattgtgttc ttcactgtct ggatcattgg aggaggcacg acacccatgt tgtcatggct   1500

taacatcaga gttggtgttg accccgatcw agacccacca cccaasamcg acagctttgc   1560

tttcnaaacg gagacggccc a                                             1581
```

<210> SEQ ID NO 23
<211> LENGTH: 922
<212> TYPE: DNA
<213> ORGANISM: Homo sapiens
<220> FEATURE:
<221> NAME/KEY: SITE
<222> LOCATION: (6)
<223> OTHER INFORMATION: n equals a,t,g, or c
<221> NAME/KEY: SITE
<222> LOCATION: (885)
<223> OTHER INFORMATION: n equals a,t,g, or c
<221> NAME/KEY: SITE
<222> LOCATION: (886)
<223> OTHER INFORMATION: n equals a,t,g, or c
<221> NAME/KEY: SITE
<222> LOCATION: (907)
<223> OTHER INFORMATION: n equals a,t,g, or c

<400> SEQUENCE: 23

```
aacggnaaaa tctcccctta ctattgggaa caaaagctgg agctccaccg cggtggcggc     60

cgctctagaa ctagtggatc ccccgggctg caggaattcg gcacgagccg aggaagagcg    120

ttttggggac gggggctggt gaggctcacg ttggagggct tcgcgtctgc ttcggagacc    180

gtaaggatat tgatgaccat gagatccctg ctcagaaccc ccttcctgtg tggcctgctc    240

tgggcctttt gtgccccagg cgccagggct gaggagcctg cagccagctt ctcccaaccc    300

ggcagcatgg gcctggataa gaacacagtg cacgaccaag agcatatcat ggagcatcta    360

gaaggtgtca tcaacaaacc agaggcggag atgtcgccac aagaattgca gctccattac    420

ttcaaaatgc atgattatga tggcaataat ttgcttgatg gcttagaact ctccacagcc    480

atcactcatg tccataagga ggaagggagt gaacaggcac cactaatgag tgaagatgaa    540

ctgattaaca taatagatgg tgttttgaga gatgatgaca agaacaatga tggatacatt    600

gactatgctg aatttgcaaa atcactgcag tagatgttat ttggccatct cctggttata    660

tacaaatgtg acccgtgata atgtgattga acactttagt aatgcaaaat aactcatttc    720

caactactgc tgcagcattt tggtaaaaac ctgtagcgat tcgttacact ggggtgagaa    780

gagataagag aaatgaaaga gaagagaaat gggacatcta atagtcccta agtgctatta    840
```

-continued aataccttat tggacaagga aaaaaaaaaa aaaaaaactc gagcnngggc ccggtaccca 900
attcggngta tgtgccgttg gt 922

<210> SEQ ID NO 24
<211> LENGTH: 2288
<212> TYPE: DNA
<213> ORGANISM: Homo sapiens
<220> FEATURE:
<221> NAME/KEY: SITE
<222> LOCATION: (66)
<223> OTHER INFORMATION: n equals a,t,g, or c
<221> NAME/KEY: SITE
<222> LOCATION: (67)
<223> OTHER INFORMATION: n equals a,t,g, or c

<400> SEQUENCE: 24
ccaataggct gccaatactc cttggactcc ccgccaggcc ctgctgtcag tgcgcctgcg 60
cgcggnntcc ggcgccgagg ttcttgactg ctgtgccgga cgccaggtgt agccatgcag 120
cgagccgatt ccgagcagcc ctccaagcgt ccccgttgcg atgacagccc gagaaccccc 180
tcaaacaccc cttccgcaga ggcagactgg tccccgggcc tggaactcca tcccgactac 240
aagacatggg gtccggagca ggtgtgctcc ttcctcaggc gcggtggctt tgaagagccg 300
gtgctgctga agaacatccg agaaaatgaa atcacaggcg cattactgcc ttgtcttgat 360
gagtctcgtt ttgaaaatct tggagtaagt tccttggggg agaggaagaa gctgcttagt 420
tatatccagc gattggttca aatccacgtt gatacaatga aggtaattaa tgatcctatc 480
catggccaca ttgagctcca ccctctcctc gtccgaatca ttgatacacc tcaatttcaa 540
cgtcttcgat acatcaaaca gctgggaggt ggttactatg tttttccagg agcttcacac 600
aatcgatttg agcatagtct aggggtgggg tatctagcag gatgtctagt tcacgcactg 660
ggtgaaaaac aaccagagct gcagataagt gaacgagatg ttctctgtgt tcagattgct 720
ggactttgtc atgatctcgg tcatgggcca ttttctcaca tgtttgatgg acgatttatt 780
ccacttgctc gcccggaggt gaaatggacg catgaacaag gctcagttat gatgtttgag 840
caccttatta attctaatgg aattaagcct gtcatggaac aatatggtct catccctgaa 900
gaagatattt gctttataaa ggaacaaatt gtaggaccac ttgaatcacc tgtcgaagat 960
tcattgtggc catataaagg gcgtcctgaa aacaaaagct tcctttatga gatagtatct 1020
aataaaagaa atggcattga tgtggacaaa tgggattatt ttgccaggga ctgccatcat 1080
cttggaatcc aaaataattt tgattacaag cgctttatta agtttgcccg tgtctgtgaa 1140
gtagacaatg agttgcgtat ttgtgctaga ratraggaag ttggaaatct gtatgacatg 1200
tyccacactc gcaactcttt acaccgtaga gcttatcaac acaaagttgg caacattatt 1260
gatacaatga ttacagatgc tttcctcaaa gcagatgact acatagagat tacaggtgct 1320
ggaggaaaaa agtatcgcat ttctacagca attgacgaca tggaagccta tactaagctg 1380
acagataaca tttttctgga gattttatac tctactgatc ccaaattgaa agacgcacga 1440
gagattttaa aacaaattga ataccgtaat ctattcaagt atgtgggtga gacgcagcca 1500
acaggacaaa taaagattaa aagggaggac tatgaatctc ttccaaaaga ggttgccagt 1560
gctaaaccca aagtattgct agacgtgaaa ctgaaggctg aagattttat agtggatgtt 1620
atcaacatgg attatggaat gcaagaaaag aatccaattg atcatgttag cttctattgt 1680
aagactgccc ccaacagagc aatcaggatt actaaaaacc aggtttcaca acttctgcca 1740
gagaaatttg cagagcagct gattcgagta tattgtaaga aggtggacag aaagagtttg 1800

-continued

```
tatgccgcaa gacaatattt tgttcagtgg tgtgcagaca gaaatttcac caagccgcag   1860

gatggcgatg ttatagcccc actcataaca cctcaaaaaa aggaatggaa cgacagtact   1920

tcagtccaaa atccaactcg cctccgagaa gcatccaaaa gcagagtcca gctttttaaa   1980

gatgacccaa tgtgaatgtc tgtagtcagt tgtttacaaa ctccctctcc tgcacaattc   2040

atttagaggc ttcaatcata gaattctgca aattaatgac aactcatgct ttaattttgt   2100

attttgaatg tacacgcatg ctgaagctaa gtaactttta atcaaagaaa taagatggta   2160

ttaggcaaat cttactatac tatgaaaagc attaccttgc ctatttttaa tattattaaa   2220

gcctttctcc ttcaaaaaaa aaaaaaaaaa aaaaaaaaaa aaaaaaaaaa aaaaaaaaaa   2280

aaactcga                                                            2288
```

<210> SEQ ID NO 25
<211> LENGTH: 908
<212> TYPE: DNA
<213> ORGANISM: Homo sapiens
<220> FEATURE:
<221> NAME/KEY: SITE
<222> LOCATION: (7)
<223> OTHER INFORMATION: n equals a,t,g, or c
<221> NAME/KEY: SITE
<222> LOCATION: (891)
<223> OTHER INFORMATION: n equals a,t,g, or c
<221> NAME/KEY: SITE
<222> LOCATION: (896)
<223> OTHER INFORMATION: n equals a,t,g, or c

<400> SEQUENCE: 25

```
tccgganttc ccgggtcgac ccacgcgtcc gcccacgcgt ccgcacagct cccttcccag     60

gacgtgaaaa tctgccttct caccatgagg cttctagtcc tttccagcct gctctgtatc    120

ctgcttctct gcttctccat cttctccaca gaagggaaga ggcgtcctgc caaggcctgg    180

tcaggcagga gaaccaggct ctgctgccac cgagtcccta gccccaactc aacaaacctg    240

aaaggacatc atgtgaggct ctgtaaacca tgcaagcttg agccagagcc ccgcctttgg    300

gtggtgcctg ggcactccc acaggtgtag cactcccaaa gcaagactcc agacagcgga    360

gaacctcatg cctggcacct gaggtaccca gcagcctcct gtctcccctt tcagccttca    420

cagcagtgag ctgcaatgtt ggagggcttc atctcgggct gcaaggaccc tgggaaagtt    480

ccagaactcc acgtccttgt ctcaattgtg ccatcaactt tcagagctat catgagccaa    540

cctcacccca cagggcctca gtcgccacca tgtgggcctc tccagtgcaa accaccgagc    600

attccaccat gaccggtcac agctacaaat ccagagacca tcaatcctgc tagagtgcag    660

ggwggcaagc acccaagggt ggctgaccaa gactgcagag tctcctccat cttcaggtcc    720

attcagcctc ctggcattta actaccagca tccagtggtc cccaaggaat cccttcctag    780

cctcctgaca tgagtctgct ggaaagagca tccaaacaaa caagtaataa ataaataaat    840

aaactcaaaa aaaaaaaaaa aaaaaaaaaa aaaaaaaaaa agggcggccg ntctanagga    900

tccaagct                                                             908
```

<210> SEQ ID NO 26
<211> LENGTH: 2090
<212> TYPE: DNA
<213> ORGANISM: Homo sapiens

<400> SEQUENCE: 26

```
ccacgcgtcc ggggtttcac tgtgttgact aggttggtct cgaactcctg acctcaagta     60

atccacccgt ctcggcctcc caaagtgccg gagttacagg cgtgagtcac cgcgcccagc    120
```

-continued

```
ctgatatgca aatattttaa acttctatga cgttccactt tatctatttg ttcttctgtt    180
gcctgtgctt ttggcgccat atccaagaaa tcattgccaa atgcaacgtc aggaagcttt    240
tcccctgtgt tttcttctaa gagttttgtg gttttagctc ttgagtttag gtctttgatg    300
caagttgagt tgatttttgc atgtggtgta agggctggtc cagcctcatg ctctgggctc    360
ttgattcact tctcttcttt tctcacgccc agctggttcc gctgggtggc ggggaggagt    420
ggggaagtcc cgggctgggc ctgcactcga tcatcccctc tcaggccagc cagggagtct    480
cagctcctgc ccaggacctg gctggacgtg ctccctaccg ggaaagcctg ggccgtcttt    540
ctaggctgat ggcagggcca gcccggggcg tcctgaggcc tgccctgcgg acatgcccct    600
tgttctaggt ggtgtggctg cccggcctgc gtgtgagacc agctgtctgt gcttcaggcc    660
atggaggctg agtgtttcca gcctgtcccc ttgctcggct ctccctctgg ggaagcccct    720
gcagcccatt ctctgcctcc gcttctgcca tctgtgcctt tgtctgcttc ctgtttggag    780
gtggtcatcc ctggggccac ccctcatgat ctggacacga gtctccatcc tgaagccacc    840
acccaaaccc ctgtgcctca aacccctccc acccaccaca tggggttcca ctgtgaccaa    900
ctcagcagct gatgaagctt cccttggggc tctcctagca acggggagct ggctttcccg    960
gaggcctggc ctctccctaa gtggaagtgg ggcagtgagg gtgtcagcct tttctgctg    1020
cctggtgctc taggttggct tgtcacccct ggaagcactt gccatcctta tacagcaccc   1080
cacacccacc tccccggctc ctaccccttc ttccaagggg tcatctctgc ttccctcccc   1140
acccaacctc acccacgtgg tccgcccagc aacctttgac ccccaacatg acaaaataaa   1200
cctcccttgc cggtcactca ttcattcatt cagcattggg tgctccctgt ggacttggcg   1260
ctggggtccc gtggaggaca aagccagaca cagtccttgc cctcatggga ctgcacaagt   1320
gcaagaccac atcagtaaac gtgaaacaca ggaagtgaca ggtgtgacaa aggggaccag   1380
tggcaggaca gaacctgggg ttcgtaggac caggtcagga gggctgcctc gggggggacac  1440
cttcgggctg agcgcagaag gatgagggga gtaaaccagg ctcaaaccca gcaggcagag   1500
gcgatcgctg caggcaaccg ccaatgtgtt caaaggccct ggggcgcggg gggctgaggc   1560
cggcagcacg gcaggaagta agactggggt tgaaagagac tgactgtcat gttgtgaaat   1620
atacacttgg ttttcatctc catttcctgg cacacaactc ctaaaatcct tggaatctcc   1680
aaagtgatgt ctttttggat gctcatgatt gacagaccag ctggcagctt caggatggtt   1740
cccagggaag accaggtaga atcacaaggt tcagcaccac cccgcaacct ccaggtaggg   1800
gagaggggct gaaggttaag cagatcatca gcggccaatg attgaatcaa tcatgccttc   1860
gtaatgaggc ctccgtgaac actcagaagg atggggttcc gggagcttct ggatggatga   1920
gcatgtggag gctcctggag ggtggagcgc ctggggagca catggaagct ctgcgtccct   1980
cccccatacc ttgccctaca catctcttcc cctgtatcct ttgtaatatc ctttataata   2040
aactagtaaa ttccatgagc cccaggaaca tgtgtaaaaa aaaaaaaaaa              2090
```

<210> SEQ ID NO 27
<211> LENGTH: 2355
<212> TYPE: DNA
<213> ORGANISM: Homo sapiens
<220> FEATURE:
<221> NAME/KEY: SITE
<222> LOCATION: (15)
<223> OTHER INFORMATION: n equals a,t,g, or c
<221> NAME/KEY: SITE
<222> LOCATION: (22)
<223> OTHER INFORMATION: n equals a,t,g, or c -continued

```
<221> NAME/KEY: SITE
<222> LOCATION: (28)
<223> OTHER INFORMATION: n equals a,t,g, or c

<400> SEQUENCE: 27

tgctcctata gaagntacgc cngcaggnac cggtccggaa ttcccgggtc gacccacgcg     60

tcsgcgcacc cacgcctcgc tgccccgctt cctgccctca acctgggcat gcgcccccca    120

cccttccggc cccccagaac ccgcgccatc ccccggagcc tccccagagc tggccgcgca    180

ggatgggcgc cctcaggccc acgctgctgc cgccttcgct gccgctgctg ctgctgctaa    240

tgctaggaat gggatgctgg gcccgggagg tgctggtccc cgaggggccc ttgtaccgcg    300

tggctggcac agctgtctcc atctcctgca atgtgaccgg ctatgagggc cctgcccagc    360

agaacttcga gtggttcctg tataggcccg aggccccaga tactgcactg ggcattgtca    420

gtaccaagga tacccagttc tcctatgctg tcttcaagtc ccgagtggtg gcgggtgagg    480

tgcaggtgca gcgcctacaa ggtgatgccg tggtgctcaa gattgcccgc ctgcaggccc    540

aggatgccgg catttatgag tgccacaccc cctccactga tacccgctac ctgggcagct    600

acagcggcaa ggtggagctg agagttcttc cagatgtcct ccaggtgtct gctgcccccc    660

cagggccccg aggccgccag gccccaacct cacccccacg catgacggtg catgaggggc    720

aggagctggc actgggctgc ctggcgagga caagcacaca gaagcacaca cacctggcag    780

tgtcctttgg gcgatctgtg cccgaggcac cagttgggcg gtcaactctg caggaagtgg    840

tgggaatccg gtcagacttg gccgtggagg ctggagctcc ctatgctgag cgattggctg    900

caggggagct tcgtctgggc aaggaaggga ccgatcggta ccgcatggta gtaggggggtg   960

cccaggcagg ggacgcaggc acctaccact gcactgccgc tgagtggatt caggatcctg   1020

atggcagctg ggcccagatt gcagagaaaa gggccgtcct ggcccacgtg gatgtgcaga   1080

cgctgtccag ccagctggca gtgacagtgg ggcctggtga acgtcggatc ggcccagggg   1140

agcccttgga actgctgtgc aatgtgtcag ggcacttcc cccagcaggc cgtcatgctg   1200

catactctgt aggttgggag atggcacctg cgggggcacc tgggcccggc cgcctggtag   1260

cccagctgga cacagagggt gtgggcagcc tgggccctgg ctatgagggc cgacacattg   1320

ccatggagaa ggtggcatcc agaacatacc ggctacggct agaggctgcc aggcctggtg   1380

atgcgggcac ctaccgctgc ctcgccaaag cctatgttcg agggtctggg acccggcttc   1440

gtgaagcagc cagtgcccgt tcccggcctc tccctgtaca ygtgcgggag gaaggtgtgg   1500

tgctggaggc tgtggcatgg ctagcaggag gcacagtgta ccgcggggag actgcctccc   1560

tgctgtgcaa catctctgtg cggggtggcc ccccaggact gcggctggcc gccagctggt   1620

gggtggagcg accagaggac ggagagctca gctctgtccc tgcccagctg gtgggtggcg   1680

taggccagga tggtgtggca ragctgggag tccggcctgg aggaggccct gtcagcgtag   1740

agctggtggg gccccgaagc catcggctga gactacacag cttggggccc gaggatgaag   1800

gcgtgtacca ctgtgccccc agcgcctggg tgcagcatgc cgactacagc tggtaccagg   1860

cgggcagtgc ccgctcaggg cctgttacag tctaccccta catgcatgcc ctggacaccc   1920

tatttgtgcc tctgctggtg ggtacagggg tggccctagt cactggtgcc actgtccttg   1980

gtaccatcac ttgctgcttc atgaagaggc ttcgaaaacg gtgatccctt actccccagg   2040

tcttgcaggt gtcractgtc ttccggccca gctccaagcc ctcctctggt tgcctggaca   2100

ccctctccct ctgtccactc ttcctttaat ttatttgacc tcccactacc cagaatggga   2160

gacgtgcctc cccttcccca ctccttccct cccaagcccc tccctctggc cttctgttct   2220
```

-continued

```
tgatctctta gggatcctat agggaggcca tttcctgtcc tggaattagt ttttctaaaa   2280
tgtgaataaa cttgttttat aaaaaaaaaa aaaaaaaaaa aaaaaaaaaa aaaaagttct   2340
agatcgcgag cggcc                                                   2355
```

<210> SEQ ID NO 28
<211> LENGTH: 1680
<212> TYPE: DNA
<213> ORGANISM: Homo sapiens

<400> SEQUENCE: 28

```
ggcacgaggt acgccgctgc cagcccggcc tgggcggccg cgcaacaaag gagtcacccg     60
gcgatgagcc ccggcacccc cggaccgacc atgggcagat cccagggcag cccaatggat    120
ccaatggtga tgaagagacc tcagttgtat ggcatgggca gtaaccctca ttctcagcct    180
cagcagagca gtccgtaccc aggaggttcc tatggccctc caggcccaca gcggtatcca    240
attggcatcc agggtcggac tcccggggcc atggccggaa tgcagtaccc tcagcagcag    300
atgccacctc agtatggaca gcaaggtgtg agtggttact gccagcaggg ccaacagcca    360
tattacagcc agcagccgca gcccccgcac ctcccacccc aggcgcagta tctgccgtcc    420
cagtcccagc agaggtacca gccgcagcag gtgagcacag tgcactgccc cgcaggccct    480
gttttctcca ccaaggcaga cccggctctg aatcatcttc ctgtccttta ttaaaaatta    540
tgttctggtg gaaaaaaaat tagttttgag aaaatgcata actgtaacct aatctaactc    600
catctccccc tccgtctttt cccctttga gattggaggg tgagaagaat gactggttta    660
atagctgctt gcattactgg ttagtggcag cagaaagtgt cagtcattgc ttgttccctg    720
tcatttgtgt tctgaacctt tcaagaaagc actctgccac tttgttaagg cttattcagg    780
agaaggattt tatcaatcat ttaatccttc tagttggcac gtgcatggta tttttatctt    840
gacctttgtt ttgttttgtt ttaatggtaa gtgctacttt gtgaaaacat tgttgccttt    900
gactgtgtta ttctatttaa actagcttat aagtagatat tcacttcagt tgcagtatat    960
taaaatacta attggaatca tgtactttaa atatatcaag cagtttctag tttaaattag   1020
tctcattaaa tactccttta ggttactggg ttatatattt cagcttacag aatttgtgga   1080
aaaatagtat atatgttatt tgataaaatg attcagtttc cttatgtttt agagactgtc   1140
actcatgagt gacatgaaaa gaagtagtga gtgagggact cttactctga atccagataa   1200
aatgttcgta gcacatccaa tcataaacat caaaatataa ttttccattt taatacttcc   1260
ttccttctct tttgtgtggt ggaggtggca aagagaaggt gaacacatgt agcatcgact   1320
ttttcctctt taaaggactt cttttgtggc ttgaatagat cgtggatatt aagcaaaata   1380
aataaattta cggagcttaa ttttaatcag tttggctggt ttcttacata ttttcttggg   1440
tttgttggag tccctttccg tatgacttac tagagaattc taaagagagt ttatgatttg   1500
aagcaaaaca tgttaaaaca acagctagga ttcgagaccc agtacaatct tgtttttaca   1560
tacatgtatt taaaagcttg aacccgggag gcggaggttg cagtgagcgg agaccacatc   1620
actgcactcc agccttgcaa cagagtgaga ctctgtctca aaaaaaaaaa aaaaaaaaaa   1680
```

<210> SEQ ID NO 29
<211> LENGTH: 1618
<212> TYPE: DNA
<213> ORGANISM: Homo sapiens

<400> SEQUENCE: 29

-continued

```
ggcagagctg tgatccgcta tctgccttgg ctttatcatc ccccctctgc aatgcagcaa     60
ggacctccgt gctgcacatg tgctccctct tccacgcgtt catctttgct cagctgtgga    120
cagtttattg cgagcaaagt gccgtcgcta caaatctcca aaatcagaat gaattcagct    180
tcacggcgat actgacagca ctagaatttt ggagtagggt gacacccagc atccttcagc    240
taatggccca taacaaagyg atggtagaaa tggtgtgtct ccatgtgatt agtttaatgg    300
aggcattgca ggwwtgcaat tcgaccattt ttgtcaagct gatacctatg tggttgccaa    360
tgattcagtc aaatatcaag cacttatctg cgggactcca gcttcgcctc caggctattc    420
agaaccacgt gaaccaccac agcctaagga cgctgccggg ctcgggccag agcagtgctg    480
gcctggcagc cctccgaaag tggttgcagt gcactcagtt caaaatggcc caggtggaga    540
tccagtcctc ggaagcagcc tctcaatttt atcctctatg agtggactcc tcggcgctca    600
gtgtcaacac tctggtttag caataatggg tttaaaaaca aacaatttga tccaagcagg    660
ttggggaaca tattggtact gtacawtctc tttctagttt agtaaaagat gtgcaaaggc    720
cagagagggc cgaaaatgaa gctttcttgc tacacatatt tctgatgact ccttgggcta    780
tctgattaag tgtttcctta cattattttt taaaaaccaa atcatttttc tttaactaac    840
ttctattttt tttaagaaaa aaaaatagac tggtgggtac tcacagaaaa gttgtataag    900
tccccctgtt gctatttttg atgatagaga ataaataggg tttttgaaac ctttgtagtg    960
tttttttctta aaatccactc ttggcaatgc aataaaaaaa accgtcacca taagccagtg   1020
acacctgact gaagcttttt gtctttatcc tgggaaaagt ggcagcttgc aaggaacatt   1080
acaaagtgca cttagaaatt aggtggttaa actgtgccaa ttgttttcgt tgttttataa   1140
tatcattttc caaaactgtc cagtaagttt tattattttt aaaactagtt tttcaactca   1200
ttagttctag gctgtactct cttgtaagct ttatgataac cactttagtt ttgtgaataa   1260
taaattttat tcttttgtta atacttgtat acaatttaat tgaaaactgt agcttgcaca   1320
ctggaccaga tgagtccctc actggcacag tgccctgcac ctggagtgat gtttcataaa   1380
acggaatttt aatagtgtaa gagcaccaag atttctctgc acctatacct agcgttggac   1440
tgtgcattcc aaatgaaatt cctcctcttt atccctgtaa tgcactgact aacagaagac   1500
ttactacaca tttaaactgt atattgacat gctattaaat gcgtttttta ttaaaaaaaa   1560
aaaaaaaaaa aaaaaaaaaa aaaaaaaaaa aaaaaaaaaa aaaaaaaagg gcggccgc     1618
```

```
<210> SEQ ID NO 30
<211> LENGTH: 973
<212> TYPE: DNA
<213> ORGANISM: Homo sapiens

<400> SEQUENCE: 30

gtcggggtgg ggtaggctgg gggtgagccc ttaactctta gaagggtggg gtgtggggca     60
gaaggagcag atgcctggat ttgagggtgc aggagatggg ctggtgcaga cgtggggcct    120
cctggctgca ggggccggca gtgaagaggt tagctcccag cccaggcagg gcataaattt    180
ggggcacagc tcccactctc aggacctgcc cgtcacaatg gccgtaggga agttcctgct    240
gggctctctg ctgctcctgt ccctgcagct gggacagggc tggggccccg atgcccgtgg    300
ggttcccgtg gccgatggag agttctcgtc tgaacaggtg gcaaaggctg gagggacctg    360
gctgggtaag gacttccagg gaccctctgt gacttcccaa ctttccccag ccctgaccct    420
gctcactgtc agcgcccttc cctcccacag gcacccaccg ccccccttgcc cgcytgcgcc   480
gagccctgtc tggtccatgc cagctgtgga gcctgaccct gtccgtggca gagctaggcc    540
```

-continued

```
tgggctacgc ctcataggag aagtcatctt ccgctactgc gccggcagct gcccccgtgg    600

tgcccgcacc cagcatggcc tggcgctggc ccggctgcag ggccagggcc garcccacgg    660

cgggccctgc tgccggccca ctcgctacac cgacgtggcc ttcctcgacg accgccacgc    720

tggcagcggc tgccccagct ctcggcggct ctgcggctgt ggtggctgag ggtgcccggc    780

ctggcaccca gaagctgcag tgctggggga gctcggctga cttatttatt ggagacctgg    840

atgcagagac aacgaggagg ggagtgggct ggggcgacca gcagtgagtg caataaagga    900

caccactctc ccggcaaaaa aaaaaaaaaa aaaaaaaaaa aaaaaaaaaa actcgagggg    960

gggtcccggt acc                                                        973


<210> SEQ ID NO 31
<211> LENGTH: 1189
<212> TYPE: DNA
<213> ORGANISM: Homo sapiens

<400> SEQUENCE: 31

cgccgctcta gaactagtgg atccccgggc tgcagaattc ggcacaraga tggcgtacca     60

gagcttgcgg ctggagtacc tgcagatccc accggtcagc cgcgcctaca ccactgcctg    120

cgtcctcacc accgccgccg tgcagttgga attgatcaca ccttttcagt tgtacttcaa    180

tcctgaatta atctttaaac actttcaaat atggagatta atcaccaact tcttattttt    240

tgggccagtt ggattcaatt ttttatttaa catgattttt ctatatcgtt actgtcgaat    300

gctagaagaa ggctctttcc gaggtcggac agcagacttt gtatttatgt tcctttttgg    360

tggattctta atgacccttt ttggtctgtt tgtgagctta gttttcttgg gccaggcctt    420

tacaataatg ctcgtctatg tgtggagccg aaggaacccc tatgtccgca tgaacttctt    480

cggccttctc aacttccagg cccccttttct gccctgggtg ctcatgggat tttccttgtt    540

gttggggaac tcaatcattg tggacctttt gggtattgca gttggacaca tatatttttt    600

cttggaagat gtatttccca atcaacctgg tggaataaga attctgaaaa caccatctat    660

tttgaaagct atttttgata caccagatga ggatccaaat tacaatccac tacctgagga    720

acggccagga ggcttcgcct ggggtgaggg ccagcggctt ggaggttaaa gcagcagtgc    780

caataatgag acccagctgg gaaggactcg gtgataccca ctgggatctt ttatcctttg    840

ttgcaaaagt gtggacactt ttgacagctt ggcagatttt aactccagaa gcactttatg    900

aaatggtaca ctgactaatc cagaagacat ttccaacagt ttgccagtgg ttcctcacta    960

cactggtact gaaagtgtaa tttcttagag ccaaaaaact ggagaaacaa atatcctgcc   1020

acctctaaca agtacatgag tacttgattt ttatggtata aggcagagcc ttttcttcct   1080

cttcttgata gatgaggcca tggtgtaaat ggaagtttca gagaggacaa aataaaacgg   1140

aattccattt ttctctcact gtaaaaaaaa aaaaaaaaag ggcggccgc               1189


<210> SEQ ID NO 32
<211> LENGTH: 1912
<212> TYPE: DNA
<213> ORGANISM: Homo sapiens

<400> SEQUENCE: 32

ccacgcgtcc gcactcgccc tcggcccgcc cggcgccgca gccccatggc cccgtccagg     60

ctgcagctcg gcctccgcgc cgcctactcc ggcatcagct ccgtggccgg cttctccatc    120

ttcctcgtct ggacggtggt ctaccgacag ccggggaccg cggctcatgg gagggctcgc    180
```

-continued

```
aggggtgctg gcactgtggg tcctggtgac gcacgtaatg tacatgcaag attattggag    240
gacctggctc aaggggctgc gcggcttctt cttcgtgggc gtcctcttct cggccgtctc    300
catcgctgcc ttctgcacct tcctcgtgct ggccatcacc cggcatcaga gcctcacaga    360
ccccaccagc tactacctct ccagcgtctg gagcttcatt tccttcaagt gggccttcct    420
gctcagcctc tatgcccacc gctaccgggc tgactttgct gacatcagca tcctcagcga    480
tttctgaccc agggggtgag gtctctgcac cctggggggg ccttaggacc tggactcagc    540
ctctgagatg ttgggagagg ctactcccac cccctggtga ccccagaact gtggcagaaa    600
atacacagca ggacgagtgt ggtctcccag gaagctgtcc tgcccgtccc ctttcgagga    660
aacctgagtg tggtagagag gggatcctgc catgttgctc ctcatcagcc tggccagagg    720
gcagctttag accttttcaa atgaatctgt tttcttttct ttcttttttt tttctttttt    780
tttttttttt gagatggagt cttactctgt cacccaggct ggagtgcagt agtgcgatct    840
cagctcactg caacctccgc ctcccaggtt caagcaattc tcctgccttg gcctctcaag    900
tagctgggat tacaggcatc tgccaccatg cccggcaaat tttgtgtttt ttagtagaga    960
cagggttttg ccatgttggc caggctggtc tcgaactcct gatctcaggt gattcacccg   1020
cctcagcctt ccaaagtgct gggattatag gtgtgagcca ccgtgcccgg cctggatctg   1080
ttttcttagc acgcagtgag gaatctttgt acttaaggcc agggcaacaa agtcaagagg   1140
tcaaggtgta gggccatgag gcctggacct atgctgcagg caagggtttc catccccgct   1200
gccctaggca ctctcttccc aaggccaggt tgggcacctg gggaggtcag ttcagaaata   1260
tctagcagag acctcttaaa cccccatccc agcaccccat cctgttgttc ccagagctgg   1320
tctcccatga gtgtgctaga gccagatagc cgtggccccc cacccatctc actcacacac   1380
acaggcatcc atacacccca gaagacttcc caaatgaggc cagactcagg gtcacgggga   1440
atgtgcttct gcccctgtaa gggctttggg gaagggggca acatagtaga ggctggaaag   1500
agcccccaaa cctgtgccca tgcccctcca gccctgcgtt tccattctgc cttctcagag   1560
ggcccttgct gcacccagac caccggccag gagagacctt gtctcccact ccagcccctc   1620
tcactgccct tcaactagag ctttcacctt tttacatttc ccttctgaag gacacaaatc   1680
tgcttttctg cccatacact ggcccaaggg ctcacctaac ttgggaggga aggggctgtt   1740
ggtacaagga tgattttctg ttagactgcc attttgcacg gtctcccccct tcccatctga   1800
tgtgtcctgc ccctcagctc tttgccttat ctgtgtcact gtcactttag caaaaataca   1860
gcggccattt gtatcaaaaa aaaaaaaaaa aaaaaaaaaa aaaaaaaaaa aa           1912
```

<210> SEQ ID NO 33
<211> LENGTH: 2394
<212> TYPE: DNA
<213> ORGANISM: Homo sapiens

<400> SEQUENCE: 33

```
cccacgcgtc cgcggaaggg taaaaagatt tttattcata tgcatgagat tattcagata     60
gatggtcata tataccagtg ccttgaatgc aagcaaaact tctgtgaaaa cttagctctt    120
attatgtgtc agagaaccca tactggggag aaaccttata aatgtgatat gtgtgagaaa    180
acctttgtcc aaagctcaga tcttacttca caccagagga tccacaatta cgagaaacct    240
tataaatgta gcaaatgtga gaagagcttt tggcatcact tagcgctttc aggacatcag    300
agaacacatg caggtaaaaa attctataca tgtgacattt gtggcaagaa ttttggtcag    360
agttctgatc tgcttgtcca ccagcgaagc catactggcg agaaaccata tctatgtagt    420
```

-continued

```
gagtgtgaca aatgcttcag tagaagtaca aacctcataa ggcatcgaag aactcacaca    480
ggtgagaaac catttaagtg tctcgagtgt gaaaaagctt ttagtgggaa atcagatctt    540
attagccacc agagaactca cactggggaa aggccctaca aatgtaataa gtgtgagaaa    600
agttaccgac accgttcagc cttcattgta cataaaagag ttcatactgg ggagaagccc    660
tataagtgtg gtgcctgtga aaaatgcttt ggccagaaat cagaccttat cgtgcaccag    720
agagtccaca caggtgagaa gccgtataaa tgcctggaat gtatgagaag ttttactcgg    780
agtgccaacc taattaggca ccaggcaact cacactcaca cttttaaatg ccttgaatat    840
gaaaaaagct ttaactgtag ctcaagatct aattgtacat cagtagaatt cacatggaag    900
aaaacaccca catcagtggt ctggcgttta gagagtggct tcctcctacg aaatggactt    960
tgttgcccaa ccagaaaatg agaactccta cagaggagca tacactatta aacaccctgt   1020
atgtgataaa agcttccacc agagttcagc ctttcttcaa catcagacag tacacattgg   1080
tgaaaaaccg tttgtctgta atgtgagtga aaaaggtctt gagcttagcc ctccccatgc   1140
gtcagaagcc tcacagatgt cttgaccagg cgagaagctg taataccaat attaaaaatt   1200
atttatgtat cagagaactc attaagatga ggacaaatct cagactttgc tcagagctca   1260
gaattcagtg gggaccagag agcctgcaat tggaaatatg agaaattctt tgcccagaga   1320
gctgcccgta acagaacact tcatcctcac tccaacgaga aatctacaga tgcccagagg   1380
ttttgaaaac ttaccgtctg agctcaaatt tgatcactca caagaggatt catacaagtg   1440
ggaaacctta gaaatgcact gagtgtgaga gagctttcta ctaatgctca gcccttctcg   1500
ttgtaagaga attcacaccg gagaacaact ttttaaatgc cttcagtgtc agttgtgctg   1560
cagacagtat gaacatctca ttggacctca gaaaacccac cctggggaga agccccagca   1620
agtgtgaaaa aagcttctaa caaaactctg acttacccat cagagaagcc atactggtga   1680
aaaattgtat atttgtctta agtatggcaa aagcattcgt tggagagcct tacttgggtt   1740
tgcacccaaa aaaaaaaaaa cccaatctga ggaaagactg caagtgtctg aatgaagagt   1800
gcttgtcaat gatcaactct tgtggtacat cagggaactc acataggtga aaaaacccat   1860
acttaccttg agtctgagaa aacctttggt agaagctcct gtcttatcag gccccaaaaa   1920
acctgttctg cagtgagaga tttaattgtg ggtgagaatc tatgtacata taatatgtat   1980
gagaagactg ttctcatagt tagttgactc atatggtaga gaggacttta catgaaatca   2040
gtatgaaaat agttttttag atacccagaa gcttgttctg ggagaagcta gggtgggtca   2100
gagtagacct gatgggtaac tcaggtaaag atgcttttct tttatctgaa ctacttaatg   2160
attgctttac ttttactttt taaaaaattc agaaatccaa taaaggaaag gacggtaacc   2220
ttatgataga aaaaaaaaaa aaaaaaaaaa aaggaaaaaa ggaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaa         2394
```

<210> SEQ ID NO 34
<211> LENGTH: 2118
<212> TYPE: DNA
<213> ORGANISM: Homo sapiens
<220> FEATURE:
<221> NAME/KEY: SITE
<222> LOCATION: (1518)
<223> OTHER INFORMATION: n equals a,t,g, or c
<221> NAME/KEY: SITE
<222> LOCATION: (1646)
<223> OTHER INFORMATION: n equals a,t,g, or c -continued

<400> SEQUENCE: 34

```
ggcacgaggg aaaggggact gcgtactccg cagatggtgt tagtttttgc ctatctgtgt     60
gttctattaa ttgtttgttg ggtaacttca aaaaccagct tggctcttaa gtacactgtt    120
tataaaaatt ttaaaagact tatttggaat aaatctattc tgatcatcac attaacaccc    180
taatcagaaa taagagaggt gtgttattgt caccagggtg gtgagctgcc tagctctgat    240
tggcacatat tgggaagttg agtttgagac tgaacacatt aagttcaaag tacagatttc    300
gtggggagac ccagaccccc accagcatta ggagtaaaat aaaataggca atataaagaa    360
gggactggca aatagatcac tagctagaat aatggcaagg gagatttatt atatctttat    420
taagacactg ctgacttgat gatgagtaaa agctcatcat ccttgagggc tgtgccatct    480
cactctcagg ccatctcctt ccttccccca ccatttctcc tctttgtttc caccacatgc    540
ctggggcctc caggagttcc gtgccactgg gtcacctgcc aggactcagc tctcagataa    600
aatcccctgg acacacagaa tggggtccct gagacgtttg atctcccata ttccagggcg    660
tctgggctgc ctgctcatcc tccttgcccc aggagccatg ctaaggatgg gactgctcct    720
tggctgtcac tgcccgcagc cacagcctca atgcccacaa tgactgatct gggcatgtct    780
gtgccaactt cacctttaaa aaggttagaa aacagcattc cactgttggg ttgacagaca    840
atacttgatg ttttgttttt aagaaagcat gcaaagaatc tgaacatgtg gaactaaatt    900
taaatgcaca tctaatatgt gcttttccta aatgcaaaga tttaccaatg taatgatttt    960
atattctttt gtcttatgaa aaatgaagaa aaataagaca aatttattta aatatctagt   1020
tggagtccaa atctggaaag aaaagtacat tctctatgag aaacatattc atatctgaca   1080
agaaatgttt ttccccaatc ccacccatcc actgctgcca agtcagtcta cctgaacctc   1140
acattaccca gctcaaaaat ctgtgttatg ggttgaattg tgtcccttcg aaattcctgt   1200
attgaagcct taacccctag aactcagcat gtgatggtat ttagaaatgg agtctttaaa   1260
gaagtgacca agttaaaatg aggctgtgag agtcggtctt aatccaatat gactggtgcc   1320
cttatatcag aggagattag gacacagaca cagaggaaga ccacatgaag atatgaggag   1380
aaggtggcca ccgataagcc aaggagagag gtctggaatg gatccttcac tcatggctct   1440
cagaaggaat caaccatgct gagaacttga ttttggactt ccagcctcca gaactatgag   1500
aaaataaatt tctgctgntt taagccaccc agcctgtggt actttggtat ggcagtctga   1560
gccaattaat ataatatgtg atcattctgc aagtcctacc aattaaattc agacacagag   1620
ccccagcaga ctcctgtctc ctctgnccca tgtgtatcct gtgttttagc cactgtggac   1680
ttgtcctcag tgttctctgc acctgtgtgt aggtaacaac catcttcaaa gcatggtgag   1740
gccatgggtg ctggacagtc ccacagttcc catccctgaa cctacagggg ctatcttggc   1800
accccaggtg tggtcccact cccctcagcc cactttccct ttttctgctc agcccctttg   1860
agggtctctg acttgggact atcatttgca tctgtctctg atgtgggtcc tggttaccaa   1920
ctttgggtct cttttgtctt catgctctgt agatcatggg acaggggacc ccaactcaaa   1980
attccagctc gaatttgagc cattccctcc atgtgaatgc ctttgtcctc tttgctactt   2040
ttcaaaaaat tatacaatgt cttccaggaa gcattccaat cagctcgtgc cgaattcgat   2100
atcaagctta tcgatacc                                                  2118
```

<210> SEQ ID NO 35
<211> LENGTH: 6065
<212> TYPE: DNA

-continued

<213> ORGANISM: Homo sapiens
<220> FEATURE:
<221> NAME/KEY: SITE
<222> LOCATION: (6035)
<223> OTHER INFORMATION: n equals a,t,g, or c
<221> NAME/KEY: SITE
<222> LOCATION: (6037)
<223> OTHER INFORMATION: n equals a,t,g, or c
<221> NAME/KEY: SITE
<222> LOCATION: (6038)
<223> OTHER INFORMATION: n equals a,t,g, or c

<400> SEQUENCE: 35
gcgttggagc tcccggaaag ttgccggacc cggaacgcag gcggagcgca agtctgtcag 60
ccagtcagtc cgccagtccg ccagcccagt acctctctct cctcggccct cgtaagctgt 120
ccgcggtctg tttggcccga acggcggcgg aggcgctgat catggcgaca ttcatctcgg 180
tgcagctgaa aaagacctca gaggtggacc tggccaagcc gctggtgaag ttcatccagc 240
agacttaccc aagcggcggg gaagagcagg cccagtactg ccgcgcggcg gaggagctca 300
gcaagctgcg ccgcgccgca gtcggtcgtc cgctggacaa gcacgagggc gcgctcgaga 360
cgctcctgag atattatgat cagatttgtt ctattgaacc caaattccca ttttctgaaa 420
atcagatctg cttgacattt acctggaagg atgctttcga taaaggttca ctttttggag 480
gctctgtaaa actggctctt gcaagcttag gatatgaaaa gagctgtgtg ttgttcaatt 540
gtgcagcctt agctagccaa attgcagcag aacagaacct ggataatgat gaaggattga 600
aaatcgctgc taaacattac cagtttgcta gtggtgcctt tttacatatt aaagagacgg 660
ttttatctgc cttaagtcga gagccgaccg tggacatatc tccagatact gttgggaccc 720
tcagtcttat tatgctggca crggctcaag aagtattttt tttaaaagcc acaagagata 780
aaatgaaaga tgccatcata gctaaattgg ctaatcaggc tgcagattat tttggtgatg 840
ctttcaaaca gtgtcaatac aaagatactc tccccaagga ggtgttccct gtcttggctg 900
caaagcactg tatcatgcag gccaatgctg agtaccatca gtctatcctg gcaaaacagc 960
agaagaaatt tggagaagaa attgcaaggt tacagcatgc agcagaactg attaaaacag 1020
tggcatctcg ctatgatgaa tatgttaatg tgaaggattt ttctgacaaa atcaatcgtg 1080
cccttrctgc agcaaagaag gataatgact tcatttatca tgatcgagtt ccagacctta 1140
aagatctaga tcctattggc aaagccacac ttgtgaaatc taccccggtc aatgtaccca 1200
tcagtcagaa atttactgat ctgtttgaga agatggttcc cgtgtcagta cagcagtctt 1260
tggctgccta taatcagagg aaagccgatt tggttaacag atcaattgct cagatgagag 1320
aagccaccac tttggcaaat ggggtgctag cttcccttaa tcttccagca gcaattgaag 1380
atgtgtctgg agacactgta cctcagtcta tattgactaa atccagatct gtgattgaac 1440
agggaggcat ccagactgtt gatcagttga ttaaagaact gcctgaatta ctgcaacgaa 1500
atagagaaat cctagatgag tcattaaggt tgttggatga agaagaagca accgataatg 1560
atttaagagc aaaatttaag gaacgttggc aaaggacacc atccaatgaa ctgtataagc 1620
ctttaagagc agagggaacc aacttcagaa cagttttaga taaagctgtg caggcagatg 1680
gacaagtgaa agaatgttac cagtctcatc gtgacaccat cgtgcttttg tgtaagccag 1740
agcctgagct gaatgctgcc atcccttctg ctaatccagc aaagaccatg cagggcagtg 1800
aggttgtaar tgtcttaaaa tccttattgt caaatcttga tgaagtaaag aaggaaagag 1860
agggtctgga gaatgacttg aaatctgtga attttgacat gacaagcaag tttttgacag 1920
ccctggctca agatggtgtg ataaatgaag aagctctttc tgttactgaa ctagatcgag 1980

-continued

```
tctatggagg tcttacaact aaagtccaag aatctctaaa gaaacaggag ggacttctta   2040
aaaatattca ggtctcacat caggaatttt caaaaatgaa acaatctaat aatgaagcta   2100
acttaagaga agaagttttg aagaatttag ctactgcata tgacaacttt gttgaacttg   2160
tagctaattt gaaggaaggc acaaagtttt acaatgagtt gactgaaatc ctggtcaggt   2220
tccagaacaa atgcagtgat atagtttttg cacggaagac agaaagagat gaactcttaa   2280
aggacttgca acaaagcatt gccagagaac ctagtgctcc ttcaattcct acacctgcgt   2340
atcagtcctt accagcagga ggacatgcac caactcctcc aactccagcg ccaagaacca   2400
tgccgcctac taagccccag cccccagcca ggcctccacc acctgtgctt ccagcaaatc   2460
gagctccttc tgctactgct ccatctccag tgggggctgg gactgctgcg ccagctccat   2520
cacaaacgcc tggctcagct cctcctccac aggcgcaggg accaccctat cccacctatc   2580
caggatatcc tgggtattgc caaatgccca tgcccatggg ctataatcct tatgcgtatg   2640
gccagtataa tatgccatat ccaccagtgt atcaccagag tcctggacag gctccgtacc   2700
cgggacccca gcagccttca taccccttcc ctcagccccc acagcagtct tactatccac   2760
agcagtaata tgtctgctca gcagctcagc tgattcagat cagagggaaa gaaataccaa   2820
ccctgcaata agtgtactaa actctacgct ctggttaatg taatgtactc tcctggactg   2880
aatgcagtgt ataatttctg tctacagcta gaagctgtgc cccagttcca catttgatta   2940
cacatgtgag atttgctgct gttgcagtat aaacactagg tataatagga tttgaaattg   3000
cattacagtt cataaaaatt gaaaatgaga aattaaacct gcaagtgaaa catttgaaac   3060
gattatactt tctacataag acatggttgg gacatcagat acttacaaag atggtttaag   3120
tatggatact agagaaaatt aagttttctt tctctttggt ttattgattt ggtttaattt   3180
ccattatgct attttgcata atcaaggcac tgtaaatctt ataattttaa aataaattac   3240
ttaagaacag ttgtcattgt tatgttttgk tattgattct cattactgtc taattttttt   3300
tctggkatta gtctcatttt gtatgtatat aagttaaaca gatactgttt ttaagtgcat   3360
gaatagtaca agttattatc aaggatgttt tacagggaaa tcaaaagaat attatcatac   3420
tttatctttc gtatgctgat tagtaaacga tttttgacat ttattttaga aagtcctata   3480
atgtggaaga aacaaacagt tgctaccaaa gattcttcaa ataaacatac aaataaatgt   3540
gtatatttaa tgttttattg ttagcttctc cagaaaattg atgcaaattc tggtaataat   3600
tcttgcattt tttccccata acctggttaa aataaatacg ccattggcaa tacttcataa   3660
tgtaatggaa ttgtttgggg aacacttact gtaccctcyc atccttttc caccttactg   3720
tgttaactta gtgacattta atgcccaata tgtatgaata gatctaagcc atttaatttt   3780
ttttccttaa agattggast attttataat tcaaggagca tacaaaacaa tggttgggaa   3840
catatgccaa ttatggaata ggctatgtat ttaatattaa tctctgccat taggatatct   3900
actcactgta taaacctcag taaaaatagt gaagacatgc atcatggaat gagaaaatga   3960
gaaaggaatg agttgtctaa catcacagtg ggatctgttt tttgtgaggt tcatttctga   4020
acacattagg catatgagca gatttccagt gaatctattt atgtttattt tctgagtttc   4080
aacgctgacc ttttcttgca ttattgtttc attttaatga tagtgttact tgtcccactg   4140
ttgttttcat tgagtttgga tttatatttt aaatgttcga atgaaagtat gattgtaaaa   4200
gggagtgaat tggkttwaaa awatatgtat attttaaact ttgttgtgtg taggaaacat   4260
gaaggcatgt taattcaata taaatgacct ttgatttcat ggaatattaa agttggttta   4320
```

-continued

```
aagtccaata gttaaacctt agcaaaaata gctttttact tcatcagttg ctaagattta   4380

atactttgga ttcatcaaag tgtgacatgg gcttgtttga cttctgtaag tggcattaag   4440

ttccacattc ttattacttg aggtacttta tactaacata agacagtgag agttagaggt   4500

attacaagtt gctagtttat aatgtcttac taatgcagaa acaaggaaaa aagcaaaatt   4560

ggcctgaata ttctcttggg gaaagagggc accaaagaaa agggtaagtg catctgaggg   4620

ccaaaagaga tgtataagcc ttttagccca ttccccatgc tgggcctgct cacagagcca   4680

caggaagatc attcagaaac taggaaagga ggcccccaca gctgatcctg ccacagcaca   4740

cctgactcac tcggctctgt tagtgtaacc ttttaaatgt agcaacacaa accctttccc   4800

tcttgtcagt tcactcatcc tttggtttct ttttaatcac ctgtgtctgg gcacagacaa   4860

tcacaataaa tgcagccctt tattactgtt aaggatcata ctgttggttt ggagttggaa   4920

gggtactact ctgtgattca ggtgtgttgt acccatattt ataattaggc tttattatct   4980

tcctaaatca aggaaaggaa atcatcccca gaccatttat gctgagcttt ggaatactat   5040

tttaaactgg attgtactta aataatgaag ctctgcatag aggaactagt cagaagtggg   5100

gaaaacactg tctaattttt atcagtctgg tataaagtat tgatctaaga gaactctccc   5160

tgtgcccctt ggtctttatt ctcaattaag aaaaacagtc acatgtcacg acaaaccaat   5220

caatctttat gagatattcc tgtatccata ccccagcttg tttgcaattt ataaacctcc   5280

ccttcaaaac taaggagttg cagaaaaaaa tggatttcac agagccttgt gtccctaaag   5340

ttctgtccca gtcagcagtc tttatagtcc aaacagatta taaaaaatgt tttccatttg   5400

aactttacag tttgcaaaag tgcttttata cattttctaa tttcagaaac aggataatat   5460

aatttgttaa gtgggtttca gtttgctaat agggattttt tgtgttttgt tttttaattt   5520

tcagcatctc ttgaagaatc ttgctacagc caaatggcat ctcacttttt aaagacgttt   5580

gcaattatta gttgattcac agtacagaac aaggtataaa ggaaaaaacc ctgctaggta   5640

gtgttataat tgctagatta aaaatagact agaacaggtt cattttaaga tttacttgga   5700

agagcaaaga aggaaaaatt atatttttaa agaaagagaa tattcaggct ttatttctgg   5760

tatgaagttt atattttta aaaaaatcct atattatcac accagagatt ttagattctt    5820

ttctggttag aaacattgct ggtagttgga ttatattttt attgtattca tttatcttag   5880

ggggaacatt gtaaagaaac aaaaaggtcc agatgaatgt atgctagaaa taaaagttga   5940

aagattctta aaaaaaaaaa aaaaaaaaaa aaaaaaaaaa aaaaaaaaaa aaaaaaaaaa   6000

aaaaaaaaac cccggggggg gccccccccc ccccngnncc cccctggggg gggggttaaa   6060

aaaaa                                                               6065
```

<210> SEQ ID NO 36
<211> LENGTH: 1365
<212> TYPE: DNA
<213> ORGANISM: Homo sapiens

<400> SEQUENCE: 36

```
ctttggagaa aacagcccag cttggcgtgg ggttaggttg ctgtttcaaa taactcacag     60

gcccaggtga catggaatct tggagcagcc ttgtgcagtg gcagccagtg gcttcctgaa    120

cgtgcctctg cgaagtgtga gatgaggggt cacataacca cactgttgac tacctcattc    180

ctggtttttg gcctccacat catctttttt cttaatattt catgttttaa tttcagggtg    240

tttatacttt ttgaaactag accagaagat agtagacttt atagagaaag accagtttta    300

cctagatact aaaggaagaa ttaaaccgct gttagtttga aatgcttttt tttttttttt    360
```

-continued

```
ttaaatggag atagggtctt aactcttgtc caggctggag gagtgcagtc gtacagtcat    420
ggctcactga agtcttgacc ccgctgcctc agcctcccaa ataactgggg ccacaggtgt    480
gcaccacaac tctcagctaa tttttaaaat tttttataga ggtggggttt tactatgctg    540
tccagactgg tcttaaactc ctgggctcaa gtgatccccc tgccttggcc tcccaaactg    600
gtgagattac aggcatgagc caccacaact ggcctgaaat tcttaaagga tgggagtgtc    660
gatgacagca ccttggcatc gttgtgccta acctgggaga cggaagaagc acgccatggg    720
aagtgtttac acttggggac aagtgctaag tattgtggag cccatagccc cttgagatag    780
atggctactt tgcctttctt cttgaactgt cttgcagaat gtggatttgg ggtaagtggt    840
cttgaaggat tcatttagtc accctcaaat taagattttt acttcatctt tcttgggcct    900
gcacctccaa gataacaaag aagaagcaat ggtcgtgcca aagaggtcca caaccaggtg    960
tgcactgttc actgcagccc atttgctgta tgaactgtgg ttgttgtgtg cccaatgaca   1020
aggctactaa gaaattcatc atttgaaacg tagaggccgc agcagtcagc gatgtttctg   1080
aaatgagcat ccttgacgcc tgtgtacttc ccaggctgga tgtgaagcta cattaccatg   1140
tgagttgtgc cattcacagc acagtggtga ggaattgagc tcatgaagca ggcaaggacc   1200
gaacacctcc accccaacgt agacctgcag gtgctgcccc atgacctcca ccaaagccca   1260
tataaggagc ggagttgtta aggactgaag aaaaacttct ctggagaaaa ataaaattgc   1320
aattctactt aaaaaaaaaa aaaaaaaaaa aaaaaaaaaa aaaaa                   1365
```

<210> SEQ ID NO 37
<211> LENGTH: 570
<212> TYPE: DNA
<213> ORGANISM: Homo sapiens

<400> SEQUENCE: 37

```
gggccatcag gcccacagag gagggcggcc tccacgtcca catggagttc ccgggggcgg     60
acggctgtaa ccaggtggat gccgagtacc tgaaggtggg ctccgaggga cacttcagag    120
tcccggcctt gggctacctg gacgtgcgca tcgtggacac agactacagc tccttcgccg    180
tcctttacat ctacaaggag ctggaggggg cgctcagcac catggtgcag ctctacagcc    240
ggacccagga tgtgagtccc caggctctga aggccttcca ggacttctac ccgaccctgg    300
ggctccccga ggacatgatg gtcatgctgc cccagtcaga tgcatgcaac cctgagagca    360
aggaggcgcc ctgacacctc cggagcccca cccccgccct tcccaggtgg agccaaagca    420
gcaggcgcct ttgcccctgg agtcaagacc cacagccctc ggggaccacc tggagtctct    480
ccatcctcca ccccccgcct gtgggatgcc ttgtgggacg tctctttcta ttcaataaac    540
agatgctgca gcctcaaaaa aaaaaaaaaa                                     570
```

<210> SEQ ID NO 38
<211> LENGTH: 3229
<212> TYPE: DNA
<213> ORGANISM: Homo sapiens
<220> FEATURE:
<221> NAME/KEY: SITE
<222> LOCATION: (3200)
<223> OTHER INFORMATION: n equals a,t,g, or c

<400> SEQUENCE: 38

```
gaaaccggaa gcggcggctg tccgcggtgc cggctggggg cggagaggcg gcggtgggct     60
ccctggggtg tgtgagcccg gtgatggagc cgggcccgac agccgcgcag cggaggtgtt    120
```

-continued

```
cgttgccgcc gtggctgccg ctggggctgc tgctgtggtc ggggctggcc ctgggcgcgc    180
tccccttcgg cagcagtccg cacagggtct tccacgacct cctgtcggag cagcagttgc    240
tggaggtgga ggacttgtcc ctgtccctcc tgcagggtgg agggctgggg cctctgtcgc    300
tgcccccgga cctgccggat ctggatcctg agtgccggga gctcctgctg gacttcgcca    360
acagcagcgc agagctgaca gggtgtctgg tgcgcascgc ccggcccgtg cgcctctgtc    420
agacctgcta cccccctcttc caacaggtcg tcagcaagat ggacaacatc agccgagccg    480
cggggaatac ttcagagagt cagagttgtg ccagaagtct cttaatggca gatagaatgc    540
aaatagttgt gattctctca gaatttttta ataccacatg gcaggaggca aattgtgcaa    600
attgtttaac aaacaacagt gaagaattat caaacagcac agtatatttc cttaatctat    660
ttaatcacac cctgacctgc tttgaacata accttcaggg gaatgcacat agtcttttac    720
agacaaaaaa ttattcagaa gtatgcaaaa actgccgtga agcatacaaa actctgagta    780
gtctgtacag tgaaatgcaa aaaatgaatg aacttgagaa taaggctgaa cctggaacac    840
atttatgcat tgatgtggaa gatgcaatga acatcactcg aaaactatgg agtcgaactt    900
tcaactgttc agtcccttgc agtgacacag tgcctgtaat tgctgtttct gtgttcattc    960
tctttctacc tgttgtcttc taccttagta gctttcttca ctcagagcaa aagaaacgca   1020
aactcattct gcccaaacgt ctcaagtcca gtaccagttt tgcaaatatt caggaaaatt   1080
caaactgaga cctacaaaat ggagaattga catatcacgt gaatgaatgg tggaagacac   1140
aacttggttt cagaaagaag ataaactgtg atttgacaag tcaagctctt aagaaataca   1200
aggacttcag atccattttt aaataagaat tttcgatttt tctttccttt tccacttctt   1260
tctaacagat ttggatattt ttaatttcca ggcatagcaa tgttatctat tttaatgtgt   1320
atttgtcaca ataacagaac atgcaagaac aatcattatt ttattttata ggcatttgat   1380
tactattcta gacttctggt atcttcttac taacataart atctcaagta gaaaagtttt   1440
tgaaaactaa catttaaaaa ttaatcagtt acagtaaaga ctttgaaaaa gaaatgtact   1500
tgttaggaag tagcttaatt accccccatt gcagtattat tgttatatat atagttaata   1560
tgttgtacat cacaataata tataattcag tctctagttt ccctagagtc atttttgaaa   1620
ccactgattg caaacctccc tgacaatttt taaaagtagt aagccacatt acatttatct   1680
ttgtaaaaag atttatggta actggtttct tacttgactt ttataaatag tattttacat   1740
cttatttttg cctttatttc ataagtaatt taaaaatcac tggattgctt tattatattc   1800
agggcaatat ggattatttt tataccaagg atttgcatcg tgaattacat taagttattt   1860
ggcaatttat aatttattac tactttaaat caaatgtagc attatcacac tgtatttaaa   1920
ttgtcatttt ttaaaggaat attttcttct taagatatat agaggatttt ggagaagaga   1980
gacaggaggg gtaaaaccag cttaaggttc agcgagcaga aagggacctg agaggatgct   2040
cactgtaaga ctgttggaca gtggtgtgta ttgaggggat gaatcggaac gatagtctca   2100
tgcagaaaat agtgagatta agatcatcct tattgtttct aaattatttc aatcagatga   2160
aagtgatacg attgaaatga aatcacatag ttcgtgctca gaaattctat tttggtatgt   2220
ttgtattagc ctttagaaaa aacactccgt ttcagaattg ttcacagttt tatttcttag   2280
gtttttagag ttcaggattt catttattaa tttcttcttg cttttttggt ggaaataggc   2340
tttgttgtaa acattaagaa tataaaatct cctctatata gaaacaagaa ttttgttaaa   2400
aagagaattt gaatcccttc ctatactata aaatgctcta tagggagaca aagtgtttct   2460
tttttctttt atgtttactg tttatgtgga gtgaaatata aggctcttgg atgtataaca   2520
```

-continued

```
tactcaaaag ctgttacact ttctctgatc tgctgtgatc cactgaaaat gtgctggggt   2580
ttgttctgct gtcactgttt atgctgctgg aacttagcac tgtcttgatt tgaagcatat   2640
gattgagagc catttgaagc aatcttcatt aatgcagata aaacaagttt acatgtgcag   2700
agttagaaaa tgacatgttc aattctgtaa gtggtgactt tttgagcacc tttcagtatt   2760
atgtatttgt aaaaaccatt gtttttggat ataaagctaa taagcacttt aaaaaggaaa   2820
aggcagcctt tactattttt tctggttgag tcattgctct ttagacctag catcagcaat   2880
agatttcaaa gataagtatt aagcgctacc ctaaagtgtg taagtttttc attttgtcat   2940
attgaaaaat gatttgcata gtactgaatg ttgacacaca gcttatatgt atttacaaga   3000
atatctttaa gtgttttttt gacacattaa aataaaggaa ataaggaaat tgtaagcttt   3060
atttggattt ttaaatacat ttttaaaatt tcagatgtaa tttaacatca catttgtttt   3120
tcaggtattg agtttagatg cctactttta tgaggtacca tcagctggga cacagtgtcc   3180
ccgtggcctg gtgttttggn aggcaccttt tggggaaggc tggaggcag               3229
```

<210> SEQ ID NO 39
<211> LENGTH: 511
<212> TYPE: DNA
<213> ORGANISM: Homo sapiens

<400> SEQUENCE: 39

```
tttaaagtta atgtctagcc aagagtttag taaacgaaga attaaactgc actgttgatc     60
ggtgctttgt gtaaatacat ctttaacatt tgggtggaga ggggccttaa gaaggacagt    120
tcattgtagg aaagcaattc tgtacatgag tttaagcatt cttgttgcat tgtctctgca    180
gattctattt ttgtttacaa tattaaaatg tatgttagca aaatgggtgg attttcaaat    240
aaaatgcagc ttccacaaaa gttttgttat ggtattctgg tctgagatgc attttcattt    300
ttcctttctc tttttattat caatattgtc atttttccct aataaaatat acccaggtga    360
ttatatttgt tgatctaata acatggaagg tttgttttat atgaattttc aaaaagatgt    420
ctctttacac tttttgttac cttgtagact cttattgata aatgcaacta cttattaaaa    480
ttgttcactt ttaaaaaaaa aaaaaaaaaa a                                   511
```

<210> SEQ ID NO 40
<211> LENGTH: 1393
<212> TYPE: DNA
<213> ORGANISM: Homo sapiens

<400> SEQUENCE: 40

```
tgtcccttcg tctccttctt cccctaacca ggcctccctc cacctgtctt ctcagagcag     60
gtaatggcaa gcatggctgc cgtgctcacc tgggctctgg ctcttctttc agcgttttcg    120
gccacccagg cacggaaagg cttctgggac tacttcagcc agaccagcgg ggacaaaggc    180
agggtggagc agatccatca gcagaagatg gctcgcgagc ccgcgaccct gaaagacagc    240
cttgagcaag acctcaacaa tatgaacaag ttcctggaaa agctgaggcc tctgagtggg    300
agcgaggctc ctcggctccc acaggacccg gtgggcatgc ggcggcagct gcaggaggag    360
ttggaggagg tgaaggctcg cctccagccc tacatggcag aggcgcacga gctggtgggc    420
tggaatttgg agggcttgcg gcagcaactg aagccctaca cgatggatct gatggagcag    480
gtggccctgc gcgtgcagga gctgcaggag cagttgcgcg tggtggggga agacaccaag    540
gcccagttgc tgggggcgt ggacgaggct tgggctttgc tgcagggact gcagagccgc    600
```

-continued

```
gtggtgcacc acaccggccg cttcaaagag ctcttccacc catacgccga gagcctggtg     660
agcggcatcg ggcgccacgt gcaggagctg caccgcagtg tggctccgca cgccccccgcc   720
agccccgcgc gcctcagtcg ctgcgtgcag gtgctctccc ggaagctcac gctcaaggcc    780
aaggccctgc acgcacgcat ccagcagaac ctggaccagc tgcgcgaaga gcttatcaga    840
gcctttgcag gcactgggac tgaggaaggg gccggcccgg acccccagat gctctccgag    900
gaggtgcgcc agcgacttca ggctttccgc caggacacct acctgcagat agctgccttc    960
actcgcgcca tcgaccagga gactgaggag gtccagcagc agctggcgcc acctccacca   1020
ggccacagtg ccttcgcccc agagtttcaa caaacagaca gtggcaaggt tctgagcaag   1080
ctgcaggccc gtctggatga cctgtgggaa gacatcactc acagccttca tgaccagggc   1140
cacagccatc tgggggaccc ctgaggatct acctgcccag gcccattccc agctccttgt   1200
ctggggagcc ttggctctga gcctctagca tggttcagtc cttgaaagtg gcctgttggg   1260
tggagggtgg aaggtcctgt gcaggacagg gaggccacca aaggggctgc tgtctcctgc   1320
atatccagcc tcctgcgact ccccaatctg gatgcattac attcaccagg ctttgcaaaa   1380
aaaaaaaaaa aaa                                                      1393
```

<210> SEQ ID NO 41
<211> LENGTH: 1651
<212> TYPE: DNA
<213> ORGANISM: Homo sapiens
<220> FEATURE:
<221> NAME/KEY: SITE
<222> LOCATION: (1522)
<223> OTHER INFORMATION: n equals a,t,g, or c
<221> NAME/KEY: SITE
<222> LOCATION: (1528)
<223> OTHER INFORMATION: n equals a,t,g, or c
<221> NAME/KEY: SITE
<222> LOCATION: (1540)
<223> OTHER INFORMATION: n equals a,t,g, or c
<221> NAME/KEY: SITE
<222> LOCATION: (1544)
<223> OTHER INFORMATION: n equals a,t,g, or c
<221> NAME/KEY: SITE
<222> LOCATION: (1556)
<223> OTHER INFORMATION: n equals a,t,g, or c
<221> NAME/KEY: SITE
<222> LOCATION: (1572)
<223> OTHER INFORMATION: n equals a,t,g, or c

<400> SEQUENCE: 41

```
ggcacgagag tcggcggtgt ttccattcgg tgatcagcac tgaacacaga ggactcacca      60
tggagtttgg gctgacctgg gttttcctcg ttgctctttt aagaggtgtc cactgtcagg     120
tacaattggt ggagtctggg ggagccgtag tccagcctgg tgggtccctg agactctcct     180
gtgcggcgtc tggtttcact ttcagtaggt acggcatgca ctgggtccgc caggctccag     240
gcaaggggct tcagtggctg gctcttgtct tacatgatgg aggtcagaaa tataatgaag     300
atgtcgtgaa gggccgattc accatctcta gagacaattc caacaataag gtctatctgc     360
aaatggacag cctgagaggc gaggacacgg ctacatacta ctgcgtgcga gggatgtggg     420
aacaactgcc ctcatattac tttgactact ggggccaggg aaccctggtc accgtctcgt     480
cagcatcccc gaccagcccc aaggtcttcc cgctgagcct ctgcagcacc cagccagatg     540
ggaacgtggt catcgcctgc ctggtccagg gcttcttccc ccaggagcca ctcagtgtga     600
cctggagcga aagcggacag ggcgtgaccg ccagaaactt cccacccagc caggatgcct     660
ccggggacct gtacaccacg agcagccagc tgaccctgcc ggccacacag tgcctagccg     720
```

-continued

```
gcaagtccgt gacatgccac gtgaagcact acacgaatcc cagccaggat gtgactgtgc    780

cctgcccagt tccctcaact ccacctaccc catctccctc aactccacct accccatctc    840

cctcatgctg ccaccccga ctgtcactgc accgaccggc cctcgaggac ctgctcttag    900

gttcagaagc gaacctcacg tgcacactga ccggcctgag agatgcctca ggtgtcacct    960

tcacctggac gccctcaagt gggaagagcg ctgttcaagg accacctgac cgtgacctct   1020

gtggctgcta cagcgtgtcc agtgtcctgc cgggctgtgc cgagccatgg aaccatggga   1080

agaccttcac ttgcactgct gcctaccccg agtccaagac cccgctaacc gccaccctct   1140

caaaatccgg aaacacattc cggcccgagg tccacctgct gccgccgccg tcggaggagc   1200

tggccctgaa cgagctggtg acgctgacgt gcctggcacg tggcttcagc cccaaggatg   1260

tgctggttcg ctggctgcag gggtcacagg agctgccccg cgagaagtac ctgacttggg   1320

catcccggca ggagcccagc cagggcacca ccaccttcgc tgtgaccagc atactgcgcg   1380

tggcagccga ggactggaag aagggggaca ccttctcctg catggtgggc cacgaggccc   1440

tgccgctggc cttcacacag aagaccatcg accgcttggc gggtaaaccc acccatgtca   1500

atgtgtctgt tgtcatggcg gnggtggncg gcccctgctn ctgngccgcc cgcctntccc   1560

ccccctgaa tnaactccat gctcccccaa aaaaaaaaaa aaaaaaaaaa aaaaaaaaaa   1620

aaaaaaaaaa aaaaaaaaaa aaaaaaaaaa a                                  1651


<210> SEQ ID NO 42
<211> LENGTH: 1108
<212> TYPE: DNA
<213> ORGANISM: Homo sapiens
<220> FEATURE:
<221> NAME/KEY: SITE
<222> LOCATION: (450)
<223> OTHER INFORMATION: n equals a,t,g, or c
<221> NAME/KEY: SITE
<222> LOCATION: (1108)
<223> OTHER INFORMATION: n equals a,t,g, or c

<400> SEQUENCE: 42

tcgacccacg cgtccgcact cagacaccgt gtcctcttgc ctgggagagg ggaagcagat     60

ctgaggacat ctctgtgcca ggccagaaac cgcccacctg cagttccttc tccgggatgg    120

acgtggggcc cagctccctg ccccaccttg ggctgaagct gctgctgctc ctgctgctgc    180

tgcccctcag ggccaagcc aacacaggct gctacgggat cccagggatg cccggcctgc    240

cyggggcacc agggaaggat gggtacgacg gactgccggg gcccaagggg gagccaggaa    300

tcccagccat tcccgggatc cgaggaccca aagggcagaw gggasaagca gaaattccag    360

tcagtgttca cggtcactcg gcagacccac cagccccctg cacccaacag cctgatcaga    420

ttcaacgcgg tcctcaccaa cccgcagagn attatgacac gagcactggc aagttcacct    480

gcaaagtccc cggcctctac tactttgtct accacgcgtc gcatacagcc aacctgtgcg    540

tgctgctgta ccgcagcggc gtcaaagtgg tcaccttctg tggccacacg tccaaaacca    600

atcaggtcaa ctcgggcggt gtgctgctga ggttgcaggt gggcgaggag gtgtggctgg    660

ctgtcaatga ctactacgac atggtgggca tccagggctc tgacagcgtc ttctccggct    720

tcctgctctt ccccgactag ggcgggcaga tgcgctcgag mcccacgggc cttccacctc    780

cctcagcttc ctgcatggac ccaccttact ggccagtctg catccttgcc tagaccattc    840

tccccaccag atggacttct cctccaggga gcccaccctg acccaccccc actgcacccc    900

ctccccatgg gttctctcct tcctctgaac ttctttagga gtcactgctt gtgtggttcc    960
```

-continued

```
tgggacactt aaccaatgcc ttctggtact gccattcttt tttttttttt ttcaagtatt   1020

ggaaggggtg gggagatata taaataaatc atgaaatcaa tacataaaaa aaaaaaaaaa   1080

aaaaaaaaaa aaaaaaaaaa aaaaaaan                                      1108
```

<210> SEQ ID NO 43
<211> LENGTH: 2286
<212> TYPE: DNA
<213> ORGANISM: Homo sapiens

<400> SEQUENCE: 43

```
ggcacgagct ccagttcagc tcgctcggcg cacccacgcc tcgctgcccc gcttcctgcc     60

ctcaacctgg gcatgcgccc cccacccttc cggcccccca gaacccgcgc catcccccgg    120

agcctcccca gagctggccg cgcaggatgg gcgccctcag gcccacgctg ctgccgcctt    180

cgctgccgct gctgctgctg ctaatgctag gaatgggatg ctgggcccgg gaggtgctgg    240

tccccgaggg gcccttgtac cgcgtggctg gcacagctgt ctccatctcc tgcaatgtga    300

ccggctatga gggccctgcc cagcagaact tcgagtggtt cctgtatagg cccgaggccc    360

cagatactgc actgggcatt gtcagtacca aggataccca gttctcctat gctgtcttca    420

agtcccgagt ggtggcgggt gaggtgcagg tgcagcgcct acaaggtgat gccgtggtgc    480

tcaagattgc ccgcctgcag gcccaggatg ccggcattta tgagtgccac acccccctcca    540

ctgatacccg ctacctgggc agctacagcg gcaaggtgga gctgagagtt cttccagatg    600

tcctccaggt gtctgctgcc cccccagggc cccgaggccg ccaggcccca acctcacccc    660

cacgcatgac ggtgcatgag ggcaggagc tggcactggg ctgcctggcg aggacaagca    720

cacagaagca cacacacctg gcagtgtcct ttgggcgatc tgtgcccgag gcaccagttg    780

ggcggtcaac tctgcaggaa gtggtgggaa tccggtcaga cttggccgtg gaggctggag    840

ctccctatgc tgagcgattg gctgcagggg agcttcgtct gggcaaggaa gggaccgatc    900

ggtaccgcat ggtagtaggg ggtgcccagg caggggacgc aggcacctac cactgcactg    960

ccgctgagtg gattcaggat cctgatggca gctgggccca gattgcatag aaaagggccc   1020

gtcctggccc acgtggatgt gcagacgctg tccagccagc tgcagtgaca gtggggcctg   1080

gtgaacgtcg gatcggccca ggggagccct tggaactgct gtgcaatgtg tcaggggcac   1140

ttcccccaag caggcccgtc atgcttgcat acttctgtag gttgggaaga tggcacctgc   1200

ggggggcact gggcccggcc gcctggtagc ccagctggac acagagggtg tgggcagctg   1260

ggccctggct atgaggccga cacattgcca tggagaaggt ggcatccaga acataccggc   1320

tacggctaga ggctgccagg cctggtgatg cgggcaccta ccgctgcctc gccaaagcct   1380

atgttcgagg gtctgggacc cggcttcgtg aagcagccag tgcccgttcc cggcctctcc   1440

ctgtacacgt gcgggaggaa ggtgtggtgc tggaagctgt ggcatggcta gcaggaggca   1500

cagtgtaccg cggggagact gcctccctgc tgtgcaacat ctctgtgcgg ggtggccccc   1560

caggactgcg gctggccgcc agctggtggg tggagcgacc agaggatgga gagctcagct   1620

ctgtccctgc ccagctggtg ggtggcgtag gccaggatgg tgtggcagag ctgggagtcc   1680

ggcctggagg aggccctgtc agcgtagagc tggtggggcc ccgaagccat cggctgagac   1740

tacacagctt ggggcccgag gatgaaggcg tgtaccactg tgcccccagc gcctgggtgc   1800

agcatgccga ctacagctgg taccaggcgg gcagtgcccg ctcagggcct gttacagtct   1860

acccctacat gcatgccctg gacaccctat ttgtgcctct gctggtgggt acaggggtgg   1920

ccctagtcac tggtgccact gtccttggta ccatcacttg ctgcttcatg aagaggcttc   1980
```

-continued gaaaacggtg atcccttact ccccaggtct tgcaggtgtc aactgtcttc cggcccagct 2040
ccaagccctc ctctggttgc ctggacaccc tctccctctg tccactcttc ctttaattta 2100
tttgacctcc cactacccag aatgggagac gtgcctcccc ttccccactc cttccctccc 2160
aagcccctcc ctctggcctt ctgttcttga tctcttaggg atcctatagg gaggccattt 2220
cctgtcctgg aattagtttt tctaaaatgt gaataaactt gttttataaa aaaaaaaaaa 2280
aaaaaa 2286

<210> SEQ ID NO 44
<211> LENGTH: 1138
<212> TYPE: DNA
<213> ORGANISM: Homo sapiens

<400> SEQUENCE: 44
gggggaagta ggaagggatg tgaaacttgg ccacagcctg gagccactcc tgctgggcag 60
cccacagggt ccctgggcgg agggcaggag catccagttg gagttgacaa caggaggcag 120
aggcatcatg gagggtcccc ggggatggct ggtgctctgt gtgctggcca tatcgctggc 180
ctctatggtg accgaggact tgtgccgagc accagacggg aagaaagggg aggcaggaag 240
acctggcaga cgggggcggc caggcctcaa gggggagcaa ggggagccgg gggcccctgg 300
catccggaca ggcatccaag gccttaaagg agaccagggg gaacctgggc cctctggaaa 360
ccccggcaag gtgggctacc cagggcccag cggcccccctc ggagcccgtg gcatcccggg 420
aattaaaggc accaagggca gcccaggaaa catcaaggac cagccgaggc cagccttctc 480
cgccattcgg cggaaccccc caatgggggg caacgtggtc atcttcgaca cggtcatcac 540
caaccaggaa gaaccgtacc agaaccactc cggccgattc gtctgcactg tacccggcta 600
ctactacttc accttccagg tgctgtccca gtgggaaatc tgcctgtcca tcgtctcctc 660
ctcaaggggc caggtccgac gctccctggg cttctgtgac accaccaaca aggggctctt 720
ccaggtggtg tcagggggca tggtgcttca gctgcagcag ggtgaccagg tctgggttga 780
aaaagacccc aaaaagggtc acatttacca gggctctgag gccgacagcg tcttcagcgg 840
cttcctcatc ttcccatctg cctgagccag ggaaggaccc cctcccccac ccacctctct 900
ggcttccatg ctccgcctgt aaaatggggg cgctattgct tcagctgctg aagggagggg 960
gctggctctg agagccccag gactggctgc cccgtgacac atgctctaag aagctcgttt 1020
cttagacctc ttcctggaat aaacatctgt gtctgtgtct gctgaaaaaa aaaaaaaaaa 1080
aaaaaaaaaa aaaaaaaaaa aaaaaaaaaa aaaaaaaaaa aaaaaaaaaa gggcggcc 1138

<210> SEQ ID NO 45
<211> LENGTH: 1071
<212> TYPE: DNA
<213> ORGANISM: Homo sapiens

<400> SEQUENCE: 45
ggagggcagg agcatccagt tggagttgac aacaggaggc agaggcatca tggagggtcc 60
ccggggatgg ctggtgctct gtgtgctggc catatcgctg gcctctatgg tgaccgagga 120
cttgtgccga gcaccagacg ggaagaaagg ggaggcagga agacctggca gacgggggcg 180
gccaggcctc aagggggagc aaggggagcc gggggcccct ggcatccgga caggcatcca 240
aggccttaaa ggagaccagg gggaacctgg gccctctgga aaccccggca aggtgggcta 300
cccagggccc agcggccccc tcggagcccg tggcatcccg ggaattaaag gcaccaaggg 360

-continued

```
cagcccagga aacatcaagg accagccgag gccagccttc tccgccattc ggcggaaccc    420

cccaatgggg gscaacgtgg tcatcttcga cacggtcatc accaaccagg aagaaccgta    480

ccagaaccac tccggccgat tcgtctgcac tgtacccggc tactactact tcaccttcca    540

ggtgctgtcc cagtgggaaa tctgcctgtc catcgtctcc tcctcaaggg gccaggtccg    600

acgctccctg ggcttctgtg acaccaccaa caaggggctc ttccaggtgg tgtcaggggg    660

catggtgctt cagytgcagc agggtgacca ggtctgggtt gaaaaagacc ccaaaaaggg    720

tcacatttac cagggctctg aggccgacag cgtcttcagc ggcttcctca tcttcccatc    780

tgcctgagcc agggaaggac cccctccccc acccacctct ytggcttcca tgctccgcct    840

gtaaaatggg ggcgctattg cttcagctgc tgaagggagg gggctggctc tgagagcccc    900

aggactggct gccccgtgac acatgctcta agaagctcgt ttcttagacc tcttcctgga    960

ataaacatct gtgtctgtgt ytgctgaaaa aaaaaaaaaa aaaaaaaaaa aaaaaaaaaa   1020

aaaaaaaaaa actcgagggg gggcccggta cccaattcgc cgtataatga g            1071
```

<210> SEQ ID NO 46
<211> LENGTH: 1050
<212> TYPE: DNA
<213> ORGANISM: Homo sapiens
<220> FEATURE:
<221> NAME/KEY: SITE
<222> LOCATION: (1026)
<223> OTHER INFORMATION: n equals a,t,g, or c
<221> NAME/KEY: SITE
<222> LOCATION: (1040)
<223> OTHER INFORMATION: n equals a,t,g, or c

<400> SEQUENCE: 46

```
gcggacgcgt gggcggacgc gtgggctcct gctgggcagc ccacagggtc cctgggcgga     60

gggcaggagc atccagttgg agttgacaac aggaggcaga ggcatcatgg agggtccccg    120

gggatggctg gtgctctgtg tgctggccat atcgctggcc tctatggtga ccgaggactt    180

gtgccgagca ccagacggga agaaagggga ggcaggaaga cctggcagac gggggcggcc    240

aggcmtcaag gsgcttaaag gagaccaggg ggaacctggg ccctctggaa accccggcaa    300

ggtgggctac ccagggccca gcggccccct cggrgcccgt ggcatcccgg gaattaaagg    360

caccaagggc agcccaggaa acatcaagga ccagccgagg ccagccttct ccgccattcg    420

gcggaacccc ccaatggggg gcaacgtggt catcttcgac acggtcatca ccaaccagga    480

agaaccgtac cagaaccact ccggccgatt cgtctgcact gtacccggct actactactt    540

caccttccag gtgctgtccc agtgggaaat ctgcctgtcc atcgtctcct cctcaagggg    600

ccaggtccga cgctccctgg gcttctgtga caccaccaac aaggggctct tccaggtggt    660

gtcagggggc atggtgcttc agctgcagca gggtgaccag gtctgggttg aaaaagaccc    720

caaaaagggt cacatttacc agggctctga ggccgacagc gtcttcagcg gcttcctcat    780

cttcccatct gcctgagcca gggaaggacc ccctccccca cccacctctc tggcttccat    840

gctccgcctg taaaatgggg gcgctattgc ttcagctgct gaagggaggg ggctggctct    900

gagagcccca ggactggctg ccccgtgaca catgctctaa gaagctcgtt tcttagacct    960

cttcctggaa taaacatctg tgtctgtgtc tgctgaaaaa aaaaaaaaaa aaaactcggg   1020

gggggncccg gaacccaatn ggccctatag                                    1050
```

<210> SEQ ID NO 47
<211> LENGTH: 1149
<212> TYPE: DNA

<213> ORGANISM: Homo sapiens

<400> SEQUENCE: 47
gggggaagta ggaagggatg tgaaacttgg ccacagcctg gagccactcc tgctgggcag 60
cccacagggt ccctgggcgg agggcaggag catccagttg gagttgacaa caggaggcag 120
aggcatcatg gagggtcccc ggggatggct ggtgctctgt gtgctggcca tatcgctggc 180
ctctatggtg accgaggact tgtgccgagc accagacggg aagaaagggg aggcaggaag 240
acctggcaga cgggggcggc caggcctcaa gggggagcaa ggggagccgg gggcccctgg 300
catccggaca ggcatccaag gccttaaagg agaccagggg gaacctgggc cctctggaaa 360
ccccggcaag gtgggctacc cagggcccag cggcccccctc ggrgcccgtg gcatcccggg 420
aattaaaggc accaagggca gcccaggaaa catcaaggac cagccgaggc cagccttctc 480
cgccattcgg cggaaccccc caatgggggg caacgtggtc atcttcgaca cggtcatcac 540
caaccaggaa gaaccgtacc agaaccactc cggccgattc gtctgcactg tacccggcta 600
ctactacttc accttccagg tgctgtccca gtgggaaatc tgcctgtcca tcgtctcctc 660
ctcaaggggc caggtccgac gctccctggg cttctgtgac accaccaaca aggggctctt 720
ccaggtggtg tcagggggca tggtgcttca gctgcagcag ggtgaccagg tctgggttga 780
aaaagacccc aaaaagggtc acatttacca gggctctgag gccgacagcg tcttcagcgg 840
cttcctcatc ttcccatctg cctgagccag ggaaggaccc cctcccccac ccacctctct 900
ggcttccatg ctccgcctgt aaaatggggg cgctattgct tcagctgctg aagggagggg 960
gctggctctg agagccccag gactggctgc cccgtgacac atgctctaag aagctcgttt 1020
cttagacctc ttcctggaat aaacatctgt gtctgtgtct gctgaaaaaa aaaaaaaaaa 1080
aaaaaaaaaa aaaaaaaaaa aaaaaaaaac tcgagggggg gcccggtacc caattcgccg 1140
tataatgag 1149

<210> SEQ ID NO 48
<211> LENGTH: 1086
<212> TYPE: DNA
<213> ORGANISM: Homo sapiens

<400> SEQUENCE: 48
ggattctagg acagggatgg gggtgcagca ctgatccagt tgacaacagg aggcagaggc 60
atcatggagg gtccccgggg atggctggtg ctctgtgtgc tggccatatc gctggcctct 120
atggtgaccg aggacttgtg ccgagcacca gacgggaaga aaggggaggc aggaagacct 180
ggcagacggg ggcggccagg cctcaagggg gagcaagggg agccgggggc ccctggcatc 240
cggacaggca tccaaggcct taaaggagac caggggggaac ctgggccctc tggaaacccc 300
ggcaaggtgg gctacccagg gcccagcggc cccctcggag cccgtggcat cccgggaatt 360
aaaggcacca agggcagccc aggaaacatc aaggaccagc cgaggccagc cttctccgcc 420
attcggcgga accccccaat ggggggcaac gtggtcatct tcgacacggt catcaccaac 480
caggaagaac cgtaccagaa ccactccggc cgattcgtct gcactgtacc cggctactac 540
tacttcacct tccaggtgct gtcccagtgg gaaatctgcc tgtccatcgt ctcctcctca 600
aggggccagg tccgacgctc cctgggcttc tgtgacacca ccaacaaggg gctcttccag 660
gtggtgtcag ggggcatggt gcttcagctg cagcagggtg accaggtctg ggttgaaaaa 720
gaccccaaaa agggtcacat ttaccagggc tctgaggccg acagcgtctt cagcggcttc 780
ctcatcttcc catctgcctg agccagggaa ggaccccctc cccccacccac ctctctggct 840

-continued

```
tccatgctcc gcctgtaaaa tgggggcgct attgcttcag ctgctgaagg gagggggctg    900

gctctgagag ccccaggact ggctgccccg tgacacatgc tctaagaagc tcgtttctta    960

gacctcttcc tggaataaac atctgtgtct gtgtctgctg aaaaaaaaaa aaaaaaaaaa   1020

aaaaaaaaaa aaaaaaaaaa aaaaaactcg aggggggggcc cggtacccaa ttcgccgtat   1080

aatgag                                                              1086
```

<210> SEQ ID NO 49
<211> LENGTH: 971
<212> TYPE: DNA
<213> ORGANISM: Homo sapiens

<400> SEQUENCE: 49

```
gcttctatcc atttattcaa gcacatattg gtcacctact gtgtgcctgg cactcatgtc     60

acaaagataa gttcctgatt cggtacactt actgagcacc tgctgtgtgc agggagctga    120

gctatgggat gggaatggga gtaaacaagg tacttttyac tttttctttt ttttcctcac    180

tgctagacgg tgtgggaact tctcactcat tggcttcttt cccacacacc tgaagagcac    240

tgactgtgtg ccgggcacta gtgatacaaa agagtgtgac agttgttcag tctgcatttt    300

cgatcatggg ctacatgccg agtgctgggg cacagagatg aacaagatcg gttccttcac    360

ttcttcatgc cacaagtgtt tattgagcac ctgtgtgcca ggcctcacag actcccagtt    420

gggttgaaga atggttgact gagtttgatt cttcctgtac cctcggtcgt ctgagctgtg    480

tgcagacaac atccccccac cacccaagag ggagggtagc tcttccgcca ccaggggcaa    540

gcacaggtcc tggtggcccc acgccacatg ttagcccccc tggagggggc gccagttgga    600

gacgggggct gggtgtccct ggcccactcc cggtcccctg tgctttacct ccttgccctt    660

gtgtctcagg tgtggtccct gcctgcttga tgaagttgct ctgttcaagc ctttggtggg    720

atcatgtgtt tgggggcttt taggggaccc agctgcactg gggcactgcc cgtggcctgg    780

gtaggacatt tcccagcaag ggctggagga gttgccgtgc cttcagcctg aatcgaatgt    840

cagaaccagc cagcggtgct tcaccctctt ggggataact tgcttagttt tttaataaat    900

gttcctggtt ggttttcaca gcaaaaaaaa aaaaaaaaaa aaaaaaaaaa aaaaaaaaaa    960

aaaaaaaaaa g                                                         971
```

<210> SEQ ID NO 50
<211> LENGTH: 2752
<212> TYPE: DNA
<213> ORGANISM: Homo sapiens

<400> SEQUENCE: 50

```
agacatagct tttctcattc accctcccac ttggggctaa tgcacagaca tgaacatcta     60

ttgaggaaaa ccacaaaaaa cttcaaaaca gctacaacgg gaaaaagaga gttttgtccc    120

acagtcagca ggccactagt ttattaactt ccagtcacct tgatttttgc taaaatgaag    180

actctgcagt ctacacttct cctgttactg cttgtgcctc tgataaagcc agcaccacca    240

acccagcagg actcacgcat tatctatgat tatggaacag ataattttga agaatccata    300

tttagccaag attatgagga taaatacctg gatggaaaaa atattaagga aaaagaaact    360

gtgataatac ccaatgagaa aagtcttcaa ttacaaaaag atgaggcaat aacaccatta    420

cctcccaaga aagaaaatga tgaaatgccc acgtgtctgc tgtgtgtttg tttaagtggc    480

tctgtatact gtgaagaagt tgacattgat gctgtaccac ccttaccaaa ggaatcagcc    540
```

-continued

```
tatctttacg cacgattcaa caaaattaaa aagctgactg ccaaagattt tgcagacata    600

cctaacttaa gaagactcga ttttacagga aatttgatag aagatataga agatggtact    660

ttttcaaaac tttctctgtt agaagaactt tcacttgctg aaaatcaact actaaaactt    720

ccagttcttc ctcccaagct cactttattt aatgcaaaat acaacaaaat caagagtagg    780

ggaatcaaag caaatgcatt caaaaaactg aataacctca ccttcctcta cttggaccat    840

aatgccctgg aatccgtgcc tcttaattta ccagaaagtc tacgtgtaat tcatcttcag    900

ttcaacaaca tagcttcaat tacagatgac acattctgca aggctaatga caccagttac    960

atccgggacc gcattgaaga gatacgcctg gagggcaatc caatcgtcct gggaaagcat   1020

ccaaacagtt ttatttgctt aaaaagatta ccgatagggt catactttta acctctattg   1080

gtacaacata taaatgaaag tacacctaca ctaatagtct gtctcaacaa tgwgtaaagg   1140

aacttaagta ttggtttaat attaaccttg tatctcattt tgaaggaatt taatatttta   1200

agcaaggatg ttcaaaatct tacatataat aagtaaaaag taagactgaa tgtctacgtt   1260

cgaaacaaag taatatgaaa atatttaaac agcattacaa aatcctagtt tatactagac   1320

taccatttaa aaatcatgtt tttatataaa tgcccaaatt tgagatgcat tattcctatt   1380

actaatgatg taagtacgag gataaatcca agaaactttc aactctttgc ctttcctggc   1440

ctttactgga tcccaaaagc atttaaggta catgttccaa aaactttgaa aagctaaatg   1500

tttcccatga tcgctcattc ttcttttatg attcatacgt tattccttat aaagtaagaa   1560

ctttgttttc ctcctatcaa ggcagctatt ttattaaatt tttcacttag tctgagaaat   1620

agcagatagt ctcatattta ggaaaacttt ccaaataaaa taaatgttat tctctgataa   1680

agagctaata cagaaatgtt caagttattt tactttctgg taatgtcttc agtaaaatat   1740

tttctttatc taaatattaa cattctaagt ctaccaaaaa aagttttaaa ctcaagcagg   1800

ccaaaaccaa tatgcttata agaaataatg aaaagttcat ccatttctga taaagttctc   1860

tatggcaaag tctttcaaat acgagataac tgcaaaatat tttcctttta tactacagaa   1920

atgagaatct catcaataaa ttagttcaag cataagatga aaacagaata ttctgtggtg   1980

ccagtgcaca ctaccttccc acccatacac atccatgttc actgtaacaa actgaatatt   2040

cacaataaag cttctgagta acactttctg attactcatg ataaactgac atggctaact   2100

gcaagaatta aatcttctat ctgagagtaa taatttatga tgactcagtg gtgccagagt   2160

aaagtttcta aaataacatt cctctcactt gtaccccact aaaagtatta gtctacacat   2220

tacattgaag ttaaacacaa aattatcagt gttttagaaa catgagtccg gactgtgtaa   2280

gtaaaagtac aaacattatt tccaccataa agtatgtatt gaaatcaagt tgtctctgtg   2340

tacagaatac atacttattc ccatttttaa gcatttgctt ctgttttccc tacctagaat   2400

gtcagatgtt tttcagttat ctccccattt gtcaaagttg acctcaagat aacatttttc   2460

attaaagcat ctgagatcta agaacacaat tattattcta acaatgatta ttagctcatt   2520

cacttatttt gataactaat gatcacagct attatactac tttctcgtta ttttgtgtgc   2580

atgcctcatt tccctgactt aaacctcact gagagcgcaa aatgcagctt tatacttttt   2640

actttcaatt gcctagcaca atagtgagta catttgaatt gaatatataa taaatattgc   2700

aaaataaaat ccatctaaat agaaaaaaaa aaaaaaaaaa aaaaaaactc ga           2752
```

<210> SEQ ID NO 51
<211> LENGTH: 2389
<212> TYPE: DNA
<213> ORGANISM: Homo sapiens -continued
<220> FEATURE:
<221> NAME/KEY: SITE
<222> LOCATION: (1965)
<223> OTHER INFORMATION: n equals a,t,g, or c

<400> SEQUENCE: 51

```
cccacgcgtc cgcttaccgc tgcttgctgg agcgagcttc cacttaactc ccgtcccggt     60

ccccgcgcgc catgtgcctc ctcggcgggc tgagcgcccc gccgctgctg ctgctgccgc    120

tgctgccgct gctgctgtgt ccgcctacgg gcagggtgac tgcagctttc ccccagagct    180

acctaatgcc atacaaagtg tgggtgacca acagagtttt cctgaaaaat tcacagtaac    240

atacaaatgt aaagaaggct ttgtaaaggt tcctggcaag gcagactccg tggtctgtct    300

caacaataaa tggtcagagg tggcagaatt ttgtaaccgt agctgtgatg ttccaaccag    360

gctacaattt gcatctctca aaaagtcttt caccaaacag aattatttcc cagtgggttc    420

cgttgtggaa tatgaatgcc gacctggcta ccaaagggac catcttctct caggaaaact    480

aacttgcctt ctgaatttta catggtccaa acccgatgaa ttttgtaaaa gaaaatcatg    540

tcctaatcct ggagatttaa gacatggtca tgtcaacatt ccaactgaca tattgtatgc    600

tgcagttatc cacttctcgt gtaacaaggg gtacaggtta gtcggtgcag cttctagtta    660

ctgttccatt gtaaatgacg atgttggctg gagtgatcca ttgcctgaat gccaagaaat    720

tttttgtccg gaaccaccaa aaattagcaa tggagtcatt ctagatcaac agaacactta    780

tgtgtatcaa caggctgtaa aatatgagtg tataaaaggc ttcaccctga tcggagagaa    840

ctctatttat tgtactgtta agggtgacca aggagaatgg agtggccgcc gcctgaatgc    900

aaaggttctc agatttctac agtcatacca gcaacagaga caccaccaca gtaagtgctt    960

cagctacaaa gccacatcag ctctcagaaa cccaccactg caaatgttac aggtaccaaa   1020

gttacatcag ctcctcagaa acccaccaca gggaatgttc caggtaccga agctacatca   1080

actcctcaga aacccactac agcggatgtt tcagagaccc cgtcagcagt ccagaatccc   1140

atcacggcaa atgcgtttgc tacacaggcc atgccagcaa cccatagatc ctccacagca   1200

aaagcttcat ttacacagag tcttccagca acacgaaagt ccactgctat acatgcccca   1260

gtgactaagg gtctccatac aacaaaaaga ttgacctctg ctcgtattac agcaaaacag   1320

agttcagcta ctcccaggac aaccagcgca cctcatggaa gagggaccct ctcttcagat   1380

gctgccatca ttgcagttgg taagtttggt tcttcggcag ttaaaaaaaa ttgtcatcac   1440

tgtgggatgt acaatcctta ttcctggagg agaatattgt ctttttactg ccttaggaat   1500

actattaaga tgaaatgttt aaggtcaggg agaagacggg taaatgcatt ttatcgacgt   1560

gtttggtgga ccccgttagg tactcggtac gttcctaagt cttcccaacc gtgttcttgt   1620

tccaaggtaa ttttagggca acttcacatc atttggccag tcaatcaagt atccctgaac   1680

gcctattgtc tcaatgcatt atcattctag gggccaaaaa caacaataag gaagctatta   1740

tcaatacagt ttttaagcct caagtgtttt acaagtactc acaaactact ccttggttgt   1800

ttctagacgt ctgttccaga taaaccagaa tgctactttt gattaacatc ctgttctttt   1860

ttccctttcc tgtcagtgat ttaaagcaaa gatagcttta aaattattct gttgctatag   1920

acttaaggac atatctatgt tgcaaatttc tttttcttgt tcccnagtct tttgttgttc   1980

attaaatata ttatttgatg ttatacattt taccaagaag attaataact cctaaagaag   2040

atggcaaaag aaatgtttaa gaagcaatac agctaagttg gcatattaaa aggatgccca   2100

gtagaaaata tgcacattaa aaagtgaata ttttaaaatt atgtccttat aagctgaggt   2160
```

-continued

```
ctcctattta tgcatgcatg agtgaaacaa gggactgaag ctgaaaaggt gtttttttaat   2220

tattattatt atttatagtt cttttatagt tcttttatat tttgaatgaa cctctcctta   2280

gctaaaatag ttatcttgaa agatttgaac agttggattc actttgtttg tttgatattt   2340

tcaatagaaa taaatgcatt ctaaatgaaa aaaaaaaaaa aaaaaaaaa              2389


<210> SEQ ID NO 52
<211> LENGTH: 2254
<212> TYPE: DNA
<213> ORGANISM: Homo sapiens
<220> FEATURE:
<221> NAME/KEY: SITE
<222> LOCATION: (6)
<223> OTHER INFORMATION: n equals a,t,g, or c

<400> SEQUENCE: 52

agggcnattg ggtacgggcc cccctcgagt tttttttttt tttttttaa tccccagctc     60

atatttattt gggcacagag tgggcactca aatatctgat gaacttgatg aactgaaaag    120

aggtctcctt aaacaagata tcatctcccg aagagagaag tcccaaccat ataaaatgta    180

tgatcaagtc ccagaaaact ttgccttccc aaggaatgtg tttctaattt ggtttcaaag    240

cacactggtt cccactttta ccactttcat gacattggac aatagtacta ctcttttcta    300

cttttcttcc agacctgggg acttgatatt ctcttagcct catatcatct ttgcaaggag    360

ttcacagaga ggattattct ccatcttaca aatagaactg aggcccagaa ggaaatccct    420

tagtgtcttt ttgatggaac acagttctgt gatgggaagc tatcccagtc tcccatcctt    480

gcaaaactgc tgcttagtac tcaggtgttc tctaggttgt tctggaacat ttacaaactt    540

ctttgggtgt gaggatgtgc tgccacaagg ccaaaaatca cattctctct ctctctcctc    600

tcctctctac cattctcctc agtgccaggt ggggacagat tccacccact gggcctggga    660

ggaagaaaag caccttggcc actagtcagg gaggagtcac agccagcaag aagagagaga    720

cctaagtaga caagagtagt ttcaatggga agaagcaggg ccaccagtaa gaaaaccagg    780

agactccttc tgaaaggctt ccacctggga ggaaagatgg cagcagygcc atgaggaggc    840

cagatccctc ctcctcaatc ctctgcgccg ggccctccca gagtcacttc ttcagggcac    900

ccaggctctt cagggtctct tgggcctggg tcagctgctg ctgcagcctc tggcgggtgc    960

tctcgttgga ggcccgcttc aggtggccct gcatctcctc caccatggct cggtggccag   1020

gagtgttgtg aaacagccgc accgcccggt ccccacagga ggccagaaag cggccagtga   1080

tgtcaaagga caagttggcg atacactcgc catggacccg ctcaaagcac tcctccttct   1140

cgccccgccg ggtattgtag agatgaatac tactgccact ggccaaggcc aagacctggg   1200

cgttggggga gagggccagg cggcacggcg cggcacccgc cgcctcttca aagcggcctg   1260

tcttcagcaa gtaggggtcc tgcttcttct tgtattccac atctgtgtcc cacagtttcc   1320

atgtaccatc cttggagaca gaagccatcc tccgtgagtc gttggagaaa gcaaacgagt   1380

gcacagccgc ggagtggccc tttagttcga aggctcgcac cacctcctgg aactccccct   1440

tctttccaaa gcagacttcc caaaccttca catctggggt gaagccacac gaggctacaa   1500

atctgccaca gggagataca gcagcgtgtg tgttgttcat ctggttggtg ttgatggtag   1560

acagcacttg acccttcagg ctccagatga ggacagtggt gtcactggag gcagtcatga   1620

taaacttccc tgtgttagca atgccaatgt cgatgacagg cgccttgtgc tttttaggga   1680

agtcctctgg ggtggctgtg aaggtgtagc ccccatcctc ccgcttggtc atcttgaaga   1740

cacggagggt gtccccgttg gccagccaga cgatgaaggc tctgcagtca gggctgaagc   1800
```

-continued gcaccagggt ggcgtggtcc agctccacgt tggctctcat gctgcggtgc tctcgctgca 1860
ggaagtcctt ggtgctccag atgcggatgg tgcgatcatc tgcacaggta gccaggtatt 1920
tgccattgct gctaaagtcc atgcaagata tgttcccgct gtggctcttc agagctgcag 1980
ccaggaggcg gtgggtgaag ttgtgttgtt gaggcttctc cttccgaatc cgctgatatt 2040
gtttctgctt cttggatccc gaagatttgt caggtggaaa tccatttgct ttttggcagg 2100
cgggccggcc gctcctctcc tcccccgcgc gcagccaccc ccgcgctacc gccgccgtcg 2160
ccatcagggc cagcagccca agcaacaccg acagccccat gagctccgac atctgcgaga 2220
gctccatgtt ggtggaaccc tcgtgccgaa ttac 2254

<210> SEQ ID NO 53
<211> LENGTH: 3559
<212> TYPE: DNA
<213> ORGANISM: Homo sapiens
<220> FEATURE:
<221> NAME/KEY: SITE
<222> LOCATION: (3363)
<223> OTHER INFORMATION: n equals a,t,g, or c

<400> SEQUENCE: 53
gaagaattgc ctttttttaac atgcagccct ttggaatgcc caccaaaagc msgtgatttc 60
cgagctcagc aatgctcagc tcataatgat gtcaagcacc atggccagtt ttatgaatgg 120
cttcctgtgt ctaatgaccc tgacaaccca tgttcactca agtgccaagc caaaggaaca 180
accctggttg ttgaactagc acctaaggtc ttagatggta cgcgttgcta tacagaatct 240
ttggatatgt gcatcagtgg tttatgccaa attgttggct gcgatcacca gctgggaagc 300
accgtcaagg aagataactg tggggtctgc aacggagatg ggtccacctg ccggctggtc 360
cgagggcagt ataaatccca gctctccgca accaaatcgg atgatactgt ggttgcaatt 420
ccctatggaa gtagacatat tcgccttgtc ttaaaaggtc ctgatcactt atatctggaa 480
accaaaaccc tccaggggac taaaggtgaa aacagtctca gctccacagg aactttcctt 540
gtggacaatt ctagtgtgga cttccagaaa tttccagaca aagagatact gagaatggct 600
ggaccactca cagcagattt cattgtcaag attcgtaact cgggctccgc tgacagtaca 660
gtccagttca tcttctatca acccatcatc caccgatgga gggagacgga tttctttcct 720
tgctcagcaa cctgtggagg aggttatcag ctgacatcgg ctgagtgcta cgatctgagg 780
agcaaccgtg tggttgctga ccaatactgt cactattacc cagagaacat caaacccaaa 840
cccaagcttc aggagtgcaa cttggatcct tgtccagcca ggtgggaggc caccccatgg 900
accgcgtgct cctcctcgtg tgggggggc atccagagcc gggcagtttc ctgtgtggag 960
gaggacatcc aggggcatgt cacttcagtg gaagagtgga aatgcatgta cacccctaag 1020
atgcccatcg cgcagccctg caacattttt gactgcccta aatggctggc acaggagtgg 1080
tctccgtgca cagtgacatg tggccagggc ctcagatacc gtgtggtcct stgcatcgac 1140
catcgaggaa tgcacacagg aggctgtagc ccaaaaacaa agccccacat aaaagaggaa 1200
tgcatcgtac ccactccctg ctataaaccc aaagagaaac ttccagtcga ggccaagttg 1260
ccatggttca aacaagctca agagctagaa gaaggagctg ctgtgtcaga ggagccctcg 1320
ttcatyycar aggcctggtc ggcctgcaca gtcacctgtg gtgtggggac ccargtgcga 1380
atagtcaggt gccaggtgct cctgtctttc tctcagtccg tggctgacct gcctattgac 1440
gagtgtgaag ggcccaagcc agcatcccag cgtgcctgtt atgcaggccc atgcagcggg 1500

-continued

```
gaaattcctg agttcaaccc agacgagaca gatgggctct ttggtggcct gcaggatttc   1560
gacgagctgt atgactggga gtatgagggg ttcaccaagt gctccgagtc ctgtggagga   1620
ggtgtccagg aggctgtggt gagctgcttg aacaaacaga ctcgggagcc tgctgaggag   1680
aacctgtgcg tgaccagccg ccggccccca cagctcctga agtcctgcaa tttggatccc   1740
tgcccagcaa ggtgggaaat tggcaagtgg agtccatgta gtctcacatg tggggtcggc   1800
ctacagacca gagacgtctt ctgcagccac ctgctttcca gagagatgaa tgaaacagtc   1860
atcctggctg atgagctgtg tcgccagccc aagcccagca cggtgcaagc ttgtaaccgc   1920
tttaattgcc ccccagcctg gtaccctgca cagtggcagc cgtgttccag aacgtgtggc   1980
gggggtgttc agaaacgtga ggttctttgc aagcagcgca tggctgatgg cagcttcctg   2040
gagcttcctg agaccttctg ttcagcttca aaacctgcct gccagcaagc atgcaagaaa   2100
gatgactgtc ccagcgagtg gcttctctca gactggacag agtgttccac aagctgcggg   2160
gaaggcaccc agactcgaag cgccatttgc cgaaagatgc tgaaaaccgg cctctcaacg   2220
gttgtcaatt ccaccctgtg cccgcccctg cctttctctt cctccatcag gccctgtatg   2280
ctggcaacct gtgcaaggcc cgggcggcca tccacgaagc acagcccgca catcgcggcc   2340
gccaggaagg tctacataca gactcgcagg cagaggaagc tgcacttcgt ggtgggggc   2400
ttcgcctacc tgctccccaa gacggcggtg gtgctgcgct gcccggcgcg caggtccgc   2460
aagcccctca tcacctggga gaaggacggc cagcacctca tcagctcgac gcacgtcacg   2520
gtggcccct tcggctatct caagatccac cgcctcaagc cctcggatgc aggcgtctac   2580
acctgctcag cgggcccggc ccgggagcac tttgtgatta agctcatcgg aggcaaccgc   2640
aagctcgtgg cccggccctt gagcccgaga agtgaggaag aggtgcttgc ggggaggaag   2700
ggcggcccga aggaggccct gcagacccac aaacaccaga acgggatctt ctccaacggc   2760
agcaaggcgg agaagcgggg cctggccgcc aacccgggga gccgctacga cgacctcgtc   2820
tcccggctgc tggagcaggg cggctggccc ggagagctgc tggcctcgtg ggaggcgcag   2880
gactctgcgg aaaggaacac gacctcggag gaggacccgg gtgcagagca agtgctcctg   2940
cacctgccct tcaccatggt gaccgagcag cggcgcctgg acgacatcct ggggaacctc   3000
tcccagcagc ccgaggagct gcgcgacctc tacagcaagc acctggtggc ccagctggcc   3060
caggagatct tccgcagcca cctggagcac caggacacgc tcctgaagcc ctcggagcgc   3120
aggacttccc cagtgactct ctcgcctcat aaacacgtgt ctggcttcag cagctccctg   3180
cggacctcct ccaccgggga cgccggggga ggctctcgaa ggccacaccg caagcccacc   3240
atcctgcgca agatctcagc ggcccagcag ctctcagcct cggaggtggt cacccacctg   3300
gggcagacgg tggccctggc cagcgggaca ctgagtgtct tctgcactgt gaggccatcg   3360
gcnacccaag gcctaccatc agctgggcca ggaatggaga agaagtcagt tcagtgacag   3420
gattcttcta cagscagatg attcyttaca gatcttgggc accagtggaa agcagatgtg   3480
ggtttctaca cttgcaatgg cacaatgcct tgggatacga mttytgctcc attggcgtca   3540
cattacaaga aaagccccc                                                 3559
```

<210> SEQ ID NO 54
<211> LENGTH: 852
<212> TYPE: DNA
<213> ORGANISM: Homo sapiens

<400> SEQUENCE: 54

```
gacggcagag gagcacttag cagcttattc agtgtccgat tctgattccg gcaaggatcc     60
```

-continued

```
aagcatggaa tgctgccgtc gggcaactcc tggcacactg ctcctctttc tggctttcct    120

gctcctgagt tccaggaccg cacgctccga ggaggaccgg gacggcctat gggatgcctg    180

gggcccatgg agtgaatgct cacgcacctg cgggggtggg gcctcctact ctctgaggcg    240

ctgcctgagc agcaagagct gtgaaggaag aaatatccga tacagaacat gcagtaatgt    300

ggactgccca ccagaagcag gtgatttccg agctcagcaa tgctcagctc ataatgatgt    360

caagcaccat ggccagtttt atgaatggct tcctgtgtct aatgaccctg acaacccatg    420

ttcactcaag tgccaagcca aaggaacaac cctggttgtt gaactagcac ctaaggtctt    480

agatggtacg cgttgctata cagaatcttt ggatatgtgc atcagtggtt tatgccaaat    540

tgttggctgc gatcaccagc tgggaagcac cgtcaaggaa gataactgtg ggtctgcaa     600

cggagatggg tccacctgcc ggctggtccg agggcagtat aaatcccagc tctccgcaac    660

caaatcggat gatactgtgg ttgcaattcc ctatggaagt agacatattc gccttgtctt    720

aaaaggtcct gatcacttat atctggaaac caaaaccctc caggggacta aaggtgaaaa    780

cagtctcagc tccacaggaa ctttccttgt ggacaattct agtgkgactt ccagaaattt    840

ccagacaaag ag                                                        852
```

<210> SEQ ID NO 55
<211> LENGTH: 609
<212> TYPE: DNA
<213> ORGANISM: Homo sapiens
<220> FEATURE:
<221> NAME/KEY: SITE
<222> LOCATION: (554)
<223> OTHER INFORMATION: n equals a,t,g, or c

<400> SEQUENCE: 55

```
gtggcagcgc tgcaacatca ccccatgtga aaacatggag tgcagagaca ccaccaggta     60

ctgcgagaag gtgaaacagc tgaaactctg ccaactcagc cagtttaaat ctcgctgctg    120

tggaacttgt ggcaaagcgt gaagataggg tgtggggaaa aactctaccc tggccacacg    180

aaggactcac gcaaccacct cggacagaac ctaagctttc ttcattttat ttatttattt    240

ccccctcccc actccacaca caccccttcca acctcctcca cctccacctt caagcataag    300

gacgtccgcg tgttttctct ttcagttagc tggaggacag gatgttggga aaggaaagga    360

cagatgtcta aaggaggttg cagagcaggc caggcagaca gtgggggcty ccttgaagag    420

cttyctccct cccaaacctg ggtctcaaag acctagaaag aggcaggcac agcccctgcg    480

gacagcaggg agccagaagg tttgtagcct attggtgcaa acattggaca aattcctgtg    540

tctttcctag aagngcagtc gacgcggccg cgaattcccg ggtcgacgtg ctcactagtc    600

ggcggccgc                                                            609
```

<210> SEQ ID NO 56
<211> LENGTH: 2099
<212> TYPE: DNA
<213> ORGANISM: Homo sapiens

<400> SEQUENCE: 56

```
gggtcgaccc acgcgtccgg gctgagcgcg tcacccacta tcgttgcggt ggtcgcttac     60

cttctgccgg cccggtccgt gccgcccttt gctgttgtgg ccrccgcggs accatggctg    120

ygytygtsgt gctcctggcg ttggtggcgg gtgttttggg gaacgagttt agtatattaa    180

aatcaccagg gtctgttgtt ttccgaaatg gaaattggcc tataccagga gagcggatcc    240
```

-continued

```
cagacgtggc tgcattgtcc atgggcttct ctgtgaaaga agacctttct tggccaggac    300

tcgcagtggg taacctgttt catcgtcctc gggctaccgt catggtgatg gtgaagggag    360

tgaacaaact ggctctaccc ccaggcagtg tcatttcgta ccctttggag aatgcagttc    420

cttttagtct tgacagtgtt gcaaattcca ttcactcctt attttctgag gaaactcctg    480

ttgttttgca gttggctccc agtgaggaaa gagtgtatat ggtagggaag gcaaactcag    540

tgtttgaaga cctttcagtc accttgcgcc agctccgtaa tcgcctgttt caagaaaact    600

ctgttctcag ttcactcccc ctcaattctc tgagtaggaa caatgaagtt gacctgctct    660

ttctttctga actgcaagtg ctacatgata tttcaagctt gctgtctcgt cataagcatc    720

tagccaagga tcattctcct gatttatatt cactggagct ggcaggtttg gatgaaattg    780

ggaagcgtta tggggaagac tctgaacaat tcagagatgc ttctaagatc cttgttgacg    840

ctctgcaaaa gtttgcagat gacatgtaca gtctttatgg tgggaatgca gtggtagagt    900

tagtcactgt caagtcattt gacacctccc tcattaggaa gacaaggact atccttgagg    960

caaaacaagc gaagaaccca gcaagtccct ataaccttgc atataagtat aattttgaat   1020

attccgtggt tttcaacatg gtactttgga taatgatcgc cttggccttg gctgtgatta   1080

tcacctctta caatatttgg aacatggatc ctggatatga tagcatcatt tataggatga   1140

caaaccagaa gattcgaatg gattgaatgt tacctgtgcc agaattagaa aaggggggttg   1200

gaaattggct gttttgttaa aatatatctt ttagtgtgct ttaaagtaga tagtatactt   1260

tacatttata aaaaaaaatc aaattttgtt ctttattttg tgtgtgcctg tgatgttttt   1320

ctagagtgaa ttatagtatt gacgtgaatc ccactgtggt atagattcca taatatgctt   1380

gaatattatg atatagccat ttaataacat tgatttcatt ctgtttaatg aatttggaaa   1440

tatgcactga aagaaatgta aaacatttag aatagctcgt gttatggaaa aaagtgcact   1500

gaatttatta gacaaactta cgaatgctta acttctttac acagcatagg tgaaaatcat   1560

atttgggcta ttgtatacta tgaacaattt gtaaatgtct taatttgatg taaataactc   1620

tgaaacaaga gaaaaggttt ttaacttaga gtagccctaa aatatggatg tgcttatata   1680

atcgcttagt tttggaactg tatctgagta acagaggaca gctgtttttt aaccctcttc   1740

tgcaagtttg ttgacctaca tgggctaata tggatactaa aaatactaca ttgatctaag   1800

aagaaactag ccttgtggag tatatagatg cttttcatta tacacacaaa aatccctgag   1860

ggacattttg aggcatgaat ataaaacatt tttatttcag taacttttcc ccctgtgtaa   1920

gttactatgg tttgtggtac aacttcattc tatagaatat taagtggaag tgggtgaatt   1980

ctacttttta tgttggagtg gaccaatgtc tatcaagagt gacaaataaa gttaatgatg   2040

attccaaaaa aaaaaaaaaa aaaaaaaaaa aaaaaaaaaa aaaaaaaagg gggggggc     2099
```

```
<210> SEQ ID NO 57
<211> LENGTH: 1688
<212> TYPE: DNA
<213> ORGANISM: Homo sapiens
<220> FEATURE:
<221> NAME/KEY: SITE
<222> LOCATION: (21)
<223> OTHER INFORMATION: n equals a,t,g, or c
<221> NAME/KEY: SITE
<222> LOCATION: (69)
<223> OTHER INFORMATION: n equals a,t,g, or c
<221> NAME/KEY: SITE
<222> LOCATION: (99)
<223> OTHER INFORMATION: n equals a,t,g, or c

<400> SEQUENCE: 57
```

-continued

```
attttactac acagaatgtc ncttttttgga gcaatcatct ctgccactga ccccagtgac     60
tgtgctggnc gatatttaat gaattgcatg cagacgtgna tctttacgca ctctttttgg    120
agagagcgtc cctaaatgat gctgttgcca ttgtactgtc ctcgtctatt gttgcctacc    180
agccagcggg actgaacact cacgcctttg atgctgctgc ctttttttaag tcagttggca    240
tttttctagg tatatttagt ggctctttta ccatgggagc tgtgactggt gttgtgactg    300
ctctagtgac taagtttacc aaactgcack gcttccccct gctggagacg gcgctgttct    360
tcctcatgtc ctggagcacg tttctcttgg cagaagcctg cggatttaca ggtgttgtag    420
ctgtcctttt ctgtggaatc acacaagctc attacaccta caacaatctg tcggtggaat    480
caagaagtcg aaccaagcag ctctttgagg tgttacattt cctggcagag aacttcatct    540
tctcctacat gggcctggca ctgtttacct tccagaagca cgttttcagc cccattttca    600
tcatcggagc ttttgttgcc atcttcctgg gcagagccgc gcacatctac ccgctctcct    660
tcttcctcaa cttgggcaga aggcataaga ttggctggaa ttttcaacac atgatgatgt    720
tttcaggcct caggggagca atggcatttg cgttggccat ccgtgacacg gcatcctatg    780
ctcgccagat gatgttcacg accacccttc tcattgtgtt cttcactgtc tggatcattg    840
gaggaggcac gacacccatg ttgtcatggc ttaacatcag agttggtgtt gaccccgatc    900
aagacccacc acccaacaac gacagctttc aagtcttaca aggggacggc ccagattctg    960
ccagaggaaa ccggacaaaa caggagagcg catggatatt caggctgtgg tacagctttg   1020
atcacaatta tctgaagccc atcctcacac acagtggtcc cccactaacc accacgctcc   1080
ccgcctggtg tggcttacta gctcgatgtc tgaccagtcc ccaggtgtac gataaccaag   1140
agccactgag agaggaagac tctgatttca tcctgaccga aggcgacctg acattgacct   1200
acggggacag cacagtgact gcaaatggct cctcaagttc gcacaccgcc tccacgagtc   1260
tggagggcag ccggagaacg aagagcagct cggaggaagt gctggagcga gacctgggaa   1320
tgggagacca gaaggtttcg agccggggca cccgcctagt gtttcccctg gaagataatg   1380
cttgactttc cccccaagcc ctggcgcgat ggggtaggct cccgatgggg tgaggacagc   1440
tgcaagccct agtgttgttg gaggtggggc agtgactaga ttgaactaac tcttctattt   1500
tattggggtc tgaagctatt gtaacactta aaatttaact cacaatgcag atggtgaggc   1560
aaaagtgtct ctaaattcag acaaacgtag acctattccc actttttttca catagtagtg   1620
cgctgtttca gagttaaaca aacaaaaaaa aatagcatgc ttaaaaaaaa aaaaaaaaaa   1680
actcgtag                                                            1688
```

```
<210> SEQ ID NO 58
<211> LENGTH: 1354
<212> TYPE: DNA
<213> ORGANISM: Homo sapiens

<400> SEQUENCE: 58

cgagcttccc cctgctggag acggcgctgt tcttcctcat gtcctggagc acgtttctct     60
tggcagaagc ctgcggattt acaggtgttg tagctgtcct tttctgtgga atcacacaag    120
ctcattacac ctacaacaat ctgtcggtgg aatcaagaag tcgaaccaag cagctctttg    180
aggtgttaca tttcctggca gagaacttca tcttctccta catgggcctg gcactgttta    240
ccttccagaa gcacgttttc agccccattt tcatcatcgg agcttttgtt gccatcttcc    300
tgggcagagc cgcgcacatc tacccgctct ccttcttcct caacttgggc agaaggcata    360
```

-continued

```
agattggctg gaattttcaa cacatgatga tgttttcagg cctcagggga gcaatggcat    420
ttgcgttggc catccgtgac acggcatcct atgctcgcca gatgatgttc acgaccaccc    480
ttctcattgt gttcttcact gtctggatca ttggaggagg cacgacaccc atgttgtcat    540
ggcttaacat cagagttggt gttgaccccg atcaagaccc accacccaac aacgacagct    600
ttcaagtctt acaaggggac ggcccagatt ctgccagagg aaaccggaca aaacaggaga    660
gcgcatggat attcaggctg tggtacagct ttgatcacaa ttatctgaag cccatcctca    720
cacacagtgg tcccccacta accaccacgc tccccgcctg gtgtggctta ctagctcgat    780
gtctgaccag tccccaggtg tacgataacc aagagccact gagagaggaa gactctgatt    840
tcatcctgac cgaaggcgac ctgacattga cctacgggga cagcacagtg actgcaaatg    900
gctcctcaag ttcgcacacc gcctccacga gtctggaggg cagccggaga acgaagagca    960
gctcggagga agtgctggag cgagacctgg gaatgggaga ccagaaggtt tcgagccggg   1020
gcacccgcct agtgtttccc ctggaagata atgcttgact ttccccccaa gccctggcgc   1080
gatggggtag gctcccgatg gggtgaggac agctgcaagc cctagtgttg ttggaggtgg   1140
ggcagtgact agattgaact aactcttcta ttttattggg gtctgaagct attgtaacac   1200
ttaaaattta actcacaatg cagatggtga ggcaaaagtg tctctaaatt cagacaaacg   1260
tagacctatt cccacttttt tcacatagta gtgcgctgtt tcagagttaa acaaacaaaa   1320
aaaaatagca tgcttaaaaa aaaaaaaaaa aaaa                                1354
```

<210> SEQ ID NO 59
<211> LENGTH: 1821
<212> TYPE: DNA
<213> ORGANISM: Homo sapiens

<400> SEQUENCE: 59

```
ccgggtcgac ccacgcgtcc gttcaaatcc acgttgatac aatgaaggta attaatgatc     60
ctatccatgg ccacattgag ctccaccacc tcccagctgt ttgatgtatc gaagacgttg    120
aaattgaggt gtatcaatga ttcggacgag gagagggtgg agctcaatgt ggccatggat    180
aggggtgggg tatctagcag gatgtctagt tcacgcactg ggtgaaaaac aaccagagct    240
gcagataagt gaacgagatg ttctctgtgt tcagattgct ggactttgtc atgatctcgg    300
tcatgggcca ttttctcaca tgtttgatgg acgatttatt ccacttgctc gcccggaggt    360
gaaatggacg catgaacaag gctcagttat gatgtttgag caccttatta attctaatgg    420
aattaagcct gtcatggaac aatatggtct catccctgaa gaagatattt gctttataaa    480
ggaacaaatt gtaggaccac ttgaatcacc tgtcgaagat tcattgtggc catataaagg    540
gcgtcctgaa aacaaaagct tcctttatga gatagtatct aataaaagaa atggcattga    600
tgtggacaaa tgggattatt ttgccaggga ctgccatcat cttggaatcc aaaataattt    660
tgattacaag cgctttatta agtttgcccg tgtctgtgaa gtagacaatg agttgcgtat    720
ttgtgctaga gataaggaag ttggaaatct gtatgacatg ttccacactc gcaactcttt    780
acaccgtaga gcttatcaac acaaagttgg caacattatt gatacaatga ttacagatgc    840
tttcctcgaa gcagatgact acatagagat tacaggtgct ggaggaaaaa agtatcgcat    900
ttctacagca attgacgaca tggaagccta tactaagctg acagataaca tttttctgga    960
gattttatac tctactgatc ccaaattgaa agacgcacga gagattttaa aacaaattga   1020
ataccgtaat ctattcaagt atgtgggtga gacgcagcca acaggacaaa taaagattaa   1080
aagggaggac tatgaatctc ttccaaaaga ggttgccagt gctaaaccca aagtattgct   1140
```

-continued

```
agacgtgaaa ctgaaggctg aagattttat agtggatgtt atcaacatgg attatggaat   1200

gcaagaaaag aatccaattg atcatgttag cttctattgt aagactgccc ccaacagagc   1260

aatcaggatt actaaaaacc aggtttcaca acttctgcca gagaaatttg cagagcagct   1320

gattcgagta tattgtaaga aggtggacag aaagagtttg tatgccgcaa gacaatattt   1380

tgttcagtgg tgtgcagaca gaaatttcac caagccgcag gatggcgatg ttatagcccc   1440

actcataaca cctcaaaaaa aggaatggaa cgacagtact tcagtccaaa atccaactcg   1500

cctccgagaa gcatccaaaa gcagagtcca gctttttaaa gatgacccaa tgtgaatgtc   1560

tgtagtcagt tgtttacaaa ctccctctcc tgcacaattc atttagaggc ttcaatcata   1620

gaattctgca aattaatgac aactcatgct ttaattttgt attttgaatg tacacgcatg   1680

ctgaagctaa gtaactttta atcaaagaaa taagatggta ttaggcaaat cttactatac   1740

tatgaaaagc attaccttgc ctatttttaa tattattaaa gcctttctcc ttcaaaaaaa   1800

aaaaaaaaaa aaaaaaaaaa a                                              1821
```

<210> SEQ ID NO 60
<211> LENGTH: 803
<212> TYPE: DNA
<213> ORGANISM: Homo sapiens

<400> SEQUENCE: 60

```
gattcggcac gagcaacagg acaaataaag attaaaaggg aggactatga atctcttcca     60

aaagaggttg ccagtgctaa acccaaagta ttgctagacg tgaaactgaa ggctgaagat    120

tttatagtgg atgttatcaa catggattat ggaatgcaag aaaagaatcc aattgatcat    180

gttagcttct attgtaagac tgcccccaac agagcaatca ggattactaa aaaccaggtt    240

tcacaacttc tgccagagaa atttgcagag cagctgattc gagtatattg taagaaggtg    300

gacagaaaga gtttgtatgc cgcaagacaa tattttgttc agtggtgtgc agacagaaat    360

ttcaccaagc cgcaggatgg cgatgttata gccccactca taacacctca aaaaaaggaa    420

tggaacgaca gtacttcagt ccaaaatcca actcgcctcc gagaagcatc caaaagcaga    480

gtccagcttt ttaaagatga cccaatgtga atgtctgtag tcagttgttt acaaactccc    540

tctcctgcac aattcattta gaggcttcaa tcatagaatt ctgcaaatta atgacaactc    600

atgctttaat tttgtatttt gaatgtacac gcatgctgaa gctaagtaac ttttaatcaa    660

agaaataaga tggtattagg caaatcttac tatactatga aaagcattac cttgcctatt    720

tttaatatta ttaaagcctt tctccttcaa aaaaaaaaaa aaaaaaaaaa aaaaaaaaaa    780

aaaaaaaaaa aaaaaaaact cga                                            803
```

<210> SEQ ID NO 61
<211> LENGTH: 1499
<212> TYPE: DNA
<213> ORGANISM: Homo sapiens

<400> SEQUENCE: 61

```
ggcacgagat gcccatacct agtgaggcag ggtgtggccc ggagctccca ctttccctca     60

gtcaccaaac tgctgctggt ctggtgggaa ggggtggtga tgtgggggtg ggggagctta    120

gtgtcagcgc ggggagggtg gggggtattt atctatttat acatgggatt gtacatagtc    180

ttgtggggca tgggggagcc ggctggaggt gagaaccctc ccctctcccc ccaccccccg    240

gggagagcaa atgtaaaact actaattttt gtgctttata tattctatat aaatatatct    300
```

-continued attttctttt tacaaaacca gtttataaat ggtagggggg tgtggggcgg acacatggag 360
ctccccttgt ggggggggccc cctccattac ccgacctacc gccctttcc tcacccccca 420 ccccactccc cacccccctgg ctgtgactgc tgtaagatgg gggtatagag gctgggcaat 480
tcccaccccc tgttgtatag ttggactatg ttataacgca caaaagagag ctgaccccag 540
ggggagccag agggtgatgg gttccttgcc tccctttcct tcccctttct gcccaagctt 600
gtgctgcagt tgaacctctt cctgggggtg ggagtaggta aggggtgggt gaggccccaa 660
acccctctct ggtagggaac cgtggggatg aagatgaagc ttatatgcag ttctcttcta 720
ggggctgtgg gcaaagggca ttttgtaatt aatattttca agaatcagat gtctggagtg 780
taggggtggg cttggtggtg gtggacgggc gggcctgctg gagggggagc ttggtcgctg 840
ttgtgatttt aggtttgttt ttgttttgtt ttgaatttgg ggggttgtgg attgttgggg 900
gtagggagat tttttttttt taaagctgct tcctcaactg tttcaagctg caaatgttta 960
agagaataac agcccccact cccacaggaa ccgctgtaat taaatcagac agtaggaaga 1020
ctgggctgct gccctcaaag ccacagccct tggatgttcc ttttccgaga gcagaaggtc 1080
taggctacag ggagggggag attggctccc gtgagtcagg ctgtgtttgg ggcttgggcc 1140
ctgggactgg gaaaagggga tggggcagac tttgtaagca tatgctaggt atccgatagt 1200
cctgtagaat ttagtgaaga aaccttatac agtttttaat ttttatataa actataactc 1260
agacccaagc tacaaggttg gaattttggt tggttttttt tttaagtacc ctgcctgtat 1320
aattgcatca gaatccccca ccccaccccc cgcccccgtg tttgtatttt gggttggttt 1380
acactcgcac atactcagtt ttcagttttc ccctttacag tcttctcccc tcacctccag 1440
gaccctcccc ctttttaaaa aataaatcgc tgacaagtgt gaaaaaaaaa aaaaaaaaa 1499

<210> SEQ ID NO 62
<211> LENGTH: 974
<212> TYPE: DNA
<213> ORGANISM: Homo sapiens
<220> FEATURE:
<221> NAME/KEY: SITE
<222> LOCATION: (563)
<223> OTHER INFORMATION: n equals a,t,g, or c

<400> SEQUENCE: 62
gtcggggtgg ggtaggctgg gggtgagccc ttaactctta gaagggtggg gtgtggggca 60
gaaggagcag atgcctggat ttgagggtgc aggagatggg ctggtgcaga cgtggggcct 120
cctggctgca ggggccggca gtgaagaggt tagctcccag cccaggcagg gcataaattt 180
ggggcacagc tcccactctc aggacctgcc cgtcacaatg gccgtaggga agttcctgct 240
gggctctctg ctgctcctgt ccctgcagct gggacagggc tggggccccg atgcccgtgg 300
ggttcccgtg gccgatggag agttctcgtc tgaacaggtg gcaaaggctg gagggacctg 360
gctgggtaag gacttccagg gaccctctgt gacttcccaa ctttccccag ccctgaccct 420
gctcactgtc agcgcccttc cctcccacag gcacccaccg ccccccttgcc cgcytgcgcc 480 gagccctgtc tggtccatgc cagctgtgga gcctgaccct gtccgtggca gagctaggcc 540
tgggctacgc ctcataggag aangtcatct tccgctactg cgccggcagc tgccccccgtg 600 gtgcccgcac ccagcatggs ctggcgctgg cccggctgca gggccagggc cgarcccacg 660
gcgggccctg ctgccggccc actcgctaca ccgacgtggc cttcctcgac gaccgccacg 720
ctggcagcgg ctgccccagc tctcggcggc tctgcggctg tggtggctga gggtgcccgg 780
cctggcaccc agaagctgca gtgctggggg agctcggctg acttatttat tggagacctg 840

-continued gatgcagaga caacgaggag gggagtgggc tggggcgacc agcagtgagt gcaataaagg 900
acaccactct cccggcaaaa aaaaaaaaaa aaaaaaaaaa aaaaaaaaaa aactcgaggg 960
ggggtcccgg tacc 974

<210> SEQ ID NO 63
<211> LENGTH: 872
<212> TYPE: DNA
<213> ORGANISM: Homo sapiens

<400> SEQUENCE: 63
ccacgcgtcc gccgaggtcg gacagcagac tttgtattta tgttcctttt tggtggattc 60
ttaatgaccc tttttggtct gtttgtgagc ttagttttct tgggccaggc ctttacaata 120
atgctcgtct atgtgtggag ccgaaggaac ccctatgtcc gcatgaactt cttcggcctt 180
ctcaacttcc aggccccctt tctgccctgg gtgctcatgg gattttcctt gttgttgggg 240
aactcaatca ttgtggacct tttgggtatt gcagttggac acatatattt tttcttggaa 300
gatgtatttc ccaatcaacc tggtggaata agaattctga aaacaccatc tattttgaaa 360
gctatttttg atacaccaga tgaggatcca aattacaatc cactacctga ggaacggcca 420
ggaggcttcg cctggggtga gggccagcgg cttggaggtt aaagcagcag tgccaataat 480
gagacccagc tgggaaggac tcggtgatac ccactgggat cttttatcct ttgttgcaaa 540
agtgtggaca cttttgacag cttggcagat tttaactcca gaagcacttt atgaaatggt 600
acactgacta atccagaaga catttccaac agtttgccag tggttcctca ctacactggt 660
actgaaagtg taatttctta gagccaaaaa actggagaaa caaatatcct gccacctcta 720
acaagtacat gagtacttga tttttatggt ataaggcaga gccttttctt cctcttcttg 780
atagatgagg ccatggtgta aatggaagtt tcagagagga caaaataaaa cggaattcca 840
tttttctctc actgtaaaaa aaaaaaaaaa aa 872

<210> SEQ ID NO 64
<211> LENGTH: 1208
<212> TYPE: DNA
<213> ORGANISM: Homo sapiens
<220> FEATURE:
<221> NAME/KEY: SITE
<222> LOCATION: (1038)
<223> OTHER INFORMATION: n equals a,t,g, or c
<221> NAME/KEY: SITE
<222> LOCATION: (1148)
<223> OTHER INFORMATION: n equals a,t,g, or c

<400> SEQUENCE: 64
gggggtgggc acgacggtgg ggaagatggc gtaccagagc ttgcggctgg agtacctgca 60
gatcccaccg gtcagccgcg cctacaccac tgcctgcgtc ctcaccaccg ccgccgtgca 120
gttggaattg atcacacctt ttcagttgta cttcaatcct gaattaatct ttaaacactt 180
tcaaatatgg agattaatca ccaacttctt attttttggg ccagttggat tcaatttttt 240
atttaacatg atttttctat atcgttactg tcgaatgcta gaagaaggct ctttccgagg 300
tcggacagca gactttgtat ttatgttcct ttttggtgga ttcttaatga cccttttttgg 360 tctgtttgtg agcttagttt tcttgggcca ggcctttaca ataatgctcg tctatgtgtg 420
gagccgaagg aacccctatg tccgcatgaa cttcttcggc cttctcaact tccaggcccc 480
ctttctgccc tgggtgctca tgggattttc cttgttgttg gggaactcaa tcattgtgga 540
ccttttgggt attgcagttg gacacatata ttttttcttg gaagatgtat ttcccaatca 600

-continued

```
acctggtgga ataagaattc tgaaaacacc atctattttg aaagctattt ttgatacacc    660
agatgaggat ccaaattaca atccactacc tgaggaacgg ccaggaggct tcgcctgggg    720
tgagggccag cggcttggag gttaaagcag cagtgccaat aatgagaccc agctgggaag    780
gactcggtga tacccactgg gatcttttat cctttgttgc aaaagtgtgg acacttttga    840
cagcttggca gattttaact ccagaagcac tttatgaaat ggtacactga ctaatccaga    900
agacatttcc aacagtttgc cagtggttcc tcactacact ggtactgaaa gtgtaatttc    960
ttagagccaa aaaactggag aaacaaatat cctgccacct ctaacaagta catgagtact   1020
tgatttttat ggtataangc agagcctttt cttcctcttc ttgatagatg aggccatggt   1080
gtaaatggaa gtttcagaga ggacaaaata aaacggaatt ccatttttct ctcactgtaa   1140
aagctttngt gtgtgatctt ttaaattctg ataatgtatt gtaaccctcc tgcgtagatc   1200
tgagctca                                                             1208
```

<210> SEQ ID NO 65
<211> LENGTH: 1167
<212> TYPE: DNA
<213> ORGANISM: Homo sapiens
<220> FEATURE:
<221> NAME/KEY: SITE
<222> LOCATION: (432)
<223> OTHER INFORMATION: n equals a,t,g, or c

<400> SEQUENCE: 65

```
gggggtgggg caggcgacgg tggggaagat ggcgtaccag agcttgcggc tggagtacct     60
gcagatccca ccggtcagcc gcgcctacac cactgcctgc gtcctcacca ccgccgccgt    120
gcagttggaa ttgatcacac cttttcagtt gtacttcaat cctgaattaa tctttaaaca    180
ctttcaaata tggagattaa tcaccaactt cttatttttt gggccagttg gattcaattt    240
tttatttaac atgattttc tatatcgtta ctgtcgaatg ctagaagaag gctctttccg    300
aggtcggaca gcagactttg tatttatgtt cctttttggt ggattcttaa tgaccctttt    360
tggtctgttt gtgagcttag ttttcttggg ccaggccttt acaataatgc tcgtctatgt    420
gtggagccga angaacccct atgtccgcat gaacttcttc ggccttctca acttccaggc    480
ccctttctg ccctgggtgc tcatgggatt ttccttgttg ttggggaact caatcattgt    540
ggaccttttg ggtattgcag ttggacacat atatttttc ttggaagatg tatttcccaa    600
tcaacctggt ggaataagaa ttctgaaaac accatctatt ttgaaagcta tttttgatac    660
accagatgag gatccaaatt acaatccact acctgaggaa cggccaggag gcttcgcctg    720
gggtgagggc cagcggcttg gaggttaaag cagcagtgcc aataatgaga cccagctggg    780
aaggactcgg tgatacccac tgggatcttt tatcctttgt tgcaaaagtg tggacacttt    840
tgacagcttg gcagatttta actccagaag cactttatga aatggtacac tgactaatcc    900
agaagacatt tccaacagtt tgccagtggt tcctcactac actggtactg aaagtgtaat    960
ttcttagagc caraaaactg gagaaacaaa tatcctgcca cctctaacaa gtacatgagt   1020
acttgatttt tatggtataa gcagagcctt ttcttcctct tcttgataga tgaggccatg   1080
gtgtaaatgg aagtttcaga gaggacaaaa taaaacggaa ttccattttt ctctcactgt   1140
aaaaaaaaaa aaaaaaaggg cggccgc                                       1167
```

<210> SEQ ID NO 66
<211> LENGTH: 2311
<212> TYPE: DNA

-continued

<213> ORGANISM: Homo sapiens

<400> SEQUENCE: 66

```
ccacgcgtcc gcggaaaggg taaaaagatt tttattcata tgcatgagat tattcagata     60
gatggtcata tataccagtg ccttgaatgc aagcaaaact tctgtgaaaa cttagctctt    120
attatgtgtc agagaaccca tactggggag aaaccttata aatgtgatat gtgtgagaaa    180
acctttgtcc aaagctcaga tcttacttca caccagagga tccacaatta cgagaaacct    240
tataaatgta gcaaatgtga gaagagcttt tggcatcact tagcgctttc aggacatcag    300
agaacacatg caggtaaaaa attctataca tgtgacattt gtggcaagaa ttttggtcag    360
agttctgatc tgcttgtcca ccagcgaagc catactggcg agaaaccata tctatgtagt    420
gagtgtgaca aatgcttcag tagaagtaca aacctcataa ggcatcgaag aactcacaca    480
ggtgagaaac catttaagtg tctcgatgtg aaaaagcttt tagtgggaaa tcagatctta    540
ttagccacca gagaactcac actggggaaa ggccctacaa atgtaataag tgtgagaaaa    600
gttaccgaca ccgttcagcc ttcattgtac ataaaagagt tcatactggg gagaagccct    660
ataagtgtgg agcctgtgaa aaatgctttg gccagaaatc agaccttatc tgtgcaccag    720
agagtccaca caggtgagaa gccgtataaa tgcctggaat gtatgagaag ttttactcgg    780
agtgccaacc taattaggca ccaggcaact cacactcaca cttttaaatg ccttgaatat    840
gaaaaaagct ttaactgtag ctcaagatct aattgtacat cagtagaatt cacatggaag    900
agaacaccca catcagtggt ctggcgttta gagagtggct tcctcctacg aaatggactt    960
tgttgcccaa ccagaaaatg agaactccta cagaggagca tacactatta aacaccctgt   1020
atgtgataaa agcttccacc agagttcagc ctttcttcaa catcagacag tacacattgg   1080
tgaaaaaccg tttgtctgta atgtgagtga aaaaggtctt gagcttagcc ctccccatgc   1140
gtcagaagcc tcacagatgt cttgaccagg cgagaagctg taataccaat attaaaaatt   1200
atttatgtat cagagaactc attaagatga ggacaaatct cagactttgc tcagagctca   1260
gaattcagtg gggaccagag agcctgcaat tggaaatatg agaaattctt tgcccagaga   1320
gctgcccgta acagaacact tcatcctcac tccaacgaga aatctacaga tgcccagagg   1380
ttttgaaaac ttaccgtctg agctcaaatt tgatcactca caagaggatt catacaagtg   1440
ggaaacctta gaaatgcact gagtgtgaga gagctttcta ctaatgctca gcccttctcg   1500
ttgtaagaga attcacaccg gagaacaact ttttaaatgc cttcagtgtc agttgtgctg   1560
cagacagtat gaacatctca ttggacctca gaaaacccac cctggggaga agccccagca   1620
agtgtgaaaa aagcttctaa caaaactctg acttacccat cagagaagcc atactggtga   1680
aaaattgtat atttgtctta agtatggcaa aagcattcgt tggagagcct tacttgggtt   1740
tgcacccaaa aaaaaaaaaa cccaatctga ggaaagactg caagtgtctg aatgaagagt   1800
gcttgtcaat gatcaactct tgtggtacat cagggaactc acataggtga aaaaacccat   1860
acttaccttg agtctgagaa aacctttggt agaagctcct gtcttatcag gccccaaaaa   1920
acctgttctg cagtgagaga tttaattgtg ggtgagaatc tatgtacata taatatgtat   1980
gagaagactg ttctcatagt tagttgactc atatggtaga gaggacttta catgaaatca   2040
gtatgaaaat agttttttag atacccagaa gcttgttctg ggagaagcta gggtgggtca   2100
gagtagacct gatgggtaac tcaggtaaag atgcttttct tttatctgaa ctacttaatg   2160
attgctttac ttttactttt taaaaaattc agaaatccaa taaaggaaag gacggtaacc   2220
ttatgataga aaaaaaaaaa aaaaaaaaaa aaggaaaaaa ggaaaaaaaa aaaaaaaaaa   2280
```

-continued aaaaaaaaaa aaaaaaaaaa aaaaaaaaaa a 2311

<210> SEQ ID NO 67
<211> LENGTH: 1049
<212> TYPE: DNA
<213> ORGANISM: Homo sapiens

<400> SEQUENCE: 67
ggcacgagga cagaaagaga tgaactctta aaggacttgc aacaaagcat tgccagagaa 60
cctagtgctc cttcaattcc tacacctgcg tatcagtcct taccagcagg aggacatgca 120
ccaactcctc caactccagc gccaagaacc atgccgccta ctaagcccca gcccccagcc 180
aggcctccac cacctgtgct tccagcaaat cgagctcctt ctgctactgc tccatctcca 240
gtgggggctg ggactgctgc gccagctcca tcacaaacgc ctggctcagc tcctcctcca 300
caggcgcagg gaccacccta tcccacctat ccaggatatc ctgggtattg ccaaatgccc 360
atgcccatgg gctataatcc ttatgcgtat ggccagtata atatgccata tccaccagtg 420
tatcaccaga gtcctggaca ggctccgtac ccgggacccc agcagccttc ataccccttc 480
cctcagcccc cacagcagtc ttactatcca cagcagtaat atgtctgctc agcagctcag 540
ctgattcaga tcagagggaa agaaatacca accctgcaat aagtgtacta aactctacgc 600
tctggttaat gtaatgtact ctcctggact gaatgcagtg tataatttct gtctacagct 660
agaagctgtg ccccagttcc acatttgatt acacatgtga gatttgctgc tgttgcagta 720
taaacactag gtataatagg atttgaaatt gcattacagt tcataaaaat tgaaaatgag 780
aaattaaacc tgcaagtgaa acatttgaaa cgattatact ttctacataa gacatggttg 840
ggacatcaga tacttacaaa gatggtttaa gtatggatac tagagaaaat taagttttct 900
ttctctttgg tttattgatt tggtttaatt tccttatgct attttgcata atcaaggcac 960
tgtaaatctt ataattttaa aataaattac ttaagaacaa aaaaaaaaaa aaaaaaaaaa 1020
aaaaaaaaaa aaaaaaaaaa aaaaaaagg 1049

<210> SEQ ID NO 68
<211> LENGTH: 3299
<212> TYPE: DNA
<213> ORGANISM: Homo sapiens

<400> SEQUENCE: 68
gcgttggagc tcccggaaag ttgccggacc cggaacgcag gcggagcgca agtctgtcag 60
ccagtcagtc cgccagtccg ccagcccagt acctctctct cctcggccct cgtaagctgt 120
ccgcggtctg tttggcccga acggcggcgg aggcgctgat catggcgaca ttcatctcgg 180
tgcagctgaa aaagacctca gaggtggacc tggccaagcc gctggtgaag ttcatccagc 240
agacttaccc aagcggcggg gaagagcagg cccagtactg ccgcgcggcg gaggagctca 300
gcaagctgcg ccgcgccgca gtcggtcgtc cgctggacaa gcacgagggc gcgctcgaga 360
cgctcctgag atattatgat cagatttgtt ctattgaacc caaattccca ttttctgaaa 420
atcagatctg cttgacattt acctggaagg atgctttcga taaaggttca ctttttggag 480
gctctgtaaa actggctctt gcaagcttag gatatgaaaa gagctgtgtg ttgttcaatt 540
gtgcagcctt agctagccaa attgcagcag aacagaacct ggataatgat gaaggattga 600
aaatcgctgc taaacattac cagtttgcta gtggtgcctt tttacatatt aaagagacgg 660
ttttatctgc cttaagtcga gagccgaccg tggacatatc tccagatact gttgggaccc 720

-continued

```
tcagtcttat tatgctggca crggctcaag aagtattttt tttaaaagcc acaagagata    780
aaatgaaaga tgccatcata gctaaattgg ctaatcaggc tgcagattat tttggtgatg    840
ctttcaaaca gtgtcaatac aaagatactc tccccaagga ggtgttccct gtcttggctg    900
caaagcactg tatcatgcag gccaatgctg agtaccatca gtctatcctg gcaaaacagc    960
agaagaaatt tggagaagaa attgcaaggt tacagcatgc agcagaactg attaaaacag   1020
tggcatctcg ctatgatgaa tatgttaatg tgaaggattt ttctgacaaa atcaatcgtg   1080
cccttrctgc agcaaagaag gataatgact tcatttatca tgatcgagtt ccagacctta   1140
aagatctaga tcctattggc aaagccacac ttgtgaaatc taccccggtc aatgtaccca   1200
tcagtcagaa atttactgat ctgtttgaga agatggttcc cgtgtcagta cagcagtctt   1260
tggctgccta taatcagagg aaagccgatt tggttaacag atcaattgct cagatgagag   1320
aagccaccac tttggcaaat ggggtgctag cttcccttaa tcttccagca gcaattgaag   1380
atgtgtctgg agacactgta cctcagtcta tattgactaa atccagatct gtgattgaac   1440
agggaggcat ccagactgtt gatcagttga ttaaagaact gcctgaatta ctgcaacgaa   1500
atagagaaat cctagatgag tcattaaggt tgttggatga agaagaagca accgataatg   1560
atttaagagc aaaatttaag gaacgttggc aaaggacacc atccaatgaa ctgtataagc   1620
ctttaagagc agagggaacc aacttcagaa cagttttaga taaagctgtg caggcagatg   1680
gacaagtgaa agaatgttac cagtctcatc gtgacaccat cgtgcttttg tgtaagccag   1740
agcctgagct gaatgctgcc atcccttctg ctaatccagc aaagaccatg cagggcagtg   1800
aggttgtaaa tgtcttaaaa tccttattgt caaatcttga tgaagtaaag aaggaaagag   1860
agggtctgga gaatgacttg aaatctgtga attttgacat gacaagcaag tttttgacag   1920
ccctggctca agatggtgtg ataaatgaag aagctctttc tgttactgaa ctagatcgag   1980
tctatggagg tcttacaact aaagtccaag aatctctaaa gaaacaggag ggacttctta   2040
aaaatattca ggtctcacat caggaatttt caaaaatgaa acaatctaat aatgaagcta   2100
acttaagaga agaagttttg aagaatttag ctactgcata tgacaacttt gttgaacttg   2160
tagctaattt gaaggaaggc acaaagtttt acaatgagtt gactgaaatc ctggtcaggt   2220
tccagaacaa atgcagtgat atagtttttg cacggaagac agaaagagat gaactcttaa   2280
aggacttgca acaaagcatt gccagagaac ctagtgctcc ttcaattcct acacctgcgt   2340
atcagtcctc accagcagga ggacatgcac caactcctcc aactccagcg ccaagaacca   2400
tgccgcctac taagccccag cccccagcca ggcctccacc acctgtgctt ccagcaaatc   2460
gagctccttc tgctactgct ccatctccag tgggggctgg gactgctgcg ccagctccat   2520
cacaaacgcc tggctcagct cctcctccac aggcgcaggg accaccctat cccacctatc   2580
caggatatcc tgggtattgc caaatgccca tgcccatggg ctataatcct tatgcgtatg   2640
gccagtataa tatgccatat ccaccagtgt atcaccagag tcctggacag gctccrtacc   2700
cgggacccca gcagccttca taccccttcc ctcagccccc acagcagtct tactatccac   2760
agcagtaata tgtctgctca gcagctcagc tgattcagat cagagggaaa gaaataccaa   2820
ccctgcaata agtgtactaa actctacgct ctggttaatg taatgtactc tcctggactg   2880
aatgcagtgt ataatttctg tctacagcta gaagctgtgc cccagttcca catttgatta   2940
cacatgtgag atttgctgct gttgcagtat aaacactagg tataatagga tttgaaattg   3000
cattacagtt cataaaaatt gaaaatgaga aattaaacct gcaagtgaaa catttgaaac   3060
gattatactt tctacataag acatggttgg gacatcagat acttacaaag atggtttaag   3120
```

-continued tatggatact agagaaaatt aagttttctt tctctttggt ttattgattt ggtttaattt 3180
ccattatgct attttgcata atcaaggcac tgtaaatctt ataattttaa aataaattac 3240
ttaagaacaa aaaaaaaaaa aaaaaaaaaa aaaaaaaaaa aaaaaaaaaa aaaaaaagg 3299

<210> SEQ ID NO 69
<211> LENGTH: 1772
<212> TYPE: DNA
<213> ORGANISM: Homo sapiens

<400> SEQUENCE: 69
ccacgcgtcc gaaaccggaa gcggcggctg tccgcggtgc cggctggggg cggagaggcg 60
gcggtgggct ccctggggtg tgtgagcccg gtgatggagc cgggcccgac agccgcgcag 120
cggaggtgtt cgttgccgcc gtggctgccg ctggggctgc tgctgtggtc ggggctggcc 180
ctgggcgcgc tccccttcgg cagcagtccg cacagggtct tccacgacct cctgtcggag 240
cagcagttgc tggaggtgga ggacttgtcc ctgtccctcc tgcagggtgg agggctgggg 300
cctctgtcgc tgcccccgga cctgccggat ctggatcctg agtgccggga gctcctgctg 360
gacttcgcca acagcagcgc agagctgaca gggtgtctgg tgcgcagcgc ccggcccgtg 420
cgcctctgtc agacctgcta ccccctcttc caacaggtcg tcagcaagat ggacaacatc 480
agccgagccg cggggaatac ttcagagagt cagagttgtg ccagaagtct cttaatggca 540
gatagaatgc aaatagttgt gattctctca gaatttttta ataccacatg gcaggaggca 600
aattgtgcaa attgtttaac aaacaacagt gaagaattat caaacagcac agtatatttc 660
cttaaatcta tttaatcaca ccctgacctg ctttgaacat aaccttcagg ggaatgcaca 720
tagtctttta cagacaaaaa attattcaga agtatgcaaa aactgccgtg aagcatacaa 780
aactctgagt agtctgtaca gtgaaatgca aaaaatgaat gaacttgaga ataaggctga 840
acctggaaca catttatgca ttgatgtgga agatgcaatg aacatcactc gaaaactatg 900
gagtcgaact ttcaactgtt cagtcccttg cagtgacaca gtgcctgtaa ttgctgtttc 960
tgtgttcatt ctctttctac ctgttgtctt ctaccttagt agctttcttc actcagagca 1020
aaagaaacgc aaactcattc tgcccaaacg tctcaagtcc agtaccagtt ttgcaaatat 1080
tcaggaaaat tcaaactgag acctacaaaa tggagaattg acatatcacg tgaatgaatg 1140
gtggaagaca caacttggtt tcagaaagaa gataaactgt gatttgacaa gtcaagctct 1200
taagaaatac aaggacttca gatccatttt taaataagaa ttttcgattt ttctttcctt 1260
ttccacttct ttctaacaga tttggatatt tttaatttcc aggcatagca atgttatcta 1320
ttttaatgtg tatttgtcac aataacagaa catgcaagaa caatcattat tttattttat 1380
aggcatttga ttactattct agacttctgg tatcttctta ctaacataag tatctcaagt 1440
agaaaagttt ttgaaaacta acatttaaaa attaatcagt tacagtaaag actttgaaaa 1500
agaaatgtac ttgttaggaa gtagcttaat taccccccat tgcagtatta ttgttatata 1560
tatagttaat atgttgtaca tcacaataat atataattca gtctctagtt tccctagagt 1620
catttttgaa accactgatt gcaaacctcc ctgacaattt ttaaaagtag taagccacat 1680
tacatttatc tttgtaaaaa gatttatggt aactggtttc ttacttgact tttataaata 1740
gtattttaca tcttaaaaaa aaaaaaaaaa aa 1772

<210> SEQ ID NO 70
<211> LENGTH: 1121
<212> TYPE: DNA

-continued

<213> ORGANISM: Homo sapiens

<400> SEQUENCE: 70
ggcacgagca aaagtggagt cctagatgaa tctaccattg ctacgatact ccgagaagta 60
ctggaagggc tggaatatct gcataaaaat ggacagatcc acagagatgt gaaagctgga 120
aacattcttc ttggagaaga tggctcagta cagattgcag actttggggt tagtgctttt 180
ttagcaactg gtggtgatat tacccgaaat aaagtgagaa agacctttgt tggcacccct 240
tgttggatgg cacctgaagt tatggaacag gtccgtggtt atgatttcaa agctgatatt 300
tggagttttg gaattacagc aattgaattg gctacagggg cggctcctta tcataaatat 360
ccaccaatga aggttttaat gctgacactg cagaacgatc ctccttcttt ggaaactggt 420
gttcaagata aagaaatgct gaaaaaatat ggaaaatcat ttagaaaaat gatttcattg 480
tgccttcaaa aagatccaga aaaaagacca acagcagcag aactattaag gcacaaattt 540
ttccagaaag caaagaataa agaatttctt caagaaaaaa cattgcagag agcaccaacc 600
atttctgaaa gagcaaaaaa ggttcggaga gtaccaggtt cctgccccta aagaactcta 660
tcttttgaga ttagcaacta acagtgtgag cccactaata ggatgtgaaa gttgtcaaaa 720
tcaagttctg gtcattgtgt taaaaatcct aacaaataga gctggggaag gccgtgaaag 780
gacgattttc atgcacagat gtctgataat gaggactatc attaaaagac tgcacaaaac 840
cacaccttgc acaaaggcca tcacaacctg acacacacaa aaaatacttc tatgaggaca 900
tttgcccagc aactccctgt ccaatgtcca actggcaaca tccttgttat tgatccttgt 960
agccaaggat aattctctca aaacaatcat ttttgcttta aaaaccgttg tcttccttga 1020
cctccctgta tatgcacata gtttactgtg gcacttgtat tcttattgca atgcctactc 1080
ctgaataaac atcattttct ttcaaaaaaa aaaaaaaaaa a 1121

<210> SEQ ID NO 71
<211> LENGTH: 938
<212> TYPE: DNA
<213> ORGANISM: Homo sapiens

<400> SEQUENCE: 71
ggcacgagag aagttgtcct caactatcag taggttttta gagatgaaca tcactcgaaa 60
actatggagt cgaactttca actgttcagt cccttgcagt gacacagtgc ctgtaattgc 120
tgtttctgtg ttcattctct ttctacctgt tgtcttctac cttagtagct ttcttcactc 180
agagcaaaag aaacgcaaac tcattctgcc caaacgtctc aagtccagta ccagttttgc 240
aaatattcag gaaaattcaa actgagacct acaaaatgga gaattgacat atcacgtgaa 300
tgaatggtgg aagacacaac ttggtttcag aaagaagata aactgtgatt tgacaagtca 360
agctcttaag aaatacaagg acttcagatc catttttaaa taagaatttt cgatttttct 420
ttccttttcc acttctttct aacagatttg gatattttta atttccaggc atagcaatgt 480
tatctatttt aatgtgtatt tgtcacaata acagaacatg caagaacaat cattatttta 540
ttttataggc atttgattac tattctagac ttctggtatc ttcttactaa cataagtatc 600
tcaagtagaa aagtttttga aaactaacat ttaaaaatta atcagttaca gtaaagactt 660
tgaaaaagaa atgtacttgt taggaagtag cttaattacc ccccattgca gtattattgt 720
tatatatata gttaatatgt tgtacatcac aataatatat aattcagtct ctagtttccc 780
tagagtcatt tttgaaacca ctgactgcaa acctccctga caatttttaa aagtagtaag 840
ccacattaca tttatctttg taaaaagatt tatggtaact ggtttcttac ttgactttta 900

-continued taaatagtat tttacatctt aaaaaaaaaa aaaaaaaa 938

<210> SEQ ID NO 72
<211> LENGTH: 943
<212> TYPE: DNA
<213> ORGANISM: Homo sapiens

<400> SEQUENCE: 72
gcgtccgggt cactacatat tcaggccaaa aaaatgccta caactacaga acagcctgtc 60
accaccacat tccctgtaac cacgggttta aaacccaccg tggccttgtg tcaacaaaag 120
tgtagacgga cggggactct ggagggcaat tattgttcaa gtgactttgt attagccggc 180
actgttatca caaccatcac tcgcgatggg agtttgcacg ccacagtctc gatcatcaac 240
atctacaaag agggaaattt ggcgattcag caggcgggca agaacatgag tgccaggctg 300
actgtcgtct gcaagcagtg ccctctcctc agaagaggtc taaattacat tattatgggc 360
caagtaggtg aagatgggcg aggcaaaatc atgccaaaca gctttatcat gatgttcaag 420
accaagaatc agaagctcct ggatgcctta aaaaataagc aatgttaaca gtgaactgtg 480
tccatttaag ctgtattctg ccattgcctt tgaaagatct atgttctctc agtagaaaaa 540
aaaatactta taaaattaca tattctgaaa gaggattccg aaagatggga ctggttgact 600
cttcacatga tggaggtatg aggcctccga gatagctgag ggaagttctt tgcctgctgt 660
cagaggagca gctatctgat tggaaacctg ccgacttagt gcggtgatag gaagctaaaa 720
gtgtcaagcg ttgacagctt ggaagcgttt atttatacat ctctgtaaaa ggatatttta 780
gaattgagtt gtgtgaagat gtcaaaaaaa gattttagaa gtgcaatatt tatagtgtta 840
tttgtttcac cttcaagcct ttgccctgag gtgttacaat cttgtcttgc gttttctaaa 900
tcaatgctta ataaaatatt tttaaaggaa aaaaaaaaaa aaa 943

<210> SEQ ID NO 73
<211> LENGTH: 1810
<212> TYPE: DNA
<213> ORGANISM: Homo sapiens
<220> FEATURE:
<221> NAME/KEY: SITE
<222> LOCATION: (1803)
<223> OTHER INFORMATION: n equals a,t,g, or c

<400> SEQUENCE: 73
tccacggatt ctctgccaca aggatatgtg gctcagtgtg gtcaagttcc ttccaaagaa 60
cctgcacttg gtctgcgtgg acatgccagg acatgagggc accacccgct cctccctgga 120
tgacctgtcc atagatgggc aagttaagag gatacaccag tttgtagaat gcctgaagct 180
gaacaaaaaa cctttccacc tggtaggcac ctccatgggt ggccaggtgg ctggggtgta 240
tgctgcttac tacccatcgg atgtctccag cctgtgtctc gtgtgtcctg ctggcctgca 300
gtactcaact gacaatcaat ttgtacaacg gctcaaagaa ctgcagggct ctgccgccgt 360
ggagaagatt cccttgatcc cgtctacccc agaagagatg agtgaaatgc ttcagctctg 420
ctcctatgtc cgcttcaagg tgccccagca gatcctgcaa ggccttgtcg atgtccgcat 480
ccctcataac aacttctacc gaaagttgtt tttggaaatc gtcagtgaga agtccagata 540
ctctctccat cagaacatgg acaagatcaa ggttccgacg cagatcatct gggggaaaca 600
agaccaggtg ctggatgtgt ctggggcaga catgttggcc aagtcaattg ccaactgcca 660
ggtggagctt ctggaaaact gtgggcactc agtagtgatg gaaagaccca ggaagacagc 720
caagctcata atcgactttt tagcttctgt gcacaacaca gacaacaaca agaagctgga 780

-continued ctgaggcccc gactgcagcc tgcattctgc acacagcatc tgctcccatc ccccaagtct 840
gacgcagcca ccactctcag ggatcctgcc ccaaatgcgg tcggagcgcc agtgaccctg 900
aggaagcccg tcccttatcc ctggtatcca cggttcccca gagctttggg gaccacgcga 960
aaacctccaa gatatttttc acaaaataga aactcatatg gaacaaaata agaaacccca 1020
gccatgaaat ctaccatgaa gtcttcaagt tcatgtcact gacaagcttg tgcaaagcag 1080
ccaccttgga ccataattaa atcaaggaca ttttctttga gacattcctt atagttggag 1140
actcaagata tttttgttgc atcaggtgta ttcccttgca tgggcagtgg cttttatagg 1200
agcattagtc ctcattcgct gaaccctgtt gtttaggtct aatttaagtt ttacatagag 1260
acccatgtat gactgcagcc cattggctgc aagaccaggg aggaaagtgg caagctgtag 1320
aaaatgttta cacgcatgga ggggcattgc tccagccctc agagcgtccg gagcagcagg 1380
rtacatgggt gggaggttca ttcagcaccc accagtcagg tatgttctga gtgaacccac 1440
agcagtcgca gaatgagcac ctggcagggt gggtttccta ggaataattt attattttta 1500
aaaataggcc taataaagca ataatgttct agacatctgt ctaagtaatc agactcaggt 1560
tccacacaca agcaacaact cgtgggcctc ttttctattt caatgtgcta ctaagaaccc 1620
ttggatgtaa catactagtt agttaatgaa ttctgtgaat tctgtgaaga gtaatgtgat 1680
tgaaaataag tctaaacagc tgtaaaagtg accacaatga catgaaataa atttaataag 1740
tctagatcag caaaaaaaaa aaaaaaaaaa aaaaaaaaaa aaaaaaaaaa aaaaaaaaaa 1800 aanaaaaaaa 1810

<210> SEQ ID NO 74
<211> LENGTH: 1543
<212> TYPE: DNA
<213> ORGANISM: Homo sapiens

<400> SEQUENCE: 74
agctcctgtg caagaacatg aaacacctgt ggttcttcct cctgctggtg gcagctccca 60
gatgggtcct gtcccaggtg cagctgcagg agtcgggccc aggactggtg aagccttcag 120
agaccctgtc cctcacctgc actgtctctg gtggctccat cagcagtggt ggtcactact 180
ggagctggat ccgccagcac ccagggaagg gcctggagtg gattgggtac atctcttaca 240
atggggtcac ctactacaat ccgtccctca agagtcgagt taccatatct gtagacacgt 300
ctcagaacca gttctccctg aggctgagct ctgtgactgc cgcggacacg gccgtctatt 360
actgtgcgaa agatcatcga gcgaccagag acgggtacca gctggaatac cgaggctttg 420
actactgggg ccagggaatc ctggtcaccg tctcctcagc atccccgacc agccccaagg 480
tcttcccgtt gagcctcgac agcaccccccc aagatgggaa cgtggtcgtc gcatgcctgg 540
tccagggctt cttcccccag gagccactca gtgtgacctg gagcgaaagc ggacagaacg 600
tgaccgccag aaacttccca cctagccagg atgcctccgg ggacctgtac accacgagca 660
gccagctgac cctgccggcc acacagtgcc cagacggcaa gtccgtgaca tgccacgtga 720
agcactacac gaatcccagc caggatgtga ctgtgccctg cccagttccc ccacctcccc 780
catgctgcca cccccgactg tcgctgcacc gaccggccct cgaggacctg ctcttaggtt 840
cagaagcgaa cctcacgtgc acactgaccg gcctgagaga tgcctctggt gccaccttca 900
cctggacgcc ctcaagtggg aagagcgctg ttcaaggacc acctgagcgt gacctctgtg 960
gctgctacag cgtgtccagt gtcctgcctg gctgtgccca gccatggaac catggggaga 1020

-continued ccttcacctg cactgctgcc caccccgagt tgaagacccc actaaccgcc aacatcacaa 1080
aatccggaaa cacattccgg cccgaggtcc acctgctgcc gccgccgtcg gaggagctgg 1140
ccctgaacga gctggtgacg ctgacgtgcc tggcacgtgg cttcagcccc aaggatgtgc 1200
tggttcgctg gctgcagggg tcacaggagc tgccccgcga gaagtacctg acttgggcat 1260
cccggcagga gcccagccag ggcaccacca ccttcgctgt gaccagcata ctgcgcgtgg 1320
cagccgagga ctggaagaag ggggacacct tctcctgcat ggtgggccac gaggccctgc 1380
cgctggcctt cacacagaag accatcgacc gcttggcggg taaacccacc catgtcaatg 1440
tgtctgttgt catggcggag gtggacggca cctgctactg agccgcccgc ctgtccccac 1500
ccctgaataa actccatgct cccccaaaaa aaaaaaaaaa aaa 1543

<210> SEQ ID NO 75
<211> LENGTH: 1806
<212> TYPE: DNA
<213> ORGANISM: Homo sapiens

<400> SEQUENCE: 75
gcgcggtggg tgcggagggg cgtgtgtgcc ggcgcgcgcg ccytggggtg caaaccccga 60
gcgtctacgy tgccatgagg ggcgcgaacg ctgggcgcca ctctgcctgc tgctggctgc 120
cgccacccag ctctcgcggc agcagtcccc agagagacct gttttcacat gtggtggcat 180
tcttactgga gagtctggat ttattggcag tgaaggtttt cctggagtgt accctccaaa 240
tagcaaatgt acttggaaaa tcacagttcc cgaaggaaaa gtagtcgttc tcaatttccg 300
attcatagac ctcgagagtg acaacctgtg ccgctatgac tttgtggatg tgtacaatgg 360
ccatgccaat ggccagcgca ttggccgctt ctgtggcact ttccggcctg gagcccttgt 420
gtccagtggc aacaagatga tggtgcagat gatttctgat gccaacacag ctggcaatgg 480
cttcatggcc atgttctccg ctgctgaacc aaacgaaaga ggggatcagt attgtggagg 540
actccttgac agaccttccg gctcttttaa aaccccccaac tggccagacc gggattaccc 600
tgcaggagtc acttgtgtgt ggcacattgt agccccaaag aatcagctta tagaattaaa 660
gtttgagaag tttgatgtgg agcgagataa ctactgccga tatgattatg tgsctgtgtt 720
taatgscggg gaagtcaacg atgctagaag aattggaaag tattgtggtg atagtccacc 780
tgcgccaatt gtgtctgaga gaaatgaact tcttattcag tttttatcag acttaagttt 840
aactgcagat gggtttattg gtcactacat attcaggcca aaaaaactgc ctacaactac 900
agaacagcct gtcaccacca cattccctgt aaccacgggt ttaaaaccca ccgtggcctt 960
gtgtcaacaa aagtgtagac ggacggggac tctggagggc aattattgtt caagtgactt 1020
tgtattagcc ggcactgtta tcacaaccat cactcgcgat gggagtttgc acgccacagt 1080
ctcgatcatc aacatctaca aagagggaaa tttggcgatt cagcaggcgg gcaagaacat 1140
gagtgccagg ctgactgtcg tctgcaagca gtgccctctc ctcagaagag gtctaaatta 1200
cattattatg ggccaagtag gtgaagatgg gcgaggcaaa atcatgccaa acagctttat 1260
catgatgttc aagaccaaga atcagaagct cctggatgcc ttaaaaaata agcaatgtta 1320
acagtgaact gtgtccattt aagctgtatt ctgccattgc ctttgaaaga tctatgttct 1380
ctcagtagaa aaaaaaatac ttataaaatt acatattctg aaagagsatt ccgaaagatg 1440
ggactggttg actcttcaca tgatggaggt atgaggcctc cgagatagct gagggaagtt 1500
ctttgcctgc tgtcagagga gcagctatct gattggaaac ctgccgactt agtgcggtga 1560
taggaagcta aaagtgtcaa gcgttgacag cttggaagcg tttatttata catctctgta 1620

-continued

```
aaaggatatt ttagaattga gttgtgtgaa gatgtcaaaa aaagatttta gaagtgcaat   1680

atttatagtg ttatttgttt caccttcaag cctttgccct gaggtgttac aatcttgtct   1740

tgcgttttct aaatcaatgc ttaataaaat atttttaaag gaaaaaaaaa aaaaaaaaaa   1800

ctcgag                                                              1806
```

<210> SEQ ID NO 76
<211> LENGTH: 1547
<212> TYPE: DNA
<213> ORGANISM: Homo sapiens

<400> SEQUENCE: 76

```
ggcagagccc agttcatctc attgggactg gttagacagt gggtgcagcc cacagaggga     60

gagcagaagc agggtggggc gttgcctcac ctgggaagcg caaggggttg aggaactccc    120

tcctctagcc aaggcaagcc atgaaggact gtgccgtgag ggacggtgct atctgaccca    180

catactacgc ttttccgatg gttttcacaa cccacagacc aaaagattcc cttgggtgcc    240

tatacaacca gggccctggg tatcaagcat aaaactggat ggccgtttgg ggagacaccg    300

agctggctgc aggagttttt tgtttttttt tgtttttttg ttttttgtac ctcagtggca    360

cctggaatgc cagcaagaca gaactgttca ctcctctgga aagggagctg aagccagggc    420

acccgagtgg tatgctcagc ggatcccacc cccacggagc ccaacaagct aaatccactg    480

gcttgaaact ctcgctgcct gcacagcagt ctgaagttga cctgggatgc tcaagcttgg    540

tgtggggagg ggcatctgcc attactgagg ctttgtaaac aaagctgaca gaaagtttga    600

actgggtgca gaacccaaca cagcatggca aagccgctgt agccagaatc tagagaggca    660

tctctagatt cctcctctct gggcagggca tctctgaaag aaaggtagca gccccagtca    720

ggagcttata gaaaaaactc ccatgtccct gggacagagc acctgggggga aggggcagct    780

gtgggcacag cttcaacaga cttaaacttt cctgcctgct ggctctgaag agaggaacag    840

atctctcacc acagcgctca agatctgcta agggacagac tgcctcttcc agtggattct    900

tgacccccgt gcctctgact gggagacacc ttccagcagg ggacgacaga cacctcaaac    960

aggagaactt cagctggcat ctggcgggtg cctctctgcg acgaagcttc cagaggaagg   1020

atcaggcagc aatatttgct gttctgcagc ctccactgga gatacccagg caaacagggt   1080

ctggaatgga acttcagtaa attccagcag acctgcagaa gaggggcctg actgttagaa   1140

ggaaaactaa caaccagaaa gcaatagcat caacatcaac aaaaaggaca cccaagcaaa   1200

aaccccatcc aaaggtcacc aacatcaaag accaaaggta gataaattca cgaagatgag   1260

gaaaaaccaa cgcaaaaagg ctgaaaattc ccaaaaccag aatgcctctt ctcctccaaa   1320

gtatcacaac tccttgccag taagggaaca aaactggacg gagaatgagt ttgatgaatt   1380

gacagaagta ggcttcagaa ggtgggtaat aacaaactct caagctaaag gagtgtgttt   1440

taacccaatg caaggaagct aagaaccttg ataaaaagtt acaggaacta tcactagaat   1500

accagttatg agaacaacat aaatacctga tggagctgaa gccaagg                 1547
```

<210> SEQ ID NO 77
<211> LENGTH: 1811
<212> TYPE: DNA
<213> ORGANISM: Homo sapiens
<220> FEATURE:
<221> NAME/KEY: SITE
<222> LOCATION: (1804)
<223> OTHER INFORMATION: n equals a,t,g, or c -continued

<400> SEQUENCE: 77
tccacggatt ctctgccaca aggatatgtg gctcagtgtg gtcaagttcc ttccaaagaa 60
cctgcacttg gtctgcgtgg acatgccagg acatgagggc accacccgct cctccctgga 120
tgacctgtcc atagatgggc aagttaagag gatacaccag tttgtagaat gcctgaagct 180
gaacaaaaaa cctttccacc tggtaggcac ctccatgggt ggccaggtgg ctggggtgta 240
tgctgcttac tacccatcgg atgtctccag cctgtgtctc gtgtgtcctg ctggcctgca 300
gtactcaact gacaatcaat ttgtacaacg gctcaaagaa ctgcagggct ctgccgccgt 360
ggagaagatt cccttgatcc cgtctacccc agaagagatg agtgaaatgc ttcagctctg 420
ctcctatgtc cgcttcaagg tgccccagca gatcctgcaa ggccttgtcg atgtccgcat 480
ccctcataac aacttctacc gaaagttgtt tttggaaatc gtcagtgaga agtccagata 540
ctctctccat cagaacatgg acaagatcaa ggttccgacg cagatcatct gggggaaaca 600
agacgcaggt gctggatgtg tctggggcag acatgttggc caagtcaatt gccaactgcc 660
aggtggagct tctggaaaac tgtgggcact cagtagtgat ggaaagaccc aggaagacag 720
ccaagctcat aatcgacttt ttagcttctg tgcacaacac agacaacaac aagaagctgg 780
actgaggccc cgactgcagc ctgcattctg cacacagcat ctgctcccat cccccaagtc 840
tgacgcagcc accactctca gggatcctgc cccaaatgcg gtcggagcgc cagtgaccct 900
gaggaagccc gtcccttatc cctggtatcc acggttcccc agagctttgg ggaccacgcg 960
aaaacctcca agatattttt cacaaaatag aaactcatat ggaacaaaat aagaaacccc 1020
agccatgaaa tctaccatga agtcttcaag ttcatgtcac tgacaagctt gtgcaaagca 1080
gccaccttgg accataatta aatcaaggac attttctttg agacattcct tatagttgga 1140
gactcaagat atttttgttg catcaggtgt attcccttgc atgggcagtg gcttttatag 1200
gagcattagt cctcattcgc tgaaccctgt tgtttaggtc taatttaagt tttacataga 1260
gacccatgta tgactgcagc ccattggctg caagaccagg gaggaaagtg gcaagctgta 1320
gaaaatgttt acacgcatgg aggggcattg ctccagccct cagagcgtcc ggagcagcag 1380
grtacatggg tgggaggttc attcagcacc caccagtcag gtatgttctg agtgaaccca 1440
cagcagtcgc agaatgagca cctggcaggg tgggtttcct aggaataatt tattattttt 1500
aaaaataggc ctaataaagc aataatgttc tagacatctg tctaagtaat cagactcagg 1560
ttccacacac aagcaacaac tcgtgggcct cttttctatt tcaatgtgct actaagaacc 1620
cttggatgta acatactagt tagttaatga attctgtgaa ttctgtgaag agtaatgtga 1680
ttgaaaataa gtctaaacag ctgtaaaagt gaccacaatg acatgaaata aatttaataa 1740
gtctagatca gcaaaaaaaa aaaaaaaaaa aaaaaaaaaa aaaaaaaaaa aaaaaaaaaa 1800
aaanaaaaaa a 1811

<210> SEQ ID NO 78
<211> LENGTH: 1141
<212> TYPE: DNA
<213> ORGANISM: Homo sapiens

<400> SEQUENCE: 78
ggcaagctca gacaccgtgt cctcttgcct gggagagggg aagcagatct gaggacatct 60
ctgtgccagg ccagaaaccg cccacctgca gttccttctc cgggatggac gtggggccca 120
gctccctgcc ccaccttggg ctgaagctgc tgctgctcct gctgctgctg cccctcaggg 180
gccaagccaa cacaggctgc tacgggatcc cagggatgcc cggcctgccc ggggcaccag 240

-continued

```
ggaaggatgg gtacgacgga ctgccggggc ccaaggggga gccaggaatc ccagccattc    300
ccgggatccg aggaccaaag ggcagataca agcagaaatt ccagtcagtg ttcacggtca    360
ctcggcagac ccaccagccc cctgcaccca acagcctgat cagattcaac gcggtcctca    420
ccaacccgca gggagattat gacacgagca ctggcaagtt cacctgcaaa gtccccggcc    480
tctactactt tgtctaccac gcgtcgcata cagccaacct gtgcgtgctg ctgtaccgca    540
gcggcgtcaa agtggtcacc ttctgtggcc acacgtccaa aaccaatcag gtcaactcgg    600
gcggtgtgct gctgaggttg caggtgggcg aggaggtgtg gctggctgtc aatgactact    660
acgacatggt gggcatccag ggctctgaca gcgtcttctc cggcttcctg ctcttccccg    720
actagggcgg gcagatgcgc tcgagcccca cgggccttcc acctccctca gcttcctgca    780
tggacccacc ttactggcca gtctgcatcc ttgcctagac cattctcccc accagatgga    840
cttctcctcc agggagccca ccctgaccca cccccactgc accccctccc catgggttct    900
ctccttcctc tgaacttctt taggagtcac tgcttgtgtg gttcctggga cacttaacca    960
atgccttctg gtactgccat tctttttttt ttttttcaa gtattggaag gggtggggag    1020
atatataaat aaatcatgaa atcaatacat aaaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa    1140
a                                                                    1141
```

<210> SEQ ID NO 79
<211> LENGTH: 990
<212> TYPE: DNA
<213> ORGANISM: Homo sapiens
<220> FEATURE:
<221> NAME/KEY: SITE
<222> LOCATION: (908)
<223> OTHER INFORMATION: n equals a,t,g, or c

<400> SEQUENCE: 79

```
gatggacatg agggtccctg ctcagctcct ggggctcctg ctgctctggc tctcaggtgc     60
cagatgcgac atccagctga cccagtctcc atcctccctg tctgcatctc ttggcgacag    120
cgtcaccatc acttgccagg cgagtcagga catcgccaac tatttgaatt ggtatcagca    180
gaagcccggg aaacccccca aactcgtgat cttcgatgga tctattttac atacaggggt    240
cccatcaagg ttcagtggag gtggatctgg gacacatttc actttcacca tcaacaacct    300
gcagcctgac gatgttgcaa catattcctg tcaacartat aatactttcc ccctcacktt    360
cggcsraggg accaaggtgg aratcaaacg aactgtggct gcaccatctg tcttcatctt    420
cccgccatct gatgagcagt tgaaatctgg aactgcctct gttgtgtgcc tgctgaataa    480
cttctatccc agagaggcca aagtacagtg gaaggtggat aacgccctcc aatcgggtaa    540
ctcccaggag agtgtcacag agcaggacag caaggacagc acctacagcc tcagcagcac    600
cctgacgctg agcaaagcag actacgagaa acacaaagtc tacgcctgcg aagtcaccca    660
tcagggcctg agctcgcccg tcacaaagag cttcaacagg ggagagtgtt agagggagaa    720
gtgcccccac ctgctcctca gttccagcct gacccctcc catcctttgg cctctgaccc    780
tttttccaca ggggacctac ccctattgcg gtcctccagc tcatctttca cctcacccc    840
ctcctcctcc ttggctttaa ttatgctaat gttggaggag aatgaataaa taaagtgaat    900
ctttgcanaa aaaaaaaaaa aaaaaaaaaa aaaaaaaaaa aaaaaaaaaa aaaaaaaaaa    960
aaaaaaaaaa aaaaaaaaaa aaaaaaaaaa                                     990
```

-continued

<210> SEQ ID NO 80
<211> LENGTH: 1297
<212> TYPE: DNA
<213> ORGANISM: Homo sapiens

<400> SEQUENCE: 80
aagctctaat acgactcact atagggaaag ctggtacgcc tgcaggtacc ggtccggaat 60
tcccgggtcg acccacgcgt ccgcactcag acaccgtgtc ctccccacgc gtccggggga 120
agcagatctg aggacatctc tgtgccaggc cagaaaccgc ccacctgcag ttccttctcc 180
gggatggacg tggggcccag ctccctgccc caccttgggc tgaagctgct gctgctcctg 240
ctgctgctgc ccctcagggg ccaagccaac acaggctgct acgggatccc agggatgccc 300
ggcctgcctg ggcaccaggg gaaggatggg tacgacggac tgccggggcc caagggggag 360
ccaggaatcc cagccattcc cgggatccga ggacccaaag ggcagaaggg agaacccggc 420
ttacccggcc atcctgggaa aaatggcccc atgggacccc ctgggatgcc aggggtgccc 480
ggccccatgg gcatccctgg agagccaggt gaggagggca gatacaagca gaaattccag 540
tcagtgttca cggtcactcg gcagacccac cagccccctg cacccaacag cctgatcaga 600
ttcaacgcgg tcctcaccaa cccgcaggag attatgacac gagcactggc aagttcacct 660
gcaaagtccc cggcctctac tactttgtct accacgcgtc gcatacagcc aacctgtgcg 720
tgctgctgta ccgcagcggc gtcaaagtgg tcaccttctg tggccacacg tccaaaacca 780
atcaggtcaa ctcgggcggt gtgctgctga ggttgcaggt gggcgaggag gtgtggctgg 840
ctgtcaatga ctactacgac atggtgggca tccagggctc tgacagcgtc ttctccggct 900
tcctgctctt ccccgactag ggcgggcaga tgcgctcgag acccacgggc cttccacctc 960
cctcagcttc ctgcatggac ccaccttact ggccagtctg catccttgcc tagaccattc 1020
tcccctccag ggagcccacc ctgacccacc cccactgcac cccctcccca tgggttctct 1080
ccttcctctg aacttcttta ggagtcactg cttgtgtggt tcctgggaca cttaaccaat 1140
gccttctggt actgccattc tttttttttt tttttcaagt attggaaggg gtggggagat 1200
atataaataa atcatgaaat caaaaaaaaa aaaaaaaaaa aaaaaaaaaa aaaaaaaaaa 1260
aaaaaaaaaa aaaaaaaaaa aaaaaaaaaa aaaaaaa 1297

<210> SEQ ID NO 81
<211> LENGTH: 941
<212> TYPE: DNA
<213> ORGANISM: Homo sapiens

<400> SEQUENCE: 81
ggcacgagaa acaacatgga catgagggtc cccgctcagc tcctggggct cctgctactc 60
tggctccgag gtgccaggtg tgatatgcag atgacccagt ctccatcctc cctgtctgca 120
tctgttggag acagagtcac catcacttgc cggacaagtc agagcattgg caaattttta 180
aattggtatc aacaaaaacc agggcaagcc cctaagctcc tgatctctgg tgcatccatt 240
ttgcaaactg gggtcccctc aagattcagt ggcagtggat ctgccacata tttcactctc 300
accatcaatg acctacaccc tgaagattct gcaacttatt actgtcaaca ggattacact 360 acccccctttt tcggccaagg gaccaaggtt gaaatcaagc gaactgtggc tgcaccatct 420
gtcttcatct tcccgccatc tgatgagcag ttgaaatctg gaactgcctc tgttgtgtgc 480
ctgctgaata acttctatcc cagagaggcc aaagtacagt ggaaggtgga taacgccctc 540
caatcgggta actcccagga gagtgtcaca gagcaggaca gcaaggacag cacctacagc 600

-continued ctcagcagca ccctgacgct gagcaaagca gactacgaga aacacaaagt ctacgcctgc 660
gaagtcaccc atcagggcct gagctcgccc gtcacaaaga gcttcaacag gggagagtgt 720
tagagggaga agtgccccca cctgctcctc agttccagcc tgacccccctc ccatcctttg 780 gcctctgacc ctttttccac aggggaccta cccctattgc ggtcctccag ctcatctttc 840
acctcacccc cctcctcctc cttggcttta attatgctaa tgttggagga gaatgaataa 900
ataaagtgaa tctttgcacc tgtaaaaaaa aaaaaaaaaa a 941

<210> SEQ ID NO 82
<211> LENGTH: 613
<212> TYPE: PRT
<213> ORGANISM: Homo sapiens

<400> SEQUENCE: 82

Met Gly Ala Leu Arg Pro Thr Leu Leu Pro Pro Ser Leu Pro Leu Leu
1 5 10 15

Leu Leu Leu Met Leu Gly Met Gly Cys Trp Ala Arg Glu Val Leu Val
20 25 30

Pro Glu Gly Pro Leu Tyr Arg Val Ala Gly Thr Ala Val Ser Ile Ser
35 40 45

Cys Asn Val Thr Gly Tyr Glu Gly Pro Ala Gln Gln Asn Phe Glu Trp
50 55 60

Phe Leu Tyr Arg Pro Glu Ala Pro Asp Thr Ala Leu Gly Ile Val Ser
65 70 75 80

Thr Lys Asp Thr Gln Phe Ser Tyr Ala Val Phe Lys Ser Arg Val Val
85 90 95

Ala Gly Glu Val Gln Val Gln Arg Leu Gln Gly Asp Ala Val Val Leu
100 105 110

Lys Ile Ala Arg Leu Gln Ala Gln Asp Ala Gly Ile Tyr Glu Cys His
115 120 125

Thr Pro Ser Thr Asp Thr Arg Tyr Leu Gly Ser Tyr Ser Gly Lys Val
130 135 140

Glu Leu Arg Val Leu Pro Asp Val Leu Gln Val Ser Ala Ala Pro Pro
145 150 155 160

Gly Pro Arg Gly Arg Gln Ala Pro Thr Ser Pro Pro Arg Met Thr Val
165 170 175

His Glu Gly Gln Glu Leu Ala Leu Gly Cys Leu Ala Arg Thr Ser Thr
180 185 190

Gln Lys His Thr His Leu Ala Val Ser Phe Gly Arg Ser Val Pro Glu
195 200 205

Ala Pro Val Gly Arg Ser Thr Leu Gln Glu Val Val Gly Ile Arg Ser
210 215 220

Asp Leu Ala Val Glu Ala Gly Ala Pro Tyr Ala Glu Arg Leu Ala Ala
225 230 235 240

Gly Glu Leu Arg Leu Gly Lys Glu Gly Thr Asp Arg Tyr Arg Met Val
245 250 255

Val Gly Gly Ala Gln Ala Gly Asp Ala Gly Thr Tyr His Cys Thr Ala
260 265 270

Ala Glu Trp Ile Gln Asp Pro Asp Gly Ser Trp Ala Gln Ile Ala Glu
275 280 285

Lys Arg Ala Val Leu Ala His Val Asp Val Gln Thr Leu Ser Ser Gln
290 295 300

Leu Ala Val Thr Val Gly Pro Gly Glu Arg Arg Ile Gly Pro Gly Glu

-continued

```
305                 310                 315                 320

Pro Leu Glu Leu Leu Cys Asn Val Ser Gly Ala Leu Pro Pro Ala Gly
                325                 330                 335

Arg His Ala Ala Tyr Ser Val Gly Trp Glu Met Ala Pro Ala Gly Ala
            340                 345                 350

Pro Gly Pro Gly Arg Leu Val Ala Gln Leu Asp Thr Glu Gly Val Gly
        355                 360                 365

Ser Leu Gly Pro Gly Tyr Glu Gly Arg His Ile Ala Met Glu Lys Val
    370                 375                 380

Ala Ser Arg Thr Tyr Arg Leu Arg Leu Glu Ala Ala Arg Pro Gly Asp
385                 390                 395                 400

Ala Gly Thr Tyr Arg Cys Leu Ala Lys Ala Tyr Val Arg Gly Ser Gly
                405                 410                 415

Thr Arg Leu Arg Glu Ala Ala Ser Ala Arg Ser Arg Pro Leu Pro Val
            420                 425                 430

His Val Arg Glu Glu Gly Val Val Leu Glu Ala Val Ala Trp Leu Ala
        435                 440                 445

Gly Gly Thr Val Tyr Arg Gly Glu Thr Ala Ser Leu Leu Cys Asn Ile
    450                 455                 460

Ser Val Arg Gly Gly Pro Pro Gly Leu Arg Leu Ala Ala Ser Trp Trp
465                 470                 475                 480

Val Glu Arg Pro Glu Asp Gly Glu Leu Ser Ser Val Pro Ala Gln Leu
                485                 490                 495

Val Gly Gly Val Gly Gln Asp Gly Val Ala Glu Leu Gly Val Arg Pro
            500                 505                 510

Gly Gly Gly Pro Val Ser Val Glu Leu Val Gly Pro Arg Ser His Arg
        515                 520                 525

Leu Arg Leu His Ser Leu Gly Pro Glu Asp Glu Gly Val Tyr His Cys
    530                 535                 540

Ala Pro Ser Ala Trp Val Gln His Ala Asp Tyr Ser Trp Tyr Gln Ala
545                 550                 555                 560

Gly Ser Ala Arg Ser Gly Pro Val Thr Val Tyr Pro Tyr Met His Ala
                565                 570                 575

Leu Asp Thr Leu Phe Val Pro Leu Leu Val Gly Thr Gly Val Ala Leu
            580                 585                 590

Val Thr Gly Ala Thr Val Leu Gly Thr Ile Thr Cys Cys Phe Met Lys
        595                 600                 605

Arg Leu Arg Lys Arg
    610


<210> SEQ ID NO 83
<211> LENGTH: 453
<212> TYPE: PRT
<213> ORGANISM: Homo sapiens

<400> SEQUENCE: 83

Met Lys Leu Leu Val Ile Leu Ile Phe Ser Gly Leu Ile Thr Cys Cys
  1               5                  10                  15

Gly Gly Asn Ser Ser His Ser Leu Pro Ser Lys Leu Leu Leu Val Ser
            20                  25                  30

Phe Asp Gly Phe Arg Ala Asp Tyr Leu Gln Asn Tyr Glu Phe Pro His
        35                  40                  45

Leu Gln Asn Phe Ile Lys Glu Gly Val Leu Val Glu His Val Lys Asn
     50                  55                  60
```

-continued

```
Val Phe Ile Thr Lys Thr Phe Pro Asn His Tyr Ser Ile Val Thr Gly
 65                  70                  75                  80

Leu Tyr Glu Glu Ser His Gly Ile Val Ala Asn Ser Met Tyr Asp Val
                 85                  90                  95

Ile Thr Lys Lys His Phe Ser Asp Phe Asp Asp Lys Asp Pro Phe Trp
            100                 105                 110

Trp Asn Glu Ala Val Pro Ile Trp Val Thr Asn Gln Leu Gln Glu Asn
        115                 120                 125

Arg Ser Ser Ala Ala Ala Met Trp Pro Gly Thr Asp Val Pro Ile His
    130                 135                 140

Asn Thr Thr Pro Ser Tyr Phe Met Asn Tyr Ser Ser Ser Val Ser Phe
145                 150                 155                 160

Glu Glu Arg Leu Asn Asn Ile Thr Met Trp Leu Met Asn Ser Asn Pro
                165                 170                 175

Pro Val Thr Phe Ala Thr Leu Tyr Trp Glu Glu Pro Asp Ala Ser Gly
            180                 185                 190

His Lys Tyr Gly Pro Glu Asp Lys Glu Asn Met Tyr Arg Val Leu Lys
        195                 200                 205

Glu Val Asp Asp Leu Ile Gly Glu Leu Val His Lys Leu Lys Val Leu
    210                 215                 220

Gly Leu Trp Glu Asn Leu Asn Val Ile Ile Thr Ser Asp His Gly Met
225                 230                 235                 240

Thr Gln Cys Ser Lys Asp Lys Leu Ile Asn Leu Asp Leu Cys Ile Asp
                245                 250                 255

Arg Ser Ser Tyr Thr Leu Val Asp Leu Thr Pro Val Ala Ala Val Leu
            260                 265                 270

Pro Lys Ile Asn Thr Thr Glu Val Tyr Asn Lys Leu Lys Val Cys Asn
        275                 280                 285

Pro His Met Asn Val Tyr Leu Lys Glu Asp Ile Pro Ala Arg Phe His
    290                 295                 300

Tyr Gln His Asn Asp Arg Ile Gln Pro Ile Ile Leu Val Ala Asp Glu
305                 310                 315                 320

Gly Trp Thr Ile Val Leu Asn Lys Ser Leu Pro Lys Leu Gly Asp His
                325                 330                 335

Gly Tyr Asp Asn Ser Leu Ser Ser Met His Pro Phe Leu Ala Ala His
            340                 345                 350

Gly Pro Ala Phe His Lys Gly Tyr Lys His Ser Thr Ile Asn Ser Val
        355                 360                 365

Asp Ile Tyr Pro Met Met Cys His Ile Leu Gly Leu Lys Pro His Pro
    370                 375                 380

Asn Asn Gly Thr Phe Gly His Thr Lys Cys Leu Leu Val Asp Gln Trp
385                 390                 395                 400

Cys Ile Asn Leu Pro Glu Ala Ile Gly Ile Val Ile Gly Ala Leu Leu
                405                 410                 415

Val Leu Thr Thr Leu Thr Cys Leu Ile Ile Ile Met Gln Asn Arg Leu
            420                 425                 430

Ser Val Pro Arg Pro Phe Ser Arg Leu Gln Leu Gln Glu Asp Asp Asp
        435                 440                 445

Asp Pro Leu Ile Glu
    450
```

<210> SEQ ID NO 84
<211> LENGTH: 152
<212> TYPE: PRT

-continued

<213> ORGANISM: Homo sapiens

<400> SEQUENCE: 84

Met Arg Arg Leu Leu Leu Val Thr Ser Leu Val Val Val Leu Leu Trp
1 5 10 15

Glu Ala Gly Ala Val Pro Ala Pro Lys Val Pro Ile Lys Met Gln Val
20 25 30

Lys His Trp Pro Ser Glu Gln Asp Pro Glu Asn Arg Ala Trp Gly Ala
35 40 45

Arg Val Val Glu Pro Pro Glu Lys Asp Asp Gln Leu Val Val Leu Phe
50 55 60

Pro Val Gln Lys Pro Lys Leu Leu Thr Thr Glu Glu Lys Pro Arg Gly
65 70 75 80

Gln Gly Arg Gly Pro Ile Leu Pro Gly Thr Lys Ala Trp Met Glu Thr
85 90 95

Glu Asp Thr Leu Gly Arg Val Leu Ser Pro Glu Pro Asp His Asp Ser
100 105 110

Leu Tyr His Pro Pro Pro Glu Glu Asp Gln Gly Glu Glu Arg Pro Arg
115 120 125

Leu Trp Val Met Pro Asn His Gln Val Leu Leu Gly Pro Glu Glu Asp
130 135 140

Gln Asp His Ile Tyr His Pro Gln
145 150

<210> SEQ ID NO 85
<211> LENGTH: 245
<212> TYPE: PRT
<213> ORGANISM: Homo sapiens

<400> SEQUENCE: 85

Met Glu Gly Pro Arg Gly Trp Leu Val Leu Cys Val Leu Ala Ile Ser
1 5 10 15

Leu Ala Ser Met Val Thr Glu Asp Leu Cys Arg Ala Pro Asp Gly Lys
20 25 30

Lys Gly Glu Ala Gly Arg Pro Gly Arg Arg Gly Arg Pro Gly Leu Lys
35 40 45

Gly Glu Gln Gly Glu Pro Gly Ala Pro Gly Ile Arg Thr Gly Ile Gln
50 55 60

Gly Leu Lys Gly Asp Gln Gly Glu Pro Gly Pro Ser Gly Asn Pro Gly
65 70 75 80

Lys Val Gly Tyr Pro Gly Pro Ser Gly Pro Leu Gly Ala Arg Gly Ile
85 90 95

Pro Gly Ile Lys Gly Thr Lys Gly Ser Pro Gly Asn Ile Lys Asp Gln
100 105 110

Pro Arg Pro Ala Phe Ser Ala Ile Arg Arg Asn Pro Pro Met Gly Gly
115 120 125

Asn Val Val Ile Phe Asp Thr Val Ile Thr Asn Gln Glu Glu Pro Tyr
130 135 140

Gln Asn His Ser Gly Arg Phe Val Cys Thr Val Pro Gly Tyr Tyr Tyr
145 150 155 160

Phe Thr Phe Gln Val Leu Ser Gln Trp Glu Ile Cys Leu Ser Ile Val
165 170 175

Ser Ser Ser Arg Gly Gln Val Arg Arg Ser Leu Gly Phe Cys Asp Thr
180 185 190

Thr Asn Lys Gly Leu Phe Gln Val Val Ser Gly Gly Met Val Leu Gln

-continued

```
        195                 200                 205

Leu Gln Gln Gly Asp Gln Val Trp Val Glu Lys Asp Pro Lys Lys Gly
    210                 215                 220

His Ile Tyr Gln Gly Ser Glu Ala Asp Ser Val Phe Ser Gly Phe Leu
225                 230                 235                 240

Ile Phe Pro Ser Ala
                245


<210> SEQ ID NO 86
<211> LENGTH: 396
<212> TYPE: PRT
<213> ORGANISM: Homo sapiens

<400> SEQUENCE: 86

Met Trp Trp Leu Leu Leu Trp Gly Val Leu Gln Ala Cys Pro Thr Arg
  1               5                  10                  15

Gly Ser Val Leu Leu Ala Gln Glu Leu Pro Gln Gln Leu Thr Ser Pro
             20                  25                  30

Gly Tyr Pro Glu Pro Tyr Gly Lys Gly Gln Glu Ser Ser Thr Asp Ile
         35                  40                  45

Lys Ala Pro Glu Gly Phe Ala Val Arg Leu Val Phe Gln Asp Phe Asp
     50                  55                  60

Leu Glu Pro Ser Gln Asp Cys Ala Gly Asp Ser Val Thr Ile Ser Phe
 65                  70                  75                  80

Val Gly Ser Asp Pro Ser Gln Phe Cys Gly Gln Gln Gly Ser Pro Leu
                 85                  90                  95

Gly Arg Pro Pro Gly Gln Arg Glu Phe Val Ser Ser Gly Arg Ser Leu
            100                 105                 110

Arg Leu Thr Phe Arg Thr Gln Pro Ser Ser Glu Asn Lys Thr Ala His
        115                 120                 125

Leu His Lys Gly Phe Leu Ala Leu Tyr Gln Thr Val Ala Val Asn Tyr
    130                 135                 140

Ser Gln Pro Ile Ser Glu Ala Ser Arg Gly Ser Glu Ala Ile Asn Ala
145                 150                 155                 160

Pro Gly Asp Asn Pro Ala Lys Val Gln Asn His Cys Gln Glu Pro Tyr
                165                 170                 175

Tyr Gln Ala Ala Ala Ala Gly Ala Leu Thr Cys Ala Thr Pro Gly Thr
            180                 185                 190

Trp Lys Asp Arg Gln Asp Gly Glu Glu Val Leu Gln Cys Met Pro Val
        195                 200                 205

Cys Gly Arg Pro Val Thr Pro Ile Ala Gln Asn Gln Thr Thr Leu Gly
    210                 215                 220

Ser Ser Arg Ala Lys Leu Gly Asn Phe Pro Trp Gln Ala Phe Thr Ser
225                 230                 235                 240

Ile His Gly Arg Gly Gly Gly Ala Leu Leu Gly Asp Arg Trp Ile Leu
                245                 250                 255

Thr Ala Ala His Thr Ile Tyr Pro Lys Asp Ser Val Ser Leu Arg Lys
            260                 265                 270

Asn Gln Ser Val Asn Val Phe Leu Gly His Thr Ala Ile Asp Glu Met
        275                 280                 285

Leu Lys Leu Gly Asn His Pro Val His Arg Val Val Val His Pro Asp
    290                 295                 300

Tyr Arg Gln Asn Glu Ser His Asn Phe Ser Gly Asp Ile Ala Leu Leu
305                 310                 315                 320
```

-continued

```
Glu Leu Gln His Ser Ile Pro Leu Gly Pro Asn Val Leu Pro Val Cys
                325                 330                 335

Leu Pro Asp Asn Glu Thr Leu Tyr Arg Ser Gly Leu Leu Gly Tyr Val
            340                 345                 350

Ser Gly Phe Gly Met Glu Met Gly Trp Leu Thr Thr Glu Leu Lys Tyr
        355                 360                 365

Ser Arg Leu Pro Val Ala Pro Arg Glu Ala Cys Asn Ala Trp Leu Gln
    370                 375                 380

Lys Arg Gln Arg Pro Glu Lys Lys Lys Lys Lys Lys
385                 390                 395


<210> SEQ ID NO 87
<211> LENGTH: 298
<212> TYPE: PRT
<213> ORGANISM: Homo sapiens

<400> SEQUENCE: 87

Met Lys Thr Leu Gln Ser Thr Leu Leu Leu Leu Leu Leu Val Pro Leu
  1               5                  10                  15

Ile Lys Pro Ala Pro Pro Thr Gln Gln Asp Ser Arg Ile Ile Tyr Asp
             20                  25                  30

Tyr Gly Thr Asp Asn Phe Glu Glu Ser Ile Phe Ser Gln Asp Tyr Glu
         35                  40                  45

Asp Lys Tyr Leu Asp Gly Lys Asn Ile Lys Glu Lys Glu Thr Val Ile
     50                  55                  60

Ile Pro Asn Glu Lys Ser Leu Gln Leu Gln Lys Asp Glu Ala Ile Thr
 65                  70                  75                  80

Pro Leu Pro Pro Lys Lys Glu Asn Asp Glu Met Pro Thr Cys Leu Leu
                 85                  90                  95

Cys Val Cys Leu Ser Gly Ser Val Tyr Cys Glu Glu Val Asp Ile Asp
            100                 105                 110

Ala Val Pro Pro Leu Pro Lys Glu Ser Ala Tyr Leu Tyr Ala Arg Phe
        115                 120                 125

Asn Lys Ile Lys Lys Leu Thr Ala Lys Asp Phe Ala Asp Ile Pro Asn
    130                 135                 140

Leu Arg Arg Leu Asp Phe Thr Gly Asn Leu Ile Glu Asp Ile Glu Asp
145                 150                 155                 160

Gly Thr Phe Ser Lys Leu Ser Leu Leu Glu Glu Leu Ser Leu Ala Glu
                165                 170                 175

Asn Gln Leu Leu Lys Leu Pro Val Leu Pro Pro Lys Leu Thr Leu Phe
            180                 185                 190

Asn Ala Lys Tyr Asn Lys Ile Lys Ser Arg Gly Ile Lys Ala Asn Ala
        195                 200                 205

Phe Lys Lys Leu Asn Asn Leu Thr Phe Leu Tyr Leu Asp His Asn Ala
    210                 215                 220

Leu Glu Ser Val Pro Leu Asn Leu Pro Glu Ser Leu Arg Val Ile His
225                 230                 235                 240

Leu Gln Phe Asn Asn Ile Ala Ser Ile Thr Asp Asp Thr Phe Cys Lys
                245                 250                 255

Ala Asn Asp Thr Ser Tyr Ile Arg Asp Arg Ile Glu Glu Ile Arg Leu
            260                 265                 270

Glu Gly Asn Pro Ile Val Leu Gly Lys His Pro Asn Ser Phe Ile Cys
        275                 280                 285

Leu Lys Arg Leu Pro Ile Gly Ser Tyr Phe
    290                 295
```

-continued

```
<210> SEQ ID NO 88
<211> LENGTH: 263
<212> TYPE: PRT
<213> ORGANISM: Homo sapiens
<220> FEATURE:
<221> NAME/KEY: SITE
<222> LOCATION: (27)
<223> OTHER INFORMATION: Xaa equals any of the naturally occurring
      L-amino acids
<221> NAME/KEY: SITE
<222> LOCATION: (112)
<223> OTHER INFORMATION: Xaa equals any of the naturally occurring
      L-amino acids

<400> SEQUENCE: 88

Met Cys Leu Leu Gly Gly Leu Ser Ala Pro Pro Leu Leu Leu Leu Pro
  1               5                  10                  15

Leu Leu Pro Leu Leu Leu Cys Pro Pro Thr Xaa Gln Gly Asp Cys Ser
             20                  25                  30

Phe Pro Pro Glu Leu Pro Asn Ala Ile Gln Ser Val Gly Asp Gln Gln
         35                  40                  45

Ser Phe Pro Glu Lys Phe Thr Val Thr Tyr Lys Cys Lys Glu Gly Phe
     50                  55                  60

Val Lys Val Pro Gly Lys Ala Asp Ser Val Val Cys Leu Asn Asn Lys
 65                  70                  75                  80

Trp Ser Glu Val Ala Glu Phe Cys Asn Arg Ser Cys Asp Val Pro Thr
                 85                  90                  95

Arg Leu Gln Phe Ala Ser Leu Lys Lys Ser Phe Thr Lys Gln Asn Xaa
            100                 105                 110

Phe Pro Val Gly Ser Val Val Glu Tyr Glu Cys Arg Pro Gly Tyr Gln
        115                 120                 125

Arg Asp His Leu Leu Ser Gly Lys Leu Thr Cys Leu Leu Asn Phe Thr
    130                 135                 140

Trp Ser Lys Pro Asp Glu Phe Cys Lys Arg Lys Ser Cys Pro Asn Pro
145                 150                 155                 160

Gly Asp Leu Arg His Gly His Val Asn Ile Pro Thr Asp Ile Leu Tyr
                165                 170                 175

Ala Ala Val Ile His Phe Ser Cys Asn Lys Gly Tyr Arg Leu Val Gly
            180                 185                 190

Ala Ala Ser Ser Tyr Cys Ser Ile Val Asn Asp Asp Val Gly Trp Ser
        195                 200                 205

Asp Pro Leu Pro Glu Cys Gln Glu Ile Phe Cys Pro Glu Pro Pro Lys
    210                 215                 220

Ile Ser Asn Gly Val Ile Leu Asp Gln Gln Asn Thr Tyr Val Tyr Gln
225                 230                 235                 240

Gln Ala Val Lys Tyr Glu Cys Ile Lys Gly Phe Thr Leu Ile Gly Glu
                245                 250                 255

Asn Ser Asp Leu Leu Tyr Cys
            260


<210> SEQ ID NO 89
<211> LENGTH: 1745
<212> TYPE: PRT
<213> ORGANISM: Homo sapiens

<400> SEQUENCE: 89

Met Glu Cys Cys Arg Arg Ala Thr Pro Gly Thr Leu Leu Leu Phe Leu
1               5                   10                  15
```

-continued

```
Ala Phe Leu Leu Leu Ser Ser Arg Thr Ala Arg Ser Glu Glu Asp Arg
            20                  25                  30

Asp Gly Leu Trp Asp Ala Trp Gly Pro Trp Ser Glu Cys Ser Arg Thr
        35                  40                  45

Cys Gly Gly Gly Ala Ser Tyr Ser Leu Arg Arg Cys Leu Ser Ser Lys
    50                  55                  60

Ser Cys Glu Gly Arg Asn Ile Arg Tyr Arg Thr Cys Ser Asn Val Asp
65                  70                  75                  80

Cys Pro Pro Glu Ala Gly Asp Phe Arg Ala Gln Gln Cys Ser Ala His
                85                  90                  95

Asn Asp Val Lys His His Gly Gln Phe Tyr Glu Trp Leu Pro Val Ser
            100                 105                 110

Asn Asp Pro Asp Asn Pro Cys Ser Leu Lys Cys Gln Ala Lys Gly Thr
        115                 120                 125

Thr Leu Val Val Glu Leu Ala Pro Lys Val Leu Asp Gly Thr Arg Cys
    130                 135                 140

Tyr Thr Glu Ser Leu Asp Met Cys Ile Ser Gly Leu Cys Gln Ile Val
145                 150                 155                 160

Gly Cys Asp His Gln Leu Gly Ser Thr Val Lys Glu Asp Asn Cys Gly
                165                 170                 175

Val Cys Asn Gly Asp Gly Ser Thr Cys Arg Leu Val Arg Gly Gln Tyr
            180                 185                 190

Lys Ser Gln Leu Ser Ala Thr Lys Ser Asp Asp Thr Val Val Ala Ile
        195                 200                 205

Pro Tyr Gly Ser Arg His Ile Arg Leu Val Leu Lys Gly Pro Asp His
    210                 215                 220

Leu Tyr Leu Glu Thr Lys Thr Leu Gln Gly Thr Lys Gly Glu Asn Ser
225                 230                 235                 240

Leu Ser Ser Thr Gly Thr Phe Leu Val Asp Asn Ser Ser Val Asp Phe
                245                 250                 255

Gln Lys Phe Pro Asp Lys Glu Ile Leu Arg Met Ala Gly Pro Leu Thr
            260                 265                 270

Ala Asp Phe Ile Val Lys Ile Arg Asn Ser Gly Ser Ala Asp Ser Thr
        275                 280                 285

Val Gln Phe Ile Phe Tyr Gln Pro Ile Ile His Arg Trp Arg Glu Thr
    290                 295                 300

Asp Phe Phe Pro Cys Ser Ala Thr Cys Gly Gly Gly Tyr Gln Leu Thr
305                 310                 315                 320

Ser Ala Glu Cys Tyr Asp Leu Arg Ser Asn Arg Val Val Ala Asp Gln
                325                 330                 335

Tyr Cys His Tyr Tyr Pro Glu Asn Ile Lys Pro Lys Pro Lys Leu Gln
            340                 345                 350

Glu Cys Asn Leu Asp Pro Cys Pro Ala Arg Trp Glu Ala Thr Pro Trp
        355                 360                 365

Thr Ala Cys Ser Ser Ser Cys Gly Gly Gly Ile Gln Ser Arg Ala Val
    370                 375                 380

Ser Cys Val Glu Glu Asp Ile Gln Gly His Val Thr Ser Val Glu Glu
385                 390                 395                 400

Trp Lys Cys Met Tyr Thr Pro Lys Met Pro Ile Ala Gln Pro Cys Asn
                405                 410                 415

Ile Phe Asp Cys Pro Lys Trp Leu Ala Gln Glu Trp Ser Pro Cys Thr
            420                 425                 430
```

-continued

```
Val Thr Cys Gly Gln Gly Leu Arg Tyr Arg Val Val Leu Cys Ile Asp
        435                 440                 445

His Arg Gly Met His Thr Gly Gly Cys Ser Pro Lys Thr Lys Pro His
    450                 455                 460

Ile Lys Glu Glu Cys Ile Val Pro Thr Pro Cys Tyr Lys Pro Lys Glu
465                 470                 475                 480

Lys Leu Pro Val Glu Ala Lys Leu Pro Trp Phe Lys Gln Ala Gln Glu
                485                 490                 495

Leu Glu Glu Gly Ala Ala Val Ser Glu Glu Pro Ser Phe Ile Pro Lys
            500                 505                 510

Ala Trp Ser Ala Cys Thr Val Thr Cys Gly Val Gly Thr Gln Val Arg
        515                 520                 525

Ile Val Arg Cys Gln Val Leu Leu Ser Phe Ser Gln Ser Val Ala Asp
    530                 535                 540

Leu Pro Ile Asp Glu Cys Glu Gly Pro Lys Pro Ala Ser Gln Arg Ala
545                 550                 555                 560

Cys Tyr Ala Gly Pro Cys Ser Gly Glu Ile Pro Glu Phe Asn Pro Asp
                565                 570                 575

Glu Thr Asp Gly Leu Phe Gly Gly Leu Gln Asp Phe Asp Glu Leu Tyr
            580                 585                 590

Asp Trp Glu Tyr Glu Gly Phe Thr Lys Cys Ser Glu Ser Cys Gly Gly
        595                 600                 605

Gly Val Gln Glu Ala Val Val Ser Cys Leu Asn Lys Gln Thr Arg Glu
    610                 615                 620

Pro Ala Glu Glu Asn Leu Cys Val Thr Ser Arg Arg Pro Pro Gln Leu
625                 630                 635                 640

Leu Lys Ser Cys Asn Leu Asp Pro Cys Pro Ala Arg Trp Glu Ile Gly
                645                 650                 655

Lys Trp Ser Pro Cys Ser Leu Thr Cys Gly Val Gly Leu Gln Thr Arg
            660                 665                 670

Asp Val Phe Cys Ser His Leu Leu Ser Arg Glu Met Asn Glu Thr Val
        675                 680                 685

Ile Leu Ala Asp Glu Leu Cys Arg Gln Pro Lys Pro Ser Thr Val Gln
    690                 695                 700

Ala Cys Asn Arg Phe Asn Cys Pro Pro Ala Trp Tyr Pro Ala Gln Trp
705                 710                 715                 720

Gln Pro Cys Ser Arg Thr Cys Gly Gly Gly Val Gln Lys Arg Glu Val
                725                 730                 735

Leu Cys Lys Gln Arg Met Ala Asp Gly Ser Phe Leu Glu Leu Pro Glu
            740                 745                 750

Thr Phe Cys Ser Ala Ser Lys Pro Ala Cys Gln Gln Ala Cys Lys Lys
        755                 760                 765

Asp Asp Cys Pro Ser Glu Trp Leu Leu Ser Asp Trp Thr Glu Cys Ser
    770                 775                 780

Thr Ser Cys Gly Glu Gly Thr Gln Thr Arg Ser Ala Ile Cys Arg Lys
785                 790                 795                 800

Met Leu Lys Thr Gly Leu Ser Thr Val Val Asn Ser Thr Leu Cys Pro
                805                 810                 815

Pro Leu Pro Phe Ser Ser Ser Ile Arg Pro Cys Met Leu Ala Thr Cys
            820                 825                 830

Ala Arg Pro Gly Arg Pro Ser Thr Lys His Ser Pro His Ile Ala Ala
        835                 840                 845

Ala Arg Lys Val Tyr Ile Gln Thr Arg Arg Gln Arg Lys Leu His Phe
```

-continued

```
    850                 855                 860

Val Val Gly Gly Phe Ala Tyr Leu Leu Pro Lys Thr Ala Val Val Leu
865                 870                 875                 880

Arg Cys Pro Ala Arg Arg Val Arg Lys Pro Leu Ile Thr Trp Glu Lys
                885                 890                 895

Asp Gly Gln His Leu Ile Ser Ser Thr His Val Thr Val Ala Pro Phe
            900                 905                 910

Gly Tyr Leu Lys Ile His Arg Leu Lys Pro Ser Asp Ala Gly Val Tyr
        915                 920                 925

Thr Cys Ser Ala Gly Pro Ala Arg Glu His Phe Val Ile Lys Leu Ile
    930                 935                 940

Gly Gly Asn Arg Lys Leu Val Ala Arg Pro Leu Ser Pro Arg Ser Glu
945                 950                 955                 960

Glu Glu Val Leu Ala Gly Arg Lys Gly Gly Pro Lys Glu Ala Leu Gln
                965                 970                 975

Thr His Lys His Gln Asn Gly Ile Phe Ser Asn Gly Ser Lys Ala Glu
            980                 985                 990

Lys Arg Gly Leu Ala Ala Asn Pro  Gly Ser Arg Tyr Asp  Asp Leu Val
        995                 1000                1005

Ser Arg  Leu Leu Glu Gln Gly  Gly Trp Pro Gly Glu  Leu Leu Ala
    1010                 1015                 1020

Ser Trp  Glu Ala Gln Asp Ser  Ala Glu Arg Asn Thr  Thr Ser Glu
    1025                 1030                 1035

Glu Asp  Pro Gly Ala Glu Gln  Val Leu Leu His Leu  Pro Phe Thr
    1040                 1045                 1050

Met Val  Thr Glu Gln Arg Arg  Leu Asp Asp Ile Leu  Gly Asn Leu
    1055                 1060                 1065

Ser Gln  Gln Pro Glu Glu Leu  Arg Asp Leu Tyr Ser  Lys His Leu
    1070                 1075                 1080

Val Ala  Gln Leu Ala Gln Glu  Ile Phe Arg Ser His  Leu Glu His
    1085                 1090                 1095

Gln Asp  Thr Leu Leu Lys Pro  Ser Glu Arg Arg Thr  Ser Pro Val
    1100                 1105                 1110

Thr Leu  Ser Pro His Lys His  Val Ser Gly Phe Ser  Ser Ser Leu
    1115                 1120                 1125

Arg Thr  Ser Ser Thr Gly Asp  Ala Gly Gly Gly Ser  Arg Arg Pro
    1130                 1135                 1140

His Arg  Lys Pro Thr Ile Leu  Arg Lys Ile Ser Ala  Ala Gln Gln
    1145                 1150                 1155

Leu Ser  Ala Ser Glu Val Val  Thr His Leu Gly Gln  Thr Val Ala
    1160                 1165                 1170

Leu Ala  Ser Gly Thr Leu Ser  Val Leu Leu His Cys  Glu Ala Ile
    1175                 1180                 1185

Gly His  Pro Arg Pro Thr Ile  Ser Trp Ala Arg Asn  Gly Glu Glu
    1190                 1195                 1200

Val Gln  Phe Ser Asp Arg Ile  Leu Leu Gln Pro Asp  Asp Ser Leu
    1205                 1210                 1215

Gln Ile  Leu Ala Pro Val Glu  Ala Asp Val Gly Phe  Tyr Thr Cys
    1220                 1225                 1230

Asn Ala  Thr Asn Ala Leu Gly  Tyr Asp Ser Val Ser  Ile Ala Val
    1235                 1240                 1245

Thr Leu  Ala Gly Lys Pro Leu  Val Lys Thr Ser Arg  Met Thr Val
    1250                 1255                 1260
```

-continued

```
Ile Asn Thr Glu Lys Pro Ala Val Thr Val Asp Ile Gly Ser Thr
    1265                1270                1275

Ile Lys Thr Val Gln Gly Val Asn Val Thr Ile Asn Cys Gln Val
    1280                1285                1290

Ala Gly Val Pro Glu Ala Glu Val Thr Trp Phe Arg Asn Lys Ser
    1295                1300                1305

Lys Leu Gly Ser Pro His His Leu His Glu Gly Ser Leu Leu Leu
    1310                1315                1320

Thr Asn Val Ser Ser Ser Asp Gln Gly Leu Tyr Ser Cys Arg Ala
    1325                1330                1335

Ala Asn Leu His Gly Glu Leu Thr Glu Ser Thr Gln Leu Leu Ile
    1340                1345                1350

Leu Asp Pro Pro Gln Val Pro Thr Gln Leu Glu Asp Ile Arg Ala
    1355                1360                1365

Leu Leu Ala Ala Thr Gly Pro Asn Leu Pro Ser Val Leu Thr Ser
    1370                1375                1380

Pro Leu Gly Thr Gln Leu Val Leu Asp Pro Gly Asn Ser Ala Leu
    1385                1390                1395

Leu Gly Cys Pro Ile Lys Gly His Pro Val Pro Asn Ile Thr Trp
    1400                1405                1410

Phe His Gly Gly Gln Pro Ile Val Thr Ala Thr Gly Leu Thr His
    1415                1420                1425

His Ile Leu Ala Ala Gly Gln Ile Leu Gln Val Ala Asn Leu Ser
    1430                1435                1440

Gly Gly Ser Gln Gly Glu Phe Ser Cys Leu Ala Gln Asn Glu Ala
    1445                1450                1455

Gly Val Leu Met Gln Lys Ala Ser Leu Val Ile Gln Asp Tyr Trp
    1460                1465                1470

Trp Ser Val Asp Arg Leu Ala Thr Cys Ser Ala Ser Cys Gly Asn
    1475                1480                1485

Arg Gly Val Gln Gln Pro Arg Leu Arg Cys Leu Leu Asn Ser Thr
    1490                1495                1500

Glu Val Asn Pro Ala His Cys Ala Gly Lys Val Arg Pro Ala Val
    1505                1510                1515

Gln Pro Ile Ala Cys Asn Arg Arg Asp Cys Pro Ser Arg Trp Met
    1520                1525                1530

Val Thr Ser Trp Ser Ala Cys Thr Arg Ser Cys Gly Gly Gly Val
    1535                1540                1545

Gln Thr Arg Arg Val Thr Cys Gln Lys Leu Lys Ala Ser Gly Ile
    1550                1555                1560

Ser Thr Pro Val Ser Asn Asp Met Cys Thr Gln Val Ala Lys Arg
    1565                1570                1575

Pro Val Asp Thr Gln Ala Cys Asn Gln Gln Leu Cys Val Glu Trp
    1580                1585                1590

Ala Phe Ser Ser Trp Gly Gln Cys Asn Gly Pro Cys Ile Gly Pro
    1595                1600                1605

His Leu Ala Val Gln His Arg Gln Val Phe Cys Gln Thr Arg Asp
    1610                1615                1620

Gly Ile Thr Leu Pro Ser Glu Gln Cys Ser Ala Leu Pro Arg Pro
    1625                1630                1635

Val Ser Thr Gln Asn Cys Trp Ser Glu Ala Cys Ser Val His Trp
    1640                1645                1650
```

-continued

```
Arg Val  Ser Leu Trp Thr Leu  Cys Thr Ala Thr Cys  Gly Asn Tyr
    1655                1660                1665

Gly Phe  Gln Ser Arg Arg Val  Glu Cys Val His Ala  Arg Thr Asn
    1670                1675                1680

Lys Ala  Val Pro Glu His Leu  Cys Ser Trp Gly Pro  Arg Pro Ala
    1685                1690                1695

Asn Trp  Gln Arg Cys Asn Ile  Thr Pro Cys Glu Asn  Met Glu Cys
    1700                1705                1710

Arg Asp  Thr Thr Arg Tyr Cys  Glu Lys Val Lys Gln  Leu Lys Leu
    1715                1720                1725

Cys Gln  Leu Ser Gln Phe Lys  Ser Arg Cys Cys Gly  Thr Cys Gly
    1730                1735                1740

Lys Ala
    1745
```

<210> SEQ ID NO 90
<211> LENGTH: 142
<212> TYPE: PRT
<213> ORGANISM: Homo sapiens

<400> SEQUENCE: 90

```
Met Arg Arg Leu Leu Leu Val Thr Ser Leu Val Val Val Leu Leu Trp
  1               5                  10                  15

Glu Ala Gly Ala Val Pro Ala Pro Lys Val Pro Ile Lys Met Gln Val
             20                  25                  30

Lys His Trp Pro Ser Glu Gln Asp Pro Glu Lys Ala Trp Gly Ala Arg
         35                  40                  45

Val Val Glu Pro Pro Glu Lys Asp Asp Gln Leu Val Val Leu Phe Pro
     50                  55                  60

Val Gln Lys Pro Lys Leu Leu Thr Thr Glu Glu Lys Pro Arg Gly Thr
 65                  70                  75                  80

Lys Ala Trp Met Glu Thr Glu Asp Thr Leu Gly Arg Val Leu Ser Pro
                 85                  90                  95

Glu Pro Asp His Asp Ser Leu Tyr His Pro Pro Pro Glu Glu Asp Gln
            100                 105                 110

Gly Glu Glu Arg Pro Arg Leu Trp Val Met Pro Asn His Gln Val Leu
        115                 120                 125

Leu Gly Pro Glu Glu Asp Gln Asp His Ile Tyr His Pro Gln
    130                 135                 140
```

<210> SEQ ID NO 91
<211> LENGTH: 350
<212> TYPE: PRT
<213> ORGANISM: Homo sapiens

<400> SEQUENCE: 91

```
Met Ala Val Phe Val Val Leu Leu Ala Leu Val Ala Gly Val Leu Gly
  1               5                  10                  15

Asn Glu Phe Ser Ile Leu Lys Ser Pro Gly Ser Val Val Phe Arg Asn
             20                  25                  30

Gly Asn Trp Pro Ile Pro Gly Glu Arg Ile Pro Asp Val Ala Ala Leu
         35                  40                  45

Ser Met Gly Phe Ser Val Lys Glu Asp Leu Ser Trp Pro Gly Leu Ala
     50                  55                  60

Val Gly Asn Leu Phe His Arg Pro Arg Ala Thr Val Met Val Met Val
 65                  70                  75                  80
```

-continued

```
Lys Gly Val Asn Lys Leu Ala Leu Pro Pro Gly Ser Val Ile Ser Tyr
                85                  90                  95

Pro Leu Glu Asn Ala Val Pro Phe Ser Leu Asp Ser Val Ala Asn Ser
            100                 105                 110

Ile His Ser Leu Phe Ser Glu Glu Thr Pro Val Val Leu Gln Leu Ala
        115                 120                 125

Pro Ser Glu Glu Arg Val Tyr Met Val Gly Lys Ala Asn Ser Val Phe
    130                 135                 140

Glu Asp Leu Ser Val Thr Leu Arg Gln Leu Arg Asn Arg Leu Phe Gln
145                 150                 155                 160

Glu Asn Ser Val Leu Ser Ser Leu Pro Leu Asn Ser Leu Ser Arg Asn
                165                 170                 175

Asn Glu Val Asp Leu Leu Phe Leu Ser Glu Leu Gln Val Leu His Asp
            180                 185                 190

Ile Ser Ser Leu Leu Ser Arg His Lys His Leu Ala Lys Asp His Ser
        195                 200                 205

Pro Asp Leu Tyr Ser Leu Glu Leu Ala Gly Leu Asp Glu Ile Gly Lys
    210                 215                 220

Arg Tyr Gly Glu Asp Ser Glu Gln Phe Arg Asp Ala Ser Lys Ile Leu
225                 230                 235                 240

Val Asp Ala Leu Gln Lys Phe Ala Asp Asp Met Tyr Ser Leu Tyr Gly
                245                 250                 255

Gly Asn Ala Val Val Glu Leu Val Thr Val Lys Ser Phe Asp Thr Ser
            260                 265                 270

Leu Ile Arg Lys Thr Arg Thr Ile Leu Glu Ala Lys Gln Ala Lys Asn
        275                 280                 285

Pro Ala Ser Pro Tyr Asn Leu Ala Tyr Lys Tyr Asn Phe Glu Tyr Ser
    290                 295                 300

Val Val Phe Asn Met Val Leu Trp Ile Met Ile Ala Leu Ala Leu Ala
305                 310                 315                 320

Val Ile Ile Thr Ser Tyr Asn Ile Trp Asn Met Asp Pro Gly Tyr Asp
                325                 330                 335

Ser Ile Ile Tyr Arg Met Thr Asn Gln Lys Ile Arg Met Asp
            340                 345                 350


<210> SEQ ID NO 92
<211> LENGTH: 102
<212> TYPE: PRT
<213> ORGANISM: Homo sapiens

<400> SEQUENCE: 92

Met Lys Pro Ala Thr Ala Ser Ala Leu Leu Leu Leu Leu Leu Gly Leu
  1               5                  10                  15

Ala Trp Thr Gln Gly Ser His Gly Trp Gly Ala Asp Ala Ser Ser Leu
            20                  25                  30

Gln Lys Arg Ala Gly Arg Ala Asp Gln Pro Gly Ala Gly Trp Gln Glu
        35                  40                  45

Val Ala Ala Val Thr Ser Lys Asn Tyr Asn Tyr Asn Gln His Ala Tyr
     50                  55                  60

Pro Thr Ala Tyr Gly Gly Lys Tyr Ser Val Lys Thr Pro Ala Lys Gly
 65                  70                  75                  80

Gly Val Ser Pro Ser Ser Ser Ala Ser Arg Val Gln Pro Gly Leu Leu
                85                  90                  95

Gln Trp Val Lys Phe Trp
            100
```

-continued

<210> SEQ ID NO 93
<211> LENGTH: 509
<212> TYPE: PRT
<213> ORGANISM: Homo sapiens
<220> FEATURE:
<221> NAME/KEY: SITE
<222> LOCATION: (20)
<223> OTHER INFORMATION: Xaa equals any of the naturally occurring L-amino acids
<221> NAME/KEY: SITE
<222> LOCATION: (168)
<223> OTHER INFORMATION: Xaa equals any of the naturally occurring L-amino acids
<221> NAME/KEY: SITE
<222> LOCATION: (198)
<223> OTHER INFORMATION: Xaa equals any of the naturally occurring L-amino acids
<221> NAME/KEY: SITE
<222> LOCATION: (199)
<223> OTHER INFORMATION: Xaa equals any of the naturally occurring L-amino acids
<221> NAME/KEY: SITE
<222> LOCATION: (244)
<223> OTHER INFORMATION: Xaa equals any of the naturally occurring L-amino acids
<221> NAME/KEY: SITE
<222> LOCATION: (246)
<223> THER INFORMATION: Xaa equals any of the naturally occurring L-amino acids
<221> NAME/KEY: SITE
<222> LOCATION: (294)
<223> OTHER INFORMATION: Xaa equals any of the naturally occurring L-amino acids
<221> NAME/KEY: SITE
<222> LOCATION: (301)
<223> OTHER INFORMATION: Xaa equals any of the naturally occurring L-amino acids
<221> NAME/KEY: SITE
<222> LOCATION: (303)
<223> OTHER INFORMATION: Xaa equals any of the naturally occurring L-amino acids
<221> NAME/KEY: SITE
<222> LOCATION: (493)
<223> OTHER INFORMATION: Xaa equals any of the naturally occurring L-amino acids
<221> NAME/KEY: SITE
<222> LOCATION: (498)
<223> OTHER INFORMATION: Xaa equals any of the naturally occurring L-amino acids
<221> NAME/KEY: SITE
<222> LOCATION: (499)
<223> OTHER INFORMATION: Xaa equals any of the naturally occurring L-amino acids
<221> NAME/KEY: SITE
<222> LOCATION: (505)
<223> OTHER INFORMATION: Xaa equals any of the naturally occurring L-amino acids

<400> SEQUENCE: 93

```
Met Glu Glu Leu Ala Thr Glu Lys Glu Ala Glu Glu Ser His Arg Gln
  1               5                  10                  15

Asp Ser Val Xaa Leu Leu Thr Phe Ile Leu Leu Leu Thr Leu Thr Ile
             20                  25                  30

Leu Thr Ile Trp Leu Phe Lys His Arg Arg Val Arg Phe Leu His Glu
         35                  40                  45

Thr Gly Leu Ala Met Ile Tyr Gly Leu Ile Val Gly Val Ile Leu Arg
     50                  55                  60

Tyr Gly Thr Pro Ala Thr Ser Gly Arg Asp Lys Ser Leu Ser Cys Thr
 65                  70                  75                  80

Gln Glu Asp Arg Ala Phe Ser Thr Leu Leu Val Asn Val Ser Gly Lys
                 85                  90                  95
```

-continued

```
Phe Phe Glu Tyr Thr Leu Lys Gly Glu Ile Ser Pro Gly Lys Ile Asn
            100                 105                 110

Ser Val Glu Gln Asn Asp Met Leu Arg Lys Val Thr Phe Asp Pro Glu
        115                 120                 125

Val Phe Phe Asn Ile Leu Leu Pro Pro Ile Ile Phe His Ala Gly Tyr
    130                 135                 140

Ser Leu Lys Lys Arg His Phe Phe Arg Asn Leu Gly Ser Ile Leu Ala
145                 150                 155                 160

Tyr Ala Phe Leu Gly Thr Ala Xaa Ser Cys Phe Ile Ile Gly Asn Leu
                165                 170                 175

Met Tyr Gly Val Val Lys Leu Met Lys Ile Met Gly Gln Leu Ser Asp
            180                 185                 190

Lys Phe Tyr Tyr Thr Xaa Xaa Leu Phe Phe Gly Ala Ile Ile Ser Ala
        195                 200                 205

Thr Asp Pro Val Thr Val Leu Ala Ile Phe Asn Glu Leu His Ala Asp
    210                 215                 220

Val Asp Leu Tyr Ala Leu Leu Phe Gly Glu Ser Val Leu Asn Asp Ala
225                 230                 235                 240

Val Ala Ile Xaa Leu Xaa Ser Ser Ile Val Ala Tyr Gln Pro Ala Gly
                245                 250                 255

Leu Asn Thr His Ala Phe Asp Ala Ala Ala Phe Phe Lys Ser Val Gly
            260                 265                 270

Ile Phe Leu Gly Ile Phe Ser Gly Ser Phe Thr Met Gly Ala Val Thr
        275                 280                 285

Gly Val Val Thr Ala Xaa Val Thr Lys Phe Thr Lys Xaa His Xaa Phe
    290                 295                 300

Pro Leu Leu Glu Thr Ala Leu Phe Phe Leu Met Ser Trp Ser Thr Phe
305                 310                 315                 320

Leu Leu Ala Glu Ala Cys Gly Phe Thr Gly Val Val Ala Val Leu Phe
                325                 330                 335

Cys Gly Ile Thr Gln Ala His Tyr Thr Tyr Asn Asn Leu Ser Val Glu
            340                 345                 350

Ser Arg Ser Arg Thr Lys Gln Leu Phe Glu Val Leu His Phe Leu Ala
        355                 360                 365

Glu Asn Phe Ile Phe Ser Tyr Met Gly Leu Ala Leu Phe Thr Phe Gln
    370                 375                 380

Lys His Val Phe Ser Pro Ile Phe Ile Ile Gly Ala Phe Val Ala Ile
385                 390                 395                 400

Phe Leu Gly Arg Ala Ala His Ile Tyr Pro Leu Ser Phe Phe Leu Asn
                405                 410                 415

Leu Gly Arg Arg His Lys Ile Gly Trp Asn Phe Gln His Met Met Met
            420                 425                 430

Phe Ser Gly Leu Arg Gly Ala Met Ala Phe Ala Leu Ala Ile Arg Asp
        435                 440                 445

Thr Ala Ser Tyr Ala Arg Gln Met Met Phe Thr Thr Thr Leu Leu Ile
    450                 455                 460

Val Phe Phe Thr Val Trp Ile Ile Gly Gly Gly Thr Thr Pro Met Leu
465                 470                 475                 480

Ser Trp Leu Asn Ile Arg Val Gly Val Asp Pro Asp Xaa Asp Pro Pro
                485                 490                 495

Pro Xaa Xaa Asp Ser Phe Ala Phe Xaa Thr Glu Thr Ala
            500                 505
```

-continued

<210> SEQ ID NO 94
<211> LENGTH: 146
<212> TYPE: PRT
<213> ORGANISM: Homo sapiens

<400> SEQUENCE: 94

```
Met Thr Met Arg Ser Leu Leu Arg Thr Pro Phe Leu Cys Gly Leu Leu
  1               5                  10                  15

Trp Ala Phe Cys Ala Pro Gly Ala Arg Ala Glu Glu Pro Ala Ala Ser
             20                  25                  30

Phe Ser Gln Pro Gly Ser Met Gly Leu Asp Lys Asn Thr Val His Asp
         35                  40                  45

Gln Glu His Ile Met Glu His Leu Glu Gly Val Ile Asn Lys Pro Glu
     50                  55                  60

Ala Glu Met Ser Pro Gln Glu Leu Gln Leu His Tyr Phe Lys Met His
 65                  70                  75                  80

Asp Tyr Asp Gly Asn Asn Leu Leu Asp Gly Leu Glu Leu Ser Thr Ala
                 85                  90                  95

Ile Thr His Val His Lys Glu Glu Gly Ser Glu Gln Ala Pro Leu Met
            100                 105                 110

Ser Glu Asp Glu Leu Ile Asn Ile Ile Asp Gly Val Leu Arg Asp Asp
        115                 120                 125

Asp Lys Asn Asn Asp Gly Tyr Ile Asp Tyr Ala Glu Phe Ala Lys Ser
    130                 135                 140

Leu Gln
145
```

<210> SEQ ID NO 95
<211> LENGTH: 626
<212> TYPE: PRT
<213> ORGANISM: Homo sapiens
<220> FEATURE:
<221> NAME/KEY: SITE
<222> LOCATION: (353)
<223> OTHER INFORMATION: Xaa equals any of the naturally occurring
      L-amino acids
<221> NAME/KEY: SITE
<222> LOCATION: (354)
<223> OTHER INFORMATION: Xaa equals any of the naturally occurring
      L-amino acids
<221> NAME/KEY: SITE
<222> LOCATION: (363)
<223> OTHER INFORMATION: Xaa equals any of the naturally occurring
      L-amino acids

<400> SEQUENCE: 95

```
Met Gln Arg Ala Asp Ser Glu Gln Pro Ser Lys Arg Pro Arg Cys Asp
  1               5                  10                  15

Asp Ser Pro Arg Thr Pro Ser Asn Thr Pro Ser Ala Glu Ala Asp Trp
             20                  25                  30

Ser Pro Gly Leu Glu Leu His Pro Asp Tyr Lys Thr Trp Gly Pro Glu
         35                  40                  45

Gln Val Cys Ser Phe Leu Arg Arg Gly Gly Phe Glu Glu Pro Val Leu
     50                  55                  60

Leu Lys Asn Ile Arg Glu Asn Glu Ile Thr Gly Ala Leu Leu Pro Cys
 65                  70                  75                  80

Leu Asp Glu Ser Arg Phe Glu Asn Leu Gly Val Ser Ser Leu Gly Glu
                 85                  90                  95

Arg Lys Lys Leu Leu Ser Tyr Ile Gln Arg Leu Val Gln Ile His Val
            100                 105                 110
```

-continued

```
Asp Thr Met Lys Val Ile Asn Asp Pro Ile His Gly His Ile Glu Leu
        115                 120                 125

His Pro Leu Leu Val Arg Ile Ile Asp Thr Pro Gln Phe Gln Arg Leu
    130                 135                 140

Arg Tyr Ile Lys Gln Leu Gly Gly Gly Tyr Tyr Val Phe Pro Gly Ala
145                 150                 155                 160

Ser His Asn Arg Phe Glu His Ser Leu Gly Val Gly Tyr Leu Ala Gly
                165                 170                 175

Cys Leu Val His Ala Leu Gly Glu Lys Gln Pro Glu Leu Gln Ile Ser
            180                 185                 190

Glu Arg Asp Val Leu Cys Val Gln Ile Ala Gly Leu Cys His Asp Leu
        195                 200                 205

Gly His Gly Pro Phe Ser His Met Phe Asp Gly Arg Phe Ile Pro Leu
    210                 215                 220

Ala Arg Pro Glu Val Lys Trp Thr His Glu Gln Gly Ser Val Met Met
225                 230                 235                 240

Phe Glu His Leu Ile Asn Ser Asn Gly Ile Lys Pro Val Met Glu Gln
                245                 250                 255

Tyr Gly Leu Ile Pro Glu Glu Asp Ile Cys Phe Ile Lys Glu Gln Ile
            260                 265                 270

Val Gly Pro Leu Glu Ser Pro Val Glu Asp Ser Leu Trp Pro Tyr Lys
        275                 280                 285

Gly Arg Pro Glu Asn Lys Ser Phe Leu Tyr Glu Ile Val Ser Asn Lys
    290                 295                 300

Arg Asn Gly Ile Asp Val Asp Lys Trp Asp Tyr Phe Ala Arg Asp Cys
305                 310                 315                 320

His His Leu Gly Ile Gln Asn Asn Phe Asp Tyr Lys Arg Phe Ile Lys
                325                 330                 335

Phe Ala Arg Val Cys Glu Val Asp Asn Glu Leu Arg Ile Cys Ala Arg
            340                 345                 350

Xaa Xaa Glu Val Gly Asn Leu Tyr Asp Met Xaa His Thr Arg Asn Ser
        355                 360                 365

Leu His Arg Arg Ala Tyr Gln His Lys Val Gly Asn Ile Ile Asp Thr
    370                 375                 380

Met Ile Thr Asp Ala Phe Leu Lys Ala Asp Asp Tyr Ile Glu Ile Thr
385                 390                 395                 400

Gly Ala Gly Gly Lys Lys Tyr Arg Ile Ser Thr Ala Ile Asp Asp Met
                405                 410                 415

Glu Ala Tyr Thr Lys Leu Thr Asp Asn Ile Phe Leu Glu Ile Leu Tyr
            420                 425                 430

Ser Thr Asp Pro Lys Leu Lys Asp Ala Arg Glu Ile Leu Lys Gln Ile
        435                 440                 445

Glu Tyr Arg Asn Leu Phe Lys Tyr Val Gly Glu Thr Gln Pro Thr Gly
    450                 455                 460

Gln Ile Lys Ile Lys Arg Glu Asp Tyr Glu Ser Leu Pro Lys Glu Val
465                 470                 475                 480

Ala Ser Ala Lys Pro Lys Val Leu Leu Asp Val Lys Leu Lys Ala Glu
                485                 490                 495

Asp Phe Ile Val Asp Val Ile Asn Met Asp Tyr Gly Met Gln Glu Lys
            500                 505                 510

Asn Pro Ile Asp His Val Ser Phe Tyr Cys Lys Thr Ala Pro Asn Arg
        515                 520                 525
```

-continued

```
Ala Ile Arg Ile Thr Lys Asn Gln Val Ser Gln Leu Leu Pro Glu Lys
    530                 535                 540

Phe Ala Glu Gln Leu Ile Arg Val Tyr Cys Lys Lys Val Asp Arg Lys
545                 550                 555                 560

Ser Leu Tyr Ala Ala Arg Gln Tyr Phe Val Gln Trp Cys Ala Asp Arg
                565                 570                 575

Asn Phe Thr Lys Pro Gln Asp Gly Asp Val Ile Ala Pro Leu Ile Thr
            580                 585                 590

Pro Gln Lys Lys Glu Trp Asn Asp Ser Thr Ser Val Gln Asn Pro Thr
        595                 600                 605

Arg Leu Arg Glu Ala Ser Lys Ser Arg Val Gln Leu Phe Lys Asp Asp
    610                 615                 620

Pro Met
625


<210> SEQ ID NO 96
<211> LENGTH: 81
<212> TYPE: PRT
<213> ORGANISM: Homo sapiens

<400> SEQUENCE: 96

Met Arg Leu Leu Val Leu Ser Ser Leu Leu Cys Ile Leu Leu Leu Cys
  1               5                  10                  15

Phe Ser Ile Phe Ser Thr Glu Gly Lys Arg Arg Pro Ala Lys Ala Trp
             20                  25                  30

Ser Gly Arg Arg Thr Arg Leu Cys Cys His Arg Val Pro Ser Pro Asn
         35                  40                  45

Ser Thr Asn Leu Lys Gly His His Val Arg Leu Cys Lys Pro Cys Lys
     50                  55                  60

Leu Glu Pro Glu Pro Arg Leu Trp Val Val Pro Gly Ala Leu Pro Gln
 65                  70                  75                  80

Val


<210> SEQ ID NO 97
<211> LENGTH: 86
<212> TYPE: PRT
<213> ORGANISM: Homo sapiens

<400> SEQUENCE: 97

Met Leu Trp Ala Leu Asp Ser Leu Leu Phe Phe Ser His Ala Gln Leu
  1               5                  10                  15

Val Pro Leu Gly Gly Gly Glu Glu Trp Gly Ser Pro Gly Leu Gly Leu
             20                  25                  30

His Ser Ile Ile Pro Ser Gln Ala Ser Gln Gly Val Ser Ala Pro Ala
         35                  40                  45

Gln Asp Leu Ala Gly Arg Ala Pro Tyr Arg Glu Ser Leu Gly Arg Leu
     50                  55                  60

Ser Arg Leu Met Ala Gly Pro Ala Arg Gly Val Leu Arg Pro Ala Leu
 65                  70                  75                  80

Arg Thr Cys Pro Leu Phe
                 85


<210> SEQ ID NO 98
<211> LENGTH: 613
<212> TYPE: PRT
<213> ORGANISM: Homo sapiens
<220> FEATURE:
<221> NAME/KEY: SITE
```

-continued

```
<222> LOCATION: (507)
<223> OTHER INFORMATION: Xaa equals any of the naturally occurring
      L-amino acids

<400> SEQUENCE: 98

Met Gly Ala Leu Arg Pro Thr Leu Leu Pro Pro Ser Leu Pro Leu Leu
  1               5                  10                  15

Leu Leu Leu Met Leu Gly Met Gly Cys Trp Ala Arg Glu Val Leu Val
             20                  25                  30

Pro Glu Gly Pro Leu Tyr Arg Val Ala Gly Thr Ala Val Ser Ile Ser
         35                  40                  45

Cys Asn Val Thr Gly Tyr Glu Gly Pro Ala Gln Gln Asn Phe Glu Trp
     50                  55                  60

Phe Leu Tyr Arg Pro Glu Ala Pro Asp Thr Ala Leu Gly Ile Val Ser
 65                  70                  75                  80

Thr Lys Asp Thr Gln Phe Ser Tyr Ala Val Phe Lys Ser Arg Val Val
                 85                  90                  95

Ala Gly Glu Val Gln Val Gln Arg Leu Gln Gly Asp Ala Val Val Leu
            100                 105                 110

Lys Ile Ala Arg Leu Gln Ala Gln Asp Ala Gly Ile Tyr Glu Cys His
        115                 120                 125

Thr Pro Ser Thr Asp Thr Arg Tyr Leu Gly Ser Tyr Ser Gly Lys Val
    130                 135                 140

Glu Leu Arg Val Leu Pro Asp Val Leu Gln Val Ser Ala Ala Pro Pro
145                 150                 155                 160

Gly Pro Arg Gly Arg Gln Ala Pro Thr Ser Pro Pro Arg Met Thr Val
                165                 170                 175

His Glu Gly Gln Glu Leu Ala Leu Gly Cys Leu Ala Arg Thr Ser Thr
            180                 185                 190

Gln Lys His Thr His Leu Ala Val Ser Phe Gly Arg Ser Val Pro Glu
        195                 200                 205

Ala Pro Val Gly Arg Ser Thr Leu Gln Glu Val Val Gly Ile Arg Ser
    210                 215                 220

Asp Leu Ala Val Glu Ala Gly Ala Pro Tyr Ala Glu Arg Leu Ala Ala
225                 230                 235                 240

Gly Glu Leu Arg Leu Gly Lys Glu Gly Thr Asp Arg Tyr Arg Met Val
                245                 250                 255

Val Gly Gly Ala Gln Ala Gly Asp Ala Gly Thr Tyr His Cys Thr Ala
            260                 265                 270

Ala Glu Trp Ile Gln Asp Pro Asp Gly Ser Trp Ala Gln Ile Ala Glu
        275                 280                 285

Lys Arg Ala Val Leu Ala His Val Asp Val Gln Thr Leu Ser Ser Gln
    290                 295                 300

Leu Ala Val Thr Val Gly Pro Gly Glu Arg Arg Ile Gly Pro Gly Glu
305                 310                 315                 320

Pro Leu Glu Leu Leu Cys Asn Val Ser Gly Ala Leu Pro Pro Ala Gly
                325                 330                 335

Arg His Ala Ala Tyr Ser Val Gly Trp Glu Met Ala Pro Ala Gly Ala
            340                 345                 350

Pro Gly Pro Gly Arg Leu Val Ala Gln Leu Asp Thr Glu Gly Val Gly
        355                 360                 365

Ser Leu Gly Pro Gly Tyr Glu Gly Arg His Ile Ala Met Glu Lys Val
    370                 375                 380

Ala Ser Arg Thr Tyr Arg Leu Arg Leu Glu Ala Ala Arg Pro Gly Asp
```

-continued

```
385                 390                 395                 400

Ala Gly Thr Tyr Arg Cys Leu Ala Lys Ala Tyr Val Arg Gly Ser Gly
                405                 410                 415

Thr Arg Leu Arg Glu Ala Ala Ser Ala Arg Ser Arg Pro Leu Pro Val
            420                 425                 430

His Val Arg Glu Glu Gly Val Val Leu Glu Ala Val Ala Trp Leu Ala
        435                 440                 445

Gly Gly Thr Val Tyr Arg Gly Glu Thr Ala Ser Leu Leu Cys Asn Ile
    450                 455                 460

Ser Val Arg Gly Gly Pro Pro Gly Leu Arg Leu Ala Ala Ser Trp Trp
465                 470                 475                 480

Val Glu Arg Pro Glu Asp Gly Glu Leu Ser Ser Val Pro Ala Gln Leu
                485                 490                 495

Val Gly Gly Val Gly Gln Asp Gly Val Ala Xaa Leu Gly Val Arg Pro
            500                 505                 510

Gly Gly Gly Pro Val Ser Val Glu Leu Val Gly Pro Arg Ser His Arg
        515                 520                 525

Leu Arg Leu His Ser Leu Gly Pro Glu Asp Glu Gly Val Tyr His Cys
    530                 535                 540

Ala Pro Ser Ala Trp Val Gln His Ala Asp Tyr Ser Trp Tyr Gln Ala
545                 550                 555                 560

Gly Ser Ala Arg Ser Gly Pro Val Thr Val Tyr Pro Tyr Met His Ala
                565                 570                 575

Leu Asp Thr Leu Phe Val Pro Leu Leu Val Gly Thr Gly Val Ala Leu
            580                 585                 590

Val Thr Gly Ala Thr Val Leu Gly Thr Ile Thr Cys Cys Phe Met Lys
        595                 600                 605

Arg Leu Arg Lys Arg
    610


<210> SEQ ID NO 99
<211> LENGTH: 60
<212> TYPE: PRT
<213> ORGANISM: Homo sapiens

<400> SEQUENCE: 99

Met Ala Trp Ala Val Thr Leu Ile Leu Ser Leu Ser Arg Ala Val Arg
  1               5                  10                  15

Thr Gln Glu Val Pro Met Ala Leu Gln Ala His Ser Gly Ile Gln Leu
             20                  25                  30

Ala Ser Arg Val Gly Leu Pro Gly Pro Trp Pro Glu Cys Ser Thr Leu
         35                  40                  45

Ser Ser Arg Cys His Leu Ser Met Asp Ser Lys Val
     50                  55                  60


<210> SEQ ID NO 100
<211> LENGTH: 167
<212> TYPE: PRT
<213> ORGANISM: Homo sapiens
<220> FEATURE:
<221> NAME/KEY: SITE
<222> LOCATION: (61)
<223> OTHER INFORMATION: Xaa equals any of the naturally occurring
      L-amino acids
<221> NAME/KEY: SITE
<222> LOCATION: (79)
<223> OTHER INFORMATION: Xaa equals any of the naturally occurring
      L-amino acids
```

-continued

<400> SEQUENCE: 100

```
Met Cys Ser Leu Phe His Ala Phe Ile Phe Ala Gln Leu Trp Thr Val
  1               5                  10                  15

Tyr Cys Glu Gln Ser Ala Val Ala Thr Asn Leu Gln Asn Gln Asn Glu
             20                  25                  30

Phe Ser Phe Thr Ala Ile Leu Thr Ala Leu Glu Phe Trp Ser Arg Val
         35                  40                  45

Thr Pro Ser Ile Leu Gln Leu Met Ala His Asn Lys Xaa Met Val Glu
     50                  55                  60

Met Val Cys Leu His Val Ile Ser Leu Met Glu Ala Leu Gln Xaa Cys
 65                  70                  75                  80

Asn Ser Thr Ile Phe Val Lys Leu Ile Pro Met Trp Leu Pro Met Ile
                 85                  90                  95

Gln Ser Asn Ile Lys His Leu Ser Ala Gly Leu Gln Leu Arg Leu Gln
            100                 105                 110

Ala Ile Gln Asn His Val Asn His His Ser Leu Arg Thr Leu Pro Gly
        115                 120                 125

Ser Gly Gln Ser Ser Ala Gly Leu Ala Ala Leu Arg Lys Trp Leu Gln
    130                 135                 140

Cys Thr Gln Phe Lys Met Ala Gln Val Glu Ile Gln Ser Ser Glu Ala
145                 150                 155                 160

Ala Ser Gln Phe Tyr Pro Leu
                165
```

<210> SEQ ID NO 101
<211> LENGTH: 183
<212> TYPE: PRT
<213> ORGANISM: Homo sapiens
<220> FEATURE:
<221> NAME/KEY: SITE
<222> LOCATION: (86)
<223> OTHER INFORMATION: Xaa equals any of the naturally occurring L-amino acids
<221> NAME/KEY: SITE
<222> LOCATION: (146)
<223> OTHER INFORMATION: Xaa equals any of the naturally occurring L-amino acids

<400> SEQUENCE: 101

```
Met Ala Val Gly Lys Phe Leu Leu Gly Ser Leu Leu Leu Leu Ser Leu
  1               5                  10                  15

Gln Leu Gly Gln Gly Trp Gly Pro Asp Ala Arg Gly Val Pro Val Ala
             20                  25                  30

Asp Gly Glu Phe Ser Ser Glu Gln Val Ala Lys Ala Gly Gly Thr Trp
         35                  40                  45

Leu Gly Lys Asp Phe Gln Gly Pro Ser Val Thr Ser Gln Leu Ser Pro
     50                  55                  60

Ala Leu Thr Leu Leu Thr Val Ser Ala Leu Pro Ser His Arg His Pro
 65                  70                  75                  80

Pro Pro Pro Cys Pro Xaa Ala Pro Ser Pro Val Trp Ser Met Pro Ala
                 85                  90                  95

Val Glu Pro Asp Pro Val Arg Gly Arg Ala Arg Pro Gly Leu Arg Leu
            100                 105                 110

Ile Gly Glu Val Ile Phe Arg Tyr Cys Ala Gly Ser Cys Pro Arg Gly
        115                 120                 125

Ala Arg Thr Gln His Gly Leu Ala Leu Ala Arg Leu Gln Gly Gln Gly
    130                 135                 140
```

-continued

```
Arg Xaa His Gly Gly Pro Cys Cys Arg Pro Thr Arg Tyr Thr Asp Val
145                 150                 155                 160

Ala Phe Leu Asp Asp Arg His Ala Gly Ser Gly Cys Pro Ser Ser Arg
                165                 170                 175

Arg Leu Cys Gly Cys Gly Gly
            180


<210> SEQ ID NO 102
<211> LENGTH: 239
<212> TYPE: PRT
<213> ORGANISM: Homo sapiens

<400> SEQUENCE: 102

Met Ala Tyr Gln Ser Leu Arg Leu Glu Tyr Leu Gln Ile Pro Pro Val
  1               5                  10                  15

Ser Arg Ala Tyr Thr Thr Ala Cys Val Leu Thr Thr Ala Ala Val Gln
            20                  25                  30

Leu Glu Leu Ile Thr Pro Phe Gln Leu Tyr Phe Asn Pro Glu Leu Ile
        35                  40                  45

Phe Lys His Phe Gln Ile Trp Arg Leu Ile Thr Asn Phe Leu Phe Phe
     50                  55                  60

Gly Pro Val Gly Phe Asn Phe Leu Phe Asn Met Ile Phe Leu Tyr Arg
 65                  70                  75                  80

Tyr Cys Arg Met Leu Glu Glu Gly Ser Phe Arg Gly Arg Thr Ala Asp
                 85                  90                  95

Phe Val Phe Met Phe Leu Phe Gly Gly Phe Leu Met Thr Leu Phe Gly
            100                 105                 110

Leu Phe Val Ser Leu Val Phe Leu Gly Gln Ala Phe Thr Ile Met Leu
        115                 120                 125

Val Tyr Val Trp Ser Arg Arg Asn Pro Tyr Val Arg Met Asn Phe Phe
    130                 135                 140

Gly Leu Leu Asn Phe Gln Ala Pro Phe Leu Pro Trp Val Leu Met Gly
145                 150                 155                 160

Phe Ser Leu Leu Leu Gly Asn Ser Ile Ile Val Asp Leu Leu Gly Ile
                165                 170                 175

Ala Val Gly His Ile Tyr Phe Phe Leu Glu Asp Val Phe Pro Asn Gln
            180                 185                 190

Pro Gly Gly Ile Arg Ile Leu Lys Thr Pro Ser Ile Leu Lys Ala Ile
        195                 200                 205

Phe Asp Thr Pro Asp Glu Asp Pro Asn Tyr Asn Pro Leu Pro Glu Glu
    210                 215                 220

Arg Pro Gly Gly Phe Ala Trp Gly Glu Gly Gln Arg Leu Gly Gly
225                 230                 235


<210> SEQ ID NO 103
<211> LENGTH: 89
<212> TYPE: PRT
<213> ORGANISM: Homo sapiens

<400> SEQUENCE: 103

Met Tyr Met Gln Asp Tyr Trp Arg Thr Trp Leu Lys Gly Leu Arg Gly
  1               5                  10                  15

Phe Phe Phe Val Gly Val Leu Phe Ser Ala Val Ser Ile Ala Ala Phe
            20                  25                  30

Cys Thr Phe Leu Val Leu Ala Ile Thr Arg His Gln Ser Leu Thr Asp
        35                  40                  45
```

-continued

```
Pro Thr Ser Tyr Tyr Leu Ser Ser Val Trp Ser Phe Ile Ser Phe Lys
     50                  55                  60

Trp Ala Phe Leu Leu Ser Leu Tyr Ala His Arg Tyr Arg Ala Asp Phe
 65                  70                  75                  80

Ala Asp Ile Ser Ile Leu Ser Asp Phe
                 85


<210> SEQ ID NO 104
<211> LENGTH: 50
<212> TYPE: PRT
<213> ORGANISM: Homo sapiens

<400> SEQUENCE: 104

Met Gln Val Lys Asn Ser Ile His Val Thr Phe Val Ala Arg Ile Leu
  1               5                  10                  15

Val Arg Val Leu Ile Cys Leu Ser Thr Ser Glu Ala Ile Leu Ala Arg
             20                  25                  30

Asn His Ile Tyr Val Val Ser Val Thr Asn Ala Ser Val Glu Val Gln
         35                  40                  45

Thr Ser
     50


<210> SEQ ID NO 105
<211> LENGTH: 49
<212> TYPE: PRT
<213> ORGANISM: Homo sapiens

<400> SEQUENCE: 105

Met Val Leu Val Phe Ala Tyr Leu Cys Val Leu Leu Ile Val Cys Trp
  1               5                  10                  15

Val Thr Ser Lys Thr Ser Leu Ala Leu Lys Tyr Thr Val Tyr Lys Asn
             20                  25                  30

Phe Lys Arg Leu Ile Trp Asn Lys Ser Ile Leu Ile Ile Thr Leu Thr
         35                  40                  45

Pro


<210> SEQ ID NO 106
<211> LENGTH: 868
<212> TYPE: PRT
<213> ORGANISM: Homo sapiens
<220> FEATURE:
<221> NAME/KEY: SITE
<222> LOCATION: (194)
<223> OTHER INFORMATION: Xaa equals any of the naturally occurring
      L-amino acids
<221> NAME/KEY: SITE
<222> LOCATION: (309)
<223> OTHER INFORMATION: Xaa equals any of the naturally occurring
      L-amino acids
<221> NAME/KEY: SITE
<222> LOCATION: (550)
<223> OTHER INFORMATION: Xaa equals any of the naturally occurring
      L-amino acids

<400> SEQUENCE: 106

Met Ala Thr Phe Ile Ser Val Gln Leu Lys Lys Thr Ser Glu Val Asp
  1               5                  10                  15

Leu Ala Lys Pro Leu Val Lys Phe Ile Gln Gln Thr Tyr Pro Ser Gly
             20                  25                  30

Gly Glu Glu Gln Ala Gln Tyr Cys Arg Ala Ala Glu Glu Leu Ser Lys
         35                  40                  45

Leu Arg Arg Ala Ala Val Gly Arg Pro Leu Asp Lys His Glu Gly Ala
```

-continued

```
     50                  55                  60

Leu Glu Thr Leu Leu Arg Tyr Tyr Asp Gln Ile Cys Ser Ile Glu Pro
 65                  70                  75                  80

Lys Phe Pro Phe Ser Glu Asn Gln Ile Cys Leu Thr Phe Thr Trp Lys
                 85                  90                  95

Asp Ala Phe Asp Lys Gly Ser Leu Phe Gly Gly Ser Val Lys Leu Ala
            100                 105                 110

Leu Ala Ser Leu Gly Tyr Glu Lys Ser Cys Val Leu Phe Asn Cys Ala
        115                 120                 125

Ala Leu Ala Ser Gln Ile Ala Ala Glu Gln Asn Leu Asp Asn Asp Glu
    130                 135                 140

Gly Leu Lys Ile Ala Ala Lys His Tyr Gln Phe Ala Ser Gly Ala Phe
145                 150                 155                 160

Leu His Ile Lys Glu Thr Val Leu Ser Ala Leu Ser Arg Glu Pro Thr
                165                 170                 175

Val Asp Ile Ser Pro Asp Thr Val Gly Thr Leu Ser Leu Ile Met Leu
            180                 185                 190

Ala Xaa Ala Gln Glu Val Phe Phe Leu Lys Ala Thr Arg Asp Lys Met
        195                 200                 205

Lys Asp Ala Ile Ile Ala Lys Leu Ala Asn Gln Ala Ala Asp Tyr Phe
    210                 215                 220

Gly Asp Ala Phe Lys Gln Cys Gln Tyr Lys Asp Thr Leu Pro Lys Glu
225                 230                 235                 240

Val Phe Pro Val Leu Ala Ala Lys His Cys Ile Met Gln Ala Asn Ala
                245                 250                 255

Glu Tyr His Gln Ser Ile Leu Ala Lys Gln Gln Lys Lys Phe Gly Glu
            260                 265                 270

Glu Ile Ala Arg Leu Gln His Ala Ala Glu Leu Ile Lys Thr Val Ala
        275                 280                 285

Ser Arg Tyr Asp Glu Tyr Val Asn Val Lys Asp Phe Ser Asp Lys Ile
    290                 295                 300

Asn Arg Ala Leu Xaa Ala Ala Lys Lys Asp Asn Asp Phe Ile Tyr His
305                 310                 315                 320

Asp Arg Val Pro Asp Leu Lys Asp Leu Asp Pro Ile Gly Lys Ala Thr
                325                 330                 335

Leu Val Lys Ser Thr Pro Val Asn Val Pro Ile Ser Gln Lys Phe Thr
            340                 345                 350

Asp Leu Phe Glu Lys Met Val Pro Val Ser Val Gln Gln Ser Leu Ala
        355                 360                 365

Ala Tyr Asn Gln Arg Lys Ala Asp Leu Val Asn Arg Ser Ile Ala Gln
    370                 375                 380

Met Arg Glu Ala Thr Thr Leu Ala Asn Gly Val Leu Ala Ser Leu Asn
385                 390                 395                 400

Leu Pro Ala Ala Ile Glu Asp Val Ser Gly Asp Thr Val Pro Gln Ser
                405                 410                 415

Ile Leu Thr Lys Ser Arg Ser Val Ile Glu Gln Gly Gly Ile Gln Thr
            420                 425                 430

Val Asp Gln Leu Ile Lys Glu Leu Pro Glu Leu Leu Gln Arg Asn Arg
        435                 440                 445

Glu Ile Leu Asp Glu Ser Leu Arg Leu Leu Asp Glu Glu Glu Ala Thr
    450                 455                 460

Asp Asn Asp Leu Arg Ala Lys Phe Lys Glu Arg Trp Gln Arg Thr Pro
465                 470                 475                 480
```

-continued

```
Ser Asn Glu Leu Tyr Lys Pro Leu Arg Ala Glu Gly Thr Asn Phe Arg
                485                 490                 495

Thr Val Leu Asp Lys Ala Val Gln Ala Asp Gly Gln Val Lys Glu Cys
            500                 505                 510

Tyr Gln Ser His Arg Asp Thr Ile Val Leu Leu Cys Lys Pro Glu Pro
        515                 520                 525

Glu Leu Asn Ala Ala Ile Pro Ser Ala Asn Pro Ala Lys Thr Met Gln
    530                 535                 540

Gly Ser Glu Val Val Xaa Val Leu Lys Ser Leu Leu Ser Asn Leu Asp
545                 550                 555                 560

Glu Val Lys Lys Glu Arg Glu Gly Leu Glu Asn Asp Leu Lys Ser Val
                565                 570                 575

Asn Phe Asp Met Thr Ser Lys Phe Leu Thr Ala Leu Ala Gln Asp Gly
            580                 585                 590

Val Ile Asn Glu Glu Ala Leu Ser Val Thr Glu Leu Asp Arg Val Tyr
        595                 600                 605

Gly Gly Leu Thr Thr Lys Val Gln Glu Ser Leu Lys Lys Gln Glu Gly
    610                 615                 620

Leu Leu Lys Asn Ile Gln Val Ser His Gln Glu Phe Ser Lys Met Lys
625                 630                 635                 640

Gln Ser Asn Asn Glu Ala Asn Leu Arg Glu Glu Val Leu Lys Asn Leu
                645                 650                 655

Ala Thr Ala Tyr Asp Asn Phe Val Glu Leu Val Ala Asn Leu Lys Glu
            660                 665                 670

Gly Thr Lys Phe Tyr Asn Glu Leu Thr Glu Ile Leu Val Arg Phe Gln
        675                 680                 685

Asn Lys Cys Ser Asp Ile Val Phe Ala Arg Lys Thr Glu Arg Asp Glu
    690                 695                 700

Leu Leu Lys Asp Leu Gln Gln Ser Ile Ala Arg Glu Pro Ser Ala Pro
705                 710                 715                 720

Ser Ile Pro Thr Pro Ala Tyr Gln Ser Leu Pro Ala Gly Gly His Ala
                725                 730                 735

Pro Thr Pro Pro Thr Pro Ala Pro Arg Thr Met Pro Pro Thr Lys Pro
            740                 745                 750

Gln Pro Pro Ala Arg Pro Pro Pro Pro Val Leu Pro Ala Asn Arg Ala
        755                 760                 765

Pro Ser Ala Thr Ala Pro Ser Pro Val Gly Ala Gly Thr Ala Ala Pro
    770                 775                 780

Ala Pro Ser Gln Thr Pro Gly Ser Ala Pro Pro Pro Gln Ala Gln Gly
785                 790                 795                 800

Pro Pro Tyr Pro Thr Tyr Pro Gly Tyr Pro Gly Tyr Cys Gln Met Pro
                805                 810                 815

Met Pro Met Gly Tyr Asn Pro Tyr Ala Tyr Gly Gln Tyr Asn Met Pro
            820                 825                 830

Tyr Pro Pro Val Tyr His Gln Ser Pro Gly Gln Ala Pro Tyr Pro Gly
        835                 840                 845

Pro Gln Gln Pro Ser Tyr Pro Phe Pro Gln Pro Pro Gln Gln Ser Tyr
    850                 855                 860

Tyr Pro Gln Gln
865
```

<210> SEQ ID NO 107
<211> LENGTH: 56

-continued

```
<212> TYPE: PRT
<213> ORGANISM: Homo sapiens

<400> SEQUENCE: 107

Met Arg Gly His Ile Thr Thr Leu Leu Thr Thr Ser Phe Leu Val Phe
  1               5                  10                  15

Gly Leu His Ile Ile Phe Phe Leu Asn Ile Ser Cys Phe Asn Phe Arg
             20                  25                  30

Val Phe Ile Leu Phe Glu Thr Arg Pro Glu Asp Ser Arg Leu Tyr Arg
         35                  40                  45

Glu Arg Pro Val Leu Pro Arg Tyr
     50                  55


<210> SEQ ID NO 108
<211> LENGTH: 110
<212> TYPE: PRT
<213> ORGANISM: Homo sapiens

<400> SEQUENCE: 108

Met Glu Phe Pro Gly Ala Asp Gly Cys Asn Gln Val Asp Ala Glu Tyr
  1               5                  10                  15

Leu Lys Val Gly Ser Glu Gly His Phe Arg Val Pro Ala Leu Gly Tyr
             20                  25                  30

Leu Asp Val Arg Ile Val Asp Thr Asp Tyr Ser Ser Phe Ala Val Leu
         35                  40                  45

Tyr Ile Tyr Lys Glu Leu Glu Gly Ala Leu Ser Thr Met Val Gln Leu
     50                  55                  60

Tyr Ser Arg Thr Gln Asp Val Ser Pro Gln Ala Leu Lys Ala Phe Gln
 65                  70                  75                  80

Asp Phe Tyr Pro Thr Leu Gly Leu Pro Glu Asp Met Met Val Met Leu
                 85                  90                  95

Pro Gln Ser Asp Ala Cys Asn Pro Glu Ser Lys Glu Ala Pro
            100                 105                 110


<210> SEQ ID NO 109
<211> LENGTH: 334
<212> TYPE: PRT
<213> ORGANISM: Homo sapiens
<220> FEATURE:
<221> NAME/KEY: SITE
<222> LOCATION: (105)
<223> OTHER INFORMATION: Xaa equals any of the naturally occurring
      L-amino acids

<400> SEQUENCE: 109

Met Glu Pro Gly Pro Thr Ala Ala Gln Arg Arg Cys Ser Leu Pro Pro
  1               5                  10                  15

Trp Leu Pro Leu Gly Leu Leu Leu Trp Ser Gly Leu Ala Leu Gly Ala
             20                  25                  30

Leu Pro Phe Gly Ser Ser Pro His Arg Val Phe His Asp Leu Leu Ser
         35                  40                  45

Glu Gln Gln Leu Leu Glu Val Glu Asp Leu Ser Leu Ser Leu Leu Gln
     50                  55                  60

Gly Gly Gly Leu Gly Pro Leu Ser Leu Pro Pro Asp Leu Pro Asp Leu
 65                  70                  75                  80

Asp Pro Glu Cys Arg Glu Leu Leu Leu Asp Phe Ala Asn Ser Ser Ala
                 85                  90                  95

Glu Leu Thr Gly Cys Leu Val Arg Xaa Ala Arg Pro Val Arg Leu Cys
            100                 105                 110
```

-continued

```
Gln Thr Cys Tyr Pro Leu Phe Gln Gln Val Val Ser Lys Met Asp Asn
        115                 120                 125

Ile Ser Arg Ala Ala Gly Asn Thr Ser Glu Ser Gln Ser Cys Ala Arg
    130                 135                 140

Ser Leu Leu Met Ala Asp Arg Met Gln Ile Val Val Ile Leu Ser Glu
145                 150                 155                 160

Phe Phe Asn Thr Thr Trp Gln Glu Ala Asn Cys Ala Asn Cys Leu Thr
                165                 170                 175

Asn Asn Ser Glu Glu Leu Ser Asn Ser Thr Val Tyr Phe Leu Asn Leu
            180                 185                 190

Phe Asn His Thr Leu Thr Cys Phe Glu His Asn Leu Gln Gly Asn Ala
        195                 200                 205

His Ser Leu Leu Gln Thr Lys Asn Tyr Ser Glu Val Cys Lys Asn Cys
    210                 215                 220

Arg Glu Ala Tyr Lys Thr Leu Ser Ser Leu Tyr Ser Glu Met Gln Lys
225                 230                 235                 240

Met Asn Glu Leu Glu Asn Lys Ala Glu Pro Gly Thr His Leu Cys Ile
                245                 250                 255

Asp Val Glu Asp Ala Met Asn Ile Thr Arg Lys Leu Trp Ser Arg Thr
            260                 265                 270

Phe Asn Cys Ser Val Pro Cys Ser Asp Thr Val Pro Val Ile Ala Val
        275                 280                 285

Ser Val Phe Ile Leu Phe Leu Pro Val Val Phe Tyr Leu Ser Ser Phe
    290                 295                 300

Leu His Ser Glu Gln Lys Lys Arg Lys Leu Ile Leu Pro Lys Arg Leu
305                 310                 315                 320

Lys Ser Ser Thr Ser Phe Ala Asn Ile Gln Glu Asn Ser Asn
                325                 330


<210> SEQ ID NO 110
<211> LENGTH: 75
<212> TYPE: PRT
<213> ORGANISM: Homo sapiens

<400> SEQUENCE: 110

Met Ser Leu Ser Ile Leu Val Ala Leu Ser Leu Gln Ile Leu Phe Leu
  1               5                  10                  15

Phe Thr Ile Leu Lys Cys Met Leu Ala Lys Trp Val Asp Phe Gln Ile
             20                  25                  30

Lys Cys Ser Phe His Lys Ser Phe Val Met Val Phe Trp Ser Glu Met
         35                  40                  45

His Phe His Phe Ser Phe Leu Phe Leu Leu Ser Ile Leu Ser Phe Phe
     50                  55                  60

Pro Asn Lys Ile Tyr Pro Gly Asp Tyr Ile Cys
 65                  70                  75


<210> SEQ ID NO 111
<211> LENGTH: 363
<212> TYPE: PRT
<213> ORGANISM: Homo sapiens

<400> SEQUENCE: 111

Met Ala Ala Val Leu Thr Trp Ala Leu Ala Leu Leu Ser Ala Phe Ser
  1               5                  10                  15

Ala Thr Gln Ala Arg Lys Gly Phe Trp Asp Tyr Phe Ser Gln Thr Ser
             20                  25                  30
```

-continued

```
Gly Asp Lys Gly Arg Val Glu Gln Ile His Gln Gln Lys Met Ala Arg
        35                  40                  45

Glu Pro Ala Thr Leu Lys Asp Ser Leu Glu Gln Asp Leu Asn Asn Met
    50                  55                  60

Asn Lys Phe Leu Glu Lys Leu Arg Pro Leu Ser Gly Ser Glu Ala Pro
65                  70                  75                  80

Arg Leu Pro Gln Asp Pro Val Gly Met Arg Arg Gln Leu Gln Glu Glu
                85                  90                  95

Leu Glu Glu Val Lys Ala Arg Leu Gln Pro Tyr Met Ala Glu Ala His
            100                 105                 110

Glu Leu Val Gly Trp Asn Leu Glu Gly Leu Arg Gln Gln Leu Lys Pro
        115                 120                 125

Tyr Thr Met Asp Leu Met Glu Gln Val Ala Leu Arg Val Gln Glu Leu
    130                 135                 140

Gln Glu Gln Leu Arg Val Val Gly Glu Asp Thr Lys Ala Gln Leu Leu
145                 150                 155                 160

Gly Gly Val Asp Glu Ala Trp Ala Leu Leu Gln Gly Leu Gln Ser Arg
                165                 170                 175

Val Val His His Thr Gly Arg Phe Lys Glu Leu Phe His Pro Tyr Ala
            180                 185                 190

Glu Ser Leu Val Ser Gly Ile Gly Arg His Val Gln Glu Leu His Arg
        195                 200                 205

Ser Val Ala Pro His Ala Pro Ala Ser Pro Ala Arg Leu Ser Arg Cys
    210                 215                 220

Val Gln Val Leu Ser Arg Lys Leu Thr Leu Lys Ala Lys Ala Leu His
225                 230                 235                 240

Ala Arg Ile Gln Gln Asn Leu Asp Gln Leu Arg Glu Glu Leu Ile Arg
                245                 250                 255

Ala Phe Ala Gly Thr Gly Thr Glu Glu Gly Ala Gly Pro Asp Pro Gln
            260                 265                 270

Met Leu Ser Glu Glu Val Arg Gln Arg Leu Gln Ala Phe Arg Gln Asp
        275                 280                 285

Thr Tyr Leu Gln Ile Ala Ala Phe Thr Arg Ala Ile Asp Gln Glu Thr
    290                 295                 300

Glu Glu Val Gln Gln Gln Leu Ala Pro Pro Pro Pro Gly His Ser Ala
305                 310                 315                 320

Phe Ala Pro Glu Phe Gln Gln Thr Asp Ser Gly Lys Val Leu Ser Lys
                325                 330                 335

Leu Gln Ala Arg Leu Asp Asp Leu Trp Glu Asp Ile Thr His Ser Leu
            340                 345                 350

His Asp Gln Gly His Ser His Leu Gly Asp Pro
        355                 360
```

```
<210> SEQ ID NO 112
<211> LENGTH: 530
<212> TYPE: PRT
<213> ORGANISM: Homo sapiens
<220> FEATURE:
<221> NAME/KEY: SITE
<222> LOCATION: (488)
<223> OTHER INFORMATION: Xaa equals any of the naturally occurring
      L-amino acids
<221> NAME/KEY: SITE
<222> LOCATION: (490)
<223> OTHER INFORMATION: Xaa equals any of the naturally occurring
      L-amino acids
<221> NAME/KEY: SITE
```

-continued

```
<222> LOCATION: (494)
<223> OTHER INFORMATION: Xaa equals any of the naturally occurring
      L-amino acids
<221> NAME/KEY: SITE
<222> LOCATION: (495)
<223> OTHER INFORMATION: Xaa equals any of the naturally occurring
      L-amino acids
<221> NAME/KEY: SITE
<222> LOCATION: (505)
<223> OTHER INFORMATION: Xaa equals any of the naturally occurring
      L-amino acids

<400> SEQUENCE: 112

Met Glu Phe Gly Leu Thr Trp Val Phe Leu Val Ala Leu Leu Arg Gly
  1               5                  10                  15

Val His Cys Gln Val Gln Leu Val Glu Ser Gly Gly Ala Val Val Gln
             20                  25                  30

Pro Gly Gly Ser Leu Arg Leu Ser Cys Ala Ala Ser Gly Phe Thr Phe
         35                  40                  45

Ser Arg Tyr Gly Met His Trp Val Arg Gln Ala Pro Gly Lys Gly Leu
     50                  55                  60

Gln Trp Leu Ala Leu Val Leu His Asp Gly Gly Gln Lys Tyr Asn Glu
 65                  70                  75                  80

Asp Val Val Lys Gly Arg Phe Thr Ile Ser Arg Asp Asn Ser Asn Asn
                 85                  90                  95

Lys Val Tyr Leu Gln Met Asp Ser Leu Arg Gly Glu Asp Thr Ala Thr
            100                 105                 110

Tyr Tyr Cys Val Arg Gly Met Trp Glu Gln Leu Pro Ser Tyr Tyr Phe
        115                 120                 125

Asp Tyr Trp Gly Gln Gly Thr Leu Val Thr Val Ser Ser Ala Ser Pro
    130                 135                 140

Thr Ser Pro Lys Val Phe Pro Leu Ser Leu Cys Ser Thr Gln Pro Asp
145                 150                 155                 160

Gly Asn Val Val Ile Ala Cys Leu Val Gln Gly Phe Phe Pro Gln Glu
                165                 170                 175

Pro Leu Ser Val Thr Trp Ser Glu Ser Gly Gln Gly Val Thr Ala Arg
            180                 185                 190

Asn Phe Pro Pro Ser Gln Asp Ala Ser Gly Asp Leu Tyr Thr Thr Ser
        195                 200                 205

Ser Gln Leu Thr Leu Pro Ala Thr Gln Cys Leu Ala Gly Lys Ser Val
    210                 215                 220

Thr Cys His Val Lys His Tyr Thr Asn Pro Ser Gln Asp Val Thr Val
225                 230                 235                 240

Pro Cys Pro Val Pro Ser Thr Pro Pro Thr Pro Ser Pro Ser Thr Pro
                245                 250                 255

Pro Thr Pro Ser Pro Ser Cys Cys His Pro Arg Leu Ser Leu His Arg
            260                 265                 270

Pro Ala Leu Glu Asp Leu Leu Leu Gly Ser Glu Ala Asn Leu Thr Cys
        275                 280                 285

Thr Leu Thr Gly Leu Arg Asp Ala Ser Gly Val Thr Phe Thr Trp Thr
    290                 295                 300

Pro Ser Ser Gly Lys Ser Ala Val Gln Gly Pro Pro Asp Arg Asp Leu
305                 310                 315                 320

Cys Gly Cys Tyr Ser Val Ser Ser Val Leu Pro Gly Cys Ala Glu Pro
                325                 330                 335

Trp Asn His Gly Lys Thr Phe Thr Cys Thr Ala Ala Tyr Pro Glu Ser
            340                 345                 350
```

-continued

```
Lys Thr Pro Leu Thr Ala Thr Leu Ser Lys Ser Gly Asn Thr Phe Arg
        355                 360                 365

Pro Glu Val His Leu Leu Pro Pro Pro Ser Glu Glu Leu Ala Leu Asn
    370                 375                 380

Glu Leu Val Thr Leu Thr Cys Leu Ala Arg Gly Phe Ser Pro Lys Asp
385                 390                 395                 400

Val Leu Val Arg Trp Leu Gln Gly Ser Gln Glu Leu Pro Arg Glu Lys
                405                 410                 415

Tyr Leu Thr Trp Ala Ser Arg Gln Glu Pro Ser Gln Gly Thr Thr Thr
            420                 425                 430

Phe Ala Val Thr Ser Ile Leu Arg Val Ala Ala Glu Asp Trp Lys Lys
        435                 440                 445

Gly Asp Thr Phe Ser Cys Met Val Gly His Glu Ala Leu Pro Leu Ala
    450                 455                 460

Phe Thr Gln Lys Thr Ile Asp Arg Leu Ala Gly Lys Pro Thr His Val
465                 470                 475                 480

Asn Val Ser Val Val Met Ala Xaa Val Xaa Gly Pro Cys Xaa Xaa Ala
                485                 490                 495

Ala Arg Leu Ser Pro Pro Leu Asn Xaa Leu His Ala Pro Pro Lys Lys
            500                 505                 510

Lys Lys Lys Lys Lys Lys Lys Lys Lys Lys Lys Lys Lys Lys Lys Lys
        515                 520                 525

Lys Lys
    530


<210> SEQ ID NO 113
<211> LENGTH: 207
<212> TYPE: PRT
<213> ORGANISM: Homo sapiens
<220> FEATURE:
<221> NAME/KEY: SITE
<222> LOCATION: (75)
<223> OTHER INFORMATION: Xaa equals any of the naturally occurring
      L-amino acids
<221> NAME/KEY: SITE
<222> LOCATION: (77)
<223> OTHER INFORMATION: Xaa equals any of the naturally occurring
      L-amino acids
<221> NAME/KEY: SITE
<222> LOCATION: (112)
<223> OTHER INFORMATION: Xaa equals any of the naturally occurring
      L-amino acids

<400> SEQUENCE: 113

Met Asp Val Gly Pro Ser Ser Leu Pro His Leu Gly Leu Lys Leu Leu
  1               5                  10                  15

Leu Leu Leu Leu Leu Leu Pro Leu Arg Gly Gln Ala Asn Thr Gly Cys
             20                  25                  30

Tyr Gly Ile Pro Gly Met Pro Gly Leu Pro Gly Ala Pro Gly Lys Asp
         35                  40                  45

Gly Tyr Asp Gly Leu Pro Gly Pro Lys Gly Glu Pro Gly Ile Pro Ala
     50                  55                  60

Ile Pro Gly Ile Arg Gly Pro Lys Gly Gln Xaa Gly Xaa Ala Glu Ile
 65                  70                  75                  80

Pro Val Ser Val His Gly His Ser Ala Asp Pro Pro Ala Pro Cys Thr
                 85                  90                  95

Gln Gln Pro Asp Gln Ile Gln Arg Gly Pro His Gln Pro Ala Glu Xaa
            100                 105                 110
```

-continued

```
Tyr Asp Thr Ser Thr Gly Lys Phe Thr Cys Lys Val Pro Gly Leu Tyr
        115                 120                 125

Tyr Phe Val Tyr His Ala Ser His Thr Ala Asn Leu Cys Val Leu Leu
    130                 135                 140

Tyr Arg Ser Gly Val Lys Val Val Thr Phe Cys Gly His Thr Ser Lys
145                 150                 155                 160

Thr Asn Gln Val Asn Ser Gly Gly Val Leu Leu Arg Leu Gln Val Gly
                165                 170                 175

Glu Glu Val Trp Leu Ala Val Asn Asp Tyr Tyr Asp Met Val Gly Ile
            180                 185                 190

Gln Gly Ser Asp Ser Val Phe Ser Gly Phe Leu Leu Phe Pro Asp
        195                 200                 205


<210> SEQ ID NO 114
<211> LENGTH: 287
<212> TYPE: PRT
<213> ORGANISM: Homo sapiens

<400> SEQUENCE: 114

Met Gly Ala Leu Arg Pro Thr Leu Leu Pro Pro Ser Leu Pro Leu Leu
  1               5                  10                  15

Leu Leu Leu Met Leu Gly Met Gly Cys Trp Ala Arg Glu Val Leu Val
            20                  25                  30

Pro Glu Gly Pro Leu Tyr Arg Val Ala Gly Thr Ala Val Ser Ile Ser
        35                  40                  45

Cys Asn Val Thr Gly Tyr Glu Gly Pro Ala Gln Gln Asn Phe Glu Trp
    50                  55                  60

Phe Leu Tyr Arg Pro Glu Ala Pro Asp Thr Ala Leu Gly Ile Val Ser
 65                  70                  75                  80

Thr Lys Asp Thr Gln Phe Ser Tyr Ala Val Phe Lys Ser Arg Val Val
                85                  90                  95

Ala Gly Glu Val Gln Val Gln Arg Leu Gln Gly Asp Ala Val Val Leu
            100                 105                 110

Lys Ile Ala Arg Leu Gln Ala Gln Asp Ala Gly Ile Tyr Glu Cys His
        115                 120                 125

Thr Pro Ser Thr Asp Thr Arg Tyr Leu Gly Ser Tyr Ser Gly Lys Val
    130                 135                 140

Glu Leu Arg Val Leu Pro Asp Val Leu Gln Val Ser Ala Ala Pro Pro
145                 150                 155                 160

Gly Pro Arg Gly Arg Gln Ala Pro Thr Ser Pro Pro Arg Met Thr Val
                165                 170                 175

His Glu Gly Gln Glu Leu Ala Leu Gly Cys Leu Ala Arg Thr Ser Thr
            180                 185                 190

Gln Lys His Thr His Leu Ala Val Ser Phe Gly Arg Ser Val Pro Glu
        195                 200                 205

Ala Pro Val Gly Arg Ser Thr Leu Gln Glu Val Val Gly Ile Arg Ser
    210                 215                 220

Asp Leu Ala Val Glu Ala Gly Ala Pro Tyr Ala Glu Arg Leu Ala Ala
225                 230                 235                 240

Gly Glu Leu Arg Leu Gly Lys Glu Gly Thr Asp Arg Tyr Arg Met Val
                245                 250                 255

Val Gly Gly Ala Gln Ala Gly Asp Ala Gly Thr Tyr His Cys Thr Ala
            260                 265                 270

Ala Glu Trp Ile Gln Asp Pro Asp Gly Ser Trp Ala Gln Ile Ala
        275                 280                 285
```

-continued

<210> SEQ ID NO 115
<211> LENGTH: 245
<212> TYPE: PRT
<213> ORGANISM: Homo sapiens

<400> SEQUENCE: 115

```
Met Glu Gly Pro Arg Gly Trp Leu Val Leu Cys Val Leu Ala Ile Ser
  1               5                  10                  15

Leu Ala Ser Met Val Thr Glu Asp Leu Cys Arg Ala Pro Asp Gly Lys
             20                  25                  30

Lys Gly Glu Ala Gly Arg Pro Gly Arg Arg Gly Arg Pro Gly Leu Lys
         35                  40                  45

Gly Glu Gln Gly Glu Pro Gly Ala Pro Gly Ile Arg Thr Gly Ile Gln
     50                  55                  60

Gly Leu Lys Gly Asp Gln Gly Glu Pro Gly Pro Ser Gly Asn Pro Gly
 65                  70                  75                  80

Lys Val Gly Tyr Pro Gly Pro Ser Gly Pro Leu Gly Ala Arg Gly Ile
                 85                  90                  95

Pro Gly Ile Lys Gly Thr Lys Gly Ser Pro Gly Asn Ile Lys Asp Gln
            100                 105                 110

Pro Arg Pro Ala Phe Ser Ala Ile Arg Arg Asn Pro Pro Met Gly Gly
        115                 120                 125

Asn Val Val Ile Phe Asp Thr Val Ile Thr Asn Gln Glu Glu Pro Tyr
    130                 135                 140

Gln Asn His Ser Gly Arg Phe Val Cys Thr Val Pro Gly Tyr Tyr Tyr
145                 150                 155                 160

Phe Thr Phe Gln Val Leu Ser Gln Trp Glu Ile Cys Leu Ser Ile Val
                165                 170                 175

Ser Ser Ser Arg Gly Gln Val Arg Arg Ser Leu Gly Phe Cys Asp Thr
            180                 185                 190

Thr Asn Lys Gly Leu Phe Gln Val Val Ser Gly Gly Met Val Leu Gln
        195                 200                 205

Leu Gln Gln Gly Asp Gln Val Trp Val Glu Lys Asp Pro Lys Lys Gly
    210                 215                 220

His Ile Tyr Gln Gly Ser Glu Ala Asp Ser Val Phe Ser Gly Phe Leu
225                 230                 235                 240

Ile Phe Pro Ser Ala
                245
```

<210> SEQ ID NO 116
<211> LENGTH: 245
<212> TYPE: PRT
<213> ORGANISM: Homo sapiens
<220> FEATURE:
<221> NAME/KEY: SITE
<222> LOCATION: (128)
<223> OTHER INFORMATION: Xaa equals any of the naturally occurring
      L-amino acids

<400> SEQUENCE: 116

```
Met Glu Gly Pro Arg Gly Trp Leu Val Leu Cys Val Leu Ala Ile Ser
  1               5                  10                  15

Leu Ala Ser Met Val Thr Glu Asp Leu Cys Arg Ala Pro Asp Gly Lys
             20                  25                  30

Lys Gly Glu Ala Gly Arg Pro Gly Arg Arg Gly Arg Pro Gly Leu Lys
         35                  40                  45
```

-continued

```
Gly Glu Gln Gly Glu Pro Gly Ala Pro Gly Ile Arg Thr Gly Ile Gln
     50                  55                  60

Gly Leu Lys Gly Asp Gln Gly Glu Pro Gly Pro Ser Gly Asn Pro Gly
 65                  70                  75                  80

Lys Val Gly Tyr Pro Gly Pro Ser Gly Pro Leu Gly Ala Arg Gly Ile
                 85                  90                  95

Pro Gly Ile Lys Gly Thr Lys Gly Ser Pro Gly Asn Ile Lys Asp Gln
            100                 105                 110

Pro Arg Pro Ala Phe Ser Ala Ile Arg Arg Asn Pro Pro Met Gly Xaa
        115                 120                 125

Asn Val Val Ile Phe Asp Thr Val Ile Thr Asn Gln Glu Glu Pro Tyr
    130                 135                 140

Gln Asn His Ser Gly Arg Phe Val Cys Thr Val Pro Gly Tyr Tyr Tyr
145                 150                 155                 160

Phe Thr Phe Gln Val Leu Ser Gln Trp Glu Ile Cys Leu Ser Ile Val
                165                 170                 175

Ser Ser Ser Arg Gly Gln Val Arg Arg Ser Leu Gly Phe Cys Asp Thr
            180                 185                 190

Thr Asn Lys Gly Leu Phe Gln Val Val Ser Gly Gly Met Val Leu Gln
        195                 200                 205

Leu Gln Gln Gly Asp Gln Val Trp Val Glu Lys Asp Pro Lys Lys Gly
    210                 215                 220

His Ile Tyr Gln Gly Ser Glu Ala Asp Ser Val Phe Ser Gly Phe Leu
225                 230                 235                 240

Ile Phe Pro Ser Ala
                245


<210> SEQ ID NO 117
<211> LENGTH: 229
<212> TYPE: PRT
<213> ORGANISM: Homo sapiens
<220> FEATURE:
<221> NAME/KEY: SITE
<222> LOCATION: (47)
<223> OTHER INFORMATION: Xaa equals any of the naturally occurring
      L-amino acids
<221> NAME/KEY: SITE
<222> LOCATION: (49)
<223> OTHER INFORMATION: Xaa equals any of the naturally occurring
      L-amino acids

<400> SEQUENCE: 117

Met Glu Gly Pro Arg Gly Trp Leu Val Leu Cys Val Leu Ala Ile Ser
  1               5                  10                  15

Leu Ala Ser Met Val Thr Glu Asp Leu Cys Arg Ala Pro Asp Gly Lys
             20                  25                  30

Lys Gly Glu Ala Gly Arg Pro Gly Arg Arg Gly Arg Pro Gly Xaa Lys
         35                  40                  45

Xaa Leu Lys Gly Asp Gln Gly Glu Pro Gly Pro Ser Gly Asn Pro Gly
     50                  55                  60

Lys Val Gly Tyr Pro Gly Pro Ser Gly Pro Leu Gly Ala Arg Gly Ile
 65                  70                  75                  80

Pro Gly Ile Lys Gly Thr Lys Gly Ser Pro Gly Asn Ile Lys Asp Gln
                 85                  90                  95

Pro Arg Pro Ala Phe Ser Ala Ile Arg Arg Asn Pro Pro Met Gly Gly
            100                 105                 110

Asn Val Val Ile Phe Asp Thr Val Ile Thr Asn Gln Glu Glu Pro Tyr
        115                 120                 125
```

-continued

```
Gln Asn His Ser Gly Arg Phe Val Cys Thr Val Pro Gly Tyr Tyr Tyr
    130                 135                 140

Phe Thr Phe Gln Val Leu Ser Gln Trp Glu Ile Cys Leu Ser Ile Val
145                 150                 155                 160

Ser Ser Ser Arg Gly Gln Val Arg Arg Ser Leu Gly Phe Cys Asp Thr
                165                 170                 175

Thr Asn Lys Gly Leu Phe Gln Val Val Ser Gly Gly Met Val Leu Gln
            180                 185                 190

Leu Gln Gln Gly Asp Gln Val Trp Val Glu Lys Asp Pro Lys Lys Gly
        195                 200                 205

His Ile Tyr Gln Gly Ser Glu Ala Asp Ser Val Phe Ser Gly Phe Leu
    210                 215                 220

Ile Phe Pro Ser Ala
225


<210> SEQ ID NO 118
<211> LENGTH: 245
<212> TYPE: PRT
<213> ORGANISM: Homo sapiens

<400> SEQUENCE: 118

Met Glu Gly Pro Arg Gly Trp Leu Val Leu Cys Val Leu Ala Ile Ser
  1               5                  10                  15

Leu Ala Ser Met Val Thr Glu Asp Leu Cys Arg Ala Pro Asp Gly Lys
             20                  25                  30

Lys Gly Glu Ala Gly Arg Pro Gly Arg Arg Gly Arg Pro Gly Leu Lys
         35                  40                  45

Gly Glu Gln Gly Glu Pro Gly Ala Pro Gly Ile Arg Thr Gly Ile Gln
     50                  55                  60

Gly Leu Lys Gly Asp Gln Gly Glu Pro Gly Pro Ser Gly Asn Pro Gly
 65                  70                  75                  80

Lys Val Gly Tyr Pro Gly Pro Ser Gly Pro Leu Gly Ala Arg Gly Ile
                 85                  90                  95

Pro Gly Ile Lys Gly Thr Lys Gly Ser Pro Gly Asn Ile Lys Asp Gln
            100                 105                 110

Pro Arg Pro Ala Phe Ser Ala Ile Arg Arg Asn Pro Pro Met Gly Gly
        115                 120                 125

Asn Val Val Ile Phe Asp Thr Val Ile Thr Asn Gln Glu Glu Pro Tyr
    130                 135                 140

Gln Asn His Ser Gly Arg Phe Val Cys Thr Val Pro Gly Tyr Tyr Tyr
145                 150                 155                 160

Phe Thr Phe Gln Val Leu Ser Gln Trp Glu Ile Cys Leu Ser Ile Val
                165                 170                 175

Ser Ser Ser Arg Gly Gln Val Arg Arg Ser Leu Gly Phe Cys Asp Thr
            180                 185                 190

Thr Asn Lys Gly Leu Phe Gln Val Val Ser Gly Gly Met Val Leu Gln
        195                 200                 205

Leu Gln Gln Gly Asp Gln Val Trp Val Glu Lys Asp Pro Lys Lys Gly
    210                 215                 220

His Ile Tyr Gln Gly Ser Glu Ala Asp Ser Val Phe Ser Gly Phe Leu
225                 230                 235                 240

Ile Phe Pro Ser Ala
                245
```

-continued

<210> SEQ ID NO 119
<211> LENGTH: 245
<212> TYPE: PRT
<213> ORGANISM: Homo sapiens

<400> SEQUENCE: 119

```
Met Glu Gly Pro Arg Gly Trp Leu Val Leu Cys Val Leu Ala Ile Ser
  1               5                  10                  15

Leu Ala Ser Met Val Thr Glu Asp Leu Cys Arg Ala Pro Asp Gly Lys
             20                  25                  30

Lys Gly Glu Ala Gly Arg Pro Gly Arg Arg Gly Arg Pro Gly Leu Lys
         35                  40                  45

Gly Glu Gln Gly Glu Pro Gly Ala Pro Gly Ile Arg Thr Gly Ile Gln
     50                  55                  60

Gly Leu Lys Gly Asp Gln Gly Glu Pro Gly Pro Ser Gly Asn Pro Gly
 65                  70                  75                  80

Lys Val Gly Tyr Pro Gly Pro Ser Gly Pro Leu Gly Ala Arg Gly Ile
                 85                  90                  95

Pro Gly Ile Lys Gly Thr Lys Gly Ser Pro Gly Asn Ile Lys Asp Gln
            100                 105                 110

Pro Arg Pro Ala Phe Ser Ala Ile Arg Arg Asn Pro Pro Met Gly Gly
        115                 120                 125

Asn Val Val Ile Phe Asp Thr Val Ile Thr Asn Gln Glu Glu Pro Tyr
    130                 135                 140

Gln Asn His Ser Gly Arg Phe Val Cys Thr Val Pro Gly Tyr Tyr Tyr
145                 150                 155                 160

Phe Thr Phe Gln Val Leu Ser Gln Trp Glu Ile Cys Leu Ser Ile Val
                165                 170                 175

Ser Ser Ser Arg Gly Gln Val Arg Arg Ser Leu Gly Phe Cys Asp Thr
            180                 185                 190

Thr Asn Lys Gly Leu Phe Gln Val Val Ser Gly Gly Met Val Leu Gln
        195                 200                 205

Leu Gln Gln Gly Asp Gln Val Trp Val Glu Lys Asp Pro Lys Lys Gly
    210                 215                 220

His Ile Tyr Gln Gly Ser Glu Ala Asp Ser Val Phe Ser Gly Phe Leu
225                 230                 235                 240

Ile Phe Pro Ser Ala
                245
```

<210> SEQ ID NO 120
<211> LENGTH: 32
<212> TYPE: PRT
<213> ORGANISM: Homo sapiens

<400> SEQUENCE: 120

```
Met Gly Val Asn Lys Val Leu Phe Thr Phe Phe Phe Phe Ser Ser Leu
  1               5                  10                  15

Leu Asp Gly Val Gly Thr Ser His Ser Leu Ala Ser Phe Pro His Thr
             20                  25                  30
```

<210> SEQ ID NO 121
<211> LENGTH: 298
<212> TYPE: PRT
<213> ORGANISM: Homo sapiens

<400> SEQUENCE: 121

```
Met Lys Thr Leu Gln Ser Thr Leu Leu Leu Leu Leu Leu Val Pro Leu
  1               5                  10                  15
```

-continued

```
Ile Lys Pro Ala Pro Pro Thr Gln Gln Asp Ser Arg Ile Ile Tyr Asp
            20                  25                  30

Tyr Gly Thr Asp Asn Phe Glu Glu Ser Ile Phe Ser Gln Asp Tyr Glu
        35                  40                  45

Asp Lys Tyr Leu Asp Gly Lys Asn Ile Lys Glu Lys Glu Thr Val Ile
    50                  55                  60

Ile Pro Asn Glu Lys Ser Leu Gln Leu Gln Lys Asp Glu Ala Ile Thr
65                  70                  75                  80

Pro Leu Pro Pro Lys Lys Glu Asn Asp Glu Met Pro Thr Cys Leu Leu
                85                  90                  95

Cys Val Cys Leu Ser Gly Ser Val Tyr Cys Glu Glu Val Asp Ile Asp
            100                 105                 110

Ala Val Pro Pro Leu Pro Lys Glu Ser Ala Tyr Leu Tyr Ala Arg Phe
        115                 120                 125

Asn Lys Ile Lys Lys Leu Thr Ala Lys Asp Phe Ala Asp Ile Pro Asn
    130                 135                 140

Leu Arg Arg Leu Asp Phe Thr Gly Asn Leu Ile Glu Asp Ile Glu Asp
145                 150                 155                 160

Gly Thr Phe Ser Lys Leu Ser Leu Leu Glu Glu Leu Ser Leu Ala Glu
                165                 170                 175

Asn Gln Leu Leu Lys Leu Pro Val Leu Pro Pro Lys Leu Thr Leu Phe
            180                 185                 190

Asn Ala Lys Tyr Asn Lys Ile Lys Ser Arg Gly Ile Lys Ala Asn Ala
        195                 200                 205

Phe Lys Lys Leu Asn Asn Leu Thr Phe Leu Tyr Leu Asp His Asn Ala
    210                 215                 220

Leu Glu Ser Val Pro Leu Asn Leu Pro Glu Ser Leu Arg Val Ile His
225                 230                 235                 240

Leu Gln Phe Asn Asn Ile Ala Ser Ile Thr Asp Asp Thr Phe Cys Lys
                245                 250                 255

Ala Asn Asp Thr Ser Tyr Ile Arg Asp Arg Ile Glu Glu Ile Arg Leu
            260                 265                 270

Glu Gly Asn Pro Ile Val Leu Gly Lys His Pro Asn Ser Phe Ile Cys
        275                 280                 285

Leu Lys Arg Leu Pro Ile Gly Ser Tyr Phe
    290                 295


<210> SEQ ID NO 122
<211> LENGTH: 55
<212> TYPE: PRT
<213> ORGANISM: Homo sapiens

<400> SEQUENCE: 122

Met Cys Leu Leu Gly Gly Leu Ser Ala Pro Pro Leu Leu Leu Leu Pro
  1               5                  10                  15

Leu Leu Pro Leu Leu Leu Cys Pro Pro Thr Gly Arg Val Thr Ala Ala
            20                  25                  30

Phe Pro Gln Ser Tyr Leu Met Pro Tyr Lys Val Trp Val Thr Asn Arg
        35                  40                  45

Val Phe Leu Lys Asn Ser Gln
    50                  55


<210> SEQ ID NO 123
<211> LENGTH: 19
<212> TYPE: PRT
```

-continued

<213> ORGANISM: Homo sapiens

<400> SEQUENCE: 123

Glu Cys Cys Glu Thr Ala Ala Pro Pro Gly Pro His Arg Arg Pro Glu
1 5 10 15

Ser Gly Gln

<210> SEQ ID NO 124
<211> LENGTH: 514
<212> TYPE: PRT
<213> ORGANISM: Homo sapiens

<400> SEQUENCE: 124

Glu Leu Cys Arg Gln Pro Lys Pro Ser Thr Val Gln Ala Cys Asn Arg
1 5 10 15

Phe Asn Cys Pro Pro Ala Trp Tyr Pro Ala Gln Trp Gln Pro Cys Ser
20 25 30

Arg Thr Cys Gly Gly Gly Val Gln Lys Arg Glu Val Leu Cys Lys Gln
35 40 45

Arg Met Ala Asp Gly Ser Phe Leu Glu Leu Pro Glu Thr Phe Cys Ser
50 55 60

Ala Ser Lys Pro Ala Cys Gln Gln Ala Cys Lys Lys Asp Asp Cys Pro
65 70 75 80

Ser Glu Trp Leu Leu Ser Asp Trp Thr Glu Cys Ser Thr Ser Cys Gly
85 90 95

Glu Gly Thr Gln Thr Arg Ser Ala Ile Cys Arg Lys Met Leu Lys Thr
100 105 110

Gly Leu Ser Thr Val Val Asn Ser Thr Leu Cys Pro Pro Leu Pro Phe
115 120 125

Ser Ser Ser Ile Arg Pro Cys Met Leu Ala Thr Cys Ala Arg Pro Gly
130 135 140

Arg Pro Ser Thr Lys His Ser Pro His Ile Ala Ala Ala Arg Lys Val
145 150 155 160

Tyr Ile Gln Thr Arg Arg Gln Arg Lys Leu His Phe Val Val Gly Gly
165 170 175

Phe Ala Tyr Leu Leu Pro Lys Thr Ala Val Val Leu Arg Cys Pro Ala
180 185 190

Arg Arg Val Arg Lys Pro Leu Ile Thr Trp Glu Lys Asp Gly Gln His
195 200 205

Leu Ile Ser Ser Thr His Val Thr Val Ala Pro Phe Gly Tyr Leu Lys
210 215 220

Ile His Arg Leu Lys Pro Ser Asp Ala Gly Val Tyr Thr Cys Ser Ala
225 230 235 240

Gly Pro Ala Arg Glu His Phe Val Ile Lys Leu Ile Gly Gly Asn Arg
245 250 255

Lys Leu Val Ala Arg Pro Leu Ser Pro Arg Ser Glu Glu Glu Val Leu
260 265 270

Ala Gly Arg Lys Gly Gly Pro Lys Glu Ala Leu Gln Thr His Lys His
275 280 285

Gln Asn Gly Ile Phe Ser Asn Gly Ser Lys Ala Glu Lys Arg Gly Leu
290 295 300

Ala Ala Asn Pro Gly Ser Arg Tyr Asp Asp Leu Val Ser Arg Leu Leu
305 310 315 320

Glu Gln Gly Gly Trp Pro Gly Glu Leu Leu Ala Ser Trp Glu Ala Gln
325 330 335

```
Asp Ser Ala Glu Arg Asn Thr Thr Ser Glu Glu Asp Pro Gly Ala Glu
            340                 345                 350

Gln Val Leu Leu His Leu Pro Phe Thr Met Val Thr Glu Gln Arg Arg
        355                 360                 365

Leu Asp Asp Ile Leu Gly Asn Leu Ser Gln Gln Pro Glu Glu Leu Arg
    370                 375                 380

Asp Leu Tyr Ser Lys His Leu Val Ala Gln Leu Ala Gln Glu Ile Phe
385                 390                 395                 400

Arg Ser His Leu Glu His Gln Asp Thr Leu Leu Lys Pro Ser Glu Arg
                405                 410                 415

Arg Thr Ser Pro Val Thr Leu Ser Pro His Lys His Val Ser Gly Phe
            420                 425                 430

Ser Ser Ser Leu Arg Thr Ser Ser Thr Gly Asp Ala Gly Gly Gly Ser
        435                 440                 445

Arg Arg Pro His Arg Lys Pro Thr Ile Leu Arg Lys Ile Ser Ala Ala
    450                 455                 460

Gln Gln Leu Ser Ala Ser Glu Val Val Thr His Leu Gly Gln Thr Val
465                 470                 475                 480

Ala Leu Ala Ser Gly Thr Leu Ser Val Phe Cys Thr Val Arg Pro Ser
                485                 490                 495

Ala Thr Gln Gly Leu Pro Ser Ala Gly Pro Gly Met Glu Lys Lys Ser
            500                 505                 510

Val Gln


<210> SEQ ID NO 125
<211> LENGTH: 262
<212> TYPE: PRT
<213> ORGANISM: Homo sapiens
<220> FEATURE:
<221> NAME/KEY: SITE
<222> LOCATION: (254)
<223> OTHER INFORMATION: Xaa equals any of the naturally occurring
      L-amino acids

<400> SEQUENCE: 125

Met Glu Cys Cys Arg Arg Ala Thr Pro Gly Thr Leu Leu Leu Phe Leu
  1               5                  10                  15

Ala Phe Leu Leu Leu Ser Ser Arg Thr Ala Arg Ser Glu Glu Asp Arg
             20                  25                  30

Asp Gly Leu Trp Asp Ala Trp Gly Pro Trp Ser Glu Cys Ser Arg Thr
         35                  40                  45

Cys Gly Gly Gly Ala Ser Tyr Ser Leu Arg Arg Cys Leu Ser Ser Lys
     50                  55                  60

Ser Cys Glu Gly Arg Asn Ile Arg Tyr Arg Thr Cys Ser Asn Val Asp
 65                  70                  75                  80

Cys Pro Pro Glu Ala Gly Asp Phe Arg Ala Gln Gln Cys Ser Ala His
                 85                  90                  95

Asn Asp Val Lys His His Gly Gln Phe Tyr Glu Trp Leu Pro Val Ser
            100                 105                 110

Asn Asp Pro Asp Asn Pro Cys Ser Leu Lys Cys Gln Ala Lys Gly Thr
        115                 120                 125

Thr Leu Val Val Glu Leu Ala Pro Lys Val Leu Asp Gly Thr Arg Cys
    130                 135                 140

Tyr Thr Glu Ser Leu Asp Met Cys Ile Ser Gly Leu Cys Gln Ile Val
145                 150                 155                 160
```

-continued

```
Gly Cys Asp His Gln Leu Gly Ser Thr Val Lys Glu Asp Asn Cys Gly
                165                 170                 175

Val Cys Asn Gly Asp Gly Ser Thr Cys Arg Leu Val Arg Gly Gln Tyr
            180                 185                 190

Lys Ser Gln Leu Ser Ala Thr Lys Ser Asp Asp Thr Val Val Ala Ile
        195                 200                 205

Pro Tyr Gly Ser Arg His Ile Arg Leu Val Leu Lys Gly Pro Asp His
    210                 215                 220

Leu Tyr Leu Glu Thr Lys Thr Leu Gln Gly Thr Lys Gly Glu Asn Ser
225                 230                 235                 240

Leu Ser Ser Thr Gly Thr Phe Leu Val Asp Asn Ser Ser Xaa Thr Ser
                245                 250                 255

Arg Asn Phe Gln Thr Lys
            260


<210> SEQ ID NO 126
<211> LENGTH: 115
<212> TYPE: PRT
<213> ORGANISM: Homo sapiens
<220> FEATURE:
<221> NAME/KEY: SITE
<222> LOCATION: (101)
<223> OTHER INFORMATION: Xaa equals any of the naturally occurring
      L-amino acids
<221> NAME/KEY: SITE
<222> LOCATION: (106)
<223> OTHER INFORMATION: Xaa equals any of the naturally occurring
      L-amino acids

<400> SEQUENCE: 126

Ile Ser Leu Leu Trp Asn Leu Trp Gln Ser Val Lys Ile Gly Cys Gly
  1               5                  10                  15

Glu Lys Leu Tyr Pro Gly His Thr Lys Asp Ser Arg Asn His Leu Gly
             20                  25                  30

Gln Asn Leu Ser Phe Leu His Phe Ile Tyr Leu Phe Pro Pro Pro His
         35                  40                  45

Ser Thr His Thr Leu Pro Thr Ser Ser Thr Ser Thr Phe Lys His Lys
     50                  55                  60

Asp Val Arg Val Phe Ser Leu Ser Val Ser Trp Arg Thr Gly Cys Trp
 65                  70                  75                  80

Glu Arg Lys Gly Gln Met Ser Lys Gly Gly Cys Arg Ala Gly Gln Ala
                 85                  90                  95

Asp Ser Gly Gly Xaa Leu Glu Glu Leu Xaa Pro Ser Gln Thr Trp Val
            100                 105                 110

Ser Lys Thr
        115


<210> SEQ ID NO 127
<211> LENGTH: 350
<212> TYPE: PRT
<213> ORGANISM: Homo sapiens
<220> FEATURE:
<221> NAME/KEY: SITE
<222> LOCATION: (3)
<223> OTHER INFORMATION: Xaa equals any of the naturally occurring
      L-amino acids
<221> NAME/KEY: SITE
<222> LOCATION: (4)
<223> OTHER INFORMATION: Xaa equals any of the naturally occurring
      L-amino acids

<400> SEQUENCE: 127
```

-continued

```
Met Ala Xaa Xaa Val Val Leu Leu Ala Leu Val Ala Gly Val Leu Gly
  1               5                  10                  15

Asn Glu Phe Ser Ile Leu Lys Ser Pro Gly Ser Val Val Phe Arg Asn
             20                  25                  30

Gly Asn Trp Pro Ile Pro Gly Glu Arg Ile Pro Asp Val Ala Ala Leu
         35                  40                  45

Ser Met Gly Phe Ser Val Lys Glu Asp Leu Ser Trp Pro Gly Leu Ala
     50                  55                  60

Val Gly Asn Leu Phe His Arg Pro Arg Ala Thr Val Met Val Met Val
 65                  70                  75                  80

Lys Gly Val Asn Lys Leu Ala Leu Pro Pro Gly Ser Val Ile Ser Tyr
                 85                  90                  95

Pro Leu Glu Asn Ala Val Pro Phe Ser Leu Asp Ser Val Ala Asn Ser
            100                 105                 110

Ile His Ser Leu Phe Ser Glu Glu Thr Pro Val Val Leu Gln Leu Ala
        115                 120                 125

Pro Ser Glu Glu Arg Val Tyr Met Val Gly Lys Ala Asn Ser Val Phe
    130                 135                 140

Glu Asp Leu Ser Val Thr Leu Arg Gln Leu Arg Asn Arg Leu Phe Gln
145                 150                 155                 160

Glu Asn Ser Val Leu Ser Ser Leu Pro Leu Asn Ser Leu Ser Arg Asn
                165                 170                 175

Asn Glu Val Asp Leu Leu Phe Leu Ser Glu Leu Gln Val Leu His Asp
            180                 185                 190

Ile Ser Ser Leu Leu Ser Arg His Lys His Leu Ala Lys Asp His Ser
        195                 200                 205

Pro Asp Leu Tyr Ser Leu Glu Leu Ala Gly Leu Asp Glu Ile Gly Lys
    210                 215                 220

Arg Tyr Gly Glu Asp Ser Glu Gln Phe Arg Asp Ala Ser Lys Ile Leu
225                 230                 235                 240

Val Asp Ala Leu Gln Lys Phe Ala Asp Asp Met Tyr Ser Leu Tyr Gly
                245                 250                 255

Gly Asn Ala Val Val Glu Leu Val Thr Val Lys Ser Phe Asp Thr Ser
            260                 265                 270

Leu Ile Arg Lys Thr Arg Thr Ile Leu Glu Ala Lys Gln Ala Lys Asn
        275                 280                 285

Pro Ala Ser Pro Tyr Asn Leu Ala Tyr Lys Tyr Asn Phe Glu Tyr Ser
    290                 295                 300

Val Val Phe Asn Met Val Leu Trp Ile Met Ile Ala Leu Ala Leu Ala
305                 310                 315                 320

Val Ile Ile Thr Ser Tyr Asn Ile Trp Asn Met Asp Pro Gly Tyr Asp
                325                 330                 335

Ser Ile Ile Tyr Arg Met Thr Asn Gln Lys Ile Arg Met Asp
            340                 345                 350


<210> SEQ ID NO 128
<211> LENGTH: 339
<212> TYPE: PRT
<213> ORGANISM: Homo sapiens

<400> SEQUENCE: 128

Met Ser Trp Ser Thr Phe Leu Leu Ala Glu Ala Cys Gly Phe Thr Gly
  1               5                  10                  15

Val Val Ala Val Leu Phe Cys Gly Ile Thr Gln Ala His Tyr Thr Tyr
             20                  25                  30
```

-continued

```
Asn Asn Leu Ser Val Glu Ser Arg Ser Arg Thr Lys Gln Leu Phe Glu
        35                  40                  45

Val Leu His Phe Leu Ala Glu Asn Phe Ile Phe Ser Tyr Met Gly Leu
    50                  55                  60

Ala Leu Phe Thr Phe Gln Lys His Val Phe Ser Pro Ile Phe Ile Ile
65                  70                  75                  80

Gly Ala Phe Val Ala Ile Phe Leu Gly Arg Ala Ala His Ile Tyr Pro
                85                  90                  95

Leu Ser Phe Phe Leu Asn Leu Gly Arg Arg His Lys Ile Gly Trp Asn
            100                 105                 110

Phe Gln His Met Met Met Phe Ser Gly Leu Arg Gly Ala Met Ala Phe
        115                 120                 125

Ala Leu Ala Ile Arg Asp Thr Ala Ser Tyr Ala Arg Gln Met Met Phe
    130                 135                 140

Thr Thr Thr Leu Leu Ile Val Phe Phe Thr Val Trp Ile Ile Gly Gly
145                 150                 155                 160

Gly Thr Thr Pro Met Leu Ser Trp Leu Asn Ile Arg Val Gly Val Asp
                165                 170                 175

Pro Asp Gln Asp Pro Pro Pro Asn Asn Asp Ser Phe Gln Val Leu Gln
            180                 185                 190

Gly Asp Gly Pro Asp Ser Ala Arg Gly Asn Arg Thr Lys Gln Glu Ser
        195                 200                 205

Ala Trp Ile Phe Arg Leu Trp Tyr Ser Phe Asp His Asn Tyr Leu Lys
    210                 215                 220

Pro Ile Leu Thr His Ser Gly Pro Pro Leu Thr Thr Thr Leu Pro Ala
225                 230                 235                 240

Trp Cys Gly Leu Leu Ala Arg Cys Leu Thr Ser Pro Gln Val Tyr Asp
                245                 250                 255

Asn Gln Glu Pro Leu Arg Glu Glu Asp Ser Asp Phe Ile Leu Thr Glu
            260                 265                 270

Gly Asp Leu Thr Leu Thr Tyr Gly Asp Ser Thr Val Thr Ala Asn Gly
        275                 280                 285

Ser Ser Ser Ser His Thr Ala Ser Thr Ser Leu Glu Gly Ser Arg Arg
    290                 295                 300

Thr Lys Ser Ser Ser Glu Glu Val Leu Glu Arg Asp Leu Gly Met Gly
305                 310                 315                 320

Asp Gln Lys Val Ser Ser Arg Gly Thr Arg Leu Val Phe Pro Leu Glu
                325                 330                 335

Asp Asn Ala


<210> SEQ ID NO 129
<211> LENGTH: 339
<212> TYPE: PRT
<213> ORGANISM: Homo sapiens

<400> SEQUENCE: 129

Met Ser Trp Ser Thr Phe Leu Leu Ala Glu Ala Cys Gly Phe Thr Gly
  1               5                  10                  15

Val Val Ala Val Leu Phe Cys Gly Ile Thr Gln Ala His Tyr Thr Tyr
            20                  25                  30

Asn Asn Leu Ser Val Glu Ser Arg Ser Arg Thr Lys Gln Leu Phe Glu
        35                  40                  45

Val Leu His Phe Leu Ala Glu Asn Phe Ile Phe Ser Tyr Met Gly Leu
    50                  55                  60
```

-continued

```
Ala Leu Phe Thr Phe Gln Lys His Val Phe Ser Pro Ile Phe Ile Ile
 65                  70                  75                  80

Gly Ala Phe Val Ala Ile Phe Leu Gly Arg Ala Ala His Ile Tyr Pro
                 85                  90                  95

Leu Ser Phe Phe Leu Asn Leu Gly Arg Arg His Lys Ile Gly Trp Asn
            100                 105                 110

Phe Gln His Met Met Met Phe Ser Gly Leu Arg Gly Ala Met Ala Phe
        115                 120                 125

Ala Leu Ala Ile Arg Asp Thr Ala Ser Tyr Ala Arg Gln Met Met Phe
    130                 135                 140

Thr Thr Thr Leu Leu Ile Val Phe Phe Thr Val Trp Ile Ile Gly Gly
145                 150                 155                 160

Gly Thr Thr Pro Met Leu Ser Trp Leu Asn Ile Arg Val Gly Val Asp
                165                 170                 175

Pro Asp Gln Asp Pro Pro Pro Asn Asn Asp Ser Phe Gln Val Leu Gln
            180                 185                 190

Gly Asp Gly Pro Asp Ser Ala Arg Gly Asn Arg Thr Lys Gln Glu Ser
        195                 200                 205

Ala Trp Ile Phe Arg Leu Trp Tyr Ser Phe Asp His Asn Tyr Leu Lys
    210                 215                 220

Pro Ile Leu Thr His Ser Gly Pro Pro Leu Thr Thr Thr Leu Pro Ala
225                 230                 235                 240

Trp Cys Gly Leu Leu Ala Arg Cys Leu Thr Ser Pro Gln Val Tyr Asp
                245                 250                 255

Asn Gln Glu Pro Leu Arg Glu Glu Asp Ser Asp Phe Ile Leu Thr Glu
            260                 265                 270

Gly Asp Leu Thr Leu Thr Tyr Gly Asp Ser Thr Val Thr Ala Asn Gly
        275                 280                 285

Ser Ser Ser Ser His Thr Ala Ser Thr Ser Leu Glu Gly Ser Arg Arg
    290                 295                 300

Thr Lys Ser Ser Ser Glu Glu Val Leu Glu Arg Asp Leu Gly Met Gly
305                 310                 315                 320

Asp Gln Lys Val Ser Ser Arg Gly Thr Arg Leu Val Phe Pro Leu Glu
                325                 330                 335

Asp Asn Ala


<210> SEQ ID NO 130
<211> LENGTH: 472
<212> TYPE: PRT
<213> ORGANISM: Homo sapiens

<400> SEQUENCE: 130

Met Ile Arg Thr Arg Arg Gly Trp Ser Ser Met Trp Pro Trp Ile Gly
  1               5                  10                  15

Val Gly Tyr Leu Ala Gly Cys Leu Val His Ala Leu Gly Glu Lys Gln
             20                  25                  30

Pro Glu Leu Gln Ile Ser Glu Arg Asp Val Leu Cys Val Gln Ile Ala
        35                  40                  45

Gly Leu Cys His Asp Leu Gly His Gly Pro Phe Ser His Met Phe Asp
     50                  55                  60

Gly Arg Phe Ile Pro Leu Ala Arg Pro Glu Val Lys Trp Thr His Glu
 65                  70                  75                  80

Gln Gly Ser Val Met Met Phe Glu His Leu Ile Asn Ser Asn Gly Ile
                 85                  90                  95
```

-continued

```
Lys Pro Val Met Glu Gln Tyr Gly Leu Ile Pro Glu Glu Asp Ile Cys
            100                 105                 110

Phe Ile Lys Glu Gln Ile Val Gly Pro Leu Glu Ser Pro Val Glu Asp
        115                 120                 125

Ser Leu Trp Pro Tyr Lys Gly Arg Pro Glu Asn Lys Ser Phe Leu Tyr
    130                 135                 140

Glu Ile Val Ser Asn Lys Arg Asn Gly Ile Asp Val Asp Lys Trp Asp
145                 150                 155                 160

Tyr Phe Ala Arg Asp Cys His His Leu Gly Ile Gln Asn Asn Phe Asp
                165                 170                 175

Tyr Lys Arg Phe Ile Lys Phe Ala Arg Val Cys Glu Val Asp Asn Glu
            180                 185                 190

Leu Arg Ile Cys Ala Arg Asp Lys Glu Val Gly Asn Leu Tyr Asp Met
        195                 200                 205

Phe His Thr Arg Asn Ser Leu His Arg Arg Ala Tyr Gln His Lys Val
    210                 215                 220

Gly Asn Ile Ile Asp Thr Met Ile Thr Asp Ala Phe Leu Glu Ala Asp
225                 230                 235                 240

Asp Tyr Ile Glu Ile Thr Gly Ala Gly Gly Lys Lys Tyr Arg Ile Ser
                245                 250                 255

Thr Ala Ile Asp Asp Met Glu Ala Tyr Thr Lys Leu Thr Asp Asn Ile
            260                 265                 270

Phe Leu Glu Ile Leu Tyr Ser Thr Asp Pro Lys Leu Lys Asp Ala Arg
        275                 280                 285

Glu Ile Leu Lys Gln Ile Glu Tyr Arg Asn Leu Phe Lys Tyr Val Gly
    290                 295                 300

Glu Thr Gln Pro Thr Gly Gln Ile Lys Ile Lys Arg Glu Asp Tyr Glu
305                 310                 315                 320

Ser Leu Pro Lys Glu Val Ala Ser Ala Lys Pro Lys Val Leu Leu Asp
                325                 330                 335

Val Lys Leu Lys Ala Glu Asp Phe Ile Val Asp Val Ile Asn Met Asp
            340                 345                 350

Tyr Gly Met Gln Glu Lys Asn Pro Ile Asp His Val Ser Phe Tyr Cys
        355                 360                 365

Lys Thr Ala Pro Asn Arg Ala Ile Arg Ile Thr Lys Asn Gln Val Ser
    370                 375                 380

Gln Leu Leu Pro Glu Lys Phe Ala Glu Gln Leu Ile Arg Val Tyr Cys
385                 390                 395                 400

Lys Lys Val Asp Arg Lys Ser Leu Tyr Ala Ala Arg Gln Tyr Phe Val
                405                 410                 415

Gln Trp Cys Ala Asp Arg Asn Phe Thr Lys Pro Gln Asp Gly Asp Val
            420                 425                 430

Ile Ala Pro Leu Ile Thr Pro Gln Lys Lys Glu Trp Asn Asp Ser Thr
        435                 440                 445

Ser Val Gln Asn Pro Thr Arg Leu Arg Glu Ala Ser Lys Ser Arg Val
    450                 455                 460

Gln Leu Phe Lys Asp Asp Pro Met
465                 470
```

<210> SEQ ID NO 131
<211> LENGTH: 42
<212> TYPE: PRT
<213> ORGANISM: Homo sapiens -continued

<400> SEQUENCE: 131

Met Glu Cys Lys Lys Arg Ile Gln Leu Ile Met Leu Ala Ser Ile Val
1 5 10 15

Arg Leu Pro Pro Thr Glu Gln Ser Gly Leu Leu Lys Thr Arg Phe His
20 25 30

Asn Phe Cys Gln Arg Asn Leu Gln Ser Ser
35 40

<210> SEQ ID NO 132
<211> LENGTH: 122
<212> TYPE: PRT
<213> ORGANISM: Homo sapiens

<400> SEQUENCE: 132

Met Trp Gly Trp Gly Ser Leu Val Ser Ala Arg Gly Gly Trp Gly Val
1 5 10 15

Phe Ile Tyr Leu Tyr Met Gly Leu Tyr Ile Val Leu Trp Gly Met Gly
20 25 30

Glu Pro Ala Gly Gly Glu Asn Pro Pro Leu Ser Pro His Pro Pro Gly
35 40 45

Arg Ala Asn Val Lys Leu Leu Ile Phe Val Leu Tyr Ile Phe Tyr Ile
50 55 60

Asn Ile Ser Ile Phe Phe Leu Gln Asn Gln Phe Ile Asn Gly Arg Gly
65 70 75 80

Val Trp Gly Gly His Met Glu Leu Pro Leu Trp Gly Gly Pro Leu His
85 90 95

Tyr Pro Thr Tyr Arg Pro Phe Pro His Pro Pro Pro His Ser Pro Pro
100 105 110

Pro Gly Cys Asp Cys Cys Lys Met Gly Val
115 120

<210> SEQ ID NO 133
<211> LENGTH: 252
<212> TYPE: PRT
<213> ORGANISM: Homo sapiens
<220> FEATURE:
<221> NAME/KEY: SITE
<222> LOCATION: (86)
<223> OTHER INFORMATION: Xaa equals any of the naturally occurring L-amino acids
<221> NAME/KEY: SITE
<222> LOCATION: (116)
<223> OTHER INFORMATION: Xaa equals any of the naturally occurring L-amino acids
<221> NAME/KEY: SITE
<222> LOCATION: (135)
<223> OTHER INFORMATION: Xaa equals any of the naturally occurring L-amino acids
<221> NAME/KEY: SITE
<222> LOCATION: (146)
<223> OTHER INFORMATION: Xaa equals any of the naturally occurring L-amino acids

<400> SEQUENCE: 133

Met Ala Val Gly Lys Phe Leu Leu Gly Ser Leu Leu Leu Leu Ser Leu
1 5 10 15

Gln Leu Gly Gln Gly Trp Gly Pro Asp Ala Arg Gly Val Pro Val Ala
20 25 30

Asp Gly Glu Phe Ser Ser Glu Gln Val Ala Lys Ala Gly Gly Thr Trp
35 40 45

Leu Gly Lys Asp Phe Gln Gly Pro Ser Val Thr Ser Gln Leu Ser Pro
50 55 60

-continued

```
Ala Leu Thr Leu Leu Thr Val Ser Ala Leu Pro Ser His Arg His Pro
 65                  70                  75                  80

Pro Pro Pro Cys Pro Xaa Ala Pro Ser Pro Val Trp Ser Met Pro Ala
                85                  90                  95

Val Glu Pro Asp Pro Val Arg Gly Arg Ala Arg Pro Gly Leu Arg Leu
            100                 105                 110

Ile Gly Glu Xaa His Leu Pro Leu Leu Arg Arg Gln Leu Pro Pro Trp
        115                 120                 125

Cys Pro His Pro Ala Trp Xaa Gly Ala Gly Pro Ala Ala Gly Pro Gly
    130                 135                 140

Pro Xaa Pro Arg Arg Ala Leu Leu Pro Ala His Ser Leu His Arg Arg
145                 150                 155                 160

Gly Leu Pro Arg Arg Pro Pro Arg Trp Gln Arg Leu Pro Gln Leu Ser
                165                 170                 175

Ala Ala Leu Arg Leu Trp Trp Leu Arg Val Pro Gly Leu Ala Pro Arg
            180                 185                 190

Ser Cys Ser Ala Gly Gly Ala Arg Leu Thr Tyr Leu Leu Glu Thr Trp
        195                 200                 205

Met Gln Arg Gln Arg Gly Gly Glu Trp Ala Gly Ala Thr Ser Ser Glu
    210                 215                 220

Cys Asn Lys Gly His His Ser Pro Gly Lys Lys Lys Lys Lys Lys Lys
225                 230                 235                 240

Lys Lys Lys Lys Lys Leu Glu Gly Gly Ser Arg Tyr
                245                 250


<210> SEQ ID NO 134
<211> LENGTH: 132
<212> TYPE: PRT
<213> ORGANISM: Homo sapiens

<400> SEQUENCE: 134

Met Thr Leu Phe Gly Leu Phe Val Ser Leu Val Phe Leu Gly Gln Ala
  1               5                  10                  15

Phe Thr Ile Met Leu Val Tyr Val Trp Ser Arg Arg Asn Pro Tyr Val
             20                  25                  30

Arg Met Asn Phe Phe Gly Leu Leu Asn Phe Gln Ala Pro Phe Leu Pro
         35                  40                  45

Trp Val Leu Met Gly Phe Ser Leu Leu Leu Gly Asn Ser Ile Ile Val
     50                  55                  60

Asp Leu Leu Gly Ile Ala Val Gly His Ile Tyr Phe Phe Leu Glu Asp
 65                  70                  75                  80

Val Phe Pro Asn Gln Pro Gly Gly Ile Arg Ile Leu Lys Thr Pro Ser
                85                  90                  95

Ile Leu Lys Ala Ile Phe Asp Thr Pro Asp Glu Asp Pro Asn Tyr Asn
            100                 105                 110

Pro Leu Pro Glu Glu Arg Pro Gly Gly Phe Ala Trp Gly Glu Gly Gln
        115                 120                 125

Arg Leu Gly Gly
    130


<210> SEQ ID NO 135
<211> LENGTH: 156
<212> TYPE: PRT
<213> ORGANISM: Homo sapiens

<400> SEQUENCE: 135
```

-continued

```
Met Leu Glu Glu Gly Ser Phe Arg Gly Arg Thr Ala Asp Phe Val Phe
  1               5                  10                  15

Met Phe Leu Phe Gly Gly Phe Leu Met Thr Leu Phe Gly Leu Phe Val
             20                  25                  30

Ser Leu Val Phe Leu Gly Gln Ala Phe Thr Ile Met Leu Val Tyr Val
         35                  40                  45

Trp Ser Arg Arg Asn Pro Tyr Val Arg Met Asn Phe Phe Gly Leu Leu
     50                  55                  60

Asn Phe Gln Ala Pro Phe Leu Pro Trp Val Leu Met Gly Phe Ser Leu
 65                  70                  75                  80

Leu Leu Gly Asn Ser Ile Ile Val Asp Leu Leu Gly Ile Ala Val Gly
                 85                  90                  95

His Ile Tyr Phe Phe Leu Glu Asp Val Phe Pro Asn Gln Pro Gly Gly
            100                 105                 110

Ile Arg Ile Leu Lys Thr Pro Ser Ile Leu Lys Ala Ile Phe Asp Thr
        115                 120                 125

Pro Asp Glu Asp Pro Asn Tyr Asn Pro Leu Pro Glu Glu Arg Pro Gly
    130                 135                 140

Gly Phe Ala Trp Gly Glu Gly Gln Arg Leu Gly Gly
145                 150                 155


<210> SEQ ID NO 136
<211> LENGTH: 140
<212> TYPE: PRT
<213> ORGANISM: Homo sapiens
<220> FEATURE:
<221> NAME/KEY: SITE
<222> LOCATION: (36)
<223> OTHER INFORMATION: Xaa equals any of the naturally occurring
      L-amino acids

<400> SEQUENCE: 136

Met Phe Leu Phe Gly Gly Phe Leu Met Thr Leu Phe Gly Leu Phe Val
  1               5                  10                  15

Ser Leu Val Phe Leu Gly Gln Ala Phe Thr Ile Met Leu Val Tyr Val
             20                  25                  30

Trp Ser Arg Xaa Asn Pro Tyr Val Arg Met Asn Phe Phe Gly Leu Leu
         35                  40                  45

Asn Phe Gln Ala Pro Phe Leu Pro Trp Val Leu Met Gly Phe Ser Leu
     50                  55                  60

Leu Leu Gly Asn Ser Ile Ile Val Asp Leu Leu Gly Ile Ala Val Gly
 65                  70                  75                  80

His Ile Tyr Phe Phe Leu Glu Asp Val Phe Pro Asn Gln Pro Gly Gly
                 85                  90                  95

Ile Arg Ile Leu Lys Thr Pro Ser Ile Leu Lys Ala Ile Phe Asp Thr
            100                 105                 110

Pro Asp Glu Asp Pro Asn Tyr Asn Pro Leu Pro Glu Glu Arg Pro Gly
        115                 120                 125

Gly Phe Ala Trp Gly Glu Gly Gln Arg Leu Gly Gly
    130                 135                 140


<210> SEQ ID NO 137
<211> LENGTH: 50
<212> TYPE: PRT
<213> ORGANISM: Homo sapiens

<400> SEQUENCE: 137
```

-continued

```
Met Gln Val Lys Asn Ser Ile His Val Thr Phe Val Ala Arg Ile Leu
  1               5                  10                  15

Val Arg Val Leu Ile Cys Leu Ser Thr Ser Glu Ala Ile Leu Ala Arg
             20                  25                  30

Asn His Ile Tyr Val Val Ser Val Thr Asn Ala Ser Val Glu Val Gln
         35                  40                  45

Thr Ser
     50


<210> SEQ ID NO 138
<211> LENGTH: 172
<212> TYPE: PRT
<213> ORGANISM: Homo sapiens

<400> SEQUENCE: 138

Gly Thr Arg Thr Glu Arg Asp Glu Leu Leu Lys Asp Leu Gln Gln Ser
  1               5                  10                  15

Ile Ala Arg Glu Pro Ser Ala Pro Ser Ile Pro Thr Pro Ala Tyr Gln
             20                  25                  30

Ser Leu Pro Ala Gly Gly His Ala Pro Thr Pro Pro Thr Pro Ala Pro
         35                  40                  45

Arg Thr Met Pro Pro Thr Lys Pro Gln Pro Pro Ala Arg Pro Pro Pro
     50                  55                  60

Pro Val Leu Pro Ala Asn Arg Ala Pro Ser Ala Thr Ala Pro Ser Pro
 65                  70                  75                  80

Val Gly Ala Gly Thr Ala Ala Pro Ala Pro Ser Gln Thr Pro Gly Ser
                 85                  90                  95

Ala Pro Pro Pro Gln Ala Gln Gly Pro Pro Tyr Pro Thr Tyr Pro Gly
            100                 105                 110

Tyr Pro Gly Tyr Cys Gln Met Pro Met Pro Met Gly Tyr Asn Pro Tyr
        115                 120                 125

Ala Tyr Gly Gln Tyr Asn Met Pro Tyr Pro Pro Val Tyr His Gln Ser
    130                 135                 140

Pro Gly Gln Ala Pro Tyr Pro Gly Pro Gln Gln Pro Ser Tyr Pro Phe
145                 150                 155                 160

Pro Gln Pro Pro Gln Gln Ser Tyr Tyr Pro Gln Gln
                165                 170


<210> SEQ ID NO 139
<211> LENGTH: 142
<212> TYPE: PRT
<213> ORGANISM: Homo sapiens
<220> FEATURE:
<221> NAME/KEY: SITE
<222> LOCATION: (111)
<223> OTHER INFORMATION: Xaa equals any of the naturally occurring
      L-amino acids

<400> SEQUENCE: 139

Met His Gln Leu Leu Gln Leu Gln Arg Gln Glu Pro Cys Arg Leu Leu
  1               5                  10                  15

Ser Pro Ser Pro Gln Pro Gly Leu His His Leu Cys Phe Gln Gln Ile
             20                  25                  30

Glu Leu Leu Leu Leu Leu Leu His Leu Gln Trp Gly Leu Gly Leu Leu
         35                  40                  45

Arg Gln Leu His His Lys Arg Leu Ala Gln Leu Leu Leu His Arg Arg
     50                  55                  60

Arg Asp His Pro Ile Pro Pro Ile Gln Asp Ile Leu Gly Ile Ala Lys
```

-continued

```
 65                  70                  75                  80

Cys Pro Cys Pro Trp Ala Ile Ile Leu Met Arg Met Ala Ser Ile Ile
                 85                  90                  95

Cys His Ile His Gln Cys Ile Thr Arg Val Leu Asp Arg Leu Xaa Thr
            100                 105                 110

Arg Asp Pro Ser Ser Leu His Thr Pro Ser Leu Ser Pro His Ser Ser
        115                 120                 125

Leu Thr Ile His Ser Ser Asn Met Ser Ala Gln Gln Leu Ser
    130                 135                 140


<210> SEQ ID NO 140
<211> LENGTH: 193
<212> TYPE: PRT
<213> ORGANISM: Homo sapiens

<400> SEQUENCE: 140

Met Glu Pro Gly Pro Thr Ala Ala Gln Arg Arg Cys Ser Leu Pro Pro
  1               5                  10                  15

Trp Leu Pro Leu Gly Leu Leu Leu Trp Ser Gly Leu Ala Leu Gly Ala
             20                  25                  30

Leu Pro Phe Gly Ser Ser Pro His Arg Val Phe His Asp Leu Leu Ser
         35                  40                  45

Glu Gln Gln Leu Leu Glu Val Glu Asp Leu Ser Leu Ser Leu Leu Gln
     50                  55                  60

Gly Gly Gly Leu Gly Pro Leu Ser Leu Pro Pro Asp Leu Pro Asp Leu
 65                  70                  75                  80

Asp Pro Glu Cys Arg Glu Leu Leu Leu Asp Phe Ala Asn Ser Ser Ala
                 85                  90                  95

Glu Leu Thr Gly Cys Leu Val Arg Ser Ala Arg Pro Val Arg Leu Cys
            100                 105                 110

Gln Thr Cys Tyr Pro Leu Phe Gln Gln Val Val Ser Lys Met Asp Asn
        115                 120                 125

Ile Ser Arg Ala Ala Gly Asn Thr Ser Glu Ser Gln Ser Cys Ala Arg
    130                 135                 140

Ser Leu Leu Met Ala Asp Arg Met Gln Ile Val Val Ile Leu Ser Glu
145                 150                 155                 160

Phe Phe Asn Thr Thr Trp Gln Glu Ala Asn Cys Ala Asn Cys Leu Thr
                165                 170                 175

Asn Asn Ser Glu Glu Leu Ser Asn Ser Thr Val Tyr Phe Leu Lys Ser
            180                 185                 190

Ile


<210> SEQ ID NO 141
<211> LENGTH: 134
<212> TYPE: PRT
<213> ORGANISM: Homo sapiens

<400> SEQUENCE: 141

Met Ala Pro Glu Val Met Glu Gln Val Arg Gly Tyr Asp Phe Lys Ala
  1               5                  10                  15

Asp Ile Trp Ser Phe Gly Ile Thr Ala Ile Glu Leu Ala Thr Gly Ala
             20                  25                  30

Ala Pro Tyr His Lys Tyr Pro Pro Met Lys Val Leu Met Leu Thr Leu
         35                  40                  45

Gln Asn Asp Pro Pro Ser Leu Glu Thr Gly Val Gln Asp Lys Glu Met
     50                  55                  60
```

-continued

Leu Lys Lys Tyr Gly Lys Ser Phe Arg Lys Met Ile Ser Leu Cys Leu
65 70 75 80

Gln Lys Asp Pro Glu Lys Arg Pro Thr Ala Ala Glu Leu Leu Arg His
85 90 95

Lys Phe Phe Gln Lys Ala Lys Asn Lys Glu Phe Leu Gln Glu Lys Thr
100 105 110

Leu Gln Arg Ala Pro Thr Ile Ser Glu Arg Ala Lys Lys Val Arg Arg
115 120 125

Val Pro Gly Ser Cys Pro
130

<210> SEQ ID NO 142
<211> LENGTH: 73
<212> TYPE: PRT
<213> ORGANISM: Homo sapiens

<400> SEQUENCE: 142

Met Asn Ile Thr Arg Lys Leu Trp Ser Arg Thr Phe Asn Cys Ser Val
1 5 10 15

Pro Cys Ser Asp Thr Val Pro Val Ile Ala Val Ser Val Phe Ile Leu
20 25 30

Phe Leu Pro Val Val Phe Tyr Leu Ser Ser Phe Leu His Ser Glu Gln
35 40 45

Lys Lys Arg Lys Leu Ile Leu Pro Lys Arg Leu Lys Ser Ser Thr Ser
50 55 60

Phe Ala Asn Ile Gln Glu Asn Ser Asn
65 70

<210> SEQ ID NO 143
<211> LENGTH: 144
<212> TYPE: PRT
<213> ORGANISM: Homo sapiens

<400> SEQUENCE: 143

Met Pro Thr Thr Thr Glu Gln Pro Val Thr Thr Thr Phe Pro Val Thr
1 5 10 15

Thr Gly Leu Lys Pro Thr Val Ala Leu Cys Gln Gln Lys Cys Arg Arg
20 25 30

Thr Gly Thr Leu Glu Gly Asn Tyr Cys Ser Ser Asp Phe Val Leu Ala
35 40 45

Gly Thr Val Ile Thr Thr Ile Thr Arg Asp Gly Ser Leu His Ala Thr
50 55 60

Val Ser Ile Ile Asn Ile Tyr Lys Glu Gly Asn Leu Ala Ile Gln Gln
65 70 75 80

Ala Gly Lys Asn Met Ser Ala Arg Leu Thr Val Val Cys Lys Gln Cys
85 90 95

Pro Leu Leu Arg Arg Gly Leu Asn Tyr Ile Ile Met Gly Gln Val Gly
100 105 110

Glu Asp Gly Arg Gly Lys Ile Met Pro Asn Ser Phe Ile Met Met Phe
115 120 125

Lys Thr Lys Asn Gln Lys Leu Leu Asp Ala Leu Lys Asn Lys Gln Cys
130 135 140

<210> SEQ ID NO 144
<211> LENGTH: 189
<212> TYPE: PRT
<213> ORGANISM: Homo sapiens -continued

<400> SEQUENCE: 144

Met Gly Gly Gln Val Ala Gly Val Tyr Ala Ala Tyr Tyr Pro Ser Asp
1 5 10 15

Val Ser Ser Leu Cys Leu Val Cys Pro Ala Gly Leu Gln Tyr Ser Thr
20 25 30

Asp Asn Gln Phe Val Gln Arg Leu Lys Glu Leu Gln Gly Ser Ala Ala
35 40 45

Val Glu Lys Ile Pro Leu Ile Pro Ser Thr Pro Glu Glu Met Ser Glu
50 55 60

Met Leu Gln Leu Cys Ser Tyr Val Arg Phe Lys Val Pro Gln Gln Ile
65 70 75 80

Leu Gln Gly Leu Val Asp Val Arg Ile Pro His Asn Asn Phe Tyr Arg
85 90 95

Lys Leu Phe Leu Glu Ile Val Ser Glu Lys Ser Arg Tyr Ser Leu His
100 105 110

Gln Asn Met Asp Lys Ile Lys Val Pro Thr Gln Ile Ile Trp Gly Lys
115 120 125

Gln Asp Gln Val Leu Asp Val Ser Gly Ala Asp Met Leu Ala Lys Ser
130 135 140

Ile Ala Asn Cys Gln Val Glu Leu Leu Glu Asn Cys Gly His Ser Val
145 150 155 160

Val Met Glu Arg Pro Arg Lys Thr Ala Lys Leu Ile Ile Asp Phe Leu
165 170 175

Ala Ser Val His Asn Thr Asp Asn Asn Lys Lys Leu Asp
180 185

<210> SEQ ID NO 145
<211> LENGTH: 487
<212> TYPE: PRT
<213> ORGANISM: Homo sapiens

<400> SEQUENCE: 145

Met Lys His Leu Trp Phe Phe Leu Leu Leu Val Ala Ala Pro Arg Trp
1 5 10 15

Val Leu Ser Gln Val Gln Leu Gln Glu Ser Gly Pro Gly Leu Val Lys
20 25 30

Pro Ser Glu Thr Leu Ser Leu Thr Cys Thr Val Ser Gly Gly Ser Ile
35 40 45

Ser Ser Gly Gly His Tyr Trp Ser Trp Ile Arg Gln His Pro Gly Lys
50 55 60

Gly Leu Glu Trp Ile Gly Tyr Ile Ser Tyr Asn Gly Val Thr Tyr Tyr
65 70 75 80

Asn Pro Ser Leu Lys Ser Arg Val Thr Ile Ser Val Asp Thr Ser Gln
85 90 95

Asn Gln Phe Ser Leu Arg Leu Ser Ser Val Thr Ala Ala Asp Thr Ala
100 105 110

Val Tyr Tyr Cys Ala Lys Asp His Arg Ala Thr Arg Asp Gly Tyr Gln
115 120 125

Leu Glu Tyr Arg Gly Phe Asp Tyr Trp Gly Gln Gly Ile Leu Val Thr
130 135 140

Val Ser Ser Ala Ser Pro Thr Ser Pro Lys Val Phe Pro Leu Ser Leu
145 150 155 160

Asp Ser Thr Pro Gln Asp Gly Asn Val Val Val Ala Cys Leu Val Gln
165 170 175

-continued

```
Gly Phe Phe Pro Gln Glu Pro Leu Ser Val Thr Trp Ser Glu Ser Gly
            180                 185                 190

Gln Asn Val Thr Ala Arg Asn Phe Pro Pro Ser Gln Asp Ala Ser Gly
        195                 200                 205

Asp Leu Tyr Thr Thr Ser Ser Gln Leu Thr Leu Pro Ala Thr Gln Cys
    210                 215                 220

Pro Asp Gly Lys Ser Val Thr Cys His Val Lys His Tyr Thr Asn Pro
225                 230                 235                 240

Ser Gln Asp Val Thr Val Pro Cys Pro Val Pro Pro Pro Pro Pro Cys
                245                 250                 255

Cys His Pro Arg Leu Ser Leu His Arg Pro Ala Leu Glu Asp Leu Leu
            260                 265                 270

Leu Gly Ser Glu Ala Asn Leu Thr Cys Thr Leu Thr Gly Leu Arg Asp
        275                 280                 285

Ala Ser Gly Ala Thr Phe Thr Trp Thr Pro Ser Ser Gly Lys Ser Ala
    290                 295                 300

Val Gln Gly Pro Pro Glu Arg Asp Leu Cys Gly Cys Tyr Ser Val Ser
305                 310                 315                 320

Ser Val Leu Pro Gly Cys Ala Gln Pro Trp Asn His Gly Glu Thr Phe
                325                 330                 335

Thr Cys Thr Ala Ala His Pro Glu Leu Lys Thr Pro Leu Thr Ala Asn
            340                 345                 350

Ile Thr Lys Ser Gly Asn Thr Phe Arg Pro Glu Val His Leu Leu Pro
        355                 360                 365

Pro Pro Ser Glu Glu Leu Ala Leu Asn Glu Leu Val Thr Leu Thr Cys
    370                 375                 380

Leu Ala Arg Gly Phe Ser Pro Lys Asp Val Leu Val Arg Trp Leu Gln
385                 390                 395                 400

Gly Ser Gln Glu Leu Pro Arg Glu Lys Tyr Leu Thr Trp Ala Ser Arg
                405                 410                 415

Gln Glu Pro Ser Gln Gly Thr Thr Thr Phe Ala Val Thr Ser Ile Leu
            420                 425                 430

Arg Val Ala Ala Glu Asp Trp Lys Lys Gly Asp Thr Phe Ser Cys Met
        435                 440                 445

Val Gly His Glu Ala Leu Pro Leu Ala Phe Thr Gln Lys Thr Ile Asp
    450                 455                 460

Arg Leu Ala Gly Lys Pro Thr His Val Asn Val Ser Val Val Met Ala
465                 470                 475                 480

Glu Val Asp Gly Thr Cys Tyr
                485


<210> SEQ ID NO 146
<211> LENGTH: 294
<212> TYPE: PRT
<213> ORGANISM: Homo sapiens
<220> FEATURE:
<221> NAME/KEY: SITE
<222> LOCATION: (93)
<223> OTHER INFORMATION: Xaa equals any of the naturally occurring
      L-amino acids
<221> NAME/KEY: SITE
<222> LOCATION: (97)
<223> OTHER INFORMATION: Xaa equals any of the naturally occurring
      L-amino acids

<400> SEQUENCE: 146

Met Met Val Gln Met Ile Ser Asp Ala Asn Thr Ala Gly Asn Gly Phe
```

-continued

```
  1               5                  10                  15

Met Ala Met Phe Ser Ala Ala Glu Pro Asn Glu Arg Gly Asp Gln Tyr
             20                  25                  30

Cys Gly Gly Leu Leu Asp Arg Pro Ser Gly Ser Phe Lys Thr Pro Asn
        35                  40                  45

Trp Pro Asp Arg Asp Tyr Pro Ala Gly Val Thr Cys Val Trp His Ile
    50                  55                  60

Val Ala Pro Lys Asn Gln Leu Ile Glu Leu Lys Phe Glu Lys Phe Asp
 65                  70                  75                  80

Val Glu Arg Asp Asn Tyr Cys Arg Tyr Asp Tyr Val Xaa Val Phe Asn
                 85                  90                  95

Xaa Gly Glu Val Asn Asp Ala Arg Arg Ile Gly Lys Tyr Cys Gly Asp
            100                 105                 110

Ser Pro Pro Ala Pro Ile Val Ser Glu Arg Asn Glu Leu Leu Ile Gln
        115                 120                 125

Phe Leu Ser Asp Leu Ser Leu Thr Ala Asp Gly Phe Ile Gly His Tyr
    130                 135                 140

Ile Phe Arg Pro Lys Lys Leu Pro Thr Thr Thr Glu Gln Pro Val Thr
145                 150                 155                 160

Thr Thr Phe Pro Val Thr Thr Gly Leu Lys Pro Thr Val Ala Leu Cys
                165                 170                 175

Gln Gln Lys Cys Arg Arg Thr Gly Thr Leu Glu Gly Asn Tyr Cys Ser
            180                 185                 190

Ser Asp Phe Val Leu Ala Gly Thr Val Ile Thr Thr Ile Thr Arg Asp
        195                 200                 205

Gly Ser Leu His Ala Thr Val Ser Ile Ile Asn Ile Tyr Lys Glu Gly
    210                 215                 220

Asn Leu Ala Ile Gln Gln Ala Gly Lys Asn Met Ser Ala Arg Leu Thr
225                 230                 235                 240

Val Val Cys Lys Gln Cys Pro Leu Leu Arg Arg Gly Leu Asn Tyr Ile
                245                 250                 255

Ile Met Gly Gln Val Gly Glu Asp Gly Arg Gly Lys Ile Met Pro Asn
            260                 265                 270

Ser Phe Ile Met Met Phe Lys Thr Lys Asn Gln Lys Leu Leu Asp Ala
        275                 280                 285

Leu Lys Asn Lys Gln Cys
    290


<210> SEQ ID NO 147
<211> LENGTH: 99
<212> TYPE: PRT
<213> ORGANISM: Homo sapiens

<400> SEQUENCE: 147

Met Ala Val Trp Gly Asp Thr Glu Leu Ala Ala Gly Val Phe Cys Phe
  1               5                  10                  15

Phe Leu Phe Phe Cys Phe Leu Tyr Leu Ser Gly Thr Trp Asn Ala Ser
             20                  25                  30

Lys Thr Glu Leu Phe Thr Pro Leu Glu Arg Glu Leu Lys Pro Gly His
        35                  40                  45

Pro Ser Gly Met Leu Ser Gly Ser His Pro His Gly Ala Gln Gln Ala
    50                  55                  60

Lys Ser Thr Gly Leu Lys Leu Ser Leu Pro Ala Gln Gln Ser Glu Val
 65                  70                  75                  80
```

-continued

```
Asp Leu Gly Cys Ser Ser Leu Val Trp Gly Gly Ala Ser Ala Ile Thr
                 85                  90                  95

Glu Ala Leu


<210> SEQ ID NO 148
<211> LENGTH: 265
<212> TYPE: PRT
<213> ORGANISM: Homo sapiens

<400> SEQUENCE: 148

Met Gly Gly Gln Val Ala Gly Val Tyr Ala Ala Tyr Tyr Pro Ser Asp
  1               5                  10                  15

Val Ser Ser Leu Cys Leu Val Cys Pro Ala Gly Leu Gln Tyr Ser Thr
             20                  25                  30

Asp Asn Gln Phe Val Gln Arg Leu Lys Glu Leu Gln Gly Ser Ala Ala
         35                  40                  45

Val Glu Lys Ile Pro Leu Ile Pro Ser Thr Pro Glu Glu Met Ser Glu
     50                  55                  60

Met Leu Gln Leu Cys Ser Tyr Val Arg Phe Lys Val Pro Gln Gln Ile
 65                  70                  75                  80

Leu Gln Gly Leu Val Asp Val Arg Ile Pro His Asn Asn Phe Tyr Arg
                 85                  90                  95

Lys Leu Phe Leu Glu Ile Val Ser Glu Lys Ser Arg Tyr Ser Leu His
            100                 105                 110

Gln Asn Met Asp Lys Ile Lys Val Pro Thr Gln Ile Ile Trp Gly Lys
        115                 120                 125

Gln Asp Ala Gly Ala Gly Cys Val Trp Gly Arg His Val Gly Gln Val
    130                 135                 140

Asn Cys Gln Leu Pro Gly Gly Ala Ser Gly Lys Leu Trp Ala Leu Ser
145                 150                 155                 160

Ser Asp Gly Lys Thr Gln Glu Asp Ser Gln Ala His Asn Arg Leu Phe
                165                 170                 175

Ser Phe Cys Ala Gln His Arg Gln Gln Gln Glu Ala Gly Leu Arg Pro
            180                 185                 190

Arg Leu Gln Pro Ala Phe Cys Thr Gln His Leu Leu Pro Ser Pro Lys
        195                 200                 205

Ser Asp Ala Ala Thr Thr Leu Arg Asp Pro Ala Pro Asn Ala Val Gly
    210                 215                 220

Ala Pro Val Thr Leu Arg Lys Pro Val Pro Tyr Pro Trp Tyr Pro Arg
225                 230                 235                 240

Phe Pro Arg Ala Leu Gly Thr Thr Arg Lys Pro Pro Arg Tyr Phe Ser
                245                 250                 255

Gln Asn Arg Asn Ser Tyr Gly Thr Lys
            260                 265


<210> SEQ ID NO 149
<211> LENGTH: 206
<212> TYPE: PRT
<213> ORGANISM: Homo sapiens

<400> SEQUENCE: 149

Met Asp Val Gly Pro Ser Ser Leu Pro His Leu Gly Leu Lys Leu Leu
  1               5                  10                  15

Leu Leu Leu Leu Leu Leu Pro Leu Arg Gly Gln Ala Asn Thr Gly Cys
             20                  25                  30

Tyr Gly Ile Pro Gly Met Pro Gly Leu Pro Gly Ala Pro Gly Lys Asp
```

-continued

```
        35                  40                  45

Gly Tyr Asp Gly Leu Pro Gly Pro Lys Gly Glu Pro Gly Ile Pro Ala
     50                  55                  60

Ile Pro Gly Ile Arg Gly Pro Lys Gly Arg Tyr Lys Gln Lys Phe Gln
 65                  70                  75                  80

Ser Val Phe Thr Val Thr Arg Gln Thr His Gln Pro Pro Ala Pro Asn
                 85                  90                  95

Ser Leu Ile Arg Phe Asn Ala Val Leu Thr Asn Pro Gln Gly Asp Tyr
            100                 105                 110

Asp Thr Ser Thr Gly Lys Phe Thr Cys Lys Val Pro Gly Leu Tyr Tyr
        115                 120                 125

Phe Val Tyr His Ala Ser His Thr Ala Asn Leu Cys Val Leu Leu Tyr
    130                 135                 140

Arg Ser Gly Val Lys Val Val Thr Phe Cys Gly His Thr Ser Lys Thr
145                 150                 155                 160

Asn Gln Val Asn Ser Gly Gly Val Leu Leu Arg Leu Gln Val Gly Glu
                165                 170                 175

Glu Val Trp Leu Ala Val Asn Asp Tyr Tyr Asp Met Val Gly Ile Gln
            180                 185                 190

Gly Ser Asp Ser Val Phe Ser Gly Phe Leu Leu Phe Pro Asp
        195                 200                 205


<210> SEQ ID NO 150
<211> LENGTH: 234
<212> TYPE: PRT
<213> ORGANISM: Homo sapiens
<220> FEATURE:
<221> NAME/KEY: SITE
<222> LOCATION: (120)
<223> OTHER INFORMATION: Xaa equals any of the naturally occurring
      L-amino acids

<400> SEQUENCE: 150

Met Arg Val Pro Ala Gln Leu Leu Gly Leu Leu Leu Leu Trp Leu Ser
  1               5                  10                  15

Gly Ala Arg Cys Asp Ile Gln Leu Thr Gln Ser Pro Ser Ser Leu Ser
            20                  25                  30

Ala Ser Leu Gly Asp Ser Val Thr Ile Thr Cys Gln Ala Ser Gln Asp
        35                  40                  45

Ile Ala Asn Tyr Leu Asn Trp Tyr Gln Gln Lys Pro Gly Lys Pro Pro
     50                  55                  60

Lys Leu Val Ile Phe Asp Gly Ser Ile Leu His Thr Gly Val Pro Ser
 65                  70                  75                  80

Arg Phe Ser Gly Gly Gly Ser Gly Thr His Phe Thr Phe Thr Ile Asn
                 85                  90                  95

Asn Leu Gln Pro Asp Asp Val Ala Thr Tyr Ser Cys Gln Gln Tyr Asn
            100                 105                 110

Thr Phe Pro Leu Thr Phe Gly Xaa Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
```

-continued

```
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 151
<211> LENGTH: 208
<212> TYPE: PRT
<213> ORGANISM: Homo sapiens

<400> SEQUENCE: 151

Met Asp Val Gly Pro Ser Ser Leu Pro His Leu Gly Leu Lys Leu Leu
  1               5                  10                  15

Leu Leu Leu Leu Leu Leu Pro Leu Arg Gly Gln Ala Asn Thr Gly Cys
             20                  25                  30

Tyr Gly Ile Pro Gly Met Pro Gly Leu Pro Gly Ala Pro Gly Lys Asp
         35                  40                  45

Gly Tyr Asp Gly Leu Pro Gly Pro Lys Gly Glu Pro Gly Ile Pro Ala
     50                  55                  60

Ile Pro Gly Ile Arg Gly Pro Lys Gly Gln Lys Gly Glu Pro Gly Leu
 65                  70                  75                  80

Pro Gly His Pro Gly Lys Asn Gly Pro Met Gly Pro Pro Gly Met Pro
                 85                  90                  95

Gly Val Pro Gly Pro Met Gly Ile Pro Gly Glu Pro Gly Glu Glu Gly
            100                 105                 110

Arg Tyr Lys Gln Lys Phe Gln Ser Val Phe Thr Val Thr Arg Gln Thr
        115                 120                 125

His Gln Pro Pro Ala Pro Asn Ser Leu Ile Arg Phe Asn Ala Val Leu
    130                 135                 140

Thr Asn Pro Gln Glu Ile Met Thr Arg Ala Leu Ala Ser Ser Pro Ala
145                 150                 155                 160

Lys Ser Pro Ala Ser Thr Thr Leu Ser Thr Thr Arg Arg Ile Gln Pro
                165                 170                 175

Thr Cys Ala Cys Cys Cys Thr Ala Ala Ala Ser Lys Trp Ser Pro Ser
            180                 185                 190

Val Ala Thr Arg Pro Lys Pro Ile Arg Ser Thr Arg Ala Val Cys Cys
        195                 200                 205


<210> SEQ ID NO 152
<211> LENGTH: 235
<212> TYPE: PRT
<213> ORGANISM: Homo sapiens

<400> SEQUENCE: 152

Met Asp Met Arg Val Pro Ala Gln Leu Leu Gly Leu Leu Leu Leu Trp
  1               5                  10                  15

Leu Arg Gly Ala Arg Cys Asp Met Gln Met Thr Gln Ser Pro Ser Ser
             20                  25                  30

Leu Ser Ala Ser Val Gly Asp Arg Val Thr Ile Thr Cys Arg Thr Ser
         35                  40                  45

Gln Ser Ile Gly Lys Phe Leu Asn Trp Tyr Gln Gln Lys Pro Gly Gln
     50                  55                  60

Ala Pro Lys Leu Leu Ile Ser Gly Ala Ser Ile Leu Gln Thr Gly Val
```

-continued

```
65                  70                  75                  80

Pro Ser Arg Phe Ser Gly Ser Gly Ser Ala Thr Tyr Phe Thr Leu Thr
                85                  90                  95

Ile Asn Asp Leu His Pro Glu Asp Ser Ala Thr Tyr Tyr Cys Gln Gln
            100                 105                 110

Asp Tyr Thr Thr Pro Leu Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235


<210> SEQ ID NO 153
<211> LENGTH: 287
<212> TYPE: PRT
<213> ORGANISM: Homo sapiens

<400> SEQUENCE: 153

Met Gly Ala Leu Arg Pro Thr Leu Leu Pro Pro Ser Leu Pro Leu Leu
  1               5                  10                  15

Leu Leu Leu Met Leu Gly Met Gly Cys Trp Ala Arg Glu Val Leu Val
             20                  25                  30

Pro Glu Gly Pro Leu Tyr Arg Val Ala Gly Thr Ala Val Ser Ile Ser
         35                  40                  45

Cys Asn Val Thr Gly Tyr Glu Gly Pro Ala Gln Gln Asn Phe Glu Trp
     50                  55                  60

Phe Leu Tyr Arg Pro Glu Ala Pro Asp Thr Ala Leu Gly Ile Val Ser
 65                  70                  75                  80

Thr Lys Asp Thr Gln Phe Ser Tyr Ala Val Phe Lys Ser Arg Val Val
                 85                  90                  95

Ala Gly Glu Val Gln Val Gln Arg Leu Gln Gly Asp Ala Val Val Leu
            100                 105                 110

Lys Ile Ala Arg Leu Gln Ala Gln Asp Ala Gly Ile Tyr Glu Cys His
        115                 120                 125

Thr Pro Ser Thr Asp Thr Arg Tyr Leu Gly Ser Tyr Ser Gly Lys Val
    130                 135                 140

Glu Leu Arg Val Leu Pro Asp Val Leu Gln Val Ser Ala Ala Pro Pro
145                 150                 155                 160

Gly Pro Arg Gly Arg Gln Ala Pro Thr Ser Pro Pro Arg Met Thr Val
                165                 170                 175

His Glu Gly Gln Glu Leu Ala Leu Gly Cys Leu Ala Arg Thr Ser Thr
            180                 185                 190

Gln Lys His Thr His Leu Ala Val Ser Phe Gly Arg Ser Val Pro Glu
        195                 200                 205
```

-continued

```
Ala Pro Val Gly Arg Ser Thr Leu Gln Glu Val Val Gly Ile Arg Ser
    210                 215                 220

Asp Leu Ala Val Glu Ala Gly Ala Pro Tyr Ala Glu Arg Leu Ala Ala
225                 230                 235                 240

Gly Glu Leu Arg Leu Gly Lys Glu Gly Thr Asp Arg Tyr Arg Met Val
                245                 250                 255

Val Gly Gly Ala Gln Ala Gly Asp Ala Gly Thr Tyr His Cys Thr Ala
            260                 265                 270

Ala Glu Trp Ile Gln Asp Pro Asp Gly Ser Trp Ala Gln Ile Ala
        275                 280                 285


<210> SEQ ID NO 154
<211> LENGTH: 203
<212> TYPE: PRT
<213> ORGANISM: Homo sapiens

<400> SEQUENCE: 154

Met Gly Leu Ile Leu Thr Val Val Gly Val His Asn Asp Thr Val Asp
  1               5                  10                  15

Arg Val Val Pro Gln Phe Gln His Leu Ile Tyr Gly Cys Val Ala Gln
             20                  25                  30

Glu His Ile His Thr Leu Val Leu Pro Glu Arg Asn Thr Val Leu Gly
         35                  40                  45

Val Asp Gly Val Gly Ser Ser Glu Asp Pro Ser Val Pro Gln Gln Gly
     50                  55                  60

Pro Ala Pro Thr Ala Val Asp Thr Gly Glu Gly Leu Pro Gly Glu Val
 65                  70                  75                  80

Ala Gln Leu Gly Ser Gly Arg Thr Glu Gly Arg Leu Ile Leu Gly Asn
                 85                  90                  95

Gly Gly Asp Trp Pro Ser Ala Asp Arg His Thr Leu Lys Asn Leu Leu
            100                 105                 110

Pro Ile Leu Ser Val Phe Pro Gly Pro Trp Gly Cys Thr Gly Glu Cys
        115                 120                 125

Pro Cys Cys Arg Gly Leu Ile Ile Gly Leu Leu Ala Val Val Leu Asp
    130                 135                 140

Leu Gly Arg Val Val Ser Arg Cys Val Asp Gly Leu Arg Ala Pro Ala
145                 150                 155                 160

Gly Leu Ala Asp Gly Leu Thr Ile Val His Ser His Gly Leu Val Glu
                165                 170                 175

Gly Gln Glu Ala Leu Val Glu Val Gly Ser Leu Val Leu Arg Gly Arg
            180                 185                 190

Leu Cys Ala Glu Gly Gln Pro Gln Thr Pro Pro
        195                 200


<210> SEQ ID NO 155
<211> LENGTH: 2165
<212> TYPE: PRT
<213> ORGANISM: Homo sapiens

<400> SEQUENCE: 155

Met Arg Ser Ile Gly Gly Ser Phe His Leu Leu Gln Pro Val Val Ala
1               5                   10                  15

Ala Leu Ile Leu Leu Val Val Cys Leu Val Tyr Ala Leu Gln Ser Gly
            20                  25                  30

Ser Gly Thr Ile Ser Glu Phe Ser Ser Asp Val Leu Phe Ser Arg Ala
        35                  40                  45
```

-continued

```
Lys Tyr Ser Gly Val Pro Val His His Ser Arg Trp Arg Gln Asp Ala
    50                  55                  60

Gly Ile His Val Ile Asp Ser His His Ile Val Arg Arg Asp Ser Tyr
65                  70                  75                  80

Gly Arg Arg Gly Lys Arg Asp Val Thr Ser Thr Asp Arg Arg Arg Arg
                85                  90                  95

Leu Gln Gly Val Ala Arg Asp Cys Gly His Ala Cys His Leu Arg Leu
            100                 105                 110

Arg Ser Asp Asp Ala Val Tyr Ile Val His Leu His Arg Trp Asn Gln
        115                 120                 125

Ile Pro Asp Ser His Asn Lys Ser Val Pro His Phe Ser Asn Ser Asn
    130                 135                 140

Phe Ala Pro Met Val Leu Tyr Leu Asp Ser Glu Glu Glu Val Arg Gly
145                 150                 155                 160

Gly Met Ser Arg Thr Asp Pro Asp Cys Ile Tyr Arg Ala His Val Lys
                165                 170                 175

Gly Val His Gln His Ser Ile Val Asn Leu Cys Asp Ser Glu Asp Gly
            180                 185                 190

Leu Tyr Gly Met Leu Ala Leu Pro Ser Gly Ile His Thr Val Glu Pro
        195                 200                 205

Ile Ile Ser Gly Asn Gly Thr Glu His Asp Gly Ala Ser Arg His Arg
    210                 215                 220

Gln His Leu Val Arg Lys Phe Asp Pro Met His Phe Lys Ser Phe Asp
225                 230                 235                 240

His Leu Asn Ser Thr Ser Val Asn Glu Thr Glu Thr Thr Val Ala Thr
                245                 250                 255

Trp Gln Asp Gln Trp Glu Asp Val Ile Glu Arg Lys Ala Arg Ser Arg
            260                 265                 270

Arg Ala Ala Asn Ser Trp Asp His Tyr Val Glu Val Leu Val Val Ala
        275                 280                 285

Asp Thr Lys Met Tyr Glu Tyr His Gly Arg Ser Leu Glu Asp Tyr Val
    290                 295                 300

Leu Thr Leu Phe Ser Thr Val Ala Ser Ile Tyr Arg His Gln Ser Leu
305                 310                 315                 320

Arg Ala Ser Ile Asn Val Val Val Val Lys Leu Ile Val Leu Lys Thr
                325                 330                 335

Glu Asn Ala Gly Pro Arg Ile Thr Gln Asn Ala Gln Gln Thr Leu Gln
            340                 345                 350

Asp Phe Cys Arg Trp Gln Gln Tyr Tyr Asn Asp Pro Asp Asp Ser Ser
        355                 360                 365

Val Gln His His Asp Val Ala Ile Leu Leu Thr Arg Lys Asp Ile Cys
    370                 375                 380

Arg Ser Gln Gly Lys Cys Asp Thr Leu Gly Leu Ala Glu Leu Gly Thr
385                 390                 395                 400

Met Cys Asp Met Gln Lys Ser Cys Ala Ile Ile Glu Asp Asn Gly Leu
                405                 410                 415

Ser Ala Ala Phe Thr Ile Ala His Glu Leu Gly His Val Phe Ser Ile
            420                 425                 430

Pro His Asp Asp Glu Arg Lys Cys Ser Thr Tyr Met Pro Val Asn Lys
        435                 440                 445

Val Cys Lys Phe Gln Ser Thr Lys Phe Asp Lys Thr Gln Phe Gln Asn
    450                 455                 460

Asn Phe His Ile Met Ala Pro Thr Leu Glu Tyr Asn Thr His Pro Trp
```

-continued

```
465                 470                 475                 480

Ser Trp Ser Pro Cys Ser Ala Gly Met Leu Glu Arg Phe Leu Glu Asn
                485                 490                 495

Asn Arg Gly Gln Thr Gln Cys Leu Phe Asp Gln Pro Val Glu Arg Arg
            500                 505                 510

Tyr Tyr Glu Asp Val Phe Val Arg Asp Glu Pro Gly Lys Lys Tyr Asp
        515                 520                 525

Ala His Gln Gln Cys Lys Phe Val Phe Gly Pro Ala Ser Glu Leu Cys
    530                 535                 540

Pro Tyr Met Pro Thr Cys Arg Arg Leu Trp Cys Ala Thr Phe Tyr Gly
545                 550                 555                 560

Ser Gln Met Gly Cys Arg Thr Gln His Met Pro Trp Ala Asp Gly Thr
                565                 570                 575

Pro Cys Asp Glu Ser Arg Ser Met Phe Cys His His Gly Ala Cys Val
            580                 585                 590

Arg Leu Ala Pro Glu Ser Leu Thr Lys Ile Asp Gly Gln Trp Gly Asp
        595                 600                 605

Trp Arg Ser Trp Gly Glu Cys Ser Arg Thr Cys Gly Gly Gly Val Gln
    610                 615                 620

Lys Gly Leu Arg Asp Cys Asp Ser Pro Lys Pro Arg Asn Gly Gly Lys
625                 630                 635                 640

Tyr Cys Val Gly Gln Arg Glu Arg Tyr Arg Ser Cys Asn Thr Gln Glu
                645                 650                 655

Cys Pro Trp Asp Thr Gln Pro Tyr Arg Glu Val Gln Cys Ser Glu Phe
            660                 665                 670

Asn Asn Lys Asp Ile Gly Ile Gln Gly Val Ala Ser Thr Asn Thr His
        675                 680                 685

Trp Val Pro Lys Tyr Ala Asn Val Ala Pro Asn Glu Arg Cys Lys Leu
    690                 695                 700

Tyr Cys Arg Leu Ser Gly Ser Ala Ala Phe Tyr Leu Leu Arg Asp Lys
705                 710                 715                 720

Val Val Asp Gly Thr Pro Cys Asp Arg Asn Gly Asp Asp Ile Cys Val
                725                 730                 735

Ala Gly Ala Cys Met Pro Ala Gly Cys Asp His Gln Leu His Ser Thr
            740                 745                 750

Leu Arg Arg Asp Lys Cys Gly Val Cys Gly Gly Asp Asp Ser Ser Cys
        755                 760                 765

Lys Val Val Lys Gly Thr Phe Asn Glu Gln Gly Thr Phe Gly Tyr Asn
    770                 775                 780

Glu Val Met Lys Ile Pro Ala Gly Ser Ala Asn Ile Asp Ile Arg Gln
785                 790                 795                 800

Lys Gly Tyr Asn Asn Met Lys Glu Asp Asp Asn Tyr Leu Ser Leu Arg
                805                 810                 815

Ala Ala Asn Gly Glu Phe Leu Leu Asn Gly His Phe Gln Val Ser Leu
            820                 825                 830

Ala Arg Gln Gln Ile Ala Phe Gln Asp Thr Val Leu Glu Tyr Ser Gly
        835                 840                 845

Ser Asp Ala Ile Ile Glu Arg Ile Asn Gly Thr Gly Pro Ile Arg Ser
    850                 855                 860

Asp Ile Tyr Val His Val Leu Ser Val Gly Ser His Pro Pro Asp Ile
865                 870                 875                 880

Ser Tyr Glu Tyr Met Thr Ala Ala Val Pro Asn Ala Val Ile Arg Pro
                885                 890                 895
```

-continued

```
Ile Ser Ser Ala Leu Tyr Leu Trp Arg Val Thr Asp Thr Trp Thr Glu
            900                 905                 910

Cys Asp Arg Ala Cys Arg Gly Gln Gln Ser Gln Lys Leu Met Cys Leu
        915                 920                 925

Asp Met Ser Thr His Arg Gln Ser His Asp Arg Asn Cys Gln Asn Val
    930                 935                 940

Leu Lys Pro Lys Gln Ala Thr Arg Met Cys Asn Ile Asp Cys Ser Thr
945                 950                 955                 960

Arg Trp Ile Thr Glu Asp Val Ser Ser Cys Ser Ala Lys Cys Gly Ser
                965                 970                 975

Gly Gln Lys Arg Gln Arg Val Ser Cys Val Lys Met Glu Gly Asp Arg
            980                 985                 990

Gln Thr Pro Ala Ser Glu His Leu  Cys Asp Arg Asn Ser  Lys Pro Ser
        995                 1000                1005

Asp Ile  Ala Ser Cys Tyr Ile  Asp Cys Ser Gly Arg  Lys Trp Asn
    1010                 1015                 1020

Tyr Gly  Glu Trp Thr Ser Cys  Ser Glu Thr Cys Gly  Ser Asn Gly
    1025                 1030                 1035

Lys Met  His Arg Lys Ser Tyr  Cys Val Asp Asp Ser  Asn Arg Arg
    1040                 1045                 1050

Val Asp  Glu Ser Leu Cys Gly  Arg Glu Gln Lys Glu  Ala Thr Glu
    1055                 1060                 1065

Arg Glu  Cys Asn Arg Ile Pro  Cys Pro Arg Trp Val  Tyr Gly His
    1070                 1075                 1080

Trp Ser  Glu Cys Ser Arg Ser  Cys Asp Gly Gly Val  Lys Met Arg
    1085                 1090                 1095

His Ala  Gln Cys Leu Asp Ala  Ala Asp Arg Glu Thr  His Thr Ser
    1100                 1105                 1110

Arg Cys  Gly Pro Ala Gln Thr  Gln Glu His Cys Asn  Glu His Ala
    1115                 1120                 1125

Cys Thr  Trp Trp Gln Phe Gly  Val Trp Ser Asp Cys  Ser Ala Lys
    1130                 1135                 1140

Cys Gly  Asp Gly Val Gln Tyr  Arg Asp Ala Asn Cys  Thr Asp Arg
    1145                 1150                 1155

His Arg  Ser Val Leu Pro Glu  His Arg Cys Leu Lys  Met Glu Lys
    1160                 1165                 1170

Ile Ile  Thr Lys Pro Cys His  Arg Glu Ser Cys Pro  Lys Tyr Lys
    1175                 1180                 1185

Leu Gly  Glu Trp Ser Gln Cys  Ser Val Ser Cys Glu  Asp Gly Trp
    1190                 1195                 1200

Ser Ser  Arg Arg Val Ser Cys  Val Ser Gly Asn Gly  Thr Glu Val
    1205                 1210                 1215

Asp Met  Ser Leu Cys Gly Thr  Ala Ser Asp Arg Pro  Ala Ser His
    1220                 1225                 1230

Gln Thr  Cys Asn Leu Gly Thr  Cys Pro Phe Trp Arg  Asn Thr Asp
    1235                 1240                 1245

Trp Ser  Ala Cys Ser Val Ser  Cys Gly Ile Gly His  Arg Glu Arg
    1250                 1255                 1260

Thr Thr  Glu Cys Ile Tyr Arg  Glu Gln Ser Val Asp  Ala Ser Phe
    1265                 1270                 1275

Cys Gly  Asp Thr Lys Met Pro  Glu Thr Ser Gln Thr  Cys His Leu
    1280                 1285                 1290
```

-continued

```
Leu Pro  Cys Thr Ser Trp Lys  Pro Ser His Trp Ser  Pro Cys Ser
    1295                 1300                 1305

Val Thr  Cys Gly Ser Gly Ile  Gln Thr Arg Ser Val  Ser Cys Thr
    1310                 1315                 1320

Arg Gly  Ser Glu Gly Thr Ile  Val Asp Glu Tyr Phe  Cys Asp Arg
    1325                 1330                 1335

Asn Thr  Arg Pro Arg Leu Lys  Lys Thr Cys Glu Lys  Asp Thr Cys
    1340                 1345                 1350

Asp Gly  Pro Arg Val Leu Gln  Lys Leu Gln Ala Asp  Val Pro Pro
    1355                 1360                 1365

Ile Arg  Trp Ala Thr Gly Pro  Trp Thr Ala Cys Ser  Ala Thr Cys
    1370                 1375                 1380

Gly Asn  Gly Thr Gln Arg Arg  Leu Leu Lys Cys Arg  Asp His Val
    1385                 1390                 1395

Arg Asp  Leu Pro Asp Glu Tyr  Cys Asn His Leu Asp  Lys Glu Val
    1400                 1405                 1410

Ser Thr  Arg Asn Cys Arg Leu  Arg Asp Cys Ser Tyr  Trp Lys Met
    1415                 1420                 1425

Ala Glu  Trp Glu Glu Cys Pro  Ala Thr Cys Gly Thr  His Val Gln
    1430                 1435                 1440

Gln Ser  Arg Asn Val Thr Cys  Val Ser Ala Glu Asp  Gly Gly Arg
    1445                 1450                 1455

Thr Ile  Leu Lys Asp Val Asp  Cys Asp Val Gln Lys  Arg Pro Thr
    1460                 1465                 1470

Ser Ala  Arg Asn Cys Arg Leu  Glu Pro Cys Pro Lys  Gly Glu Glu
    1475                 1480                 1485

His Ile  Gly Ser Trp Ile Ile  Gly Asp Trp Ser Lys  Cys Ser Ala
    1490                 1495                 1500

Ser Cys  Gly Gly Gly Trp Arg  Arg Arg Ser Val Ser  Cys Thr Ser
    1505                 1510                 1515

Ser Ser  Cys Asp Glu Thr Arg  Lys Pro Lys Met Phe  Asp Lys Cys
    1520                 1525                 1530

Asn Glu  Glu Leu Cys Pro Pro  Leu Thr Asn Asn Ser  Trp Gln Ile
    1535                 1540                 1545

Ser Pro  Trp Thr His Cys Ser  Val Ser Cys Gly Gly  Gly Val Gln
    1550                 1555                 1560

Arg Arg  Lys Ile Trp Cys Glu  Asp Val Leu Ser Gly  Arg Lys Gln
    1565                 1570                 1575

Asp Asp  Ile Glu Cys Ser Glu  Ile Lys Pro Arg Glu  Gln Arg Asp
    1580                 1585                 1590

Cys Glu  Met Pro Pro Cys Arg  Ser His Tyr His Asn  Lys Thr Ser
    1595                 1600                 1605

Ser Ala  Ser Met Thr Ser Leu  Ser Ser Ser Asn Ser  Asn Thr Thr
    1610                 1615                 1620

Ser Ser  Ala Ser Ala Ser Ser  Leu Pro Ile Leu Pro  Pro Val Val
    1625                 1630                 1635

Ser Trp  Gln Thr Ser Ala Trp  Ser Ala Cys Ser Ala  Lys Cys Gly
    1640                 1645                 1650

Arg Gly  Thr Lys Arg Arg Val  Val Glu Cys Val Asn  Pro Ser Leu
    1655                 1660                 1665

Asn Val  Thr Val Ala Ser Thr  Glu Cys Asp Gln Thr  Lys Lys Pro
    1670                 1675                 1680

Val Glu  Glu Val Arg Cys Arg  Thr Lys His Cys Pro  Arg Trp Lys
```

-continued

```
    1685                1690                1695

Thr Thr  Thr Trp Ser Ser Cys  Ser Val Thr Cys Gly  Arg Gly Ile
    1700                1705                1710

Arg Arg  Arg Glu Val Gln Cys  Tyr Arg Gly Arg Lys  Asn Leu Val
    1715                1720                1725

Ser Asp  Ser Glu Cys Asn Pro  Lys Thr Lys Leu Asn  Ser Val Ala
    1730                1735                1740

Asn Cys  Phe Pro Val Ala Cys  Pro Ala Tyr Arg Trp  Asn Val Thr
    1745                1750                1755

Pro Trp  Ser Lys Cys Lys Asp  Glu Cys Ala Arg Gly  Gln Lys Gln
    1760                1765                1770

Thr Arg  Arg Val His Cys Ile  Ser Thr Ser Gly Lys  Arg Ala Ala
    1775                1780                1785

Pro Arg  Met Cys Glu Leu Ala  Arg Ala Pro Thr Ser  Ile Arg Glu
    1790                1795                1800

Cys Asp  Thr Ser Asn Cys Pro  Tyr Glu Trp Val Pro  Gly Asp Trp
    1805                1810                1815

Gln Thr  Cys Ser Lys Ser Cys  Gly Glu Gly Val Gln  Thr Arg Glu
    1820                1825                1830

Val Arg  Cys Arg Arg Lys Ile  Asn Phe Asn Ser Thr  Ile Pro Ile
    1835                1840                1845

Ile Phe  Met Leu Glu Asp Glu  Pro Ala Val Pro Lys  Glu Lys Cys
    1850                1855                1860

Glu Leu  Phe Pro Lys Pro Asn  Glu Ser Gln Thr Cys  Glu Leu Asn
    1865                1870                1875

Pro Cys  Asp Ser Glu Phe Lys  Trp Ser Phe Gly Pro  Trp Gly Glu
    1880                1885                1890

Cys Ser  Lys Asn Cys Gly Gln  Gly Ile Arg Arg Arg  Arg Val Lys
    1895                1900                1905

Cys Val  Ala Asn Asp Gly Arg  Arg Val Glu Arg Val  Lys Cys Thr
    1910                1915                1920

Thr Lys  Lys Pro Arg Arg Thr  Gln Tyr Cys Phe Glu  Arg Asn Cys
    1925                1930                1935

Leu Pro  Ser Thr Cys Gln Glu  Leu Lys Ser Gln Asn  Val Lys Ala
    1940                1945                1950

Lys Asp  Gly Asn Tyr Thr Ile  Leu Leu Asp Gly Phe  Thr Ile Glu
    1955                1960                1965

Ile Tyr  Cys His Arg Met Asn  Ser Thr Ile Pro Lys  Ala Tyr Leu
    1970                1975                1980

Asn Val  Asn Pro Arg Thr Asn  Phe Ala Glu Val Tyr  Gly Lys Lys
    1985                1990                1995

Leu Ile  Tyr Pro His Thr Cys  Pro Phe Asn Gly Asp  Arg Asn Asp
    2000                2005                2010

Ser Cys  His Cys Ser Glu Asp  Gly Asp Ala Ser Ala  Gly Leu Thr
    2015                2020                2025

Arg Phe  Asn Lys Val Arg Ile  Asp Leu Leu Asn Arg  Lys Phe His
    2030                2035                2040

Leu Ala  Asp Tyr Thr Phe Ala  Lys Arg Glu Tyr Gly  Val His Val
    2045                2050                2055

Pro Tyr  Gly Thr Ala Gly Asp  Cys Tyr Ser Met Lys  Asp Cys Pro
    2060                2065                2070

Gln Gly  Ile Phe Ser Ile Asp  Leu Lys Ser Ala Gly  Leu Lys Leu
    2075                2080                2085
```

-continued

```
Val Asp  Asp Leu Asn Trp Glu  Asp Gln Gly His Arg  Thr Ser Ser
    2090                 2095                 2100

Arg Ile  Asp Arg Phe Tyr Asn  Asn Ala Lys Val Ile  Gly His Cys
    2105                 2110                 2115

Gly Gly  Phe Cys Gly Lys Cys  Ser Pro Glu Arg Tyr  Lys Gly Leu
    2120                 2125                 2130

Ile Phe  Glu Val Asn Thr Lys  Leu Leu Asn His Val  Lys Asn Gly
    2135                 2140                 2145

Gly His  Ile Asp Asp Glu Leu  Asp Asp Asp Gly Phe  Ser Gly Asp
    2150                 2155                 2160

Met Asp
    2165


<210> SEQ ID NO 156
<211> LENGTH: 446
<212> TYPE: DNA
<213> ORGANISM: Homo sapiens
<220> FEATURE:
<221> NAME/KEY: SITE
<222> LOCATION: (14)
<223> OTHER INFORMATION: n equals a,t,g, or c
<221> NAME/KEY: SITE
<222> LOCATION: (15)
<223> OTHER INFORMATION: n equals a,t,g, or c
<221> NAME/KEY: SITE
<222> LOCATION: (380)
<223> OTHER INFORMATION: n equals a,t,g, or c
<221> NAME/KEY: SITE
<222> LOCATION: (391)
<223> OTHER INFORMATION: n equals a,t,g, or c
<221> NAME/KEY: SITE
<222> LOCATION: (394)
<223> OTHER INFORMATION: n equals a,t,g, or c
<221> NAME/KEY: SITE
<222> LOCATION: (401)
<223> OTHER INFORMATION: n equals a,t,g, or c
<221> NAME/KEY: SITE
<222> LOCATION: (429)
<223> OTHER INFORMATION: n equals a,t,g, or c

<400> SEQUENCE: 156

gccaattgtc actnncacag gactgacgca tcacatcttg gcagctggac agatccttca     60

agttgcaaac cttagcggtg ggtctcaagg ggaattcagc tgccttgctc agaatgaggc    120

aggggtgctc atgcagaagg catctttagt gatccaagat tactggtggt ctgtggacag    180

actggcaacc tgctcagcct cctgtggtaa ccggggggtt cagcagcccc gcttgaggtg    240

cctgctgaac agcacggagg tcaaccctgc ccactgcgca gggaaggttc gccctgcggt    300

gcagcccatc gtgtgcaacc ggagagactg cccttctcgg tggatggtga cctcctggtc    360

tgcctgtacc cggagctgtn ggggaggtgt ncanacccca nggtgacctg tcaaaagctg    420

aaaagcctnt gggatctcca cccctg                                         446


<210> SEQ ID NO 157
<211> LENGTH: 354
<212> TYPE: DNA
<213> ORGANISM: Homo sapiens
<220> FEATURE:
<221> NAME/KEY: SITE
<222> LOCATION: (38)
<223> OTHER INFORMATION: n equals a,t,g, or c
<221> NAME/KEY: SITE
<222> LOCATION: (63)
<223> OTHER INFORMATION: n equals a,t,g, or c
<221> NAME/KEY: SITE
<222> LOCATION: (98)
```

-continued

<223> OTHER INFORMATION: n equals a,t,g, or c
<221> NAME/KEY: SITE
<222> LOCATION: (281)
<223> OTHER INFORMATION: n equals a,t,g, or c
<221> NAME/KEY: SITE
<222> LOCATION: (284)
<223> OTHER INFORMATION: n equals a,t,g, or c
<221> NAME/KEY: SITE
<222> LOCATION: (301)
<223> OTHER INFORMATION: n equals a,t,g, or c
<221> NAME/KEY: SITE
<222> LOCATION: (307)
<223> OTHER INFORMATION: n equals a,t,g, or c
<221> NAME/KEY: SITE
<222> LOCATION: (353)
<223> OTHER INFORMATION: n equals a,t,g, or c

<400> SEQUENCE: 157
agcagcagtg tgtggagtgg gccttctcca gctggggnca gtgcaatggg ccttgcatcg 60
ggnctcacct agctgtgcaa cacagacaag tcttctgnca gacacgggat ggcatcacct 120
taccatcaga gcagtgcagt gctcttccga ggcctgtgag cacccagaac tgctggtcag 180
aggcctgcag tgtacactgg agagtcagcc tgtggaccct gtgcacagct acctgtggca 240
actacggctt ccagtcccgg cgtgtggagt gtgtgcatgc ncgnaccaac aaaggcagtg 300
ncttgancac ctgtgctacc tgggggaccc ggacttgccc aattggcagc gcng 354

<210> SEQ ID NO 158
<211> LENGTH: 318
<212> TYPE: DNA
<213> ORGANISM: Homo sapiens
<220> FEATURE:
<221> NAME/KEY: SITE
<222> LOCATION: (9)
<223> OTHER INFORMATION: n equals a,t,g, or c
<221> NAME/KEY: SITE
<222> LOCATION: (42)
<223> OTHER INFORMATION: n equals a,t,g, or c
<221> NAME/KEY: SITE
<222> LOCATION: (50)
<223> OTHER INFORMATION: n equals a,t,g, or c
<221> NAME/KEY: SITE
<222> LOCATION: (51)
<223> OTHER INFORMATION: n equals a,t,g, or c
<221> NAME/KEY: SITE
<222> LOCATION: (80)
<223> OTHER INFORMATION: n equals a,t,g, or c
<221> NAME/KEY: SITE
<222> LOCATION: (134)
<223> OTHER INFORMATION: n equals a,t,g, or c
<221> NAME/KEY: SITE
<222> LOCATION: (163)
<223> OTHER INFORMATION: n equals a,t,g, or c
<221> NAME/KEY: SITE
<222> LOCATION: (270)
<223> OTHER INFORMATION: n equals a,t,g, or c
<221> NAME/KEY: SITE
<222> LOCATION: (273)
<223> OTHER INFORMATION: n equals a,t,g, or c
<221> NAME/KEY: SITE
<222> LOCATION: (276)
<223> OTHER INFORMATION: n equals a,t,g, or c
<221> NAME/KEY: SITE
<222> LOCATION: (295)
<223> OTHER INFORMATION: n equals a,t,g, or c
<221> NAME/KEY: SITE
<222> LOCATION: (317)
<223> OTHER INFORMATION: n equals a,t,g, or c

<400> SEQUENCE: 158
ggcagaggng aaaaactcta ccctggccac acgaaggact cncgcaaccn nctcggacag 60
aacctaagct ttcttcattn tatttattta tttccccctc cccactccac acacaccctt 120

-continued ccaacctcct ccanctccac cttcaagcat aaggacgtcc gcntgttttc tctttcagtt 180
agctggagga caggatgttg ggaaaggaaa ggacagatgt ctaaaggagg ttgcagagca 240
ggccaggcag acagtggggg ggcttccttn ganggngctt tcctccctcc caaanctggg 300
ggttttcaaa gaccttng 318

<210> SEQ ID NO 159
<211> LENGTH: 442
<212> TYPE: DNA
<213> ORGANISM: Homo sapiens
<220> FEATURE:
<221> NAME/KEY: SITE
<222> LOCATION: (9)
<223> OTHER INFORMATION: n equals a,t,g, or c
<221> NAME/KEY: SITE
<222> LOCATION: (98)
<223> OTHER INFORMATION: n equals a,t,g, or c
<221> NAME/KEY: SITE
<222> LOCATION: (191)
<223> OTHER INFORMATION: n equals a,t,g, or c
<221> NAME/KEY: SITE
<222> LOCATION: (273)
<223> OTHER INFORMATION: n equals a,t,g, or c
<221> NAME/KEY: SITE
<222> LOCATION: (303)
<223> OTHER INFORMATION: n equals a,t,g, or c
<221> NAME/KEY: SITE
<222> LOCATION: (323)
<223> OTHER INFORMATION: n equals a,t,g, or c
<221> NAME/KEY: SITE
<222> LOCATION: (340)
<223> OTHER INFORMATION: n equals a,t,g, or c
<221> NAME/KEY: SITE
<222> LOCATION: (402)
<223> OTHER INFORMATION: n equals a,t,g, or c
<221> NAME/KEY: SITE
<222> LOCATION: (408)
<223> OTHER INFORMATION: n equals a,t,g, or c
<221> NAME/KEY: SITE
<222> LOCATION: (415)
<223> OTHER INFORMATION: n equals a,t,g, or c
<221> NAME/KEY: SITE
<222> LOCATION: (419)
<223> OTHER INFORMATION: n equals a,t,g, or c
<221> NAME/KEY: SITE
<222> LOCATION: (441)
<223> OTHER INFORMATION: n equals a,t,g, or c

<400> SEQUENCE: 159
ggcagaggna cttccccagt gactctctcg cctcataaac acgtgtctgg cttcagcagc 60
tccctgcgga cctcctccac cggggacgcc gggggagnct ctcgaaggcc acaccgcaag 120
cccaccatcc tgcggcaaga tctcagcggc ccagcagctc tcagcctcgg aggtggtcac 180
ccacctgggg ncagacggtg gccctggcca gcgggacact gagtgttctt ctgcactgtg 240
aggccatcgg caacccaagg ccttaccatc agntgggcca ggaatgggag aaggaagttt 300
canttcagtg gacaggattc ttnttacagc cagatgattn ctttacagat tttgggcacc 360
atgggaagca gatgtgggtt ttttacaatt tgcaatggcc ancaatgnct tgggntaang 420
attttgtttc cattggcctt na 442

<210> SEQ ID NO 160
<211> LENGTH: 429
<212> TYPE: DNA
<213> ORGANISM: Homo sapiens
<220> FEATURE:
<221> NAME/KEY: SITE
<222> LOCATION: (323)
<223> OTHER INFORMATION: n equals a,t,g, or c -continued
<221> NAME/KEY: SITE
<222> LOCATION: (361)
<223> OTHER INFORMATION: n equals a,t,g, or c
<221> NAME/KEY: SITE
<222> LOCATION: (363)
<223> OTHER INFORMATION: n equals a,t,g, or c
<221> NAME/KEY: SITE
<222> LOCATION: (376)
<223> OTHER INFORMATION: n equals a,t,g, or c
<221> NAME/KEY: SITE
<222> LOCATION: (387)
<223> OTHER INFORMATION: n equals a,t,g, or c
<221> NAME/KEY: SITE
<222> LOCATION: (410)
<223> OTHER INFORMATION: n equals a,t,g, or c

<400> SEQUENCE: 160

```
ctgcggacag cagggagcca gaaggtttgt agcctattgg tgcaaacatt ggacaaattc     60

ctgtgtcttt cctagaagcg cactatcaca aacacaggag tgttttgctc ctttgtctcc    120

tcttccccat ctatgtccct ttagtcacag ttaggacaaa tggggagggg acaccatgct    180

gaggcagaaa ctagcccaga actcactcag ttcttctagt gggtgagtgc agagagagaa    240

gaactcagat caccagtagg gagaggtaaa aaagcaaaca aagcaggctc taaggcacac    300

aacattgcca gaaaatgagg aanggagggg gagggaaggg acagaagcca aaagggacct    360

ntnggtgttc cccatngggg caggttnaac aggggtttcc aggtgcatgn ggctctggga    420

ccactttga                                                            429
```

<210> SEQ ID NO 161
<211> LENGTH: 50
<212> TYPE: PRT
<213> ORGANISM: Homo sapiens

<400> SEQUENCE: 161

```
Asp Gly Leu Trp Asp Ala Trp Gly Pro Trp Ser Glu Cys Ser Arg Thr
  1               5                  10                  15

Cys Gly Gly Gly Ala Ser Tyr Ser Leu Arg Arg Cys Leu Ser Ser Lys
             20                  25                  30

Ser Cys Glu Gly Arg Asn Ile Arg Tyr Arg Thr Cys Ser Asn Val Asp
         35                  40                  45

Cys Pro
     50
```

<210> SEQ ID NO 162
<211> LENGTH: 60
<212> TYPE: PRT
<213> ORGANISM: Homo sapiens

<400> SEQUENCE: 162

```
Trp Arg Glu Thr Asp Phe Phe Pro Cys Ser Ala Thr Cys Gly Gly Gly
  1               5                  10                  15

Tyr Gln Leu Thr Ser Ala Glu Cys Tyr Asp Leu Arg Ser Asn Arg Val
             20                  25                  30

Val Ala Asp Gln Tyr Cys His Tyr Tyr Pro Glu Asn Ile Lys Pro Lys
         35                  40                  45

Pro Lys Leu Gln Glu Cys Asn Leu Asp Pro Cys Pro
     50                  55                  60
```

<210> SEQ ID NO 163
<211> LENGTH: 59
<212> TYPE: PRT
<213> ORGANISM: Homo sapiens -continued

<400> SEQUENCE: 163

Trp Glu Ala Thr Pro Trp Thr Ala Cys Ser Ser Ser Cys Gly Gly Gly
1 5 10 15

Ile Gln Ser Arg Ala Val Ser Cys Val Glu Glu Asp Ile Gln Gly His
20 25 30

Val Thr Ser Val Glu Glu Trp Lys Cys Met Tyr Thr Pro Lys Met Pro
35 40 45

Ile Ala Gln Pro Cys Asn Ile Phe Asp Cys Pro
50 55

<210> SEQ ID NO 164
<211> LENGTH: 53
<212> TYPE: PRT
<213> ORGANISM: Homo sapiens

<400> SEQUENCE: 164

Trp Leu Ala Gln Glu Trp Ser Pro Cys Thr Val Thr Cys Gly Gln Gly
1 5 10 15

Leu Arg Tyr Arg Val Val Leu Cys Ile Asp His Arg Gly Met His Thr
20 25 30

Gly Gly Cys Ser Pro Lys Thr Lys Pro His Ile Lys Glu Glu Cys Ile
35 40 45

Val Pro Thr Pro Cys
50

<210> SEQ ID NO 165
<211> LENGTH: 53
<212> TYPE: PRT
<213> ORGANISM: Homo sapiens

<400> SEQUENCE: 165

Trp Ser Ala Cys Thr Val Thr Cys Gly Val Gly Thr Gln Val Arg Ile
1 5 10 15

Val Arg Cys Gln Val Leu Leu Ser Phe Ser Gln Ser Val Ala Asp Leu
20 25 30

Pro Ile Asp Glu Cys Glu Gly Pro Lys Pro Ala Ser Gln Arg Ala Cys
35 40 45

Tyr Ala Gly Pro Cys
50

<210> SEQ ID NO 166
<211> LENGTH: 61
<212> TYPE: PRT
<213> ORGANISM: Homo sapiens

<400> SEQUENCE: 166

Glu Leu Tyr Asp Trp Glu Tyr Glu Gly Phe Thr Lys Cys Ser Glu Ser
1 5 10 15

Cys Gly Gly Gly Val Gln Glu Ala Val Val Ser Cys Leu Asn Lys Gln
20 25 30

Thr Arg Glu Pro Ala Glu Glu Asn Leu Cys Val Thr Ser Arg Arg Pro
35 40 45

Pro Gln Leu Leu Lys Ser Cys Asn Leu Asp Pro Cys Pro
50 55 60

<210> SEQ ID NO 167
<211> LENGTH: 60
<212> TYPE: PRT

-continued

<213> ORGANISM: Homo sapiens

<400> SEQUENCE: 167

Trp Glu Ile Gly Lys Trp Ser Pro Cys Ser Leu Thr Cys Gly Val Gly
1 5 10 15

Leu Gln Thr Arg Asp Val Phe Cys Ser His Leu Leu Ser Arg Glu Met
20 25 30

Asn Glu Thr Val Ile Leu Ala Asp Glu Leu Cys Arg Gln Pro Lys Pro
35 40 45

Ser Thr Val Gln Ala Cys Asn Arg Phe Asn Cys Pro
50 55 60

<210> SEQ ID NO 168
<211> LENGTH: 58
<212> TYPE: PRT
<213> ORGANISM: Homo sapiens

<400> SEQUENCE: 168

Trp Tyr Pro Ala Gln Trp Gln Pro Cys Ser Arg Thr Cys Gly Gly Gly
1 5 10 15

Val Gln Lys Arg Glu Val Leu Cys Lys Gln Arg Met Ala Asp Gly Ser
20 25 30

Phe Leu Glu Leu Pro Glu Thr Phe Cys Ser Ala Ser Lys Pro Ala Cys
35 40 45

Gln Gln Ala Cys Lys Lys Asp Asp Cys Pro
50 55

<210> SEQ ID NO 169
<211> LENGTH: 58
<212> TYPE: PRT
<213> ORGANISM: Homo sapiens

<400> SEQUENCE: 169

Trp Leu Leu Ser Asp Trp Thr Glu Cys Ser Thr Ser Cys Gly Glu Gly
1 5 10 15

Thr Gln Thr Arg Ser Ala Ile Cys Arg Lys Met Leu Lys Thr Gly Leu
20 25 30

Ser Thr Val Val Asn Ser Thr Leu Cys Pro Pro Leu Pro Phe Ser Ser
35 40 45

Ser Ile Arg Pro Cys Met Leu Ala Thr Cys
50 55

<210> SEQ ID NO 170
<211> LENGTH: 57
<212> TYPE: PRT
<213> ORGANISM: Homo sapiens

<400> SEQUENCE: 170

Trp Trp Ser Val Asp Arg Leu Ala Thr Cys Ser Ala Ser Cys Gly Asn
1 5 10 15

Arg Gly Val Gln Gln Pro Arg Leu Arg Cys Leu Leu Asn Ser Thr Glu
20 25 30

Val Asn Pro Ala His Cys Ala Gly Lys Val Arg Pro Ala Val Gln Pro
35 40 45

Ile Ala Cys Asn Arg Arg Asp Cys Pro
50 55

<210> SEQ ID NO 171
<211> LENGTH: 59

-continued

<212> TYPE: PRT
<213> ORGANISM: Homo sapiens

<400> SEQUENCE: 171

Trp Met Val Thr Ser Trp Ser Ala Cys Thr Arg Ser Cys Gly Gly Gly
1 5 10 15

Val Gln Thr Arg Arg Val Thr Cys Gln Lys Leu Lys Ala Ser Gly Ile
20 25 30

Ser Thr Pro Val Ser Asn Asp Met Cys Thr Gln Val Ala Lys Arg Pro
35 40 45

Val Asp Thr Gln Ala Cys Asn Gln Gln Leu Cys
50 55

<210> SEQ ID NO 172
<211> LENGTH: 58
<212> TYPE: PRT
<213> ORGANISM: Homo sapiens

<400> SEQUENCE: 172

Trp Ala Phe Ser Ser Trp Gly Gln Cys Asn Gly Pro Cys Ile Gly Pro
1 5 10 15

His Leu Ala Val Gln His Arg Gln Val Phe Cys Gln Thr Arg Asp Gly
20 25 30

Ile Thr Leu Pro Ser Glu Gln Cys Ser Ala Leu Pro Arg Pro Val Ser
35 40 45

Thr Gln Asn Cys Trp Ser Glu Ala Cys Ser
50 55

<210> SEQ ID NO 173
<211> LENGTH: 56
<212> TYPE: PRT
<213> ORGANISM: Homo sapiens

<400> SEQUENCE: 173

Trp Arg Val Ser Leu Trp Thr Leu Cys Thr Ala Thr Cys Gly Asn Tyr
1 5 10 15

Gly Phe Gln Ser Arg Arg Val Glu Cys Val His Ala Arg Thr Asn Lys
20 25 30

Ala Val Pro Glu His Leu Cys Ser Trp Gly Pro Arg Pro Ala Asn Trp
35 40 45

Gln Arg Cys Asn Ile Thr Pro Cys
50 55

<210> SEQ ID NO 174
<211> LENGTH: 138
<212> TYPE: PRT
<213> ORGANISM: Homo sapiens

<400> SEQUENCE: 174

Pro Glu Ala Gly Asp Phe Arg Ala Gln Gln Cys Ser Ala His Asn Asp
1 5 10 15

Val Lys His His Gly Gln Phe Tyr Glu Trp Leu Pro Val Ser Asn Asp
20 25 30

Pro Asp Asn Pro Cys Ser Leu Lys Cys Gln Ala Lys Gly Thr Thr Leu
35 40 45

Val Val Glu Leu Ala Pro Lys Val Leu Asp Gly Thr Arg Cys Tyr Thr
50 55 60

Glu Ser Leu Asp Met Cys Ile Ser Gly Leu Cys Gln Ile Val Gly Cys
65 70 75 80

-continued

```
Asp His Gln Leu Gly Ser Thr Val Lys Glu Asp Asn Cys Gly Val Cys
                85                  90                  95

Asn Gly Asp Gly Ser Thr Cys Arg Leu Val Arg Gly Gln Tyr Lys Ser
            100                 105                 110

Gln Leu Ser Ala Thr Lys Ser Asp Asp Thr Val Val Ala Ile Pro Tyr
        115                 120                 125

Gly Ser Arg His Ile Arg Leu Val Leu Lys
    130                 135


<210> SEQ ID NO 175
<211> LENGTH: 292
<212> TYPE: PRT
<213> ORGANISM: Homo sapiens

<400> SEQUENCE: 175

Ser Val Leu Leu His Cys Glu Ala Ile Gly His Pro Arg Pro Thr Ile
  1               5                  10                  15

Ser Trp Ala Arg Asn Gly Glu Glu Val Gln Phe Ser Asp Arg Ile Leu
            20                  25                  30

Leu Gln Pro Asp Asp Ser Leu Gln Ile Leu Ala Pro Val Glu Ala Asp
        35                  40                  45

Val Gly Phe Tyr Thr Cys Asn Ala Thr Asn Ala Leu Gly Tyr Asp Ser
     50                  55                  60

Val Ser Ile Ala Val Thr Leu Ala Gly Lys Pro Leu Val Lys Thr Ser
 65                  70                  75                  80

Arg Met Thr Val Ile Asn Thr Glu Lys Pro Ala Val Thr Val Asp Ile
                85                  90                  95

Gly Ser Thr Ile Lys Thr Val Gln Gly Val Asn Val Thr Ile Asn Cys
            100                 105                 110

Gln Val Ala Gly Val Pro Glu Ala Glu Val Thr Trp Phe Arg Asn Lys
        115                 120                 125

Ser Lys Leu Gly Ser Pro His His Leu His Glu Gly Ser Leu Leu Leu
    130                 135                 140

Thr Asn Val Ser Ser Ser Asp Gln Gly Leu Tyr Ser Cys Arg Ala Ala
145                 150                 155                 160

Asn Leu His Gly Glu Leu Thr Glu Ser Thr Gln Leu Leu Ile Leu Asp
                165                 170                 175

Pro Pro Gln Val Pro Thr Gln Leu Glu Asp Ile Arg Ala Leu Leu Ala
            180                 185                 190

Ala Thr Gly Pro Asn Leu Pro Ser Val Leu Thr Ser Pro Leu Gly Thr
        195                 200                 205

Gln Leu Val Leu Asp Pro Gly Asn Ser Ala Leu Leu Gly Cys Pro Ile
    210                 215                 220

Lys Gly His Pro Val Pro Asn Ile Thr Trp Phe His Gly Gly Gln Pro
225                 230                 235                 240

Ile Val Thr Ala Thr Gly Leu Thr His His Ile Leu Ala Ala Gly Gln
                245                 250                 255

Ile Leu Gln Val Ala Asn Leu Ser Gly Gly Ser Gln Gly Glu Phe Ser
            260                 265                 270

Cys Leu Ala Gln Asn Glu Ala Gly Val Leu Met Gln Lys Ala Ser Leu
        275                 280                 285

Val Ile Gln Asp
    290
```

-continued

<210> SEQ ID NO 176
<211> LENGTH: 50
<212> TYPE: PRT
<213> ORGANISM: Homo sapiens

<400> SEQUENCE: 176

```
Met Lys Pro Ala Thr Ala Ser Ala Leu Leu Leu Leu Leu Leu Gly Leu
  1               5                  10                  15

Ala Trp Thr Gln Gly Ser His Gly Trp Gly Ala Asp Ala Ser Ser Leu
             20                  25                  30

Gln Lys Arg Ala Gly Arg Ala Asp Gln Pro Gly Ala Gly Trp Gln Glu
         35                  40                  45

Val Ala
     50
```

<210> SEQ ID NO 177
<211> LENGTH: 67
<212> TYPE: PRT
<213> ORGANISM: Homo sapiens

<400> SEQUENCE: 177

```
Met Lys Pro Ala Thr Ala Ser Ala Leu Leu Leu Leu Leu Leu Gly Leu
  1               5                  10                  15

Ala Trp Thr Gln Gly Ser His Gly Trp Gly Ala Asp Ala Ser Ser Leu
             20                  25                  30

Gln Lys Arg Ala Gly Arg Ala Asp Gln Pro Gly Ala Gly Trp Gln Glu
         35                  40                  45

Val Ala Ala Val Thr Ser Lys Asn Tyr Asn Tyr Asn Gln His Ala Tyr
     50                  55                  60

Pro Thr Ala
 65
```

<210> SEQ ID NO 178
<211> LENGTH: 83
<212> TYPE: PRT
<213> ORGANISM: Homo sapiens

<400> SEQUENCE: 178

```
Met Lys Pro Ala Thr Ala Ser Ala Leu Leu Leu Leu Leu Leu Gly Leu
  1               5                  10                  15

Ala Trp Thr Gln Gly Ser His Gly Trp Gly Ala Asp Ala Ser Ser Leu
             20                  25                  30

Gln Lys Arg Ala Gly Arg Ala Asp Gln Pro Gly Ala Gly Trp Gln Glu
         35                  40                  45

Val Ala Ala Val Thr Ser Lys Asn Tyr Asn Tyr Asn Gln His Ala Tyr
     50                  55                  60

Pro Thr Ala Tyr Gly Gly Lys Tyr Ser Val Lys Thr Pro Ala Lys Gly
 65                  70                  75                  80

Gly Val Ser
```

<210> SEQ ID NO 179
<211> LENGTH: 96
<212> TYPE: PRT
<213> ORGANISM: Homo sapiens

<400> SEQUENCE: 179

```
Met Ala Gly Gly Gly Ser Cys Asn Phe Gln Glu Leu Gln Leu Gln Pro
  1               5                  10                  15

Ala Cys Val Ser His Cys Leu Trp Trp Glu Val Leu Ser Gln Asp Pro
```

-continued

```
            20                  25                  30

Cys Lys Gly Gly Ser Leu Thr Phe Phe Leu Gly Phe Pro Gly Ala Thr
        35                  40                  45

Trp Pro Ala Ala Val Gly Glu Val Leu Val Gly Asn Phe Leu Gln Pro
    50                  55                  60

Pro Pro Arg Pro Arg Lys Ala Leu Val Val Arg Glu Leu Leu Pro Leu
65                  70                  75                  80

Ala Pro Ser Leu Cys Gln Pro Trp Pro Gly Cys His Thr Ser Val Ser
                85                  90                  95


<210> SEQ ID NO 180
<211> LENGTH: 526
<212> TYPE: PRT
<213> ORGANISM: Homo sapiens
<220> FEATURE:
<221> NAME/KEY: SITE
<222> LOCATION: (37)
<223> OTHER INFORMATION: Xaa equals any of the naturally occurring
      L-amino acids
<221> NAME/KEY: SITE
<222> LOCATION: (185)
<223> OTHER INFORMATION: Xaa equals any of the naturally occurring
      L-amino acids
<221> NAME/KEY: SITE
<222> LOCATION: (215)
<223> OTHER INFORMATION: Xaa equals any of the naturally occurring
      L-amino acids
<221> NAME/KEY: SITE
<222> LOCATION: (216)
<223> OTHER INFORMATION: Xaa equals any of the naturally occurring
      L-amino acids
<221> NAME/KEY: SITE
<222> LOCATION: (261)
<223> OTHER INFORMATION: Xaa equals any of the naturally occurring
      L-amino acids
<221> NAME/KEY: SITE
<222> LOCATION: (263)
<223> OTHER INFORMATION: Xaa equals any of the naturally occurring
      L-amino acids
<221> NAME/KEY: SITE
<222> LOCATION: (311)
<223> OTHER INFORMATION: Xaa equals any of the naturally occurring
      L-amino acids
<221> NAME/KEY: SITE
<222> LOCATION: (318)
<223> OTHER INFORMATION: Xaa equals any of the naturally occurring
      L-amino acids
<221> NAME/KEY: SITE
<222> LOCATION: (320)
<223> OTHER INFORMATION: Xaa equals any of the naturally occurring
      L-amino acids
<221> NAME/KEY: SITE
<222> LOCATION: (510)
<223> OTHER INFORMATION: Xaa equals any of the naturally occurring
      L-amino acids
<221> NAME/KEY: SITE
<222> LOCATION: (515)
<223> OTHER INFORMATION: Xaa equals any of the naturally occurring
      L-amino acids
<221> NAME/KEY: SITE
<222> LOCATION: (516)
<223> OTHER INFORMATION: Xaa equals any of the naturally occurring
      L-amino acids
<221> NAME/KEY: SITE
<222> LOCATION: (522)
<223> OTHER INFORMATION: Xaa equals any of the naturally occurring
      L-amino acids

<400> SEQUENCE: 180

Arg Pro Arg Leu Gly Ser Ser Ser Gly Ala Ala Ala Glu Asp Ser Ser
  1               5                  10                  15

Ala Met Glu Glu Leu Ala Thr Glu Lys Glu Ala Glu Glu Ser His Arg
```

-continued

```
            20                  25                  30

Gln Asp Ser Val Xaa Leu Leu Thr Phe Ile Leu Leu Leu Thr Leu Thr
        35                  40                  45

Ile Leu Thr Ile Trp Leu Phe Lys His Arg Arg Val Arg Phe Leu His
    50                  55                  60

Glu Thr Gly Leu Ala Met Ile Tyr Gly Leu Ile Val Gly Val Ile Leu
65                  70                  75                  80

Arg Tyr Gly Thr Pro Ala Thr Ser Gly Arg Asp Lys Ser Leu Ser Cys
                85                  90                  95

Thr Gln Glu Asp Arg Ala Phe Ser Thr Leu Leu Val Asn Val Ser Gly
            100                 105                 110

Lys Phe Phe Glu Tyr Thr Leu Lys Gly Glu Ile Ser Pro Gly Lys Ile
        115                 120                 125

Asn Ser Val Glu Gln Asn Asp Met Leu Arg Lys Val Thr Phe Asp Pro
    130                 135                 140

Glu Val Phe Phe Asn Ile Leu Leu Pro Pro Ile Ile Phe His Ala Gly
145                 150                 155                 160

Tyr Ser Leu Lys Lys Arg His Phe Phe Arg Asn Leu Gly Ser Ile Leu
                165                 170                 175

Ala Tyr Ala Phe Leu Gly Thr Ala Xaa Ser Cys Phe Ile Ile Gly Asn
            180                 185                 190

Leu Met Tyr Gly Val Val Lys Leu Met Lys Ile Met Gly Gln Leu Ser
        195                 200                 205

Asp Lys Phe Tyr Tyr Thr Xaa Xaa Leu Phe Phe Gly Ala Ile Ile Ser
    210                 215                 220

Ala Thr Asp Pro Val Thr Val Leu Ala Ile Phe Asn Glu Leu His Ala
225                 230                 235                 240

Asp Val Asp Leu Tyr Ala Leu Leu Phe Gly Glu Ser Val Leu Asn Asp
                245                 250                 255

Ala Val Ala Ile Xaa Leu Xaa Ser Ser Ile Val Ala Tyr Gln Pro Ala
            260                 265                 270

Gly Leu Asn Thr His Ala Phe Asp Ala Ala Ala Phe Phe Lys Ser Val
        275                 280                 285

Gly Ile Phe Leu Gly Ile Phe Ser Gly Ser Phe Thr Met Gly Ala Val
    290                 295                 300

Thr Gly Val Val Thr Ala Xaa Val Thr Lys Phe Thr Lys Xaa His Xaa
305                 310                 315                 320

Phe Pro Leu Leu Glu Thr Ala Leu Phe Phe Leu Met Ser Trp Ser Thr
                325                 330                 335

Phe Leu Leu Ala Glu Ala Cys Gly Phe Thr Gly Val Val Ala Val Leu
            340                 345                 350

Phe Cys Gly Ile Thr Gln Ala His Tyr Thr Tyr Asn Asn Leu Ser Val
        355                 360                 365

Glu Ser Arg Ser Arg Thr Lys Gln Leu Phe Glu Val Leu His Phe Leu
    370                 375                 380

Ala Glu Asn Phe Ile Phe Ser Tyr Met Gly Leu Ala Leu Phe Thr Phe
385                 390                 395                 400

Gln Lys His Val Phe Ser Pro Ile Phe Ile Ile Gly Ala Phe Val Ala
                405                 410                 415

Ile Phe Leu Gly Arg Ala Ala His Ile Tyr Pro Leu Ser Phe Phe Leu
            420                 425                 430

Asn Leu Gly Arg Arg His Lys Ile Gly Trp Asn Phe Gln His Met Met
        435                 440                 445
```

-continued

```
Met Phe Ser Gly Leu Arg Gly Ala Met Ala Phe Ala Leu Ala Ile Arg
    450                 455                 460

Asp Thr Ala Ser Tyr Ala Arg Gln Met Met Phe Thr Thr Thr Leu Leu
465                 470                 475                 480

Ile Val Phe Phe Thr Val Trp Ile Ile Gly Gly Gly Thr Thr Pro Met
                485                 490                 495

Leu Ser Trp Leu Asn Ile Arg Val Gly Val Asp Pro Asp Xaa Asp Pro
            500                 505                 510

Pro Pro Xaa Xaa Asp Ser Phe Ala Phe Xaa Thr Glu Thr Ala
        515                 520                 525


<210> SEQ ID NO 181
<211> LENGTH: 210
<212> TYPE: PRT
<213> ORGANISM: Homo sapiens

<400> SEQUENCE: 181

Asn Gly Lys Ile Ser Pro Tyr Tyr Trp Glu Gln Lys Leu Glu Leu His
  1               5                  10                  15

Arg Gly Gly Gly Arg Ser Arg Thr Ser Gly Ser Pro Gly Leu Gln Glu
             20                  25                  30

Phe Gly Thr Ser Arg Gly Arg Ala Phe Trp Gly Arg Gly Leu Val Arg
         35                  40                  45

Leu Thr Leu Glu Gly Phe Ala Ser Ala Ser Glu Thr Val Arg Ile Leu
     50                  55                  60

Met Thr Met Arg Ser Leu Leu Arg Thr Pro Phe Leu Cys Gly Leu Leu
 65                  70                  75                  80

Trp Ala Phe Cys Ala Pro Gly Ala Arg Ala Glu Glu Pro Ala Ala Ser
                 85                  90                  95

Phe Ser Gln Pro Gly Ser Met Gly Leu Asp Lys Asn Thr Val His Asp
            100                 105                 110

Gln Glu His Ile Met Glu His Leu Glu Gly Val Ile Asn Lys Pro Glu
        115                 120                 125

Ala Glu Met Ser Pro Gln Glu Leu Gln Leu His Tyr Phe Lys Met His
    130                 135                 140

Asp Tyr Asp Gly Asn Asn Leu Leu Asp Gly Leu Glu Leu Ser Thr Ala
145                 150                 155                 160

Ile Thr His Val His Lys Glu Glu Gly Ser Glu Gln Ala Pro Leu Met
                165                 170                 175

Ser Glu Asp Glu Leu Ile Asn Ile Ile Asp Gly Val Leu Arg Asp Asp
            180                 185                 190

Asp Lys Asn Asn Asp Gly Tyr Ile Asp Tyr Ala Glu Phe Ala Lys Ser
        195                 200                 205

Leu Gln
    210


<210> SEQ ID NO 182
<211> LENGTH: 119
<212> TYPE: PRT
<213> ORGANISM: Homo sapiens
<220> FEATURE:
<221> NAME/KEY: SITE
<222> LOCATION: (118)
<223> OTHER INFORMATION: Xaa equals any of the naturally occurring
      L-amino acids

<400> SEQUENCE: 182
```

-continued

```
Met Leu His Asp Met Leu Leu Val Val His Cys Val Leu Ile Gln Ala
  1               5                  10                  15

His Ala Ala Gly Leu Gly Glu Ala Gly Cys Arg Leu Leu Ser Pro Gly
             20                  25                  30

Ala Trp Gly Thr Lys Gly Pro Glu Gln Ala Thr Gln Glu Gly Gly Ser
         35                  40                  45

Glu Gln Gly Ser His Gly His Gln Tyr Pro Tyr Gly Leu Arg Ser Arg
     50                  55                  60

Arg Glu Ala Leu Gln Arg Glu Pro His Gln Pro Pro Ser Pro Lys Arg
 65                  70                  75                  80

Ser Ser Ser Ala Arg Ala Glu Phe Leu Gln Pro Gly Gly Ser Thr Ser
                 85                  90                  95

Ser Arg Ala Ala Ala Thr Ala Val Glu Leu Gln Leu Leu Phe Pro Ile
            100                 105                 110

Val Arg Gly Asp Phe Xaa Val
        115


<210> SEQ ID NO 183
<211> LENGTH: 116
<212> TYPE: PRT
<213> ORGANISM: Homo sapiens

<400> SEQUENCE: 183

Met Thr Pro Ser Arg Cys Ser Met Ile Cys Ser Trp Ser Cys Thr Val
  1               5                  10                  15

Phe Leu Ser Arg Pro Met Leu Pro Gly Trp Glu Lys Leu Ala Ala Gly
             20                  25                  30

Ser Ser Ala Leu Ala Pro Gly Ala Gln Lys Ala Gln Ser Arg Pro His
         35                  40                  45

Arg Lys Gly Val Leu Ser Arg Asp Leu Met Val Ile Asn Ile Leu Thr
     50                  55                  60

Val Ser Glu Ala Asp Ala Lys Pro Ser Asn Val Ser Leu Thr Ser Pro
 65                  70                  75                  80

Arg Pro Gln Asn Ala Leu Pro Arg Leu Val Pro Asn Ser Cys Ser Pro
                 85                  90                  95

Gly Asp Pro Leu Val Leu Glu Arg Pro Pro Pro Arg Trp Ser Ser Ser
            100                 105                 110

Phe Cys Ser Gln
        115


<210> SEQ ID NO 184
<211> LENGTH: 109
<212> TYPE: PRT
<213> ORGANISM: Homo sapiens
<220> FEATURE:
<221> NAME/KEY: SITE
<222> LOCATION: (3)
<223> OTHER INFORMATION: Xaa equals any of the naturally occurring
      L-amino acids

<400> SEQUENCE: 184

Ser Gly Xaa Pro Gly Ser Thr His Ala Ser Ala His Ala Ser Ala Gln
  1               5                  10                  15

Leu Pro Ser Gln Asp Val Lys Ile Cys Leu Leu Thr Met Arg Leu Leu
             20                  25                  30

Val Leu Ser Ser Leu Leu Cys Ile Leu Leu Leu Cys Phe Ser Ile Phe
         35                  40                  45

Ser Thr Glu Gly Lys Arg Arg Pro Ala Lys Ala Trp Ser Gly Arg Arg
```

-continued

```
     50                  55                  60

Thr Arg Leu Cys Cys His Arg Val Pro Ser Pro Asn Ser Thr Asn Leu
 65                  70                  75                  80

Lys Gly His His Val Arg Leu Cys Lys Pro Cys Lys Leu Glu Pro Glu
                 85                  90                  95

Pro Arg Leu Trp Val Val Pro Gly Ala Leu Pro Gln Val
            100                 105


<210> SEQ ID NO 185
<211> LENGTH: 122
<212> TYPE: PRT
<213> ORGANISM: Homo sapiens

<400> SEQUENCE: 185

Met Trp Gly Trp Gly Ser Leu Val Ser Ala Arg Gly Gly Trp Gly Val
  1               5                  10                  15

Phe Ile Tyr Leu Tyr Met Gly Leu Tyr Ile Val Leu Trp Gly Met Gly
            20                  25                  30

Glu Pro Ala Gly Gly Glu Asn Pro Pro Leu Ser Pro His Pro Pro Gly
        35                  40                  45

Arg Ala Asn Val Lys Leu Leu Ile Phe Val Leu Tyr Ile Phe Tyr Ile
     50                  55                  60

Asn Ile Ser Ile Phe Phe Leu Gln Asn Gln Phe Ile Asn Gly Arg Gly
 65                  70                  75                  80

Val Trp Gly Gly His Met Glu Leu Pro Leu Trp Gly Gly Pro Leu His
                 85                  90                  95

Tyr Pro Thr Tyr Arg Pro Phe Pro His Pro Pro Pro His Ser Pro Pro
            100                 105                 110

Pro Gly Cys Asp Cys Cys Lys Met Gly Val
        115                 120


<210> SEQ ID NO 186
<211> LENGTH: 177
<212> TYPE: PRT
<213> ORGANISM: Homo sapiens

<400> SEQUENCE: 186

Gly Thr Arg Tyr Ala Ala Ala Ser Pro Ala Trp Ala Ala Ala Gln Gln
  1               5                  10                  15

Arg Ser His Pro Ala Met Ser Pro Gly Thr Pro Gly Pro Thr Met Gly
            20                  25                  30

Arg Ser Gln Gly Ser Pro Met Asp Pro Met Val Met Lys Arg Pro Gln
        35                  40                  45

Leu Tyr Gly Met Gly Ser Asn Pro His Ser Gln Pro Gln Gln Ser Ser
     50                  55                  60

Pro Tyr Pro Gly Gly Ser Tyr Gly Pro Pro Gly Pro Gln Arg Tyr Pro
 65                  70                  75                  80

Ile Gly Ile Gln Gly Arg Thr Pro Gly Ala Met Ala Gly Met Gln Tyr
                 85                  90                  95

Pro Gln Gln Gln Met Pro Pro Gln Tyr Gly Gln Gln Gly Val Ser Gly
            100                 105                 110

Tyr Cys Gln Gln Gly Gln Gln Pro Tyr Tyr Ser Gln Gln Pro Gln Pro
        115                 120                 125

Pro His Leu Pro Pro Gln Ala Gln Tyr Leu Pro Ser Gln Ser Gln Gln
    130                 135                 140

Arg Tyr Gln Pro Gln Gln Val Ser Thr Val His Cys Pro Ala Gly Pro
```

-continued

```
145                 150                 155                 160

Val Phe Ser Thr Lys Ala Asp Pro Ala Leu Asn His Leu Pro Val Leu
                165                 170                 175

Tyr


<210> SEQ ID NO 187
<211> LENGTH: 132
<212> TYPE: PRT
<213> ORGANISM: Homo sapiens

<400> SEQUENCE: 187

Pro Ser Phe Ser Ala Ser Ala Glu Gln Ser Val Pro Arg Arg Phe Leu
  1               5                  10                  15

Trp Pro Ser Arg Pro Thr Ala Val Ser Asn Trp His Pro Gly Ser Asp
             20                  25                  30

Ser Arg Gly His Gly Arg Asn Ala Val Pro Ser Ala Ala Asp Ala Thr
         35                  40                  45

Ser Val Trp Thr Ala Arg Cys Glu Trp Leu Leu Pro Ala Gly Pro Thr
     50                  55                  60

Ala Ile Leu Gln Pro Ala Ala Ala Ala Pro Ala Pro Pro Thr Pro Gly
 65                  70                  75                  80

Ala Val Ser Ala Val Pro Val Pro Ala Glu Val Pro Ala Ala Ala Gly
                 85                  90                  95

Glu His Ser Ala Leu Pro Arg Arg Pro Cys Phe Leu His Gln Gly Arg
            100                 105                 110

Pro Gly Ser Glu Ser Ser Ser Cys Pro Leu Leu Lys Ile Met Phe Trp
        115                 120                 125

Trp Lys Lys Asn
    130


<210> SEQ ID NO 188
<211> LENGTH: 172
<212> TYPE: PRT
<213> ORGANISM: Homo sapiens

<400> SEQUENCE: 188

Met Ile Gln Ser Arg Val Cys Leu Gly Gly Glu Asn Arg Ala Cys Gly
  1               5                  10                  15

Ala Val His Cys Ala His Leu Leu Arg Leu Val Pro Leu Leu Gly Leu
             20                  25                  30

Gly Arg Gln Ile Leu Arg Leu Gly Trp Glu Val Arg Gly Leu Arg Leu
         35                  40                  45

Leu Ala Val Ile Trp Leu Leu Ala Leu Leu Ala Val Thr Thr His Thr
     50                  55                  60

Leu Leu Ser Ile Leu Arg Trp His Leu Leu Leu Arg Val Leu His Ser
 65                  70                  75                  80

Gly His Gly Pro Gly Ser Pro Thr Leu Asp Ala Asn Trp Ile Pro Leu
                 85                  90                  95

Trp Ala Trp Arg Ala Ile Gly Thr Ser Trp Val Arg Thr Ala Leu Leu
            100                 105                 110

Arg Leu Arg Met Arg Val Thr Ala His Ala Ile Gln Leu Arg Ser Leu
        115                 120                 125

His His His Trp Ile His Trp Ala Ala Leu Gly Ser Ala His Gly Arg
    130                 135                 140

Ser Gly Gly Ala Gly Ala His Arg Arg Val Thr Pro Leu Leu Arg Gly
145                 150                 155                 160
```

-continued

```
Arg Pro Gly Arg Ala Gly Ser Gly Val Pro Arg Ala
                165                 170


<210> SEQ ID NO 189
<211> LENGTH: 132
<212> TYPE: PRT
<213> ORGANISM: Homo sapiens

<400> SEQUENCE: 189

Met Thr Leu Phe Gly Leu Phe Val Ser Leu Val Phe Leu Gly Gln Ala
  1               5                  10                  15

Phe Thr Ile Met Leu Val Tyr Val Trp Ser Arg Arg Asn Pro Tyr Val
             20                  25                  30

Arg Met Asn Phe Phe Gly Leu Leu Asn Phe Gln Ala Pro Phe Leu Pro
         35                  40                  45

Trp Val Leu Met Gly Phe Ser Leu Leu Leu Gly Asn Ser Ile Ile Val
     50                  55                  60

Asp Leu Leu Gly Ile Ala Val Gly His Ile Tyr Phe Phe Leu Glu Asp
 65                  70                  75                  80

Val Phe Pro Asn Gln Pro Gly Gly Ile Arg Ile Leu Lys Thr Pro Ser
                 85                  90                  95

Ile Leu Lys Ala Ile Phe Asp Thr Pro Asp Glu Asp Pro Asn Tyr Asn
            100                 105                 110

Pro Leu Pro Glu Glu Arg Pro Gly Gly Phe Ala Trp Gly Glu Gly Gln
        115                 120                 125

Arg Leu Gly Gly
    130


<210> SEQ ID NO 190
<211> LENGTH: 310
<212> TYPE: PRT
<213> ORGANISM: Homo sapiens

<400> SEQUENCE: 190

Cys Thr Cys Lys Ile Ile Gly Gly Pro Gly Ser Arg Gly Cys Ala Ala
  1               5                  10                  15

Ser Ser Ser Trp Ala Ser Ser Ser Arg Pro Ser Pro Ser Leu Pro Ser
             20                  25                  30

Ala Pro Ser Ser Cys Trp Pro Ser Pro Gly Ile Arg Ala Ser Gln Thr
         35                  40                  45

Pro Pro Ala Thr Thr Ser Pro Ala Ser Gly Ala Ser Phe Pro Ser Ser
     50                  55                  60

Gly Pro Ser Cys Ser Ala Ser Met Pro Thr Ala Thr Gly Leu Thr Leu
 65                  70                  75                  80

Leu Thr Ser Ala Ser Ser Ala Ile Ser Asp Pro Gly Gly Glu Val Ser
                 85                  90                  95

Ala Pro Trp Gly Gly Leu Arg Thr Trp Thr Gln Pro Leu Arg Cys Trp
            100                 105                 110

Glu Arg Leu Leu Pro Pro Pro Gly Asp Pro Arg Thr Val Ala Glu Asn
        115                 120                 125

Thr Gln Gln Asp Glu Cys Gly Leu Pro Gly Ser Cys Pro Ala Arg Pro
    130                 135                 140

Leu Ser Arg Lys Pro Glu Cys Gly Arg Glu Gly Ile Leu Pro Cys Cys
145                 150                 155                 160

Ser Ser Ser Ala Trp Pro Glu Gly Ser Phe Arg Pro Phe Gln Met Asn
                165                 170                 175
```

-continued

```
Leu Phe Ser Phe Leu Ser Phe Phe Phe Leu Phe Phe Phe Phe Leu Arg
            180                 185                 190

Trp Ser Leu Thr Leu Ser Pro Arg Leu Glu Cys Ser Ser Ala Ile Ser
        195                 200                 205

Ala His Cys Asn Leu Arg Leu Pro Gly Ser Ser Asn Ser Pro Ala Leu
    210                 215                 220

Ala Ser Gln Val Ala Gly Ile Thr Gly Ile Cys His His Ala Arg Gln
225                 230                 235                 240

Ile Phe Val Phe Leu Val Glu Thr Gly Phe Cys His Val Gly Gln Ala
                245                 250                 255

Gly Leu Glu Leu Leu Ile Ser Gly Asp Ser Pro Ala Ser Ala Phe Gln
            260                 265                 270

Ser Ala Gly Ile Ile Gly Val Ser His Arg Ala Arg Pro Gly Ser Val
        275                 280                 285

Phe Leu Ala Arg Ser Glu Glu Ser Leu Tyr Leu Arg Pro Gly Gln Gln
    290                 295                 300

Ser Gln Glu Val Lys Val
305                 310


<210> SEQ ID NO 191
<211> LENGTH: 160
<212> TYPE: PRT
<213> ORGANISM: Homo sapiens

<400> SEQUENCE: 191

Met Arg Pro Gly Pro Met Leu Gln Ala Arg Val Ser Ile Pro Ala Ala
  1               5                  10                  15

Leu Gly Thr Leu Phe Pro Arg Pro Gly Trp Ala Pro Gly Glu Val Ser
            20                  25                  30

Ser Glu Ile Ser Ser Arg Asp Leu Leu Asn Pro His Pro Ser Thr Pro
        35                  40                  45

Ser Cys Cys Ser Gln Ser Trp Ser Pro Met Ser Val Leu Glu Pro Asp
     50                  55                  60

Ser Arg Gly Pro Pro Pro Ile Ser Leu Thr His Thr Gly Ile His Thr
 65                  70                  75                  80

Pro Gln Lys Thr Ser Gln Met Arg Pro Asp Ser Gly Ser Arg Gly Met
                85                  90                  95

Cys Phe Cys Pro Cys Lys Gly Phe Gly Glu Gly Gly Asn Ile Val Glu
            100                 105                 110

Ala Gly Lys Ser Pro Gln Thr Cys Ala His Ala Pro Pro Ala Leu Arg
        115                 120                 125

Phe His Ser Ala Phe Ser Glu Gly Pro Cys Cys Thr Gln Thr Thr Gly
    130                 135                 140

Gln Glu Arg Pro Cys Leu Pro Leu Gln Pro Leu Ser Leu Pro Phe Asn
145                 150                 155                 160


<210> SEQ ID NO 192
<211> LENGTH: 161
<212> TYPE: PRT
<213> ORGANISM: Homo sapiens

<400> SEQUENCE: 192

His Ala Ser Ala Leu Ala Leu Gly Pro Pro Gly Ala Ala Ala Pro Trp
  1               5                  10                  15

Pro Arg Pro Gly Cys Ser Ser Ala Ser Ala Pro Pro Thr Pro Ala Ser
            20                  25                  30
```

```
Ala Pro Trp Pro Ala Ser Pro Ser Ser Ser Ser Gly Arg Trp Ser Thr
        35                  40                  45

Asp Ser Arg Gly Pro Arg Leu Met Gly Gly Leu Ala Gly Val Leu Ala
    50                  55                  60

Leu Trp Val Leu Val Thr His Val Met Tyr Met Gln Asp Tyr Trp Arg
65                  70                  75                  80

Thr Trp Leu Lys Gly Leu Arg Gly Phe Phe Phe Val Gly Val Leu Phe
                85                  90                  95

Ser Ala Val Ser Ile Ala Ala Phe Cys Thr Phe Leu Val Leu Ala Ile
            100                 105                 110

Thr Arg His Gln Ser Leu Thr Asp Pro Thr Ser Tyr Tyr Leu Ser Ser
        115                 120                 125

Val Trp Ser Phe Ile Ser Phe Lys Trp Ala Phe Leu Leu Ser Leu Tyr
    130                 135                 140

Ala His Arg Tyr Arg Ala Asp Phe Ala Asp Ile Ser Ile Leu Ser Asp
145                 150                 155                 160

Phe
```

<210> SEQ ID NO 193
<211> LENGTH: 239
<212> TYPE: PRT
<213> ORGANISM: Homo sapiens

<400> SEQUENCE: 193

```
Met Pro Thr Ala Thr Gly Leu Thr Leu Leu Thr Ser Ala Ser Ser Ala
  1               5                  10                  15

Ile Ser Asp Pro Gly Gly Glu Val Ser Ala Pro Trp Gly Gly Leu Arg
            20                  25                  30

Thr Trp Thr Gln Pro Leu Arg Cys Trp Glu Arg Leu Leu Pro Pro Pro
        35                  40                  45

Gly Asp Pro Arg Thr Val Ala Glu Asn Thr Gln Gln Asp Glu Cys Gly
    50                  55                  60

Leu Pro Gly Ser Cys Pro Ala Arg Pro Leu Ser Arg Lys Pro Glu Cys
65                  70                  75                  80

Gly Arg Glu Gly Ile Leu Pro Cys Cys Ser Ser Ser Ala Trp Pro Glu
                85                  90                  95

Gly Ser Phe Arg Pro Phe Gln Met Asn Leu Phe Ser Phe Leu Ser Phe
            100                 105                 110

Phe Phe Leu Phe Phe Phe Phe Leu Arg Trp Ser Leu Thr Leu Ser Pro
        115                 120                 125

Arg Leu Glu Cys Ser Ser Ala Ile Ser Ala His Cys Asn Leu Arg Leu
    130                 135                 140

Pro Gly Ser Ser Asn Ser Pro Ala Leu Ala Ser Gln Val Ala Gly Ile
145                 150                 155                 160

Thr Gly Ile Cys His His Ala Arg Gln Ile Phe Val Phe Leu Val Glu
                165                 170                 175

Thr Gly Phe Cys His Val Gly Gln Ala Gly Leu Glu Leu Leu Ile Ser
            180                 185                 190

Gly Asp Ser Pro Ala Ser Ala Phe Gln Ser Ala Gly Ile Ile Gly Val
        195                 200                 205

Ser His Arg Ala Arg Pro Gly Ser Val Phe Leu Ala Arg Ser Glu Glu
    210                 215                 220

Ser Leu Tyr Leu Arg Pro Gly Gln Gln Ser Gln Glu Val Lys Val
225                 230                 235
```

-continued

<210> SEQ ID NO 194
<211> LENGTH: 135
<212> TYPE: PRT
<213> ORGANISM: Homo sapiens

<400> SEQUENCE: 194

```
Met Ala Pro Ser Arg Leu Gln Leu Gly Leu Arg Ala Ala Tyr Ser Gly
  1               5                  10                  15

Ile Ser Ser Val Ala Gly Phe Ser Ile Phe Leu Val Trp Thr Val Val
             20                  25                  30

Tyr Arg Gln Pro Gly Thr Ala Ala His Gly Arg Ala Arg Arg Gly Ala
         35                  40                  45

Gly Thr Val Gly Pro Gly Asp Ala Arg Asn Val His Ala Arg Leu Leu
     50                  55                  60

Glu Asp Leu Ala Gln Gly Ala Ala Arg Leu Leu Leu Arg Gly Arg Pro
 65                  70                  75                  80

Leu Leu Gly Arg Leu His Arg Cys Leu Leu His Leu Pro Arg Ala Gly
                 85                  90                  95

His His Pro Ala Ser Glu Pro His Arg Pro His Gln Leu Leu Pro Leu
            100                 105                 110

Gln Arg Leu Glu Leu His Phe Leu Gln Val Gly Leu Pro Ala Gln Pro
        115                 120                 125

Leu Cys Pro Pro Leu Pro Gly
    130                 135
```

<210> SEQ ID NO 195
<211> LENGTH: 326
<212> TYPE: PRT
<213> ORGANISM: Homo sapiens

<400> SEQUENCE: 195

```
Pro Arg Val Arg Gly Lys Gly Lys Lys Ile Phe Ile His Met His Glu
  1               5                  10                  15

Ile Ile Gln Ile Asp Gly His Ile Tyr Gln Cys Leu Glu Cys Lys Gln
             20                  25                  30

Asn Phe Cys Glu Asn Leu Ala Leu Ile Met Cys Gln Arg Thr His Thr
         35                  40                  45

Gly Glu Lys Pro Tyr Lys Cys Asp Met Cys Glu Lys Thr Phe Val Gln
     50                  55                  60

Ser Ser Asp Leu Thr Ser His Gln Arg Ile His Asn Tyr Glu Lys Pro
 65                  70                  75                  80

Tyr Lys Cys Ser Lys Cys Glu Lys Ser Phe Trp His His Leu Ala Leu
                 85                  90                  95

Ser Gly His Gln Arg Thr His Ala Gly Lys Lys Phe Tyr Thr Cys Asp
            100                 105                 110

Ile Cys Gly Lys Asn Phe Gly Gln Ser Ser Asp Leu Leu Val His Gln
        115                 120                 125

Arg Ser His Thr Gly Glu Lys Pro Tyr Leu Cys Ser Glu Cys Asp Lys
    130                 135                 140

Cys Phe Ser Arg Ser Thr Asn Leu Ile Arg His Arg Arg Thr His Thr
145                 150                 155                 160

Gly Glu Lys Pro Phe Lys Cys Leu Asp Val Lys Lys Leu Leu Val Gly
                165                 170                 175

Asn Gln Ile Leu Leu Ala Thr Arg Glu Leu Thr Leu Gly Lys Gly Pro
            180                 185                 190
```

-continued

```
Thr Asn Val Ile Ser Val Arg Lys Val Thr Asp Thr Val Gln Pro Ser
        195                 200                 205

Leu Tyr Ile Lys Glu Phe Ile Leu Gly Arg Ser Pro Ile Ser Val Glu
    210                 215                 220

Pro Val Lys Asn Ala Leu Ala Arg Asn Gln Thr Leu Ser Val His Gln
225                 230                 235                 240

Arg Val His Thr Gly Glu Lys Pro Tyr Lys Cys Leu Glu Cys Met Arg
                245                 250                 255

Ser Phe Thr Arg Ser Ala Asn Leu Ile Arg His Gln Ala Thr His Thr
            260                 265                 270

His Thr Phe Lys Cys Leu Glu Tyr Glu Lys Ser Phe Asn Cys Ser Ser
        275                 280                 285

Arg Ser Asn Cys Thr Ser Val Glu Phe Thr Trp Lys Arg Thr Pro Thr
    290                 295                 300

Ser Val Val Trp Arg Leu Glu Ser Gly Phe Leu Leu Arg Asn Gly Leu
305                 310                 315                 320

Cys Cys Pro Thr Arg Lys
                325


<210> SEQ ID NO 196
<211> LENGTH: 313
<212> TYPE: PRT
<213> ORGANISM: Homo sapiens

<400> SEQUENCE: 196

Met His Glu Ile Ile Gln Ile Asp Gly His Ile Tyr Gln Cys Leu Glu
  1               5                  10                  15

Cys Lys Gln Asn Phe Cys Glu Asn Leu Ala Leu Ile Met Cys Gln Arg
            20                  25                  30

Thr His Thr Gly Glu Lys Pro Tyr Lys Cys Asp Met Cys Glu Lys Thr
        35                  40                  45

Phe Val Gln Ser Ser Asp Leu Thr Ser His Gln Arg Ile His Asn Tyr
    50                  55                  60

Glu Lys Pro Tyr Lys Cys Ser Lys Cys Glu Lys Ser Phe Trp His His
 65                  70                  75                  80

Leu Ala Leu Ser Gly His Gln Arg Thr His Ala Gly Lys Lys Phe Tyr
                85                  90                  95

Thr Cys Asp Ile Cys Gly Lys Asn Phe Gly Gln Ser Ser Asp Leu Leu
            100                 105                 110

Val His Gln Arg Ser His Thr Gly Glu Lys Pro Tyr Leu Cys Ser Glu
        115                 120                 125

Cys Asp Lys Cys Phe Ser Arg Ser Thr Asn Leu Ile Arg His Arg Arg
    130                 135                 140

Thr His Thr Gly Glu Lys Pro Phe Lys Cys Leu Glu Cys Glu Lys Ala
145                 150                 155                 160

Phe Ser Gly Lys Ser Asp Leu Ile Ser His Gln Arg Thr His Thr Gly
                165                 170                 175

Glu Arg Pro Tyr Lys Cys Asn Lys Cys Glu Lys Ser Tyr Arg His Arg
            180                 185                 190

Ser Ala Phe Ile Val His Lys Arg Val His Thr Gly Glu Lys Pro Tyr
        195                 200                 205

Lys Cys Gly Ala Cys Glu Lys Cys Phe Gly Gln Lys Ser Asp Leu Ile
    210                 215                 220

Val His Gln Arg Val His Thr Gly Glu Lys Pro Tyr Lys Cys Leu Glu
```

-continued

```
225                 230                 235                 240

Cys Met Arg Ser Phe Thr Arg Ser Ala Asn Leu Ile Arg His Gln Ala
                245                 250                 255

Thr His Thr His Thr Phe Lys Cys Leu Glu Tyr Glu Lys Ser Phe Asn
            260                 265                 270

Cys Ser Ser Arg Ser Asn Cys Thr Ser Val Glu Phe Thr Trp Lys Lys
        275                 280                 285

Thr Pro Thr Ser Val Val Trp Arg Leu Glu Ser Gly Phe Leu Leu Arg
    290                 295                 300

Asn Gly Leu Cys Cys Pro Thr Arg Lys
305                 310


<210> SEQ ID NO 197
<211> LENGTH: 60
<212> TYPE: PRT
<213> ORGANISM: Homo sapiens

<400> SEQUENCE: 197

Gly Thr Arg Glu Arg Gly Leu Arg Thr Pro Gln Met Val Leu Val Phe
  1               5                  10                  15

Ala Tyr Leu Cys Val Leu Leu Ile Val Cys Trp Val Thr Ser Lys Thr
             20                  25                  30

Ser Leu Ala Leu Lys Tyr Thr Val Tyr Lys Asn Phe Lys Arg Leu Ile
         35                  40                  45

Trp Asn Lys Ser Ile Leu Ile Ile Thr Leu Thr Pro
     50                  55                  60


<210> SEQ ID NO 198
<211> LENGTH: 142
<212> TYPE: PRT
<213> ORGANISM: Homo sapiens

<400> SEQUENCE: 198

Met His Gln Leu Leu Gln Leu Gln Arg Gln Glu Pro Cys Arg Leu Leu
  1               5                  10                  15

Ser Pro Ser Pro Gln Pro Gly Leu His His Leu Cys Phe Gln Gln Ile
             20                  25                  30

Glu Leu Leu Leu Leu Leu Leu His Leu Gln Trp Gly Leu Gly Leu Leu
         35                  40                  45

Arg Gln Leu His His Lys Arg Leu Ala Gln Leu Leu Leu His Arg Arg
     50                  55                  60

Arg Asp His Pro Ile Pro Pro Ile Gln Asp Ile Leu Gly Ile Ala Lys
 65                  70                  75                  80

Cys Pro Cys Pro Trp Ala Ile Ile Leu Met Arg Met Ala Ser Ile Ile
                 85                  90                  95

Cys His Ile His Gln Cys Ile Thr Arg Val Leu Asp Arg Leu Arg Thr
            100                 105                 110

Arg Asp Pro Ser Ser Leu His Thr Pro Ser Leu Ser Pro His Ser Ser
        115                 120                 125

Leu Thr Ile His Ser Ser Asn Met Ser Ala Gln Gln Leu Ser
    130                 135                 140


<210> SEQ ID NO 199
<211> LENGTH: 921
<212> TYPE: PRT
<213> ORGANISM: Homo sapiens
<220> FEATURE:
<221> NAME/KEY: SITE
```

-continued

```
<222> LOCATION: (247)
<223> OTHER INFORMATION: Xaa equals any of the naturally occurring
      L-amino acids
<221> NAME/KEY: SITE
<222> LOCATION: (362)
<223> OTHER INFORMATION: Xaa equals any of the naturally occurring
      L-amino acids
<221> NAME/KEY: SITE
<222> LOCATION: (603)
<223> OTHER INFORMATION: Xaa equals any of the naturally occurring
      L-amino acids

<400> SEQUENCE: 199

Val Gly Ala Pro Gly Lys Leu Pro Asp Pro Glu Arg Arg Arg Ser Ala
  1               5                  10                  15

Ser Leu Ser Ala Ser Gln Ser Ala Ser Pro Pro Ala Gln Tyr Leu Ser
            20                  25                  30

Leu Leu Gly Pro Arg Lys Leu Ser Ala Val Cys Leu Ala Arg Thr Ala
        35                  40                  45

Ala Glu Ala Leu Ile Met Ala Thr Phe Ile Ser Val Gln Leu Lys Lys
     50                  55                  60

Thr Ser Glu Val Asp Leu Ala Lys Pro Leu Val Lys Phe Ile Gln Gln
 65                  70                  75                  80

Thr Tyr Pro Ser Gly Gly Glu Glu Gln Ala Gln Tyr Cys Arg Ala Ala
                 85                  90                  95

Glu Glu Leu Ser Lys Leu Arg Arg Ala Ala Val Gly Arg Pro Leu Asp
            100                 105                 110

Lys His Glu Gly Ala Leu Glu Thr Leu Leu Arg Tyr Tyr Asp Gln Ile
        115                 120                 125

Cys Ser Ile Glu Pro Lys Phe Pro Phe Ser Glu Asn Gln Ile Cys Leu
    130                 135                 140

Thr Phe Thr Trp Lys Asp Ala Phe Asp Lys Gly Ser Leu Phe Gly Gly
145                 150                 155                 160

Ser Val Lys Leu Ala Leu Ala Ser Leu Gly Tyr Glu Lys Ser Cys Val
                165                 170                 175

Leu Phe Asn Cys Ala Ala Leu Ala Ser Gln Ile Ala Ala Glu Gln Asn
            180                 185                 190

Leu Asp Asn Asp Glu Gly Leu Lys Ile Ala Ala Lys His Tyr Gln Phe
        195                 200                 205

Ala Ser Gly Ala Phe Leu His Ile Lys Glu Thr Val Leu Ser Ala Leu
    210                 215                 220

Ser Arg Glu Pro Thr Val Asp Ile Ser Pro Asp Thr Val Gly Thr Leu
225                 230                 235                 240

Ser Leu Ile Met Leu Ala Xaa Ala Gln Glu Val Phe Phe Leu Lys Ala
                245                 250                 255

Thr Arg Asp Lys Met Lys Asp Ala Ile Ile Ala Lys Leu Ala Asn Gln
            260                 265                 270

Ala Ala Asp Tyr Phe Gly Asp Ala Phe Lys Gln Cys Gln Tyr Lys Asp
        275                 280                 285

Thr Leu Pro Lys Glu Val Phe Pro Val Leu Ala Ala Lys His Cys Ile
    290                 295                 300

Met Gln Ala Asn Ala Glu Tyr His Gln Ser Ile Leu Ala Lys Gln Gln
305                 310                 315                 320

Lys Lys Phe Gly Glu Glu Ile Ala Arg Leu Gln His Ala Ala Glu Leu
                325                 330                 335

Ile Lys Thr Val Ala Ser Arg Tyr Asp Glu Tyr Val Asn Val Lys Asp
            340                 345                 350
```

-continued

```
Phe Ser Asp Lys Ile Asn Arg Ala Leu Xaa Ala Ala Lys Lys Asp Asn
        355                 360                 365

Asp Phe Ile Tyr His Asp Arg Val Pro Asp Leu Lys Asp Leu Asp Pro
    370                 375                 380

Ile Gly Lys Ala Thr Leu Val Lys Ser Thr Pro Val Asn Val Pro Ile
385                 390                 395                 400

Ser Gln Lys Phe Thr Asp Leu Phe Glu Lys Met Val Pro Val Ser Val
                405                 410                 415

Gln Gln Ser Leu Ala Ala Tyr Asn Gln Arg Lys Ala Asp Leu Val Asn
            420                 425                 430

Arg Ser Ile Ala Gln Met Arg Glu Ala Thr Thr Leu Ala Asn Gly Val
        435                 440                 445

Leu Ala Ser Leu Asn Leu Pro Ala Ala Ile Glu Asp Val Ser Gly Asp
    450                 455                 460

Thr Val Pro Gln Ser Ile Leu Thr Lys Ser Arg Ser Val Ile Glu Gln
465                 470                 475                 480

Gly Gly Ile Gln Thr Val Asp Gln Leu Ile Lys Glu Leu Pro Glu Leu
                485                 490                 495

Leu Gln Arg Asn Arg Glu Ile Leu Asp Glu Ser Leu Arg Leu Leu Asp
            500                 505                 510

Glu Glu Glu Ala Thr Asp Asn Asp Leu Arg Ala Lys Phe Lys Glu Arg
        515                 520                 525

Trp Gln Arg Thr Pro Ser Asn Glu Leu Tyr Lys Pro Leu Arg Ala Glu
    530                 535                 540

Gly Thr Asn Phe Arg Thr Val Leu Asp Lys Ala Val Gln Ala Asp Gly
545                 550                 555                 560

Gln Val Lys Glu Cys Tyr Gln Ser His Arg Asp Thr Ile Val Leu Leu
                565                 570                 575

Cys Lys Pro Glu Pro Glu Leu Asn Ala Ala Ile Pro Ser Ala Asn Pro
            580                 585                 590

Ala Lys Thr Met Gln Gly Ser Glu Val Val Xaa Val Leu Lys Ser Leu
        595                 600                 605

Leu Ser Asn Leu Asp Glu Val Lys Lys Glu Arg Glu Gly Leu Glu Asn
    610                 615                 620

Asp Leu Lys Ser Val Asn Phe Asp Met Thr Ser Lys Phe Leu Thr Ala
625                 630                 635                 640

Leu Ala Gln Asp Gly Val Ile Asn Glu Glu Ala Leu Ser Val Thr Glu
                645                 650                 655

Leu Asp Arg Val Tyr Gly Gly Leu Thr Thr Lys Val Gln Glu Ser Leu
            660                 665                 670

Lys Lys Gln Glu Gly Leu Leu Lys Asn Ile Gln Val Ser His Gln Glu
        675                 680                 685

Phe Ser Lys Met Lys Gln Ser Asn Asn Glu Ala Asn Leu Arg Glu Glu
    690                 695                 700

Val Leu Lys Asn Leu Ala Thr Ala Tyr Asp Asn Phe Val Glu Leu Val
705                 710                 715                 720

Ala Asn Leu Lys Glu Gly Thr Lys Phe Tyr Asn Glu Leu Thr Glu Ile
                725                 730                 735

Leu Val Arg Phe Gln Asn Lys Cys Ser Asp Ile Val Phe Ala Arg Lys
            740                 745                 750

Thr Glu Arg Asp Glu Leu Leu Lys Asp Leu Gln Gln Ser Ile Ala Arg
        755                 760                 765
```

-continued

```
Glu Pro Ser Ala Pro Ser Ile Pro Thr Pro Ala Tyr Gln Ser Leu Pro
    770                 775                 780

Ala Gly Gly His Ala Pro Thr Pro Pro Thr Pro Ala Pro Arg Thr Met
785                 790                 795                 800

Pro Pro Thr Lys Pro Gln Pro Pro Ala Arg Pro Pro Pro Pro Val Leu
                805                 810                 815

Pro Ala Asn Arg Ala Pro Ser Ala Thr Ala Pro Ser Pro Val Gly Ala
            820                 825                 830

Gly Thr Ala Ala Pro Ala Pro Ser Gln Thr Pro Gly Ser Ala Pro Pro
        835                 840                 845

Pro Gln Ala Gln Gly Pro Pro Tyr Pro Thr Tyr Pro Gly Tyr Pro Gly
    850                 855                 860

Tyr Cys Gln Met Pro Met Pro Met Gly Tyr Asn Pro Tyr Ala Tyr Gly
865                 870                 875                 880

Gln Tyr Asn Met Pro Tyr Pro Pro Val Tyr His Gln Ser Pro Gly Gln
                885                 890                 895

Ala Pro Tyr Pro Gly Pro Gln Gln Pro Ser Tyr Pro Phe Pro Gln Pro
            900                 905                 910

Pro Gln Gln Ser Tyr Tyr Pro Gln Gln
        915                 920


<210> SEQ ID NO 200
<211> LENGTH: 91
<212> TYPE: PRT
<213> ORGANISM: Homo sapiens

<400> SEQUENCE: 200

Val Ala Val Ser Asn Asn Ser Gln Ala Gln Val Thr Trp Asn Leu Gly
  1               5                  10                  15

Ala Ala Leu Cys Ser Gly Ser Gln Trp Leu Pro Glu Arg Ala Ser Ala
             20                  25                  30

Lys Cys Glu Met Arg Gly His Ile Thr Thr Leu Leu Thr Thr Ser Phe
         35                  40                  45

Leu Val Phe Gly Leu His Ile Ile Phe Phe Leu Asn Ile Ser Cys Phe
     50                  55                  60

Asn Phe Arg Val Phe Ile Leu Phe Glu Thr Arg Pro Glu Asp Ser Arg
 65                  70                  75                  80

Leu Tyr Arg Glu Arg Pro Val Leu Pro Arg Tyr
                 85                  90


<210> SEQ ID NO 201
<211> LENGTH: 123
<212> TYPE: PRT
<213> ORGANISM: Homo sapiens

<400> SEQUENCE: 201

Ala Ile Arg Pro Thr Glu Glu Gly Gly Leu His Val His Met Glu Phe
  1               5                  10                  15

Pro Gly Ala Asp Gly Cys Asn Gln Val Asp Ala Glu Tyr Leu Lys Val
             20                  25                  30

Gly Ser Glu Gly His Phe Arg Val Pro Ala Leu Gly Tyr Leu Asp Val
         35                  40                  45

Arg Ile Val Asp Thr Asp Tyr Ser Ser Phe Ala Val Leu Tyr Ile Tyr
     50                  55                  60

Lys Glu Leu Glu Gly Ala Leu Ser Thr Met Val Gln Leu Tyr Ser Arg
 65                  70                  75                  80
```

-continued

```
Thr Gln Asp Val Ser Pro Gln Ala Leu Lys Ala Phe Gln Asp Phe Tyr
                 85                  90                  95

Pro Thr Leu Gly Leu Pro Glu Asp Met Met Val Met Leu Pro Gln Ser
            100                 105                 110

Asp Ala Cys Asn Pro Glu Ser Lys Glu Ala Pro
        115                 120


<210> SEQ ID NO 202
<211> LENGTH: 183
<212> TYPE: PRT
<213> ORGANISM: Homo sapiens

<400> SEQUENCE: 202

Met Lys Gly Leu Val Leu Ser Phe Ala Leu Val Ala Leu Ser Ala Leu
  1               5                  10                  15

Cys Val Tyr Gly Asp Val Pro Ile Gln Pro Asp Phe Gln Glu Asp Lys
             20                  25                  30

Ile Leu Gly Lys Trp Tyr Gly Ile Gly Leu Ala Ser Asn Ser Asn Trp
         35                  40                  45

Phe Gln Ser Lys Lys Gln Gln Leu Lys Met Cys Thr Thr Val Ile Thr
     50                  55                  60

Pro Thr Ala Asp Gly Asn Leu Asp Val Val Ala Thr Phe Pro Lys Leu
 65                  70                  75                  80

Asp Arg Cys Glu Lys Lys Ser Met Thr Tyr Ile Lys Thr Glu Gln Pro
                 85                  90                  95

Gly Arg Phe Leu Ser Lys Ser Pro Arg Tyr Gly Ser Asp His Val Ile
            100                 105                 110

Arg Val Val Glu Ser Asn Tyr Asp Glu Tyr Thr Leu Met His Thr Ile
        115                 120                 125

Lys Thr Lys Gly Asn Glu Val Asn Thr Ile Val Ser Leu Phe Gly Arg
    130                 135                 140

Arg Lys Thr Leu Ser Pro Glu Leu Leu Asp Lys Phe Gln Gln Phe Ala
145                 150                 155                 160

Lys Glu Gln Gly Leu Thr Asp Asp Asn Ile Leu Ile Leu Pro Gln Thr
                165                 170                 175

Asp Ser Cys Met Ser Glu Val
            180


<210> SEQ ID NO 203
<211> LENGTH: 184
<212> TYPE: PRT
<213> ORGANISM: Homo sapiens

<400> SEQUENCE: 203

Met Met Arg Ile Leu Leu Ala Leu Ser Leu Gly Val Ala Cys Cys Ser
  1               5                  10                  15

Leu Trp Val Gly Ala Glu Val Gln Val Gln Pro Asp Phe Gln Lys Glu
             20                  25                  30

Lys Val Leu Gly Lys Trp Tyr Gly Ile Gly Leu Ala Ser Asn Ser Asn
         35                  40                  45

Trp Phe Lys Asp Arg Lys Ser His Met Lys Met Cys Thr Thr Ile Ile
     50                  55                  60

Thr Pro Thr Ala Asp Gly Asn Val Glu Val Thr Ala Thr Tyr Pro Lys
 65                  70                  75                  80

Met Asp Arg Cys Glu Thr Lys Ser Met Thr Tyr Phe Lys Thr Glu Gln
                 85                  90                  95
```

-continued

```
Leu Gly Arg Phe Arg Ala Lys Ser Pro Arg Tyr Gly Ser Glu His Asp
            100                 105                 110

Met Arg Val Val Glu Thr Asn Tyr Asp Glu Tyr Ile Leu Met Tyr Thr
        115                 120                 125

Val Lys Thr Lys Gly Ser Glu Thr Asn Gln Ile Val Ser Leu Phe Gly
    130                 135                 140

Arg Asp Lys Asp Leu Arg Pro Glu Leu Leu Asp Lys Phe Gln Asn Phe
145                 150                 155                 160

Ala Lys Ser Gln Gly Leu Ala Asp Asp Asn Ile Ile Ile Leu Pro His
                165                 170                 175

Thr Asp Gln Cys Met Thr Glu Ala
            180


<210> SEQ ID NO 204
<211> LENGTH: 184
<212> TYPE: PRT
<213> ORGANISM: Homo sapiens

<400> SEQUENCE: 204

Met Met Arg Ile Leu Leu Ala Leu Ser Leu Gly Val Ala Cys Cys Ser
  1               5                  10                  15

Leu Trp Val Gly Ala Glu Val Gln Val Gln Pro Asp Phe Gln Lys Glu
            20                  25                  30

Lys Val Leu Gly Lys Trp Tyr Gly Ile Gly Leu Ala Ser Asn Ser Asn
        35                  40                  45

Trp Phe Lys Asp Arg Lys Ser His Met Lys Met Cys Thr Thr Ile Ile
     50                  55                  60

Thr Pro Thr Ala Asp Gly Asn Leu Glu Val Thr Ala Thr Tyr Pro Lys
 65                  70                  75                  80

Met Asp Arg Cys Glu Thr Lys Ser Met Thr Tyr Phe Lys Thr Glu Gln
                 85                  90                  95

Leu Gly Gly Phe Arg Ala Lys Ser Pro Arg Tyr Gly Ser Glu His Asp
            100                 105                 110

Met Arg Val Val Glu Thr Asn Tyr Asp Glu Tyr Ile Leu Met Tyr Thr
        115                 120                 125

Val Lys Thr Lys Gly Ser Glu Thr Asn Gln Ile Val Ser Leu Phe Gly
    130                 135                 140

Arg Asp Lys Asp Leu Arg Pro Glu Leu Leu Asp Lys Phe Gln Asn Phe
145                 150                 155                 160

Ala Lys Ser Gln Gly Leu Ala Asp Asp Asn Ile Ile Ile Leu Pro His
                165                 170                 175

Thr Asp Gln Cys Met Thr Glu Ala
            180


<210> SEQ ID NO 205
<211> LENGTH: 224
<212> TYPE: PRT
<213> ORGANISM: Homo sapiens

<400> SEQUENCE: 205

Pro Arg Val Arg Asn Arg Lys Arg Arg Leu Ser Ala Val Pro Ala Gly
  1               5                  10                  15

Gly Gly Glu Ala Ala Val Gly Ser Leu Gly Cys Val Ser Pro Val Met
            20                  25                  30

Glu Pro Gly Pro Thr Ala Ala Gln Arg Arg Cys Ser Leu Pro Pro Trp
        35                  40                  45
```

-continued

```
Leu Pro Leu Gly Leu Leu Leu Trp Ser Gly Leu Ala Leu Gly Ala Leu
     50                  55                  60

Pro Phe Gly Ser Ser Pro His Arg Val Phe His Asp Leu Leu Ser Glu
 65                  70                  75                  80

Gln Gln Leu Leu Glu Val Glu Asp Leu Ser Leu Ser Leu Leu Gln Gly
                 85                  90                  95

Gly Gly Leu Gly Pro Leu Ser Leu Pro Pro Asp Leu Pro Asp Leu Asp
            100                 105                 110

Pro Glu Cys Arg Glu Leu Leu Leu Asp Phe Ala Asn Ser Ser Ala Glu
        115                 120                 125

Leu Thr Gly Cys Leu Val Arg Ser Ala Arg Pro Val Arg Leu Cys Gln
    130                 135                 140

Thr Cys Tyr Pro Leu Phe Gln Gln Val Val Ser Lys Met Asp Asn Ile
145                 150                 155                 160

Ser Arg Ala Ala Gly Asn Thr Ser Glu Ser Gln Ser Cys Ala Arg Ser
                165                 170                 175

Leu Leu Met Ala Asp Arg Met Gln Ile Val Val Ile Leu Ser Glu Phe
            180                 185                 190

Phe Asn Thr Thr Trp Gln Glu Ala Asn Cys Ala Asn Cys Leu Thr Asn
        195                 200                 205

Asn Ser Glu Glu Leu Ser Asn Ser Thr Val Tyr Phe Leu Lys Ser Ile
    210                 215                 220


<210> SEQ ID NO 206
<211> LENGTH: 382
<212> TYPE: PRT
<213> ORGANISM: Homo sapiens

<400> SEQUENCE: 206

Met Phe Leu Lys Ala Val Val Leu Ser Leu Ala Leu Val Ala Val Thr
  1               5                  10                  15

Gly Ala Arg Ala Glu Val Asn Ala Asp Gln Val Ala Thr Val Met Trp
            20                  25                  30

Asp Tyr Phe Ser Gln Leu Gly Ser Asn Ala Lys Lys Ala Val Glu His
        35                  40                  45

Leu Gln Lys Ser Glu Leu Thr Gln Gln Leu Asn Thr Leu Phe Gln Asp
    50                  55                  60

Lys Leu Gly Glu Val Asn Thr Tyr Thr Glu Asp Leu Gln Lys Lys Leu
 65                  70                  75                  80

Val Pro Phe Ala Thr Glu Leu His Glu Arg Leu Thr Lys Asp Ser Glu
                 85                  90                  95

Lys Leu Lys Glu Glu Ile Arg Arg Glu Leu Glu Glu Leu Arg Ala Arg
            100                 105                 110

Leu Leu Pro His Ala Thr Glu Val Ser Gln Lys Ile Gly Asp Asn Val
        115                 120                 125

Arg Glu Leu Gln Gln Arg Leu Gly Pro Phe Thr Gly Gly Leu Arg Thr
    130                 135                 140

Gln Val Asn Thr Gln Val Gln Gln Leu Gln Arg Gln Leu Lys Pro Tyr
145                 150                 155                 160

Ala Glu Arg Met Glu Ser Val Leu Arg Gln Asn Ile Arg Asn Leu Glu
                165                 170                 175

Ala Ser Val Ala Pro Tyr Ala Asp Glu Phe Lys Ala Lys Ile Asp Gln
            180                 185                 190

Asn Val Glu Glu Leu Lys Gly Ser Leu Thr Pro Tyr Ala Glu Glu Leu
        195                 200                 205
```

-continued

```
Lys Ala Lys Ile Asp Gln Asn Val Glu Glu Leu Arg Arg Ser Leu Ala
    210                 215                 220

Pro Tyr Ala Gln Asp Val Gln Glu Lys Leu Asn His Gln Leu Glu Gly
225                 230                 235                 240

Leu Ala Phe Gln Met Lys Lys Gln Ala Glu Glu Leu Lys Ala Lys Ile
                245                 250                 255

Ser Ala Asn Ala Asp Glu Leu Arg Gln Lys Leu Val Pro Val Ala Glu
            260                 265                 270

Asn Val His Gly His Leu Lys Gly Asn Thr Glu Gly Leu Gln Lys Ser
        275                 280                 285

Leu Leu Glu Leu Arg Ser His Leu Asp Gln Gln Val Glu Glu Phe Arg
    290                 295                 300

Leu Lys Val Glu Pro Tyr Gly Glu Thr Phe Asn Lys Ala Leu Val Gln
305                 310                 315                 320

Gln Val Glu Asp Leu Arg Gln Lys Leu Gly Pro Leu Ala Gly Asp Val
                325                 330                 335

Glu Gly His Leu Ser Phe Leu Glu Lys Asp Leu Arg Asp Lys Val Asn
            340                 345                 350

Thr Phe Phe Ser Thr Leu Lys Glu Glu Ala Ser Gln Gly Gln Ser Gln
        355                 360                 365

Ala Leu Pro Ala Gln Glu Lys Ala Gln Ala Pro Leu Glu Gly
    370                 375                 380


<210> SEQ ID NO 207
<211> LENGTH: 396
<212> TYPE: PRT
<213> ORGANISM: Homo sapiens

<400> SEQUENCE: 207

Met Phe Leu Lys Ala Val Val Leu Thr Leu Ala Leu Val Ala Val Ala
  1               5                  10                  15

Gly Ala Arg Ala Glu Val Ser Ala Asp Gln Val Ala Thr Val Met Trp
             20                  25                  30

Asp Tyr Phe Ser Gln Leu Ser Asn Asn Ala Lys Glu Ala Val Glu His
         35                  40                  45

Leu Gln Lys Ser Glu Leu Thr Gln Gln Leu Asn Ala Leu Phe Gln Asp
     50                  55                  60

Lys Leu Gly Glu Val Asn Thr Tyr Ala Gly Asp Leu Gln Lys Lys Leu
 65                  70                  75                  80

Val Pro Phe Ala Thr Glu Leu His Glu Arg Leu Ala Lys Asp Ser Glu
                 85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Asp Pro Leu
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
```

-continued

```
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
    370                 375                 380

Gln Glu Gln Val Gln Met Leu Ala Pro Leu Glu Ser
385                 390                 395


<210> SEQ ID NO 208
<211> LENGTH: 391
<212> TYPE: PRT
<213> ORGANISM: Homo sapiens

<400> SEQUENCE: 208

Met Phe Leu Lys Ala Ala Val Leu Thr Leu Ala Leu Val Ala Ile Thr
  1               5                  10                  15

Gly Thr Arg Ala Glu Val Thr Ser Asp Gln Val Ala Asn Val Val Trp
            20                  25                  30

Asp Tyr Phe Thr Gln Leu Ser Asn Asn Ala Lys Glu Ala Val Glu Gln
        35                  40                  45

Phe Gln Lys Thr Asp Val Thr Gln Gln Leu Ser Thr Leu Phe Gln Asp
     50                  55                  60

Lys Leu Gly Asp Ala Ser Thr Tyr Ala Asp Gly Val His Asn Lys Leu
 65                  70                  75                  80

Val Pro Phe Val Val Gln Leu Ser Gly His Leu Ala Lys Glu Thr Glu
                85                  90                  95

Arg Val Lys Glu Glu Ile Lys Lys Glu Leu Glu Asp Leu Arg Asp Arg
            100                 105                 110

Met Met Pro His Ala Asn Lys Val Thr Gln Thr Phe Gly Glu Asn Met
        115                 120                 125

Gln Lys Leu Gln Glu His Leu Lys Pro Tyr Ala Val Asp Leu Gln Asp
    130                 135                 140

Gln Ile Asn Thr Gln Thr Gln Glu Met Lys Leu Gln Leu Thr Pro Tyr
145                 150                 155                 160

Ile Gln Arg Met Gln Thr Thr Ile Lys Glu Asn Val Asp Asn Leu His
                165                 170                 175
```

-continued

```
Thr Ser Met Met Pro Leu Ala Thr Asn Leu Lys Asp Lys Phe Asn Arg
            180                 185                 190

Asn Met Glu Glu Leu Lys Gly His Leu Thr Pro Arg Ala Asn Glu Leu
        195                 200                 205

Lys Ala Thr Ile Asp Gln Asn Leu Glu Asp Leu Arg Arg Ser Leu Ala
    210                 215                 220

Pro Leu Thr Val Gly Val Gln Glu Lys Leu Asn His Gln Met Glu Gly
225                 230                 235                 240

Leu Ala Phe Gln Met Lys Lys Asn Ala Glu Glu Leu Gln Thr Lys Val
                245                 250                 255

Ser Ala Lys Ile Asp Gln Leu Gln Lys Asn Leu Ala Pro Leu Val Glu
            260                 265                 270

Asp Val Gln Ser Lys Val Lys Gly Asn Thr Glu Gly Leu Gln Lys Ser
        275                 280                 285

Leu Glu Asp Leu Asn Arg Gln Leu Glu Gln Gln Val Glu Glu Phe Arg
    290                 295                 300

Arg Thr Val Glu Pro Met Gly Glu Met Phe Asn Lys Ala Leu Val Gln
305                 310                 315                 320

Gln Leu Glu Gln Phe Arg Gln Gln Leu Gly Pro Asn Ser Gly Glu Val
                325                 330                 335

Glu Ser His Leu Ser Phe Leu Glu Lys Ser Leu Arg Glu Lys Val Asn
            340                 345                 350

Ser Phe Met Ser Thr Leu Glu Lys Lys Gly Ser Pro Asp Gln Pro Gln
        355                 360                 365

Ala Leu Pro Leu Pro Glu Gln Ala Gln Glu Gln Ala Gln Glu Gln Val
    370                 375                 380

Gln Pro Lys Pro Leu Glu Ser
385                 390
```

<210> SEQ ID NO 209
<211> LENGTH: 468
<212> TYPE: DNA
<213> ORGANISM: Homo sapiens
<220> FEATURE:
<221> NAME/KEY: SITE
<222> LOCATION: (431)
<223> OTHER INFORMATION: n equals a,t,g, or c
<221> NAME/KEY: SITE
<222> LOCATION: (452)
<223> OTHER INFORMATION: n equals a,t,g, or c
<221> NAME/KEY: SITE
<222> LOCATION: (464)
<223> OTHER INFORMATION: n equals a,t,g, or c

<400> SEQUENCE: 209

```
gtgaaagaca gccttgagca agacctcaac aatatgaaca agttcctgga aaagctgagg     60

cctctgagtg ggagcgaggc tcctcggctc ccacaggacc cggtgggcat gcggcggcag    120

ctgcaggagg agttggagga ggtgaaggct cgcctccagc cctacatggc agaggcgcac    180

gagctggtgg gctggaattt ggagggcttg cggcacaact gaagccctac acgatggatc    240

tgatggagca ggtggccctg cgcgtgcagg agctgcagga gcagttgcgc gtggtggggg    300

aagacaccaa ggcccagttg ctgggggcgg tggacgaggc ttgggctttg ctgcagggac    360

tgcagagccg cgtggtgcac cacaccggcc gcttcaaaga gctcttccaa ccatacgccg    420

agagcctggt naacggcatc gggcgccacg tncaggagct gcancgca                 468
```

<210> SEQ ID NO 210
<211> LENGTH: 331

-continued

```
<212> TYPE: DNA
<213> ORGANISM: Homo sapiens

<400> SEQUENCE: 210

ggcaaggttc tgagcaagct gcaggcccgt ctggatgacc tgtgggaaga catcactcac     60

agccttcatg accagggcca cagccatctg ggggacccct gaggatctac ctgcccaggc    120

ccattcccag ctccttgtct ggggagcctt ggctctgagc ctctagcatg gttcagtcct    180

tgaaagtggc ctgttgggtg gagggtggaa ggtcctgtgc aggacaggga ggccaccaaa    240

ggggctgctg tctcctgcat atccagcctc ctgcgactcc ccaatctgga tgcattacat    300

tcaccaggct ttgcaaaaaa aaaaaaaaaa a                                   331


<210> SEQ ID NO 211
<211> LENGTH: 451
<212> TYPE: DNA
<213> ORGANISM: Homo sapiens
<220> FEATURE:
<221> NAME/KEY: SITE
<222> LOCATION: (390)
<223> OTHER INFORMATION: n equals a,t,g, or c
<221> NAME/KEY: SITE
<222> LOCATION: (438)
<223> OTHER INFORMATION: n equals a,t,g, or c
<221> NAME/KEY: SITE
<222> LOCATION: (450)
<223> OTHER INFORMATION: n equals a,t,g, or c

<400> SEQUENCE: 211

gacctgccca ggcccattcc cagctccttg tctggggagc cttggctctg agcctctagc     60

atggttcagt ccttgaaagt ggcctgttgg gtggagggtg gaaggtcctg tgcaggacag    120

ggaggccacc aaaggggctg ctgtctcctg catatccagc ctcctgcgac tccccaatct    180

ggatgcatta cattcaccag gctttgcaaa cccagcctcc cagtgctcat ttgggaatgc    240

tcatgagtta ctccattcaa gggtgaggga gtagggaggg agaggcacca tgcatgtggg    300

tgattatctg caagcctgtt tgccgtgatg ctggaagcct gtgccactac atcctggagt    360

ttggctctag tcacttctgg ctgcctggtn gccactgcta cagtggtcca cagagaggag    420

cacttgtctc cccagggntt ccatggcaan a                                   451


<210> SEQ ID NO 212
<211> LENGTH: 366
<212> TYPE: PRT
<213> ORGANISM: Homo sapiens

<400> SEQUENCE: 212

Met Ala Ser Met Ala Ala Val Leu Thr Trp Ala Leu Ala Leu Leu Ser
  1               5                  10                  15

Ala Phe Ser Ala Thr Gln Ala Arg Lys Gly Phe Trp Asp Tyr Phe Ser
             20                  25                  30

Gln Thr Ser Gly Asp Lys Gly Arg Val Glu Gln Ile His Gln Gln Lys
         35                  40                  45

Met Ala Arg Glu Pro Ala Thr Leu Lys Asp Ser Leu Glu Gln Asp Leu
     50                  55                  60

Asn Asn Met Asn Lys Phe Leu Glu Lys Leu Arg Pro Leu Ser Gly Ser
 65                  70                  75                  80

Glu Ala Pro Arg Leu Pro Gln Asp Pro Val Gly Met Arg Arg Gln Leu
                 85                  90                  95

Gln Glu Glu Leu Glu Glu Val Lys Ala Arg Leu Gln Pro Tyr Met Ala
            100                 105                 110
```

-continued

```
Glu Ala His Glu Leu Val Gly Trp Asn Leu Glu Gly Leu Arg Gln Gln
        115                 120                 125

Leu Lys Pro Tyr Thr Met Asp Leu Met Glu Gln Val Ala Leu Arg Val
    130                 135                 140

Gln Glu Leu Gln Glu Gln Leu Arg Val Val Gly Glu Asp Thr Lys Ala
145                 150                 155                 160

Gln Leu Leu Gly Gly Val Asp Glu Ala Trp Ala Leu Leu Gln Gly Leu
                165                 170                 175

Gln Ser Arg Val Val His His Thr Gly Arg Phe Lys Glu Leu Phe His
            180                 185                 190

Pro Tyr Ala Glu Ser Leu Val Ser Gly Ile Gly Arg His Val Gln Glu
        195                 200                 205

Leu His Arg Ser Val Ala Pro His Ala Pro Ala Ser Pro Ala Arg Leu
    210                 215                 220

Ser Arg Cys Val Gln Val Leu Ser Arg Lys Leu Thr Leu Lys Ala Lys
225                 230                 235                 240

Ala Leu His Ala Arg Ile Gln Gln Asn Leu Asp Gln Leu Arg Glu Glu
                245                 250                 255

Leu Ile Arg Ala Phe Ala Gly Thr Gly Thr Glu Glu Gly Ala Gly Pro
            260                 265                 270

Asp Pro Gln Met Leu Ser Glu Glu Val Arg Gln Arg Leu Gln Ala Phe
        275                 280                 285

Arg Gln Asp Thr Tyr Leu Gln Ile Ala Ala Phe Thr Arg Ala Ile Asp
    290                 295                 300

Gln Glu Thr Glu Glu Val Gln Gln Gln Leu Ala Pro Pro Pro Pro Gly
305                 310                 315                 320

His Ser Ala Phe Ala Pro Glu Phe Gln Gln Thr Asp Ser Gly Lys Val
                325                 330                 335

Leu Ser Lys Leu Gln Ala Arg Leu Asp Asp Leu Trp Glu Asp Ile Thr
            340                 345                 350

His Ser Leu His Asp Gln Gly His Ser His Leu Gly Asp Pro
        355                 360                 365


<210> SEQ ID NO 213
<211> LENGTH: 372
<212> TYPE: PRT
<213> ORGANISM: Homo sapiens

<400> SEQUENCE: 213

Met Cys Leu Leu Gly Gly Leu Ser Ala Pro Pro Leu Leu Leu Leu Pro
  1               5                  10                  15

Leu Leu Pro Leu Leu Leu Cys Pro Pro Thr Ala Gln Gly Asp Cys Ser
             20                  25                  30

Phe Pro Pro Glu Leu Pro Asn Ala Ile Gln Ser Val Gly Asp Gln Gln
         35                  40                  45

Ser Phe Pro Glu Lys Phe Thr Val Thr Tyr Lys Cys Lys Glu Gly Phe
     50                  55                  60

Val Lys Val Pro Gly Lys Ala Asp Ser Val Val Cys Leu Asn Asn Lys
 65                  70                  75                  80

Trp Ser Glu Val Ala Glu Phe Cys Asn Arg Ser Cys Asp Val Pro Thr
                 85                  90                  95

Arg Leu Gln Phe Ala Ser Leu Lys Lys Ser Phe Thr Lys Gln Asn Tyr
            100                 105                 110

Phe Pro Val Gly Ser Val Val Glu Tyr Glu Cys Arg Pro Gly Tyr Gln
```

-continued

```
        115                 120                 125

Arg Asp His Leu Leu Ser Gly Lys Leu Thr Cys Leu Leu Asn Phe Thr
    130                 135                 140

Trp Ser Lys Pro Asp Glu Phe Cys Lys Arg Lys Ser Cys Pro Asn Pro
145                 150                 155                 160

Gly Asp Leu Arg His Gly His Val Asn Ile Pro Thr Asp Ile Leu Tyr
                165                 170                 175

Ala Ala Val Ile His Phe Ser Cys Asn Lys Gly Tyr Arg Leu Val Gly
            180                 185                 190

Ala Ala Ser Ser Tyr Cys Ser Ile Val Asn Asp Asp Val Gly Trp Ser
        195                 200                 205

Asp Pro Leu Pro Glu Cys Gln Glu Ile Phe Cys Pro Glu Pro Pro Lys
    210                 215                 220

Ile Ser Asn Gly Val Ile Leu Asp Gln Gln Asn Thr Tyr Val Tyr Gln
225                 230                 235                 240

Gln Ala Val Lys Tyr Glu Cys Ile Lys Gly Phe Thr Leu Ile Gly Glu
                245                 250                 255

Asn Ser Ile Tyr Cys Thr Val Lys Gly Asp Gln Gly Glu Trp Ser Gly
            260                 265                 270

Arg Arg Leu Asn Ala Lys Val Leu Arg Phe Leu Gln Ser Tyr Gln Gln
        275                 280                 285

Gln Arg His His His Ser Lys Cys Phe Ser Tyr Lys Ala His Ile Ser
    290                 295                 300

Ser Ser Glu Thr His His Cys Lys Cys Tyr Arg Tyr Gln Ser Tyr Ile
305                 310                 315                 320

Ser Ser Ser Glu Thr His His Arg Glu Cys Ser Arg Tyr Arg Ser Tyr
                325                 330                 335

Ile Asn Ser Ser Glu Thr His Tyr Ser Gly Cys Phe Arg Asp Pro Val
            340                 345                 350

Ser Ser Pro Glu Ser His His Gly Lys Cys Val Cys Tyr Thr Gly His
        355                 360                 365

Ala Ser Asn Pro
    370


<210> SEQ ID NO 214
<211> LENGTH: 2464
<212> TYPE: DNA
<213> ORGANISM: Homo sapiens
<220> FEATURE:
<221> NAME/KEY: misc_feature
<222> LOCATION: (7)
<223> OTHER INFORMATION: n equals a,t,g, or c
<221> NAME/KEY: misc_feature
<222> LOCATION: (9)
<223> OTHER INFORMATION: n equals a,t,g, or c
<221> NAME/KEY: misc_feature
<222> LOCATION: (1049)
<223> OTHER INFORMATION: n equals a,t,g, or c
<221> NAME/KEY: misc_feature
<222> LOCATION: (2030)
<223> OTHER INFORMATION: n equals a,t,g, or c
<221> NAME/KEY: misc_feature
<222> LOCATION: (2157)
<223> OTHER INFORMATION: n equals a,t,g, or c

<400> SEQUENCE: 214

gaacgantng gtgacactat agaaggtacg cctgcaggta ccggtccgga attcccgggt      60

cgacccacgc gtccgcttac cgctgcttgc tggagcgagc ttccacttaa ctcccgtccc     120

ggtccccgcg cgccatgtgc ctcctcggcg ggctgagcgc cccgccgctg ctgctgctgc     180
```

-continued

```
cgctgctgcc gctgctgctg tgtccgccta cggcgcaggg tgactgcagc tttcccccag    240
agctacctaa tgccatacaa agtgtgggtg accaacagag ttttcctgaa aaattcacag    300
taacatacaa atgtaaagaa ggctttgtaa aggttcctgg caaggcagac tccgtggtct    360
gtctcaacaa taaatggtca gaggtggcag aattttgtaa ccgtagctgt gatgttccaa    420
ccaggctaca atttgcatct ctcaaaaagt ctttcaccaa acagaattat ttcccagtgg    480
gttccgttgt ggaatatgaa tgccgacctg gctaccaaag ggaccatctt ctctcaggaa    540
aactaacttg ccttctgaat tttacatggt ccaaacccga tgaattttgt aaaagaaaat    600
catgtcctaa tcctggagat ttaagacatg gtcatgtcaa cattccaact gacatattgt    660
atgctgcagt tatccacttc tcgtgtaaca aggggtacag gttagtcggt gcagcttcta    720
gttactgttc cattgtaaat gacgatgttg gctggagtga tccattgcct gaatgccaag    780
aaattttttg tccggaacca ccaaaaaatta gcaatggagt cattctagat caacagaaca    840
cttatgtgta tcaacaggct gtwaaatatg agtgtataaa aggcttcacc ctgatcggag    900
agaactctat ttattgtact gttaagggtg accaaggaga atggagtggc cgccgcctga    960
atgcaaaggt tctcagattt ctacagtcat accagcaaca gagacaccac cacagtaagt   1020
gcttcagcta caaagcccac atcagctcnt cagaaaccca ccactgcaaa tgttacaggt   1080
accaaagtta catcagctcc tcagaaaccc accacaggga atgttccagg taccgaagct   1140
acatcaactc ctcagaaacc cactacagcg gatgtttcag agaccccgtc agcagtccag   1200
aatcccatca cggcaaatgc gtytgctaca caggccatgc cagcaaccca tagatcctcc   1260
acagcaaaag cttcatttac acagagtctt ccagcaacac gaaagtccac tgctatacat   1320
gccccagtga ctaagggtct ccatacaaca aaaagattga cctctgctcg tattacagca   1380
aaacagagtt cagctactcc caggacaacc agcgcacctc atggaagagg gaccctctct   1440
tcagatgctg ccatcattgc agttggtaag tttggttctt cggcagttaa aaaaaattgt   1500
catcactgtg ggatgtacaa tccttattcc tggaggagaa tattgtcttt ttactgcctt   1560
aggaatacta ttaagatgaa atgtttaagg tcagggagaa gacgggtaaa tgcattttat   1620
cgacgtgttt ggtggacccc gttaggtact cggtacgttc ctaagtcttc ccaaccgtgt   1680
tcttgttcca aggtaatttt agggcaactt cacatcattt ggccagtcaa tcaagtatcc   1740
ctgaacgcct attgtctcaa tgcattatca ttctaggggc caaaaacaac mataaggaag   1800
ctattatcaa tacagttttt aagcctcaag tgktttacaa gtactcacaa actactcctt   1860
ggttgkttct agacgtctgt tccagataaa ccagaatgct acytttgatt acatcctgtt   1920
ctttttttccc tttcctgtca gtgatttaaa gcaaagatag ctttaaaatt attctgttgc   1980
tatagactta aggacatatc tatgttgcaa atttcttttt cttgttcccn agtcttttgt   2040
tgttcattaa atatattatt tgatgttata cattttacca agaagattaa taactcctaa   2100
agaagatggc aaaagaaatg tttaagaagc aatacagcta agttggcata ttaaaangga   2160
atgcccagta gaaaatatgc acattaaaaa gtgaatattt taaaattatg tccttataag   2220
ctgaggtctc ctatttatgc atgcatgagt gaaacaaggg actgaagctg aaaaggtgtt   2280
ttttaattat tattattatt tatagttctt ttatagttct tttatatttt gaatgaacct   2340
ctccttagct aaaatagtta tcttgaaaga tttgaacagt tggattcact ttgtttgttt   2400
gatattttca atagaaataa atgcattcta aatgaaaaaa aaaaaaaaaa aaaaaagggc   2460
ggcc                                                                2464
```

-continued

<210> SEQ ID NO 215
<211> LENGTH: 370
<212> TYPE: PRT
<213> ORGANISM: Homo sapiens

<400> SEQUENCE: 215

```
Met Gly Ala Val Thr Gly Val Val Thr Ala Leu Val Thr Lys Phe Thr
  1               5                  10                  15

Lys Leu His Cys Phe Pro Leu Leu Glu Thr Ala Leu Phe Phe Leu Met
             20                  25                  30

Ser Trp Ser Thr Phe Leu Leu Ala Glu Ala Cys Gly Phe Thr Gly Val
         35                  40                  45

Val Ala Val Leu Phe Cys Gly Ile Thr Gln Ala His Tyr Thr Tyr Asn
     50                  55                  60

Asn Leu Ser Val Glu Ser Arg Ser Arg Thr Lys Gln Leu Phe Glu Val
 65                  70                  75                  80

Leu His Phe Leu Ala Glu Asn Phe Ile Phe Ser Tyr Met Gly Leu Ala
                 85                  90                  95

Leu Phe Thr Phe Gln Lys His Val Phe Ser Pro Ile Phe Ile Ile Gly
            100                 105                 110

Ala Phe Val Ala Ile Phe Leu Gly Arg Ala Ala His Ile Tyr Pro Leu
        115                 120                 125

Ser Phe Phe Leu Asn Leu Gly Arg Arg His Lys Ile Gly Trp Asn Phe
    130                 135                 140

Gln His Met Met Met Phe Ser Gly Leu Arg Gly Ala Met Ala Phe Ala
145                 150                 155                 160

Leu Ala Ile Arg Asp Thr Ala Ser Tyr Ala Arg Gln Met Met Phe Thr
                165                 170                 175

Thr Thr Leu Leu Ile Val Phe Phe Thr Val Trp Ile Ile Gly Gly Gly
            180                 185                 190

Thr Thr Pro Met Leu Ser Trp Leu Asn Ile Arg Val Gly Val Asp Pro
        195                 200                 205

Asp Gln Asp Pro Pro Pro Asn Asn Asp Ser Phe Gln Val Leu Gln Gly
    210                 215                 220

Asp Gly Pro Asp Ser Ala Arg Gly Asn Arg Thr Lys Gln Glu Ser Ala
225                 230                 235                 240

Trp Ile Phe Arg Leu Trp Tyr Ser Phe Asp His Asn Tyr Leu Lys Pro
                245                 250                 255

Ile Leu Thr His Ser Gly Pro Pro Leu Thr Thr Thr Leu Pro Ala Trp
            260                 265                 270

Cys Gly Leu Leu Ala Arg Cys Leu Thr Ser Pro Gln Val Tyr Asp Asn
        275                 280                 285

Gln Glu Pro Leu Arg Glu Glu Asp Ser Asp Phe Ile Leu Thr Glu Gly
    290                 295                 300

Asp Leu Thr Leu Thr Tyr Gly Asp Ser Thr Val Thr Ala Asn Gly Ser
305                 310                 315                 320

Ser Ser Ser His Thr Ala Ser Thr Ser Leu Glu Gly Ser Arg Arg Thr
                325                 330                 335

Lys Ser Ser Ser Glu Glu Val Leu Glu Arg Asp Leu Gly Met Gly Asp
            340                 345                 350

Gln Lys Val Ser Ser Arg Gly Thr Arg Leu Val Phe Pro Leu Glu Asp
        355                 360                 365

Asn Ala
    370
```

-continued

<210> SEQ ID NO 216
<211> LENGTH: 494
<212> TYPE: PRT
<213> ORGANISM: Homo sapiens

<400> SEQUENCE: 216

```
Met Glu Phe Gly Leu Thr Trp Val Phe Leu Val Ala Leu Leu Arg Gly
  1               5                  10                  15

Val His Cys Gln Val Gln Leu Val Glu Ser Gly Gly Ala Val Val Gln
             20                  25                  30

Pro Gly Gly Ser Leu Arg Leu Ser Cys Ala Ala Ser Gly Phe Thr Phe
         35                  40                  45

Ser Arg Tyr Gly Met His Trp Val Arg Gln Ala Pro Gly Lys Gly Leu
     50                  55                  60

Gln Trp Leu Ala Leu Val Leu His Asp Gly Gly Gln Lys Tyr Asn Glu
 65                  70                  75                  80

Asp Val Val Lys Gly Arg Phe Thr Ile Ser Arg Asp Asn Ser Asn Asn
                 85                  90                  95

Lys Val Tyr Leu Gln Met Asp Ser Leu Arg Gly Glu Asp Thr Ala Thr
            100                 105                 110

Tyr Tyr Cys Val Arg Gly Met Trp Glu Gln Leu Pro Ser Tyr Tyr Phe
        115                 120                 125

Asp Tyr Trp Gly Gln Gly Thr Leu Val Thr Val Ser Ser Ala Ser Pro
    130                 135                 140

Thr Ser Pro Lys Val Phe Pro Leu Ser Leu Cys Ser Thr Gln Pro Asp
145                 150                 155                 160

Gly Asn Val Val Ile Ala Cys Leu Val Gln Gly Phe Phe Pro Gln Glu
                165                 170                 175

Pro Leu Ser Val Thr Trp Ser Glu Ser Gly Gln Gly Val Thr Ala Arg
            180                 185                 190

Asn Phe Pro Pro Ser Gln Asp Ala Ser Gly Asp Leu Tyr Thr Thr Ser
        195                 200                 205

Ser Gln Leu Thr Leu Pro Ala Thr Gln Cys Leu Ala Gly Lys Ser Val
    210                 215                 220

Thr Cys His Val Lys His Tyr Thr Asn Pro Ser Gln Asp Val Thr Val
225                 230                 235                 240

Pro Cys Pro Val Pro Ser Thr Pro Pro Thr Pro Ser Pro Ser Thr Pro
                245                 250                 255

Pro Thr Pro Ser Pro Ser Cys Cys His Pro Arg Leu Ser Leu His Arg
            260                 265                 270

Pro Ala Leu Glu Asp Leu Leu Leu Gly Ser Glu Ala Asn Leu Thr Cys
        275                 280                 285

Thr Leu Thr Gly Leu Arg Asp Ala Ser Gly Ala Thr Phe Thr Trp Thr
    290                 295                 300

Pro Ser Ser Gly Lys Ser Ala Val Gln Gly Pro Pro Glu Arg Asp Leu
305                 310                 315                 320

Cys Gly Cys Tyr Ser Val Ser Ser Val Leu Pro Gly Cys Ala Gln Pro
                325                 330                 335

Trp Asn His Gly Glu Thr Phe Thr Cys Thr Ala Ala Tyr Pro Glu Leu
            340                 345                 350

Lys Thr Pro Leu Thr Ala Asn Ile Thr Lys Ser Gly Asn Thr Phe Arg
        355                 360                 365

Pro Glu Val His Leu Leu Pro Pro Pro Ser Glu Glu Leu Ala Leu Asn
```

-continued

```
    370                 375                 380

Glu Leu Val Thr Leu Thr Cys Leu Ala Arg Gly Phe Ser Pro Lys Asp
385                 390                 395                 400

Val Leu Val Arg Trp Leu Gln Gly Ser Gln Glu Leu Pro Arg Glu Lys
                405                 410                 415

Tyr Leu Thr Trp Ala Ser Arg Gln Glu Pro Ser Gln Gly Thr Thr Thr
            420                 425                 430

Phe Ala Val Thr Ser Ile Leu Arg Val Ala Ala Glu Asp Trp Lys Lys
        435                 440                 445

Gly Asp Thr Phe Ser Cys Met Val Gly His Glu Ala Leu Pro Leu Ala
    450                 455                 460

Phe Thr Gln Lys Thr Ile Asp Arg Leu Ala Gly Lys Pro Thr His Val
465                 470                 475                 480

Asn Val Ser Val Val Met Ala Glu Val Asp Gly Thr Cys Tyr
                485                 490


<210> SEQ ID NO 217
<211> LENGTH: 1059
<212> TYPE: PRT
<213> ORGANISM: Homo sapiens

<400> SEQUENCE: 217

Met Lys Cys Ser Tyr Thr Val Val Phe Leu Leu Phe Tyr Leu Leu Ile
  1               5                  10                  15

Ala Ser Phe His Val Asp Ala Leu Ser Trp Ala Ala Trp Ser Pro Trp
            20                  25                  30

Ser Ser Cys Thr Lys Thr Cys Gly Gly Gly Val Ser Arg Gln Leu Arg
        35                  40                  45

Arg Cys Leu Thr Ser Lys Cys Ser Gly Glu Ser Val Arg Phe Lys Val
    50                  55                  60

Cys Ala Gln Lys Thr Cys Glu Ser Lys Ser Arg Leu Ala Arg Asp Thr
 65                  70                  75                  80

Ile Cys Gly Gly Glu Glu Ile Val Ser Arg Gly Gln Cys Glu Val Val
                 85                  90                  95

Cys Arg Ser Arg Leu Thr Gly Ala Asn Phe Leu Trp Arg Val Asp Asp
            100                 105                 110

Gly Thr Pro Cys Gln Ala Ala Thr Ser Arg Ala Val Cys Ser Lys Gly
        115                 120                 125

Ser Cys Gln Ile Val Gly Cys Asp Gly Leu Ile Ser Ser Ser Phe Arg
    130                 135                 140

Phe Asp Ala Cys Gly Val Cys Gly Gly Arg Gly Asp Thr Cys Asp Asn
145                 150                 155                 160

Gly Lys Phe Ile Trp Lys Val Ser Glu Glu Tyr Thr Ala Cys Ala Ser
                165                 170                 175

Asn Cys Asp Asp Ile Val Asp Trp Ser Gly Ala Gly Arg Ser Ile Ala
            180                 185                 190

Ser Thr Ser Gln Pro Ile Val Val Cys Val Asn Ala Ile Thr Gly Arg
        195                 200                 205

Val Val Pro Glu Lys Leu Cys Ala Asp Lys Leu Arg Pro Lys Val Glu
    210                 215                 220

Ala Arg Pro Cys Pro Met Leu Ile Cys Pro Ser Arg Trp Met Ala Ala
225                 230                 235                 240

Asp Trp Thr Glu Cys Val Pro His Cys Gly Glu Gly Thr Arg Lys Arg
                245                 250                 255
```

-continued

```
Glu Val Tyr Cys Val Gln Thr Ala His Asn Val Thr Val His Val Pro
            260                 265                 270

Asp Thr Phe Cys Glu Asn Gly Thr Arg Pro Ala Ala Glu Glu Asn Cys
        275                 280                 285

Val Ser Thr Ser Cys Gly Arg Trp Glu Ala Gly Lys Trp Ser Lys Cys
    290                 295                 300

Thr Ala Ser Cys Gly Gln Gly Val Arg Arg Arg His Val Ala Cys Val
305                 310                 315                 320

Gly Gly Ser Asp Cys Asp Glu Gly Gly Arg Pro Arg Gln Glu Thr Thr
                325                 330                 335

Cys Tyr Ala Gly Ile Pro Cys Ser Ile Ala Thr Asn Ser Leu Asp Trp
            340                 345                 350

Asn Asp Arg Ala Tyr Leu Asp Gly Asn Thr Phe Gly Ser Met Asp Asn
        355                 360                 365

His Asn Asp Trp Gln Ala Pro Arg Leu Val Ala Gly Glu Trp Ser Thr
    370                 375                 380

Cys Ser Ser Thr Cys Gly Thr Gly Val Met Ser Arg Thr Val Glu Cys
385                 390                 395                 400

Val Ala Val Asn Pro Ile Ser Ser Ala Pro Ile Lys Leu Pro Met Ser
                405                 410                 415

Glu Cys Gln Asp Gln Glu Gln Pro Lys Leu Phe Glu Ser Cys Glu Val
            420                 425                 430

Arg Ser Cys Pro Leu Gln Glu Asp Ser Lys Leu Ser Glu Asp Glu Ala
        435                 440                 445

Pro Tyr Gln Trp Arg Tyr Gly Asp Trp Thr Gln Cys Ser Ala Ser Cys
    450                 455                 460

Leu Gly Gly Lys Gln Lys Ala Ala Leu Lys Cys Ile Gln Val Ser Thr
465                 470                 475                 480

Gly Lys Ser Val Gln Trp Ser Gln Cys Asp Ala Arg Arg Arg Pro Pro
                485                 490                 495

Glu Lys Ser Arg Pro Cys Asn Gln His Pro Cys Pro Pro Phe Trp Leu
            500                 505                 510

Thr Ser Lys Tyr Ser Asp Cys Ser Met Ser Cys Gly Ser Gly Thr Ala
        515                 520                 525

Arg Arg Ser Val Lys Cys Ala Gln Thr Val Ser Lys Thr Asp Gly Ala
    530                 535                 540

Asp Ala His Ile Val Leu Arg Asp Asp Arg Cys His Phe Lys Lys Pro
545                 550                 555                 560

Gln Glu Thr Glu Thr Cys Asn Val Val Ala Cys Pro Ala Thr Trp Val
                565                 570                 575

Ser Ser Leu Asn Lys Arg His Asn Lys Ile Lys Leu Asn Lys Leu Lys
            580                 585                 590

Thr Ala Gln Trp Thr Glu Cys Ser Arg Ser Cys Asp Ser Gly Glu Arg
        595                 600                 605

Arg Arg Gln Val Trp Cys Glu Ile Arg Asp Ser Arg Gly Lys Thr Gln
    610                 615                 620

Arg Arg Pro Asp Val Glu Cys Asp Ala Asn Thr Lys Pro Gln Thr Val
625                 630                 635                 640

Glu Val Cys Ser Phe Gly Ser Cys Ser Arg Pro Glu Leu Leu Ser Asn
                645                 650                 655
```

-continued

```
Arg Val Phe Glu Gln Asn Ala Glu Gln Lys Lys Leu Thr Leu Gly Ile
            660                 665                 670

Gly Gly Val Ala Thr Leu Tyr Gln Gly Thr Ser Ile Lys Ile Lys Cys
        675                 680                 685

Pro Ala Lys Lys Phe Asp Lys Lys Lys Ile Tyr Trp Lys Lys Asn Gly
    690                 695                 700

Lys Lys Ile Lys Asn Asp Ala His Ile Lys Val Ser Ala Asn Gly Asn
705                 710                 715                 720

Leu Arg Val Phe His Ala Arg Met Glu Asp Ala Gly Val Tyr Glu Cys
                725                 730                 735

Phe Thr Asp Arg Leu Gln Gly Asn Val Thr Leu Asn Phe Lys Tyr Arg
            740                 745                 750

Asp Phe Pro Ala Ser Arg Val Asp Leu Ala Pro Lys Pro Gln Ile Pro
        755                 760                 765

Ser Thr Lys Asn Arg Gln Arg Val Gln Val Ser Lys Glu Asp Val Leu
    770                 775                 780

Arg Glu Gln Ala Ser Val Leu His Lys Met Asn Val Ser Leu Ile Glu
785                 790                 795                 800

Ala Leu Leu Thr Ala Pro Asn Asp Glu Lys Ala Arg Glu Gln Leu Arg
                805                 810                 815

Lys Tyr Gly Asn Glu Leu Val Ala Arg Trp Asp Ile Gly His Trp Ser
            820                 825                 830

Glu Cys Arg Gln Lys Thr Cys His Val Ala Gly Tyr Gln Ala Arg Gly
        835                 840                 845

Ile Ser Cys Lys Val Thr Phe His Gly Glu Ile Arg Asn Val Asp Asn
    850                 855                 860

Ser Ile Cys Glu Ser Leu Ala Ser Val Arg Pro Pro Glu Thr Arg Pro
865                 870                 875                 880

Cys His Arg Glu Asp Cys Pro Arg Trp Glu Ala Ser Gln Trp Ser Glu
                885                 890                 895

Cys Ser Ser Gln Arg Cys Val Ser Ser Met Leu Ala Gln Lys Arg Arg
            900                 905                 910

Asn Val Thr Cys Arg Phe Thr Asn Gly Thr Ser Val Asp Ile Gln His
        915                 920                 925

Cys Asp Ile Thr Asn Arg Pro Ala Thr Thr Met Asp Cys Pro Asn Gln
    930                 935                 940

Asn Cys Lys Ala Glu Trp Arg Thr Ser Asp Trp Gly Ser Cys Ser Ser
945                 950                 955                 960

Glu Cys Gly Thr Gly Gly Val Gln Leu Arg Leu Leu Ser Cys Val Trp
                965                 970                 975

Ile Ser Ser Gly Arg Pro Ala Gly Arg Asn Cys Glu Gln Met Arg Arg
            980                 985                 990

Pro His Ser Ala Arg Ala Cys Val  Ala Asp Glu Pro Leu  Pro Pro Cys
        995                 1000                1005

Met Pro  Thr Ala Ser Ala Leu  Tyr Gln Arg Asp Ala  Ser Cys Gln Asp
    1010                1015                1020

Gln  Ser Arg Phe Cys Asp  Ile Ile Lys Leu Phe  His Ser Cys Asp
1025                1030                1035

Ser  Leu Glu Val Arg Gln  Lys Cys Cys Ser Thr  Cys Thr Phe Val
1040                1045                1050

Glu  Arg Lys Lys Phe
1055
```